(12) United States Patent
Malhotra et al.

(10) Patent No.: US 12,084,429 B2
(45) Date of Patent: Sep. 10, 2024

(54) FUSED RING COMPOUNDS

(71) Applicant: Genentech, Inc., South San Francisco, CA (US)

(72) Inventors: Sushant Malhotra, South San Francisco, CA (US); Jianfeng Xin, Beijing (CN); Steven Do, South San Francisco, CA (US); Jack Terrett, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 93 days.

(21) Appl. No.: 17/644,993

(22) Filed: Dec. 17, 2021

(65) Prior Publication Data

US 2023/0089126 A1 Mar. 23, 2023

Related U.S. Application Data

(63) Continuation of application No. 16/679,104, filed on Nov. 8, 2019, now Pat. No. 11,236,068.

(30) Foreign Application Priority Data

Nov. 9, 2018 (WO) ................ PCT/CN2018/114788

(51) Int. Cl.
| | |
|---|---|
| *C07D 401/04* | (2006.01) |
| *A61K 9/00* | (2006.01) |
| *A61K 31/517* | (2006.01) |
| *A61P 35/00* | (2006.01) |
| *C07D 401/14* | (2006.01) |
| *C07D 403/04* | (2006.01) |
| *C07D 403/14* | (2006.01) |
| *C07D 405/14* | (2006.01) |
| *C07D 471/14* | (2006.01) |

(52) U.S. Cl.
CPC .......... *C07D 401/14* (2013.01); *A61K 9/0019* (2013.01); *A61K 9/0053* (2013.01); *A61P 35/00* (2018.01); *C07D 405/14* (2013.01)

(58) Field of Classification Search
CPC ................ C07D 401/04; C07D 401/14; C07D 403/04; C07D 403/14; C07D 405/14; C07D 471/14; A61K 31/517; A61P 35/00
See application file for complete search history.

(56) References Cited

U.S. PATENT DOCUMENTS

| | | | |
|---|---|---|---|
| 9,810,690 B2 | 11/2017 | Patricelli et al. | |
| 9,840,516 B2 | 12/2017 | Li et al. | |
| 9,862,701 B2 | 1/2018 | Li et al. | |
| 9,988,357 B2 | 6/2018 | Mani et al. | |
| 10,011,600 B2 | 7/2018 | Li et al. | |
| 10,023,588 B2 | 7/2018 | Ostrem et al. | |
| 10,111,874 B2 | 10/2018 | Janes et al. | |
| 10,125,134 B2 | 11/2018 | Blake et al. | |
| 10,144,724 B2 | 12/2018 | Li et al. | |
| 10,246,424 B2 | 4/2019 | Li et al. | |
| 10,370,386 B2 | 8/2019 | Li et al. | |
| 10,414,757 B2 | 9/2019 | Li et al. | |
| 2010/0048557 A1 | 2/2010 | Zhu et al. | |
| 2018/0015087 A1 | 1/2018 | Liu et al. | |
| 2019/0062313 A1 | 2/2019 | Li et al. | |
| 2019/0062314 A1 | 2/2019 | Li et al. | |
| 2019/0144444 A1 | 5/2019 | Blake et al. | |
| 2019/0233440 A1 | 8/2019 | Planken et al. | |

FOREIGN PATENT DOCUMENTS

| | | |
|---|---|---|
| WO | 9902558 A1 | 1/1999 |
| WO | 2016044772 A1 | 3/2015 |
| WO | 2015054572 A1 | 4/2015 |
| WO | 2016164675 A1 | 10/2016 |
| WO | 2017172979 A1 | 10/2017 |
| WO | 2017201161 A1 | 11/2017 |
| WO | 2018218069 | 11/2018 |
| WO | 2019125849 A1 | 6/2019 |

OTHER PUBLICATIONS

Fleisher et al., "Improved oral drug delivery: solubility limitations overcome by the use of prodrugs", Advanced Drug Delivery Reviews, 1996, vol. 19, No. 2, pp. 115-130.
Robinson et al., "Discovery of the Hemifumarate and (α-L-Alanyloxy)methyl Ether as Prodrugs of an Antirheumatic Oxindole: Prodrugs for the Enolic OH Group", Journal of Medicinal Chemistry, 1996, vol. 39, No. 1, pp. 10-18.
Stella et al., "Prodrugs: A Chemical Approach to Targeted Drug Delivery", Directed Drug Delivery, Borchardt et al., (ed.), 1985, pp. 247-267.
Wilman, Derry E.V., "Prodrugs in Cancer Chemotherapy", Biochemical Society Transactions, 615th Meeting Belfast, 1986, vol. 14, pp. 375-382.
International Search Report for PCT/US2019/060578, mailed May 8, 2020, 5 pages.
Written Opinion for PCT/US2019/060578, mailed May 8, 2020, 9 pages.

*Primary Examiner* — Brenda L Coleman

(74) *Attorney, Agent, or Firm* — Armstrong Teasdale LLP

(57) ABSTRACT

This invention pertains to fused ring compounds of Formula (I), as further detailed herein, which are used for the inhibition of Ras proteins, as well as compositions comprising these compounds and methods of treatment by their administration.

15 Claims, No Drawings

FUSED RING COMPOUNDS

CROSS-REFERENCE TO RELATED APPLICATIONS

This application is a continuation of U.S. patent application Ser. No. 16/679,104, filed on Nov. 8, 2019 and claims priority to International Application Serial Number PCT/CN2018/114788, filed on Nov. 9, 2018, each of which are herein incorporated by reference in their entirety.

FIELD OF THE DISCLOSURE

This invention pertains to fused ring compounds of Formula (I), as further detailed herein, which are used for the inhibition of Ras proteins, such as K-Ras, H-Ras, and N-Ras, as well as compositions comprising these compounds and methods of treatment by their administration.

BACKGROUND OF THE DISCLOSURE

Ras is a small GTP-binding protein that functions as a nucleotide-dependent switch for central growth signaling pathways. In response to extracellular signals, Ras is converted from a GDP-bound ($Ras^{GDP}$) to a GTP-bound ($Ras^{GTP}$) state, as catalyzed by guanine nucleotide exchange factors (GEFs), notably the SOS1 protein. Active $Ras^{GTP}$ mediates its diverse growth-stimulating functions through its direct interactions with effectors including Raf, PI3K, and Ral guanine nucleotide dissociation stimulator. The intrinsic GTPase activity of Ras then hydrolyzes GTP to GDP to terminate Ras signaling. The Ras GTPase activity can be further accelerated by its interactions with GTPase-activating proteins (GAPs), including the neurofibromin 1 tumor suppressor.

Mutant Ras has a reduced GTPase activity, which prolongs its activated conformation, thereby promoting Ras-dependent signaling and cancer cell survival or growth. Mutation in Ras which affects its ability to interact with GAP or to convert GTP back to GDP will result in a prolonged activation of the protein and consequently a prolonged signal to the cell telling it to continue to grow and divide. Because these signals result in cell growth and division, overactive RAS signaling may ultimately lead to cancer. Mutations in any one of the three main isoforms of RAS (H-Ras, N-Ras, or K-Ras) genes are common events in human tumorigenesis. Among the three Ras isoforms (K, N, and H), K-Ras is most frequently mutated.

The most common K-Ras mutations are found at residue G12 and G13 in the P-loop and at residue Q61. G12C is a frequent mutation of K-Ras gene (glycine-12 to cysteine). G12D and G13D are other frequent mutations. Mutations of Ras in cancer are associated with poor prognosis. Inactivation of oncogenic Ras in mice results in tumor shrinkage. Thus, Ras is widely considered an oncology target of exceptional importance.

SUMMARY OF THE DISCLOSURE

In one aspect, the present disclosure is directed to a compound of Formula (I):

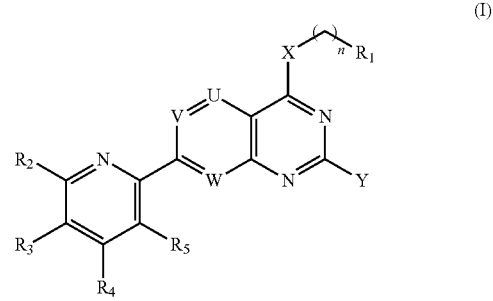

or a pharmaceutically acceptable salt thereof;
wherein,
$R_1$, $R_2$, $R_3$, $R_4$, $R_5$, X, Y, U, V, W, and n are as defined herein.

Another aspect of the disclosure includes a compound of Formula (II):

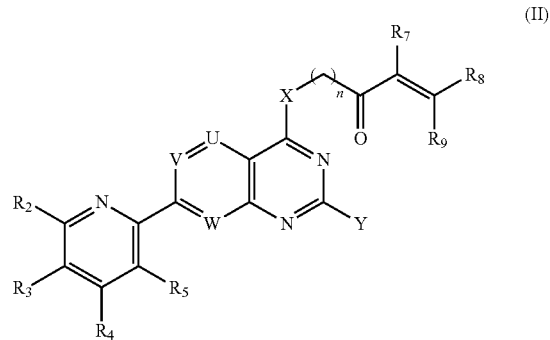

or a pharmaceutically acceptable salt thereof;
wherein, $R_2$, $R_3$, $R_4$, $R_5$, $R_7$, $R_8$, $R_9$, X, Y, U, V, W, and n are as defined herein.

Also disclosed, is a compound of Formula (III):

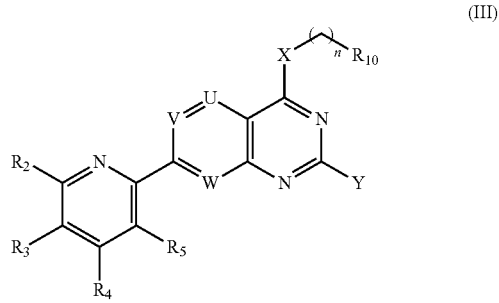

or a pharmaceutically acceptable salt thereof;
wherein, $R_2$, $R_3$, $R_4$, $R_5$, $R_{10}$, X, Y, U, V, W, and n are as defined herein.

In another aspect, the present disclosure is directed to a compound of Formula (IV):

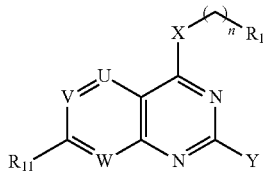

or a pharmaceutically acceptable salt thereof;
wherein, $R_1$, $R_{11}$, X, Y, U, V, W, and n are as defined herein.

Also provided is a pharmaceutical composition comprising a compound of the invention, or a pharmaceutically acceptable salt thereof, and a pharmaceutically acceptable excipient.

Another aspect includes a method of treating cancer comprising administering to an individual in need thereof a therapeutically effective amount of a compound of the invention, or a pharmaceutically acceptable salt thereof.

Another aspect includes a method of regulating activity of a mutant K-Ras G12C protein, the method comprising reacting the mutant protein with the compound of the invention, or a pharmaceutically acceptable salt thereof.

Another aspect includes a method of treating a disorder mediated by a K-Ras G12C mutation in an individual in need thereof, the method comprising: determining if the individual has the mutation; and if the individual is determined to have the mutation, then administering to the individual a therapeutically effective amount of the pharmaceutical composition of the invention.

Another aspect includes a method of inhibiting tumor metastasis, the method comprising administering a therapeutically effective amount of the pharmaceutical composition of the invention to an individual in need thereof.

DETAILED DESCRIPTION OF THE DISCLOSURE

Definitions

The term "halogen" or "halo" refers to F, Cl, Br or I. Additionally, terms such as "haloalkyl," are meant to include monohaloalkyl and polyhaloalkyl.

The term "alkyl" refers to a saturated linear or branched-chain monovalent hydrocarbon radical. In one example, the alkyl radical is one to eighteen carbon atoms ($C_{1-18}$). In other examples, the alkyl radical is $C_{1-12}$, $C_{1-10}$, $C_{1-8}$, $C_{1-6}$, $C_{1-5}$, $C_{1-4}$, or $C_{1-3}$. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl and 1-octyl.

The term "amino" refers to —$NH_2$.
The term "alkylamino" refers to —NH-alkyl.
The term "dialkylamino" refers to —N(alkyl)$_2$.
The term "oxo" refers to =O.
The term "carboxy" refers to —C(=O)OH.
The term "carbamoyl" refers to —C(=O)$NH_2$.
The term "alkanoyl" refers to —C(=O)-alkyl.
The term "hydroxyalkanoyl" refers to —C(=O)-hydroxyalkyl.
The term "alkanoylamino" refers to —NH—C(=O)-alkyl.
The term "alkoxy" refers to —O-alkyl.
The term "alkoxyalkyl" refers to an alkyl substituted with one alkoxy substituent.
The term "dialkylamino cyclopropyl" refers to a cyclopropyl substituted with one dialkylamino substituent.
The term "alkylsulfanyl" refers to —S(=O)-alkyl.
The term "alkylsulfonyl" refers to —S(=O)$_2$-alkyl.
The term "alkylsulfonylamino" refers to —NH—S(=O)$_2$-alkyl.
The term "alkylthio" refers to —S-alkyl.
The term "haloalkylthio" refers to —S-haloalkyl.
The term "aminoalkyl" refers to alkyl substituted with one amino substituent.
The term "carbamoylalkyl" refers to alkyl substituted with one carbamoyl substituent.
The term "carboxyalkyl" refers to alkyl substituted with one carboxy substituent.
The terms "cyano" or "nitrile" refers to —C≡N or —CN.
The term "cyanoalkyl" refers to alkyl substituted with one cyano substituent.
The term "haloalkoxy" refers to —O-haloalkyl.
The term "heterocyclylamino" refers to —NH-heterocyclyl.
The term "hydroxy" refers to —OH.
The term "hydroxyalkyl" refers to alkyl substituted with one hydroxy substituent.
The term "alkenyl" refers to linear or branched-chain monovalent hydrocarbon radical with at least one carbon-carbon double bond, and includes radicals having "cis" and "trans" orientations, or alternatively, "E" and "Z" orientations. In one example, the alkenyl radical is two to eighteen carbon atoms ($C_{2-18}$). In other examples, the alkenyl radical is $C_{2-12}$, $C_{2-10}$, $C_{2-8}$, $C_{2-6}$, or $C_{2-3}$. Examples include, but are not limited to, ethenyl or vinyl (—CH=$CH_2$), prop-1-enyl (—CH=$CHCH_3$), prop-2-enyl (—$CH_2$CH=$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl.

The term "alkynyl" refers to a linear or branched monovalent hydrocarbon radical with at least one carbon-carbon, triple bond. In one example, the alkynyl radical is two to eighteen carbon atoms ($C_{2-18}$). In other examples, the alkynyl radical is $C_{2-12}$, $C_{2-10}$, $C_{2-8}$, $C_{2-6}$, or $C_{2-3}$. Examples include, but are not limited to, ethynyl (—C≡CH), prop-1-ynyl (—C≡$CCH_3$), prop-2-ynyl (propargyl, —$CH_2$C≡CH), but-1-ynyl, but-2-ynyl, and but-3-ynyl.

The term "alkylene" refers to a saturated, branched, or straight chain hydrocarbon group having two monovalent radical centers derived by the removal of two hydrogen atoms from the same or two different carbon atoms of a parent alkane. In one example, the divalent alkylene group is one to eighteen carbon atoms ($C_{1-18}$). In other examples, the divalent alkylene group is $C_{1-12}$, $C_{1-10}$, $C_{1-8}$, $C_{1-6}$, $C_{1-5}$, $C_{1-4}$, or $C_{1-3}$. Example alkylene groups include methylene (—CH$_2$—), 1,1-ethyl (—CH(CH$_3$)—), (1,2-ethyl (—CH$_2$CH$_2$—), 1,1-propyl (—CH(CH$_2$CH$_3$)—), 2,2-propyl (—C(CH$_3$)$_2$—), 1,2-propyl (—CH(CH$_3$)CH$_2$—), 1,3-propyl (—CH$_2$CH$_2$CH$_2$—), 1,1-dimethyleth-1,2-yl (—C(CH$_3$)$_2$CH$_2$—), 1,4-butyl (—CH$_2$CH$_2$CH$_2$CH$_2$—), and the like.

The term "aryl" refers to a carbocyclic aromatic group, whether or not fused to one or more groups, having the number of carbon atoms designated, or if no number is designated, up to 14 carbon atoms. One example includes aryl groups having 6-14 carbon atoms. Another example includes aryl groups having 6-10 carbon atoms. Examples of aryl groups include phenyl, naphthyl, biphenyl, phenanthrenyl, naphthacenyl, 1,2,3,4-tetrahydronaphthalenyl, 1H-indenyl, 2,3-dihydro-1H-indenyl, and the like (see, e.g., Lang's Handbook of Chemistry (Dean, J. A., ed.) 13$^{th}$ ed. Table 7-2 [1985]). A particular aryl is phenyl.

The term "cycloalkyl" refers to a saturated hydrocarbon ring group. Cycloalkyl encompasses mono-, bi-, tricyclic, spiro and bridged, saturated ring systems. In one example, the cycloalkyl group is 3 to 12 carbon atoms ($C_{3-12}$). In other examples, cycloalkyl is $C_{3-7}$, $C_{3-8}$, $C_{3-10}$, or $C_{5-10}$. In other examples, the cycloalkyl group, as a monocycle, is $C_{3-8}$, $C_{3-6}$, or $C_{5-6}$. In another example, the cycloalkyl group, as a bicycle, is $C_7$-$C_{12}$. In another example, the cycloalkyl group, as a spiro system, is $C_{5-12}$. Examples of monocyclic cycloalkyl include cyclopropyl, cyclobutyl, cyclopentyl, cyclohexyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spirocycloalkyl include, spiro[2.2]pentane, spiro[2.3]hexane, spiro[2.4]heptane, spiro[2.5]octane and spiro[4.5]decane.

The term "cycloalkenyl" refers to a non-aromatic, hydrocarbon ring group with at least one carbon-carbon double bond. Cycloalkenyl encompasses mono-, bi-, tricyclic, spiro or bridged, saturated ring systems. Examples of monocyclic cycloalkenyl include 1-cyclopent-1-enyl, 1-cyclopent-2-enyl, 1-cyclopent-3-enyl, 1-cyclohex-1-enyl, 1-cyclohex-2-enyl, 1-cyclohex-3-enyl, and cyclohexadienyl. Exemplary arrangements of bicyclic cycloalkenyls having 7 to 12 ring atoms include, but are not limited to, [4,4], [4,5], [5,5], [5,6] or [6,6] ring systems. Exemplary bridged bicyclic cycloalkenyls include, but are not limited to, bicyclo[2.2.1]heptene, bicyclo[2.2.2]octene and bicyclo[3.2.2]nonene. Examples of spiro cycloalkyl include, spiro[2.2]pentene, spiro[2.3]hexene, spiro[2.4]heptene, spiro[2.5]octene and spiro[4.5]decene.

The terms "heterocyclic group", "heterocyclic", "heterocycle", "heterocyclyl", or "heterocyclo" are used interchangeably and refer to any mono-, bi-, tricyclic, spiro or bridged, saturated, partially saturated or unsaturated, non-aromatic ring system, having 3 to 20 ring atoms, where the ring atoms are carbon, and at least one atom in the ring or ring system is a heteroatom selected from nitrogen, sulfur or oxygen. If any ring atom of a cyclic system is a heteroatom, that system is a heterocycle, regardless of the point of attachment of the cyclic system to the rest of the molecule. In one example, heterocyclyl includes 3-11 ring atoms ("members") and includes monocycles, bicycles, tricycles, spiro, and bridged ring systems, wherein the ring atoms are carbon, where at least one atom in the ring or ring system is a heteroatom selected from nitrogen, sulfur or oxygen. In other examples, heterocyclyl includes 4-10 or 5-10 ring atoms. In one example, heterocyclyl includes 1 to 4 heteroatoms. In one example, heterocyclyl includes 1 to 3 heteroatoms. In another example, heterocyclyl includes 3- to 7-membered monocycles having 1-2, 1-3 or 1-4 heteroatoms selected from nitrogen, sulfur or oxygen. In another example, heterocyclyl includes 4- to 6-membered monocycles having 1-2, 1-3 or 1-4 heteroatoms selected from nitrogen, sulfur or oxygen. In another example, heterocyclyl includes 3-membered monocycles. In another example, heterocyclyl includes 4-membered monocycles. In another example, heterocyclyl includes 5-6 membered monocycles. In some embodiments, a heterocycloalkyl includes at least one nitrogen. In one example, the heterocyclyl group includes 0 to 3 double bonds. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$, [NR$_4$]$^+$OH$^-$). Example heterocycles are oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, isoquinolinyl, tetrahydroisoquinolinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, 1,1-dioxoisothiazolyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-onyl, azaspiro[5.5]undecanyl, tetrahydroindolyl, octahydroindolyl, tetrahydroisoindolyl, tetrahydroindazolyl, 1,1-dioxohexahydrothiopyranyl.

The term "methylheterocyclyl" refers to a heterocyclyl substituted with a methyl group.

The term "heteroaryl" refers to any mono-, bi-, or tricyclic aromatic ring system containing from 1 to 4 heteroatoms selected from nitrogen, oxygen, and sulfur, and in an example embodiment, at least one heteroatom is nitrogen. See, for example, Lang's Handbook of Chemistry (Dean, J. A., ed.) 13$^{th}$ ed. Table 7-2 [1985]. Included in the definition are any bicyclic groups where any of the above heteroaryl rings are fused to an aryl ring, wherein the aryl ring or the heteroaryl ring is joined to the remainder of the molecule. In one embodiment, heteroaryl includes 5-6 membered monocyclic aromatic groups where one or more ring atoms is nitrogen, sulfur or oxygen. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl and purinyl, as well as benzo-fused derivatives, for example benzoxazolyl, benzofuryl, benzothiazolyl, benzothiadiazolyl, benzotriazolyl, benzoimidazolyl, indazolyl and indolyl.

In particular embodiments, a heterocyclyl group or a heteroaryl group is attached at a carbon atom of the heterocyclyl group or the heteroaryl group. By way of example, carbon bonded heterocyclyl groups include bonding arrangements at position 2, 3, 4, 5, or 6 of a pyridine ring, position 3, 4, 5, or 6 of a pyridazine ring, position 2, 4, 5, or 6 of a pyrimidine ring, position 2, 3, 5, or 6 of a pyrazine ring, position 2, 3, 4, or 5 of a furan, tetrahydrofuran, thiofuran, thiophene, pyrrole or tetrahydropyrrole ring, position 2, 4, or 5 of an oxazole, imidazole or thiazole ring, position 3, 4, or 5 of an isoxazole, pyrazole, or isothiazole ring, position 2 or 3 of an aziridine ring, position 2, 3, or 4 of an azetidine ring, position 2, 3, 4, 5, 6, 7, or 8 of a quinoline ring or position 1, 3, 4, 5, 6, 7, or 8 of an isoquinoline ring.

In certain embodiments, the heterocyclyl group or heteroaryl group is N-attached. By way of example, nitrogen bonded heterocyclyl or heteroaryl groups include bonding arrangements at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Fused" refers to any ring structure described herein that shares one or more atoms (e.g., carbon or nitrogen atoms) with an existing ring structure in the compounds of the invention.

The term "acyl" refers to a carbonyl containing substituent represented by the formula —C(=O)—R in which R is a substituent such as hydrogen, alkyl, cycloalkyl, aryl or heterocyclyl, wherein the alkyl, cycloalkyl, aryl and heterocyclyl are as defined herein. Acyl groups include alkanoyl (e.g., acetyl), aroyl (e.g., benzoyl), and heteroaroyl (e.g., pyridinoyl).

The term "haloalkyl" refers to an alkyl chain in which one or more hydrogen has been replaced by a halogen. Examples of haloalkyls are trifluoromethyl, difluoromethyl, and fluoromethyl.

The terms "compound(s) of the invention," and "compound(s) of the present invention" and the like, unless otherwise indicated, include compounds of Formula (I), Formula (II), Formula (III), Formula (IV), Formulas (Ia)-(Ik), and the compounds listed in the Tables herein, including stereoisomers (including atropisomers), geometric isomers, tautomers, isotopes, and salts (e.g., pharmaceutically acceptable salts) thereof.

The term "optionally substituted" unless otherwise specified means that a group may be unsubstituted or substituted by one or more (e.g., 0, 1, 2, 3, 4, or 5 or more, or any range derivable therein) of the substituents listed for that group in which said substituents may be the same or different. In an embodiment, an optionally substituted group has 1 substituent. In another embodiment an optionally substituted group has 2 substituents. In another embodiment an optionally substituted group has 3 substituents. In another embodiment an optionally substituted group has 4 substituents. In another embodiment an optionally substituted group has 5 substituents.

As used herein a wavy line "$\sim$" that intersects a bond in a chemical structure indicate the point of attachment of the atom to which the wavy bond is connected in the chemical structure to the remainder of a molecule, or to the remainder of a fragment of a molecule.

In certain embodiments, divalent groups are described generically without specific bonding configurations. It is understood that the generic description is meant to include both bonding configurations, unless specified otherwise. For example, in the group $R^1$-$R^2$-$R^3$, if the group $R^2$ is described as —$CH_2C(O)$—, then it is understood that this group can be bonded both as $R^1$—$CH_2C(O)$—$R^3$, and as $R^1$—$C(O)$$CH_2$—$R^3$, unless specified otherwise.

The term "pharmaceutically acceptable" refers to molecular entities and compositions that do not produce an adverse, allergic or other untoward reaction when administered to an animal, such as, for example, a human, as appropriate.

Compounds of the invention may be in the form of a salt, such as a pharmaceutically acceptable salt. "Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

The term "pharmaceutically acceptable base addition salts" include those derived from inorganic bases such as sodium, potassium, lithium, ammonium, calcium, magnesium, iron, zinc, copper, manganese, aluminum salts and the like. Particular base addition salts are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particular organic non-toxic bases include isopropylamine, diethylamine, ethanolamine, tromethamine, dicyclohexylamine, choline, and caffeine.

In some embodiments, a salt is selected from a hydrochloride, hydrobromide, trifluoroacetate, sulfate, phosphate, acetate, fumarate, maleate, tartrate, lactate, citrate, pyruvate, succinate, oxalate, methanesulfonate, p-toluenesulfonate, bisulfate, benzenesulfonate, ethanesulfonate, malonate, xinafoate, ascorbate, oleate, nicotinate, saccharinate, adipate, formate, glycolate, palmitate, L-lactate, D-lactate, aspartate, malate, L-tartrate, D-tartrate, stearate, furoate (e.g., 2-furoate or 3-furoate), napadisylate (naphthalene-1,5-disulfonate or naphthalene-1-(sulfonic acid)-5-sulfonate), edisylate (ethane-1,2-disulfonate or ethane-1-(sulfonic acid)-2-sulfonate), isothionate (2-hydroxyethylsulfonate), 2-mesitylenesulfonate, 2-naphthalenesulfonate, 2,5-dichlorobenzenesulfonate, D-mandelate, L-mandelate, cinnamate, benzoate, adipate, esylate, malonate, mesitylate (2-mesitylenesulfonate), napsylate (2-naphthalenesulfonate), camsylate (camphor-10-sulfonate, for example (1S)-(+)-10-camphorsulfonic acid salt), glutamate, glutarate, hippurate (2-(benzoylamino)acetate), orotate, xylate (p-xylene-2-sulfonate), and pamoic (2,2'-dihydroxy-1,1'-dinaphthylmethane-3,3'-dicarboxylate).

A "sterile" formulation is aseptic or free from all living microorganisms and their spores.

The term "stereoisomers" refer to compounds that have identical chemical constitution, but differ with regard to the arrangement of the atoms or groups in space. Stereoisomers include diastereomers, enantiomers, conformers and the like.

The term "chiral" refers to molecules which have the property of non-superimposability of the mirror image partner, while the term "achiral" refers to molecules which are superimposable on their mirror image partner.

The term "diastereomer" refers to a stereoisomer with two or more centers of chirality and whose molecules are not mirror images of one another. Diastereomers have different physical properties, e.g., melting points, boiling points, spectral properties or biological activities. Mixtures of diastereomers may separate under high resolution analytical procedures such as electrophoresis and chromatography such as HPLC.

The term "enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

"Atropisomers" are stereoisomers arising because of hindered rotation around a single bond, where energy differences due to steric strain or other contributors create a barrier to rotation that is high enough to allow for isolation of individual conformers.

Certain compounds of the invention can exist in unsolvated forms as well as solvated forms, including hydrated forms. A "solvate" refers to an association or complex of one or more solvent molecules and a compound of the present invention. Examples of solvents that form solvates include water, isopropanol, ethanol, methanol, DMSO, ethyl acetate, acetic acid, and ethanolamine. Certain compounds of the invention can exist in multiple crystalline or amorphous forms. In general, all physical forms are intended to be within the scope of the present invention. The term "hydrate" refers to the complex where the solvent molecule is water.

A "metabolite" refers to a product produced through metabolism in the body of a specified compound or salt thereof. Such products can result, for example, from the oxidation, reduction, hydrolysis, amidation, deamidation, esterification, deesterification, enzymatic cleavage, and the like, of the administered compound.

Metabolite products typically are identified by preparing a radiolabeled (e.g., $^{14}C$ or $^{3}H$) isotope of a compound of the invention, administering it in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

The invention described herein also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$. Certain isotopically-labeled compounds of the present invention (e.g., those labeled with $^{3}H$ and $^{14}C$) are useful in compound and/or substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}$F are useful for positron emission tomography (PET) studies to examine substrate receptor occupancy. Isotopically labeled compounds of the present invention can generally be prepared by following procedures analogous to those disclosed in the Examples herein below, by substituting an isotopically labeled reagent for a non-isotopically labeled reagent.

The term "amino-protecting group" as used herein refers to a derivative of the groups commonly employed to block or protect an amino group while reactions are carried out on other functional groups on the compound. Examples of such protecting groups include carbamates, amides, alkyl and aryl groups, and imines, as well as many N-heteroatom derivatives which can be removed to regenerate the desired amine group. Particular amino protecting groups are Pmb (p-methoxybenzyl), Boc (tert-butyloxycarbonyl), Fmoc (9-fluorenylmethyloxycarbonyl) and Cbz (carbobenzyloxy). Further examples of these groups are found in T. W. Greene and P. G. M. Wuts, "Protecting Groups in Organic Synthesis, 3$^{rd}$ ed., John Wiley & Sons, Inc., 1999. The term "protected amino" refers to an amino group substituted with one of the above amino-protecting groups.

The term "carboxy-protecting group" as used herein refers to those groups that are stable to the conditions of subsequent reaction(s) at other positions of the molecule, which may be removed at the appropriate point without disrupting the remainder of the molecule, to give the unprotected carboxy-group. Examples of carboxy protecting groups include, ester groups and heterocyclyl groups. Ester derivatives of the carboxylic acid group may be employed to block or protect the carboxylic acid group while reactions are carried out on other functional groups on the compound. Examples of such ester groups include substituted arylalkyl, including substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl or substituted alkyl esters such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. Another example of carboxy-protecting groups are heterocyclyl groups such as 1,3-oxazolinyl. Further examples of these groups are found in T. W. Greene and P. G. M. Wuts, "Protecting Groups in Organic Synthesis, 3$^{rd}$ ed., John Wiley & Sons, Inc., 1999. The term "protected carboxy" refers to a carboxy group substituted with one of the above carboxy-protecting groups.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Mixtures of particular diastereomeric compounds may be separated, or enriched in one or more particular diastereomers, by chromatographic or crystallization methods. Similarly, enantiomeric mixtures may be separated, or enantiomerically enriched, using the same techniques or others known in the art. Each of the asymmetric carbon or nitrogen atoms may be in the R or S configuration and both of these configurations are within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. Unless otherwise specified, if solid wedges or dashed lines are used, relative stereochemistry is intended.

Another aspect includes prodrugs of the compounds of the invention including known amino-protecting and carboxy-protecting groups which are released, for example hydrolyzed, to yield the compound of the present invention under physiologic conditions.

The term "prodrug" refers to a precursor or derivative form of a pharmaceutically active substance that is less efficacious to the patient compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, and 5-fluorocytosine and 5-fluorouridine prodrugs.

A particular class of prodrugs are compounds in which a nitrogen atom in an amino, amidino, aminoalkyleneamino, iminoalkyleneamino or guanidino group is substituted with a hydroxy group, —CO—R, —CO—OR, or —CO—O—R—O—CO—R, where R is a monovalent or divalent group, for example alkyl, alkylene or aryl, or a group having the Formula —C(O)—O—CP1P2-haloalkyl, where P1 and P2 are the same or different and are hydrogen, alkyl, alkoxy, cyano, halogen, alkyl or aryl. In a particular embodiment, the nitrogen atom is one of the nitrogen atoms of the amidino group of the compounds of the invention. Prodrugs may be prepared by reacting a compound of the present invention with an activated group, such as acyl groups, to bond, for example, a nitrogen atom in the compound to the exemplary carbonyl of the activated acyl group. Examples of activated carbonyl compounds are those containing a leaving group bonded to the carbonyl group, and include, for example, acyl halides, acyl amines, acyl pyridinium salts, acyl alkoxides, acyl phenoxides such as p-nitrophenoxy acyl, dinitrophenoxy acyl, fluorophenoxy acyl, and difluorophenoxy acyl. The reactions are generally carried out in inert solvents at temperatures such as about −78 to about 50° C. The reactions may also be carried out in the presence of an inorganic base, for example potassium carbonate or sodium bicarbonate, or an organic base such as an amine, including pyridine, trimethylamine, triethylamine, triethanolamine, or the like.

Additional types of prodrugs are also encompassed. For instance, a free carboxyl group of a compound of the invention can be derivatized as an amide or alkyl ester. As another example, compounds of the invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-$((C_{1-6})$alkanoyloxy)ethyl, 1-methyl-1-$((C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})$alkyl$)_2$ or glycosyl (the radical resulting from the removal of a hydroxyl group of the hemiacetal form of a carbohydrate).

The term "leaving group" refers to a portion of a first reactant in a chemical reaction that is displaced from the first reactant in the chemical reaction. Examples of leaving groups include, but are not limited to, halogen atoms, alkoxy and sulfonyloxy groups. Example sulfonyloxy groups include, but are not limited to, alkylsulfonyloxy groups (for example methyl sulfonyloxy (mesylate group) and trifluoromethylsulfonyloxy (triflate group)) and arylsulfonyloxy groups (for example p-toluenesulfonyloxy (tosylate group) and p-nitrosulfonyloxy (nosylate group)).

A "subject," "individual," or "patient" is a vertebrate. In certain embodiments, the vertebrate is a mammal. Mammals include, but are not limited to, farm animals (such as cows), sport animals, pets (such as guinea pigs, cats, dogs, rabbits and horses), primates, mice and rats. In certain embodiments, a mammal is a human. In embodiments comprising administration of a compound of to a patient, the patient is typically in need thereof.

The terms "inhibiting" and "reducing," or any variation of these terms, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal.

A "therapeutically effective amount" means an amount of a compound of the present invention, such as a compound of Formula (I), Formula (II), Formula (III), or Formula (IV), or a pharmaceutically acceptable salt thereof, that (i) treats or prevents the particular disease, condition or disorder, or (ii) attenuates, ameliorates or eliminates one or more symptoms of the particular disease, condition, or disorder, and optionally (iii) prevents or delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; or relieve to some extent one or more of the symptoms associated with the cancer. To the extent the drug may prevent growth or kill existing cancer cells, it may be cytostatic or cytotoxic. For cancer therapy, efficacy can, for example, be measured by assessing the time to disease progression (TTP) or determining the response rate (RR).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, stabilized (i.e., not worsening) state of disease, decreasing the rate of disease progression, amelioration or palliation of the disease state, prolonging survival as compared to expected survival if not receiving treatment and remission or improved prognosis. In some embodiments, compounds of the invention, are used to delay development of a disease or disorder or to slow the progression of a disease or disorder. Those in need of treatment include those already with the condition or disorder as well as those prone to have the condition or disorder, (for example, through a genetic mutation) or those in which the condition or disorder is to be prevented.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

The terms "antagonist" and "inhibitor" are used interchangeably, and they refer to a compound having the ability to inhibit a biological function of a target protein, whether by inhibiting the activity or expression of the protein, such as K-Ras, H-Ras or N-Ras G12C. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

The terms "cancer" and "cancerous", "neoplasm", and "tumor" and related terms refer to or describe the physiological condition in mammals that is typically characterized by unregulated cell growth. A "tumor" comprises one or more cancerous cells. Examples of cancer include carcinoma, blastoma, sarcoma, seminoma, glioblastoma, melanoma, leukemia, and myeloid or lymphoid malignancies. More particular examples of such cancers include squamous cell cancer (e.g., epithelial squamous cell cancer) and lung cancer including small-cell lung cancer, non-small cell lung cancer ("NSCLC"), adenocarcinoma of the lung and squamous carcinoma of the lung. Other cancers include skin, keratoacanthoma, follicular carcinoma, hairy cell leukemia, buccal cavity, pharynx (oral), lip, tongue, mouth, salivary gland, esophageal, larynx, hepatocellular, gastric, stomach, gastrointestinal, small intestine, large intestine, pancreatic, cervical, ovarian, liver, bladder, hepatoma, breast, colon, rectal, colorectal, genitourinary, biliary passage, thyroid, papillary, hepatic, endometrial, uterine, salivary gland, kidney or renal, prostate, testis, vulval, peritoneum, anal, penile, bone, multiple myeloma, B-cell lymphoma, diffuse large B-Cell lymphoma (DLBCL), central nervous system, brain, head and neck, Hodgkin's, and associated metastases. Examples of neoplastic disorders include myeloproliferative disorders, such as polycythemia vera, essential thrombocytosis, myelofibrosis, such as primary myelofibrosis, and chronic myelogenous leukemia (CML).

A "chemotherapeutic agent" is an agent useful in the treatment of a given disorder, for example, cancer or inflammatory disorders. Examples of chemotherapeutic agents are well-known in the art and include examples such as those disclosed in U.S. Publ. Appl. No. 2010/0048557, incorporated herein by reference. Additionally, chemotherapeutic agents include pharmaceutically acceptable salts, acids or derivatives of any of chemotherapeutic agents, as well as combinations of two or more of them.

Unless otherwise stated, structures depicted herein are also meant to include compounds that differ only in the presence of one or more isotopically enriched atoms. Exemplary isotopes that can be incorporated into compounds of the invention, include isotopes of hydrogen, carbon, nitrogen, oxygen, phosphorus, sulfur, fluorine, chlorine, and iodine, such $^{2}$H, $^{3}$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Isotopically-labeled compounds (e.g., those labeled with $^{3}$H and $^{14}$C) can be useful in compound or substrate tissue distribution assays. Tritiated (i.e., $^{3}$H) and carbon-14 (i.e., $^{14}$C) isotopes can be useful for their ease of preparation and detectability. Further, substitution with heavier isotopes such as deuterium (i.e., $^{2}$H) may afford certain therapeutic advantages resulting from greater metabolic stability (e.g., increased in vivo half-life or reduced dosage requirements). In some embodiments, in compounds of the invention, one or more carbon atoms are replaced by $^{13}$C- or $^{14}$C-enriched carbon. Positron emitting isotopes such as $^{15}$O, $^{13}$N, $^{11}$C, and $^{18}$F are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

It is specifically contemplated that any limitation discussed with respect to one embodiment of the invention may apply to any other embodiment of the invention. Furthermore, any compound or composition of the invention may be used in any method of the invention, and any method of the invention may be used to produce or to utilize any compound or composition of the invention.

The use of the term "or" is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

As used herein, "a" or "an" means one or more, unless clearly indicated otherwise. As used herein, "another" means at least a second or more.

Headings used herein are intended only for organizational purposes.

Ras Inhibitors

In an aspect, the invention provides compounds which are capable of selectively binding to and/or modulating a G12C, G12D, or G13D mutant K-Ras, H-Ras or N-Ras protein.

As noted, one aspect of the invention includes a compound of Formula (I):

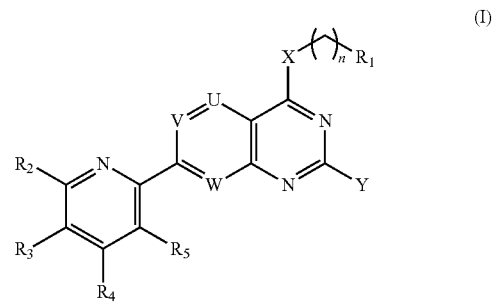

or a pharmaceutically acceptable salt thereof;
wherein,
$R_1$ is an electrophilic moiety capable of forming a covalent bond with a cysteine residue at position 12 of a K-Ras G12C mutant protein;
$R_2$ is selected from the group consisting of H, OH, $NH_2$, halo, $C_{1-6}$ alkyl, $C_{1-6}$ haloalkyl, cyclopropyl, and —NHR, wherein R is selected from the group consisting of $C_{1-6}$ alkyl, $C_{1-6}$ alkoxy, $C_{1-6}$ alkanoyl, $C_{1-6}$ hydroxyalkanoyl, $C_{1-6}$ cyanoalkyl, $C_{1-6}$ alkylamino, —($C_{1-6}$ alkylenyl)NH($CH_3$)—($C_{1-6}$ alkylenyl)N($CH_3$)$_2$, and —($C_{1-3}$ alkylenyl)(3-7 membered-heterocyclyl);
$R_3$ and $R_4$ are each independently selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and cyclopropyl;
$R_5$ is selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_{3-7}$ cycloalkyl,
wherein at least one of $R_2$, $R_3$, $R_4$, and $R_5$ is other than H; or
$R_2$ and $R_3$, $R_3$ and $R_4$, or $R_4$ and $R_5$, together with the atoms to which they are each bonded, form a $C_{3-7}$ cycloalkyl, 3 to 7 membered heterocycloalkyl, $C_{6-14}$ aryl, or 5- to 10-membered heteroaryl; each of which is optionally substituted with 1 to 4 substituents, wherein each substituent is independently selected from the group consisting of OH, $NH_2$, halo, $C_{1-3}$ alkyl, $C_{1-3}$ haloalkyl, $C_{1-3}$ alkoxy, and $C_{1-3}$ haloalkoxy;
X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

Y is selected from the group consisting of -L-$Y_1$ or $Y_1$;

$Y_1$ is selected from the group consisting of H, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$ aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{3-7}$ cycloalkyl substituted with a $C_{1-6}$ dialkylamino, $C_{1-6}$ haloalkoxy, $C_{1-6}$ haloalkyl, 5- to 10-membered heteroaryl, 4- to 10-membered heterocyclyl, 4- to 10-membered heterocyclyl substituted with methyl, hydroxy, and oxo;

each $Y_{1a}$ is independently selected from the group consisting of halo, $C_{1-6}$ alkyl, $C_{1-6}$ alkoxy, 3- to 7-membered heterocyclyl, $C_{1-6}$ alkoxy$C_{1-6}$ alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkoxy;

L is selected from the group consisting of a bond, O, S, and $N(L^a)$;

$L^a$ is selected from the group consisting of hydrogen and $C_{1-3}$ alkyl;

U is $C(R_{6a})$;

V is $C(R_{6b})$;

W is $C(R_{6c})$ or N;

each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{1-6}$ haloalkoxy, $C_{1-6}$ haloalkyl, 5- to 10-membered heteroaryl, and 4- to 10-membered heterocyclyl; and n is selected from the group consisting of 0, 1, and 2.

According to some embodiments of the compound of Formula (I), or a pharmaceutically acceptable salt thereof $R^1$ is an electrophilic moiety capable of forming a covalent bond with a cysteine residue at position 12 of a K-Ras G12C mutant protein.

According to some embodiments of the compound of Formula (I), or a pharmaceutically acceptable salt thereof $R^1$ is an electrophilic moiety capable of forming a covalent bond with a cysteine residue at position 12 of a H-Ras G12C mutant protein.

According to some embodiments of the compound of Formula (I), or a pharmaceutically acceptable salt thereof $R^1$ is an electrophilic moiety capable of forming a covalent bond with a cysteine residue at position 12 of a N-Ras G12C mutant protein.

In the above definition of $R^1$, the electrophilic moiety that is capable of forming a covalent bond with a cysteine residue is determined via K-Ras G12C-alkylation studies and Homogeneous Time Resolved Fluorescence (HTRF) assays. The G12C mutation of the K-Ras gene is a change in amino acid from glycine to cysteine at the 12th amino acid. The compounds according to the present disclosure were discovered using the HTRF assay and the K-Ras G12C-alkylation assay, as further detailed elsewhere herein below, and then NMR spectroscopy was later used to validate the specificity with which the molecule was attaching to G12C.

In another aspect, the invention includes a compound of Formula (II):

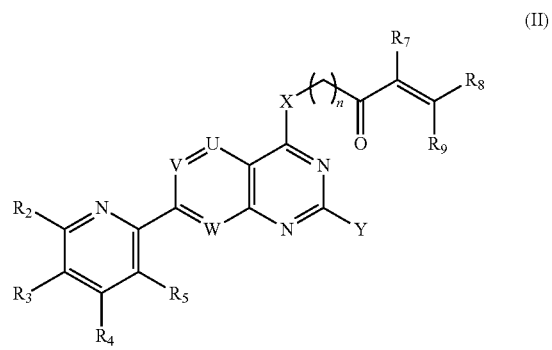

or a pharmaceutically acceptable salt thereof;
wherein,
$R_2$ is selected from the group consisting of H, OH, $NH_2$, halo, $C_{1-6}$ alkyl, $C_{1-6}$ haloalkyl, cyclopropyl, and —NHR, wherein R is selected from the group consisting of $C_{1-6}$ alkyl, $C_{1-6}$ alkoxy, $C_{1-6}$ alkanoyl, $C_{1-6}$ hydroxyalkanoyl, $C_{1-6}$ cyanoalkyl, $C_{1-6}$ alkylamino, —($C_{1-6}$ alkylenyl)$NH(CH_3)$—($C_{1-6}$ alkylenyl)$N(CH_3)_2$, and —($C_{1-3}$ alkylenyl)(3-7 membered-heterocyclyl);

$R_3$ and $R_4$ are each independently selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and cyclopropyl;

$R_5$ is selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_{3-7}$ cycloalkyl, wherein at least one of $R_2$, $R_3$, $R_4$, and $R_5$ is other than H; or $R_2$ and $R_3$, $R_3$ and $R_4$, or $R_4$ and $R_5$, together with the atoms to which they are each bonded, form a $C_{3-7}$ cycloalkyl, 3 to 7 membered heterocycloalkyl, $C_{6-14}$ aryl, or 5- to 10-membered heteroaryl; each of which is optionally substituted with 1 to 4 substituents, wherein each substituent is independently selected from the group consisting of OH, $NH_2$, halo, $C_{1-3}$ alkyl, $C_{1-3}$ haloalkyl, $C_{1-3}$ alkoxy, and $C_{1-3}$ haloalkoxy;

$R_7$ is selected from the group consisting of H, cyano, and halo; and $R_8$ and $R_9$ are each independently selected from the group consisting of H, $C_{1-6}$ alkyl, $C_{1-6}$ haloalkyl, $C_{1-6}$ hydroxyalkyl, cyano, and halo; wherein $C_{1-6}$ alkyl is optionally substituted with one substituent selected from the group consisting of: methanesulfonyl (mesyl), p-toluenesulfonyl (tosyl), an alkyl or aryl sulfonate leaving group, $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy;

or $R_7$ and $R_8$ together form a triple bond between the carbons to which they are attached, or $R_7$ and $R_8$ together with the carbons to which they are each bonded form a $C_{3-7}$ cycloalkenyl optionally substituted with one or two halo substituents; and $R_9$ is selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy;

X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

Y is selected from the group consisting of -L-$Y_1$ or $Y_1$;

$Y_1$ is selected from the group consisting of H, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$ aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{3-7}$ cycloalkyl substituted with a $C_{1-6}$ dialkylamino, $C_{1-6}$ haloalkoxy, $C_{1-6}$ haloalkyl, 5- to 10-membered heteroaryl, 4- to 10-membered heterocyclyl, 4- to 10-membered heterocyclyl substituted with methyl, hydroxy, and oxo;

each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkoxy;

L is selected from the group consisting of a bond, O, S, and $N(L^a)$;

$L_a$ is selected from the group consisting of hydrogen and $C_{1-3}$ alkyl;

U is $C(R_{6a})$;

V is $C(R_{6b})$;

W is $C(R_{6c})$ or N;

each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, haloalkoxy, $C_{1-6}$ haloalkyl, 5- to 10-membered heteroaryl, and 4- to 10-membered heterocyclyl; and n is selected from the group consisting of 0, 1, and 2.

In another aspect, the invention includes a compound of Formula (III):

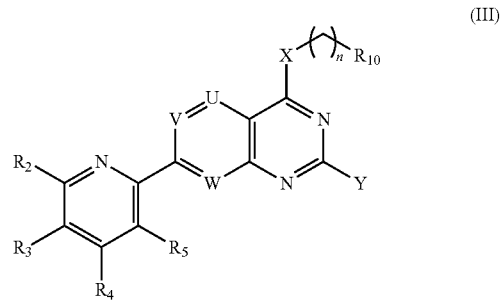

(III)

or a pharmaceutically acceptable salt thereof;

wherein, $R_2$ is selected from the group consisting of H, OH, $NH_2$, halo, $C_{1-6}$ alkyl, $C_{1-6}$ haloalkyl, cyclopropyl, and —NHR, wherein R is selected from the group consisting of $C_{1-6}$ alkyl, $C_{1-6}$ alkoxy, $C_{1-6}$ alkanoyl, $C_{1-6}$ hydroxyalkanoyl, $C_{1-6}$ cyanoalkyl, $C_{1-6}$ alkylamino, —($C_{1-6}$ alkylenyl)$NH(CH_3)$—($C_{1-6}$ alkylenyl)$N(CH_3)_2$, and —($C_{1-3}$ alkylenyl)(3-7 membered-heterocyclyl);

$R_3$ and $R_4$ are each independently selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and cyclopropyl;

$R_5$ is selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_{3-7}$ cycloalkyl, wherein at least one of $R_2$, $R_3$, $R_4$, and $R_5$ is other than H; or $R_2$ and $R_3$, $R_3$ and $R_4$, or $R_4$ and $R_5$, together with the atoms to which they are each bonded, form a $C_{3-7}$ cycloalkyl, 3 to 7 membered heterocycloalkyl, $C_{6-14}$ aryl, or 5- to 10-membered heteroaryl; each of which is optionally substituted with 1 to 4 substituents, wherein each substituent is independently selected from the group consisting of OH, $NH_2$, halo, $C_{1-3}$ alkyl, $C_{1-3}$ haloalkyl, $C_{1-3}$ alkoxy, and $C_{1-3}$ haloalkoxy;

$R_{10}$ is selected from the group consisting of $R_{10a}$ and —C(O)—$R_{10a}$;

$R_{10a}$ is selected from the group consisting of oxiranyl and aziridinyl;

X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

Y is selected from the group consisting of -L-$Y_1$ or $Y_1$;

$Y_1$ is selected from the group consisting of H, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$ aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{3-7}$ cycloalkyl substituted with a $C_{1-6}$ dialkylamino, $C_{1-6}$ haloalkoxy, $C_{1-6}$ haloalkyl, 5- to 10-membered heteroaryl, 4- to 10-membered heterocyclyl, 4- to 10-membered heterocyclyl substituted with methyl, hydroxy, and oxo;

each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkoxy;

L is selected from the group consisting of a bond, O, S, and N($L^a$);

$L^a$ is selected from the group consisting of hydrogen and $C_{1-3}$ alkyl;

U is C($R_{6a}$);

V is C($R_{6b}$);

W is C($R_{6c}$) or N;

each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{1-6}$ haloalkoxy, $C_{1-6}$ haloalkyl, 5- to 10-membered heteroaryl, and 4- to 10-membered heterocyclyl; and n is selected from the group consisting of 0, 1, and 2.

According to some embodiments of the compound of Formula (I), Formula (II), or Formula (III), or a pharmaceutically acceptable salt thereof, $R_2$ is selected from the group consisting of $NH_2$ and —NHR; and R is $C_{1-6}$ alkyl.

According to some embodiments of the compound of Formula (I), Formula (II), or Formula (III), or a pharmaceutically acceptable salt thereof, $R_2$ is $NH_2$. In one embodiment, of the compound of Formula (I), Formula (II), or Formula (III), or a pharmaceutically acceptable salt thereof, $R_2$ is —NHR, where R is $C_{1-6}$ alkyl or $C_{1-6}$ alkoxy. In another embodiment, of the compound of Formula (I), Formula (II), or Formula (III), or a pharmaceutically acceptable salt thereof, $R_2$ is —NHR where R is C(O)$CH_3$, C(O)$CH_2$OH, CH($CH_3$)$_2$, $CH_2$CN, or $CH_3$.

According to some embodiments of the compound of Formula (I), Formula (II), or Formula (III), or a pharmaceutically acceptable salt thereof, $R_3$ and $R_4$ are independently selected from the group consisting of H, halo, $C_{1-6}$ alkyl, $C_{1-6}$ haloalkyl, and cyclopropyl. In one embodiment, of the compound of Formula (I), Formula (II), or Formula (III), or a pharmaceutically acceptable salt thereof, $R_3$ is $C_{1-3}$ alkyl (e.g., methyl or ethyl) or $C_{1-3}$ haloalkyl (e.g. —$CF_3$ or —$CH_2CF_3$). In another embodiment of the compound of Formula (I), Formula (II), or Formula (III), or a pharmaceutically acceptable salt thereof, $R_3$ is hydrogen. In one embodiment of the compound of Formula (I), Formula (II), or Formula (III), or a pharmaceutically acceptable salt thereof, $R_4$ is hydrogen, halo, $C_{1-3}$ alkyl, $C_{1-3}$ haloalkyl, or cyclopropyl. In another embodiment of the compound of Formula (I), Formula (II), or Formula (III), or a pharmaceutically acceptable salt thereof, $R_4$ is hydrogen or halo. In another embodiment of the compound of Formula (I), Formula (II), or Formula (III), or a pharmaceutically acceptable salt thereof, $R_4$ is $C_{1-3}$ alkyl (e.g., methyl or ethyl). In another embodiment of the compound of Formula (I), Formula (II), or Formula (III), or a pharmaceutically acceptable salt thereof, $R_4$ is methyl. In still another embodiment of the compound of Formula (I), Formula (II), or Formula (III), or a pharmaceutically acceptable salt thereof, $R_4$ is —$CF_3$. In another embodiment of the compound of Formula (I), Formula (II), or Formula (III), or a pharmaceutically acceptable salt thereof, $R_4$ is hydrogen.

According to some embodiments of the compound of Formula (I), Formula (II), or Formula (III), or a pharmaceutically acceptable salt thereof, $R_5$ is selected from the group consisting of H, halo, $C_{1-6}$ alkyl, $C_{1-6}$ haloalkyl, $C_{1-6}$ haloalkoxy, $C_{1-6}$ alkylamino, and $C_{3-7}$ cycloalkyl. In one embodiment of the compound of Formula (I), Formula (II), or Formula (III), or a pharmaceutically acceptable salt thereof, $R_5$ is $C_{1-6}$ haloalkyl. In another embodiment of the compound of Formula (I), Formula (II), or Formula (III), or a pharmaceutically acceptable salt thereof, $R_5$ is $C_{1-3}$ haloalkyl. In another embodiment of the compound of Formula (I), Formula (II), or Formula (III), or a pharmaceutically acceptable salt thereof, $R_5$ is $C_{1-3}$ alkyl. In another embodiment of the compound of Formula (I), Formula (II), or Formula (III), or a pharmaceutically acceptable salt thereof, $R_5$ is $C_{1-3}$ haloalkoxy. In still another embodiment of the compound of Formula (I), Formula (II), or Formula (III), or a pharmaceutically acceptable salt thereof, $R_5$ is H, $CH_3$, $CHF_2$, $CF_3$, $OCF_3$, $CH_2CF_3$, halo, or cyclopropyl. In still another embodiment of the compound of Formula (I), Formula (II), or Formula (III), or a pharmaceutically acceptable salt thereof, $R_5$ is $CF_3$.

In another embodiment of the compound of Formula (I), Formula (II), or Formula (III), or a pharmaceutically acceptable salt thereof, $R_5$ is $CF_3$ and $R_2$ is $NH_2$.

In another embodiment of the compound of Formula (I), Formula (II), or Formula (III), or a pharmaceutically acceptable salt thereof, $R_2$ is $NH_2$, $R_4$ is $C_{1-3}$ alkyl, and $R_5$ is $CF_3$.

According to some embodiments of the compound of Formula (I), Formula (II), or Formula (III), or a pharmaceutically acceptable salt thereof, $R_5$ is cyclopropyl.

According to some embodiments of the compound of Formula (I), Formula (II), or Formula (III), or a pharmaceutically acceptable salt thereof, at least two of $R_2$, $R_3$, $R_4$, and $R_5$ is other than H.

According to some embodiments of the compound of Formula (I), Formula (II), or Formula (III), or a pharmaceutically acceptable salt thereof, at least three of $R_2$, $R_3$, $R_4$, and $R_5$ is other than H.

According to some embodiments of the compound of Formula (I), Formula (II), or Formula (III), or a pharmaceutically acceptable salt thereof, $R_4$ and $R_5$, together with the atoms to which they are each bonded, form a $C_{3-7}$ cycloalkyl, 3 to 7 membered heterocycloalkyl, $C_{6-14}$ aryl, or 5- to 10-membered heteroaryl; each of which is optionally substituted with 1 to 4 substituents, wherein each substituent is independently selected from the group consisting of OH, NH₂, halo, C$_{1-3}$ alkyl, C$_{1-3}$ haloalkyl, C$_{1-3}$ alkoxy, and C$_{1-3}$ haloalkoxy.

According to some embodiments of the compound of Formula (I), Formula (II), or Formula (III), or a pharmaceutically acceptable salt thereof, R₄ and R₅, together with the atoms to which they are each bonded, form a C$_{6-14}$ aryl, which is optionally substituted with 1 to 4 substituents, wherein each substituent is independently selected from the group consisting of OH, NH₂, halo, C$_{1-3}$ alkyl, C$_{1-3}$ haloalkyl, C$_{1-3}$ alkoxy, and C$_{1-3}$ haloalkoxy.

According to some embodiments of the compound of Formula (I), Formula (II), or Formula (III), or a pharmaceutically acceptable salt thereof, R₄ and R₅, together with the atoms to which they are each bonded, form a C₆ aryl, which is optionally substituted with 1 to 4 substituents, wherein each substituent is independently selected from the group consisting of OH, NH₂, halo, C$_{1-3}$ alkyl, C$_{1-3}$ haloalkyl, C$_{1-3}$ alkoxy, and C$_{1-3}$ haloalkoxy. According to some embodiments of the compound of Formula (I), Formula (II), or Formula (III), or a pharmaceutically acceptable salt thereof, the C₆ aryl is unsubstituted. According to some embodiments of the compound of Formula (I), Formula (II), or Formula (III), or a pharmaceutically acceptable salt thereof, the C₆ aryl is substituted with 1 to 4 substituents, wherein each substituent is independently halo.

According to some embodiments of the compound of Formula (I), Formula (II), or Formula (III), or a pharmaceutically acceptable salt thereof, Y is -L-Y₁. In one embodiment of the compound of Formula (I), Formula (II), or Formula (III), or a pharmaceutically acceptable salt thereof, L is O or N(L$^a$). In another embodiment of the compound of Formula (I), Formula (II), or Formula (III), or a pharmaceutically acceptable salt thereof, L is O. In one embodiment of the compound of Formula (I), Formula (II), or Formula (III), or a pharmaceutically acceptable salt thereof, Y₁ is C$_{2-6}$ alkenyl, C$_{1-6}$ alkyl, or C$_{1-6}$ alkyl substituted with a 4- to 10-membered heterocyclyl or methylheterocyclyl substituent. In another embodiment of the compound of Formula (I), Formula (II), or Formula (III), or a pharmaceutically acceptable salt thereof, Y₁ is C$_{1-6}$ alkyl, or C$_{1-6}$ alkyl substituted with a 4- to 10-membered heterocyclyl or methylheterocyclyl substituent. In still another embodiment of the compound of Formula (I), Formula (II), or Formula (III), or a pharmaceutically acceptable salt thereof, Y₁ is C$_{1-6}$ alkyl substituted with a 4- to 10-membered heterocyclyl or methylheterocyclyl substituent. In another embodiment of the compound of Formula (I), Formula (II), or Formula (III), or a pharmaceutically acceptable salt thereof, Y₁ is C$_{1-6}$ alkyl substituted with a 4- to 10-membered heterocyclyl or d methylheterocyclyl substituent, where the heterocyclyl or methylheterocyclyl substituent comprises at least 1 nitrogen heteroatom. In one embodiment, the heterocyclyl or methylheterocyclyl substituent is a pyrrolidinyl moiety. In one embodiment, the pyrrolidinyl is substituted with F. In one embodiment, the heterocyclyl and methylheterocyclyl moieties are each independently optionally substituted with 1-3 substituents selected from the group consisting of consisting of OH, NH₂, halo, cyano, C$_{1-6}$ alkyl, C$_{1-6}$ carboxyalkyl, C$_{1-6}$ cyanoalkyl, C$_{1-6}$ haloalkyl, or C$_{1-6}$ hydroxyalkyl.

In one embodiment of the compound of Formula (I), Formula (II), or Formula (III), or a pharmaceutically acceptable salt thereof, Y is

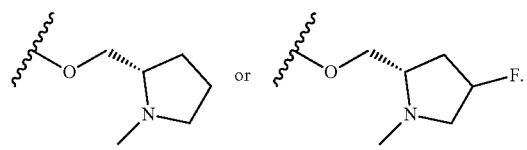

In one embodiment, Y is

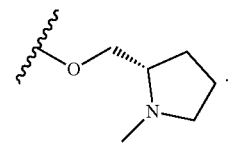 [SMILES: *OC[C@@H]1CCCN1C]

In another embodiment of the compound of Formula (I), Formula (II), or Formula (III), or a pharmaceutically acceptable salt thereof, Y is

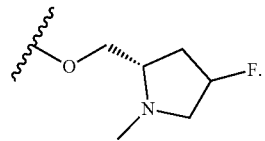 [SMILES: *OC[C@@H]1CC(F)CN1C]

In still another embodiment of the compound of Formula (I), Formula (II), or Formula (III), or a pharmaceutically acceptable salt thereof, Y is

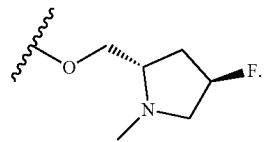 [SMILES: *OC[C@@H]1C[C@@H](F)CN1C]

In still another embodiment of the compound of Formula (I), Formula (II), or Formula (III), or a pharmaceutically acceptable salt thereof, Y is

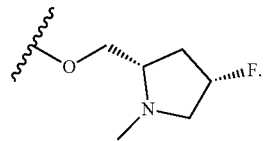 [SMILES: *OC[C@@H]1C[C@H](F)CN1C]

According to some embodiments of the compound of Formula (I), Formula (II), or Formula (III), or a pharmaceutically acceptable salt thereof, R$_{6a}$ is hydrogen, halo, or C$_{1-3}$ alkyl. According to some embodiments of the compound of Formula (I), Formula (II), or Formula (III), or a pharmaceutically acceptable salt thereof, R$_{6b}$ is hydrogen, halo, C$_{1-3}$ alkyl, C$_{1-3}$ haloalkyl, C$_{1-3}$ alkoxy, or cyclopropyl. In one embodiment of the compound of Formula (I), Formula (II), or Formula (III), or a pharmaceutically acceptable salt thereof, R$_{6b}$ is hydrogen, halo, or C$_{1-3}$ haloalkyl. In another embodiment of the compound of Formula (I), Formula (II), or Formula (III), or a pharmaceutically acceptable salt thereof, R$_{6b}$ is halo or C$_{1-3}$ haloalkyl. In another embodiment, R$_{6b}$ is halo (e.g. Cl or F). In still another embodiment of the compound of Formula (I), Formula (II), or Formula (III), or a pharmaceutically acceptable salt thereof, $R_{6b}$ is Cl. In another embodiment, $R_{6b}$ is $CF_3$ or $CHF_2$. According to some embodiments of the compound of Formula (I), Formula (II), or Formula (III), or a pharmaceutically acceptable salt thereof, $R_{6c}$ is hydrogen or halo. In one embodiment of the compound of Formula (I), Formula (II), or Formula (III), or a pharmaceutically acceptable salt thereof, $R_{6c}$ is hydrogen. In one embodiment, $R_{6c}$ is halo. In one embodiment of the compound of Formula (I), Formula (II), or Formula (III), or a pharmaceutically acceptable salt thereof, $R_{6b}$ and $R_{6c}$ are independently halo. In another embodiment, $R_{6b}$ is halo and $R_{6c}$ is hydrogen.

Further provided herein are compounds of Formula (I), Formula (II), or Formula (III), or a pharmaceutically acceptable salt thereof, wherein:

Y is

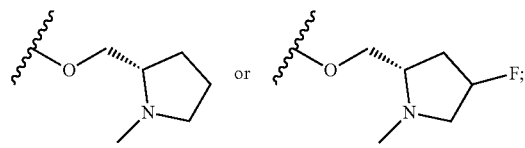

X is

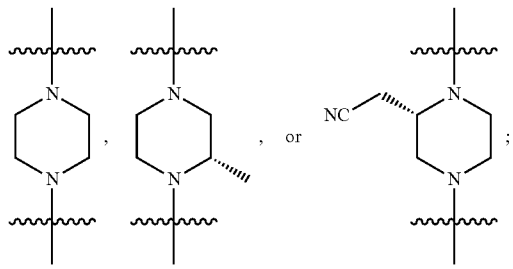

$R_2$ is $NH_2$; $R_3$ is hydrogen; $R_4$ is hydrogen or $C_{1-3}$ methyl; and $R_5$ is $CF_3$.

According to some embodiments of Formula (I), Formula (II), or Formula (III), or a pharmaceutically acceptable salt thereof, the compound is selected from the group consisting of the compounds in Table 1, shown below, or a pharmaceutically acceptable salt thereof.

TABLE 1

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
| --- | --- | --- |
| 1 | 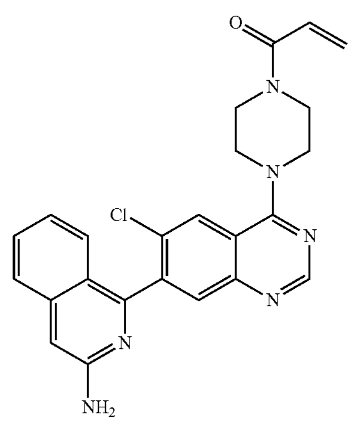 [SMILES: C=CC(=O)N1CCN(c2ncnc3cc(-c4nc(N)cc5ccccc45)c(Cl)cc23)CC1] | 1-[4-[7-(3-amino-1-isoquinolyl)-6-chloro-quinazolin-4-yl]piperazin-1-yl]prop-2-en-1-one |
| 2 | 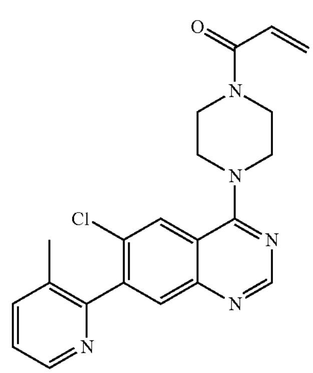 [SMILES: C=CC(=O)N1CCN(c2ncnc3cc(-c4ncccc4C)c(Cl)cc23)CC1] | 1-[4-[6-chloro-7-(3-methyl-2-pyridyl)quinazolin-4-yl]piperazin-1-yl]prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 3 | 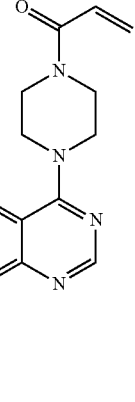 | 1-[4-[7-(6-amino-1,7-naphthyridin-8-yl)-6-chloro-quinazolin-4-yl]piperazin-1-yl]prop-2-en-1-one |
| 4 | 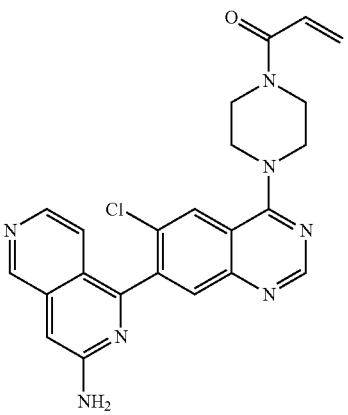 [SMILES: C=CC(=O)N1CCN(c2ncnc3cc(-c4nc(N)cc5cnccc45)c(Cl)cc23)CC1] | 1-[4-[7-(3-amino-2,6-naphthyridin-1-yl)-6-chloro-quinazolin-4-yl]piperazin-1-yl]prop-2-en-1-one |
| 5 | 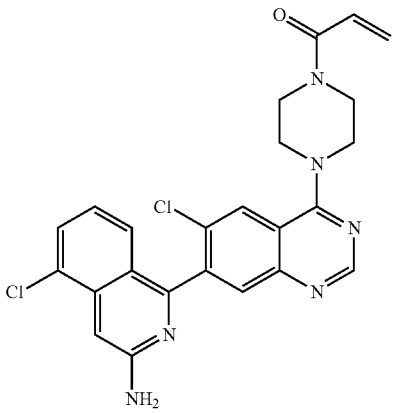 [SMILES: C=CC(=O)N1CCN(c2ncnc3cc(-c4nc(N)cc5c(Cl)cccc45)c(Cl)cc23)CC1] | 1-[4-[7-(3-amino-5-chloro-1-isoquinolyl)-6-chloro-quinazolin-4-yl]piperazin-1-yl]prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 6 | 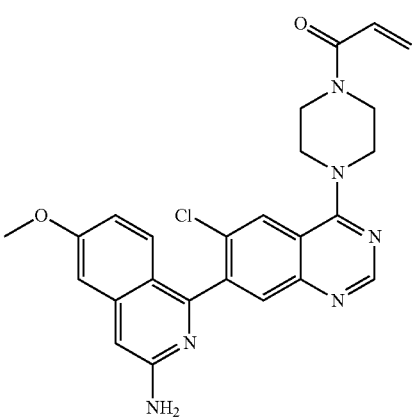 [SMILES: C=CC(=O)N1CCN(c2ncnc3cc(-c4nc(N)cc5cc(OC)ccc45)c(Cl)cc23)CC1] | 1-[4-[7-(3-amino-6-methoxy-1-isoquinolyl)-6-chloro-quinazolin-4-yl]piperazin-1-yl]prop-2-en-1-one |
| n/a | 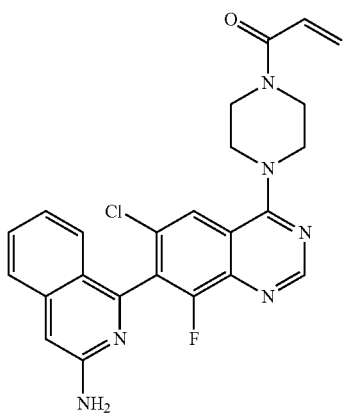 [SMILES: C=CC(=O)N1CCN(c2ncnc3c(F)c(-c4nc(N)cc5ccccc45)c(Cl)cc23)CC1] | 1-(4-(7-(3-aminoisoquinolin-1-yl)-6-chloro-8-fluoroquinazolin-4-yl)piperazin-1-yl)prop-2-en-1-one |
| 7 | 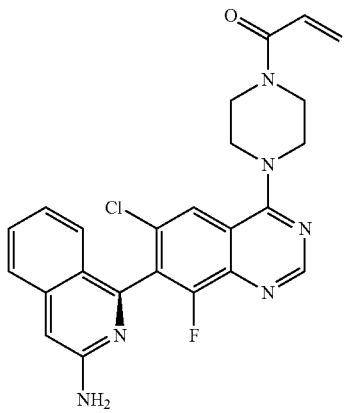 | (S)-1-(4-(7-(3-aminoisoquinolin-1-yl)-6-chloro-8-fluoroquinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 8 | 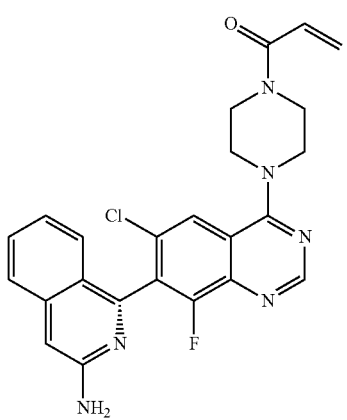 | (R)-1-(4-(7-(3-aminoisoquinolin-1-yl)-6-chloro-8-fluoroquinazolin-4-yl)piperazin-1-yl)prop-2-en-1-one |
| n/a | 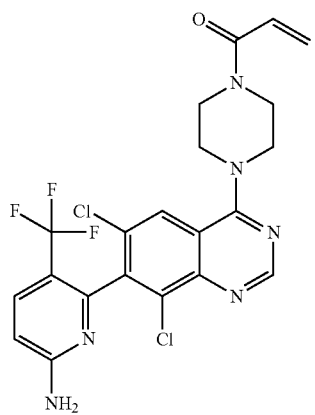 [SMILES: C=CC(=O)N1CCN(c2ncnc3c(Cl)c(-c4nc(N)ccc4C(F)(F)F)c(Cl)cc23)CC1] | 1-(4-(7-(6-amino-3-(trifluoromethyl)pyridin-2-yl)-6-chloro-8-fluoroquinazolin-4-yl)piperazin-1-yl)prop-2-en-1-one |
| 9 | 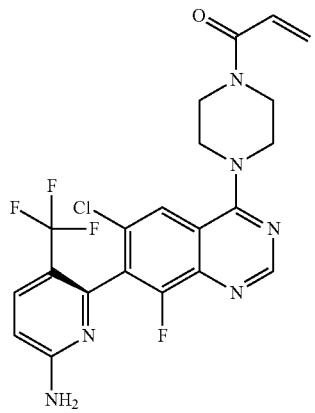 | (S)-1-(4-(7-(6-amino-3-(trifluoromethyl)pyridin-2-yl)-6-chloro-8-fluoroquinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 10 | 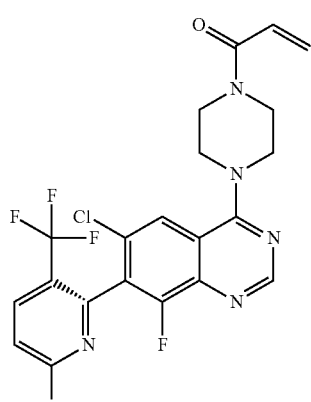 | (R)-1-(4-(7-(6-amino-3-(trifluoromethyl)pyridin-2-yl)-6-chloro-8-fluoroquinazolin-4-yl)piperazin-1-yl)prop-2-en-1-one |
| 11 | 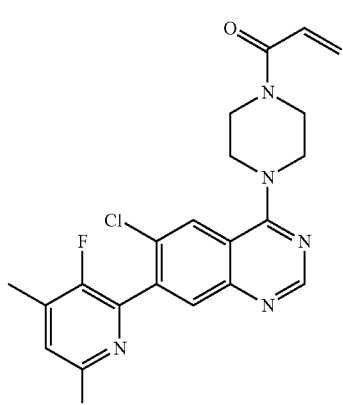 | 1-(4-(7-(6-amino-3-fluoro-4-methylpyridin-2-yl)-6-chloroquinazolin-4-yl)piperazin-1-yl)prop-2-en-1-one |
| n/a | 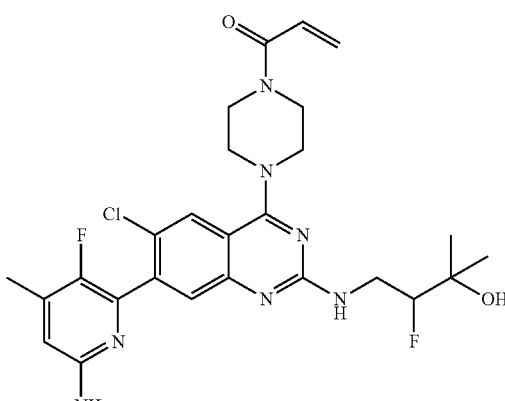 | 1-(4-(7-(6-amino-3-fluoro-4-methylpyridin-2-yl)-6-chloro-2-((2-fluoro-3-hydroxy-3-methylbutyl)amino)quinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 12 | 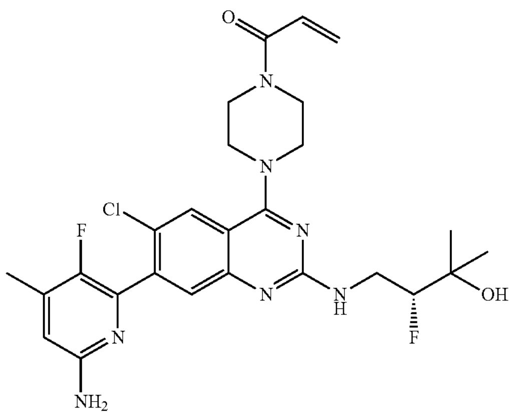 [SMILES: C=CC(=O)N1CCN(c2nc(NC[C@@H](F)C(C)(C)O)nc3cc(-c4nc(N)cc(C)c4F)c(Cl)cc23)CC1] | (R)-1-(4-(7-(6-amino-3-fluoro-4-methylpyridin-2-yl)-6-chloro-2-((2-fluoro-3-hydroxy-3-methylbutyl)amino)quinazolin-4-yl)piperazin-1-yl)prop-2-en-1-one |
| 13 | 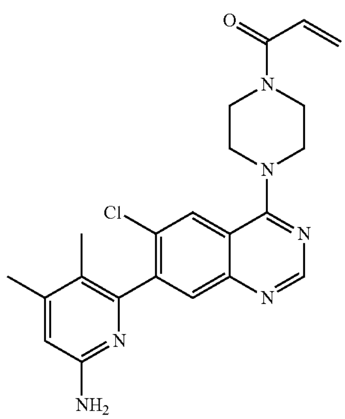 [SMILES: C=CC(=O)N1CCN(c2ncnc3cc(-c4nc(N)cc(C)c4C)c(Cl)cc23)CC1] | 1-(4-(7-(6-amino-3,4-dimethylpyridin-2-yl)-6-chloroquinazolin-4-yl)piperazin-1-yl)prop-2-en-1-one |
| 14 | 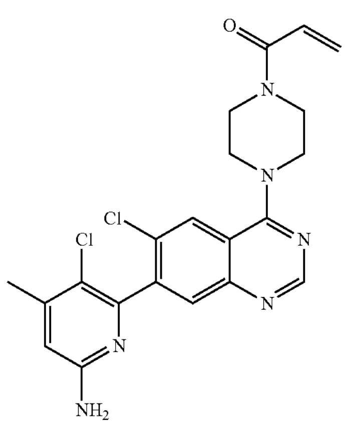 | 1-(4-(7-(6-amino-3-chloro-4-methylpyridin-2-yl)-6-chloroquinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 15 | 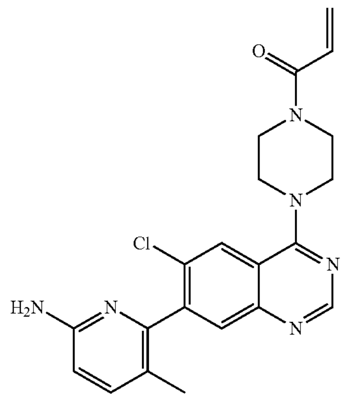 [SMILES: C=CC(=O)N1CCN(c2ncnc3cc(-c4nc(N)ccc4C)c(Cl)cc23)CC1] | 1-(4-(7-(6-amino-3-methylpyridin-2-yl)-6-chloroquinazolin-4-yl)piperazin-1-yl)prop-2-en-1-one |
| 16 | 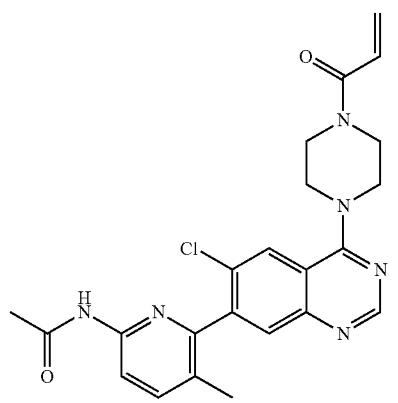 [SMILES: C=CC(=O)N1CCN(c2ncnc3cc(-c4nc(NC(C)=O)ccc4C)c(Cl)cc23)CC1] | N-(6-[6-chloro-4-[4-(prop-2-enoyl)piperazin-1-yl]quinazolin-7-yl]-5-methylpyridin-2-yl)acetamide |
| n/a | 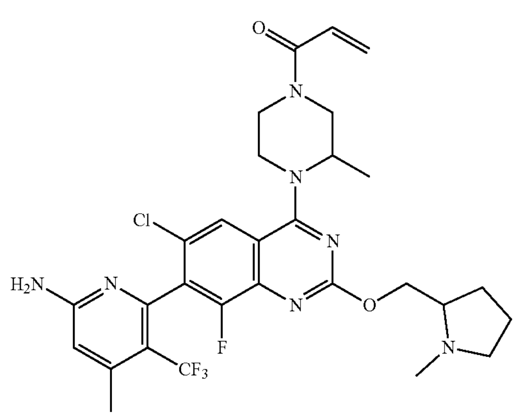 [SMILES: C=CC(=O)N1CCN(c2nc(OCC3CCCN3C)nc3c(F)c(-c4nc(N)cc(C)c4C(F)(F)F)c(Cl)cc23)C(C)C1] | 1-(4-(7-(6-amino-4-methyl-3-(trifluoromethyl)pyridin-2-yl)-6-chloro-8-fluoro-2-((1-methylpyrrolidin-2-yl)methoxy)quinazolin-4-yl)-3-methylpiperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 17a | 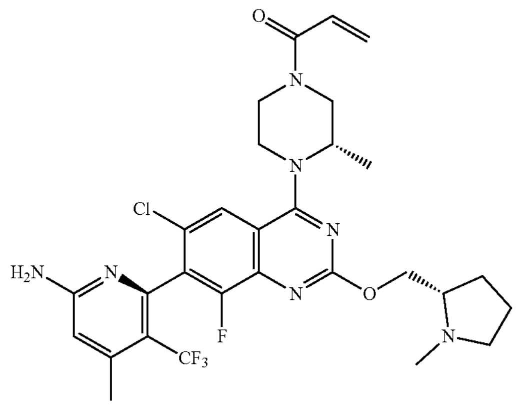 | 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one |
| 17b | 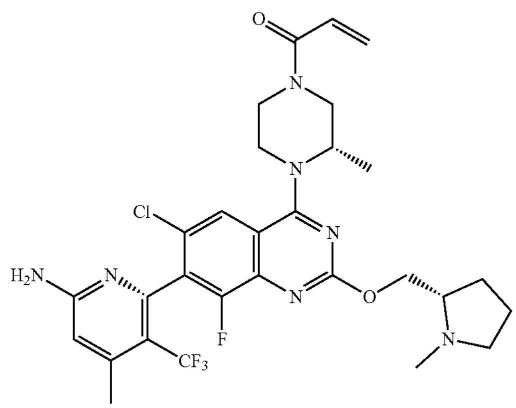 | 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one |
| n/a | 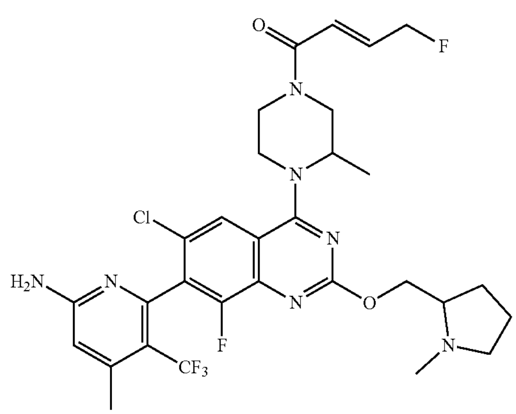 [SMILES: Cc1cc(N)nc(-c2c(Cl)cc3c(N4CCN(C(=O)/C=C/CF)CC4C)nc(OCC4CCCN4C)nc3c2F)c1C(F)(F)F] | (E)-1-(4-(7-(6-amino-4-methyl-3-(trifluoromethyl)pyridin-2-yl)-6-chloro-8-fluoro-2-((1-methylpyrrolidin-2-yl)methoxy)quinazolin-4-yl)-3-methylpiperazin-1-yl)-4-fluorobut-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 18a/18b | | (E)-1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-fluorobut-2-en-1-one |
| 18a/18b | | (E)-1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-fluorobut-2-en-1-one |
| n/a | 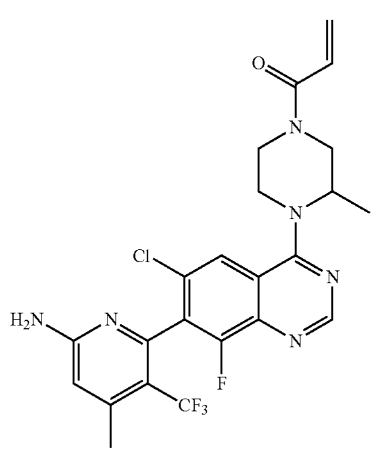 [SMILES: C=CC(=O)N1CCN(c2ncnc3c(F)c(-c4nc(N)cc(C)c4C(F)(F)F)c(Cl)cc23)[C@@H](C)C1] | 1-(4-(7-(6-amino-4-methyl-3-(trifluoromethyl)pyridin-2-yl)-6-chloro-8-fluoroquinazolin-4-yl)-3-methylpiperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 19 | 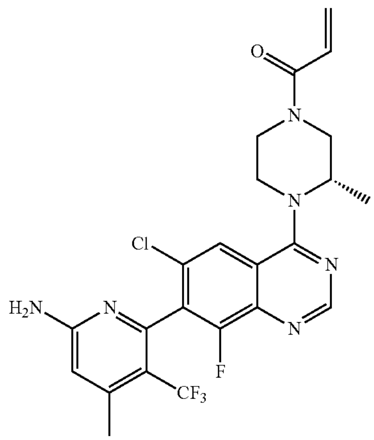 | 1-((3S)-4-(7-(6-amino-4-methyl-3-(trifluoromethyl)pyridin-2-yl)-6-chloro-8-fluoroquinazolin-4-yl)-3-methylpiperazin-1-yl)prop-2-en-1-one |
| 20 | 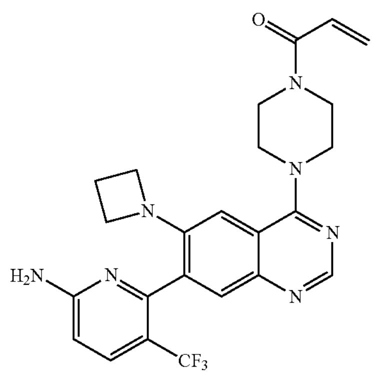 [SMILES: C=CC(=O)N1CCN(c2ncnc3cc(-c4nc(N)ccc4C(F)(F)F)c(N4CCC4)cc23)CC1] | 1-[4-[7-[6-amino-3-(trifluoromethyl)-2-pyridyl]-6-(azetidin-1-yl)quinazolin-4-yl]piperazin-1-yl]prop-2-en-1-one |
| 21 | 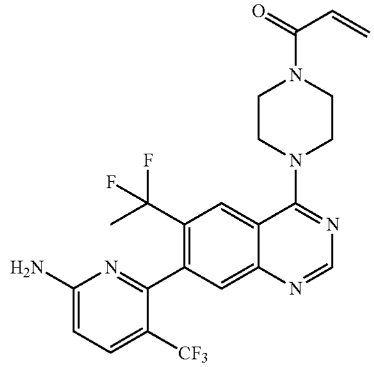 [SMILES: C=CC(=O)N1CCN(c2ncnc3cc(-c4nc(N)ccc4C(F)(F)F)c(C(C)(F)F)cc23)CC1] | 1-(4-(7-(6-amino-3-(trifluoromethyl)pyridin-2-yl)-6-(1,1-difluoroethyl)quinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 22 | 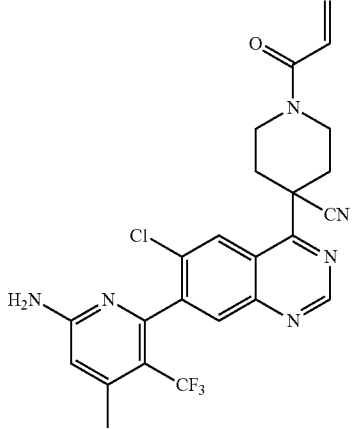 [SMILES: C=CC(=O)N1CCC(C#N)(c2ncnc3cc(-c4nc(N)cc(C)c4C(F)(F)F)c(Cl)cc23)CC1] | 4-[7-[6-amino-4-methyl-3-(trifluoromethyl)-2-pyridyl]-6-chloro-quinazolin-4-yl]-1-prop-2-enoyl-piperidine-4-carbonitrile |
| 23 | 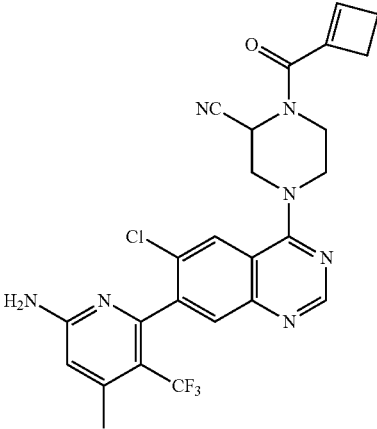 [SMILES: Cc1cc(N)nc(-c2cc3ncnc(N4CCN(C(=O)C5=CCC5)C(C#N)C4)c3cc2Cl)c1C(F)(F)F] | 4-[7-[6-amino-4-methyl-3-(trifluoromethyl)-2-pyridyl]-6-chloro-quinazolin-4-yl]-1-(cyclobutene-1-carbonyl)piperazine-2-carbonitrile |
| 24 | 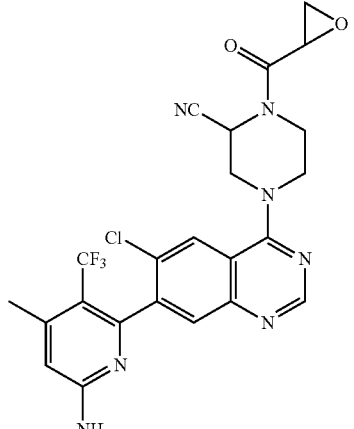 | 4-[7-[6-amino-4-methyl-3-(trifluoromethyl)-2-pyridyl]-6-chloro-quinazolin-4-yl]-1-(oxirane-2-carbonyl)piperazine-2-carbonitrile |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 25 | 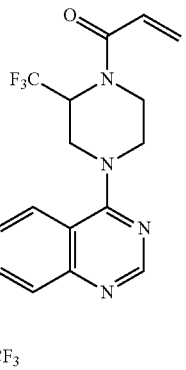 | 4-[7-[6-amino-4-methyl-3-(trifluoromethyl)-2-pyridyl]-6-chloro-quinazolin-4-yl]-1-prop-2-enoyl-piperidine-4-carbonitrile |
| 26 | 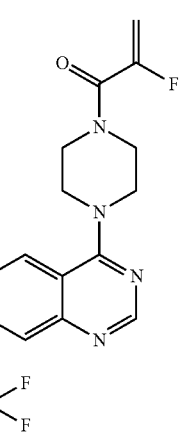 | 1-(4-[7-[6-amino-4-methyl-3-(trifluoromethyl)pyridin-2-yl]-6-chloroquinazolin-4-yl]piperazin-1-yl)-2-fluoroprop-2-en-1-one |
| 27 | 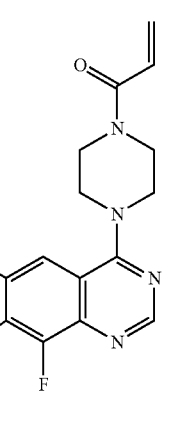 | 1-[4-[7-(3-amino-8-fluoro-1-isoquinolyl)-6-chloro-8-fluoro-quinazolin-4-yl]piperazin-1-yl]prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 28 | 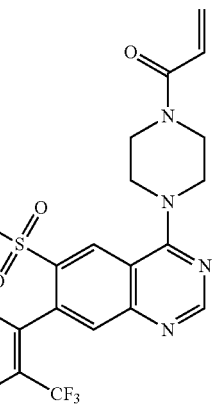 | 1-[4-[7-[6-amino-3-(trifluoromethyl)-2-pyridyl]-6-methylsulfonyl-quinazolin-4-yl]piperazin-1-yl]prop-2-en-1-one |
| 29 | 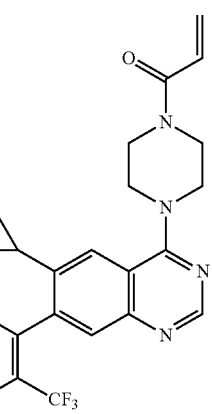 | 1-[4-[7-[6-amino-3-(trifluoromethyl)-2-pyridyl]-6-cyclopropyl-quinazolin-4-yl]piperazin-1-yl]prop-2-en-1-one |
| 30 | 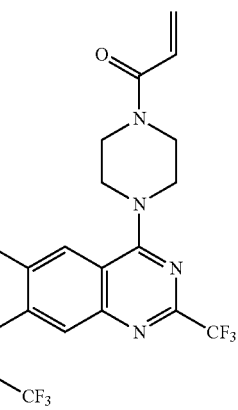 | 1-(4-[7-[6-amino-4-methyl-3-(trifluoromethyl)pyridin-2-yl]-6-chloro-2-(trifluoromethyl)quinazolin-4-yl]piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 31 | 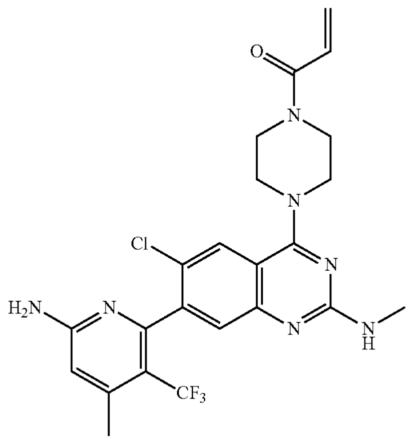 [SMILES: C=CC(=O)N1CCN(c2nc(NC)nc3cc(-c4nc(N)cc(C)c4C(F)(F)F)c(Cl)cc23)CC1] | 1-(4-[7-[6-amino-4-methyl-3-(trifluoromethyl)pyridin-2-yl]-6-chloro-2-(methylamino)quinazolin-4-yl]piperazin-1-yl)prop-2-en-1-one |
| 32 | 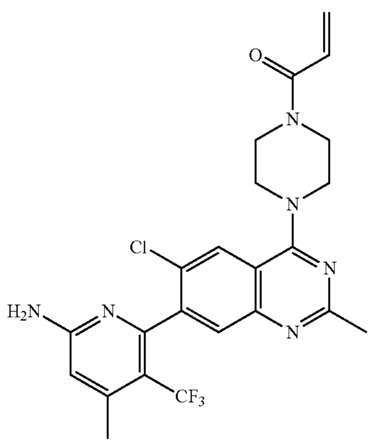 [SMILES: C=CC(=O)N1CCN(c2nc(C)nc3cc(-c4nc(N)cc(C)c4C(F)(F)F)c(Cl)cc23)CC1] | 1-(4-[7-[6-amino-4-methyl-3-(trifluoromethyl)pyridin-2-yl]-6-chloro-2-methylquinazolin-4-yl]piperazin-1-yl)prop-2-en-1-one |
| 33 | 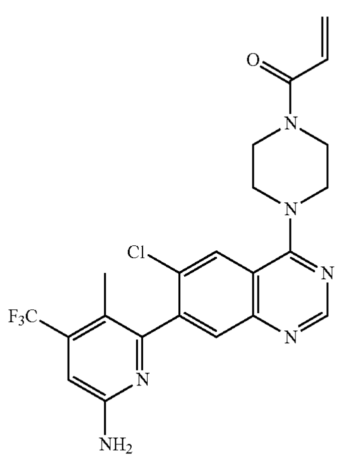 [SMILES: C=CC(=O)N1CCN(c2ncnc3cc(-c4nc(N)cc(C(F)(F)F)c4C)c(Cl)cc23)CC1] | 1-(4-[7-[6-amino-3-methyl-4-(trifluoromethyl)pyridin-2-yl]-6-chloroquinazolin-4-yl]piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 34 | 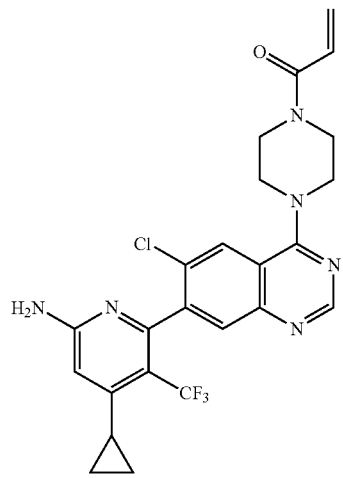 | 1-(4-(7-(6-amino-4-cyclopropyl-3-(trifluoromethyl)pyridin-2-yl)-6-chloroquinazolin-4-yl)piperazin-1-yl)prop-2-en-1-one |
| 35 | 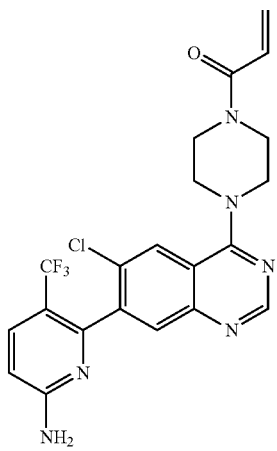 [SMILES: C=CC(=O)N1CCN(c2ncnc3cc(-c4nc(N)ccc4C(F)(F)F)c(Cl)cc23)CC1] | 1-(4-[7-[6-amino-3-(trifluoromethyl)pyridin-2-yl]-6-chloroquinazolin-4-yl]piperazin-1-yl)prop-2-en-1-one |
| 36 | 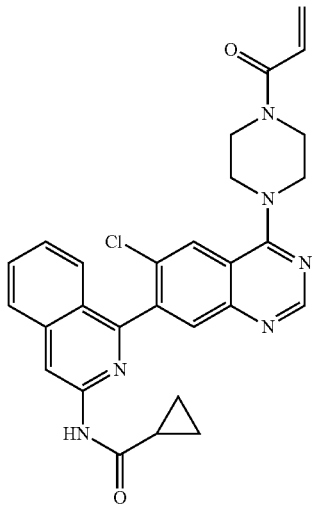 [SMILES: C=CC(=O)N1CCN(c2ncnc3cc(-c4nc(NC(=O)C5CC5)cc5ccccc45)c(Cl)cc23)CC1] | N-(1-(4-(4-acryloylpiperazin-1-yl)-6-chloroquinazolin-7-yl)isoquinolin-3-yl)cyclopropane-carboxamide |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 37 | 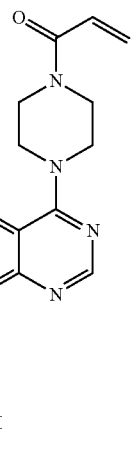 | N-(1-[6-chloro-4-[4-(prop-2-enoyl)piperazin-1-yl]quinazolin-7-yl]isoquinolin-3-yl)-2-hydroxyacetamide |
| 38 | 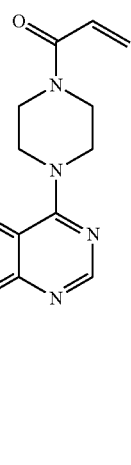 | 1-[4-(6-chloro-7-[3-[(propan-2-yl)amino]isoquinolin-1-yl]quinazolin-4-yl)piperazin-1-yl]prop-2-en-1-one |
| 39 | 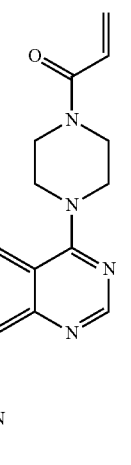 | 2-[(1-[6-chloro-4-[4-(prop-2-enoyl)piperazin-1-yl]quinazolin-7-yl]isoquinolin-3-yl)amino]acetonitrile |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 40 | 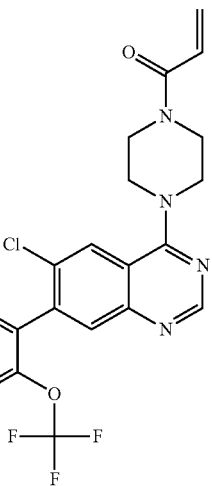 | 1-(4-[7-[6-amino-3-(trifluoromethoxy)pyridin-2-yl]-6-chloroquinazolin-4-yl]piperazin-1-yl)prop-2-en-1-one |
| 41 | 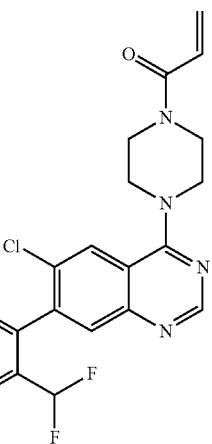 | 1-(4-[7-[6-amino-3-(difluoromethyl)pyridin-2-yl]-6-chloroqiuinazolin-4-yl]piperazin-1-yl)prop-2-en-1-one |
| 42 | 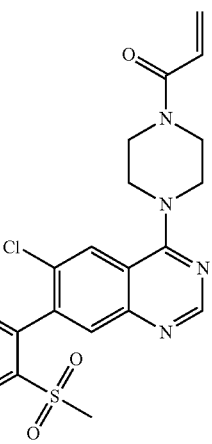 | 1-[4-[7-(6-amino-3-methanesulfonylpyridin-2-yl)-6-chloroquinazolin-4-yl]piperazin-1-yl]prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 43 | 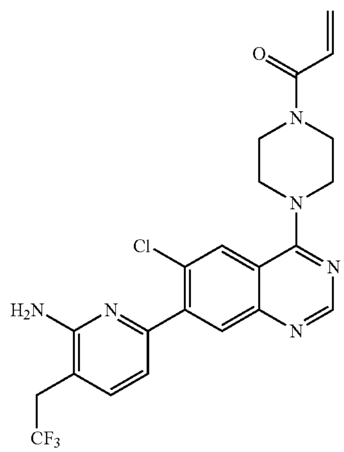 [SMILES: C=CC(=O)N1CCN(c2ncnc3cc(-c4ccc(CC(F)(F)F)c(N)n4)c(Cl)cc23)CC1] | 1-(4-[7-[6-amino-3-(2,2,2-trifluoroethyl)pyridin-2-yl]-6-chloroquinazolin-4-yl]piperazin-1-yl)prop-2-en-1-one |
| 44 | 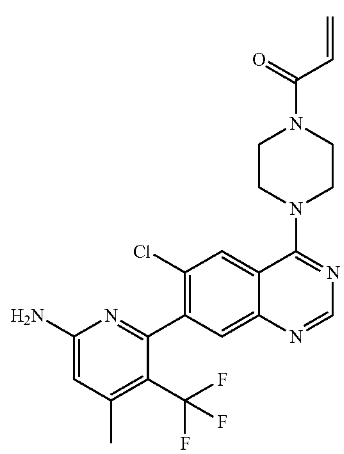 [SMILES: C=CC(=O)N1CCN(c2ncnc3cc(-c4nc(N)cc(C)c4C(F)(F)F)c(Cl)cc23)CC1] | 1-(4-[7-[6-amino-4-methyl-3-(trifluoromethyl)pyridin-2-yl]-6-chloroquinazolin-4-yl]piperazin-1-yl)prop-2-en-1-one |
| 45 | 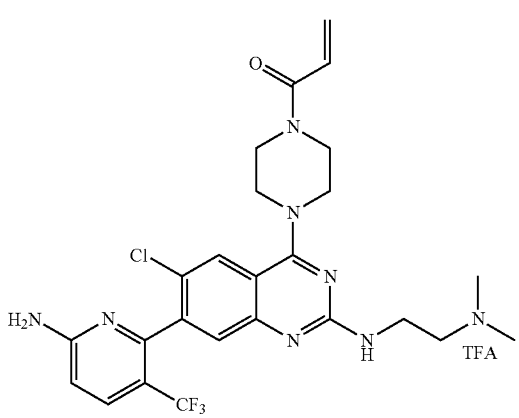 [SMILES: C=CC(=O)N1CCN(c2nc(NCCN(C)C)nc3cc(-c4nc(N)ccc4C(F)(F)F)c(Cl)cc23)CC1] | 1-(4-[7-[6-amino-3-(trifluoromethyl)pyridin-2-yl]-6-chloro-2-[[2-(dimethylamino)ethyl]amino]quinazolin-4-yl]piperazin-1-yl)prop-2-en-1-one•trifluoroacetic acid salt |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| n/a | 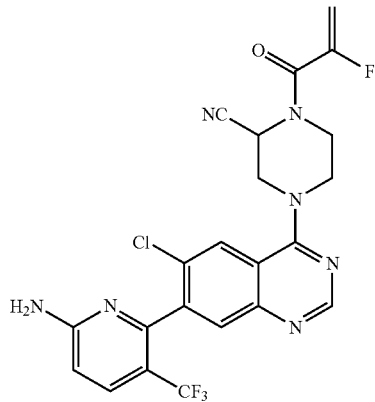 [SMILES: C=C(F)C(=O)N1CCN(c2ncnc3cc(-c4nc(N)ccc4C(F)(F)F)c(Cl)cc23)CC1C#N] | 4-(7-(6-amino-3-(trifluoromethyl)pyridin-2-yl)-6-chloroquinazolin-4-yl)-1-(2-fluoroacryloyl)piperazine-2-carbonitrile |
| 46a | 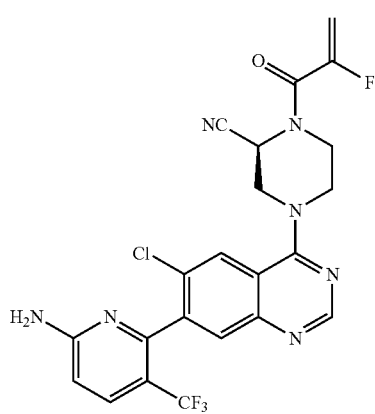 [SMILES: C=C(F)C(=O)N1CCN(c2ncnc3cc(-c4nc(N)ccc4C(F)(F)F)c(Cl)cc23)C[C@H]1C#N] | (S)-4-(7-(6-amino-3-(trifluoromethyl)pyridin-2-yl)-6-chloroquinazolin-4-yl)-1-(2-fluoroacryloyl)piperazine-2-carbonitrile |
| 46b | 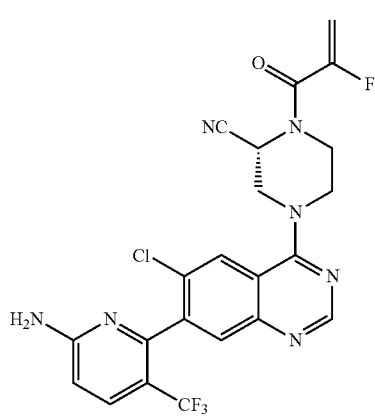 [SMILES: C=C(F)C(=O)N1CCN(c2ncnc3cc(-c4nc(N)ccc4C(F)(F)F)c(Cl)cc23)C[C@@H]1C#N] | (R)-4-(7-(6-amino-3-(trifluoromethyl)pyridin-2-yl)-6-chloroquinazolin-4-yl)-1-(2-fluoroacryloyl)piperazine-2-carbonitrile |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
| --- | --- | --- |
| 47 | 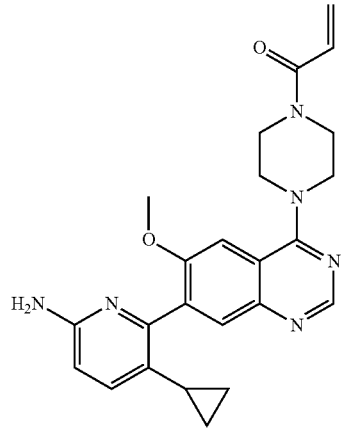 [SMILES: C=CC(=O)N1CCN(c2ncnc3cc(-c4nc(N)ccc4C4CC4)c(OC)cc23)CC1] | 1-[4-[7-(6-amino-3-cyclopropylpyridin-2-yl)-6-methoxyquinazolin-4-yl]piperazin-1-yl]prop-2-en-1-one |
| 48 | 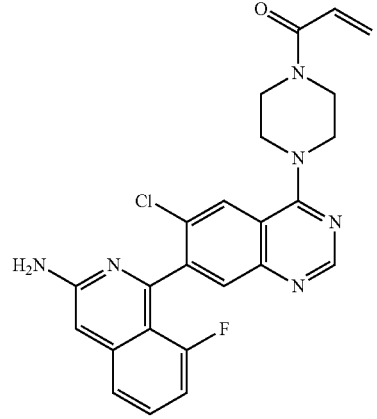 [SMILES: C=CC(=O)N1CCN(c2ncnc3cc(-c4nc(N)cc5cccc(F)c45)c(Cl)cc23)CC1] | 1-[4-[7-(3-amino-8-fluoroisoquinolin-1-yl)-6-chloroquinazolin-4-yl]piperazin-1-yl]prop-2-en-1-one |
| 49 | 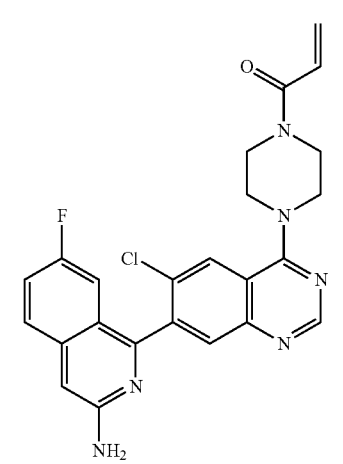 [SMILES: C=CC(=O)N1CCN(c2ncnc3cc(-c4nc(N)cc5ccc(F)cc45)c(Cl)cc23)CC1] | 1-[4-[7-(3-amino-7-fluoroisoquinolin-1-yl)-6-chloroquinazolin-4-yl]piperazin-1-yl]prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 50 | 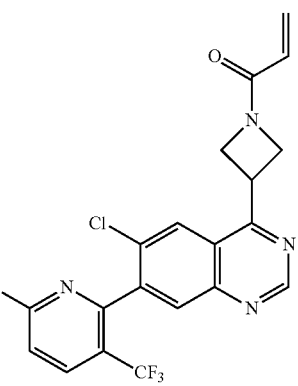 | 1-(3-[7-[6-amino-3-(trifluoromethyl)pyridin-2-yl]-6-chloroquinazolin-4-yl]azetidin-1-yl)prop-2-en-1-one |
| 51 | 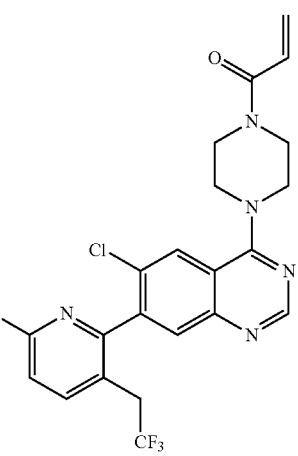 | 1-[4-[7-[6-amino-3-(2,2,2-trifluoroethyl)-2-pyridyl]-6-chloro-quinazolin-4-yl]piperazin-1-yl]prop-2-en-1-one |
| 52 | 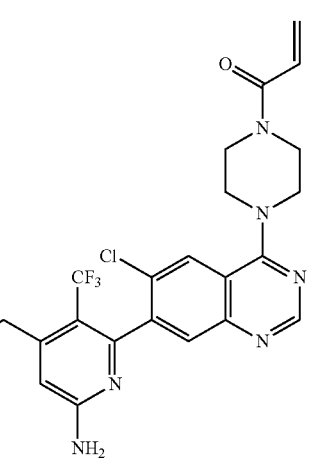 | 1-[4-[7-[6-amino-4-ethyl-3-(trifluoromethyl)-2-pyridyl]-6-chloro-quinazolin-4-yl]piperazin-1-yl]prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
| --- | --- | --- |
| 53 | 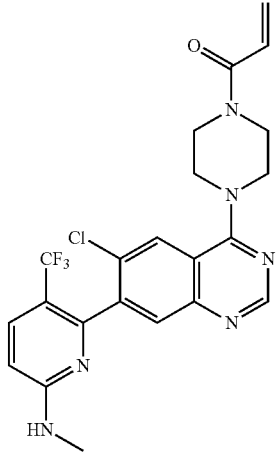 [SMILES: C=CC(=O)N1CCN(c2ncnc3cc(-c4nc(NC)ccc4C(F)(F)F)c(Cl)cc23)CC1] | 1-(4-[6-chloro-7-[6-(methylamino)-3-(trifluoromethyl)pyridin-2-yl]quinazolin-4-yl]piperazin-1-yl)prop-2-en-1-one |
| n/a | 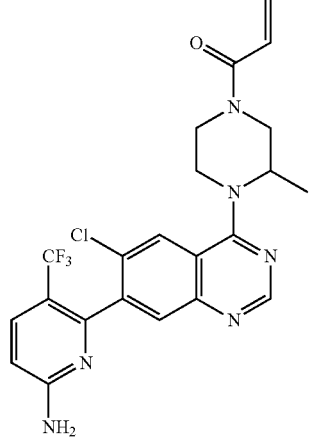 [SMILES: C=CC(=O)N1CCN(c2ncnc3cc(-c4nc(N)ccc4C(F)(F)F)c(Cl)cc23)C(C)C1] | 1-(4-(7-(6-amino-3-(trifluoromethyl)pyridin-2-yl)-6-chloroquinazolin-4-yl)-3-methylpiperazin-1-yl)prop-2-en-1-one |
| 54 | 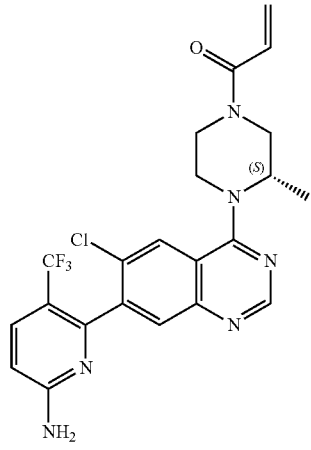 | 1-[(3S)-4-[7-[6-amino-3-(trifluoromethyl)pyridin-2-yl]-6-chloroquinazolin-4-yl]-3-methylpiperazin-1-yl]prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| n/a | | 2-(4-(7-(6-amino-4-methyl-3-(trifluoromethyl)pyridin-2-yl)-6-chloro-2-((1-methylpyrrolidin-2-yl)methoxy)quinazolin-4-yl)-1-(2-fluoroacryloyl)piperazin-2-yl)acetonitrile |
| 55 | 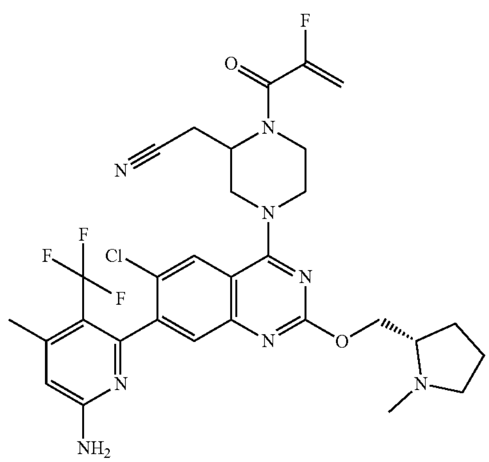 [SMILES: C=C(F)C(=O)N1CCN(c2nc(OC[C@@H]3CCCN3C)nc3cc(-c4nc(N)cc(C)c4C(F)(F)F)c(Cl)cc23)CC1CC#N] | 2-[4-[7-[6-amino-4-methyl-3-(trifluoromethyl)-2-pyridyl]-6-chloro-2-[[(2S)-1-methylpyrrolidin-2-yl]methoxy]quinazolin-4-yl]-1-(2-fluoroprop-2-enoyl)piperazin-2-yl]acetonitrile |
| n/a | | 2-(4-(7-(6-amino-4-methyl-3-(trifluoromethyl)pyridin-2-yl)-6-chloro-2-((4-fluoro-1-methylpyrrolidin-2-yl)methoxy)quinazolin-4-yl)-1-(2-fluoroacryloyl)piperazin-2-yl)acetonitrile |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 56 | 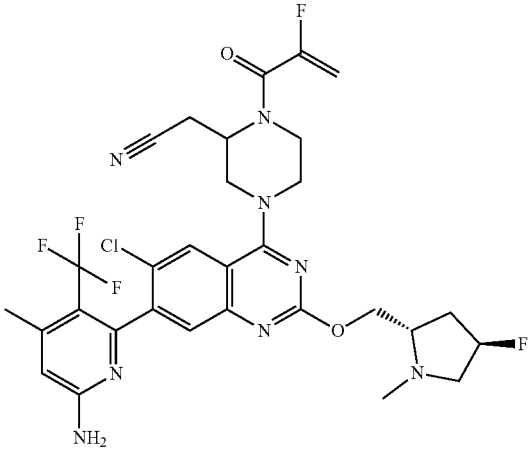 [SMILES: C=C(F)C(=O)N1CCN(c2nc(OC[C@@H]3C[C@@H](F)CN3C)nc3cc(-c4nc(N)cc(C)c4C(F)(F)F)c(Cl)cc23)CC1CC#N] | 2-[4-[7-[6-amino-4-methyl-3-(trifluoromethyl)-2-pyridyl]-6-chloro-2-[[(2S,4R)-4-fluoro-1-methyl-pyrrolidin-2-yl]methoxy]quinazolin-4-yl]-1-(2-fluoroprop-2-enoyl)piperazin-2-yl]acetonitrile |
| n/a | 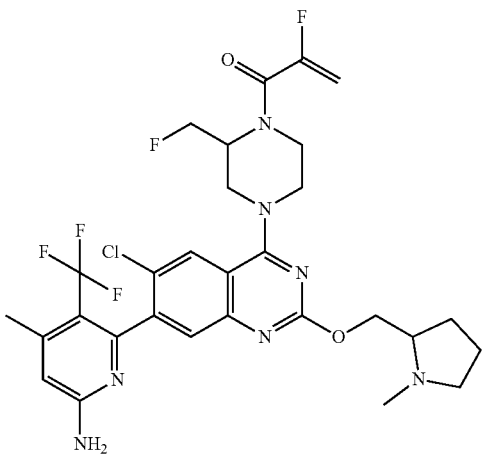 [SMILES: C=C(F)C(=O)N1CCN(c2nc(OCC3CCCN3C)nc3cc(-c4nc(N)cc(C)c4C(F)(F)F)c(Cl)cc23)CC1CF] | 1-(4-(7-(6-amino-4-methyl-3-(trifluoromethyl)pyridin-2-yl)-6-chloro-2-((1-methylpyrrolidin-2-yl)methoxy)quinazolin-4-yl)-2-(fluoromethyl)piperazin-1-yl)-2-fluoroprop-2-en-1-one |
| 57 | 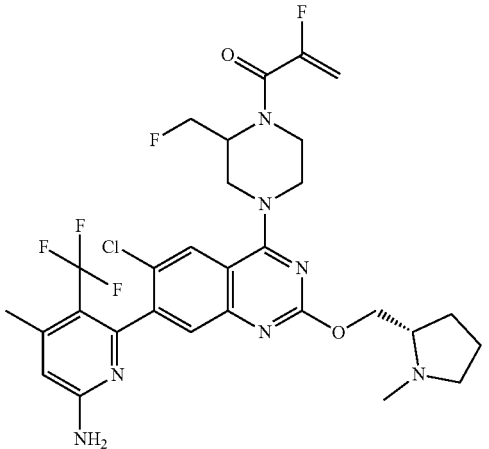 [SMILES: C=C(F)C(=O)N1CCN(c2nc(OC[C@@H]3CCCN3C)nc3cc(-c4nc(N)cc(C)c4C(F)(F)F)c(Cl)cc23)CC1CF] | 1-[4-[7-[6-amino-4-methyl-3-(trifluoromethyl)-2-pyridyl]-6-chloro-2-[[(2S)-1-methylpyrrolidin-2-yl]methoxy]quinazolin-4-yl]-2-(fluoromethyl)piperazin-1-yl]-2-fluoro-prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
| --- | --- | --- |
| n/a | | 2-(4-(7-(6-amino-4-methyl-3-(trifluoromethyl)pyridin-2-yl)-6-chloro-2-(((2S)-4-fluoro-1-methylpyrrolidin-2-yl)methoxy)quinazolin-4-yl)-1-(2-fluoroacryloyl)-5-methylpiperazin-2-yl)acetonitrile |
| 58 | 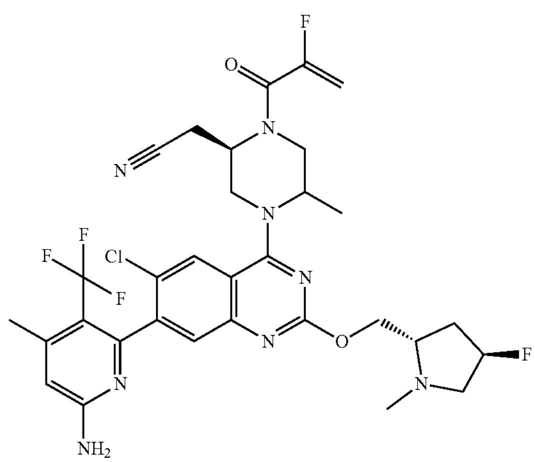 [SMILES: C=C(F)C(=O)N1CC(C)N(c2nc(OC[C@@H]3C[C@@H](F)CN3C)nc3cc(-c4nc(N)cc(C)c4C(F)(F)F)c(Cl)cc23)C[C@H]1CC#N] | 2-[(2R)-4-[7-[6-amino-4-methyl-3-(trifluoromethyl)-2-pyridyl]-6-chloro-2-[[(2S,4R)-4-fluoro-1-methyl-pyrrolidin-2-yl]methoxy]quinazolin-4-yl]-1-(2-fluoroprop-2-enoyl)-5-methyl-piperazin-2-yl]acetonitrile |
| n/a | | 1-(4-(7-(6-amino-4-methyl-3-(trifluoromethyl)pyridin-2-yl)-8-fluoro-2-((1-methylpyrrolidin-2-yl)methoxy)-6-((trifluoromethyl)thio)quinazolin-4-yl)-3-methylpiperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 59a | 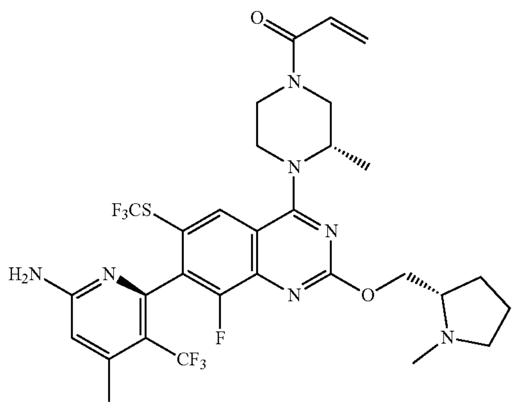 | 1-((S)-4-((R)-7-(6-amino-4-methyl-3-(trifluoromethyl)pyridin-2-yl)-8-fluoro-2-(((S)-1-methylpyrrolidin-2-yl)methoxy)-6-((trifluoromethyl)thio)quinazolin-4-yl)-3-methylpiperazin-1-yl)prop-2-en-1-one |
| 59b | 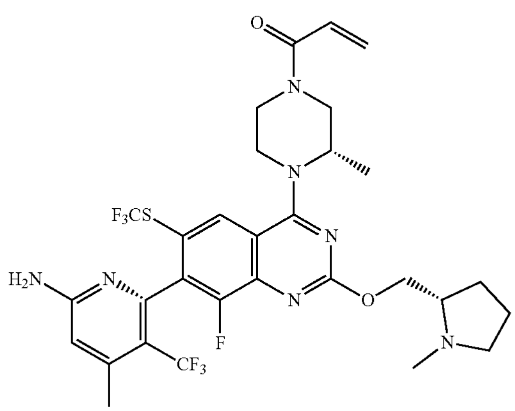 | 1-((S)-4-((S)-7-(6-amino-4-methyl-3-(trifluoromethyl)pyridin-2-yl)-8-fluoro-2-(((S)-1-methylpyrrolidin-2-yl)methoxy)-6-((trifluoromethyl)thio)quinazolin-4-yl)-3-methylpiperazin-1-yl)prop-2-en-1-one |
| n/a | 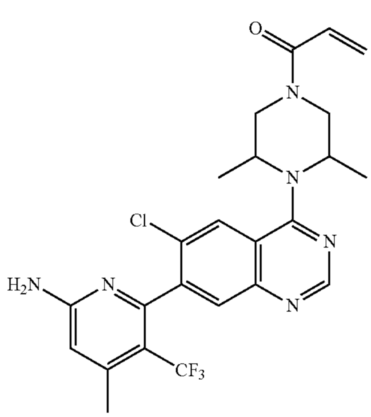 [SMILES: C=CC(=O)N1CC(C)N(c2ncnc3cc(-c4nc(N)cc(C)c4C(F)(F)F)c(Cl)cc23)C(C)C1] | 1-(4-(7-(6-amino-4-methyl-3-(trifluoromethyl)pyridin-2-yl)-6-chloroquinazolin-4-yl)-3,5-dimethylpiperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 60 | 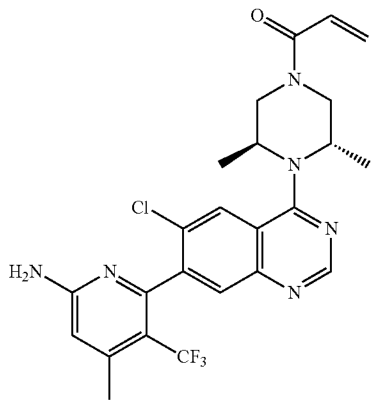 [SMILES: C=CC(=O)N1C[C@H](C)N(c2ncnc3cc(-c4nc(N)cc(C)c4C(F)(F)F)c(Cl)cc23)[C@@H](C)C1] | 1-[(3S,5S)-4-[7-[6-amino-4-methyl-3-(trifluoromethyl)-2-pyridyl]-6-chloro-quinazolin-4-yl]-3,5-dimethyl-piperazin-1-yl]prop-2-en-1-one |
| n/a | 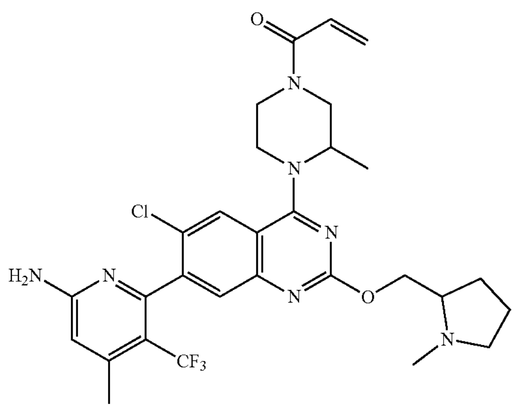 [SMILES: C=CC(=O)N1CCN(c2nc(OCC3CCCN3C)nc3cc(-c4nc(N)cc(C)c4C(F)(F)F)c(Cl)cc23)C(C)C1] | 1-(4-(7-(6-amino-4-methyl-3-(trifluoromethyl)pyridin-2-yl)-6-chloro-2-((1-methylpyrrolidin-2-yl)methoxy)quinazolin-4-yl)-3-methylpiperazin-1-yl)prop-2-en-1-one |
| 61 | 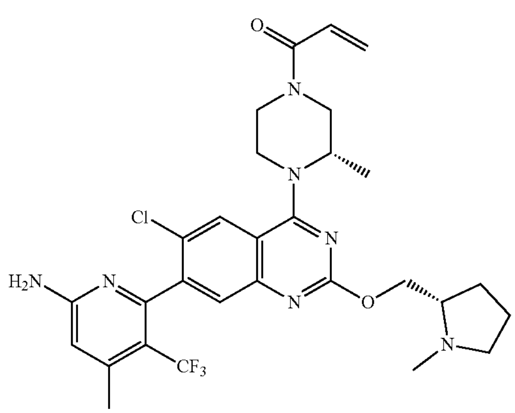 [SMILES: C=CC(=O)N1CCN(c2nc(OC[C@@H]3CCCN3C)nc3cc(-c4nc(N)cc(C)c4C(F)(F)F)c(Cl)cc23)[C@@H](C)C1] | 1-((S)-4-(7-(6-amino-4-methyl-3-(trifluoromethyl)pyridin-2-yl)-6-chloro-2-(((S)-1-methylpyrrolidin-2-yl)methoxy)quinazolin-4-yl)-3-methylpiperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| n/a | 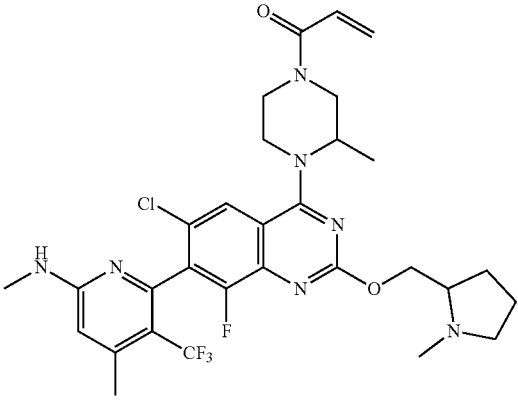 [SMILES: C=CC(=O)N1CCN(c2nc(OCC3CCCN3C)nc3c(F)c(-c4nc(NC)cc(C)c4C(F)(F)F)c(Cl)cc23)C(C)C1] | 1-(4-(6-chloro-8-fluoro-7-(4-methyl-6-(methylamino)-3-(trifluoromethyl)pyridin-2-yl)-2-((1-methylpyrrolidin-2-yl)methoxy)quinazolin-4-yl)-3-methylpiperazin-1-yl)prop-2-en-1-one |
| 62a | 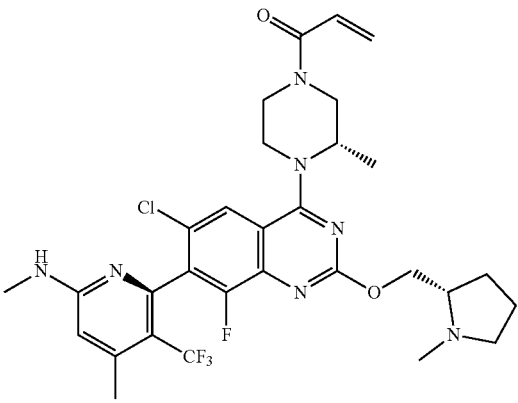 | 1-((S)-4-((R)-6-chloro-8-fluoro-7-(4-methyl-6-(methylamino)-3-(trifluromethyl)pyridin-2-yl)-2-(((S)-1-methylpyrrolidin-2-yl)methoxy)quinazolin-4-yl)-3-methylpiperazin-1-yl)prop-2-en-1-one |
| 62b | 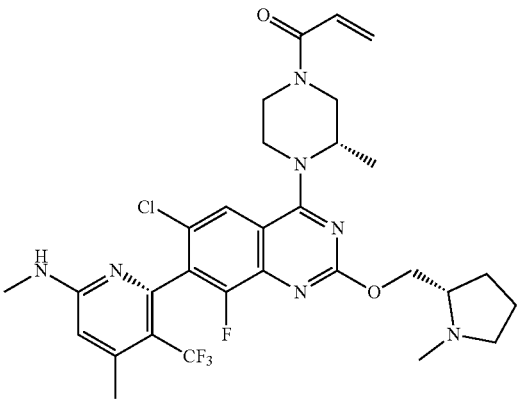 | 1-((S)-4-((S)-6-chloro-8-fluoro-7-(4-methyl-6-(methylamino)-3-(trifluoromethyl)pyridin-2-yl)-2-(((S)-1-methylpyrrolidin-2-yl)methoxy)quinazolin-4-yl)-3-methylpiperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| n/a | 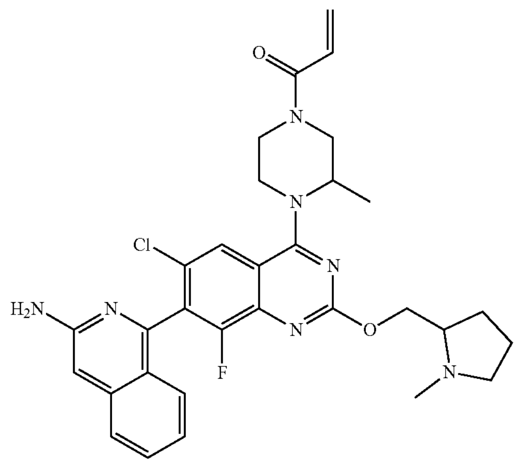 [SMILES: C=CC(=O)N1CCN(c2nc(OCC3CCCN3C)nc3c(F)c(-c4nc(N)cc5ccccc45)c(Cl)cc23)C(C)C1] | 1-(4-(7-(3-aminoisoquinolin-1-yl)-6-chloro-8-fluoro-2-((1-methylpyrrolidin-2-yl)methoxy)quinazolin-4-yl)-3-methylpiperazin-1-yl)prop-2-en-1-one |
| 63a | 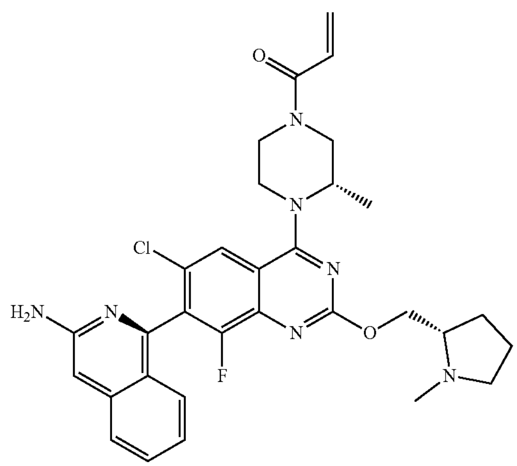 | 1-((S)-4-((R)-7-(3-aminoisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one |
| 63b | 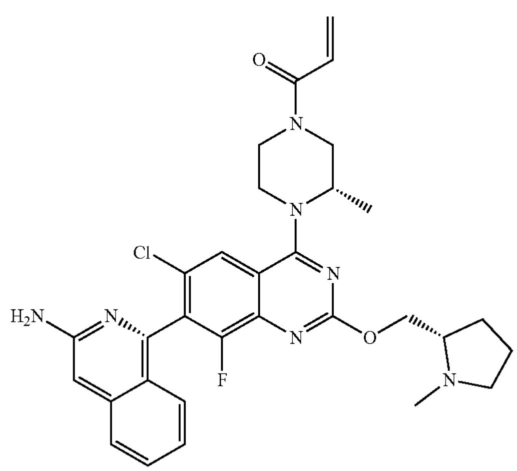 | 1-((S)-4-((S)-7-(3-aminoisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
| --- | --- | --- |
| n/a | 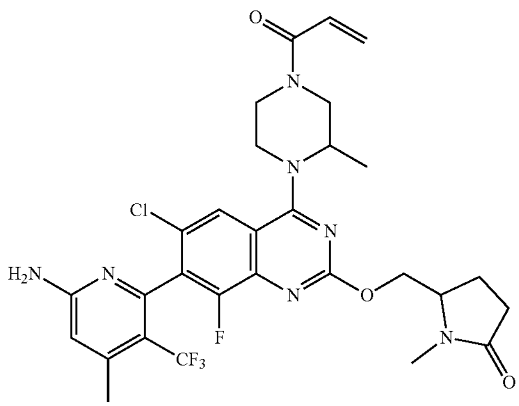 [SMILES: C=CC(=O)N1CCN(c2nc(OCC3CCC(=O)N3C)nc3c(F)c(-c4nc(N)cc(C)c4C(F)(F)F)c(Cl)cc23)C(C)C1] | 5-(((4-(4-acryloyl-2-methylpiperazin-1-yl)-7-(6-amino-4-methyl-3-(trifluoromethyl)pyridin-2-yl)-6-chloro-8-fluoroquinazolin-2-yl)oxy)methyl)-1-methylpyrrolidin-2-one |
| 64a | 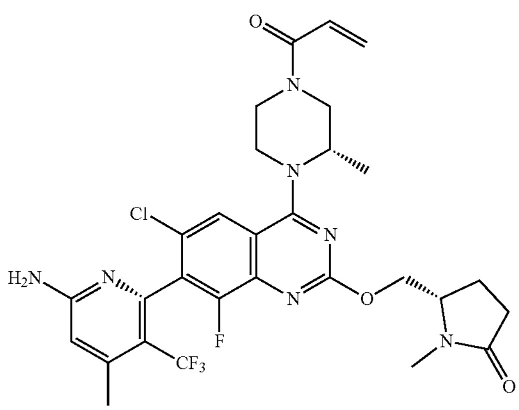 | (S)-5-((((S)-4-((S)-4-acryloyl-2-methylpiperazin-1-yl)-7-(6-amino-4-methyl-3-(trifluoromethyl)pyridin-2-yl)-6-chloro-8-fluoroquinazolin-2-yl)oxy)methyl)-1-methylpyrrolidin-2-one |
| 64b | 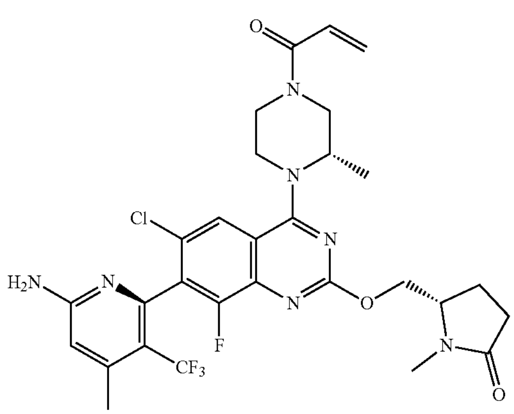 | (S)-5-((((R)-4-((S)-4-acryloyl-2-methylpiperazin-1-yl)-7-(6-amino-4-methyl-3-(trifluoromethyl)pyridin-2-yl)-6-chloro-8-fluoroquinazolin-2-yl)oxy)methyl)-1-methylpyrrolidin-2-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| n/a | | (E)-1-(4-(7-(6-amino-4-methyl-3-(trifluoromethyl)pyridin-2-yl)-6-chloro-2-((1-methylpyrrolidin-2-yl)methoxy)quinazolin-4-yl)-3-methylpiperazin-1-yl)-4,4-difluorobut-2-en-1-one |
| 65 | 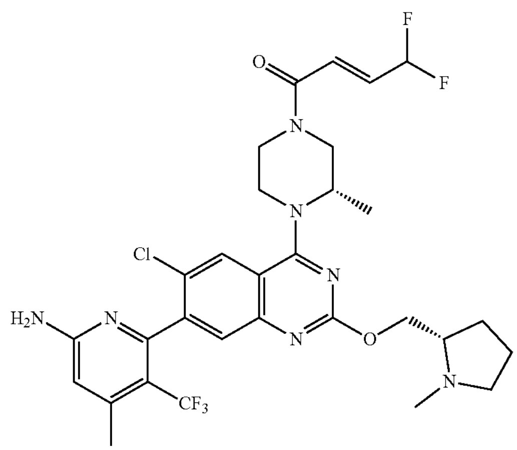 [SMILES: Cc1cc(N)nc(-c2cc3nc(OC[C@@H]4CCCN4C)nc(N4CCN(C(=O)/C=C/C(F)F)C[C@@H]4C)c3cc2Cl)c1C(F)(F)F] | (E)-1-((S)-4-(7-(6-amino-4-methyl-3-(trifluoromethyl)pyridin-2-yl)-6-chloro-2-(((S)-1-methylpyrrolidin-2-yl)methoxy)quinazolin-4-yl)-3-methylpiperazin-1-yl)-4,4-difluorobut-2-en-1-one |
| n/a | | 1-(4-(7-(6-amino-4-methyl-3-(trifluoromethyl)pyridin-2-yl)-6-chloro-2-((2-(dimethylamino)cyclopentyl)oxy)quinazolin-4-yl)-3-methylpiperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 66 | 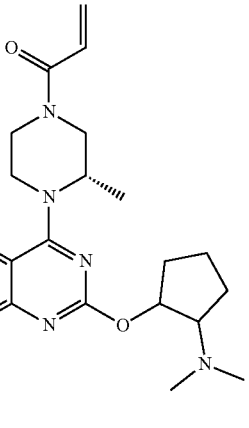 | 1-[(3S)-4-[7-[6-amino-4-methyl-3-(trifluoromethyl)-2-pyridyl]-6-chloro-2-[2-(dimethylamino)cyclopentoxy]quinazolin-4-yl]-3-methyl-piperazin-1-yl]prop-2-en-1-one |
| n/a | 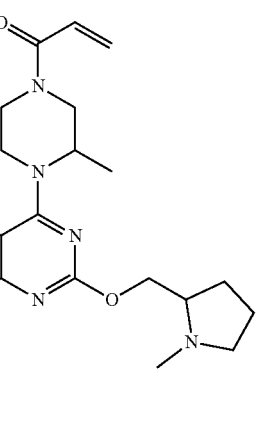 | 1-(4-(7-(3-amino-4-fluoroisoquinolin-1-yl)-6-chloro-8-fluoro-2-((1-methylpyrrolidin-2-yl)methoxy)quinazolin-4-yl)-3-methylpiperazin-1-yl)prop-2-en-1-one |
| 67a | 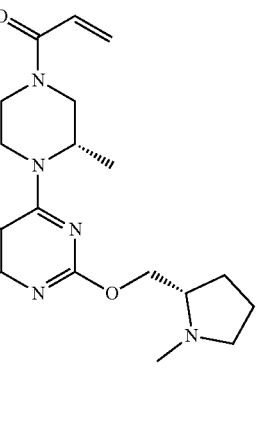 | 1-((S)-4-((R)-7-(3-amino-4-fluoroisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 67b | 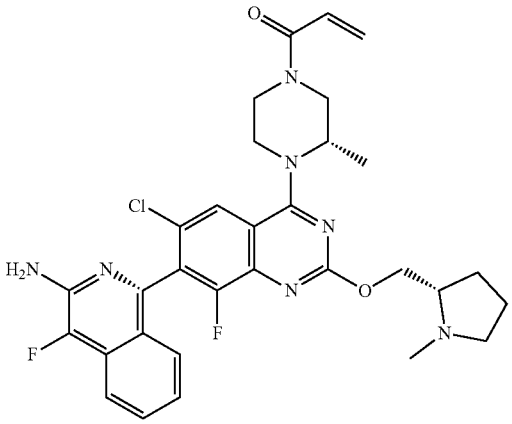 | 1-((S)-4-((S)-7-(3-amino-4-fluoroisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one |
| n/a | 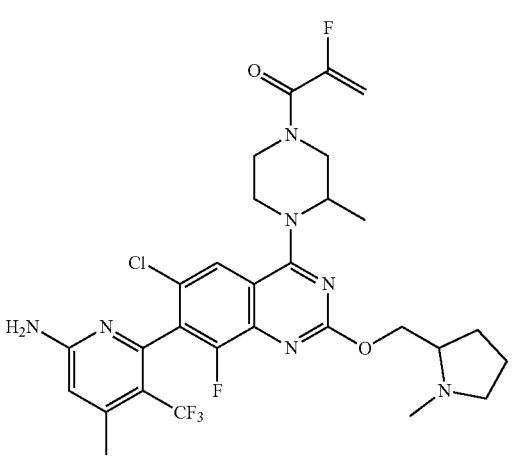 [SMILES: C=C(F)C(=O)N1CCN(c2nc(OCC3CCCN3C)nc3c(F)c(-c4nc(N)cc(C)c4C(F)(F)F)c(Cl)cc23)C(C)C1] | 1-(4-(7-(6-amino-4-methyl-3-(trifluoromethyl)pyridin-2-yl)-6-chloro-8-fluoro-2-((1-methylpyrrolidin-2-yl)methoxy)quinazolin-4-yl)-3-methylpiperazin-1-yl)-2-fluoroprop-2-en-1-one |
| 68a | 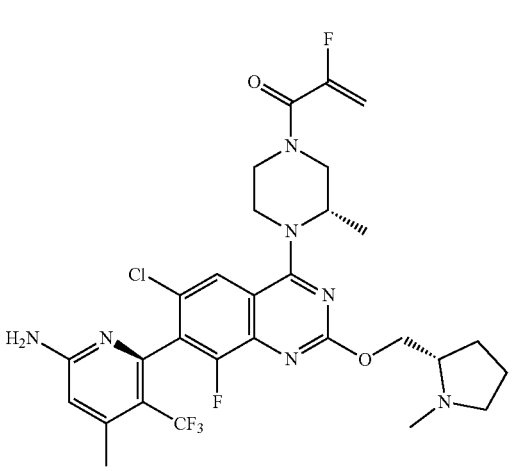 | 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-2-fluoroprop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 68b | 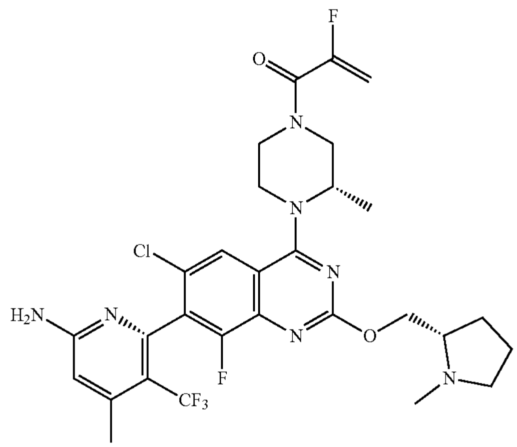 | 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-2-fluoroprop-2-en-1-one |
| n/a | 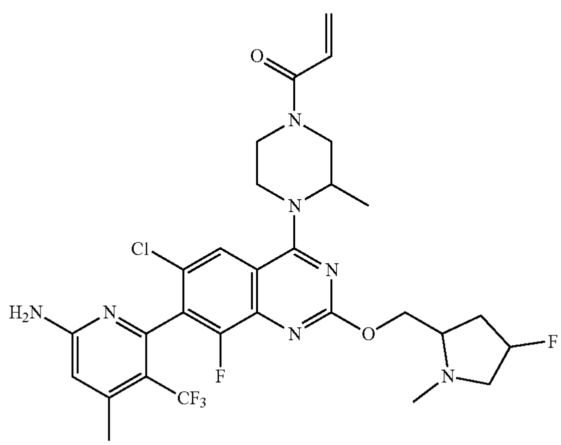 [SMILES: C=CC(=O)N1CCN(c2nc(OCC3CC(F)CN3C)nc3c(F)c(-c4nc(N)cc(C)c4C(F)(F)F)c(Cl)cc23)C(C)C1] | 1-(4-(7-(6-amino-4-methyl-3-(trifluoromethyl)pyridin-2-yl)-6-chloro-8-fluoro-2-((4-fluoro-1-methylpyrrolidin-2-yl)methoxy)quinazolin-4-yl)-3-methylpiperazin-1-yl)prop-2-en-1-one |
| 69 | 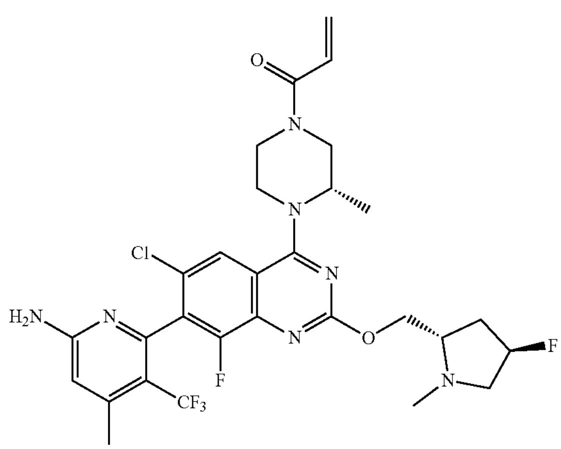 [SMILES: C=CC(=O)N1CCN(c2nc(OC[C@@H]3C[C@@H](F)CN3C)nc3c(F)c(-c4nc(N)cc(C)c4C(F)(F)F)c(Cl)cc23)[C@@H](C)C1] | 1-[(3S)-4-[7-[6-amino-4-methyl-3-(trifluoromethyl)-2-pyridyl]-6-chloro-8-fluoro-2-[[(2S,4R)-4-fluoro-1-methyl-pyrrolidin-2-yl]methoxy]quinazolin-4-yl]-3-methyl-piperazin-1-yl]prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| n/a | 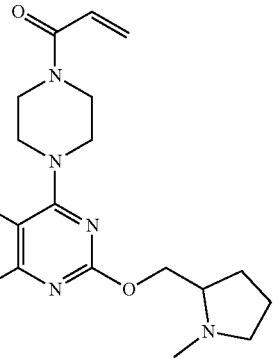 | 1-(4-(7-(6-amino-3-(trifluoromethyl)pyridin-2-yl)-6-chloro-2-((1-methylpyrrolidin-2-yl)methoxy)quinazolin-4-yl)piperazin-1-yl)prop-2-en-1-one |
| 70 | 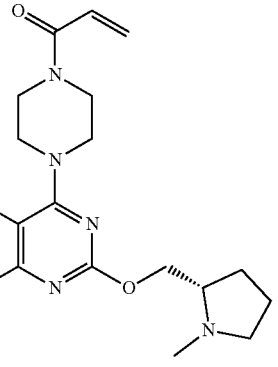 | (S)-1-(4-(7-(6-amino-3-(trifluoromethyl)pyridin-2-yl)-6-chloro-2-((1-methylpyrrolidin-2-yl)methoxy)quinazolin-4-yl)piperazin-1-yl)prop-2-en-1-one |
| n/a | 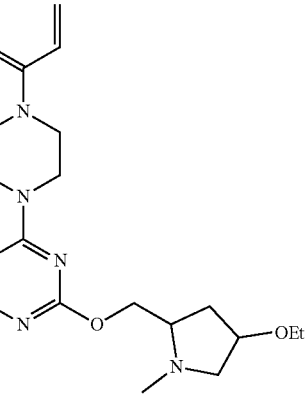 | 1-(4-(7-(6-amino-3-(trifluoromethyl)pyridin-2-yl)-6-chloro-2-((4-ethoxy-1-methylpyrrolidin-2-yl)methoxy)quinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 71 | 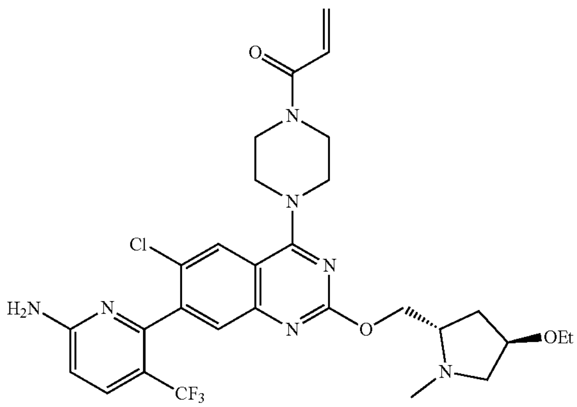 [SMILES: C=CC(=O)N1CCN(c2nc(OC[C@@H]3C[C@@H](OCC)CN3C)nc3cc(-c4nc(N)ccc4C(F)(F)F)c(Cl)cc23)CC1] | 1-(4-(7-(6-amino-3-(trifluoromethyl)pyridin-2-yl)-6-chloro-2-(((2S,4R)-4-ethoxy-1-methylpyrrolidin-2-yl)methoxy)quinazolin-4-yl)piperazin-1-yl)prop-2-en-1-one |
| n/a | 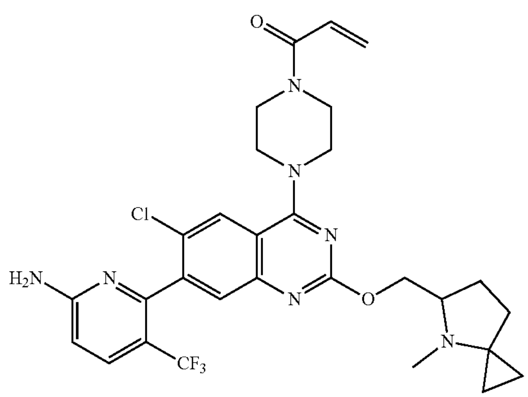 [SMILES: C=CC(=O)N1CCN(c2nc(OCC3CCC4(CC4)N3C)nc3cc(-c4nc(N)ccc4C(F)(F)F)c(Cl)cc23)CC1] | 1-(4-(7-(6-amino-3-(trifluoromethyl)pyridin-2-yl)-6-chloro-2-((4-methyl-4-azaspiro[2,4]heptan-5-yl)methoxy)quinazolin-4-yl)piperazin-1-yl)prop-2-en-1-one |
| 72 | 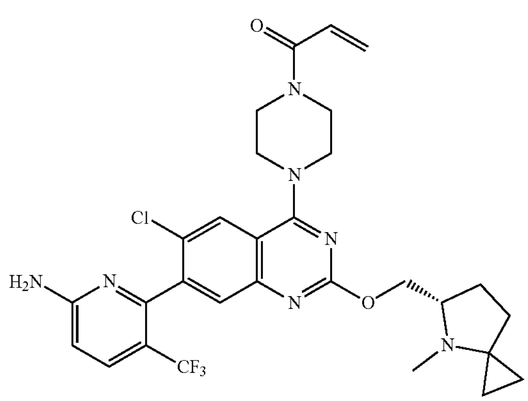 [SMILES: C=CC(=O)N1CCN(c2nc(OC[C@@H]3CCC4(CC4)N3C)nc3cc(-c4nc(N)ccc4C(F)(F)F)c(Cl)cc23)CC1] | (S)-1-(4-(7-(6-amino-3-(trifluoromethyl)pyridin-2-yl)-6-chloro-2-((4-methyl-4-azaspiro[2.4]heptan-5-yl)methoxy)quinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 73 | 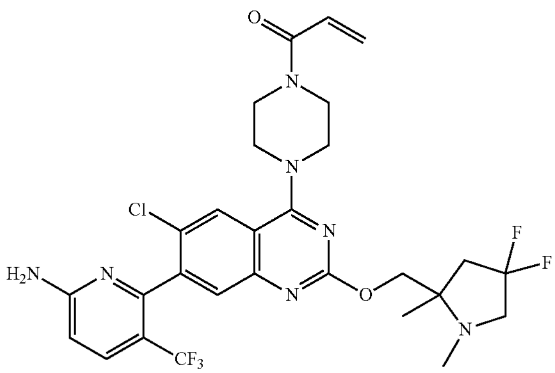 [SMILES: C=CC(=O)N1CCN(c2nc(OCC3(C)CC(F)(F)CN3C)nc3cc(-c4nc(N)ccc4C(F)(F)F)c(Cl)cc23)CC1] | 1-(4-(7-(6-amino-3-(trifluoromethyl)pyridin-2-yl)-6-chloro-2-((4,4-difluoro-1,2-dimethylpyrrolidin-2-yl)methoxy)quinazolin-4-yl)piperazin-1-yl)prop-2-en-1-one |
| n/a | | 1-(4-(7-(6-amino-3-(trifluoromethyl)pyridin-2-yl)-6-chloro-2-((2-(1-methylpyrrolidin-2-yl)propan-2-yl)oxy)quinazolin-4-yl)piperazin-1-yl)prop-2-en-1-one |
| 74 | 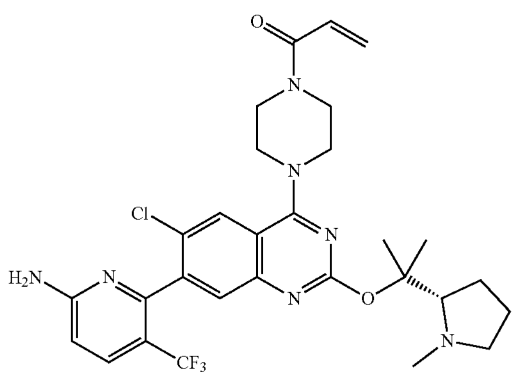 [SMILES: C=CC(=O)N1CCN(c2nc(OC(C)(C)[C@@H]3CCCN3C)nc3cc(-c4nc(N)ccc4C(F)(F)F)c(Cl)cc23)CC1] | 1-[4-[7-[6-amino-3-(trifluoromethyl)-2-pyridyl]-6-chloro-2-[1-methyl-1-[(2S)-1-methylpyrrolidin-2-yl]ethoxy]quinazolin-4-yl]piperazin-1-yl]prop-2-en-1-one |
| n/a | | 1-(4-(7-(6-amino-3-(trifluoromethyl)pyridin-2-yl)-6-chloro-2-((1-methylazetidin-2-yl)methoxy)quinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 75a | 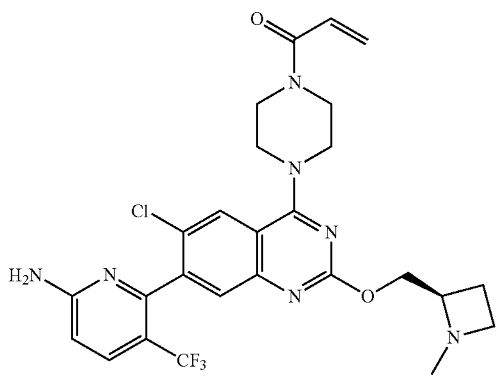 [SMILES: C=CC(=O)N1CCN(c2nc(OC[C@H]3CCN3C)nc3cc(-c4nc(N)ccc4C(F)(F)F)c(Cl)cc23)CC1] | (R)-1-(4-(7-(6-amino-3-(trifluoromethyl)pyridin-2-yl)-6-chloro-2-((1-methylazetidin-2-yl)methoxy)quinazolin-4-yl)piperazin-1-yl)prop-2-en-1-one |
| 75b | 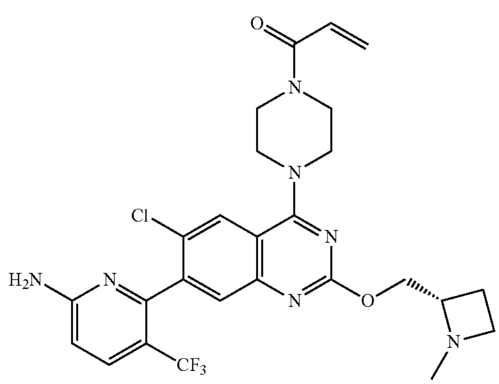 [SMILES: C=CC(=O)N1CCN(c2nc(OC[C@@H]3CCN3C)nc3cc(-c4nc(N)ccc4C(F)(F)F)c(Cl)cc23)CC1] | (S)-1-(4-(7-(6-amino-3-(trifluoromethyl)pyridin-2-yl)-6-chloro-2-((1-methylazetidin-2-yl)methoxy)quinazolin-4-yl)piperazin-1-yl)prop-2-en-1-one |
| 76 | 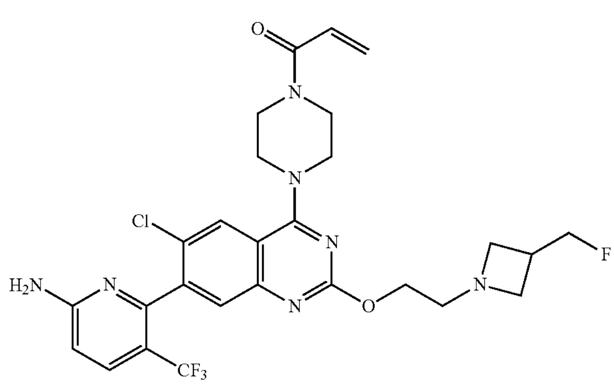 | 1-(4-(7-(6-amino-3-(trifluoromethyl)pyridin-2-yl)-6-chloro-2-(2-(3-(fluoromethyl)azetidin-1-yl)ethoxy)quinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| n/a | 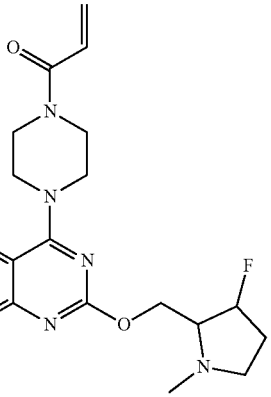 | 1-(4-(7-(6-amino-3-(trifluoromethyl)pyridin-2-yl)-6-chloro-2-((3-fluoro-1-methylpyrrolidin-2-yl)methoxy)quinazolin-4-yl)piperazin-1-yl)prop-2-en-1-one |
| 77 | 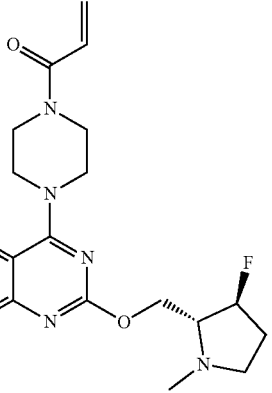 | 1-[4-[7-[6-amino-3-(trifluoromethyl)-2-pyridyl]-6-chloro-2-[[(2R,3S)-3-fluoro-1-methyl-pyrrolidin-2-yl]methoxy]quinazolin-4-yl]piperazin-1-yl]prop-2-en-1-one |
| n/a | 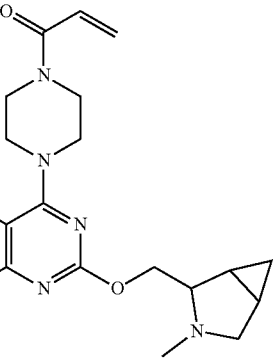 | 1-(4-(7-(6-amino-3-(trifluoromethyl)pyridin-2-yl)-6-chloro-2-((3-methyl-3-azabicyclo[3.1.0]hexan-2-yl)methoxy)quinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 78a | 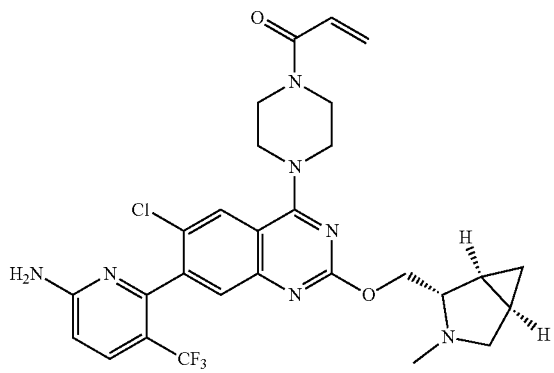 [SMILES: C=CC(=O)N1CCN(c2nc(OC[C@@H]3[C@H]4C[C@H]4CN3C)nc3cc(-c4nc(N)ccc4C(F)(F)F)c(Cl)cc23)CC1] | 1-(4-(7-(6-amino-3-(trifluoromethyl)pyridin-2-yl)-6-chloro-2-(((1S,2S,5R)-3-methyl-3-azabicyclo[3.1.0]hexan-2-yl)methoxy)quinazolin-4-yl)piperazin-1-yl)prop-2-en-1-one |
| 78b | 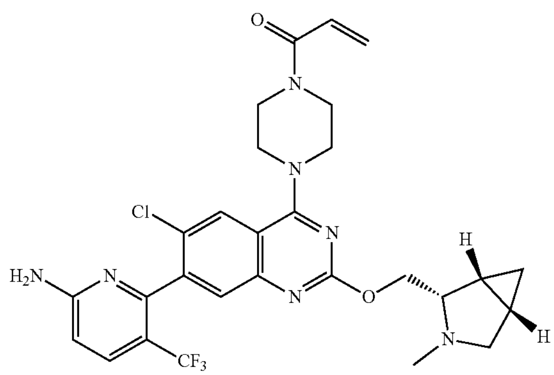 [SMILES: C=CC(=O)N1CCN(c2nc(OC[C@@H]3[C@@H]4C[C@@H]4CN3C)nc3cc(-c4nc(N)ccc4C(F)(F)F)c(Cl)cc23)CC1] | 1-(4-(7-(6-amino-3-(trifluoromethyl)pyridin-2-yl)-6-chloro-2-(((1R,2S,5S)-3-methyl-3-azabicyclo[3.1.0]hexan-2-yl)methoxy)quinazolin-4-yl)piperazin-1-yl)prop-2-en-1-one |
| n/a | 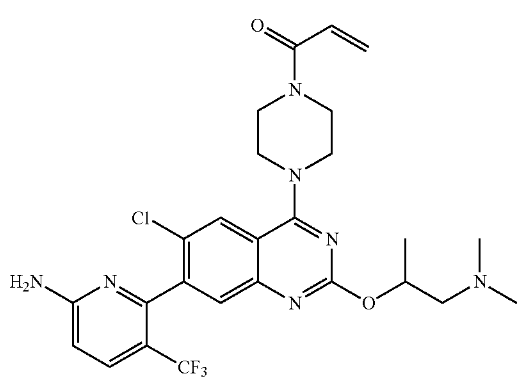 [SMILES: C=CC(=O)N1CCN(c2nc(OC(C)CN(C)C)nc3cc(-c4nc(N)ccc4C(F)(F)F)c(Cl)cc23)CC1] | 1-(4-(7-(6-amino-3-(trifluoromethyl)pyridin-2-yl)-6-chloro-2-((1-(dimethylamino)propan-2-yl)oxy)quinazolin-4-yl)piperazin-1-yl)prop-2-en-1-one |
| 79a/79b | 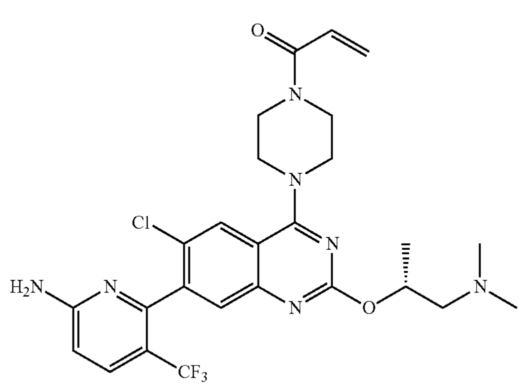 [SMILES: C=CC(=O)N1CCN(c2nc(O[C@H](C)CN(C)C)nc3cc(-c4nc(N)ccc4C(F)(F)F)c(Cl)cc23)CC1] | (R)-1-(4-(7-(6-amino-3-(trifluoromethyl)pyridin-2-yl)-6-chloro-2-((1-(dimethylamino)propan-2-yl)oxy)quinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 79a/79b | 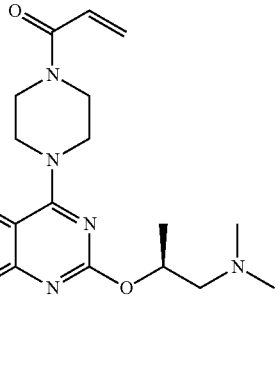 | (S)-1-(4-(7-(6-amino-3-(trifluoromethyl)pyridin-2-yl)-6-chloro-2-((1-(dimethylamino)propan-2-yl)oxy)quinazolin-4-yl)piperazin-1-yl)prop-2-en-1-one |
| 80 | 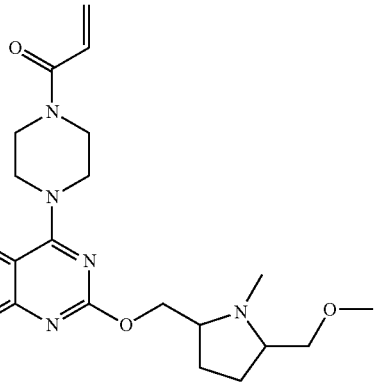 | 1-(4-(7-(6-amino-3-(trifluoromethyl)pyridin-2-yl)-6-chloro-2-((5-(methoxymethyl)-1-methylpyrrolidin-2-yl)methoxy)quinazolin-4-yl)piperazin-1-yl)prop-2-en-1-one |
| n/a | 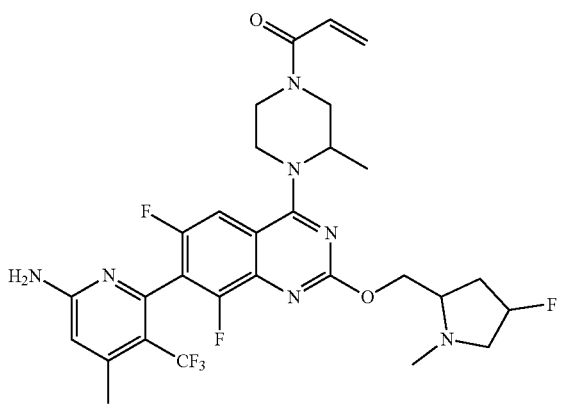 [SMILES: C=CC(=O)N1CCN(c2nc(OCC3CC(F)CN3C)nc3c(F)c(-c4nc(N)cc(C)c4C(F)(F)F)c(F)cc23)C(C)C1] | 1-(4-(7-(6-amino-4-methyl-3-(trifluoromethyl)pyridin-2-yl)-6,8-difluoro-2-((4-fluoro-1-methylpyrrolidin-2-yl)methoxy)quinazolin-4-yl)-3-methylpiperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 81a | 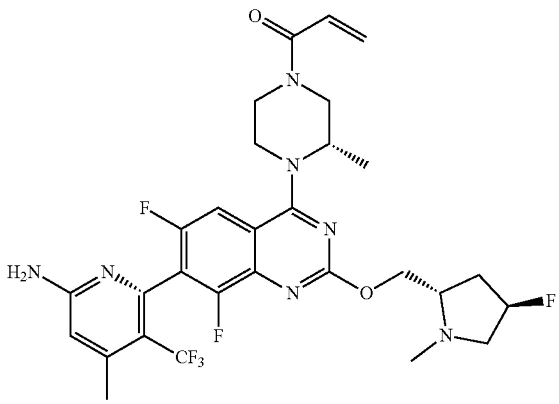 | 1-((S)-4-((R)-7-(6-amino-4-methyl-3-(trifluoromethyl)pyridin-2-yl)-6,8-difluoro-2-(((2S,4R)-4-fluoro-1-methylpyrrolidin-2-yl)methoxy)quinazolin-4-yl)-3-methylpiperazin-1-yl)prop-2-en-1-one |
| 81b | 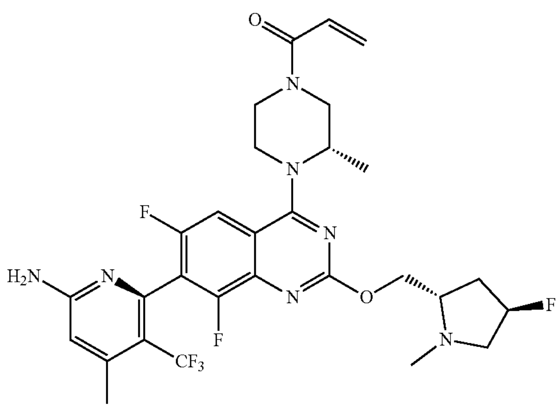 | 1-((S)-4-((S)-7-(6-amino-4-methyl-3-(trifluoromethyl)pyridin-2-yl)-6,8-difluoro-2-(((2S,4R)-4-fluoro-1-methylpyrrolidin-2-yl)methoxy)quinazolin-4-yl)-3-methylpiperazin-1-yl)prop-2-en-1-one |
| n/a | 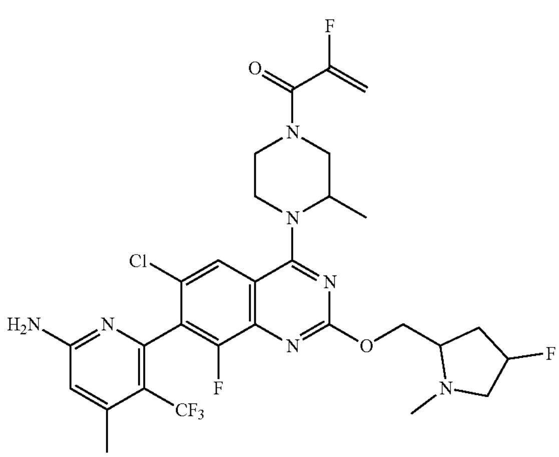 [SMILES: C=C(F)C(=O)N1CCN(c2nc(OCC3CC(F)CN3C)nc3c(F)c(-c4nc(N)cc(C)c4C(F)(F)F)c(Cl)cc23)C(C)C1] | 1-(4-(7-(6-amino-4-methyl-3-(trifluoromethyl)pyridin-2-yl)-6-chloro-8-fluoro-2-((4-fluoro-1-methylpyrrolidin-2-yl)methoxy)quinazolin-4-yl)-3-methylpiperazin-1-yl)-2-fluoroprop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 82a | 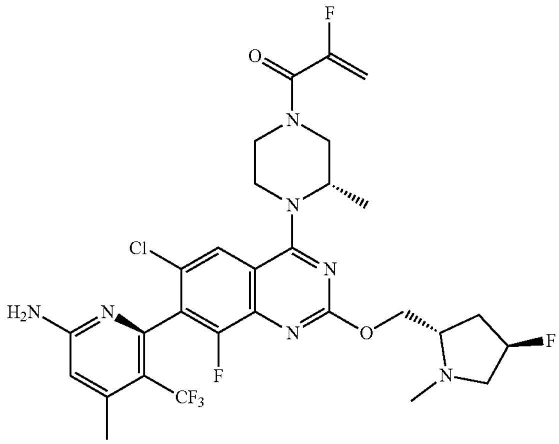 | 1-((S)-4-((R)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)-2-fluoroprop-2-en-1-one |
| 82b | 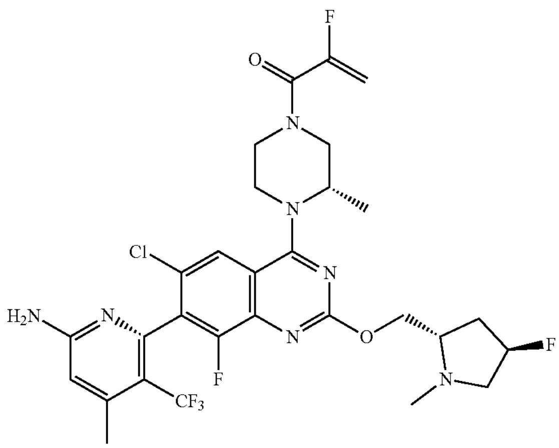 | 1-((S)-4-((S)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)-2-fluoroprop-2-en-1-one |
| n/a | 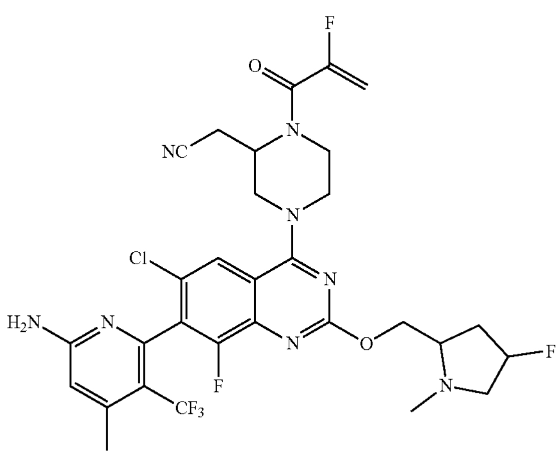 [SMILES: C=C(F)C(=O)N1CCN(c2nc(OCC3CC(F)CN3C)nc3c(F)c(-c4nc(N)cc(C)c4C(F)(F)F)c(Cl)cc23)CC1CC#N] | 2-(4-(7-(6-amino-4-methyl-3-(trifluoromethyl)pyridin-2-yl)-6-chloro-8-fluoro-2-((4-fluoro-1-methylpyrrolidin-2-yl)methoxy)quinazolin-4-yl)-1-(2-fluoroacryloyl)piperazin-2-yl)acetonitrile |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 83a | 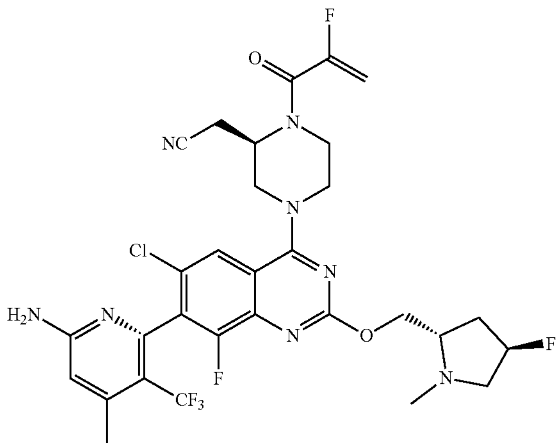 | 2-((R)-4-((S)-7-(6-amino-4-methyl-3-(trifluoromethyl)pyridin-2-yl)-6-chloro-8-fluoro-2-((((2S,4R)-4-fluoro-1-methylpyrrolidin-2-yl)methoxy)quinazolin-4-yl)-1-(2-fluoroacryloyl)piperazin-2-yl)acetonitrile |
| 83b | 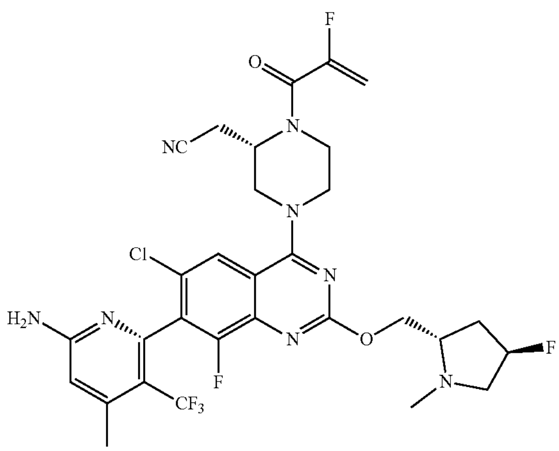 | 2-((S)-4-((S)-7-(6-amino-4-methyl-3-(trifluoromethyl)pyridin-2-yl)-6-chloro-8-fluoro-2-((((2S,4R)-4-fluoro-1-methylpyrrolidin-2-yl)methoxy)quinazolin-4-yl)-1-(2-fluoroacryloyl)piperazin-2-yl)acetonitrile |
| 83c | 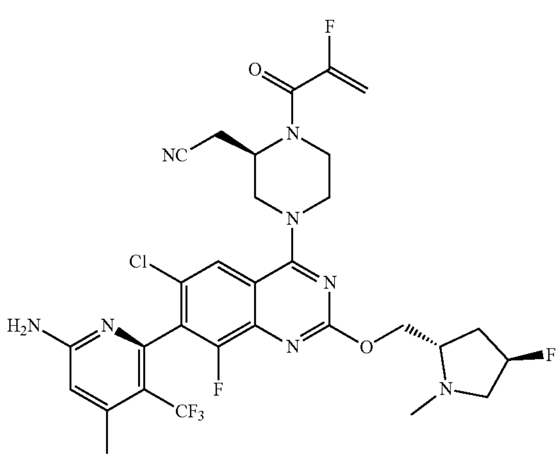 | 2-((R)-4-((R)-7-(6-amino-4-methyl-3-(trifluoromethyl)pyridin-2-yl)-6-chloro-8-fluoro-2-((((2S,4R)-4-fluoro-1-methylpyrrolidin-2-yl)methoxy)quinazolin-4-yl)-1-(2-fluoroacryloy)piperazin-2-yl)acetonitrile |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 83d | 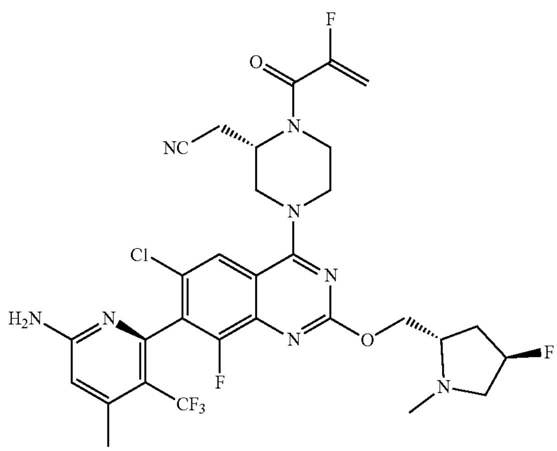 | 2-((S)-4-((R)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-1-(2-fluoroacryloyl)piperazin-2-yl)acetonitrile |
| n/a | 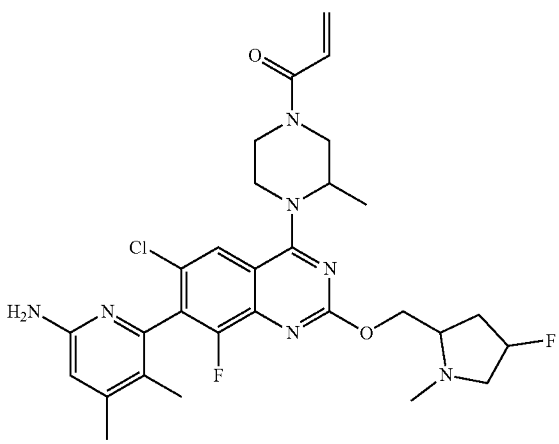 [SMILES: C=CC(=O)N1CCN(c2nc(OCC3CC(F)CN3C)nc3c(F)c(-c4nc(N)cc(C)c4C)c(Cl)cc23)C(C)C1] | 1-(4-(7-(6-amino-3,4-dimethylpyridin-2-yl)-6-chloro-8-fluoro-2-((4-fluoro-1-methylpyrrolidin-2-yl)methoxy)quinazolin-4-yl)-3-methylpiperazin-1-yl)prop-2-en-1-one |
| 84a | 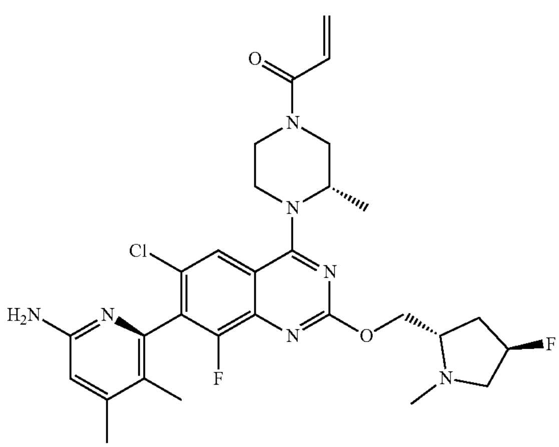 | 1-((S)-4-((R)-7-(6-amino-3,4-dimethylpyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 84b | 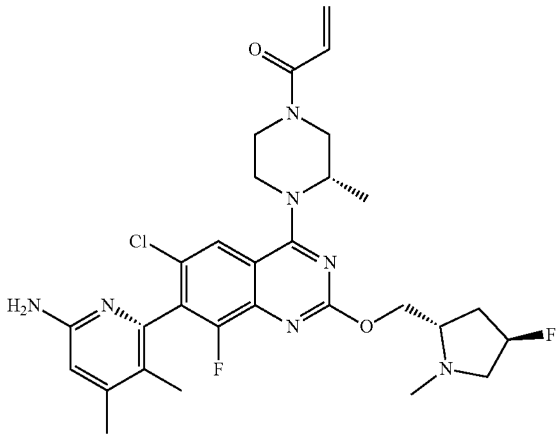 | 1-((S)-4-((S)-7-(6-amino-3,4-dimethylpyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)prop-2-en-1-one |
| n/a | 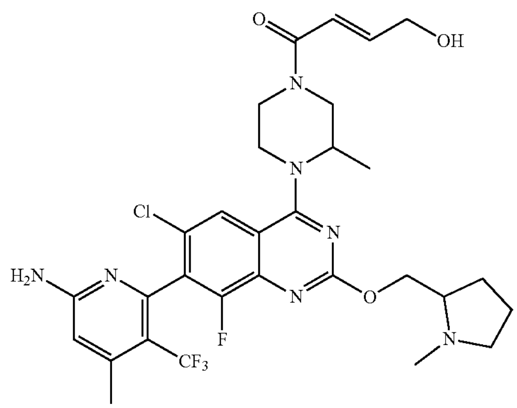 [SMILES: Cc1cc(N)nc(-c2c(Cl)cc3c(N4CCN(C(=O)/C=C/CO)CC4C)nc(OCC4CCCN4C)nc3c2F)c1C(F)(F)F] | (E)-1-(4-(7-(6-amino-4-methyl-3-(trifluoromethyl)pyridin-2-yl)-6-chloro-8-fluoro-2-((1-methylpyrrolidin-2-yl)methoxy)quinazolin-4-yl)-3-methylpiperazin-1-yl)-4-hydroxybut-2-en-1-one |
| 85 | 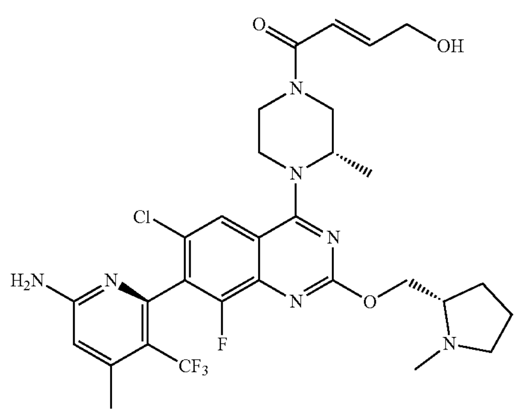 | (E)-1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-hydroxybut-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| n/a | 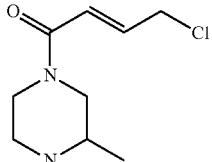 | (E)-1-(4-(7-(6-amino-4-methyl-3-(trifluoromethyl)pyridin-2-yl)-6-chloro-8-fluoro-2-((1-methylpyrrolidin-2-yl)methoxy)quinazolin-4-yl)-3-methylpiperazin-1-yl)-4-chlorobut-2-en-1-one |
| 86 | 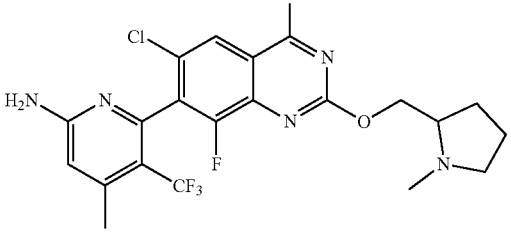 | (E)-1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-chlorobut-2-en-1-one |
| n/a | 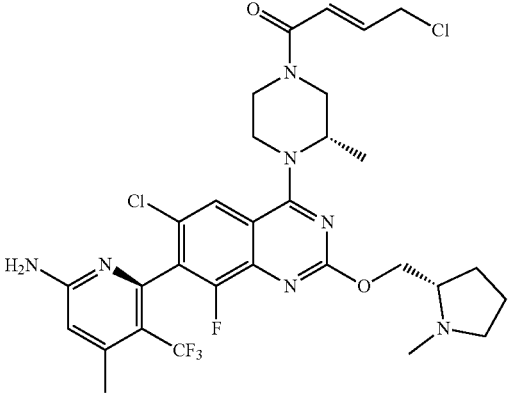 | 1-(4-(7-(6-amino-3-(trifluoromethyl)pyridin-2-yl)-6-chloro-2-((1-(oxetan-3-yl)pyrrolidin-2-yl)methoxy)quinazolin-4-yl)piperazin-1-yl)prop-2-en-1-one |

| Compound # | Structure | Compound Name |
|---|---|---|
| 87 | 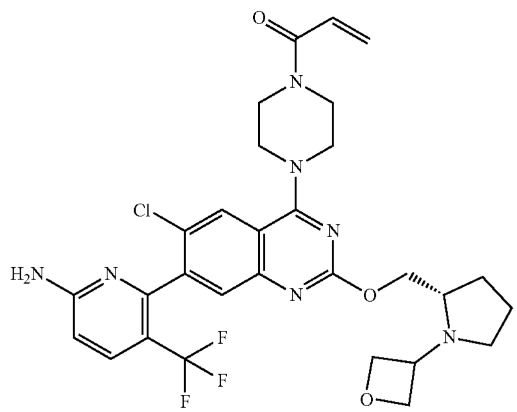 [SMILES: C=CC(=O)N1CCN(c2nc(OC[C@@H]3CCCN3C3COC3)nc3cc(-c4nc(N)ccc4C(F)(F)F)c(Cl)cc23)CC1] | 1-[4-[7-[6-amino-3-(trifluoromethyl)-2-pyridyl]-6-chloro-2-[[(2S)-1-(oxetan-3-yl)pyrrolidin-2-yl]methoxy]quinazolin-4-yl]piperazin-1-yl]prop-2-en-1-one |
| 88 | 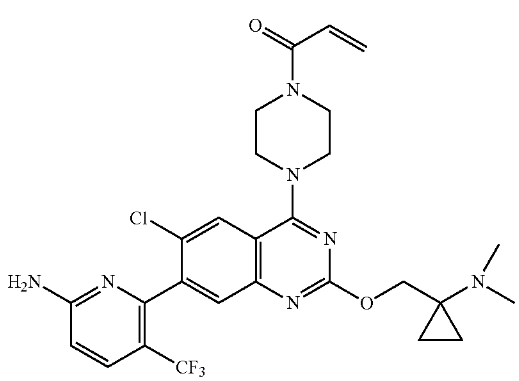 [SMILES: C=CC(=O)N1CCN(c2nc(OCC3(N(C)C)CC3)nc3cc(-c4nc(N)ccc4C(F)(F)F)c(Cl)cc23)CC1] | 1-(4-(7-(6-amino-3-(trifluoromethyl)pyridin-2-yl)-6-chloro-2-((1-(dimethylamino)cyclopropyl)methoxy)quinazolin-4-yl)piperazin-1-yl)prop-2-en-1-one |
| n/a | 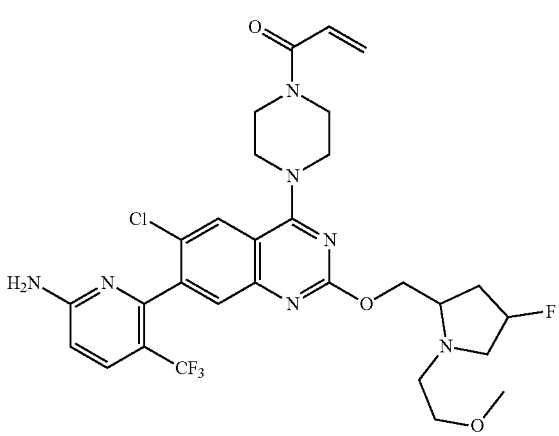 [SMILES: C=CC(=O)N1CCN(c2nc(OCC3CC(F)CN3CCOC)nc3cc(-c4nc(N)ccc4C(F)(F)F)c(Cl)cc23)CC1] | 1-(4-(7-(6-amino-3-(trifluoromethyl)pyridin-2-yl)-6-chloro-2-((4-fluoro-1-(2-methoxyethyl)pyrrolidin-2-yl)methoxy)quinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 89 | 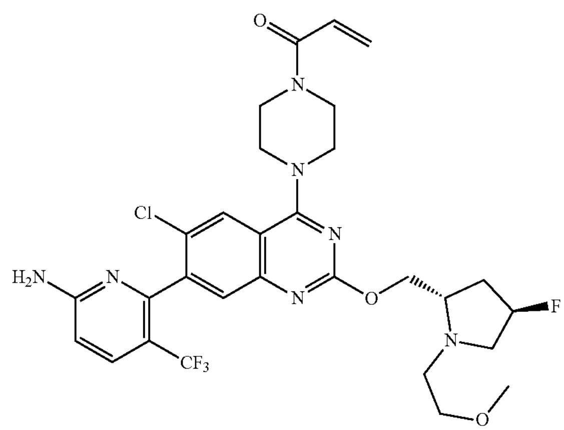 [SMILES: C=CC(=O)N1CCN(c2nc(OC[C@@H]3C[C@@H](F)CN3CCOC)nc3cc(-c4nc(N)ccc4C(F)(F)F)c(Cl)cc23)CC1] | 1-[4-[7-[6-amino-3-(trifluoromethyl)-2-pyridyl]-6-chloro-2-[[(2S,4R)-4-fluoro-1-(2-methoxyethyl)pyrrolidin-2-yl]methoxy]quinazolin-4-yl]piperazin-1-yl]prop-2-en-1-one |
| n/a | 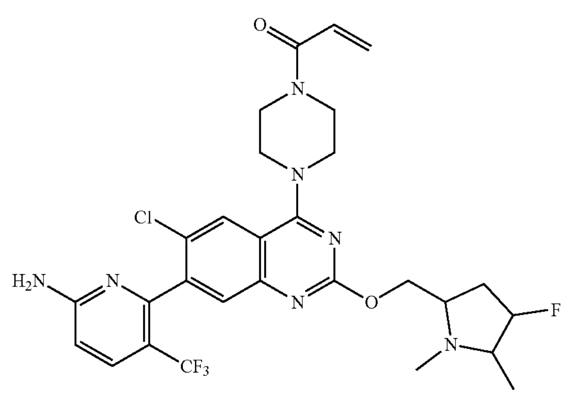 [SMILES: C=CC(=O)N1CCN(c2nc(OCC3CC(F)C(C)N3C)nc3cc(-c4nc(N)ccc4C(F)(F)F)c(Cl)cc23)CC1] | 1-(4-(7-(6-amino-3-(trifluoromethyl)pyridin-2-yl)-6-chloro-2-((4-fluoro-1,5-dimethylpyrrolidin-2-yl)methoxy)quinazolin-4-yl)piperazin-1-yl)prop-2-en-1-one |
| 90 | 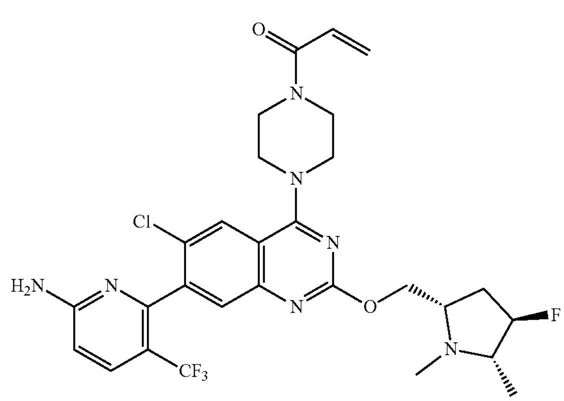 [SMILES: C=CC(=O)N1CCN(c2nc(OC[C@@H]3C[C@@H](F)[C@H](C)N3C)nc3cc(-c4nc(N)ccc4C(F)(F)F)c(Cl)cc23)CC1] | 1-[4-[7-[6-amino-3-(trifluoromethyl)-2-pyridyl]-6-chloro-2-[[(2S,4R,5S)-4-fluoro-1,5-dimethyl-pyrrolidin-2-yl]methoxy]quinazolin-4-yl]piperazin-1-yl]prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| n/a | 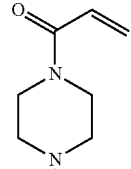 | 1-(4-(7-(6-amino-3-(trifluoromethyl)pyridin-2-yl)-6-chloro-2-((1-(2-methoxyethyl)pyrrolidin-2-yl)methoxy)quinazolin-4-yl)piperazin-1-yl)prop-2-en-1-one |
| 91 | 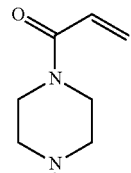 | 1-[4-[7-[6-amino-3-(trifluoromethyl)-2-pyridyl]-6-chloro-2-[[(2S)-1-(2-methoxyethyl)pyrrolidin-2-yl]methoxy]quinazolin-4-yl]piperazin-1-yl]prop-2-en-1-one |
| n/a | 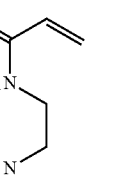 | 1-(4-(7-(6-amino-3-(trifluoromethyl)pyridin-2-yl)-6-chloro-2-((4-(difluoromethoxy)-1-methylpyrrolidin-2-yl)methoxy)quinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 92 | 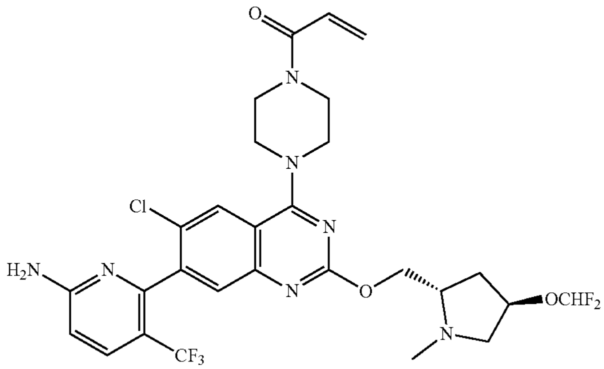 [SMILES: C=CC(=O)N1CCN(c2nc(OC[C@@H]3C[C@@H](OC(F)F)CN3C)nc3cc(-c4nc(N)ccc4C(F)(F)F)c(Cl)cc23)CC1] | 1-[4-[7-[6-amino-3-(trifluoromethyl)-2-pyridyl]-6-chloro-2-[[(2S,4R)-4-(difluoromethoxy)-1-methyl-pyrrolidin-2-yl]methoxy]quinazolin-4-yl]piperazin-1-yl]prop-2-en-1-one |
| n/a | 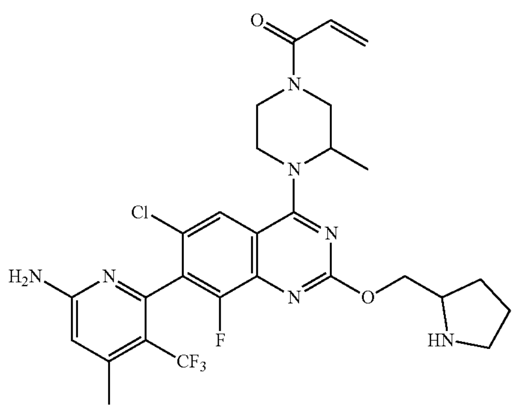 [SMILES: C=CC(=O)N1CCN(c2nc(OCC3CCCN3)nc3c(F)c(-c4nc(N)cc(C)c4C(F)(F)F)c(Cl)cc23)C(C)C1] | 1-(4-(7-(6-amino-4-methyl-3-(trifluoromethyl)pyridin-2-yl)-6-chloro-8-fluoro-2-(pyrrolidin-2-ylmethoxy)quinazolin-4-yl)-3-methylpiperazin-1-yl)prop-2-en-1-one |
| 93 | 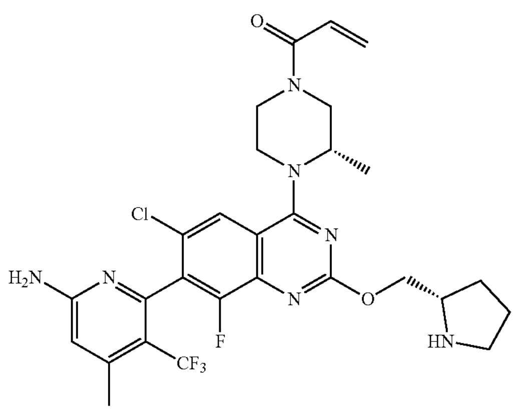 [SMILES: C=CC(=O)N1CCN(c2nc(OC[C@@H]3CCCN3)nc3c(F)c(-c4nc(N)cc(C)c4C(F)(F)F)c(Cl)cc23)[C@@H](C)C1] | 1-((3S)-4-(7-(6-amino-4-methyl-3-(trifluoromethyl)pyridin-2-yl)-6-chloro-8-fluoro-2-(((S)-pyrrolidin-2-yl)methoxy)quinazolin-4-yl)-3-methylpiperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| n/a | | 1-(4-(7-(6-amino-3-(trifluoromethyl)pyridin-2-yl)-6-chloro-2-((1-(2,2-difluoroethyl)pyrrolidin-2-yl)methoxy)quinazolin-4-yl)piperazin-1-yl)prop-2-en-1-one |
| 94 | 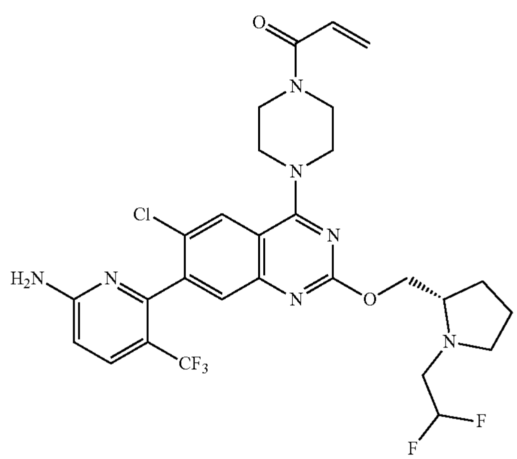 [SMILES: C=CC(=O)N1CCN(c2nc(OC[C@@H]3CCCN3CC(F)F)nc3cc(-c4nc(N)ccc4C(F)(F)F)c(Cl)cc23)CC1] | (S)-1-(4-(7-(6-amino-3-(trifluoromethyl)pyridin-2-yl)-6-chloro-2-((1-(2,2-difluoroethyl)pyrrolidin-2-yl)methoxy)quinazolin-4-yl)piperazin-1-yl)prop-2-en-1-one |
| n/a | | 1-(4-(7-(6-amino-3-(trifluoromethyl)pyridin-2-yl)-6-chloro-2-((4-methoxy-1-(2-methoxyethyl)pyrrolidin-2-yl)methoxy)quinazolin-4-yl)piperazin-1-yl)prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| 95 | 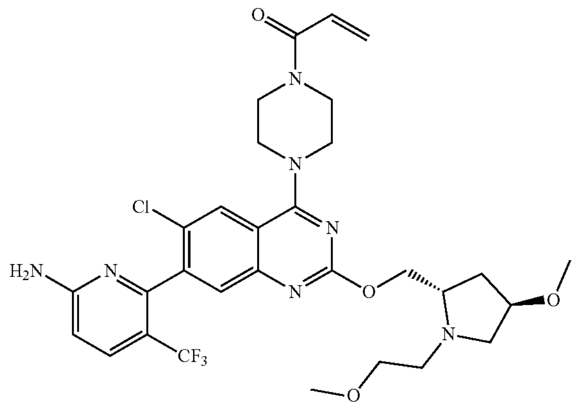 [SMILES: C=CC(=O)N1CCN(c2nc(OC[C@@H]3C[C@@H](OC)CN3CCOC)nc3cc(-c4nc(N)ccc4C(F)(F)F)c(Cl)cc23)CC1] | 1-(4-(7-(6-amino-3-(trifluoromethyl)pyridin-2-yl)-6-chloro-2-(((2S,4R)-4-methoxy-1-(2-methoxyethyl)pyrrolidin-2-yl)methoxy)quinazolin-4-yl)piperazin-1-yl)prop-2-en-1-one |
| n/a | 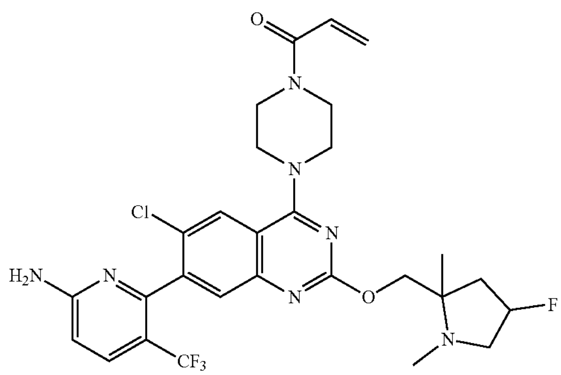 [SMILES: C=CC(=O)N1CCN(c2nc(OCC3(C)CC(F)CN3C)nc3cc(-c4nc(N)ccc4C(F)(F)F)c(Cl)cc23)CC1] | 1-(4-(7-(6-amino-3-(trifluoromethyl)pyridin-2-yl)-6-chloro-2-((4-fluoro-1,2-dimethylpyrrolidin-2-yl)methoxy)quinazolin-4-yl)piperazin-1-yl)prop-2-en-1-one |
| 96 | 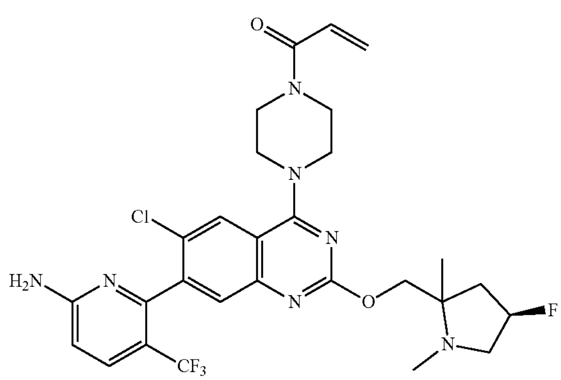 [SMILES: C=CC(=O)N1CCN(c2nc(OCC3(C)C[C@@H](F)CN3C)nc3cc(-c4nc(N)ccc4C(F)(F)F)c(Cl)cc23)CC1] | 1-[4-[7-[6-amino-3-(trifluoromethyl)-2-pyridyl]-6-chloro-2-[[(4R)-4-fluoro-1,2-dimethyl-pyrrolidin-2-yl]methoxy]quinazolin-4-yl]piperazin-1-yl]prop-2-en-1-one |

TABLE 1-continued

Exemplary compounds of the present disclosure. Salts of such compounds are also contemplated. See the Examples section for preparation of such compounds. Compounds that do not have preparation details explicitly described in the Examples may be prepared by modifying the preparation details for other compounds provided herein, using methods generally known in the art.

| Compound # | Structure | Compound Name |
|---|---|---|
| n/a | 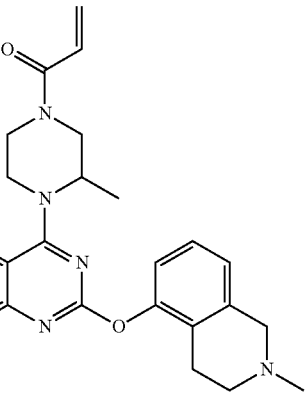 | 1-(4-(7-(6-amino-4-methyl-3-(trifluoromethyl)pyridin-2-yl)-6-chloro-8-fluoro-2-((2-methyl-1,2,3,4-tetrahydroisoquinolin-5-yl)oxy)quinazolin-4-yl)-3-methylpiperazin-1-yl)prop-2-en-1-one |
| 97 | 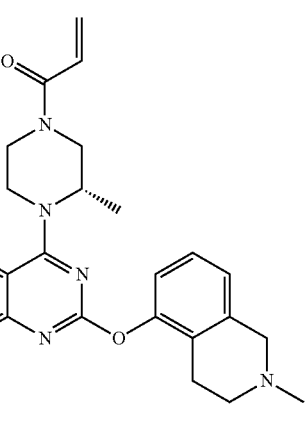 | 1-((S)-4-((R)-7-(6-amino-4-methyl-3-(trifluoromethyl)pyridin-2-yl)-6-chloro-8-fluoro-2-((2-methyl-1,2,3,4-tetrahydroisoquinolin-5-yl)oxy)quinazolin-4-yl)-3-methylpiperazin-1-yl)prop-2-en-1-one | n/a = not applicable

In another embodiment, according to some embodiments of the compound of Formula (I), Formula (II), or Formula (III), or a pharmaceutically acceptable salt thereof:

$R_2$ is selected from the group consisting of H, OH, $NH_2$, halo, $C_{1-6}$ alkyl, $C_{1-6}$ haloalkyl, cyclopropyl, and —NHR, wherein R is selected from the group consisting of linear $C_{1-6}$ alkyl, $C_{1-6}$ alkoxy, $C_{1-6}$ alkanoyl, $C_{1-6}$ hydroxyalkanoyl, $C_{1-6}$ cyanoalkyl, $C_{1-6}$ alkylamino, —($C_{1-6}$ alkylenyl)NH($CH_3$)—($C_{1-6}$ alkylenyl)N($CH_3$)$_2$, and —($C_{1-3}$ alkylenyl)(3-7 membered-heterocyclyl);

$R_3$ and $R_4$ are each independently selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, and $C_{1-6}$ alkylamino;

$R_5$ is selected from the group consisting of H, Cl, Br, I, $NH_2$, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_{3-7}$ cycloalkyl, wherein at least two of $R_2$, $R_3$, $R_4$, and $R_5$ is other than H; or $R_2$ and $R_3$, $R_3$ and $R_4$, or $R_4$ and $R_5$, together with the atoms to which they are each bonded, form a $C_{3-7}$ cycloalkyl, 3 to 7 membered heterocycloalkyl, or $C_{6-14}$ aryl; each of which is optionally substituted with 1 to 4 substituents, wherein each substituent is independently selected from the group consisting of OH, $NH_2$, halo, $C_{1-3}$ alkyl, $C_{1-3}$ haloalkyl, and $C_{1-3}$ haloalkoxy;

X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

Y is selected from the group consisting of -L-$Y_1$ or $Y_1$;

$Y_1$ is selected from the group consisting of H, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$ aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{3-7}$ cycloalkyl substituted with a $C_{1-6}$ dialkylamino, $C_{1-6}$ haloalkoxy, $C_{1-6}$ haloalkyl, 5- to 10-membered heteroaryl, 4- to 10-membered heterocyclyl, 4- to 10-membered heterocyclyl substituted with methyl, hydroxy, and oxo;

each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkyl;

L is selected from the group consisting of a bond, O, S, and $N(L^a)$;

$L^a$ is selected from the group consisting of hydrogen and $C_{1-3}$ alkyl;

U is $C(R_{6a})$;
V is $C(R_{6b})$;
W is $C(R_{6c})$ or N;

each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{1-6}$ haloalkoxy, $C_{1-6}$ haloalkyl, 5- to 10-membered heteroaryl, and 4- to 10-membered heterocyclyl; and n is selected from the group consisting of 0, 1, and 2.

It is to be understood that, according to embodiments of the compound of Formula (I), Formula (II), or Formula (III), or a pharmaceutically acceptable salt thereof, when one of $R_2$ and $R_3$, $R_3$ and $R_4$, or $R_4$ and $R_5$, together with the atoms to which they are each bonded, form a ring, the substituents not forming the ring, are defined as set forth above for Formula (I).

In another aspect, the invention includes a compound of Formula (IV):

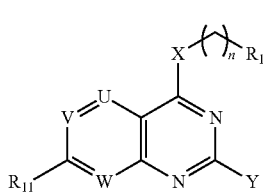

(IV)

or a pharmaceutically acceptable salt thereof;
wherein,
$R_1$ is an electrophilic moiety capable of forming a covalent bond with a cysteine residue at position 12 of a K-Ras G12C mutant protein;

X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

Y is selected from the group consisting of -L-$Y_1$ or $Y_1$;
$Y_1$ is selected from the group consisting of H, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$ aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{3-7}$ cycloalkyl substituted with a $C_{1-6}$ dialkylamino, $C_{1-6}$ haloalkoxy, $C_{1-6}$ haloalkyl, 5- to 10-membered heteroaryl, 4- to 10-membered heterocyclyl, 4- to 10-membered heterocyclyl substituted with methyl, hydroxy, and oxo;

each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkyl;

L is selected from the group consisting of a bond, O, S, and $N(L^a)$;

$L^a$ is selected from the group consisting of hydrogen and $C_{1-3}$ alkyl;

U is $C(R_{6a})$;
V is $C(R_{6b})$;
W is $C(R_{6c})$ or N;

each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{1-6}$ haloalkoxy, $C_{1-6}$ haloalkyl, 5- to 10-membered heteroaryl, and 4- to 10-membered heterocyclyl;

n is selected from the group consisting of 0, 1, and 2; and
$R_{11}$ is selected from the group consisting of:

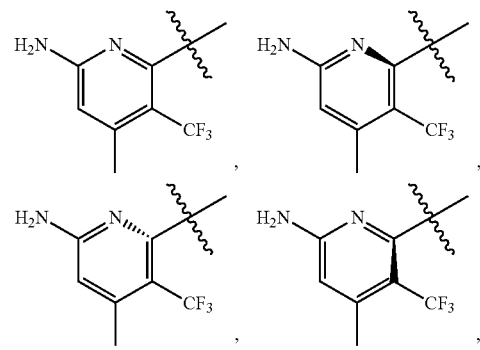

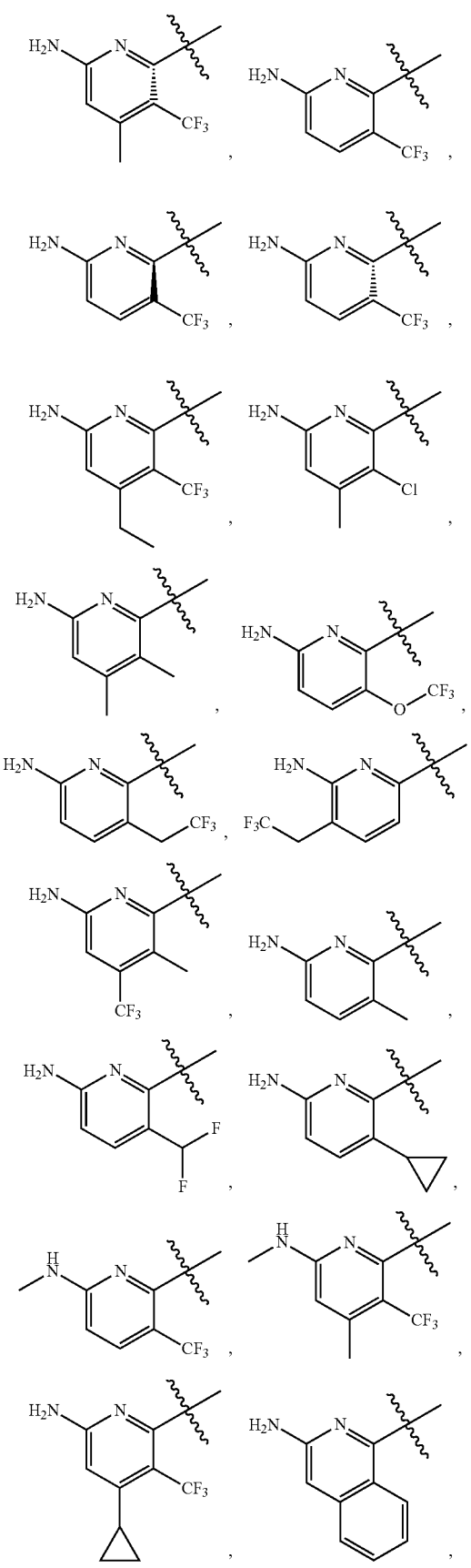

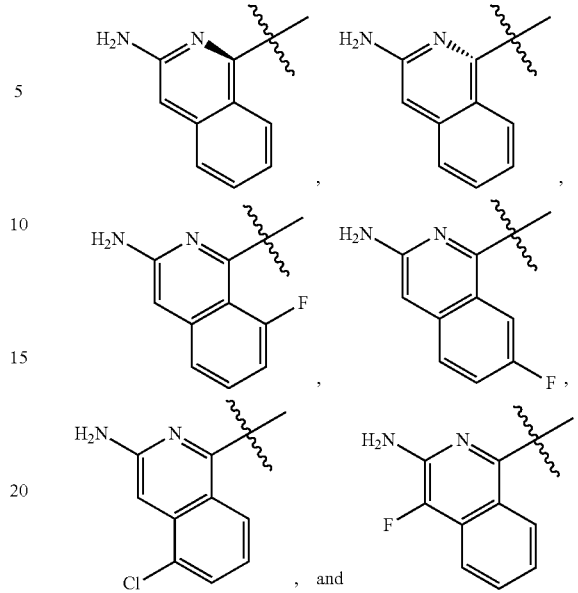

According to some embodiments of the compound of Formula (I), Formula (II), Formula (III), or Formula (IV), or a pharmaceutically acceptable salt thereof, Y is $Y_1$, and $Y_1$ is selected from the group consisting of H, $C_{1-6}$ alkyl, and $C_{1-6}$ haloalkyl.

According to some embodiments of the compound of Formula (I), Formula (II), Formula (III), or Formula (IV), or a pharmaceutically acceptable salt thereof, $Y_1$ is H.

According to some embodiments of the compound of Formula (I), Formula (II), Formula (III), or Formula (IV), or a pharmaceutically acceptable salt thereof, Y is -L-$Y_1$; L is selected form the group consisting of O and N($L^a$); $L^a$ is H; and $Y_1$ is selected from the group consisting of $C_{1-6}$ alkyl, $C_{1-6}$ alkyl substituted with a methylheterocyclyl substituent, and $C_{1-6}$ alkyl substituted with a $C_{1-6}$ dialkylamino substituent.

According to some embodiments of the compound of Formula (I), Formula (II), Formula (III), or Formula (IV), or a pharmaceutically acceptable salt thereof, $Y_1$ is a monocyclic aryl or a monocyclic heteroaryl.

According to some embodiments of the compound of Formula (I), Formula (II), Formula (III), or Formula (IV), or a pharmaceutically acceptable salt thereof, Y is -L-$Y_1$; L is selected form the group consisting of O and N($L^a$); $L^a$ is H; $Y_1$ is selected from the group consisting of $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{3-7}$ cycloalkyl substituted with a $C_{1-6}$ dialkylamino, and 4- to 10-membered heterocyclyl substituted with methyl; and each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkoxy.

According to some embodiments of the compound of Formula (I), Formula (II), Formula (III), or Formula (IV), or a pharmaceutically acceptable salt thereof, Y is -L-$Y_1$; L is N($L^a$); $L^a$ is H; and $Y_1$ is $C_{1-6}$ alkyl or $C_{1-6}$ alkyl substituted with a $C_{1-6}$ dialkylamino substituent.

According to some embodiments of the compound of Formula (I), Formula (II), Formula (III), or Formula (IV), or a pharmaceutically acceptable salt thereof, Y is -L-$Y_1$; L is O; $Y_1$ is selected from the group consisting of $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{3-7}$ cycloalkyl substituted with a $C_{1-6}$ dialkylamino, and 4- to 10-membered heterocyclyl substituted with methyl; and each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkoxy.

According to some embodiments of the compound of Formula (I), Formula (II), Formula (III), or Formula (IV), or a pharmaceutically acceptable salt thereof, Y is -L-$Y_1$; L is selected form the group consisting of O and N($L^a$); $L^a$ is H; $Y_1$ is $C_{1-6}$ alkyl substituted with a 4- to 10-membered methylheterocyclyl substituent.

According to some embodiments of the compound of Formula (I), Formula (II), Formula (III), or Formula (IV), or a pharmaceutically acceptable salt thereof, Y is selected from the group consisting of:

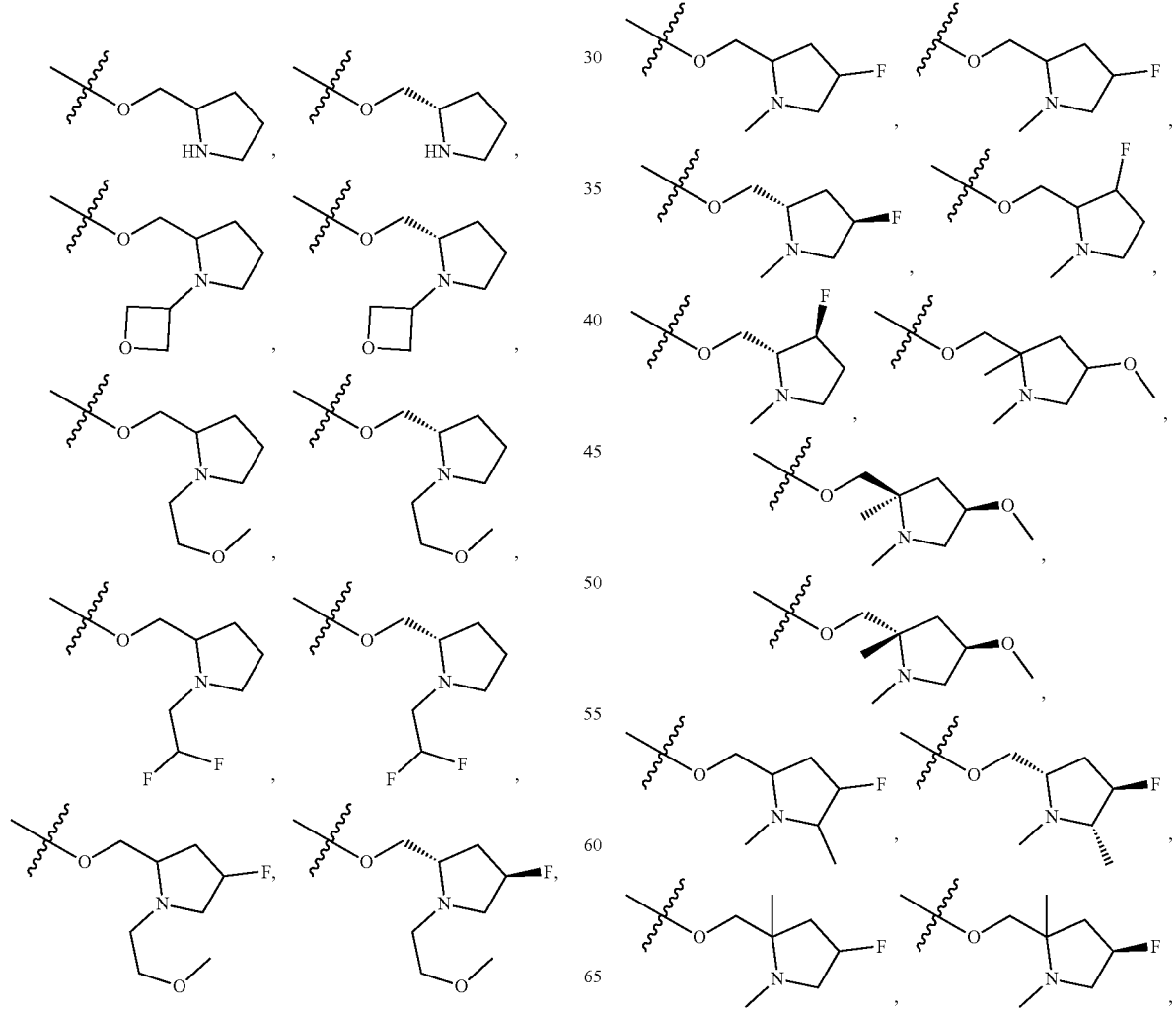

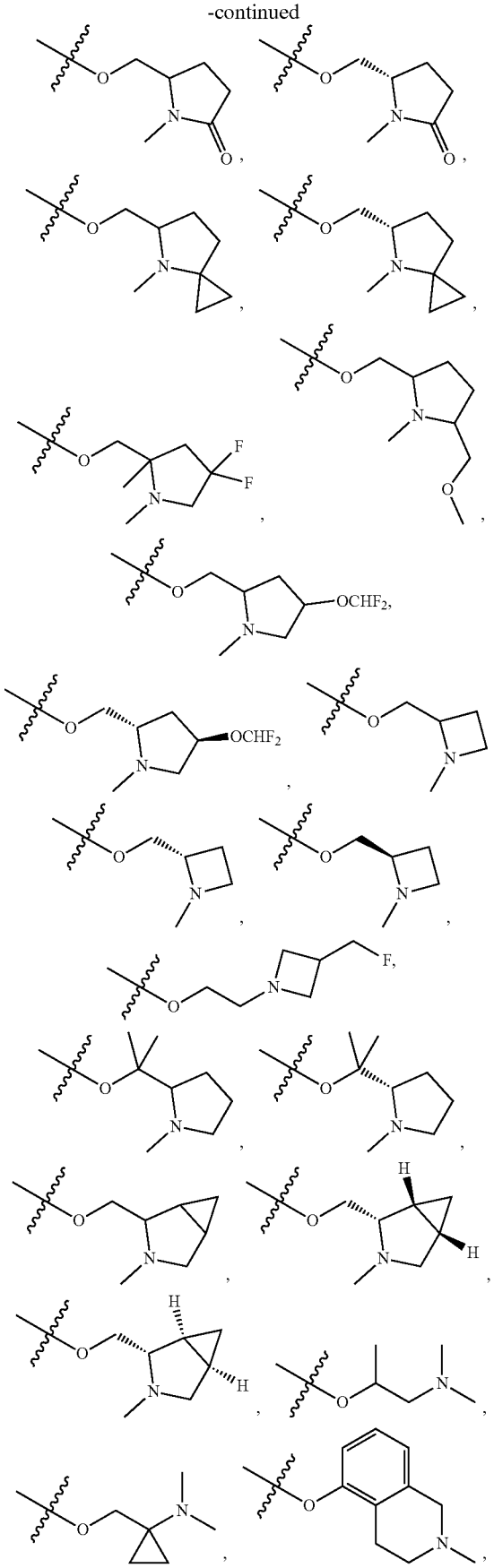

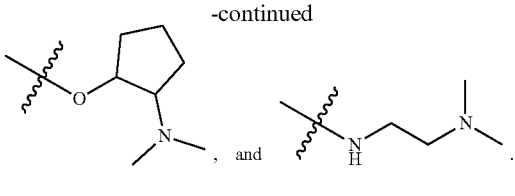

According to some embodiments of the compound of Formula (I), Formula (II), Formula (III), or Formula (IV), or a pharmaceutically acceptable salt thereof, Y is:

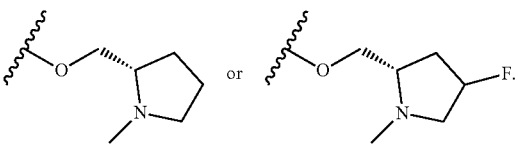

In one embodiment of the compound of Formula (I), Formula (II), Formula (III), or Formula (IV), or a pharmaceutically acceptable salt thereof, Y is

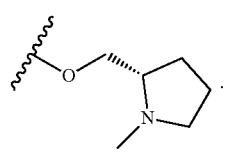 [SMILES: *OC[C@@H]1CCCN1C]

In another embodiment of the compound of Formula (I), Formula (II), Formula (III), or Formula (IV), or a pharmaceutically acceptable salt thereof, Y is

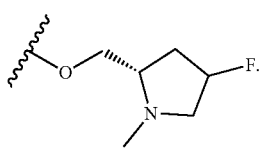 [SMILES: *OC[C@@H]1CC(F)CN1C]

In still another embodiment of the compound of Formula (I), Formula (II), Formula (III), or Formula (IV), or a pharmaceutically acceptable salt thereof, Y is

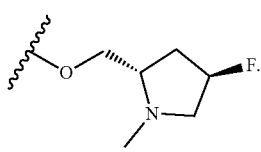 [SMILES: *OC[C@@H]1C[C@@H](F)CN1C]

In still another embodiment of the compound of Formula (I), Formula (II), Formula (III), or Formula (IV), or a pharmaceutically acceptable salt thereof, Y is

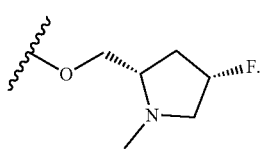 [SMILES: *OC[C@@H]1C[C@H](F)CN1C]

According to some embodiments of the compound of Formula (I), Formula (II), Formula (III), or Formula (IV), or a pharmaceutically acceptable salt thereof, wherein $R_{6a}$ is H.

According to some embodiments of the compound of Formula (I), Formula (II), Formula (III), or Formula (IV), or a pharmaceutically acceptable salt thereof, $R_{6b}$ is selected from the group consisting of H, halo, $C_{1-6}$ alkoxy, $C_{1-6}$ alkylsulfonyl, $C_{1-6}$ haloalkyl, $C_{3-7}$ cycloalkyl, $C_{1-6}$ haloalkylthio, and 4- to 10-membered heterocyclyl.

According to some embodiments of the compound of Formula (I), Formula (II), Formula (III), or Formula (IV), or a pharmaceutically acceptable salt thereof, $R_{6b}$ is selected from the group consisting of H, halo, $C_{1-3}$ haloalkyl.

According to some embodiments of the compound of Formula (I), Formula (II), Formula (III), or Formula (IV), or a pharmaceutically acceptable salt thereof, W is $C(R_{6c})$, and $R_{6c}$ is selected from the group consisting of H and halo.

According to some embodiments of the compound of Formula (I), Formula (II), Formula (III), or Formula (IV), or a pharmaceutically acceptable salt thereof, W is $C(R_{6c})$, and $R_{6c}$ is halo.

According to some embodiments of the compound of Formula (I), Formula (II), Formula (III), or Formula (IV), or a pharmaceutically acceptable salt thereof, $R_{6a}$, $R_{6b}$, and $R_{6c}$ are independently selected from the group consisting of a monocyclic aryl and a monocyclic heteroaryl.

According to some embodiments of the compound of Formula (I), Formula (II), Formula (III), or Formula (IV), or a pharmaceutically acceptable salt thereof, X is $C_{3-7}$ cycloalkyl, 4- to 7-membered heterocyclyl, or 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ haloalkyl, and 4- to 7-membered heterocyclyl. In one embodiment of the compound of Formula (I), Formula (II), Formula (III), or Formula (IV), or a pharmaceutically acceptable salt thereof, X is $C_{3-7}$ cycloalkyl or 4- to 7-membered heterocyclyl, each of which is optionally substituted with 1 to 4 substituents, wherein each substituent is independently selected from the group consisting of OH, $NH_2$, halo, cyano, $C_{1-6}$ alkyl, and $C_{1-6}$ haloalkyl. In another embodiment of the compound of Formula (I), Formula (II), Formula (III), or Formula (IV), or a pharmaceutically acceptable salt thereof, X is a piperazinyl or azetidinyl moiety each of which is optionally substituted with 1 to 4 substituents, wherein each substituent is independently selected from the group consisting of OH, $NH_2$, halo, cyano, $C_{1-6}$ alkyl, and $C_{1-6}$ haloalkyl. In still another embodiment of the compound of Formula (I), Formula (II), Formula (III), or Formula (IV), or a pharmaceutically acceptable salt thereof, X is a piperazinyl moiety optionally substituted with 1 to 4 substituents, wherein each substituent is independently selected from the group consisting of halo, cyano, $C_{1-3}$ alkyl, and $C_{1-3}$ haloalkyl.

According to some embodiments of the compound of Formula (I), Formula (II), Formula (III), or Formula (IV), or a pharmaceutically acceptable salt thereof, X is a 4- to 7-membered heterocyclyl.

According to some embodiments of the compound of Formula (I), Formula (II), Formula (III), or Formula (IV), or a pharmaceutically acceptable salt thereof, X is a 4- to 7-membered heterocyclyl substituted with 1 to 4 substituents, wherein each substituent is independently selected from the group consisting of cyano, $C_{1-6}$ alkyl, $C_{1-6}$ cyanoalkyl, and $C_{1-6}$ haloalkyl.

According to some embodiments of the compound of Formula (I), Formula (II), Formula (III), or Formula (IV), or a pharmaceutically acceptable salt thereof, X is selected from the group consisting of:

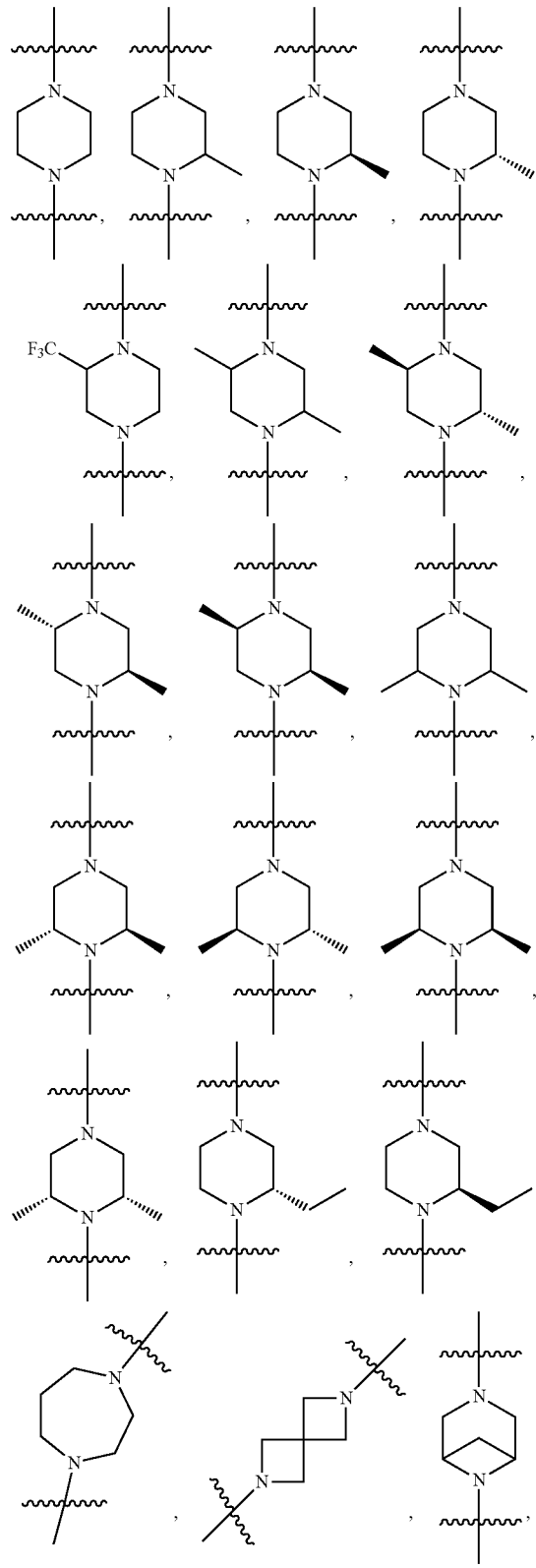

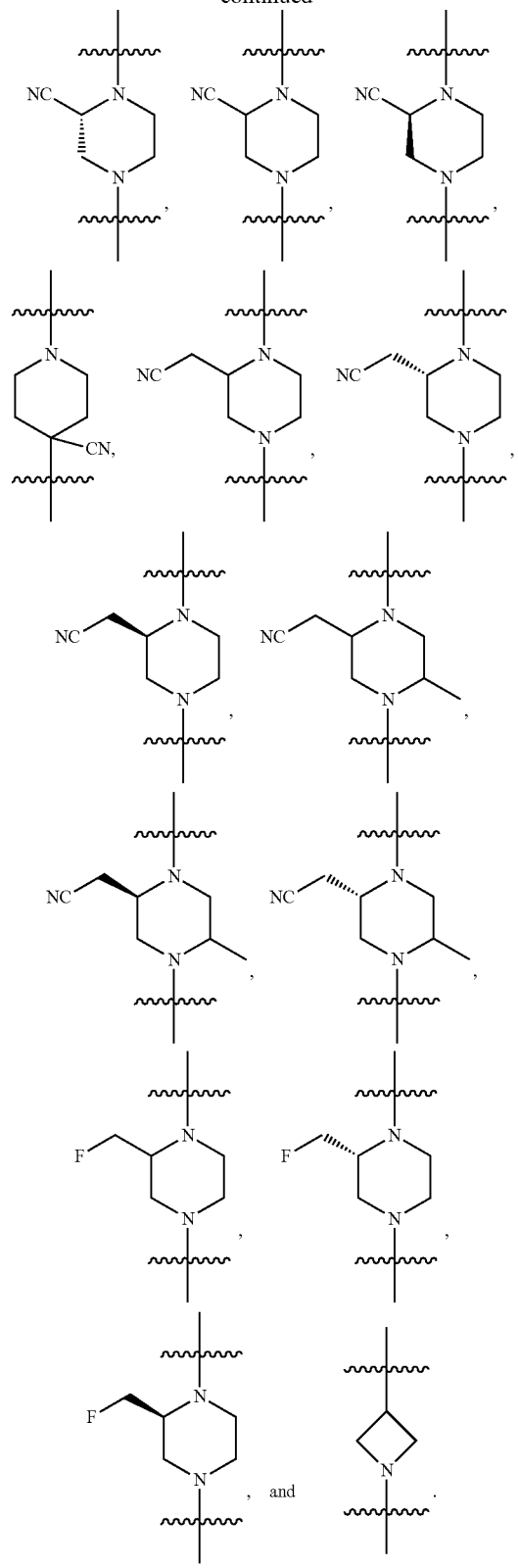

According to some embodiments of the compound of Formula (I), Formula (II), Formula (III), or Formula (IV), or a pharmaceutically acceptable salt thereof, X is selected from the group consisting of:

According to some embodiments of the compound of Formula (I), Formula (II), Formula (III), or Formula (IV), or a pharmaceutically acceptable salt thereof, X is selected from the group consisting of:

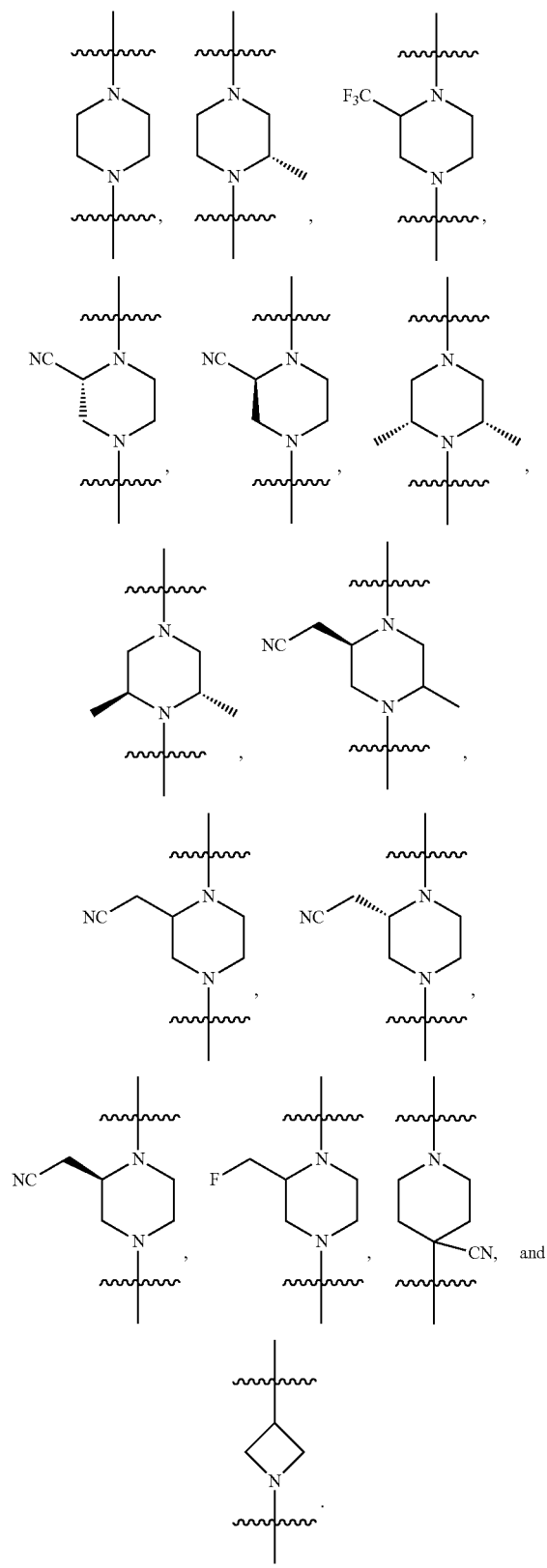

According to some embodiments of the compound of Formula (I), Formula (II), Formula (III), or Formula (IV), or a pharmaceutically acceptable salt thereof, X is

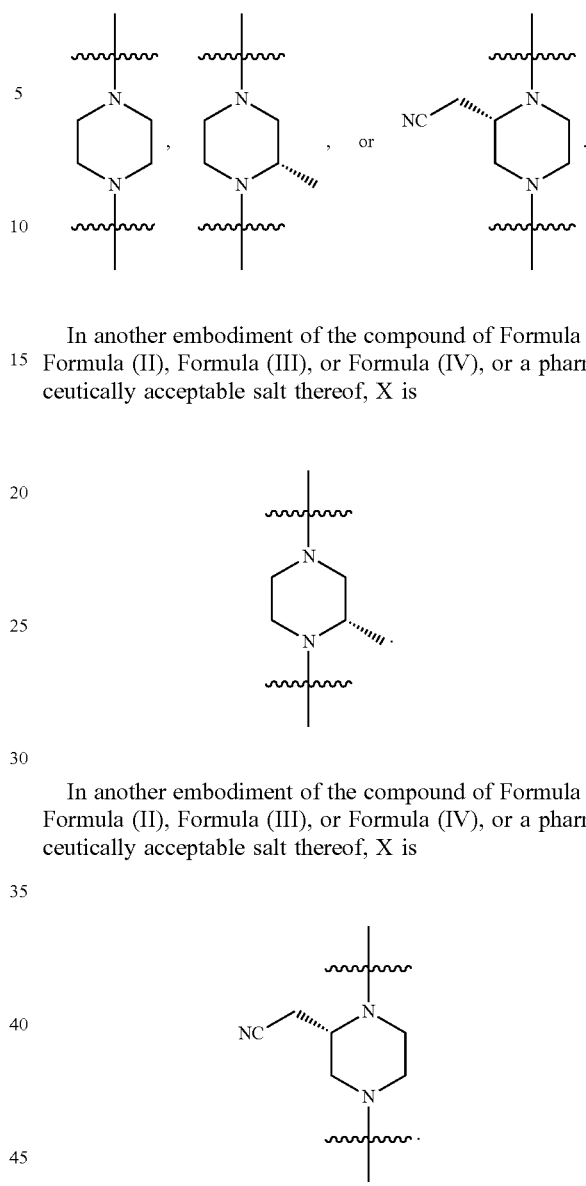

In another embodiment of the compound of Formula (I), Formula (II), Formula (III), or Formula (IV), or a pharmaceutically acceptable salt thereof, X is In another embodiment of the compound of Formula (I), Formula (II), Formula (III), or Formula (IV), or a pharmaceutically acceptable salt thereof, X is According to some embodiments of the compound of Formula (IV), or a pharmaceutically acceptable salt thereof, $R_{11}$ is

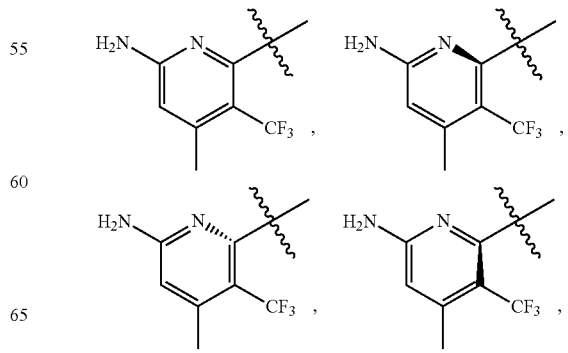

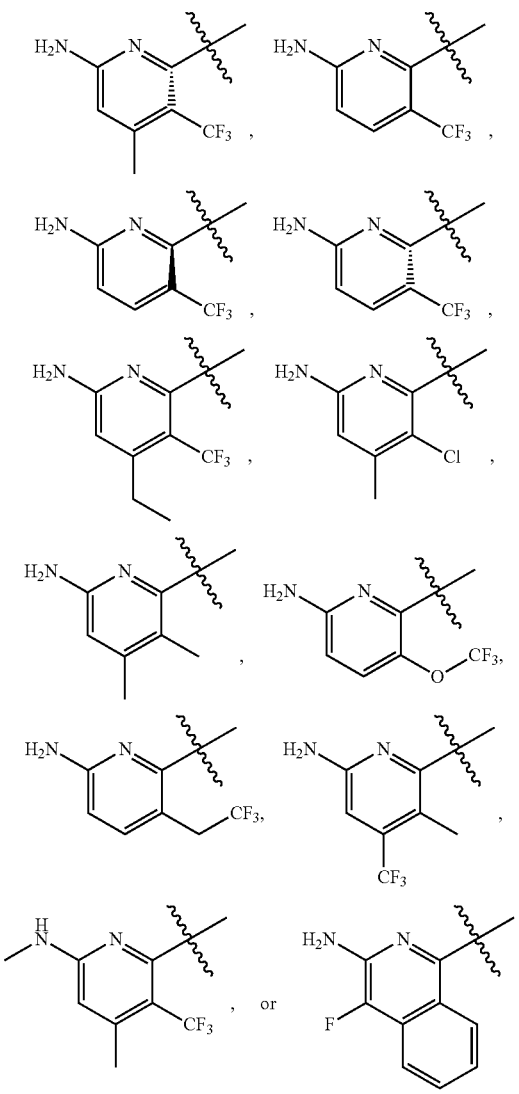

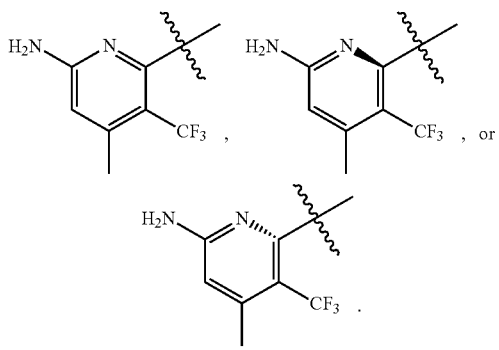

According to some embodiments of the compound of Formula (IV), or a pharmaceutically acceptable salt thereof, $R_{11}$ is:

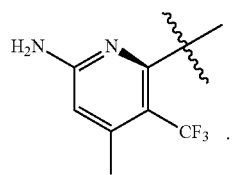

According to some embodiments of the compound of Formula (I), Formula (II), Formula (III), or Formula (IV), or a pharmaceutically acceptable salt thereof, n is 0.

According to some embodiments of the compound of Formula (I) or Formula (IV), or a pharmaceutically acceptable salt thereof, $R_1$ is selected from the group consisting of:

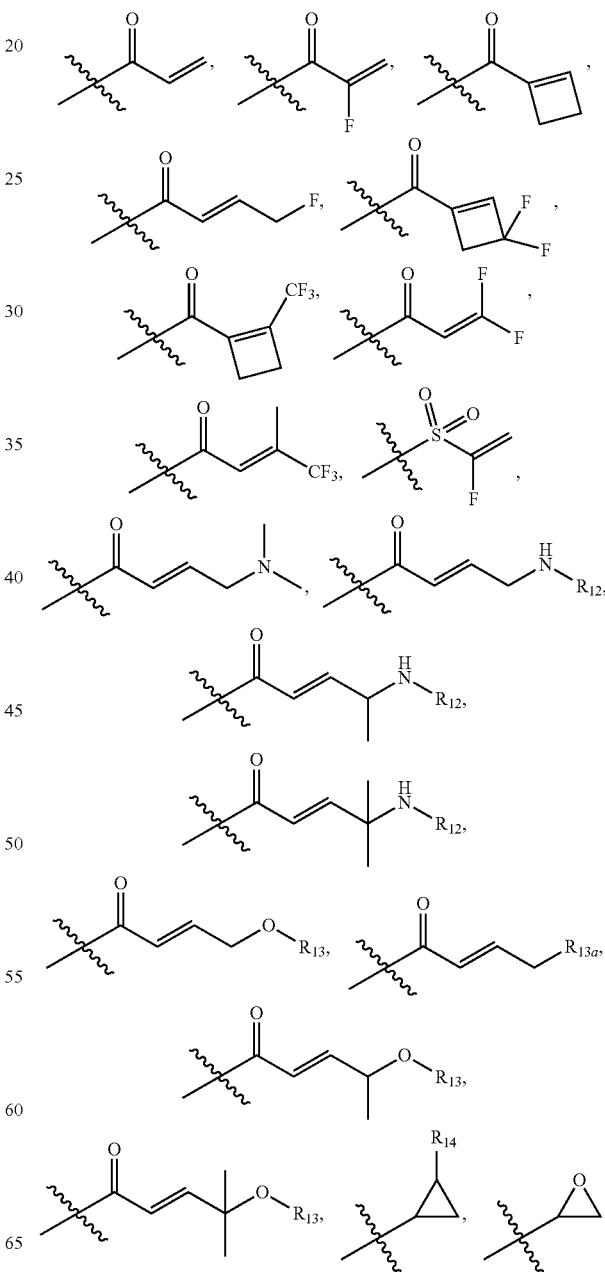

-continued

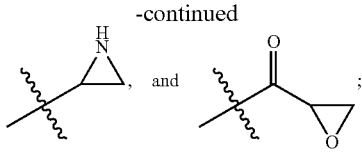 and 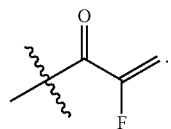;

wherein:

$R_{12}$ is selected from the group consisting of $C_{1-6}$ alkanoyl, $C_{1-6}$ alkyl, and $C_{1-6}$ alkylsulfonyl;

$R_{13}$ is selected from the group consisting of H, $C_{1-6}$ alkyl and $C_{1-6}$ haloalkyl;

$R_{13a}$ is halo; and $R_{14}$ is halo.

According to some embodiments of the compound of Formula (I) or Formula (IV), or a pharmaceutically acceptable salt thereof, $R_1$ is selected from the group consisting of:

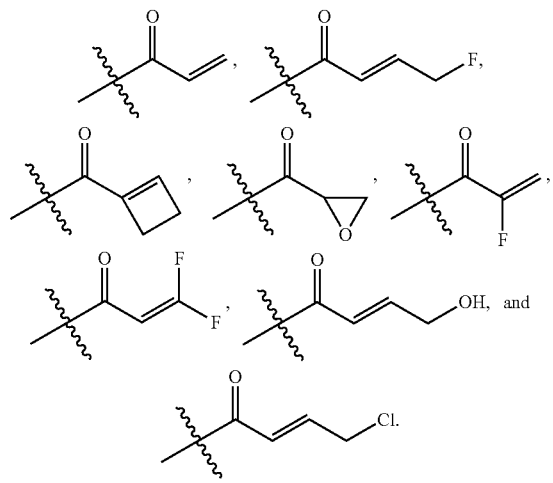

According to some embodiments of the compound of Formula (I) or Formula (IV), or a pharmaceutically acceptable salt thereof, $R_1$ is

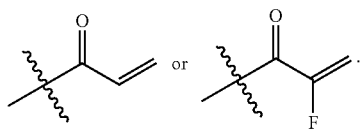

According to some embodiments of the compound of Formula (I) or Formula (IV), or a pharmaceutically acceptable salt thereof, $R_1$ is

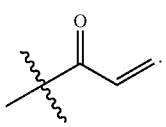 [SMILES: *C(=O)C=C]

According to some embodiments of the compound of Formula (I) or Formula (IV), or a pharmaceutically acceptable salt thereof, $R_1$ is

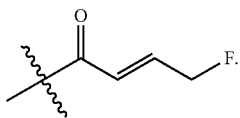 [SMILES: *C(=O)/C=C/CF]

According to some embodiments of the compound of Formula (I) or Formula (IV), or a pharmaceutically acceptable salt thereof, $R_1$ According to some embodiments of the compound of Formula (II), or a pharmaceutically acceptable salt thereof, $R_7$ is selected from the group consisting of H, cyano, and halo; and $R_8$ and $R_9$ are each independently selected from the group consisting of H, $C_{1-6}$ alkyl, $C_{1-6}$ haloalkyl, $C_{1-6}$ hydroxyalkyl, cyano, and halo; wherein $C_{1-6}$ alkyl is optionally substituted with one substituent selected from the group consisting of: methanesulfonyl (mesyl), p-toluenesulfonyl (tosyl), an alkyl or aryl sulfonate leaving group, $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy.

According to some embodiments of the compound of Formula (II), or a pharmaceutically acceptable salt thereof, $R_7$ and $R_8$ together form a triple bond between the carbons to which they are attached, or $R_7$ and $R_8$ together with the carbons to which they are each bonded form a $C_{3-7}$ cycloalkenyl optionally substituted with one or two halo substituents; and $R_9$ is selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy.

According to some embodiments of the compound of Formula (II), or a pharmaceutically acceptable salt thereof, $R_7$, $R_8$, and $R_9$ are each H.

According to some embodiments of the compound of Formula (III), or a pharmaceutically acceptable salt thereof, $R_{10}$ is —C(O)—$R_{10a}$, and $R_{10a}$ is oxiranyl.

According to some embodiments of the compound of Formula (III), or a pharmaceutically acceptable salt thereof, $R_{10}$ is —C(O)—$R_{10a}$, and $R_{10a}$ is aziridinyl.

According to some embodiments of the compound of Formula (I), the compound has a formula selected from the group consisting of:

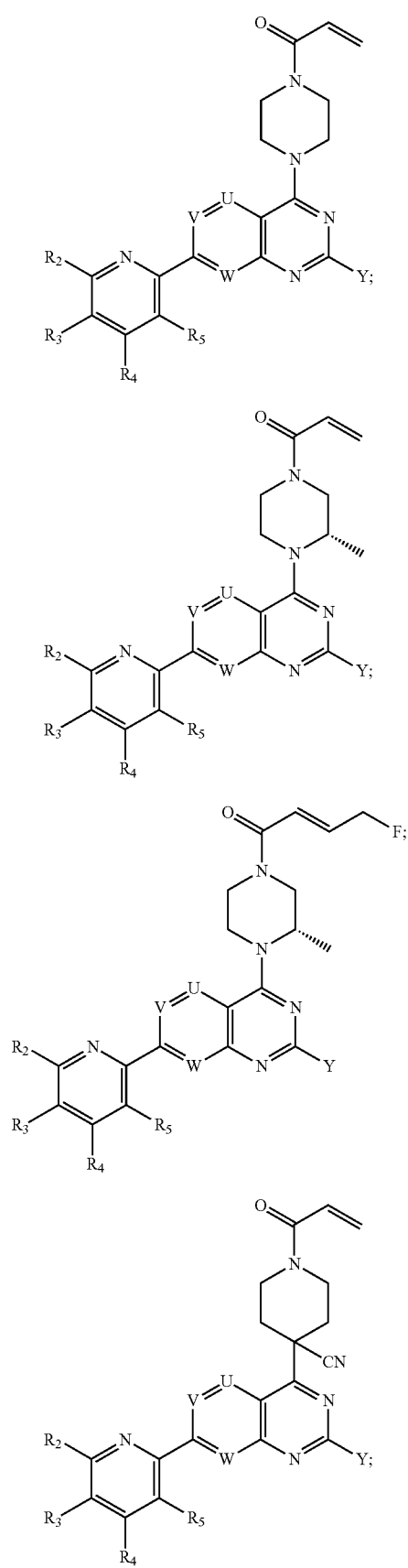
(Ia)
(Ib)
(Ic)
(Id)
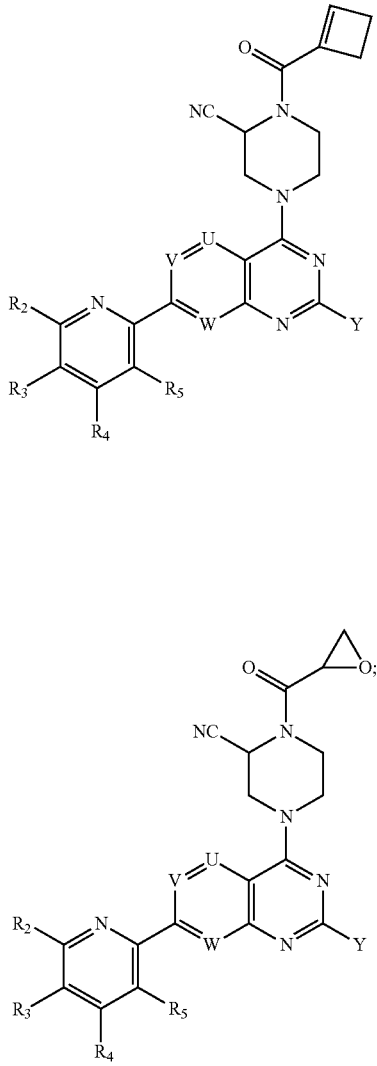
(Ie)
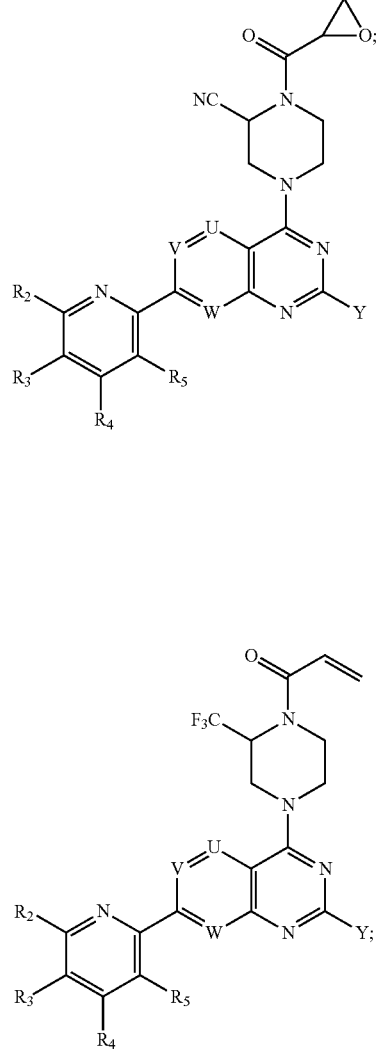
(If)
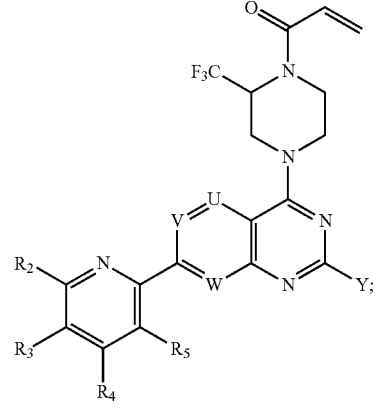
(Ig)

(Ih)
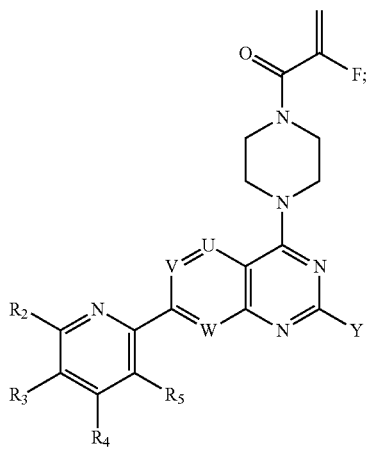

(Ii)
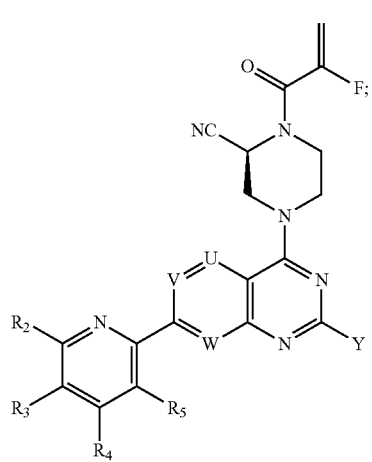

(Ij)
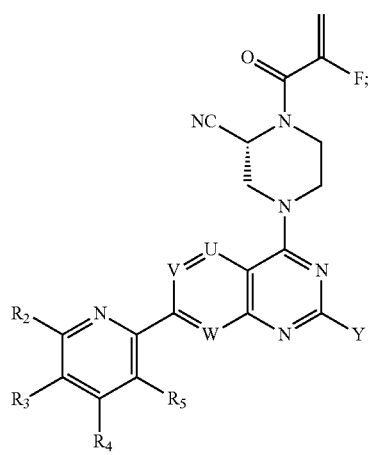

(Ik)
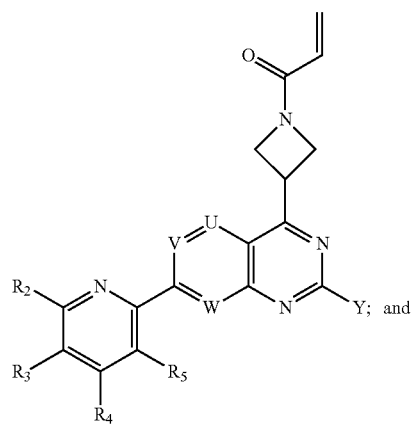

(Il)
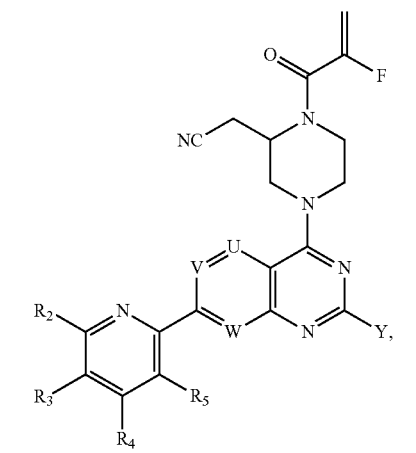

or a pharmaceutically acceptable salt thereof.

In one embodiment of the compound of Formula (Ia), (Ib), (Ic), (Id), (Ie), (If), (Ig), (Ih), (Ij), (Ik), or (Il), or a pharmaceutically acceptable salt thereof, Y is

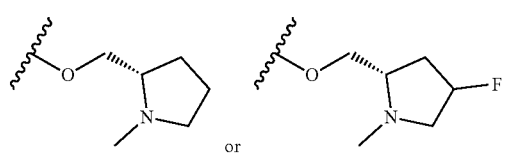

In one embodiment of the compound of Formula (Ia), (Ib), (Ic), (Id), (Ie), (If), (Ig), (Ih), (Ij), (Ik), or (Il), or a pharmaceutically acceptable salt thereof, Y is

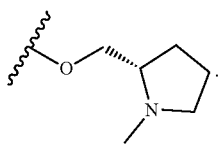 [SMILES: *OC[C@@H]1CCCN1C ; "."]

In one embodiment of the compound of Formula (Ia), (Ib), (Ic), (Id), (Ie), (If), (Ig), (Ih), (Ij), (Ik), or (Il), or a pharmaceutically acceptable salt thereof, Y is

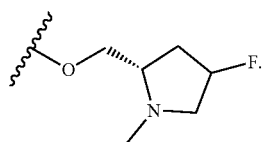

In one embodiment of the compound of Formula (Ia), (Ib), (Ic), (Id), (Ie), (If), (Ig), (Ih), (Ij), (Ik), or (Il), or a pharmaceutically acceptable salt thereof, Y is

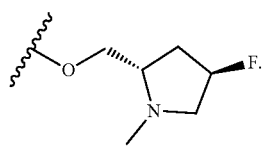 [SMILES: *OC[C@@H]1C[C@@H](F)CN1C]

In still another embodiment of the compound of Formula (Ia), (Ib), (Ic), (Id), (Ie), (If), (Ig), (Ih), (Ij), (Ik), or (Il), or a pharmaceutically acceptable salt thereof, Y is

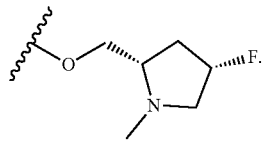 [SMILES: *OC[C@@H]1C[C@H](F)CN1C]

According to some embodiments of the compound of Formula (I), the compound has a formula (Ia) or (Ic), or a pharmaceutically acceptable salt thereof.

According to some embodiments of the compound of Formula (I), the compound has a formula (Ib) or (Il), or a pharmaceutically acceptable salt thereof.

According to some embodiments of the compound of Formula (I), the compound has Formula (Ia), or a pharmaceutically acceptable salt thereof.

According to some embodiments of the compound of Formula (I), the compound has Formula (Ib), or a pharmaceutically acceptable salt thereof.

According to some embodiments of the compound of Formula (I), the compound has Formula (Ic), or a pharmaceutically acceptable salt thereof.

According to some embodiments of the compound of Formula (I), the compound has Formula (Il), or a pharmaceutically acceptable salt thereof.

According to some embodiments of the compound of Formula (IV), or a pharmaceutically acceptable salt thereof, the compound has a formula selected from the group consisting of:

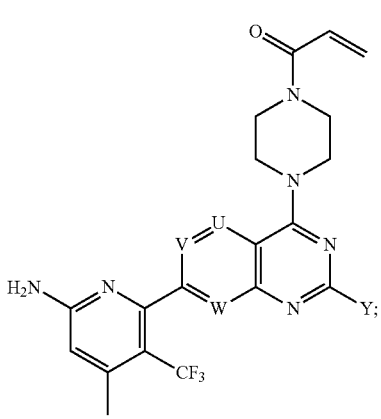

(IVa)

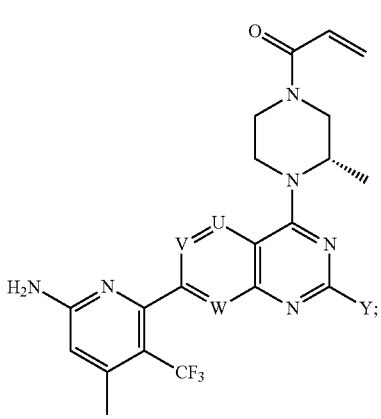

(IVb)

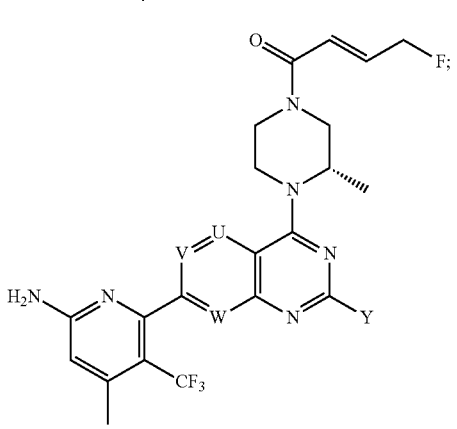

(IVc)

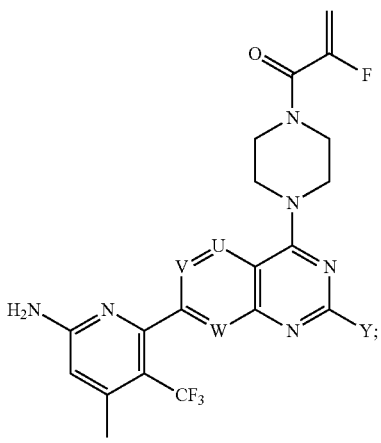

(IVd)

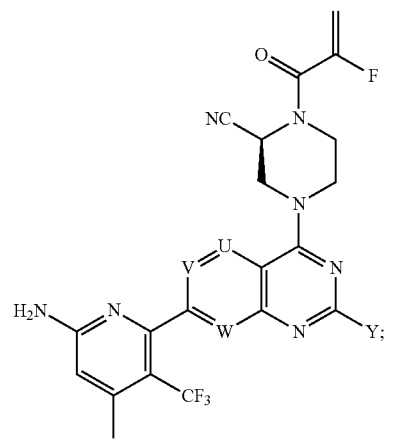
(IVe)

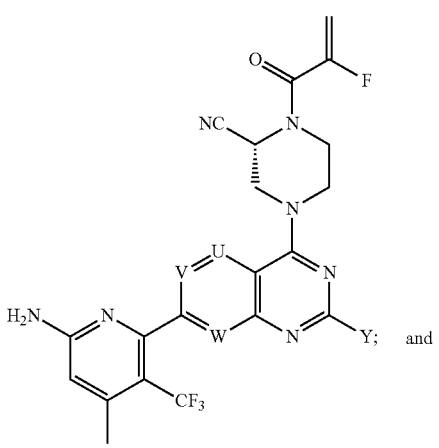
(IVf) and

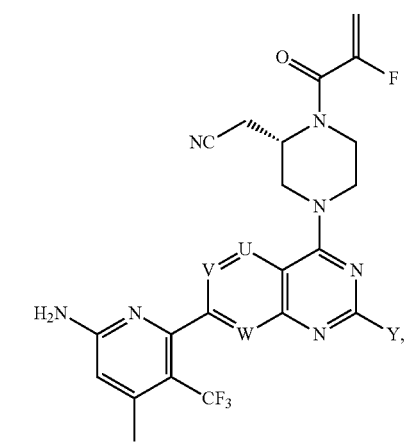
(IVg)

or a pharmaceutically acceptable salt thereof.

According to some embodiments of the compound of Formula (IV), the compound comprises a compound of formula (IVa), (IVb), (IVd), or (IVg), or a pharmaceutically acceptable salt thereof. According to some embodiments of the compound of Formula (IV), the compound comprises a compound of formula (IVa) or (IVb), or a pharmaceutically acceptable salt thereof. According to some embodiments of the compound of Formula (IV), the compound comprises a compound of formula (IVd) or (IVg), or a pharmaceutically acceptable salt thereof.

In one embodiment of the compound of Formula (I), (II), (III), or (IV), the compound is a compound or pharmaceutically acceptable salt thereof as set forth in Table 1 herein.

In another embodiment of the compound of Formula (I), (II), (III), or (IV), the compound is a compound corresponding to Compound 9, Compound 17a, Compound 17b, Compound 18a, Compound 18b, Compound 19, Compound 44, Compound 83a, Compound 83b, Compound 83c, Compound 83d, or Compound 69, or a pharmaceutically acceptable salt thereof.

In one embodiment, the compound is Compound 9. In one embodiment, the compound is Compound 17a. In one embodiment, the compound is Compound 17b. In one embodiment, the compound is Compound 18a. In one embodiment, the compound is Compound 18b. In one embodiment, the compound is Compound 19. In one embodiment, the compound is Compound 83a. In one embodiment, the compound is Compound 83b. In one embodiment, the compound is Compound 83c. In one embodiment, the compound is Compound 83d. In one embodiment, the compound is Compound 69.

According to some embodiments of Formula (I), the compound is selected from the group consisting of Compounds 1, 5, 7-10, 13-15, 17a, 17b, 18a, 18b, 19-33, 35, 40-41, 43-45, 46a, 46b, 47-58, 59a, 59b, 60-61, 62a, 62b, 63a, 63b, 64a, 64b, 65, 66, 67a, 67b, 68a, 68b, 69-74, 75a, 75b, 76, 77, 78a, 78b, 79a, 79b, 80, 81a, 81b, 82a, 82b, 83a, 83b, 83c, 83d, 84a, 84b, and 85-97 of Table 1, or a pharmaceutically acceptable salt thereof. According to other embodiments of Formula (I), the compound is selected from the group consisting of compounds 1, 5, 7-10, 13-15, 17a, 17b, 18a, 18b, 19-33, 35, 40-41, 43-45, 46a, 46b, and 47-54 of Table 1, or a pharmaceutically acceptable salt thereof. According to another embodiment of Formula (I), the compound is selected from the group consisting of compounds 55-58, 59a, 59b, 60-61, 62a, 62b, 63a, 63b, 64a, 64b, 65, 66, 67a, 67b, 68a, 68b, 69-74, 75a, 75b, 76, 77, 78a, 78b, 79a, 79b, 80, 81a, 81b, 82a, 82b, 83a, 83b, 83c, 83d, 84a, 84b, and 85-97 of Table 1, or a pharmaceutically acceptable salt thereof.

The compounds of the invention (e.g., compounds of Formula (I), (II), (III), or (IV)), or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. Embodiments thus include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

Embodiments of the present invention include all manner of rotamers and conformationally restricted states of a compound of the invention. Atropisomers, which are stereoisomers arising because of hindered rotation about a single bond, where energy differences due to steric strain or other contributors create a barrier to rotation that is high enough to allow for isolation of individual conformers, are also included. As an example, certain compounds of the invention may exist as mixtures of atropisomers or purified or enriched for the presence of one atropisomer.

In some embodiments, the compound of Formula (I) is a mixture of atropisomers. In other embodiments, the compound of Formula (I) is a substantially purified atropisomer. In some embodiments, the compound of Formula (I) is a substantially purified R-atropisomer. In some other embodiments, the compound of Formula (I) is a substantially purified R-atropisomer.

Synthesis of Ras Inhibitors

Compounds of the present disclosure can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, vol. 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds.) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, vol. 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained herein.

For illustrative purposes, reaction Schemes below provide routes for synthesizing the compounds of the invention as well as key intermediates. For a more detailed description of the individual reaction steps, see the Examples section below. Those skilled in the art will appreciate that other synthetic routes may be used. Although some specific starting materials and reagents are depicted in the Schemes and discussed below, other starting materials and reagents can be substituted to provide a variety of derivatives or reaction conditions. In addition, many of the compounds prepared by the methods described below can be further modified in light of this disclosure using conventional chemistry well known to those skilled in the art.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, or, about 20° C.

Some compounds in following schemes are depicted with generalized substituents; however, one skilled in the art will immediately appreciate that the nature of the substituents can varied to afford the various compounds contemplated in this invention. Moreover, the reaction conditions are exemplary and alternative conditions are well known. The reaction sequences in the following examples are not meant to limit the scope of the invention as set forth in the claims.

Persons skilled in the art will recognize that the chemical reactions described may be readily adapted to prepare other compounds of the present invention. For example, the synthesis of non-exemplified compounds according to the invention may be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

Methods of Treatment with and Uses of Ras Inhibitors

Compounds of the present disclosure are useful as Ras inhibitors. In one aspect, the compounds of the present disclosure are useful as K-Ras inhibitors. In another aspect, the compounds of the present disclosure are useful as N-Ras inhibitors. In another aspect, the compounds of the present disclosure are useful as H-Ras inhibitors. Accordingly, in one embodiment is provided a method of contacting a cell, such as an ex vivo cell, with a compound of the present invention, or a pharmaceutically acceptable salt thereof, to inhibit Ras activity (e.g., K-Ras, H-Ras, and/or N-Ras activity) in the cell. It is understood that the therapeutic methods described herein can further include in certain embodiments, determination of the presence or absence of a G12 Ras mutation prior to administration of a compound or pharmaceutically acceptable salt thereof described herein.

Further provided is a method of preventing, treating, or lessening the severity of a disease or condition responsive to the inhibition of Ras (e.g., K-Ras, H-Ras, and/or N-Ras) in a patient, comprising administering to the patient a therapeutically effective amount of a compound of the present invention, or a pharmaceutically acceptable salt thereof.

In one aspect, the present disclosure is directed to a method of preventing, treating, or lessening the severity of a disease or condition responsive to the inhibition of K-Ras in a patient, comprising administering to the patient a therapeutically effective amount of a compound of the present invention, or a pharmaceutically acceptable salt thereof.

In one aspect, the present disclosure is directed to a method of preventing, treating, or lessening the severity of a disease or condition responsive to the inhibition of H-Ras in a patient, comprising administering to the patient a therapeutically effective amount of a compound of the present invention, or a pharmaceutically acceptable salt thereof.

In one aspect, the present disclosure is directed to a method of preventing, treating, or lessening the severity of a disease or condition responsive to the inhibition of N-Ras in a patient, comprising administering to the patient a therapeutically effective amount of a compound of the present invention, or a pharmaceutically acceptable salt thereof.

Also provided is a method for treating cancer in a patient, comprising administering to the patient a therapeutically effective amount of a compound of the present invention, or a pharmaceutically acceptable salt thereof.

Also provided is a method of inhibiting Ras (e.g., K-Ras, H-Ras, and/or N-Ras) in a patient in need of therapy, comprising administering to the patient a therapeutically effective amount of a compound of the present invention, or a pharmaceutically acceptable salt thereof.

In one aspect, the present disclosure is directed to a method of inhibiting K-Ras in a patient in need of therapy, comprising administering to the patient a therapeutically effective amount of a compound of the present invention, or a pharmaceutically acceptable salt thereof.

In one aspect, the present disclosure is directed to a method of inhibiting H-Ras in a patient in need of therapy, comprising administering to the patient a therapeutically effective amount of a compound of the present invention, or a pharmaceutically acceptable salt thereof.

In one aspect, the present disclosure is directed to a method of inhibiting N-Ras in a patient in need of therapy, comprising administering to the patient a therapeutically effective amount of a compound of the present invention, or a pharmaceutically acceptable salt thereof.

Also provided is a pharmaceutical composition comprising a therapeutically effective amount of a compound of the present invention, or a pharmaceutically acceptable salt thereof, and a pharmaceutically acceptable excipient. Compounds of the invention, including pharmaceutical compositions comprising such compounds, may be used in the methods described herein.

Embodiments of the present disclosure provide a method of inhibiting Ras-mediated cell signaling comprising contacting a cell with a therapeutically effective amount of one or more compounds disclosed herein, or a pharmaceutically acceptable salt thereof. Inhibition of Ras-mediated signal transduction can be assessed and demonstrated by a wide variety of ways known in the art. Non-limiting examples include a showing of (a) a decrease in GTPase activity of Ras; (b) a decrease in GTP binding affinity or an increase in GDP binding affinity; (c) an increase in K off of GTP or a decrease in K off of GDP; (d) a decrease in the levels of signaling transduction molecules downstream in the Ras pathway, such as a decrease in pMEK level; and/or (e) a decrease in binding of Ras complex to downstream signaling molecules including but not limited to Raf. Kits and commercially available assays can be utilized for determining one or more of the above.

Embodiments also provide methods of using the compounds or pharmaceutical compositions of the present invention to treat disease conditions, including but not limited to conditions implicated by G12C K-Ras mutation, G12C H-Ras mutation and/or G12C N-Ras mutation (e.g., cancer).

In some embodiments the invention provides a method of treating a disorder in a subject in need thereof, wherein the said method comprises determining if the subject has a K-Ras, H-Ras or N-Ras G12C mutation and if the subject is determined to have a K-Ras, H-Ras or N-Ras G12C mutation, then administering to the subject a therapeutically effective amount of at least one compound of the present invention, or a pharmaceutically acceptable salt thereof.

K-Ras, H-Ras or N-Ras G12C mutations have also been identified in hematological malignancies (e.g., cancers that affect blood, bone marrow, and/or lymph nodes). Accordingly, certain embodiments are directed to administration of a disclosed compound of the present invention, or a pharmaceutically acceptable salt thereof (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMoL) and/or other leukemias. In other embodiments, the compounds of the present invention, or a pharmaceutically acceptable salt thereof are useful for treatment of lymphomas such as all subtypes of Hodgkin's lymphoma or non-Hodgkin's lymphoma.

Determining whether a tumor or cancer comprises a G12C K-Ras, H-Ras or N-Ras mutation can be undertaken by assessing the nucleotide sequence encoding the K-Ras, H-Ras or N-Ras protein, by assessing the amino acid sequence of the K-Ras, H-Ras or N-Ras protein, or by assessing the characteristics of a putative K-Ras, H-Ras or N-Ras mutant protein. The sequences of wild-type human K-Ras (e.g. Accession No. NP203524), H-Ras (e.g. Accession No. NP001123914) and N-Ras (e.g. Accession No. NP002515) are known in the art.

Methods for detecting a mutation in a K-Ras, H-Ras or N-Ras nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C K-Ras, H-Ras or N-Ras mutations by real-time PCR. In real-time PCR, fluorescent probes specific for the K-Ras, H-Ras or N-Ras G12C mutation are used. When a mutation is present, the probe binds and fluorescence is detected. In some embodiments, the K-Ras, H-Ras or N-Ras G12C mutation is identified using a direct sequencing method of specific regions (e.g., exon 2 and/or exon 3) in the K-Ras, H-Ras or N-Ras gene. This technique will identify all possible mutations in the region sequenced.

Methods for detecting a mutation in a K-Ras, H-Ras or N-Ras protein are known by those of skill in the art. These methods include, but are not limited to, detection of a K-Ras, H-Ras or N-Ras mutant using a binding agent (e.g., an antibody) specific for the mutant protein, protein electrophoresis and Western blotting, and direct peptide sequencing. Methods for determining whether a tumor or cancer comprises a G12C K-Ras, H-Ras or N-Ras mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

Embodiments also relate to a method of treating a hyperproliferative disorder in a mammal that comprises administering to said mammal a therapeutically effective amount of a compound of the present invention, or a pharmaceutically acceptable salt thereof. In some embodiments, said method relates to the treatment of cancer such as acute myeloid leukemia, cancer in adolescents, childhood adrenocortical carcinoma, AIDS-related cancers (e.g. lymphoma and Kaposi's sarcoma), anal cancer, appendix cancer, astrocytomas, atypical teratoid rhabdoid tumor, basal cell carcinoma, bile duct cancer, bladder cancer, bone cancer, brain stem glioma, brain tumor, breast cancer, bronchial tumors, Burkitt lymphoma, carcinoid tumor, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, Ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin's lymphoma, hypopharyngeal cancer, intraocular melanoma, islet cell tumors, pancreatic neuroendocrine tumors, kidney cancer, laryngeal cancer, lip and oral cavity cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/ myeloproliferative neoplasms, multiple myeloma, Merkel cell carcinoma, malignant mesothelioma, malignant fibrous histiocytoma of bone and osteosarcoma, nasal cavity and paranasal sinus cancer, nasopharyngeal cancer, neuroblastoma, non-Hodgkin's lymphoma, non-small cell lung cancer (NSCLC), oral cancer, oropharyngeal cancer, ovarian cancer, pancreatic cancer, papillomatosis, paraganglioma, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or viral-induced cancer. In some embodiments, said method relates to the treatment of a non-cancerous hyperproliferative disorder such as benign hyperplasia of the skin (e. g., psoriasis), restenosis, or benign prostatic hyperplasia (BPH).

In certain particular embodiments, the invention relates to methods for treatment of lung cancers, the methods comprise administering a therapeutically effective amount of a compound of the present invention, or a pharmaceutically acceptable salt thereof (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

In some embodiments, the invention provides methods of inhibiting K-Ras, H-Ras, or N-Ras G12C activity in a cell by contacting said cell with an amount of a compound of the present invention, or a pharmaceutically acceptable salt thereof sufficient to inhibit the activity of K-Ras, H-Ras or N-Ras G12C in said cell. In some embodiments, the invention provides methods of inhibiting K-Ras, H-Ras or N-Ras G12C activity in a tissue by contacting said tissue with an amount of a compound of the present invention, or a pharmaceutically acceptable salt thereof sufficient to inhibit the activity of K-Ras, H-Ras or N-Ras G12C in said tissue. In some embodiments, the invention provides methods of inhibiting K-Ras, H-Ras or N-Ras G12C activity in an organism by contacting said organism with an amount of a compound of the present invention, or a pharmaceutically acceptable salt thereof sufficient to inhibit the activity of K-Ras, H-Ras or N-Ras G12C in said organism. In some embodiments, the invention provides methods of inhibiting K-Ras, H-Ras or N-Ras G12C activity in an animal by contacting said animal with an amount of a compound of the present invention, or a pharmaceutically acceptable salt thereof sufficient to inhibit the activity of K-Ras, H-Ras or N-Ras G12C in said animal. In some embodiments, the invention provides methods of inhibiting K-Ras, H-Ras or N-Ras G12C activity in a mammal by contacting said mammal with an amount of a compound of the present invention, or a pharmaceutically acceptable salt thereof sufficient to inhibit the activity of K-Ras, H-Ras or N-Ras G12C in said mammal. In some embodiments, the invention provides methods of inhibiting K-Ras, H-Ras or N-Ras G12C activity in a human by contacting said human with an amount of a compound of the present invention, or a pharmaceutically acceptable salt thereof sufficient to inhibit the activity of K-Ras, H-Ras or N-Ras G12C in said human. In other embodiments, the present invention provides methods of treating a disease mediated by K-Ras, H-Ras or N-Ras G12C activity in a subject in need of such treatment.

In some embodiments, the invention provides methods of treating cancer comprising administering to an individual in need thereof a therapeutically effective amount of the compound of the present invention, or a pharmaceutically acceptable salt thereof, or the pharmaceutical composition of the present invention. In some embodiments, the individual is a human. In some embodiments, the administering is via the oral route. In some embodiments, the administering is via injection. In some embodiments, the cancer is mediated by a K-Ras G12C, H-Ras G12C or N-Ras G12C mutation. In some embodiments, the cancer is mediated by a K-Ras G12C mutation. In some embodiments, the cancer is a hematological cancer, pancreatic cancer, MYH associated polyposis, colorectal cancer or lung cancer. In one embodiment, the cancer is lung cancer, colorectal cancer, appendicial cancer, or pancreatic cancer. In one embodiment, the cancer is colorectal cancer. In another embodiment, the cancer is pancreatic cancer. In some embodiments, the cancer is lung adenocarcinoma.

In some embodiments, the invention provides methods for regulating activity of a mutant protein selected from the group consisting of K-Ras G12C, H-Ras G12C and N-Ras G12C, the method comprising reacting the mutant protein with the compound of the present invention, or a pharmaceutically acceptable salt thereof.

In some embodiments, the invention provides methods for inhibiting proliferation of a cell population, the method comprising contacting the cell population with the compound of the present invention, or a pharmaceutically acceptable salt thereof. In some embodiments, the inhibition of proliferation is measured as a decrease in cell viability of the cell population.

In some embodiments, the invention provides methods for treating a disorder mediated by a mutation selected from the group consisting of K-Ras G12C, H-Ras G12C and N-Ras G12C in an individual in need thereof, the method comprising: determining if the individual has the mutation; and if the individual is determined to have the mutation, then administering to the individual a therapeutically effective amount of the compound of the present invention, or a pharmaceutically acceptable salt thereof, or the pharmaceutical composition of the present invention. In some embodiments, the disorder is mediated by a K-Ras G12C mutation. In some embodiments, the disorder is a cancer. In some embodiments, the cancer is a hematological cancer, pancreatic cancer, MYH associated polyposis, colorectal cancer or lung cancer. In one embodiment, the cancer is lung cancer, colorectal cancer, appendicial cancer, or pancreatic cancer. In one embodiment, the cancer is colorectal cancer. In another embodiment, the cancer is pancreatic cancer. In some embodiments, the cancer is lung adenocarcinoma.

In some embodiments, the invention provides methods for preparing a labeled K-Ras G12C, H-Ras G12C or N-Ras G12C mutant protein, the method comprising reacting a K-Ras G12C, H-Ras G12C or N-Ras G12C mutant protein with a compound of the present invention, or a pharmaceutically acceptable salt thereof, to result in the labeled K-Ras G12C, H-Ras G12C or N-Ras G12C mutant protein.

In some embodiments, the invention provides methods for inhibiting tumor metastasis comprising administering to an individual in need thereof a therapeutically effective amount of the compound of the present invention, or a pharmaceutically acceptable salt thereof, or the pharmaceutical composition of the present invention to a subject in need thereof.

In some embodiments, the invention provides uses of a compound of the present invention, or a pharmaceutically acceptable salt thereof, in the manufacture of a medicament for treating cancer. In some embodiments, the medicament is formulated for oral administration. In some embodiments, the medicament is formulated for injection. In some embodiments, the cancer is mediated by a K-Ras G12C, H-Ras G12C or N-Ras G12C mutation. In some embodiments, the cancer is mediated by a K-Ras G12C mutation. In some embodiments, the cancer is mediated by a H-Ras G12C mutation. In some embodiments, the cancer is mediated by a N-Ras G12C mutation. In some embodiments, the cancer is a hematological cancer, pancreatic cancer, MYH associated polyposis, colorectal cancer or lung cancer. In one embodiment, the cancer is lung cancer, colorectal cancer, appendicial cancer, or pancreatic cancer. In one embodiment, the cancer is colorectal cancer. In another embodiment, the cancer is pancreatic cancer. In some embodiments, the cancer is lung adenocarcinoma. In some embodiments, the invention provides uses of a compound of the present invention, or a pharmaceutically acceptable salt thereof, in the manufacture of a medicament for inhibiting tumor metastasis.

In some embodiments, the invention provides a compound of the present invention, or a pharmaceutically acceptable salt thereof, or a pharmaceutical composition of the present invention, for use in a method of treatment of the human or animal body by therapy. In some embodiments, the invention provides a compound of the present invention, or a pharmaceutically acceptable salt thereof, or a pharmaceutical composition of the present invention, for use in a method of treating cancer. In some embodiments, the cancer is mediated by a K-Ras G12C, H-Ras G12C or N-Ras G12C mutation. In some embodiments, the cancer is mediated by a K-Ras G12C mutation. In some embodiments, the cancer is mediated by a H-Ras G12C mutation. In some embodiments, the cancer is mediated by a N-Ras G12C mutation. In some embodiments, the cancer is a hematological cancer, pancreatic cancer, MYH associated polyposis, colorectal cancer or lung cancer. In one embodiment, the cancer is lung cancer, colorectal cancer, appendicial cancer, or pancreatic cancer. In one embodiment, the cancer is colorectal cancer.

In another embodiment, the cancer is pancreatic cancer. In some embodiments, the cancer is lung adenocarcinoma. In some embodiments, the invention provides a compound of the present invention, or a pharmaceutically acceptable salt thereof, or a pharmaceutical composition of the present invention, for use in a method of inhibiting tumor metastasis.

Further provided herein are methods of treating lung cancer in a patient having lung cancer, comprising administering a therapeutically effective amount of a compound or a pharmaceutically acceptable salt thereof (or a pharmaceutical composition comprising the same) described herein to the patient. In one embodiment, the lung cancer is non-small cell lung carcinoma (NSCLC). The NSCLC can be, for example, adenocarcinoma, squamous-cell lung carcinoma or large-cell lung carcinoma. In another embodiment, the lung cancer is small cell lung carcinoma. In still another embodiment, the lung cancer is glandular tumors, carcinoid tumors or undifferentiated carcinomas. The lung cancer can be stage I or II lung cancer. In one embodiment, the lung cancer is stage III or IV lung cancer. The methods provided herein include administration of the compound as a 1L therapy. In one embodiment, the lung cancer comprises a G12C KRas mutation.

Still further provided herein are methods of treating pancreatic cancer in a patient having pancreatic cancer, the method comprising administering a therapeutically effective amount of a compound or pharmaceutically acceptable salt thereof described herein to the patient. In one embodiment, the patient has been previously treated with radiation and one or more chemotherapy agents. In one embodiment, the pancreatic cancer is stage 0, I, or II. In another embodiment, the pancreatic cancer is stage III or stage IV. In one embodiment, the pancreatic cancer comprises a G12C KRas mutation.

Still further provided herein are methods of treating colon cancer in a patient having colon cancer, the method comprising administering a therapeutically effective amount of a compound or pharmaceutically acceptable salt thereof described herein to the patient. In one embodiment, the colon cancer is stage I or II. In another embodiment, the colon cancer is stage III or stage IV. In one embodiment, the colon cancer comprises a G12C KRas mutation.

Further provided herein are methods of treating tumor agnostic G12C mutant KRas mediated cancer. In one embodiment of such methods, the method comprises:
a. determining the absence or presence of a KRas G12C mutation in a sample taken from a patient with a suspected diagnosed cancer; and
b. administering to the patient a therapeutically effective amount of a compound or pharmaceutically acceptable salt thereof described herein.

In one embodiment of such methods, the patient is diagnosed with a cancer described herein. In another embodiment of such methods, the sample is a tumor sample taken from the subject. In one such embodiment, the sample is taken before administration of any therapy. In another such embodiment, the sample is taken before administration of a compound of pharmaceutically acceptable salt thereof described herein and after administration of another chemotherapeutic agent. In another embodiment of such methods, the compound or pharmaceutically acceptable salt thereof described herein is administered as provided herein (e.g. orally).

Dosage & Administration

The present invention provides pharmaceutical compositions or medicaments containing a therapeutically effective amount of a compound of the present invention, or a pharmaceutically acceptable salt thereof and at least one therapeutically inert excipient, as well as methods of using the compounds of the invention to prepare such compositions and medicaments.

An embodiment, therefore, includes a pharmaceutical composition comprising a therapeutically effective amount of a compound of the present invention, or a pharmaceutically acceptable salt thereof. A further embodiment includes a pharmaceutical composition comprising a therapeutically effective amount of a compound of the present invention, or a pharmaceutically acceptable salt thereof, together with a pharmaceutically acceptable excipient.

In one example, a therapeutically effective amount of a compound of the present invention, or a pharmaceutically acceptable salt thereof, with the desired degree of purity may be formulated by mixing with physiologically acceptable excipients, i.e., excipients that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of the present invention, or a pharmaceutically acceptable salt thereof is formulated in an acetate buffer, at pH 5. In another embodiment, compound of the present invention, or a pharmaceutically acceptable salt thereof is sterile. The compound of the present invention, or a pharmaceutically acceptable salt thereof may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the severity of the disorder, the particular patient being treated, the clinical condition of the individual patient, the cause of the disorder, the site of delivery of the agent, the method of administration, the scheduling of administration, and other factors known to medical practitioners. The "therapeutically effective amount" of the compound of the present invention, or a pharmaceutically acceptable salt thereof to be administered will be governed by such considerations, and is the minimum amount necessary to inhibit K-Ras, H-Ras, and/or N-Ras activity. Typically such amount may be below the amount that is toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container may have deposited thereon a label that describes the contents of the container. The label may also include appropriate warnings.

Sustained-release preparations may be prepared. Suitable examples of sustained-release preparations include semipermeable matrices of solid hydrophobic polymers containing a therapeutically effective amount of a compound of the present invention, or a pharmaceutically acceptable salt thereof, which matrices are in the form of shaped articles, e.g. films, or microcapsules. Examples of sustained-release matrices include polyesters, hydrogels (for example, poly (2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

A dose to treat human patients may range from about 0.01 mg to about 1000 mg of a compound of the present invention, or a pharmaceutically acceptable salt thereof. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

A therapeutically effective amount of a compound of the present invention, or a pharmaceutically acceptable salt thereof may be administered by any suitable means, including oral, topical (including buccal and sublingual), rectal, vaginal, transdermal, parenteral, subcutaneous, intraperitoneal, intrapulmonary, intradermal, intrathecal, epidural and intranasal, and, if desired for local treatment, intralesional administration. Parenteral infusions include intramuscular, intravenous, intraarterial, intraperitoneal, or subcutaneous administration.

A therapeutically effective amount of a compound of the present invention, or a pharmaceutically acceptable salt thereof may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a therapeutically effective amount of a compound of the present invention, or a pharmaceutically acceptable salt thereof and an excipient. Suitable excipients include carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and taste and/or odour correctants, and are well known to those skilled in the art and are described in detail in, e.g., Ansel, H. C., et al., Ansel's *Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, R. C., *Handbook of Pharmaceutical Excipients*, Chicago, Pharmaceutical Press, 2005. The formulations may also include one or more buffers, surfactants, lubricating agents, suspending agents, preservatives, opaquing agents, glidants, processing aids, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the compound of the present invention, or a pharmaceutically acceptable salt thereof are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In certain embodiments, pharmaceutical compositions are formulated in any conventional manner using one or more physiologically acceptable excipients and auxiliaries which facilitate processing of the active compounds into preparations which can be used pharmaceutically. Proper formulation is dependent upon the route of administration chosen. Any pharmaceutically acceptable techniques and excipients are optionally used as suitable. Pharmaceutical compositions comprising a therapeutically effective amount of a compound of the present invention, or a pharmaceutically acceptable salt thereof are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable excipient and a therapeutically effective amount of a compound of the present invention, or a pharmaceutically acceptable salt thereof, described herein as an active ingredient. The active ingredient is in free-acid or freebase form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, excipients, such as preserving, stabilizing, wetting or emulsifying agents, solution promoters, salts for regulating the osmotic pressure, buffers, and/or other therapeutically valuable substances.

Methods for the preparation of compositions comprising a therapeutically effective amount of a compound of the present invention, or a pharmaceutically acceptable salt thereof described herein include formulating the compound of the present invention, or a pharmaceutically acceptable salt thereof with one or more inert, pharmaceutically acceptable excipients to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising a therapeutically effective amount of a compound of the present invention, or a pharmaceutically acceptable salt thereof illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of the present invention, or a pharmaceutically acceptable salt thereof. The term "solubilizing agent" generally includes agents that result in formation of a micellar solution or a true solution of the agent. Certain acceptable nonionic surfactants, for example polysorbate 80, are useful as solubilizing agents, as are ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or excipients useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days.

The invention further provides veterinary compositions comprising at least one active ingredient as above defined together with a veterinary excipient therefore. Veterinary excipients are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of the present invention, or a pharmaceutically acceptable salt thereof may be employed alone or in combination with other therapeutic agents for the treatment of a disease or disorder described herein. The second compound of the pharmaceutical combination formulation or dosing regimen preferably has complementary activities to the compound of the present invention, or a pharmaceutically acceptable salt thereof such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Combination therapies according to the present invention thus comprise the administration of a compound of the present invention, or a pharmaceutically acceptable salt thereof, and the use of at least one other treatment method. The amounts of the compound of the present invention, or a pharmaceutically acceptable salt thereof and the other pharmaceutically active agent(s) and the relative timings of administration will be selected in order to achieve the desired combined therapeutic effect.

In various embodiments of the method, the additional therapeutic agent is an epidermal growth factor receptor (EGFR) inhibitor, phosphatidylinositol kinase (PI3K) inhibitor, insulin-like growth factor receptor (IGF1R) inhibitor, a Janus kinase (JAK) inhibitor, a Met kinase inhibitor, a SRC family kinase inhibitor, a mitogen-activated protein kinase (MEK) inhibitor, an extracellular-signal-regulated kinase (ERK) inhibitor, a topoisomerase inhibitor (such as irinotecan, or such as etoposide, or such as doxorubicin), a taxane (such as anti-microtubule agents including paclitaxel and docetaxel), an anti-metabolite agent (such as 5-FU or such as gemcitabine), or an alkylating agent (such as cisplatin or such as cyclophosphamide), or a taxane.

In some embodiments, the additional therapeutic agent is an epidermal growth factor receptor (EGFR) inhibitor, such as Erlotinib or such as Afatinib. In some embodiments the additional therapeutic agent is Iressa. In some embodiments the additional therapeutic agent is a monoclonal antibody such as cetuximab (Erbitux) or panitumumab (Vectibix). In some embodiments the GFR inhibitor is a dual or pan-HER inhibitor. In other embodiments, the additional therapeutic agent is a phosphatidylinositol-3-kinase (PI3K) inhibitor, such as GDC-0941, MLN1117, BYL719 (Alpelisib) or BKM120 (Buparlisib). GDC-0941 refers to 2-(1H-indazol-4-yl)-6-(4-methanesulfonyl-piperazin-1-ylmethyl)-4-morpholin-4-yl-thieno[3,2-d]pyrimidine or a salt thereof (e.g., bismesylate salt).

In still different embodiments, the additional therapeutic agent is an insulin-like growth factor receptor (IGF1R) inhibitor. For example, in some embodiments the insulin-like growth factor receptor (IGF1R) inhibitor is NVP-AEW541. In other embodiments, the additional therapeutic agent is IGOSI-906 (Linsitinib), BMS-754807, or in other embodiments the additional therapeutic agent is a neutralizing monoclonal antibody specific to IGF1R such as AMG-479 (ganitumab), CP-751,871 (figitumumab), IMC-A12 (cixutumumab), MK-0646 (dalotuzumab), or R-1507 (robatumumab).

In some other embodiments, the additional therapeutic agent is a Janus kinase (JAK) inhibitor. In some embodiments, the additional therapeutic agent is CYT387, GLPG0634, Baricitinib, Lestaurtinib, momelotinib, Pacritinib, Ruxolitinib, or TG101348.

In some other embodiments, the additional therapeutic agent is an anti-glypican 3 antibody. In some embodiments, the anti-glypican 3 antibody is codrituzumab.

In some other embodiments, the additional therapeutic agent is an antibody drug conjugate (ADC). In some embodiments, the ADC is polatuzumab vedotin, RG7986, RG7882, RG6109, or RO7172369.

In some other embodiments, the additional therapeutic agent is an MDM2 antagonist. In some embodiments, the MDM2 antagonist is idasanutlin.

In some other embodiments, the additional therapeutic agent is an agonistic antibody against CD40. In some embodiments, the agonistic antibody against CD40 is selicrelumab (RG7876).

In some other embodiments, the additional therapeutic agent is a bispecific antibody. In some embodiments, the bispecific antibody is RG7828 (BTCT4465A), RG7802, RG7386 (FAP-DR5), RG6160, RG6026, ERY974, or anti-HER2/CD3.

In some other embodiments, the additional therapeutic agent is a targeted immunocytokine. In some embodiments, the targeted immunocytokine is RG7813 or RG7461.

In some other embodiments, the additional therapeutic agent is an antibody targeting colony stimulating factor-1 receptor (CSF-1R). In some embodiments, the CSF-1R antibody is emactuzumab.

In some other embodiments, the additional therapeutic agent is a personalised cancer vaccine. In some embodiments, the personalised cancer vaccine is RG6180.

In some other embodiments, the additional therapeutic agent is an inhibitor of BET (bromodomain and extraterminal family) proteins (BRD2/3/4/T). In some embodiments, the BET inhibitor is RG6146.

In some other embodiments, the additional therapeutic agent is an antibody designed to bind to TIGIT. In some embodiments, the anti-TIGIT antibody is RG6058 (MTIG7192A).

In some other embodiments, the additional therapeutic agent is a selective estrogen receptor degrader (SERD). In some other embodiments, the SERD is RG6047 (GDC-0927) or RG6171 (GDC-9545).

In some other embodiments the additional therapeutic agent is an MET kinase inhibitor, such as Crizotinib, tivantinib, AMG337, cabozantinib, or foretinib. In other embodiments the additional therapeutic agent is a neutralizing monoclonal antibody to MET such as onartuzumab.

In more embodiments, the additional therapeutic agent is a SRC family non-receptor tyrosine kinase inhibitor. For example in some embodiments the additional therapeutic agent is an inhibitor of the subfamily of SRC family non-receptor tyrosine kinases. Exemplary inhibitors in this respect include Dasatinib. Other examples in this regard include Ponatinib, saracatinib, and bosutinib.

In yet different embodiments, the additional therapeutic agent is a mitogen-activated protein kinase (MEK) inhibitor. In some of these embodiments, the mitogen-activated protein kinase (MEK) inhibitor is trametinib, selumetinib, COTELLIC® (cobimetinib), PD0325901, or RO5126766. In other embodiments the MEK inhibitor is GSK-1120212, also known as trametinib.

In yet different embodiments, the additional therapeutic agent is an extracellular-signal-regulated kinase (ERK) inhibitor. In some of these embodiments, the mitogen-activated protein kinase (MEK) inhibitor is $SCH_{722984}$ or GDC-0994.

In other embodiments the protein kinase inhibitor is taselisib, ipatasertib, GDC-0575, GDC-5573 (HM95573), RG6114 (GDC-0077), CKI27, Afatinib, Axitinib, Atezolizumab, Bevacizumab, Bostutinib, Cetuximab, Crizotinib, Dasatinib, Erlotinib, Fostamatinib, Gefitinib, Imatinib, Lapatinib, Lenvatinib, Ibrutinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib, or Vemurafenib. In still more embodiments, the additional therapeutic agent is a topoisomerase inhibitor. In some of these embodiments, the topoisomerase inhibitor is Irinotecan. In some more embodiments, the additional therapeutic agent is a taxane. Exemplary taxanes include Taxol and Docetaxel.

In addition to the above additional therapeutic agent, other chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methyl melamines including altretamine, triethylenemelamine, triethylenephosphoramide, triethylenethiophosphaoramide and trimethylol melamine; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide K; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; Xeloda®; ibandronate; camptothecin-11 (CPT-11); topoisomerase inhibitor RFS 2000; and difluoromethylornithine (DMFO). Where desired, the compounds or pharmaceutical composition of the present invention can be used in combination with commonly prescribed anti-cancer drugs such as Herceptin®, Avastin®, Gazyva®, Tecentriq®, Alecensa®, Perjeta®, Venclexta™, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Amino-pyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

The exact method for administering the compound and the additional therapeutic agent will be apparent to one of ordinary skill in the art. In some exemplary embodiments the compound and the additional therapeutic agent are co-administered. In other embodiments, the compound and the additional therapeutic agent are separately administered.

In some embodiments, the compound and the additional therapeutic agent are administered with the second agent simultaneously or separately. This administration in combination can include simultaneous administration of the two agents in the same dosage form, simultaneous administration in separate dosage forms, and separate administration. That is, the compound and any of the additional therapeutic agents described herein can be formulated together in the same dosage form and administered simultaneously. Alternatively, the compound and any of the additional therapeutic agents described herein can be simultaneously administered, wherein both the agents are present in separate formulations. In another alternative, the compound can be administered just followed by and any of the additional therapeutic agents described herein, or vice versa. In some embodiments of the separate administration protocol, the compound and any of the additional therapeutic agents described herein are administered a few minutes apart, or a few hours apart, or a few days apart.

Articles of Manufacture

In another embodiment of the invention, an article of manufacture, or "kit", containing materials useful for the treatment of the diseases and disorders described above is provided. In one embodiment, the kit comprises a container comprising compound of the present invention, or a pharmaceutically acceptable salt thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of the present invention, or a pharmaceutically acceptable salt thereof or a formulation thereof which is effective for treating the condition and may have a sterile access port (for example, the container may be an intravenous solution bag or a vial having a stopper pierceable by a hypodermic injection needle). At least one active agent in the composition is a compound of the present invention, or a pharmaceutically acceptable salt thereof. Alternatively, or additionally, the article of manufacture may further comprise a second container comprising a pharmaceutical diluent, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

In another embodiment, the kits are suitable for the delivery of solid oral forms of a compound of the present invention, or a pharmaceutically acceptable salt thereof, such as tablets or capsules. Such a kit can include a number of unit dosages. An example of such a kit is a "blister pack". Blister packs are well known in the packaging industry and are widely used for packaging pharmaceutical unit dosage forms.

Additional Embodiments

Additional embodiments are provided herein below.

Embodiment 1: A compound of Formula (I):

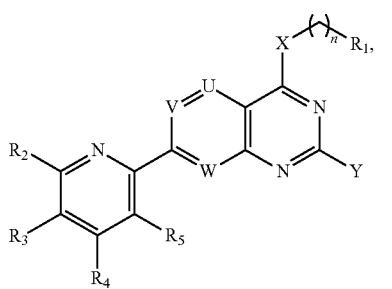

(I)

or a pharmaceutically acceptable salt thereof;
wherein,
$R_1$ is an electrophilic moiety capable of forming a covalent bond with a cysteine residue at position 12 of a K-Ras G12C mutant protein;
$R_2$ is selected from the group consisting of H, OH, NH$_2$, halo, $C_{1-6}$ alkyl, $C_{1-6}$ haloalkyl, cyclopropyl, and —NHR, wherein R is selected from the group consisting of $C_{1-6}$ alkyl, $C_{1-6}$ alkoxy, $C_{1-6}$ alkanoyl, $C_{1-6}$ hydroxyalkanoyl, $C_{1-6}$ cyanoalkyl, $C_{1-6}$ alkylamino, —($C_{1-6}$ alkylenyl)NH(CH$_3$)—($C_{1-6}$ alkylenyl)N(CH$_3$)$_2$, and —($C_{1-3}$ alkylenyl)(3-7 membered-heterocyclyl);
$R_3$ and $R_4$ are each independently selected from the group consisting of H, NH$_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and cyclopropyl;
$R_5$ is selected from the group consisting of H, NH$_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_{3-7}$ cycloalkyl,
wherein at least one of $R_2$, $R_3$, $R_4$, and $R_5$ is other than H; or
$R_2$ and $R_3$, $R_3$ and $R_4$, or $R_4$ and $R_5$, together with the atoms to which they are each bonded, form a $C_{3-7}$ cycloalkyl, 3 to 7 membered heterocycloalkyl, $C_{6-14}$ aryl, or 5- to 10-membered heteroaryl; each of which is optionally substituted with 1 to 4 substituents, wherein each substituent is independently selected from the group consisting of OH, NH$_2$, halo, $C_{1-3}$ alkyl, $C_{1-3}$ haloalkyl, $C_{1-3}$ alkoxy, and $C_{1-3}$ haloalkoxy;
X is selected from the group consisting of NH$_2$, $C_{1-6}$ alkoxy, $C_{1-6}$ alkyl, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, NH$_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;
Y is selected from the group consisting of -L-Y$_1$ or Y$_1$;
Y$_1$ is selected from the group consisting of H, NH$_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 Y$_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$ aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{3-7}$ cycloalkyl substituted with a $C_{1-6}$ dialkylamino, $C_{1-6}$ haloalkoxy, $C_{1-6}$ haloalkyl, 5- to 10-membered heteroaryl, 4- to 10-membered heterocyclyl, a 4- to 10-membered heterocyclyl substituted with methyl, hydroxy, and oxo;
each Y$_{1a}$ is independently selected from the group consisting of halo, $C_{1-6}$ alkyl, $C_{1-6}$ alkoxy, 3- to 7-membered heterocyclyl, $C_{1-6}$alkoxyC$_{1-6}$alkyl, $C_{1-6}$ haloalkyl, oxo, hydroxy, NH$_2$, cyano, $C_{1-6}$ carboxyalkyl, $C_{1-6}$ cyanoalkyl, $C_{1-6}$ hydroxyalkyl, and $C_{1-6}$ haloalkoxy;
L is selected from the group consisting of a bond, O, S, and N(L$^a$);
L$^a$ is selected from the group consisting of hydrogen and $C_{1-3}$ alkyl;
U is C(R$_{6a}$);
V is C(R$_{6b}$);
W is C(R$_{6c}$) or N;
each of R$_{6a}$, R$_{6b}$, and R$_{6c}$ are independently selected from the group consisting of H, OH, NH$_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{1-6}$ haloalkoxy, $C_{1-6}$ haloalkyl, 5- to 10-membered heteroaryl, and 4- to 10-membered heterocyclyl; and n is selected from the group consisting of 0, 1, and 2.

Embodiment 2: The compound of Embodiment 1 having a Formula (II):

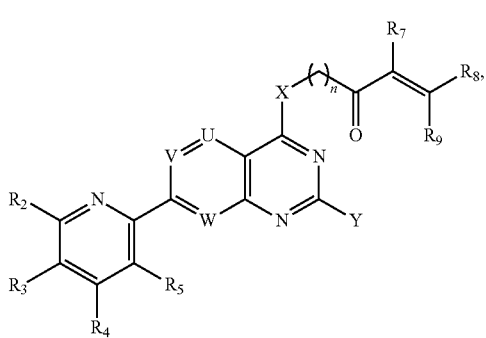

(II)

or a pharmaceutically acceptable salt thereof;

wherein, $R_2$ is selected from the group consisting of H, OH, $NH_2$, halo, $C_{1-6}$ alkyl, $C_{1-6}$ haloalkyl, cyclopropyl, and —NHR, wherein R is selected from the group consisting of $C_{1-6}$ alkyl, $C_{1-6}$ alkoxy, $C_{1-6}$ alkanoyl, $C_{1-6}$ hydroxyalkanoyl, $C_{1-6}$ cyanoalkyl, $C_{1-6}$ alkylamino, —($C_{1-6}$ alkylenyl)NH($CH_3$)—($C_{1-6}$ alkylenyl)N($CH_3$)$_2$, and —($C_{1-3}$ alkylenyl)(3-7 membered-heterocyclyl);

$R_3$ and $R_4$ are each independently selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and cyclopropyl;

$R_5$ is selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_{3-7}$ cycloalkyl, wherein at least one of $R_2$, $R_3$, $R_4$, and $R_5$ is other than H; or $R_2$ and $R_3$, $R_3$ and $R_4$, or $R_4$ and $R_5$, together with the atoms to which they are each bonded, form a $C_{3-7}$ cycloalkyl, 3 to 7 membered heterocycloalkyl, $C_{6-14}$ aryl, or 5- to 10-membered heteroaryl; each of which is optionally substituted with 1 to 4 substituents, wherein each substituent is independently selected from the group consisting of OH, $NH_2$, halo, $C_{1-3}$ alkyl, $C_{1-3}$ haloalkyl, $C_{1-3}$ alkoxy, and $C_{1-3}$ haloalkoxy;

$R_7$ is selected from the group consisting of H, cyano, and halo; and $R_8$ and $R_9$ are each independently selected from the group consisting of H, $C_{1-6}$ alkyl, $C_{1-6}$ haloalkyl, $C_{1-6}$ hydroxyalkyl, cyano, and halo; wherein $C_{1-6}$ alkyl is optionally substituted with one substituent selected from the group consisting of: methanesulfonyl (mesyl), p-toluenesulfonyl (tosyl), an alkyl or aryl sulfonate leaving group, $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy; or $R_7$ and $R_8$ together form a triple bond between the carbons to which they are attached, or $R_7$ and $R_8$ together with the carbons to which they are each bonded form a $C_{3-7}$ cycloalkenyl optionally substituted with one or two halo substituents; and $R_9$ is selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy;

X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;

Y is selected from the group consisting of -L-$Y_1$ or $Y_1$;

$Y_1$ is selected from the group consisting of H, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$ aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{3-7}$ cycloalkyl substituted with a $C_{1-6}$ dialkylamino, $C_{1-6}$ haloalkoxy, $C_{1-6}$ haloalkyl, 5- to 10-membered heteroaryl, 4- to 10-membered heterocyclyl, 4- to 10-membered heterocyclyl substituted with methyl, hydroxy, and oxo;

each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkoxy;

L is selected from the group consisting of a bond, O, S, and N($L^a$);

$L^a$ is selected from the group consisting of hydrogen and $C_{1-3}$ alkyl;

U is C($R_{6a}$);

V is C($R_{6b}$);

W is C($R_{6c}$) or N;

each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{1-6}$ haloalkoxy, $C_{1-6}$ haloalkyl, 5- to 10-membered heteroaryl, and 4- to 10-membered heterocyclyl; and n is selected from the group consisting of 0, 1, and 2.

Embodiment 3: The compound of Embodiment 1 having a Formula (III):

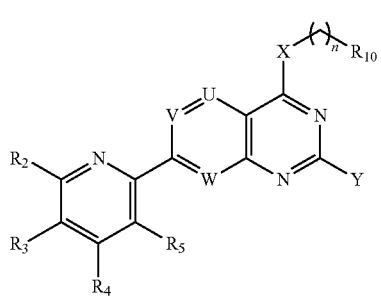

or a pharmaceutically acceptable salt thereof;
wherein,
$R_2$ is selected from the group consisting of H, OH, $NH_2$, halo, $C_{1-6}$ alkyl, $C_{1-6}$ haloalkyl, cyclopropyl, and —NHR, wherein R is selected from the group consisting of $C_{1-6}$ alkyl, $C_{1-6}$ alkoxy, $C_{1-6}$ alkanoyl, $C_{1-6}$ hydroxyalkanoyl, $C_{1-6}$ cyanoalkyl, $C_{1-6}$ alkylamino, —($C_{1-6}$ alkylenyl)NH($CH_3$)—($C_{1-6}$ alkylenyl)N($CH_3$)$_2$, and —($C_{1-3}$ alkylenyl)(3-7 membered-heterocyclyl);
$R_3$ and $R_4$ are each independently selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and cyclopropyl;
$R_5$ is selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_{3-7}$ cycloalkyl,
wherein at least one of $R_2$, $R_3$, $R_4$, and $R_5$ is other than H; or
$R_2$ and $R_3$, $R_3$ and $R_4$, or $R_4$ and $R_5$, together with the atoms to which they are each bonded, form a $C_{3-7}$ cycloalkyl, 3 to 7 membered heterocycloalkyl, $C_{6-14}$ aryl, or 5- to 10-membered heteroaryl; each of which is optionally substituted with 1 to 4 substituents, wherein each substituent is independently selected from the group consisting of OH, $NH_2$, halo, $C_{1-3}$ alkyl, $C_{1-3}$ haloalkyl, $C_{1-3}$ alkoxy, and $C_{1-3}$ haloalkoxy;
$R_{10}$ is selected from the group consisting of $R_{10a}$ and —C(O)—$R_{10a}$;
$R_{10a}$ is selected from the group consisting of oxiranyl and aziridinyl;
X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;
Y is selected from the group consisting of -L-$Y_1$ or $Y_1$;
$Y_1$ is selected from the group consisting of H, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 $Y_{1a}$ substituents $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$ aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{3-7}$ cycloalkyl substituted with a $C_{1-6}$ dialkylamino, $C_{1-6}$ haloalkoxy, $C_{1-6}$ haloalkyl, 5- to 10-membered heteroaryl, 4- to 10-membered heterocyclyl, a 4- to 10-membered heterocyclyl substituted with methyl, hydroxy, and oxo;
each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkoxy;
L is selected from the group consisting of a bond, O, S, and N($L^a$);
$L^a$ is selected from the group consisting of hydrogen and $C_{1-3}$ alkyl;
U is C($R_{6a}$);
V is C($R_{6b}$);
W is C($R_{6c}$) or N;
each of $R_{6a}$, $R_{6b}$, and $R_6$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{1-6}$ haloalkoxy, $C_{1-6}$ haloalkyl, 5- to 10-membered heteroaryl, and 4- to 10-membered heterocyclyl; and
n is selected from the group consisting of 0, 1, and 2.

Embodiment 4: The compound of any one of Embodiments 1-3, or a pharmaceutically acceptable salt thereof, wherein $R_2$ is selected from the group consisting of $NH_2$ and —NHR; and R is $C_{1-6}$ alkyl.

Embodiment 5: The compound of any one of Embodiments 1-4, or a pharmaceutically acceptable salt thereof, wherein $R_2$ is $NH_2$.

Embodiment 6: The compound of any one of Embodiments 1-5, or a pharmaceutically acceptable salt thereof, wherein $R_3$ and $R_4$ are independently selected from the group consisting of H, halo, $C_{1-6}$ alkyl, $C_{1-6}$ haloalkyl, and cyclopropyl.

Embodiment 7: The compound of any one of Embodiments 1-6, or a pharmaceutically acceptable salt thereof, wherein $R_5$ is selected from the group consisting of H, halo, $C_{1-6}$ alkyl, $C_{1-6}$ haloalkyl, $C_{1-6}$ haloalkoxy, $C_{1-6}$ alkylamino, and $C_{3-7}$ cycloalkyl.

Embodiment 8: The compound of any one of Embodiments 1-7, or a pharmaceutically acceptable salt thereof, wherein $R^5$ is $C_{1-3}$ haloalkyl.

Embodiment 9: The compound of any one of Embodiments 1-7, or a pharmaceutically acceptable salt thereof, wherein $R_5$ is $CF_3$ and $R_2$ is $NH_2$.

Embodiment 10: The compound of any one of Embodiments 1-7, or a pharmaceutically acceptable salt thereof, wherein $R_5$ is cyclopropyl.

Embodiment 11: The compound of any one of Embodiments 1-5, or a pharmaceutically acceptable salt thereof, wherein $R_4$ and $R_5$, together with the atoms to which they are each bonded, form a $C_{3-7}$ cycloalkyl, 3 to 7 membered heterocycloalkyl, $C_{6-14}$ aryl, or 5- to 10-membered heteroaryl; each of which is optionally substituted with 1 to 4 substituents, wherein each substituent is independently selected from the group consisting of OH, $NH_2$, halo, $C_{1-3}$ alkyl, $C_{1-3}$ haloalkyl, $C_{1-3}$ alkoxy, and $C_{1-3}$ haloalkoxy.

Embodiment 12: The compound of Embodiment 11, or a pharmaceutically acceptable salt thereof, wherein $R_4$ and $R_5$, together with the atoms to which they are each bonded, form a $C_{6-14}$ aryl, which is optionally substituted with 1 to 4 substituents, wherein each substituent is independently selected from the group consisting of OH, $NH_2$, halo, $C_{1-3}$ alkyl, $C_{1-3}$ haloalkyl, $C_{1-3}$ alkoxy, and $C_{1-3}$ haloalkoxy.

Embodiment 13: The compound of Embodiment 12, or a pharmaceutically acceptable salt thereof, wherein $R_4$ and $R_5$, together with the atoms to which they are each bonded, form a $C_6$ aryl, which is optionally substituted with 1 to 4 substituents, wherein each substituent is independently selected from the group consisting of OH, $NH_2$, halo, $C_{1-3}$ alkyl, $C_{1-3}$ haloalkyl, $C_{1-3}$ alkoxy, and $C_{1-3}$ haloalkoxy.

Embodiment 14: The compound of Embodiment 13, or a pharmaceutically acceptable salt thereof, wherein the $C_6$ aryl is unsubstituted.

Embodiment 15: The compound of Embodiment 13, or a pharmaceutically acceptable salt thereof, wherein the $C_6$ aryl is substituted with 1 to 4 substituents, wherein each substituent is independently halo.

Embodiment 16: The compound of any one of Embodiments 1-3, or a pharmaceutically acceptable salt thereof, wherein:
  $R_2$ is selected from the group consisting of H, OH, $NH_2$, halo, $C_{1-6}$ alkyl, $C_{1-6}$ haloalkyl, cyclopropyl, and —NHR, wherein R is selected from the group consisting of linear $C_{1-6}$ alkyl, $C_{1-6}$ alkoxy, $C_{1-6}$ alkanoyl, $C_{1-6}$ hydroxyalkanoyl, $C_{1-6}$ cyanoalkyl, $C_{1-6}$ alkylamino, —($C_{1-6}$ alkylenyl)NH($CH_3$)—($C_{1-6}$ alkylenyl)N($CH_3$)$_2$, and —($C_{1-3}$ alkylenyl)(3-7 membered-heterocyclyl);
  $R_3$ and $R_4$ are each independently selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, and $C_{1-6}$ alkylamino;
  $R_5$ is selected from the group consisting of H, Cl, Br, I, $NH_2$, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_{3-7}$ cycloalkyl,
  wherein at least two of $R_2$, $R_3$, $R_4$, and $R_5$ is other than H; or
  $R_2$ and $R_3$, $R_3$ and $R_4$, or $R_4$ and $R_5$, together with the atoms to which they are each bonded, form a $C_{3-7}$ cycloalkyl, 3 to 7 membered heterocycloalkyl, or $C_{6-14}$ aryl; each of which is optionally substituted with 1 to 4 substituents, wherein each substituent is independently selected from the group consisting of OH, $NH_2$, halo, $C_{1-3}$ alkyl, $C_{1-3}$ haloalkyl, and $C_{1-3}$ haloalkoxy;
  X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;
  Y is selected from the group consisting of -L-$Y_1$ or $Y_1$;
  $Y_1$ is selected from the group consisting of H, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{1-6}$ alkylsulfanyl, $C_{1-6}$ alkylsulfonyl, $C_{1-6}$ alkylthio, $C_{2-6}$ alkynyl, $C_{1-6}$ alkylamino, $C_{6-14}$ aryl, $C_{6-14}$ aryl substituted with a $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{3-7}$ cycloalkyl substituted with a $C_{1-6}$ dialkylamino, $C_{1-6}$ haloalkoxy, $C_{1-6}$ haloalkyl, 5- to 10-membered heteroaryl, 4- to 10-membered heterocyclyl, 4- to 10-membered heterocyclyl substituted with methyl, hydroxy, and oxo;
  each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkoxy;
  L is selected from the group consisting of a bond, O, S, and N($L^a$);
  $L^a$ is selected from the group consisting of hydrogen and $C_{1-3}$ alkyl;
  U is C($R_{6a}$);
  V is C($R_{6b}$);
  W is C($R_{6c}$) or N;
  each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{1-6}$ haloalkoxy, $C_{1-6}$ haloalkyl, 5- to 10-membered heteroaryl, and 4- to 10-membered heterocyclyl; and
  n is selected from the group consisting of 0, 1, and 2.

Embodiment 17: A compound of Formula (I) having a Formula (IV):

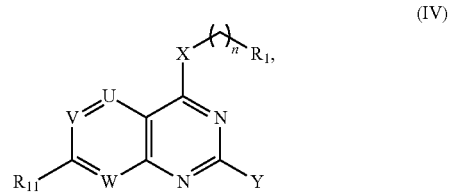

(IV)

or a pharmaceutically acceptable salt thereof;
wherein,
  $R_1$ is an electrophilic moiety capable of forming a covalent bond with a cysteine residue at position 12 of a K-Ras G12C mutant protein;
  X is selected from the group consisting of $NH_2$, $C_{1-6}$ alkoxy, $C_{1-6}$ alkyl, $C_{1-6}$ alkylamino, $C_{1-6}$ alkylsulfanyl, $C_{1-6}$ alkylsulfonyl, $C_{1-6}$ alkylthio, $C_{3-7}$ cycloalkyl, 4- to 7-membered heterocyclyl, and 4- to 7-membered heterocyclylamino; each of which is optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form C$_{3-7}$ spirocycloalkyl or 4- to 7-membered spiroheterocyclyl;

Y is selected from the group consisting of -L-Y$_1$ or Y$_1$;

Y$_1$ is selected from the group consisting of H, NH$_2$, halo, cyano, carbamoyl, C$_{2-6}$ alkenyl, C$_{1-6}$ alkoxy, C$_{1-6}$ alkyl, C$_{1-6}$ alkyl substituted with a 4- to 10-membered heterocyclyl optionally substituted with 1-4 Y$_{1a}$ substituents, C$_{1-6}$ alkyl substituted with a C$_{1-6}$ dialkylamino substituent, C$_{1-6}$ alkyl substituted with a C$_{1-6}$ dialkylamino cyclopropyl C$_{1-6}$ alkylsulfanyl, C$_{1-6}$ alkylsulfonyl, C$_{1-6}$ alkylthio, C$_{2-6}$ alkynyl, C$_{1-6}$ alkylamino, C$_{6-14}$ aryl, C$_{6-14}$ aryl substituted with a C$_{1-6}$ alkyl, C$_{1-6}$ aminoalkyl, C$_{1-6}$ carbamoylalkyl, C$_{1-6}$ carboxyalkyl, C$_{1-6}$ cyanoalkyl, C$_{3-7}$ cycloalkyl, C$_{3-7}$ cycloalkyl substituted with a C$_{1-6}$ dialkylamino, C$_{1-6}$ haloalkoxy, C$_{1-6}$ haloalkyl, 5- to 10-membered heteroaryl, 4- to 10-membered heterocyclyl, 4- to 10-membered heterocyclyl substituted with methyl, hydroxy, and oxo;

each Y$_{1a}$ is independently selected from the group consisting of halo, C$_{1-6}$ alkyl, C$_{1-6}$ alkoxy, 3- to 7-membered heterocyclyl, C$_{1-6}$alkoxyC$_{1-6}$alkyl, C$_{1-6}$ haloalkyl, oxo, hydroxy, NH$_2$, cyano, C$_{1-6}$ carboxyalkyl, C$_{1-6}$ cyanoalkyl, C$_{1-6}$ hydroxyalkyl, C$_{1-6}$ haloalkoxy;

L is selected from the group consisting of a bond, O, S, and N(L$^a$);

L$^a$ is selected from the group consisting of hydrogen and C$_{1-3}$ alkyl;

U is C(R$_{6a}$);

V is C(R$_{6b}$);

W is C(R$_{6c}$) or N;

each of R$_{6a}$, R$_{6b}$, and R$_{6c}$ are independently selected from the group consisting of H, OH, NH$_2$, halo, cyano, carbamoyl, C$_{2-6}$ alkenyl, C$_{1-6}$ alkoxy, C$_{1-6}$ alkyl, C$_{1-6}$ alkyl substituted with a 4- to 10-membered heterocyclyl substituent, C$_{1-6}$ alkylsulfanyl, C$_{1-6}$ alkylsulfonyl, C$_{1-6}$ alkylthio, C$_{1-6}$ haloalkylthio, C$_{2-6}$ alkynyl, C$_{1-6}$ alkylamino, C$_{6-14}$ aryl, C$_{1-6}$ aminoalkyl, C$_{1-6}$ carbamoylalkyl, C$_{1-6}$ carboxyalkyl, C$_{1-6}$ cyanoalkyl, C$_{3-7}$ cycloalkyl, C$_{1-6}$ haloalkoxy, C$_{1-6}$ haloalkyl, 5- to 10-membered heteroaryl, and 4- to 10-membered heterocyclyl;

n is selected from the group consisting of 0, 1, and 2; and

R$_{11}$ is selected from the group consisting of:

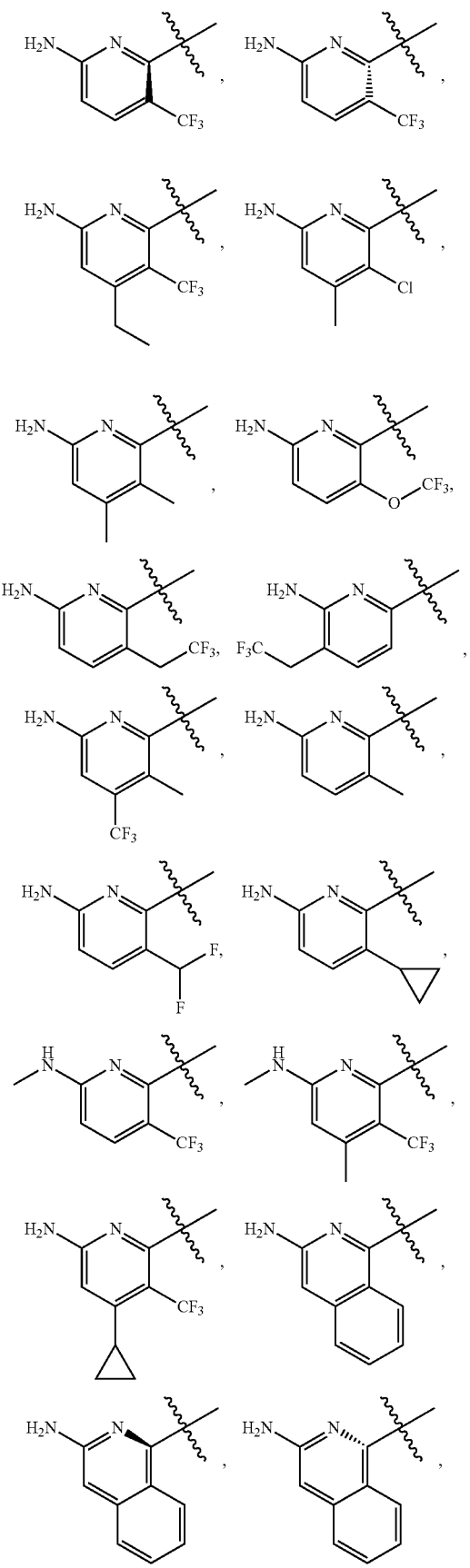

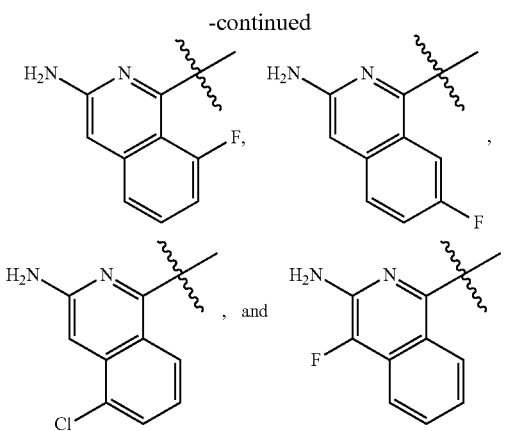

Embodiment 18: The compound of any one of Embodiments 1-17, or a pharmaceutically acceptable salt thereof, wherein Y is $Y_1$, and $Y_1$ is selected from the group consisting of H, $C_{1-6}$ alkyl, and $C_{1-6}$ haloalkyl.

Embodiment 19: The compound of any one of Embodiments 1-17, or a pharmaceutically acceptable salt thereof, wherein:

Y is -L-$Y_1$;

L is selected form the group consisting of O and N($L^a$);

$L^a$ is H; and $Y_1$ is selected from the group consisting of $C_{1-6}$ alkyl, $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{3-7}$ cycloalkyl substituted with a $C_{1-6}$ dialkylamino, and 4- to 10-membered heterocyclyl substituted with methyl; and each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkoxy.

Embodiment 20: The compound of Embodiment 19, or a pharmaceutically acceptable salt thereof, wherein L is N($L^a$), $L^a$ is H, and $Y_1$ is $C_{1-6}$ alkyl or $C_{1-6}$ alkyl substituted with a $C_{1-6}$ dialkylamino substituent.

Embodiment 21: The compound of Embodiment 19, or a pharmaceutically acceptable salt thereof, wherein:

L is O;

$Y_1$ is selected from the group consisting of $C_{1-6}$ alkyl substituted with a 4- to 10-membered heterocyclyl that is optionally substituted with 1-4 $Y_{1a}$ substituents, $C_{1-6}$ alkyl substituted with a $C_{1-6}$ dialkylamino substituent, $C_{1-6}$ alkyl substituted with a $C_{1-6}$ dialkylamino cyclopropyl, $C_{3-7}$ cycloalkyl substituted with a $C_{1-6}$ dialkylamino, and 4- to 10-membered heterocyclyl substituted with methyl; and each $Y_{1a}$ is independently selected from the group consisting of halo, $C_{1-6}$ alkyl, $C_{1-6}$ alkoxy, 3- to 7-membered heterocyclyl, $C_{1-6}$alkoxy$C_{1-6}$alkyl, $C_{1-6}$ haloalkyl, oxo, hydroxy, $NH_2$, cyano, $C_{1-6}$ carboxyalkyl, $C_{1-6}$ cyanoalkyl, $C_{1-6}$ hydroxyalkyl, and $C_{1-6}$ haloalkoxy.

Embodiment 22: The compound of Embodiment 19, or a pharmaceutically acceptable salt thereof, wherein $Y_1$ is a $C_{1-6}$ alkyl substituted with a 4- to 10-membered methylheterocyclyl substituent.

Embodiment 23: The compound of Embodiment 19, or a pharmaceutically acceptable salt thereof, wherein Y is selected from the group consisting of:

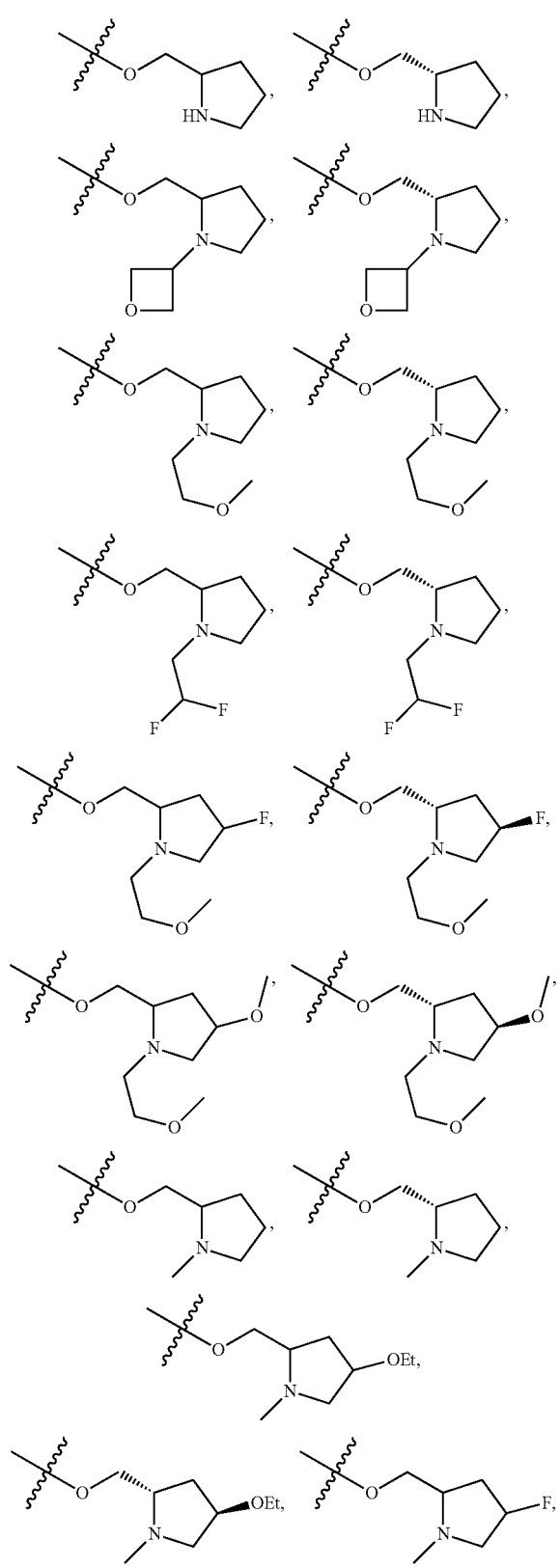

189
-continued
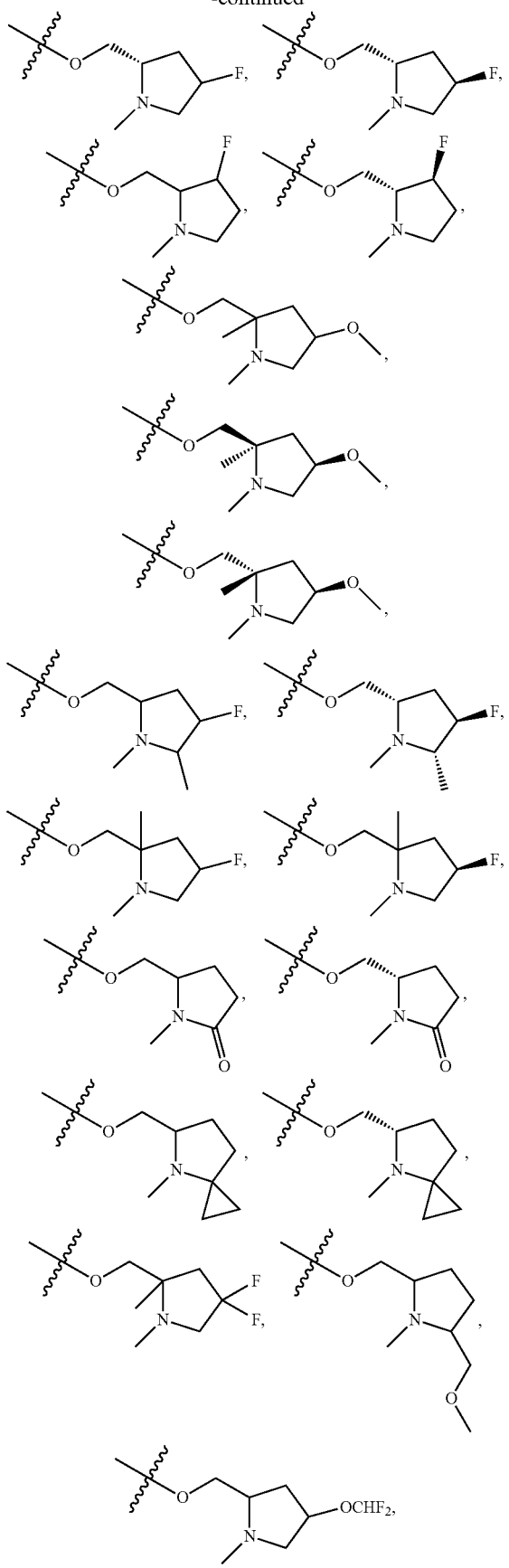
190
-continued
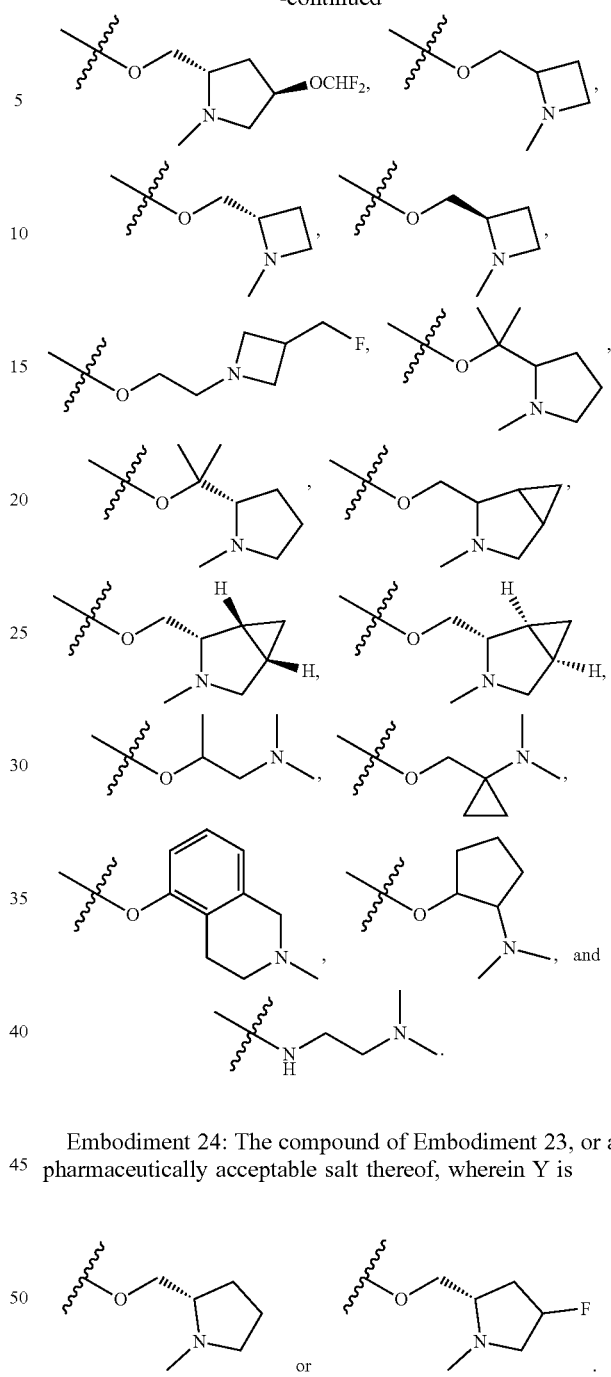
Embodiment 24: The compound of Embodiment 23, or a pharmaceutically acceptable salt thereof, wherein Y is
Embodiment 25: The compound of any one of Embodiments 17-24, or a pharmaceutically acceptable salt thereof, wherein $R_{11}$ is
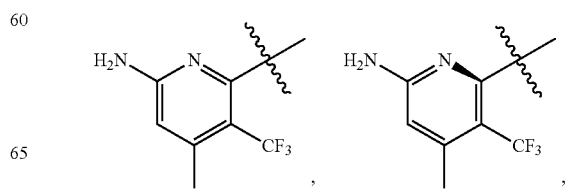

-continued

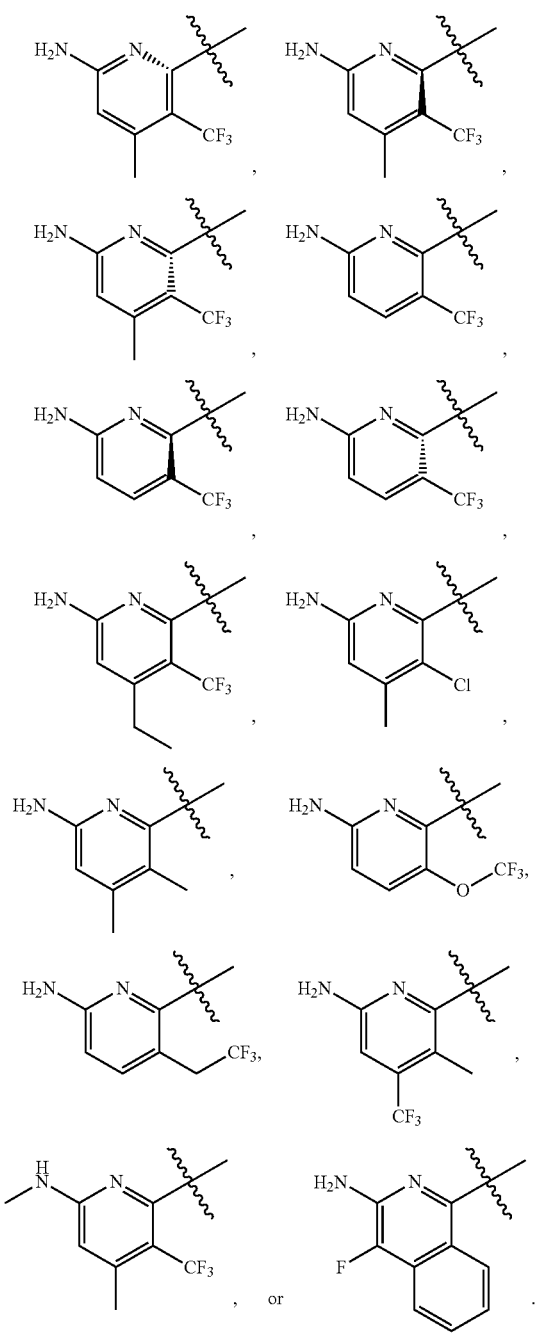

Embodiment 26: The compound of any one of Embodiments 17-25, or a pharmaceutically acceptable salt thereof, wherein R₁₁ is

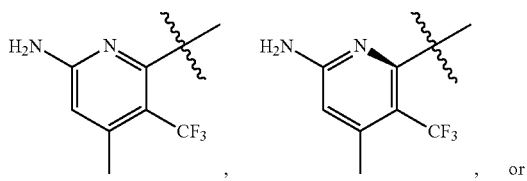

or

-continued

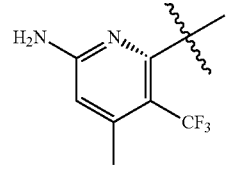

Embodiment 27: The compound of any one of Embodiments 17-25, or a pharmaceutically acceptable salt thereof, wherein R₁₁ is

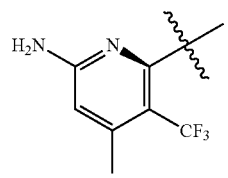

Embodiment 28: The compound of any one of Embodiments 1-27, or a pharmaceutically acceptable salt thereof, wherein $R_{6a}$ is H.

Embodiment 29: The compound of any one of Embodiments 1-28, or a pharmaceutically acceptable salt thereof, wherein $R_{6b}$ is selected from the group consisting of H, halo, $C_{1-6}$ alkoxy, $C_{1-6}$ alkylsulfonyl, $C_{1-6}$ haloalkyl, $C_{3-7}$ cycloalkyl, $C_{1-6}$ haloalkylthio, and 4- to 10-membered heterocyclyl.

Embodiment 30: The compound of any one of Embodiments 1-28, or a pharmaceutically acceptable salt thereof, wherein $R_{6b}$ is hydrogen, halo, or $C_{1-3}$ haloalkyl.

Embodiment 31: The compound of any one of Embodiments 1-30, or a pharmaceutically acceptable salt thereof, wherein W is $C(R_{6c})$, and $R_{6c}$ is hydrogen or halo.

Embodiment 32: The compound of any one of Embodiments 1-31, or a pharmaceutically acceptable salt thereof, wherein W is $C(R_{6c})$, and $R_{6c}$ is halo.

Embodiment 33: The compound of any one of Embodiments 1-32, or a pharmaceutically acceptable salt thereof, wherein X is a 4- to 7-membered heterocyclyl.

Embodiment 34: The compound of any one of Embodiments 1-32, or a pharmaceutically acceptable salt thereof, wherein X is a 4- to 7-membered heterocyclyl substituted with 1 to 4 substituents, wherein each substituent is independently selected from the group consisting of cyano, $C_{1-6}$ alkyl, $C_{1-6}$ cyanoalkyl, and $C_{1-6}$ haloalkyl.

Embodiment 35: The compound of any one of Embodiments 1-32, or a pharmaceutically acceptable salt thereof, wherein X is selected from the group consisting of:

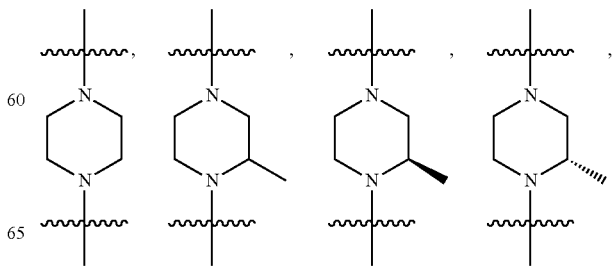

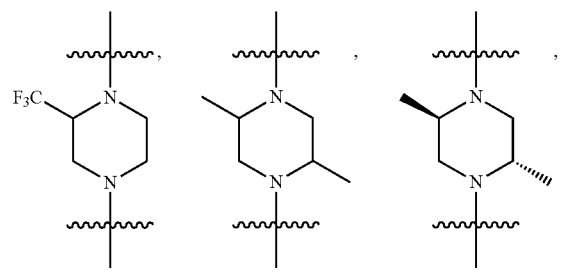
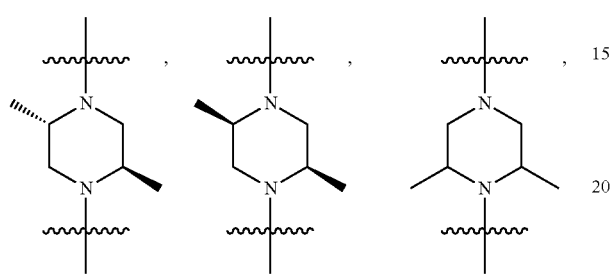
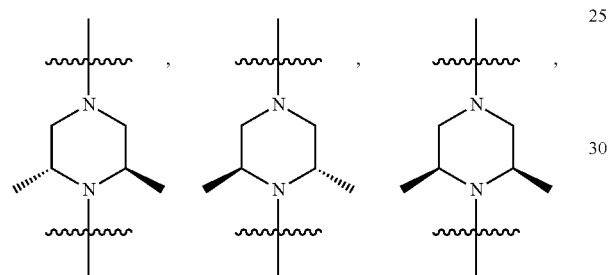
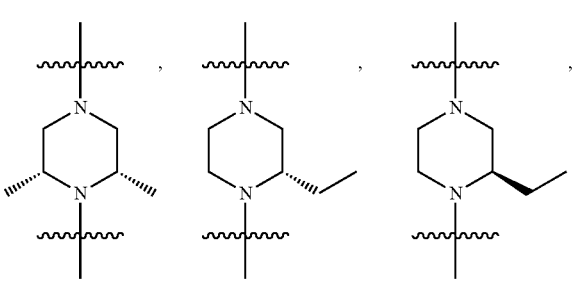
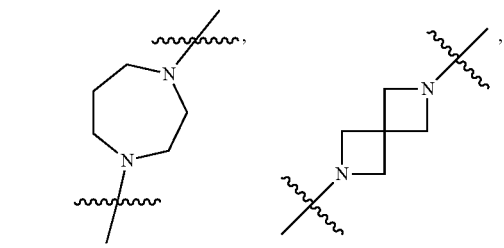
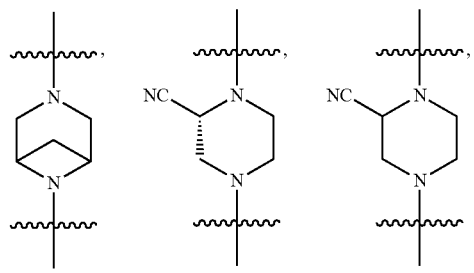
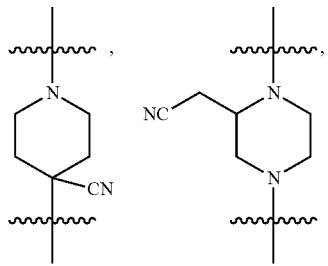
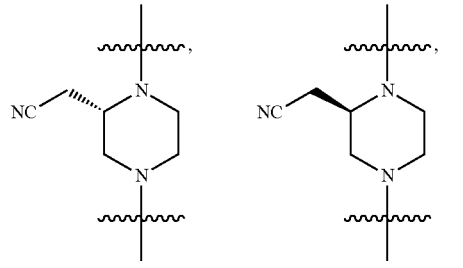
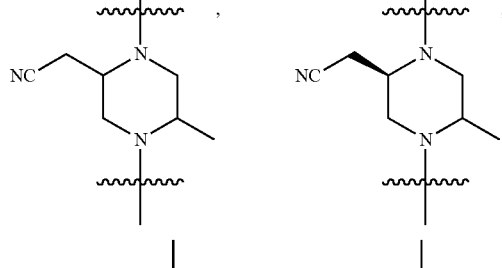
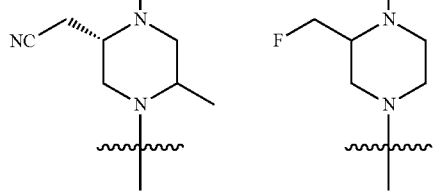
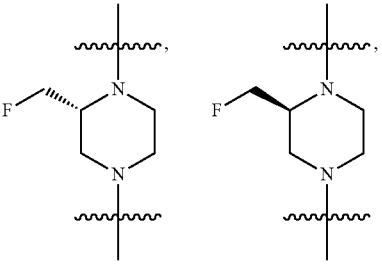
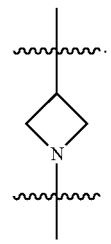
Embodiment 36: The compound of any one of Embodiments 1-32, or a pharmaceutically acceptable salt thereof, wherein X is selected from the group consisting of:

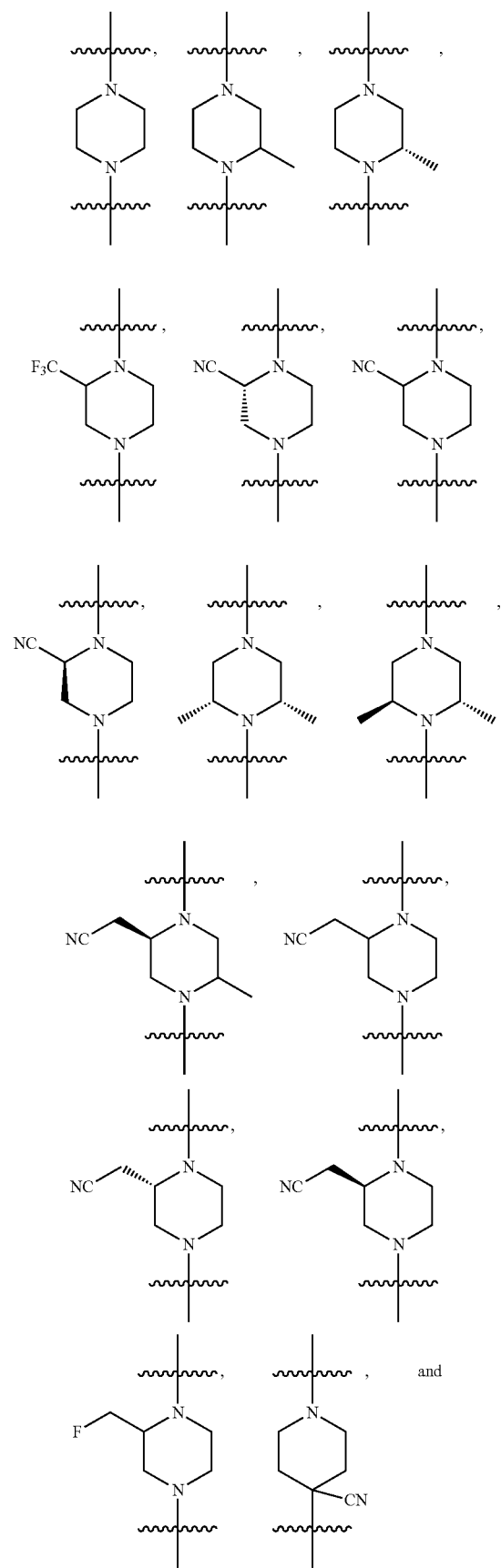
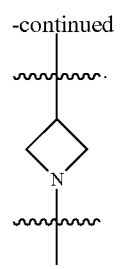
Embodiment 37: The compound of any one of Embodiments 1-32, or a pharmaceutically acceptable salt thereof, wherein X is selected from the group consisting of:
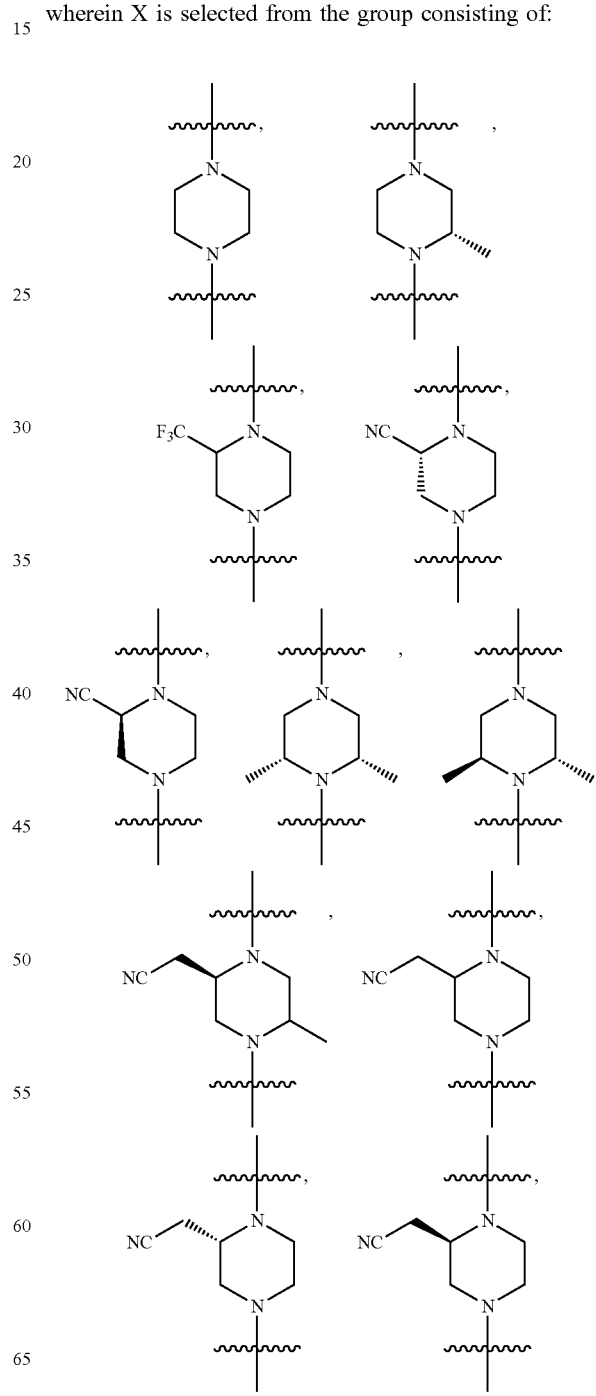

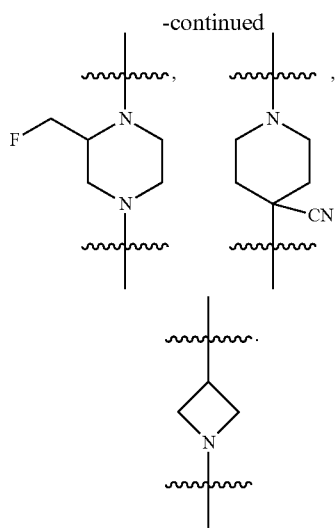

Embodiment 38: The compound of any one of Embodiments 1-32, or a pharmaceutically acceptable salt thereof, wherein X is

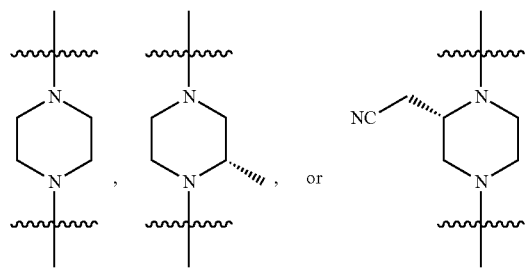

Embodiment 39: The compound of any one of Embodiments 1-38, or a pharmaceutically acceptable salt thereof, wherein n is 0.

Embodiment 40: The compound of Embodiment 1 or 17, or a pharmaceutically acceptable salt thereof, wherein $R_1$ is selected from the group consisting of:

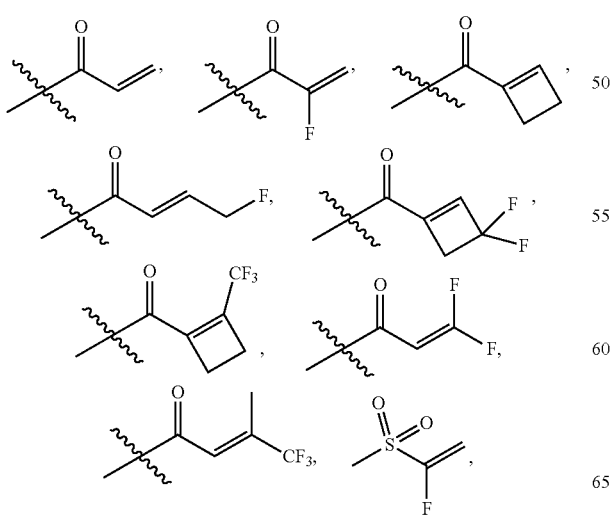

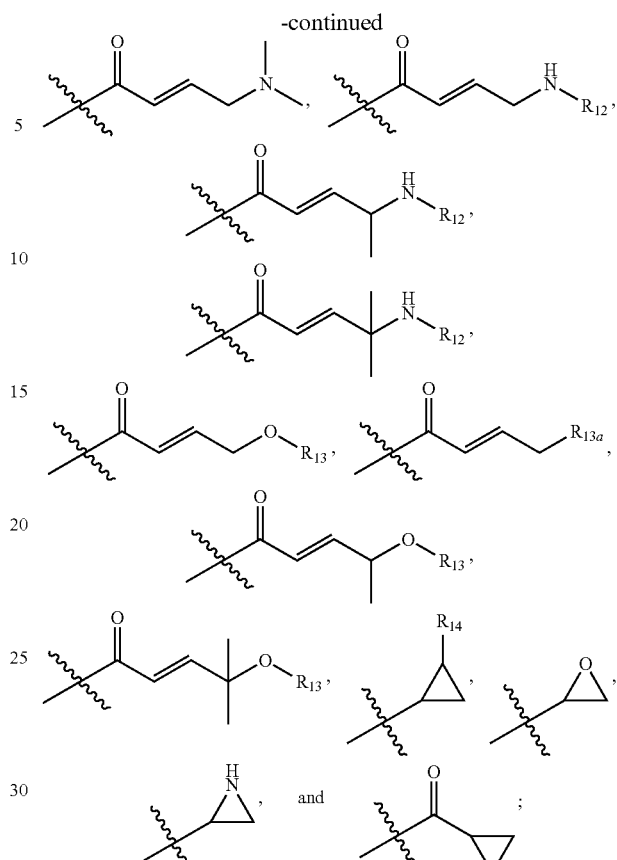

wherein:
$R_{12}$ is selected from the group consisting of $C_{1-6}$ alkanoyl, $C_{1-6}$ alkyl, and $C_{1-6}$ alkylsulfonyl;
$R_{13}$ is selected from the group consisting of H, $C_{1-6}$ alkyl and $C_{1-6}$ haloalkyl;
$R_{13a}$ is halo; and
$R_{14}$ is halo.

Embodiment 41: The compound of Embodiment 40, or a pharmaceutically acceptable salt thereof, wherein $R_1$ is selected from the group consisting of:

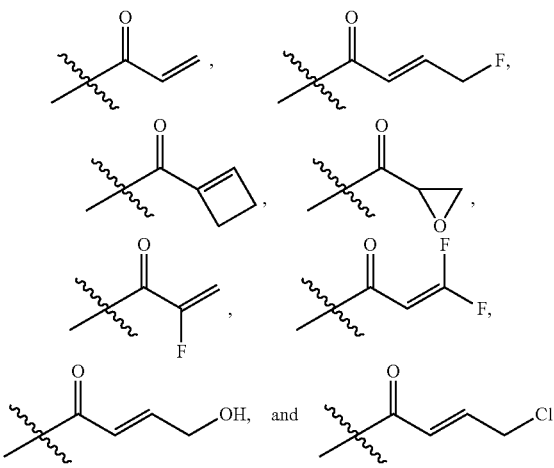

Embodiment 42: The compound of Embodiment 41, or a pharmaceutically acceptable salt thereof, wherein $R^1$ is

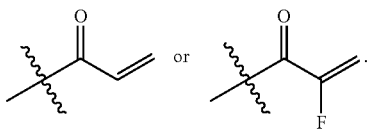

Embodiment 43: The compound of Embodiment 2, or a pharmaceutically acceptable salt thereof, wherein $R_7$ is selected from the group consisting of H, cyano, and halo; and $R_8$ and $R_9$ are each independently selected from the group consisting of H, $C_{1-6}$ alkyl, $C_{1-6}$ haloalkyl, $C_{1-6}$ hydroxyalkyl, cyano, and halo; wherein $C_{1-6}$ alkyl is optionally substituted with one substituent selected from the group consisting of: methanesulfonyl (mesyl), p-toluenesulfonyl (tosyl), an alkyl or aryl sulfonate leaving group, $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy.

Embodiment 44: The compound of Embodiment 1 or 17, or a pharmaceutically acceptable salt thereof, having a Formula selected from the group consisting of:

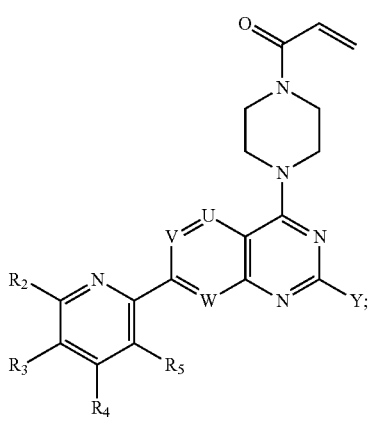

(Ia)

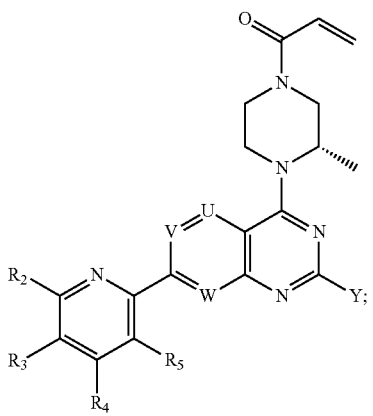

(Ib)

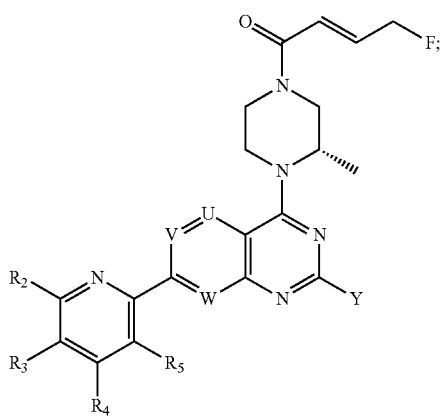

(Ic)

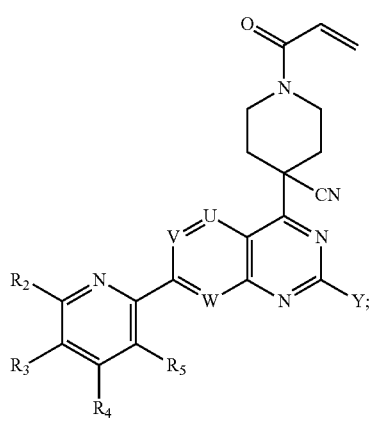

(Id)

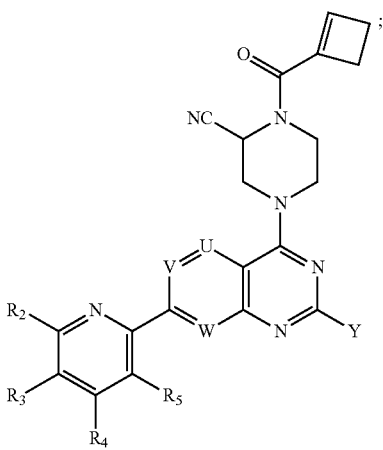

(Ie)

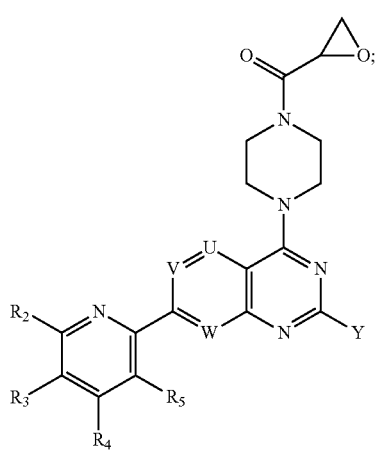
(If)
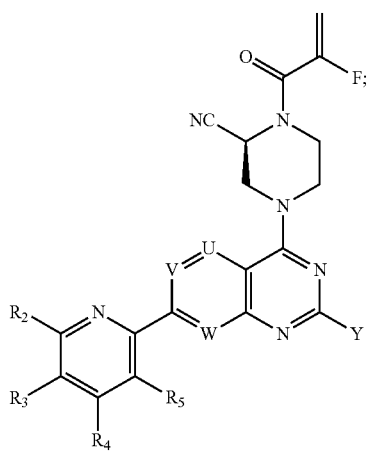
(Ii)
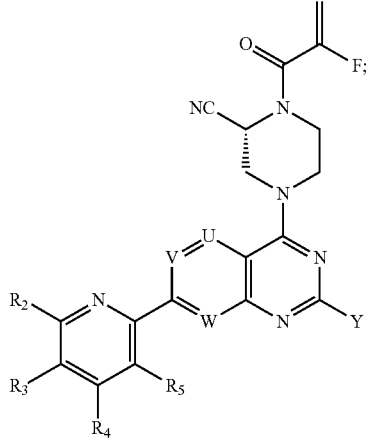
(Ij)
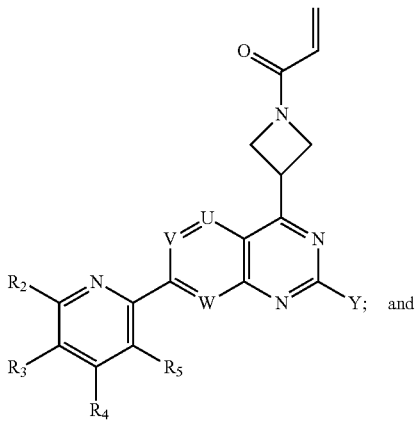
(Ik)
(Ig)
(Ih)

-continued

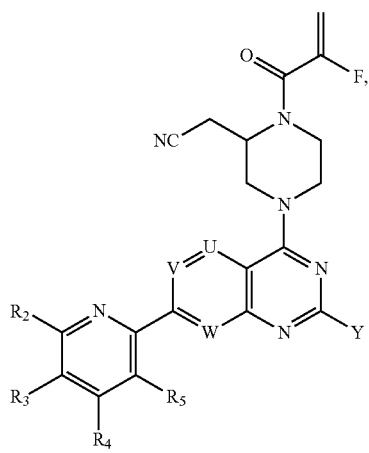

(II)

or a pharmaceutically acceptable salt thereof.

Embodiment 45: The compound of Embodiment 44, or a pharmaceutically acceptable salt thereof, having a Formula selected from the group consisting of Formula (Ib) or (II).

Embodiment 46: The compound of any one of Embodiments 17-41, wherein the compound of formula (IV) comprises formula selected from the group consisting of:

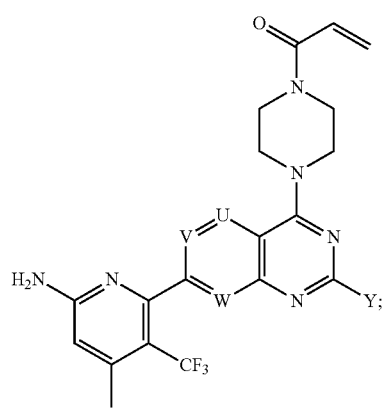

(IVa)

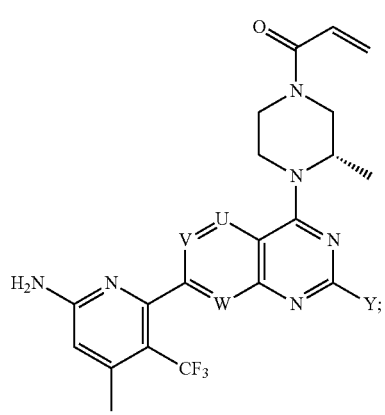

(IVb)

-continued

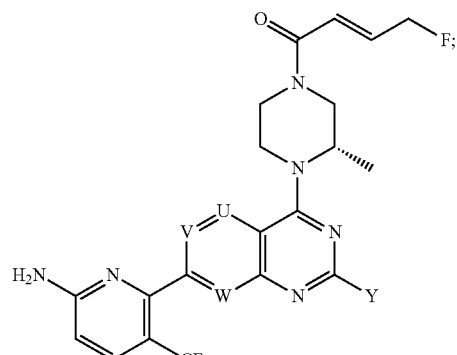

(IVc)

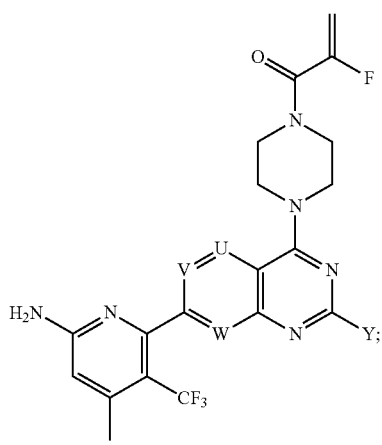

(IVd)

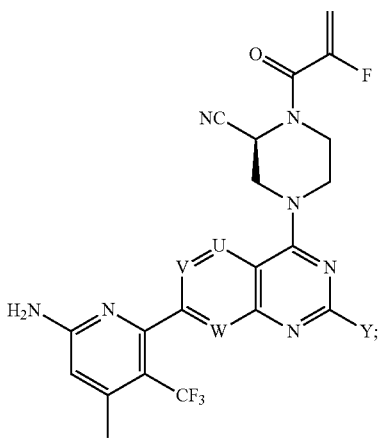

(IVe)

-continued

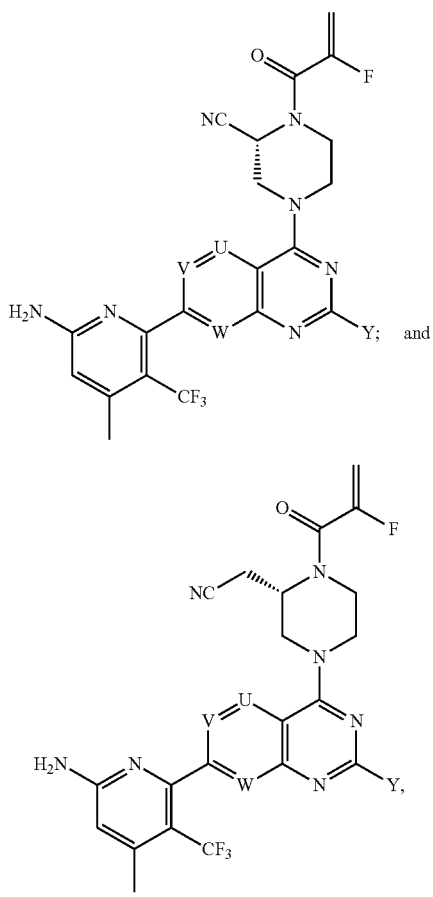

or a pharmaceutically acceptable salt thereof.

Embodiment 47: The compound of Embodiment 46, wherein the compound of formula (IV) comprises a compound of formula (IVa), (IVb), (IVd), or (IVg), or a pharmaceutically acceptable salt thereof.

Embodiment 48: The compound of Embodiment 46, wherein the compound of formula (IV) comprises a compound of formula (IVa) or (IVb), or a pharmaceutically acceptable salt thereof.

Embodiment 49: The compound of Embodiment 46, wherein the compound of formula (IV) comprises a compound of formula (IVd) or (IVg), or a pharmaceutically acceptable salt thereof.

Embodiment 50: The compound of Embodiment 2, or a pharmaceutically acceptable salt thereof, wherein $R_7$ and $R_8$ together form a triple bond between the carbons to which they are attached, or $R_7$ and $R_8$ together with the carbons to which they are each bonded form a $C_{3-7}$ cycloalkenyl optionally substituted with one or two halo substituents; and $R_9$ is selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy.

Embodiment 51: The compound of Embodiment 2, or a pharmaceutically acceptable salt thereof, wherein $R_7$, $R_8$, and $R_9$ are each H.

Embodiment 52: A compound or a pharmaceutically acceptable salt thereof as provided in Table 1.

Embodiment 53: A pharmaceutical composition comprising the compound of any one of Embodiments 1-52, or a pharmaceutically acceptable salt thereof, and a pharmaceutically acceptable excipient.

Embodiment 54: The pharmaceutical composition of Embodiment 53, wherein the pharmaceutical composition is formulated for oral administration.

Embodiment 55: The pharmaceutical composition of Embodiment 53, wherein the pharmaceutical composition is formulated for injection.

Embodiment 56: A method of treating cancer comprising administering to an individual in need thereof a therapeutically effective amount of the compound of any one of Embodiments 1-52, or a pharmaceutically acceptable salt thereof, or the pharmaceutical composition of any one of Embodiments 53-55.

Embodiment 57: The method of Embodiment 56, wherein the individual is a human.

Embodiment 58: The method of Embodiment 55 or 56, wherein the administering is via the oral route.

Embodiment 59: The method of Embodiment 55 or 56, wherein the administering is via injection.

Embodiment 60: The method of any one of Embodiments 56-59, wherein the cancer is mediated by a K-Ras G12C mutation.

Embodiment 61: The method of any one of Embodiments 56-60, wherein the cancer is a hematological cancer, pancreatic cancer, MYH associated polyposis, colorectal cancer or lung cancer.

Embodiment 62: The method of any one of Embodiments 56-61, wherein the cancer is lung adenocarcinoma.

Embodiment 63: A method for regulating activity of a K-Ras G12C mutant protein, the method comprising reacting the mutant protein with the compound of any one of Embodiments 1-52, or a pharmaceutically acceptable salt thereof.

Embodiment 64: A method for inhibiting proliferation of a cell population, the method comprising contacting the cell population with the compound of any one of Embodiments 1-52, or a pharmaceutically acceptable salt thereof.

Embodiment 65: The method of Embodiment 64, wherein the inhibition of proliferation is measured as a decrease in cell viability of the cell population.

Embodiment 66: A method for treating a disorder mediated by a K-Ras G12C mutation in an individual in need thereof, the method comprising:
  determining if the individual has the mutation; and
  if the individual is determined to have the mutation, then administering to the individual a therapeutically effective amount of the compound of any one of Embodiments 1-52, or a pharmaceutically acceptable salt thereof, or the pharmaceutical composition of any one of Embodiments 53-55.

Embodiment 67: The method of Embodiment 66, wherein the disorder is a cancer.

Embodiment 68: The method of Embodiment 67, wherein the cancer is a hematological cancer, pancreatic cancer, MYH associated polyposis, colorectal cancer or lung cancer.

Embodiment 69: The method of Embodiment 66, wherein the cancer is a lung cancer, colorectal cancer, appendicial cancer, or pancreatic cancer.

Embodiment 70: The method of any one of Embodiments 66-69, wherein the cancer is lung adenocarcinoma.

Embodiment 71: A method for preparing a labeled K-Ras G12C mutant protein, the method comprising reacting a K-Ras G12C mutant protein with a labeled compound of any one of Embodiments 1-52, or a pharmaceutically acceptable salt thereof, to result in the labeled K-Ras G12C mutant protein.

Embodiment 72: A method for inhibiting tumor metastasis comprising administering to an individual in need thereof a therapeutically effective amount of the compound of any one of Embodiments 1-52, or a pharmaceutically acceptable salt thereof, or the pharmaceutical composition of any one of Embodiments 53-55 to a subject in need thereof.

Embodiment 73: Use of a compound of any one of Embodiments 1-52, or a pharmaceutically acceptable salt thereof, in the manufacture of a medicament for treating cancer.

Embodiment 74: The use of Embodiment 73, wherein the medicament is formulated for oral administration.

Embodiment 75: The use of Embodiment 73, wherein the medicament is formulated for injection.

Embodiment 76: The use of any one of Embodiments 73-75, wherein the cancer is mediated by a K-Ras G12C mutation.

Embodiment 77: The use of any one of Embodiments 73-76, wherein the cancer is a hematological cancer, pancreatic cancer, MYH associated polyposis, colorectal cancer or lung cancer.

Embodiment 78: The use of any one of Embodiments 73-76, wherein the cancer is a lung cancer, colorectal cancer, appendicial cancer, or pancreatic cancer.

Embodiment 79: The use of any one of Embodiments 73-78, wherein the cancer is lung adenocarcinoma.

Embodiment 80: Use of a compound of any one of Embodiments 1-52, or a pharmaceutically acceptable salt thereof, in the manufacture of a medicament for inhibiting tumor metastasis.

Embodiment 81: The compound of any one of Embodiments 1-52, or a pharmaceutically acceptable salt thereof, or the pharmaceutical composition of any one of Embodiments 53-55, for use in a method of treatment of the human or animal body by therapy.

Embodiment 82: The compound of any one of Embodiments 1-52, or a pharmaceutically acceptable salt thereof, or the pharmaceutical composition of any one of Embodiments 53-55, for use in a method of treating cancer.

Embodiment 83: The compound, pharmaceutically acceptable salt thereof, or pharmaceutical composition of Embodiment 82, wherein the cancer is mediated by a K-Ras G12C mutation.

Embodiment 84: The compound, pharmaceutically acceptable salt thereof, or pharmaceutical composition of Embodiment 82 or 83, wherein the cancer is a hematological cancer, pancreatic cancer, MYH associated polyposis, colorectal cancer or lung cancer.

Embodiment 85: The compound, pharmaceutically acceptable salt thereof, or pharmaceutical composition of Embodiment 82 or 83, wherein the cancer is a lung cancer, colorectal cancer, appendicial cancer, or pancreatic cancer.

Embodiment 86: The compound, pharmaceutically acceptable salt thereof, or pharmaceutical composition of any one of Embodiments 82-85, wherein the cancer is lung adenocarcinoma.

Embodiment 87: The compound of any one of Embodiments 1-52, or a pharmaceutically acceptable salt thereof, or the pharmaceutical composition of any one of Embodiments 53-55 for use in a method of inhibiting tumor metastasis.

EXAMPLES

The following examples illustrate the preparation and biological evaluation of compounds within the scope of the invention. These examples and preparations which follow are provided to enable those skilled in the art to more clearly understand to practice the present invention. They should not be considered as limiting the scope of the invention, but merely as being illustrative and representative thereof.

The following abbreviations are used in the Examples:
ACN—acetonitrile
$Ac_2O$—acetyl acetate
BINAP—(+/−)-2,2'-bis(diphenylphosphino)-1,1'-binaphthyl
$Boc_2O$—di-tert-butyl dicarbonate
BOP—(benzotriazol-1-yloxy)tris(dimethylamino)phosphonium hexafluorophosphate
$CH_3Ti(O_i$—$Pr)_3$—methyltitanium(IV) triisopropoxide
DBU—1,8-diazabicyclo[5.4.0]undec-7-ene
DCE—1,2-dichloroethane
DCM—dichloromethane
DIEA or DIPEA—N,N-diisopropylethylamine
DMA—N,N-dimethylacetamide
DMAc—N,N-dimethylacetamide
DMAP—4-dimethylaminopyridine
DMF—N,N-dimethylformamide
DMSO—dimethyl sulfoxide
EA—ethyl acetate
EtOAc—ethyl acetate
EtOH—ethanol
HATU—2-(7-azabenzotriazol-1-yl)-N,N,N',N'-tetramethyluronium hexafluorophosphate
HFIP—hexafluoroisopropanol
HOAc—acetic acid
iPrOAc—isopropyl acetate
KF—potassium fluoride
KOAc—potassium acetate
LDA—lithium diisopropylamide
LiHMDS—lithium bis(trimethylsilyl)amide
LCMS—a
mCPBA—3-chloroperoxybenzoic acid
MeCN—acetonitrile
MeI—iodomethane
MeOH—methanol
MeONa—sodium methoxide or sodium methanolate
MTBE—methyl tert-butyl ether
MW—microwave
$NaBH(OAc)_3$—sodium triacetoxyborohydride
NIS—N-iodosuccinimide
$P(Cy)_3$ or $PCy_3$—tricyclohexylphosphine
$P(t-Bu)_3HBF_4$—tri-tert-butylphosphonium tetrafluoroborate
Pd/C—palladium on carbon
$Pd_2(dba)_3$—tris(dibenzylideneacetone)dipalladium(0)
$Pd_2(dba)_3CHCl_3$—tris(dibenzylidenacetone)dipalladium (0) chloroform
$Pd(dppf)Cl_2 \cdot CH_2Cl_2$-[1,1'-bis(diphenylphosphino)ferrocene]dichloropalladium(II) or dichloro[1,1-bis(diphenylphosphino)ferrocene]palladium(II), complexed with dichloromethane
$Pd(PPh_3)_4$—tetrakis(triphenylphosphine)palladium(0)
$Pd(PPh_3)_2Cl_2$—bis(triphenylphosphine)palladium(II) dichloride
PE—petroleum ether
PMBCl—4-methoxybenzylchloride
pTsA—p-toluenesulfonic acid
r.t.—room temperature
$Sn_2(n-Bu)_6$—hexabutylditin
TBSCl—tert-butyldimethylsilyl chloride or tert-butyldimethylchlorosilane

[Rh(COD)Cl]₂—chloro(1,5-cyclooctadiene)rhodium(I) dimer
TEA—triethylamine
TFA—trifluoroacetic acid or 2,2,2-trifluoroacetic acid
THF—tetrahydrofuran
THP—tetrahydropyran
TsOH—p-toluenesulfonic acid Compound Examples Intermediate 1: tert-butyl 4-(7-bromo-6-chloroquinazolin-4-yl)piperazine-1-carboxylate Intermediate tert-butyl 4-(7-bromo-6-chloroquinazolin-4-yl)piperazine-1-carboxylate was prepared according to the following synthetic scheme:

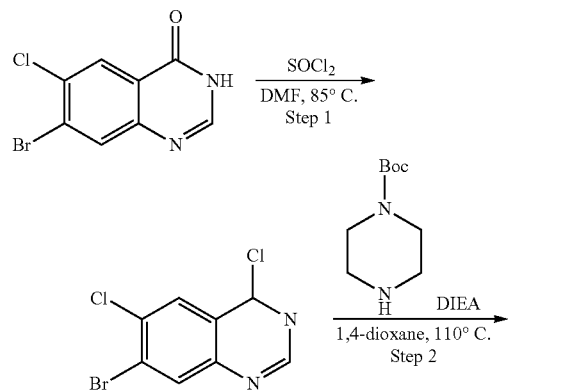

Step 1

7-bromo-4,6-dichloroquinazoline

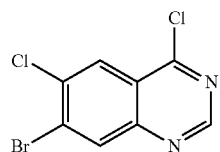 [SMILES: Clc1cc2c(Cl)ncnc2cc1Br]

To a solution of 7-bromo-6-chloro-3,4-dihydroquinazolin-4-one (330 g, 1.28 mol) in thionyl chloride (4.0 L) was added N,N-dimethylformamide (4 mL). The mixture was stirred for 12 h at 80° C. After completion, the resulting mixture was concentrated under vacuum to give 7-bromo-4,6-dichloroquinazoline (350 g, crude) as a yellow solid. LCMS (ESI, m/z): 277.1 [M+H]⁺.

Step 2: tert-butyl 4-(7-bromo-6-chloroquinazolin-4-yl)piperazine-1-carboxylate

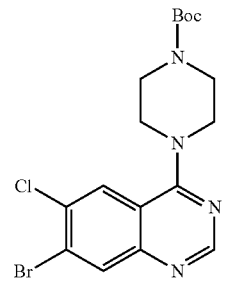 [SMILES: CC(C)(C)OC(=O)N1CCN(c2ncnc3cc(Br)c(Cl)cc23)CC1]

A solution of 7-bromo-4,6-dichloroquinazoline (330 g, 1.20 mol), tert-butyl piperazine-1-carboxylate (340 g, 1.80 mol, 1.50 equiv) and DIPEA (586 mL, 3.60 mol) in 1,4-dioxane (3.0 L) was stirred for 60 min at 110° C. After completion, the solids were collected by filtration, washed with PE (500 mL) and water (500 mL) and then dried to afford tert-butyl 4-(7-bromo-6-chloroquinazolin-4-yl)piperazine-1-carboxylate (446 g, 87.4%) as a light yellow solid.
¹H NMR (400 MHz, CDCl₃) δ 8.71 (s, 1H), 8.22 (s, 1H), 7.95 (s, 1H), 3.76 (dd, J=6.2, 3.7 Hz, 4H), 3.65 (dd, J=6.4, 3.8 Hz, 4H), 1.50 (s, 9H). LCMS (ESI, m/z): 429.2 [M+H]⁺.

Intermediate 2: 2((2R)-5-methylpiperizin-2-yl)acetonitrile

Intermediate compound 2((2R)-5-methylpiperizin-2-yl)acetonitrile was prepared according to the following reaction scheme:

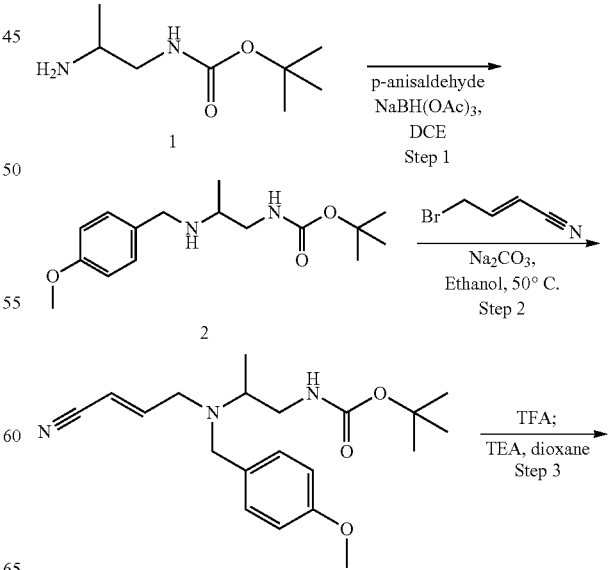

-continued

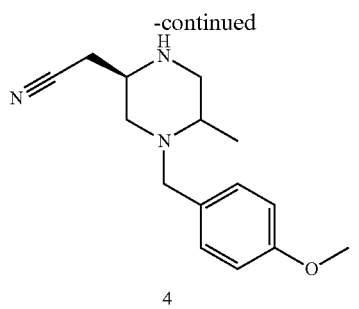

4

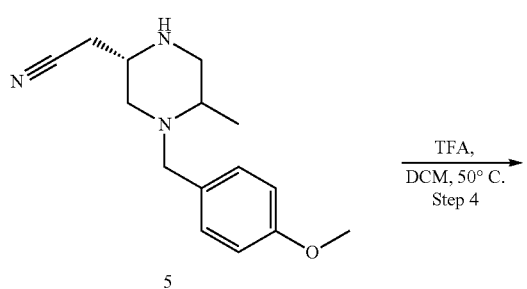

5

TFA,
DCM, 50° C.
Step 4

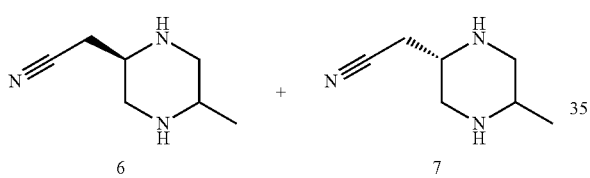

6       7

Step 1: tert-butyl (2-((4-methoxybenzyl)amino)propyl)carbamate

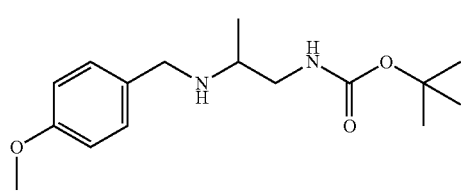 [SMILES: COc1ccc(CNC(C)CNC(=O)OC(C)(C)C)cc1]

To a solution of tert-butyl N-(2-aminopropyl)carbamate (8.3 g, 47.6 mmol) and p-anisaldehyde (5.8 mL, 47.6 mmol) in 1,2-dichloroethane (175 mL) was added sodium triacetoxyborohydride (15 g, 71.5 mmol). The reaction mixture was stirred at r.t. for 18 hours. The reaction was diluted with DCM then washed with sat·Na₂CO₃. The organic layers was dried with sodium sulfate, filtered, and concentrated via rotovap. The crude product was purified by flash chromatography on silica (eluting with iPrOAc/Hep) to give tert-butyl (2-((4-methoxybenzyl)amino)propyl)carbamate (10.2 g, 71%). LCMS (ESI, m/z): 295.5 [M+H]$^+$.

Step 2: tert-butyl (E)-(2-((3-cyanoallyl)(4-methoxybenzyl)amino)propyl)carbamate

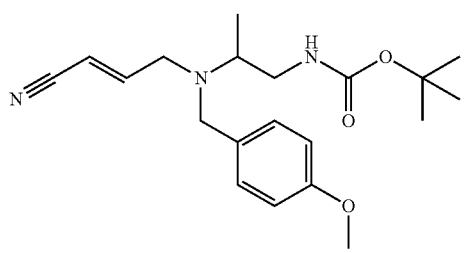 [SMILES: COc1ccc(CN(C/C=C/C#N)C(C)CNC(=O)OC(C)(C)C)cc1]

To a solution of tert-butyl (2-((4-methoxybenzyl)amino)propyl)carbamate (2.9 g, 9.8 mmol), (E)-4-bromobut-2-enenitrile (1.2 mg, 8.22 mmol) and sodium carbonate (2.8 g, 26.3 mmol) in ethanol (30 mL) was stirred at 50° C. for 18 hours. The reaction was concentrated then diluted in EtOAc. The organic layer was washed with water. The organic layers was dried with sodium sulfate, filtered, and concentrated via rotovap. The crude product was purified by flash chromatography on silica (eluting with iPrOAc/Hep) then (eluting with MeOH/DCM)) to give tert-butyl (E)-(2-((3-cyanoallyl)(4-methoxybenzyl)amino)propyl)carbamate. LCMS (ESI, m/z): 360.6 [M+H]$^+$.

Step 3: 2-((2R)-4-(4-methoxybenzyl)-5-methylpiperazin-2-yl)acetonitrile and 2-((2S)-4-(4-methoxybenzyl)-5-methylpiperazin-2-yl)acetonitrile

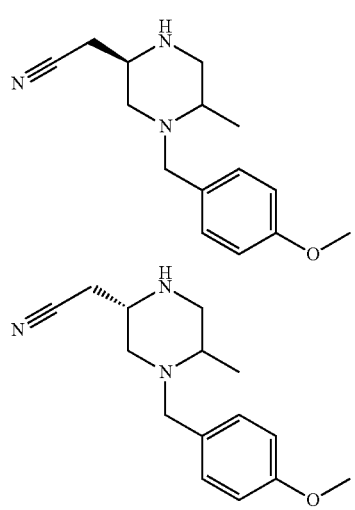

A solution of tert-butyl (E)-(2-((3-cyanoallyl)(4-methoxybenzyl)amino)propyl)carbamate (2.3 g, 6.4 mmol) in 5% trifluoroacetic acid in hexafluoro-2-propanol (75 mL, 49.3 mmol) was stirred r.t. for 18 hours. The reaction was concentrated then added 1,4-dioxane (80 mL) and triethylamine (5.75 mL, 41.1 mmol). The reaction mixture was stirred at r.t. for 60 minutes. The crude product was concentrated and purified by HPLC (NH₄OH 5-50%) to give 2-((2R)-4-(4-methoxybenzyl)-5-methylpiperazin-2-yl)acetonitrile as HPLC peak 1 (1.05 g, 49%) and 2-((2S)-4-(4-methoxybenzyl)-5-methylpiperazin-2-yl)acetonitrile as HPLC peak 2 (0.76 g, 35%). Stereochemistry was arbitrary assigned. LCMS (ESI, m/z): 260.1 [M+H]$^+$.

Step 4: 2-((2R)-5-methylpiperazin-2-yl)acetonitrile and 2-((2S)-5-methylpiperazin-2-yl)acetonitrile

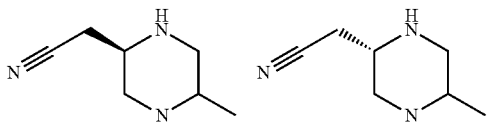

To a solution of 2-((2R)-4-(4-methoxybenzyl)-5-methylpiperazin-2-yl)acetonitrile (600 mg, 2.313 mmol) in dichloromethane (10 mL) was added trifluoroacetic acid (17.5 mL, 231.3 mmol). The reaction mixture was stirred at 50° C. for 48 hours. The reaction was concentrated and the crude product was carried to next step. LCMS (ESI, m/z): 140.1 [M+H]$^+$.

Intermediate 3: tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate The compound tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate was prepared according to the following synthetic scheme:

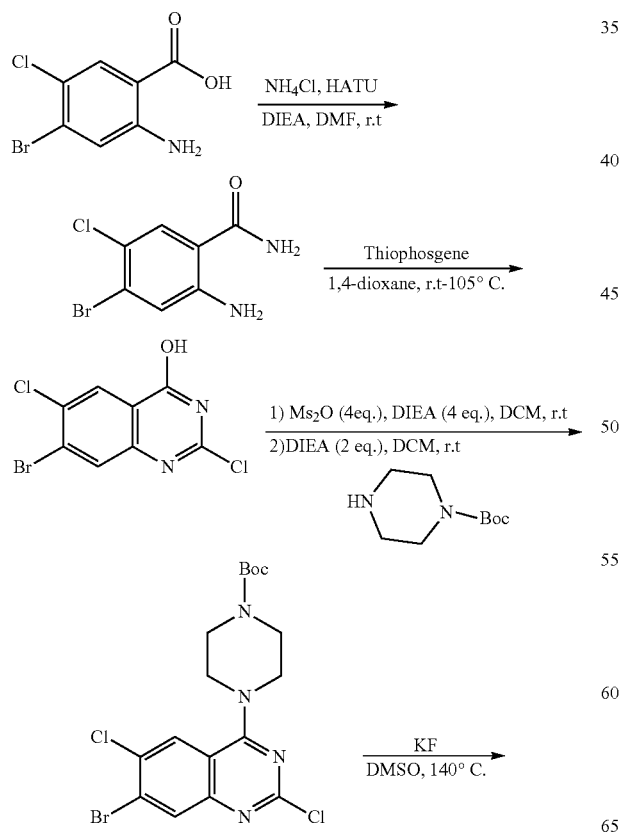

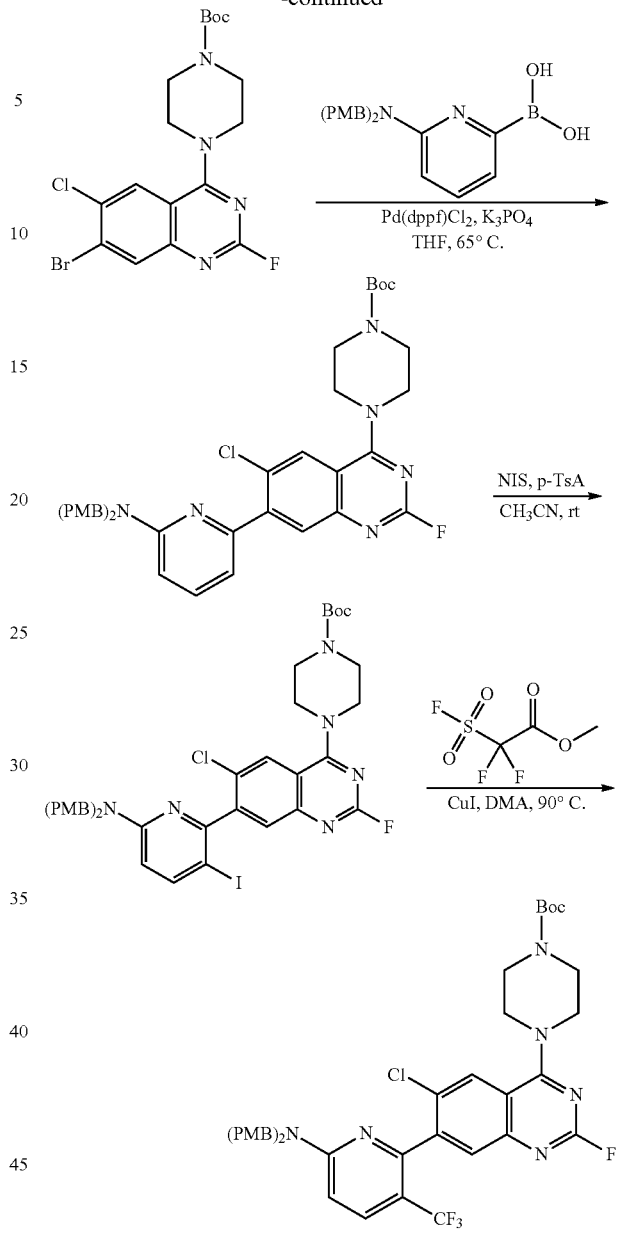

Step 1: 2-amino-4-bromo-5-chloro-benzamide

A solution of 2-amino-4-bromo-5-chlorobenzoic acid (10.0 g, 39.92 mmol), N,N-diisopropylethylamine (15.45 g, 119.77 mmol) and ammonium chloride (6.41 g, 119.77 mmol) in N,N-dimethylformamide (50 mL) was stirred at room temperature for 5 minutes. Then HATU (18.22 g, 47.91 mmol) was added and stirred at room temperature for 2 hours. After completion, the reaction was quenched with water. The reaction mixture was filtrated, and the filter cake was collected and dried under vacuum to afford 2-amino-4-bromo-5-chloro-benzamide (8 g, 32.0 mmol, 80.3% yield) as a yellow solid. LCMS (ESI, m/z): 248.9 [M+H]+.

Step 2: 7-bromo-2, 6-dichloro-quinazolin-4-ol

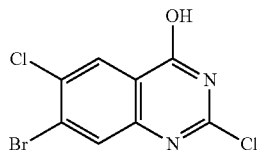 [SMILES: Oc1nc(Cl)nc2cc(Br)c(Cl)cc12]

A solution of 2-amino-4-bromo-5-chloro-benzamide (20.0 g, 80.16 mmol) in 1, 4-dioxane (100 mL) was followed by the addition of thiophosgene (20.3 g, 176.52 mmol) dropwise with stirring. The resulting solution was stirred for 1 hour at room temperature then stirred for 1 hour at 105° C. After completion, the resulting solution was concentrated under vacuum. The organic layer was washed with diethyl ether to afford 7-bromo-2, 6-dichloro-quinazolin-4-ol (20 g, 68.043 mmol, 84.9% yield) as a brown solid. LCMS (ESI, m/z): 292.9 [M+H]+.

Step 3: tert-butyl 4-(7-bromo-2, 6-dichloro-quinazolin-4-yl)piperazine-1-carboxylate

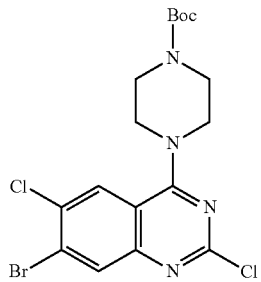 [SMILES: CC(C)(C)OC(=O)N1CCN(c2nc(Cl)nc3cc(Br)c(Cl)cc23)CC1]

A solution of 7-bromo-2,6-dichloro-quinazolin-4-ol (15.0 g, 51.03 mmol), methanesulfonic anhydride (35.6 g, 204.11 mmol) and N,N-diisopropylethylamine (26.3 g, 203.88 mmol) in dichloromethane (200 mL) was stirred at 25° C. for 0.5 hour. Then tert-butyl 1-piperazinecarboxylate (14.2 g, 76.24 mmol) and N,N-diisopropylethylamine (13.2 g, 102.33 mmol) was added and stirred at 25° C. for 2 hours. After completion, the resulting solution was diluted with ethyl acetate and washed with water. The organic layer was dried over anhydrous sodium sulfate and concentrated under vacuum. The residue was purified by flash chromatography on silica gel eluting with ethyl acetate/petroleum ether (1/6) to afford tert-butyl 4-(7-bromo-2,6-dichloro-quinazolin-4-yl)piperazine-1-carboxylate (13 g, 28.13 mmol, 55.1% yield) as a yellow solid. LCMS (ESI, m/z): 461.0 [M+H]+.

Step 4: tert-butyl 4-(7-bromo-6-chloro-2-fluoro-quinazolin-4-yl)piperazine-1-carboxylate

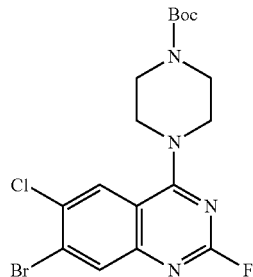 [SMILES: CC(C)(C)OC(=O)N1CCN(c2nc(F)nc3cc(Br)c(Cl)cc23)CC1]

A solution of tert-butyl 4-(7-bromo-2,6-dichloro-quinazolin-4-yl)piperazine-1-carboxylate (15.6 g, 33.75 mmol) and KF (40.0 g, 688.47 mmol) in dimethyl sulfoxide (100 mL) was stirred at 140° C. for 4 hours. After completion, the reaction system was cooled to room temperature, diluted with water and extracted with ethyl acetate. Then the organic layers were combined, washed with brine, dried over anhydrous sodium sulfate and concentrated under vacuum. The residue was purified by flash chromatography on silica gel eluting with petroleum ether/ethyl acetate (3/1) to afford tert-butyl 4-(7-bromo-6-chloro-2-fluoro-quinazolin-4-yl)piperazine-1-carboxylate (10 g, 22.44 mmol, 66.5% yield) as a yellow solid. LCMS (ESI, m/z): 445.0 [M+H]+.

Step 5: tert-butyl 4-(7-(6-(bis(4-methoxybenzyl)amino)pyridin-2-yl)-6-chloro-2-fluoroquinazolin-4-yl)piperazine-1-carboxylate

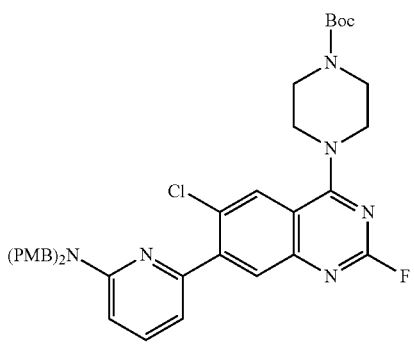

Under nitrogen, a solution of tert-butyl 4-(7-bromo-6-chloro-2-fluoro-quinazolin-4-yl)piperazine-1-carboxylate (50.0 g, 104.66 mmol), (6-(bis(4-methoxyphenyl)amino)pyridin-2-yl)boronic acid (90.0 g, 229.44 mmol), potassium phosphate (45.0 g, 212.26 mmol) and 1,1'-bis(diphenylphosphino)ferrocene-Palladium(II)dichloride (11.5 g, 15.73 mmol) in tetrahydrofuran (1.5 L) and water (300 mL) was stirred at 65° C. for 3 hours. After completion, the resulting solution was diluted with ethyl acetate and washed with water. The organic layer was dried over anhydrous sodium sulfate and concentrated under vacuum. The residue was purified by flash chromatography on silica gel eluting with ethyl acetate/petroleum ether (1/6) to afford tert-butyl 4-(7-(6-(bis(4-methoxybenzyl)amino)pyridin-2-yl)-6-chloro-2- fluoroquinazolin-4-yl)piperazine-1-carboxylate. (52 g, 69.77 mmol, 66.7% yield) as a yellow solid. LCMS (ESI, m/z): 713.3 [M+H]⁺.

Step 6: tert-butyl 4-(7-(6-(bis(4-methoxybenzyl)amino)-3-iodopyridin-2-yl)-6-chloro-2-fluoroquinazolin-4-yl)piperazine-1-carboxylate

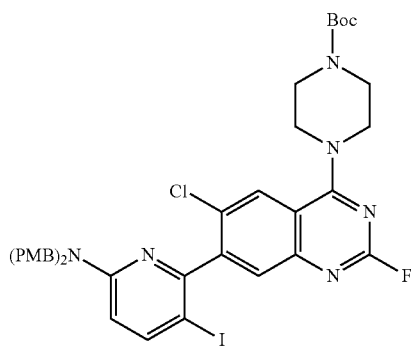

A solution of tert-butyl 4-(7-(6-(bis(4-methoxybenzyl)amino)pyridin-2-yl)-6-chloro-2-fluoroquinazolin-4-yl)piperazine-1-carboxylate (9.61 g, 12.9 mmol), N-iodosuccinimide (14.45 g, 64.49 mmol) and p-toluenesulfonic acid (0.09 g, 0.52 mmol) in acetonitrile (180 mL) was stirred at 25° C. for 24 hours. After completion, the resulting solution was diluted with ethyl acetate and washed with brine. The organic layer was dried over anhydrous sodium sulfate and concentrated under vacuum. The residue was purified by flash chromatography on silica gel eluting with ethyl acetate/petroleum ether (1/7) to afford tert-butyl 4-(7-(6-(bis(4-methoxybenzyl)amino)-3-iodopyridin-2-yl)-6-chloro-2-fluoroquinazolin-4-yl)piperazine-1-carboxylate (7.71 g, 8.85 mmol, 68.6% yield) as a yellow solid. LCMS (ESI, m/z): 839.2 [M+H]⁺.

Step 7: tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate

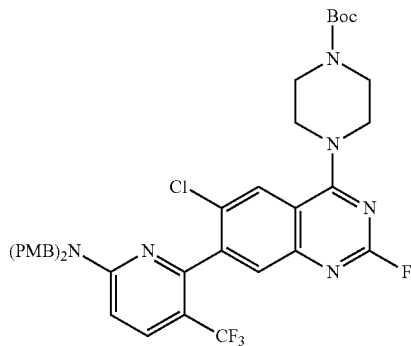

To a solution of tert-butyl 4-(7-(6-(bis(4-methoxybenzyl)amino)-3-iodopyridin-2-yl)-6-chloro-2-fluoroquinazolin-4-yl)piperazine-1-carboxylate (15.35 g, 17.62 mmol) and copper(I) iodide (40.17 g, 211.44 mmol) in N,N-dimethylacetamide (380 mL) was added methyl 2,2-difluoro-2-(fluorosulfonyl)acetate (84.63 g, 440.51 mmol) and stirred at 90° C. for 6 hours. After completion, the resulting solution was diluted with ethyl acetate and washed with brine. The organic layer was dried over anhydrous sodium sulfate and concentrated under vacuum. The residue was purified by flash chromatography on silica gel eluting with ethyl acetate/petroleum ether (1/5) to afford tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (11.8 g, 14.51 mmol, 82.3% yield) as a yellow solid. LCMS (ESI, m/z): 781.3 [M+H]⁺.

Intermediate 4: tert-butyl 4-(7-bromo-2,6-dichloroquinazolin-4-yl)piperazine-1-carboxylate The compound tert-butyl 4-(7-bromo-2,6-dichloro-quinazolin-4-yl)piperazine-1-carboxylate was prepared according to the following synthetic scheme:

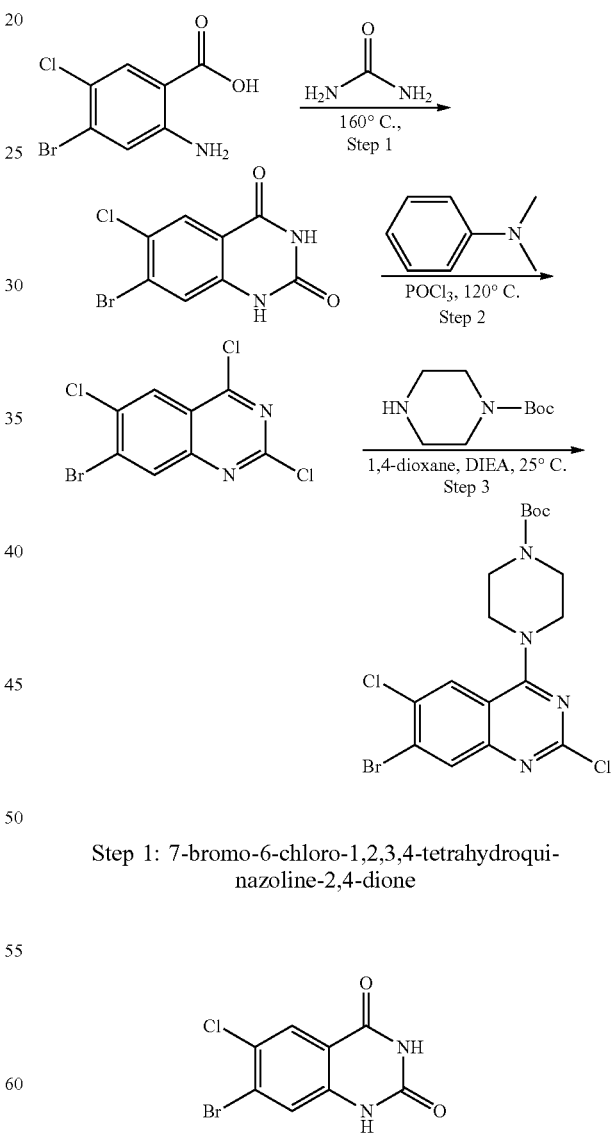

Step 1: 7-bromo-6-chloro-1,2,3,4-tetrahydroquinazoline-2,4-dione

Into a 3000-mL round-bottom flask was placed 2-amino-4-bromo-5-chlorobenzoic acid (200 g, 0.8 mol) and urea (720 g, 12 mol). The resulting solution was stirred at 160° C. for 12 hours. The mixture was cooled to 80° C. and quenched with water then refluxed for 5-10 minutes. The mixture was cooled to room temperature to form the precipitate. The solids were collected by filtration and washed with H₂O and dried under oven to afford 200 g (90%) of crude 7-bromo-6-chloro-1,2,3,4-tetrahydroquinazoline-2,4-dione as a yellow solid. The crude material was taken to the next step without further purification.

Step 2: 7-bromo-2,4,6-trichloroquinazoline

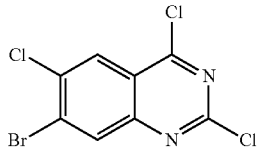 [SMILES: Clc1nc(Cl)c2cc(Cl)c(Br)cc2n1]

A solution of 7-bromo-6-chloro-1,2,3,4-tetrahydroquinazoline-2,4-dione (200 g, 0.72 mol) and N,N-dimethylaniline (264 g, 2.16 mol) in POCl₃ (750 mL) was stirred at 120° C. for 8 hours and concentrated under vacuum and taken to the next step without further purification.

Step 3: tert-butyl 4-(7-bromo-2,6-dichloro-quinazolin-4-yl)piperazine-1-carboxylate (Intermediate 4)

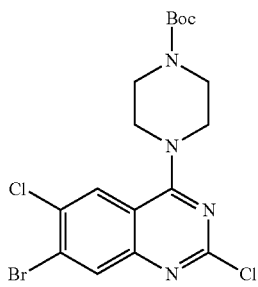 [SMILES: CC(C)(C)OC(=O)N1CCN(c2nc(Cl)nc3cc(Br)c(Cl)cc23)CC1]

A solution of 7-bromo-2,4,6-trichloroquinazoline (200 g, 0.64 mol), tert-butyl piperazine-1-carboxylate (178 g, 0.92 mol), and DIEA (3 equiv.) in 1,4-dioxane (2000 mL) was stirred at 25° C. for 8 hours. The resulting solution was diluted with 2000 ml of water then extracted with 3×3000 mL of ethyl acetate. The combined organic layer was washed with brine (1×100 mL), dried over anhydrous sodium sulfate, and concentrated under vacuum. The residue was purified by a silica gel column eluted with ethyl acetate/petroleum ether (1:10) to afford 126 g (43%) of tert-butyl 4-(7-bromo-2,6-dichloro-quinazolin-4-yl)piperazine-1-carboxylate as a yellow solid.

¹H NMR (400 MHz, DMSO-d₆) δ 8.20-8.14 (m, 1H), 8.16-8.10 (m, 1H), 3.95-3.87 (m, 4H), 3.60-3.52 (m, 4H), 1.44 (s, 9H). LCMS (ESI, m/z): 461.1 [M+H]⁺.

Intermediate 5: tert-butyl (S)-4-(7-bromo-2,6-dichloroquinazolin-4-yl)-3-methylpiperazine-1-carboxylate

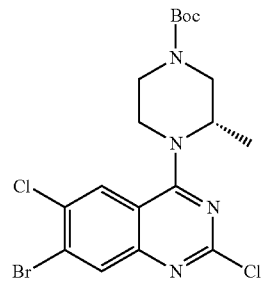 [SMILES: C[C@H]1CN(C(=O)OC(C)(C)C)CCN1c1nc(Cl)nc2cc(Br)c(Cl)cc12]

The compound tert-butyl (S)-4-(7-bromo-2,6-dichloroquinazolin-4-yl)-3-methylpiperazine-1-carboxylate (Intermediate 5) was prepared according to the protocol set forth for Intermediate 4, except in Step 3, tert-butyl (S)-3-methylpiperazine-1-carboxylate was used instead of tert-butyl piperazine-1-carboxylate.

Example 1

1-[4-[7-(3-amino-1-isoquinolyl)-6-chloro-quinazolin-4-yl]piperazin-1-yl]prop-2-en-1-one The compound 1-[4-[7-(3-amino-1-isoquinolyl)-6-chloro-quinazolin-4-yl]piperazin-1-yl]prop-2-en-1-one was prepared according to the following synthetic scheme:

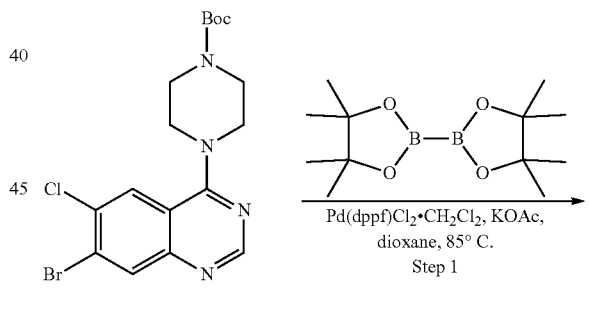

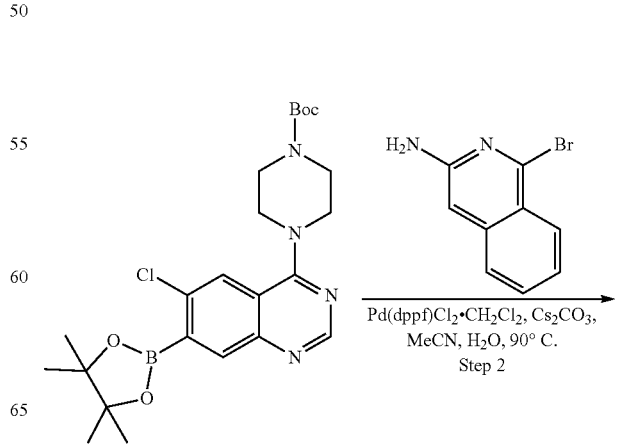

221
-continued

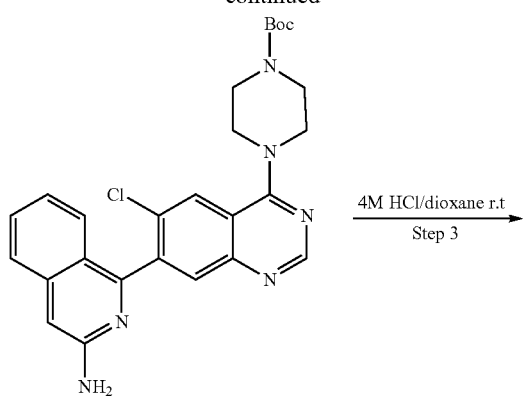

4M HCl/dioxane r.t
Step 3

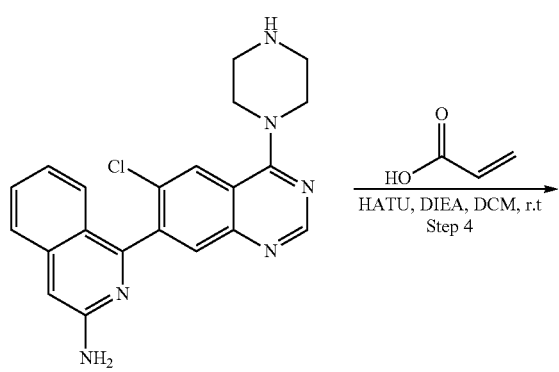

HATU, DIEA, DCM, r.t
Step 4

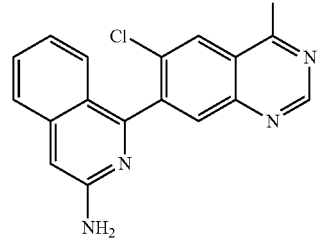

222

Step 1: tert-butyl 4-(6-chloro-7-(4,4,5,5-tetramethyl-1,3,2-dioxaborolan-2-yl)quinazolin-4-yl)piperazine-1-carboxylate

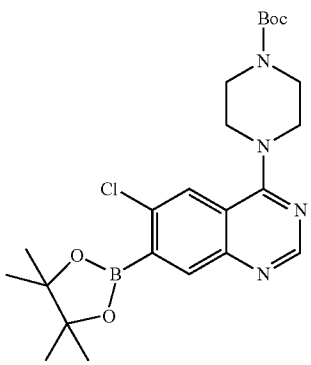 [SMILES: CC(C)(C)OC(=O)N1CCN(c2ncnc3cc(B4OC(C)(C)C(C)(C)O4)c(Cl)cc23)CC1]

To a solution of tert-butyl 4-(7-bromo-6-chloroquinazolin-4-yl)piperazine-1-carboxylate (550 mg, 1.29 mmol) and bis(pinacolato)diboron (733 mg, 2.83 mmol) in 1,4-dioxane (25.0 mL) was added potassium acetate (189.3 mg, 0.121 ml, 1.929 mmol) and [1,1'-bis(diphenylphosphino) ferrocene] dichloropalladium(II) (95.0 mg, 0.129 mmol). The reaction mixture was degassed then heated at 85° C. for 18 h. The reaction was filtered thru celite concentrated and the crude product was purified by flash chromatography on silica (eluting with MeOH/DCM) to give tert-butyl 4-(6-chloro-7-(4,4,5,5-tetramethyl-1,3,2-dioxaborolan-2-yl)quinazolin-4-yl)piperazine-1-carboxylate (514 mg, 84%). LCMS shows mass of boronic acid. LCMS (ESI, m/z): 393.1 [M+H]$^+$.

Step 2: tert-butyl 4-(7-(3-aminoisoquinolin-1-yl)-6-chloroquinazolin-4-yl)piperazine-1-carboxylate

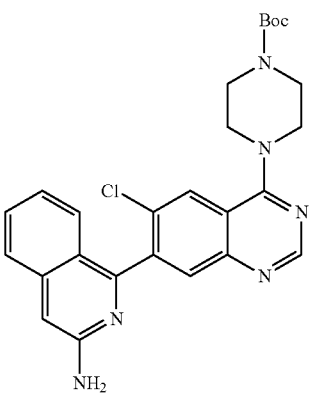 [SMILES: CC(C)(C)OC(=O)N1CCN(c2ncnc3cc(-c4nc(N)cc5ccccc45)c(Cl)cc23)CC1]

A solution of 1-bromoisoquinolin-3-amine (196 mg, 0.85 mmol), tert-butyl 4-[6-chloro-7-(4,4,5,5-tetramethyl-1,3,2-dioxaborolan-2-yl)quinazolin-4-yl]piperazine-1-carboxylate (270 mg, 0.57 mmol), cesium carbonate (371 mg, 1.14 mmol) and [1,1'-bis(diphenylphosphino)ferrocene]dichloropalladium(II) dichloromethane adduct (47 mg, 0.057 mmol) in acetonitrile (6 mL) and water (3 mL, 157.8 mmol) was degassed. The reaction mixture was heated at 90° C. for 5 h. The reaction was filtered thru celite and the crude product was purified by flash chromatography on silica (eluting with MeOH/DCM) to afford 235 mg of tert-butyl 4-(7-(3-aminoisoquinolin-1-yl)-6-chloroquinazolin-4-yl)piperazine-1-carboxylate as a yellow solid. LCMS (ESI, m/z): 491.2 [M+H]$^+$.

Step 3: 1-(6-chloro-4-(piperazin-1-yl)quinazolin-7-yl)isoquinolin-3-amine

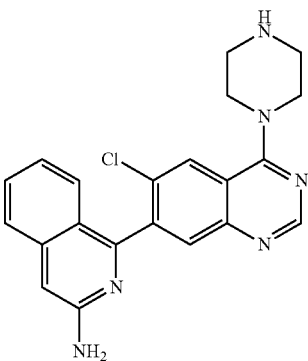 [SMILES: Nc1cc2ccccc2c(-c2cc3ncnc(N4CCNCC4)c3cc2Cl)n1]

To a solution of tert-butyl 4-[7-(3-amino-1-isoquinolyl)-6-chloro-quinazolin-4-yl]piperazine-1-carboxylate (235 mg, 0.48 mmol) in 1,4-dioxane (2.0 mL) was added hydrochloric acid (4 mol/L) in 1,4-dioxane (1.2 mL, 4.8 mmol). The reaction mixture was stirred at r.t. for 18 h. The reaction was concentrated to afford 136 mg crude of 1-(6-chloro-4-(piperazin-1-yl)quinazolin-7-yl)isoquinolin-3-amine. The crude product was used for next step without purification. LCMS (ESI, m/z): 391.1 [M+H]$^+$.

Step 4: 1-[4-[7-(3-amino-1-isoquinolyl)-6-chloro-quinazolin-4-yl]piperazin-1-yl]prop-2-en-1-one

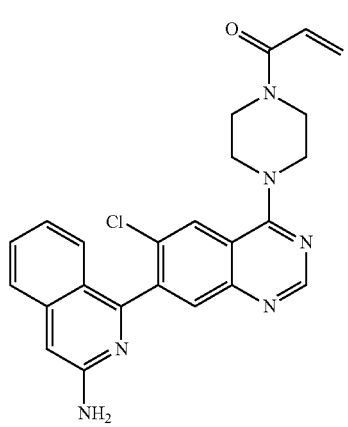 [SMILES: C=CC(=O)N1CCN(c2ncnc3cc(-c4nc(N)cc5ccccc45)c(Cl)cc23)CC1]

To a solution of 1-(6-chloro-4-(piperazin-1-yl)quinazolin-7-yl)isoquinolin-3-amine (136 mg, 0.35 mmol) and acrylic acid (0.026 mL, 0.383 mmol) in N,N-dimethylformamide (3.5 mL) was added N,N-diisopropylethylamine (0.30 mL, 1.74 mmol) and HATU (203 mg, 0.52 mmol). The reaction mixture was stirred at r.t. for 15 min. The reaction was quenched with water and extracted with EtOAc. The organic layers was dried with sodium sulfate, filtered, and concentrated via rotovap. The crude product was purified by flash chromatography on silica (eluting with MeOH/DCM) then submitted for reverse-phase HPLC to afford 8 mg 1-(4-(7-(3-aminoisoquinolin-1-yl)-6-chloroquinazolin-4-yl)piperazin-1-yl)prop-2-en-1-one as a white solid.

Example 1

$^1$H NMR (400 MHz, DMSO-d$_6$) δ 8.70 (s, 1H), 8.21 (s, 1H), 7.84 (s, 1H), 7.63 (dd, J=8.5, 1.0 Hz, 1H), 7.47 (ddd, J=8.3, 6.6, 1.2 Hz, 1H), 7.25 (dq, J=8.5, 0.9 Hz, 1H), 7.07 (ddd, J=8.5, 6.7, 1.2 Hz, 1H), 6.85 (dd, J=16.7, 10.4 Hz, 1H), 6.75 (d, J=0.9 Hz, 1H), 6.18 (dd, J=16.7, 2.4 Hz, 1H), 6.10 (s, 2H), 5.75 (dd, J=10.4, 2.4 Hz, 1H), 4.01-3.73 (m, 8H). LCMS (ESI, m/z): 445.1 [M+H]$^+$.

Example 2

1-[4-[6-chloro-7-(3-methyl-2-pyridyl)quinazolin-4-yl]piperazin-1-yl]prop-2-en-1-one Procedure same as Example 1 except that in Step 2 of Example 2, commercially available 2-bromo-3-methylpyridine was used instead of 1-bromoisoquinoline-3-amine as the alternative reagent Example 2

$^1$H NMR (400 MHz, DMSO-d$_6$) δ 8.69 (s, 1H), 8.51 (ddd, J=4.8, 1.6, 0.7 Hz, 1H), 8.19 (s, 1H), 7.81 (ddd, J=7.8, 1.7, 0.8 Hz, 1H), 7.76 (s, 1H), 7.42 (dd, J=7.7, 4.7 Hz, 1H), 6.84 (dd, J=16.7, 10.4 Hz, 1H), 6.18 (dd, J=16.7, 2.4 Hz, 1H), 5.74 (dd, J=10.4, 2.4 Hz, 1H), 3.95-3.75 (m, 8H), 2.14 (d, J=0.8 Hz, 3H). LCMS (ESI, m/z): 394.1 [M+H]$^+$.

Example 3

1-[4-[7-(6-amino-1,7-naphthyridin-8-yl)-6-chloro-quinazolin-4-yl]piperazin-1-yl]prop-2-en-1-one

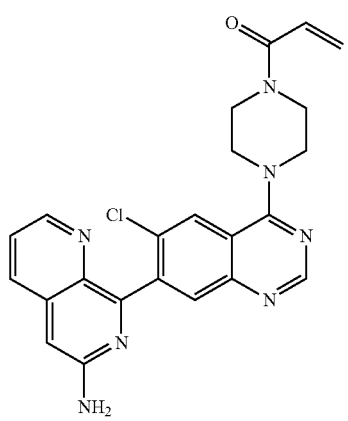 [SMILES: C=CC(=O)N1CCN(c2ncnc3cc(-c4nc(N)cc5cccnc45)c(Cl)cc23)CC1]

Procedure same as Example 1 except that in Step 2 of Example 3, commercially available 8-bromo-1,7-naphthyridin-6-amine was used instead of 1-bromoisoquinoline-3-amine as the alternative reagent Example 3

$^1$H NMR (400 MHz, DMSO-d$_6$) δ 8.69 (s, 1H), 8.44 (dd, J=4.0, 1.6 Hz, 1H), 8.14 (s, 1H), 8.07 (dd, J=8.6, 1.6 Hz, 1H), 7.84 (s, 1H), 7.44 (dd, J=8.5, 4.0 Hz, 1H), 6.84 (dd, J=16.7, 10.5 Hz, 1H), 6.75 (s, 1H), 6.32 (s, 2H), 6.18 (dd, J=16.7, 2.4 Hz, 1H), 5.75 (dd, J=10.5, 2.3 Hz, 1H), 3.85 (d, J=43.6 Hz, 8H). LCMS (ESI, m/z): 446.1 [M+H]$^+$.

Example 4

1-[4-[7-(3-amino-2,6-naphthyridin-1-yl)-6-chloro-quinazolin-4-yl]piperazin-1-yl]prop-2-en-1-one

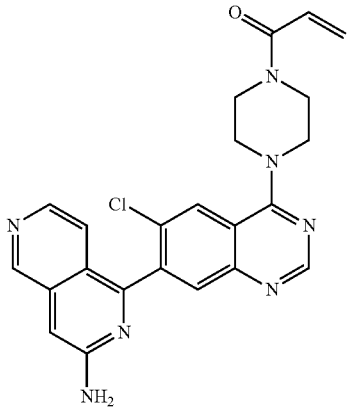 [SMILES: C=CC(=O)N1CCN(c2ncnc3cc(-c4nc(N)cc5cnccc45)c(Cl)cc23)CC1]

Procedure same as Example 1 except that in Step 2 of Example 4, commercially available 1-bromo-2,6-naphthyridin-3-amine was used instead of 1-bromoisoquinoline-3-amine as the alternative reagent Example 4

$^1$H NMR (400 MHz, DMSO-d$_6$) δ 9.13 (d, J=1.1 Hz, 1H), 8.71 (s, 1H), 8.23 (s, 1H), 8.09 (d, J=5.9 Hz, 1H), 7.89 (s, 1H), 7.09 (dt, J=5.9, 1.1 Hz, 1H), 6.88 (t, J=1.1 Hz, 1H), 6.87-6.79 (m, 1H), 6.49 (s, 2H), 6.18 (dd, J=16.7, 2.4 Hz, 1H), 5.75 (dd, J=10.4, 2.4 Hz, 1H), 3.99-3.74 (m, 8H). LCMS (ESI, m/z): 446.1 [M+H]$^+$.

Example 5

1-[4-[7-(3-amino-5-chloro-1-isoquinolyl)-6-chloro-quinazolin-4-yl]piperazin-1-yl]prop-2-en-1-one

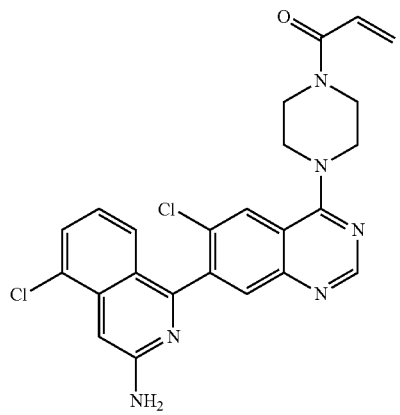 [SMILES: C=CC(=O)N1CCN(c2ncnc3cc(-c4nc(N)cc5c(Cl)cccc45)c(Cl)cc23)CC1]

Procedure same as Example 1 except that in Step 2 of Example 5, commercially available 1-bromo-5-chloro-isoquinolin-3-amine was used instead of 1-bromoisoquinoline-3-amine as the alternative reagent Example 5

$^1$H NMR (400 MHz, DMSO-d$_6$) δ 8.70 (s, 1H), 8.22 (s, 1H), 7.88 (s, 1H), 7.67 (dd, J=7.4, 1.1 Hz, 1H), 7.25 (dt, J=8.5, 1.0 Hz, 1H), 7.03 (dd, J=8.5, 7.3 Hz, 1H), 6.98 (d, J=1.0 Hz, 1H), 6.85 (dd, J=16.7, 10.5 Hz, 1H), 6.49 (s, 2H), 6.18 (dd, J=16.7, 2.4 Hz, 1H), 5.75 (dd, J=10.5, 2.4 Hz, 1H), 3.99-3.75 (m, 8H). LCMS (ESI, m/z): 479.1 [M+H]$^+$.

Example 6

1-[4-[7-(3-amino-6-methoxy-1-isoquinolyl)-6-chloro-quinazolin-4-yl]piperazin-1-yl]prop-2-en-1-one

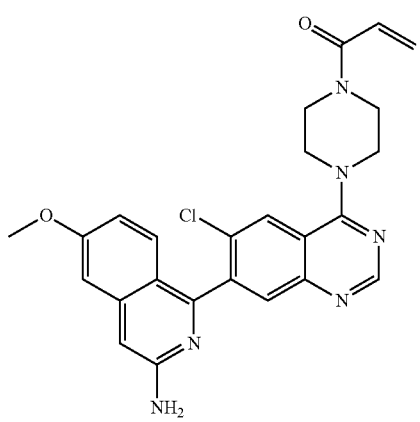 [SMILES: C=CC(=O)N1CCN(c2ncnc3cc(-c4nc(N)cc5cc(OC)ccc45)c(Cl)cc23)CC1]

Procedure same as Example 1 except that in Step 2 of Example 6, commercially available 1-bromo-6-methoxyisoquinolin-3-amine was used instead of 1-bromoisoquinoline-3-amine as the alternative reagent

Example 6

$^1$H NMR (400 MHz, DMSO-d$_6$) δ 8.69 (s, 1H), 8.19 (s, 1H), 7.80 (s, 1H), 7.14 (d, J=9.2 Hz, 1H), 6.98 (d, J=2.4 Hz, 1H), 6.84 (dd, J=16.7, 10.5 Hz, 1H), 6.74-6.63 (m, 2H), 6.18 (dd, J=16.7, 2.4 Hz, 1H), 6.03 (s, 2H), 5.75 (dd, J=10.4, 2.4 Hz, 1H), 3.78-3.99 (m, 11H). LCMS (ESI, m/z): 475.1 [M+H]$^+$.

Example 7

(S)-1-(4-(7-(3-aminoisoquinolin-1-yl)-6-chloro-8-fluoroquinazolin-4-yl)piperazin-1-yl)prop-2-en-1-one The compound (S)-1-(4-(7-(3-aminoisoquinolin-1-yl)-6-chloro-8-fluoroquinazolin-4-yl)piperazin-1-yl)prop-2-en-1-one was prepared according to the following synthetic scheme

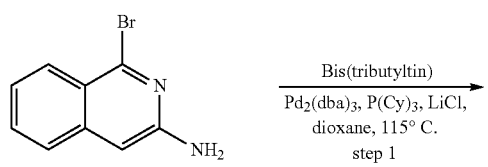

Bis(tributyltin)
Pd$_2$(dba)$_3$, P(Cy)$_3$, LiCl, dioxane, 115° C.
step 1

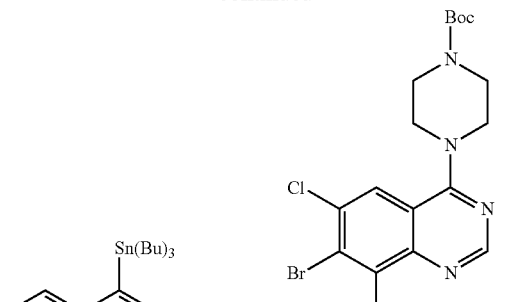

Pd(PPh$_3$)$_4$, CuI, LiCl
DMF, Microwave
150° C.
step 2

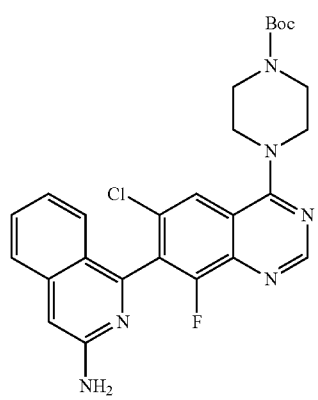

4M HCl/dioxane r.t
step 3

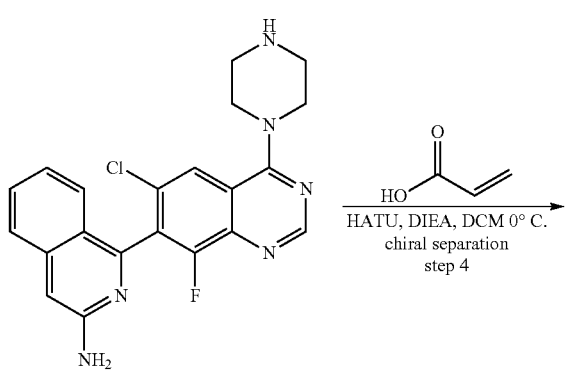

HO—acrylic acid
HATU, DIEA, DCM 0° C.
chiral separation
step 4

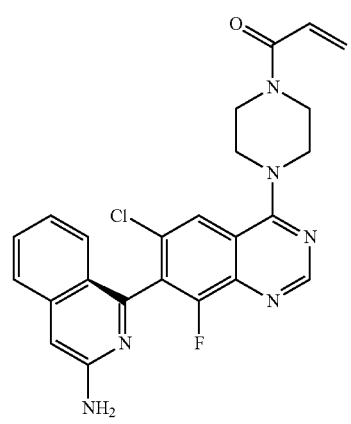

229

Step 1: 1-(tributylstannyl)isoquinolin-3-amine

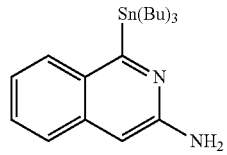

To a solution of 1-bromoisoquinolin-3-amine (500 mg, 2.17 mmol), bis(tributyltin) (1.21 mL, 2.39 mmol), tris(dibenzylideneacetone)dipalladium(0) (205 mg, 0.217 mmol), tricyclohexylphosphine (122 mg, 0.435 mmol) and lithium chloride (460 mg, 10.9 mmol) in 1,4-dioxane (10 mL) was degassed. The reaction mixture was stirred at 115° C. for 18 h. The reaction was filtered thru celite. The crude product was used in next step. LCMS (ESI, m/z): 434.1 [M+H]$^+$.

Step 2: tert-butyl 4-(7-(3-aminoisoquinolin-1-yl)-6-chloro-8-fluoroquinazolin-4-yl)piperazine-1-carboxylate

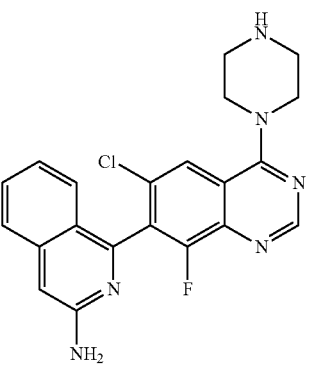 [SMILES: Nc1cc2ccccc2c(-c2c(Cl)cc3c(N4CCNCC4)ncnc3c2F)n1]

A solution of 1-tributylstannylisoquinolin-3-amine (300 mg, 0.693 mmol), tert-butyl 4-(7-bromo-6-chloro-8-fluoroquinazolin-4-yl)piperazine-1-carboxylate (617 mg, 1.39 mmol), tetrakis(triphenylphosphine)palladium(0) (80.0 mg, 0.069 mmol), cuprous iodide (39.6 mg, 0.21 mmol) and lithium chloride (124 mg, 2.77 mmol) in N,N-dimethylformamide (14 mL) was degassed. The reaction mixture heated at 150° C. for 15 min in microwave. The reaction mixture was filtered thru celite and concentrated. The crude product was concentrated and purified by flash chromatography on silica (eluting with MeOH/DCM) to afford tert-butyl 4-(7-(3-aminoisoquinolin-1-yl)-6-chloro-8-fluoroquinazolin-4-yl)piperazine-1-carboxylate (94 mg, 27%). LCMS (ESI, m/z): 444.9 [M+H]$^+$.

230

Step 3: 1-(6-chloro-8-fluoro-4-(piperazin-1-yl)quinazolin-7-yl)isoquinolin-3-amine

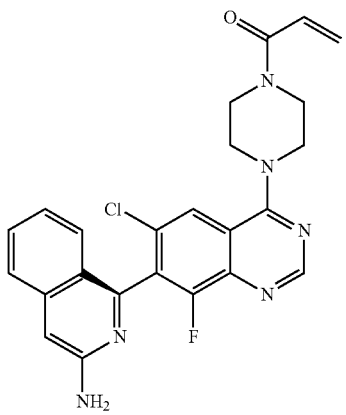

To a solution of tert-butyl 4-[7-(3-amino-1-isoquinolyl)-6-chloro-8-fluoro-quinazolin-4-yl]piperazine-1-carboxylate (410 mg, 0.806 mmol) in 1,4-dioxane (3.0 mL) was added hydrochloric acid (4 mol/L) in 1,4-dioxane (2.0 mL, 8.1 mmol). The reaction mixture was stirred at r.t. for 18 h. The reaction was concentrated to afford 329 mg crude of 1-(6-chloro-8-fluoro-4-(piperazin-1-yl)quinazolin-7-yl)isoquinolin-3-amine. The crude product was used for next step without purification. LCMS (ESI, m/z): 409.1 [M+H]$^+$.

Step 4: (S)-1-(4-(7-(3-aminoisoquinolin-1-yl)-6-chloro-8-fluoroquinazolin-4-yl)piperazin-1-yl)prop-2-en-1-one

To a solution of 1-(6-chloro-8-fluoro-4-piperazin-1-yl-quinazolin-7-yl)isoquinolin-3-amine (329 mg, 0.805 mmol) and N,N-diisopropylethylamine (0.70 mL, 4.02 mmol) in dichloromethane (8.0 mL) was added acrylic acid (0.061 mL, 0.885 mmol) and HATU (468.3 mg, 1.21 mmol) at 0° C. The reaction mixture was stirred at 0° C. for 10 min. The reaction was quenched with water and extracted with EtOAc. The organic layers was dried with sodium sulfate, filtered, and concentrated via rotovap. The crude product was purified by flash chromatography on silica (eluting with MeOH/DCM) to give 1-(4-(7-(3-aminoisoquinolin-1-yl)-6-chloro-8-fluoroquinazolin-4-yl)piperazin-1-yl)prop-2-en-1-one then submitted for chiral SFC purification to afford 30.6 mg of (S)-1-(4-(7-(3-aminoisoquinolin-1-yl)-6-chloro-8-fluoroquinazolin-4-yl)piperazin-1-yl)prop-2-en-1-one as a white solid (8.2% yield).

Example 7

$^1$H NMR (400 MHz, DMSO-d$_6$) δ 8.73 (s, 1H), 8.08 (d, J=1.5 Hz, 1H), 7.65 (dt, J=8.7, 0.9 Hz, 1H), 7.49 (ddd, J=8.3, 6.7, 1.2 Hz, 1H), 7.25 (dt, J=8.6, 1.0 Hz, 1H), 7.09 (ddd, J=8.5, 6.7, 1.1 Hz, 1H), 6.84 (dd, J=16.7, 10.4 Hz, 1H), 6.79 (d, J=0.9 Hz, 1H), 6.24-6.08 (m, 3H), 5.75 (dd, J=10.4, 2.4 Hz, 1H), 4.04-3.90 (m, 4H), 3.90-3.74 (m, 4H). LCMS (ESI, m/z): 463.1 [M+H]$^+$.

Example 8

(R)-1-(4-(7-(3-aminoisoquinolin-1-yl)-6-chloro-8-fluoroquinazolin-4-yl)piperazin-1-yl)prop-2-en-1-one

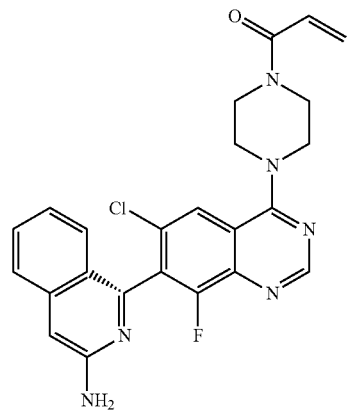

Chiral separation of 1-(4-(7-(3-aminoisoquinolin-1-yl)-6-chloro-8-fluoroquinazolin-4-yl)piperazin-1-yl)prop-2-en-1-one afforded example 8

Example 8

$^1$H NMR (400 MHz, DMSO-d$_6$) δ 8.73 (s, 1H), 8.08 (d, J=1.5 Hz, 1H), 7.65 (dt, J=8.5, 0.9 Hz, 1H), 7.49 (ddd, J=8.3, 6.7, 1.2 Hz, 1H), 7.25 (dt, J=8.6, 1.0 Hz, 1H), 7.09 (ddd, J=8.5, 6.7, 1.2 Hz, 1H), 6.84 (dd, J=16.7, 10.5 Hz, 1H), 6.80-6.76 (m, 1H), 6.23-6.10 (m, 3H), 5.75 (dd, J=10.5, 2.4 Hz, 1H), 4.05-3.90 (m, 4H), 3.82 (d, J=29.0 Hz, 4H). LCMS (ESI, m/z): 463.1 [M+H]$^+$.

Example 9

(S)-1-(4-(7-(6-amino-3-(trifluoromethyl)pyridin-2-yl)-6-chloro-8-fluoroquinazolin-4-yl)piperazin-1-yl)prop-2-en-1-one

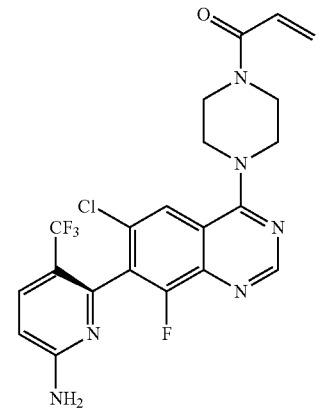

Procedure same as Example 7 except that in Step 1 of Example 9, commercially available 6-chloro-5-(trifluoromethyl)pyridin-2-amine was used instead of 1-bromoisoquinoline-3-amine as the alternative reagent Example 9

$^1$H NMR (400 MHz, DMSO-d$_6$) δ 8.70 (s, 1H), 8.01 (d, J=1.5 Hz, 1H), 7.84 (d, J=8.9 Hz, 1H), 7.00 (s, 2H), 6.82 (dd, J=16.7, 10.4 Hz, 1H), 6.69-6.61 (m, 1H), 6.17 (dd, J=16.7, 2.4 Hz, 1H), 5.74 (dd, J=10.4, 2.4 Hz, 1H), 3.92 (t, J=5.2 Hz, 4H), 3.84 (s, 2H), 3.77 (s, 2H). LCMS (ESI, m/z): 481.1 [M+H]$^+$.

Example 10

(R)-1-(4-(7-(6-amino-3-(trifluoromethyl)pyridin-2-yl)-6-chloro-8-fluoroquinazolin-4-yl)piperazin-1-yl)prop-2-en-1-one

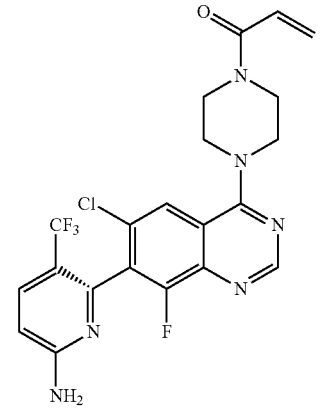

Procedure same as Example 7 except that in Step 1 of Example 10, commercially available 6-chloro-5-(trifluoromethyl)pyridin-2-amine was used instead of 1-bromoisoquinoline-3-amine as the alternative reagent.

Example 10

$^1$H NMR (400 MHz, DMSO-d$_6$) δ 8.70 (s, 1H), 8.01 (d, J=1.6 Hz, 1H), 7.84 (d, J=8.9 Hz, 1H), 7.00 (s, 2H), 6.82 (dd, J=16.7, 10.4 Hz, 1H), 6.69-6.61 (m, 1H), 6.17 (dd, J=16.7, 2.4 Hz, 1H), 5.74 (dd, J=10.4, 2.4 Hz, 1H), 3.91 (dd, J=6.5, 4.0 Hz, 4H), 3.84 (s, 2H), 3.77 (s, 2H). LCMS (ESI, m/z): 481.1 [M+H]$^+$.

Example 11

1-(4-(7-(6-amino-3-fluoro-4-methylpyridin-2-yl)-6-chloroquinazolin-4-yl)piperazin-1-yl)prop-2-en-1-one The compound 1-(4-(7-(6-amino-3-fluoro-4-methylpyridin-2-yl)-6-chloroquinazolin-4-yl)piperazin-1-yl)prop-2-en-1-one was prepared according to the following synthetic scheme:

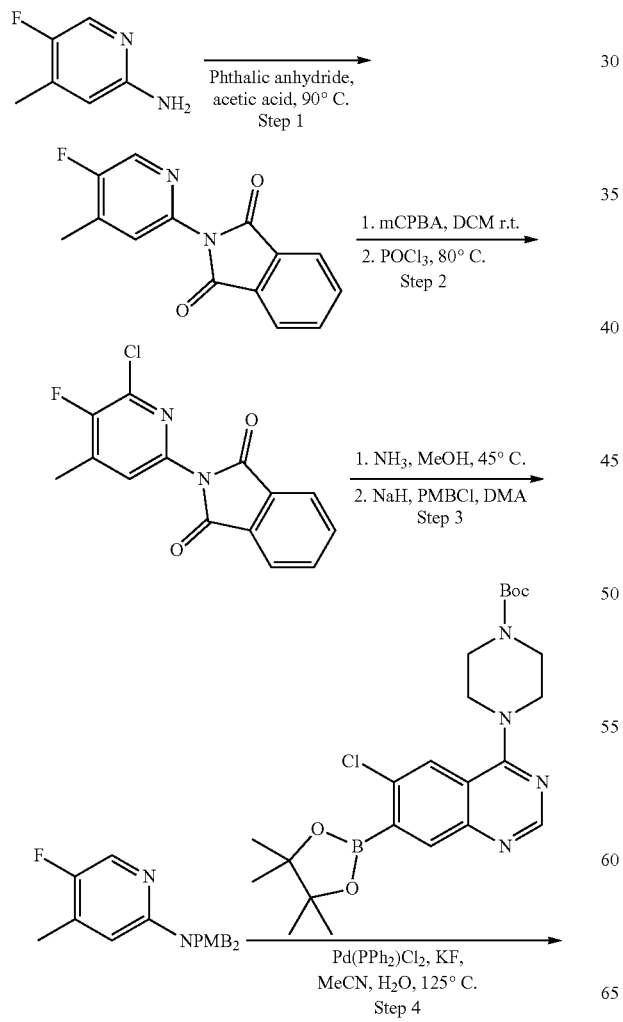

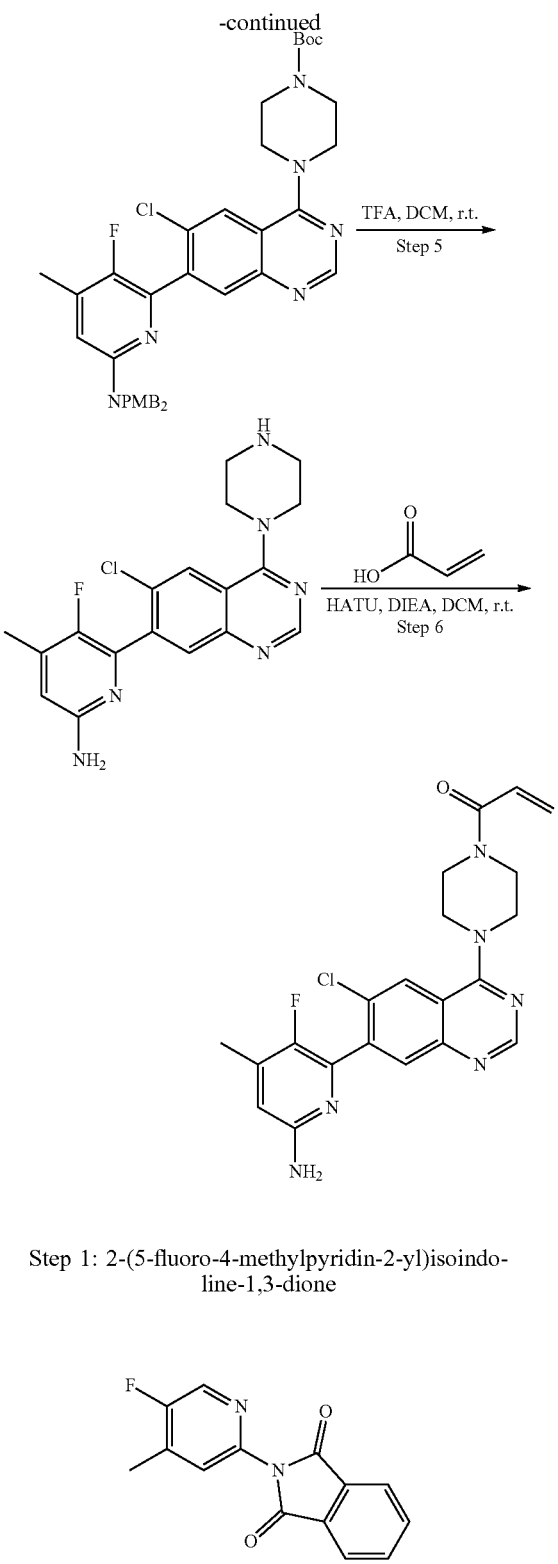

Step 1: 2-(5-fluoro-4-methylpyridin-2-yl)isoindoline-1,3-dione

A solution of 2-amino-5-fluoro-4-picoline (500 mg, 3.77 mmol) and phthalic anhydride (836 mg, 5.65 mmol) in acetic acid (9.5 mL) was heated at 90° C. for 18 h. The reaction was quenched with sat. sodium bicarbonate then extracted with EtOAc. The organic layers was dried with sodium sulfate, filtered, and concentrated via rotovap. The crude product was purified by flash chromatography on silica (eluting with iPrOAc/Hep) to afford 2-(5-fluoro-4-methylpyridin-2-yl)isoindoline-1,3-dione (834 mg, 86.5%). LCMS (ESI, m/z): 257.1 [M+H]⁺.

Step 2: 2-(6-chloro-5-fluoro-4-methylpyridin-2-yl)isoindoline-1,3-dione

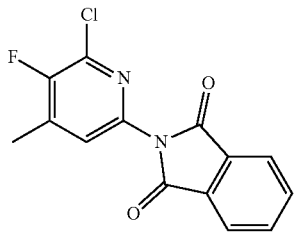 [SMILES: Cc1cc(N2C(=O)c3ccccc3C2=O)nc(Cl)c1F]

To a solution of 2-(5-fluoro-4-methylpyridin-2-yl)isoindoline-1,3-dione (964 mg, 3.76 mmol) in dichloromethane (37 mL) was added 3-chloroperoxybenzoic acid (1.30 g, 7.53 mmol). The reaction mixture was stirred at r.t. for 18 h. The reaction was quenched with a saturated aqueous Na$_2$S$_2$O$_3$ solution and extracted with EtOAc. The organic layers was dried with sodium sulfate, filtered, and concentrated via rotovap to afford 2-(1,3-dioxoisoindolin-2-yl)-5-fluoro-4-methylpyridine 1-oxide (945 mg, 92.3%).

A solution of 2-(1,3-dioxoisoindolin-2-yl)-5-fluoro-4-methylpyridine 1-oxide (550 mg, 2.02 mmol) in phosphorus oxychloride (5.0 mL, 50.51 mmol) was heated to 80° C. for 2 h. The reaction was quenched with iced water and satd. NaHCO$_3$ then extracted with EtOAc. The organic layers was dried with sodium sulfate, filtered, and concentrated via rotovap. The crude product was purified by flash chromatography on silica (eluting with iPrOAc/Hep) to afford 2-(6-chloro-5-fluoro-4-methylpyridin-2-yl)isoindoline-1,3-dione (234 mg, 39.8%). LCMS (ESI, m/z): 290.9 [M+H]⁺.

Step 3: 6-chloro-5-fluoro-N,N-bis(4-methoxybenzyl)-4-methylpyridin-2-amine

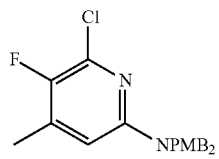

A solution of 2-(6-chloro-5-fluoro-4-methylpyridin-2-yl)isoindoline-1,3-dione (633 mg, 2.18 mmol) in ammonia (7 mol/L) in methanol 3.1 mL) was stirred at 45° C. for 5 h. The solid was filtered to give to afford 136 mg crude of 6-chloro-5-fluoro-4-methylpyridin-2-amine. The crude product was used for next step without purification. LCMS (ESI, m/z): 161.1 [M+H]⁺.

To a solution of 6-chloro-5-fluoro-4-methyl-pyridin-2-amine (250 mg, 1.56 mmol) in N,N-dimethylacetamide (6.0 mL) at 0° C. was added sodium hydride (60 mass %) in oil (75.0 mg, 1.87 mmol). The reaction was stirred at 0° C. for 30 min then 4-methoxybenzyl chloride (0.24 mL, 1.71 mmol) was added dropwise. The reaction mixture was stirred at r.t. for 18 h. The reaction was quenched with water and extracted with EtOAc. The organic layers was dried with sodium sulfate, filtered, and concentrated via rotovap. The crude product was purified by flash chromatography on silica (eluting with iPrOAc/Hep) to afford 6-chloro-5-fluoro-N,N-bis(4-methoxybenzyl)-4-methylpyridin-2-amine (521 mg, 83.4%). LCMS (ESI, m/z): 401.9 [M+H]⁺.

Step 4: tert-butyl 4-(7-(6-(bis(4-methoxybenzyl)amino)-3-fluoro-4-methylpyridin-2-yl)-6-chloroquinazolin-4-yl)piperazine-1-carboxylate

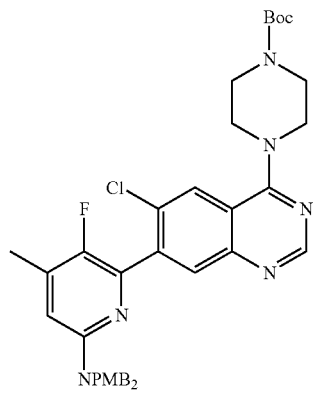

A suspension of tert-butyl 4-[6-chloro-7-(4,4,5,5-tetramethyl-1,3,2-dioxaborolan-2-yl)quinazolin-4-yl]piperazine-1-carboxylate (250 mg, 0.527 mmol) 6-chloro-5-fluoro-N,N-bis(4-methoxybenzyl)-4-methylpyridin-2-amine (190.0 mg, 0.474 mmol), bis(triphenylphosphine)palladium(ii) dichloride (37.3 mg, 0.053 mmol) and potassium fluoride (92 mg, 1.58 mmol) in acetonitrile (5.0 mL) and water (1.0 mL) was degassed. The reaction mixture was heated in microwave at 125° C. for 30 min. The reaction was filtered thru celite. The crude product was purified by flash chromatography on silica (eluting with MeOH/DCM) to afford tert-butyl 4-(7-(6-(bis(4-methoxybenzyl)amino)-3-fluoro-4-methylpyridin-2-yl)-6-chloroquinazolin-4-yl)piperazine-1-carboxylate (145 mg, 38.6%). LCMS (ESI, m/z): 657.1 [M+H]⁺.

Step 5: 6-(6-chloro-4-(piperazin-1-yl)quinazolin-7-yl)-5-fluoro-4-methylpyridin-2-amine

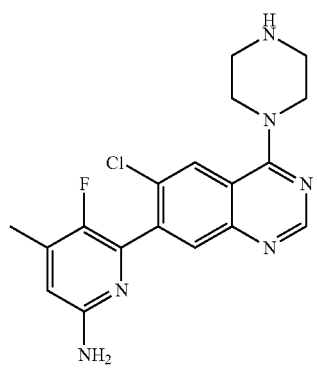 [SMILES: Cc1cc(N)nc(-c2cc3ncnc(N4CCNCC4)c3cc2Cl)c1F]

To a solution of tert-butyl 4-(7-(6-(bis(4-methoxybenzyl)amino)-3-fluoro-4-methylpyridin-2-yl)-6-chloroquinazolin-4-yl)piperazine-1-carboxylate (200 mg, 0.280 mmol) in dichloromethane (3.0 mL) was added trifluoroacetic acid (0.106 mL, 1.40 mmol). The reaction mixture was stirred at r.t. for 18 h. The reaction was concentrated and diluted in EtOAc. The solution was washed with sat. NaHCO$_3$. The organic layers was dried with sodium sulfate, filtered, and concentrated via rotovap to afford 105 mg crude of 6-(6-chloro-4-(piperazin-1-yl)quinazolin-7-yl)-5-fluoro-4-methylpyridin-2-amine. The crude product was used for next step without purification. LCMS (ESI, m/z): 373.1 [M+H]$^+$.

Step 6: 1-(4-(7-(6-amino-3-fluoro-4-methylpyridin-2-yl)-6-chloroquinazolin-4-yl)piperazin-1-yl)prop-2-en-1-one

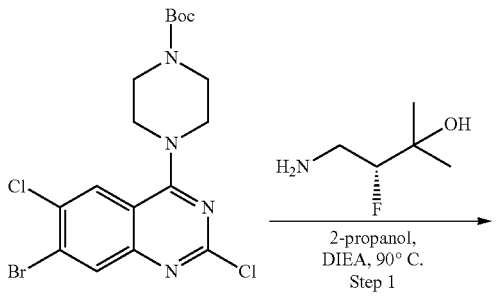

To a solution of 6-(6-chloro-4-piperazin-1-yl-quinazolin-7-yl)-5-fluoro-4-methyl-pyridin-2-amine (210 mg, 0.563 mmol) and N,N-diisopropylethylamine (0.50 mL, 2.82 mmol) in dichloromethane (5.5 mL) was added acrylic acid 0.042 mL, 0.620 mmol) and HATU (328 mg, 0.845 mmol) at 0° C. The reaction mixture was stirred at 0° C. for 10 min. The reaction was quenched with water and extracted with EtOAc. The organic layers was dried with sodium sulfate, filtered, and concentrated via rotovap. The crude product was purified by flash chromatography on silica (eluting with MeOH/DCM) then submitted for reverse-phase HPLC to afford 1-(4-(7-(6-amino-3-fluoro-4-methylpyridin-2-yl)-6-chloroquinazolin-4-yl)piperazin-1-yl)prop-2-en-1-one (54.1 mg, 20.7%).

Example 11

$^1$H NMR (400 MHz, DMSO-d$_6$) δ 8.67 (s, 1H), 8.14 (s, 1H), 7.81 (s, 1H), 6.83 (dd, J=16.7, 10.4 Hz, 1H), 6.45 (dd, J=4.7, 1.0 Hz, 1H), 6.17 (dd, J=16.7, 2.4 Hz, 1H), 5.93 (s, 2H), 5.74 (dd, J=10.4, 2.4 Hz, 1H), 3.91-3.73 (m, 8H), 2.21 (dd, J=1.7, 0.9 Hz, 3H). LCMS (ESI, m/z): 427.1 [M+H]$^+$.

Example 12

(R)-1-(4-(7-(6-amino-3-fluoro-4-methylpyridin-2-yl)-6-chloro-2-((2-fluoro-3-hydroxy-3-methylbutyl)amino)quinazolin-4-yl)piperazin-1-yl)prop-2-en-1-one The compound (R)-1-(4-(7-(6-amino-3-fluoro-4-methylpyridin-2-yl)-6-chloro-2-((2-fluoro-3-hydroxy-3-methylbutyl)amino)quinazolin-4-yl)piperazin-1-yl)prop-2-en-1-one was prepared according to the following synthetic scheme:

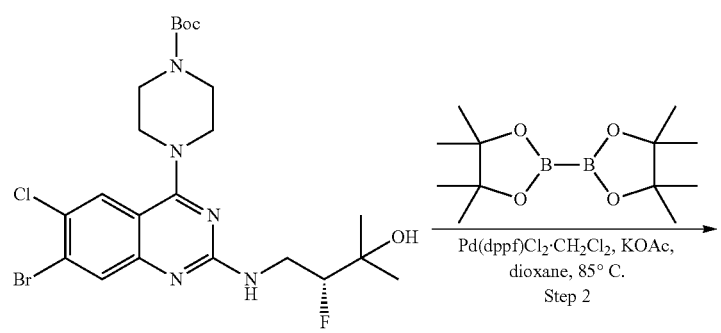

-continued
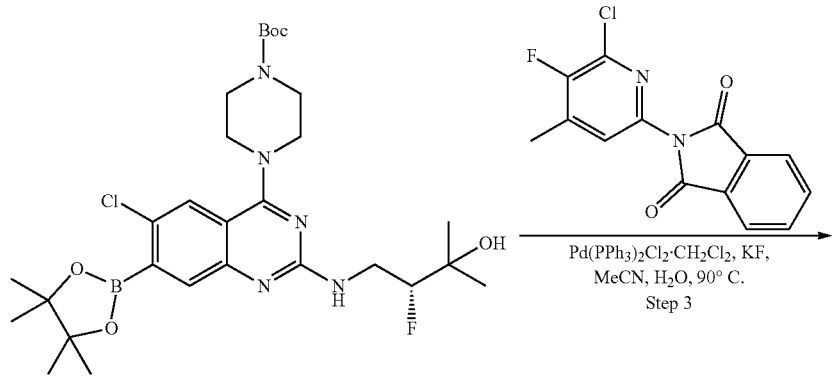
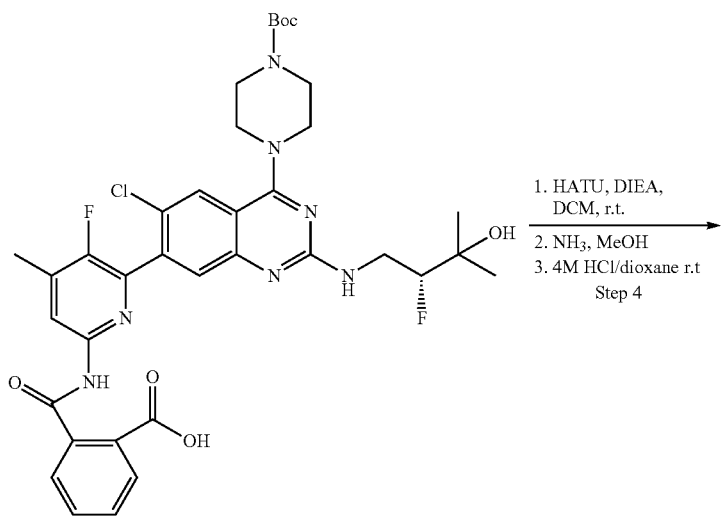
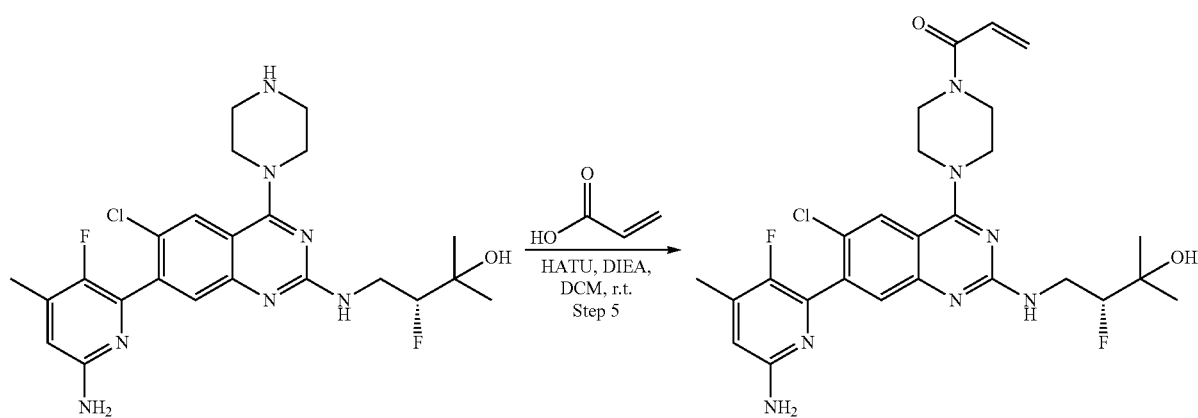

Step 1: tert-butyl (R)-4-(7-bromo-6-chloro-2-((2-fluoro-3-hydroxy-3-methylbutyl)amino)quinazolin-4-yl)piperazine-1-carboxylate

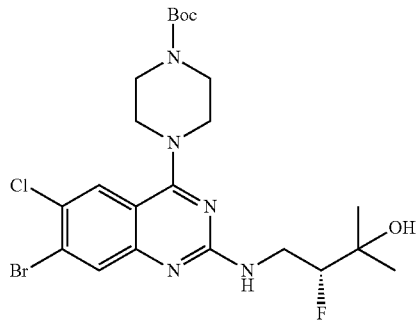 [SMILES: CC(C)(C)OC(=O)N1CCN(c2nc(NC[C@@H](F)C(C)(C)O)nc3cc(Br)c(Cl)cc23)CC1]

To a solution of tert-butyl 4-(7-bromo-2,6-dichloro-quinazolin-4-yl)piperazine-1-carboxylate (Intermediate 4) (500 mg, 1.08 mmol) and (3R)-4-amino-3-fluoro-2-methyl-butan-2-ol hydrochloride (375 mg, 2.38 mmol) in 2-propanol (10.0 mL) was added N,N-diisopropylethylamine (1.90 mL, 10.8 mmol). The reaction mixture was stirred at 65° C. for 18 h. The reaction was concentrated and the crude product was purified by flash chromatography on silica (eluting with MeOH/DCM) to afford tert-butyl (R)-4-(7-bromo-6-chloro-2-((2-fluoro-3-hydroxy-3-methylbutyl)amino)quinazolin-4-yl)piperazine-1-carboxylate (558 mg, 94.3%). LCMS (ESI, m/z): 548.1 [M+H]$^+$.

Step 2: tert-butyl (R)-4-(6-chloro-2-((2-fluoro-3-hydroxy-3-methylbutyl)amino)-7-(4,4,5,5-tetramethyl-1,3,2-dioxaborolan-2-yl)quinazolin-4-yl)piperazine-1-carboxylate

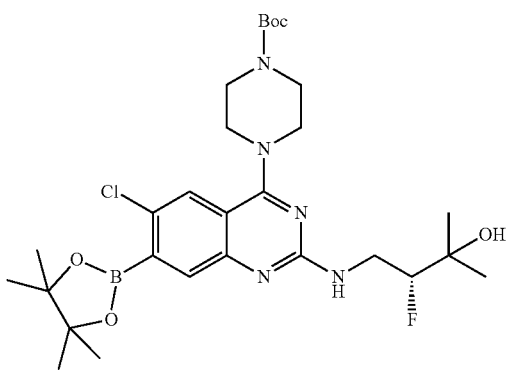 [SMILES: CC(C)(C)OC(=O)N1CCN(c2nc(NC[C@@H](F)C(C)(C)O)nc3cc(B4OC(C)(C)C(C)(C)O4)c(Cl)cc23)CC1]

To a solution of tert-butyl (R)-4-(7-bromo-6-chloro-2-((2-fluoro-3-hydroxy-3-methylbutyl)amino)quinazolin-4-yl)piperazine-1-carboxylate (100 mg, 0.183 mmol) and bis(pinacolato)diboron (142 mg, 0.549 mmol) in 1,4-dioxane (3.5 mL) was added potassium acetate (54 mg, 0.548 mmol) and 1,1'-bis(diphenylphosphino)ferrocene-palladium(II)dichloride dichloromethane complex (9.0 mg, 0.0091 mmol). The reaction mixture was degassed then stirred at 125° C. for 1 h. The reaction was filtered thru celite and concentrated to afford 108 mg crude of tert-butyl (R)-4-(6-chloro-2-((2-fluoro-3-hydroxy-3-methylbutyl)amino)-7-(4,4,5,5-tetramethyl-1,3,2-dioxaborolan-2-yl)quinazolin-4-yl)piperazine-1-carboxylate. The crude material was used for next step without purification. LCMS (ESI, m/z): 595.1 [M+H]$^+$.

Step 3: (R)-2-((6-(4-(4-(tert-butoxy carbonyl)piperazin-1-yl)-6-chloro-2-((2-fluoro-3-hydroxy-3-methylbutyl)amino)quinazolin-7-yl)-5-fluoro-4-methylpyridin-2-yl)carbamoyl)benzoic acid

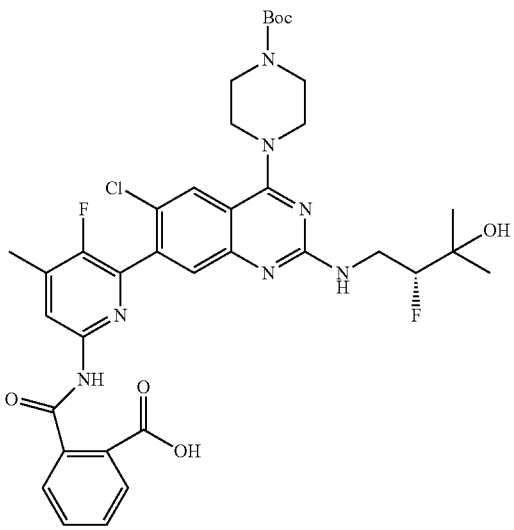 [SMILES: Cc1cc(NC(=O)c2ccccc2C(=O)O)nc(-c2cc3nc(NC[C@@H](F)C(C)(C)O)nc(N4CCN(C(=O)OC(C)(C)C)CC4)c3cc2Cl)c1F]

A solution of tert-butyl (R)-4-(6-chloro-2-((2-fluoro-3-hydroxy-3-methylbutyl)amino)-7-(4,4,5,5-tetramethyl-1,3,2-dioxaborolan-2-yl)quinazolin-4-yl)piperazine-1-carboxylate (108 mg, 0.182 mmol), 2-(6-chloro-5-fluoro-4-methyl-2-pyridyl)isoindoline-1,3-dione (74.0 mg, 0.255 mmol), bis(triphenylphosphine)palladium(II) dichloride (13.0 mg, 0.0182 mmol) and potassium fluoride (42.0 mg, 0.727 mmol) in acetonitrile (2.0 mL) and water (0.5 mL) was degassed. The reaction mixture was heated in microwave at 125° C. for 30 min. The reaction was filtered thru celite. The crude product was purified by flash chromatography on silica (eluting with MeOH/DCM) to afford (R)-2-((6-(4-(4-(tert-butoxycarbonyl)piperazin-1-yl)-6-chloro-2-((2-fluoro-3-hydroxy-3-methylbutyl)amino)quinazolin-7-yl)-5-fluoro-4-methylpyridin-2-yl)carbamoyl)benzoic acid (38 mg, 28.2%). LCMS (ESI, m/z): 741.1 [M+H]$^+$.

Step 4: (R)-4-((7-(6-amino-3-fluoro-4-methylpyridin-2-yl)-6-chloro-4-(piperazin-1-yl)quinazolin-2-yl)amino)-3-fluoro-2-methylbutan-2-ol

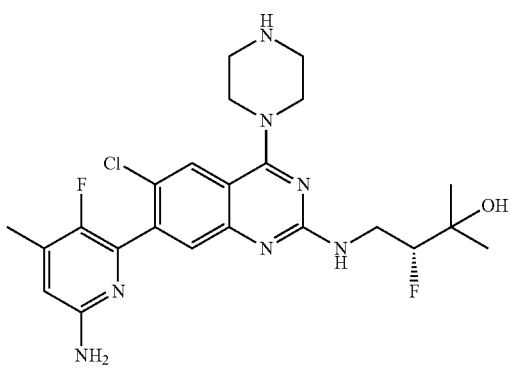 [SMILES: Cc1cc(N)nc(-c2cc3nc(NC[C@@H](F)C(C)(C)O)nc(N4CCNCC4)c3cc2Cl)c1F]

To a solution of (R)-2-((6-(4-(4-(tert-butoxycarbonyl)piperazin-1-yl)-6-chloro-2-((2-fluoro-3-hydroxy-3-methylbutyl)amino)quinazolin-7-yl)-5-fluoro-4-methylpyridin-2-yl)carbamoyl)benzoic acid (270 mg, 0.365 mmol) and N,N-diisopropylethylamine (0.32 mL, 1.80 mmol) in dichloromethane (3.5 mL) was added HATU (212.0 mg, 0.547 mmol). The reaction mixture was stirred at r.t. for 18 h. The reaction was quenched with water and extracted with EtOAc. The organic layers was dried with sodium sulfate, filtered, and concentrated via rotovap. The crude product was purified by flash chromatography on silica (eluting with MeOH/DCM) to afford tert-butyl 4-[6-chloro-7-[6-(1,3-dioxoisoindolin-2-yl)-3-fluoro-4-methyl-2-pyridyl]-2-[[(2R)-2-fluoro-3-hydroxy-3-methyl-butyl]amino]quinazolin-4-yl]piperazine-1-carboxylate (151 mg, 57.3%). LCMS (ESI, m/z): 723.1 [M+H]+.

A solution of tert-butyl 4-[6-chloro-7-[6-(1,3-dioxoisoindolin-2-yl)-3-fluoro-4-methyl-2-pyridyl]-2-[[(2R)-2-fluoro-3-hydroxy-3-methyl-butyl]amino]quinazolin-4-yl]piperazine-1-carboxylate (190 mg, 0.263 mmol) in ammonia (7 mol/L) in methanol (1.90 mL, 13.2 mmol) was stirred at 45° C. for 2 h. The reaction was concentrated and the crude product was carried to next step without further purification.

To a solution of tert-butyl 4-[7-(6-amino-3-fluoro-4-methyl-2-pyridyl)-6-chloro-2-[[(2R)-2-fluoro-3-hydroxy-3-methyl-butyl]amino]quinazolin-4-yl]piperazine-1-carboxylate (156 mg, 0.263 mmol) in 1,4-dioxane (1.0 mL) was added hydrochloric acid (4 mol/L) in 1,4-dioxane (0.65 mL, 2.63 mmol). The reaction mixture was stirred at r.t. for 18 h. The reaction was concentrated to afford 129 mg of crude (R)-4-((7-(6-amino-3-fluoro-4-methylpyridin-2-yl)-6-chloro-4-(piperazin-1-yl)quinazolin-2-yl)amino)-3-fluoro-2-methylbutan-2-ol. The crude product was used for next step without purification. LCMS (ESI, m/z): 493.1 [M+H]+.

Step 5: (R)-1-(4-(7-(6-amino-3-fluoro-4-methylpyridin-2-yl)-6-chloro-2-((2-fluoro-3-hydroxy-3-methylbutyl)amino)quinazolin-4-yl)piperazin-1-yl)prop-2-en-1-one

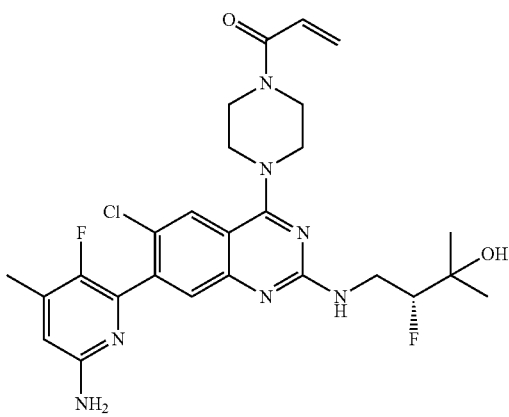 [SMILES: C=CC(=O)N1CCN(c2nc(NC[C@@H](F)C(C)(C)O)nc3cc(-c4nc(N)cc(C)c4F)c(Cl)cc23)CC1]

To a solution of (R)-4-((7-(6-amino-3-fluoro-4-methylpyridin-2-yl)-6-chloro-4-(piperazin-1-yl)quinazolin-2-yl)amino)-3-fluoro-2-methylbutan-2-ol (129 mg, 0.262 mmol) and N,N-diisopropylethylamine (0.23 mL, 1.31 mmol) in dichloromethane 2.5 mL) was added acrylic acid (0.020 mL, 0.290 mmol) and HATU (153 mg, 0.393 mmol) at 0° C. The reaction mixture was stirred at 0° C. for 10 min. The reaction was quenched with water and extracted with EtOAc. The organic layers was dried with sodium sulfate, filtered, and concentrated via rotovap. The crude product was purified by flash chromatography on silica (eluting with MeOH/DCM) then submitted for reverse-phase HPLC to afford (R)-1-(4-(7-(6-amino-3-fluoro-4-methylpyridin-2-yl)-6-chloro-2-((2-fluoro-3-hydroxy-3-methylbutyl)amino)quinazolin-4-yl)piperazin-1-yl)prop-2-en-1-one (25 mg, 17.3%).

Example 12

$^1$H NMR (400 MHz, DMSO-$d_6$) δ 7.84 (s, 1H), 7.25 (d, J=58.3 Hz, 2H), 6.84 (dd, J=16.7, 10.5 Hz, 1H), 6.41 (dd, J=4.7, 1.0 Hz, 1H), 6.16 (dd, J=16.7, 2.4 Hz, 1H), 5.88 (s, 2H), 5.73 (dd, J=10.4, 2.4 Hz, 1H), 4.77 (s, 1H), 4.36 (s, 1H), 3.90-3.59 (m, 10H), 2.19 (dd, J=1.7, 0.8 Hz, 3H), 1.20-1.09 (m, 6H). LCMS (ESI, m/z): 526.2 [M+H]+.

Example 13

1-(4-(7-(6-amino-3,4-dimethylpyridin-2-yl)-6-chloroquinazolin-4-yl)piperazin-1-yl)prop-2-en-1-one

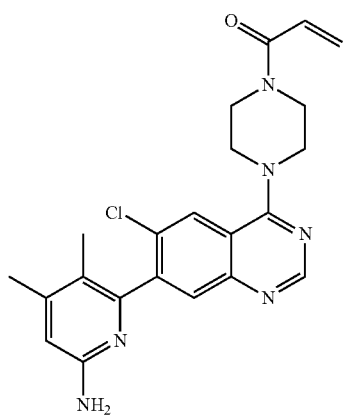 [SMILES: C=CC(=O)N1CCN(c2ncnc3cc(-c4nc(N)cc(C)c4C)c(Cl)cc23)CC1]

Procedure same as Example 11 except that in Step 1 of Example 12, commercially available 4,5-dimethylpyridin-2-amine was used instead of 2-amino-5-fluoro-4-picoline as the alternative reagent.

Example 13

$^1$H NMR (400 MHz, DMSO-$d_6$) δ 8.66 (s, 1H), 8.12 (s, 1H), 7.64 (s, 1H), 6.83 (dd, J=16.7, 10.5 Hz, 1H), 6.40-6.36 (m, 1H), 6.17 (dd, J=16.7, 2.4 Hz, 1H), 5.79-5.69 (m, 3H), 3.90-3.74 (m, 8H), 2.18 (d, J=0.8 Hz, 3H), 1.83 (s, 3H). LCMS (ESI, m/z): 423.1 [M+H]+.

Example 14

1-(4-(7-(6-amino-3-chloro-4-methylpyridin-2-yl)-6-chloroquinazolin-4-yl)piperazin-1-yl)prop-2-en-1-one

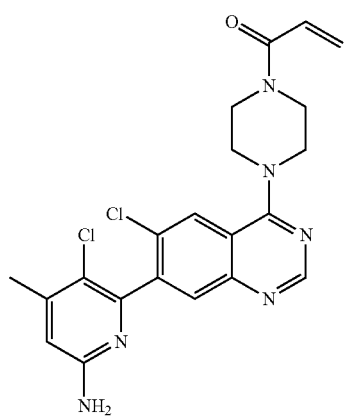 [SMILES: C=CC(=O)N1CCN(c2ncnc3cc(-c4nc(N)cc(C)c4Cl)c(Cl)cc23)CC1]

Procedure same as Example 11 except that in Step 1 of Example 13, commercially available 2-amino-5-chloro-4-picoline was used instead of 2-amino-5-fluoro-4-picoline as the alternative reagent.

Example 14

$^1$H NMR (400 MHz, DMSO-$d_6$) δ 8.67 (s, 1H), 8.14 (s, 1H), 7.72 (s, 1H), 6.83 (dd, J=16.7, 10.5 Hz, 1H), 6.51 (d, J=0.9 Hz, 1H), 6.23-6.14 (m, 3H), 5.74 (dd, J=10.4, 2.4 Hz, 1H), 3.83 (dd, J=39.2, 5.3 Hz, 8H), 2.28 (d, J=0.7 Hz, 3H). LCMS (ESI, m/z): 443.1 [M+H]$^+$.

Example 15

1-(4-(7-(6-amino-3-methylpyridin-2-yl)-6-chloroquinazolin-4-yl)piperazin-1-yl)prop-2-en-1-one

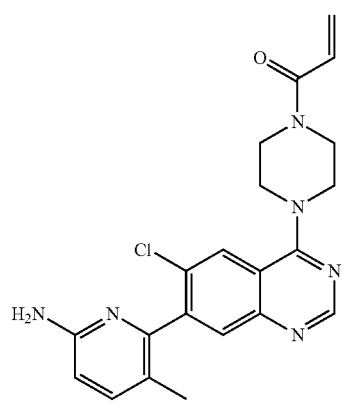

Synthetic Route

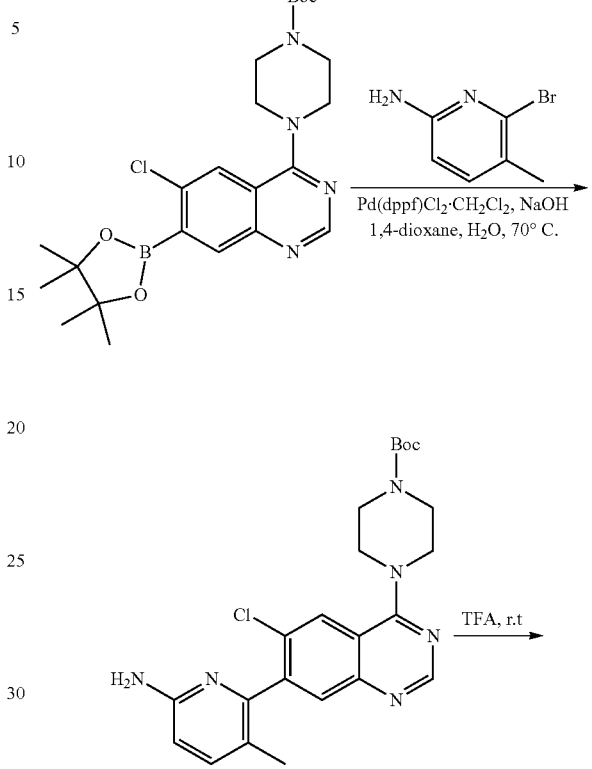

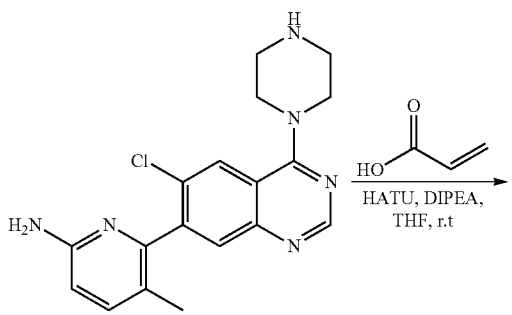

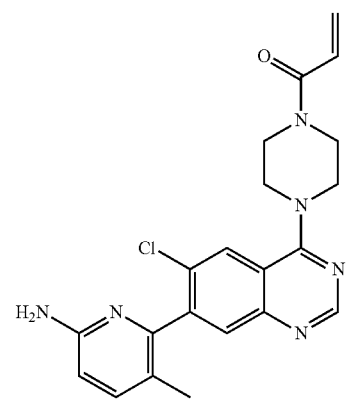 [SMILES: C=CC(=O)N1CCN(c2ncnc3cc(-c4nc(N)ccc4C)c(Cl)cc23)CC1]

247

Step 1: tert-butyl 4-(7-(6-amino-3-methylpyridin-2-yl)-6-chloroquinazolin-4-yl)piperazine-1-carboxylate

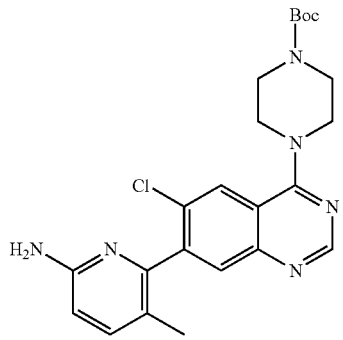 [SMILES: Cc1ccc(N)nc1-c1cc2ncnc(N3CCN(C(=O)OC(C)(C)C)CC3)c2cc1Cl]

Under nitrogen, a solution of tert-butyl 4-[6-chloro-7-(tetramethyl-1,3,2-dioxaborolan-2-yl)quinazolin-4-yl]piperazine-1-carboxylate (2.5 g, 5.2 mmol), 6-bromo-5-methylpyridin-2-amine (1 g, 5.3 mmol), 1,1'-bis(diphenylphosphino)ferrocene-palladium(II)dichloride dichloromethane complex (432 mg, 0.52 mmol), sodium hydroxide (430 mg, 10.75 mmol) in 1,4-dioxane (15 mL) and water (2 mL) was stirred for 2 h at 100° C. After completion, the solution was diluted with water (30 mL) and extracted with ethyl acetate (3×50 mL) and the organic layers were combined. The organic layer was dried over anhydrous sodium sulfate and concentrated under vacuum. The residue was applied onto a silica gel column eluting with dichloromethane/methanol (10/1) to afford 1.6 g (67%) of tert-butyl 4-[7-(6-amino-3-methylpyridin-2-yl)-6-chloroquinazolin-4-yl]piperazine-1-carboxylate (1.6 g, 3.5 mmol, 67% yield) as yellow oil. LC-MS (ESI, m/z): 455.2 [M+H]$^+$.

Step 2: 6-(6-chloro-4-(piperazin-1-yl)quinazolin-7-yl)-5-methylpyridin-2-amine

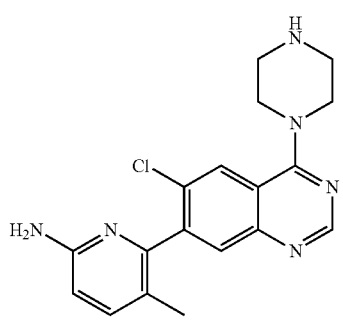 [SMILES: Cc1ccc(N)nc1-c1cc2ncnc(N3CCNCC3)c2cc1Cl]

A solution of tert-butyl 4-[7-(6-amino-3-methylpyridin-2-yl)-6-chloroquinazolin-4-yl]piperazine-1-carboxylate (1.5 g, 3.29 mmol) and trifluoroacetic acid (1.12 g, 9.82 mmol) in dichloromethane (20 mL) was stirred for 3 h at 25° C. After completion, the resulting mixture was concentrated under vacuum to afford 1.8 g (crude) of 6-[6-chloro-4-(piperazin-1-yl)quinazolin-7-yl]-5-methylpyridin-2-amine as brown oil which was used for next step without purification. LC-MS (ESI, m/z): 355.1 [M+H]$^+$.

248

Step 3: 1-[4-[7-(6-amino-3-methylpyridin-2-yl)-6-chloroquinazolin-4-yl]piperazin-1-yl]prop-2-en-1-one

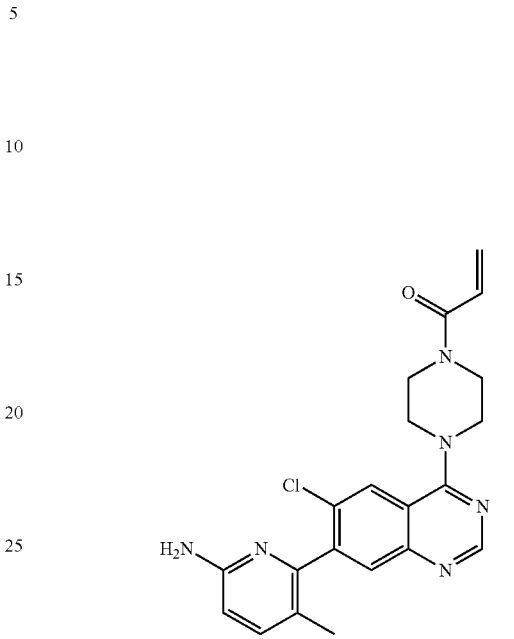

A solution of 6-[6-chloro-4-(piperazin-1-yl)quinazolin-7-yl]-5-methylpyridin-2-amine (600 mg, 1.69 mmol), prop-2-enoic acid (140 mg, 1.94 mmol), HATU (1.3 g, 3.41 mmol), N,N-diisopropylethylamine (877 mg, 6.78 mmol) in dichloromethane (20 mL) was stirred for 2 h at 25° C. After completion, the solution was quenched with water (5 mL), diluted with dichloromethane (50 mL) and washed with brine (3×10 mL). The organic layer was dried over anhydrous sodium sulfate and concentrated under vacuum. The crude product was further isolated by Prep-HPLC with the following conditions Column: CHIRALPAK IE, 2*25 cm, 5 um; Mobile Phase A:MTBE(10 mM NH$_3$-methanol)-HPLC, Mobile Phase B: methanol-HPLC; Flow rate: 20 mL/min; Gradient: 15 B to 15 B in 27 min; 220/254 nm; RT1:17.672; RT2:23.294 to afford 1-[4-[7-(6-amino-3-methylpyridin-2-yl)-6-chloroquinazolin-4-yl]piperazin-1-yl]prop-2-en-1-one (20.2 mg, 0.048 mmol 3% yield) as a white solid. LC-MS (ESI, m/z): 409.1 [M+H]$^+$.

Example 15

$^1$H NMR (400 MHz, Methanol-d$_4$, ppm) δ 8.68 (s, 1H), 8.23 (s, 1H), 7.76 (s, 1H), 7.48 (dd, J=8.4, 0.4 Hz, 1H), 6.88-6.81 (m, 1H), 6.66 (d, J=8.4 Hz, 1H), 6.29 (dd, J=16.8, 2.0 Hz, 1H), 5.83 (dd, J=10.8, 2.0 Hz, 1H), 4.02 (s, 4H), 3.94 (s, 4H), 2.00 (s, 3H).

Example 16

N-(6-[6-chloro-4-[4-(prop-2-enoyl)piperazin-1-yl]quinazolin-7-yl]-5-methylpyridin-2-yl)acetamide Synthetic Route

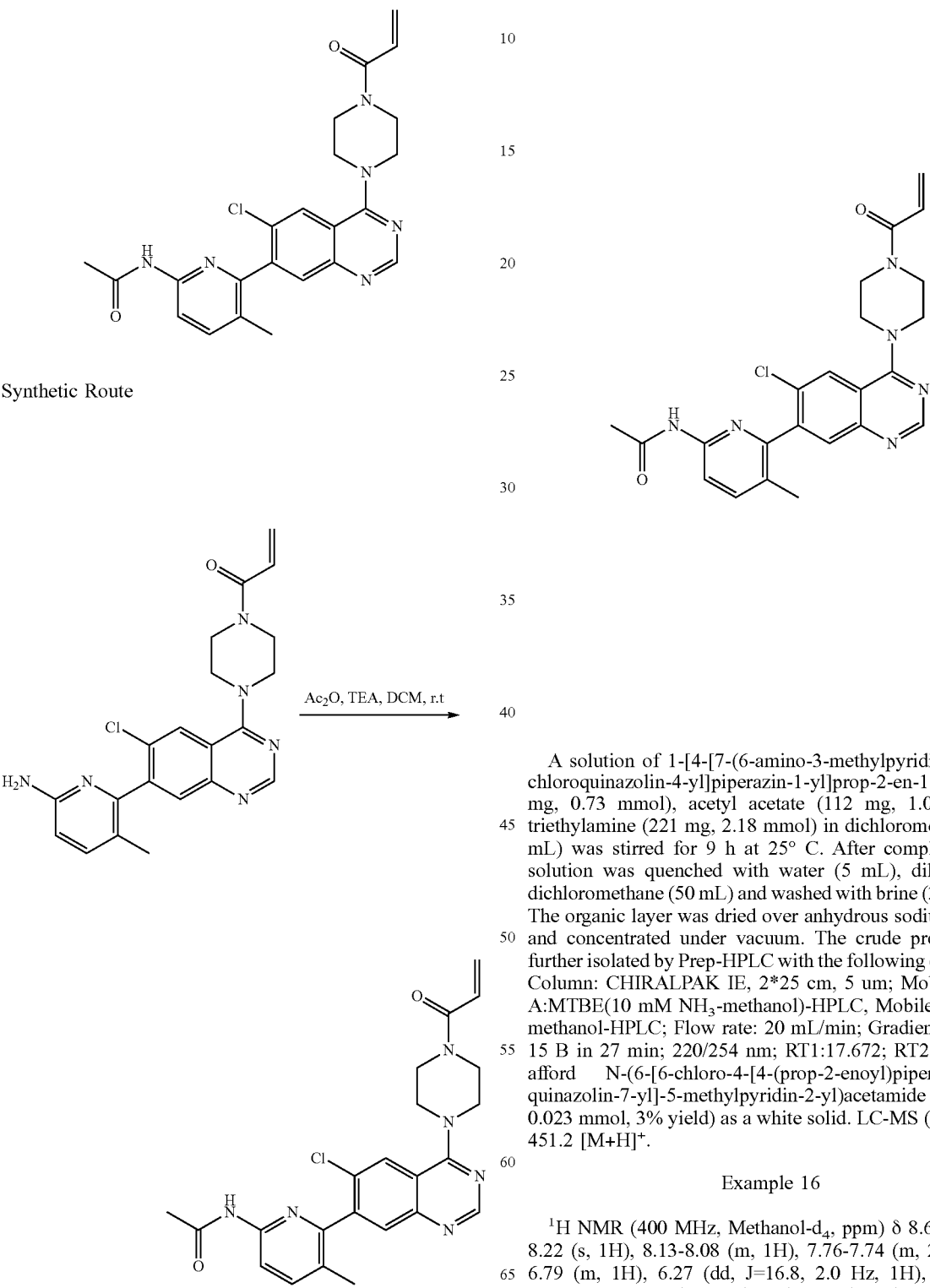

Step 1: N-(6-[6-chloro-4-[4-(prop-2-enoyl)piperazin-1-yl]quinazolin-7-yl]-5-methylpyridin-2-yl)acetamide A solution of 1-[4-[7-(6-amino-3-methylpyridin-2-yl)-6-chloroquinazolin-4-yl]piperazin-1-yl]prop-2-en-1-one (300 mg, 0.73 mmol), acetyl acetate (112 mg, 1.09 mmol), triethylamine (221 mg, 2.18 mmol) in dichloromethane (20 mL) was stirred for 9 h at 25° C. After completion, the solution was quenched with water (5 mL), diluted with dichloromethane (50 mL) and washed with brine (3×10 mL). The organic layer was dried over anhydrous sodium sulfate and concentrated under vacuum. The crude product was further isolated by Prep-HPLC with the following conditions Column: CHIRALPAK IE, 2*25 cm, 5 um; Mobile Phase A:MTBE(10 mM $NH_3$-methanol)-HPLC, Mobile Phase B: methanol-HPLC; Flow rate: 20 mL/min; Gradient: 15 B to 15 B in 27 min; 220/254 nm; RT1:17.672; RT2:23.294 to afford N-(6-[6-chloro-4-[4-(prop-2-enoyl)piperazin-1-yl]quinazolin-7-yl]-5-methylpyridin-2-yl)acetamide (10.2 mg, 0.023 mmol, 3% yield) as a white solid. LC-MS (ESI, m/z): 451.2 $[M+H]^+$.

Example 16

$^1$H NMR (400 MHz, Methanol-$d_4$, ppm) δ 8.68 (s, 1H), 8.22 (s, 1H), 8.13-8.08 (m, 1H), 7.76-7.74 (m, 2H), 6.86-6.79 (m, 1H), 6.27 (dd, J=16.8, 2.0 Hz, 1H), 5.80 (dd, J=14.4, 2.0 Hz, 1H), 4.00 (s, 4H), 3.92 (s, 4H), 2.16 (s, 3H), 2.13 (s, 3H).

Examples 17a&17b
1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (Example 17a) and 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (Example 17b)
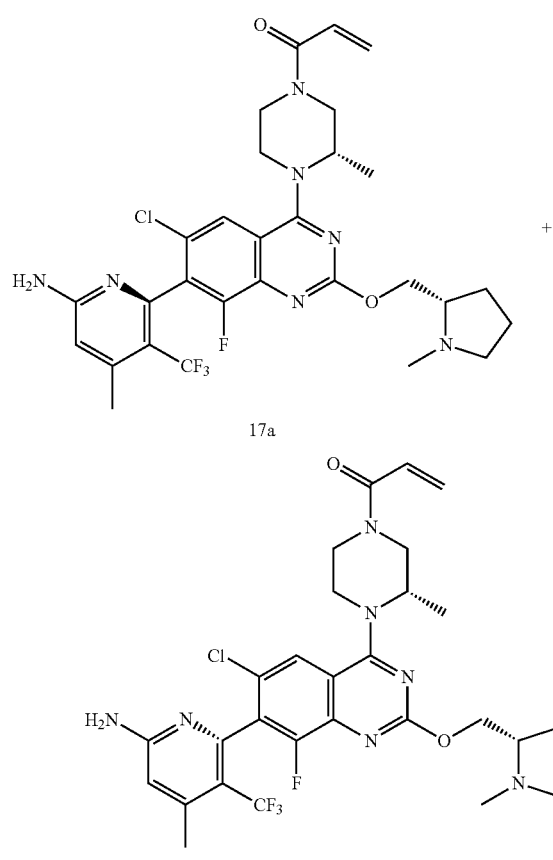
Synthetic Route
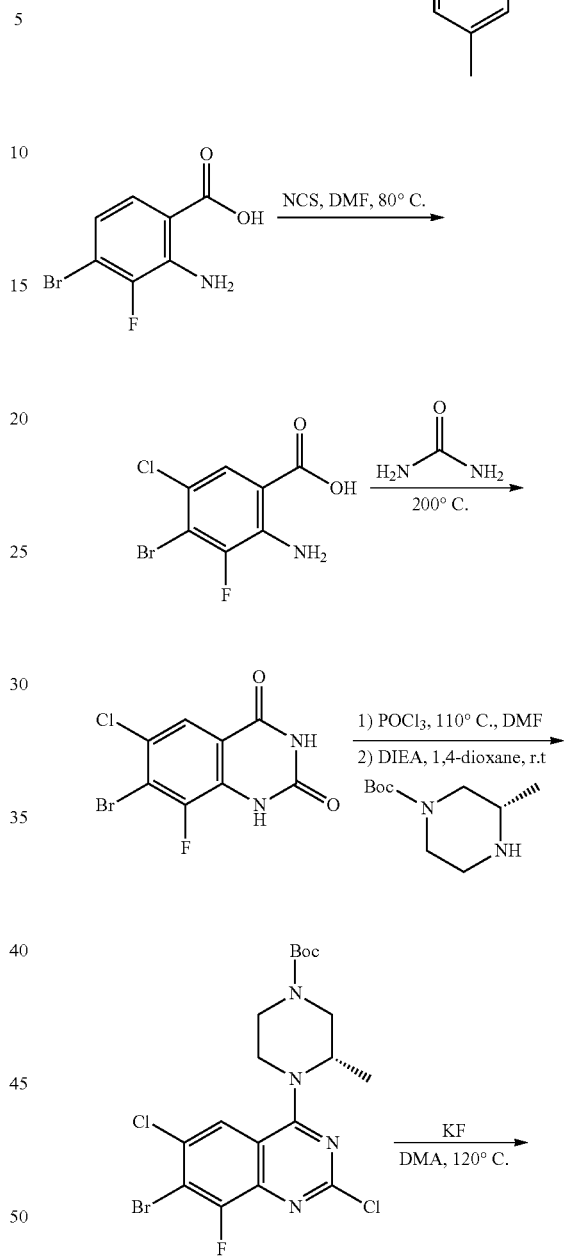

253
-continued

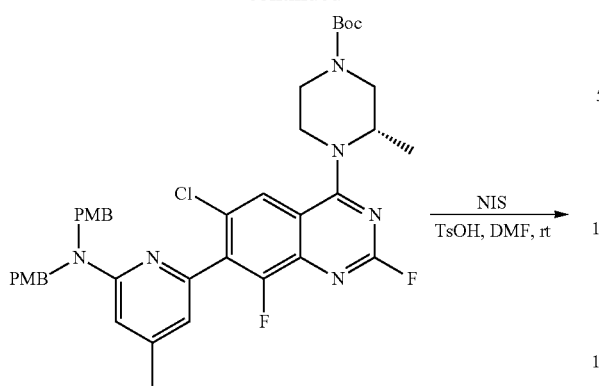

254
-continued

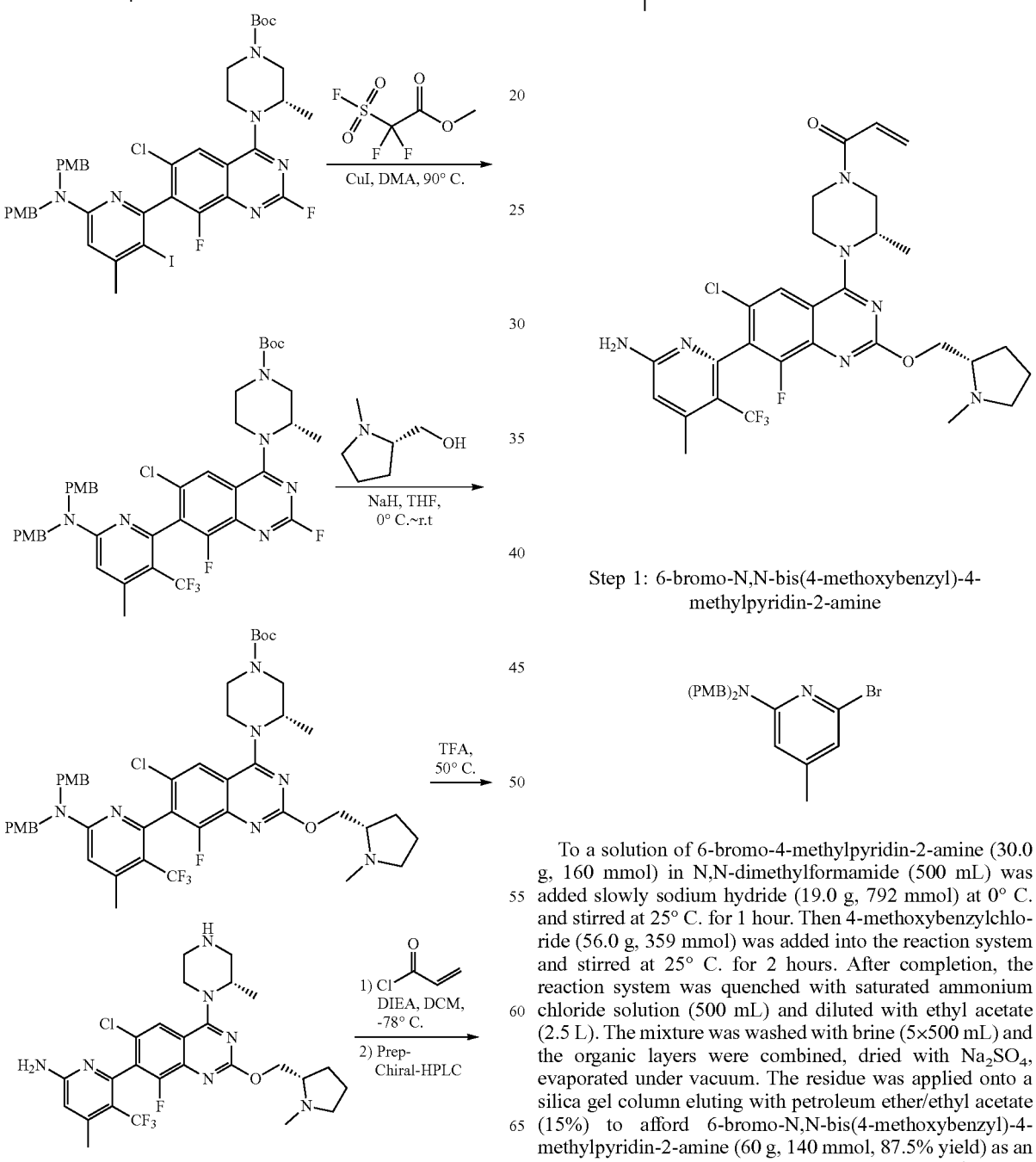

Step 1: 6-bromo-N,N-bis(4-methoxybenzyl)-4-methylpyridin-2-amine

To a solution of 6-bromo-4-methylpyridin-2-amine (30.0 g, 160 mmol) in N,N-dimethylformamide (500 mL) was added slowly sodium hydride (19.0 g, 792 mmol) at 0° C. and stirred at 25° C. for 1 hour. Then 4-methoxybenzylchloride (56.0 g, 359 mmol) was added into the reaction system and stirred at 25° C. for 2 hours. After completion, the reaction system was quenched with saturated ammonium chloride solution (500 mL) and diluted with ethyl acetate (2.5 L). The mixture was washed with brine (5×500 mL) and the organic layers were combined, dried with Na$_2$SO$_4$, evaporated under vacuum. The residue was applied onto a silica gel column eluting with petroleum ether/ethyl acetate (15%) to afford 6-bromo-N,N-bis(4-methoxybenzyl)-4-methylpyridin-2-amine (60 g, 140 mmol, 87.5% yield) as an off-white solid. LC-MS: (ESI, m/z): 427.1 [M+H]$^+$.

Step 2: N,N-bis[(4-methoxyphenyl)methyl]-4-methyl-6-tributylstannyl-pyridin-2-amine

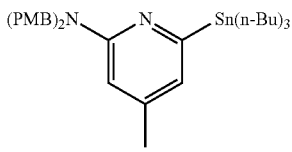

Under nitrogen, a solution of 6-bromo-N,N-bis[(4-methoxyphenyl)methyl]-4-methyl-pyridin-2-amine (35.0 g, 82 mmol), hexabutylditin (143.0 g, 247 mmol), tris(dibenzylideneacetone)dipalladium (7.53 g, 8.2 mmol), tricyclohexyl phosphine (4.6 g, 16.4 mmol) and Lithium chloride (17.3 g, 412 mmol) in 1,4-dioxane (220 mL) was stirred at 110° C. for 5 hours. After completion, the reaction system was concentrated under vacuum. The residue was purified by flash chromatography on silica gel eluting with petroleum ether/ethyl acetate (10/1) to afford N,N-bis[(4-methoxyphenyl)methyl]-4-methyl-6-tributylstannyl-pyridin-2-amine (45 g, 71 mmol, 86.2% yield) as a red oil. LC-MS: (ESI, m/z): 639.3 [M+H]⁺.

Step 3: 2-amino-4-bromo-5-chloro-3-fluoro-benzoic acid

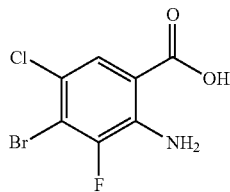 [SMILES: Nc1c(C(=O)O)cc(Cl)c(Br)c1F]

A solution of 2-amino-4-bromo-3-fluoro-benzoic acid (100.0 g, 427 mmol) and N-chlorosuccinimide (66.0 g, 494 mmol) in N,N-dimethylformamide (1 L) was stirred at 80° C. for 2 hours. After completion, the system was poured into water (2.0 L), a large amount of solids were precipitated. Then the solids were collected after filtration. The solids were washed with hot water (1 L). Then the solids were dried under infrared lamp to afford 2-amino-4-bromo-5-chloro-3-fluoro-benzoic acid (100 g, 373 mmol, 87.2% yield) as off-white solid. LC-MS: (ESI, m/z): 265.9 [M–H]⁺.

Step 4: 7-bromo-6-chloro-8-fluoroquinazoline-2,4(1H,3H)-dione

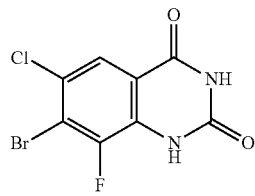

A solution of 2-amino-4-bromo-5-chloro-3-fluoro-benzoic acid (120.0 g, 447 mmol) in urea (806.0 g, 13.4 mol) was stirred at 200° C. for 1.5 hours. After completion, the reaction system was cooled to 80° C., and water (1.5 L) was added into the system with stirring for 20 mins. After filtration, the solids were collected and washed with hot water (1 L). Then the solids were dried under infrared lamp to afford 7-bromo-6-chloro-8-fluoroquinazoline-2,4(1H,3H)-dione (120 g, 409 mmol, 91.5% yield) as a light brown solid. LC-MS: (ESI, m/z): 290.9 [M–H]⁺.

Step 5: tert-butyl (3S)-4-(7-bromo-2,6-dichloro-8-fluoroquinazolin-4-yl)-3-methylpiperazine-1-carboxylate

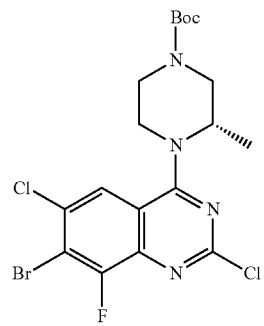 [SMILES: C[C@H]1CN(C(=O)OC(C)(C)C)CCN1c1nc(Cl)nc2c(F)c(Br)c(Cl)cc12]

A solution of 7-bromo-6-chloro-8-fluoro-quinazoline-2,4-diol (65.0 g, 222 mmol) and DMF (500.0 mg, 6.85 mmol) in POCl₃ (1.0 L) was stirred at 110° C. for 60 hours. After the starting material was completely, the resulting mixture was concentrated under vacuum. Then 1,4-dioxane (1.0 L), N,N-diisopropylethylamine (286.0 g, 2217 mmol) and tert-butyl (3S)-3-methyl-1-piperazinecarboxylate (90.0 g, 449 mmol) was added into the reaction system and stirred at 25° C. for 1 hours. After completion, the solvent was concentrated under vacuum. The residue was purified by flash chromatography on silica gel eluting with petroleum ether/ethyl acetate (20%) to afford tert-butyl (3S)-4-(7-bromo-2,6-dichloro-8-fluoroquinazolin-4-yl)-3-methylpiperazine-1-carboxylate (65 g, 132 mmol, 59.4% yield) as a yellow solid. LC-MS: (ESI, m/z): 493.0 [M+H]⁺.

Step 6: tert-butyl (3S)-4-(7-bromo-6-chloro-2,8-difluoroquinazolin-4-yl)-3-methylpiperazine-1-carboxylate

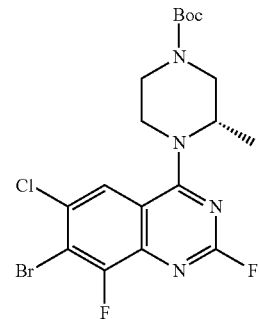 [SMILES: C[C@H]1CN(C(=O)OC(C)(C)C)CCN1c1nc(F)nc2c(F)c(Br)c(Cl)cc12]

A mixture of tert-butyl (3S)-4-(7-bromo-2,6-dichloro-8-fluoroquinazolin-4-yl)-3-methylpiperazine-1-carboxylate (30.0 g, 61 mmol) and potassium fluoride (71.0 g, 1224 mmol) in N,N-dimethylacetamide (300 mL) was stirred at 120° C. for 18 hours. After completion, the reaction system was cooled to room temperature. Then ethyl acetate (1.5 L) was added into the system and the mixture was washed with water (3×500 mL). The organic layer was dried over anhydrous sodium sulfate and concentrated under vacuum. The residue was purified by flash chromatography on silica gel eluting with petroleum ether/ethyl acetate (20%) to afford tert-butyl (3S)-4-(7-bromo-6-chloro-2,8-difluoroquinazolin-4-yl)-3-methylpiperazine-1-carboxylate (23 g, 48 mmol, 79.3% yield) as a yellow solid. LC-MS: (ESI, m/z): 477.0 [M+H]+.

Step 7: tert-butyl (3S)-4-(7-(6-(bis(4-methoxybenzyl)amino)-4-methylpyridin-2-yl)-6-chloro-2,8-difluoroquinazolin-4-yl)-3-methylpiperazine-1-carboxylate

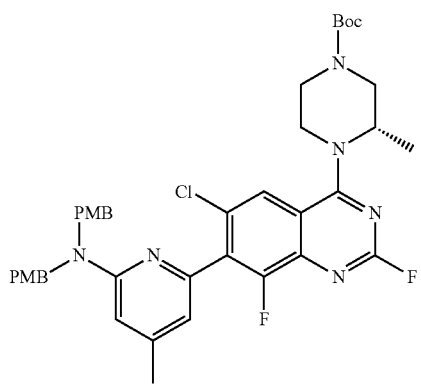

Under nitrogen, a solution of tert-butyl (3S)-4-(7-bromo-6-chloro-2,8-difluoroquinazolin-4-yl)-3-methylpiperazine-1-carboxylate (23.0 g, 48 mmol), N,N-bis[(4-methoxyphenyl)methyl]-4-methyl-6-tributylstannyl-pyridin-2-amine (62.0 g, 97 mmol), tetrakis(triphenylphosphine)palladium (11.2 g, 9.7 mmol), cuprous iodide (2.8 g, 15 mmol) and Lithium chloride (5.0 g, 119 mmol) in 1,4-dioxane (320 mL) was stirred at 120° C. for 16 hours. After completion, the reaction system was diluted with water (100 mL) and extracted with ethyl acetate (100 mL). Then the organic layers were combined, dried over anhydrous sodium sulfate and concentrated under vacuum. The residue was purified by flash chromatography on silica gel eluting with petroleum ether/ethyl acetate (30%) to afford tert-butyl (3S)-4-(7-(6-(bis(4-methoxybenzyl)amino)-4-methylpyridin-2-yl)-6-chloro-2,8-difluoroquinazolin-4-yl)-3-methylpiperazine-1-carboxylate (18.5 g, 25 mmol, 51.6% yield) as a yellow solid. LC-MS: (ESI, m/z): 745.3 [M+H]+.

Step 8: tert-butyl (3S)-4-(7-(6-(bis(4-methoxybenzyl)amino)-3-iodo-4-methylpyridin-2-yl)-6-chloro-2,8-difluoroquinazolin-4-yl)-3-methylpiperazine-1-carboxylate

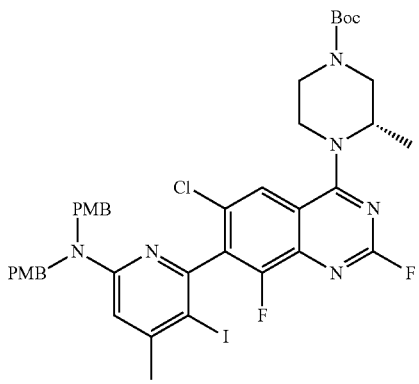

A solution of tert-butyl (3S)-4-(7-(6-(bis(4-methoxybenzyl)amino)-4-methylpyridin-2-yl)-6-chloro-2,8-difluoroquinazolin-4-yl)-3-methylpiperazine-1-carboxylate (18.5 g, 25 mmol), p-toluenesulfonic acid (171.0 mg, 0.99 mmol) and N-iodosuccinimide (28.0 g, 125 mmol) in N,N-dimethylformamide (350 mL) was stirred at 25° C. for 5 hours. After completion, the reaction system was diluted with ethyl acetate (1.5 L) and washed with saturated sodium thiosulfate solution (4×350 mL). The organic layer was dried over anhydrous sodium sulfate and concentrated under vacuum. The residue was purified by flash chromatography on silica gel eluting with petroleum ether/ethyl acetate (25%) to afford tert-butyl (3S)-4-(7-(6-(bis(4-methoxybenzyl)amino)-3-iodo-4-methylpyridin-2-yl)-6-chloro-2,8-difluoroquinazolin-4-yl)-3-methylpiperazine-1-carboxylate (16 g, 18.4 mmol, 74% yield) as a yellow solid. LC-MS: (ESI, m/z): 871.2 [M+H]+.

Step 9: tert-butyl (3S)-4-(7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate

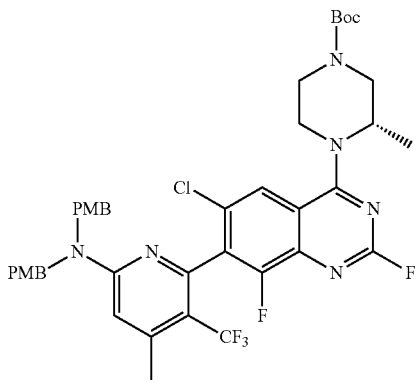

Under nitrogen, a solution of tert-butyl (3S)-4-(7-(6-(bis(4-methoxybenzyl)amino)-3-iodo-4-methylpyridin-2-yl)-6-chloro-2,8-difluoroquinazolin-4-yl)-3-methylpiperazine-1-carboxylate (16.0 g, 18.4 mmol), methyl 2,2-difluoro-2-

(fluorosulfonyl)acetate (88.3 g, 460 mmol) and cuprous iodide (42.0 g, 221 mmol) in N,N-dimethylacetamide (400 mL) was stirred at 90° C. for 18 hours. After completion, the reaction system was diluted with ethyl acetate (2.0 L) and washed with brine (4×350 mL). The organic layer was dried over anhydrous sodium sulfate and concentrated under vacuum. The residue was purified by flash chromatography on silica gel eluting with petroleum ether/ethyl acetate (30%) to afford tert-butyl (3S)-4-(7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate (12.2 g, 15 mmol, 81.7% yield) as a yellow solid. LC-MS: (ESI, m/z): 813.3 [M+H]+.

Step 10: tert-butyl (3S)-4-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazine-1-carboxylate

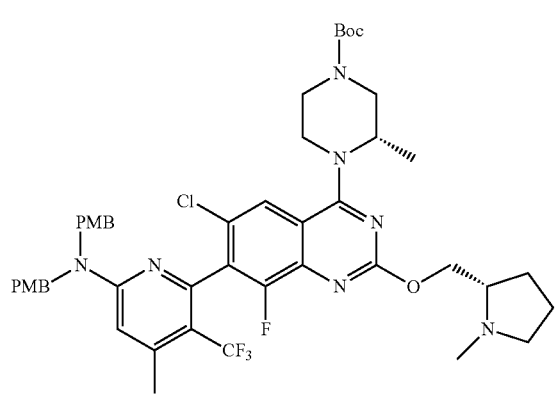

To a solution of (S)-(1-methylpyrrolidin-2-yl)methanol (4.32 g, 37.5 mmol) in tetrahydrofuran (300 mL) was added slowly sodium hydride (2.1 g, 87.5 mmol) at 0° C. and stirred for 1 h at 25° C. Then tert-butyl (3S)-4-(7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate (12.2 g, 15 mmol) was added into the reaction system and stirred at 25° C. for 1 hours. After completion, the reaction system was quenched with methanol (50 mL). Then the mixture was concentrated under vacuum and the residue was purified by flash chromatography on silica gel eluting with dichloromethane/methanol (6/94) to afford tert-butyl (3S)-4-(7-(6-(bis(4-methoxybenzyl)amino)-4-methyl-3-(trifluoromethyl)pyridin-2-yl)-6-chloro-8-fluoro-2-4(S)-1-methylpyrrolidin-2-yl)methoxy)quinazolin-4-yl)-3-methylpiperazine-1-carboxylate (8.6 g, 9.5 mmol, 63.1% yield) as a brown solid. LC-MS: (ESI, m/z): 908.4 [M+H]+.

Step 11: 6-(6-chloro-8-fluoro-4-((S)-2-methylpiperazin-1-yl)-2-(((S)-1-methylpyrrolidin-2-yl)methoxy)quinazolin-7-yl)-4-methyl-5-(trifluoromethyl)pyridin-2-amine

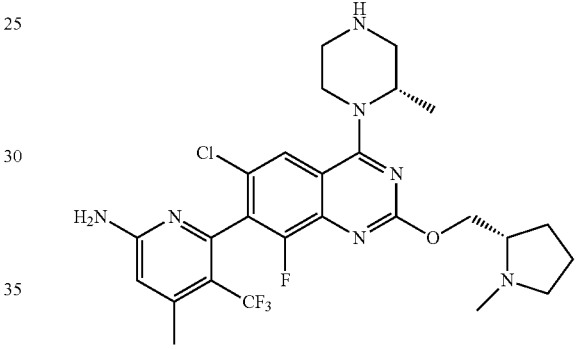

A solution of tert-butyl (3S)-4-(7-(6-(bis(4-methoxybenzyl)amino)-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazine-1-carboxylate (8.6 g, 9.5 mmol) in trifluoroacetic acid (100 mL) was stirred at 50° C. for 4 hours. After completion, the reaction system was concentrated under vacuum. The residue was dissolved with dichloromethane (50 mL) and the PH was adjusted to pH=9 with N,N-diisopropylethylamine. After concentrated under vacuum, the residue was purified by a reversed-phase chromatography directly with the following conditions: Column, C18 silica gel; mobile phase, A: water, B:ACN, B % (5%~40% in 30 min); Detector, UV 254 nm to afford 6-(6-chloro-8-fluoro-4-((S)-2-methylpiperazin-1-yl)-2-(((S)-1-methylpyrrolidin-2-yl)methoxy)quinazolin-7-yl)-4-methyl-5-(trifluoromethyl)pyridin-2-amine (3.5 g, 6.17 mmol, 65.1% yield) as a yellow solid. LC-MS: (ESI, m/z): 568.2 [M+H]+.

Step 12: 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (Example 17a) and 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (Example 17b)

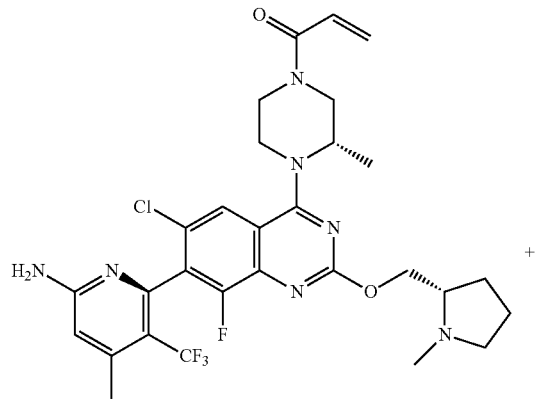

17a

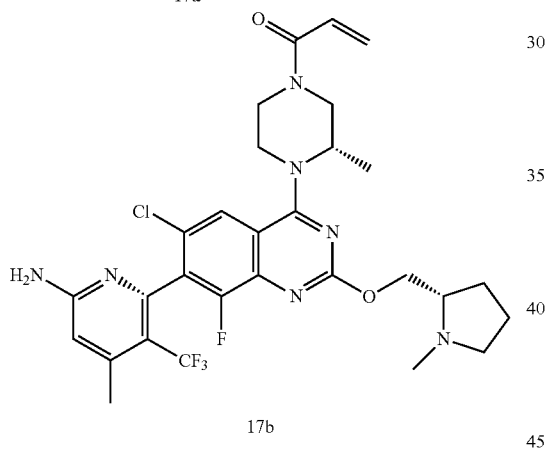

17b

To a solution of 6-(6-chloro-8-fluoro-4-((S)-2-methylpiperazin-1-yl)-2-(((S)-1-methylpyrrolidin-2-yl)methoxy)quinazolin-7-yl)-4-methyl-5-(trifluoromethyl)pyridin-2-amine (2.5 g, 4.4 mmol) and N,N-diisopropylethylamine (2.9 g, 22.5 mmol) in dichloromethane (120 mL) was added acryloyl chloride (359.0 mg, 3.97 mmol) at −78° C. and stirred at −78° C. for 25 mins. The reaction was quenched by water and extracted with dichloromethane. The organic layers were combined. The organic layer was dried over anhydrous sodium sulfate and concentrated under vacuum. The residue was purified by a reversed-phase chromatography directly with the following conditions: Column, C18 silica gel; mobile phase, A: water, B:ACN, B % (5%~60% in 30 min); Detector, UV 254 nm to afford 1-[(3S)-4-[7-[6-amino-4-methyl-3-(trifluoromethyl)-2-pyridyl]-6-chloro-8-fluoro-2-[[(2S)-1-methylpyrrolidin-2-yl]methoxy]quinazolin-4-yl]-3-methyl-piperazin-1-yl]prop-2-en-1-one (1.3 g, 2.09 mmol, 47.5% yield) as a brown solid. The mixture of diasteroisomer was separated by Prep-Chiral-HPLC with the following condition: Column, CHIRALPAK IC-3 0.46*5 Cm 3 um; mobile phase, (Hex:dichloromethane=3:1) (0.1% DEA);

EtOH=50:50; Detector, 254 nm; Flow, 1.0 ml/min; Temperature: 25° C. to afford 657.7 mg of 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy) quinazolin-4-yl)-3-methylpiperazin-1-yl)prop-2-en-1-one (Example 17a) as a white solid and 352.1 mg of 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)prop-2-en-1-one (Example 17b) as a white solid.

Example 17a

LC-MS: (ESI, m/z): 622.2 [M+H]$^+$, $^1$H NMR: (400 MHz, CDCl$_3$, ppm) δ 7.64 (s, 1H), 6.70-6.55 (m, 1H), 6.48 (s, 1H), 6.42-6.35 (m, 1H), 5.82-5.75 (m, 1H), 4.90-4.79 (m, 2H), 4.78-4.40 (m, 3H), 4.35-4.28 (m, 1H), 4.18-4.00 (m, 1H), 3.99-3.76 (m, 1H), 3.72-3.45 (m, 2H), 3.31-2.98 (m, 2H), 2.81-2.70 (m, 1H), 2.55-2.45 (m, 6H), 2.35-2.25 (m, 1H), 2.11-2.01 (m, 1H), 1.95-1.72 (m, 3H), 1.36-1.34 (m, 3H).

Example 17b

LC-MS: (ESI, m/z): 622.2 [M+H]$^+$, $^1$H NMR: (400 MHz, CDCl$_3$, ppm) δ 7.63 (s, 1H), 6.70-6.55 (m, 1H), 6.50 (s, 1H), 6.42-6.35 (m, 1H), 5.82-5.75 (m, 1H), 4.85-4.70 (m, 2H), 4.78-4.68 (m, 2H), 4.65-4.55 (m, 1H), 4.50-4.40 (m, 1H), 4.30-4.10 (m, 1H), 4.05-3.75 (m, 1H), 3.80-3.76 (m, 2H), 3.25-3.08 (m, 2H), 2.85-2.75 (m, 1H), 2.60-2.45 (m, 6H), 2.40-2.25 (m, 1H), 2.15-2.05 (m, 1H), 1.95-1.72 (m, 3H), 1.45-1.32 (m, 3H).

Examples 18a&18b (E)-1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-fluorobut-2-en-1-one and
(E)-1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-fluorobut-2-en-1-one

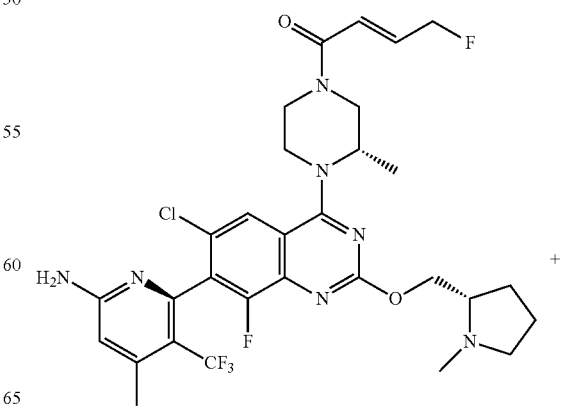

-continued

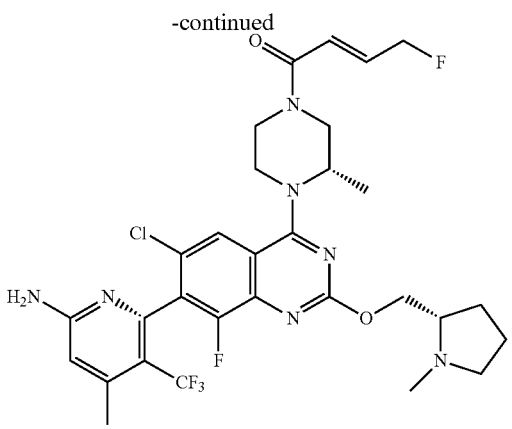

Synthetic Route

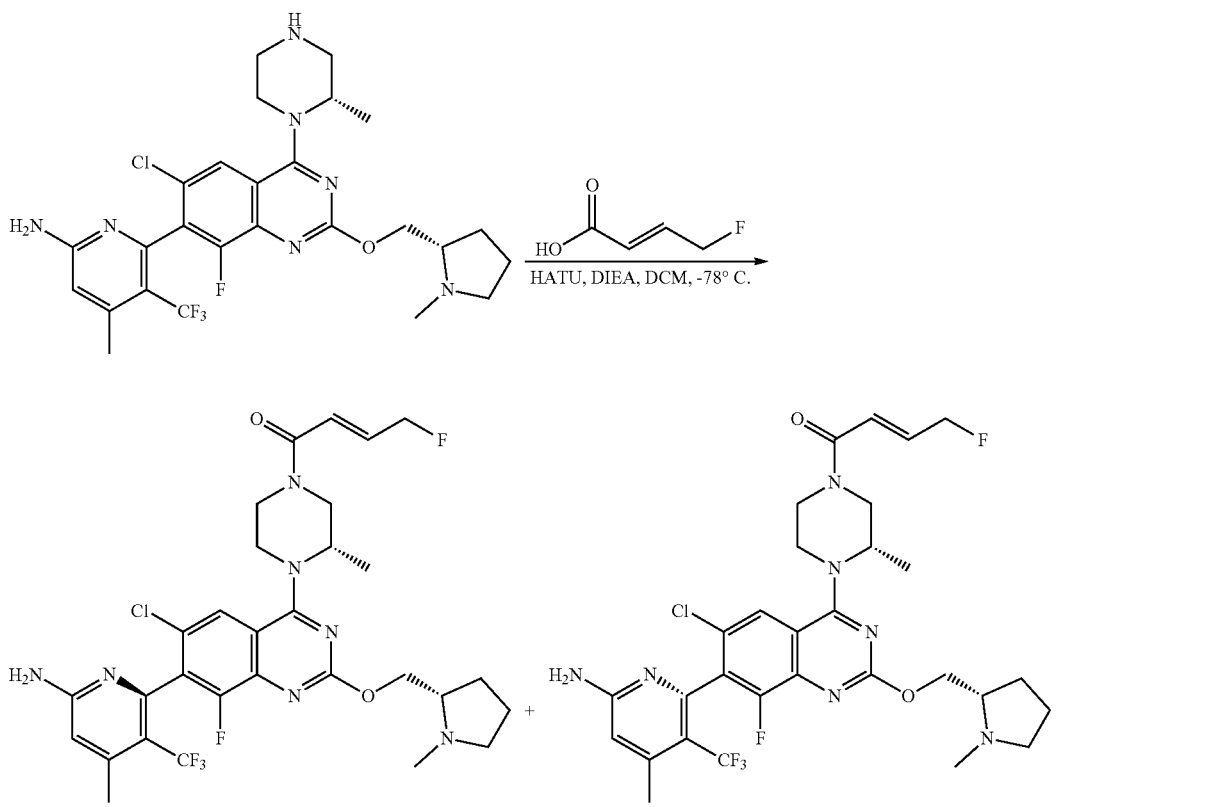

To a solution of 6-[6-chloro-8-fluoro-4-[(2S)-2-methylpiperazin-1-yl]-2-[[(2S)-1-methylpyrrolidin-2-yl]methoxy]quinazolin-7-yl]-4-methyl-5-(trifluoromethyl)pyridin-2-amine (500 mg, 0.88 mmol), HATU (401 mg, 1.06 mmol) and N,N-diisopropylethylamine (228 mg, 0.96 mmol) in dichloromethane (25 mL) was added (E)-4-fluorobut-2-enoic acid (100 mg, 3.97 mmol) at 25° C. and the mixture solution was stirred for 0.5 h. After completion, the reaction was quenched by water and extracted with dichloromethane. The organic layers were combined. The organic layer was dried over anhydrous sodium sulfate and concentrated under vacuum. The residue was purified by a reversed-phase chromatography directly with the following conditions: Column, C18 silica gel; mobile phase, A: water, B:ACN, B % (5%~60% in 30 min); Detector, UV 254 nm to afford a mixture of (E)-1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-fluorobut-2-en-1-one and (E)-1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-fluorobut-2-en-1-one (130 mg, 0.20 mmol, 23% yield) as a white solid. The mixture of diastereoisomers was separated by Prep-Chiral-HPLC with the following condition: Column:CHIRAL Cellulose-SB, Column Size: 0.46*10 cm; 3 um, Mobile phase Hex:EtOH=50:50, Flow: 1.0 mL/min, Temperature: 25° C. to afford 32 mg of (E)-1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-fluorobut-2-en-1-one as a white solid and 29.9 mg of (E)-1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-fluorobut-2-en-1-one as a white solid.

Example 18a

LC-MS: (ESI, m/z): 654.2 [M+H]$^+$, $^1$HNMR: (400 MHz, DMSO-$d_6$, ppm) δ 7.82 (s, 1H), 6.85 (s, 2H), 6.83-6.68 (m, 2H), 6.50 (s, 1H), 5.20 (d, J=2.8 Hz, 1H), 5.08 (d, J=2.8 Hz, 1H), 4.75 (s, 1H), 4.41-4.23 (m, 2H), 4.19-3.94 (m, 3H), 3.73-3.65 (m, 1H), 3.43-3.07 (m, 2H), 2.96-2.93 (m, 1H), 2.60-2.50 (m, 1H), 2.37-2.36 (m, 6H), 2.18 (dd, J=16.4, 8.0 Hz, 1H), 1.99-1.90 (m, 1H), 1.72-1.59 (m, 3H), 1.27 (t, J=6.8 Hz, 3H).

Example 18b
LC-MS: (ESI, m/z): 654.2 [M+H]$^+$, $^1$HNMR: (400 MHz, DMSO-d$_6$, ppm) δ 7.80 (s, 1H), 6.85 (s, 2H), 6.83-6.68 (m, 2H), 6.50 (s, 1H), 5.20 (d, J=2.8 Hz, 1H), 5.08 (d, J=2.8 Hz, 1H), 4.71 (s, 1H), 4.39-4.23 (m, 2H), 4.20-3.93 (m, 3H), 3.70-3.60 (m, 1H), 3.51-3.09 (m, 2H), 2.96-2.93 (m, 1H), 2.60-2.52 (m, 1H), 2.37-2.36 (m, 6H), 2.18 (dd, J=16.4, 8.0 Hz, 1H), 1.99-1.90 (m, 1H), 1.72-1.59 (m, 3H), 1.30 (t, J=8.0 Hz, 3H).
Example 19
1-((3S)-4-(7-(6-amino-4-methyl-3-(trifluoromethyl)pyridin-2-yl)-6-chloro-8-fluoroquinazolin-4-yl)-3-methylpiperazin-1-yl)prop-2-en-1-one
Synthetic Route
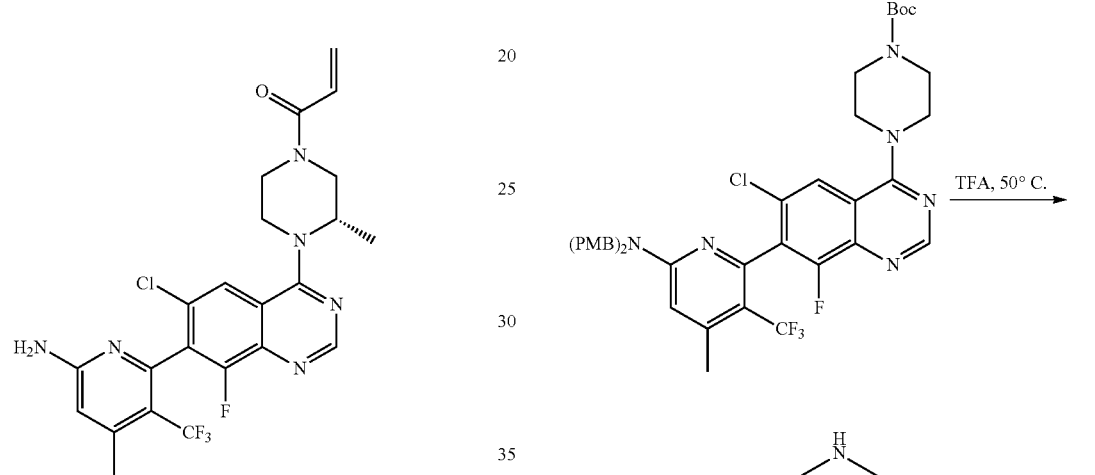
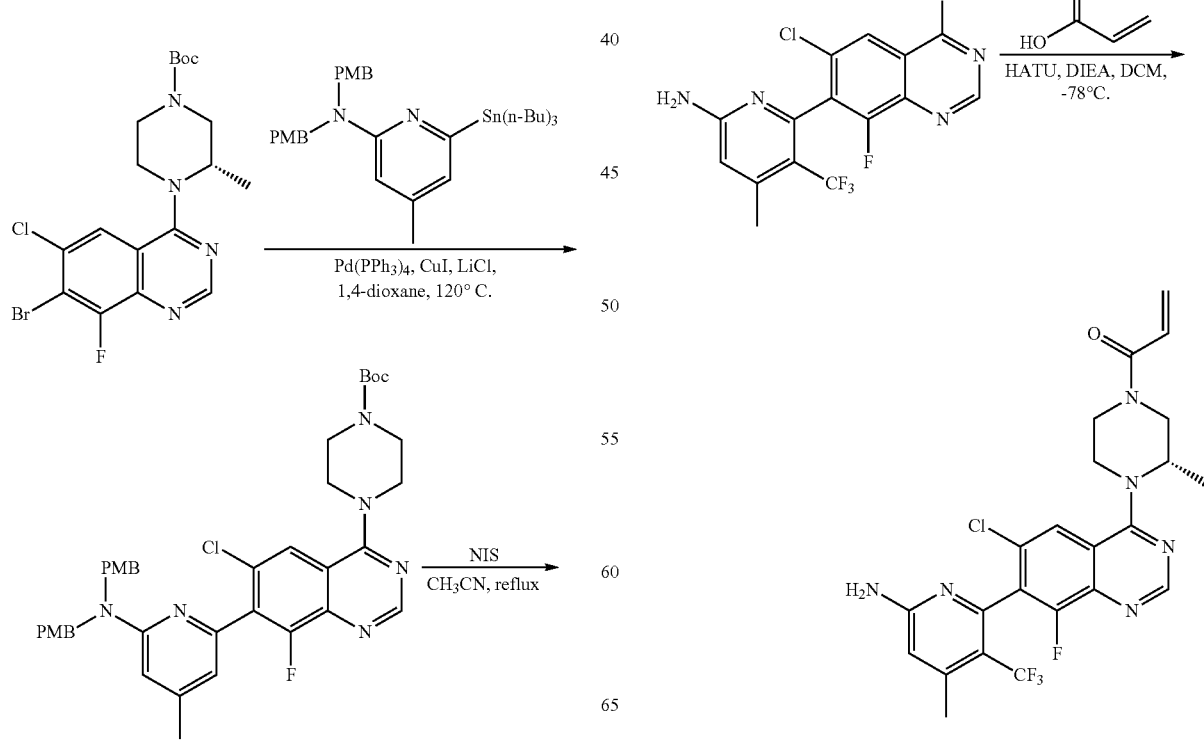

Step 1: tert-butyl 4-[7-[6-[bis[(4-methoxyphenyl)methyl]amino]-4-methyl-2-pyridyl]-6-chloro-8-fluoro-quinazolin-4-yl]piperazine-1-carboxylate

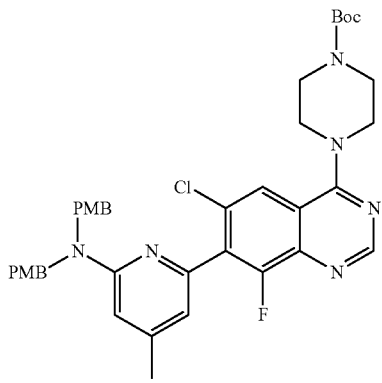

Under nitrogen, a solution of N,N-bis[(4-methoxyphenyl)methyl]-4-methyl-6-tributylstannyl-pyridin-2-amine (4.0 g, 6.27 mmol) and tert-butyl 4-[7-[6-[bis[(4-methoxyphenyl)methyl]amino]-4-methyl-2-pyridyl]-6-chloro-8-fluoro-quinazolin-4-yl]piperazine-1-carboxylate (2.31 g, 5.02 mmol), tetrakis(triphenylphosphine)palladium (0.72 g, 0.63 mmol), Lithium chloride (0.66 g, 15.69 mmol) and cuprous iodide (0.12 g, 0.63 mmol) in 1,4-dioxane (100 mL) was stirred at 120° C. for 3 hours. After completion, the solution was diluted with water (200 mL) and extracted with of ethyl acetate (3×50 mL). Then the organic layers were combined and dried over anhydrous sodium sulfate. The organic layers was concentrated under vacuum and the residue was purified by flash chromatography on silica gel eluting with ethyl acetate/petroleum ether (1/20) to afford tert-butyl 4-[7-[6-[bis[(4-methoxyphenyl)methyl]amino]-4-methyl-2-pyridyl]-6-chloro-8-fluoro-quinazolin-4-yl]piperazine-1-carboxylate (1.1 g, 1.54 mmol, 24.6% yield) as a yellow oil. LC-MS (ESI, m/z): 713.3 [M+H]$^+$.

Step 2: tert-butyl (3S)-4-[7-[6-[bis[(4-methoxyphenyl)methyl]amino]-3-iodo-4-methyl-2-pyridyl]-6-chloro-8-fluoro-quinazolin-4-yl]-3-methyl-piperazine-1-carboxylate

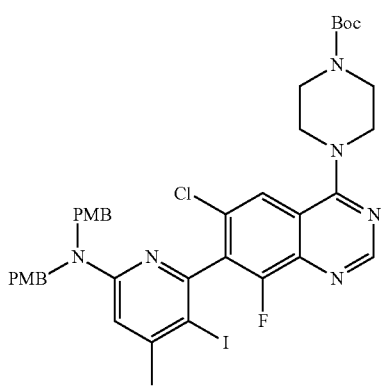

A solution of tert-butyl 4-[7-[6-[bis[(4-methoxyphenyl)methyl]amino]-4-methyl-2-pyridyl]-6-chloro-8-fluoro-quinazolin-4-yl]piperazine-1-carboxylate (2 g, 3 mmol) and N-iodosuccinimide (1 g, 3.00 mmol) in acetonitrile (200 mL) was stirred at 50° C. for 4 hours. After completion, the solution was diluted with water (30 mL) and extracted with ethyl acetate (4×50 mL) and the organic layers were combined. The organic layer was dried over anhydrous sodium sulfate and concentrated under vacuum. The residue was purified by flash chromatography on silica gel eluting with ethyl acetate/petroleum ether (1/20) to afford tert-butyl (3S)-4-[7-[6-[bis[(4-methoxyphenyl)methyl]amino]-3-iodo-4-methyl-2-pyridyl]-6-chloro-8-fluoro-quinazolin-4-yl]-3-methyl-piperazine-1-carboxylate (1.3 g, 1.55 mmol, 656.5% yield) as a yellow oil. LC-MS (ESI, m/z): 839.2 [M+H]$^+$.

Step 3: tert-butyl (3S)-4-[7-[6-[bis[(4-methoxyphenyl)methyl]amino]-4-methyl-3-(trifluoromethyl)-2-pyridyl]-6-chloro-8-fluoro-quinazolin-4-yl]-3-methyl-piperazine-1-carboxylate

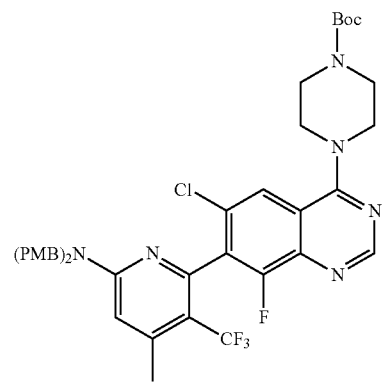

Under nitrogen, a solution of tert-butyl (3S)-4-[7-[6-[bis[(4-methoxyphenyl)methyl]amino]-4-methyl-3-(trifluoromethyl)-2-pyridyl]-6-chloro-8-fluoro-quinazolin-4-yl]-3-methyl-piperazine-1-carboxylate (0.1 g, 0.12 mmol), (1,10-Phenanthroline)(trifluoromethyl)copper(I) (0.73 g, 2.34 mmol) and cuprous iodide (0.45 g, 2.34 mmol) in N,N-dimethylformamide (5 mL) was stirred at 50° C. for 5 hours. After completion, the solution was diluted with water (30 mL) and extracted with ethyl acetate (4×350 mL) and the organic layers were combined. The organic layer was dried over anhydrous sodium sulfate and concentrated under vacuum. The residue was purified by flash chromatography on silica gel eluting with ethyl acetate/petroleum ether (1/5) to afford tert-butyl (3S)-4-[7-[6-[bis[(4-methoxyphenyl)methyl]amino]-4-methyl-3-(trifluoromethyl)-2-pyridyl]-6-chloro-8-fluoro-quinazolin-4-yl]-3-methyl-piperazine-1-carboxylate (60 mg, 0.075 mmol, 64.4% yield) as a yellow solid. LC-MS (ESI, m/z): 781.3 [M+H]$^+$.

Step 4: 6-[6-chloro-8-fluoro-4-[(2S)-2-methylpiperazin-1-yl]quinazolin-7-yl]-4-methyl-5-(trifluoromethyl)pyridin-2-amine

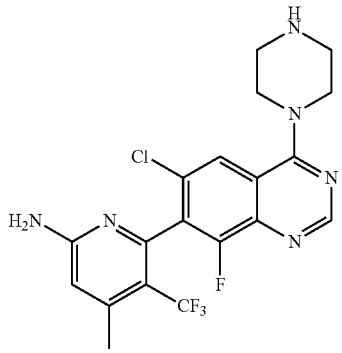 [SMILES: Cc1cc(N)nc(-c2c(Cl)cc3c(N4CCNCC4)ncnc3c2F)c1C(F)(F)F]

A solution of tert-butyl (3S)-4-[7-[6-[bis[(4-methoxyphenyl)methyl]amino]-4-methyl-3-(trifluoromethyl)-2-pyridyl]-6-chloro-8-fluoro-quinazolin-4-yl]-3-methyl-piperazine-1-carboxylate (0.1 g, 0.13 mmol) in trifluoroacetic acid (5.0 mL) was stirred at 50° C. for 3 hours. After completion, the solution was diluted with water (30 mL) and extracted with ethyl acetate (3×50 mL) and the organic layers were combined. The organic layer was dried over anhydrous sodium sulfate and concentrated under vacuum. The residue was purified by flash chromatography on silica gel eluting with methanol/dichloromethane (1/9) to afford 6-[6-chloro-8-fluoro-4-[(2S)-2-methylpiperazin-1-yl]quinazolin-7-yl]-4-methyl-5-(trifluoromethyl)pyridin-2-amine (40 mg, 0.08 mmol, 69.9% yield) as a yellow oil. LC-MS (ESI, m/z): 441.1 [M+H]$^+$.

Step 5: 1-((3S)-4-(7-(6-amino-4-methyl-3-(trifluoromethyl)pyridin-2-yl)-6-chloro-8-fluoroquinazolin-4-yl)-3-methylpiperazin-1-yl)prop-2-en-1-one

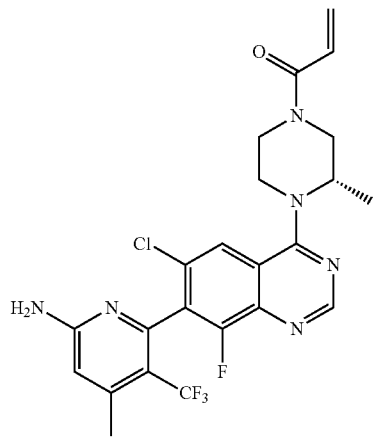 [SMILES: C=CC(=O)N1CCN(c2ncnc3c(F)c(-c4nc(N)cc(C)c4C(F)(F)F)c(Cl)cc23)[C@@H](C)C1]

A solution of 6-[6-chloro-8-fluoro-4-[(2S)-2-methylpiperazin-1-yl]quinazolin-7-yl]-4-methyl-5-(trifluoromethyl)pyridin-2-amine (0.04 g, 0.09 mmol) and HATU (0.07 g, 0.18 mmol), N,N-diisopropylethylamine (0.03 g, 0.26 mmol) in dichloromethane (3 mL) was stirred at −78° C. for 0.5 hours. Then acrylic acid (0.01 g, 0.13 mmol) was added and stirred at −78° C. for 4 hours. After completion, the solution was diluted with water (30 mL) and extracted with ethyl acetate (3×50 mL) and the organic layers were combined. The organic layer was dried over anhydrous sodium sulfate and concentrated under vacuum. The crude product was further isolated by Prep-HPLC with the following conditions Column: CHIRALPAK IE, 2*25 cm, 5 um; Mobile Phase A: MTBE (10 mM NH$_3$-methanol)-HPLC, Mobile Phase B: methanol-HPLC; Flow rate: 20 mL/min; Gradient: 15 B to 15 B in 27 min; 220/254 nm; RT1:17.672; RT2:23.294 to afford 1-[(3S)-4-[7-[6-amino-4-methyl-3-(trifluoromethyl)-2-pyridyl]-6-chloro-8-fluoro-quinazolin-4-yl]-3-methyl-piperazin-1-yl]prop-2-en-1-one (10 mg, 0.019 mmol, 22.3% yield) as a white solid. LC-MS (ESI, m/z): 509.1 [M+H]$^+$.

Example 19

$^1$H NMR (400 MHz, Methanol-d$_4$, ppm) δ 8.67 (s, 1H), 7.92 (s, 1H), 6.89-6.82 (m, 1H), 6.62 (s, 1H), 6.32-6.26 (m, 1H), 5.83-5.80 (m, 1H), 4.56-4.39 (m, 1H), 4.38-4.30 (m, 1H), 4.20-4.02 (m, 1H), 3.80-3.52 (m, 2H), 3.33-3.30 (m, 1H), 3.22-3.13 (m, 1H), 2.45 (s, 3H), 1.42 (d, J=1.6 Hz, 3H).

Example 20

1-[4-[7-[6-amino-3-(trifluoromethyl)-2-pyridyl]-6-(azetidin-1-yl)quinazolin-4-yl]piperazin-1-yl]prop-2-en-1-one

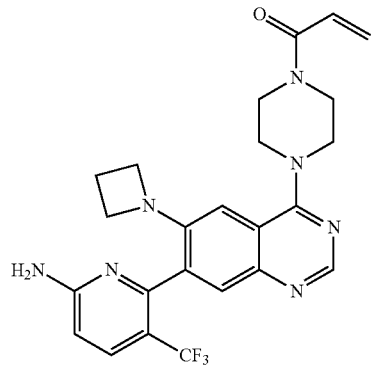 [SMILES: C=CC(=O)N1CCN(c2ncnc3cc(-c4nc(N)ccc4C(F)(F)F)c(N4CCC4)cc23)CC1]

Synthetic Route

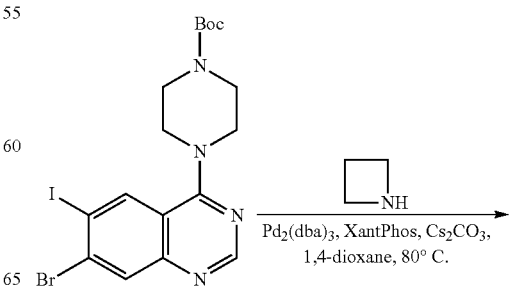

-continued

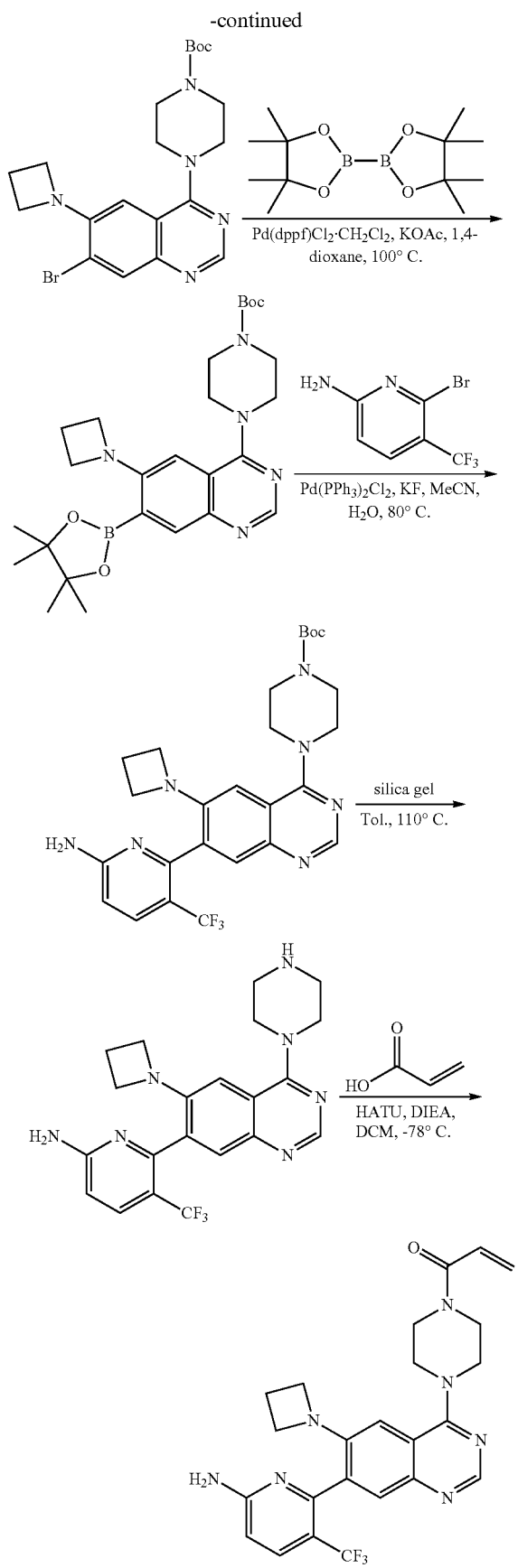

Step 1: tert-butyl 4-[6-(azetidin-1-yl)-7-bromo-quinazolin-4-yl]piperazine-1-carboxylate

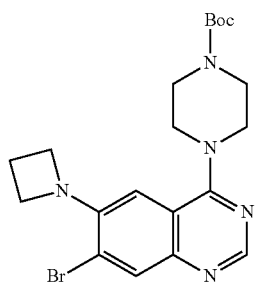 [SMILES: CC(C)(C)OC(=O)N1CCN(c2ncnc3cc(Br)c(N4CCC4)cc23)CC1]

Under nitrogen, a solution of tert-butyl 4-(7-bromo-6-iodo-quinazolin-4-yl)piperazine-1-carboxylate (5.5 g, 10.59 mmol), azetidine (1.2 g, 21.19 mmol), tris(dibenzylideneacetone)dipalladium (609.15 mg, 1.06 mmol), XantPhos (1.22 g, 2.12 mmol) and cesium carbonate (6.9 g, 21.19 mmol) in 1,4-dioxane (20 mL) was stirred at 80° C. for 2 hours. After completion, the solution was diluted with ethyl acetate (200 mL) and washed with brine (50 mL). The organic layer was dried over anhydrous sodium sulfate and concentrated under vacuum. The residue was purified by flash chromatography on silica gel eluting with ethyl acetate/petroleum ether (45/55) to afford tert-butyl 4-[6-(azetidin-1-yl)-7-bromo-quinazolin-4-yl]piperazine-1-carboxylate (1.0 g, 2.24 mmol, 21.1% yield) as a yellow solid. LC-MS (ESI, m/z): 448.1 [M+H]$^+$.

Step 2: tert-butyl 4-[6-(azetidin-1-yl)-7-(4,4,5,5-tetramethyl-1,3,2-dioxaborolan-2-yl)quinazolin-4-yl]piperazine-1-carboxylate

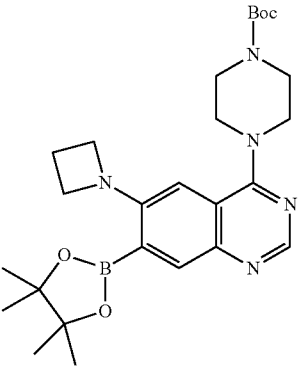 [SMILES: CC(C)(C)OC(=O)N1CCN(c2ncnc3cc(B4OC(C)(C)C(C)(C)O4)c(N4CCC4)cc23)CC1]

Under nitrogen, a solution of tert-butyl 4-[6-(azetidin-1-yl)-7-bromo-quinazolin-4-yl]piperazine-1-carboxylate (1.0 g, 2.23 mmol), bis(pinacolato)diboron (5.66 g, 22.3 mmol), 1,1'-bis(diphenylphosphino)ferrocene-palladium(II)dichloride dichloromethane complex (182.0 mg, 0.22 mmol) and potassium acetate (437.15 mg, 4.46 mmol) in 1,4-dioxane (15 mL) was stirred at 80° C. for 3 hours. After completion, the solution was diluted with dichloromethane (100 mL). After filtration, the filtrate was concentrated under reduced pressure. The residue was dissolved with petroleum ether (100 mL). After filtration, the filter cake was purified by flash chromatography on silica gel eluting with ethyl acetate/petroleum ether (1/1) to afford tert-butyl 4-[6-(azetidin-1- yl)-7-(4,4,5,5-tetramethyl-1,3,2-dioxaborolan-2-yl)quinazolin-4-yl]piperazine-1-carboxylate (500 mg, 1.01 mmol, 45.3% yield) as a yellow solid. LC-MS (ESI, m/z): 496.3 [M+H]⁺.

Step 3: tert-butyl 4-[7-[6-amino-3-(trifluoromethyl)-2-pyridyl]-6-(azetidin-1-yl)quinazolin-4-yl]piperazine-1-carboxylate

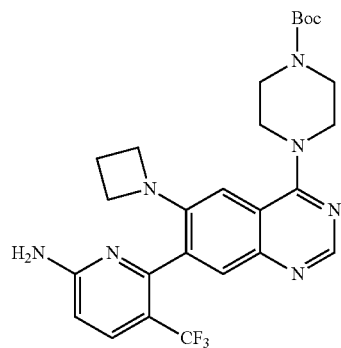 [SMILES: CC(C)(C)OC(=O)N1CCN(c2ncnc3cc(-c4nc(N)ccc4C(F)(F)F)c(N4CCC4)cc23)CC1]

Under nitrogen, a solution of tert-butyl 4-[6-(azetidin-1-yl)-7-(4,4,5,5-tetramethyl-1,3,2-dioxaborolan-2-yl)quinazolin-4-yl]piperazine-1-carboxylate (500.0 mg, 1.01 mmol), 6-bromo-5-(trifluoromethyl)pyridin-2-amine (243.24 mg, 1.01 mmol), bis(triphenylphosphine)palladium(II) chloride (70.85 mg, 0.10 mmol) and potassium fluoride (117.07 mg, 2.02 mmol) in acetonitrile (10 mL) and water (2 mL) was stirred at 80° C. for 2 hours. After completion, the solution was concentrated under vacuum. The residue was purified by flash chromatography on silica gel eluting with methanol/dichloromethane (3/97) to afford tert-butyl 4-[7-[6-amino-3-(trifluoromethyl)-2-pyridyl]-6-(azetidin-1-yl)quinazolin-4-yl]piperazine-1-carboxylate (280 mg, 0.53 mmol, 52.4% yield) as a yellow solid. LC-MS (ESI, m/z): 530.2 [M+H]⁺.

Step 4: 6-[6-(azetidin-1-yl)-4-piperazin-1-yl-quinazolin-7-yl]-5-(trifluoromethyl)pyridin-2-amine

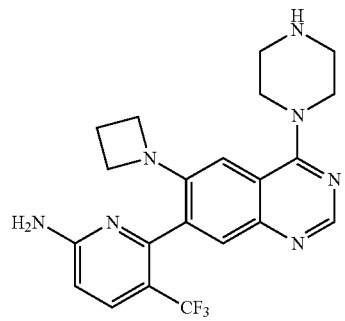 [SMILES: Nc1ccc(C(F)(F)F)c(-c2cc3ncnc(N4CCNCC4)c3cc2N2CCC2)n1]

A solution of tert-butyl 4-[7-[6-amino-3-(trifluoromethyl)-2-pyridyl]-6-(azetidin-1-yl)quinazolin-4-yl]piperazine-1-carboxylate (200.0 mg, 0.38 mmol) and silica gel (1.0 g) in toluene (20 mL) was stirred at 110° C. for 12 hours. After completion, the solution was concentrated under vacuum. The residue was purified by flash chromatography on silica gel eluting with methanol/dichloromethane (1/9) to afford 6-[6-(azetidin-1-yl)-4-piperazin-1-yl-quinazolin-7-yl]-5-(trifluoromethyl)pyridin-2-amine (150 mg, 0.35 mmol, 92.5% yield) as a yellow solid. LC-MS (ESI, m/z): 430.2 [M+H]⁺.

Step 5: 1-[4-[7-[6-amino-3-(trifluoromethyl)-2-pyridyl]-6-(azetidin-1-yl)quinazolin-4-yl]piperazin-1-yl]prop-2-en-1-one

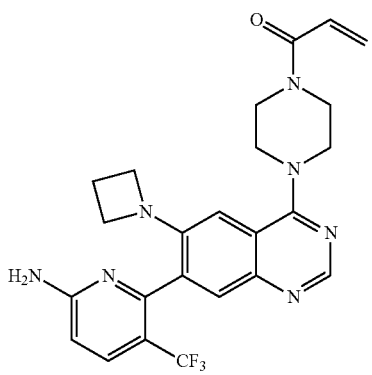 [SMILES: C=CC(=O)N1CCN(c2ncnc3cc(-c4nc(N)ccc4C(F)(F)F)c(N4CCC4)cc23)CC1]

A solution of 6-[6-(azetidin-1-yl)-4-piperazin-1-yl-quinazolin-7-yl]-5-(trifluoromethyl)pyridin-2-amine (150.0 mg, 0.35 mmol), acrylic acid (25.17 mg, 0.35 mmol), HATU (159.37 mg, 0.42 mmol) and N,N-diisopropylethylamine (45 mg, 0.35 mmol) in dichloromethane (10 mL) was stirred at 25° C. for 1 h. After completion, the solution was diluted with dichloromethane and washed with brine. The organic layer was dried over anhydrous sodium sulfate and concentrated under vacuum. The residue was purified by reverse-phase column eluting with acetonitrile/water (1/1) to afford 1-[4-[7-[6-amino-3-(trifluoromethyl)-2-pyridyl]-6-(azetidin-1-yl)quinazolin-4-yl]piperazin-1-yl]prop-2-en-1-one (5.9 mg, 3.5% yield) as a yellow solid. LC-MS (ESI, m/z): 484.2 [M+H]⁺.

Example 20

¹H NMR (300 MHz, Methanol-d₄, ppm) δ 8.50 (s, 1H), 7.83 (d, J=9.0 Hz, 1H), 7.54 (s, 1H), 6.91-6.82 (m, 1H), 6.75-6.70 (m, 2H), 6.30 (dd, J=16.8, 2.0 Hz, 1H), 5.83 (dd, J=10.6, 2.0 Hz, 1H), 3.99-3.81 (m, 8H), 3.78-3.61 (m, 4H), 2.29-2.19 (m, 2H).

Example 21
1-(4-(7-(6-amino-3-(trifluoromethyl)pyridin-2-yl)-6-(1,1-difluoroethyl)quinazolin-4-yl)piperazin-1-yl)prop-2-en-1-one
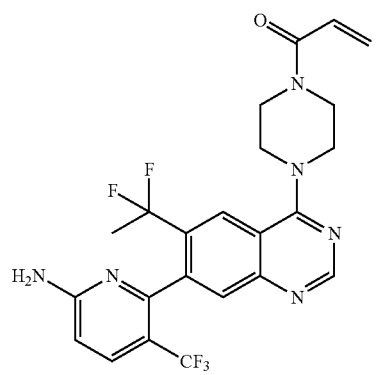 [SMILES: C=CC(=O)N1CCN(c2ncnc3cc(-c4nc(N)ccc4C(F)(F)F)c(C(C)(F)F)cc23)CC1]
Synthetic Route
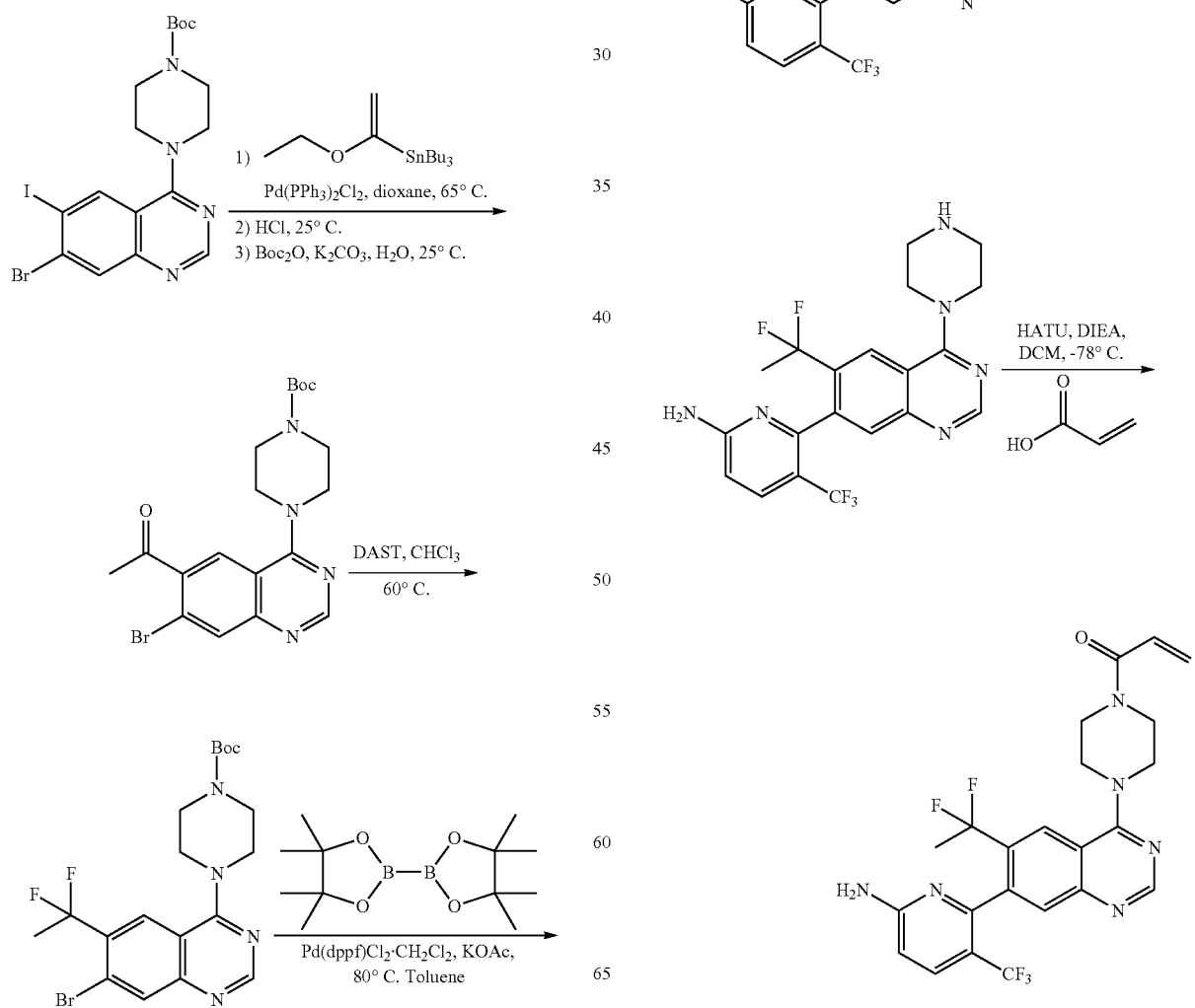

Step 1: tert-butyl 4-(6-acetyl-7-bromoquinazolin-4-yl)piperazine-1-carboxylate

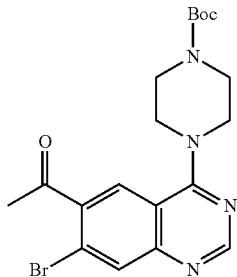 [SMILES: CC(=O)c1cc2c(N3CCN(C(=O)OC(C)(C)C)CC3)ncnc2cc1Br]

Under nitrogen, a solution of tert-butyl 4-(7-bromo-6-iodo-quinazolin-4-yl)piperazine-1-carboxylate (1.8 g, 3.47 mmol), tributyl(1-ethoxyvinyl)tin (2.5 g, 6.93 mmol), bis(triphenylphosphine)palladium(II) chloride (243.4 mg, 0.35 mmol) in 1,4-dioxane (40 mL) was stirred at 65° C. for 30 hours. After completion, the solution was added hydrochloric acid (40 mL, 2 M) was stirred at 25° C. for 0.5 hours. Then the solvent was concentrated under vacuum. The residue was dissolved with water (40 mL), and the pH of the resulting solution was adjusted to pH=9 with potassium carbonate. Then di-tert-butyl dicarbonate (1.67 g, 7.61 mmol) was added and the solution was stirred at 25° C. for 2 hours. After completion, the solution was extracted with ethyl acetate (100 mL) and the organic layer was dried over anhydrous sodium sulfate and concentrated under vacuum. The residue was purified by reverse-phase eluting with acetonitrile/water (1:1) to afford tert-butyl 4-(6-acetyl-7-bromoquinazolin-4-yl)piperazine-1-carboxylate (1.0 g, 2.30 mmol, 66.3% yield) as a yellow oil. LC-MS: (ESI, m/z): 435.1, 437.1 [M+H]$^+$.

Step 2: tert-butyl 4-[7-bromo-6-(1,1-difluoroethyl)quinazolin-4-yl]piperazine-1-carboxylate

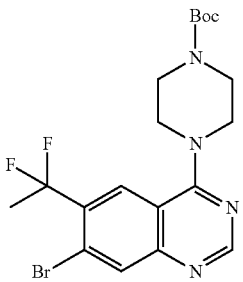 [SMILES: CC(C)(C)OC(=O)N1CCN(c2ncnc3cc(Br)c(C(C)(F)F)cc23)CC1]

A solution of tert-butyl 4-(6-acetyl-7-bromoquinazolin-4-yl)piperazine-1-carboxylate (1.2 g, 2.8 mmol), diethylaminosulfur trifluoride (3.6 mL, 27.6 mmol) in chloroform (30 mL) was stirred at 25° C. for 36 hours. After completion, the solution was quenched with water (5 mL) and concentrated under vacuum. The residue was purified by reverse-phase column eluting with acetonitrile/water (5/1) to afford tert-butyl 4-[7-bromo-6-(1,1-difluoroethyl)quinazolin-4-yl]piperazine-1-carboxylate (570 mg, 1.2 mmol, 45.2% yield) as a light brown solid. LC-MS: (ESI, m/z): 457.1, 459.1 [M+H]$^+$.

Step 3: tert-butyl 4-[6-(1,1-difluoroethyl)-7-(4,4,5,5-tetramethyl-1,3,2-dioxaborolan-2-yl)quinazolin-4-yl]piperazine-1-carboxylate

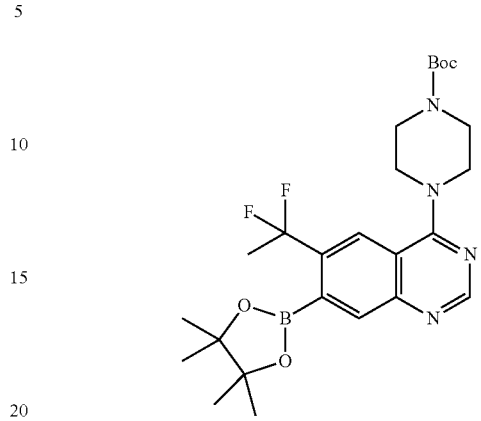

Under nitrogen, a solution of tert-butyl 4-[7-bromo-6-(1,1-difluoroethyl)quinazolin-4-yl]piperazine-1-carboxylate (550.0 mg, 1.2 mmol), bis(pinacolato)diboron (1.5 g, 6.0 mmol) 1,1'-bis(diphenylphosphino)ferrocene-palladium(II) dichloride dichloromethane complex (88.0 mg, 0.1 mmol), potassium acetate (353.6 mg, 3.6 mmol) in toluene (20.0 mL) at 95° C. for 4 hours. After completion, the solution was concentrated under vacuum. The residue was purified by reverse-phase eluting with acetonitrile/water (4/1) to afford tert-butyl 4-[6-(1,1-difluoroethyl)-7-(4,4,5,5-tetramethyl-1,3,2-dioxaborolan-2-yl)quinazolin-4-yl]piperazine-1-carboxylate (350.0 mg, 0.7 mmol, 57.7% yield) as a light yellow oil. LC-MS: (ESI, m/z): 505.3 [M+H]$^+$.

Step 4: tert-butyl 4-[7-[6-amino-3-(trifluoromethyl)-2-pyridyl]-6-(1,1-difluoroethyl)quinazolin-4-yl]piperazine-1-carboxylate

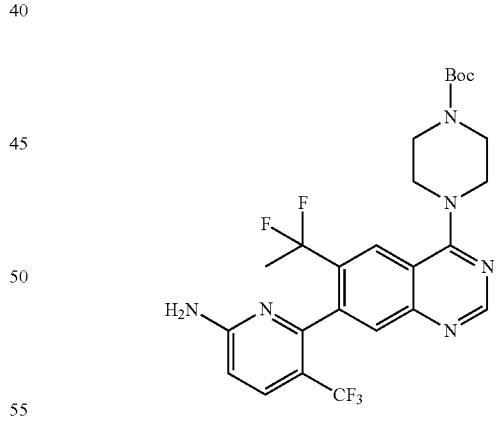

Under nitrogen, a solution of tert-butyl 4-[6-(1,1-difluoroethyl)-7-(4,4,5,5-tetramethyl-1,3,2-dioxaborolan-2-yl)quinazolin-4-yl]piperazine-1-carboxylate (350.0 mg, 0.7 mmol), 6-bromo-5-(trifluoromethyl)pyridin-2-amine (167.2 mg, 0.7 mmol), potassium carbonate (287.3 mg, 2.1 mmol) and bis(triphenylphosphine)palladium(II) chloride (48.7 mg, 0.1 mmol) in acetonitrile (20 mL) and water (2 mL) was stirred for 4 h at 95° C. After completion, the solution was concentrated under vacuum. The residue was purified by reverse-phase acetonitrile/water (6:1) to afford tert-butyl 4-[7-[6-amino-3-(trifluoromethyl)-2-pyridyl]-6-(1,1-difluoroethyl)quinazolin-4-yl]piperazine-1-carboxylate (170 mg, 0.3 mmol, 45.5% yield) as a light brown oil. LC-MS: (ESI, m/z): 539.2 [M+H]+.

Step 5: 6-[6-(1,1-difluoroethyl)-4-piperazin-1-yl-quinazolin-7-yl]-5-(trifluoromethyl)pyridin-2-amine

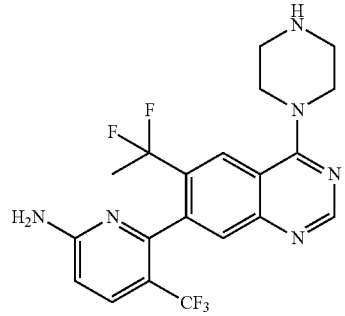 [SMILES: CC(F)(F)c1cc2c(N3CCNCC3)ncnc2cc1-c1nc(N)ccc1C(F)(F)F]

A solution of tert-butyl 4-[7-[6-amino-3-(trifluoromethyl)-2-pyridyl]-6-(1,1-difluoroethyl)quinazolin-4-yl]piperazine-1-carboxylate (160.0 mg, 0.3 mmol) in dichloromethane (10 mL) and trifluoroacetic acid (2 mL) was stirred at 25° C. for 3 hours. After completion, the solution was concentrated under vacuum to afford 6-[6-(1,1-difluoroethyl)-4-piperazin-1-yl-quinazolin-7-yl]-5-(trifluoromethyl)pyridin-2-amine (170 mg crude) as a light brown oil which was used for next step without purification. LC-MS: (ESI, m/z): 439.2 [M+H]+

Step 6: 1-[4-[7-[6-amino-3-(trifluoromethyl)-2-pyridyl]-6-(1,1-difluoroethyl)quinazolin-4-yl]piperazin-1-yl]prop-2-en-1-one

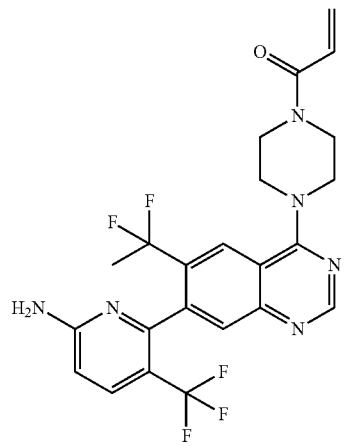 [SMILES: C=CC(=O)N1CCN(c2ncnc3cc(-c4nc(N)ccc4C(F)(F)F)c(C(C)(F)F)cc23)CC1]

A solution of (6-[6-(1,1-difluoroethyl)-4-piperazin-1-yl-quinazolin-7-yl]-5-(trifluoromethyl)pyridin-2-amine (160.0 mg, 0.4 mmol), HATU (346.9 mg, 0.9 mmol), acrylic acid (52.6 mg, 0.7 mmol) and N,N-diisopropylethylamine (235.4 mg, 1.8 mmol) in dichloromethane (10 mL) was stirred at −78° C. for 1.0 h. After completion, the solution was quenched with water (5 mL). The resulting solution was extracted with dichloromethane (3×20 mL) and the organic layers were combined. The organic layer was dried over anhydrous sodium sulfate and concentrated under vacuum. The residue was purified by reverse-phase eluting with acetonitrile/water (6/1) to afford 100 mg of crude product. Then the crude product was purified by Prep-HPLC to afford 1-(4-(7-(6-amino-3-(trifluoromethyl)pyridin-2-yl)-6-(1,1-difluoroethyl)quinazolin-4-yl)piperazin-1-yl)prop-2-en-1-one (22.1 mg, 0.04 mmol, 12.3% yield) as an off-white solid. LC-MS: (ESI, m/z): 493.2 [M+H]+.

Example 21

$^1$H NMR (400 MHz, Methanol-$d_4$, ppm) δ 8.69 (s, 1H), 8.26 (s, 1H), 7.78 (d, J=7.2 Hz, 1H), 7.67 (s, 1H), 6.84 (dd, J=16.8, 10.4 Hz, 1H), 6.67 (d, J=8.8 Hz, 1H), 6.29 (dd, J=16.8, 2.0 Hz, 1H), 5.82 (dd, J=10.4, 2.0 Hz, 1H), 4.15-4.00 (m, 4H), 3.99-3.86 (m, 4H), 2.02 (dd, J=19.2, 18.4 Hz, 3H).

Example 22

4-[7-[6-amino-4-methyl-3-(trifluoromethyl)-2-pyridyl]-6-chloro-quinazolin-4-yl]-1-prop-2-enoyl-piperidine-4-carbonitrile

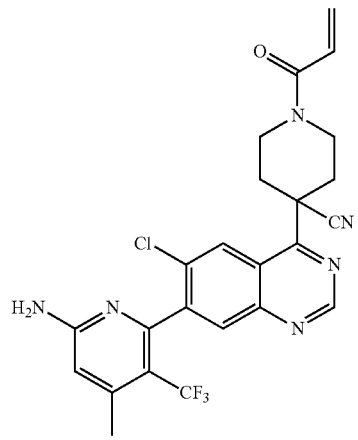 [SMILES: C=CC(=O)N1CCC(C#N)(c2ncnc3cc(-c4nc(N)cc(C)c4C(F)(F)F)c(Cl)cc23)CC1]

Synthetic Route

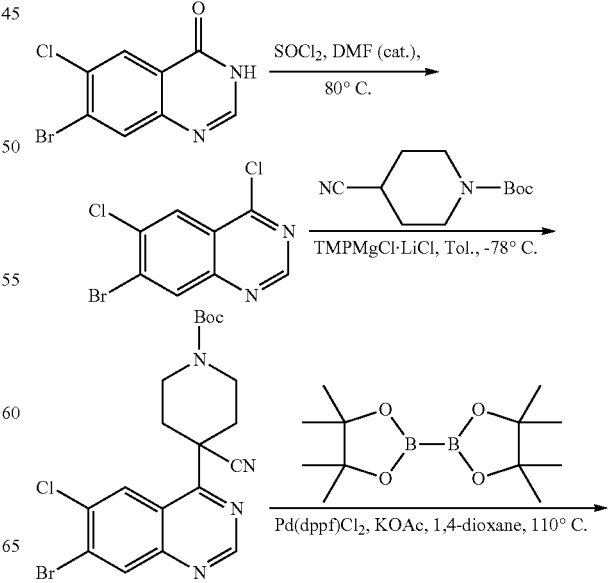

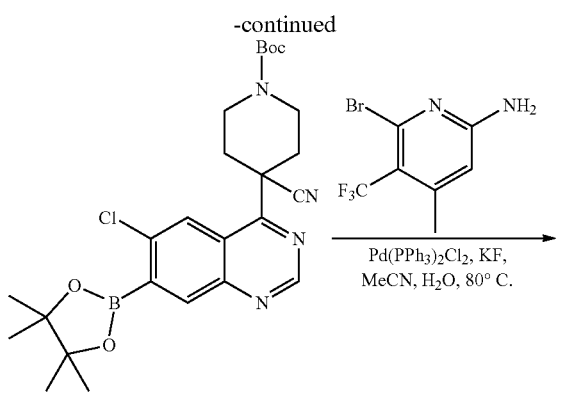

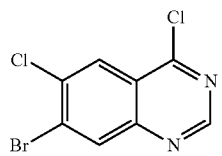 [SMILES: Clc1cc2c(Cl)ncnc2cc1Br]

Step 1: 7-bromo-4,6-dichloroquinazoline

A solution of 7-bromo-6-chloro-3H-quinazolin-4-one (50 g, 38.5 mmol), N,N-dimethylformamide (1.0 mL) in thionyl chloride (500 mL, 192.7 mmol) was stirred at 80° C. for 3 hours. After completion, the solution was concentrated under vacuum. Then the residue was purified by flash chromatography on silica gel eluting with ethyl acetate/petroleum ether (1/10) to afford 7-bromo-4,6-dichloro-quinazoline (26 g, 98% yield) as an white solid.

Step 2: 7 tert-butyl 4-(7-bromo-6-chloro-quinazolin-4-yl)-4-cyano-piperidine-1-carboxylate

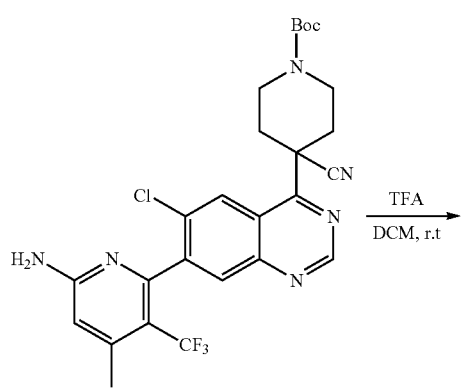

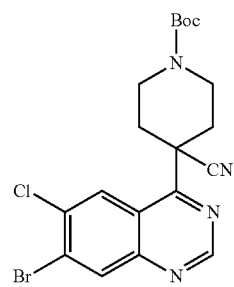 [SMILES: CC(C)(C)OC(=O)N1CCC(C#N)(c2ncnc3cc(Br)c(Cl)cc23)CC1]

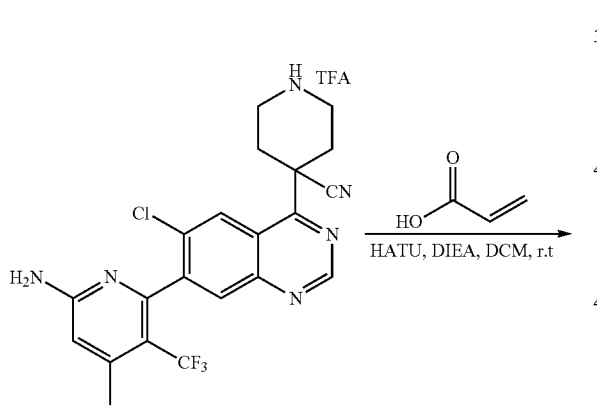

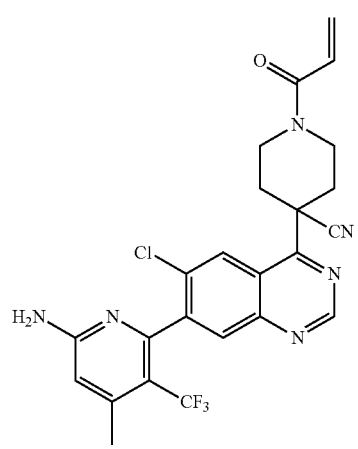

Under nitrogen, to a solution of 1-Boc-4-cyanopiperidine (18.9 g, 90.0 mmol) and 7-bromo-4,6-dichloro-quinazoline (5.0 g, 18.0 mmol) in dry toluene (100 mL) was added TMPMgCl·LiCl (54.0 mL, 54.0 mmol, 1.0 M in THF) at −78° C. for 0.5 h. After completion, the solution was quenched with water (50 mL) and extracted with ethyl acetate (3×100 mL) and the organic layers were combined. The organic layer was dried over anhydrous sodium sulfate and concentrated under vacuum. The residue was purified by flash chromatography eluting with ethyl acetate/petroleum ether (1/2) to afford crude product. Then the crude material was repurified by reverse phase chromatography eluting with acetonitrile/water (7/3) to afford tert-butyl 4-(7-bromo-6-chloro-quinazolin-4-yl)-4-cyano-piperidine-1-carboxylate (1.6 g, 3.5 mmol, 19.7% yield). LC-MS: (ESI, m/z): 451.0 [M+H]$^+$ Step 3: tert-butyl 4-[6-chloro-7-(4,4,5,5-tetramethyl-1,3,2-dioxaborolan-2-yl)quinazolin-4-yl]-4-cyano-piperidine-1-carboxylate

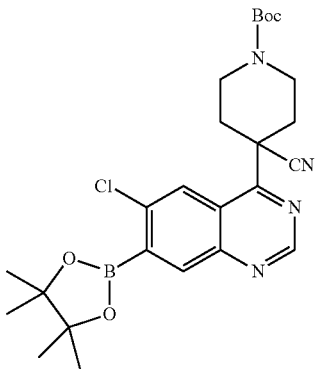 [SMILES: CC(C)(C)OC(=O)N1CCC(C#N)(c2ncnc3cc(B4OC(C)(C)C(C)(C)O4)c(Cl)cc23)CC1]

Under nitrogen, a solution of tert-butyl 4-(7-bromo-6-chloro-quinazolin-4-yl)-4-cyano-piperidine-1-carboxylate (1.0 g, 2.2 mmol), bis(pinacolato)diboron (2.8 g, 11.1 mmol), 1,1'-bis(diphenylphosphino)ferrocene-palladium(II) dichloride dichloromethane complex (310.4 mg, 0.4 mmol) and potassium acetate (650.8 mg, 6.6 mmol) in 1,4-dioxane (30 mL) was stirred at 110° C. for 2 hours. After completion, the solution was diluted with water (30 mL) and extracted with dichloromethane (3×50 mL) and the organic layers were combined. The organic layer was dried over anhydrous sodium sulfate and concentrated under vacuum. The residue was purified by reverse phase chromatography eluting with acetonitrile/water (7/3) to afford tert-butyl 4-[6-chloro-7-(4,4,5,5-tetramethyl-1,3,2-dioxaborolan-2-yl)quinazolin-4-yl]-4-cyano-piperidine-1-carboxylate (300 mg, 0.6 mmol, 27.2% yield) as an off-white solid, LC-MS: (ESI, m/z): 499.2 [M+H]$^+$.

Step 4: tert-butyl 4-[7-[6-amino-4-methyl-3-(trifluoromethyl)-2-pyridyl]-6-chloro-quinazolin-4-yl]-4-cyano-piperidine-1-carboxylate

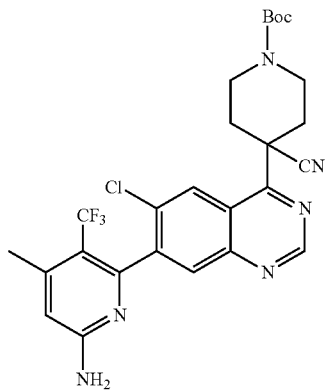 [SMILES: Cc1cc(N)nc(-c2cc3ncnc(C4(C#N)CCN(C(=O)OC(C)(C)C)CC4)c3cc2Cl)c1C(F)(F)F]

Under nitrogen, a solution of tert-butyl 4-[6-chloro-7-(4,4,5,5-tetramethyl-1,3,2-dioxaborolan-2-yl)quinazolin-4-yl]-4-cyano-piperidine-1-carboxylate (200.0 mg, 0.48 mmol), 6-bromo-4-methyl-5-(trifluoromethyl)pyridin-2-amine (134.7 mg, 0.5 mmol), bis(triphenylphosphine)palladium(II) chloride (33.7 mg, 0.05 mmol), potassium fluoride (83.5 mg, 1.4 mmol) in acetonitrile (10 mL) and water (1 mL) was stirred at 80° C. for 1 hour. After completion, the solution was diluted with water (20 mL) and extracted with dichloromethane (3×50 mL) and the organic layers were combined. The organic layer was dried over anhydrous sodium sulfate and concentrated under vacuum. The residue was purified by silica gel column eluting with petroleum ether/ethyl acetate (2/1) to afford tert-butyl 4-[7-[6-amino-4-methyl-3-(trifluoromethyl)-2-pyridyl]-6-chloro-quinazolin-4-yl]-4-cyano-piperidine-1-carboxylate (140 mg, 0.26 mmol, 53.3% yield) as a white solid. LC-MS: (ESI, m/z): 547.2 [M+H]$^+$.

Step 5: 4-(7-(6-amino-4-methyl-3-(trifluoromethyl)pyridin-2-yl)-6-chloroquinazolin-4-yl)piperidine-4-carbonitrile 2,2,2-trifluoroacetate

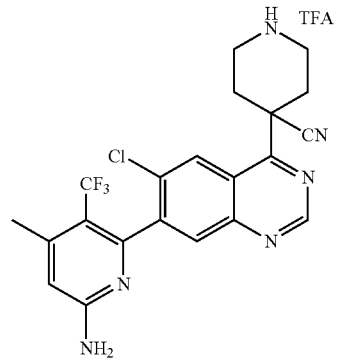 [SMILES: Cc1cc(N)nc(-c2cc3ncnc(C4(C#N)CCNCC4)c3cc2Cl)c1C(F)(F)F]

A solution of tert-butyl 4-[7-[6-amino-4-methyl-3-(trifluoromethyl)-2-pyridyl]-6-chloro-quinazolin-4-yl]-4-cyano-piperidine-1-carboxylate (140.0 mg, 0.26 mmol) in dichloromethane (5 mL) and trifluoroacetic acid (0.5 mL) was stirred at 25° C. for 3 hours. After completion, the solution was concentrated under vacuum to afford 150 mg crude which was used for next step without purification. LC-MS: (ESI, m/z): 447.1 [M+H]$^+$.

Step 6: 4-[7-[6-amino-4-methyl-3-(trifluoromethyl)-2-pyridyl]-6-chloro-quinazolin-4-yl]-1-prop-2-enoyl-piperidine-4-carbonitrile

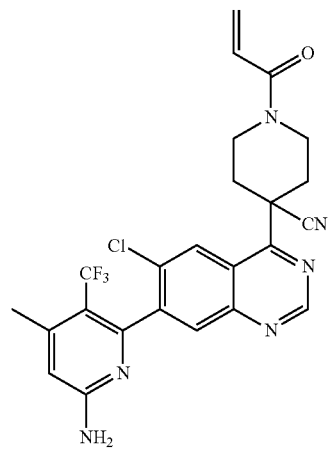 [SMILES: C=CC(=O)N1CCC(C#N)(c2ncnc3cc(-c4nc(N)cc(C)c4C(F)(F)F)c(Cl)cc23)CC1]

A solution of acrylic acid (32.3 mg, 0.5 mmol), HATU (85.1 mg, 0.2 mmol), N,N-diisopropylethylamine (86.6 mg, 0.7 mmol) and 4-(7-(6-amino-4-methyl-3-(trifluoromethyl)pyridin-2-yl)-6-chloroquinazolin-4-yl)piperidine-4-carbonitrile 2,2,2-trifluoroacetate in dichloromethane (5 mL) was stirred at 25° C. for 20 mins. After completion, the solution was quenched with water (30 mL) and extracted with dichloromethane (3×30 mL) and the organic layers were combined. The organic layer was dried over anhydrous sodium sulfate and concentrated under vacuum. The residue was purified by flash chromatography on silica gel eluting with dichloromethane/methanol (1/49) to afford a crude product. Then the crude material was purified by reverse-phase eluting with acetonitrile/water (6/1) to afford 4-[7-[6-amino-4-methyl-3-(trifluoromethyl)-2-pyridyl]-6-chloro-quinazolin-4-yl]-1-prop-2-enoyl-piperidine-4-carbonitrile (2.1 mg, 0.0042 mmol, 1.9% yield) as a white solid. LC-MS: (ESI, m/z): 501.1 [M+H]$^+$.

Example 22

$^1$H NMR (400 MHz, Methanol-d$_4$, ppm) δ 9.34 (s, 1H), 8.87 (s, 1H), 8.02 (s, 1H), 6.91-6.87 (m, 1H), 6.63 (s, 1H), 6.27 (dd, J=16.8, 2.0 Hz, 1H), 5.82 (dd, J=10.8, 2.0 Hz, 1H), 4.82-4.78 (m, 1H), 4.65 (m, 1H), 4.44-4.35 (m, 1H), 3.81-3.72 (m, 1H), 3.40-3.35 (m, 1H), 2.69-2.60 (m, 2H), 2.48 (s, 3H), 2.45-2.35 (m, 1H).

Example 23

4-[7-[6-amino-4-methyl-3-(trifluoromethyl)-2-pyridyl]-6-chloro-quinazolin-4-yl]-1-(cyclobutene-1-carbonyl)piperazine-2-carbonitrile

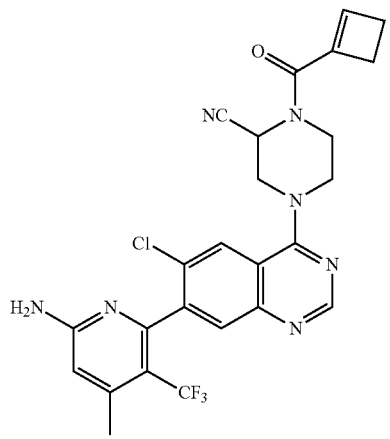 [SMILES: Cc1cc(N)nc(-c2cc3ncnc(N4CCN(C(=O)C5=CCC5)C(C#N)C4)c3cc2Cl)c1C(F)(F)F]

Synthetic Route

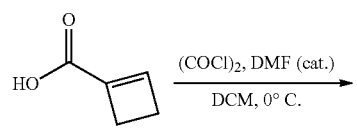

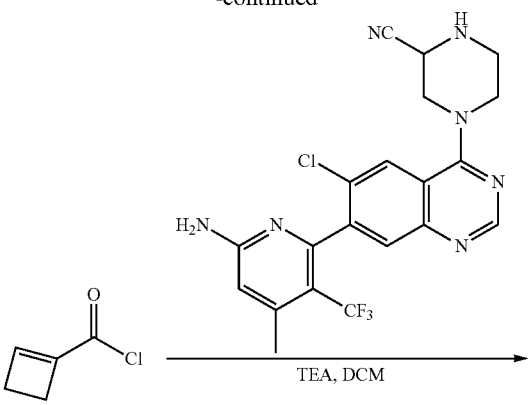

Step 1: cyclobutene-1-carbonyl chloride

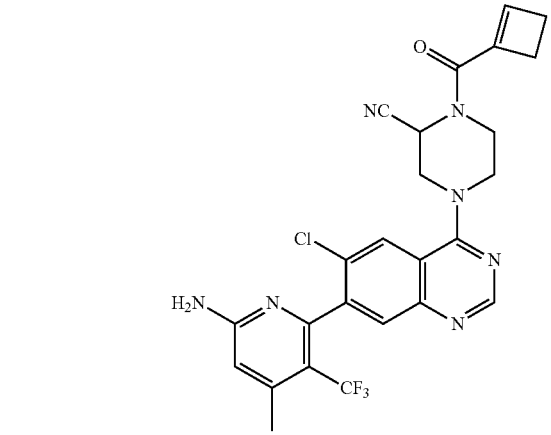 [SMILES: Cc1cc(N)nc(-c2cc3ncnc(N4CCN(C(=O)C5=CCC5)C(C#N)C4)c3cc2Cl)c1C(F)(F)F]

A solution of cyclobutene-1-carboxylic acid (300.0 mg, 3.1 mmol), N,N-dimethylformamide (22.3 mg, 0.3 mmol) in dichloromethane (20 mL) was stirred at 0° C. for 0.5 hours. Then oxalic acid chloride (582.3 mg, 4.6 mmol) was added and stirred at 0° C. for 3 h. After completion, the solution was concentrated under vacuum to afford 350 mg crude product which was used directly for next step.

Step 2: 4-[7-[6-amino-4-methyl-3-(trifluoromethyl)-2-pyridyl]-6-chloro-quinazolin-4-yl]-1-(cyclobutene-1-carbonyl)piperazine-2-carbonitrile

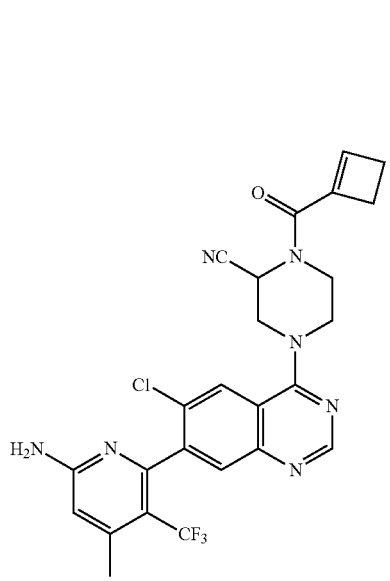

A solution of 4-[7-[6-amino-4-methyl-3-(trifluoromethyl)-2-pyridyl]-6-chloro-quinazolin-4-yl]piperazine-2-carbonitrile (150.0 mg, 0.3 mmol) and triethylamine (507.4 mg, 5.0 mmol) in dichloromethane (25 mL) was stirred at 25° C. for 0.5 hours. Then cyclobutene-1-carbonyl chloride (195.2 mg, crude) was added and stirred at 25° C. for 16 hours. The reaction was quenched with methanol. After completion, the solution was concentrated under vacuum. The residue was purified by Prep-HPLC with the following conditions: Column, XBridge Shield RP18 OBD Column 30*150 mm, 5 um; Phase A: Water (10 MMOL/L NH$_4$HCO$_3$), Phase B:ACN. Flow rate:60 ml/min, RT: 6.15 min, to afford 4-[7-[6-amino-4-methyl-3-(trifluoromethyl)-2-pyridyl]-6-chloro-quinazolin-4-yl]-1-(cyclobutene-1-carbonyl)piperazine-2-carbonitrile (50.6 mg, 0.0958 mmol, 28.6% yield) as a light yellow solid. LC-MS: (ESI, m/z): 528.1 [M+H]$^+$.

Example 23

$^1$H NMR (300 MHz, CDCl$_3$, ppm) δ 8.88 (s, 1H), 8.15 (d, J=12.3 Hz, 1H), 7.91 (s, 1H), 6.69 (d, J=0.9 Hz, 1H), 6.51 (s, 1H), 5.82 (s, 1H), 4.85 (s, 2H), 4.47 (dd, J=13.8, 7.8 Hz, 2H), 4.28 (d, J=12.9 Hz, 1H), 3.88 (s, 1H), 3.40 (t, J=15.8 Hz, 1H), 3.32-3.14 (m, 1H), 2.94 (s, 2H), 2.66-2.57 (m, 2H), 2.51 (s, 3H).

Example 24

4-[7-[6-amino-4-methyl-3-(trifluoromethyl)-2-pyridyl]-6-chloro-quinazolin-4-yl]-1-(oxirane-2-carbonyl)piperazine-2-carbonitrile

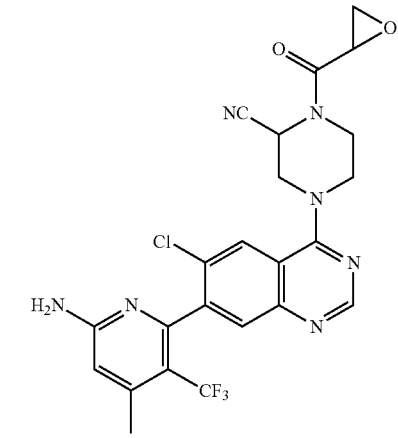 [SMILES: Cc1cc(N)nc(-c2cc3ncnc(N4CCN(C(=O)C5CO5)C(C#N)C4)c3cc2Cl)c1C(F)(F)F]

Synthetic Route

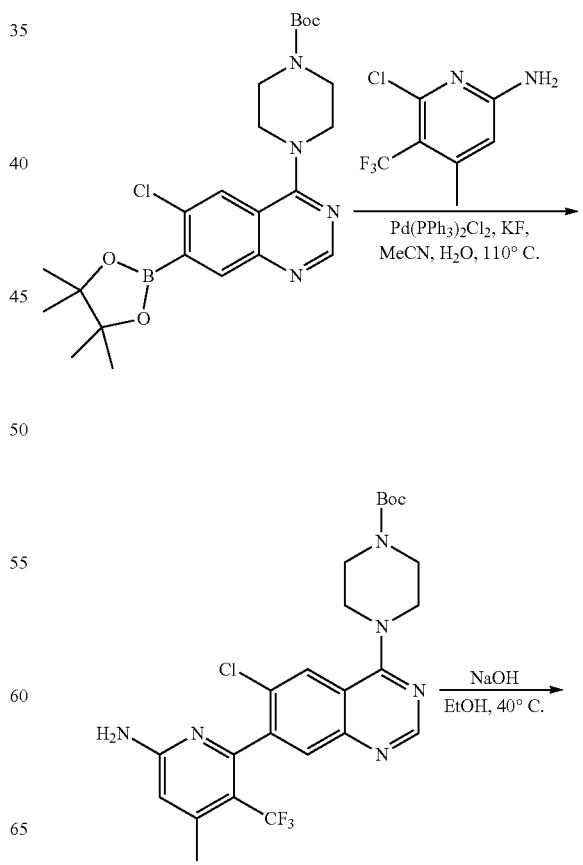

-continued

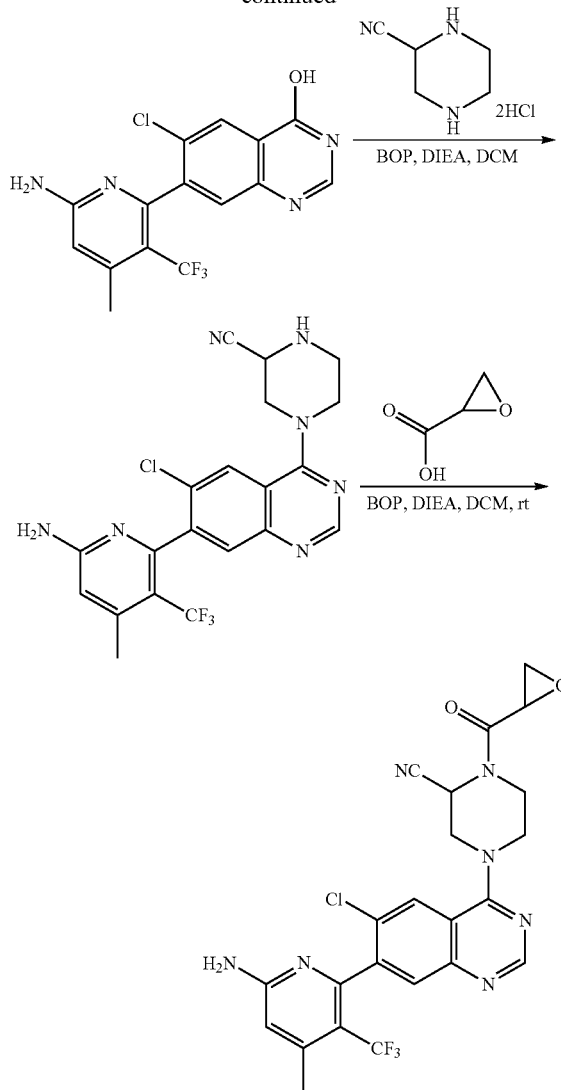

Step 1: tert-butyl 4-[7-[6-amino-4-methyl-3-(trifluoromethyl)-2-pyridyl]-6-chloro-quinazolin-4-yl]piperazine-1-carboxylate

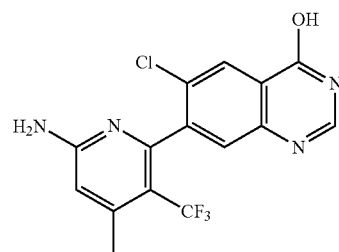

Under nitrogen, a solution of tert-butyl 4-[6-chloro-7-(4,4,5,5-tetramethyl-1,3,2-dioxaborolan-2-yl)quinazolin-4-yl]piperazine-1-carboxylate (4.3 g, 9.0 mmol), 6-chloro-4-methyl-5-(trifluoromethyl)pyridin-2-amine (1.5 g, 7.2 mmol), bis(triphenylphosphine)palladium(II) chloride (504.1 mg, 0.7 mmol), potassium fluoride (1.6 g, 26.9 mmol) in acetonitrile (15 mL) and water (1.5 mL) was stirred at 100° C. for 18 hours. After completion, the solution was concentrated under vacuum. The residue was purified by flash chromatography on silica gel eluting with ethyl acetate/petroleum ether (10/1) to afford tert-butyl 4-[7-[6-amino-4-methyl-3-(trifluoromethyl)-2-pyridyl]-6-chloro-quinazolin-4-yl]piperazine-1-carboxylate (2.8 g, 5.4 mmol, 59.8% yield) as a light brown solid. LC-MS: (ESI, m/z): 523.2 [M+H]$^+$.

Step 2: 7-[6-amino-4-methyl-3-(trifluoromethyl)-2-pyridyl]-6-chloro-quinazolin-4-ol

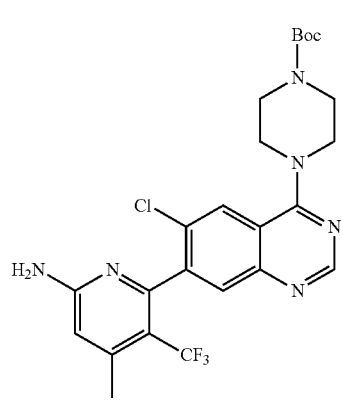 [SMILES: Cc1cc(N)nc(-c2cc3ncnc(N4CCN(C(=O)OC(C)(C)C)CC4)c3cc2Cl)c1C(F)(F)F]

A solution of tert-butyl 4-[7-[6-amino-4-methyl-3-(trifluoromethyl)-2-pyridyl]-6-chloro-quinazolin-4-yl]piperazine-1-carboxylate (2.5 g, 4.8 mmol), sodium hydroxide (573.7 mg, 14.3 mmol) in ethanol (30 mL) and water (10 mL) was stirred at 40° C. for 16 hours. After completion, the solution was concentrated under vacuum. The residue was purified by flash chromatography on silica gel eluting with ethyl acetate/petroleum ether (1/1) to afford 7-[6-amino-4-methyl-3-(trifluoromethyl)-2-pyridyl]-6-chloro-quinazolin-4-ol (1.5 g, 4.2 mmol, 88.5% yield) as light yellow solid. LC-MS: (ESI, m/z): 355.0 [M+H]$^+$.

Step 3: 4-[7-[6-amino-4-methyl-3-(trifluoromethyl)-2-pyridyl]-6-chloro-quinazolin-4-yl]piperazine-2-carbonitrile A solution of piperazine-2-carbonitrile dihydrochloride (3.6 mg, 19.7 mmol), 7-[6-amino-4-methyl-3-(trifluoromethyl)-2-pyridyl]-6-chloro-quinazolin-4-ol (1.4 g, 4.0 mmol), BOP (1.0 g, 23.7 mmol), N,N-diisopropylethylamine (5.1 g, 39.5 mmol) in dichloromethane (50 mL) was stirred at 25° C. for 18 hours. After completion, the solution was concentrated under vacuum. The residue was purified by flash chromatography on silica gel eluting with dichloromethane/methanol (10/1) to afford 4-[7-[6-amino-4-methyl-3-(trifluoromethyl)-2-pyridyl]-6-chloro-quinazolin-4-yl]piperazine-2-carbonitrile (950 mg, 2.1 mmol, 53.7% yield) as a yellow solid. LC-MS: (ESI, m/z): 448.1 [M+H]$^+$.

Step 4: 4-[7-[6-amino-4-methyl-3-(trifluoromethyl)-2-pyridyl]-6-chloro-quinazolin-4-yl]-1-(oxirane-2-carbonyl)piperazine-2-carbonitrile

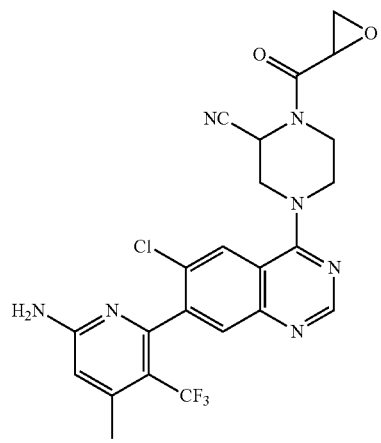 [SMILES: Cc1cc(N)nc(-c2cc3ncnc(N4CCN(C(=O)C5CO5)C(C#N)C4)c3cc2Cl)c1C(F)(F)F]

A solution of 4-[7-[6-amino-4-methyl-3-(trifluoromethyl)-2-pyridyl]-6-chloro-quinazolin-4-yl]piperazine-2-carbonitrile (300.0 mg, 0.7 mmol), oxirane-2-carboxylic acid (88.5 mg, 1.0 mmol), BOP (592.6 mg, 1.3 mmol), N,N-diisopropylethylamine (432.1 mg, 3.4 mmol) in N,N-dimethylformamide (20 mL) was stirred at 25° C. for 24 hours. After completion, the solution was quenched with water (40 mL) and extracted with dichloromethane (3×100 mL). The combined organic layer was washed with brine (50 mL), dried over anhydrous sodium sulfate, filtered and filtrate was concentrated under concentrated under vacuum. The residue was purified by flash chromatography on silica gel eluting with dichloromethane/methanol (10/1) to afford 220 mg of crude product. The crude product was purified by Prep-HPLC with the following conditions: Column, X Bridge C18, 19*150 mm, 5 um; Mobile Phase A:Water/ 0.05% NH$_4$HCO$_3$, Mobile Phase B: ACN; (conditions); Detector, UV 254 nm. 4-[7-[6-amino-4-methyl-3-(trifluoromethyl)-2-pyridyl]-6-chloro-quinazolin-4-yl]-1-(oxirane-2-carbonyl)piperazine-2-carbonitrile (10.6 mg, 0.02 mmol, 3.1% yield) as a white solid. LC-MS: (ESI, m/z): 518.1 [M+H]$^+$.

Example 24

$^1$H NMR (300 MHz, CDCl$_3$, ppm) δ 8.90 (s, 1H), 8.21-8.09 (m, 1H), 7.91 (s, 1H), 6.50 (s, 1H), 5.85-5.75 (m, 1H), 4.82 (s, 2H), 4.47-4.21 (m, 3H), 4.05-3.95 (m, 1H), 3.73 (t, J=3.4 Hz, 1H), 3.59-3.09 (m, 4H), 2.51 (s, 3H).

Example 25

1-[4-[7-[6-amino-3-(trifluoromethyl)-2-pyridyl]-6-chloro-quinazolin-4-yl]-2-(trifluoromethyl)piperazin-1-yl]prop-2-en-1-one

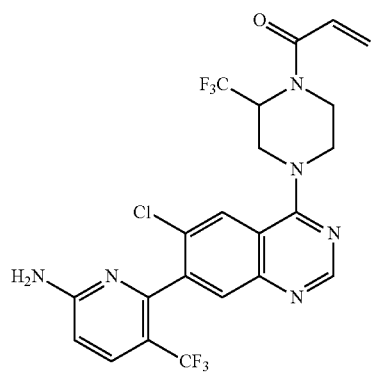 [SMILES: C=CC(=O)N1CCN(c2ncnc3cc(-c4nc(N)ccc4C(F)(F)F)c(Cl)cc23)CC1C(F)(F)F]

Synthetic Route

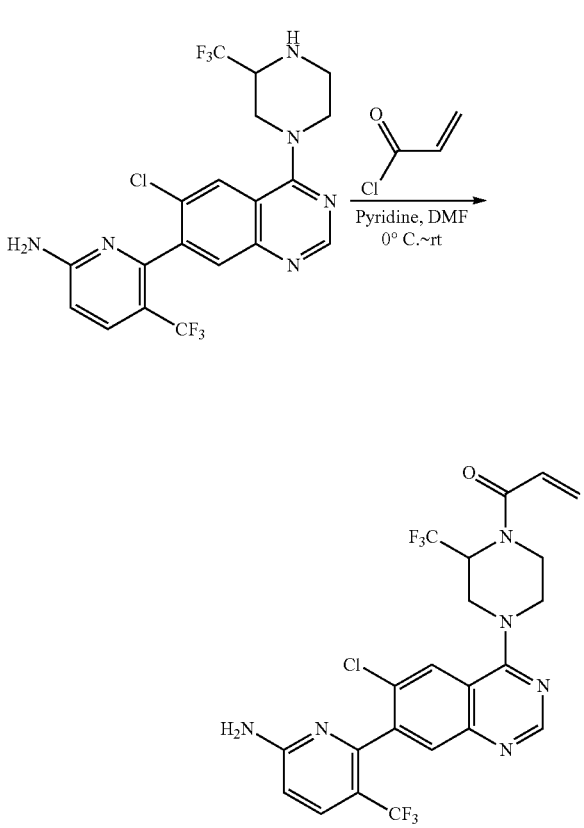

Step 1: 1-[4-[7-[6-amino-3-(trifluoromethyl)-2-pyridyl]-6-chloro-quinazolin-4-yl]-2-(trifluoromethyl)piperazin-1-yl]prop-2-en-1-one

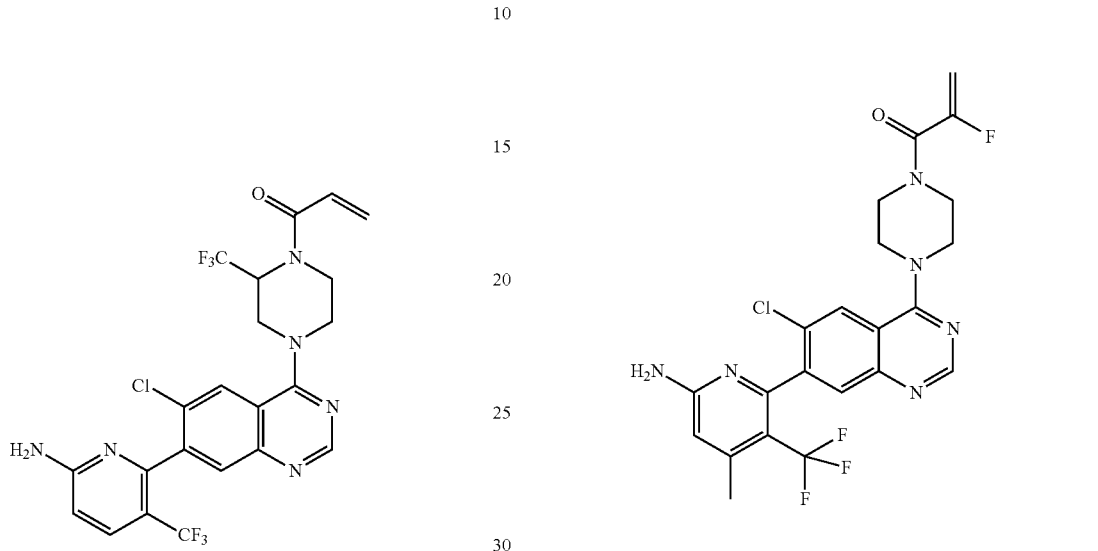

A solution of 6-[6-chloro-4-[3-(trifluoromethyl)piperazin-1-yl]quinazolin-7-yl]-5-(trifluoromethyl)pyridin-2-amine (200.0 mg, 0.4 mmol) and acryloyl chloride (45.6 mg, 0.5 mmol), pyridine (0.07 mL, 0.8 mmol) in N,N-dimethylformamide (3 mL) was stirred at 0° C. for 3 hours. After completion, the solution was quenched with water (10 mL) and extracted with dichloromethane (3×20 mL). The combined organic layer was washed with brine (10 mL), dried over anhydrous sodium sulfate, filtered and filtrate was concentrated under concentrated under vacuum. The residue was purified by flash chromatography on silica gel eluting with methanol/dichloromethane (1/10) to afford 1-[4-[7-[6-amino-3-(trifluoromethyl)-2-pyridyl]-6-chloro-quinazolin-4-yl]-2-(trifluoromethyl)piperazin-1-yl]prop-2-en-1-one (19.4 mg, 0.04 mmol, 8.7% yield) as a white solid. LC-MS (ESI, m/z): 531.1 [M+H]$^+$.

Example 25

$^1$H NMR (300 MHz, DMSO-d$_6$, ppm) δ 8.73 (s, 1H), 8.10 (s, 1H), 7.86-7.75 (m, 2H), 6.96 (s, 2H), 6.93-6.88 (m, 1H), 6.63 (d, 0.9 Hz, 1H), 6.27 (t, J=12 Hz, 1H), 5.90-5.80 (m, 1H), 5.50-5.38 (m, 1H), 4.55-4.20 (m, 3H), 3.90-3.68 (m, 2H), 3.56-3.40 (m, 1H).

Example 26

1-(4-[7-[6-amino-4-methyl-3-(trifluoromethyl)pyridin-2-yl]-6-chloroquinazolin-4-yl]piperazin-1-yl)-2-fluoroprop-2-en-1-one Synthetic Route

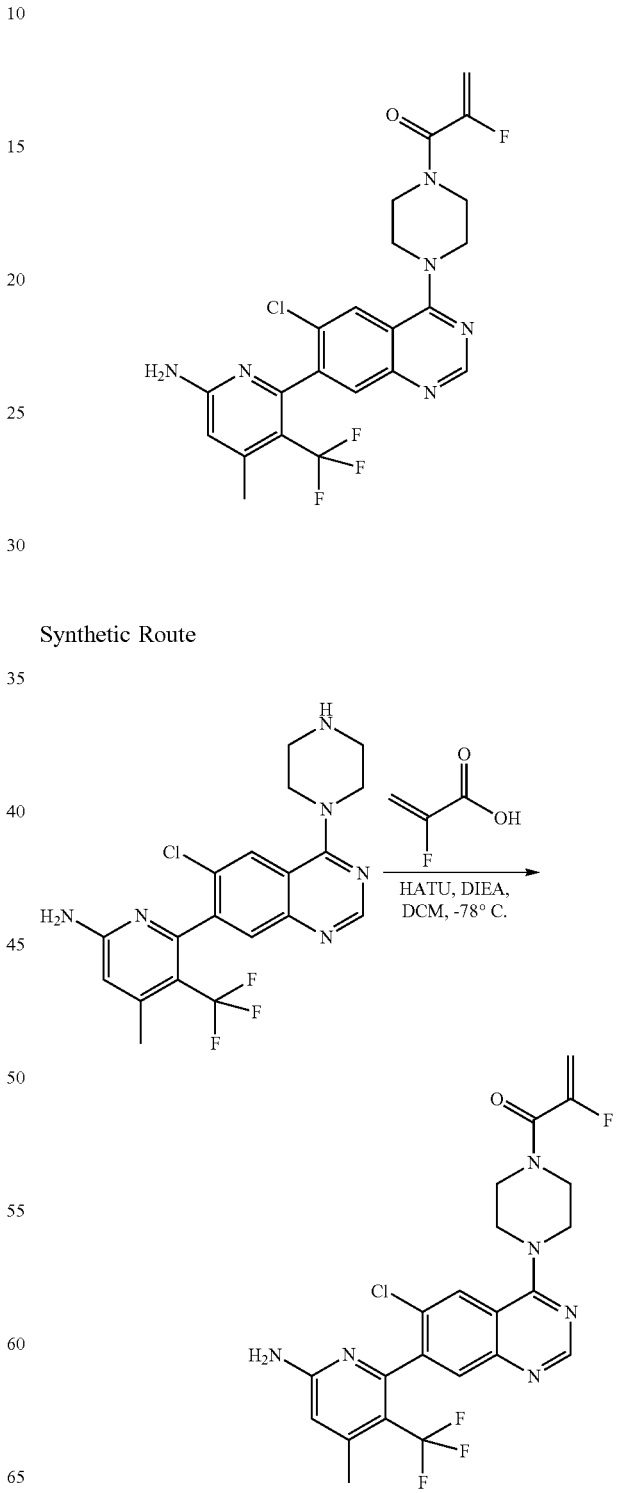

295

Step 1: 1-(4-[7-[6-amino-4-methyl-3-(trifluoromethyl)pyridin-2-yl]-6-chloroquinazolin-4-yl]piperazin-1-yl)-2-fluoroprop-2-en-1-one

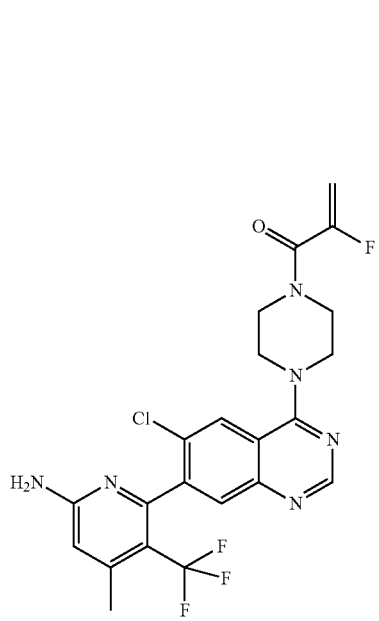 [SMILES: C=C(F)C(=O)N1CCN(c2ncnc3cc(-c4nc(N)cc(C)c4C(F)(F)F)c(Cl)cc23)CC1]

A solution of 6-[6-chloro-4-(piperazin-1-yl)quinazolin-7-yl]-4-methyl-5-(trifluoromethyl)pyridin-2-amine (240.0 mg, 0.6 mmol), 2-fluoroprop-2-enoic acid (60 mg, 0.7 mmol), HATU (260 mg, 0.7 mmol), N,N-diisopropylethylamine (150 mg, 1.2 mmol) in dichloromethane (10 mL) was stirred for 30 min at −78° C. After completion, the solution was quenched with water (20 mL) and extracted with dichloromethane (3×30 mL). The combined organic layer was washed with brine (20 mL), dried over anhydrous sodium sulfate, filtered and filtrate was concentrated under concentrated under vacuum. The residue was applied onto a silica gel column eluting with dichloromethane/methanol (10/1) to afford 108 mg (38%) of 1-(4-[7-[6-amino-4-methyl-3-(trifluoromethyl)pyridin-2-yl]-6-chloroquinazolin-4-yl]piperazin-1-yl)-2-fluoroprop-2-en-1-one as a white solid. LC-MS: (ESI, m/z) 495.1 [M+H]$^+$.

Example 26

$^1$H NMR (400 MHz, Methanol-d$_4$, ppm) δ 8.68 (s, 1H), 8.18 (s, 1H), 7.71 (s, 1H), 6.61 (s, 1H), 5.38-5.32 (dd, J=18.8, 3.6 Hz, 1H), 5.29-5.25 (dd, J=13.2, 4.0 Hz, 1H), 4.09-3.96 (m, 4H), 3.92 (s, 4H), 2.47 (s, 3H).

296

Example 27

1-[4-[7-(3-amino-8-fluoro-1-isoquinolyl)-6-chloro-8-fluoro-quinazolin-4-yl]piperazin-1-yl]prop-2-en-1-one

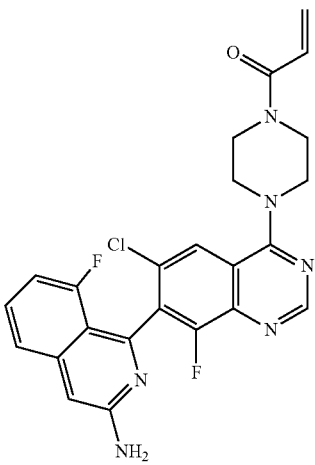 [SMILES: C=CC(=O)N1CCN(c2ncnc3c(F)c(-c4nc(N)cc5cccc(F)c45)c(Cl)cc23)CC1]

Synthetic Route

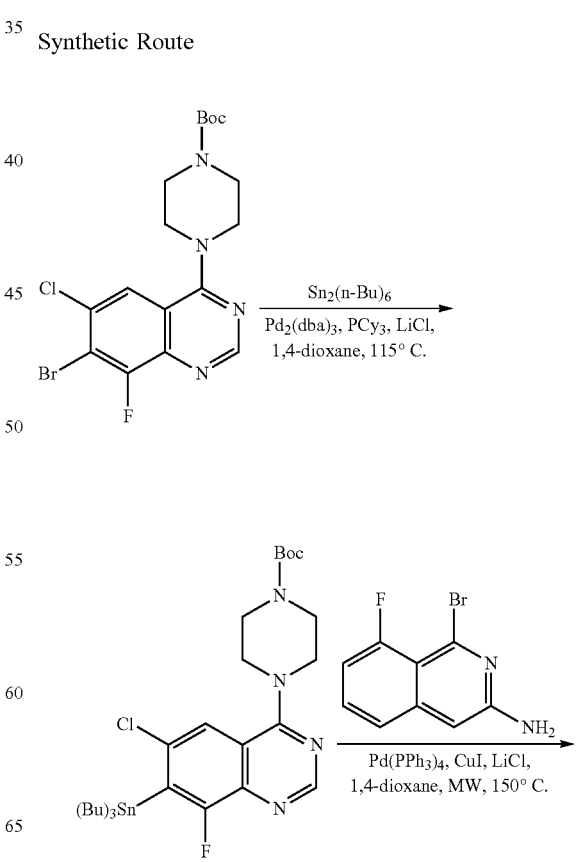

-continued

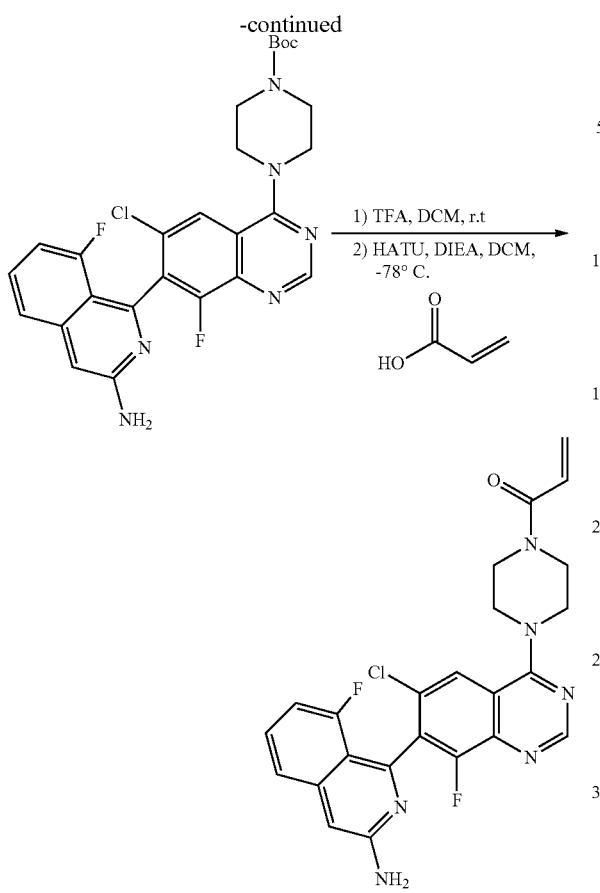

1) TFA, DCM, r.t
2) HATU, DIEA, DCM, -78° C.

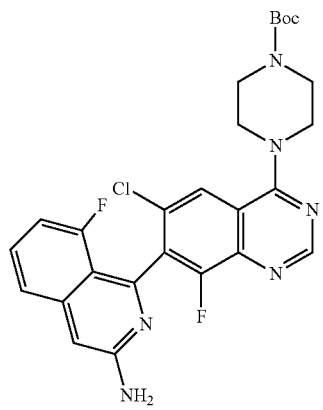 [SMILES: CC(C)(C)OC(=O)N1CCN(c2ncnc3c(F)c(-c4nc(N)cc5cccc(F)c45)c(Cl)cc23)CC1]

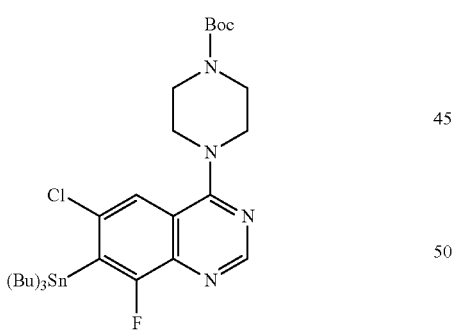

Step 1: tert-butyl 4-(6-chloro-8-fluoro-7-(tributyl-stannyl)quinazolin-4-yl)piperazine-1-carboxylate Under nitrogen, a solution of tert-butyl 4-(7-bromo-6-chloro-8-fluoroquinazolin-4-yl)piperazine-1-carboxylate (2.0 g, 4.5 mmol), hexabutylditin (5.2 g, 9.0 mmol), tris(dibenzylideneacetone)dipalladium (413 mg, 0.45 mmol), tricyclohexyl phosphine (230 mg, 0.9 mmol) and Lithium chloride (565 mg, 13.5 mmol) in 1,4-dioxane (20 mL) was stirred at 110° C. for 5 hours. After completion, the reaction system was concentrated under vacuum. The residue was purified by flash chromatography on silica gel eluting with petroleum ether/ethyl acetate (10/1) to afford tert-butyl 4-(6-chloro-8-fluoro-7-(tributylstannyl)quinazolin-4-yl)piperazine-1-carboxylate (1.5 g, 2.3 mmol) as a red oil. LC-MS: (ESI, m/z): 657.2 [M+H]$^+$.

Step 2: tert-butyl 4-(7-(3-amino-8-fluoroisoquino-lin-1-yl)-6-chloro-8-fluoroquinazolin-4-yl)pipera-zine-1-carboxylate

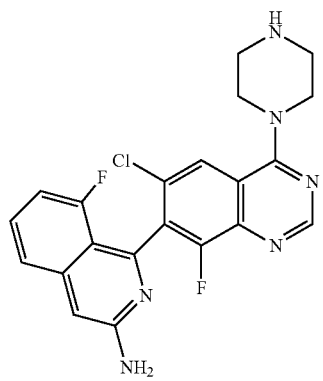 [SMILES: Nc1cc2cccc(F)c2c(-c2c(Cl)cc3c(N4CCNCC4)ncnc3c2F)n1]

Under nitrogen, a solution of tert-butyl 4-(6-chloro-8-fluoro-7-(tributylstannyl)quinazolin-4-yl)piperazine-1-carboxylate (500 mg, 0.76 mmol), 1-bromo-8-fluoroisoquino-lin-3-amine (183 mg, 0.76 mmol), tetrakis(triphenylphosphine)palladium (88 mg, 0.076 mmol), cuprous iodide (14.4 mg, 0.076 mmol) and Lithium chloride (96 mg, 2.28 mmol) in 1,4-dioxane (5 mL) was stirred at 120° C. for 16 hours. After completion, the reaction system was diluted with water (10 mL) and extracted with ethyl acetate (3×20 mL). Then the organic layers were combined, dried over anhydrous sodium sulfate and concentrated under vacuum. The residue was purified by flash chromatography on silica gel eluting with petroleum ether/ethyl acetate (2/1) to afford tert-butyl 4-(7-(3-amino-8-fluoroisoquinolin-1-yl)-6-chloro-8-fluoroquinazolin-4-yl)piperazine-1-carboxylate (40 mg, 0.076 mmol, 10% yield) as a yellow solid. LC-MS: (ESI, m/z): 527.2 [M+H]$^+$.

Step 3: 1-(6-chloro-8-fluoro-4-(piperazin-1-yl)qui-nazolin-7-yl)-8-fluoroisoquinolin-3-amine A solution of tert-butyl 4-(7-(3-amino-8-fluoroisoquino-lin-1-yl)-6-chloro-8-fluoroquinazolin-4-yl)piperazine-1-carboxylate (60 mg, 0.1 mmol), trifluoroacetic acid (1.0 mL) in dichloromethane (5.0 mL) was stirred for 30 min at 25° C. After completion, the solution was concentrated under vacuum. Then the residue was dissolved with dichloromethane (10 mL), and the pH value of the resulting solution was adjusted to pH=8 with N,N-diisopropylethylamine and concentrated under vacuum. The residue was applied onto a silica gel column eluting with dichloromethane/methanol (10/1) to afford 30 mg of 1-(6-chloro-8-fluoro-4-(piperazin-1-yl)quinazolin-7-yl)-8-fluoroisoquinolin-3-amine as a white solid. LC-MS: (ESI, m/z): 427.1 [M+H]⁺.

Step 4: 1-[4-[7-(3-amino-8-fluoro-1-isoquinolyl)-6-chloro-8-fluoro-quinazolin-4-yl]piperazin-1-yl]prop-2-en-1-one

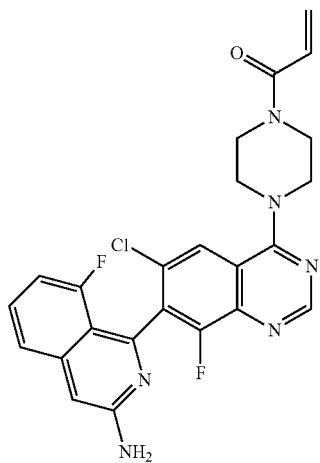 [SMILES: C=CC(=O)N1CCN(c2ncnc3c(F)c(-c4nc(N)cc5cccc(F)c45)c(Cl)cc23)CC1]

A solution of 1-(6-chloro-8-fluoro-4-piperazin-1-yl-quinazolin-7-yl)-8-fluoro-isoquinolin-3-amine (30.0 mg, 0.07 mmol), acrylic acid (5.1 mg, 0.07 mmol), N,N-diisopropylethylamine (18.1 mg, 0.14 mmol) and HATU (32.1 mg, 0.08 mmol) in dichloromethane (2 mL) was stirred at −78° C. for 30 min. After completion, the reaction was quenched by water (20 mL) and extracted with ethyl acetate (3×50 mL). The solvent was concentrated under vacuum. The residue was purified by flash chromatography on silica gel eluting with methanol/dichloromethane (4/96) to afford 50 mg crude. Then the crude product was further purified by Prep-HPLC with the following condition to afford 1-[4-[7-(3-amino-8-fluoro-1-isoquinolyl)-6-chloro-8-fluoro-quinazolin-4-yl]piperazin-1-yl]prop-2-en-1-one (4.2 mg, 0.0087 mmol, 12.4% yield) as a white solid.

Prep-HPLC condition Column: XBridge Prep C18 OBD Column, 5 um, 19*150 mm; Mobile Phase A:Water (10 MMOL/L NH4HCO3), Mobile Phase B: ACN; Flow rate: 20 mL/min; Gradient: 35% B to 49% B in 7 min; 254/220 nm; Rt: 5.68 min Example 27

LC-MS: (ESI, m/z): 481.1 [M+H]⁺. ¹H NMR (300 MHz, DMSO-d₆, ppm) δ 8.71 (s, 1H), 8.04 (s, 1H), 7.51-7.45 (m, 2H), 6.87-6.80 (m, 3H), 6.41 (d, J=5.2 Hz, 2H), 6.18 (d, J=16.4, 2.0 Hz, 1H), 5.75 (dd, J=10.4, 2.4 Hz, 1H), 3.94-3.77 (m, 8H).

Example 28

1-[4-[7-[6-amino-3-(trifluoromethyl)-2-pyridyl]-6-methylsulfonyl-quinazolin-4-yl]piperazin-1-yl]prop-2-en-1-one

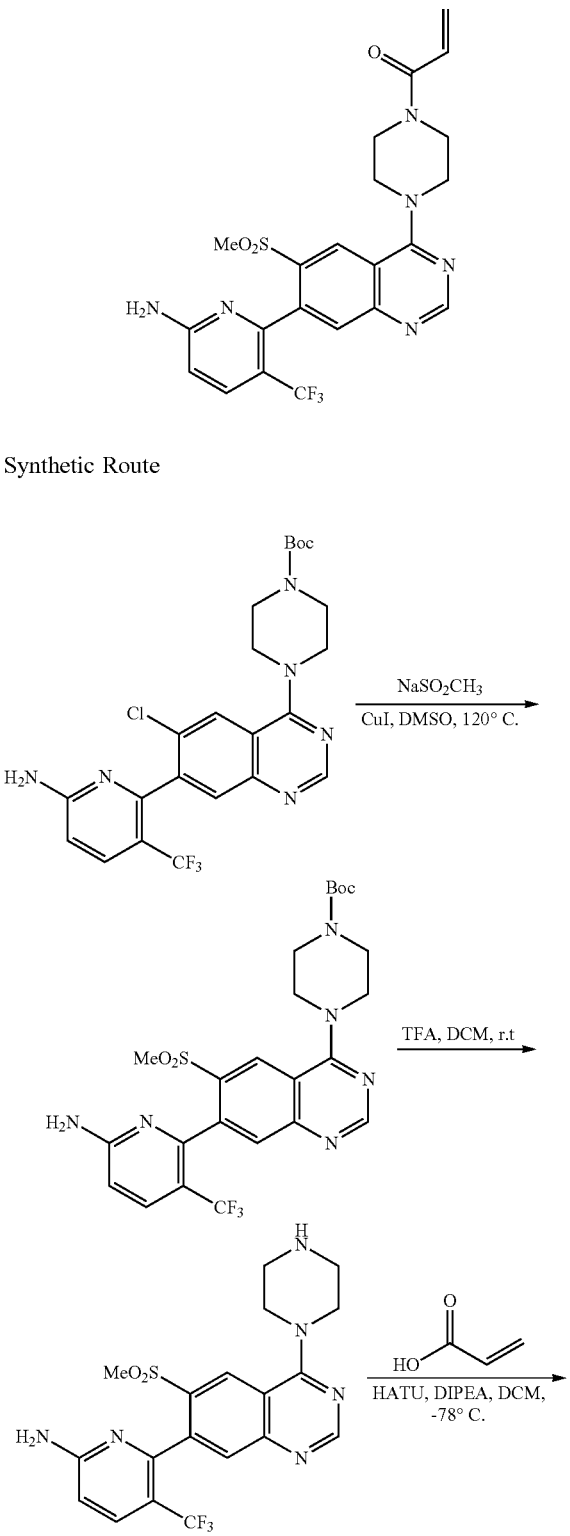

Synthetic Route

301
-continued

Step 1: tert-butyl 4-[7-[6-amino-3-(trifluoromethyl)-2-pyridyl]-6-methylsulfonyl-quinazolin-4-yl]piperazine-1-carboxylate

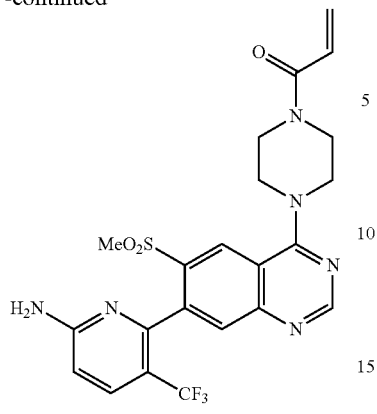

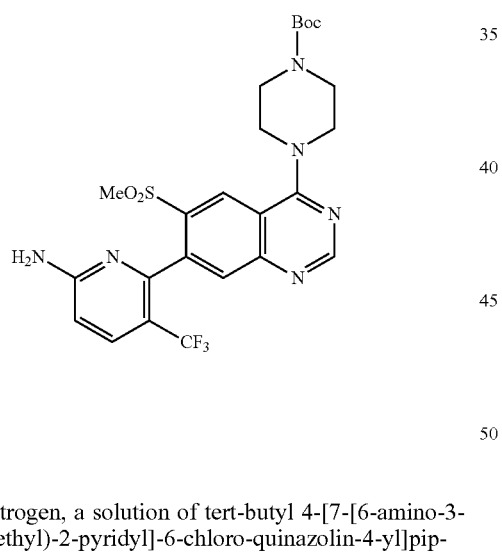

Under nitrogen, a solution of tert-butyl 4-[7-[6-amino-3-(trifluoromethyl)-2-pyridyl]-6-chloro-quinazolin-4-yl]piperazine-1-carboxylate (1.0 g, 1.96 mmol), sodiummethanesulfinate (810.3 mg, 7.86 mmol) and copper(I) iodide (74.8 mg, 0.39 mmol) in dimethyl sulfoxide (20 mL) was stirred for 10 hours at 80° C. After completion, the reaction mixture was diluted with water (100 mL) and extracted with ethyl acetate (3×150 mL). The organic layer was collected and dried over anhydrous sodium sulfate and concentrated under vacuum. The residue was purified by flash chromatography on silica gel eluting with methanol/dichloromethane (4/96) to afford tert-butyl 4-[7-[6-amino-3-(trifluoromethyl)-2-pyridyl]-6-methylsulfonyl-quinazolin-4-yl]piperazine-1-carboxylate (250 mg, 0.45 mmol, 23% yield) as a yellow solid. LC-MS (ESI, m/z): 553.2 [M+H]$^+$.

302

Step 2: 6-(6-methylsulfonyl-4-piperazin-1-yl-quinazolin-7-yl)-5-(trifluoromethyl)pyridin-2-amine

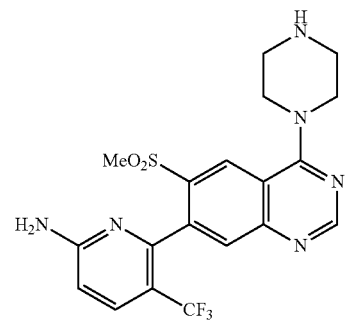 [SMILES: CS(=O)(=O)c1cc2c(N3CCNCC3)ncnc2cc1-c1nc(N)ccc1C(F)(F)F]

A solution of tert-butyl 4-[7-[6-amino-3-(trifluoromethyl)-2-pyridyl]-6-methylsulfonyl-quinazolin-4-yl]piperazine-1-carboxylate (240.0 mg, 0.43 mmol) and trifluoroacetic acid (1 mL) in dichloromethane (5 mL) was stirred at 25° C. for 1 hour. After completion, the resulting solution was concentrated under vacuum. The residue was dissolved with dichloromethane (5 mL) and the pH of the resulting solution was adjusted to pH=9 with N,N-diisopropylethylamine. After concentrated under vacuum, the residue was purified by reverse-phase column eluting with water/acetonitrile (62/38) to afford 6-(6-methylsulfonyl-4-piperazin-1-yl-quinazolin-7-yl)-5-(trifluoromethyl)pyridin-2-amine (150 mg, 0.33 mmol, 76.3% yield) as a yellow solid. LC-MS (ESI, m/z): 453.1 [M+H]$^+$.

Step 3: 1-[4-[7-[6-amino-3-(trifluoromethyl)-2-pyridyl]-6-methylsulfonyl-quinazolin-4-yl]piperazin-1-yl]prop-2-en-1-one

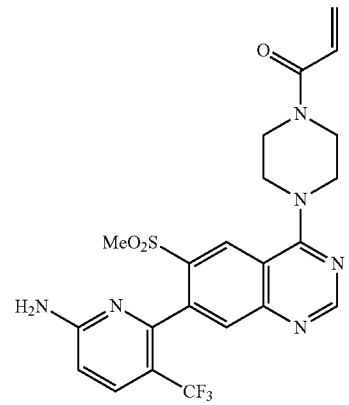 [SMILES: C=CC(=O)N1CCN(c2ncnc3cc(-c4nc(N)ccc4C(F)(F)F)c(S(C)(=O)=O)cc23)CC1]

A solution of 6-(6-methylsulfonyl-4-piperazin-1-yl-quinazolin-7-yl)-5-(trifluoromethyl)pyridin-2-amine (140.0 mg, 0.31 mmol), HATU (141.2 mg, 0.37 mmol), acrylic acid (22.3 mg, 0.31 mmol) and N,N-diisopropylethylamine (0.11 mL, 0.62 mmol) in dichloromethane (5 mL) was stirred at −78° C. for 1 hour. After completion, the reaction was quenched with water (20 mL) and extracted with dichloromethane (3×50 mL). The organic layer was collected and dried over anhydrous sodium sulfate and concentrated under vacuum. The residue was purified by reverse-phase column eluting with water/acetonitrile (75/25) to afford 1-[4-[7-[6- amino-3-(trifluoromethyl)-2-pyridyl]-6-methylsulfonyl-quinazolin-4-yl]piperazin-1-yl]prop-2-en-1-one (20.5 mg, 0.0405 mmol, 13.1% yield) as a white solid. LC-MS (ESI, m/z): 507.1 [M+H]+.

Example 28

1H NMR (300 MHz, DMSO-d6, ppm) δ 8.74 (s, 1H), 8.68 (s, 1H), 7.79 (d, J=9.0 Hz, 1H), 7.66 (s, 1H), 6.89 (s, 2H), 6.86-6.80 (m, 1H), 6.60 (d, J=8.1 Hz, 1H), 6.19 (dd, J=16.8, 2.4 Hz, 1H), 5.75 (dd, J=10.5, 2.4 Hz, 1H), 4.05 (m, 4H), 3.86-3.72 (m, 4H), 3.42 (s, 3H).

Example 29

1-[4-[7-[6-amino-3-(trifluoromethyl)-2-pyridyl]-6-cyclopropyl-quinazolin-4-yl]piperazin-1-yl]prop-2-en-1-one

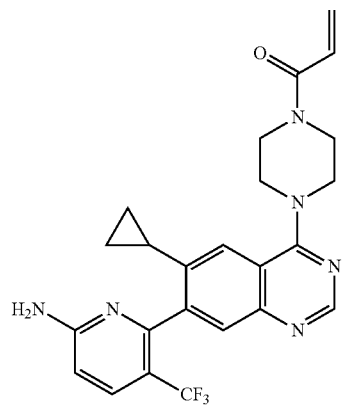 [SMILES: C=CC(=O)N1CCN(c2ncnc3cc(-c4nc(N)ccc4C(F)(F)F)c(C4CC4)cc23)CC1]

Synthetic Route

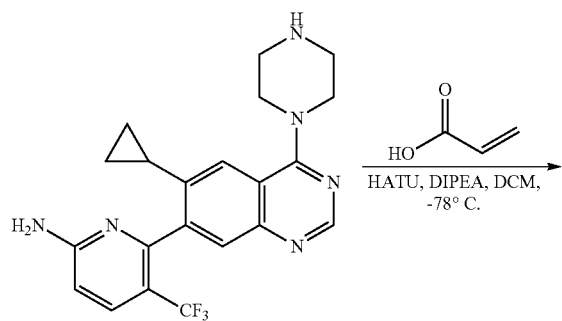

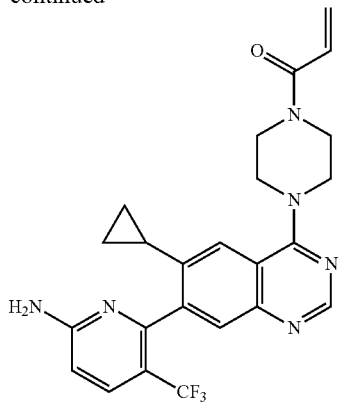

1-[4-[7-[6-amino-3-(trifluoromethyl)-2-pyridyl]-6-cyclopropyl-quinazolin-4-yl]piperazin-1-yl]prop-2-en-1-one

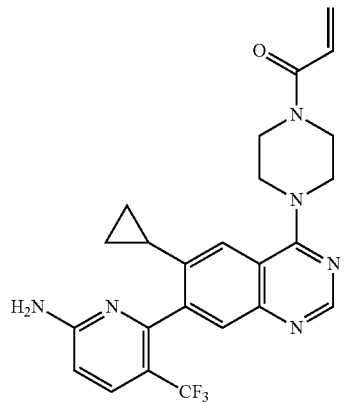 [SMILES: C=CC(=O)N1CCN(c2ncnc3cc(-c4nc(N)ccc4C(F)(F)F)c(C4CC4)cc23)CC1]

A solution of 6-(6-cyclopropyl-4-piperazin-1-yl-quinazolin-7-yl)-5-(trifluoromethyl)pyridin-2-amine (50.0 mg, 0.12 mmol), acrylic acid (8.7 mg, 0.12 mmol), HATU (45.87 mg, 0.12 mmol), N,N-diisopropylethylamine (15.6 mg, 0.12 mmol) in dichloromethane (10 mL) was stirred for 20 min at −78° C. After completion, the reaction was quenched with water (20 mL) and extracted with dichloromethane (3×50 mL). The organic layer was collected and dried over anhydrous sodium sulfate and concentrated under vacuum. The residue was applied onto a silica gel column eluting with dichloromethane/methanol (4/96) to afford the crude. Then the crude product was purified by reverse phase chromatography eluting with water/acetonitrile (3/2) to afford 1-[4-[7-[6-amino-3-(trifluoromethyl)-2-pyridyl]-6-cyclopropyl-quinazolin-4-yl]piperazin-1-yl]prop-2-en-1-one (2.8 mg, 0.006 mmol, 5% yield) as a white solid. LC-MS: (ESI, m/z): 469.2 [M+H]+.

Example 29

1H NMR (300 MHz, Methanol-d4, ppm) δ 8.62 (s, 1H), 7.85 (d, J=8.7 Hz, 1H), 7.63 (d, J=11.4 Hz, 2H), 6.85 (dd, J=16.8, 10.6 Hz, 1H), 6.71 (d, J=9.0 Hz, 1H), 6.29 (dd, J=16.8, 2.0 Hz, 1H), 5.82 (dd, J=10.6, 1.9 Hz, 1H), 3.94 (s, 8H), 1.82 (t, J=5.8 Hz, 1H), 0.97-0.83 (m, 3H), 0.71 (d, J=5.6 Hz, 1H).

Example 30

1-(4-[7-[6-amino-4-methyl-3-(trifluoromethyl)pyridin-2-yl]-6-chloro-2-(trifluoromethyl)quinazolin-4-yl]piperazin-1-yl)prop-2-en-1-one

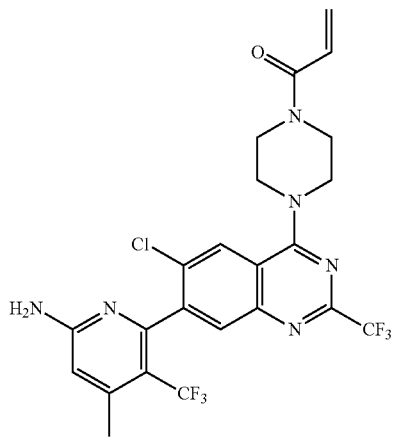 [SMILES: C=CC(=O)N1CCN(c2nc(C(F)(F)F)nc3cc(-c4nc(N)cc(C)c4C(F)(F)F)c(Cl)cc23)CC1]

Synthetic Route

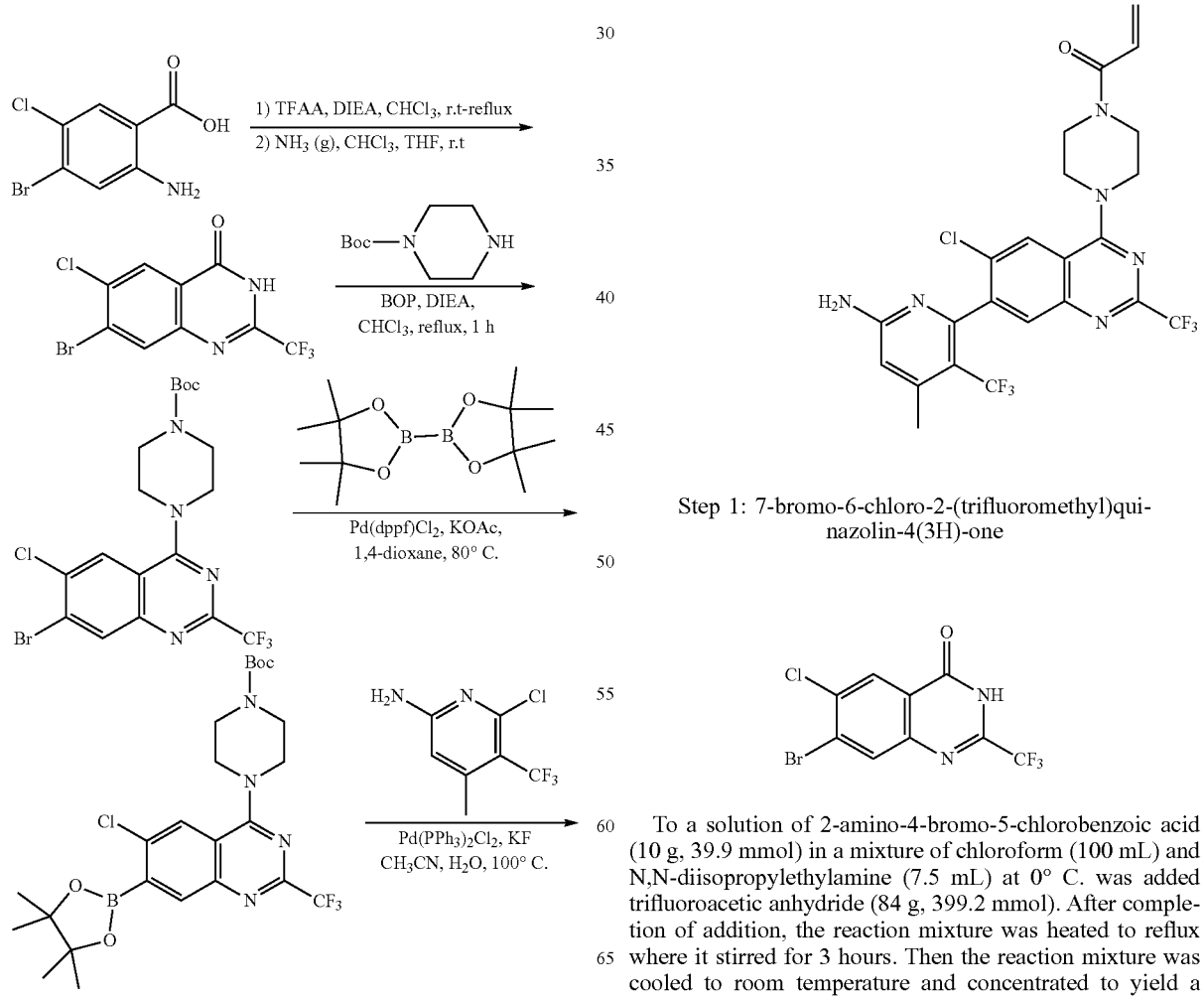

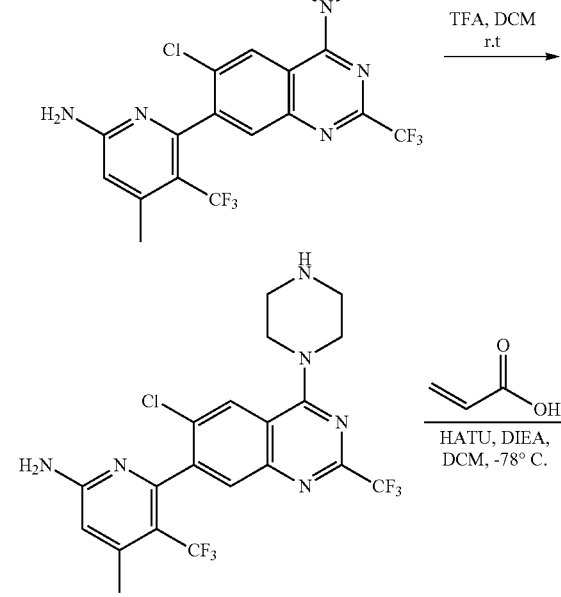

Step 1: 7-bromo-6-chloro-2-(trifluoromethyl)quinazolin-4(3H)-one

To a solution of 2-amino-4-bromo-5-chlorobenzoic acid (10 g, 39.9 mmol) in a mixture of chloroform (100 mL) and N,N-diisopropylethylamine (7.5 mL) at 0° C. was added trifluoroacetic anhydride (84 g, 399.2 mmol). After completion of addition, the reaction mixture was heated to reflux where it stirred for 3 hours. Then the reaction mixture was cooled to room temperature and concentrated to yield a crude material. The crude material was dissolved in chloroform (100 mL) saturated with ammonia gas and then stirred for 2 hours at room temperature. After completion, the mixture was concentrated under vacuum and the resulting solid was washed with water (100 mL). After filtration, the filtrate cake was collected and followed by recrystallization from toluene to afford 2.1 g (16%) of 7-bromo-6-chloro-2-(trifluoromethyl)quinazolin-4(3H)-one as a yellow solid. LC-MS: (ESI, m/z): 326.9 [M+H]+.

Step 2: tert-butyl 4-(7-bromo-6-chloro-2-(trifluoromethyl)quinazolin-4-yl)piperazine-1-carboxylate

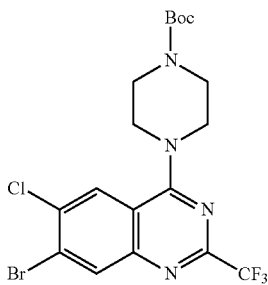 [SMILES: CC(C)(C)OC(=O)N1CCN(c2nc(C(F)(F)F)nc3cc(Br)c(Cl)cc23)CC1]

A solution of 7-bromo-6-chloro-2-(trifluoromethyl)quinazolin-4(3H)-one (4.0 g, 12.2 mmol, 1.00 equiv), tert-butyl piperazine-1-carboxylate (4.6 g, 24.4 mmol), BOP (8.1 g, 18.3 mmol) and N,N-diisopropylethylamine (4.7 g, 36.5 mmol) in chloroform (100 mL) was stirred for 15 h at 80° C. After completion, the solution was concentrated under vacuum. The residue was purified by a silica gel column eluting with ethyl acetate/petroleum ether (1/2) to afford 5.2 g (85%) of tert-butyl 4-(7-bromo-6-chloro-2-(trifluoromethyl)quinazolin-4-yl)piperazine-1-carboxylate as a light yellow solid. LC-MS: (ESI, m/z): 495.0 [M+H]+.

Step 3: tert-butyl 4-(6-chloro-7-(4,4,5,5-tetramethyl-1,3,2-dioxaborolan-2-yl)-2-(trifluoromethyl)quinazolin-4-yl)piperazine-1-carboxylate

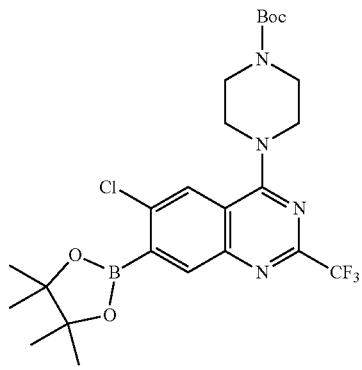 [SMILES: CC(C)(C)OC(=O)N1CCN(c2nc(C(F)(F)F)nc3cc(B4OC(C)(C)C(C)(C)O4)c(Cl)cc23)CC1]

Under nitrogen, a solution of tert-butyl 4-(7-bromo-6-chloro-2-(trifluoromethyl)quinazolin-4-yl)piperazine-1-carboxylate (3.0 g, 6.0 mmol), bis(pinacolato)diboron (7.6 g, 30.3 mmol) 1,1'-bis(diphenylphosphino)ferrocene-palladium(II)dichloride dichloromethane complex (490.2 mg, 0.6 mmol) and potassium acetate (1.8 g, 18.0 mmol) in 1,4-dioxane (50 mL) was stirred at 80° C. for 2 hours. After completion, the resulting solution was diluted with dichloromethane (50 mL) and filtered. The filter was collected and concentrated under vacuum. The solid was washed with petroleum ether (3×30 mL) and collected by filtration to afford 2.0 crude (80% purity) of tert-butyl 4-(6-chloro-7-(4,4,5,5-tetramethyl-1,3,2-dioxaborolan-2-yl)-2-(trifluoromethyl)quinazolin-4-yl)piperazine-1-carboxylate as an off-white solid. LC-MS: (ESI, m/z): 543.2 [M+H]+.

Step 4: tert-butyl 4-[7-[6-amino-4-methyl-3-(trifluoromethyl)pyridin-2-yl]-6-chloro-2-(trifluoromethyl)quinazolin-4-yl]piperazine-1-carboxylate

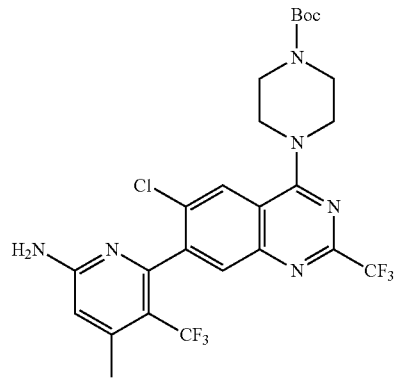 [SMILES: Cc1cc(N)nc(-c2cc3nc(C(F)(F)F)nc(N4CCN(C(=O)OC(C)(C)C)CC4)c3cc2Cl)c1C(F)(F)F]

Under nitrogen, a solution of tert-butyl 4-[6-chloro-7-(tetramethyl-1,3,2-dioxaborolan-2-yl)-2-(trifluoromethyl)quinazolin-4-yl]piperazine-1-carboxylate (1.0 g crude, 80% purity, 1.5 mmol), 6-chloro-4-methyl-5-(trifluoromethyl)pyridin-2-amine (300 mg, 1.4 mmol), bis(triphenylphosphine)palladium(II) chloride (50 mg, 0.07 mmol), potassium fluoride (250 mg, 4.3 mmol) in acetonitrile (4 mL) and water (1 mL) was stirred for 30 min at 100° C. After completion, the resulting solution was diluted with water (50 mL) and extracted with ethyl acetate (3×50 mL). Then the organic layers were combined, washed with brine (3×20 mL) and dried over anhydrous sodium sulfate and concentrated under vacuum. The residue was purified by a silica gel column eluting with ethyl acetate/petroleum ether (1/2) to afford 400 mg (46%) of tert-butyl 4-[7-[6-amino-4-methyl-3-(trifluoromethyl)pyridin-2-yl]-6-chloro-2-(trifluoromethyl)quinazolin-4-yl]piperazine-1-carboxylate as an off-white solid. LC-MS: (ESI, m/z): 591.2 [M+H]+.

Step 5: 6-[6-chloro-4-(piperazin-1-yl)-2-(trifluoromethyl)quinazolin-7-yl]-4-methyl-5-(trifluoromethyl)pyridin-2-amine

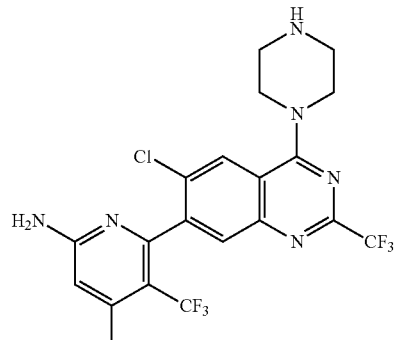

A solution of tert-butyl 4-[7-[6-amino-4-methyl-3-(trifluoromethyl)pyridin-2-yl]-6-chloro-2-(trifluoromethyl)quinazolin-4-yl]piperazine-1-carboxylate (490 mg, 0.8 mmol) in dichloromethane (5 mL) and trifluoroacetic acid (5 mL) was stirred for 30 min at 25° C., After completion, the resulting solution was concentrated under vacuum. The residue was dissolved with dichloromethane (5 mL) and the pH of the resulting solution was adjusted to pH=9 with N,N-diisopropylethylamine. After concentrated under vacuum, the residue was purified by silica gel column eluting with dichloromethane/methanol (85/15) to afford 230 mg (57%) of 6-[6-chloro-4-(piperazin-1-yl)-2-(trifluoromethyl)quinazolin-7-yl]-4-methyl-5-(trifluoromethyl)pyridin-2-amine as a light brown solid. LC-MS: (ESI, m/z): 491.1 [M+H]+.

Step 6: 1-(4-[7-[6-amino-4-methyl-3-(trifluoromethyl)pyridin-2-yl]-6-chloro-2-(trifluoromethyl)quinazolin-4-yl]piperazin-1-yl)prop-2-en-1-one

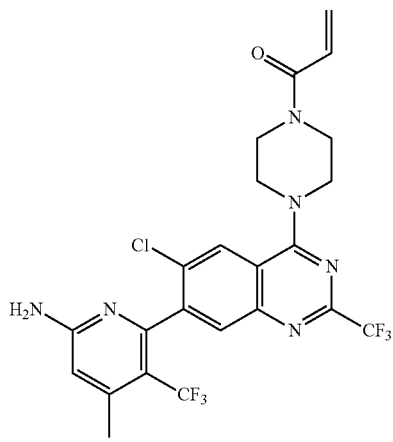 [SMILES: C=CC(=O)N1CCN(c2nc(C(F)(F)F)nc3cc(-c4nc(N)cc(C)c4C(F)(F)F)c(Cl)cc23)CC1]

A solution of 6-[6-chloro-4-(piperazin-1-yl)-2-(trifluoromethyl)quinazolin-7-yl]-4-methyl-5-(trifluoromethyl)pyridin-2-amine (210 mg, 0.4 mmol), prop-2-enoic acid (40 mg, 0.6 mmol), HATU (200 mg, 0.5 mmol) and N,N-diisopropylethylamine (300 mg, 2.3 mmol) in dichloromethane (5 mL) was stirred for 30 min at −78° C. After completion, the solution was quenched with water (20 mL) and extracted with dichloromethane (3×50 mL). The organic layer was collected and dried over anhydrous sodium sulfate and concentrated under vacuum. Then the residue was purified by reverse phase chromatography eluting with water/acetonitrile (3/2) to afford 49.6 mg (21%) of 1-(4-[7-[6-amino-4-methyl-3-(trifluoromethyl)pyridin-2-yl]-6-chloro-2-(trifluoromethyl)quinazolin-4-yl]piperazin-1-yl)prop-2-en-1-one as a white solid. LC-MS: (ESI, m/z): 545.1 [M+H]+.

Example 30

$^1$H NMR (300 MHz, DMSO-$d_6$, ppm) δ 8.24 (s, 1H), 7.78 (s, 1H), 6.85-6.78 (m, 3H), 6.49 (s, 1H), 6.22-6.15 (m, 1H), 5.78-5.72 (m, 1H), 4.08-4.00 (m, 4H), 3.88-3.70 (m, 4H), 2.37 (s, 3H).

Example 31

1-(4-[7-[6-amino-4-methyl-3-(trifluoromethyl)pyridin-2-yl]-6-chloro-2-(methylamino)quinazolin-4-yl]piperazin-1-yl)prop-2-en-1-one

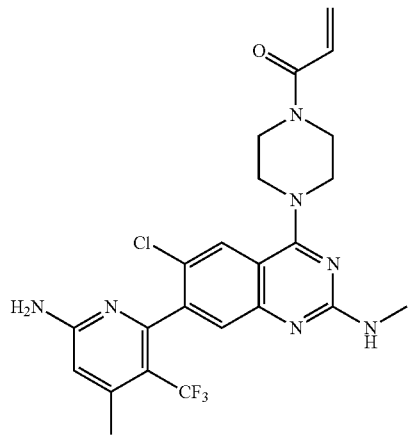 [SMILES: C=CC(=O)N1CCN(c2nc(NC)nc3cc(-c4nc(N)cc(C)c4C(F)(F)F)c(Cl)cc23)CC1]

Synthetic Route

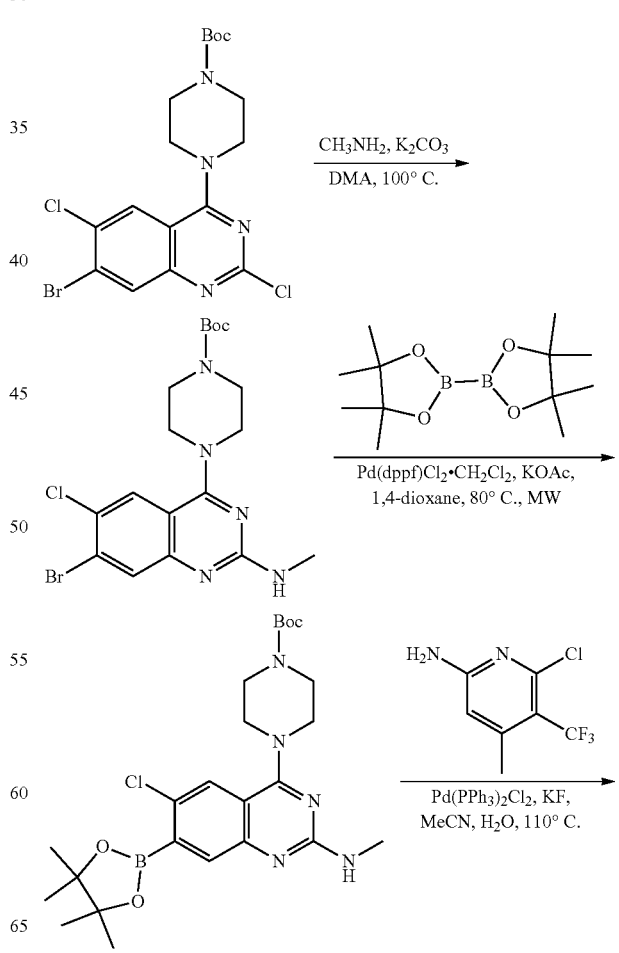

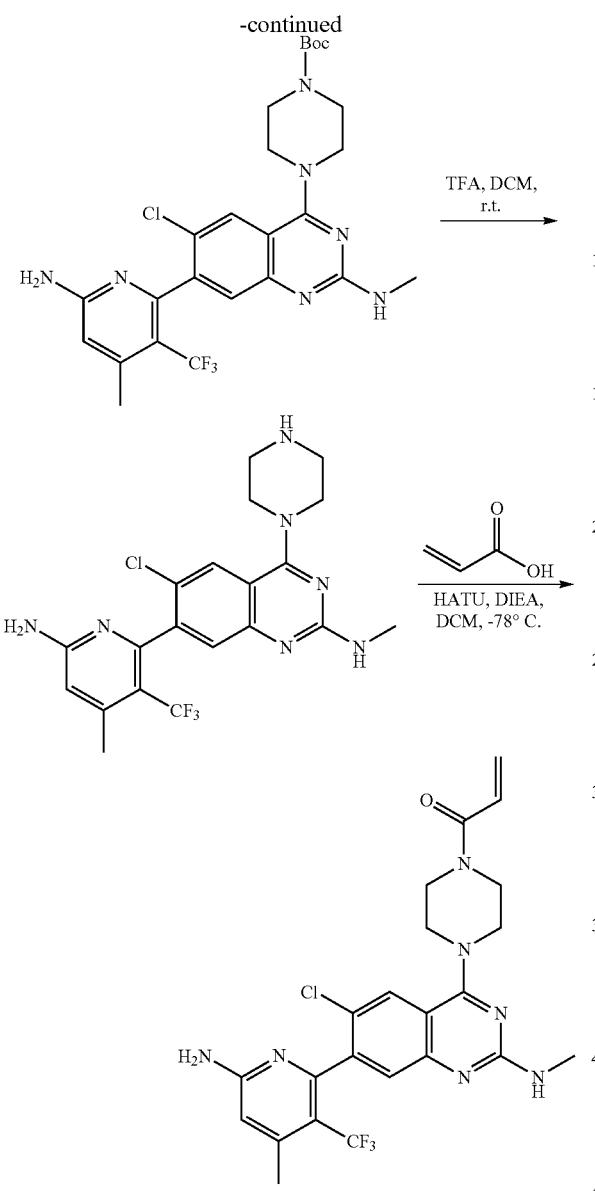

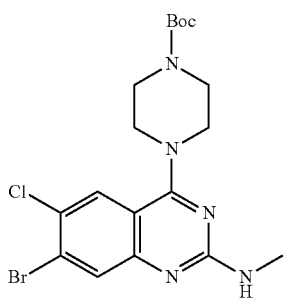 [SMILES: CNc1nc(N2CCN(C(=O)OC(C)(C)C)CC2)c2cc(Cl)c(Br)cc2n1]

Step 1: tert-butyl 4-[7-bromo-6-chloro-2-(methylamino)quinazolin-4-yl]piperazine-1-carboxylate A solution of tert-butyl 4-(7-bromo-2,6-dichloroquinazolin-4-yl)piperazine-1-carboxylate (3 g, 6.5 mmol), methylamine hydrochloride (900 mg, 13.3 mmol), potassium carbonate (2.3 g, 16.6 mmol), N,N-dimethylacetamide (60 mL) was stirred for 12 h at 100° C. After completion, the solution was diluted with water (150 mL) and extracted with ethyl acetate (3×150 mL). Then the organic layers were combined and washed with brine (3×100 mL). The organic layer was dried over anhydrous sodium sulfate and concentrated under vacuum. The residue was applied onto a silica gel column eluting with dichloromethane/methanol (10/1) to afford 1.5 g (51%) of tert-butyl 4-[7-bromo-6-chloro-2-(methylamino)quinazolin-4-yl]piperazine-1-carboxylate as a yellow solid. LC-MS: (ESI, m/z): 456.1 [M+H]+.

Step 2: tert-butyl 4-[6-chloro-2-(methylamino)-7-(tetramethyl-1,3,2-dioxaborolan-2-yl)quinazolin-4-yl]piperazine-1-carboxylate

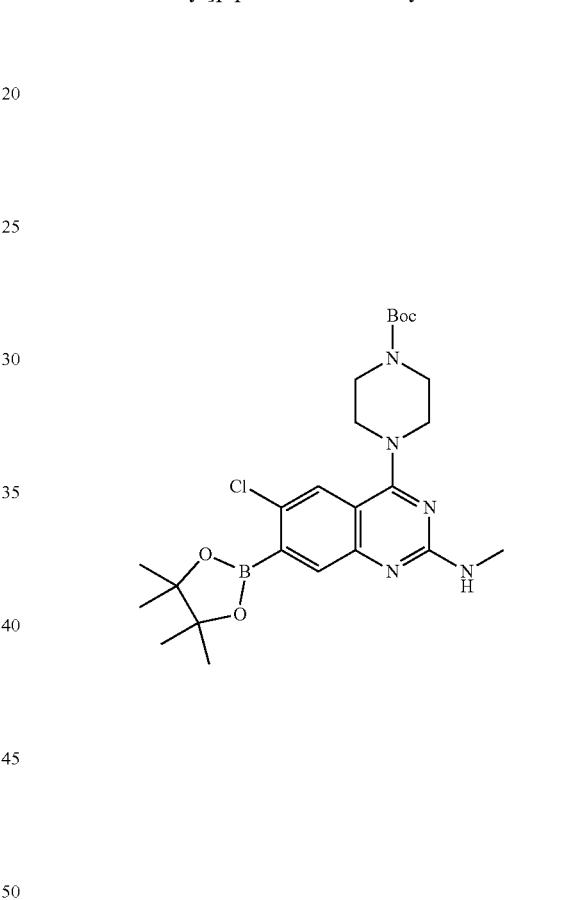

Under nitrogen, a solution of tert-butyl 4-[7-bromo-6-chloro-2-(methylamino)quinazolin-4-yl]piperazine-1-carboxylate (500 mg, 1.1 mmol), bis(pinacolato)diboron (1.4 g, 5.5 mmol), potassium acetate (323.1 mg, 3.3 mmol), 1,1'-Bis(diphenylphosphino)ferrocene-palladium(II)dichloride dichloromethane complex (89.8 mg, 0.1 mmol) in 1,4-dioxane (20 mL) was irradiated with microwave radiation for 2 h at 80° C. After completion, the resulting solution was diluted with dichloromethane (20 mL) and filtered. The filter was collected and concentrated under vacuum. The solid was washed with petroleum ether (3×30 mL) and collected by filtration to 600 mg (crude) of tert-butyl 4-(6-chloro-2-(methylamino)-7-(4,4,5,5-tetramethyl-1,3,2-dioxaborolan-2-yl)quinazolin-4-yl)piperazine-1-carboxylate. LC-MS: (ESI, m/z): 504.2 [M+H]+.

Step 3: tert-butyl 4-[7-[6-amino-4-methyl-3-(trifluoromethyl)pyridin-2-yl]-6-chloro-2-(methylamino)quinazolin-4-yl]piperazine-1-carboxylate

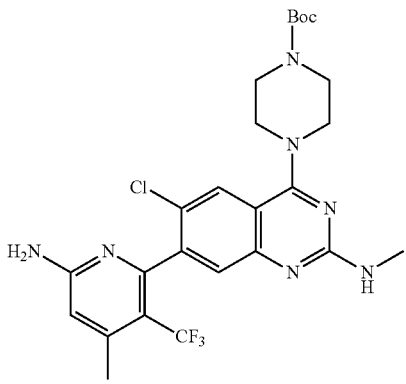 [SMILES: CNc1nc(N2CCN(C(=O)OC(C)(C)C)CC2)c2cc(Cl)c(-c3nc(N)cc(C)c3C(F)(F)F)cc2n1]

Under nitrogen, a solution of tert-butyl 4-(6-chloro-2-(methylamino)-7-(4,4,5,5-tetramethyl-1,3,2-dioxaborolan-2-yl)quinazolin-4-yl)piperazine-1-carboxylate (500 mg, 1.0 mmol), bis(triphenylphosphine)palladium(II) chloride (69.8 mg, 0.1 mmol), potassium fluoride (115.5 mg, 2.0 mmol) and 6-chloro-4-methyl-5-(trifluoromethyl)pyridin-2-amine (229.9 mg, 1.1 mmol) in acetonitrile (10 mL) and water (2 mL) was stirred for 1 h at 110° C. After completion, the resulting solution was diluted with water (50 mL) and extracted with of ethyl acetate (3×50 mL). Then the organic layers were combined, washed with brine (3×20 mL) and dried over anhydrous sodium sulfate and concentrated under vacuum. The residue was applied onto a silica gel column eluting with dichloromethane/methanol (10/1) to afford 300 mg (55%) of tert-butyl 4-[7-[6-amino-4-methyl-3-(trifluoromethyl)pyridin-2-yl]-6-chloro-2-(methylamino)quinazolin-4-yl]piperazine-1-carboxylate as a yellow solid. LC-MS: (ESI, m/z): 552.2 [M+H]$^+$.

Step 4: 7-[6-amino-4-methyl-3-(trifluoromethyl)pyridin-2-yl]-6-chloro-N-methyl-4-(piperazin-1-yl)quinazolin-2-amine

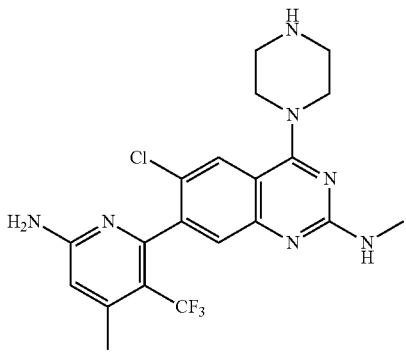 [SMILES: CNc1nc(N2CCNCC2)c2cc(Cl)c(-c3nc(N)cc(C)c3C(F)(F)F)cc2n1]

A solution of tert-butyl 4-[7-[6-amino-4-methyl-3-(trifluoromethyl)pyridin-2-yl]-6-chloro-2-(methylamino)quinazolin-4-yl]piperazine-1-carboxylate (110 mg, 0.2 mmol) in dichloromethane (5 mL) and trifluoroacetic acid (1 mL) was stirred for 30 min at 25° C. After completion, the resulting solution was concentrated under vacuum to afford 110 mg (crude) of 7-[6-amino-4-methyl-3-(trifluoromethyl)pyridin-2-yl]-6-chloro-N-methyl-4-(piperazin-1-yl)quinazolin-2-amine as a dark red solid which was used for next step without purification. LC-MS: (ESI, m/z): 452.1 [M+H]$^+$.

Step 5: 1-(4-[7-[6-amino-4-methyl-3-(trifluoromethyl)pyridin-2-yl]-6-chloro-2-(methylamino)quinazolin-4-yl]piperazin-1-yl)prop-2-en-1-one

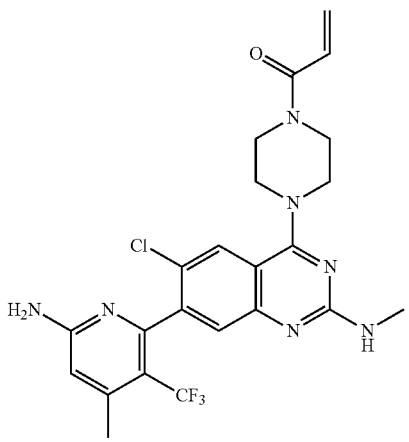 [SMILES: C=CC(=O)N1CCN(c2nc(NC)nc3cc(-c4nc(N)cc(C)c4C(F)(F)F)c(Cl)cc23)CC1]

A solution of 7-[6-amino-4-methyl-3-(trifluoromethyl)pyridin-2-yl]-6-chloro-N-methyl-4-(piperazin-1-yl)quinazolin-2-amine (110 mg crude), prop-2-enoic acid (17.5 mg, 0.2 mmol), HATU (92.6 mg, 0.2 mmol) and N,N-diisopropylethylamine (125.6 mg, 1.0 mmol) in dichloromethane (10 mL) was stirred for 30 min at −78° C. After completion, the solution was quenched with water (20 mL) and extracted with dichloromethane (3×50 mL). The organic layer was collected and dried over anhydrous sodium sulfate and concentrated under vacuum. The residue was applied onto a silica gel column eluting with dichloromethane/methanol (10/1) to afford crude product. Then the crude product was purified by Prep-HPLC with the following conditions: Column: XSelect CSH Prep C18 OBD Column, 5 um, 19*150 mm; Mobile Phase A:Water (0.05% TFA), Mobile Phase B: ACN; Flow rate: 20 mL/min; Gradient: 15% B to 58% B in 7 min; 254/220 nm; Rt: 6.15 min to afford 32.8 mg (27%) of 1-(4-[7-[6-amino-4-methyl-3-(trifluoromethyl)pyridin-2-yl]-6-chloro-2-(methylamino)quinazolin-4-yl]piperazin-1-yl)prop-2-en-1-one as a white solid. LC-MS: (ESI, m/z): 506.2 [M+H]$^+$ Example 31

$^1$H NMR (300 MHz, Methanol-d$_4$, ppm) δ 8.16 (s, 1H), 7.59-7.25 (m, 1H), 6.79 (dd, J=16.8, 10.5 Hz, 1H), 6.65 (s, 1H), 6.30 (dd, J=16.5, 1.8 Hz, 1H), 5.82 (dd, J=10.8, 2.1 Hz, 1H), 4.27 (s, 4H), 3.94 (s, 4H), 3.09 (s, 3H), 2.45 (s, 3H).

Example 32

1-(4-[7-[6-amino-4-methyl-3-(trifluoromethyl)pyridin-2-yl]-6-chloro-2-methylquinazolin-4-yl]piperazin-1-yl)prop-2-en-1-one

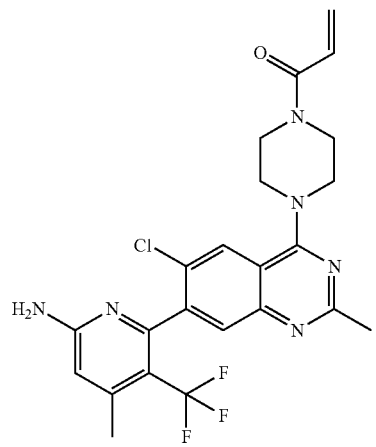 [SMILES: C=CC(=O)N1CCN(c2nc(C)nc3cc(-c4nc(N)cc(C)c4C(F)(F)F)c(Cl)cc23)CC1]

Synthetic Route

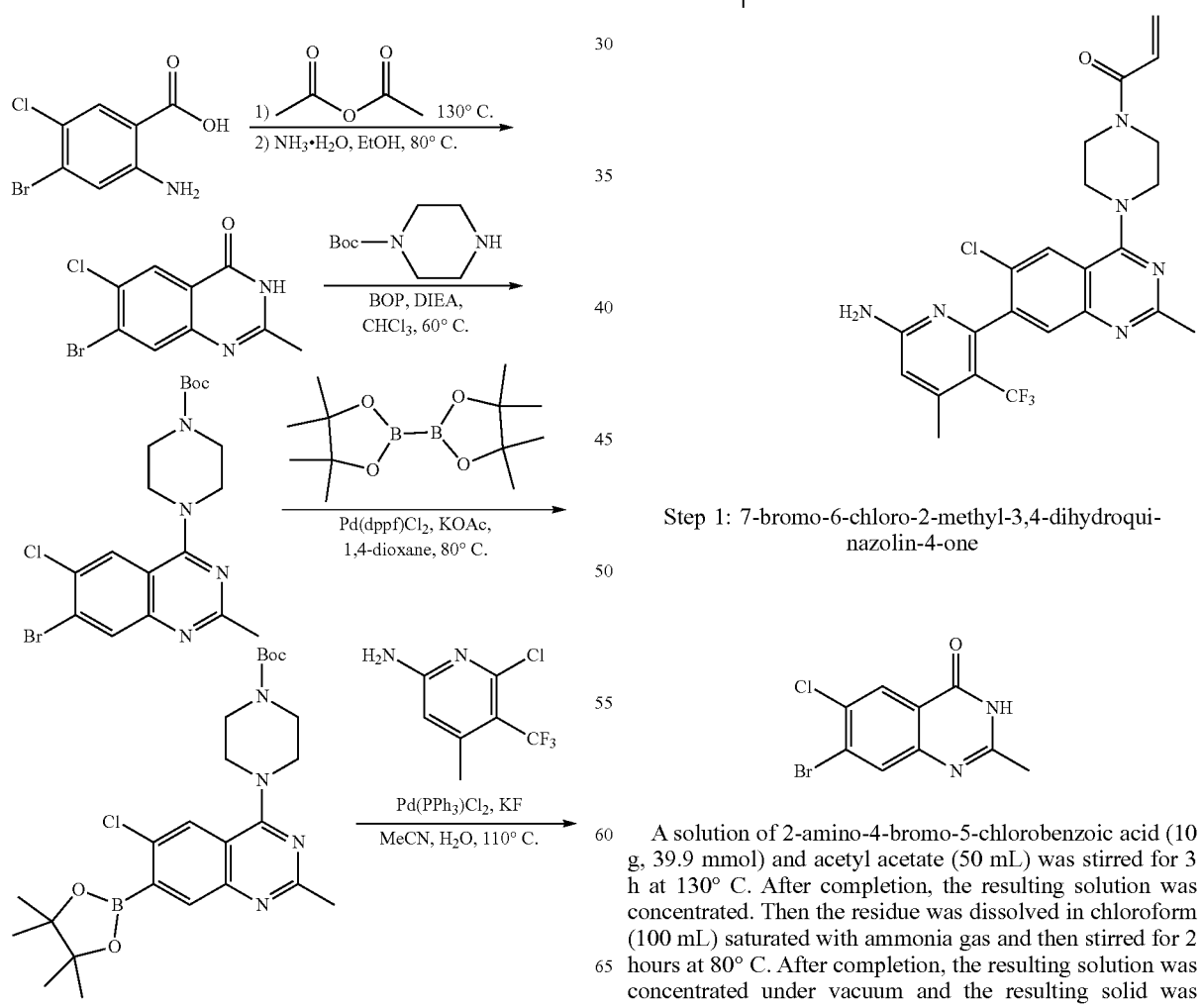

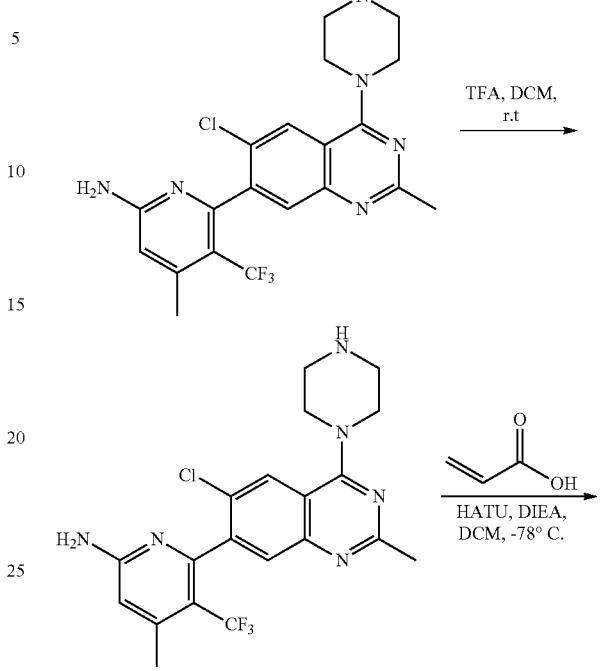

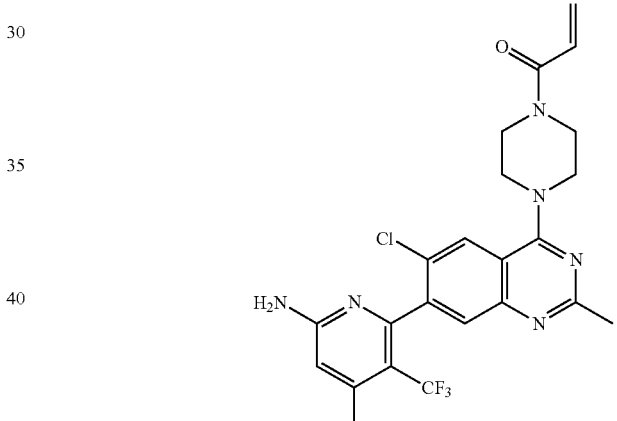

Step 1: 7-bromo-6-chloro-2-methyl-3,4-dihydroquinazolin-4-one

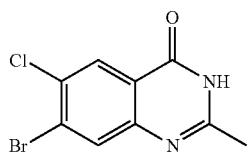

A solution of 2-amino-4-bromo-5-chlorobenzoic acid (10 g, 39.9 mmol) and acetyl acetate (50 mL) was stirred for 3 h at 130° C. After completion, the resulting solution was concentrated. Then the residue was dissolved in chloroform (100 mL) saturated with ammonia gas and then stirred for 2 hours at 80° C. After completion, the resulting solution was concentrated under vacuum and the resulting solid was washed with water (100 mL). After filtration, the filtrate cake was collected and followed by recrystallization from toluene to afford 8.4 g (77%) of 7-bromo-6-chloro-2-methyl-3,4-dihydroquinazolin-4-one as a yellow solid. LC-MS: (ESI, m/z): 272.9 [M+H]+

Step 2: tert-butyl 4-(7-bromo-6-chloro-2-methylquinazolin-4-yl)piperazine-1-carboxylate

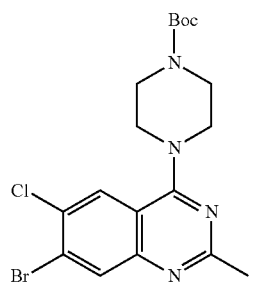 [SMILES: Cc1nc(N2CCN(C(=O)OC(C)(C)C)CC2)c2cc(Cl)c(Br)cc2n1]

A solution of 7-bromo-6-chloro-2-methyl-3,4-dihydroquinazolin-4-one (1 g, 3.66 mmol), tert-butyl piperazine-1-carboxylate (1.37 g, 7.36 mmol), BOP (2.45 g, 5.54 mmol) and N,N-diisopropylethylamine (1.8 mL, 10.89 mmol) in chloroform (30 mL) was stirred for 15 hours at 8° C. After completion, the solution was concentrated under vacuum. The residue was purified by a silica gel column eluting with ethyl acetate/petroleum ether (1/2) to afford 850 mg (53%) of tert-butyl 4-(7-bromo-6-chloro-2-methylquinazolin-4-yl)piperazine-1-carboxylate as a light yellow solid. LC-MS: (ESI, m/z): 441.1 [M+H]+.

Step 3: tert-butyl 4-[6-chloro-2-methyl-7-(tetramethyl-1,3,2-dioxaborolan-2-yl)quinazolin-4-yl]piperazine-1-carboxylate

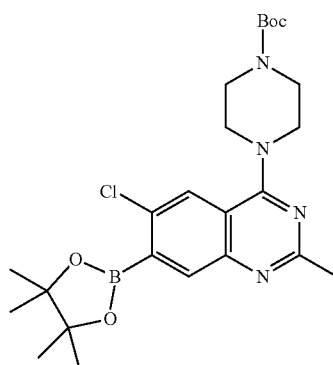

Under nitrogen, a solution of tert-butyl 4-(7-bromo-6-chloro-2-methylquinazolin-4-yl)piperazine-1-carboxylate (2 g, 4.5 mmol), bis(pinacolato)diboron (3.3 g, 13.0 mmol), potassium acetate (1.3 g, 13.6 mmol, 3.0 equiv) and 1,1'-bis(diphenylphosphino)ferrocene-palladium(II)dichloride dichloromethane complex (196 mg, 0.24 mmol) in 1,4-dioxane (30 mL) was stirred for 12 hours at 80° C. After completion, the resulting solution was diluted with dichloromethane (30 mL) and filtered. The filter was collected and concentrated under vacuum. The solid was washed with petroleum ether (3×30 mL) and collected by filtration to afford 1.9 g crude (85% purity) of tert-butyl 4-[6-chloro-2-methyl-7-(tetramethyl-1,3,2-dioxaborolan-2-yl)quinazolin-4-yl]piperazine-1-carboxylate as a brown solid. LC-MS: (ESI, m/z): 489.2 [M+H]+.

Step 4: tert-butyl 4-[7-[6-amino-4-methyl-3-(trifluoromethyl)pyridin-2-yl]-6-chloro-2-methylquinazolin-4-yl]piperazine-1-carboxylate

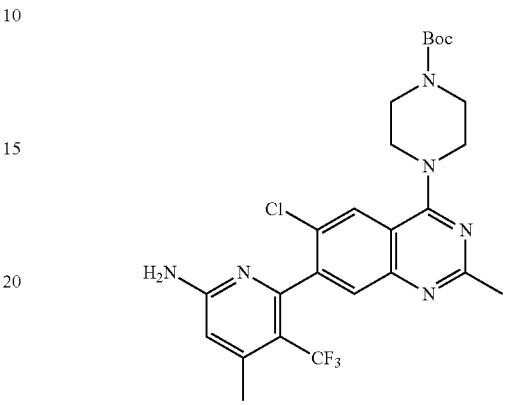

Under nitrogen, a solution of tert-butyl 4-[6-chloro-2-methyl-7-(tetramethyl-1,3,2-dioxaborolan-2-yl)quinazolin-4-yl]piperazine-1-carboxylate (1 g, 2.1 mmol), 6-chloro-4-methyl-5-(trifluoromethyl)pyridin-2-amine (430 mg, 2.04 mmol), bis(triphenylphosphine)palladium(II) chloride (144 mg, 0.2 mmol) and potassium fluoride (195 mg, 3.4 mmol) in acetonitrile (20 mL) and water (4 mL) was stirred for 1 h at 100° C. After completion, the resulting solution was diluted with water (100 mL) and extracted with of ethyl acetate (3×100 mL). Then the organic layers were combined, washed with brine (3×30 mL) and dried over anhydrous sodium sulfate and concentrated under vacuum. The residue was purified by a silica gel column eluting with dichloromethane/methanol (20/1) to afford 460 mg (42%) of tert-butyl 4-[7-[6-amino-4-methyl-3-(trifluoromethyl)pyridin-2-yl]-6-chloro-2-methylquinazolin-4-yl]piperazine-1-carboxylate as a light yellow solid. LC-MS: (ESI, m/z): 537.2 [M+H]+.

Step 5: 6-[6-chloro-2-methyl-4-(piperazin-1-yl)quinazolin-7-yl]-4-methyl-5-(trifluoromethyl)pyridin-2-amine

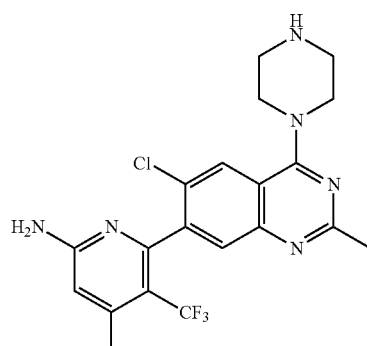

A solution of tert-butyl 4-[7-[6-amino-4-methyl-3-(trifluoromethyl)pyridin-2-yl]-6-chloro-2-methylquinazolin-4- yl]piperazine-1-carboxylate (350 mg, 0.65 mmol) in trifluoroacetic acid (3 mL) and dichloromethane (10 mL) was stirred for 30 min at room temperature. After completion, the resulting solution was concentrated under vacuum to afford 700 mg (crude) of 6-[6-chloro-2-methyl-4-(piperazin-1-yl) quinazolin-7-yl]-4-methyl-5-(trifluoromethyl)pyridin-2-amine as a brown solid. LC-MS: (ESI, m/z): 437.1 [M+H]+.

Step 6: 1-(4-[7-[6-amino-4-methyl-3-(trifluoromethyl)pyridin-2-yl]-6-chloro-2-methylquinazolin-4-yl]piperazin-1-yl)prop-2-en-1-one

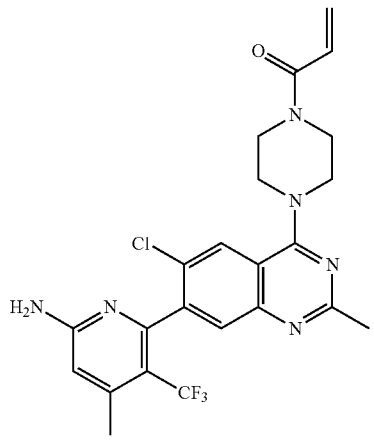 [SMILES: C=CC(=O)N1CCN(c2nc(C)nc3cc(-c4nc(N)cc(C)c4C(F)(F)F)c(Cl)cc23)CC1]

A solution of 6-[6-chloro-2-methyl-4-(piperazin-1-yl)quinazolin-7-yl]-4-methyl-5-(trifluoromethyl)pyridin-2-amine (285 mg, crude), prop-2-enoic acid (94 mg, 1.30 mmol), HATU (370 mg, 1.0 mmol) and N,N-diisopropylethylamine (2 mL) in dichloromethane (15 mL) was stirred for 30 min at −78° C. After completion, the solution was quenched with water (20 mL) and extracted with dichloromethane (3×50 mL). The organic layer was collected and dried over anhydrous sodium sulfate and concentrated under vacuum. The residue was purified by a silica gel column eluting with dichloromethane/methanol (20/1) to afford a crude product. The crude product was purified by Prep-HPLC with the following conditions: Column: X Bridge C18, 19*150 mm, 5 um; Mobile Phase A:Water/0.05% TFA, Mobile Phase B: ACN; Flow rate: 20 mL/min; Gradient: 30% B to 70% B in 10 min; 254 nm to afford 79.2 mg (12%) of 1-(4-[7-[6-amino-4-methyl-3-(trifluoromethyl)pyridin-2-yl]-6-chloro-2-methylquinazolin-4-yl]piperazin-1-yl)prop-2-en-1-one as a white solid. LC-MS: (ESI, m/z): 491.1 [M+H]+.

Example 32

1H NMR (300 MHz, Methanol-d4, ppm) δ 8.12 (s, 1H), 7.62 (s, 1H), 6.84 (dd, J=16.8, 10.6 Hz, 1H), 6.64-6.57 (m, 1H), 6.29 (dd, J=16.8, 2.0 Hz, 1H), 5.82 (dd, J=10.6, 2.0 Hz, 1H), 3.98-3.89 (m, 8H), 2.63 (s, 3H), 2.46 (s, 3H).

Example 33

1-(4-[7-[6-amino-3-methyl-4-(trifluoromethyl)pyridin-2-yl]-6-chloroquinazolin-4-yl]piperazin-1-yl)prop-2-en-1-one

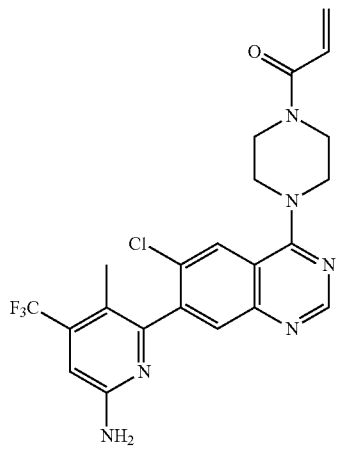 [SMILES: C=CC(=O)N1CCN(c2ncnc3cc(-c4nc(N)cc(C(F)(F)F)c4C)c(Cl)cc23)CC1]

Synthetic Route

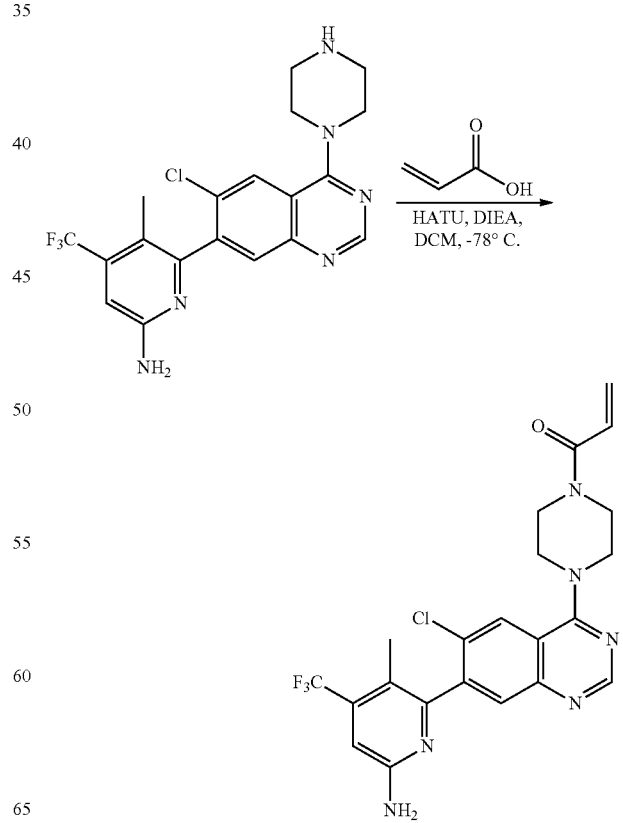

321

Step 1: 1-(4-[7-[6-amino-3-methyl-4-(trifluoromethyl)pyridin-2-yl]-6-chloroquinazolin-4-yl]piperazin-1-yl)prop-2-en-1-one

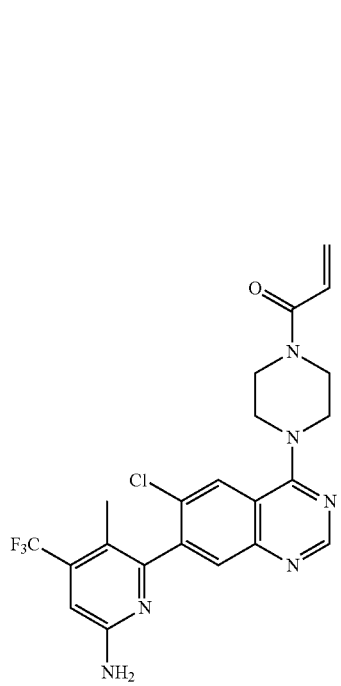 [SMILES: C=CC(=O)N1CCN(c2ncnc3cc(-c4nc(N)cc(C(F)(F)F)c4C)c(Cl)cc23)CC1]

A solution of 6-[6-chloro-4-(piperazin-1-yl)quinazolin-7-yl]-5-methyl-4-(trifluoromethyl)pyridin-2-amine (290.0 mg, 0.7 mmol), HATU (312.9 mg, 0.8 mmol), N,N-diisopropylethylamine (177.3 mg, 1.4 mmol), prop-2-enoic acid (49.4 mg, 0.7 mmol) in dichloromethane (10 mL) was stirred for 1 h at −78° C. After completion, the solution was quenched with water (20 mL) and extracted with dichloromethane (3×50 mL). The organic layer was collected and dried over anhydrous sodium sulfate and concentrated under vacuum. The crude product was purified by reverse-phase column eluting with acetonitrile/water (3/7) to afford 50.8 mg (16%) of 1-(4-[7-[6-amino-3-methyl-4-(trifluoromethyl)pyridin-2-yl]-6-chloroquinazolin-4-yl]piperazin-1-yl)prop-2-en-1-one as a white solid. LC-MS: (ESI, m/z): 477.1 [M+H]$^+$.

Example 33

$^1$H NMR (300 MHz, DMSO-d$_6$, ppm) 8.68 (s, 1H), 8.17 (s, 1H), 7.76 (s, 1H), 6.89-6.70 (m, 2H), 6.50 (s, 2H), 6.21-6.15 (m, 1H), 5.78-5.72 (m, 1H), 3.88-3.78 (m, 8H), 1.99 (s, 3H)

322

Example 34

1-(4-(7-(6-amino-4-cyclopropyl-3-(trifluoromethyl)pyridin-2-yl)-6-chloroquinazolin-4-yl)piperazin-1-yl)prop-2-en-1-one

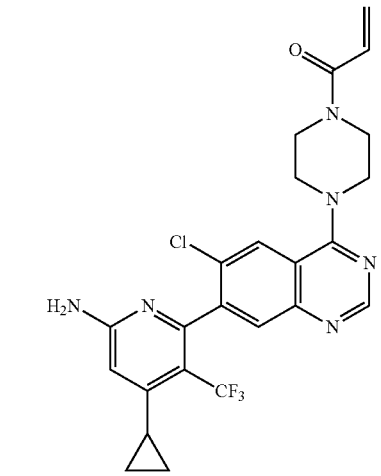 [SMILES: C=CC(=O)N1CCN(c2ncnc3cc(-c4nc(N)cc(C5CC5)c4C(F)(F)F)c(Cl)cc23)CC1]

Synthetic Route

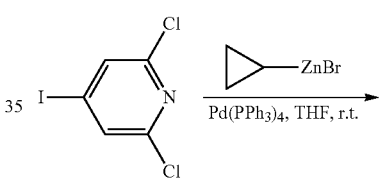

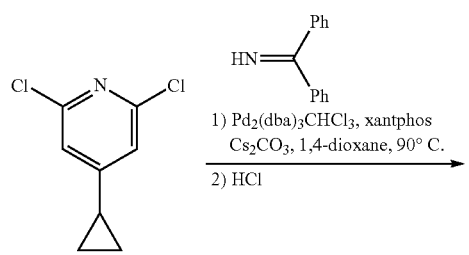

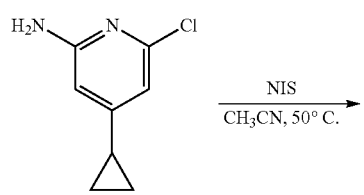

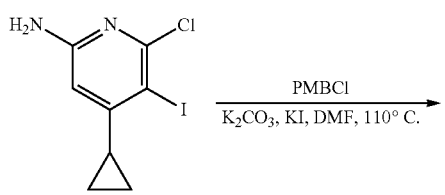

323
-continued

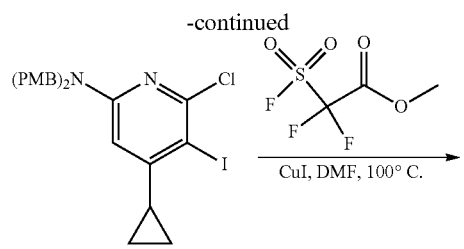

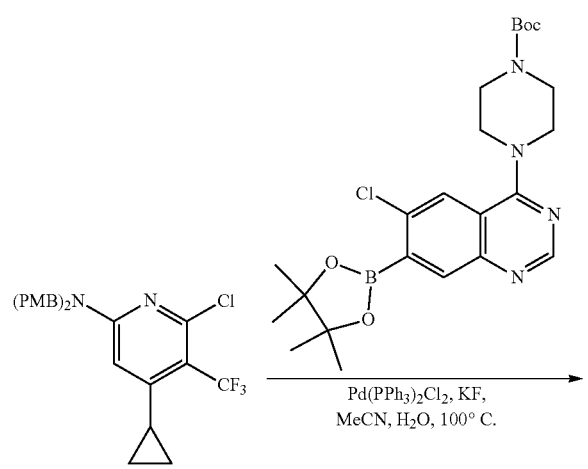

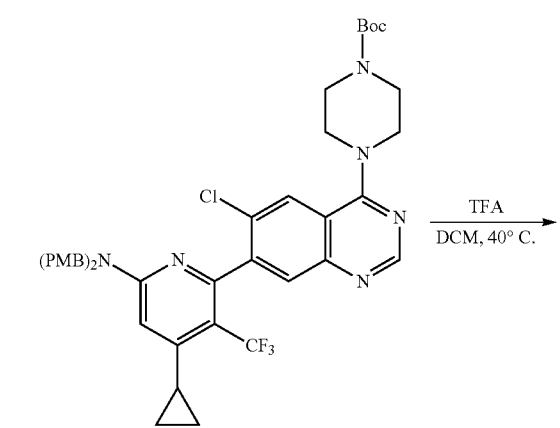

324
-continued

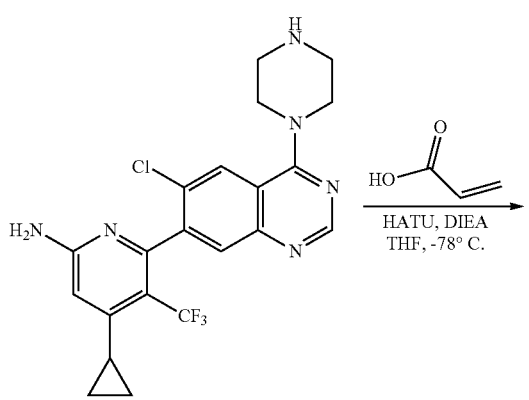

Step 1: 2,6-dichloro-4-cyclopropylpyridine

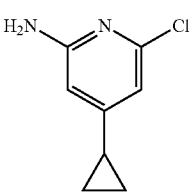 [SMILES: Nc1cc(C2CC2)cc(Cl)n1]

Under nitrogen, to a solution of 2,6-dichloro-4-iodopyridine (3.6 g, 13.2 mmol), tetrakis(triphenylphosphine)palladium (1.5 g, 1.3 mmol) in dry THF (30 mL) was added a solution of bromo(cyclopropyl)zinc (26.4 mL, 26.4 mmol, 1.0 M in THF), then the solution was stirred for 1 h at 25° C. After completion, the solution was quenched with water (20 mL) and extracted with dichloromethane (3×50 mL). The organic layer was collected and dried over anhydrous sodium sulfate and concentrated under vacuum. The crude product was The residue was applied on a silica gel column eluting with petroleum ether/ethyl acetate (10/1) to afford 2.2 g (79%) 2,6-dichloro-4-cyclopropylpyridine as an orange solid. LC-MS: (ESI, m/z): 188.0 [M+H]$^+$.

Step 2: 6-chloro-4-cyclopropylpyridin-2-amine

Under nitrogen, a solution of 2,6-dichloro-4-cyclopropylpyridine (1.2 g, 6.4 mmol), diphenylmethanimine (1.16 g, 6.4 mmol), tris(dibenzylideneacetone)dipalladium chloroform complex (662 mg, 0.64 mmol), xantphos (370 mg, 0.64 mmol), cesium carbonate (4.2 g, 12.8 mmol) in 1,4-dioxane (25 mL) was stirred for 2 h at 90° C. After completion, the solution was diluted with water (50 mL) and extracted with ethyl acetate (3×50 mL). The organic layers were collected, dried over anhydrous sodium sulfate and concentrated under vacuum. The residue was dissolved with hydrogen chloride (10 mL, 3M in 1,4-dioxane) and stirred for 1 h at 25° C. After completion, the solution was concentrated under vacuum. Then residue was dissolved with dichloromethane (50 mL), and the pH of the resulting solution was adjusted to pH=9 with N,N-diisopropylethylamine. Then the resulting solution was concentrated under vacuum and the residue was purified by a silica gel column eluting with ethyl acetate/petroleum ether (1/3) to afford 690 mg (64%) of 6-chloro-4-cyclopropylpyridin-2-amine as a white solid. LC-MS: (ESI, m/z): 169.0 [M+H]+.

Step 3:
6-chloro-4-cyclopropyl-5-iodopyridin-2-amine

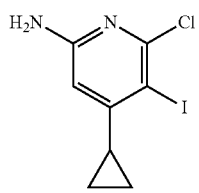 [SMILES: Nc1cc(C2CC2)c(I)c(Cl)n1]

A solution of 6-chloro-4-cyclopropylpyridin-2-amine (690 mg, 4.1 mmol), N-iodosuccinimide (1.2 g, 5.3 mmol) in acetonitrile (10 mL) was stirred for 1 h at 50° C. After completion, the solution was diluted with saturated sodium thiosulfate solution (50 mL) and extracted with ethyl acetate (4×50 mL). Then the organic layers were combined dried over anhydrous sodium sulfate and concentrated under vacuum. The residue was applied onto a silica gel column eluting with ethyl acetate/petroleum ether (1/4) to afford 950 mg (79%) of 6-chloro-4-cyclopropyl-5-iodopyridin-2-amine as a brown solid. LC-MS: (ESI, m/z): 294.9 [M+H]+.

Step 4: 6-chloro-4-cyclopropyl-5-iodo-N,N-bis(4-methoxybenzyl)pyridin-2-amine

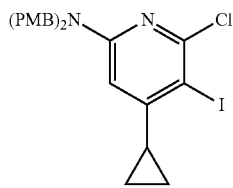

A solution of 6-chloro-4-cyclopropyl-5-iodopyridin-2-amine (690 mg, 2.3 mmol), potassium carbonate (1.3 g, 9.4 mmol), 1-(chloromethyl)-4-methoxybenzene (1.5 g, 9.6 mmol), potassium iodide (200 mg, 1.2 mmol) in N,N-dimethylformamide (5 mL) was stirred for 2 h at 110° C. After completion, the solution was diluted with water (25 mL) and extracted with ethyl acetate (3×30 mL). The organic layers combined and dried over anhydrous sodium sulfate and concentrated under vacuum. The residue was applied onto a silica gel column eluting with ethyl acetate/ petroleum ether (3/97) to afford 1.2 g (96%) of 6-chloro-4-cyclopropyl-5-iodo-N,N-bis[(4-methoxyphenyl)methyl] pyridin-2-amine as colorless oil. LC-MS: (ESI, m/z): 535.1 [M+H]+.

Step 5: 6-chloro-4-cyclopropyl-N,N-bis(4-methoxybenzyl)-5-(trifluoromethyl)pyridin-2-amine

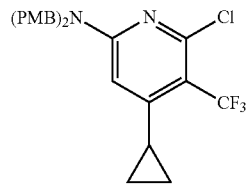

Under nitrogen, a solution of 6-chloro-4-cyclopropyl-5-iodo-N,N-bis[(4-methoxyphenyl)methyl]pyridin-2-amine (1.2 g, 2.2 mmol), methyl 2,2-difluoro-2-(fluorosulfonyl) acetate (960 mg, 4.9 mmol) and cuprous iodide (880 mg, 4.621 mmol) in N,N-dimethylformamide (10 mL) was stirred and for 1 h at 100° C. After completion, the solution was diluted with water (25 mL) and extracted with ethyl acetate (3×30 mL). The organic layers combined and dried over anhydrous sodium sulfate and concentrated under vacuum. The residue was applied onto a silica gel column eluting with ethyl acetate/petroleum ether (3/97) to afford 1.0 g (93%) of 6-chloro-4-cyclopropyl-N,N-bis[(4-methoxyphenyl)methyl]-5-(trifluoromethyl)pyridin-2-amine as light yellow oil. LC-MS: (ESI, m/z): 477.1 [M+H]+.

Step 6: tert-butyl 4-(7-(6-(bis(4-methoxybenzyl) amino)-4-cyclopropyl-3-(trifluoromethyl)pyridin-2-yl)-6-chloroquinazolin-4-yl)piperazine-1-carboxylate

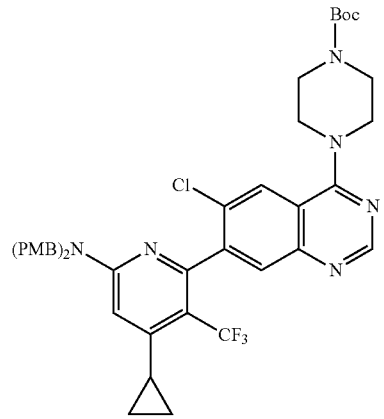

Under nitrogen, a solution of tert-butyl 4-(6-chloro-7-(4, 4,5,5-tetramethyl-1,3,2-dioxaborolan-2-yl)quinazolin-4-yl) piperazine-1-carboxylate (500 mg, 1.05 mmol), 6-chloro-4-cyclopropyl-N,N-bis[(4-methoxyphenyl)methyl]-5-(trifluoromethyl)pyridin-2-amine (553 mg, 1.16 mmol), bis (triphenylphosphine)palladium(II) chloride (77.2 mg, 0.1 mmol), potassium fluoride (122 mg, 2.1 mmol) in acetonitrile (10 mL) and water (1 mL) was stirred for 30 min at 100° C. After completion, the resulting solution was diluted with water (50 mL) and extracted with ethyl acetate (3×50 mL). Then the organic layers were combined, washed with brine (3×20 mL) and dried over anhydrous sodium sulfate and concentrated under vacuum. The residue was purified by a silica gel column eluting with ethyl acetate/petroleum ether (1/2) to afford 491 mg (59%) of tert-butyl 4-(7-(6-(bis(4-methoxybenzyl)amino)-4-cyclopropyl-3-(trifluoromethyl)pyridin-2-yl)-6-chloroquinazolin-4-yl)piperazine-1-carboxylate as an off-white solid. LC-MS: (ESI, m/z): 789.3 [M+H]+.

Step 7: 6-(6-chloro-4-(piperazin-1-yl)quinazolin-7-yl)-4-cyclopropyl-5-(trifluoromethyl)pyridin-2-amine

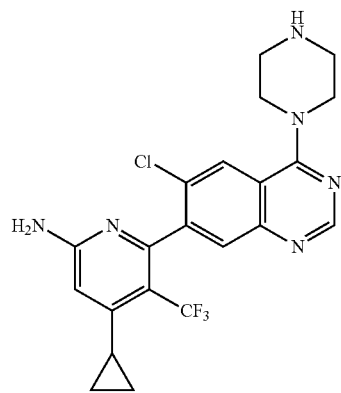 [SMILES: Nc1cc(C2CC2)c(C(F)(F)F)c(-c2cc3ncnc(N4CCNCC4)c3cc2Cl)n1]

A solution of tert-butyl 4-(7-(6-(bis(4-methoxybenzyl)amino)-4-cyclopropyl-3-(trifluoromethyl)pyridin-2-yl)-6-chloroquinazolin-4-yl)piperazine-1-carboxylate (491 mg, 0.62 mmol) in dichloromethane (5 mL) and trifluoroacetic acid (5 mL) was stirred for 30 min at 25° C., After completion, the resulting solution was concentrated under vacuum. The residue was dissolved with dichloromethane (5 mL) and the pH of the resulting solution was adjusted to pH=9 with N,N-diisopropylethylamine. After concentrated under vacuum, the residue was purified by silica gel column eluting with dichloromethane/methanol (83/17) to afford 205 mg (74%) of 6-(6-chloro-4-(piperazin-1-yl)quinazolin-7-yl)-4-cyclopropyl-5-(trifluoromethyl)pyridin-2-amine as a light brown solid. LC-MS: (ESI, m/z): 449.1 [M+H]+.

Step 8: 1-(4-(7-(6-amino-4-cyclopropyl-3-(trifluoromethyl)pyridin-2-yl)-6-chloroquinazolin-4-yl)piperazin-1-yl)prop-2-en-1-one

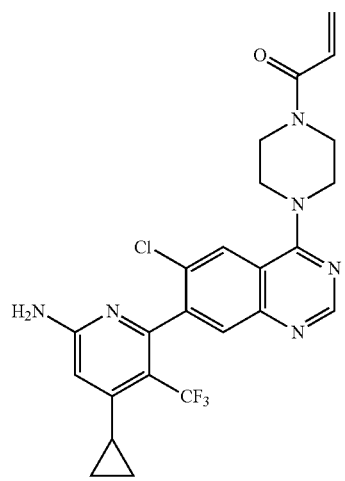 [SMILES: C=CC(=O)N1CCN(c2ncnc3cc(-c4nc(N)cc(C5CC5)c4C(F)(F)F)c(Cl)cc23)CC1]

A solution of 6-(6-chloro-4-(piperazin-1-yl)quinazolin-7-yl)-4-cyclopropyl-5-(trifluoromethyl)pyridin-2-amine (205 mg, 0.46 mmol), prop-2-enoic acid (33 mg, 0.46 mmol), HATU (210 mg, 0.55 mmol) and N,N-diisopropylethylamine (89 mg, 0.69 mmol) in dichloromethane (10 mL) was stirred for 30 min at −78° C. After completion, the solution was quenched with water (30 mL) and extracted with dichloromethane (3×50 mL). The organic layer was collected and dried over anhydrous sodium sulfate and concentrated under vacuum. Then the residue was purified by reverse phase chromatography eluting with water/acetonitrile (3/2) to afford 49.6 mg (21%) of 1-(4-[7-[6-amino-4-methyl-3-(trifluoromethyl)pyridin-2-yl]-6-chloro-2-(trifluoromethyl)quinazolin-4-yl]piperazin-1-yl)prop-2-en-1-one as a white solid. LC-MS: (ESI, m/z): 503.1 [M+H]+.

Example 34

$^1$H NMR (400 MHz, CDCl$_3$, ppm) δ 8.75 (s, 1H), 8.09 (s, 1H), 7.97 (s, 1H), 6.75-6.65 (m, 1H), 6.42-6.37 (m, 1H), 6.22 (s, 1H), 5.81 (dd, J=7.2, 2.4 Hz, 1H), 4.98 (s, 1H), 4.05-3.80 (m, 8H), 2.19 (s, 1H), 1.25 (s, 1H), 1.14-1.07 (m, 2H), 0.88 (s, 2H).

Example 35

1-(4-[7-[6-amino-3-(trifluoromethyl)pyridin-2-yl]-6-chloroquinazolin-4-yl]piperazin-1-yl)prop-2-en-1-one

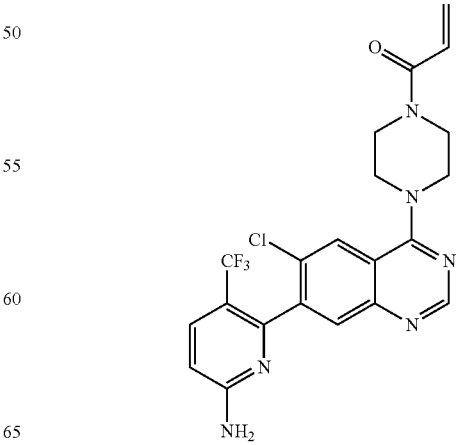

Synthetic Route

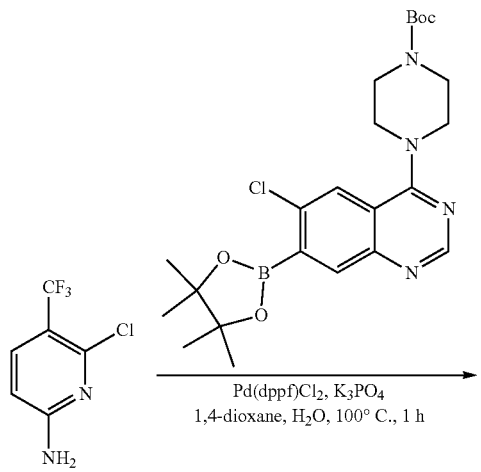

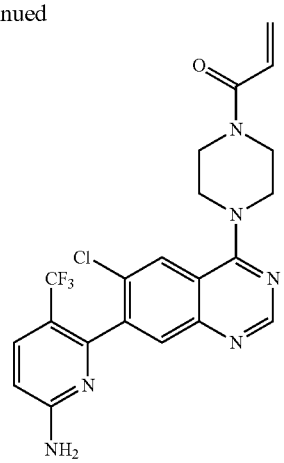

Step 1: tert-butyl 4-[7-[6-amino-3-(trifluoromethyl) pyridin-2-yl]-6-chloroquinazolin-4-yl]piperazine-1-carboxylate

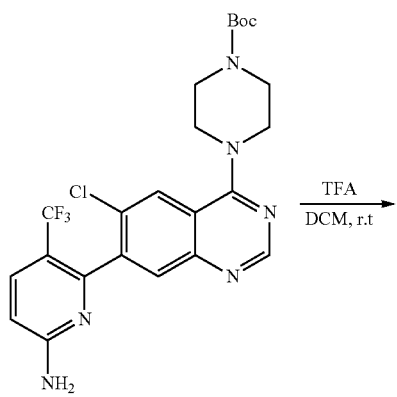

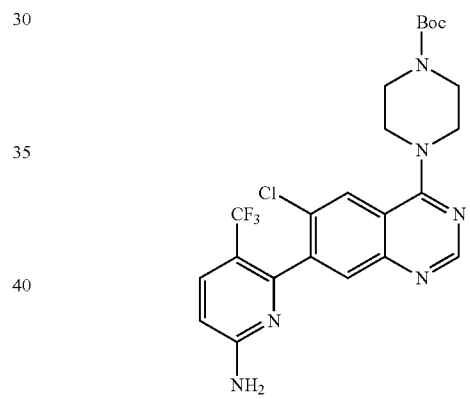

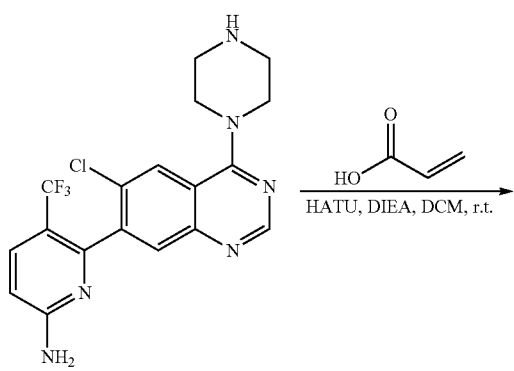

A solution of 6-chloro-5-(trifluoromethyl)pyridin-2-amine (400.0 mg, 2.04 mmol), tert-butyl 4-[6-chloro-7-(tetramethyl-1,3,2-dioxaborolan-2-yl)quinazolin-4-yl]piperazine-1-carboxylate (1.00 g, 2.11 mmol), 1,1'-bis(diphenylphosphino)ferrocene-palladium(II)dichloride dichloromethane complex (164.1 mg, 0.20 mmol) and $K_3PO_4$ (848.0 mg, 3.99 mmol) in 1,4-dioxane (8 mL) and water (0.5 mL) was stirred for 60 min at 100° C. After completion, the resulting solution was concentrated, diluted with dichloromethane (150 mL), washed by water (80 mL×3), dried over anhydrous sodium sulfate and concentrated under vacuum. The residue was purified by a silica gel column eluting with dichloromethane/methanol (20/1) to give 200.0 mg (19%) of tert-butyl 4-[7-[6-amino-3-(trifluoromethyl)pyridin-2-yl]-6-chloroquinazolin-4-yl]piperazine-1-carboxylate as a yellow solid. LC-MS (ESI, m/z): 509.2 [M+H]$^+$.

Step 2: 6-[6-chloro-4-(piperazin-1-yl)quinazolin-7-yl]-5-(trifluoromethyl)pyridin-2-amine

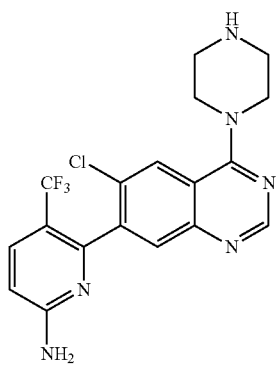 [SMILES: Nc1ccc(C(F)(F)F)c(-c2cc3ncnc(N4CCNCC4)c3cc2Cl)n1]

A solution of tert-butyl 4-[7-[6-amino-3-(trifluoromethyl)pyridin-2-yl]-6-chloroquinazolin-4-yl]piperazine-1-carboxylate (500.0 mg, 0.98 mmol) in trifluoroacetic acid (3 mL) and dichloromethane (10 mL) was stirred for 60 min at room temperature. After completion, the resulting solution was concentrated. This resulted in 600.0 mg (crude) of 6-[6-chloro-4-(piperazin-1-yl)quinazolin-7-yl]-5-(trifluoromethyl)pyridin-2-amine as a brown oil. LC-MS (ESI, m/z): 409.1 [M+H]$^+$.

Step 3: 1-(4-[7-[6-amino-3-(trifluoromethyl)pyridin-2-yl]-6-chloroquinazolin-4-yl]piperazin-1-yl)prop-2-en-1-one

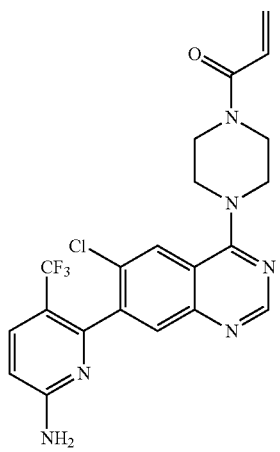 [SMILES: C=CC(=O)N1CCN(c2ncnc3cc(-c4nc(N)ccc4C(F)(F)F)c(Cl)cc23)CC1]

A solution of prop-2-enoic acid (10.0 mg, 0.14 mmol), 6-[6-chloro-4-(piperazin-1-yl)quinazolin-7-yl]-5-(trifluoromethyl)pyridin-2-amine (60.0 mg, 0.15 mmol), HATU (56.0 mg, 0.15 mmol) and N,N-diisopropylethylamine (1 mL, 5.69 mmol) in dichloromethane (5 mL) was stirred for 30 min at room temperature. After completion, the resulting solution was concentrated and diluted with dichloromethane (150 mL), washed with brine (40 mL×3), dried over anhydrous sodium sulfate and concentrated under vacuum. The residue was purified by a silica gel column eluting with dichloromethane/methanol (20/1). The product was prepare by HPLC with following condition: Column: X Bridge C18, 19*150 mm, 5 um; Mobile Phase A: Water/0.05% TFA, Mobile Phase B: ACN; Flow rate: 20 mL/min; Gradient: 30% B to 70% B in 10 min; 254 nm. This resulted in 9.7 mg (15%) of 1-(4-[7-[6-amino-3-(trifluoromethyl)pyridin-2-yl]-6-chloroquinazolin-4-yl]piperazin-1-yl)prop-2-en-1-one as a white solid. LC-MS (ESI, m/z): 463.1 [M+H]$^+$.

Example 35

$^1$H NMR (300 MHz, DMSO-d$_6$, ppm) δ 8.68 (s, 1H), 8.14 (s, 1H), 7.81 (d, J=8.9 Hz, 1H), 7.72 (s, 1H), 6.95 (s, 2H), 6.84 (dd, J=16.5, 10.2 Hz, 1H), 6.62 (d, J=9.0 Hz, 1H), 6.18 (dd, J=16.8, 2.4 Hz, 1H), 5.75 (dd, J=10.5, 2.4 Hz, 1H), 3.87-3.79 (m, 8H).

Example 36

N-(1-(4-(4-acryloylpiperazin-1-yl)-6-chloroquinazolin-7-yl)isoquinolin-3-yl)cyclopropanecarboxamide

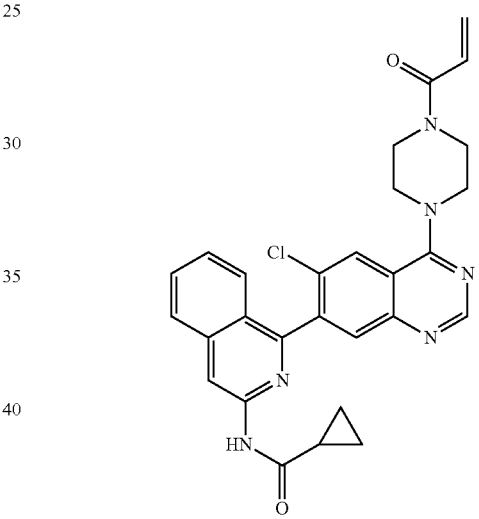

Synthetic Route

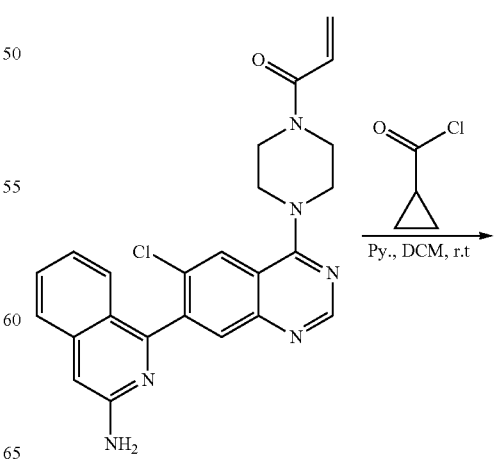

333

-continued

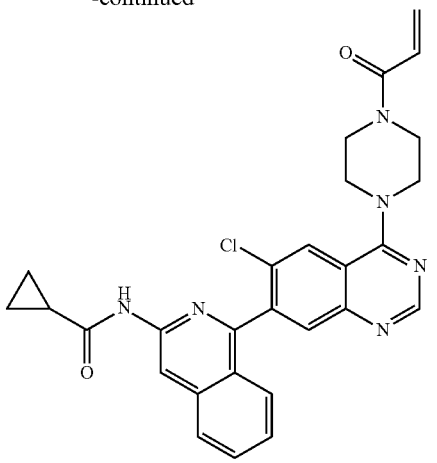

Step 1: N-(1-(4-(4-acryloylpiperazin-1-yl)-6-chloro-quinazolin-7-yl)isoquinolin-3-yl)cyclopropanecarboxamide

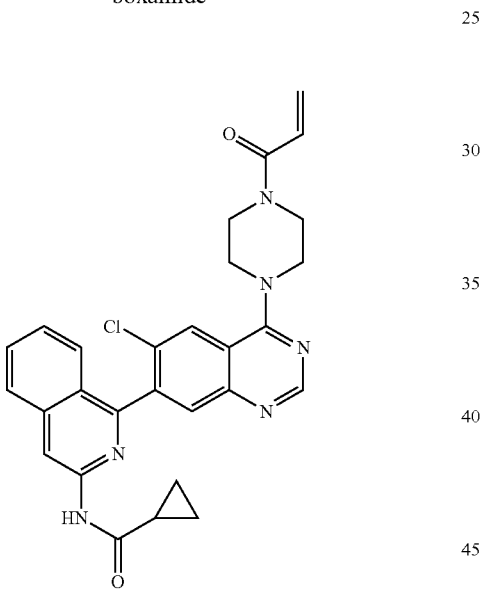

To a solution of 1-(4-(7-(3-aminoisoquinolin-1-yl)-6-chloroquinazolin-4-yl)piperazin-1-yl)prop-2-en-1-one (160 mg, 0.36 mmol), pyridine (57 mg, 0.72 mmol) in dichloromethane (10 mL) was added cyclopropanecarbonyl chloride (41 mg, 0.4 mmol), then the solution was stirred for 30 min at 25° C. After completion, the resulting solution was quenched with water (30 mL), extracted with dichloromethane (3×30 mL), washed with brine (3×10 mL), dried over anhydrous sodium sulfate and concentrated under vacuum. The residue was applied onto a silica gel column eluting with dichloromethane/methanol (20/1) to afford a crude product. The crude product was purified by Prep-HPLC with the following conditions: Column, XBridge Shield RP18 OBD Column 5 um, 19*150 mm; mobile phase, Waters (0.05% NH3 water) and ACN (10% ACN up to 45% in 10 min); Detector, UV 254/220 nm. This resulted in 53.9 mg (29.3%) of N-(1-(4-(4-acryloylpiperazin-1-yl)-6-chloroquinazolin-7-yl)isoquinolin-3-yl)cyclopropanecarboxamide as a white solid. LC-MS (ESI, m/z): 513.2 [M+H]⁺.

334

Example 36

¹H NMR (300 MHz, Methanol-d₄, ppm) δ 8.71 (s, 1H), 8.55 (s, 1H), 8.31 (s, 1H), 7.95-7.92 (m, 2H), 7.74-7.69 (m, 1H), 7.55 (d, J=8.4 Hz, 1H), 7.47-7.42 (m, 1H), 6.85 (dd, J=16.8, 10.8 Hz, 1H), 6.30 (dd, J=16.8, 1.8 Hz, 1H), 5.83 (dd, J=10.6, 1.9 Hz, 1H), 4.08-4.04 (m, 4H), 3.98-3.92 (m, 4H), 1.95-1.92 (m, 1H), 1.05-1.01 (m, 2H), 0.94-0.89 (m, 2H).

Example 37

N-(1-[6-chloro-4-[4-(prop-2-enoyl)piperazin-1-yl]quinazolin-7-yl]isoquinolin-3-yl)-2-hydroxyacetamide

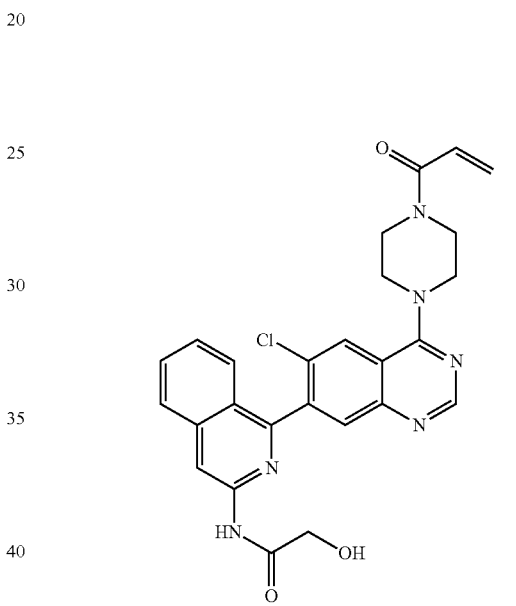

Synthetic Route

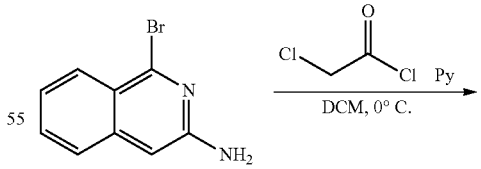

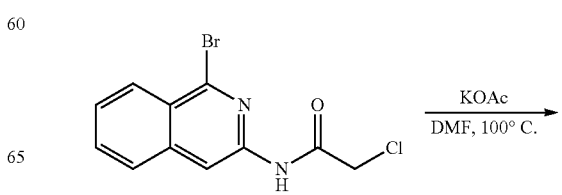

335
-continued

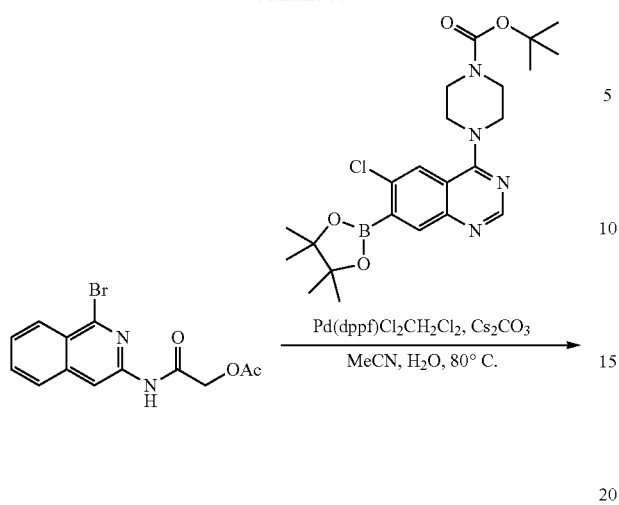

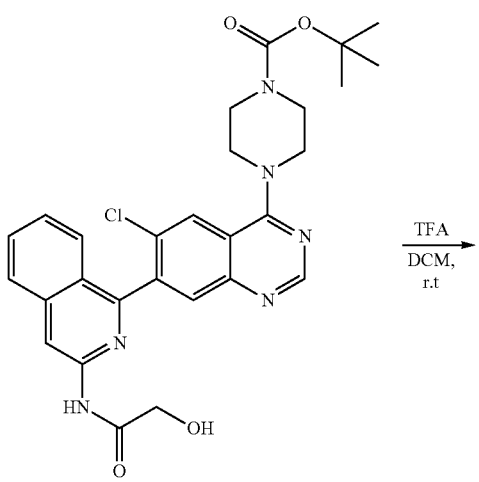

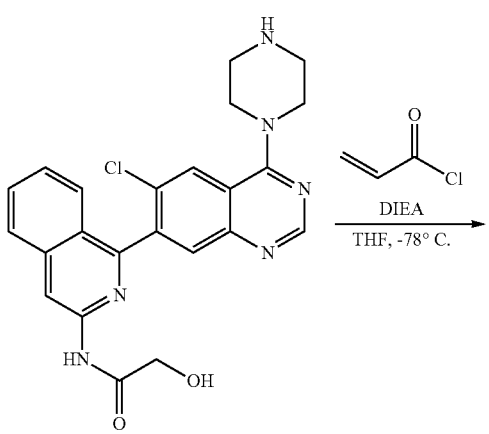

336
-continued

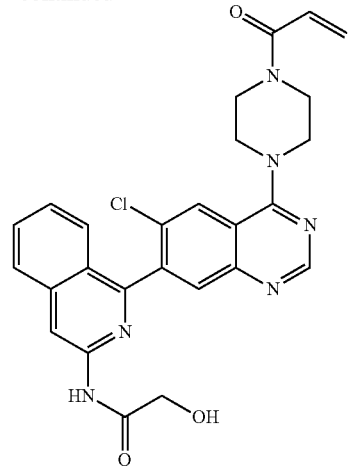 [SMILES: C=CC(=O)N1CCN(c2ncnc3cc(-c4nc(NC(=O)CO)cc5ccccc45)c(Cl)cc23)CC1]

Step 1:
N-(1-bromoisoquinolin-3-yl)-2-chloroacetamide

To a solution of 1-bromoisoquinolin-3-amine (200.0 mg, 0.9 mmol) and pyridine (100.0 mg, 1.3 mmol) in dichloromethane (5 mL) was added 2-chloroacetyl chloride (150.0 mg, 1.3 mmol). The resulting solution was stirred for 30 min at 0° C. and concentrated under vacuum. The residue was applied onto a silica gel column eluting with ethyl acetate/petroleum ether (5/1) to afford 210.0 mg (78%) of N-(1-bromoisoquinolin-3-yl)-2-chloroacetamide as a light yellow solid. LC-MS (ESI, m/z): 299.0 [M+H]$^+$.

Step 2:
2-((1-bromoisoquinolin-3-yl)amino)-2-oxoethyl acetate

A solution of N-(1-bromoisoquinolin-3-yl)-2-chloroacetamide (150.0 mg, 0.50 mmol) and potassium acetate (75.0 mg, 0.76 mmol) in N,N-dimethylformamide (5 mL) was stirred for 2 h at 100° C. After completion, the resulting solution was cooled to room temperature and diluted with water (50 mL). After filtration, the solids were collected and dried under vacuum to afford 120 mg (66%) of 2-((1-bromoisoquinolin-3-yl)amino)-2-oxoethyl acetate as a white solid. LC-MS (ESI, m/z): 323.0 [M+H]$^+$.

Step 3: tert-butyl 4-[6-chloro-7-[3-(2-hydroxyacetamido)isoquinolin-1-yl]quinazolin-4-yl]piperazine-1-carboxylate

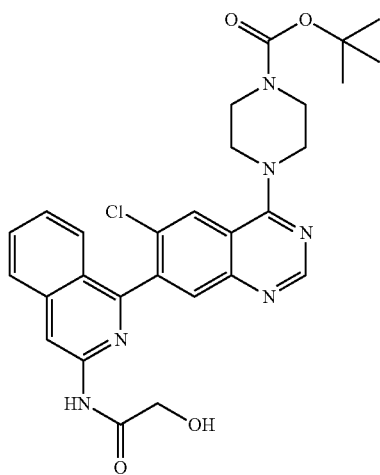 [SMILES: CC(C)(C)OC(=O)N1CCN(c2ncnc3cc(-c4nc(NC(=O)CO)cc5ccccc45)c(Cl)cc23)CC1]

Under nitrogen, a solution of 2-((1-bromoisoquinolin-3-yl)amino)-2-oxoethyl acetate (150.0 mg, 0.46 mmol), tert-butyl 4-[6-chloro-7-(tetramethyl-1,3,2-dioxaborolan-2-yl)quinazolin-4-yl]piperazine-1-carboxylate (250.0 mg, 0.53 mmol), 1,1'-bis(diphenylphosphino)ferrocene-palladium(II) dichloride dichloromethane complex (75.0 mg, 0.10 mmol) and cesium carbonate (400.0 mg, 1.20 mmol) in water (1 mL) and acetonitrile (5 mL) was stirred for 30 min at 80° C. After completion, the resulting solution was concentrated, diluted with 150 mL of dichloromethane, washed by water (3×80 mL), dried over anhydrous sodium sulfate and concentrated under vacuum. The residue was purified by a silica gel column eluting with dichloromethane/methanol (20/1) to afford 200.0 mg (78%) of tert-butyl 4-[6-chloro-7-[3-(2-hydroxyacetamido)isoquinolin-1-yl]quinazolin-4-yl]piperazine-1-carboxylate as a light yellow solid. LC-MS (ESI, m/z): 549.2 [M+H]$^+$.

Step 4: N-[1-[6-chloro-4-(piperazin-1-yl)quinazolin-7-yl]isoquinolin-3-yl]-2-hydroxyacetamide

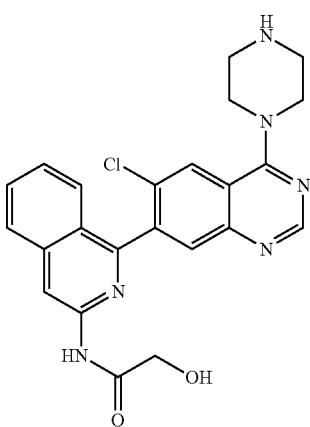 [SMILES: O=C(CO)Nc1cc2ccccc2c(-c2cc3ncnc(N4CCNCC4)c3cc2Cl)n1]

A solution of tert-butyl 4-[6-chloro-7-[3-(2-hydroxyacetamido)isoquinolin-1-yl]quinazolin-4-yl]piperazine-1-carboxylate (200.0 mg, 0.36 mmol) in dichloromethane (5 mL) and trifluoroacetic acid (3 mL) was stirred for 1 h at 25° C. After completion, the solution was concentrated under vacuum. Then the residue was dissolved with dichloromethane (20 mL) and the pH value of the resulting solution was adjusted to pH=8 with N,N-diisopropylethylamine and concentrated under vacuum. The residue was applied onto a silica gel column eluting with dichloromethane/methanol (85/15) to afford 100.0 mg (61%) of N-[1-[6-chloro-4-(piperazin-1-yl)quinazolin-7-yl]isoquinolin-3-yl]-2-hydroxyacetamide as a light yellow solid. LC-MS (ESI, m/z): 449.1 [M+H]$^+$.

Step 5: N-(1-[6-chloro-4-[4-(prop-2-enoyl)piperazin-1-yl]quinazolin-7-yl]isoquinolin-3-yl)-2-hydroxyacetamide

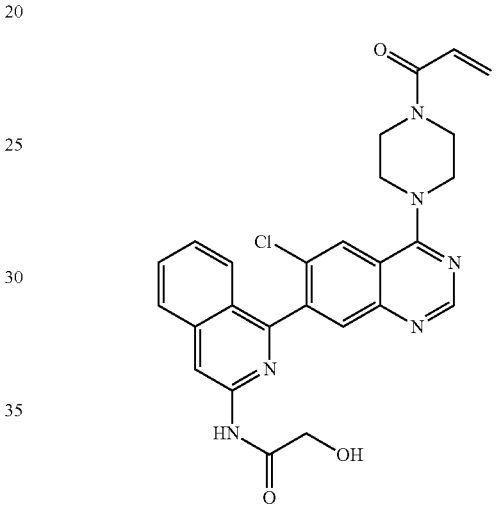

To a solution of N-[1-[6-chloro-4-(piperazin-1-yl)quinazolin-7-yl]isoquinolin-3-yl]-2-hydroxyacetamide (50.0 mg, 0.10 mmol) and N,N-diisopropylethylamine (1 mL) in THF (5 mL) was added prop-2-enoyl chloride (11.0 mg, 0.10 mmol) and stirred for 30 min at −78° C. After completion, the solution was quenched with water (30 mL) and extracted with dichloromethane (3×50 mL). The organic layer was collected and dried over anhydrous sodium sulfate and concentrated under vacuum. The residue was purified by Prep-HPLC with the following conditions: Column, XBridge Shield RP18 OBD Column 5 um, 19*150 mm; mobile phase, Water (0.05% NH3 water) and ACN (20% ACN up to 45% in 7 min). This resulted in 6.0 mg (11%) of N-(1-[6-chloro-4-[4-(prop-2-enoyl)piperazin-1-yl]quinazolin-7-yl]isoquinolin-3-yl)-2-hydroxyacetamide as a white solid. LC-MS (ESI, m/z): 503.2 [M+H]$^+$.

Example 37

$^1$H NMR (300 MHz, Methanol-d$_4$, ppm): δ 8.71 (d, J=4.6 Hz, 2H), 8.33 (s, 1H), 8.01 (d, J=8.4 Hz, 1H), 7.95 (s, 1H), 7.80-7.74 (m, 1H), 7.60-7.57 (m, 1H), 7.53-7.47 (m, 1H), 6.86 (dd, J=16.8, 10.6 Hz, 1H), 6.31 (dd, J=16.8, 1.9 Hz, 1H), 5.84 (dd, J=10.6, 2.0 Hz, 1H), 4.23 (s, 2H), 4.10-4.06 (m, 4H), 3.99-3.94 (m, 4H).

Example 38
1-[4-(6-chloro-7-[3-[(propan-2-yl)amino]isoquinolin-1-yl]quinazolin-4-yl)piperazin-1-yl]prop-2-en-1-one
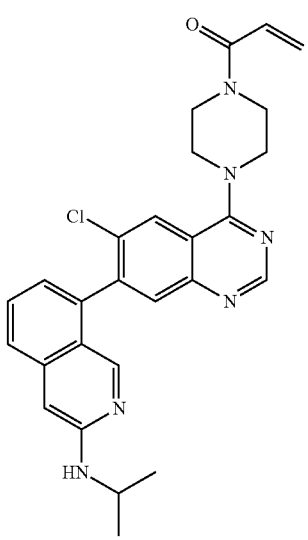 [SMILES: C=CC(=O)N1CCN(c2ncnc3cc(-c4cccc5cc(NC(C)C)ncc45)c(Cl)cc23)CC1]
Synthetic Route
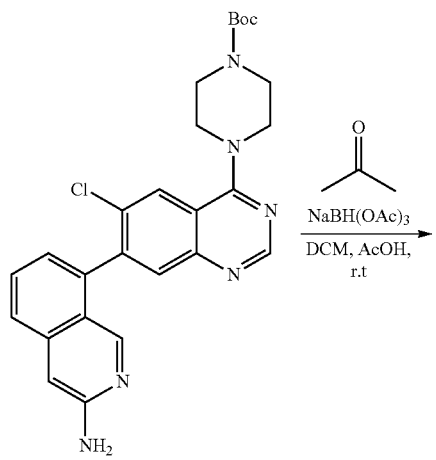
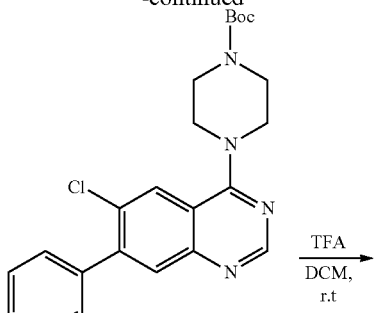
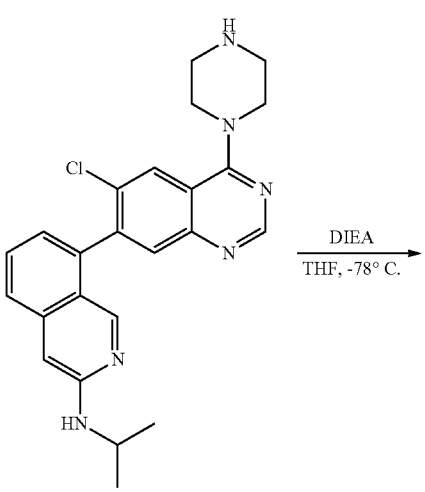
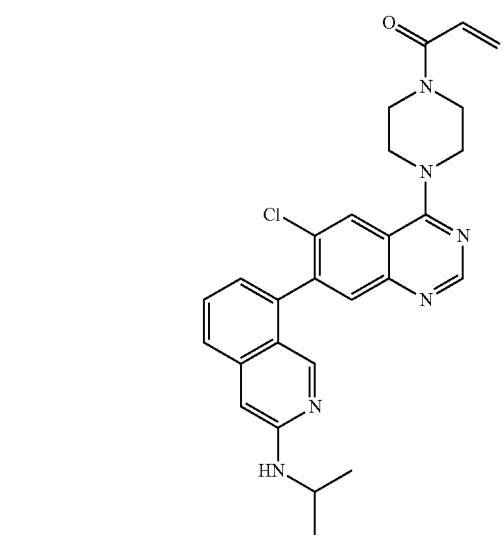 [SMILES: C=CC(=O)N1CCN(c2ncnc3cc(-c4cccc5cc(NC(C)C)ncc45)c(Cl)cc23)CC1]

Step 1: tert-butyl 4-(6-chloro-7-[3-[(propan-2-yl)amino]isoquinolin-1-yl]quinazolin-4-yl)piperazine-1-carboxylate

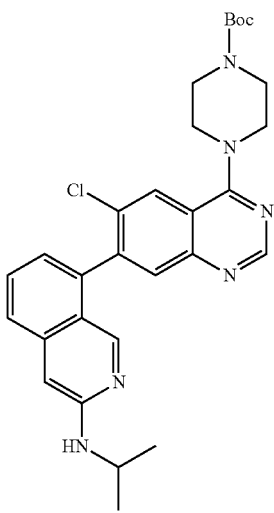 [SMILES: CC(C)Nc1cc2cccc(-c3cc4ncnc(N5CCN(C(=O)OC(C)(C)C)CC5)c4cc3Cl)c2cn1]

A solution of tert-butyl 4-[7-(3-aminoisoquinolin-1-yl)-6-chloroquinazolin-4-yl]piperazine-1-carboxylate (400.0 mg, 0.82 mmol), AcOH (1 mL, 17.45 mmol), propan-2-one (60.0 mg, 1.00 mmol) in dichloromethane (5 mL) was added NaBH(OAc)₃ (500 mg, 2.4 mmol) and stirred for 2 h at 25° C. After completion, the resulting solution was diluted with dichloromethane (150 mL), washed by water (80 mL×3), dried over anhydrous sodium sulfate and concentrated under vacuum. The residue was purified by a silica gel column eluting with dichloromethane/methanol (20/1) to afford to 350 mg (81%) of tert-butyl 4-(6-chloro-7-[3-[(propan-2-yl)amino]isoquinolin-1-yl]quinazolin-4-yl)piperazine-1-carboxylate as a yellow solid. LC-MS (ESI, m/z): 533.2 [M+H]⁺.

Step 2: 1-[6-chloro-4-(piperazin-1-yl)quinazolin-7-yl]-N-(propan-2-yl)isoquinolin-3-amine

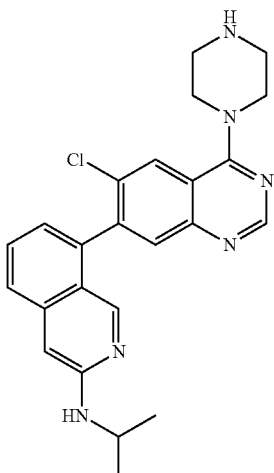

A solution of tert-butyl 4-(6-chloro-7-[3-[(propan-2-yl)amino]isoquinolin-1-yl]quinazolin-4-yl)piperazine-1-carboxylate (350.0 mg, 0.66 mmol) in TFA (2 mL) and dichloromethane (10 mL) was stirred for 1 h at 25° C. After completion, the solution was concentrated under vacuum. Then the residue was dissolved with dichloromethane (10 mL), and the pH value of the resulting solution was adjusted to pH=8 with N,N-diisopropylethylamine and concentrated under vacuum. The residue was applied onto a silica gel column eluting with dichloromethane/methanol (85/15) to afford 230.0 mg (81%) of 1-[6-chloro-4-(piperazin-1-yl)quinazolin-7-yl]-N-(propan-2-yl)isoquinolin-3-amine as a yellow solid. LC-MS (ESI, m/z): 433.2 [M+H]⁺.

Step 3: 1-[4-(6-chloro-7-[3-[(propan-2-yl)amino]isoquinolin-1-yl]quinazolin-4-yl)piperazin-1-yl]prop-2-en-1-one

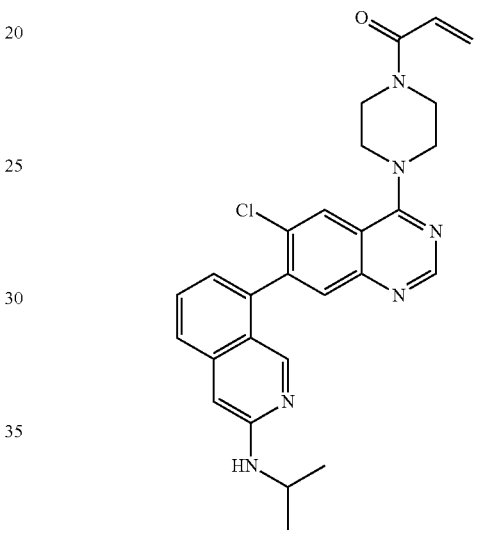

To a solution of 1-[6-chloro-4-(piperazin-1-yl)quinazolin-7-yl]-N-(propan-2-yl)isoquinolin-3-amine (200.0 mg, 0.46 mmol) in THF (5 mL) was added N,N-diisopropylethylamine (120.0 mg, 0.93 mmol) and prop-2-enoyl chloride (42.0 mg, 0.46 mmol) was stirred for 60 min at −78° C. After completion, the solution was quenched with water (30 mL) and extracted with dichloromethane (3×50 mL). The organic layer was collected and dried over anhydrous sodium sulfate and concentrated under vacuum. The residue was applied onto a silica gel column eluting with dichloromethane/methanol (10:1). The product was purified by Prep-HPLC with the following conditions: Column, XBridge Shield RP18 OBD Column 5 um, 19*150 mm; mobile phase, Water (0.05% NH3 water) and ACN (28.0% ACN up to 70.0% in 7 min); Detector, UV 220 nm. This resulted in 10.3 mg (4.6%) of 1-[4-(6-chloro-7-[3-[(propan-2-yl)amino]isoquinolin-1-yl]quinazolin-4-yl)piperazin-1-yl]prop-2-en-1-one as a yellow solid. LC-MS (ESI, m/z): 487.2 [M+H]⁺.

Example 38

¹H NMR (400 MHz, CDCl₃, ppm) δ 8.80 (s, 1H), 8.18-8.06 (s, 2H), 7.64 (d, J=8.4 Hz, 1H), 7.52-7.47 (m, 1H), 7.35-7.33 (m, 1H), 7.13-7.11 (m, 1H), 6.66-6.59 (m, 2H), 6.39 (dd, J=16.8, 1.8 Hz, 1H), 5.80 (dd, J=10.5, 1.8 Hz, 1H), 3.95-3.82 (m, 9H), 1.35-1.34 (m, 6H).

Example 39

2-[(1-[6-chloro-4-[4-(prop-2-enoyl)piperazin-1-yl]quinazolin-7-yl]isoquinolin-3-yl)amino]acetonitrile

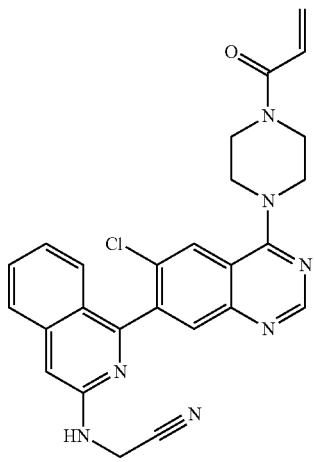 [SMILES: C=CC(=O)N1CCN(c2ncnc3cc(-c4nc(NCC#N)cc5ccccc45)c(Cl)cc23)CC1]

Synthetic Route

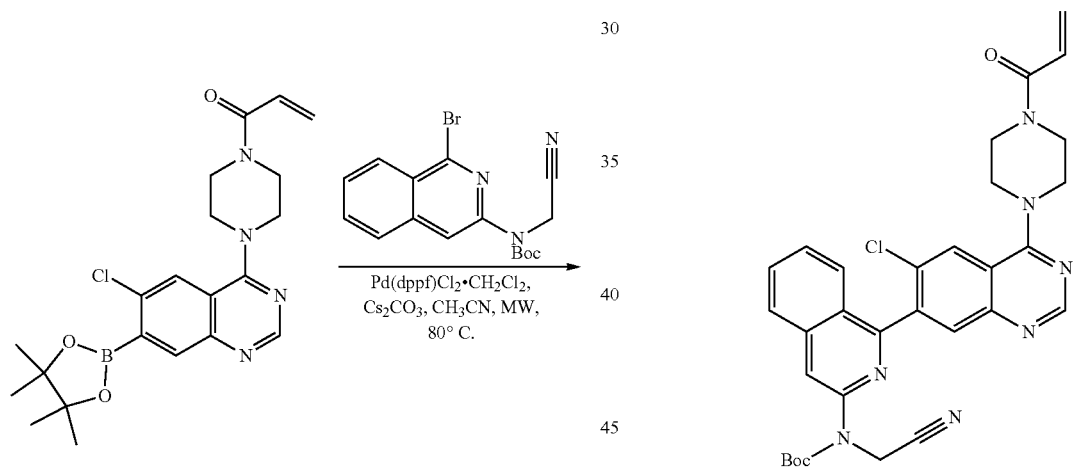

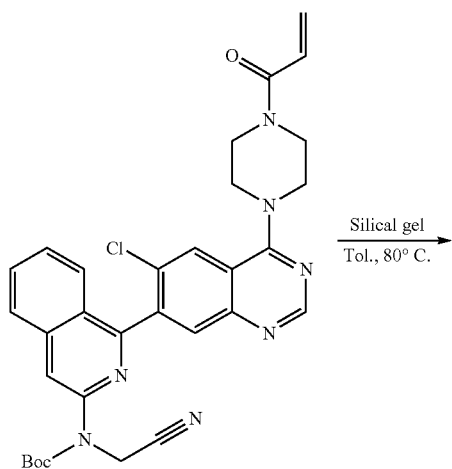

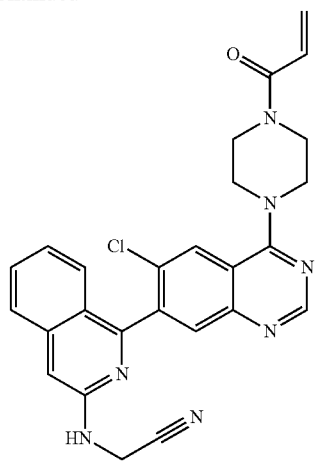 [SMILES: C=CC(=O)N1CCN(c2ncnc3cc(-c4nc(NCC#N)cc5ccccc45)c(Cl)cc23)CC1]

Step 1: tert-butyl N-(1-[6-chloro-4-[4-(prop-2-enoyl)piperazin-1-yl]quinazolin-7-yl]isoquinolin-3-yl)-N-(cyanomethyl)carbamate Under nitrogen, a solution of [6-chloro-4-[4-(prop-2-enoyl)piperazin-1-yl]quinazolin-7-yl]boronic acid (200.0 mg, 0.58 mmol), tert-butyl N-(1-bromoisoquinolin-3-yl)-N-(cyanomethyl)carbamate (167.0 mg, 0.46 mmol), 1,1'-bis(diphenylphosphino)ferrocene-palladium(II)dichloride dichloromethane complex (47.0 mg, 0.06 mmol) and cesium carbonate (373.0 mg, 1.14 mmol) in acetonitrile (5 mL) was irradiated with microwave radiation for 1.5 h at 80° C. After completion, the resulting solution was diluted with dichloromethane (150 mL), washed by water (80 mL×3), dried over anhydrous sodium sulfate and concentrated under vacuum. The residue was purified by a silica gel column eluting with dichloromethane/methanol (20/1) to afford 150 mg (45%) of tert-butyl N-(1-[6-chloro-4-[4-(prop-2-enoyl)piperazin-1-yl]quinazolin-7-yl]isoquinolin-3-yl)-N-(cyanomethyl)carbamate as a yellow solid. LC-MS (ESI, m/z): 584.2 [M+H]$^+$.

345

Step 2: 2-[(1-[6-chloro-4-[4-(prop-2-enoyl)piper-azin-1-yl]quinazolin-7-yl]isoquinolin-3-yl)amino]acetonitrile A solution of tert-butyl N-(1-[6-chloro-4-[4-(prop-2-enoyl)piperazin-1-yl]quinazolin-7-yl]isoquinolin-3-yl)-N-(cyanomethyl)carbamate (200.0 mg, 0.34 mmol) and silica gel (205.0 mg, 3.41 mmol) in toluene (3 mL) was stirred for 2 h at 80° C. After completion, the resulting solution was concentrated under vacuum. The residue was applied onto a silica gel column eluting with methanol/dichloromethane (1/10) to afford 15.7 mg (9%) of 2-[(1-[6-chloro-4-[4-(prop-2-enoyl)piperazin-1-yl]quinazolin-7-yl]isoquinolin-3-yl)amino]acetonitrile as a yellow solid. LC-MS (ESI, m/z): 484.2 [M+H]$^+$.

Example 39

$^1$H NMR (400 MHz, Methanol-d$_4$, ppm) δ 8.71 (s, 1H), 8.31 (s, 1H), 7.93 (s, 1H), 7.77 (d, J=8.4 Hz, 1H), 7.58 (ddd, J=8.3, 6.7, 1.2 Hz, 1H), 7.45-7.42 (m, 1H), 7.23 (ddd, J=8.4, 6.8, 1.2 Hz, 1H), 7.03 (s, 1H), 6.86 (dd, J=16.8, 10.6 Hz, 1H), 6.31 (dd, J=16.8, 1.9 Hz, 1H), 5.84 (dd, J=10.6, 1.9 Hz, 1H), 4.44 (d, J=1.9 Hz, 2H), 4.09-4.06 (m, 4H), 3.97-3.95 (m, 4H).

346

Example 40

1-(4-[7-[6-amino-3-(trifluoromethoxy)pyridin-2-yl]-6-chloroquinazolin-4-yl]piperazin-1-yl)prop-2-en-1-one

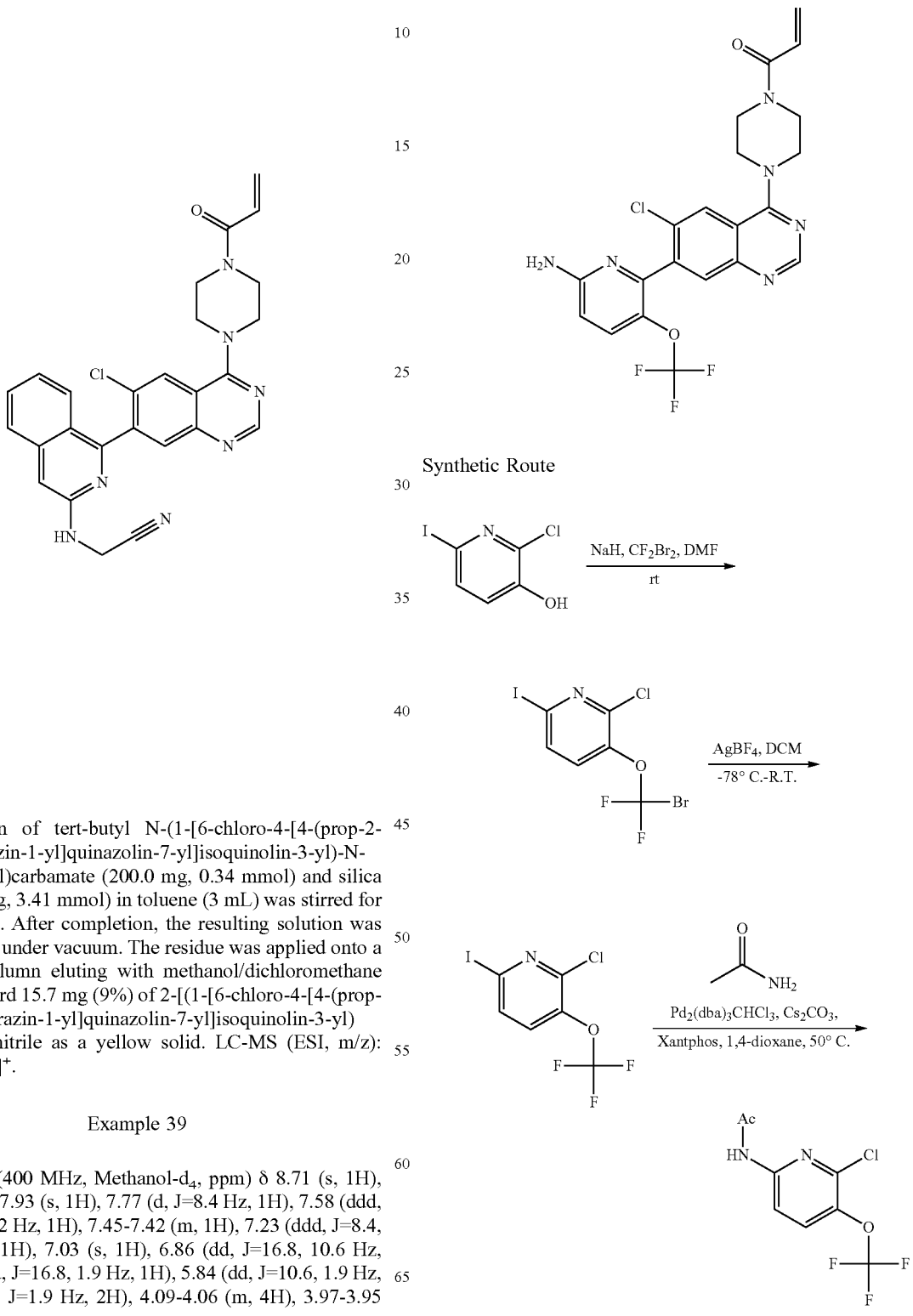

Synthetic Route

347
-continued

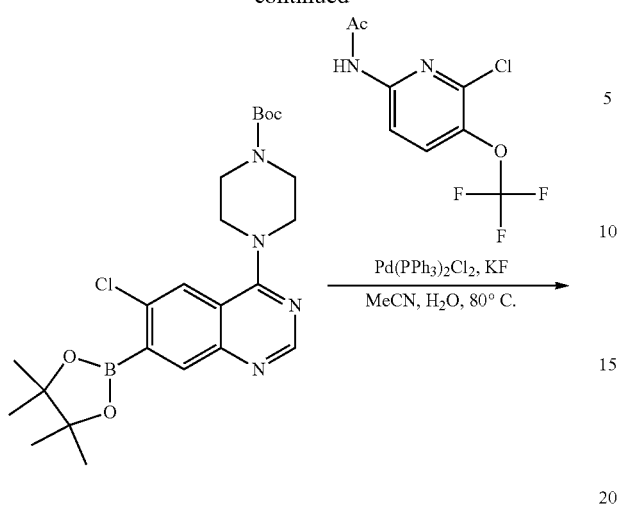

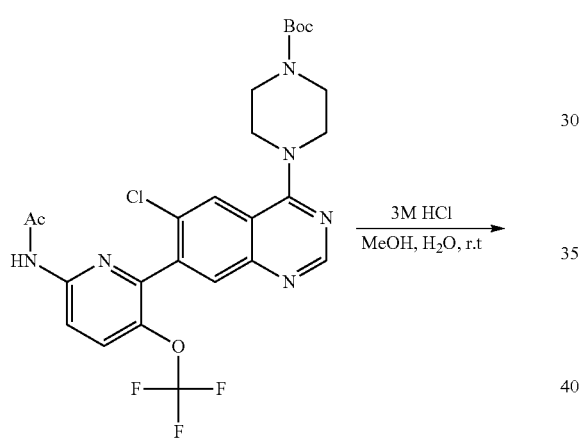

348
-continued

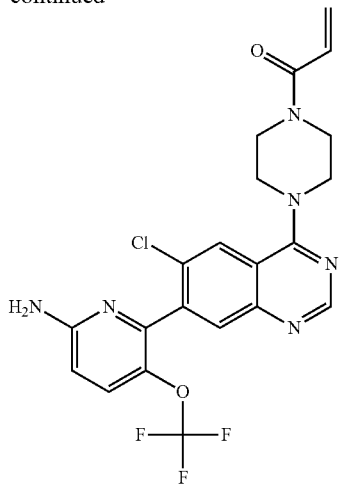

Step 1:
3-(bromodifluoromethoxy)-2-chloro-6-iodopyridine

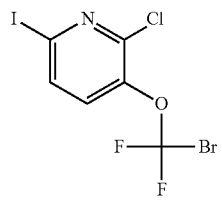 [SMILES: FC(F)(Br)Oc1ccc(I)nc1Cl]

A solution of 2-chloro-6-iodopyridin-3-ol (2.0 g, 7.8 mmol) in N,N-dimethylformamide (15 mL) was added sodium hydride (1.0 g, 41.7 mmol) and followed by a solution of dibromodifluoromethane (5.0 g, 23.8 mmol) in N,N-dimethylformamide (10 mL) was stirred for 3 h at 25° C. After completion, the resulting solution was quenched by the addition of water (50 mL), extracted with dichloromethane (100 mL×3), washed with water (100 mL×3), dried over anhydrous sodium sulfate and concentrated under vacuum. The residue was applied onto a silica gel column and purified eluting with petroleum ether to afford 1.8 g (60%) of 3-(bromodifluoromethoxy)-2-chloro-6-iodopyridine as light yellow oil. LC-MS (ESI, m/z): 383.8 [M+H]$^+$.

Step 2:
2-chloro-6-iodo-3-(trifluoromethoxy)pyridine

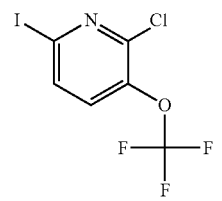

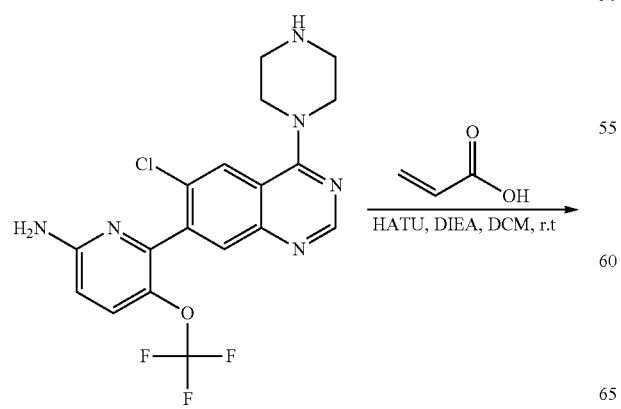

Under nitrogen, a solution of 3-(bromodifluoromethoxy)-2-chloro-6-iodopyridine (1.8 g, 4.7 mmol) in dichloromethane (10 mL) was added silver tetrafluoroborate (2.00 g, 10.30 mmol) and stirred for 16 h at −78° C. The solids were filtered out and the filtrate was concentrated under vacuum to afford 1.0 g (crude) of 2-chloro-6-iodo-3-(trifluoromethoxy)pyridine as light yellow oil. LC-MS (ESI, m/z): 323.9 [M+H]$^+$.

Step 3: N-(6-chloro-5-(trifluoromethoxy)pyridin-2-yl)acetamide

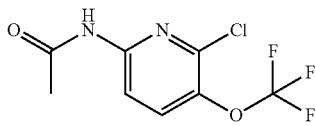 [SMILES: CC(=O)Nc1ccc(OC(F)(F)F)c(Cl)n1]

Under nitrogen, a solution of 2-chloro-6-iodo-3-(trifluoromethoxy)pyridine (500.0 mg, 1.50 mmol), acetamide (100.0 mg, 1.7 mmol), tris(dibenzylideneacetone)dipalladium-chloroform adduct (80.0 mg, 0.1 mmol), xantphos (90.0 mg, 0.2 mmol) and cesium carbonate (1.0 g, 3.1 mmol) in 1,4-dioxane (5 mL) was stirred for 20 min at 50° C. After completion, the resulting solution was diluted with ethyl acetate (200 mL), washed with brine (80 mL×3), dried over anhydrous sodium sulfate and concentrated under vacuum. The residue was applied onto a silica gel column eluting with ethyl acetate/petroleum ether (93/7) to afford 300.0 mg (76%) of N-[6-chloro-5-(trifluoromethoxy)pyridin-2-yl]acetamide as a light brown solid. LC-MS (ESI, m/z): 255.0 [M+H]$^+$.

Step 4: tert-butyl 4-[6-chloro-7-[6-acetamido-3-(trifluoromethoxy)pyridin-2-yl]quinazolin-4-yl]piperazine-1-carboxylate

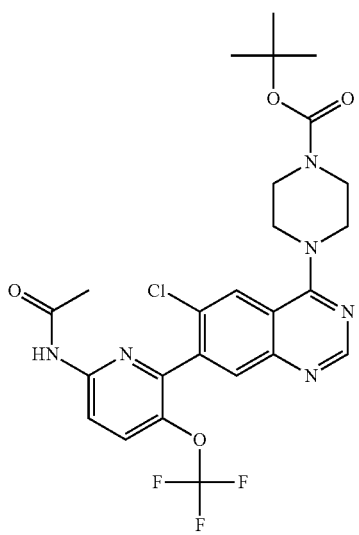 [SMILES: CC(=O)Nc1ccc(OC(F)(F)F)c(-c2cc3ncnc(N4CCN(C(=O)OC(C)(C)C)CC4)c3cc2Cl)n1]

Under nitrogen, a solution of N-[6-chloro-5-(trifluoromethoxy)pyridin-2-yl]acetamide (200.0 mg, 0.79 mmol), tert-butyl 4-[6-chloro-7-(tetramethyl-1,3,2-dioxaborolan-2-yl)quinazolin-4-yl]piperazine-1-carboxylate (400.0 mg, 0.84 mmol), bis(triphenylphosphine)palladium(II) chloride (40.0 mg, 0.06 mmol) and potassium fluoride (100.0 mg, 1.70 mmol) in acetonitrile (5 mL) and water (1 mL) was stirred for 20 min at 80° C. After completion, the resulting solution was diluted with ethyl acetate (200 mL), washed with water (80 mL×3), dried over anhydrous sodium sulfate and concentrated under vacuum. The residue was applied onto a silica gel column eluting with dichloromethane/methanol (97/3) to afford 420 mg (94%) of tert-butyl 4-[6-chloro-7-[6-acetamido-3-(trifluoromethoxy)pyridin-2-yl]quinazolin-4-yl]piperazine-1-carboxylate as a light yellow solid. LC-MS (ESI, m/z): 567.2 [M+H]$^+$.

Step 5: 6-[6-chloro-4-(piperazin-1-yl)quinazolin-7-yl]-5-(trifluoromethoxy)pyridin-2-amine

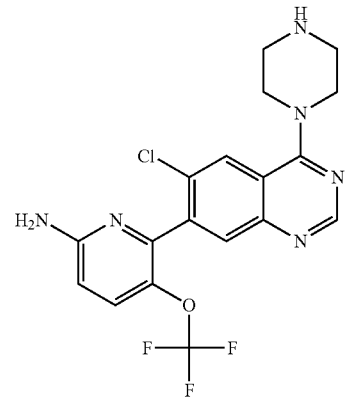 [SMILES: Nc1ccc(OC(F)(F)F)c(-c2cc3ncnc(N4CCNCC4)c3cc2Cl)n1]

A solution of 4-[6-chloro-7-[6-acetamido-3-(trifluoromethoxy)pyridin-2-yl]quinazolin-4-yl]piperazine-1-carboxylate (400.0 mg, 0.70 mmol) in hydrochloric acid (5 mL, 3 M in methanol) stirred for 2 h at room temperature. After completion, the resulting solution was concentrated under vacuum. The residue was dissolved with water (2 mL), and the pH of the resulting solution was adjusted to pH=10 with potassium carbonate saturated solution. Then the mixture was extracted with n-butanol (60 mL×3) and concentrated under vacuum. The residue was applied onto a silica gel column eluting with dichloromethane/methanol (9:1) to afford 150.0 mg (50%) of 6-[6-chloro-4-(piperazin-1-yl)quinazolin-7-yl]-5-(trifluoromethoxy)pyridin-2-amine as a light yellow solid. LC-MS (ESI, m/z): 425.1 [M+H]$^+$.

351

Step 6: 1-(4-[7-[6-amino-3-(trifluoromethoxy)pyridin-2-yl]-6-chloroquinazolin-4-yl]piperazin-1-yl)prop-2-en-1-one A solution of 6-[6-chloro-4-(piperazin-1-yl)quinazolin-7-yl]-5-(trifluoromethoxy)pyridin-2-amine (100.0 mg, 0.24 mmol), HATU (150.0 mg, 0.39 mmol), prop-2-enoic acid (20.0 mg, 0.28 mmol) and N,N-diisopropylethylamine (100.0 mg, 0.80 mmol) in dichloromethane (10 mL) was stirred for 30 min at 25° C. After completion, the solution was quenched with water (20 mL) and extracted with dichloromethane (3×30 mL). The organic layer was collected and dried over anhydrous sodium sulfate and concentrated under vacuum. The residue was applied onto a silica gel column eluting with dichloromethane/methanol (20/1) to afford 68.0 mg (60%) of 1-(4-[7-[6-amino-3-(trifluoromethoxy)pyridin-2-yl]-6-chloroquinazolin-4-yl]piperazin-1-yl)prop-2-en-1-one as a white solid. LC-MS (ESI, m/z): 479.1 [M+H]$^+$.

Example 40

$^1$H NMR (300 MHz, Methanol-d$_4$, ppm) δ 8.68 (s, 1H), 8.22 (s, 1H), 7.85 (s, 1H), 7.64-7.55 (m, 1H), 6.84 (dd, J=16.8, 10.6 Hz, 1H), 6.74 (d, J=9.1 Hz, 1H), 6.29 (dd, J=16.8, 2.0 Hz, 1H), 5.82 (dd, J=10.7, 2.0 Hz, 1H), 4.04-4.00 (m, 4H), 3.95-3.92 (m, 4H).

352

Example 41

1-(4-[7-[6-amino-3-(difluoromethyl)pyridin-2-yl]-6-chloroquinazolin-4-yl]piperazin-1-yl)prop-2-en-1-one

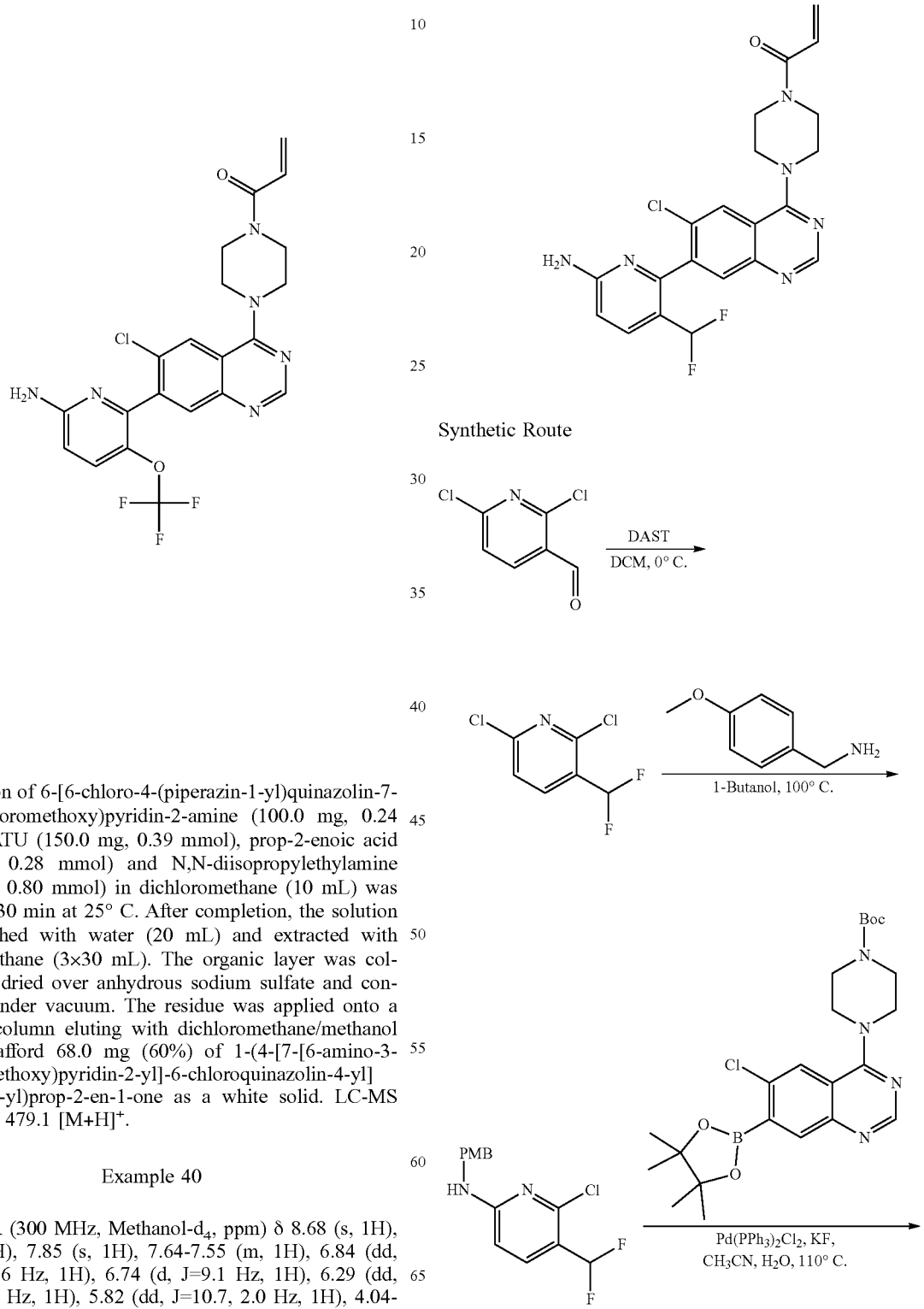

Synthetic Route

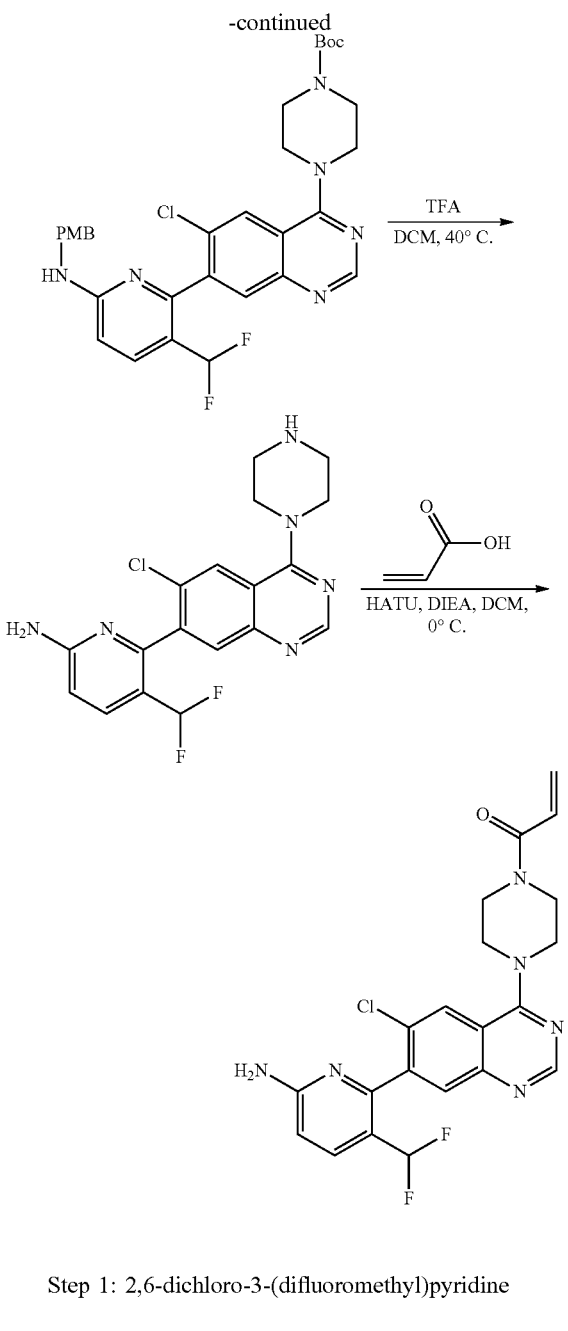

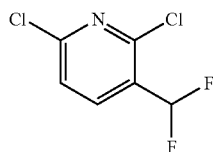 [SMILES: FC(F)c1ccc(Cl)nc1Cl]

A solution of 2,6-dichloropyridine-3-carbaldehyde (20.00 g, 113.64 mmol) in dichloromethane (100 mL) was added diethylaminosulfur trifluoride (55.27 g, 342.86 mmol) and stirred for 60 min at 0° C. After completion, the reaction was quenched by the addition of 400 mL of sodium carbonate saturated aqueous solution, extracted with dichloromethane (200 mL×3), dried over anhydrous sodium sulfate and concentrated under vacuum. The residue was applied onto a silica gel column eluting with ethyl acetate/petroleum ether (1:10) to afford 15.7 g (70%) of 2,6-dichloro-3-(difluoromethyl)pyridine as colorless oil. LC-MS (ESI, m/z): 198.0 [M+H]$^+$.

Step 2: 6-chloro-5-(difluoromethyl)-N-[(4-methoxyphenyl)methyl]pyridin-2-amine

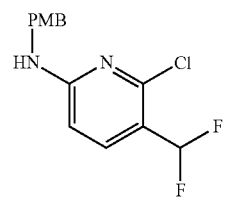

A solution of (4-methoxyphenyl)methanamine (459.0 mg, 3.35 mmol) and 2,6-dichloro-3-(difluoromethyl)pyridine (600.0 mg, 3.03 mmol) in n-butanol (5 mL) was stirred for 60 min at 100° C. After completion, the resulting solution was concentrated under vacuum. The residue was applied onto a silica gel column eluting with ethyl acetate/petroleum ether (1/5) to afford 100.0 mg (10%) of 6-chloro-5-(difluoromethyl)-N-[(4-methoxyphenyl)methyl]pyridin-2-amine as a yellow solid. LC-MS (ESI, m/z): 299.1 [M+H]$^+$.

Step 3: tert-butyl 4-[6-chloro-7-[3-(difluoromethyl)-6-[[(4-methoxyphenyl)methyl]amino]pyridin-2-yl]quinazolin-4-yl]piperazine-1-carboxylate

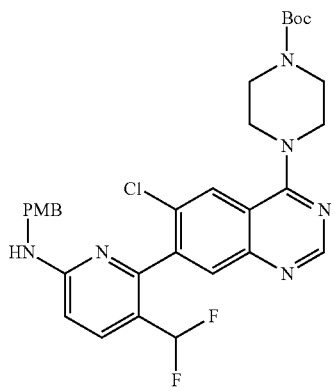

Under nitrogen, a solution of 6-chloro-5-(difluoromethyl)-N-[(4-methoxyphenyl)methyl]pyridin-2-amine (300.0 mg, 1.00 mmol), potassium fluoride (116.2 mg, 2.00 mmol), tert-butyl 4-[6-chloro-7-(tetramethyl-1,3,2-dioxaborolan-2-yl)quinazolin-4-yl]piperazine-1-carboxylate (568.0 mg, 1.20 mmol) and bis(triphenylphosphine)palladium(II) chloride (70.7 mg, 0.10 mmol) in acetonitrile (5 mL) and water (1 mL) was stirred for 60 min at 110° C. The resulting mixture was concentrated under vacuum, diluted with ethyl acetate (200 mL), washed with brine (50 mL×3), dried over anhydrous sodium sulfate and concentrated under vacuum. The residue was applied onto a silica gel column eluting with ethyl acetate/petroleum ether (1/5) to afford 280.0 mg (46%) of tert-butyl 4-[6-chloro-7-[3-(difluoromethyl)-6-[[(4-methoxyphenyl)methyl]amino]pyridin-2-yl]

quinazolin-4-yl]piperazine-1-carboxylate as a white solid. LC-MS (ESI, m/z): 611.2 [M+H]⁺.

Step 4: 6-[6-chloro-4-(piperazin-1-yl)quinazolin-7-yl]-5-(difluoromethyl)pyridin-2-amine

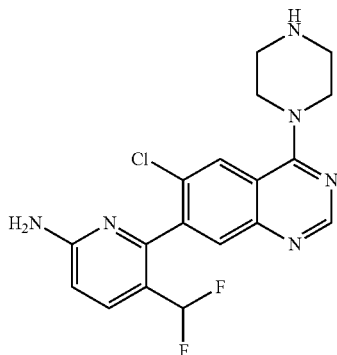 [SMILES: Nc1ccc(C(F)F)c(-c2cc3ncnc(N4CCNCC4)c3cc2Cl)n1]

A solution of tert-butyl 4-[6-chloro-7-[3-(difluoromethyl)-6-[[(4-methoxyphenyl)methyl]amino]pyridin-2-yl]quinazolin-4-yl]piperazine-1-carboxylate (280.0 mg, 0.46 mmol) in dichloromethane (2 mL) and trifluoroacetic acid (2 mL) was stirred for 60 min at 40° C. After completion, the resulting solution was concentrated under vacuum. The residue was dissolved with water (2 mL), and the pH of the resulting solution was adjusted to pH=10 with potassium carbonate saturated solution. Then the mixture was extracted with ethyl acetate (50 mL×3), dried over anhydrous sodium sulfate and concentrated under vacuum. The residue was applied onto a silica gel column eluting with ethyl acetate/petroleum ether (1/5) to afford 150.0 mg (84%) of 6-[6-chloro-4-(piperazin-1-yl)quinazolin-7-yl]-5-(difluoromethyl)pyridin-2-amine as a white solid. LC-MS (ESI, m/z): 391.1 [M+H]⁺.

Step 5: 1-(4-[7-[6-amino-3-(difluoromethyl)pyridin-2-yl]-6-chloroquinazolin-4-yl]piperazin-1-yl)prop-2-en-1-one

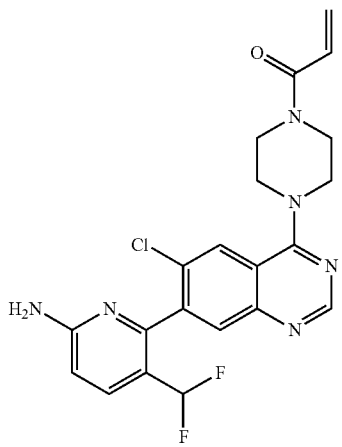 [SMILES: C=CC(=O)N1CCN(c2ncnc3cc(-c4nc(N)ccc4C(F)F)c(Cl)cc23)CC1]

A solution of 6-[6-chloro-4-(piperazin-1-yl)quinazolin-7-yl]-5-(difluoromethyl)pyridin-2-amine (100.0 mg, 0.26 mmol), N,N-diisopropylethylamine (33.0 mg, 0.26 mmol), HATU (97.44 mg, 0.26 mmol) and prop-2-enoic acid (18.48 mg, 0.26 mmol) in dichloromethane (5 mL) was stirred for 60 min at 0° C. After completion, the solution was quenched with water (30 mL) and extracted with dichloromethane (3×50 mL). The organic layer was collected and dried over anhydrous sodium sulfate and concentrated under vacuum. The residue was applied onto a silica gel column eluting with methanol/dichloromethane (1/10) to afford a crude product. Then the crude product was purified by reverse-phase column eluting with acetonitrile/water (3/7) to afford 3.2 mg (3%) of 1-(4-[7-[6-amino-3-(difluoromethyl)pyridin-2-yl]-6-chloroquinazolin-4-yl]piperazin-1-yl)prop-2-en-1-one as a white solid. LC-MS (ESI, m/z): 445.1 [M+H]⁺.

Example 41

¹H NMR (300 MHz, Methanol-d₄, ppm) δ 8.68 (s, 1H), 8.22 (s, 1H), 7.81-7.78 (m, 2H), 6.87-6.73 (m, 2H), 6.53-6.16 (m, 2H), 5.81 (dd, J=10.6, 1.9 Hz, 1H), 4.03-3.99 (m, 4H), 3.93-3.91 (m, 4H).

Example 42

1-[4-[7-(6-amino-3-methanesulfonylpyridin-2-yl)-6-chloroquinazolin-4-yl]piperazin-1-yl]prop-2-en-1-one

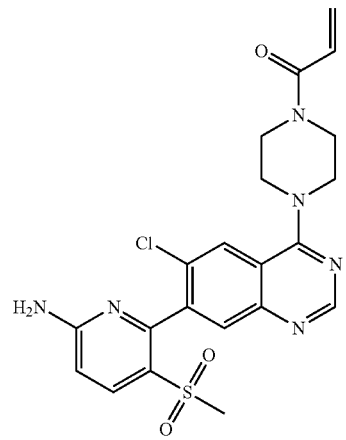 [SMILES: C=CC(=O)N1CCN(c2ncnc3cc(-c4nc(N)ccc4S(C)(=O)=O)c(Cl)cc23)CC1]

Synthetic Route

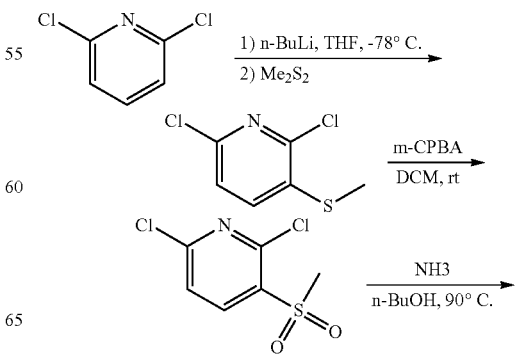

-continued

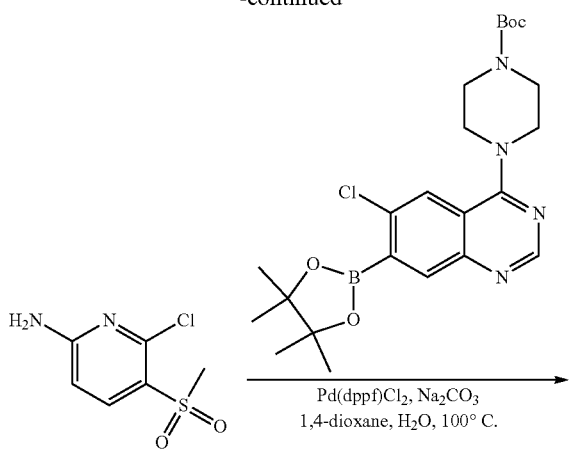

Pd(dppf)Cl$_2$, Na$_2$CO$_3$
1,4-dioxane, H$_2$O, 100° C.

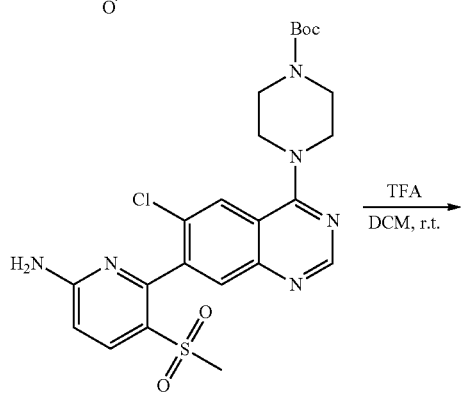

TFA
DCM, r.t.

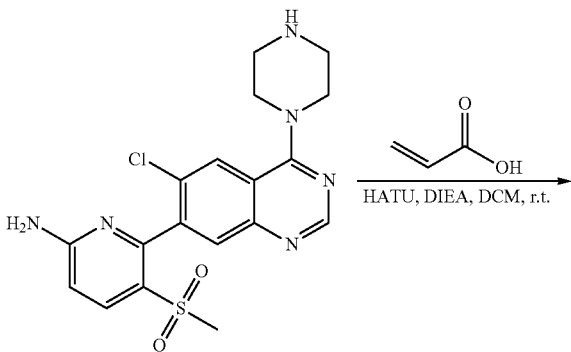

HATU, DIEA, DCM, r.t.

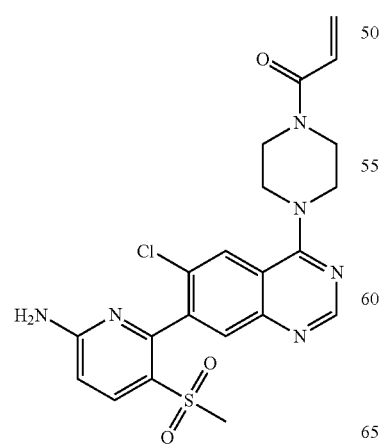

Step 1: 2,6-dichloro-3-(methylsulfanyl)pyridine

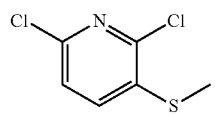

Under nitrogen, a solution of 2,6-dichloropyridine (10.00 g, 67.57 mmol) in tetrahydrofuran (200 mL) was slowly added n-butyllithium (35.0 mL, 81.96 mmol, 2.5 M solution in Hexane) and stirred for 1 h at −78° C. Then (methyldisulfanyl)methane (6.50 g, 69.00 mmol) was slowly added at −78° C. and stirred for 5 h at room temperature. After completion, the resulting solution was quenched by ammonium chloride saturated solution, concentrated under vacuum, diluted with dichloromethane (200 mL), washed with water (80 mL×3), dried over anhydrous sodium sulfate and concentrated under vacuum. The residue was applied onto a silica gel column eluting with ethyl acetate/petroleum ether (1/5) to afford 5.0 g (38%) of 2,6-dichloro-3-(methylsulfanyl)pyridine as yellow oil. LC-MS (ESI, m/z): 194.0 [M+H]$^+$.

Step 2: 2,6-dichloro-3-methanesulfonylpyridine

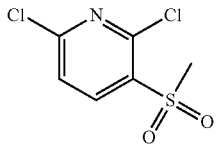

A solution of 2,6-dichloro-3-(methylsulfanyl)pyridine (1.00 g, 5.15 mmol) in dichloromethane (10 mL) was added m-chloro-peroxybenzoic acid (3.50 g, 20.28 mmol) was stirred for 12 hours at room temperature. After completion, the resulting mixture was quenched by sodium sulfite saturated solution (40 mL) and extracted with dichloromethane (80 mL×3). Then the organic layers was collected and dried over anhydrous sodium sulfate and concentrated under vacuum. This resulted in 1.6 g (crude) of 2,6-dichloro-3-methanesulfonylpyridine as a yellow solid. LC-MS (ESI, m/z): 225.9 [M+H]$^+$.

Step 3: 6-chloro-5-methanesulfonylpyridin-2-amine

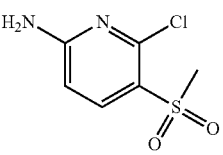

Under ammonia, a solution of 2,6-dichloro-3-methanesulfonylpyridine (1.80 g, 7.96 mmol) in n-butanol (20 mL) was stirred for 1 h at 90° C. The resulting mixture was concentrated under vacuum to afford 1.50 g (crude) of 6-chloro-5-methanesulfonylpyridin-2-amine as a yellow solid. LC-MS (ESI, m/z): 207.0 [M+H]$^+$.

Step 4: tert-butyl 4-[7-(6-amino-3-methanesulfonylpyridin-2-yl)-6-chloroquinazolin-4-yl]piperazine-1-carboxylate

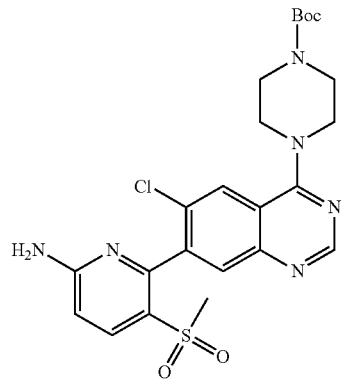 [SMILES: CC(C)(C)OC(=O)N1CCN(c2ncnc3cc(-c4nc(N)ccc4S(C)(=O)=O)c(Cl)cc23)CC1]

Under nitrogen, a solution of tert-butyl 4-[6-chloro-7-(tetramethyl-1,3,2-dioxaborolan-2-yl)quinazolin-4-yl]piperazine-1-carboxylate (400.0 mg, 0.84 mmol), 6-chloro-5-methanesulfonylpyridin-2-amine (200.0 mg, 0.97 mmol), 1,1'-bis(diphenylphosphino)ferrocene-palladium(II)dichloride (80.0 mg, 0.10 mmol) and sodium carbonate (200.0 mg, 1.89 mmol) in dioxane (10 mL) and water (2 mL) was stirred for 1 h at 100° C. After completion, the resulting mixture was diluted with dichloromethane (100 mL), washed with brine (30 mL×3). Then the organic layers was dried over anhydrous sodium sulfate and concentrated under vacuum. The residue was applied onto a silica gel column eluting with dichloromethane/methanol (96/4) to afford 250 mg (57%) of tert-butyl 4-[7-(6-amino-3-methanesulfonylpyridin-2-yl)-6-chloroquinazolin-4-yl]piperazine-1-carboxylate as a yellow solid. LC-MS (ESI, m/z): 519.2 [M+H]$^+$.

Step 5: 6-[6-chloro-4-(piperazin-1-yl)quinazolin-7-yl]-5-methanesulfonylpyridin-2-amine

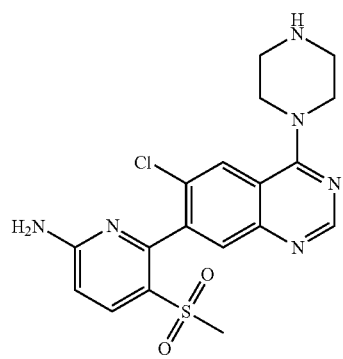 [SMILES: CS(=O)(=O)c1ccc(N)nc1-c1cc2ncnc(N3CCNCC3)c2cc1Cl]

A solution of tert-butyl 4-[7-(6-amino-3-methanesulfonylpyridin-2-yl)-6-chloroquinazolin-4-yl]piperazine-1-carboxylate (240.0 mg, 0.46 mmol) in dichloromethane (10 mL) and trifluoroacetic acid (3 mL) was stirred for 2 h at room temperature. After completion, the resulting mixture was concentrated under vacuum. This resulted in 200 mg (crude) of 6-[6-chloro-4-(piperazin-1-yl)quinazolin-7-yl]-5-methanesulfonylpyridin-2-amine as yellow oil. LC-MS (ESI, m/z): 419.1 [M+H]$^+$.

Step 6: 1-[4-[7-(6-amino-3-methanesulfonylpyridin-2-yl)-6-chloroquinazolin-4-yl]piperazin-1-yl]prop-2-en-1-one

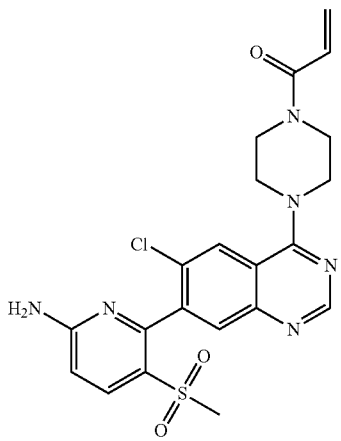 [SMILES: C=CC(=O)N1CCN(c2ncnc3cc(-c4nc(N)ccc4S(C)(=O)=O)c(Cl)cc23)CC1]

A solution of 6-[6-chloro-4-(piperazin-1-yl)quinazolin-7-yl]-5-methanesulfonylpyridin-2-amine (100.0 mg crude), HATU (110.0 mg, 0.29 mmol), prop-2-enoic acid (20.0 mg, 0.28 mmol) and N,N-diisopropylethylamine (60 mg, 0.46 mmol) in dichloromethane (5 mL) was stirred for 30 min at room temperature. After completion, the solution was quenched with water (20 mL) and extracted with dichloromethane (3×30 mL). The organic layer was collected and dried over anhydrous sodium sulfate and concentrated under vacuum. The residue was applied onto a silica gel column eluting with dichloromethane/methanol (10/1) to afford 40 mg crude product. The crude product was purified by Prep-HPLC with the following conditions: Column, XBridge Shield RP18 OBD Column 5 um, 19*150 mm; mobile phase, Water (0.05% NH3 water) and ACN (28.0% ACN up to 70.0% in 7 min); Detector, UV 220 nm. This resulted in 2.6 mg (2%) of 1-[4-[7-(6-amino-3-methanesulfonylpyridin-2-yl)-6-chloroquinazolin-4-yl]piperazin-1-yl]prop-2-en-1-one as a white solid. LC-MS (ESI, m/z): 473.1 [M+H]$^+$.

Example 42

$^1$H NMR (300 MHz, Methanol-d$_4$, ppm) δ 8.68 (s, 1H), 8.17 (s, 1H), 8.07 (d, J=9.0 Hz, 1H), 7.84 (s, 1H), 6.84 (dd, J=16.8, 10.6 Hz, 1H), 6.76 (d, J=9.0 Hz, 1H), 6.29 (dd, J=16.8, 2.0 Hz, 1H), 5.82 (dd, J=10.6, 2.0 Hz, 1H), 4.05-3.92 (m, 8H), 2.99 (s, 3H).

Example 43
1-(4-[7-[6-amino-3-(2,2,2-trifluoroethyl)pyridin-2-yl]-6-chloroquinazolin-4-yl]piperazin-1-yl)prop-2-en-1-one
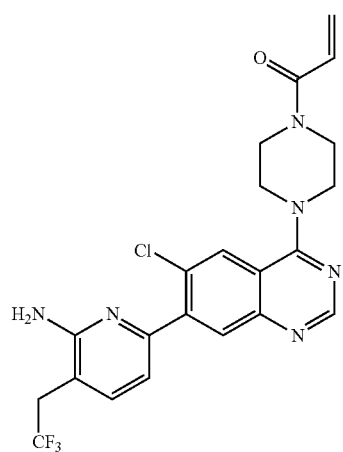 [SMILES: C=CC(=O)N1CCN(c2ncnc3cc(-c4ccc(CC(F)(F)F)c(N)n4)c(Cl)cc23)CC1]
Synthetic Route
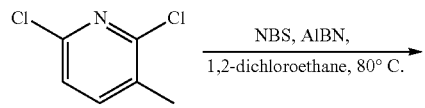
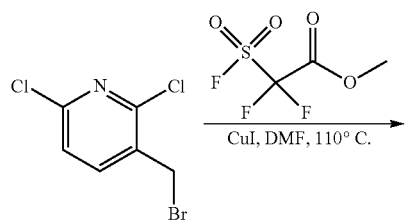
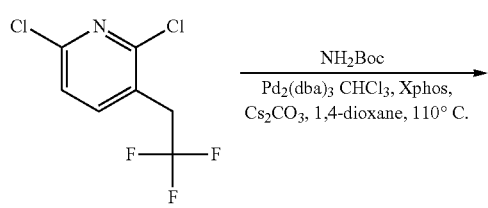
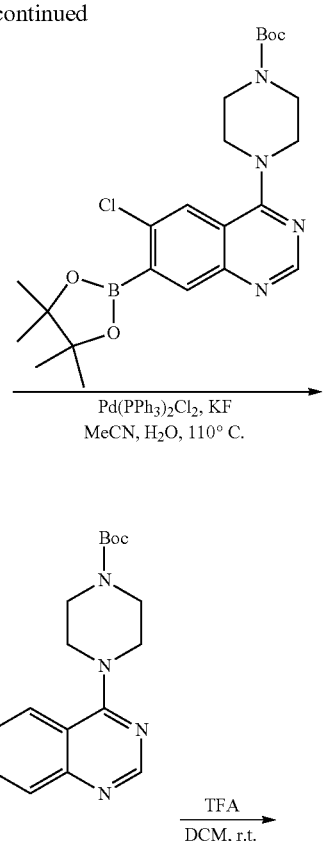
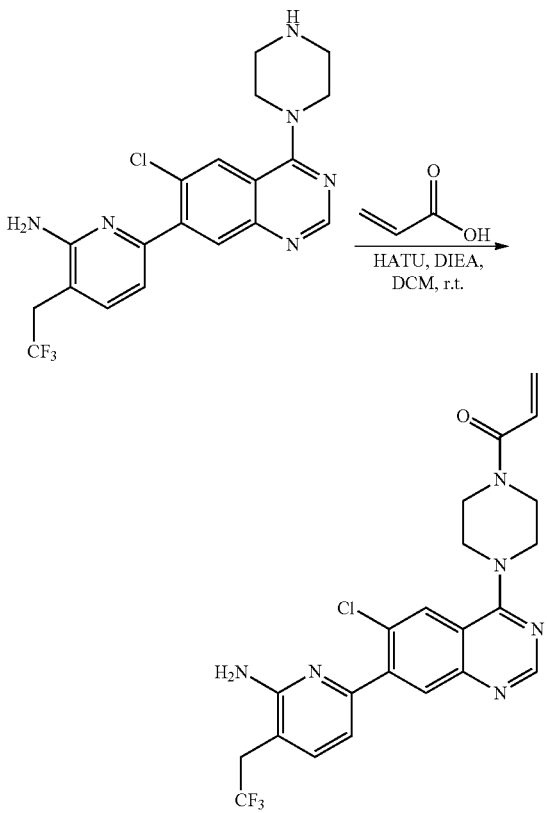

Step 1: 3-(bromomethyl)-2,6-dichloropyridine

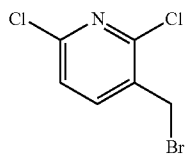

A solution of 2,6-dichloro-3-methylpyridine (3.00 g, 18.52 mmol), 2,2'-Azobis(isobutyronitrile) (300.0 mg, 1.83 mmol) and N-bromosuccinimide (3.50 g, 19.44 mmol) in 1,2-dichloroethane (20 mL) was stirred for 12 h at 80° C. After completion, the resulting mixture was diluted with dichloromethane (200 mL), washed with brine (80 mL×3), dried over anhydrous sodium sulfate and concentrated under vacuum. The residue was applied onto a silica gel column eluting with petroleum ether/ethyl acetate (10/1) to afford 2.5 g (56%) of 3-(bromomethyl)-2,6-dichloropyridine as a white solid. LC-MS (ESI, m/z): 239.9 [M+H]⁺.

Step 2: 2,6-dichloro-3-(2,2,2-trifluoroethyl)pyridine

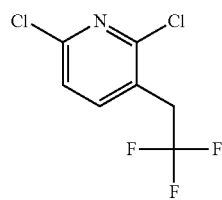 [SMILES: FC(F)(F)Cc1ccc(Cl)nc1Cl]

Under nitrogen, a solution of 3-(bromomethyl)-2,6-dichloropyridine (1.00 g, 4.15 mmol), methyl 2,2-difluoro-2-(fluorosulfonyl)acetate (1.00 g, 5.21 mmol) and cuprous iodide (79.05 mg, 0.42 mmol) in N,N-dimethylformamide (15 mL) was stirred for 2 h at 110° C. After completion, the resulting mixture was diluted with dichloromethane (100 mL), washed with brine (20 mL×3). The organic layer was collected and dried over anhydrous sodium sulfate and concentrated under vacuum. The residue was applied onto a silica gel column eluting with petroleum ether:ethyl acetate (50:1) to afford 560.0 mg (59%) of 2,6-dichloro-3-(2,2,2-trifluoroethyl)pyridine as yellow oil. LC-MS (ESI, m/z): 230.0 [M+H]⁺.

Step 3: tert-butyl N-[6-chloro-5-(2,2,2-trifluoroethyl)pyridin-2-yl]carbamate

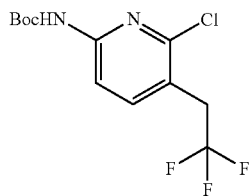 [SMILES: CC(C)(C)OC(=O)Nc1ccc(CC(F)(F)F)c(Cl)n1]

Under nitrogen, a solution of 2,6-dichloro-3-(2,2,2-trifluoroethyl)pyridine (560.0 mg, 2.44 mmol), tert-butyl carbamate (570.4 mg, 4.87 mmol), tris(dibenzylideneacetone)dipalladium-chloroform adduct (126.0 mg, 0.12 mmol), XantPhos (140.9 mg, 0.24 mmol) and cesium carbonate (1.59 g, 4.87 mmol) in 1,4-dioxane (20 mL) was stirred for 1 h at 110° C. After completion, the resulting mixture was diluted with ethyl acetate (200 mL), washed with brine (80 mL×3). The organic layer was collected and dried over anhydrous sodium sulfate and concentrated under vacuum. The residue was applied onto a silica gel column eluting with petroleum ether/ethyl acetate (50/1) to afford 230.0 mg (30%) of tert-butyl N-[6-chloro-5-(2,2,2-trifluoroethyl)pyridin-2-yl]carbamate as a white solid. LC-MS (ESI, m/z): 311.1 [M+H]⁺.

Step 4: tert-butyl 4-[7-(6-[[(tert-butoxy)carbonyl]amino]-3-(2,2,2-trifluoroethyl)pyridin-2-yl)-6-chloroquinazolin-4-yl]piperazine-1-carboxylate

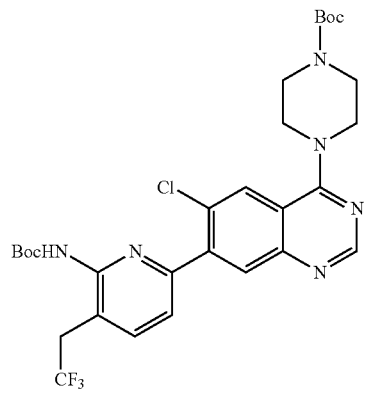 [SMILES: CC(C)(C)OC(=O)Nc1nc(-c2cc3ncnc(N4CCN(C(=O)OC(C)(C)C)CC4)c3cc2Cl)ccc1CC(F)(F)F]

Under nitrogen, a solution of tert-butyl N-[6-chloro-5-(2,2,2-trifluoroethyl)pyridin-2-yl]carbamate (200.0 mg, 0.64 mmol), tert-butyl 4-[6-chloro-7-(tetramethyl-1,3,2-dioxaborolan-2-yl)quinazolin-4-yl]piperazine-1-carboxylate (305.6 mg, 0.64 mmol), bis(triphenylphosphine)palladium(II) chloride (49.7 mg, 0.07 mmol) and potassium fluoride (112.2 mg, 1.93 mmol) in acetonitrile (10 mL) and water (1 mL) was stirred for 30 min at 110° C. After completion, the resulting mixture was concentrated under vacuum. The residue was applied onto a silica gel column eluting with dichloromethane/methanol (20/1) to afford 200.0 mg (50%) of tert-butyl 4-[7-(6-[[(tert-butoxy)carbonyl]amino]-3-(2,2,2-trifluoroethyl)pyridin-2-yl)-6-chloroquinazolin-4-yl]piperazine-1-carboxylate as a yellow oil. LC-MS (ESI, m/z): 623.2 [M+H]⁺.

Step 5: 6-[6-chloro-4-(piperazin-1-yl)quinazolin-7-yl]-5-(2,2,2-trifluoroethyl)pyridin-2-amine

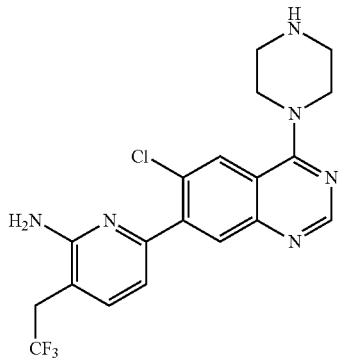 [SMILES: Nc1nc(-c2cc3ncnc(N4CCNCC4)c3cc2Cl)ccc1CC(F)(F)F]

A solution of tert-butyl 4-[7-(6-[[(tert-butoxy)carbonyl]amino]-3-(2,2,2-trifluoroethyl)pyridin-2-yl)-6-chloroquinazolin-4-yl]piperazine-1-carboxylate (100.0 mg, 0.16 mmol) in trifluoroacetic acid (2 mL) and dichloromethane (10 mL) was stirred for 2 h at 25° C. After completion, the resulting mixture was concentrated under vacuum to afford 100 mg (crude) of 6-[6-chloro-4-(piperazin-1-yl)quinazolin-7-yl]-5-(2,2,2-trifluoroethyl)pyridin-2-amine as yellow oil. LC-MS (ESI, m/z): 423.1 [M+H]$^+$.

Step 6: 1-(4-[7-[6-amino-3-(2,2,2-trifluoroethyl)pyridin-2-yl]-6-chloroquinazolin-4-yl]piperazin-1-yl)prop-2-en-1-one

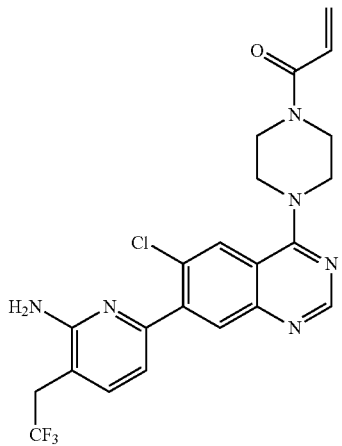 [SMILES: C=CC(=O)N1CCN(c2ncnc3cc(-c4ccc(CC(F)(F)F)c(N)n4)c(Cl)cc23)CC1]

A solution of 6-[6-chloro-4-(piperazin-1-yl)quinazolin-7-yl]-5-(2,2,2-trifluoroethyl)pyridin-2-amine (60.0 mg crude), prop-2-enoic acid (10.2 mg, 0.14 mmol), HATU (64.7 mg, 0.17 mmol) and N,N-diisopropylethylamine (36.7 mg, 0.28 mmol) in dichloromethane (4 mL) was stirred for 30 min at −78° C. After completion, the solution was quenched with water (20 mL) and extracted with dichloromethane (3×20 mL). The organic layer was collected and dried over anhydrous sodium sulfate and concentrated under vacuum. The residue was applied onto a silica gel column eluting with dichloromethane/methanol (10/1) to afford 22.0 mg (33%) of 1-(4-[7-[6-amino-3-(2,2,2-trifluoroethyl)pyridin-2-yl]-6-chloroquinazolin-4-yl]piperazin-1-yl)prop-2-en-1-one as a white solid. LC-MS (ESI, m/z): 477.1 [M+H]$^+$.

Example 43

$^1$H NMR (300 MHz, CDCl$_3$, ppm) δ 8.80 (s, 1H), 8.01 (s, 1H), 7.97 (s, 1H), 7.62 (d, J=9.0 Hz, 1H), 6.70 (d, J=8.6 Hz, 1H), 6.64 (dd, J=16.8, 10.5 Hz, 1H), 6.40 (dd, J=16.8, 1.9 Hz, 1H), 5.80 (dd, J=10.5, 1.9 Hz, 1H), 5.12 (brs, 2H), 3.94-3.85 (m, 8H), 3.34-2.99 (m, 2H).

Example 44

1-(4-[7-[6-amino-4-methyl-3-(trifluoromethyl)pyridin-2-yl]-6-chloroquinazolin-4-yl]piperazin-1-yl)prop-2-en-1-one

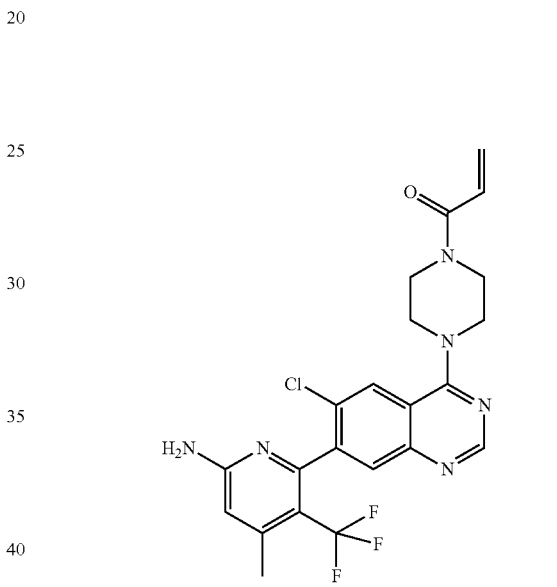

Synthetic Route

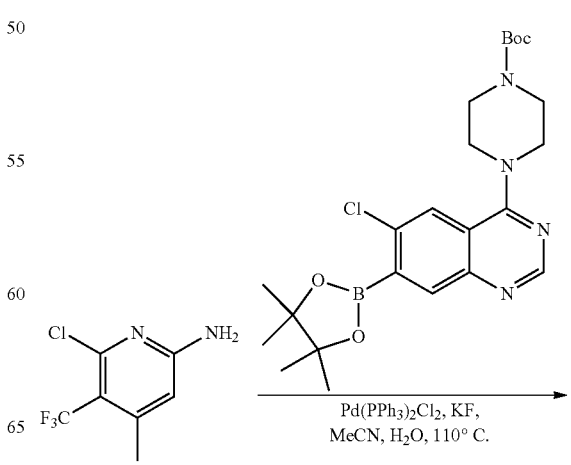

367
-continued

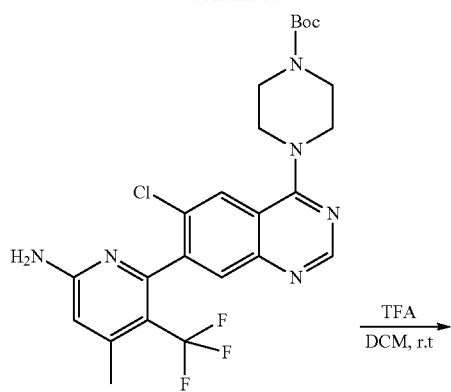

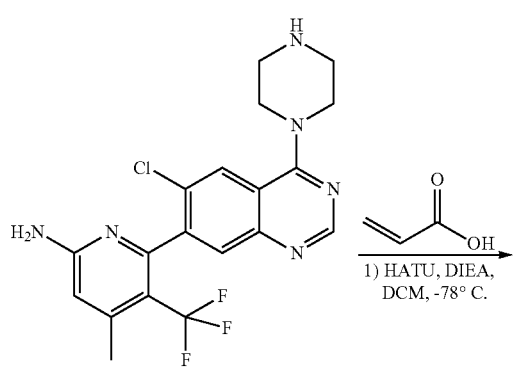

368

Step 1: tert-butyl 4-[7-[6-amino-4-methyl-3-(trifluoromethyl)pyridin-2-yl]-6-chloroquinazolin-4-yl]piperazine-1-carboxylate

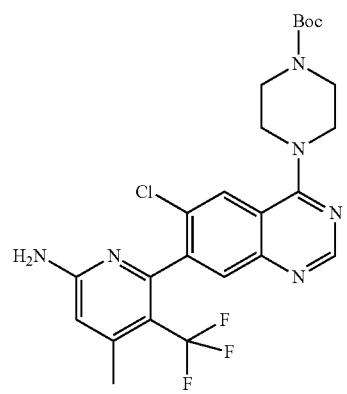 [SMILES: Cc1cc(N)nc(-c2cc3ncnc(N4CCN(C(=O)OC(C)(C)C)CC4)c3cc2Cl)c1C(F)(F)F]

Under nitrogen, a solution of 6-chloro-4-methyl-5-(trifluoromethyl)pyridin-2-amine (2.00 g, 9.50 mmol), tert-butyl 4-[6-chloro-7-(tetramethyl-1,3,2-dioxaborolan-2-yl)quinazolin-4-yl]piperazine-1-carboxylate (5.40 g, 11.42 mmol), bis(triphenylphosphine)palladium(II) chloride (666.6 mg, 0.95 mmol) and potassium fluoride (1.60 g, 28.50 mmol) in acetonitrile (50 mL) and water (5 mL) was stirred for 30 min at 100° C. After completion, the solids were filtered out. The resulting mixture was diluted with dichloromethane (200 mL), washed with brine (80 mL×3), dried over anhydrous sodium sulfate and concentrated under vacuum. The residue was applied onto a silica gel column eluting with dichloromethane/methanol (10/1) to afford 3.1 g (62%) of tert-butyl 4-[7-[6-amino-4-methyl-3-(trifluoromethyl)pyridin-2-yl]-6-chloroquinazolin-4-yl]piperazine-1-carboxylate as a yellow solid. LC-MS (ESI, m/z): 523.2 [M+H]$^+$.

Step 2: 6-[6-chloro-4-(piperazin-1-yl)quinazolin-7-yl]-4-methyl-5-(trifluoromethyl)pyridin-2-amine

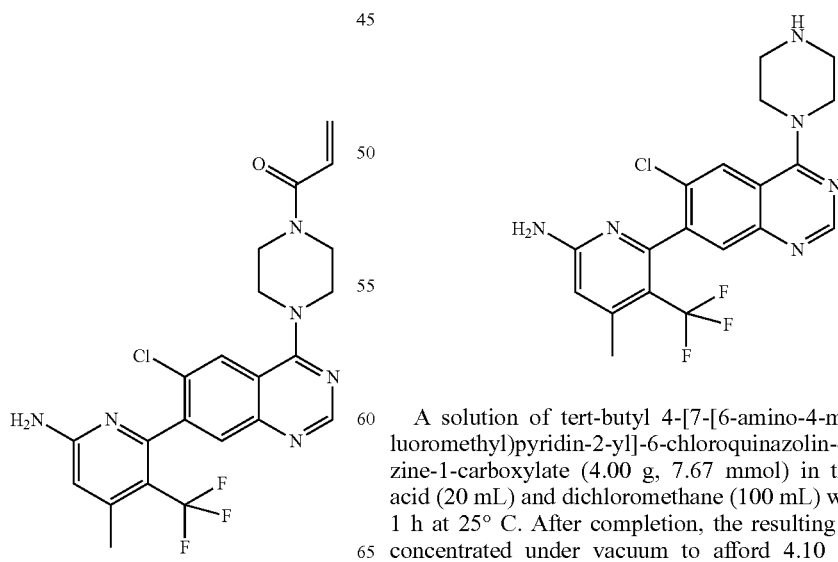

A solution of tert-butyl 4-[7-[6-amino-4-methyl-3-(trifluoromethyl)pyridin-2-yl]-6-chloroquinazolin-4-yl]piperazine-1-carboxylate (4.00 g, 7.67 mmol) in trifluoroacetic acid (20 mL) and dichloromethane (100 mL) was stirred for 1 h at 25° C. After completion, the resulting mixture was concentrated under vacuum to afford 4.10 g (crude) of 6-[6-chloro-4-(piperazin-1-yl)quinazolin-7-yl]-4-methyl-5-(trifluoromethyl)pyridin-2-amine as a yellow oil. $^1$H NMR (400 MHz, Methanol-d$_4$, ppm) δ 8.70 (s, 1H), 8.09 (s, 1H), 7.68 (s, 1H), 6.61 (s, 1H), 3.95-3.81 (m, 4H), 3.10-3.00 (m, 4H), 2.46 (s, 3H) LC-MS (ESI, m/z): 423.1 [M+H]$^+$.

Step 3: 1-(4-[7-[6-amino-4-methyl-3-(trifluoromethyl)pyridin-2-yl]-6-chloroquinazolin-4-yl]piperazin-1-yl)prop-2-en-1-one

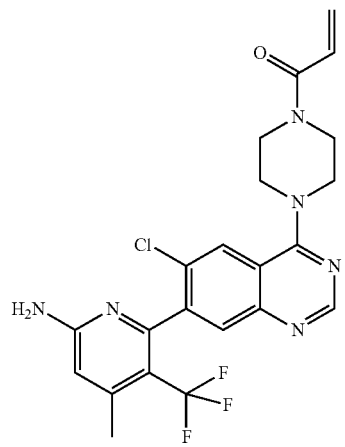 [SMILES: C=CC(=O)N1CCN(c2ncnc3cc(-c4nc(N)cc(C)c4C(F)(F)F)c(Cl)cc23)CC1]

A solution of 6-[6-chloro-4-(piperazin-1-yl)quinazolin-7-yl]-4-methyl-5-(trifluoromethyl)pyridin-2-amine (3.00 g, 7.10 mmol), prop-2-enoic acid (600.3 mg, 8.33 mmol), HATU (4.20 g, 11.05 mmol) and N,N-diisopropylethylamine (4.60 g, 35.47 mmol) in dichloromethane (50 mL) was stirred for 30 min at −78° C. After completion, the solution was quenched with water (50 mL) and extracted with dichloromethane (3×80 mL). The organic layer was collected and dried over anhydrous sodium sulfate and concentrated under vacuum. The residue was applied onto a silica gel column eluting with dichloromethane/methanol (20/1) to afford a crude product. Then the crude product was purified by reverse phase chromatography (acetonitrile 0-40/0.1% ammonium bicarbonate in water) to afford 2.1 g (62%) of 1-(4-[7-[6-amino-4-methyl-3-(trifluoromethyl)pyridin-2-yl]-6-chloroquinazolin-4-yl]piperazin-1-yl)prop-2-en-1-one as a white solid. LC-MS (ESI, m/z): 477.1 [M+H]$^+$.

Example 44

$^1$H NMR (300 MHz, Methanol-d$_4$, ppm) δ 8.67 (s, 1H), 8.18 (s, 1H), 7.71 (s, 1H), 6.84 (dd, J=16.8, 10.6 Hz, 1H), 6.61 (m, 1H), 6.29 (dd, J=16.8, 2.0 Hz, 1H), 5.82 (dd, J=10.6, 2.0 Hz, 1H), 4.03-3.91 (m, 8H), 2.48-2.46 (m, 3H).

Example 45

1-(4-[7-[6-amino-3-(trifluoromethyl)pyridin-2-yl]-6-chloro-2-[[2-(dimethylamino)ethyl]amino]quinazolin-4-yl]piperazin-1-yl)prop-2-en-1-one.trifluoroacetic acid salt

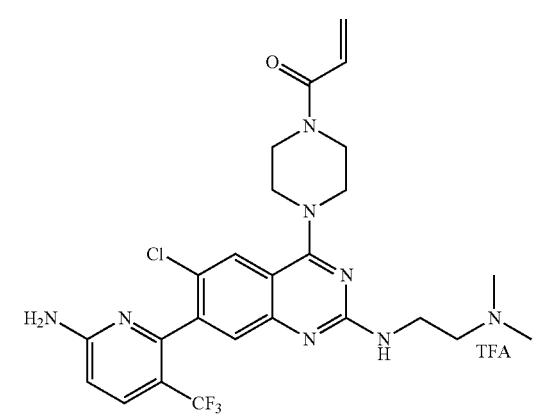 [SMILES: C=CC(=O)N1CCN(c2nc(NCCN(C)C)nc3cc(-c4nc(N)ccc4C(F)(F)F)c(Cl)cc23)CC1]

Synthetic Route

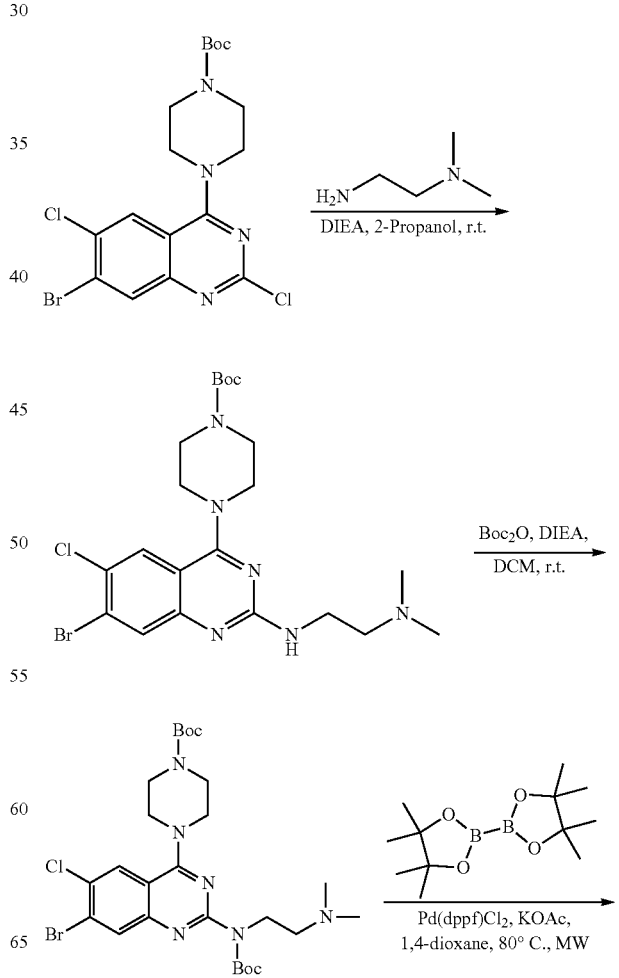

371
-continued

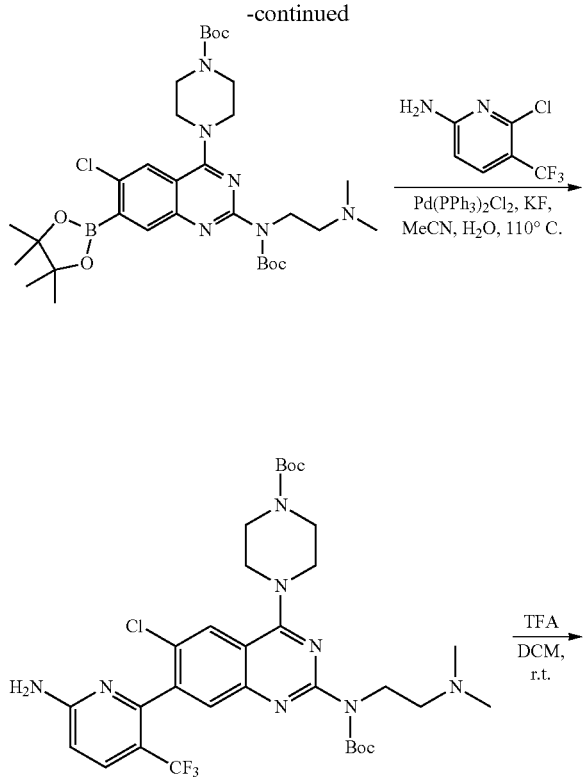

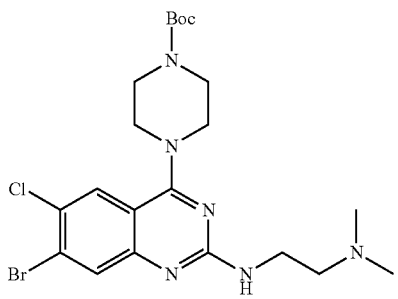 [SMILES: CN(C)CCNc1nc(N2CCN(C(=O)OC(C)(C)C)CC2)c2cc(Cl)c(Br)cc2n1]

Pd(PPh₃)₂Cl₂, KF,
MeCN, H₂O, 110° C.

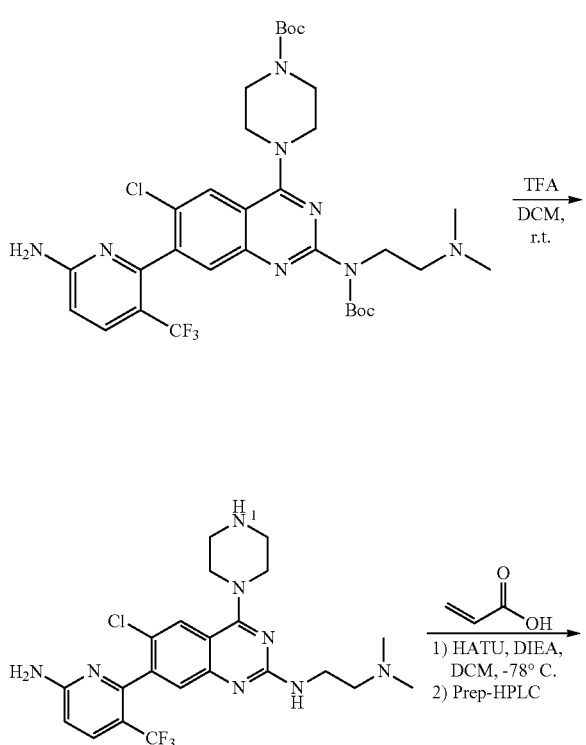

1) HATU, DIEA,
DCM, -78° C.
2) Prep-HPLC

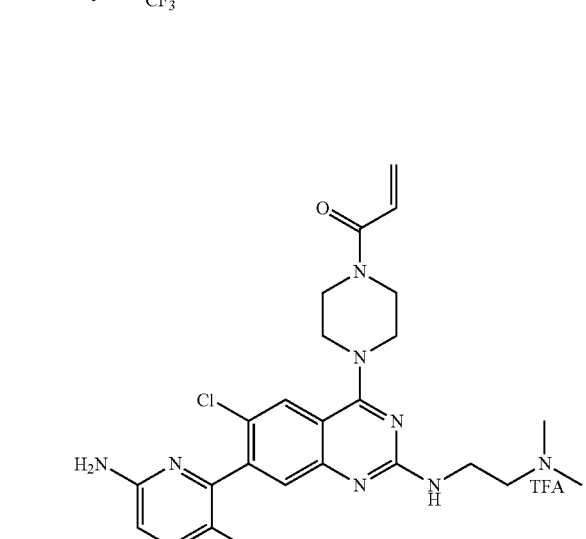

372

Step 1: tert-butyl 4-(7-bromo-6-chloro-2-[[2-(dimethylamino)ethyl]amino]quinazolin-4-yl)piperazine-1-carboxylate

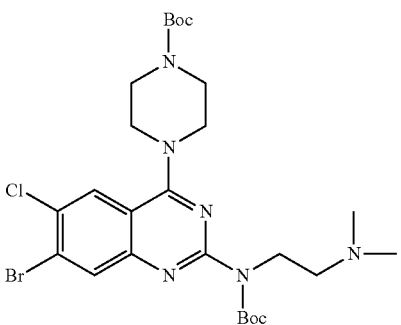 [SMILES: CN(C)CCN(C(=O)OC(C)(C)C)c1nc(N2CCN(C(=O)OC(C)(C)C)CC2)c2cc(Cl)c(Br)cc2n1]

A solution of tert-butyl 4-(7-bromo-2,6-dichloroquinazolin-4-yl)piperazine-1-carboxylate (4.00 g, 8.65 mmol), N,N-diisopropylethylamine (2.20 g, 17.38 mmol) and (2-aminoethyl)dimethylamine (3.80 g, 43.40 mmol) in 2-propanol (10 mL) was stirred for 3 days at 25° C. After completion, the resulting mixture was concentrated under vacuum to afford 2.70 g (crude) of tert-butyl 4-(7-bromo-6-chloro-2-[[2-(dimethylamino)ethyl]amino]quinazolin-4-yl)piperazine-1-carboxylate as a solid. LC-MS (ESI, m/z): 513.1 [M+H]⁺.

Step 2: tert-butyl 4-(7-bromo-2-[[(tert-butoxy)carbonyl][2-(dimethylamino)ethyl]amino]-6-chloroquinazolin-4-yl)piperazine-1-carboxylate A solution of tert-butyl 4-(7-bromo-6-chloro-2-[[2-(dimethylamino)ethyl]amino]quinazolin-4-yl)piperazine-1-carboxylate (2.70 g crude), di-tert-butyl dicarbonate (1.70 g, 7.88 mmol) and N,N-diisopropylethylamine (1.40 g, 10.52 mmol) in dichloromethane (10 mL) was stirred for 1 h at 25° C. After completion, the resulting mixture was diluted with dichloromethane (200 mL), washed with brine (80 mL×3), dried over anhydrous sodium sulfate and concentrated under vacuum. The residue was applied onto a silica gel column eluting with dichloromethane/methanol (10/1) to afford 1.50 g (46%) of tert-butyl 4-(7-bromo-2-[[(tert-butoxy)carbonyl][2-(dimethylamino)ethyl]amino]-6-chloroquinazolin-4-yl)piperazine-1-carboxylate as a yellow solid. LC-MS (ESI, m/z): 613.2 [M+H]⁺.

Step 3: tert-butyl 4-(2-[[(tert-butoxy)carbonyl][2-(dimethylamino)ethyl]amino]-6-chloro-7-(tetramethyl-1,3,2-dioxaborolan-2-yl)quinazolin-4-yl)piperazine-1-carboxylate

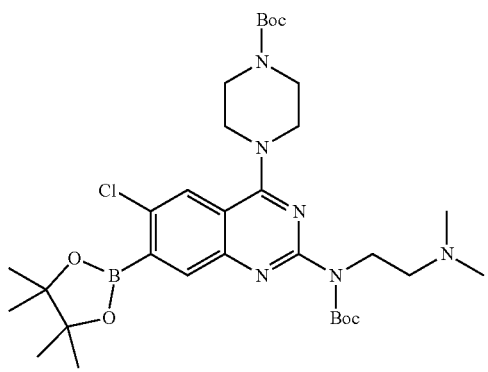

Under nitrogen, a solution of tert-butyl 4-(7-bromo-2-[[(tert-butoxy)carbonyl][2-(dimethylamino)ethyl]amino]-6-chloroquinazolin-4-yl)piperazine-1-carboxylate (500.0 mg, 0.81 mmol), 4,4,5,5-tetramethyl-2-(tetramethyl-1,3,2-dioxaborolan-2-yl)-1,3,2-dioxaborolane (1.00 g, 4.08 mmol) and 1,1'-bis(diphenylphosphino)ferrocene-palladium(II)dichloride (66.7 mg, 0.09 mmol), potassium acetate (240.2 mg, 2.45 mmol) in 1,4-dioxane (10 mL) was irradiated with microwave radiation for 2 h at 80° C. After completion, the resulting mixture was diluted with dichloromethane (200 mL) and washed with brine (80 mL×3). Then the organic layer was collected and dried over anhydrous sodium sulfate and concentrated under vacuum to 480 mg (crude) of tert-butyl 4-(2-[[(tert-butoxy)carbonyl][2-(dimethylamino)ethyl]amino]-6-chloro-7-(tetramethyl-1,3,2-dioxaborolan-2-yl)quinazolin-4-yl)piperazine-1-carboxylate as a dark red solid. LC-MS (ESI, m/z): 661.4 [M+H]$^+$.

Step 4: tert-butyl 4-[7-[6-amino-3-(trifluoromethyl)pyridin-2-yl]-2-[[(tert-butoxy)carbonyl][2-(dimethylamino)ethyl]amino]-6-chloroquinazolin-4-yl]piperazine-1-carboxylate

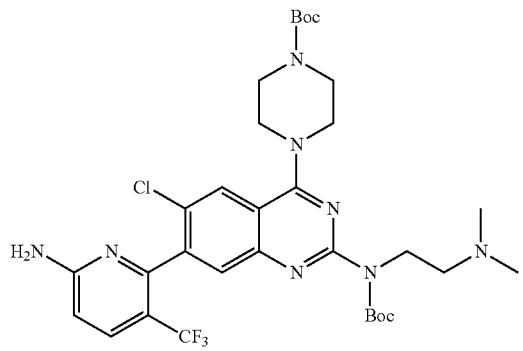 [SMILES: CN(C)CCN(C(=O)OC(C)(C)C)c1nc(N2CCN(C(=O)OC(C)(C)C)CC2)c2cc(Cl)c(-c3nc(N)ccc3C(F)(F)F)cc2n1]

Under nitrogen, a solution of tert-butyl 4-(2-[[(tert-butoxy)carbonyl][2-(dimethylamino)ethyl]amino]-6-chloro-7-(tetramethyl-1,3,2-dioxaborolan-2-yl)quinazolin-4-yl)piperazine-1-carboxylate (500.0 mg, 0.76 mmol), potassium fluoride (88.0 mg, 1.52 mmol), bis(triphenylphosphine)palladium(II) chloride (53.18 mg, 0.08 mmol) and 6-chloro-5-(trifluoromethyl)pyridin-2-amine (178.0 mg, 0.91 mmol) in acetonitrile (10 mL) and water (2 mL) was stirred for 60 min at 110° C. After completion, the resulting mixture was concentrated under vacuum. The residue was applied onto a silica gel column eluting with dichloromethane/methanol (10:1) to afford 200.0 mg (38%) of tert-butyl 4-[7-[6-amino-3-(trifluoromethyl)pyridin-2-yl]-2-[[(tert-butoxy)carbonyl][2-(dimethylamino)ethyl]amino]-6-chloroquinazolin-4-yl]piperazine-1-carboxylate as a black solid. LC-MS (ESI, m/z): 695.3 [M+H]$^+$.

Step 5: 6-(6-chloro-2-[[2-(dimethylamino)ethyl]amino]-4-(piperazin-1-yl)quinazolin-7-yl)-5-(trifluoromethyl)pyridin-2-amine

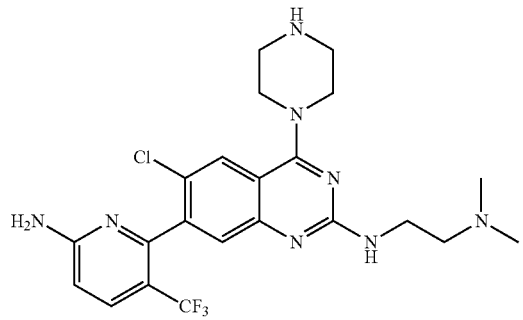 [SMILES: CN(C)CCNc1nc(N2CCNCC2)c2cc(Cl)c(-c3nc(N)ccc3C(F)(F)F)cc2n1]

A solution of tert-butyl 4-[7-[6-amino-3-(trifluoromethyl)pyridin-2-yl]-2-[[(tert-butoxy)carbonyl][2-(dimethylamino)ethyl]amino]-6-chloroquinazolin-4-yl]piperazine-1-carboxylate (200.0 mg, 0.29 mmol) in dichloromethane (8 mL) and trifluoroacetic acid (2 mL) was stirred for 30 min at 25° C. After completion, the resulting mixture was concentrated under vacuum to afford 200.0 mg (crude) of 6-(6-chloro-2-[[2-(dimethylamino)ethyl]amino]-4-(piperazin-1-yl)quinazolin-7-yl)-5-(trifluoromethyl)pyridin-2-amine. LC-MS (ESI, m/z): 495.2 [M+H]$^+$.

Step 6: 1-(4-[7-[6-amino-3-(trifluoromethyl)pyridin-2-yl]-6-chloro-2-[[2-(dimethylamino)ethyl]amino]quinazolin-4-yl]piperazin-1-yl)prop-2-en-1-one; trifluoroacetic acid salt

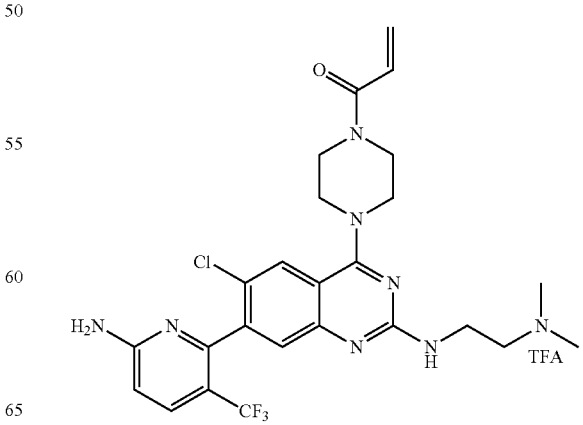

A solution of 6-(6-chloro-2-[[2-(dimethylamino)ethyl]amino]-4-(piperazin-1-yl)quinazolin-7-yl)-5-(trifluoromethyl)pyridin-2-amine (150.0 mg, 0.30 mmol), HATU (138.4 mg, 0.36 mmol), N,N-diisopropylethylamine (469.8 mg, 3.63 mmol) and prop-2-enoic acid (21.9 mg, 0.30 mmol) in dichloromethane (10 mL) was stirred for 30 min at −78° C. After completion, the reaction was quenched by the water (60 mL), extracted with dichloromethane (100 mL×3), dried over anhydrous sodium sulfate and concentrated under vacuum. The residue was applied onto a silica gel column eluting with dichloromethane/methanol (10/1) to afford a crude product. Then the crude product was purified by Prep-HPLC with the following conditions: Column: XSelect CSH Prep C18 OBD Column, 5 um, 19*150 mm; Mobile Phase A: Water (0.05% TFA), Mobile Phase B: ACN; Flow rate: 20 mL/min; Gradient: 15% B to 26% B in 7 min; 254/220 nm; Rt: 5.92 min to afford 22.5 mg (11%) of 1-(4-[7-[6-amino-3-(trifluoromethyl)pyridin-2-yl]-6-chloro-2-[[2-(dimethylamino)ethyl]amino]quinazolin-4-yl]piperazin-1-yl)prop-2-en-1-one; trifluoroacetic acid as a white solid. LC-MS (ESI, m/z): 549.2 [M+H]+.

Example 45

¹H NMR (300 MHz, Methanol-d₄, ppm) δ 8.22 (s, 1H), 7.85 (d, J=9.0 Hz, 1H), 7.56 (s, 1H), 6.84-6.75 (m, 2H), 6.31 (dd, J=16.8, 1.9 Hz, 1H), 5.84 (dd, J=10.6, 1.9 Hz, 1H), 4.31 (brs, 4H), 4.04-3.92 (m, 6H), 3.49 (t, J=5.9 Hz, 2H), 2.99 (s, 6H).

Example 46a (2S)-4-[7-[6-amino-3-(trifluoromethyl)pyridin-2-yl]-6-chloroquinazolin-4-yl]-1-(2-fluoroprop-2-enoyl)piperazine-2-carbonitrile Example 46b (2R)-4-[7-[6-amino-3-(trifluoromethyl)pyridin-2-yl]-6-chloroquinazolin-4-yl]-1-(2-fluoroprop-2-enoyl)piperazine-2-carbonitrile

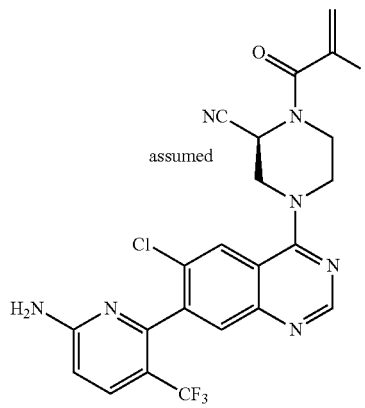

-continued

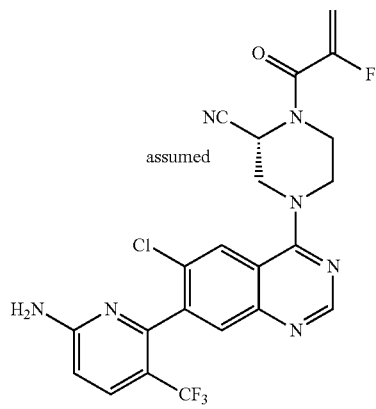

Synthetic Route

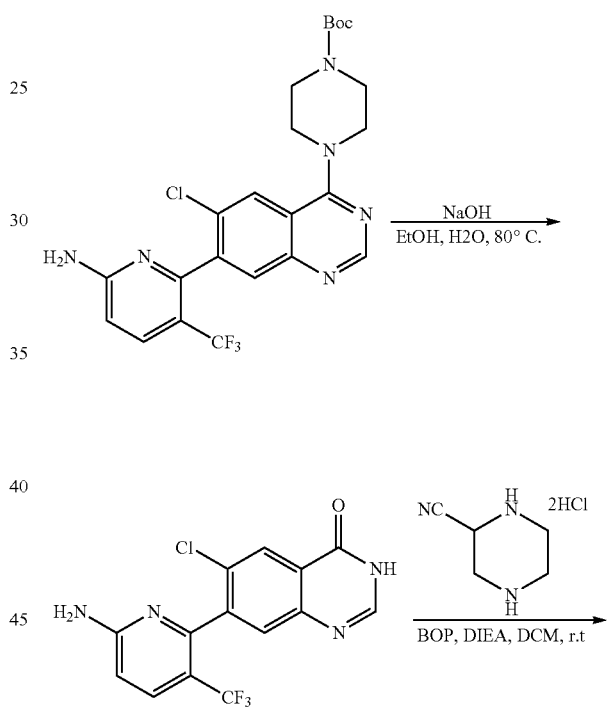

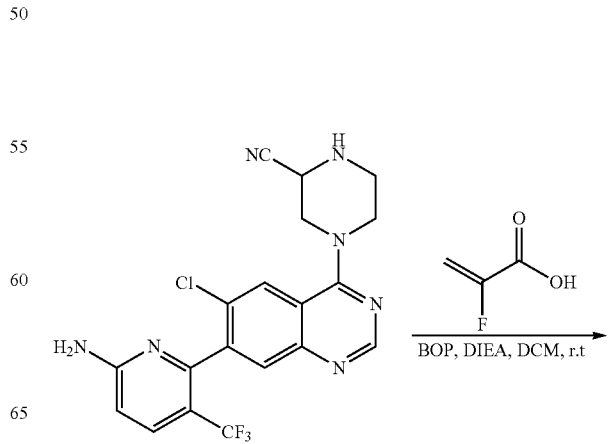

377
-continued

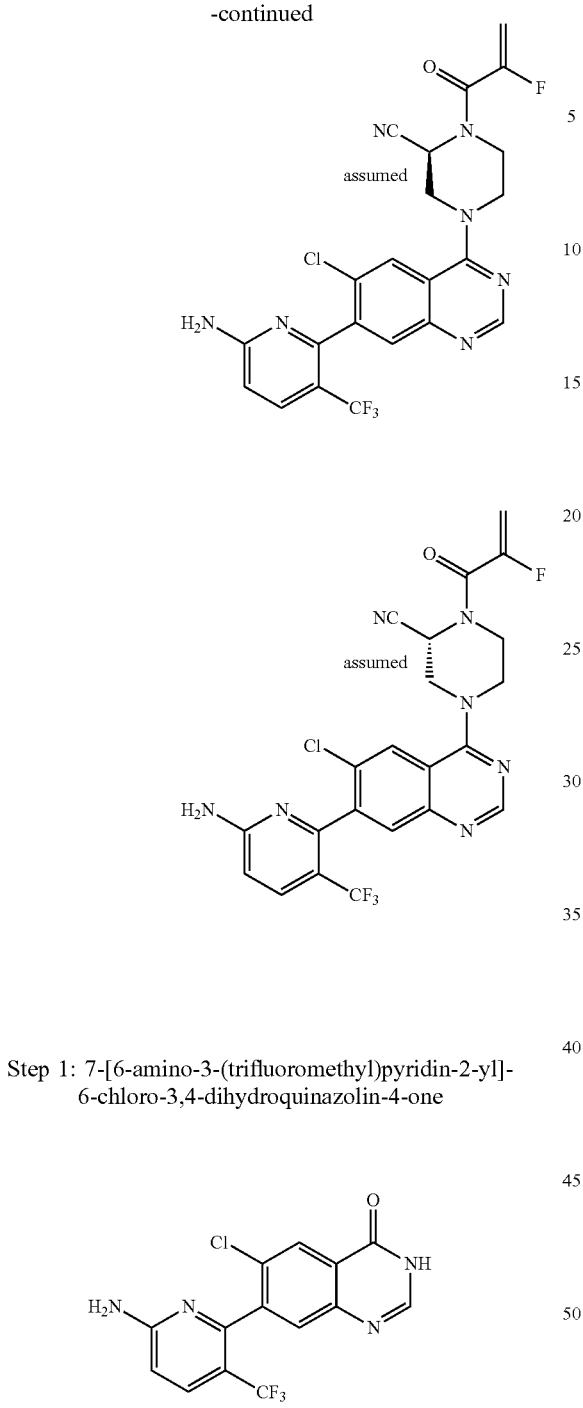

Step 1: 7-[6-amino-3-(trifluoromethyl)pyridin-2-yl]-6-chloro-3,4-dihydroquinazolin-4-one A solution of tert-butyl 4-[7-[6-amino-3-(trifluoromethyl)pyridin-2-yl]-6-chloroquinazolin-4-yl]piperazine-1-carboxylate (500.0 mg, 0.98 mmol) and sodium hydroxide (80.0 mg, 2.00 mmol) in ethanol (10 mL) and water (1 mL) was stirred for 2 h at 80° C. After completion, the pH of the resulting solution was adjusted to pH=7.0 with hydrochloric acid in 1,4-dioxane solution, concentrated under vacuum. The residue was purified by a silica gel column eluting with dichloromethane/methanol (10:1) to afford 150.0 mg (45%) of 7-[6-amino-3-(trifluoromethyl)pyridin-2-yl]-6-chloro-3,4-dihydroquinazolin-4-one as a white solid. LC-MS (ESI, m/z): 341.0 [M+H]+.

378

Step 2: 4-[7-[6-amino-3-(trifluoromethyl)pyridin-2-yl]-6-chloroquinazolin-4-yl]piperazine-2-carbonitrile

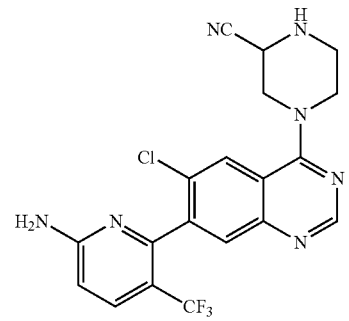 [SMILES: N#CC1CN(c2ncnc3cc(-c4nc(N)ccc4C(F)(F)F)c(Cl)cc23)CCN1]

A solution of piperazine-2-carbonitrile (94.0 mg, 0.85 mmol), 7-[6-amino-3-(trifluoromethyl)pyridin-2-yl]-6-chloro-3,4-dihydroquinazolin-4-one (150.0 mg, 0.44 mmol), BOP (234.0 mg, 0.53 mmol) and N,N-diisopropylethylamine (0.4 mL, 2.42 mmol) in dichloromethane (10 mL) was stirred for 12 hours at room temperature. After completion, the resulting solution was concentrated and diluted with dichloromethane (150 mL), washed with brine (50 mL×3), dried over anhydrous sodium sulfate and concentrated under vacuum. The residue was purified by a silica gel column eluting with dichloromethane/methanol (10/1) to afford 70.0 mg (37%) of 4-[7-[6-amino-3-(trifluoromethyl)pyridin-2-yl]-6-chloroquinazolin-4-yl]piperazine-2-carbonitrile as a white solid. LC-MS (ESI, m/z): 434.1 [M+H]+.

Step 3: (2S)-4-[7-[6-amino-3-(trifluoromethyl)pyridin-2-yl]-6-chloroquinazolin-4-yl]-1-(2-fluoroprop-2-enoyl)piperazine-2-carbonitrile and (2R)-4-[7-[6-amino-3-(trifluoromethyl)pyridin-2-yl]-6-chloroquinazolin-4-yl]-1-(2-fluoroprop-2-enoyl)piperazine-2-carbonitrile

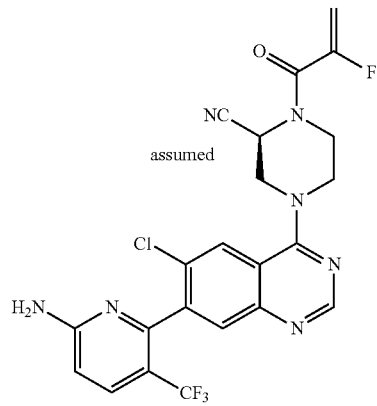

-continued

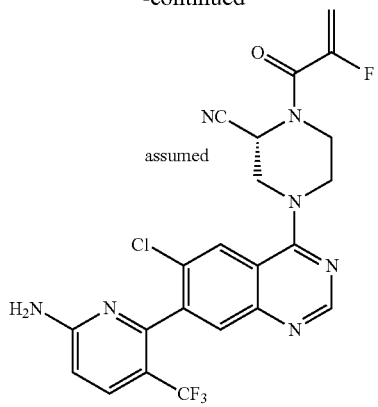

A solution of 4-[7-[6-amino-3-(trifluoromethyl)pyridin-2-yl]-6-chloroquinazolin-4-yl]piperazine-2-carbonitrile (70.0 mg, 0.16 mmol), 2-fluoroprop-2-enoic acid (15.0 mg, 0.17 mmol), BOP (85.0 mg, 0.19 mmol) and N,N-diisopropylethylamine (62.0 mg, 0.48 mmol) in dichloromethane (5 mL) was stirred for 60 min at room temperature. After completion, the solution was quenched with water (20 mL) and extracted with dichloromethane (3×30 mL). The organic layer was collected and dried over anhydrous sodium sulfate and concentrated under vacuum. The residue was purified by a silica gel column eluting with dichloromethane/methanol (10:1) to afford a crude product. Then the crude product was prepared by Prep-HPLC with following condition: Column: X Bridge C18, 19*150 mm, 5 um; Mobile Phase A:Water/0.05% TFA, Mobile Phase B: ACN; Flow rate: 20 mL/min; Gradient: 30% B to 70% B in 10 min; 254 nm. The product was purified by Chiral-Prep-HPLC with the following conditions (Prep-HPLC-009): Column, CHIRAL ART Cellulose-SB, 2*25 cm, 5 um; mobile phase, Hex-HPLC and ethanol-HPLC (hold 40% ethanol-HPLC in 10 min); Detector, UV 220/254 nm. This resulted in 5.6 mg (7%) of (2S)-4-[7-[6-amino-3-(trifluoromethyl)pyridin-2-yl]-6-chloroquinazolin-4-yl]-1-(2-fluoroprop-2-enoyl)piperazine-2-carbonitrile (assumed) as a white solid. LC-MS (ESI, m/z): 506.1 [M+H]$^+$ and 6.0 mg (7%) of (2R)-4-[7-[6-amino-3-(trifluoromethyl)pyridin-2-yl]-6-chloroquinazolin-4-yl]-1-(2-fluoroprop-2-enoyl)piperazine-2-carbonitrile (assumed) as a white solid. LC-MS (ESI, m/z): 506.1 [M+H]$^+$.

Example 46a $^1$H NMR (400 MHz, Methanol-d$_4$, ppm) δ 8.79 (s, 1H), 8.31 (d, J=1.8 Hz, 1H), 7.85-7.83 (m, 2H), 6.74 (dd, J=8.9, 0.9 Hz, 1H), 5.67 (brs, 1H), 5.55 (dd, J=4.0, 1.3 Hz, 1H), 5.45-5.40 (m, 1H), 4.71 (dq, J=14.1, 2.3 Hz, 1H), 4.52-4.47 (m, 1H), 4.38-4.34 (m, 1H), 3.83 (brs, 1H), 3.72 (ddd, J=13.9, 10.2, 3.6 Hz, 1H), 3.54-3.43 (m, 1H).

Example 46b $^1$H NMR (400 MHz, Methanol-d$_4$, ppm) δ 8.79 (s, 1H), 8.31 (d, J=1.8 Hz, 1H), 7.85-7.83 (m, 2H), 6.74 (dd, J=8.9, 0.9 Hz, 1H), 5.67 (brs, 1H), 5.55 (dd, J=4.0, 1.3 Hz, 1H), 5.45-5.40 (m, 1H), 4.71 (dq, J=14.1, 2.3 Hz, 1H), 4.52-4.47 (m, 1H), 4.38-4.34 (m, 1H), 3.83 (brs, 1H), 3.72 (ddd, J=13.9, 10.2, 3.6 Hz, 1H), 3.54-3.43 (m, 1H).

Example 47

1-[4-[7-(6-amino-3-cyclopropylpyridin-2-yl)-6-methoxyquinazolin-4-yl]piperazin-1-yl]prop-2-en-1-one

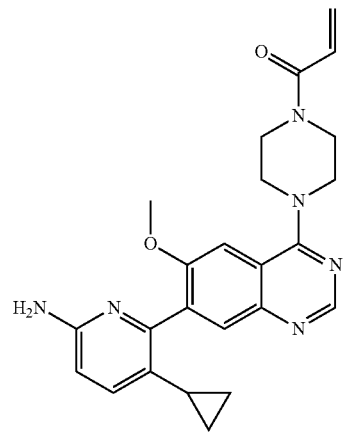 [SMILES: C=CC(=O)N1CCN(c2ncnc3cc(-c4nc(N)ccc4C4CC4)c(OC)cc23)CC1]

Synthetic Route

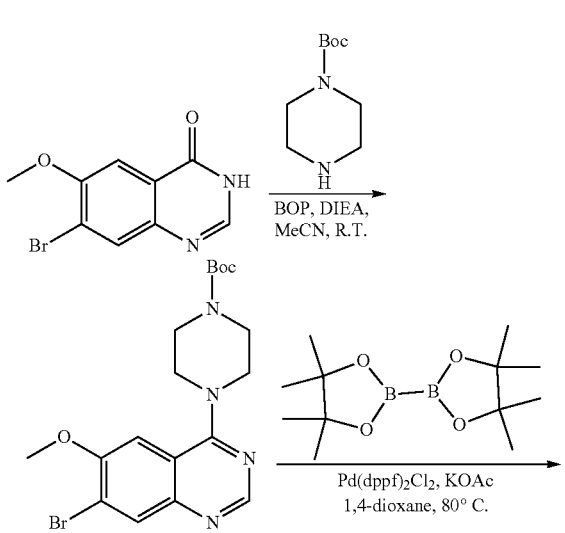

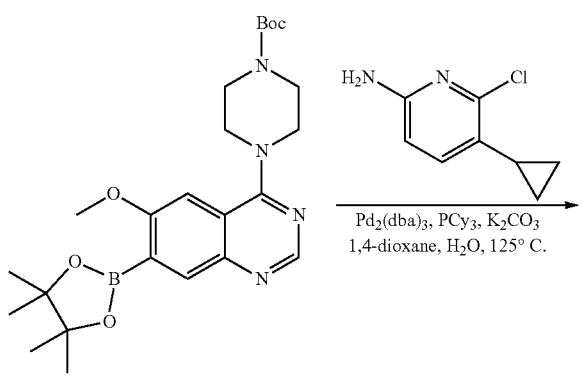

-continued

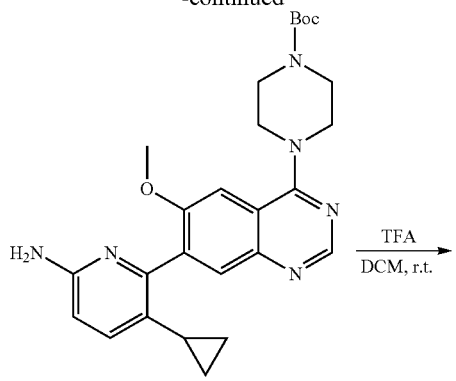

TFA
DCM, r.t.

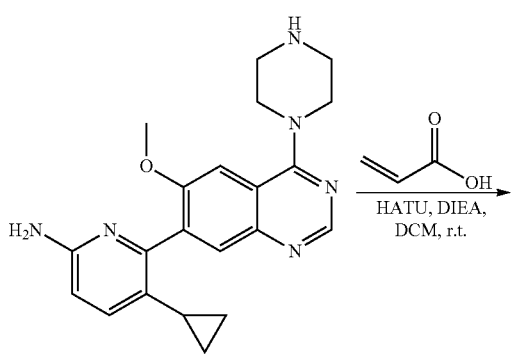

HATU, DIEA,
DCM, r.t.

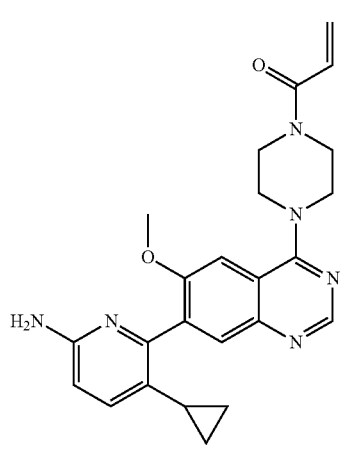 [SMILES: C=CC(=O)N1CCN(c2ncnc3cc(-c4nc(N)ccc4C4CC4)c(OC)cc23)CC1]

Step 1: tert-butyl 4-(7-bromo-6-methoxyquinazolin-4-yl)piperazine-1-carboxylate

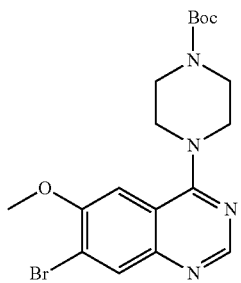 [SMILES: COc1cc2c(N3CCN(C(=O)OC(C)(C)C)CC3)ncnc2cc1Br]

A solution of 7-bromo-6-methoxy-3,4-dihydroquinazolin-4-one (5.00 g, 19.60 mmol), tert-butyl piperazine-1-carboxylate (7.30 g, 39.19 mmol), BOP (17.30 g, 39.21 mmol) and N,N-diisopropylethylamine (5.07 g, 39.23 mmol) in acetonitrile (120 mL) was stirred for 4 h at 25° C. After completion, the resulting mixture was concentrated under vacuum and diluted with ethyl acetate (150 mL), washed with brine (40 mL×3), dried over anhydrous sodium sulfate and concentrated under vacuum. The residue was applied onto a silica gel column eluting with petroleum ether/ethyl acetate (1/1). This resulted in 5.00 g (60%) of tert-butyl 4-(7-bromo-6-methoxyquinazolin-4-yl)piperazine-1-carboxylate as a yellow solid. LC-MS (ESI, m/z): 506.1 [M+H]$^+$.

Step 2: tert-butyl 4-[6-methoxy-7-(tetramethyl-1,3,2-dioxaborolan-2-yl)quinazolin-4-yl]piperazine-1-carboxylate

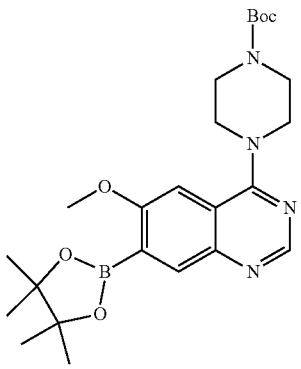 [SMILES: COc1cc2c(N3CCN(C(=O)OC(C)(C)C)CC3)ncnc2cc1B1OC(C)(C)C(C)(C)O1]

Under nitrogen, a solution of tert-butyl 4-(7-bromo-6-methoxyquinazolin-4-yl)piperazine-1-carboxylate (2.00 g, 4.73 mmol), 4,4,5,5-tetramethyl-2-(tetramethyl-1,3,2-dioxaborolan-2-yl)-1,3,2-dioxaborolane (4.80 g, 18.90 mmol), 1,1'-bis(diphenylphosphino)ferrocene-palladium(II)dichloride (139.3 mg, 0.24 mmol), potassium acetate (927.4 mg, 9.45 mmol) in 1,4-dioxane (100 mL) was stirred for 2 h at 80° C. After completion, the resulting solution was concentrated and diluted with ethyl acetate (150 mL), washed with brine (40 mL×3), dried over anhydrous sodium sulfate and concentrated under vacuum. The residue was applied onto a silica gel column eluting with dichloromethane/methanol (10/1). This resulted in 700.0 mg (31%) of tert-butyl 4-[6-methoxy-7-(tetramethyl-1,3,2-dioxaborolan-2-yl)quinazolin-4-yl]piperazine-1-carboxylate as a yellow solid. LC-MS (ESI, m/z): 471.3 [M+H]$^+$.

Step 3: tert-butyl 4-[7-(6-amino-3-cyclopropylpyridin-2-yl)-6-methoxyquinazolin-4-yl]piperazine-1-carboxylate

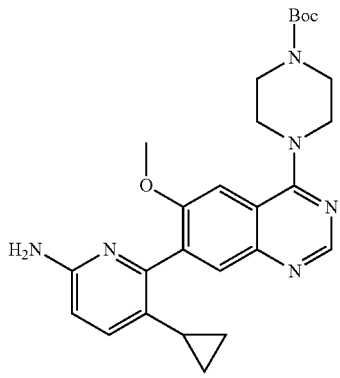 [SMILES: COc1cc2c(N3CCN(C(=O)OC(C)(C)C)CC3)ncnc2cc1-c1nc(N)ccc1C1CC1]

Under nitrogen, a solution of tert-butyl 4-[6-methoxy-7-(tetramethyl-1,3,2-dioxaborolan-2-yl)quinazolin-4-yl]piperazine-1-carboxylate (200.0 mg, 0.43 mmol), 6-chloro-5-cyclopropylpyridin-2-amine (71.6 mg, 0.43 mmol), Pd$_2$(dba)$_3$ (19.5 mg, 0.02 mmol), tricyclohexyl phosphine (12.0 mg, 0.04 mmol) and potassium carbonate (117.5 mg, 0.85 mmol) in dioxane (5 mL) and water (1 mL) was stirred for 30 min at 110° C. After completion, the resulting mixture was concentrated under vacuum. The residue was applied onto a silica gel column eluting with dichloromethane/methanol (20/1). This resulted in 100.0 mg (49%) of tert-butyl 4-[7-(6-amino-3-cyclopropylpyridin-2-yl)-6-methoxyquinazolin-4-yl]piperazine-1-carboxylate as off-white oil. LC-MS (ESI, m/z): 477.3 [M+H]$^+$.

Step 4: 5-cyclopropyl-6-[6-methoxy-4-(piperazin-1-yl)quinazolin-7-yl]pyridin-2-amine

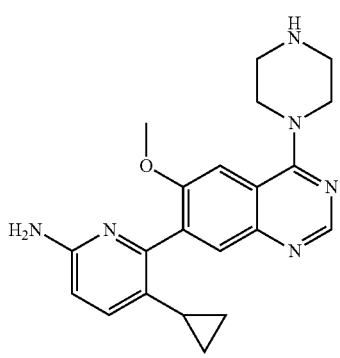 [SMILES: COc1cc2c(N3CCNCC3)ncnc2cc1-c1nc(N)ccc1C1CC1]

A solution of tert-butyl 4-[7-(6-amino-3-cyclopropylpyridin-2-yl)-6-methoxyquinazolin-4-yl]piperazine-1-carboxylate (100.0 mg, 0.21 mmol) in trifluoroacetic acid (2 mL) and dichloromethane (10 mL) was stirred for 1 h at 25° C. After completion, the resulting mixture was concentrated under vacuum. This resulted in 100 mg (crude) of 5-cyclopropyl-6-[6-methoxy-4-(piperazin-1-yl)quinazolin-7-yl]pyridin-2-amine as yellow oil. LC-MS (ESI, m/z): 377.2 [M+H]$^+$.

Step 5: 1-[4-[7-(6-amino-3-cyclopropylpyridin-2-yl)-6-methoxyquinazolin-4-yl]piperazin-1-yl]prop-2-en-1-one

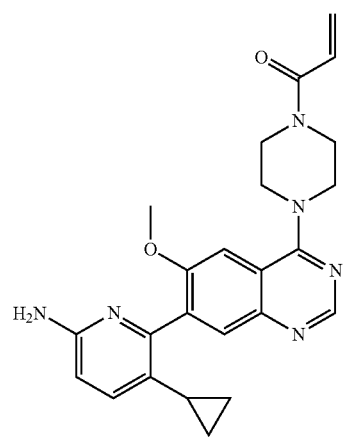 [SMILES: C=CC(=O)N1CCN(c2ncnc3cc(-c4nc(N)ccc4C4CC4)c(OC)cc23)CC1]

A solution of 5-cyclopropyl-6-[6-methoxy-4-(piperazin-1-yl)quinazolin-7-yl]pyridin-2-amine (50.0 mg, 0.13 mmol), prop-2-enoic acid (10.0 mg, 0.14 mmol), HATU (60.6 mg, 0.16 mmol) and N,N-diisopropylethylamine (20.6 mg, 0.16 mmol) in dichloromethane (5 mL) was stirred for 1 h at −78° C. After completion, the resulting solution was quenched with (1 mL) and diluted with dichloromethane (150 mL), washed with brine (40 mL×3), dried over anhydrous sodium sulfate and concentrated under vacuum. The residue was applied onto a silica gel column eluting with dichloromethane/methanol (10/1). This resulted in 19.6 mg (34%) of 1-[4-[7-(6-amino-3-cyclopropylpyridin-2-yl)-6-methoxyquinazolin-4-yl]piperazin-1-yl]prop-2-en-1-one as a white solid. LC-MS (ESI, m/z): 431.2 [M+H]$^+$.

Example 47

$^1$H NMR (300 MHz, Chloroform-d) δ 8.77 (s, 1H), 7.91 (s, 1H), 7.22-7.18 (m, 2H), 6.66 (dd, J=16.8, 10.5 Hz, 1H), 6.56 (d, J=8.5 Hz, 1H), 6.38 (dd, J=16.8, 1.9 Hz, 1H), 5.79 (dd, J=10.5, 1.9 Hz, 1H), 4.65 (brs, 2H), 3.92-3.78 (m, 11H), 1.65-1.55 (m, 1H), 0.69-0.66 (m, 2H), 0.55-0.49 (m, 2H).

Example 48
1-[4-[7-(3-amino-8-fluoroisoquinolin-1-yl)-6-chloro-quinazolin-4-yl]piperazin-1-yl]prop-2-en-1-one
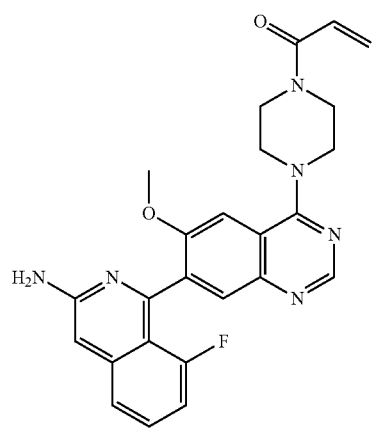
Synthetic Route
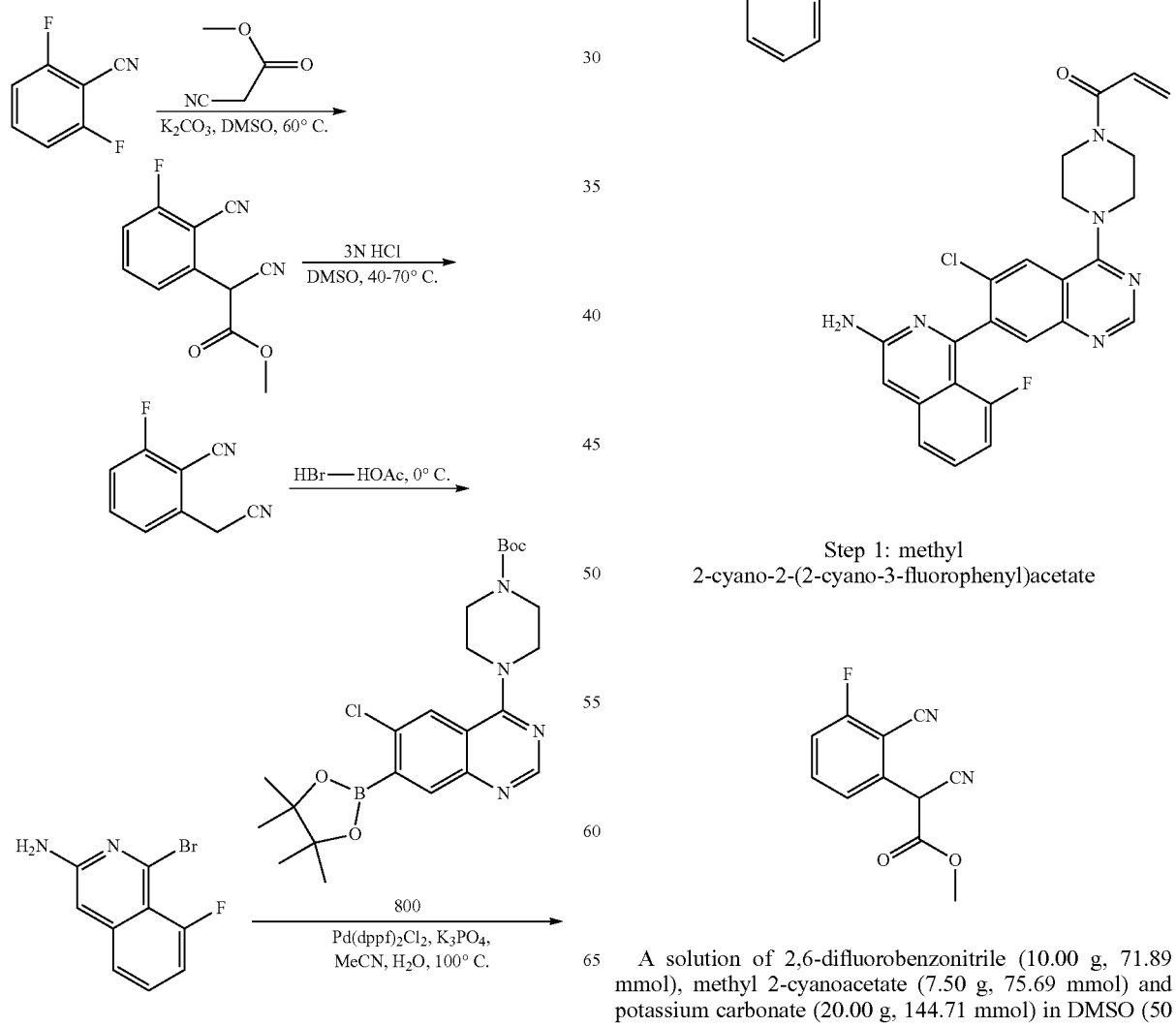
-continued
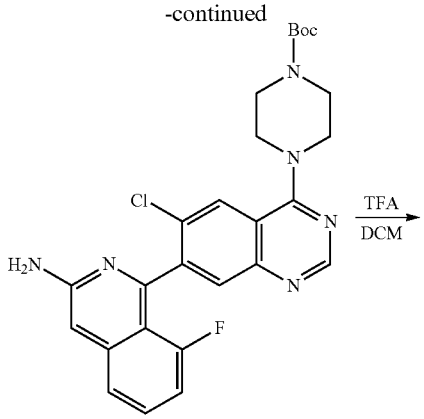
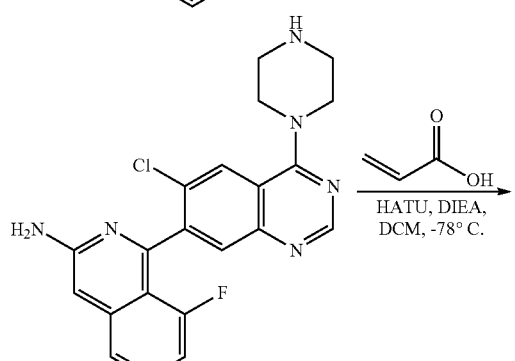
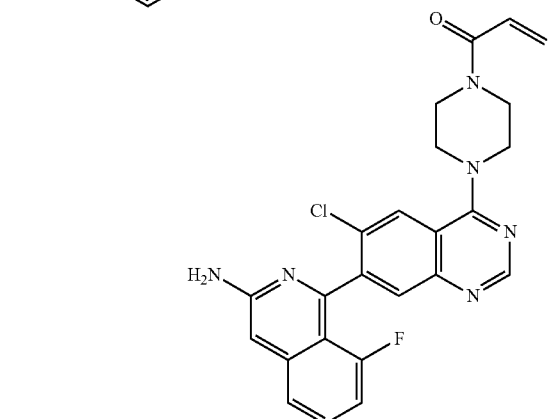
Step 1: methyl 2-cyano-2-(2-cyano-3-fluorophenyl)acetate
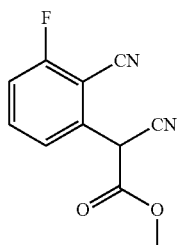
A solution of 2,6-difluorobenzonitrile (10.00 g, 71.89 mmol), methyl 2-cyanoacetate (7.50 g, 75.69 mmol) and potassium carbonate (20.00 g, 144.71 mmol) in DMSO (50 mL) was stirred for 12 h at room temperature. After completion, the resulting solution was diluted with water (100 mL). The solids were collected by filtration. This resulted in 11.5 g (73%) of methyl 2-cyano-2-(2-cyano-3-fluorophenyl)acetate as a yellow solid. LC-MS (ESI, m/z): 219.0 [M+H]⁺.

Step 2: 2-(cyanomethyl)-6-fluorobenzonitrile

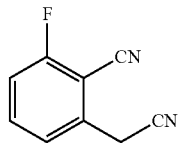 [SMILES: N#CCc1cccc(F)c1C#N]

A solution of methyl 2-cyano-2-(2-cyano-3-fluorophenyl)acetate (1.00 g, 4.58 mmol) in DMSO (8 mL) and hydrogen chloride solution (6M) (2 mL) was stirred for 12 hours at 70° C. After completion, the pH of the resulting solution was adjusted to pH=9.0 with sodium carbonate solution. The solids were collected by filtration. This resulted in 700.0 mg (95%) of 2-(cyanomethyl)-6-fluorobenzonitrile as a gray solid. LC-MS (ESI, m/z): 161.0 [M+H]⁺.

Step 3: 1-bromo-8-fluoroisoquinolin-3-amine

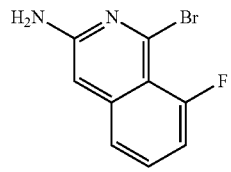 [SMILES: Nc1cc2cccc(F)c2c(Br)n1]

A solution of 2-(cyanomethyl)-6-fluorobenzonitrile (3.00 g, 18.73 mmol) in HBr/AcOH(40%) (15 mL) was stirred for 30 min at 0° C. After completion, the pH of the resulting solution was adjusted to pH=8.0 with sodium carbonate saturated aqueous solution. The solids were collected by filtration. This resulted in 1.70 g (38%) of 1-bromo-8-fluoroisoquinolin-3-amine as a light yellow solid. LC-MS (ESI, m/z): 241.0 [M+H]⁺.

Step 4: tert-butyl 4-[7-(3-amino-8-fluoroisoquinolin-1-yl)-6-chloroquinazolin-4-yl]piperazine-1-carboxylate

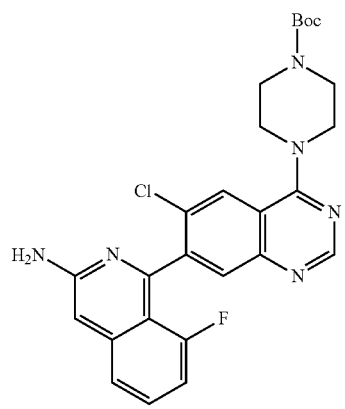 [SMILES: CC(C)(C)OC(=O)N1CCN(c2ncnc3cc(-c4nc(N)cc5cccc(F)c45)c(Cl)cc23)CC1]

A suspension of 4-[6-chloro-7-(tetramethyl-1,3,2-dioxaborolan-2-yl)quinazolin-4-yl]piperazine-1-carboxylate (1.2 g, 2.48 mmol), 1-bromo-8-fluoroisoquinolin-3-amine (600.0 mg, 2.49 mmol), Pd(dppf)Cl₂ (183.0 mg, 0.25 mmol) and K₃PO₄ (1.00 g, 4.71 mmol) in acetonitrile (10 mL) and water (0.2 mL) was stirred for 60 min at 100° C. After completion, the resulting solution was concentrated and diluted with ethyl acetate (250 mL), washed with brine (80 mL×3), dried over anhydrous sodium sulfate and concentrated under vacuum. The residue was purified by a silica gel column eluting with dichloromethane/methanol (10/1) to afford 200.0 mg (9%) of tert-butyl 4-[7-(3-amino-8-fluoroisoquinolin-1-yl)-6-chloroquinazolin-4-yl]piperazine-1-carboxylate as a brown solid. LC-MS (ESI, m/z): 509.2 [M+H]⁺.

Step 5: 1-[6-chloro-4-(piperazin-1-yl)quinazolin-7-yl]-8-fluoroisoquinolin-3-amine

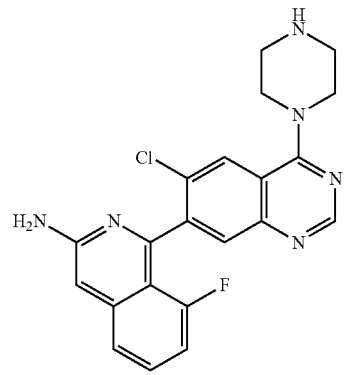 [SMILES: Nc1cc2cccc(F)c2c(-c2cc3ncnc(N4CCNCC4)c3cc2Cl)n1]

A solution of tert-butyl 4-[7-(3-amino-8-fluoroisoquinolin-1-yl)-6-chloroquinazolin-4-yl]piperazine-1-carboxylate (200.0 mg, 0.39 mmol) in trifluoroacetic acid (2 mL) and dichloromethane (6 mL) was stirred for 60 min at room temperature. After completion, the resulting solution was concentrated under vacuum. This resulted in 300 mg (crude) of 1-[6-chloro-4-(piperazin-1-yl)quinazolin-7-yl]-8-fluoroisoquinolin-3-amine as brown oil. LC-MS (ESI, m/z): 409.2 [M+H]⁺.

Step 6: 1-[4-[7-(3-amino-8-fluoroisoquinolin-1-yl)-6-chloroquinazolin-4-yl]piperazin-1-yl]prop-2-en-1-one

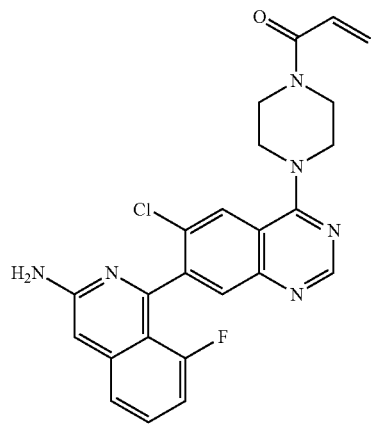 [SMILES: C=CC(=O)N1CCN(c2ncnc3cc(-c4nc(N)cc5cccc(F)c45)c(Cl)cc23)CC1]

A solution of 1-[6-chloro-4-(piperazin-1-yl)quinazolin-7-yl]-8-fluoroisoquinolin-3-amine (100.0 mg crude), prop-2-enoic acid (53.0 mg, 0.73 mmol), HATU (109.0 mg, 0.29 mmol) and N,N-diisopropylethylamine (155.0 mg, 1.20 mmol) in dichloromethane (5 mL) was stirred for 30 min at −78° C. After completion, the resulting solution was quenched with water (1 mL), diluted with dichloromethane (150 mL), washed with brine (40 mL×3), dried over anhydrous sodium sulfate and concentrated under vacuum. The residue was purified by Prep-HPLC with the following conditions: Column: X Bridge C18, 19*150 mm, 5 um; Mobile Phase A:Water/0.05% TFA, Mobile Phase B: ACN; Flow rate: 20 mL/min; Gradient: 30% B to 70% B in 10 min; 254 nm. This resulted in 9.1 mg (8%) of 1-[4-[7-(3-amino-8-fluoroisoquinolin-1-yl)-6-chloroquinazolin-4-yl]piperazin-1-yl]prop-2-en-1-one as a light yellow solid. LC-MS (ESI, m/z): 463.1 [M+H]⁺.

Example 48

¹H NMR (300 MHz, DMSO-d₆, ppm) δ 8.69 (s, 1H), 8.14 (s, 1H), 7.83 (s, 1H), 7.49-7.40 (m, 2H), 6.89-6.76 (m, 3H), 6.35 (s, 2H), 6.18 (dd, J=16.7, 2.4 Hz, 1H), 5.75 (dd, J=10.4, 2.4 Hz, 1H), 3.88 (brs, 6H), 3.79 (brs, 2H).

Example 49

1-[4-[7-(3-amino-7-fluoroisoquinolin-1-yl)-6-chloroquinazolin-4-yl]piperazin-1-yl]prop-2-en-1-one

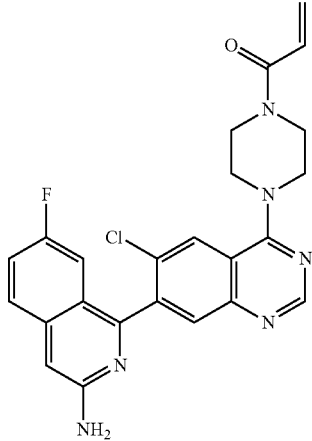 [SMILES: C=CC(=O)N1CCN(c2ncnc3cc(-c4nc(N)cc5ccc(F)cc45)c(Cl)cc23)CC1]

Synthetic Route

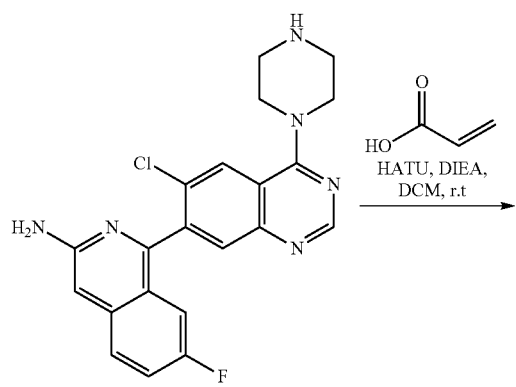

Step 1: 1-[4-[7-(3-amino-7-fluoroisoquinolin-1-yl)-6-chloroquinazolin-4-yl]piperazin-1-yl]prop-2-en-1-one

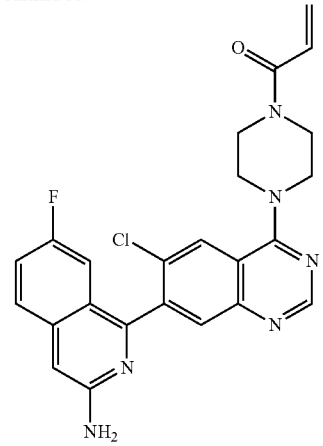 [SMILES: C=CC(=O)N1CCN(c2ncnc3cc(-c4nc(N)cc5ccc(F)cc45)c(Cl)cc23)CC1]

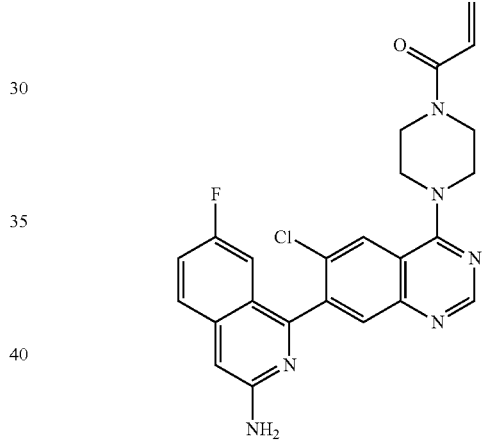

A solution of 1-[6-chloro-4-(piperazin-1-yl)quinazolin-7-yl]-7-fluoroisoquinolin-3-amine (100.0 mg, 0.24 mmol), HATU (111.6 mg, 0.29 mmol), N,N-diisopropylethylamine (63.2 mg, 0.49 mmol) and prop-2-enoic acid (17.6 mg, 0.25 mmol) in dichloromethane (5 mL) was stirred for 30 min at room temperature. After completion, the resulting solution was quenched with water (1 mL), diluted with dichloromethane (150 mL), washed with brine (40 mL×3), dried over anhydrous sodium sulfate and concentrated under vacuum. The residue was purified by Prep-HPLC with the following conditions: Column: X Bridge C18, 19*150 mm, 5 um; Mobile Phase A:Water/0.05% TFA, Mobile Phase B: ACN; Flow rate: 20 mL/min; Gradient: 30% B to 70% B in 10 min; 254 nm. This resulted in 3.8 mg (3%) of 1-[4-[7-(3-amino-7-fluoroisoquinolin-1-yl)-6-chloroquinazolin-4-yl]piperazin-1-yl]prop-2-en-1-one as a yellow solid. LC-MS (ESI, m/z): 463.1 [M+H]⁺.

Example 49

¹H NMR (300 MHz, Methanol-d₄, ppm) δ 8.70 (s, 1H), 8.31 (s, 1H), 7.90 (s, 1H), 7.73 (dd, J=9.2, 5.4 Hz, 1H), 7.42-7.35 (m, 1H), 6.99-6.93 (m, 2H), 6.85 (dd, J=16.8, 10.6 Hz, 1H), 6.29 (dd, J=16.8, 1.9 Hz, 1H), 5.82 (dd, J=10.6, 2.0 Hz, 1H), 4.09-4.04 (m, 4H), 3.96-3.93 (m, 4H).

Example 50

1-(3-[7-[6-amino-3-(trifluoromethyl)pyridin-2-yl]-6-chloroquinazolin-4-yl]azetidin-1-yl)prop-2-en-1-one

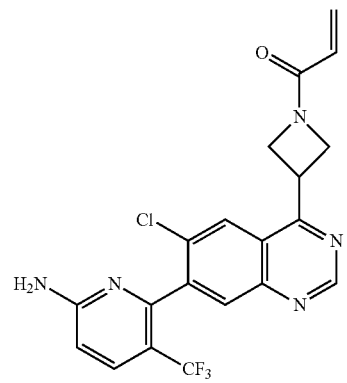 [SMILES: C=CC(=O)N1CC(c2ncnc3cc(-c4nc(N)ccc4C(F)(F)F)c(Cl)cc23)C1]

Synthetic Route

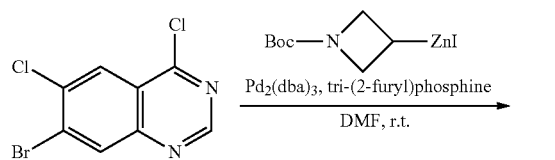

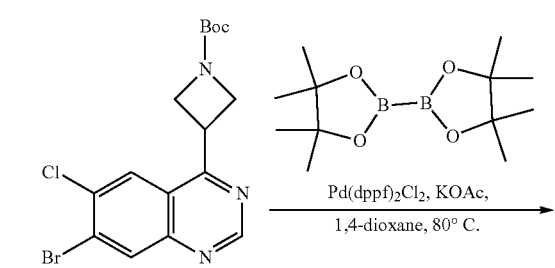

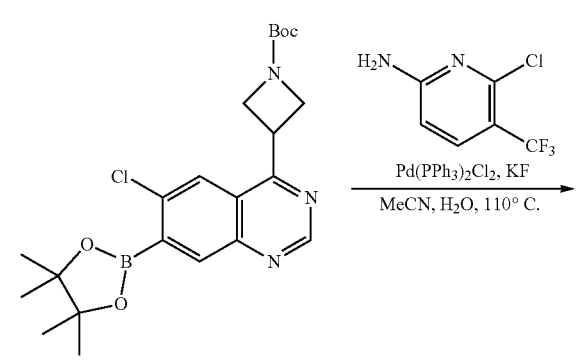

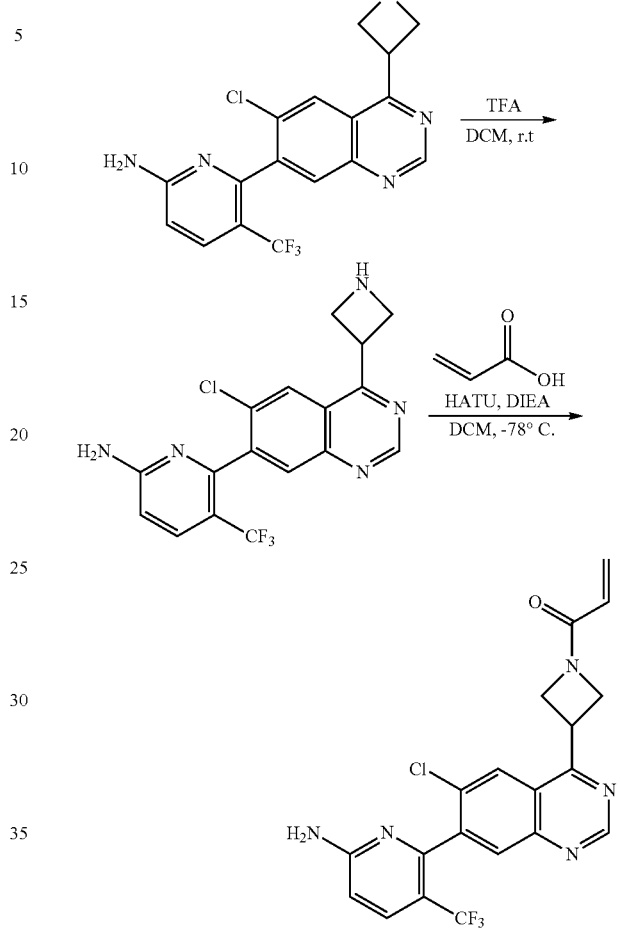

Step 1: tert-butyl 3-(7-bromo-6-chloroquinazolin-4-yl)azetidine-1-carboxylate

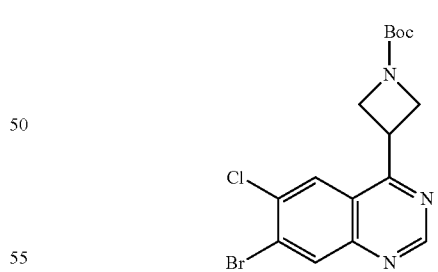

Under nitrogen, a solution of 7-bromo-4,6-dichloroquinazoline (6.00 g, 21.59 mmol), [1-[(tert-butoxy)carbonyl]azetidin-3-yl](iodo)zinc (30 mL, 15.49 mmol), tris(dibenzylideneacetone)dipalladium-chloroform adduct (998.0 mg, 0.96 mmol) and tri-2-furylphosphine (500.0 mg, 2.15 mmol) in N,N-dimethylformamide (30 mL) was stirred for 30 min at room temperature. After completion, the resulting solution was diluted with water (100 mL), extracted with ethyl acetate (100 mL×3), washed with brine (100 mL×3), dried over anhydrous sodium sulfate and concentrated under vacuum. The residue was applied onto a silica gel column eluting with ethyl acetate/petroleum ether (1/5) to afford 3.3 g (42%) of tert-butyl 3-(7-bromo-6-chloroquinazolin-4-yl)azetidine-1-carboxylate as a light yellow solid. LC-MS (ESI, m/z): 398.0 [M+H]⁺.

Step 2: tert-butyl 3-[6-chloro-7-(tetramethyl-1,3,2-dioxaborolan-2-yl)quinazolin-4-yl]azetidine-1-carboxylate

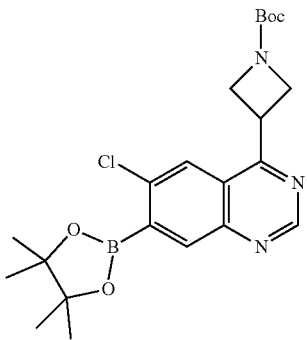 [SMILES: CC(C)(C)OC(=O)N1CC(c2ncnc3cc(B4OC(C)(C)C(C)(C)O4)c(Cl)cc23)C1]

Under nitrogen, a solution of tert-butyl 3-(7-bromo-6-chloroquinazolin-4-yl)azetidine-1-carboxylate (2.00 g, 5.02 mmol), 1,1'-bis(diphenylphosphino)ferrocene-palladium(II) dichloride (400.6 mg, 0.55 mmol), potassium acetate (1.48 g, 15.08 mmol) and 4,4,5,5-tetramethyl-2-(tetramethyl-1,3,2-dioxaborolan-2-yl)-1,3,2-dioxaborolane (3.88 g, 15.28 mmol) in 1,4-dioxane (30 mL) was stirred for 2 h at 80° C. After completion, the resulting solution was concentrated under vacuum, diluted with dichloromethane (150 mL). After filtration, the filtrate were collected, concentrated under vacuum, washed with petroleum ether (10 mL×3). This resulted in 1.4 g (crude) of tert-butyl 3-[6-chloro-7-(tetramethyl-1,3,2-dioxaborolan-2-yl)quinazolin-4-yl]azetidine-1-carboxylate as a brown solid. LC-MS (ESI, m/z): 446.2 [M+H]⁺.

Step 3: tert-butyl 3-[7-[6-amino-3-(trifluoromethyl)pyridin-2-yl]-6-chloroquinazolin-4-yl]azetidine-1-carboxylate

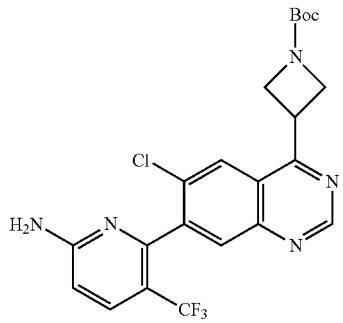 [SMILES: CC(C)(C)OC(=O)N1CC(c2ncnc3cc(-c4nc(N)ccc4C(F)(F)F)c(Cl)cc23)C1]

Under nitrogen, a solution of tert-butyl 3-[6-chloro-7-(tetramethyl-1,3,2-dioxaborolan-2-yl)quinazolin-4-yl]azetidine-1-carboxylate (1.40 g, 3.14 mmol), bis(triphenylphosphine)palladium(II) chloride (220.5 mg, 0.31 mmol), potassium fluoride (380.0 mg, 6.54 mmol) and 6-chloro-5-(trifluoromethyl)pyridin-2-amine (620.0 mg, 3.15 mmol) in acetonitrile (20 mL) and water (5 mL) was stirred for 60 min at 110° C. After completion, the resulting solution was diluted with ethyl acetate (200 mL), washed with brine (80 mL×3), dried over anhydrous sodium sulfate and concentrated under vacuum. The residue was applied onto a silica gel column eluting with dichloromethane/methanol (10/1). This resulted in 600.0 mg (40%) of tert-butyl 3-[7-[6-amino-3-(trifluoromethyl)pyridin-2-yl]-6-chloroquinazolin-4-yl]azetidine-1-carboxylate as a dark red solid. LC-MS (ESI, m/z): 480.1 [M+H]⁺.

Step 4: 6-[4-(azetidin-3-yl)-6-chloroquinazolin-7-yl]-5-(trifluoromethyl)pyridin-2-amine

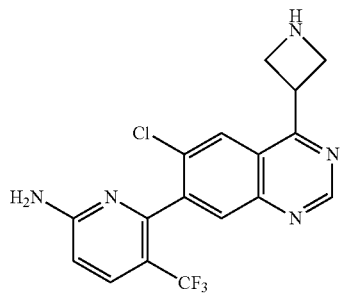 [SMILES: Nc1ccc(C(F)(F)F)c(-c2cc3ncnc(C4CNC4)c3cc2Cl)n1]

A solution of tert-butyl 3-[7-[6-amino-3-(trifluoromethyl)pyridin-2-yl]-6-chloroquinazolin-4-yl]azetidine-1-carboxylate (300.0 mg, 0.63 mmol) in trifluoroacetic acid (5 mL) and dichloromethane (15 mL) was stirred for 20 min at 25° C. After completion, the resulting solution was concentrated under vacuum. The resulted in 320 mg (crude) of 6-[4-(azetidin-3-yl)-6-chloroquinazolin-7-yl]-5-(trifluoromethyl)pyridin-2-amine as a dark red solid. LC-MS (ESI, m/z): 380.1 [M+H]⁺.

Step 5: 1-(3-[7-[6-amino-3-(trifluoromethyl)pyridin-2-yl]-6-chloroquinazolin-4-yl]azetidin-1-yl)prop-2-en-1-one

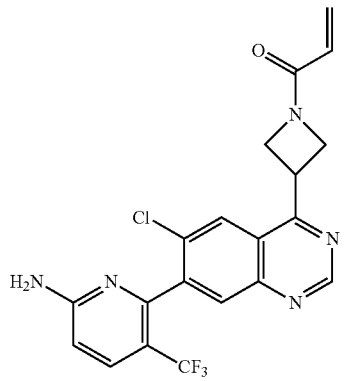 [SMILES: C=CC(=O)N1CC(c2ncnc3cc(-c4nc(N)ccc4C(F)(F)F)c(Cl)cc23)C1]

A solution of 6-[4-(azetidin-3-yl)-6-chloroquinazolin-7-yl]-5-(trifluoromethyl)pyridin-2-amine (300.0 mg, 0.79 mmol), HATU (300.8 mg, 0.79 mmol), N,N-diisopropylethylamine (408.4 mg, 3.16 mmol) and prop-2-enoic acid (57.0 mg, 0.79 mmol) in dichloromethane (15 mL) was stirred for 60 min at −78° C. After completion, the resulting solution was quenched with water (1 mL), diluted with dichloromethane (200 mL), washed with brine (80 mL×3), dried over anhydrous sodium sulfate and concentrated under vacuum. The residue was applied onto a silica gel column eluting with dichloromethane/methanol (10:1). Then the crude product was purified by Prep-HPLC with the following conditions: Column: (Bridge Prep OBD C18 Column 30×150 mm 5 um; Mobile Phase A:Water (10 MMOL/L NH4HCO3), Mobile Phase B: ACN; Flow rate: 60 mL/min; Gradient: 20% B to 50% B in 7 min; 254/220 nm; Rt: 6.62 min to afford 141.2 mg (41%) of 1-(3-[7-[6-amino-3-(trifluoromethyl)pyridin-2-yl]-6-chloroquinazolin-4-yl]azetidin-1-yl)prop-2-en-1-one as a white solid. LC-MS (ESI, m/z): 434.1 [M+H]⁺.

Example 50

¹H NMR (300 MHz, Methanol-d₄, ppm) δ 9.33 (s, 1H), 8.33 (s, 1H), 7.98 (s, 1H), 7.82 (d, J=8.9 Hz, 1H), 6.73 (dd, J=9.0, 1.1 Hz, 1H), 6.47-6.38 (m, 1H), 6.29 (dd, J=17.0, 2.1 Hz, 1H), 5.78 (ddd, J=10.2, 2.3, 1.0 Hz, 1H), 5.00-4.88 (m, 2H), 4.84-4.76 (m, 1H), 4.64-4.50 (m, 2H).

Example 51

1-[4-[7-[6-amino-3-(2,2,2-trifluoroethyl)-2-pyridyl]-6-chloro-quinazolin-4-yl]piperazin-1-yl]prop-2-en-1-one

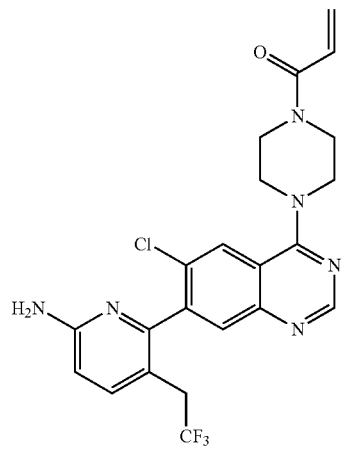 [SMILES: C=CC(=O)N1CCN(c2ncnc3cc(-c4nc(N)ccc4CC(F)(F)F)c(Cl)cc23)CC1]

Synthetic Route

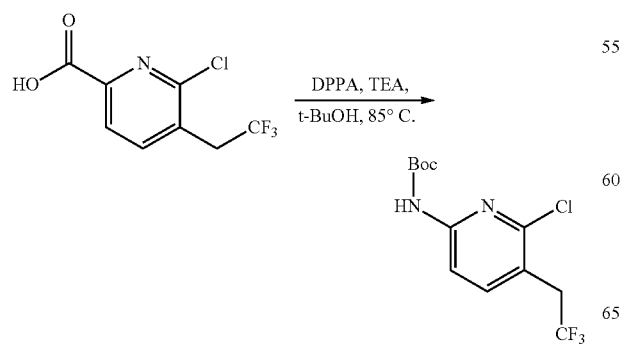

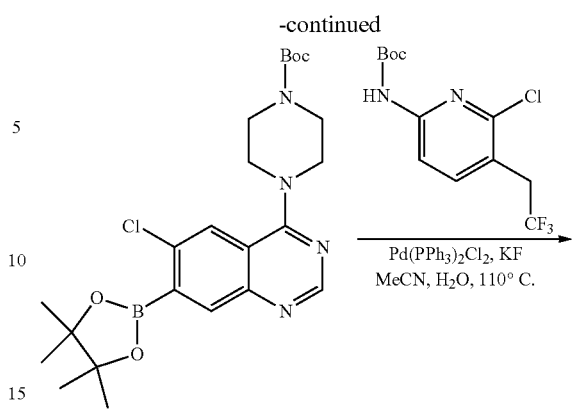

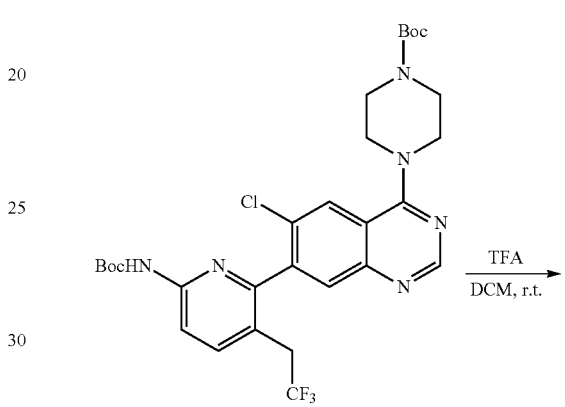

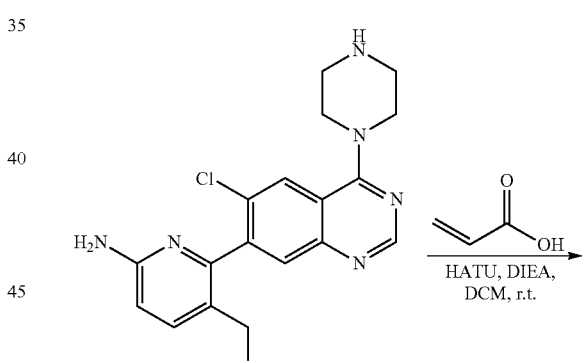

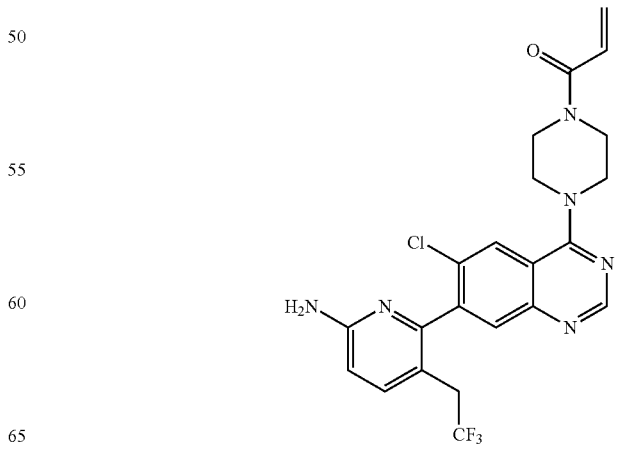

Step 1: tert-butyl N-[6-chloro-5-(2,2,2-trifluoro-ethyl)-2-pyridyl]carbamate

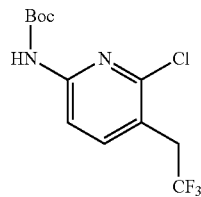

A solution of 6-chloro-5-(2,2,2-trifluoroethyl)pyridine-2-carboxylic acid (300.0 mg, 1.25 mmol), diphenylphosphoryl azide (0.27 mL, 1.25 mmol) and triethylamine (0.17 mL, 1.25 mmol) in 2-methyl-1-propanol (10 mL) was stirred at 85° C. for 2 hours. After completion, the solvent was concentrated under vacuum. The residue was purified by flash chromatography on silica gel eluting with petroleum ether/ethyl acetate (90/10) to afford tert-butyl N-[6-chloro-5-(2,2,2-trifluoroethyl)-2-pyridyl]carbamate (100.0 mg, 0.32 mmol, 25.7% yield) as a yellow oil. LC-MS (ESI, m/z): 311.1 [M+H]$^+$.

Step 2: tert-butyl 4-[7-[6-(tert-butoxycarbonylamino)-3-(2,2,2-trifluoroethyl)-2-pyridyl]-6-chloro-quinazolin-4-yl]piperazine-1-carboxylate

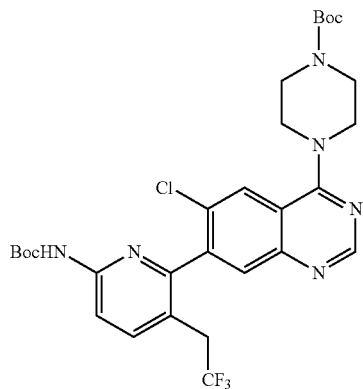 [SMILES: CC(C)(C)OC(=O)Nc1ccc(CC(F)(F)F)c(-c2cc3ncnc(N4CCN(C(=O)OC(C)(C)C)CC4)c3cc2Cl)n1]

Under nitrogen, a solution of tert-butyl 4-[6-chloro-7-(4,4,5,5-tetramethyl-1,3,2-dioxaborolan-2-yl)quinazolin-4-yl]piperazine-1-carboxylate (183.4 mg, 0.39 mmol), tert-butyl N-[6-chloro-5-(2,2,2-trifluoroethyl)-2-pyridyl]carbamate (100.0 mg, 0.32 mmol), bis(triphenylphosphine)palladium (ii)dichloride (22.7 mg, 0.03 mmol) and potassium fluoride (56.0 mg, 0.97 mmol) in acetonitrile (3 mL) and water (0.5 mL) was stirred at 110° C. for 20 min. After completion, the resulting solution was diluted with dichloromethane (200 mL), washed with brine (80 mL×3), dried over anhydrous sodium sulfate and concentrated under vacuum. The residue was purified by flash chromatography on silica gel eluting with dichloromethane/methanol (95/5) to afford tert-butyl 4-[7-[6-(tert-butoxycarbonylamino)-3-(2,2,2-trifluoroethyl)-2-pyridyl]-6-chloro-quinazolin-4-yl]piperazine-1-carboxylate (80 mg, 0.13 mmol, 39.9% yield) as a solid. LC-MS (ESI, m/z): 623.1 [M+H]$^+$.

Step 3: 6-(6-chloro-4-piperazin-1-yl-quinazolin-7-yl)-5-(2,2,2-trifluoroethyl)pyridin-2-amine

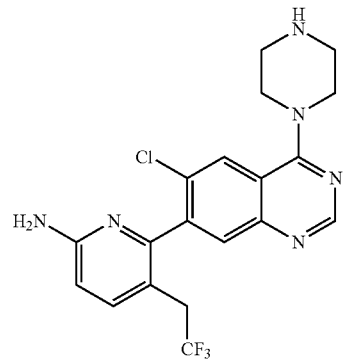 [SMILES: Nc1ccc(CC(F)(F)F)c(-c2cc3ncnc(N4CCNCC4)c3cc2Cl)n1]

A solution of tert-butyl 4-[7-[6-(tert-butoxycarbonylamino)-3-(2,2,2-trifluoroethyl)-2-pyridyl]-6-chloro-quinazolin-4-yl]piperazine-1-carboxylate (50.0 mg, 0.08 mmol) in TFA (2 mL) and dichloromethane (10 mL) was stirred at 25° C. for 3 hours. After completion, the solvent was concentrated under vacuum. The material was taken to next step without further purification. LC-MS (ESI, m/z): 423.1 [M+H]$^+$.

Step 4: 1-[4-[7-[6-amino-3-(2,2,2-trifluoroethyl)-2-pyridyl]-6-chloro-quinazolin-4-yl]piperazin-1-yl]prop-2-en-1-one

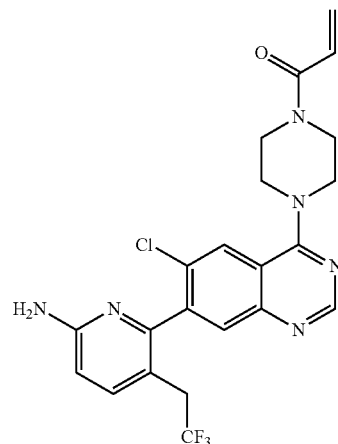

A solution of 6-(6-chloro-4-piperazin-1-yl-quinazolin-7-yl)-5-(2,2,2-trifluoroethyl)pyridin-2-amine (50.0 mg, 0.12 mmol), acrylic acid (8.5 mg, 0.12 mmol), HATU (54.0 mg, 0.14 mmol) and N,N-diisopropylethylamine (22.9 mg, 0.18 mmol) in dichloromethane (5 mL) was stirred at −78° C. for 30 min. After completion, the resulting solution was quenched with water (1 mL), diluted with dichloromethane (200 mL), washed with brine (80 mL×3), dried over anhydrous sodium sulfate and concentrated under vacuum. The residue was purified by flash chromatography on silica gel eluting with dichloromethane/methanol (95/5) to afford 1-[4-[7-[6-amino-3-(2,2,2-trifluoroethyl)-2-pyridyl]-6- chloro-quinazolin-4-yl]piperazin-1-yl]prop-2-en-1-one (7.6 mg, 13.5% yield) as a white solid. LC-MS (ESI, m/z): 477.1 [M+H]$^+$.
Example 51
$^1$H NMR (300 MHz, Methanol-d$_4$, ppm) δ 8.68 (s, 1H), 8.24 (s, 1H), 7.80 (s, 1H), 7.62 (d, J=8.6 Hz, 1H), 6.84 (dd, J=16.8, 10.6 Hz, 1H), 6.72 (d, J=8.7 Hz, 1H), 6.29 (dd, J=16.8, 2.0 Hz, 1H), 5.82 (dd, J=10.6, 2.0 Hz, 1H), 4.06-4.01 (m, 4H), 3.98-3.93 (m, 4H), 3.43-3.36 (m, 1H), 3.16-3.00 (m, 1H).
Example 52
1-[4-[7-[6-amino-4-ethyl-3-(trifluoromethyl)-2-pyridyl]-6-chloro-quinazolin-4-yl]piperazin-1-yl]prop-2-en-1-one
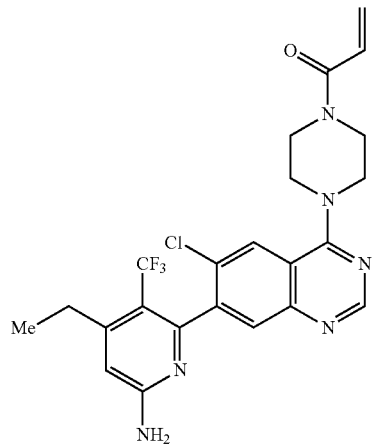 [SMILES: C=CC(=O)N1CCN(c2ncnc3cc(-c4nc(N)cc(CC)c4C(F)(F)F)c(Cl)cc23)CC1]
Synthetic Route
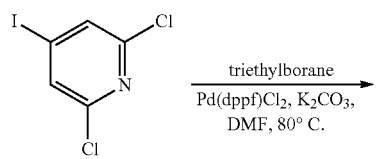
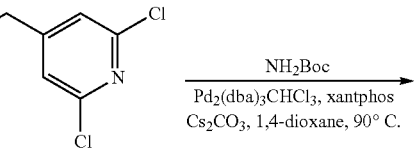
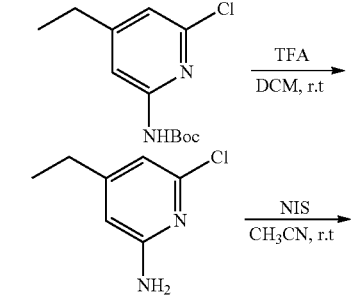
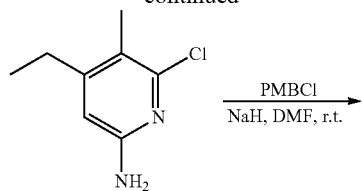
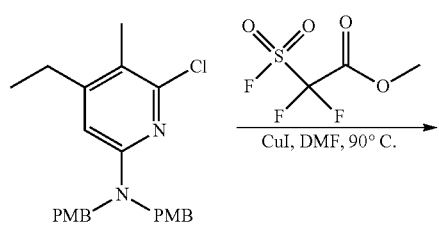
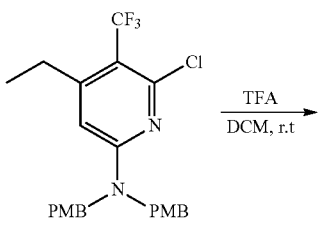
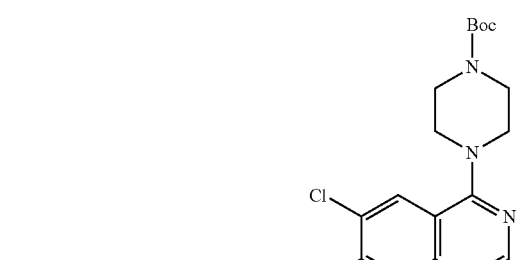

401

-continued

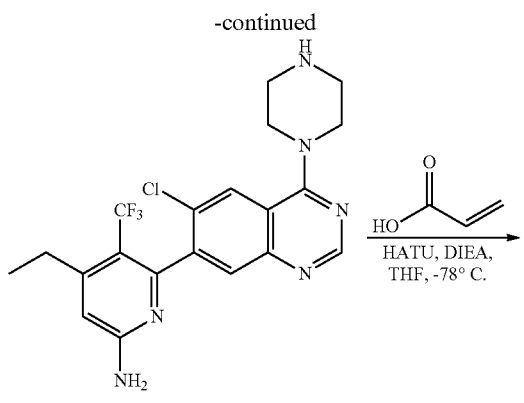

10

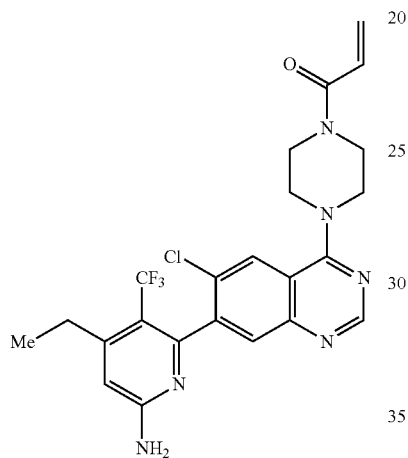

Step 1: 2,6-dichloro-4-ethylpyridine

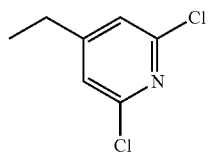

Under nitrogen, a solution of 2,6-dichloro-4-iodopyridine (10.00 g, 36.51 mmol), triethylborane (36.0 mL, 36.00 mmol), 1,1′-bis(diphenylphosphino)ferrocene-palladium(II) dichloride (2.67 g, 3.65 mmol) and potassium carbonate (10.00 g, 72.36 mmol) in N,N-dimethylformamide (80 mL) was stirred for 60 min at 80° C. After completion, the resulting solution was diluted with water (100 mL), extracted with ethyl acetate (150 mL×3), washed with brine (150 mL×3), dried over anhydrous sodium sulfate and concentrated under vacuum. The residue was applied onto a silica gel column eluting with ethyl acetate/petroleum ether (3/97) to afford 6.3 g (98%) of 2,6-dichloro-4-ethylpyridine as a solid. LC-MS (ESI, m/z): 176.0 [M+H]⁺.

402

Step 2: tert-butyl N-(6-chloro-4-ethylpyridin-2-yl)carbamate

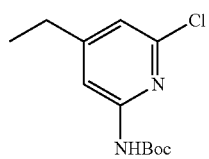

A solution of 2,6-dichloro-4-ethylpyridine (3.00 g, 17.04 mmol), tert-butyl carbamate (2.20 g, 18.78 mmol), tris(dibenzylideneacetone)dipalladium-chloroform adduct (880.0 mg, 0.85 mmol), XantPhos (985.0 mg, 1.70 mmol) and cesium carbonate (11.00 g, 33.76 mmol) in 1,4-dioxane (50 mL) was stirred for 60 min at 90° C. After completion, the resulting solution was concentrated under vacuum, diluted with dichloromethane (200 mL), washed with brine (80 mL×3), dried over anhydrous sodium sulfate and concentrated under vacuum. The residue was applied onto a silica gel column eluting with ethyl acetate/petroleum ether (1/10). This resulted in 3.3 g (69%) of tert-butyl N-(6-chloro-4-ethylpyridin-2-yl)carbamate as a solid. LC-MS (ESI, m/z): 257.1 [M+H]⁺.

Step 3: 6-chloro-4-ethylpyridin-2-amine

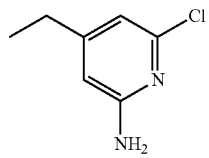

A solution of tert-butyl N-(6-chloro-4-ethylpyridin-2-yl)carbamate (3.00 g, 11.68 mmol) in trifluoroacetic acid (20 mL) and dichloromethane (70 mL) was stirred for 60 min at 25° C. After completion, the resulting solution was concentrated under vacuum, diluted with water (30 mL), the pH of the resulting solution was adjusted to pH=7.0 with sodium carbonate saturated aqueous solution, extracted with ethyl acetate (100 mL×3), dried over anhydrous sodium sulfate and concentrated under vacuum. The residue was applied onto a silica gel column eluting with ethyl acetate/petroleum ether (1/3) to afford 1.52 g (83%) of 6-chloro-4-ethylpyridin-2-amine as a solid. LC-MS (ESI, m/z): 157.0 [M+H]⁺.

Step 4: 6-chloro-4-ethyl-5-iodopyridin-2-amine

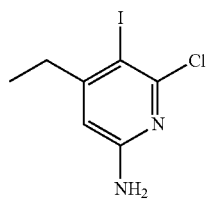

A solution of 6-chloro-4-ethylpyridin-2-amine (1.50 g, 9.58 mmol) and NIS (2.16 g, 9.60 mmol) in acetonitrile (70 mL) was stirred for 2 h at 25° C. After completion, the resulting solution was concentrated under vacuum, diluted with dichloromethane (200 mL), washed with brine (80 mL×3), dried over anhydrous sodium sulfate and concentrated under vacuum. The residue was applied onto a silica gel column eluting with ethyl acetate/petroleum ether (1/10) to afford 1.73 g (64%) of 6-chloro-4-ethyl-5-iodopyridin-2-amine as a solid. LC-MS (ESI, m/z): 282.9 [M+H]⁺.

Step 5: 6-chloro-4-ethyl-5-iodo-N,N-bis[(4-methoxyphenyl)methyl]pyridin-2-amine

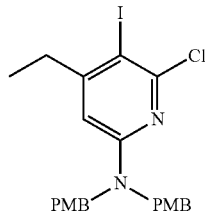

A solution of 6-chloro-4-ethyl-5-iodopyridin-2-amine (1.05 g, 3.72 mmol), 1-(chloromethyl)-4-methoxybenzene (1.75 g, 11.17 mmol) and sodium hydride (270.0 mg, 11.25 mmol) in N,N-dimethylformamide (15.00 mL) was stirred for 60 min at 25° C. After completion, the resulting solution was quenched with ammonium chloride saturated solution, extracted with ethyl acetate (100 mL×3), washed with brine (80 mL×3), dried over anhydrous sodium sulfate and concentrated under vacuum. The residue was applied onto a silica gel column eluting with ethyl acetate/petroleum ether (1/10) to afford 1.10 g (57%) of 6-chloro-4-ethyl-5-iodo-N,N-bis[(4-methoxyphenyl)methyl]pyridin-2-amine as a solid. LC-MS (ESI, m/z): 523.1 [M+H]⁺.

Step 6: 6-chloro-4-ethyl-N,N-bis[(4-methoxyphenyl)methyl]-5-(trifluoromethyl)pyridin-2-amine

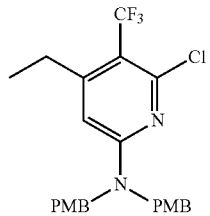

A solution of 6-chloro-4-ethyl-5-iodo-N,N-bis[(4-methoxyphenyl)methyl]pyridin-2-amine (1.20 g, 2.30 mmol), copper(I) iodide (0.87 g, 4.60 mmol) and methyl 2,2-difluoro-2-(fluorosulfonyl)acetate (0.58 mL, 4.59 mmol) in N,N-dimethylformamide (10 mL) was stirred at 90° C. for 2 hours. After completion, the resulting solution was diluted with water (50 mL), extracted with ethyl acetate (100 mL×3), washed with brine (80 mL×3), dried over anhydrous sodium sulfate and concentrated under vacuum. The residue was applied onto a silica gel column eluting with ethyl acetate/petroleum ether (1/10) to afford 0.70 g (70%) of 6-chloro-4-ethyl-N,N-bis[(4-methoxyphenyl)methyl]-5-(trifluoromethyl)pyridin-2-amine. LC-MS (ESI, m/z): 465.1 [M+H]

Step 7: 6-chloro-4-ethyl-5-(trifluoromethyl)pyridin-2-amine

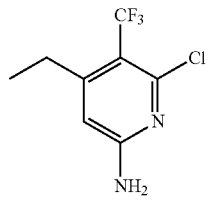

A solution of 6-chloro-4-ethyl-N,N-bis[(4-methoxyphenyl)methyl]-5-(trifluoromethyl)pyridin-2-amine (1.20 g, 2.58 mmol) in dichloromethane (10 mL) and trifluoroacetic acid (10 mL) was stirred at 40° C. for 2 hours. After completion, the resulting solution was concentrated under vacuum, diluted with water (50 mL), the pH of the resulting solution was adjusted to pH=8 with sodium carbonate saturated aqueous solution, extracted with ethyl acetate (100 mL×3), washed with brine (80 mL×3), dried over anhydrous sodium sulfate and concentrated under vacuum. The residue was purified by flash chromatography on silica gel eluting with petroleum ether/ethyl acetate (1/10) to afford 0.59 g (89.6%) of 6-chloro-4-ethyl-5-(trifluoromethyl)pyridin-2-amine. LC-MS (ESI, m/z): 225.0 [M+H]⁺.

Step 8: tert-butyl 4-[7-[6-amino-4-ethyl-3-(trifluoromethyl)-2-pyridyl]-6-chloro-quinazolin-4-yl]piperazine-1-carboxylate

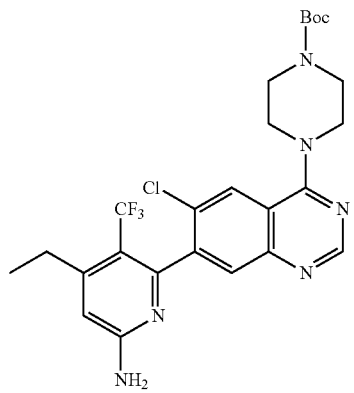 [SMILES: CCc1cc(N)nc(-c2cc3ncnc(N4CCN(C(=O)OC(C)(C)C)CC4)c3cc2Cl)c1C(F)(F)F]

Under nitrogen, a solution of 6-chloro-4-ethyl-5-(trifluoromethyl)pyridin-2-amine (560.0 mg, 2.49 mmol), tert-butyl 4-[6-chloro-7-(4,4,5,5-tetramethyl-1,3,2-dioxaborolan-2-yl)quinazolin-4-yl]piperazine-1-carboxylate (1.42 g, 2.99 mmol), bis(triphenylphosphine)palladium(II)dichloride (175.5 mg, 0.25 mmol) and potassium fluoride (289.7 mg, 4.99 mmol) in acetonitrile (10 mL) and water (2 mL) was stirred at 90° C. for 1 hour. After completion, the resulting solution was concentrated under vacuum, diluted with dichloromethane (200 mL), washed with brine (80 mL×3), dried over anhydrous sodium sulfate and concentrated under vacuum. The residue was purified by flash chromatography on silica gel eluting with methanol/dichloromethane (1/20) to afford 250.0 mg (18.7%) tert-butyl 4-[7-[6-amino-4- ethyl-3-(trifluoromethyl)-2-pyridyl]-6-chloro-quinazolin-4-yl]piperazine-1-carboxylate. LC-MS (ESI, m/z): 537.2 [M+H]⁺.

Step 9: 6-(6-chloro-4-piperazin-1-yl-quinazolin-7-yl)-4-ethyl-5-(trifluoromethyl)pyridin-2-amine

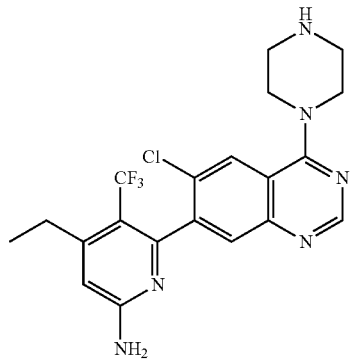 [SMILES: CCc1cc(N)nc(-c2cc3ncnc(N4CCNCC4)c3cc2Cl)c1C(F)(F)F]

A solution of tert-butyl 4-[7-[6-amino-4-ethyl-3-(trifluoromethyl)-2-pyridyl]-6-chloro-quinazolin-4-yl]piperazine-1-carboxylate (250.0 mg, 0.47 mmol) in dichloromethane (10 mL) and trifluoroacetic acid (2 mL) was stirred at 25° C. for 0.5 hour. After completion, the resulting solution was concentrated under vacuum, diluted with water (50 mL), the pH of the resulting solution was adjusted to pH=8 with sodium carbonate saturated aqueous solution, extracted with ethyl acetate (100 mL×3), washed with brine (80 mL×3), dried over anhydrous sodium sulfate and concentrated under vacuum. The residue was purified by flash chromatography on silica gel eluting with methanol/dichloromethane (1/5) to afford 142.0 mg (70%) of 6-(6-chloro-4-piperazin-1-yl-quinazolin-7-yl)-4-ethyl-5-(trifluoromethyl)pyridin-2-amine. LC-MS (ESI, m/z): 437.1 [M+H]⁺.

Step 10: 1-[4-[7-[6-amino-4-ethyl-3-(trifluoromethyl)-2-pyridyl]-6-chloro-quinazolin-4-yl]piperazin-1-yl]prop-2-en-1-one

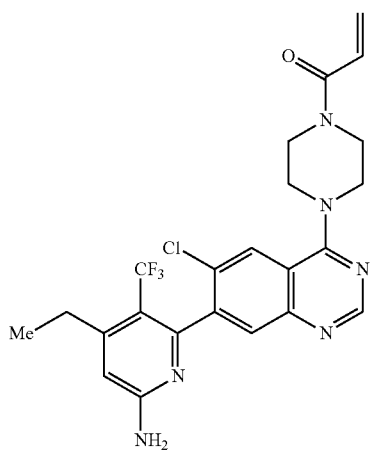 [SMILES: C=CC(=O)N1CCN(c2ncnc3cc(-c4nc(N)cc(CC)c4C(F)(F)F)c(Cl)cc23)CC1]

A solution of 6-(6-chloro-4-piperazin-1-yl-quinazolin-7-yl)-4-ethyl-5-(trifluoromethyl)pyridin-2-amine (211.0 mg, 0.48 mmol), acrylic acid (0.05 mL, 0.72 mmol), N,N-diisopropylethylamine (1.0 mL, 5.74 mmol) and HATU (220.4 mg, 0.58 mmol) in dichloromethane (7 mL) was stirred at −78° C. for 0.5 hour. After completion, the resulting solution was diluted with dichloromethane (200 mL), washed with brine (80 mL×3), dried over anhydrous sodium sulfate and concentrated under vacuum. The residue was purified by flash chromatography on silica gel eluting with dichloromethane/methanol (10/1) to afford 48.4 mg (20.1%) of 1-[4-[7-[6-amino-4-ethyl-3-(trifluoromethyl)-2-pyridyl]-6-chloro-quinazolin-4-yl]piperazin-1-yl]prop-2-en-1-one. LC-MS (ESI, m/z): 491.1 [M+H]⁺.

Example 52

¹H NMR (400 MHz, DMSO-d₆, ppm) δ 8.67 (s, 1H), 8.11 (s, 1H), 7.65 (s, 1H), 6.88-6.81 (m, 3H), 6.54 (s, 1H), 6.18 (dd, J=16.7, 2.4 Hz, 1H), 5.75 (dd, J=10.4, 2.4 Hz, 1H), 3.86 (brs, 7H), 3.78 (brs, 1H), 2.74-2.68 (m, 2H), 1.24 (t, J=7.4 Hz, 3H).

Example 53

1-(4-[6-chloro-7-[6-(methylamino)-3-(trifluoromethyl)pyridin-2-yl]quinazolin-4-yl]piperazin-1-yl)prop-2-en-1-one

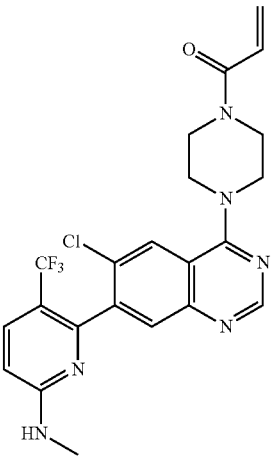 [SMILES: C=CC(=O)N1CCN(c2ncnc3cc(-c4nc(NC)ccc4C(F)(F)F)c(Cl)cc23)CC1]

Synthetic Route

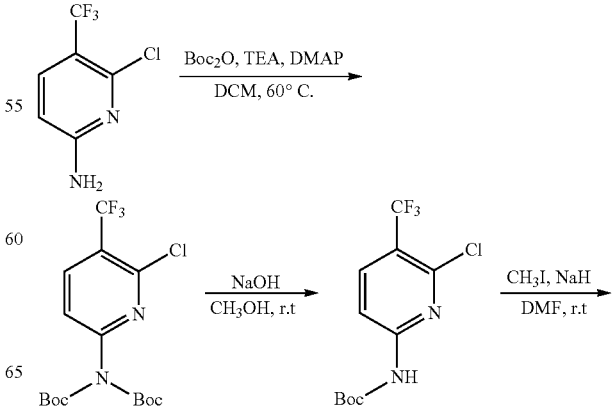

-continued

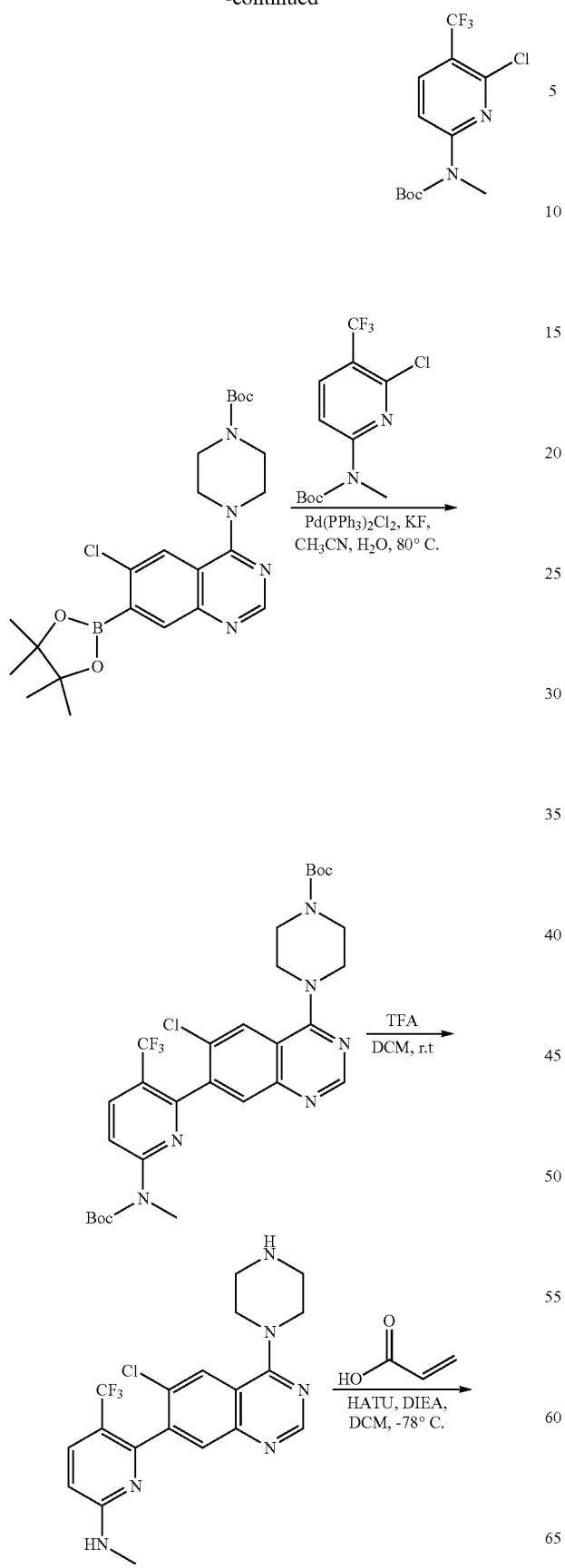

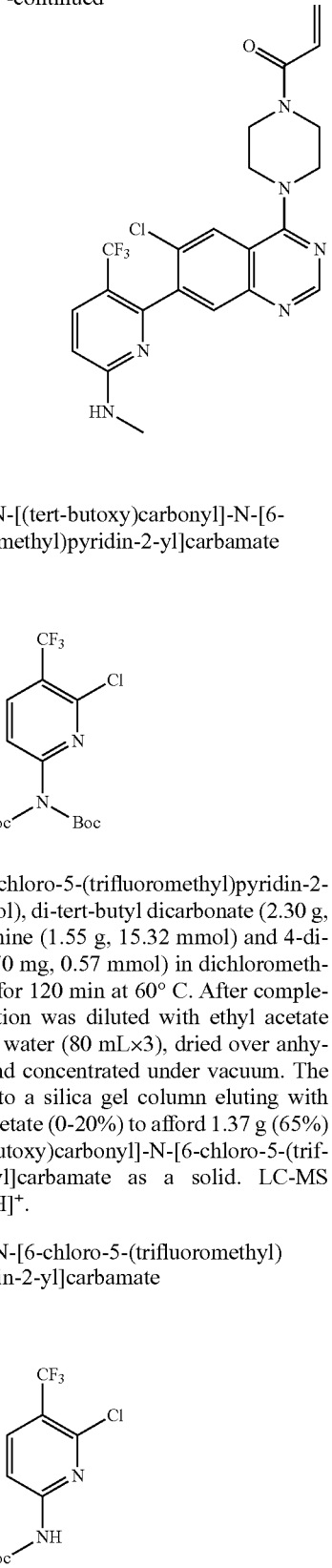

Step 1: tert-butyl N-[(tert-butoxy)carbonyl]-N-[6-chloro-5-(trifluoromethyl)pyridin-2-yl]carbamate A solution of 6-chloro-5-(trifluoromethyl)pyridin-2-amine (1.04 g, 5.29 mmol), di-tert-butyl dicarbonate (2.30 g, 10.54 mmol), triethylamine (1.55 g, 15.32 mmol) and 4-dimethylaminopyridine (70 mg, 0.57 mmol) in dichloromethane (6 mL) was stirred for 120 min at 60° C. After completion, the resulting solution was diluted with ethyl acetate (200 mL), washed with water (80 mL×3), dried over anhydrous sodium sulfate and concentrated under vacuum. The residue was applied onto a silica gel column eluting with petroleum ether/ethyl acetate (0-20%) to afford 1.37 g (65%) of tert-butyl N-[(tert-butoxy)carbonyl]-N-[6-chloro-5-(trifluoromethyl)pyridin-2-yl]carbamate as a solid. LC-MS (ESI, m/z): 397.1 [M+H]$^+$.

Step 2: tert-butyl N-[6-chloro-5-(trifluoromethyl)pyridin-2-yl]carbamate

A solution of tert-butyl N-[(tert-butoxy)carbonyl]-N-[6-chloro-5-(trifluoromethyl)pyridin-2-yl]carbamate (1.37 g, 3.45 mmol) and sodium hydroxide (848.0 mg, 21.20 mmol)

in water (7 mL) and tetrahydrofuran (7 mL) was stirred for 120 min at 70° C. After completion, the pH of the resulting solution was adjusted to pH=7.0 with HCl/1,4-dioxane, diluted with ethyl acetate (200 mL), washed with water (80 mL×3), dried over anhydrous sodium sulfate and concentrated under vacuum. The residue was applied onto a silica gel column eluting with petroleum ether/ethyl acetate (0-30%) to afford 523.0 mg (70%) of tert-butyl N-[6-chloro-5-(trifluoromethyl)pyridin-2-yl]carbamate as a solid. LC-MS (ESI, m/z): 297.1 [M+H]$^+$.

Step 3: tert-butyl N-[6-chloro-5-(trifluoromethyl)pyridin-2-yl]-N-methylcarbamate

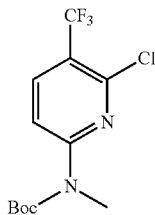

A solution of tert-butyl N-[6-chloro-5-(trifluoromethyl)pyridin-2-yl]carbamate (1.00 g, 3.37 mmol) in N,N-dimethylformamide (11 mL) was added sodium hydride (206.0 mg, 8.58 mmol) stirred for 5 min at 0° C. Then iodomethane (1.00 g, 7.04 mmol) was added and stirred for 30 min at 0° C. After completion, the resulting solution was quenched with ammonium chloride saturated solution, extracted with (80 mL×3), washed with (80 mL×3), dried over anhydrous sodium sulfate and concentrated under vacuum. The residue was applied onto a silica gel column eluting with petroleum ether/ethyl acetate (0-30%) to afford 1.00 g (95%) of tert-butyl N-[6-chloro-5-(trifluoromethyl)pyridin-2-yl]-N-methylcarbamate as a solid. LC-MS (ESI, m/z): 311.1 [M+H]$^+$.

Step 4: tert-butyl 4-[7-(6-[[(tert-butoxy)carbonyl](methyl)amino]-3-(trifluoromethyl)pyridin-2-yl)-6-chloroquinazolin-4-yl]piperazine-1-carboxylate

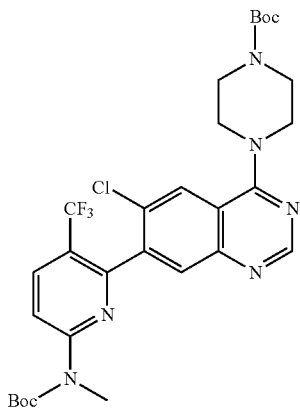 [SMILES: CN(C(=O)OC(C)(C)C)c1ccc(C(F)(F)F)c(-c2cc3ncnc(N4CCN(C(=O)OC(C)(C)C)CC4)c3cc2Cl)n1]

Under nitrogen, a solution of tert-butyl N-[6-chloro-5-(trifluoromethyl)pyridin-2-yl]-N-methylcarbamate (200.0 mg, 0.64 mmol), tert-butyl 4-[6-chloro-7-(tetramethyl-1,3,2-dioxaborolan-2-yl)quinazolin-4-yl]piperazine-1-carboxylate (360.0 mg, 0.76 mmol), bis(triphenylphosphine)palladium(II) chloride (45.0 mg, 0.064 mmol) and potassium fluoride (120.0 mg, 2.07 mmol) in acetonitrile (3 mL) and water (0.6 mL) was stirred for 30 min at 80° C. After completion, the resulting solution was diluted with ethyl acetate (200 mL), washed with water (80 mL×3), dried over anhydrous sodium sulfate and concentrated under vacuum. The residue was applied onto a silica gel column eluting with dichloromethane/methanol (0-10%) to afford 380 mg (95%) of tert-butyl 4-[7-(6-[[(tert-butoxy)carbonyl](methyl)amino]-3-(trifluoromethyl)pyridin-2-yl)-6-chloroquinazolin-4-yl]piperazine-1-carboxylate as a solid. LC-MS (ESI, m/z): 623.2 [M+H]$^+$.

Step 5: 6-[6-chloro-4-(piperazin-1-yl)quinazolin-7-yl]-N-methyl-5-(trifluoromethyl)pyridin-2-amine

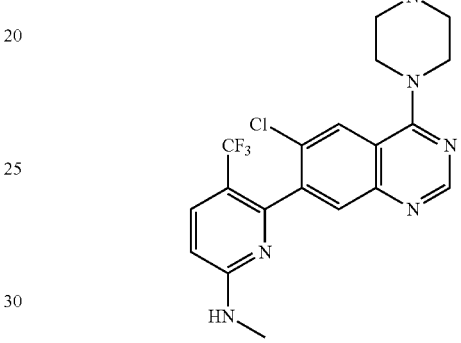

A solution of tert-butyl 4-[7-(6-[[(tert-butoxy)carbonyl](methyl)amino]-3-(trifluoromethyl)pyridin-2-yl)-6-chloroquinazolin-4-yl]piperazine-1-carboxylate (380.0 mg, 0.61 mmol) in trifluoroacetic acid (3 mL) and dichloromethane (10 mL) was stirred for 30 min at 25° C. After completion, the resulting solution was concentrated under vacuum to afford 450.0 mg (crude) of 6-[6-chloro-4-(piperazin-1-yl)quinazolin-7-yl]-N-methyl-5-(trifluoromethyl)pyridin-2-amine as brown oil. LC-MS (ESI, m/z): 523.2 [M+H]$^+$.

Step 6: 1-(4-[6-chloro-7-[6-(methylamino)-3-(trifluoromethyl)pyridin-2-yl]quinazolin-4-yl]piperazin-1-yl)prop-2-en-1-one

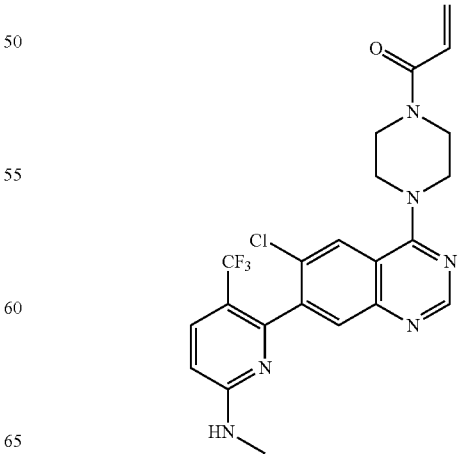

411

A solution of 6-[6-chloro-4-(piperazin-1-yl)quinazolin-7-yl]-N-methyl-5-(trifluoromethyl)pyridin-2-amine (420.0 mg, 0.99 mmol), prop-2-enoic acid (97.0 mg, 1.35 mmol), HATU (410.0 mg, 1.08 mmol) and N,N-diisopropylethyl-amine (1 mL, 6.05 mmol) in dichloromethane (10 mL) was stirred for 30 min at −78° C. After completion, the resulting solution was quenched with water (1 mL), diluted with dichloromethane (200 mL), washed with water (80 mL×3), dried over anhydrous sodium sulfate and concentrated under vacuum. The residue was applied onto a silica gel column eluting with dichloromethane/methanol (0-10%) to afford 40.1 mg (8%) of 1-(4-[6-chloro-7-[6-(methylamino)-3-(tri-fluoromethyl)pyridin-2-yl]quinazolin-4-yl]piperazin-1-yl) prop-2-en-1-one as a solid. LC-MS (ESI, m/z): 477.1 [M+H]$^+$.

Example 53

$^1$H NMR (400 MHz, Methanol-d$_4$, ppm) δ 8.68 (s, 1H), 8.20 (s, 1H), 7.80-7.76 (m, 2H), 6.85 (dd, J=16.8, 10.6 Hz, 1H), 6.65 (dd, J=9.0, 0.9 Hz, 1H), 6.30 (dd, J=16.8, 1.9 Hz, 1H), 5.83 (dd, J=10.6, 2.0 Hz, 1H), 4.03-4.01 (m, 4H), 3.96-3.91 (m, 4H), 2.91 (s, 3H).

Example 54

1-[(3S)-4-[7-[6-amino-3-(trifluoromethyl)pyridin-2-yl]-6-chloroquinazolin-4-yl]-3-methylpiperazin-1-yl] prop-2-en-1-one Synthetic Route

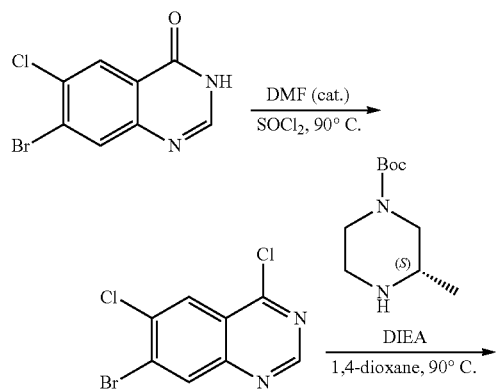

412

-continued

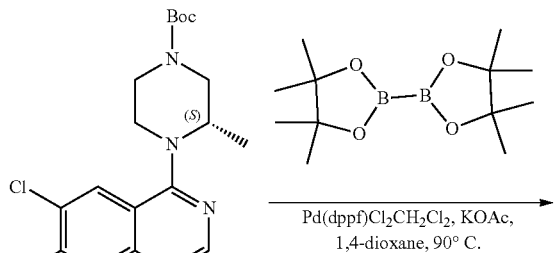

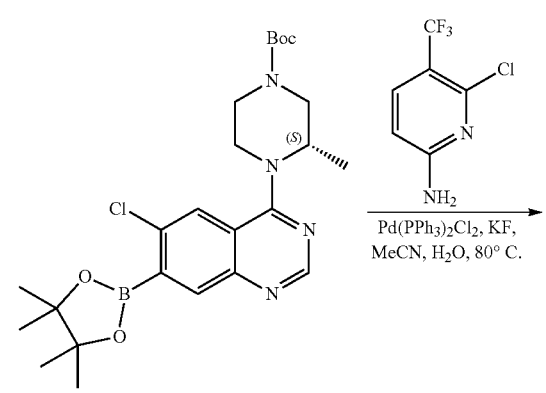

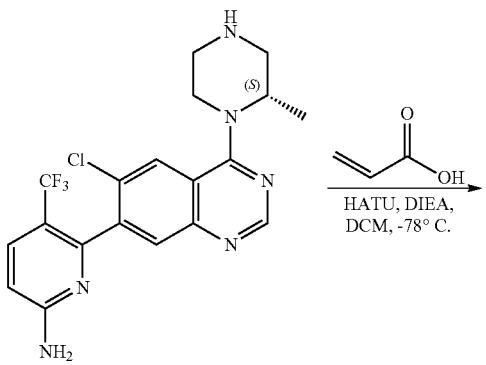

-continued

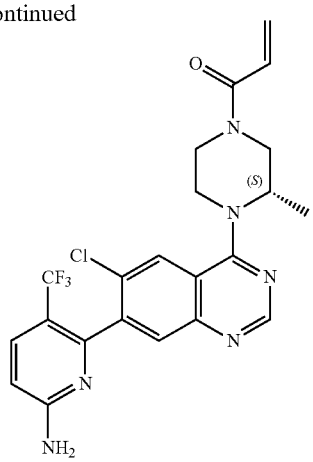

Step 1: 7-bromo-4,6-dichloroquinazoline

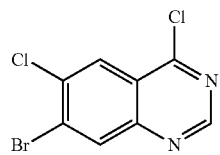 [SMILES: Clc1cc2c(Cl)ncnc2cc1Br]

A solution of 7-bromo-6-chloro-3,4-dihydroquinazolin-4-one (10.00 g, 38.54 mmol) in thionyl chloride (40 mL) was added N,N-dimethylformamide (0.2 mL) and stirred for 3 h at 90° C. After completion, the resulting solution was concentrated under vacuum. This resulted in 11.00 g (crude) of 7-bromo-4,6-dichloroquinazoline as a white solid. LC-MS (ESI, m/z): 276.9 [M+H]$^+$.

Step 2: tert-butyl (3S)-4-(7-bromo-6-chloroquinazolin-4-yl)-3-methylpiperazine-1-carboxylate

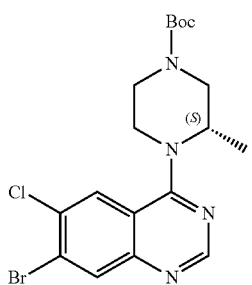

A solution of 7-bromo-4,6-dichloroquinazoline (10.00 g, 35.98 mmol), tert-butyl (3S)-3-methylpiperazine-1-carboxylate (10.90 g, 54.424 mmol) and N,N-diisopropylethylam the (9.3 g, 71.96 mmol) in 1,4-dioxane (50 mL) was stirred for 1 h at 90° C. After completion, the resulting solution was concentrated under vacuum, diluted with dichloromethane (300 mL), washed with brine (80 mL×3), dried over anhydrous sodium sulfate and concentrated under vacuum. The residue was purified by flash chromatography on silica gel eluting with dichloromethane/methanol (20/1) to afford 10.00 g (63%) of tert-butyl (3S)-4-(7-bromo-6-chloroquinazolin-4-yl)-3-methylpiperazine-1-carboxylate as a yellow solid. LC-MS (ESI, m/z): 441.1 [M+H]$^+$.

Step 3: tert-butyl (3S)-4-[6-chloro-7-(tetramethyl-1,3,2-dioxaborolan-2-yl)quinazolin-4-yl]-3-methylpiperazine-1-carboxylate

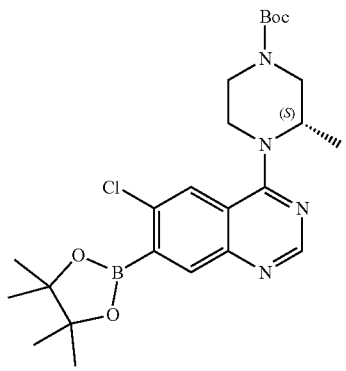

Under nitrogen, a solution of tert-butyl (3S)-4-(7-bromo-6-chloroquinazolin-4-yl)-3-methylpiperazine-1-carboxylate (1.00 g, 2.26 mmol), 4,4,5,5-tetramethyl-2-(tetramethyl-1,3,2-dioxaborolan-2-yl)-1,3,2-dioxaborolane (1.73 g, 6.81 mmol), 1,1'-bis(diphenylphosphino)ferrocene-palladium(II) dichloride dichloromethane complex (186.0 mg, 0.23 mmol) and potassium acetate (450 mg, 4.585 mmol) in 1,4-dioxane (8 mL) was stirred for 1 h at 90° C. After completion, the resulting solution was diluted with dichloromethane (200 mL), washed with brine (80 mL×3), dried over anhydrous sodium sulfate and concentrated under vacuum. The residue was applied onto reverse phase with water:acetonitrile (5%~60%). This resulted in 1.2 g (36%) of tert-butyl (3S)-4-[6-chloro-7-(tetramethyl-1,3,2-dioxaborolan-2-yl)quinazolin-4-yl]-3-methylpiperazine-1-carboxylate as a white solid. LC-MS (ESI, m/z): 489.2 [M+H]$^+$.

Step 4: tert-butyl (3S)-4-[7-[6-amino-3-(trifluoromethyl)pyridin-2-yl]-6-chloroquinazolin-4-yl]-3-methylpiperazine-1-carboxylate

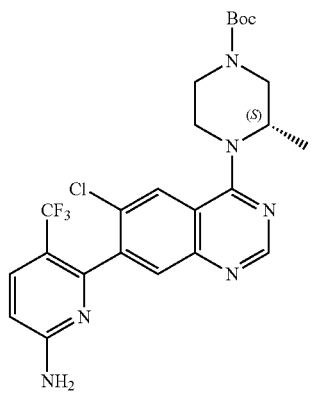

Under nitrogen, a solution of tert-butyl (3S)-4-[6-chloro-7-(tetramethyl-1,3,2-dioxaborolan-2-yl)quinazolin-4-yl]-3-methylpiperazine-1-carboxylate (800.0 mg, 1.64 mmol), 6-chloro-5-(trifluoromethyl)pyridin-2-amine (257.0 mg,

415

1.31 mmol), bis(triphenylphosphine)palladium(II) chloride (115.0 mg, 0.16 mmol) and potassium fluoride (190.0 mg, 3.27 mmol) in acetonitrile (6 mL) and water (1 mL) was stirred for 1 h at 110° C. After completion, the resulting solution was diluted with dichloromethane (200 mL), washed with brine (80 mL×3), dried over anhydrous sodium sulfate and concentrated under vacuum. The residue was applied onto a silica gel column eluting with methanol/dichloromethane (1/20) to afford 80.0 mg (9%) of tert-butyl (3S)-4-[7-[6-amino-3-(trifluoromethyl)pyridin-2-yl]-6-chloroquinazolin-4-yl]-3-methylpiperazine-1-carboxylate as a yellow solid. LC-MS (ESI, m/z): 523.2 [M+H]$^+$.

Step 5: 6-[6-chloro-4-[(2S)-2-methylpiperazin-1-yl]quinazolin-7-yl]-5-(trifluoromethyl)pyridin-2-amine

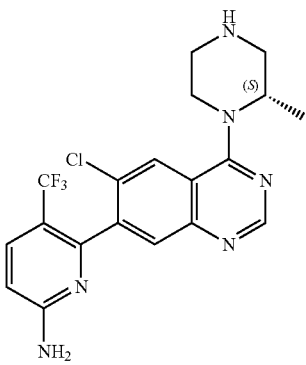

A solution of tert-butyl (3S)-4-[7-[6-amino-3-(trifluoromethyl)pyridin-2-yl]-6-chloroquinazolin-4-yl]-3-methylpiperazine-1-carboxylate (100.0 mg, 0.19 mmol) in trifluoroacetic acid (1 mL) and dichloromethane (3 mL) was stirred for 1 h at room temperature. After completion, the resulting solution was concentrated under vacuum, diluted with water (50 mL), the pH of the resulting solution was adjusted to pH=8 with sodium carbonate saturated aqueous solution, extracted with ethyl acetate (100 mL×3), dried over anhydrous sodium sulfate and concentrated under vacuum. This resulted in 90 mg (crude) of 6-[6-chloro-4-[(2S)-2-methylpiperazin-1-yl]quinazolin-7-yl]-5-(trifluoromethyl)pyridin-2-amine as a gray solid. LC-MS (ESI, m/z): 423.1 [M+H]$^+$.

416

Step 6: 1-[(3S)-4-[7-[6-amino-3-(trifluoromethyl)pyridin-2-yl]-6-chloroquinazolin-4-yl]-3-methylpiperazin-1-yl]prop-2-en-1-one

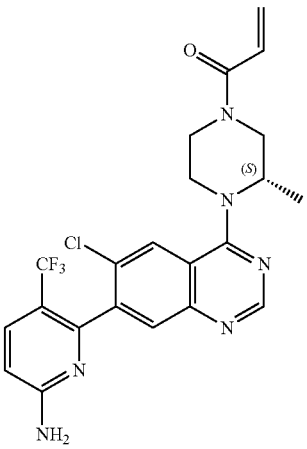

A solution of 6-[6-chloro-4-[(2S)-2-methylpiperazin-1-yl]quinazolin-7-yl]-5-(trifluoromethyl)pyridin-2-amine (200.0 mg, 0.47 mmol), prop-2-enoic acid (41.0 mg, 0.57 mmol), HATU (270.0 mg, 0.71 mmol) and N,N-diisopropylethylamine (122.0 mg, 0.94 mmol) in dichloromethane (5 mL) was stirred for 30 min at −78° C. After completion, the resulting solution was quenched with water (1 mL), diluted with dichloromethane (200 mL), washed with brine (80 mL×3), dried over anhydrous sodium sulfate and concentrated under vacuum. The residue was applied onto a silica gel column eluting with dichloromethane/methanol (20/1). The product was prepare by Pre-HPLC with following condition: Column: X Bridge C18, 19*150 mm, 5 um; Mobile Phase A:Water/0.05% TFA, Mobile Phase B: ACN; Flow rate: 20 mL/min; Gradient: 30% B to 70% B in 10 min; 254 nm. This resulted in 30.5 mg (14%) of 1-[(3S)-4-[7-[6-amino-3-(trifluoromethyl)pyridin-2-yl]-6-chloroquinazolin-4-yl]-3-methylpiperazin-1-yl]prop-2-en-1-one as a white solid. LC-MS (ESI, m/z): 477.1 [M+H]$^+$.

Example 54

$^1$H NMR (400 MHz, Methanol-d$_4$, ppm) δ 8.69 (s, 1H), 8.12 (s, 1H), 7.84 (d, J=8.9 Hz, 1H), 7.77 (s, 1H), 6.92-6.80 (m, 1H), 6.74 (dd, J=8.9, 0.8 Hz, 1H), 6.31 (dd, J=16.9, 5.7 Hz, 1H), 5.84 (dd, J=10.7, 1.9 Hz, 1H), 4.59-4.41 (m, 1H), 4.34-4.29 (m, 1H), 4.23-4.05 (m, 1H), 3.85-3.60 (m, 2H), 3.39-3.37 (m, 1H), 3.26-3.19 (m, 1H), 1.44 (d, J=6.8 Hz, 3H).

Example 55
2-[4-[7-[6-amino-4-methyl-3-(trifluoromethyl)-2-pyridyl]-6-chloro-2-[[(2S)-1-methylpyrrolidin-2-yl]methoxy]quinazolin-4-yl]-1-(2-fluoroprop-2-enoyl)piperazin-2-yl]acetonitrile
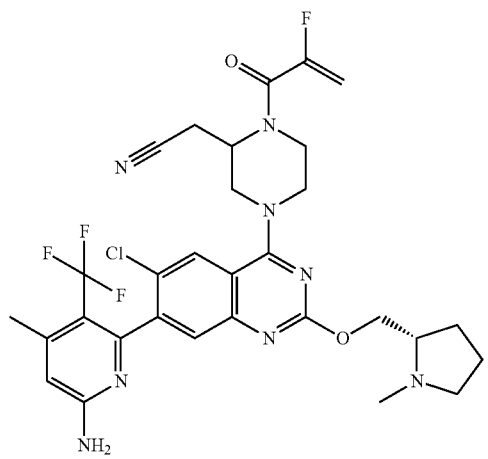 [SMILES: C=C(F)C(=O)N1CCN(c2nc(OC[C@@H]3CCCN3C)nc3cc(-c4nc(N)cc(C)c4C(F)(F)F)c(Cl)cc23)CC1CC#N]
Synthetic Route
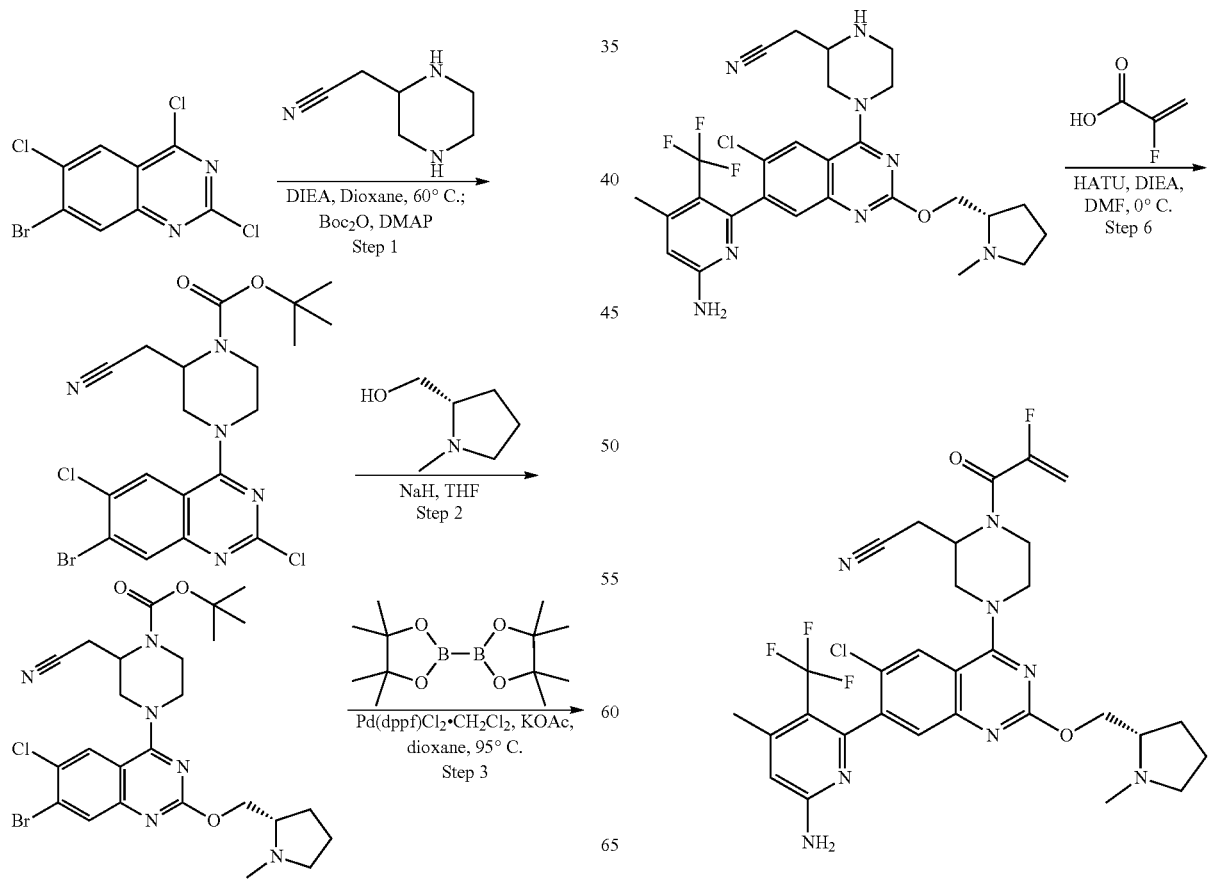
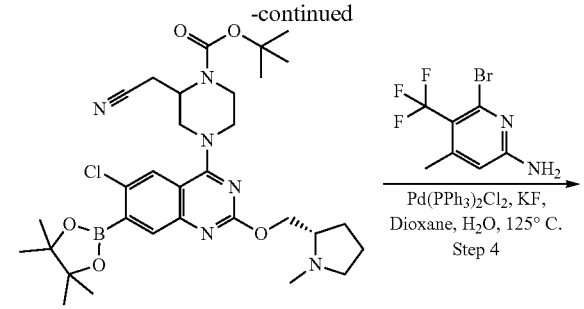
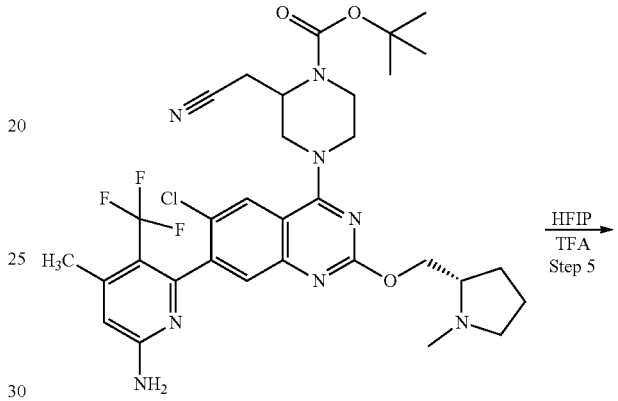

Step 1: tert-butyl 4-(7-bromo-2,6-dichloroquinazolin-4-yl)-2-(cyanomethyl)piperazine-1-carboxylate

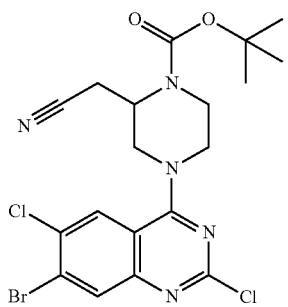 [SMILES: CC(C)(C)OC(=O)N1CCN(c2nc(Cl)nc3cc(Br)c(Cl)cc23)CC1CC#N]

To a solution of 7-bromo-2,4,6-trichloroquinazoline (536.5 mg, 1.67 mmol) in 1,4-dioxane (7.5 ml) was added N,N-diisopropylethylamine (1.00 ml, 6.00 mmol) and 2-piperazin-2-ylacetonitrile dihydrochloride (300 mg, 1.50 mmol). The reaction mixture was stirred at 60° C. for 1 hour. The reaction mixture was cooled to r.t. then 4-dimethylaminopyridine (37.5 mg, 0.303 mmol) and di-tert-butyl dicarbonate (1022 mg, 4.54 mmol) was added. The reaction mixture was stirred at r.t. for 18 hours. The reaction was quenched with water and extracted with EtOAc. The organic layers was dried with sodium sulfate, filtered, and concentrated via rotovap. The crude product was purified by flash chromatography on silica (eluting with MeOH/DCM) to give tert-butyl 4-(7-bromo-2,6-dichloroquinazolin-4-yl)-2-(cyanomethyl)piperazine-1-carboxylate (562 mg, 74%). LCMS (ESI, m/z): 501.9 [M+H]$^+$.

Step 2: tert-butyl 4-(7-bromo-6-chloro-2-(((S)-1-methylpyrrolidin-2-yl)methoxy)quinazolin-4-yl)-2-(cyanomethyl)piperazine-1-carboxylate

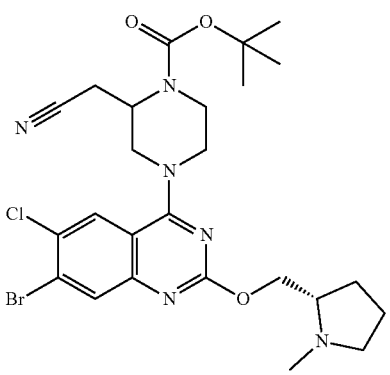 [SMILES: CN1CCC[C@H]1COc1nc(N2CCN(C(=O)OC(C)(C)C)C(CC#N)C2)c2cc(Cl)c(Br)cc2n1]

To a solution of [(2S)-1-methylpyrrolidin-2-yl]methanol (0.334 mL, 2.70 mmol) in tetrahydrofuran (18 mL) was added sodium hydride (60 mass %) in oil (108 mg, 2.70 mmol) at room temperature then stirred for 20 minutes. The reaction was cooled to 0° C. and a solution of tert-butyl 4-(7-bromo-2,6-dichloroquinazolin-4-yl)-2-(cyanomethyl)piperazine-1-carboxylate (450 mg, 0.90 mmol) in tetrahydrofuran (3 mL) was added. The reaction was warm to room temperature and stirred for 1 hour. The reaction mixture was quenched with water and extracted with EtOAc. The organic layers was dried with sodium sulfate, filtered, and concentrated via rotovap. The crude product was purified by flash chromatography on silica (eluting with MeOH/DCM) to give tert-butyl 4-(7-bromo-6-chloro-2-(((S)-1-methylpyrrolidin-2-yl)methoxy)quinazolin-4-yl)-2-(cyanomethyl)piperazine-1-carboxylate (224 mg, 43%). LCMS (ESI, m/z): 579.1 [M+H]$^+$.

Step 3: tert-butyl 4-(6-chloro-2-(((S)-1-methylpyrrolidin-2-yl)methoxy)-7-(4,4,5,5-tetramethyl-1,3,2-dioxaborolan-2-yl)quinazolin-4-yl)-2-(cyanomethyl)piperazine-1-carboxylate

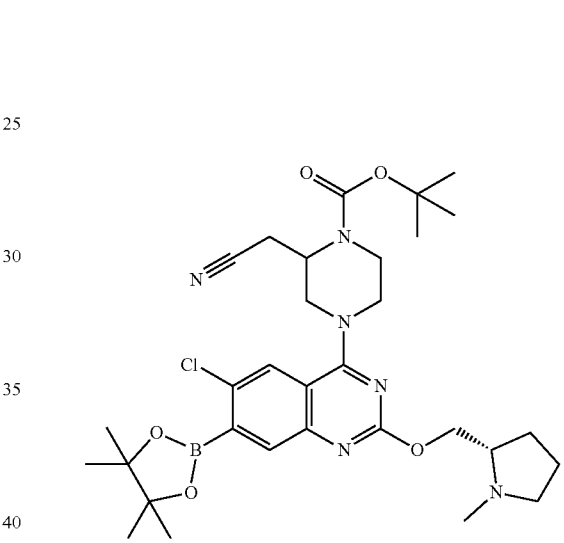

To a solution of tert-butyl 4-(7-bromo-6-chloro-2-(((S)-1-methylpyrrolidin-2-yl)methoxy)quinazolin-4-yl)-2-(cyanomethyl)piperazine-1-carboxylate (220 mg, 0.379 mmol) and bis(pinacolato)diboron (147 mg, 0.570 mmol) in 1,4-dioxane (7.0 mL) was added potassium acetate (55.9 mg, 0.570 mmol) and [1,1'-bis(diphenylphosphino)ferrocene]dichloropalladium(II) dichloromethane complex (28.0 mg, 0.038 mmol). The reaction mixture was degassed then heated at 95° C. for 2 hours. The reaction was filtered thru celite concentrated to give tert-butyl 4-(6-chloro-2-(((S)-1-methylpyrrolidin-2-yl)methoxy)-7-(4,4,5,5-tetramethyl-1,3,2-dioxaborolan-2-yl)quinazolin-4-yl)-2-(cyanomethyl)piperazine-1-carboxylate. The crude product was carried to next step. LCMS (ESI, m/z): 545.1 [M+H]$^+$ (LCMS shows mass of boronic acid).

Step 4: tert-butyl 4-(7-(6-amino-4-methyl-3-(trifluoromethyl)pyridin-2-yl)-6-chloro-2-(((S)-1-methylpyrrolidin-2-yl)methoxy)quinazolin-4-yl)-2-(cyanomethyl)piperazine-1-carboxylate

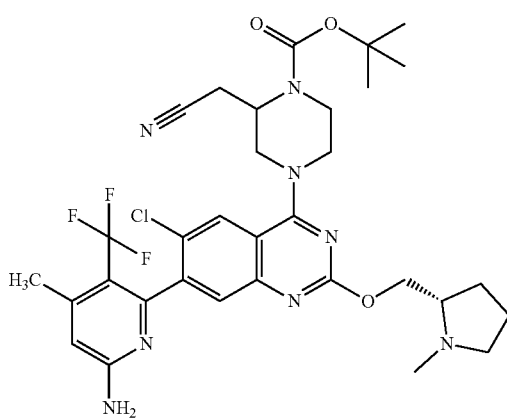 [SMILES: Cc1cc(N)nc(-c2cc3nc(OC[C@@H]4CCCN4C)nc(N4CCN(C(=O)OC(C)(C)C)C(CC#N)C4)c3cc2Cl)c1C(F)(F)F]

A suspension of tert-butyl 4-(6-chloro-2-(((S)-1-methylpyrrolidin-2-yl)methoxy)-7-(4,4,5,5-tetramethyl-1,3,2-dioxaborolan-2-yl)quinazolin-4-yl)-2-(cyanomethyl)piperazine-1-carboxylate (240 mg, 0.383 mmol), 6-bromo-4-methyl-5-(trifluoromethyl)pyridin-2-amine (195.0 mg, 0.766 mmol), bis(triphenylphosphine)palladium(II) dichloride (27.0 mg, 0.038 mmol), potassium fluoride (223 mg, 3.83 mmol) in 1,4-dioxane (7.0 mL) and water (3.5 mL) was degassed. The reaction mixture was heated microwave at 125° C. for 25 minutes. The reaction was filtered thru celite. The crude product was purified by flash chromatography on silica (eluting with MeOH/DCM) to give tert-butyl 4-(7-(6-amino-4-methyl-3-(trifluoromethyl)pyridin-2-yl)-6-chloro-2-(((S)-1-methylpyrrolidin-2-yl)methoxy)quinazolin-4-yl)-2-(cyanomethyl)piperazine-1-carboxylate (112 mg, 43%). LCMS (ESI, m/z): 675.4 [M+H]+.

Step 5: 2-(4-(7-(6-amino-4-methyl-3-(trifluoromethyl)pyridin-2-yl)-6-chloro-2-(((S)-1-methylpyrrolidin-2-yl)methoxy)quinazolin-4-yl)piperazin-2-yl)acetonitrile

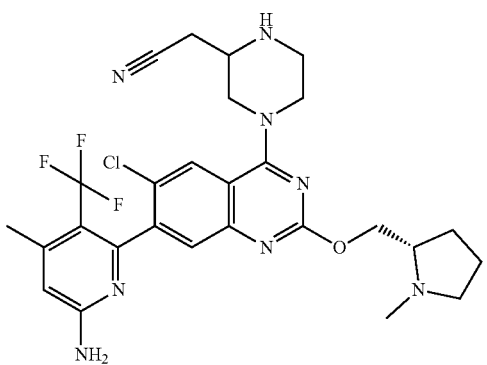 [SMILES: Cc1cc(N)nc(-c2cc3nc(OC[C@@H]4CCCN4C)nc(N4CCNC(CC#N)C4)c3cc2Cl)c1C(F)(F)F]

A solution of tert-butyl 4-(7-(6-amino-4-methyl-3-(trifluoromethyl)pyridin-2-yl)-6-chloro-2-(((S)-1-methylpyrrolidin-2-yl)methoxy)quinazolin-4-yl)-2-(cyanomethyl)piperazine-1-carboxylate (112 mg, 0.166 mmol) in 5% trifluoroacetic acid in hexafluoroisopropanol (2.509 mL, 1.66 mmol) was stirred at r.t. for 4 hours. The organic layers was dried with sodium sulfate, filtered, and concentrated via rotovap. The reaction was concentrated and the crude product was purified by HPLC to give 2-(4-(7-(6-amino-4-methyl-3-(trifluoromethyl)pyridin-2-yl)-6-chloro-2-(((S)-1-methylpyrrolidin-2-yl)methoxy)quinazolin-4-yl)piperazin-2-yl)acetonitrile (50 mg, 52%). LCMS (ESI, m/z): 575.2 [M+H]+.

Step 6: 2-[4-[7-[6-amino-4-methyl-3-(trifluoromethyl)-2-pyridyl]-6-chloro-2-[[(2S)-1-methylpyrrolidin-2-yl]methoxy]quinazolin-4-yl]-1-(2-fluoroprop-2-enoyl)piperazin-2-yl]acetonitrile

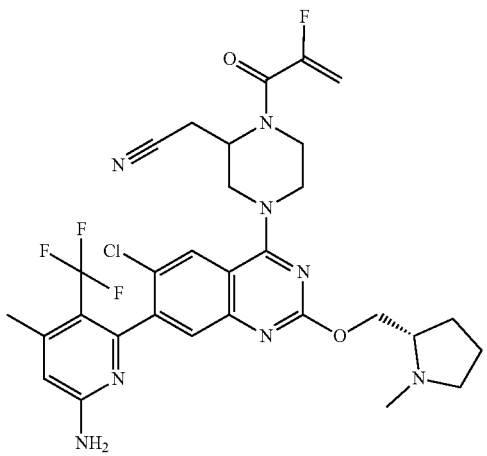 [SMILES: C=C(F)C(=O)N1CCN(c2nc(OC[C@@H]3CCCN3C)nc3cc(-c4nc(N)cc(C)c4C(F)(F)F)c(Cl)cc23)CC1CC#N]

To a solution of 2-(4-(7-(6-amino-4-methyl-3-(trifluoromethyl)pyridin-2-yl)-6-chloro-2-(((S)-1-methylpyrrolidin-2-yl)methoxy)quinazolin-4-yl)piperazin-2-yl)acetonitrile (60 mg, 0.10 mmol), 2-fluoroprop-2-enoyloxysodium (14 mg, 0.13 mmol) and N,N-diisopropylethylamine (0.09 mL, 0.52 mmol) in N,N-dimethylformamide (2.0 mL) was added HATU (83.5 mg, 0.21 mmol) at 0° C. and stirred for 20 minutes. The reaction was quenched with water and extracted with EtOAc. The organic layers was dried with sodium sulfate, filtered, and concentrated via rotovap. The crude product was purified by HPLC FA 5-50% 15 min to give 2-[4-[7-[6-amino-4-methyl-3-(trifluoromethyl)-2-pyridyl]-6-chloro-2-[[(2S)-1-methylpyrrolidin-2-yl]methoxy]quinazolin-4-yl]-1-(2-fluoroprop-2-enoyl)piperazin-2-yl]acetonitrile (34 mg, 50%).

Example 55

$^1$H NMR (400 MHz, DMSO-d$_6$) δ 8.17-8.06 (m, 1H), 7.42 (d, J=3.2 Hz, 1H), 6.77 (d, J=2.9 Hz, 2H), 6.46 (s, 1H), 5.48-5.18 (m, 2H), 4.86 (s, 1H), 4.36 (dt, J=11.3, 5.7 Hz, 1H), 4.21 (qd, J=10.4, 9.0, 6.0 Hz, 3H), 3.11-2.93 (m, 2H), 2.63 (s, 1H), 2.40-2.34 (m, 6H), 2.23 (q, J=8.4 Hz, 2H), 2.02-1.88 (m, 1H), 1.67 (tdd, J=16.1, 9.6, 4.8 Hz, 3H). LCMS (ESI, m/z): 647.3 [M+H]+.

Example 56

2-[4-[7-[6-amino-4-methyl-3-(trifluoromethyl)-2-pyridyl]-6-chloro-2-[[(2S,4R)-4-fluoro-1-methyl-pyrrolidin-2-yl]methoxy]quinazolin-4-yl]-1-(2-fluoroprop-2-enoyl)piperazin-2-yl]acetonitrile

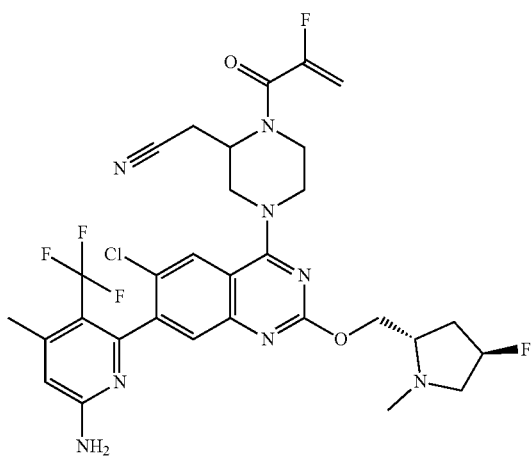 [SMILES: C=C(F)C(=O)N1CCN(c2nc(OC[C@@H]3C[C@@H](F)CN3C)nc3cc(-c4nc(N)cc(C)c4C(F)(F)F)c(Cl)cc23)CC1CC#N]

Example 56 was prepared according to the same protocol as Example 55 except that in Step 2 of Example 56, ((2S,4R)-4-fluoro-1-methylpyrrolidin-2-yl)methanol was used instead of [(2S)-1-methylpyrrolidin-2-yl]methanol as the alternative reagent.

Example 56

$^1$H NMR (400 MHz, DMSO-$d_6$) δ 8.10 (d, J=3.9 Hz, 1H), 7.43 (d, J=3.1 Hz, 1H), 6.77 (d, J=2.8 Hz, 2H), 6.46 (s, 1H), 5.41 (dd, J=18.0, 4.1 Hz, 1H), 5.37-5.08 (m, 2H), 4.39 (ddd, J=11.5, 7.6, 4.7 Hz, 1H), 4.25 (ddq, J=24.9, 12.6, 5.3 Hz, 3H), 2.92 (dd, J=10.2, 5.3 Hz, 2H), 2.40 (s, 3H), 2.38-2.33 (m, 3H), 2.22-2.04 (m, 1H), 1.91 (dddd, J=33.6, 14.8, 9.8, 5.9 Hz, 1H). LCMS (ESI, m/z): 665.3 [M+H]$^+$.

Example 57

1-[4-[7-[6-amino-4-methyl-3-(trifluoromethyl)-2-pyridyl]-6-chloro-2-[[(2S)-1-methylpyrrolidin-2-yl]methoxy]quinazolin-4-yl]-2-(fluoromethyl)piper-azin-1-yl]-2-fluoro-prop-2-en-1-one

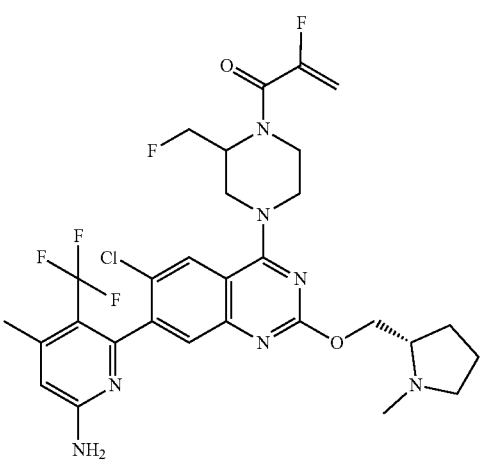 [SMILES: C=C(F)C(=O)N1CCN(c2nc(OC[C@@H]3CCCN3C)nc3cc(-c4nc(N)cc(C)c4C(F)(F)F)c(Cl)cc23)CC1CF]

Example 57 was prepared according to the same protocol as Example 55 except that in Step 1 of Example 57, tert-butyl 2-(fluoromethyl)piperazine-1-carboxylate hydrochloride was used instead of 2-piperazin-2-ylacetonitrile dihydrochloride as the alternative reagent.

Example 57

$^1$H NMR (400 MHz, DMSO-$d_6$) δ 8.04 (d, J=1.5 Hz, 1H), 7.42 (d, J=1.7 Hz, 1H), 6.78 (d, J=2.9 Hz, 2H), 6.46 (s, 1H), 5.43-5.18 (m, 2H), 4.74 (d, J=43.0 Hz, 3H), 4.43-4.12 (m, 5H), 2.99-2.93 (m, 1H), 2.63-2.53 (m, 1H), 2.36 (s, 6H), 2.18 (q, J=8.6 Hz, 1H), 2.01-1.89 (m, 1H), 1.74-1.56 (m, 4H). LCMS (ESI, m/z): 640.3 [M+H]$^+$.

Example 58

2-[(2R)-4-[7-[6-amino-4-methyl-3-(trifluoromethyl)-2-pyridyl]-6-chloro-2-[[(2 S,4R)-4-fluoro-1-methyl-pyrrolidin-2-yl]methoxy]quinazolin-4-yl]-1-(2-fluoroprop-2-enoyl)-5-methyl-piperazin-2-yl]acetonitrile

Examples 59a and 59b 1-((S)-4-((R)-7-(6-amino-4-methyl-3-(trifluoromethyl)pyridin-2-yl)-8-fluoro-2-(((S)-1-methylpyrrolidin-2-yl)methoxy)-6-((trifluoromethyl)thio)quinazolin-4-yl)-3-methylpiperazin-1-yl)prop-2-en-1-one (Example 59a) and 1-((S)-4-((S)-7-(6-amino-4-methyl-3-(trifluoromethyl)pyridin-2-yl)-8-fluoro-2-(((S)-1-methylpyrrolidin-2-yl)methoxy)-6-((trifluoromethyl)thio)quinazolin-4-yl)-3-methylpiperazin-1-yl)prop-2-en-1-one (Example 59b)

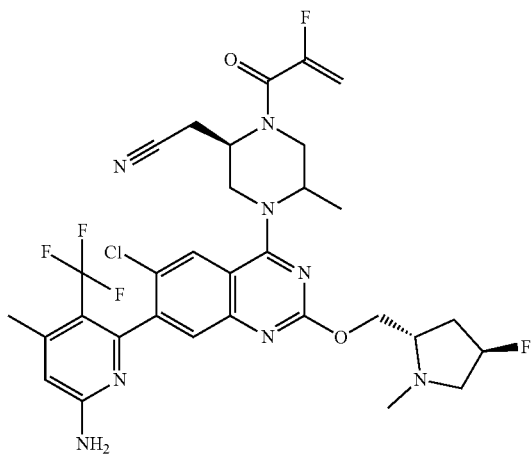 [SMILES: C=C(F)C(=O)N1CC(C)N(c2nc(OC[C@@H]3C[C@@H](F)CN3C)nc3cc(-c4nc(N)cc(C)c4C(F)(F)F)c(Cl)cc23)C[C@H]1CC#N]

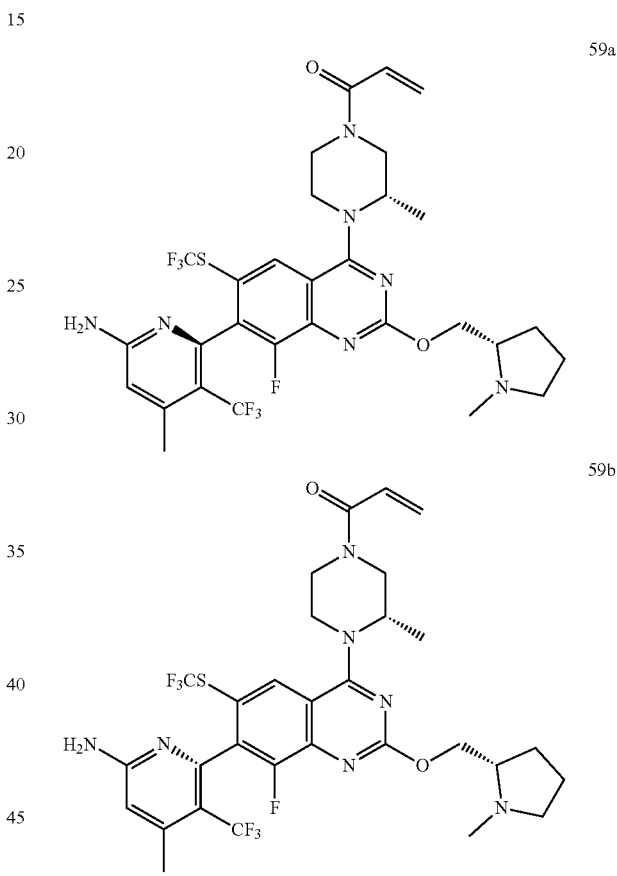

Example 58 was produced according to the same protocol as Example 55 except that in Step 1 of Example 58, 2-((2R)-5-methylpiperazin-2-yl)acetonitrile (Intermediate 2) was used instead of 2-piperazin-2-ylacetonitrile dihydrochloride, and in Step 2 of Example 58, instead of [(2S)-1-methylpyrrolidin-2-yl]methanol, ((2S,4R)-4-fluoro-1-methylpyrrolidin-2-yl)methanol was used as the alternative reagent.

Example 58

$^1$H NMR (400 MHz, DMSO-d$_6$) δ 8.08 (d, J=10.5 Hz, 1H), 7.43 (d, J=2.5 Hz, 1H), 6.77 (s, 2H), 6.46 (d, J=1.5 Hz, 1H), 5.49-4.92 (m, 4H), 4.64 (s, 1H), 4.38 (dt, J=10.6, 5.1 Hz, 1H), 4.34-4.22 (m, 1H), 4.21-3.93 (m, 2H), 3.71 (d, J=29.2 Hz, 2H), 3.53-3.37 (m, 2H), 3.07-2.84 (m, 2H), 2.40 (dd, J=2.4, 1.1 Hz, 4H), 2.38-2.34 (m, 3H), 2.13 (ddd, J=25.1, 10.7, 4.0 Hz, 1H), 2.02-1.80 (m, 1H), 1.15 (d, J=8.5 Hz, 3H). LCMS (ESI, m/z): 679.3 [M+H]$^+$.

Synthetic Route

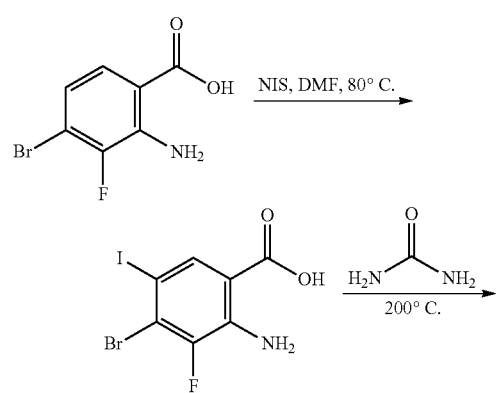

427
-continued
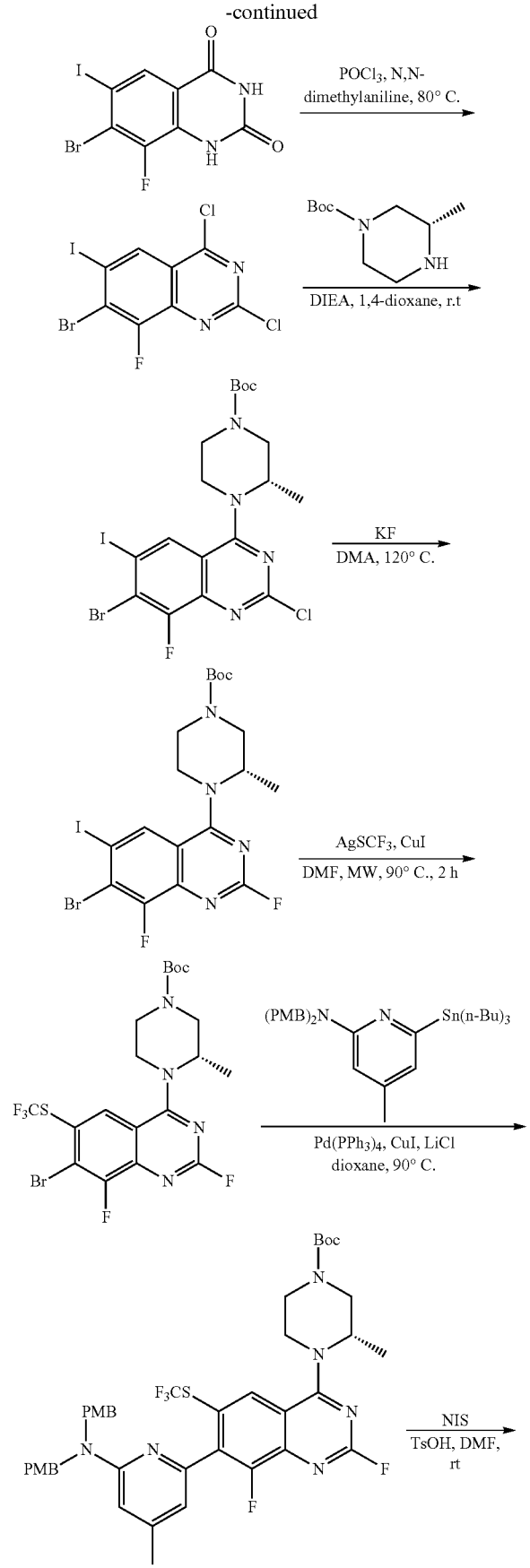
428
-continued
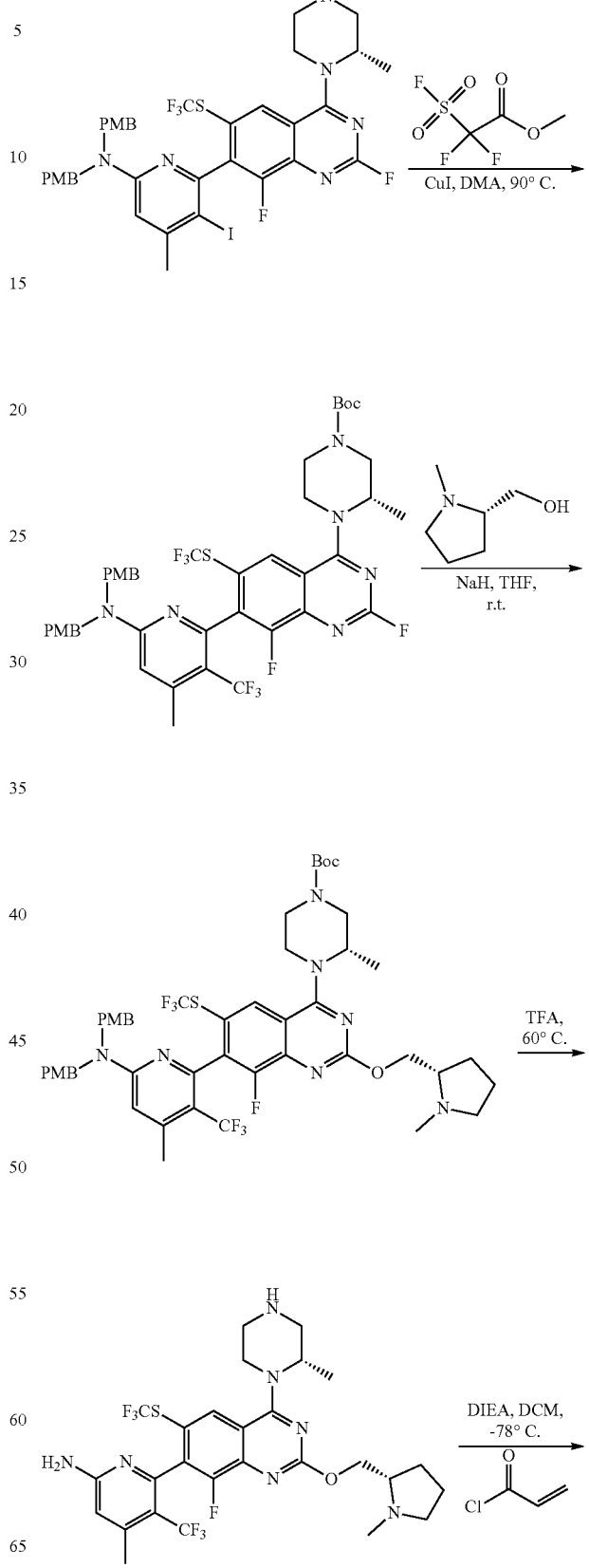

-continued

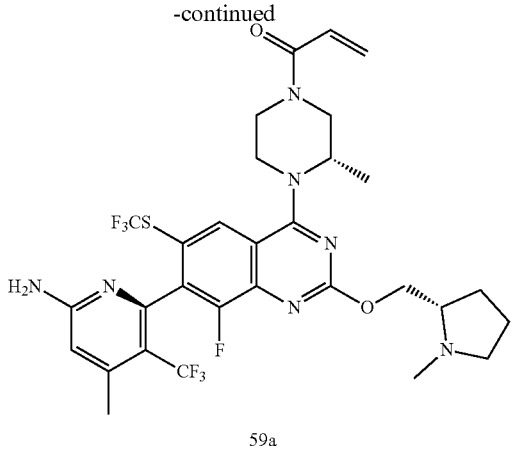

59a

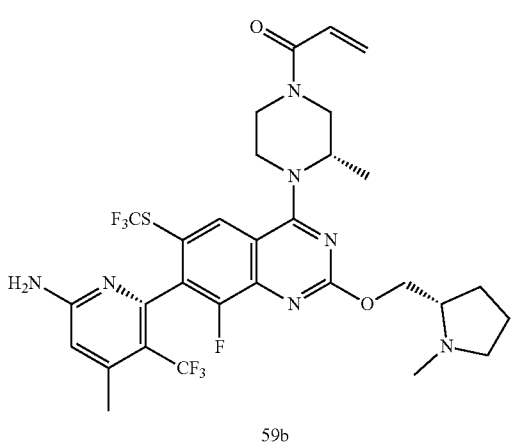

59b

Step 1: 2-amino-4-bromo-3-fluoro-5-iodobenzoic acid

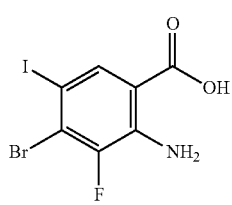 [SMILES: Nc1c(C(=O)O)cc(I)c(Br)c1F]

A solution of 2-amino-4-bromo-3-fluorobenzoic acid (31.0 g, 132.47 mmol) and N-iodosuccinimide (32.86 g, 146.05 mmol) in N,N-dimethylformamide (100 mL) was stirred at 80° C. for 2 hours. LC-MS showed the formation of the desired product. The resulting solution was diluted with water (2 L), filtered, and the solids were collected and washed with water to afford 2-amino-4-bromo-3-fluoro-5-iodo-benzoic acid (45 g, 125.03 mmol, 94.4% yield) as a yellow solid. LC-MS: (ESI, m/z): 357.9 [M−H]+

Step 2: 7-bromo-8-fluoro-6-iodoquinazoline-2,4(1H,3H)-dione

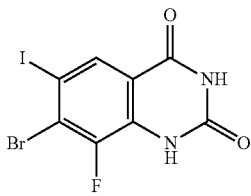 [SMILES: O=c1[nH]c(=O)c2cc(I)c(Br)c(F)c2[nH]1]

A solution of urea (352.0 g, 5860.8 mmol) and 2-amino-4-bromo-3-fluoro-5-iodobenzoic acid (44.0 g, 122.25 mmol) was stirred at 200° C. for 1 hour. LC-MS showed the formation of the desired product. The reaction was cooled to 80° C. and subsequently diluted with water. After filtration, the solids were collected and washed with water (~50° C.) to afford 7-bromo-8-fluoro-6-iodoquinazoline-2,4(1H,3H)-dione (45 g, 116.9 mmol, 95.6% yield) as a yellow solid. LC-MS: (ESI, m/z): 382.8 [M−H]+

Step 3: 7-bromo-2,4-dichloro-8-fluoro-6-iodoquinazoline

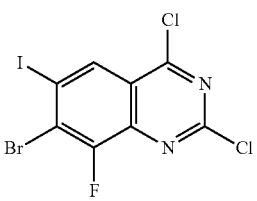 [SMILES: Fc1c(Br)c(I)cc2c(Cl)nc(Cl)nc12]

A solution of 7-bromo-8-fluoro-6-iodoquinazoline-2,4 (1H,3H)-dione (1.0 g, 2.6 mmol) and N,N-dimethylaniline (0.99 mL, 7.79 mmol) in phosphorus oxychloride (10 mL, 107.28 mmol) was stirred at 80° C. for 2 hours. Upon completion, the crude product was directly used in the next step.

Step 4: tert-butyl (S)-4-(7-bromo-2-chloro-8-fluoro-6-iodoquinazolin-4-yl)-3-methylpiperazine-1-carboxylate

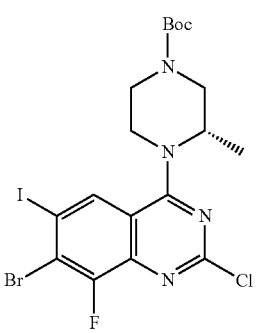

A solution of 7-bromo-2,4-dichloro-8-fluoro-6-iodoquinazoline (2.2 g, 5.22 mmol) and N,N-diisopropylethylamine (4.58 mL, 26.31 mmol) in 1,4-dioxane (20 mL) was stirred at 25° C. for 2 minutes. Tert-butyl (3S)-3-methyl-1-piperazinecarboxylate (3.1 g, 15.48 mmol) was added and stirred at 25° C. for 1 hour. Upon completion, the reaction was concentrated under vacuum and the residue was purified by flash chromatography on silica gel eluting with petroleum ether/ethyl acetate (85:15) to afford tert-butyl (S)-4-(7-bromo-2-chloro-8-fluoro-6-iodoquinazolin-4-yl)-3-methylpiperazine-1-carboxylate (700 mg, 1.1953 mmol, 22.9% yield) as a yellow solid. LC-MS: (ESI, m/z): 584.9 [M+H]+

Step 5: tert-butyl (S)-4-(7-bromo-2,8-difluoro-6-iodoquinazolin-4-yl)-3-methylpiperazine-1-carboxylate

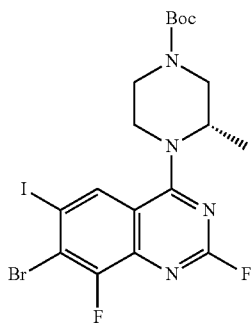

A solution of tert-butyl (S)-4-(7-bromo-2-chloro-8-fluoro-6-iodoquinazolin-4-yl)-3-methylpiperazine-1-carboxylate (5.0 g, 8.54 mmol) and potassium fluoride (2.5 g, 43.03 mmol) in N,N-dimethylacetamide (10 mL) was stirred at 120° C. for 2 hours. Upon completion, the solution was diluted with ethyl acetate and washed with water. The organic layer was dried over anhydrous sodium sulfate and concentrated under vacuum. The residue was purified by flash chromatography on silica gel eluting with petroleum ether/ethyl acetate (9:1) to afford tert-butyl (S)-4-(7-bromo-2,8-difluoro-6-iodoquinazolin-4-yl)-3-methylpiperazine-1-carboxylate (3.1 g, 5.4 mmol, 63.8% yield) as a yellow solid. LC-MS: (ESI, m/z): 569.0 [M+H]+

Step 6: tert-butyl (S)-4-(7-bromo-2,8-difluoro-6-((trifluoromethyl)thio)quinazolin-4-yl)-3-methylpiperazine-1-carboxylate

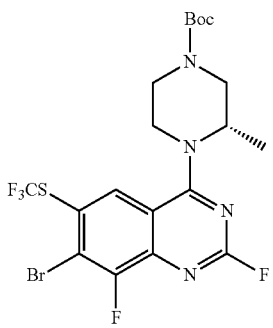

Under nitrogen, a solution of tert-butyl (S)-4-(7-bromo-2,8-difluoro-6-iodoquinazolin-4-yl)-3-methylpiperazine-1-carboxylate (1.0 g, 1.76 mmol), copper(I) iodide (3400 mg, 17.85 mmol) and silver(I) trifluoromethanethiolate (1.1 g, 5.26 mmol) in N,N-dimethylformamide (10 mL) was stirred at 90° C. for 2 hours under microwave. Upon completion, the residue was purified by flash chromatography on C18 gel eluting with methanol/water (97:3) to afford tert-butyl (S)-4-(7-bromo-2,8-difluoro-6-((trifluoromethyl)thio)quinazolin-4-yl)-3-methylpiperazine-1-carboxylate. LC-MS: (ESI, m/z): 543.1 [M+H]+

Step 7: tert-butyl (S)-4-(7-(6-(bis(4-methoxybenzyl)amino)-4-methylpyridin-2-yl)-2,8-difluoro-6-((trifluoromethyl)thio)quinazolin-4-yl)-3-methylpiperazine-1-carboxylate Under nitrogen, a solution of tert-butyl (S)-4-(7-bromo-2,8-difluoro-6-((trifluoromethyl)thio)quinazolin-4-yl)-3-methylpiperazine-1-carboxylate (2.0 g, 3.68 mmol), N,N-bis[(4-methoxyphenyl)methyl]-4-methyl-6-tributylstannyl-pyridin-2-amine (3.5 g, 5.49 mmol), tetrakis(triphenylphosphine)palladium(0) (2.1 g, 1.82 mmol), copper(I) iodide (400 mg, 2.1 mmol) and lithium chloride (400.0 mg, 9.22 mmol) in 1,4-dioxane (20 mL) was added and stirred at 90° C. for 16 hours. Upon completion, the reaction was filtered, the filtrate was diluted with ethyl acetate and washed with water. The organic layer was concentrated under reduced pressure. The residue was purified by flash chromatography on silica gel eluting with petroleum ether/ethyl acetate (80:20) to afford tert-butyl (S)-4-(7-(6-(bis(4-methoxybenzyl)amino)-4-methylpyridin-2-yl)-2,8-difluoro-6-((trifluoromethyl)thio)quinazolin-4-yl)-3-methylpiperazine-1-carboxylate (1.6 g, 1.9 mmol, 53.6% yield) as a yellow oil. LC-MS: (ESI, m/z): 811.3 [M+H]+

Step 8: tert-butyl (3S)-4-(7-(6-(bis(4-methoxybenzyl)amino)-3-iodo-4-methylpyridin-2-yl)-2,8-difluoro-6-(((trifluoromethyl)thio)quinazolin-4-yl)-3-methylpiperazine-1-carboxylate

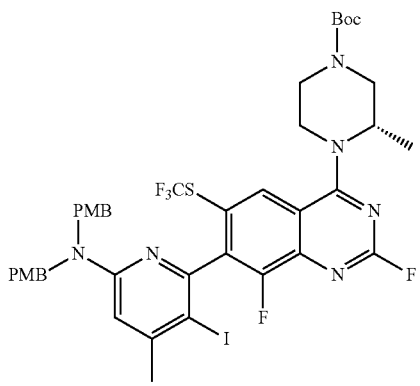

A solution of tert-butyl (S)-4-(7-(6-(bis(4-methoxybenzyl)amino)-4-methylpyridin-2-yl)-2,8-difluoro-6-((trifluoromethyl)thio)quinazolin-4-yl)-3-methylpiperazine-1-carboxylate (3.7 g, 4.56 mmol), N-iodosuccinimide (1.25 g, 5.59 mmol) and p-toluenesulfonicacid monohydrate (44.0 mg, 0.23 mmol) in N,N-dimethylformamide (20 mL) was stirred at 25° C. for 1 hour. Upon completion, the solution was diluted with ethyl acetate, transferred to a reparatory funnel and washed with water. The organic layer was combined and dried over anhydrous sodium sulfate and concentrated under vacuum. The residue was purified by flash chromatography on silica gel eluting with petroleum ether/ethyl acetate (75:25) to afford tert-butyl (3S)-4-(7-(6-(bis(4-methoxybenzyl)amino)-3-iodo-4-methylpyridin-2-yl)-2,8-difluoro-6-((trifluoromethyl)thio)quinazolin-4-yl)-3-methylpiperazine-1-carboxylate (1.1 g, 1.1 mmol, 25.7% yield) as a yellow oil. LC-MS: (ESI, m/z): 937.1 [M+H]⁺

Step 9: tert-butyl (3S)-4-(7-(6-(bis(4-methoxybenzyl)amino)-4-methyl-3-(trifluoromethyl)pyridin-2-yl)-2,8-difluoro-6-((trifluoromethyl)thio)quinazolin-4-yl)-3-methylpiperazine-1-carboxylate

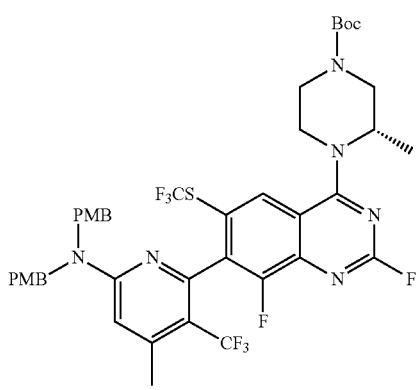

Under nitrogen, a solution of tert-butyl (3S)-4-(7-(6-(bis(4-methoxybenzyl)amino)-3-iodo-4-methylpyridin-2-yl)-2,8-difluoro-6-((trifluoromethyl)thio)quinazolin-4-yl)-3-methylpiperazine-1-carboxylate (200.0 mg, 0.21 mmol), methyl 2,2-difluoro-2-(fluorosulfonyl)acetate (1000.0 mg, 5.21 mmol) and copper(I) iodide (404 mg, 2.12 mmol) in N,N-dimethylacetamide (10 mL) was added and stirred at 90° C. for 2 hours. Upon completion, the reaction was filtered, the filtrate was concentrated under reduced pressure and diluted with ethyl acetate and washed with water. The organic layer was combined, dried over anhydrous sodium sulfate and concentrated under vacuum. The residue was purified by flash chromatography on silica gel eluting with petroleum ether/ethyl acetate (80:20) to afford tert-butyl (3S)-4-(7-(6-(bis(4-methoxybenzyl)amino)-4-methyl-3-(trifluoromethyl)pyridin-2-yl)-2,8-difluoro-6-((trifluoromethyl)thio)quinazolin-4-yl)-3-methylpiperazine-1-carboxylate (160 mg, 0.18 mmol, 85.3% yield) as a yellow oil. LC-MS: (ESI, m/z): 879.2 [M+H]⁺

Step 10: tert-butyl (3S)-4-(7-(6-(bis(4-methoxybenzyl)amino)-4-methyl-3-(trifluoromethyl)pyridin-2-yl)-8-fluoro-2-(((S)-1-methylpyrrolidin-2-yl)methoxy)-6-((trifluoromethyl)thio)quinazolin-4-yl)-3-methylpiperazine-1-carboxylate

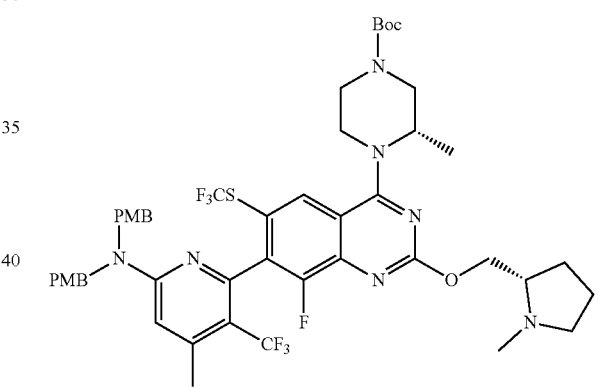

A solution of sodium hydride (165.0 mg, 4.12 mmol) in tetrahydrofuran (50 mL) was stirred at 25° C. for 5 minutes. N-methyl-1-prolinol (412.5 mg, 3.58 mmol) was added and stirred at 25° C. for 10 minutes. Then tert-butyl (3S)-4-(7-(6-(bis(4-methoxybenzyl)amino)-4-methyl-3-(trifluoromethyl)pyridin-2-yl)-2,8-difluoro-6-((trifluoromethyl)thio)quinazolin-4-yl)-3-methylpiperazine-1-carboxylate (1650.0 mg, 1.88 mmol) was added and stirred at 25° C. for 10 minutes. Upon completion, the reaction was concentrated to afford crude tert-butyl (3S)-4-(7-(6-(bis(4-methoxybenzyl)amino)-4-methyl-3-(trifluoromethyl)pyridin-2-yl)-8-fluoro-2-(((S)-1-methylpyrrolidin-2-yl)methoxy)-6-((trifluoromethyl)thio)quinazolin-4-yl)-3-methylpiperazine-1-carboxylate (1.5 g, 1.54 mmol, 82% yield) that was directly used in the next step without purification. LC-MS: (ESI, m/z): 974.4 [M+H]⁺

Step 11: 6-(8-fluoro-4-((S)-2-methylpiperazin-1-yl)-2-(((S)-1-methylpyrrolidin-2-yl)methoxy)-6-((trifluoromethyl)thio)quinazolin-7-yl)-4-methyl-5-(trifluoromethyl)pyridin-2-amine

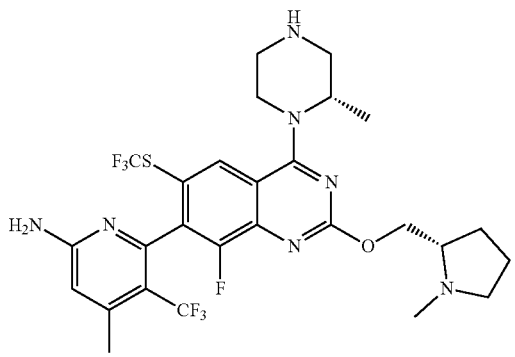

A solution of tert-butyl (3S)-4-(7-(6-(bis(4-methoxybenzyl)amino)-4-methyl-3-(trifluoromethyl)pyridin-2-yl)-8-fluoro-2-(((S)-1-methylpyrrolidin-2-yl)methoxy)-6-((trifluoromethyl)thio)quinazolin-4-yl)-3-methylpiperazine-1-carboxylate (1.3 g, 1.33 mmol) in 2,2,2-trifluoroacetic acid (20 mL) was stirred at 60° C. for 16 hours. Upon completion, the reaction was concentrated. The residue was purified by flash chromatography on silica gel eluting with methanol/water (25/75) and (60/40) to afford 6-(8-fluoro-4-((S)-2-methylpiperazin-1-yl)-2-(((S)-1-methylpyrrolidin-2-yl)methoxy)-6-((trifluoromethyl)thio)quinazolin-7-yl)-4-methyl-5-(trifluoromethyl)pyridin-2-amine (410 mg, 0.6 mmol, 48.5% yield) as a yellow oil. LC-MS: (ESI, m/z): 634.2 [M+H]$^+$ Step 12: 1-((S)-4-((R)-7-(6-amino-4-methyl-3-(trifluoromethyl)pyridin-2-yl)-8-fluoro-2-(((S)-1-methylpyrrolidin-2-yl)methoxy)-6-((trifluoromethyl)thio)quinazolin-4-yl)-3-methylpiperazin-1-yl)prop-2-en-1-one (Example 59a) and 1-((S)-4-((S)-7-(6-amino-4-methyl-3-(trifluoromethyl)pyridin-2-yl)-8-fluoro-2-(((S)-1-methylpyrrolidin-2-yl)methoxy)-6-((trifluoromethyl)thio)quinazolin-4-yl)-3-methylpiperazin-1-yl)prop-2-en-1-one (Example 59b)

59a

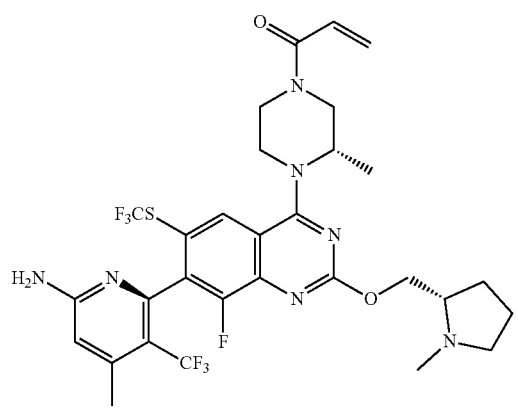

59b

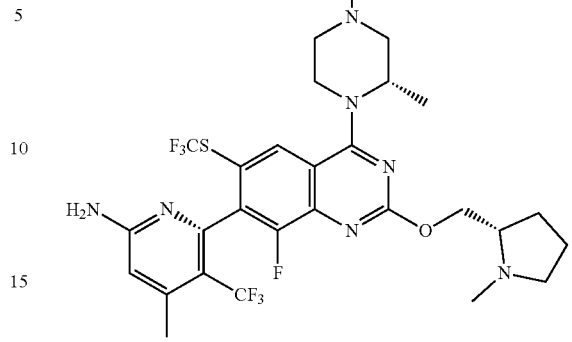

A solution of N,N-diisopropylethylamine (288.0 mg, 2.23 mmol) and 6-(8-fluoro-4-((S)-2-methylpiperazin-1-yl)-2-(((S)-1-methylpyrrolidin-2-yl)methoxy)-6-((trifluoromethyl)thio)quinazolin-7-yl)-4-methyl-5-(trifluoromethyl)pyridin-2-amine (720.0 mg, 1.14 mmol) in dichloromethane (50 mL) was stirred at −78° C. for 5 minutes. Then acryloyl chloride (108.0 mg, 1.19 mmol) was added and the reaction was stirred at −78° C. for 30 minutes. Upon completion, the reaction was quenched with methanol and diluted with dichloromethane. The resulting mixture was poured into a separatory funnel and washed with water. The organic layer was dried over anhydrous sodium sulfate and concentrated under vacuum. The residue was purified by flash chromatography on C18 gel eluting with acetonitrile/water (65:35) to afford crude product. The crude product was purified by Prep-HPLC-Column: Xselect CSH OBD Column 30*150 mm 5 um, n; Mobile Phase A:Water(0.1% FA), Mobile Phase B:ACN; Flow rate:60 mL/min. The resulting product was purified by Chiral Prep-HPLC-Column: CHIRALPAK IC, 2*25 cm, 5 um; Mobile Phase A:Hex:DCM=3:1(10 mM NH$_3$-MeOH)-HPLC, Mobile Phase B:EtOH-HPLC; Flow rate:15 mL/min; to afford 1-((S)-4-((R)-7-(6-amino-4-methyl-3-(trifluoromethyl)pyridin-2-yl)-8-fluoro-2-(((S)-1-methylpyrrolidin-2-yl)methoxy)-6-((trifluoromethyl)thio)quinazolin-4-yl)-3-methylpiperazin-1-yl)prop-2-en-1-one as a white solid and 1-((S)-4-((S)-7-(6-amino-4-methyl-3-(trifluoromethyl)pyridin-2-yl)-8-fluoro-2-(((S)-1-methylpyrrolidin-2-yl)methoxy)-6-((trifluoromethyl)thio)quinazolin-4-yl)-3-methylpiperazin-1-yl)prop-2-en-1-one (44.5 mg, 0.06 mmol, 5.7% yield) as a white solid.

Example 59a

LC-MS: (ESI, m/z): 688.2 [M+H]$^+$, $^1$H NMR (300 MHz, DMSO, ppm) δ 8.12 (d, J=21 Hz, 1H), 6.84 (s, 3H), 6.50 (s, 1H), 6.18 (d, J=36.0 Hz, 1H), 5.75 (dd, J=2.4, 10.2 Hz, 1H), 4.75-4.63 (m, 1H), 4.47-4.00 (m, 5H), 3.67-3.55 (m, 2H), 3.25-3.16 (m, 1H), 3.02-2.92 (m, 1H), 2.66-2.55 (m, 1H), 2.38 (s, 6H), 2.25-2.15 (m, 1H), 2.02-1.85 (m, 1H), 1.75-1.55 (m, 3H), 1.45-1.26 (m, 3H). Chiral HPLC: CHIRALPAK IC-3 (0.46*5 cm; 3 um); detected at 254 nm; n-hexane/dichloromethane=3/1(0.1% diethylamine); flow rate=1.0 mL/min; Retention time: 0.9 min (faster peak).

Example 59b

LC-MS: (ESI, m/z): 688.2 [M+H]$^+$, $^1$H NMR (300 MHz, DMSO, ppm) δ 8.13 (s, 1H), 6.92-6.84 (m, 3H), 6.51 (s, 1H), 6.20 (d, J=30.0 Hz, 1H), 5.75 (dd, J=2.4, 10.2 Hz, 1H), 4.75 (s, 1H), 4.45-4.35 (m, 1H), 4.30-3.90 (m, 4H), 3.80-3.55 (m, 2H), 3.28-3.04 (m, 1H), 3.01-2.90 (m, 1H), 2.65-2.55 (m, 1H), 2.43-2.31 (m, 6H), 2.23-2.11 (m, 1H), 2.04-1.87 (m, 1H), 1.75-1.55 (m, 3H), 1.34 (d, J=6.6 Hz, 3H). Chiral HPLC: CHIRALPAK IC-3 (0.46*5 cm; 3 um); detected at 254 nm; n-hexane/dichloromethane=3/1(0.1% diethylamine); flow rate=1.0 mL/min; Retention time: 1.8 min (slower peak).

Example 60

1-[(3S,5S)-4-[7-[6-amino-4-methyl-3-(trifluoromethyl)-2-pyridyl]-6-chloro-quinazolin-4-yl]-3,5-dimethyl-piperazin-1-yl]prop-2-en-1-one Synthetic Route

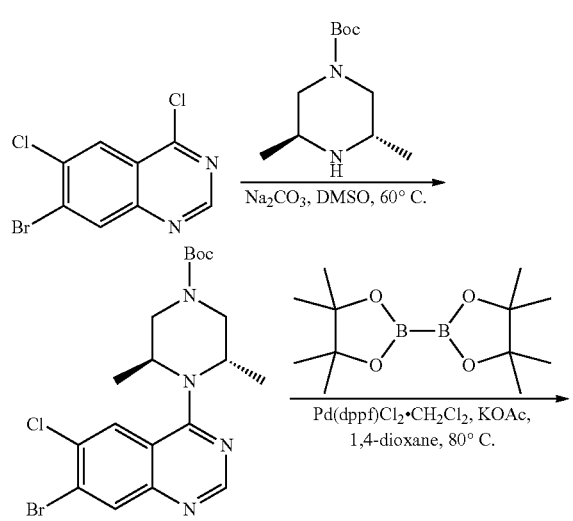

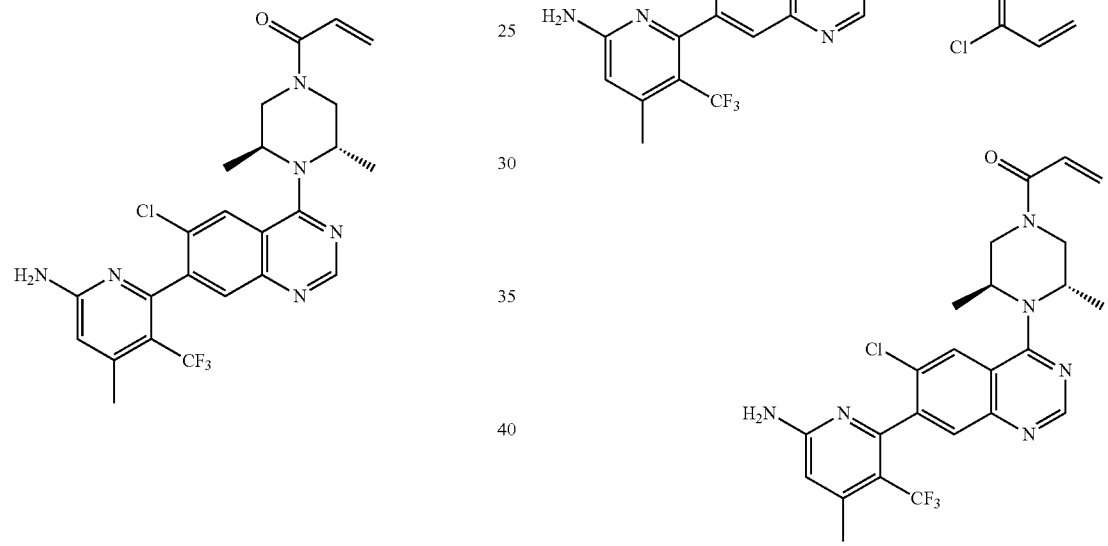

Step 1: tert-butyl (3S,5S)-4-(7-bromo-6-chloro-quinazolin-4-yl)-3,5-dimethyl-piperazine-1-carboxylate A mixture of 7-bromo-4,6-dichloro-quinazoline (see Example 22, Step 1) (1.0 g, 3.6 mmol), tert-butyl(3S,5S)-3,5-dimethylpiperazine-1-carboxylate (1.1 g, 5.4 mmol) and sodium carbonate (1.1 g, 10.7 mmol) in dimethyl sulfoxide (10 mL) was stirred at 60° C. for 16 hours. Upon completion, the reaction was concentrated under reduced pressure. The residue was purified by flash chromatography on silica gel eluting with petroleum ether/ethyl acetate (9:1) to afford tert-butyl (3S,5S)-4-(7-bromo-6-chloro-quinazolin-4-yl)-3,5-dimethyl-piperazine-1-carboxylate (0.50 g, 1.0 mmol, 30.5% yield) as a yellow oil. LC-MS: (ESI, m/z): 455.1 [M+H]$^+$ Step 2: tert-butyl (3S,5S)-4-[6-chloro-7-(4,4,5,5-tetramethyl-1,3,2-dioxaborolan-2-yl)quinazolin-4-yl]-3,5-dimethyl-piperazine-1-carboxylate

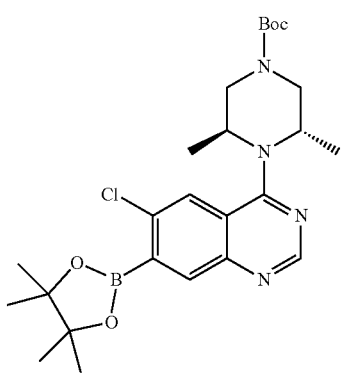

Under nitrogen, a solution of tert-butyl (3S,5S)-4-(7-bromo-6-chloro-quinazolin-4-yl)-3,5-dimethyl-piperazine-1-carboxylate (900.0 mg, 1.9 mmol), bis(pinacolato)diboron (5.0 g, 19.7 mmol), [1,1'-bis(diphenylphosphino)ferrocene]dichloropalladium(II) dichloromethane complex (144.3 mg, 0.20 mmol) and potassium acetate (387.0 mg, 3.9 mmol) in 1,4-dioxane (90 mL) was stirred at 80° C. for 1 hour. Upon completion, the reaction was filtered and the resulting solid was washed with hexane. The crude product was be directly used in the next step. LC-MS: (ESI, m/z): 503.3 [M+H]$^+$ Step 3: tert-butyl (3S,5S)-4-[7-[6-amino-4-methyl-3-(trifluoromethyl)-2-pyridyl]-6-chloro-quinazolin-4-yl]-3,5-dimethyl-piperazine-1-carboxylate

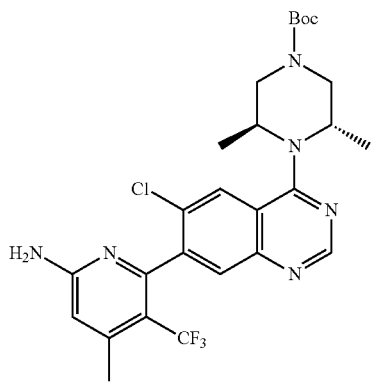 [SMILES: Cc1cc(N)nc(-c2cc3ncnc(N4[C@@H](C)CN(C(=O)OC(C)(C)C)C[C@@H]4C)c3cc2Cl)c1C(F)(F)F]

A solution of tert-butyl (3S,5S)-4-[6-chloro-7-(4,4,5,5-tetramethyl-1,3,2-dioxaborolan-2-yl)quinazolin-4-yl]-3,5-dimethyl-piperazine-1-carboxylate (1.0 g, 1.9 mmol), 6-bromo-4-methyl-5-(trifluoromethyl)pyridin-2-amine (1.0 g, 3.9 mmol), potassium fluoride (230.6 mg, 3.9 mmol) and bis(triphenylphosphine)palladium(II) chloride (139.4 mg, 0.2 mmol) in acetonitrile (10 mL) and water (2 mL) was stirred at 80° C. for 1 hour under nitrogen. Upon completion, the reaction was diluted with dichloromethane, washed with water and dried over anhydrous sodium sulfate. The mixture was concentrated and the residue was purified by flash chromatography on silica gel eluting with dichloromethane/methanol (20:1) to afford tert-butyl (3S,5S)-4-[7-[6-amino-4-methyl-3-(trifluoromethyl)-2-pyridyl]-6-chloro-quinazolin-4-yl]-3,5-dimethyl-piperazine-1-carboxylate (300 mg, 0.5 mmol, 27.4% yield) as a brown solid. LC-MS: (ESI, m/z): 551.2 [M+H]$^+$ Step 4: 1-[(3S,5S)-4-[7-[6-amino-4-methyl-3-(trifluoromethyl)-2-pyridyl]-6-chloro-quinazolin-4-yl]-3,5-dimethyl-piperazin-1-yl]prop-2-en-1-one

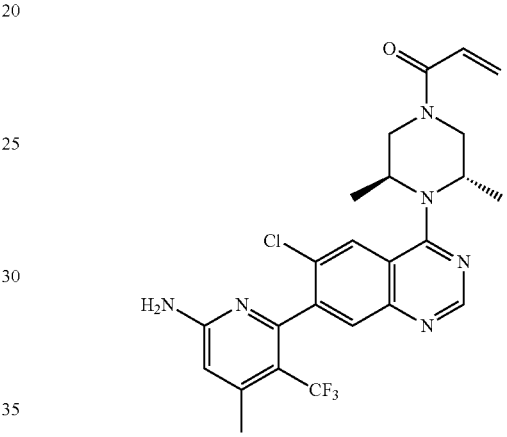

A solution of tert-butyl (3S,5S)-4-[7-[6-amino-4-methyl-3-(trifluoromethyl)-2-pyridyl]-6-chloro-quinazolin-4-yl]-3,5-dimethyl-piperazine-1-carboxylate (300.0 mg, 0.5 mmol) in dichloromethane (6 mL) was added trifluoroacetic acid (1.2 mL, 15.7 mmol). The reaction was stirred at 25° C. for 30 minutes and concentrated. The resulting mixture was diluted with dichloromethane (6 mL) and to it was added N,N-diisopropylethylamine (343.3 mg, 2.6 mmol). Acryloyl chloride (48.1 mg, 0.5 mmol) was added at −78° C. and the reaction was stirred for 30 minutes. Upon completion, the reaction was concentrated and the residue purified by flash chromatography on silica gel eluting with dichloromethane/methanol (20:1) to afford crude solid. The crude product was purified by Prep-HPLC to afford 1-[(3S,5S)-4-[7-[6-amino-4-methyl-3-(trifluoromethyl)-2-pyridyl]-6-chloro-quinazolin-4-yl]-3,5-dimethyl-piperazin-1-yl]prop-2-en-1-one (90.1 mg, 0.18 mmol, 33.5% yield) as a white solid. The crude product was purified by Prep-HPLC-Column: XBridge Prep C18 OBD Column 19×150 mm 5 um; Mobile Phase A: Water (10 mmol/L NH$_4$HCO$_3$), Mobile Phase B: ACN; Flow rate: 60 mL/min.

Example 60

1H NMR (400 MHz, DMSO-d6, ppm) δ 8.97 (d, J=4.9 Hz, 1H), 8.22 (d, J=5.2 Hz, 1H), 7.79 (d, J=5.3 Hz, 1H), 6.97-6.71 (m, 3H), 6.55-6.46 (m, 1H), 6.20 (dd, J=16.7, 2.4 Hz, 1H), 5.75 (dd, J=10.4, 2.4 Hz, 1H), 4.15-3.89 (m, 4H), 3.65 (s, 2H), 2.38 (d, J=2.5 Hz, 3H), 1.01 (d, J=6.4 Hz, 6H). LC-MS: (ESI, m/z): 505.1 [M+H]$^+$

Example 61

1-((S)-4-(7-(6-amino-4-methyl-3-(trifluoromethyl)pyridin-2-yl)-6-chloro-2-(((S)-1-methylpyrrolidin-2-yl)methoxy)quinazolin-4-yl)-3-methylpiperazin-1-yl)prop-2-en-1-one

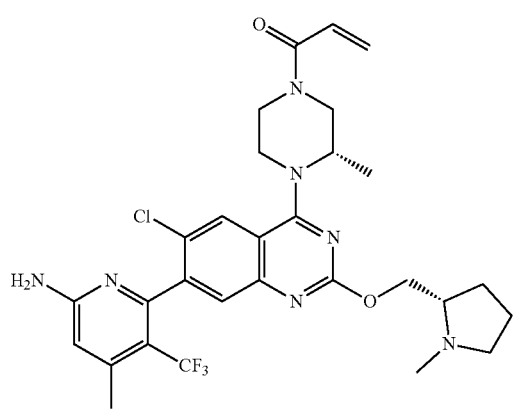 [SMILES: C=CC(=O)N1CCN(c2nc(OC[C@@H]3CCCN3C)nc3cc(-c4nc(N)cc(C)c4C(F)(F)F)c(Cl)cc23)[C@@H](C)C1]

Synthetic Route

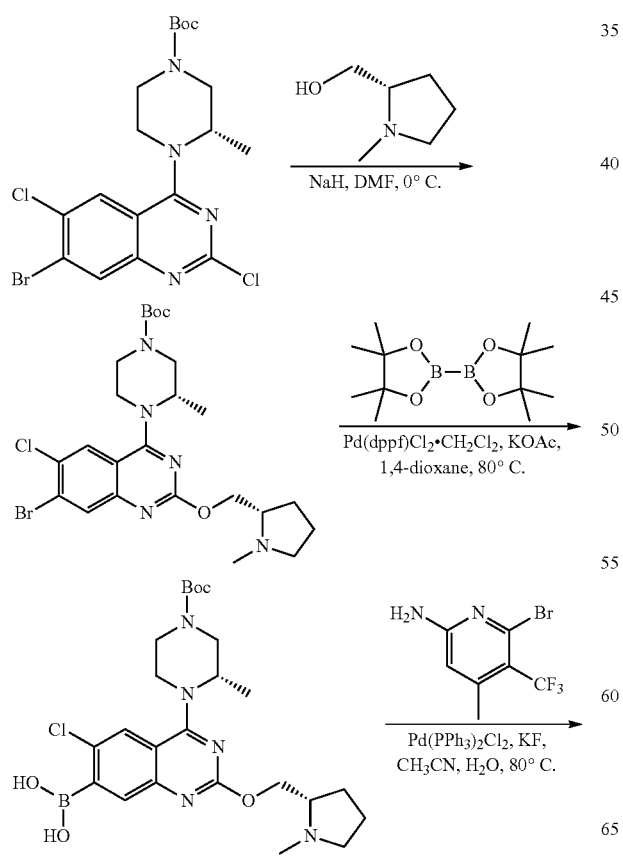

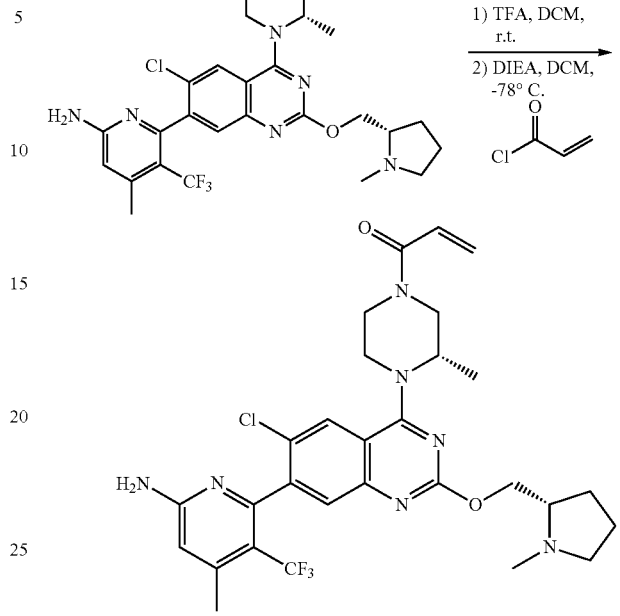

Step 1: tert-butyl (S)-4-(7-bromo-6-chloro-2-(((S)-1-methylpyrrolidin-2-yl)methoxy)quinazolin-4-yl)-3-methylpiperazine-1-carboxylate Sodium hydride (1.01 g, 42.00 mmol) was added to a solution of (S)-(1-methylpyrrolidin-2-yl)methanol (4.84 g, 42.00 mmol) in N,N-dimethylformamide (40 mL) and stirred at 0° C. for 5 minutes. Then tert-butyl (S)-4-(7-bromo-2,6-dichloroquinazolin-4-yl)-3-methylpiperazine-1-carboxylate (Intermediate 5) (10.00 g, 21.00 mmol) was added and the resulting mixture was stirred at 0° C. for 1 hour. Upon completion, the reaction was quenched with aqueous ammonium chloride, diluted with water, extracted with ethyl acetate, washed with water, dried with sodium sulfate and concentrated. The residue was purified by silica gel chromatography eluting with dichloromethane/methanol (20:1) to afford tert-butyl (S)-4-(7-bromo-6-chloro-2-(((S)-1-methylpyrrolidin-2-yl)methoxy)quinazolin-4-yl)-3-methylpiperazine-1-carboxylate (10.50 g, 17.98 mmol, 85.6% yield) as a yellow oil. LCMS: (ESI, m/z): 556.4 [M+H]$^+$ Step 2: 4-((S)-4-(tert-butoxycarbonyl)-2-methylpiperazin-1-yl)-6-chloro-2-(((S)-1-methylpyrrolidin-2-yl)methoxy)quinazolin-7-ylboronic acid

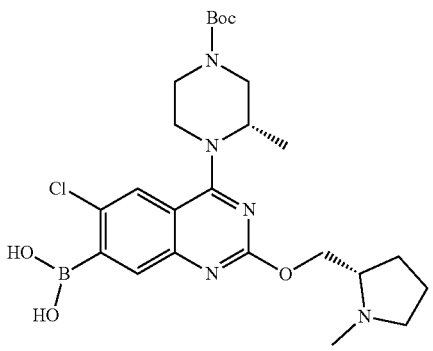 [SMILES: C[C@H]1CN(C(=O)OC(C)(C)C)CCN1c1nc(OC[C@@H]2CCCN2C)nc2cc(B(O)O)c(Cl)cc12]

A solution of tert-butyl (S)-4-(7-bromo-6-chloro-2-(((S)-1-methylpyrrolidin-2-yl)methoxy)quinazolin-4-yl)-3-methylpiperazine-1-carboxylate (2.00 g, 3.60 mmol), bis(pinacolato)diboron (2.75 g, 10.81 mmol), potassium acetate (1.06 g, 10.81 mmol) and [1,1'-bis(diphenylphosphino)ferrocene]dichloropalladium(II) dichloromethane complex (0.27 g, 0.36 mmol) in 1,4-dioxane (15 mL) was stirred at 80° C. for 2 hours under nitrogen. Upon completion, the resulting solution was concentrated, diluted with dichloromethane and filtered. The filtrate was concentrated under vacuum to afford 4-((S)-4-(tert-butoxycarbonyl)-2-methylpiperazin-1-yl)-6-chloro-2-(((S)-1-methylpyrrolidin-2-yl)methoxy)quinazolin-7-ylboronic acid (3.00 g, crude) as a black oil. The crude product was directly used in the next step. LCMS: (ESI, m/z): 520.2 [M+H]$^+$ Step 3: tert-butyl (S)-4-(7-(6-amino-4-methyl-3-(trifluoromethyl)pyridin-2-yl)-6-chloro-2-(((S)-1-methylpyrrolidin-2-yl)methoxy)quinazolin-4-yl)-3-methylpiperazine-1-carboxylate

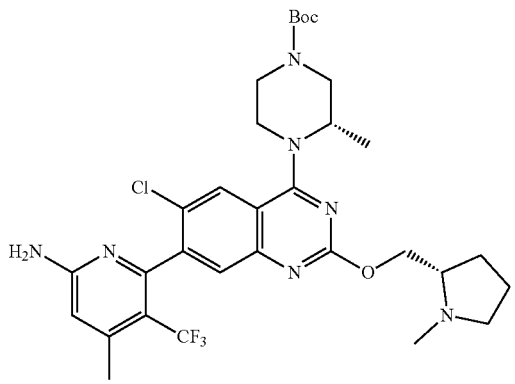 [SMILES: Cc1cc(N)nc(-c2cc3nc(OC[C@@H]4CCCN4C)nc(N4CCN(C(=O)OC(C)(C)C)C[C@@H]4C)c3cc2Cl)c1C(F)(F)F]

A solution of 4-((S)-4-(tert-butoxycarbonyl)-2-methylpiperazin-1-yl)-6-chloro-2-(((S)-1-methylpyrrolidin-2-yl)methoxy)quinazolin-7-ylboronic acid (2.20 g, 2.12 mmol), 6-bromo-4-methyl-5-(trifluoromethyl)pyridin-2-amine (0.54 g, 2.12 mmol), potassium fluoride (0.25 g, 4.23 mmol) and bis(triphenylphosphine)palladium(II) dichloride (0.15 g, 0.21 mmol) in the mixed solvent of acetonitrile (35 mL) and water (7 mL) was stirred at 80° C. for 2 hours under nitrogen. Upon completion, the resulting solution was diluted with dichloromethane, washed with water, dried over anhydrous sodium sulfate and concentrated. The residue was purified by silica gel column eluting with dichloromethane/methanol (10:1) to afford tert-butyl (S)-4-(7-(6-amino-4-methyl-3-(trifluoromethyl)pyridin-2-yl)-6-chloro-2-(((S)-1-methylpyrrolidin-2-yl)methoxy)quinazolin-4-yl)-3-methylpiperazine-1-carboxylate (0.50 g, 0.72 mmol, 34.2% yield) as a brown solid. LCMS: (ESI, m/z): 650.3 [M+H]$^+$ Step 4: 1-((S)-4-(7-(6-amino-4-methyl-3-(trifluoromethyl)pyridin-2-yl)-6-chloro-2-(((S)-1-methylpyrrolidin-2-yl)methoxy)quinazolin-4-yl)-3-methylpiperazin-1-yl)prop-2-en-1-one

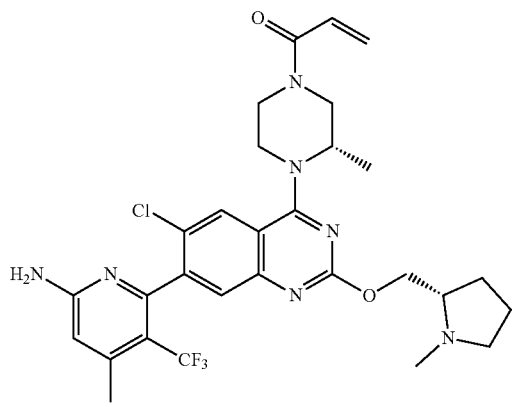 [SMILES: C=CC(=O)N1CCN(c2nc(OC[C@@H]3CCCN3C)nc3cc(-c4nc(N)cc(C)c4C(F)(F)F)c(Cl)cc23)[C@@H](C)C1]

A solution of tert-butyl (S)-4-(7-(6-amino-4-methyl-3-(trifluoromethyl)pyridin-2-yl)-6-chloro-2-(((S)-1-methylpyrrolidin-2-yl)methoxy)quinazolin-4-yl)-3-methylpiperazine-1-carboxylate (0.30 g, 0.46 mmol) and trifluoroacetic acid (0.6 mL, 7.79 mmol) in dichloromethane (3 mL) was stirred at 25° C. for 1 hour. Upon completion, the reaction mixture was concentrated, diluted with dichloromethane and adjusted to pH>7 with N,N-diisopropylethylamine. Then acryloyl chloride (0.03 g, 0.37 mmol) was added and the reaction was stirred at −78° C. for 1 hour. Upon completion, the resulting solution was diluted with water, extracted with dichloromethane, dried with sodium sulfate and concentrated. The crude product was purified by Prep-HPLC to afford 1-((S)-4-(7-(6-amino-4-methyl-3-(trifluoromethyl)pyridin-2-yl)-6-chloro-2-(((S)-1-methylpyrrolidin-2-yl)methoxy)quinazolin-4-yl)-3-methylpiperazin-1-yl)prop-2-en-1-one (28.7 mg, 0.05 mmol, 15.1% yield) as a white solid. LCMS: (ESI, m/z): 604.2 [M+H]$^+$. Prep-HPLC conditions: Column: XBridge Prep C18 OBD Column; mobile phase, A: water, B: acetonitrile, B % (33% to 50% in 7 min); Detector, UV 254 nm to Example 61

$^1$H NMR (300 MHz, DMSO-d6, ppm) δ 7.94 (d, J=3.9 Hz, 1H), 7.41 (s, 1H), 6.95-6.72 (m, 3H), 6.47 (s, 1H), 6.18 (d, J=18.3 Hz, 1H), 5.75 (d, J=10.5, 2.4 Hz, 1H), 4.70 (s, 1H), 4.46-4.31 (m, 2H), 4.31-3.92 (m, 4H), 3.73-3.51 (m, 2H), 3.01-2.91 (m, 1H), 2.64-2.53 (m, 1H), 2.36 (s, 6H), 2.25-2.12 (m, 1H), 2.00-1.90 (m, 1H), 1.77-1.56 (m, 3H), 1.26 (d, J=6.0 Hz, 3H).

Examples 62a and 62b
1-((S)-4-((R)-6-chloro-8-fluoro-7-(4-methyl-6-(methylamino)-3-(trifluoromethyl)pyridin-2-yl)-2-(((S)-1-methylpyrrolidin-2-yl)methoxy)quinazolin-4-yl)-3-methylpiperazin-1-yl)prop-2-en-1-one (Example 62a) and 1-((S)-4-((S)-6-chloro-8-fluoro-7-(4-methyl-6-(methylamino)-3-(trifluoromethyl)pyridin-2-yl)-2-(((S)-1-methylpyrrolidin-2-yl)methoxy)quinazolin-4-yl)-3-methylpiperazin-1-yl)prop-2-en-1-one (Example 62b) (2 atropisomers)
Synthetic Route
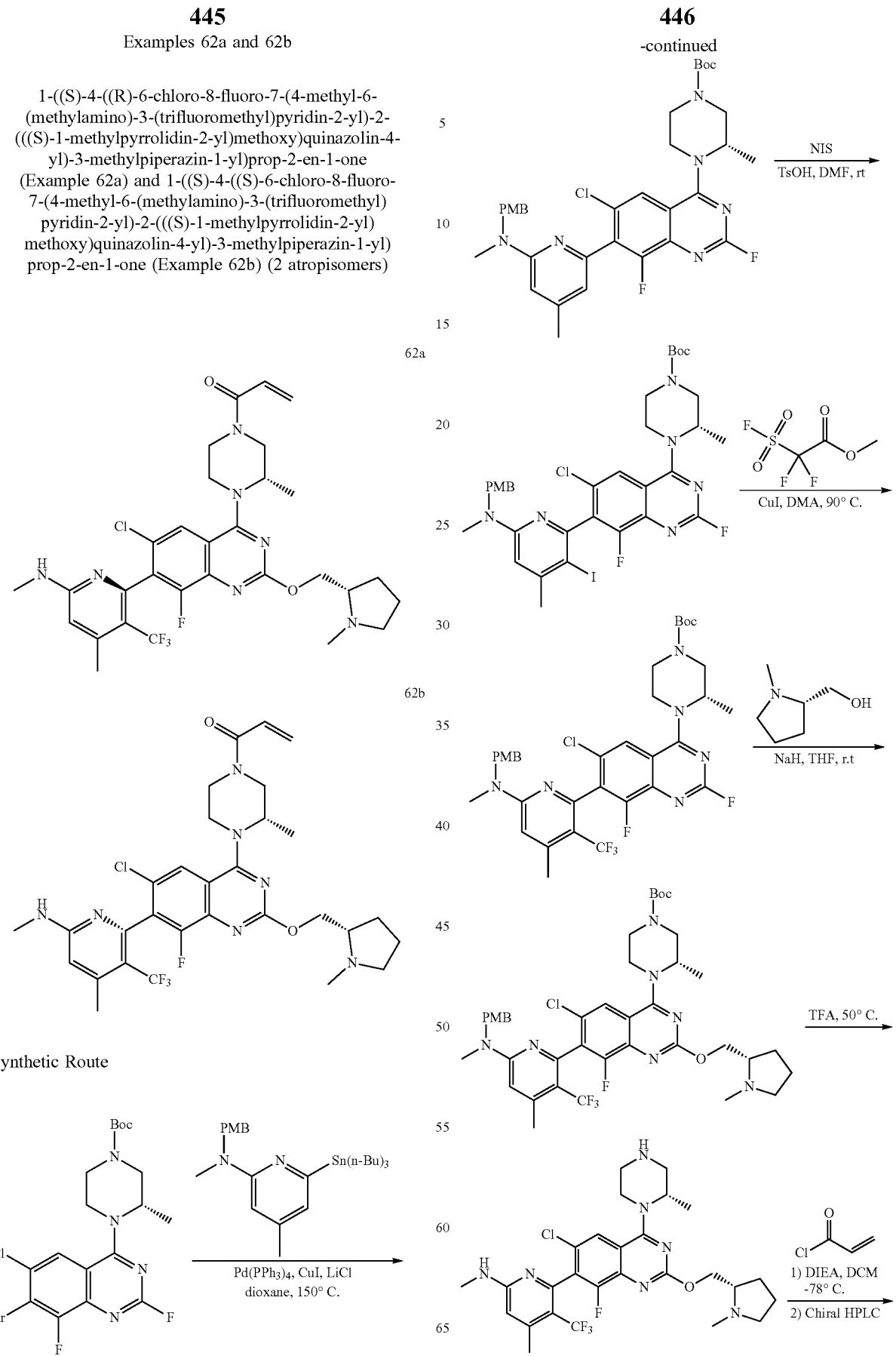

447

-continued

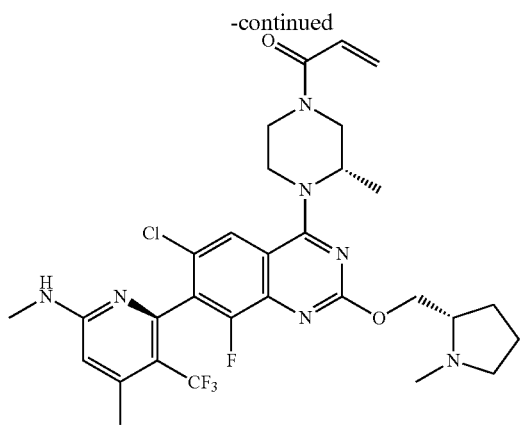

62a

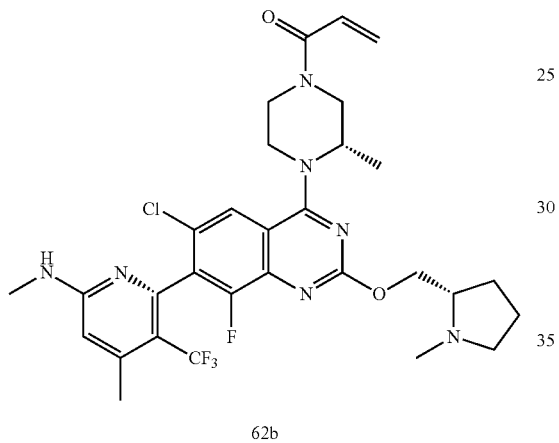

62b

Step 1: tert-butyl (S)-4-(6-chloro-2,8-difluoro-7-(6-((4-methoxybenzyl)(methyl)amino)-4-methylpyridin-2-yl)quinazolin-4-yl)-3-methylpiperazine-1-carboxylate

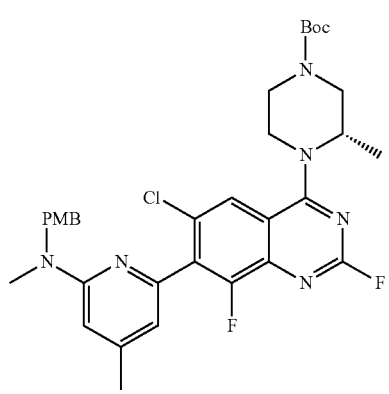

448

A solution of N-[(4-methoxyphenyl)methyl]-N,4-dimethyl-6-tributylstannyl-pyridin-2-amine (5.5 g, 10.35 mmol), tert-butyl (3S)-4-(7-bromo-6-chloro-2,8-difluoro-quinazolin-4-yl)-3-methyl-piperazine-1-carboxylate (2.47 g, 5.17 mmol), tetrakis(triphenylphosphine)palladium (1.2 g, 1.03 mmol), cuprous iodide (296.1 mg, 1.55 mmol) and lithium chloride (548.4 mg, 12.94 mmol) in 1,4-dioxane (100 mL) was stirred overnight at 150° C. under nitrogen. The reaction was concentrate and the residue was purified by flash chromatography on silica gel eluting with petroleum ether/ethyl acetate (7/3) to afford tert-butyl (S)-4-(6-chloro-2,8-difluoro-7-(6-((4-methoxybenzyl)(methyl)amino)-4-methylpyridin-2-yl)quinazolin-4-yl)-3-methylpiperazine-1-carboxylate (2.2 g, 3.48 mmol, 67.2% yield) as a yellow solid. LC-MS: (ESI, m/z): 639.3 [M+H]$^+$ Step 2: tert-butyl (3S)-4-(6-chloro-2,8-difluoro-7-(3-iodo-6-((4-methoxybenzyl)(methyl)amino)-4-methylpyridin-2-yl)quinazolin-4-yl)-3-methylpiperazine-1-carboxylate

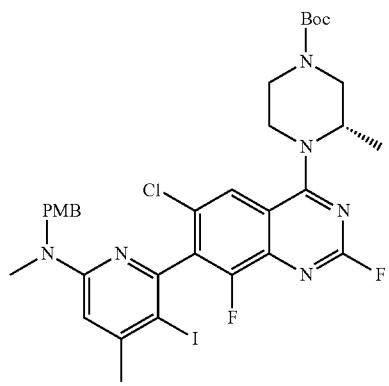

A solution of tert-butyl (S)-4-(6-chloro-2,8-difluoro-7-(6-((4-methoxybenzyl)(methyl)amino)-4-methylpyridin-2-yl)quinazolin-4-yl)-3-methylpiperazine-1-carboxylate (2.22 g, 3.48 mmol), N-iodosuccinimide (1.57 g, 6.96 mmol) and p-toluenesulfonic acid (129.5 mg, 0.75 mmol) were dissolved in N,N-dimethylformamide (100 mL) and stirred for overnight at room temperature. The reaction mixture was diluted with water and extracted with ethyl acetate. The organic layer was dried over anhydrous sodium sulfate and concentrated under vacuum. The residue was purified by flash chromatography on silica gel eluting with petroleum ether/ethyl acetate (75/25) to afford tert-butyl (3S)-4-(6-chloro-2,8-difluoro-7-(3-iodo-6-((4-methoxybenzyl)(methyl)amino)-4-methylpyridin-2-yl)quinazolin-4-yl)-3-methylpiperazine-1-carboxylate (1.53 g, 2.00 mmol, 57.5% yield) as a yellow solid. LC-MS: (ESI, m/z): 765.1 [M+H]$^+$.

Step 3: tert-butyl (3S)-4-(6-chloro-2,8-difluoro-7-(6-((4-methoxybenzyl)(methyl)amino)-4-methyl-3-(trifluoromethyl)pyridin-2-yl)quinazolin-4-yl)-3-methylpiperazine-1-carboxylate

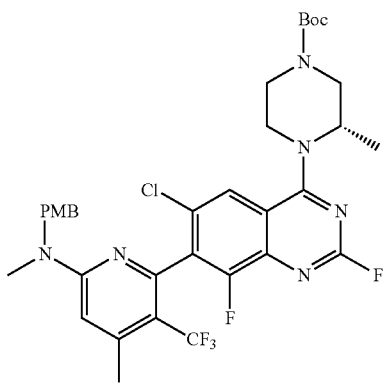

A solution of methyl 2,2-difluoro-2-(fluorosulfonyl)acetate (4.39 g, 22.85 mmol), tert-butyl (3S)-4-(6-chloro-2,8-difluoro-7-(3-iodo-6-((4-methoxybenzyl)(methyl)amino)-4-methylpyridin-2-yl)quinazolin-4-yl)-3-methylpiperazine-1-carboxylate (3.5 g, 4.57 mmol) and cuprous iodide (870.0 mg, 4.57 mmol) in N,N-dimethylformamide (70 mL) was stirred for 6 hours at 90° C. under nitrogen. The reaction was diluted with water and extracted with ethyl acetate. The organic layer was dried over anhydrous sodium sulfate and concentrated. The residue was purified by flash chromatography on silica gel eluting with petroleum ether/ethyl acetate (75/25) to afford tert-butyl (3S)-4-(6-chloro-2,8-difluoro-7-(6-((4-methoxybenzyl)(methyl)amino)-4-methyl-3-(trifluoromethyl)pyridin-2-yl)quinazolin-4-yl)-3-methylpiperazine-1-carboxylate (2.5 g, 3.54 mmol, 77.5% yield) as a yellow solid. LC-MS: (ESI, m/z): 707.3 [M+H]$^+$ Step 4: tert-butyl (3S)-4-(6-chloro-8-fluoro-7-(6-((4-methoxybenzyl)(methyl)amino)-4-methyl-3-(trifluoromethyl)pyridin-2-yl)-2-(((S)-1-methylpyrrolidin-2-yl)methoxy)quinazolin-4-yl)-3-methylpiperazine-1-carboxylate

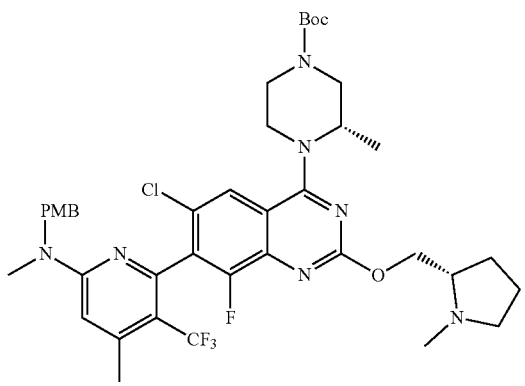

To a solution of N-methyl-1-prolinol (70 mg, 0.57 mmol) in tetrahydrofuran (3 mL) was added sodium hydride (23 mg, 0.57 mmol, 60% dispersion in mineral oil) at 0° C. The reaction was stirred for 0.5 hours. To the resulting mixture was added tert-butyl (3S)-4-(6-chloro-2,8-difluoro-7-(6-((4-methoxybenzyl)(methyl)amino)-4-methyl-3-(trifluoromethyl)pyridin-2-yl)quinazolin-4-yl)-3-methylpiperazine-1-carboxylate (0.2 g, 0.28 mmol) and the reaction was stirred at room temperature for an additional 0.5 hours. The reaction was quenched with water and extracted with ethyl acetate. Then the organic layer was dried over anhydrous sodium sulfate and concentrated. The residue was purified by flash chromatography on silica gel eluting with eluting with petroleum ether/ethyl acetate (30%) to afford tert-butyl (3S)-4-(6-chloro-8-fluoro-7-(6-((4-methoxybenzyl)(methyl)amino)-4-methyl-3-(trifluoromethyl)pyridin-2-yl)-2-(((S)-1-methylpyrrolidin-2-yl)methoxy)quinazolin-4-yl)-3-methylpiperazine-1-carboxylate (100 mg, 0.12 mmol, 44.1% yield) as a yellow solid. LCMS (ESI, m/z): 802.1 [M+H]$^+$.

Step 5: 6-(6-chloro-8-fluoro-4-((S)-2-methylpiperazin-1-yl)-2-(((S)-1-methylpyrrolidin-2-yl)methoxy)quinazolin-7-yl)-N,4-dimethyl-5-(trifluoromethyl)pyridin-2-amine

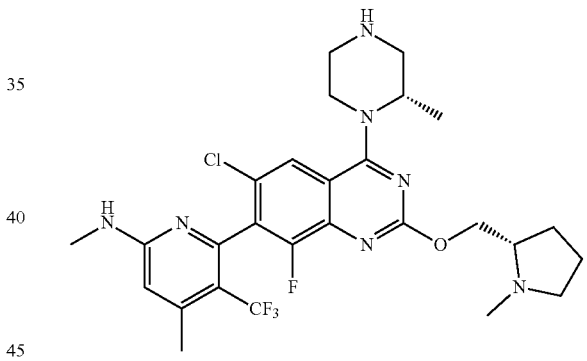

A solution of tert-butyl (3S)-4-(6-chloro-8-fluoro-7-(6-((4-methoxybenzyl)(methyl)amino)-4-methyl-3-(trifluoromethyl)pyridin-2-yl)-2-(((S)-1-methylpyrrolidin-2-yl)methoxy)quinazolin-4-yl)-3-methylpiperazine-1-carboxylate (2.1 g, 2.66 mmol) in trifluoroacetic acid (40 mL) was stirred at 50° C. for 2 hours. The reaction solution was concentrated and the residue was purified by flash chromatography on silica gel eluting with methanol/dichloromethane (2/10) to afford 6-(6-chloro-8-fluoro-4-((S)-2-methylpiperazin-1-yl)-2-(((S)-1-methylpyrrolidin-2-yl)methoxy)quinazolin-7-yl)-N,4-dimethyl-5-(trifluoromethyl)pyridin-2-amine (1.2 g, 2.11 mmol, 79.3% yield) as a yellow solid. LCMS (ESI, m/z): 582.1 [M+H]$^+$.

Step 6: 1-((S)-4-((R)-6-chloro-8-fluoro-7-(4-methyl-6-(methylamino)-3-(trifluoromethyl)pyridin-2-yl)-2-(((S)-1-methylpyrrolidin-2-yl)methoxy)quinazolin-4-yl)-3-methylpiperazin-1-yl)prop-2-en-1-one (Example 62a) and 1-((S)-4-((S)-6-chloro-8-fluoro-7-(4-methyl-6-(methylamino)-3-(trifluoromethyl)pyridin-2-yl)-2-(((S)-1-methylpyrrolidin-2-yl)methoxy)quinazolin-4-yl)-3-methylpiperazin-1-yl)prop-2-en-1-one (Example 62b) (2 atropisomers)

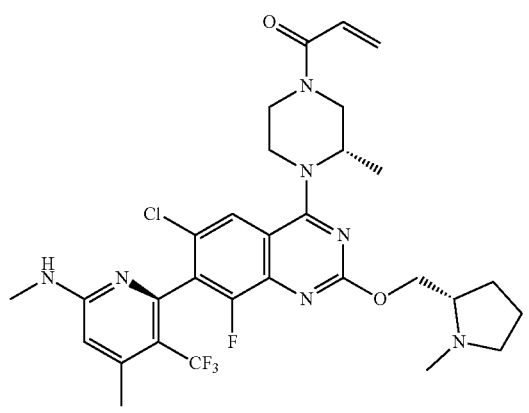

62a

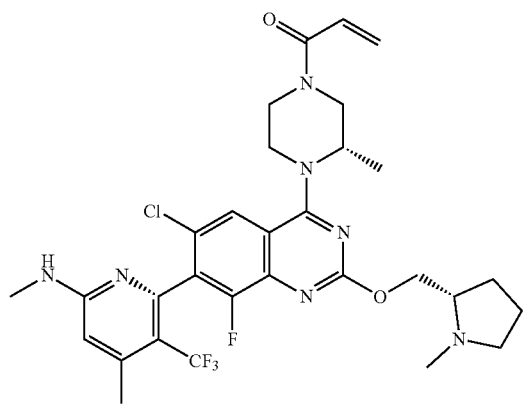

62b

A solution of 6-(6-chloro-8-fluoro-4-((S)-2-methylpiperazin-1-yl)-2-(((S)-1-methylpyrrolidin-2-yl)methoxy)quinazolin-7-yl)-N,4-dimethyl-5-(trifluoromethyl)pyridin-2-amine (400.0 mg, 0.69 mmol) and N,N-diisopropylethylamine (177.3 mg, 1.37 mmol) in dichloromethane (10 mL) was cooled to −78° C. To the reaction was added acryloyl chloride (62 mg, 0.69 mmol) and the mixture was stirred at −78° C. for 2 hours. The reaction was quenched with water and extracted with ethyl acetate. The organic layer was dried over anhydrous sodium sulfate and concentrated. The residue was isolated by Prep-HPLC-Column, CHIRAL ART Cellulose-SB, 2*25 cm, 5 um; mobile phase, Hex-HPLC and ethanol-HPLC (hold 40% ethanol-HPLC in 10 min); Detector, UV 220/254 nm to afford the title compounds. The stereo chemistry of title compounds was assigned based on potency.

Example 62a 1-((S)-4-((R)-6-chloro-8-fluoro-7-(4-methyl-6-(methylamino)-3-(trifluoromethyl)pyridin-2-yl)-2-(((S)-1-methylpyrrolidin-2-yl)methoxy)quinazolin-4-yl)-3-methylpiperazin-1-yl)prop-2-en-1-one (70.9 mg, 0.11 mmol, 16.2% yield, white solid). $^1$H NMR (400 MHz, Methanol-$d_4$, ppm) δ 7.84 (d, J=1.7 Hz, 1H), 6.93-6.76 (m, 1H), 6.53 (s, 1H), 6.31 (d, J=16.8 Hz, 1H), 5.87-5.79 (m, 1H), 4.59-4.38 (m, 3H), 4.28-4.22 (m, 2H), 4.20-4.15 (m, 2H), 4.05 (d, J=14.1 Hz, 1H), 3.76-3.72 (m, 1H), 3.61 (s, 1H), 3.40 (s, 3H), 3.23-3.20 (m, 1H), 3.15-3.08 (m, 3H), 2.89 (s, 3H), 2.81-2.73 (m, 1H), 2.54-2.50 (m, 1H), 2.49-2.44 (m, 3H), 1.43 (s, 3H).

Example 62b 1-((S)-4-((S)-6-chloro-8-fluoro-7-(4-methyl-6-(methylamino)-3-(trifluoromethyl)pyridin-2-yl)-2-(((S)-1-methylpyrrolidin-2-yl)methoxy)quinazolin-4-yl)-3-methylpiperazin-1-yl)prop-2-en-1-one (65.1 mg, 0.10 mmol, 14.9% yield, white solid). $^1$H NMR (300 MHz, Methanol-$d_4$) δ 7.84 (d, J=1.7 Hz, 1H), 6.85 (d, J=10.7 Hz, 1H), 6.53 (s, 1H), 6.31 (d, J=17.5 Hz, 1H), 5.83 (d, J=10.6 Hz, 1H), 4.51-4.48 (m, 3H), 4.31 (d, J=13.9 Hz, 2H), 4.05 (d, J=13.2 Hz, 1H), 3.76 (d, J=14.0 Hz, 2H), 3.18-3.09 (m, 1H), 2.88 (s, 4H), 2.56 (s, 4H), 2.46 (s, 3H), 2.45-2.34 (m, 2H), 1.92-1.73 (m, 3H), 1.45 (d, J=6.8 Hz, 3H). LC-MS: (ESI, m/z): 636.1 [M+H]$^+$.

Examples 63a and 63b 1-((S)-4-((R)-7-(3-aminoisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one (Example 63a) and 1-((S)-4-((S)-7-(3-aminoisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one (Example 63b)

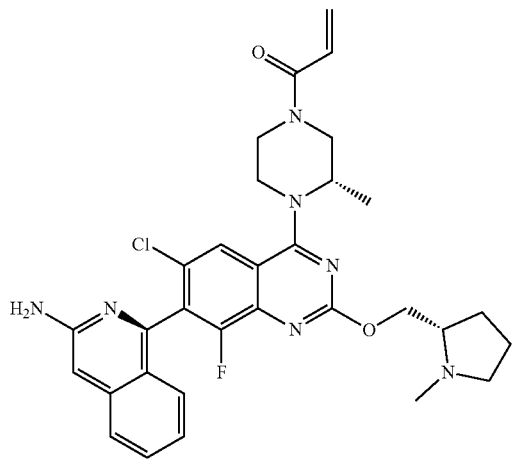

63a

-continued
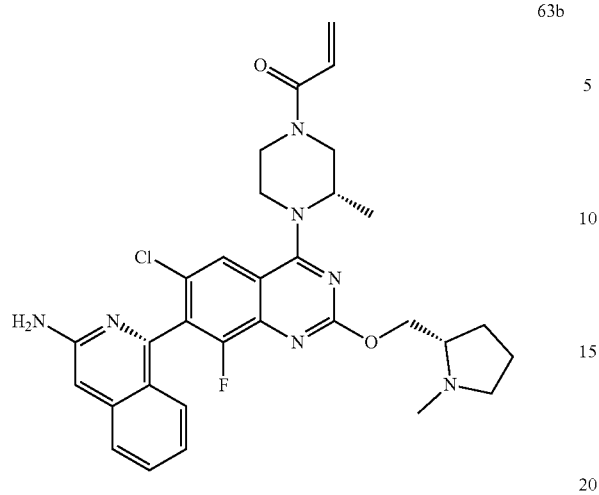
63b
Synthetic Route
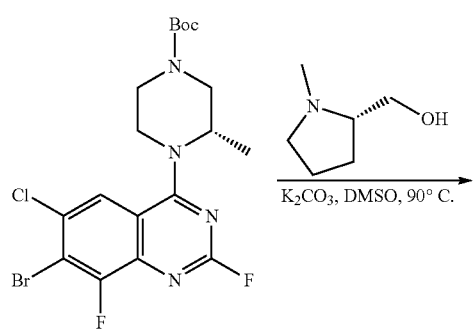
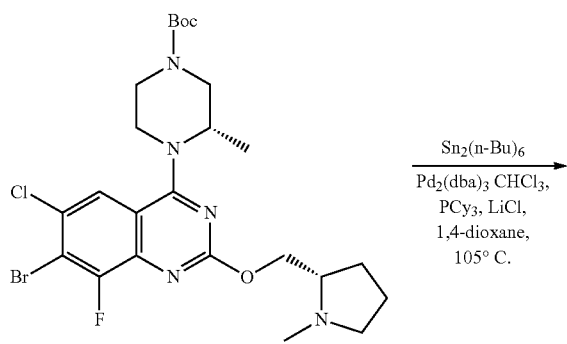
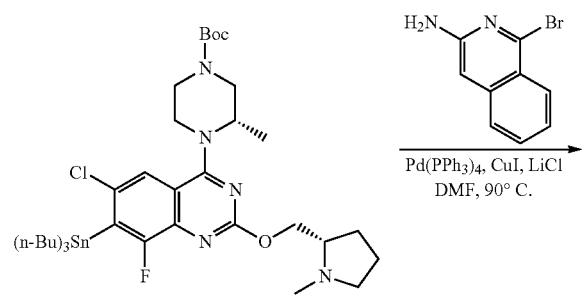

-continued
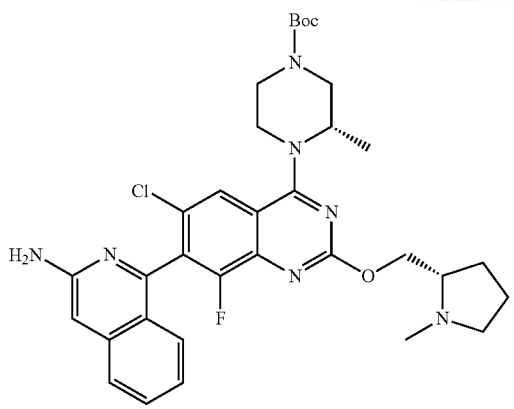
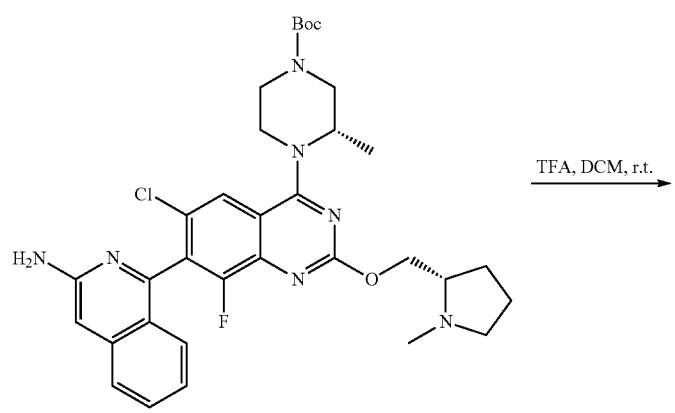
TFA, DCM, r.t.
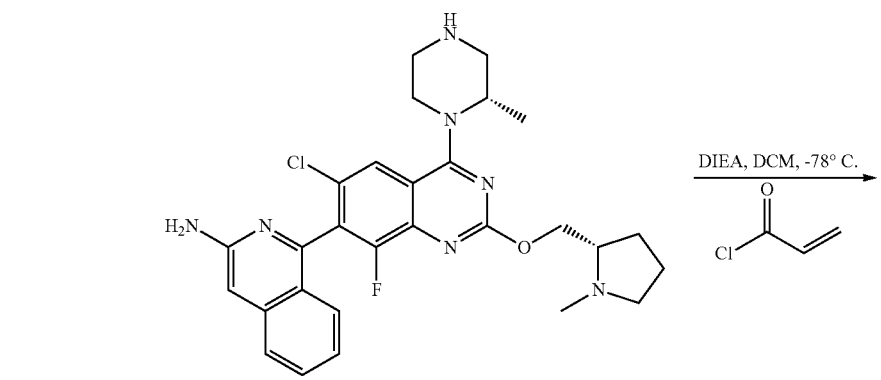
DIEA, DCM, −78° C.
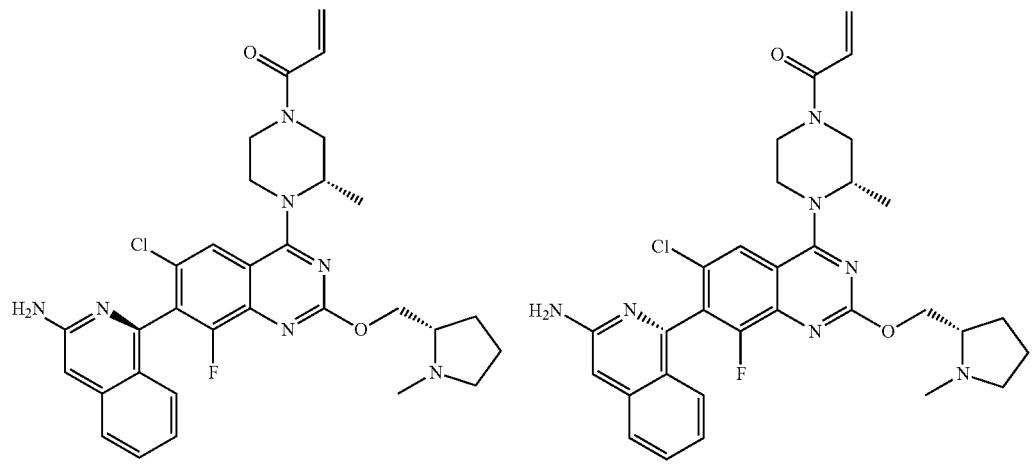
63a
63b Step 1: tert-butyl (S)-4-(7-bromo-6-chloro-8-fluoro-2-(((S)-1-methylpyrrolidin-2-yl)methoxy)quinazolin-4-yl)-3-methylpiperazine-1-carboxylate

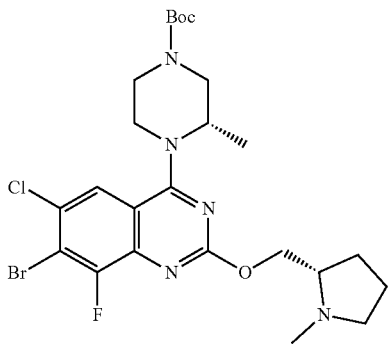 [SMILES: C[C@H]1CN(C(=O)OC(C)(C)C)CCN1c1nc(OC[C@@H]2CCCN2C)nc2c(F)c(Br)c(Cl)cc12]

A solution of N-methyl-1-prolinol (3.5 g, 30.39 mmol) and potassium carbonate (5.6 g, 40.58 mmol) in dimethyl sulfoxide (20 mL) was stirred at 90° C. for 0.5 hours. Then tert-butyl (S)-4-(7-bromo-6-chloro-2,8-difluoroquinazolin-4-yl)-3-methylpiperazine-1-carboxylate (10.0 g, 20.24 mmol) was added and stirred at 90° C. for 1 hour. Upon completion, the reaction mixture was diluted with water. The resulting solution was extracted with dichloromethane and washed with water. The organic layer was dried over anhydrous sodium sulfate and concentrated under vacuum. The residue was purified by flash chromatography on silica gel eluting with dichloromethane/methanol (94:6) to afford tert-butyl (S)-4-(7-bromo-6-chloro-8-fluoro-2-(((S)-1-methylpyrrolidin-2-yl)methoxy)quinazolin-4-yl)-3-methylpiperazine-1-carboxylate (6.5 g, 11.3 mmol, 56.1% yield) as a yellow oil. LC-MS: (ESI, m/z): 572.1 [M+H]$^+$ Step 2: tert-butyl (S)-4-(6-chloro-8-fluoro-2-(((S)-1-methylpyrrolidin-2-yl)methoxy)-7-(tributylstannyl)quinazolin-4-yl)-3-methylpiperazine-1-carboxylate

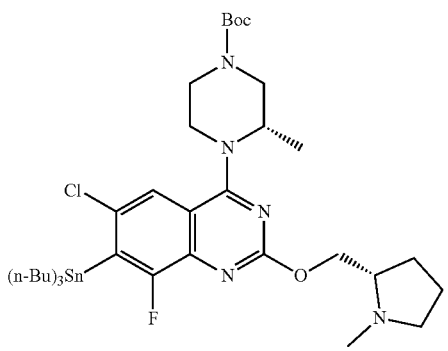

A solution of tert-butyl (S)-4-(7-bromo-6-chloro-8-fluoro-2-(((S)-1-methylpyrrolidin-2-yl)methoxy)quinazolin-4-yl)-3-methylpiperazine-1-carboxylate (1.0 g, 1.75 mmol), hexabutylditin (2.9 g, 8.85 mmol), tris(dibenzylideneacetone)dipalladium-chloroformadduct (181.0 mg, 0.1700 mmol), tricyclohexylphosphine (100.0 mg, 0.3600 mmol) and lithium chloride (189.0 mg, 4.35 mmol) in 1,4-dioxane (100 mL) was stirred at 105° C. for 2 hours under nitrogen. Upon completion, the reaction mixture was diluted with dichloromethane. The resulting solution was washed with water. The organic layer was dried over anhydrous sodium sulfate and concentrated under vacuum. The residue was purified by flash chromatography on C18 gel eluting with methanol/water (19:1) to afford tert-butyl (S)-4-(6-chloro-8-fluoro-2-(((S)-1-methylpyrrolidin-2-yl)methoxy)-7-(tributylstannyl)quinazolin-4-yl)-3-methylpiperazine-1-carboxylate (340 mg, 0.4 mmol, 24.9% yield) as a brown solid. LC-MS: (ESI, m/z): 784.3 [M+H]$^+$ Step 3: tert-butyl (3S)-4-(7-(3-aminoisoquinolin-1-yl)-6-chloro-8-fluoro-2-(((S)-1-methylpyrrolidin-2-yl)methoxy)quinazolin-4-yl)-3-methylpiperazine-1-carboxylate

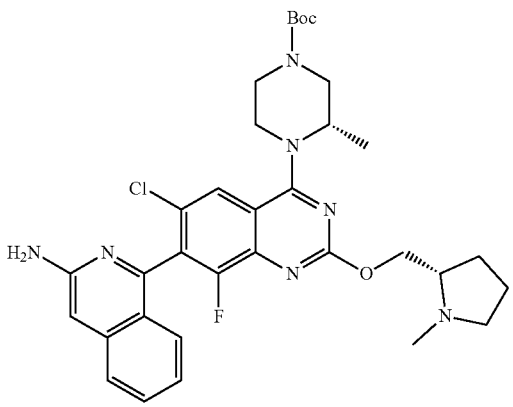 [SMILES: C[C@H]1CN(C(=O)OC(C)(C)C)CCN1c1nc(OC[C@@H]2CCCN2C)nc2c(F)c(-c3nc(N)cc4ccccc34)c(Cl)cc12]

A solution of tert-butyl (S)-4-(6-chloro-8-fluoro-2-(((S)-1-methylpyrrolidin-2-yl)methoxy)-7-(tributylstannyl)quinazolin-4-yl)-3-methylpiperazine-1-carboxylate (212.5 mg, 0.27 mmol), 1-bromoisoquinolin-3-amine (50.0 mg, 0.2200 mmol), tetrakis(triphenylphosphine)Palladium(0) (130.0 mg, 0.1100 mmol), copper(I) iodide (22.5 mg, 0.1200 mmol) and lithium chloride (22.5 mg, 0.5200 mmol) in N,N-dimethylformamide (5 mL) was stirred at 90° C. for 1 hour under nitrogen. Upon completion, the solution was concentrated and the residue was purified by flash chromatography on C18 gel eluting with methanol/water (97:3) to afford tert-butyl (3S)-4-(7-(3-aminoisoquinolin-1-yl)-6-chloro-8-fluoro-2-(((S)-1-methylpyrrolidin-2-yl)methoxy)quinazolin-4-yl)-3-methylpiperazine-1-carboxylate (100 mg, 0.15 mmol, 70.1% yield) as a yellow solid. LC-MS: (ESI, m/z): 636.2 [M+H]$^+$

Step 4: 1-(6-chloro-8-fluoro-4-((S)-2-methylpiperazin-1-yl)-2-(((S)-1-methylpyrrolidin-2-yl)methoxy)quinazolin-7-yl)isoquinolin-3-amine

Step 5: 1-((S)-4-((R)-7-(3-aminoisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one (Example 63a) and 1-((S)-4-((S)-7-(3-aminoisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one (Example 63b)

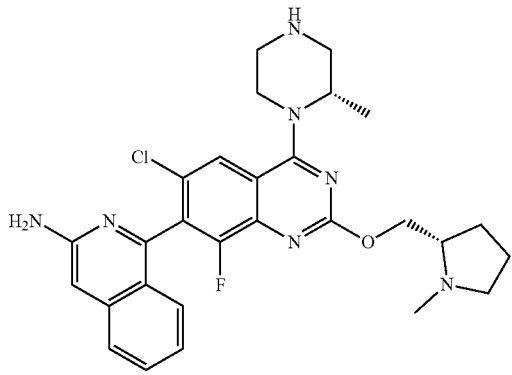 [SMILES: C[C@H]1CNCCN1c1nc(OC[C@@H]2CCCN2C)nc2c(F)c(-c3nc(N)cc4ccccc34)c(Cl)cc12]

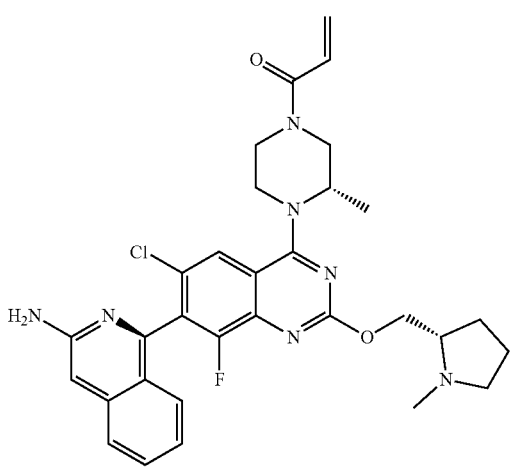

63a

A solution of tert-butyl (3S)-4-(7-(3-aminoisoquinolin-1-yl)-6-chloro-8-fluoro-2-(((S)-1-methylpyrrolidin-2-yl)methoxy)quinazolin-4-yl)-3-methylpiperazine-1-carboxylate (600.0 mg, 0.94 mmol) in dichloromethane (20 mL) and trifluoroacetic acid (10 mL, 129.8 mmol) was stirred at 25° C. for 1 hour. Upon completion, the reaction was concentrated and residue was purified by flash chromatography on C18 gel eluting with methanol/water (40:60) to afford 1-(6-chloro-8-fluoro-4-((S)-2-methylpiperazin-1-yl)-2-(((S)-1-methylpyrrolidin-2-yl)methoxy)quinazolin-7-yl)isoquinolin-3-amine (410 mg, 0.76 mmol, 81.1% yield) as a yellow solid. LC-MS: (ESI, m/z): 536.2 [M+H]$^+$

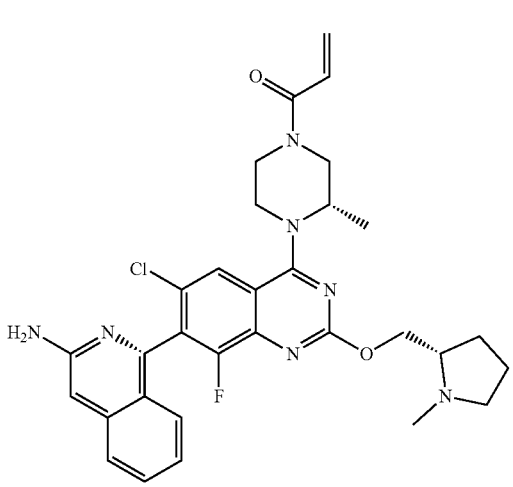

63b

A solution of 1-(6-chloro-8-fluoro-4-((S)-2-methylpiperazin-1-yl)-2-(((S)-1-methylpyrrolidin-2-yl)methoxy)quinazolin-7-yl)isoquinolin-3-amine (410.0 mg, 0.76 mmol) and N,N-diisopropylethylamine (0.13 mL, 0.77 mmol) in dichloromethane (10 mL) was stirred at −78° C. for 5 minutes. Then acryloyl chloride (76.0 mg, 0.84 mmol) was added and stirred at −78° C. for 30 minutes. Upon completion, the reaction was quenched with water and the reaction was concentrated. The residue was purified by flash chromatography on C18 gel eluting with methanol/water (9:1) and further purified by Prep-HPLC-Column: Xcelect CSH F-pheny OBD Column 19*250 mm, 5 um; mobile phase A:water(10 mmol/L $NH_4HCO_3$), mobile Phase B: methanol; flow rate: 25 mL/min. The product was purified by Chiral-Prep-HPLC-Column: CHIRALPAK IC, 2*25 cm, 5 um; Mobile Phase A:Hex:DCM=1:1(10 mM NH3-MeOH)-HPLC, Mobile Phase B: EtOH-HPLC; Flow rate: 18 mL/min. The residue was freeze-dried to get 1-((S)-4-((R)-7-(3-aminoisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one (Example 63) (39.7 mg, 0.06 mmol, 8.8% yield) as a yellow solid and 1-((S)-4-((S)-7-(3-aminoisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one (Example 63b) (47.0 mg, 0.079 mmol, 10.4% yield) as a yellow solid.

Example 63a

LC-MS: (ESI, m/z): 590.2 [M+H]$^+$, 1H NMR (300 MHz, CDCl3, ppm) δ 7.74 (s, 1H), 7.64 (d, J=8.4 Hz, 1H), 7.54-7.49 (m, 1H), 7.39 (d, J=8.4 Hz, 1H), 7.28-7.15 (m, 1H), 6.88 (s, 1H), 6.69-6.55 (m, 1H), 6.39 (dd, J=1.8, 16.5 Hz, 1H), 5.79 (dd, J=1.8, 10.5 Hz, 1H), 4.90-4.70 (m, 1H), 4.67-4.50 (m, 3H), 4.39-4.27 (m, 1H), 4.23-4.11 (m, 1H), 4.05-3.85 (m, 1H), 3.72-3.41 (m, 2H), 3.40-2.95 (m, 2H), 2.82-2.75 (m, 1H), 2.52 (s, 3H), 2.42-1.95 (m, 3H), 1.95-1.69 (m, 3H), 1.50-1.25 (m, 3H). Chiral HPLC: CHIRALPAK IG-3 (0.46*5 cm; 3 um); detected at 254 nm; (n-hexane/dichloromethane=1/1)(0.1% diethylamine)/ethanol=1/1; flow rate=1.0 mL/min; Retention time: 1.5 min (faster peak)

Example 63b

LC-MS: (ESI, m/z): 590.2 [M+H]$^+$, $^1$H NMR (300 MHz, CDCl$_3$, ppm) δ 7.73 (s, 1H), 7.65 (d, J=8.1 Hz, 1H), 7.55-7.50 (m, 1H), 7.40 (d, J=8.4 Hz, 1H), 7.21-7.18 (m, 1H), 6.89 (s, 1H), 6.78-6.50 (m, 1H), 6.40 (dd, J=2.1, 16.8 Hz, 1H), 5.80 (d, J=11.1 Hz, 1H), 4.80-4.67 (m, 1H), 4.65-4.45 (m, 3H), 4.45-4.32 (m, 1H), 4.32-4.17 (m, 1H), 4.12-3.75 (m, 1H), 3.78-3.43 (m, 2H), 3.30-3.00 (m, 2H), 2.97-2.70 (m, 1H), 2.55 (s, 3H), 2.45-2.30 (m, 1H), 2.17-2.03 (m, 1H), 1.99-1.66 (m, 4H), 1.54-1.35 (m, 3H). Chiral HPLC: CHIRALPAK IG-3 (0.46*5 cm; 3 um); detected at 254 nm; (n-hexane/dichloromethane=1/1)(0.1% diethylamine)/ethanol=1/1; flow rate=1.0 mL/min; Retention time: 2.5 min (slower peak)

Examples 64a and 64b (S)-5-(4(S)-4-((S)-4-acryloyl-2-methylpiperazin-1-yl)-7-(6-amino-4-methyl-3-(trifluoromethyl)pyridin-2-yl)-6-chloro-8-fluoroquinazolin-2-yl)oxy)methyl)-1-methylpyrrolidin-2-one (Example 64a) and (S)-5-(4(R)-4-((S)-4-acryloyl-2-methylpiperazin-1-yl)-7-(6-amino-4-methyl-3-(trifluoromethyl)pyridin-2-yl)-6-chloro-8-fluoroquinazolin-2-yl)oxy)methyl)-1-methylpyrrolidin-2-one (Example 64b) (2 atropisomers)

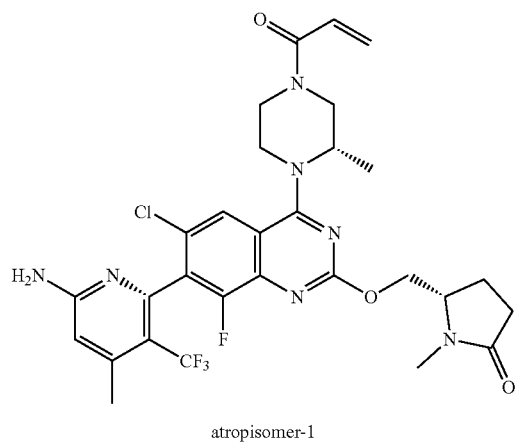

atropisomer-1

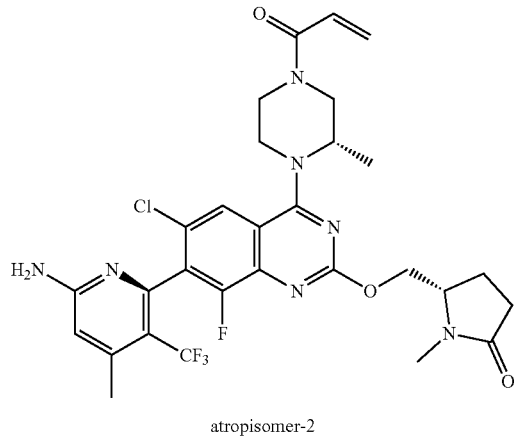

atropisomer-2

Synthetic Route

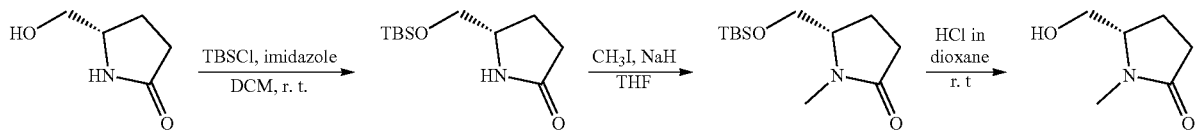

-continued
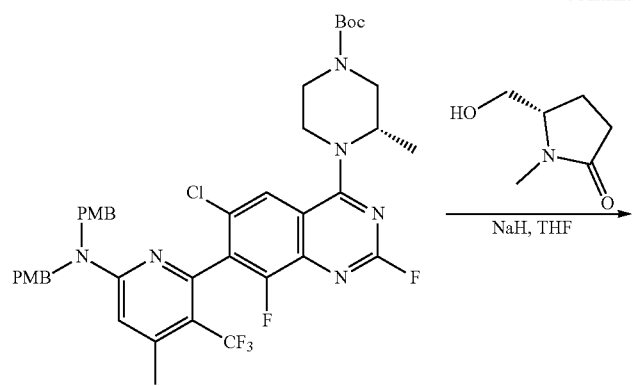
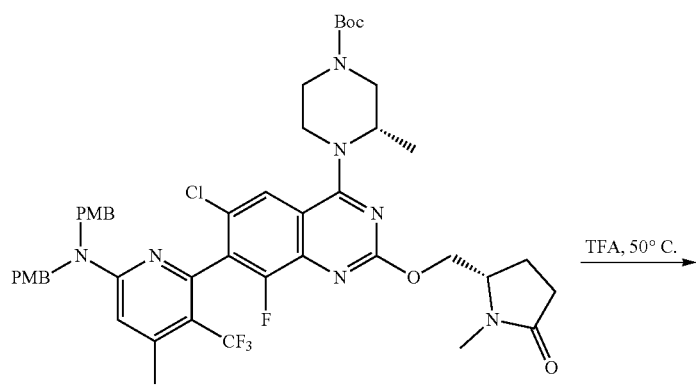
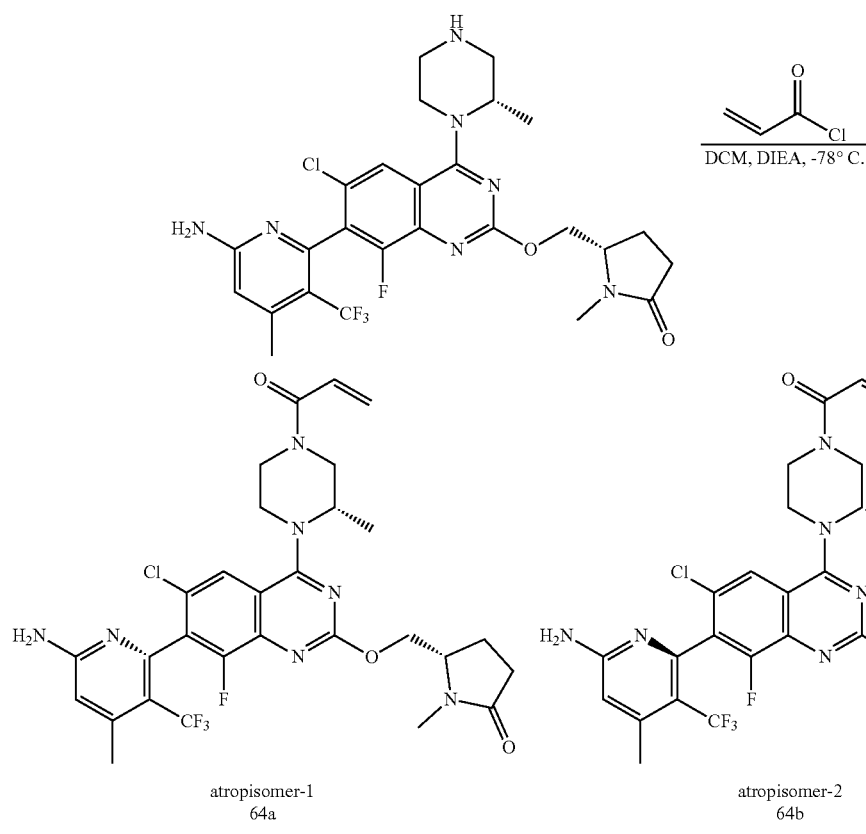

Step 1: (5S)-5-[[tert-butyl(dimethyl)silyl]oxymethyl]pyrrolidin-2-one

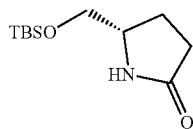 [SMILES: CC(C)(C)[Si](C)(C)OC[C@@H]1CCC(=O)N1]

A solution of (5S)-5-(hydroxymethyl)-2-pyrrolidinone (15.0 g, 130.29 mmol), imidazole (17.74 g, 260.58 mmol) and tert-butyldimethylsilyl chloride (29.31 g, 195.43 mmol) in dichloromethane (300 mL) was stirred at 25° C. for 1 hour. Upon completion, the reaction was concentrated and the residue was purified by flash chromatography on silica gel eluting with dichloromethane/methanol (97/3) to afford 25 g (83.6%) of (5S)-5-[[tert-butyl(dimethyl)silyl]oxymethyl]pyrrolidin-2-one as a colorless oil. LC-MS: (ESI, m/z): 230.1 [M+H]$^+$ Step 2: (5S)-5-[[tert-butyl(dimethyl)silyl]oxymethyl]-1-methyl-pyrrolidin-2-one

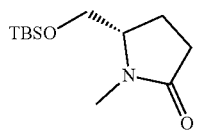 [SMILES: CN1C(=O)CC[C@H]1CO[Si](C)(C)C(C)(C)C]

A solution of (5S)-5-[[tert-butyl(dimethyl)silyl]oxymethyl]pyrrolidin-2-one (18.0 g, 78.47 mmol) in tetrahydrofuran (300 mL) was added sodium hydride (10.99 g, 274.64 mmol, 60% dispersion in mineral oil) stirred at 25° C. for 10 minutes. Then iodomethane (22.29 g, 156.94 mmol) was added stirred at 25° C. for 1 hour. Upon completion, the resulting solution was quenched with water and the mixture was concentrated. The residue was purified by flash chromatography on silica gel eluting with dichloromethane/methanol (20/1) to afford 10 g (52.4%) of (5S)-5-[[tert-butyl(dimethyl)silyl]oxymethyl]-1-methyl-pyrrolidin-2-one as a colorless oil. LC-MS: (ESI, m/z): 244.1 [M+H]$^+$ Step 3: (5S)-5-(hydroxymethyl)-1-methyl-pyrrolidin-2-one

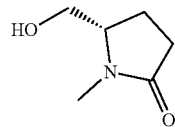

A solution of (5 S)-5-[[tert-butyl(dimethyl)silyl]oxymethyl]-1-methyl-pyrrolidin-2-one (1.06 g, 4.35 mmol) in HCl/dioxane (30 mL, 4.35 mmol) was stirred at 25° C. for 2 hours. Upon completion, the reaction was concentrated, the pH was adjusted to 7-8 with aqueous sodium bicarbonate. The reaction was concentrated and the resulting mixture was purified by flash chromatography on silica gel eluting with dichloromethane/methanol (95/5) to afford 550 mg (97.8%) of (5S)-5-(hydroxymethyl)-1-methyl-pyrrolidin-2-one as a yellow oil. LC-MS: (ESI, m/z): 130.1 [M+H]$^+$ Step 4: tert-butyl (3S)-4-[7-[6-[bis[(4-methoxyphenyl)methyl]amino]-4-methyl-3-(trifluoromethyl)-2-pyridyl]-6-chloro-8-fluoro-2-[[(2S)-1-methyl-5-oxopyrrolidin-2-yl]methoxy]quinazolin-4-yl]-3-methylpiperazine-1-carboxylate

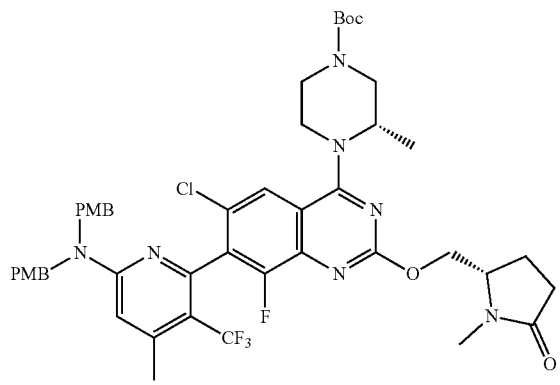

A solution of (5S)-5-(hydroxymethyl)-1-methyl-pyrrolidin-2-one (0.54 g, 4.18 mmol) in tetrahydrofuran (8 mL) was added sodium hydride (292.65 mg, 7.32 mmol, 60% dispersion in mineral oil) at 0° C. and stirred at 25° C. for 1 hour. Then tert-butyl (3S)-4-[7-[6-[bis[(4-methoxyphenyl)methyl]amino]-4-methyl-3-(trifluoromethyl)-2-pyridyl]-6-chloro-2,8-difluoro-quinazolin-4-yl]-3-methyl-piperazine-1-carboxylate (see Step 9 of Example 17a/17b) (1.7 g, 2.09 mmol) was added and stirred at 25° C. for 1 hour. Upon completion, the reaction was quenched with water and extracted with dichloromethane. Then the organic layers were combined, washed with water, dried over anhydrous sodium sulfate and concentrated. The residue was purified by flash chromatography on silica gel eluting with dichloromethane/methanol (95/5) to afford 1.676 g (86.9%) of tert-butyl (3S)-4-[7-[6-[bis[(4-methoxyphenyl)methyl] amino]-4-methyl-3-(trifluoromethyl)-2-pyridyl]-6-chloro-8-fluoro-2-[[(2S)-1-methyl-5-oxo-pyrrolidin-2-yl]methoxy] quinazolin-4-yl]-3-methyl-piperazine-1-carboxylate as a yellow solid. LC-MS: (ESI, m/z): 922.3 [M+H]$^+$ Step 5: (5S)-5-[[7-[6-amino-4-methyl-3-(trifluoromethyl)-2-pyridyl]-6-chloro-8-fluoro-4-[(2S)-2-methylpiperazin-1-yl]quinazolin-2-yl]oxymethyl]-1-methyl-pyrrolidin-2-one

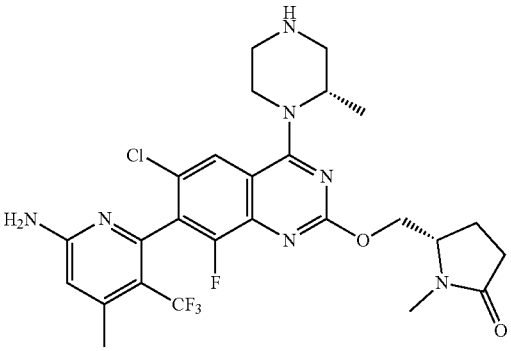 [SMILES: Cc1cc(N)nc(-c2c(Cl)cc3c(N4CCNC[C@@H]4C)nc(OC[C@@H]4CCC(=O)N4C)nc3c2F)c1C(F)(F)F]

A solution of tert-butyl (3S)-4-[7-[6-[bis[(4-methoxyphenyl)methyl]amino]-4-methyl-3-(trifluoromethyl)-2-pyridyl]-6-chloro-8-fluoro-2-[[(2S)-1-methyl-5-oxo-pyrrolidin-2-yl]methoxy]quinazolin-4-yl]-3-methyl-piperazine-1-carboxylate (1.63 g, 1.77 mmol) in trifluoroacetic acid (8 mL) was stirred at 50° C. for 24 hours. Upon completion, the reaction was concentrated. The pH was adjusted to 8 with N,N-diisopropylethylamine. The residue was purified by a reversed-phase chromatography-Column, C18 silica gel; mobile phase, A: water, B: acetonitrile, B % (5% 70% in 30 min); Detector, UV 254 nm to afford 785 mg (76.1%) of (5S)-5-[[7-[6-amino-4-methyl-3-(trifluoromethyl)-2-pyridyl]-6-chloro-8-fluoro-4-[(2S)-2-methylpiperazin-1-yl]quinazolin-2-yl]oxymethyl]-1-methyl-pyrrolidin-2-one as a light yellow solid. LC-MS: (ESI, m/z): 582.2 [M+H]+

Step 6: (S)-5-(4(S)-4-((S)-4-acryloyl-2-methylpiperazin-1-yl)-7-(6-amino-4-methyl-3-(trifluoromethyl)pyridin-2-yl)-6-chloro-8-fluoroquinazolin-2-yl)oxy)methyl)-1-methylpyrrolidin-2-one (Example 64a) and (S)-5-(4(R)-4-((S)-4-acryloyl-2-methylpiperazin-1-yl)-7-(6-amino-4-methyl-3-(trifluoromethyl)pyridin-2-yl)-6-chloro-8-fluoroquinazolin-2-yl)oxy)methyl)-1-methylpyrrolidin-2-one (Example 64b) (2 atropisomers)

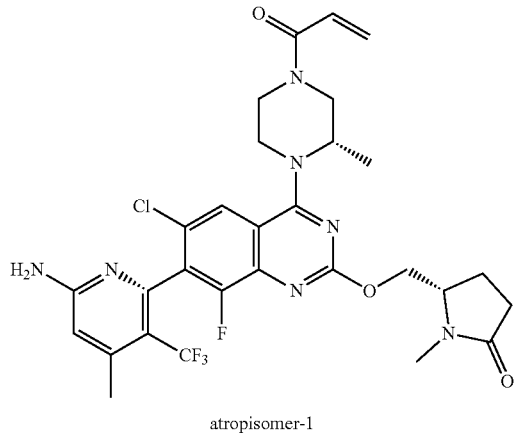

atropisomer-1

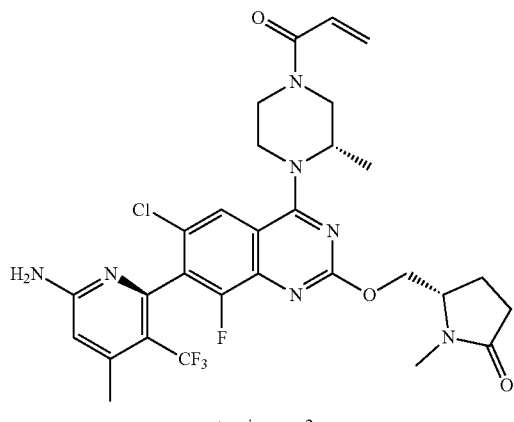

atropisomer-2

To a solution (5S)-5-[[7-[6-amino-4-methyl-3-(trifluoromethyl)-2-pyridyl]-6-chloro-8-fluoro-4-[(2S)-2-methylpiperazin-1-yl]quinazolin-2-yl]oxymethyl]-1-methyl-pyrrolidin-2-one (463.0 mg, 0.80 mmol) and N,N-diisopropylethylamine (513.13 mg, 3.98 mmol) in dichloromethane (12 mL) was added acryloyl chloride (57.6 mg, 0.6400 mmol) at −78° C. and stirred at −78° C. for 1 hour. Upon completion, the reaction was quenched by water and extracted with dichloromethane. The organic layers were combined, dried over anhydrous sodium sulfate and concentrated under vacuum. The residue was purified by a reversed-phase chromatography-Column, C18 silica gel; mobile phase, A: water, B: acetonitrile, B % (5%~70% in 30 min); Detector, UV 254 nm to afford 251 mg of crude product as a white solid. The mixture of diastereoisomers was separated by Prep-Chiral-HPLC-Column, CHIRALPAK IE-3 0.46*5 cm 3 um; mobile phase, (Hex:dichloromethane=3:1) (0.1% DEA):EtOH=50:50; Detector, 254 nm; Flow, 1.0 ml/min; Temperature: 25° C. to afford 96.5 mg (19.1%) of (S)-5-(4(S)-4-((S)-4-acryloyl-2-methylpiperazin-1-yl)-7-(6-amino-4-methyl-3-(trifluoromethyl)pyridin-2-yl)-6-chloro-8-fluoroquinazolin-2-yl)oxy)methyl)-1-methylpyrrolidin-2-one as a white solid and 95.1 mg (18.8%) of (S)-5-((((R)-4-((S)-4-acryloyl-2-methylpiperazin-1-yl)-7-(6-amino-4-methyl-3-(trifluoromethyl)pyridin-2-yl)-6-chloro-8-fluoroquinazolin-2-yl)oxy)methyl)-1-methylpyrrolidin-2-one as a white solid. LC-MS: (ESI, m/z): 636.2 [M+H]+

Example 64a $^1$H NMR (400 MHz, Methanol-$d_4$, ppm) δ 7.85 (d, J=1.6 Hz, 1H), 6.92-6.77 (m, 1H), 6.62 (s, 1H), 6.30 (dd, J=16.8, 3.2 Hz, 1H), 5.82 (dd, J=10.8, 8.8 Hz, 1H), 4.82-4.78 (m, 1H), 4.52-4.48 (m, 2H), 4.31-4.28 (m, 1H), 4.28-4.01 (m, 2H), 3.87-3.52 (m, 2H), 3.40-3.44 (m, 1H), 3.32-3.17 (m, 1H), 2.92 (s, 3H), 2.61-2.58 (m, 1H), 2.46 (d, J=1.2 Hz, 3H), 2.37-2.27 (m, 2H), 2.10-2.05 (m, 1H), 1.43 (d, J=6.8 Hz, 3H). LC-MS: (ESI, m/z): 636.2 [M+H]+ Chiral HPLC: CHIRALPAK IE-3 (0.46*5 cm; 3 um); detected at 254 nm; Hex:DCM=3:1)(0.1% DEA):EtOH=50:50; flow=1 mL/min; Retention time: 1.74 min (faster peak).

Example 64b $^1$H NMR (400 MHz, Methanol-$d_4$, ppm) δ 7.85 (d, J=1.6 Hz, 1H), 6.92-6.77 (m, 1H), 6.62 (s, 1H), 6.30 (dd, J=16.8, 3.2 Hz, 1H), 5.81 (dd, J=10.8, 8.8 Hz, 1H), 4.85-4.77 (m, 1H), 4.53-4.49 (m, 2H), 4.31-4.28 (m, 1H), 4.28-4.01 (m, 2H), 3.87-3.52 (m, 2H), 3.36-3.34 (m, 1H), 3.30-3.17 (m, 1H), 2.92 (s, 3H), 2.61-2.58 (m, 1H), 2.46 (d, J=1.2 Hz, 3H), 2.37-2.27 (m, 2H), 2.11-2.05 (m, 1H), 1.43 (d, J=6.8 Hz, 3H). LC-MS: (ESI, m/z): 636.2 [M+H]+ Chiral HPLC: CHIRALPAK IE-3 (0.46*5 cm; 3 um); detected at 254 nm; Hex:DCM=3:1)(0.1% DEA):EtOH=50:50; flow=1 mL/min; Retention time: 3.48 min (slower peak).

Example 65

(E)-1-((S)-4-(7-(6-amino-4-methyl-3-(trifluoromethyl)pyridin-2-yl)-6-chloro-2-(((S)-1-methylpyrrolidin-2-yl)methoxy)quinazolin-4-yl)-3-methylpiperazin-1-yl)-4,4-difluorobut-2-en-1-one

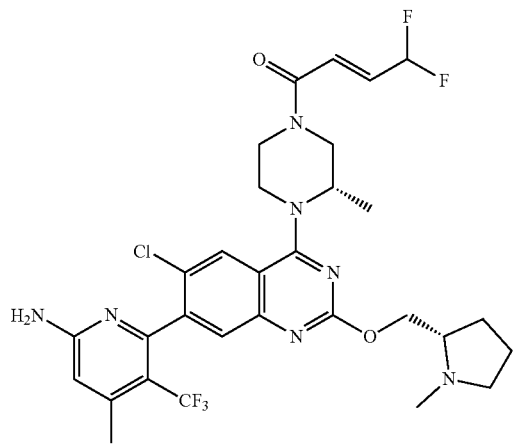 [SMILES: Cc1cc(N)nc(-c2cc3nc(OC[C@@H]4CCCN4C)nc(N4CCN(C(=O)/C=C/C(F)F)C[C@@H]4C)c3cc2Cl)c1C(F)(F)F]

Synthetic Route

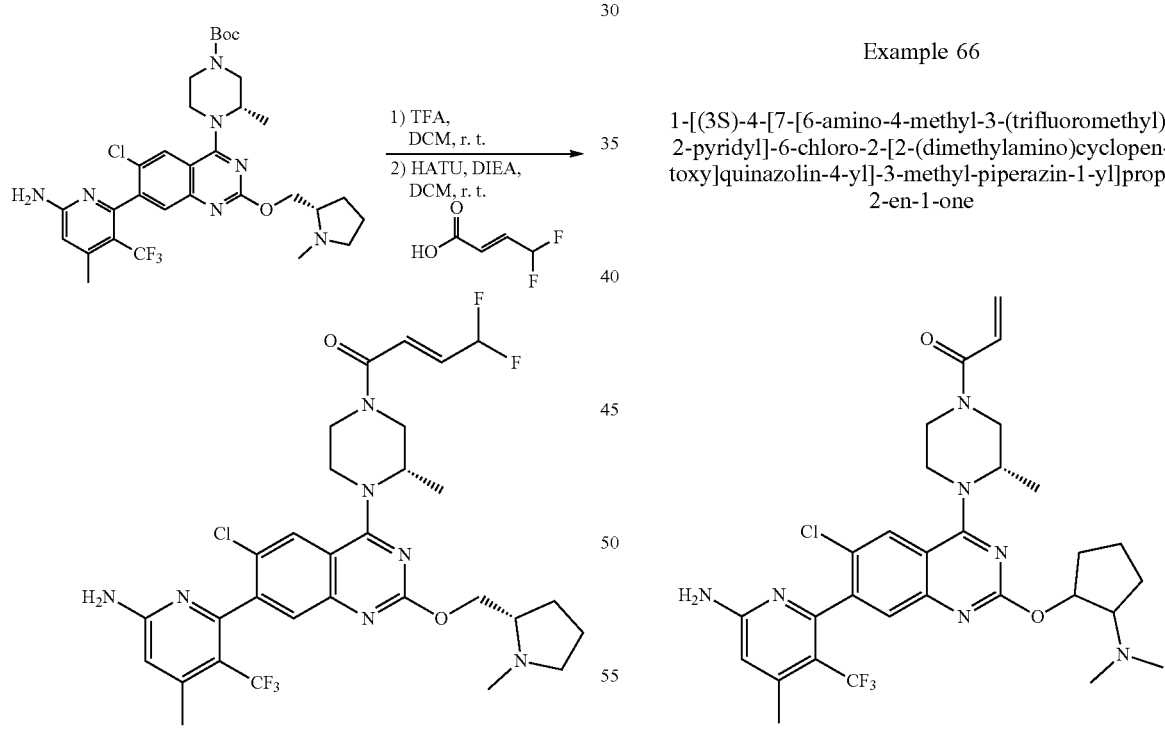

A solution of tert-butyl (S)-4-(7-(6-amino-4-methyl-3-(trifluoromethyl)pyridin-2-yl)-6-chloro-2-(((S)-1-methylpyrrolidin-2-yl)methoxy)quinazolin-4-yl)-3-methylpiperazine-1-carboxylate (see step 3, Example 61) (0.29 g, 0.53 mmol) and trifluoroacetic acid (0.6 mL, 7.79 mmol) in dichloromethane (3 mL) was stirred at 25° C. for 1 hour. Upon completion, the reaction mixture was concentrated. The resulting mixture was redissolved in dichloromethane (3 mL) and N,N-diisopropylethylamine (0.18 mL, 1.05 mmol), (E)-4,4-difluorobut-2-enoic acid (0.07 g, 0.58 mmol) and 2-(7-azabenzotriazol-1-yl)-N,N,N',N'-tetramethyluronium hexafluorophosphate (0.26 g, 0.69 mmol) were added. The mixture was stirred at 25° C. for 1 hour. Upon completion, the resulting solution was diluted with water, extracted with dichloromethane, dried with sodium sulfate and concentrated under vacuum. The residue was purified by silica gel column eluting with dichloromethane/methanol (10/1) to afford product. The crude product was purified by Prep-HPLC to afford 23 mg of (E)-1-((S)-4-(7-(6-amino-4-methyl-3-(trifluoromethyl)pyridin-2-yl)-6-chloro-2-(((S)-1-methylpyrrolidin-2-yl)methoxy)quinazolin-4-yl)-3-methylpiperazin-1-yl)-4,4-difluorobut-2-en-1-one as a white solid. LCMS: (ESI, m/z): 654.3 [M+H]$^+$. Prep-HPLC conditions: Column: XBridge Shield RP18 OBD Column; mobile phase, A: water, B: acetonitrile, B % (40%~62% in 7 min); Detector, UV 220 nm.

Example 65

$^1$H NMR (400 MHz, DMSO-d6, ppm) δ 7.94 (t, J=7.2 Hz, 1H), 7.41 (s, 1H), 7.23-7.08 (m, 1H), 6.78 (s, 2H), 6.69-6.62 (m, 1H), 6.53-6.45 (m, 1H), 4.84-4.63 (m, 1H), 4.43-4.22 (m, 2H), 4.19-3.98 (m, 3H), 3.98-3.80 (m, 1H), 3.78-3.42 (m, 2H), 3.28-3.08 (m, 1H), 2.97-2.92 (m, 1H), 2.63-2.55 (m, 1H), 2.41-2.33 (m, 6H), 2.18 (q, J=8.4 Hz, 1H), 2.01-1.92 (m, 1H), 1.73-1.58 (m, 3H), 1.35-1.23 (m, 3H).

Example 66

1-[(3S)-4-[7-[6-amino-4-methyl-3-(trifluoromethyl)-2-pyridyl]-6-chloro-2-[2-(dimethylamino)cyclopentoxy]quinazolin-4-yl]-3-methyl-piperazin-1-yl]prop-2-en-1-one Synthetic Route

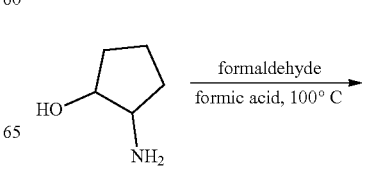

471

-continued

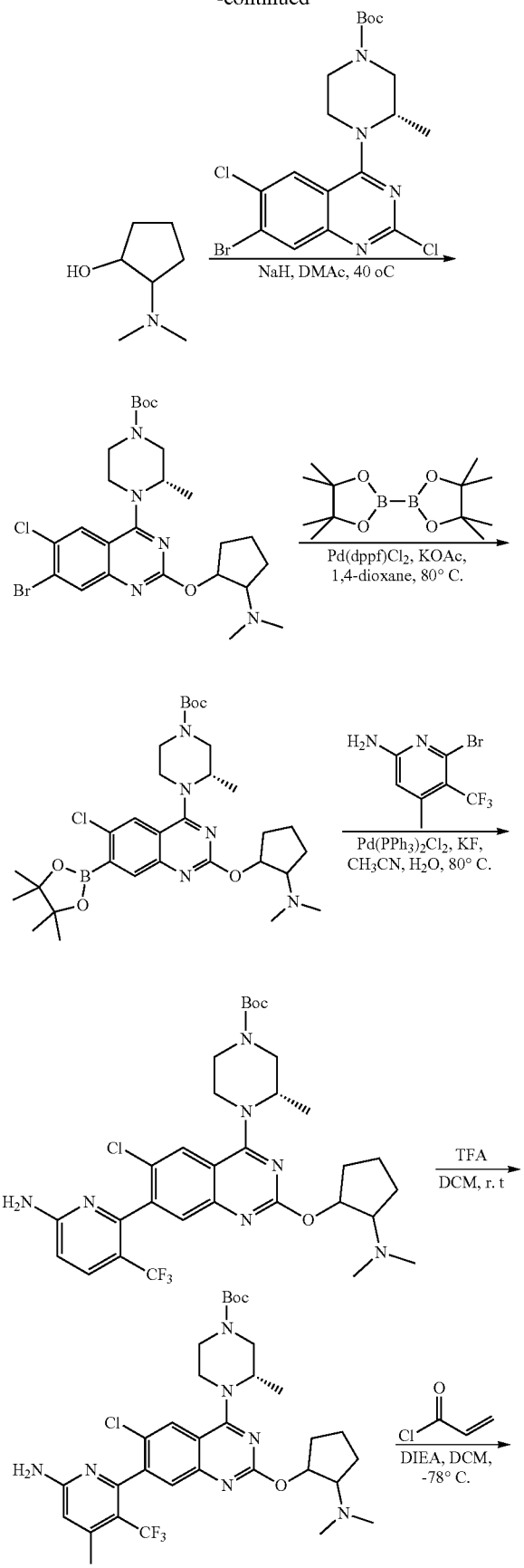

472

-continued

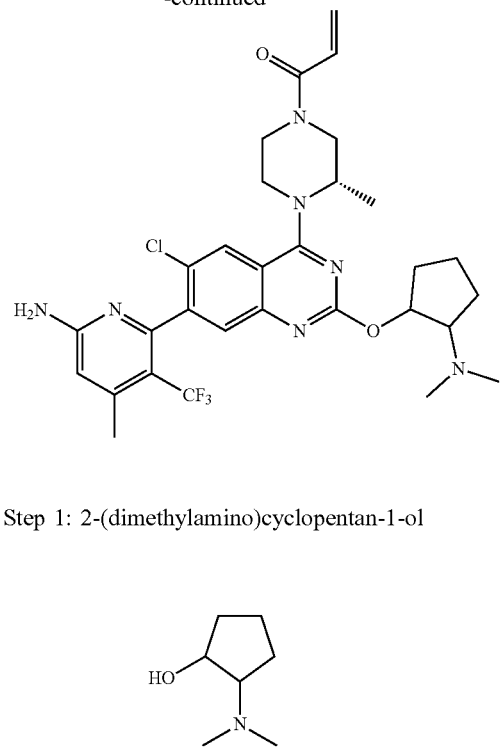

Step 1: 2-(dimethylamino)cyclopentan-1-ol

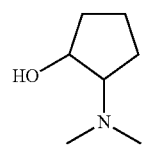

A solution of 2-aminocyclopentan-1-ol (5.0 g, 49.4 mmol) was added formic acid (10 mL) at room temperature under nitrogen. Formaldehyde (2.8 g) was added and the reaction was stirred at 100° C. for 2 hours. The reaction was cooled to room temperature, diluted with water, and the pH of solution was adjusted to 9 with sodium bicarbonate. The resulting mixture was extracted with dichloromethane, the organic layer was dried over anhydrous sodium sulfate and concentrated to afford 2-(dimethylamino)cyclopentan-1-ol (5 g, crude) as a yellow oil which was used for next step without purification. LC-MS: (ESI, m/z): 129.2 [M+H]$^+$.

Step 2: tert-butyl (3S)-4-(7-bromo-6-chloro-2-((2-(dimethylamino)cyclopentyl)oxy)quinazolin-4-yl)-3-methylpiperazine-1-carboxylate

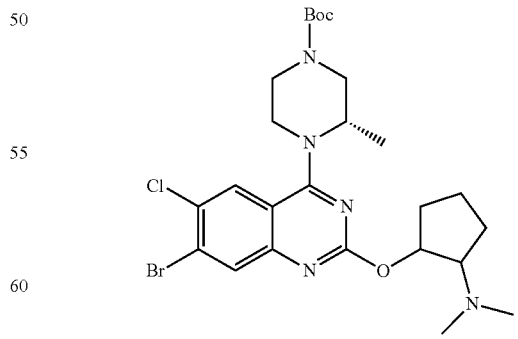

To a solution 2-(dimethylamino)cyclopentan-1-ol (1.0 g, 7.7 mmol) in N,N-dimethylacetamide (30 mL) was added sodium hydride (584 mg, 14.6 mmol, 60% dispersion in mineral oil) at room temperature. The resulting solution was stirred for 30 mins at room temperature. Then tert-butyl (3S)-4-(7-bromo-2,6-dichloro-quinazolin-4-yl)-3-methyl-piperazine-1-carboxylate (Intermediate 5) (2.0 g, 4.2 mmol) was added and stirred at 40° C. for 2 hours. The reaction was quenched with water and extracted with ethyl acetate. Then the organic layers were combined, dried over anhydrous sodium sulfate and concentrated. The residue was purified by flash chromatography on silica gel eluting with ethyl acetate/petroleum ether (1/8) to afford tert-butyl (3S)-4-(7-bromo-6-chloro-2-((2-(dimethylamino)cyclopentyl)oxy) quinazolin-4-yl)-3-methylpiperazine-1-carboxylate (2 g, 3.52 mmol, 83% yield) as a yellow solid. LC-MS: (ESI, m/z): 568.9 [M+H]$^+$.

Step 3: tert-butyl (3S)-4-(6-chloro-2-((2-(dimethyl-amino)cyclopentyl)oxy)-7-(4,4,5,5-tetramethyl-1,3,2-dioxaborolan-2-yl)quinazolin-4-yl)-3-methylpiperazine-1-carboxylate

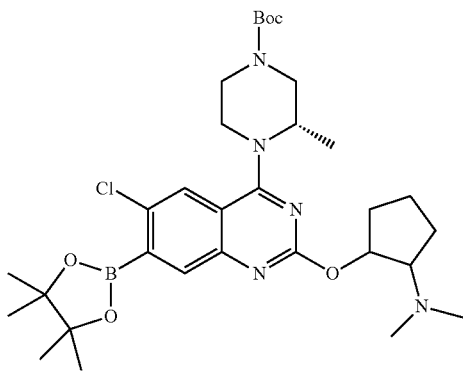

A solution of tert-butyl (3S)-4-(7-bromo-6-chloro-2-((2-(dimethylamino)cyclopentyl)oxy)quinazolin-4-yl)-3-methylpiperazine-1-carboxylate (2.0 g, 3.52 mmol), bis(pinacolato)diboron (8.0 g, 31.3 mmol), dichloro[1,1-bis(diphenylphosphino)ferrocene]palladium(II) (256 mg, 0.35 mmol) and potassium acetate (1400 mg, 10.9 mmol) in 1,4-Dioxane (20 mL) was stirred at 80° C. for 2 hours under nitrogen. The reaction mixture was diluted with ethyl acetate (100 mL) and washed with water (3×100 mL) to afford tert-butyl (3S)-4-(6-chloro-2-((2-(dimethylamino)cyclopentyl)oxy)-7-(4,4,5,5-tetramethyl-1,3,2-dioxaborolan-2-yl) quinazolin-4-yl)-3-methylpiperazine-1-carboxylate (1 g, 1.6 mmol, 5.2% yield) as a yellow solid. LC-MS: (ESI, m/z): 616.0 [M+H]$^+$.

Step 4: tert-butyl (3S)-4-(7-(6-amino-3-(trifluoromethyl)pyridin-2-yl)-6-chloro-2-((2-(dimethylamino) cyclopentyl)oxy)quinazolin-4-yl)-3-methylpiperazine-1-carboxylate

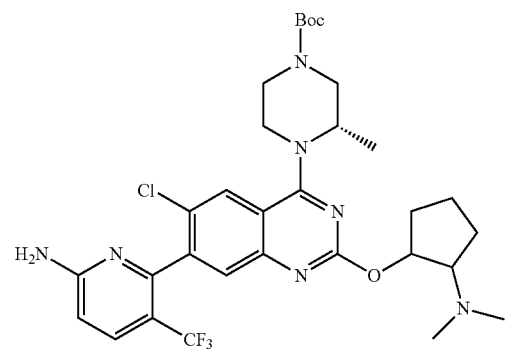 [SMILES: C[C@H]1CN(C(=O)OC(C)(C)C)CCN1c1nc(OC2CCCC2N(C)C)nc2cc(-c3nc(N)ccc3C(F)(F)F)c(Cl)cc12]

A solution of tert-butyl (3S)-4-(6-chloro-2-((2-(dimethyl-amino)cyclopentyl)oxy)-7-(4,4,5,5-tetramethyl-1,3,2-dioxaborolan-2-yl)quinazolin-4-yl)-3-methylpiperazine-1-carboxylate (1000 mg, 1.8 mmol), 6-bromo-4-methyl-5-(trifluoromethyl)pyridin-2-amine (500 mg, 1.9 mmol), Pd(PPh3)2Cl2 (120 mg, 0.2 mmol) and potassium fluoride (300 mg, 6.5 mmol) in acetonitrile (10 mL) and water (1 mL) was stirred at 80° C. for 3 hours under nitrogen. The reaction mixture was diluted with dichloromethane (50 mL). The mixture was filtered through a Celite pad and the filtrate was concentrated under vacuum. The residue was purified by flash chromatography on silica gel eluting with methyl alcohol/dichloromethane (1:13) to afford tert-butyl (3S)-4-(7-(6-amino-3-(trifluoromethyl)pyridin-2-yl)-6-chloro-2-((2-(dimethylamino)cyclopentyl)oxy)quinazolin-4-yl)-3-methylpiperazine-1-carboxylate (200 mg, 0.2 mmol, 14.5% yield) as a yellow solid. LC-MS: (ESI, m/z): 650.1 [M+H]$^+$ Step 5: 6-[6-chloro-2-[2-(dimethylamino)cyclopentoxy]-4-[(2S)-2-methylpiperazin-1-yl]quinazolin-7-yl]-4-methyl-5-(trifluoromethyl)pyridin-2-amine

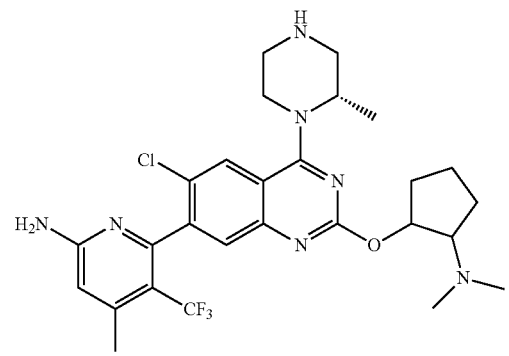 [SMILES: Cc1cc(N)nc(-c2cc3nc(OC4CCCC4N(C)C)nc(N4CCNC[C@@H]4C)c3cc2Cl)c1C(F)(F)F]

A solution of tert-butyl (3S)-4-(7-(6-amino-3-(trifluoromethyl)pyridin-2-yl)-6-chloro-2-((2-(dimethylamino)cyclopentyl)oxy)quinazolin-4-yl)-3-methylpiperazine-1-carboxylate (200 mg, 0.3 mmol) in 2,2,2-trifluoroacetic acid (5 mL) and dichloromethane (20 mL) was stirred at room temperature for 1 hour. The solvent was concentrated under vacuum to afford 6-[6-chloro-2-[2-(dimethylamino)cyclopentoxy]-

4-[(2S)-2-methylpiperazin-1-yl]quinazolin-7-yl]-4-methyl-5-(trifluoromethyl)pyridin-2-amine (150 mg, 0.3 mmol, 79.5% yield) as a yellow solid. LC-MS: (ESI, m/z): 564.1 [M+H]+

Step 6: 1-[(3S)-4-[7-[6-amino-4-methyl-3-(trifluoromethyl)-2-pyridyl]-6-chloro-2-[2-(dimethylamino)cyclopentoxy]quinazolin-4-yl]-3-methyl-piperazin-1-yl]prop-2-en-1-one

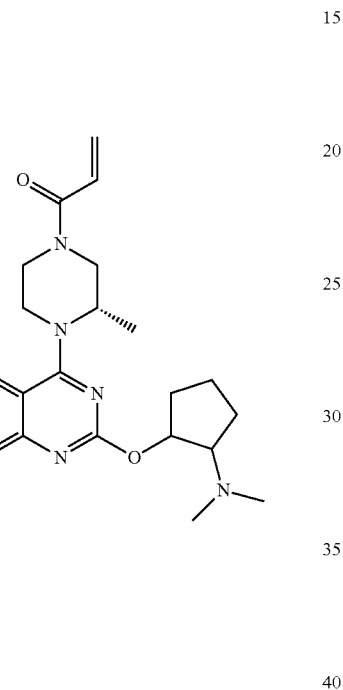

A solution of 6-[6-chloro-2-[2-(dimethylamino)cyclopentoxy]-4-[(2S)-2-methylpiperazin-1-yl]quinazolin-7-yl]-4-methyl-5-(trifluoromethyl)pyridin-2-amine (250 mg, 0.4 mmol) in dichloromethane (5 mL) and DIEA (171 mg, 1.3 mmol) was added acryloyl chloride (32 mg, 0.3 mmol) at −78° C. for 1 hour. The solvent was concentrated under vacuum. The residue was purified by Pre HPLC to afford 1-[(3S)-4-[7-[6-amino-4-methyl-3-(trifluoromethyl)-2-pyridyl]-6-chloro-2-[2-(dimethylamino)cyclopentoxy]quinazolin-4-yl]-3-methyl-piperazin-1-yl]prop-2-en-1-one (32 mg, 0.1 mmol, 11.6% yield) as a white solid.

Example 66

$^1$H NMR (400 MHz, DMSO-$d_6$, ppm) δ 7.93 (s, 1H), 7.42 (d, J=3.4 Hz, 1H), 6.89-6.80 (m, 1H), 6.77 (s, 2H), 6.46 (s, 1H), 6.19 (d, J=16.4 Hz, 1H), 5.75 (dd, J=10.4, 2.4 Hz, 1H), 5.40 (s, 1H), 4.70 (s, 1H), 4.40-4.19 (m, 1H), 4.15-3.89 (m, 2H), 3.62-3.40 (m, 2H), 3.25-3.05 (m, 2H), 2.40-2.25 (m, 8H), 2.13-1.97 (m, 3H), 1.68-1.52 (s, 4H), 1.39-1.25 (m, 3H). LC-MS: (ESI, m/z): 618.2 [M+H]+

Examples 67a and 67b 1-((S)-4-((R)-7-(3-amino-4-fluoroisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one (Example 67a) and 1-((S)-4-((S)-7-(3-amino-4-fluoroisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one (Example 67b) (2 atropisomers)

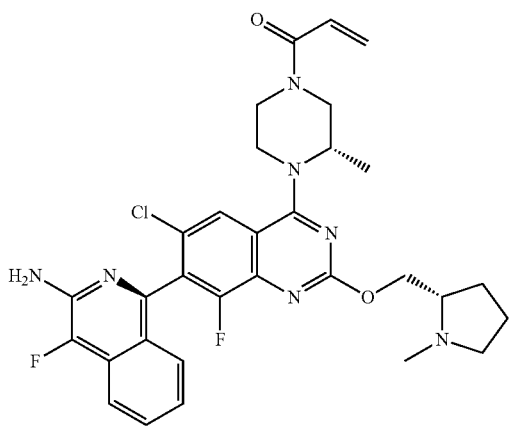

atropisomer-1

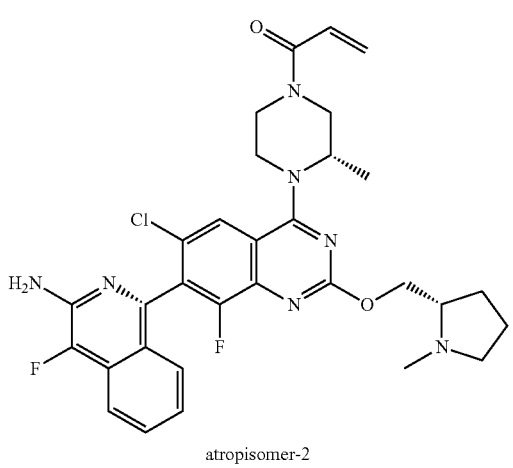

atropisomer-2

Synthetic Route
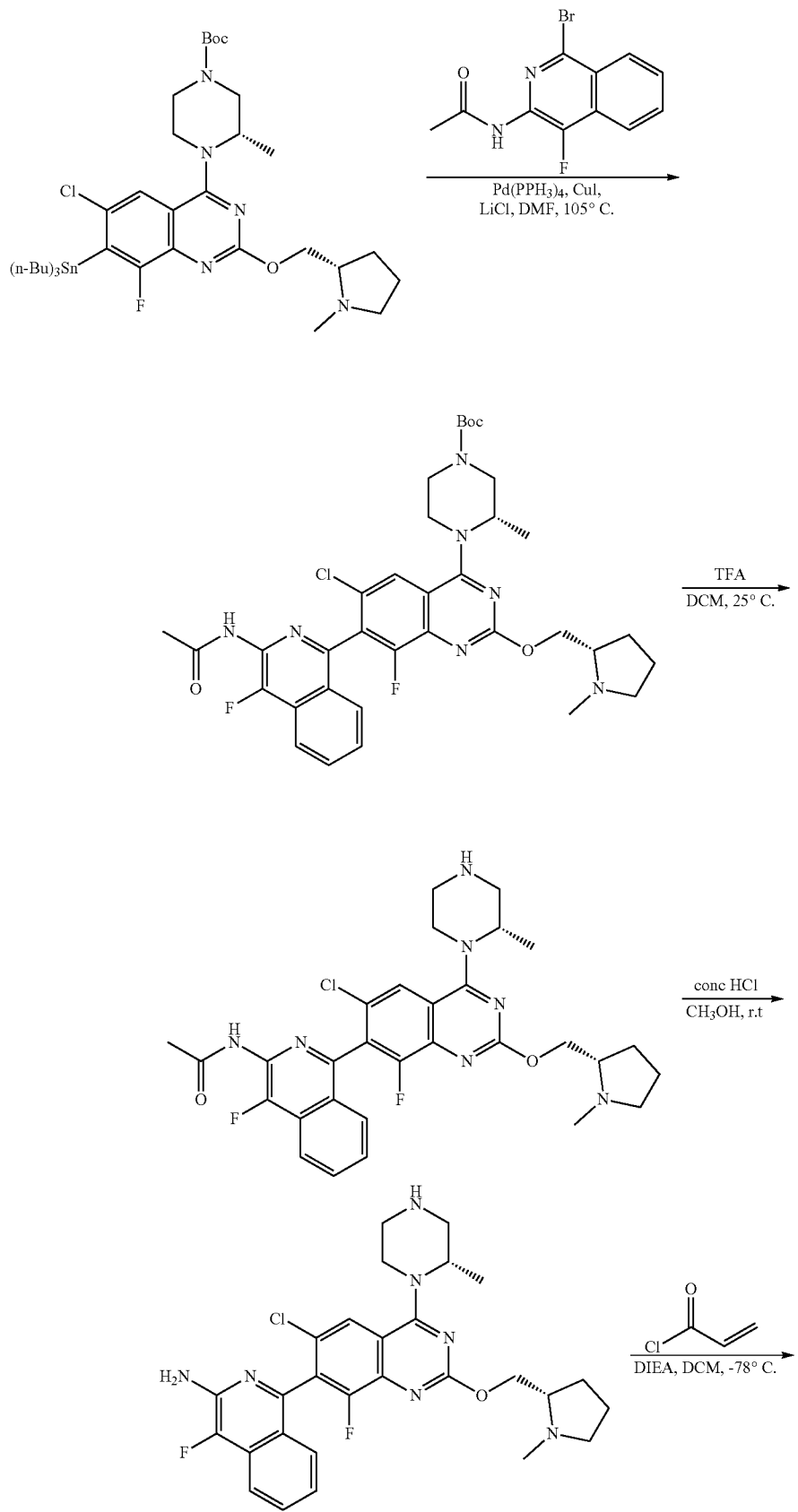

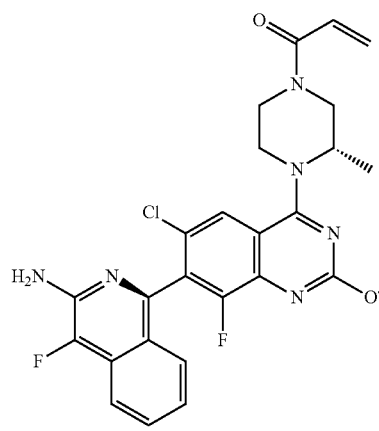

atropisomer-1
67a

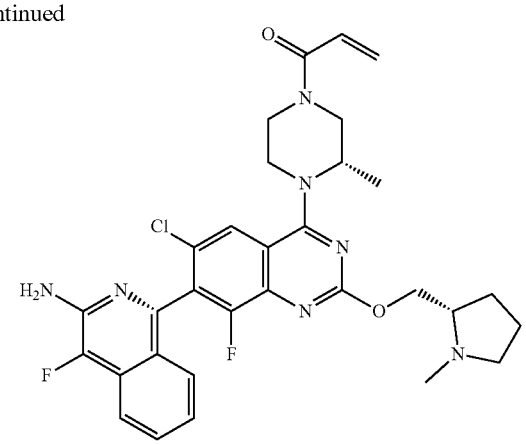

atropisomer-2
67b

Step 1: tert-butyl (3S)-4-(7-(3-acetamido-4-fluoroisoquinolin-1-yl)-6-chloro-8-fluoro-2-(((S)-1-methylpyrrolidin-2-yl)methoxy)quinazolin-4-yl)-3-methylpiperazine-1-carboxylate Step 2: N-(1-(6-chloro-8-fluoro-4-((S)-2-methylpiperazin-1-yl)-2-(((S)-1-methylpyrrolidin-2-yl)methoxy)quinazolin-7-yl)-4-fluoroisoquinolin-3-yl)acetamide

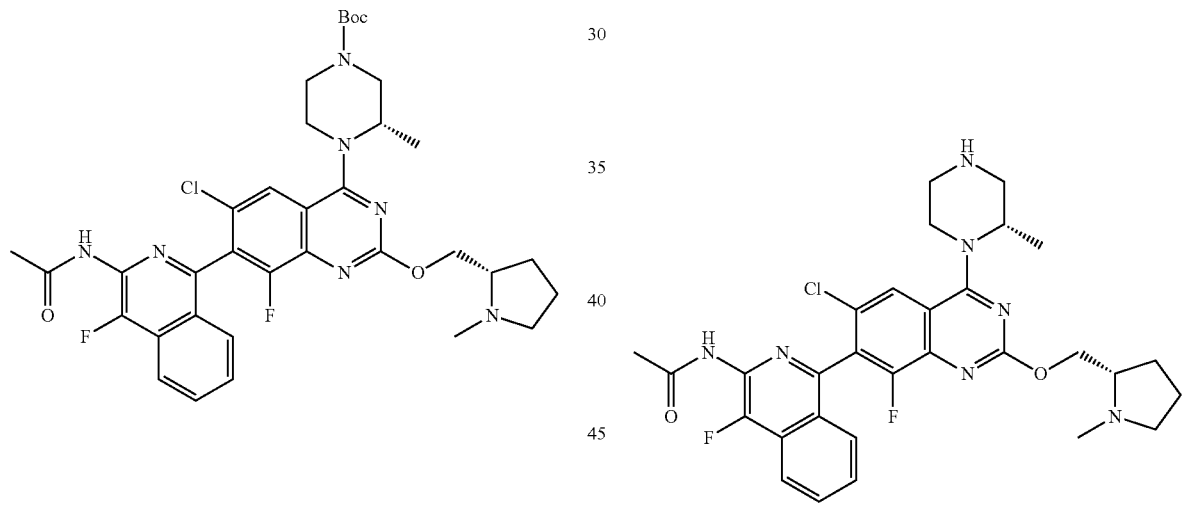

A solution of tert-butyl (S)-4-(6-chloro-8-fluoro-2-(((S)-1-methylpyrrolidin-2-yl)methoxy)-7-(tributylstannyl)quinazolin-4-yl)-3-methylpiperazine-1-carboxylate (see Example 63a/63b, Step 2) (138.0 mg, 0.18 mmol), N-(1-bromo-4-fluoro-3-isoquinolyl)acetamide (50.0 mg, 0.18 mmol), tetrakis(triphenylphosphine)Palladium(0) (102.0 mg, 0.09 mmol), copper(I) iodide (17.0 mg, 0.09 mmol) and lithium chloride (19.0 mg, 0.4400 mmol) in N,N-dimethylformamide (2 mL) was stirred at 105° C. for 16 hours under nitrogen. Upon completion, the reaction was filtered, the filtrate was diluted with ethyl acetate and washed with water. The organic layer was dried over anhydrous sodium sulfate and concentrated. The residue was purified by flash chromatography on silica gel eluting with dichloromethane/methanol (92:8) to afford tert-butyl (3S)-4-(7-(3-acetamido-4-fluoroisoquinolin-1-yl)-6-chloro-8-fluoro-2-(((S)-1-methylpyrrolidin-2-yl)methoxy)quinazolin-4-yl)-3-methylpiperazine-1-carboxylate (60 mg, 0.08 mmol, 48.8% yield) as a yellow oil. LC-MS: (ESI, m/z): 696.3 [M+H]+

A solution of tert-butyl (3S)-4-(7-(3-acetamido-4-fluoroisoquinolin-1-yl)-6-chloro-8-fluoro-2-(((S)-1-methylpyrrolidin-2-yl)methoxy)quinazolin-4-yl)-3-methylpiperazine-1-carboxylate (800.0 mg, 1.15 mmol) in 2,2,2-trifluoroacetic acid (10 mL) and dichloromethane (10 mL) was stirred at 25° C. for 1 hour. Upon completion, the reaction was concentrated and the resulting residue was purified by flash chromatography on C18 gel eluting with methanol/water (3:7) to afford N-(1-(6-chloro-8-fluoro-4-((S)-2-methylpiperazin-1-yl)-2-(((S)-1-methylpyrrolidin-2-yl)methoxy)quinazolin-7-yl)-4-fluoroisoquinolin-3-yl)acetamide (500 mg, 0.83 mmol, 73% yield) as a yellow solid. LC-MS: (ESI, m/z): 596.2 [M+H]+

Step 3: 1-(6-chloro-8-fluoro-4-((S)-2-methylpiper-azin-1-yl)-2-(((S)-1-methylpyrrolidin-2-yl)methoxy)quinazolin-7-yl)-4-fluoroisoquinolin-3-amine

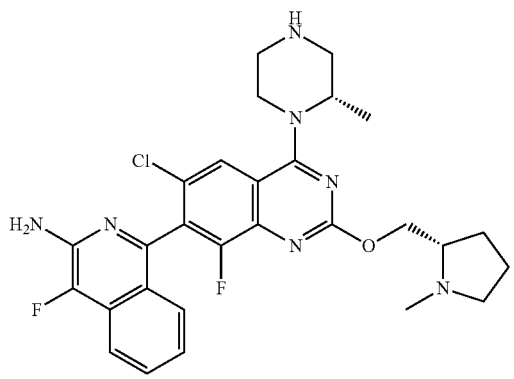 [SMILES: C[C@H]1CNCCN1c1nc(OC[C@@H]2CCCN2C)nc2c(F)c(-c3nc(N)c(F)c4ccccc34)c(Cl)cc12]

A solution of N-(1-(6-chloro-8-fluoro-4-((S)-2-methylpiperazin-1-yl)-2-(((S)-1-methylpyrrolidin-2-yl)methoxy)quinazolin-7-yl)-4-fluoroisoquinolin-3-yl)acetamide (400.0 mg, 0.67 mmol) in methyl alcohol (20 mL) and hydrochloric acid (1 mL, 10 mmol) was stirred at 25° C. for 16 hours. Upon completion, the solution was concentrated under vacuum. The crude product of 1-(6-chloro-8-fluoro-4-((S)-2-methylpiperazin-1-yl)-2-(((S)-1-methylpyrrolidin-2-yl)methoxy)quinazolin-7-yl)-4-fluoroisoquinolin-3-amine (350 mg, 0.63 mmol, 94.1% yield) was directly used in the next step without purification. LC-MS: (ESI, m/z): 554.3 [M+H]$^+$ Step 4: 1-((S)-4-((R)-7-(3-amino-4-fluoroisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one (Example 67a) and 1-((S)-4-((S)-7-(3-amino-4-fluoroisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one (Example 67b) (2 atropisomers)

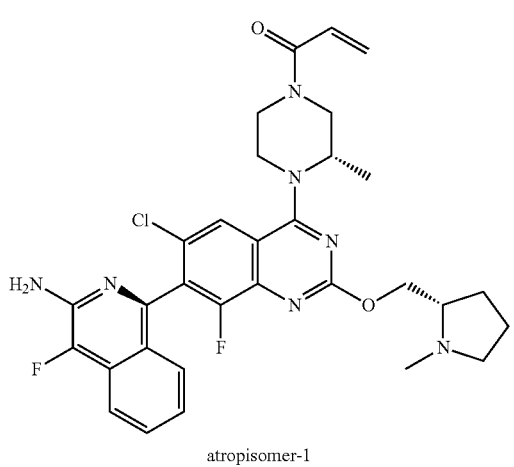

atropisomer-1

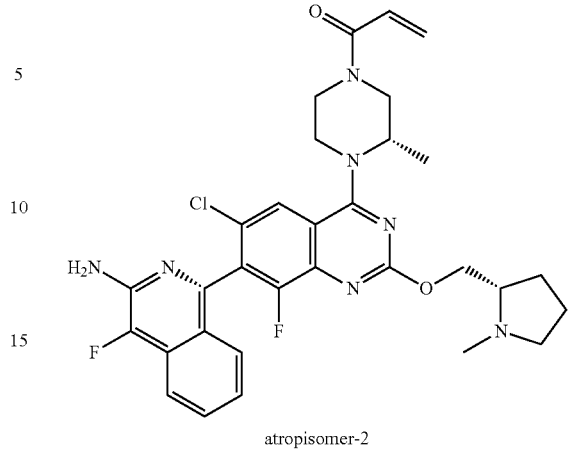

atropisomer-2

A solution of 1-(6-chloro-8-fluoro-4-((S)-2-methylpiperazin-1-yl)-2-(((S)-1-methylpyrrolidin-2-yl)methoxy)quinazolin-7-yl)-4-fluoroisoquinolin-3-amine (220.0 mg, 0.4000 mmol) and N,N-diisopropylethylamine (1 mL, 5.74 mmol) in dichloromethane (20 mL) was stirred at −78° C. for 5 minutes. Then acryloyl chloride (36.0 mg, 0.4000 mmol) was added and the reaction was stirred at −78° C. for an additional 30 minutes. The reaction was concentrated and the residue was purified by flash chromatography on C18 gel eluting with acetonitrile/water (7:3) to afford crude product. The product was purified by Chiral-Prep-HPLC-Column: CHIRALPAK IC, 2*25 cm, 5 um; Mobile Phase A:Hex: DCM=1:1(10 mM NH$_3$-MeOH)-HPLC, Mobile Phase B:EtOH-HPLC; Flow rate: 17 mL/min to afford 1-((S)-4-((R)-7-(3-amino-4-fluoroisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one (36.9 mg, 0.060 mmol, 15.3% yield) as a white solid and 1-((S)-4-((S)-7-(3-amino-4-fluoroisoquinolin-1-yl)-6-chloro-8-fluoro-2-(((S)-1-methylpyrrolidin-2-yl)methoxy)quinazolin-4-yl)-3-methylpiperazin-1-yl)prop-2-en-1-one (41.4 mg, 0.068 mmol, 17.1% yield) as a white solid.

Example 67a

LC-MS: (ESI, m/z): 608.2 [M+H]$^+$, $^1$H NMR (300 MHz, DMSO, ppm) δ 8.01-7.74 (m, 2H), 7.73-7.60 (m, 1H), 7.40-7.30 (m, 1H), 7.25-7.17 (m, 1H), 6.75-7.00 (m, 1H), 6.33 (s, 2H), 6.22-6.09 (m, 1H), 5.74 (dd, J=2.4, 10.5 Hz, 1H), 4.80 (s, 1H), 4.42-3.95 (m, 5H), 3.87-3.37 (m, 2H), 3.29-3.02 (m, 1H), 2.98-2.83 (m, 1H), 2.68-2.54 (m, 1H), 2.32 (s, 3H), 2.19-2.09 (m, 1H), 2.00-1.85 (m, 1H), 1.70-1.52 (m, 3H), 1.38-1.25 (m, 3H). Chiral HPLC: CHIRALPAK IC-3 (0.46*5 cm; 3 um); detected at 254 nm; (n-hexane/dichloromethane=1/1)(0.1% diethylamine)/ethanol=1/1; flow rate=1.0 mL/min; Retention time: 1.4 min (faster peak).

Example 67b

LC-MS: (ESI, m/z): 608.2 [M+H]$^+$, $^1$H NMR (300 MHz, DMSO, ppm) δ 8.05-7.75 (m, 2H), 7.73-7.53 (m, 1H), 7.51-7.30 (m, 1H), 7.27-7.10 (m, 1H), 7.00-6.6.63 (m, 1H), 6.33 (s, 2H), 6.22-6.15 (d, J=21, 1H), 5.74 (dd, J=2.4, 10.5 Hz, 1H), 4.80 (s, 1H), 4.42-3.95 (m, 5H), 3.87-3.37 (m, 2H), 3.29-3.02 (m, 1H), 2.98-2.83 (m, 1H), 2.68-2.54 (m, 1H), 2.32 (s, 3H), 2.19-2.09 (m, 1H), 2.01-1.87 (m, 1H), 1.80-1.53 (m, 3H), 1.33-1.17 (m, 3H). Chiral HPLC: CHIRALPAK IC-3 (0.46*5 cm; 3 um); detected at 254 nm; (n-hexane/dichloromethane=1/1)(0.1% diethylamine)/ethanol=1/1; flow rate=1.0 mL/min; Retention time: 2.4 min (slower peak).

Examples 68a and 68b 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-2-fluoroprop-2-en-1-one (Example 68a) and 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-2-fluoroprop-2-en-1-one (Example 68b) (2 atropisomers)

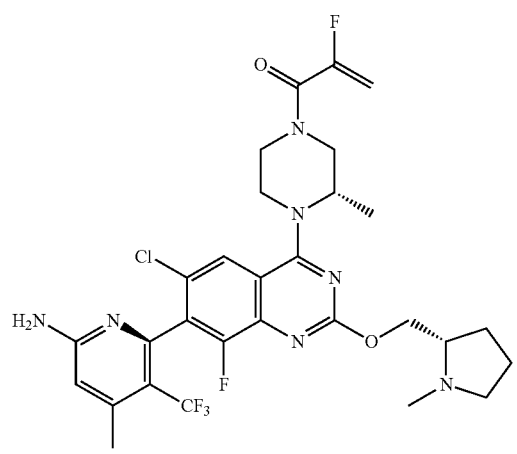

atropisomer-1

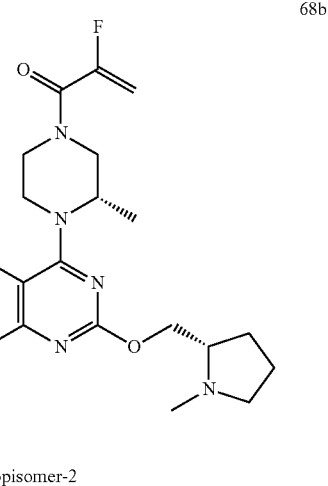

atropisomer-2

Synthetic Route

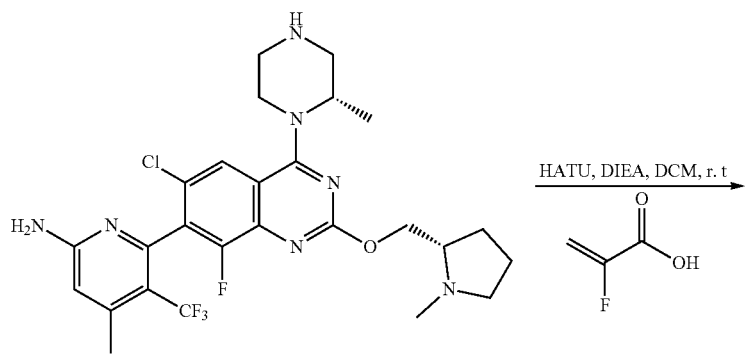

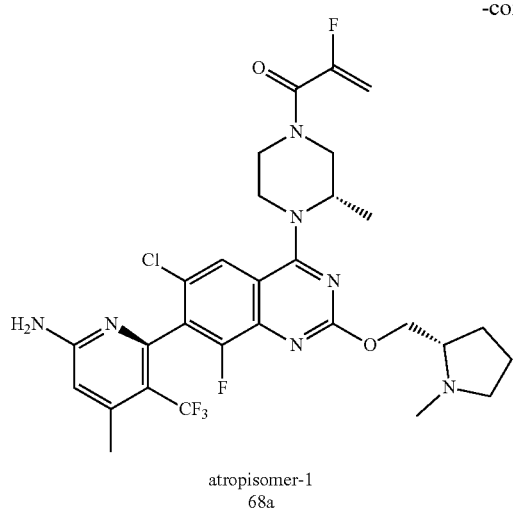

atropisomer-1
68a

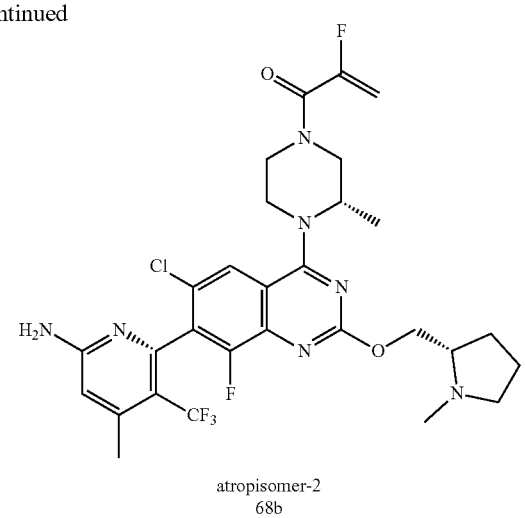

atropisomer-2
68b

A solution of 6-[6-chloro-8-fluoro-4-[(2S)-2-methylpiperazin-1-yl]-2-[[(2S)-1-methylpyrrolidin-2-yl]methoxy]quinazolin-7-yl]-4-methyl-5-(trifluoromethyl)pyridin-2-amine (see Step 11, Example 17) (450.0 mg, 0.79 mmol), 2-fluoroacrylic acid (64.21 mg, 0.71 mmol), HATU (451.85 mg, 1.19 mmol) and N,N-diisopropylethylamine (408.8 mg, 3.17 mmol) in dichloromethane (4 mL) was stirred at 25° C. for 1 hour. Upon completion, the reaction was diluted with dichloromethane and washed with water. Then the organic layer was dried over anhydrous sodium sulfate and concentrated. The residue was purified by a reversed-phase chromatography-Column, C18 silica gel; mobile phase, A: water, B: acetonitrile, B % (5%~70% in 30 min); Detector, UV 254 nm to afford 150 mg of 1-[(3S)-4-[7-[6-amino-4-methyl-3-(trifluoromethyl)-2-pyridyl]-6-chloro-8-fluoro-2-[[(2S)-1-methylpyrrolidin-2-yl]methoxy]quinazolin-4-yl]-3-methyl-piperazin-1-yl]-2-fluoro-prop-2-en-1-one as a white solid. The crude product was purified directly by Prep-HPLC-Column, XBridge Prep C18 OBD Column19*15 mm 5 umC-0013; mobile phase, A: 10 mmol HCOOH in water, B: ACN and B % (51%~73% in 7 min); Detector, UV 254 nm to afford crude product (130 mg) as a white solid. The mixture of diasteroisomers was separated by Prep-Chiral-HPLC-Column, CHIRALPAK IC-3 0.45*5 cm 3 um; mobile phase, (Hex:dichloromethane=3:1)(0.1% DEA): EtOH=50:50; Detector, 254 nm; Flow, 1.0 ml/min; Temperature:25° C. to afford 32 mg (6.3%) of 1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-2-fluoroprop-2-en-1-one (at 1.01 min) as a white solid and 48 mg (9.5%) 1-((S)-4-((S)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-2-fluoroprop-2-en-1-one (at 1.41 min) as a white solid. LC-MS: (ESI, m/z): 640.2 [M+H]$^+$ Example 68a $^1$H NMR (400 MHz, DMSO-d$_6$, ppm) δ 7.81 (s, 1H), 6.85 (s, 2H), 6.49 (s, 1H), 5.37-5.20 (m, 2H), 4.76 (s, 1H), 4.39 (dd, J=10.8, 6.0 Hz, 1H), 4.18-4.11 (m, 3H), 4.11-3.93 (m, 1H), 3.91-3.69 (m, 2H), 3.20-3.03 (m, 1H), 2.96-2.92 (m, 1H), 2.60-2.57 (m, 1H), 2.37-2.35 (m, 6H), 2.19-2.14 (m, 1H), 1.96-1.92 (m, 1H), 1.70-1.62 (m, 3H), 1.28 (d, J=6.8 Hz, 3H). LC-MS: (ESI, m/z): 640.2 [M+H]$^+$ Chiral HPLC: CHIRALPAK IC-3 (0.46*5 cm; 3 um); detected at 254 nm; Hex:DCM=3:1)(0.1% DEA):EtOH=50:50; flow=1 mL/min; Retention time: 1.00 min (faster peak).

Example 68b $^1$H NMR (400 MHz, DMSO-d$_6$, ppm) δ 7.79 (s, 1H), 6.84 (s, 2H), 6.49 (s, 1H), 5.37-5.19 (m, 2H), 4.73 (s, 1H), 4.37 (dd, J=10.8, 6.0 Hz, 1H), 4.18-4.01 (m, 3H), 4.01-3.79 (m, 1H), 3.79-3.66 (m, 2H), 3.31-3.03 (m, 1H), 2.96-2.92 (m, 1H), 2.59-2.56 (m, 1H), 2.37-2.35 (m, 6H), 2.18-2.14 (m, 1H), 1.97-1.93 (m, 1H), 1.70-1.62 (m, 3H), 1.31 (d, J=6.8 Hz, 3H). LC-MS: (ESI, m/z): 640.2 [M+H]$^+$ Chiral HPLC: CHIRALPAK IC-3 (0.46*5 cm; 3 um); detected at 254 nm; Hex:DCM=3:1)(0.1% DEA):EtOH=50:50; flow=1 mL/min; Retention time: 1.41 min (slower peak).

Example 69

1-[(3S)-4-[7-[6-amino-4-methyl-3-(trifluoromethyl)-2-pyridyl]-6-chloro-8-fluoro-2-[[(2 S,4R)-4-fluoro-1-methyl-pyrrolidin-2-yl]methoxy]quinazolin-4-yl]-3-methyl-piperazin-1-yl]prop-2-en-1-one

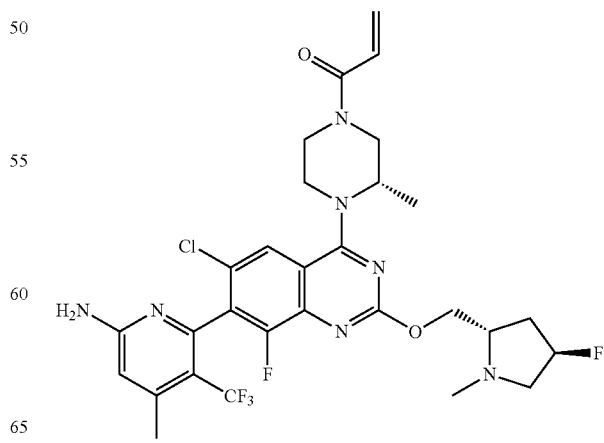

Synthetic Route
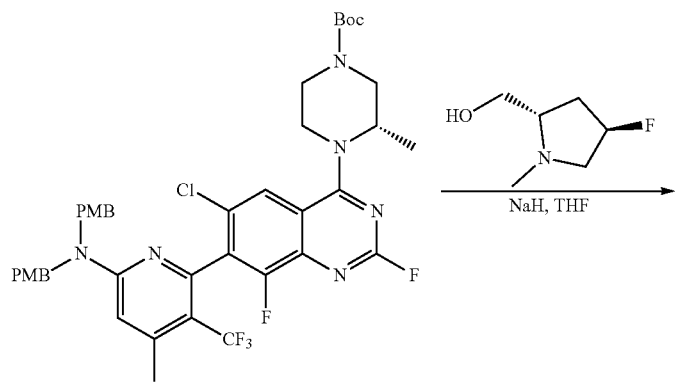
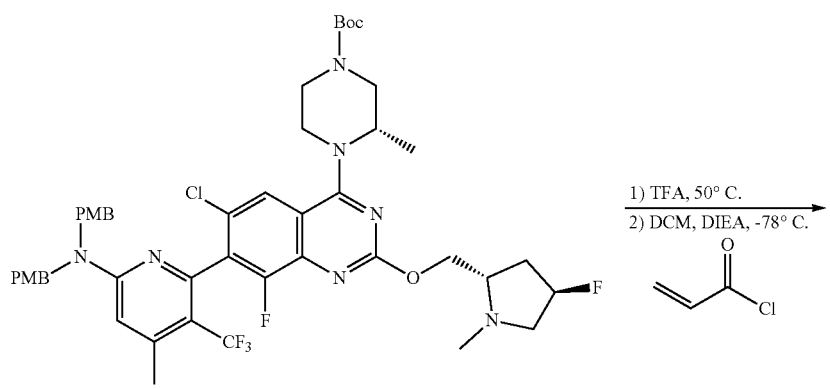
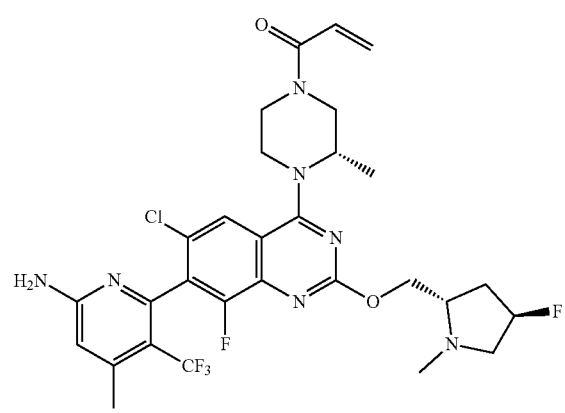

Step 1: tert-butyl (3S)-4-(7-(6-(bis(4-methoxyben-zyl)amino)-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-3-methylpiperazine-1-carboxylate Step 2: 1-[(3S)-4-[7-[6-amino-4-methyl-3-(trifluoromethyl)-2-pyridyl]-6-chloro-8-fluoro-2-[[(2S,4R)-4-fluoro-1-methyl-pyrrolidin-2-yl]methoxy]quinazolin-4-yl]-3-methyl-piperazin-1-yl]prop-2-en-1-one

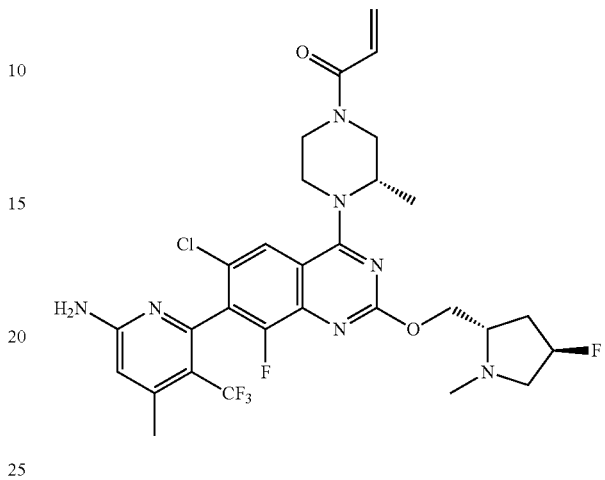

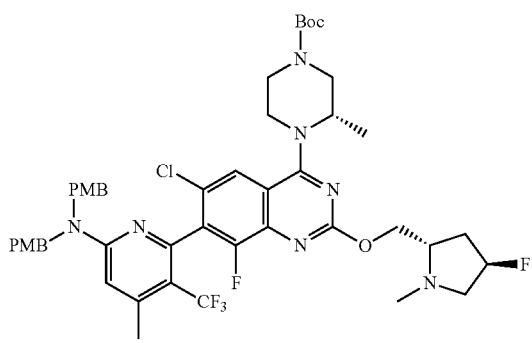

A solution of [(2S,4R)-4-fluoro-1-methyl-pyrrolidin-2-yl]methanol (300 mg, 2.2 mmol) in tetrahydrofuran (20 mL) was added sodium hydride (206 mg, 1.9 mmol) at room temperature. The resulting solution was stirred for 30 mins at room temperature. Then tert-butyl (3S)-4-[7-[6-[bis[(4-methoxyphenyl)methyl]amino]-4-methyl-3-(trifluoromethyl)-2-pyridyl]-6-chloro-2,8-difluoro-quinazolin-4-yl]-3-methyl-piperazine-1-carboxylate (see Step 9 of Example 17a/17b) (1.6 g, 1.9 mmol) was added and stirred at room temperature for an additional 1 hour. The reaction was quenched with water. The resulting solution was extracted with ethyl acetate (3×100 mL) and the organic layers were combined. The organic layer was dried over anhydrous sodium sulfate and concentrated under vacuum. The residue was purified by flash chromatography on silica gel eluting with eluting with petroleum ether/ethyl acetate (30%) to afford tert-butyl (3S)-4-(7-(6-(bis(4-methoxybenzyl)amino)-4-methyl-3-(trifluoromethyl)pyridin-2-yl)-6-chloro-8-fluoro-2-4(2S,4R)-4-fluoro-1-methylpyrrolidin-2-yl)methoxy)quinazolin-4-yl)-3-methylpiperazine-1-carboxylate (900 mg, 0.8 mmol, 44.4% yield) as a yellow solid. LC-MS: (ESI, m/z): 926.4 [M+H]$^+$ A solution of tert-butyl (3S)-4-(7-(6-(bis(4-methoxybenzyl)amino)-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-3-methylpiperazine-1-carboxylate (900 mg, 0.9 mmol) in 2,2,2-trifluoroacetic acid (10 mL) was stirred at 50° C. for 5 hours. The reaction was concentrated to afford 6-[6-chloro-8-fluoro-2-[[(2S,4R)-4-fluoro-1-methyl-pyrrolidin-2-yl]methoxy]-4-[(2S)-2-methylpiperazin-1-yl]quinazolin-7-yl]-4-methyl-5-(trifluoromethyl)pyridin-2-amine (500 mg, 0.7 mmol, 79% yield) as a yellow solid. Then, a solution of 6-[6-chloro-8-fluoro-2-[[(2S,4R)-4-fluoro-1-methyl-pyrrolidin-2-yl]methoxy]-4-[(2S)-2-methylpiperazin-1-yl]quinazolin-7-yl]-4-methyl-5-(trifluoromethyl)pyridin-2-amine (500 mg, 0.7 mmol) and N,N-diisopropylethylamine (1.2 g, 2.7 mmol) in dichloromethane (30 mL) was added acryloyl chloride (70 mg, 0.7 mmol) at −78° C. The resulting solution was stirred for 1 hour at −78° C., quenched with water and extracted with dichloromethane (3×100 mL). The organic layers were combined and concentrated and the residue was purified by Prep-HPLC-Column, CHIRALPAK IC-3 0.46*5 cm 3 um; mobile phase, (Hex:DCM=3:1)(0.1% DEA):EtOH=50:50; Detector, 254 nm; Flow, 1.0 ml/min; Temperature: 25° C. to afford 1-[(3S)-4-[7-[6-amino-4-methyl-3-(trifluoromethyl)-2-pyridyl]-6-chloro-8-fluoro-2-[[(2 S,4R)-4-fluoro-1-methyl-pyrrolidin-2-yl]methoxy]quinazolin-4-yl]-3-methyl-piperazin-1-yl]prop-2-en-1-one (53 mg, 0.1 mmol, 9.5% yield) (at 1.058 min) as a white solid. LC-MS: (ESI, m/z): 640.2 [M+H]$^+$ Example 69

$^1$H NMR (400 MHz, DMSO-d$_6$, ppm) δ 7.80 (s, 1H), 6.85 (s, 3H), 6.50 (s, 1H), 6.25-6.12 (m, 1H), 5.74 (dd, J=10.4, 2.4 Hz, 1H), 5.19 (d, J=56.6 Hz, 1H), 4.71 (s, 1H), 4.51-4.19 (m, 3H), 4.19-3.91 (m, 2H), 3.61 (d, J=12.3 Hz, 2H), 3.45 (m, J=25.6, 11.5, 5.3 Hz, 1H), 3.25-3.02 (m, 1H), 2.93 (dd, J=10.1, 5.3 Hz, 1H), 2.42-2.34 (m, 7H), 2.24-2.05 (m, 1H), 1.92 (m, J=33.7, 14.9, 10.0, 6.0 Hz, 1H), 1.30 (d, J=6.6 Hz, 3H).

Example 70

(S)-1-(4-(7-(6-amino-3-(trifluoromethyl)pyridin-2-yl)-6-chloro-2-((1-methylpyrrolidin-2-yl)methoxy)quinazolin-4-yl)piperazin-1-yl)prop-2-en-1-one

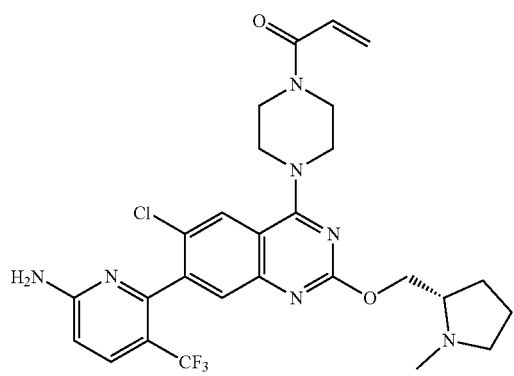

Synthetic Route

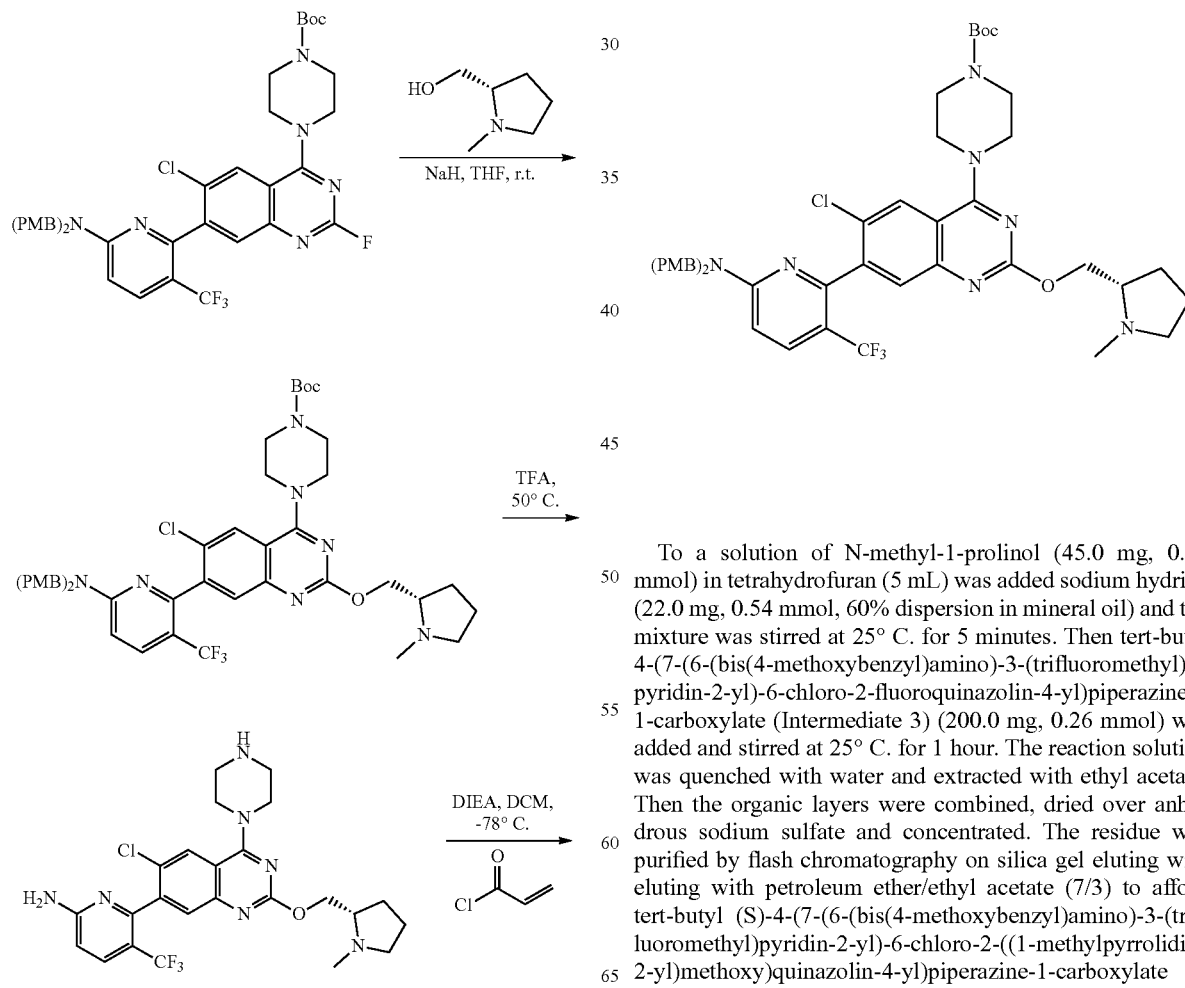

Step 1: tert-butyl (S)-4-(7-(6-(bis(4-methoxybenzyl)amino)-3-(trifluoromethyl)pyridin-2-yl)-6-chloro-2-((1-methylpyrrolidin-2-yl)methoxy)quinazolin-4-yl)piperazine-1-carboxylate

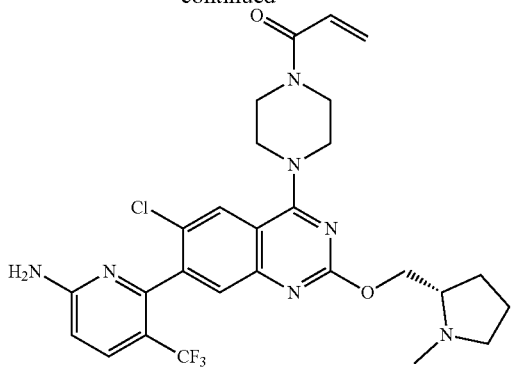

To a solution of N-methyl-1-prolinol (45.0 mg, 0.39 mmol) in tetrahydrofuran (5 mL) was added sodium hydride (22.0 mg, 0.54 mmol, 60% dispersion in mineral oil) and the mixture was stirred at 25° C. for 5 minutes. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (200.0 mg, 0.26 mmol) was added and stirred at 25° C. for 1 hour. The reaction solution was quenched with water and extracted with ethyl acetate. Then the organic layers were combined, dried over anhydrous sodium sulfate and concentrated. The residue was purified by flash chromatography on silica gel eluting with eluting with petroleum ether/ethyl acetate (7/3) to afford tert-butyl (S)-4-(7-(6-(bis(4-methoxybenzyl)amino)-3-(trifluoromethyl)pyridin-2-yl)-6-chloro-2-((1-methylpyrrolidin-2-yl)methoxy)quinazolin-4-yl)piperazine-1-carboxylate (210 mg, 0.24 mmol, 93.4% yield). LC-MS: (ESI, m/z): 862.2 [M+H]$^+$

Step 2: (S)-6-(6-chloro-2-((1-methylpyrrolidin-2-yl)methoxy)-4-(piperazin-1-yl)quinazolin-7-yl)-5-(trifluoromethyl)pyridin-2-amine

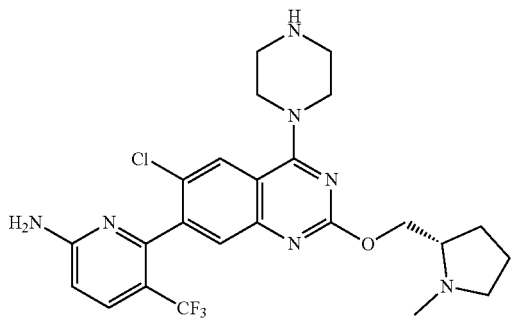 [SMILES: CN1CCC[C@H]1COc1nc(N2CCNCC2)c2cc(Cl)c(-c3nc(N)ccc3C(F)(F)F)cc2n1]

A solution of tert-butyl (S)-4-(7-(6-(bis(4-methoxybenzyl)amino)-3-(trifluoromethyl)pyridin-2-yl)-6-chloro-2-((1-methylpyrrolidin-2-yl)methoxy)quinazolin-4-yl)piperazine-1-carboxylate (200.0 mg, 0.2300 mmol) in trifluoroacetic acid (5 mL) was stirred at 50° C. for 2 hours. After completion, the solvent was concentrated under vacuum. The residue was purified by flash chromatography on C18 gel eluting with acetonitrile/water (7/3) to afford (S)-6-(6-chloro-2-((1-methylpyrrolidin-2-yl)methoxy)-4-(piperazin-1-yl)quinazolin-7-yl)-5-(trifluoromethyl)pyridin-2-amine (90 mg, 0.17 mmol, 74.3% yield) as a yellow oil. LC-MS: (ESI, m/z): 522.2 [M+H]$^+$

Step 3: (S)-1-(4-(7-(6-amino-3-(trifluoromethyl)pyridin-2-yl)-6-chloro-2-((1-methylpyrrolidin-2-yl)methoxy)quinazolin-4-yl)piperazin-1-yl)prop-2-en-1-one

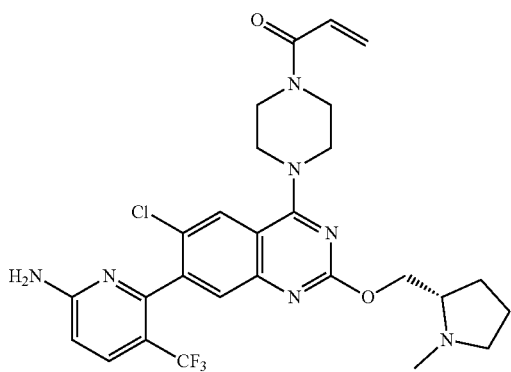

A solution of (S)-6-(6-chloro-2-((1-methylpyrrolidin-2-yl)methoxy)-4-(piperazin-1-yl)quinazolin-7-yl)-5-(trifluoromethyl)pyridin-2-amine (100.0 mg, 0.19 mmol) and N,N-diisopropylethylamine (1.0 mL, 5.74 mmol) in dichloromethane (10 mL) was stirred at −78° C. for 5 minutes. Then acryloyl chloride (17.0 mg, 0.19 mmol) was added and stirred at −78° C. for 30 minutes. After completion, the solvent was concentrated under vacuum. The crude product was purified by Prep-HPLC to afford (S)-1-(4-(7-(6-amino-3-(trifluoromethyl)pyridin-2-yl)-6-chloro-2-((1-methylpyrrolidin-2-yl)methoxy)quinazolin-4-yl)piperazin-1-yl)prop-2-en-1-one (19.3 mg, 0.034 mmol, 17.5% yield) as a white solid. LC-MS: (ESI, m/z): 576.2 [M+H]$^+$

Example 70

$^1$H NMR (400 MHz, DMSO-d$_6$, ppm) δ 8.04 (s, 1H), 7.78 (d, J=8.8 Hz, 1H), 7.46 (s, 1H), 6.90 (s, 2H), 6.82 (dd, J=10.0, 16.4 Hz, 1H), 6.60 (d, J=8.8 Hz, 1H), 6.17 (dd, J=2.4, 16.8 Hz, 1H), 5.74 (dd, J=2.0, 10.4 Hz, 1H), 4.36-4.33 (m, 1H), 4.19-4.15 (m, 1H), 3.85-3.77 (m, 8H), 2.96-2.95 (m, 1H), 2.68-2.65 (s, 1H), 2.35 (s, 3H), 2.19-2.13 (m, 1H), 1.97-1.88 (m, 1H), 1.68-1.60 (m, 3H). LC-MS: (ESI, m/z): 576.2 [M+H]$^+$.

Example 71

1-(4-(7-(6-amino-3-(trifluoromethyl)pyridin-2-yl)-6-chloro-2-(((2S,4R)-4-ethoxy-1-methylpyrrolidin-2-yl)methoxy)quinazolin-4-yl)piperazin-1-yl)prop-2-en-1-one

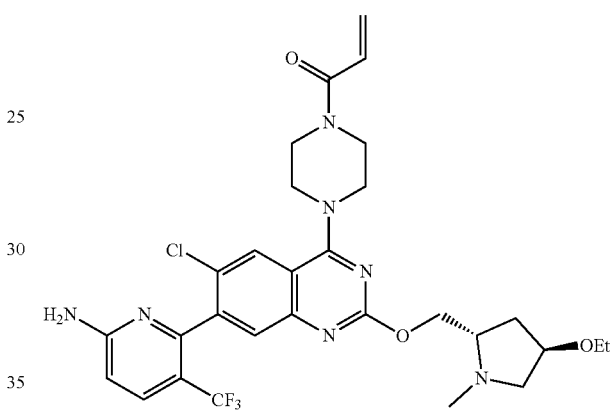

Synthetic Route

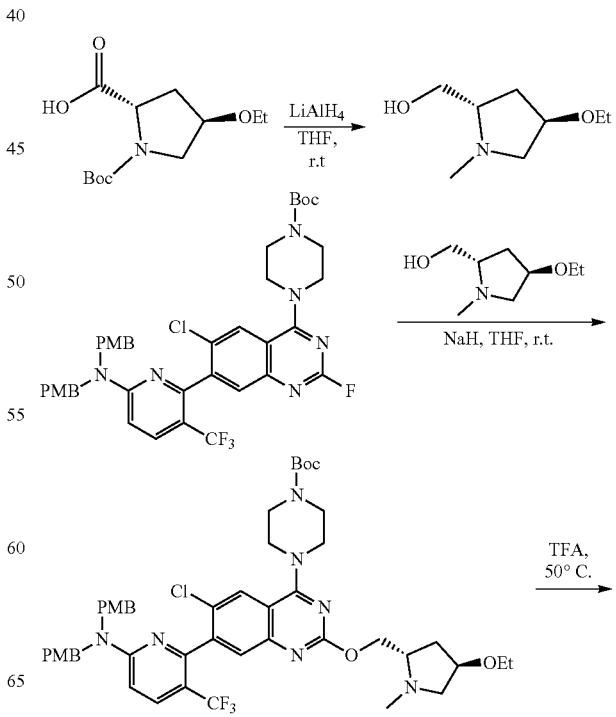

495

-continued

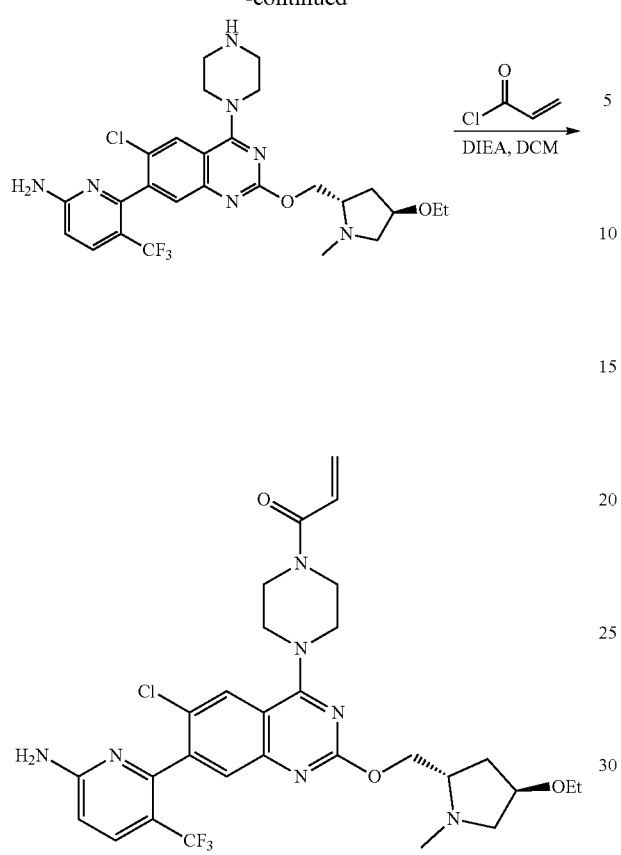

Step 1:
((2S,4R)-4-ethoxy-1-methylpyrrolidin-2-yl)methanol

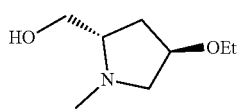

A solution of (2S,4R)-1-tert-butoxycarbonyl-4-ethoxy-pyrrolidine-2-carboxylic acid (600.0 mg, 2.31 mmol) in tetrahydrofuran (10 mL) was stirred at room temperature for 5 minutes. Then lithium aluminium hydride (352.0 mg, 9.26 mmol) was added and stirred at 25° C. for 6 hours. The reaction was quenched with water and extracted with water and ethyl acetate. The organic layer was dried over anhydrous sodium sulfate and concentrated under vacuum to afford ((2S,4R)-4-ethoxy-1-methylpyrrolidin-2-yl)methanol (150 mg, crude) as a yellow oil. LC-MS: (ESI, m/z): 160.1 [M+H]$^+$

496

Step 2: tert-butyl 4-(7-(6-(bis(4-methoxybenzyl)amino)-3-(trifluoromethyl)pyridin-2-yl)-6-chloro-2-(((2S,4R)-4-ethoxy-1-methylpyrrolidin-2-yl)methoxy)quinazolin-4-yl)piperazine-1-carboxylate

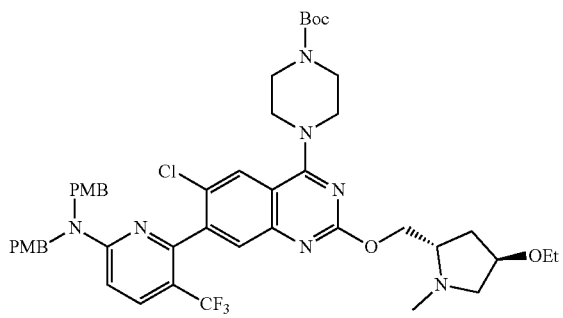

To a solution of ((2S,4R)-4-ethoxy-1-methylpyrrolidin-2-yl)methanol (84.0 mg, 0.53 mmol) in tetrahydrofuran (10 mL) was added sodium hydride (21.6 mg, 0.54 mmol, 60% dispersion in mineral oil) and the mixture was stirred at 25° C. for 30 minutes. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (200.0 mg, 0.26 mmol) was added and stirred at 25° C. for 6 hours. The reaction was quenched with water and extracted with ethyl acetate. Then the organic layer was dried over anhydrous sodium sulfate and concentrated. The residue was purified by flash chromatography on silica gel eluting with petroleum ether/ethyl acetate (4/1) to afford tert-butyl 4-(7-(6-(bis(4-methoxybenzyl)amino)-3-(trifluoromethyl)pyridin-2-yl)-6-chloro-2-(((2S,4R)-4-ethoxy-1-methylpyrrolidin-2-yl)methoxy)quinazolin-4-yl)piperazine-1-carboxylate (160 mg, 0.18 mmol, 67.7% yield) as a yellow solid. LC-MS: (ESI, m/z): 906.4 [M+H]$^+$ Step 3: 6-(6-chloro-2-(((2S,4R)-4-ethoxy-1-methylpyrrolidin-2-yl)methoxy)-4-(piperazin-1-yl)quinazolin-7-yl)-5-(trifluoromethyl)pyridin-2-amine

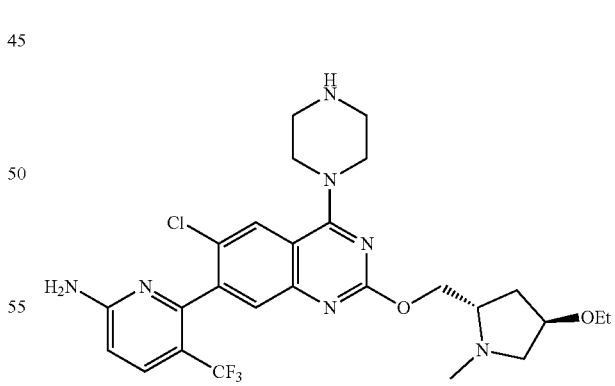

A solution of tert-butyl 4-(7-(6-(bis(4-methoxybenzyl)amino)-3-(trifluoromethyl)pyridin-2-yl)-6-chloro-2-(((2S,4R)-4-ethoxy-1-methylpyrrolidin-2-yl)methoxy)quinazolin-4-yl)piperazine-1-carboxylate (150.0 mg, 0.17 mmol) in trifluoroacetic acid (20 mL) was stirred at 50° C. for 6 hours. The reaction was concentrated and the residue was purified by C18 flash chromatography eluting with acetonitrile/water (7/3) to afford 6-(6-chloro-2-(((2S,4R)-4-ethoxy-1-methylpyrrolidin-2-yl)methoxy)-4-(piperazin-1-yl)quinazolin-7-yl)-5-(trifluoromethyl)pyridin-2-amine (80 mg, 0.14 mmol, 85.4% yield) as an off-white solid. LC-MS: (ESI, m/z): 566.2 [M+H]⁺

Step 4: 1-(4-(7-(6-amino-3-(trifluoromethyl)pyridin-2-yl)-6-chloro-2-(((2S,4R)-4-ethoxy-1-methylpyrrolidin-2-yl)methoxy)quinazolin-4-yl)piperazin-1-yl)prop-2-en-1-one

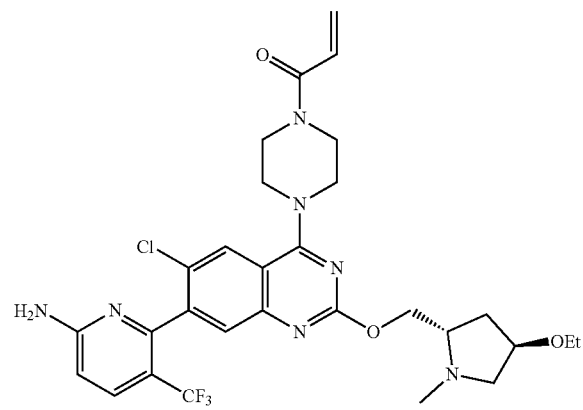

A solution of 6-(6-chloro-2-(((2S,4R)-4-ethoxy-1-methylpyrrolidin-2-yl)methoxy)-4-(piperazin-1-yl)quinazolin-7-yl)-5-(trifluoromethyl)pyridin-2-amine (70.1 mg, 0.12 mmol) and N,N-diisopropylethylamine (48.1 mg, 0.37 mmol) in dichloromethane (10 mL) was stirred at −78° C. for 5 minutes. Then acryloyl chloride (12.0 mg, 0.13 mmol) was added dropwise into the reaction system and stirred at −78° C. for 30 minutes. After completion, the reaction was quenched with water and concentrated. The residue was purified by Prep-HPLC to afford 1-(4-(7-(6-amino-3-(trifluoromethyl)pyridin-2-yl)-6-chloro-2-(((2S,4R)-4-ethoxy-1-methylpyrrolidin-2-yl)methoxy)quinazolin-4-yl)piperazin-1-yl)prop-2-en-1-one (32.9 mg, 0.053 mmol, 42.9% yield) as a white solid.

Example 71

¹H NMR (300 MHz, Methanol-d₄, ppm) δ 8.09 (s, 1H), 7.80 (d, J=9.0 Hz, 1H), 7.54 (s, 1H), 6.89-6.77 (m, 1H), 6.71-6.66 (m, 1H), 6.31-6.25 (m, 1H), 5.86-5.75 (m, 1H), 4.52-4.48 (m, 2H), 4.10 (s, 1H), 3.98 (s, 4H), 3.93 (s, 4H), 3.56-3.36 (m, 3H), 3.17 (s, 1H), 2.60 (s, 3H), 2.56-2.47 (m, 1H), 2.12 (s, 1H), 2.00 (d, J=8.2 Hz, 1H), 1.18 (t, J=7.0 Hz, 3H). LC-MS: (ESI, m/z): 620.3 [M+H]⁺.

Example 72

(S)-1-(4-(7-(6-amino-3-(trifluoromethyl)pyridin-2-yl)-6-chloro-2-((4-methyl-4-azaspiro[2.4]-heptan-5-yl)methoxy)quinazolin-4-yl)piperazin-1-yl)prop-2-en-1-one

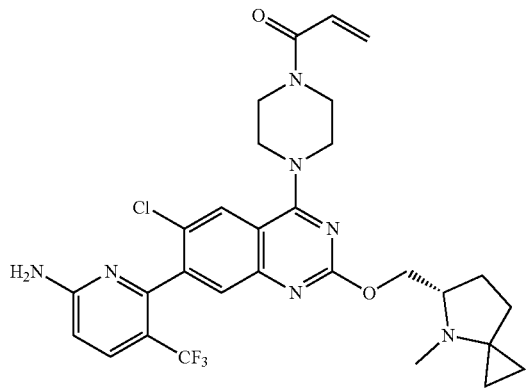 [SMILES: C=CC(=O)N1CCN(c2nc(OC[C@@H]3CCC4(CC4)N3C)nc3cc(-c4nc(N)ccc4C(F)(F)F)c(Cl)cc23)CC1]

Synthetic Route

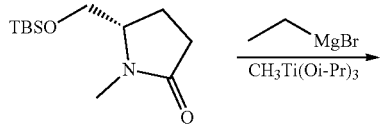

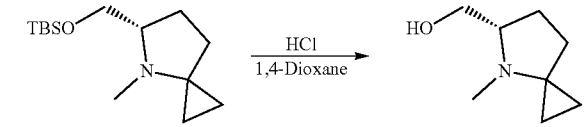

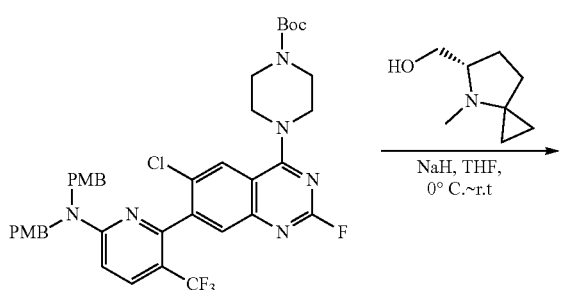

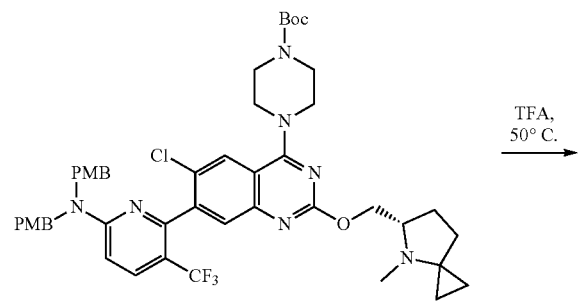

-continued

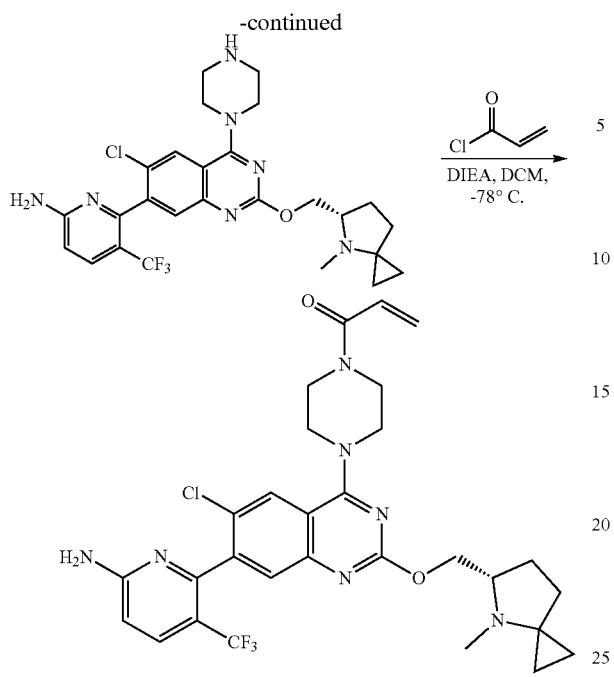

Step 1: (S)-5-(((tert-butyldimethylsilyl)oxy)methyl)-4-methyl-4-azaspiro[2.4]heptane

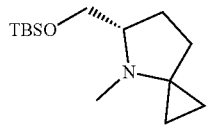 [SMILES: CN1[C@H](CO[Si](C)(C)C(C)(C)C)CCC12CC2]

A solution of (S)-5-(((tert-butyldimethylsilyl)oxy)methyl)-1-methylpyrrolidin-2-one (see Step 2 of Examples 64a and 64b) (3.0 g, 12.32 mmol) in tetrahydrofuran (40 mL) was added $CH_3Ti(Oi-Pr)_3$ (13.96 g, 49.3 mmol) at 25° C. under nitrogen. The resulting solution was stirred for 0.5 hours. Ethylmagnesium bromide (13.14 g, 98.6 mmol) was added at 0° C. and stirred at 25° C. for 6 hours. Upon completion, the solution was quenched with water and extracted with dichloromethane. The organic layer was collected and dried over anhydrous sodium sulfate and concentrated under vacuum. The residue was applied on a silica gel column eluting with petroleum ether/ethyl acetate (7/1) to afford (S)-5-(((tert-butyldimethylsilyl)oxy)methyl)-4-methyl-4-azaspiro[2.4]heptane (1.5 g, 5.87 mmol, 47.6% yield) as yellow oil. LC-MS: (ESI, m/z): 256.2 [M+H]$^+$

Step 2: (S)-(4-methyl-4-azaspiro[2.4]heptan-5-yl)methanol

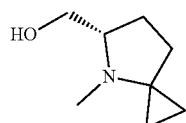

A solution of (S)-5-(((tert-butyldimethylsilyl)oxy)methyl)-4-methyl-4-azaspiro[2.4]heptane (1.4 g, 5.48 mmol) in HCl/1,4-dioxane (20 mL) was stirred at 50° C. for 6 hours. Upon completion, the solution was quenched with water and extracted with dichloromethane. The organic layer was collected and dried over anhydrous sodium sulfate and concentrated. The residue was applied on a silica gel column eluting with petroleum ether/ethyl acetate (5/1) to afford (S)-(4-methyl-4-azaspiro[2.4]heptan-5-yl)methanol (300 mg, 2.12 mmol, 38.8% yield) as a yellow oil. LC-MS: (ESI, m/z): 142.1 [M+H]+

Step 3: tert-butyl (S)-4-(7-(6-(bis(4-methoxybenzyl)amino)-3-(trifluoromethyl)pyridin-2-yl)-6-chloro-2-((4-methyl-4-azaspiro[2.4]heptan-5-yl)methoxy)quinazolin-4-yl)piperazine-1-carboxylate

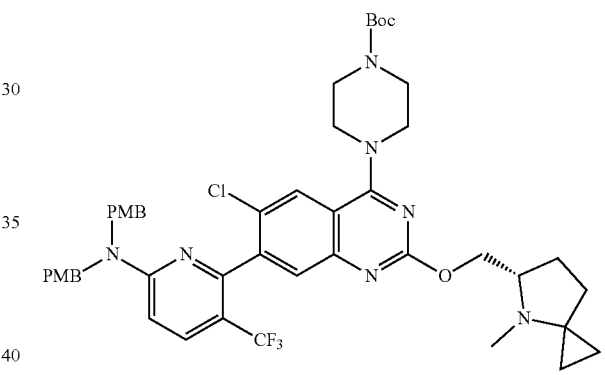

A solution of (S)-(4-methyl-4-azaspiro[2.4]heptan-5-yl)methanol (148.0 mg, 1.05 mmol) and sodium hydride (60%) (50.0 mg, 2.08 mmol) in tetrahydrofuran (10 mL) was stirred at 25° C. for 0.5 hours. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (200.0 mg, 0.26 mmol) was added and stirred at 25° C. for 6 hours. Upon completion, the solution was quenched with water and extracted with dichloromethane. The organic layer was collected and dried over anhydrous sodium sulfate and concentrated under vacuum. The residue was applied on a silica gel column eluting with petroleum ether/ethyl acetate (8/1) to afford tert-butyl (S)-4-(7-(6-(bis(4-methoxybenzyl)amino)-3-(trifluoromethyl)pyridin-2-yl)-6-chloro-2-((4-methyl-4-azaspiro[2.4]heptan-5-yl)methoxy)quinazolin-4-yl)piperazine-1-carboxylate (96 mg, 0.11 mmol, 41.5% yield) as a yellow solid. LC-MS: (ESI, m/z): 888.5 [M+H]$^+$ Step 4: (S)-6-(6-chloro-2-((4-methyl-4-azaspiro[2.4]heptan-5-yl)methoxy)-4-(piperazin-1-yl)quinazolin-7-yl)-5-(trifluoromethyl)pyridin-2-amine

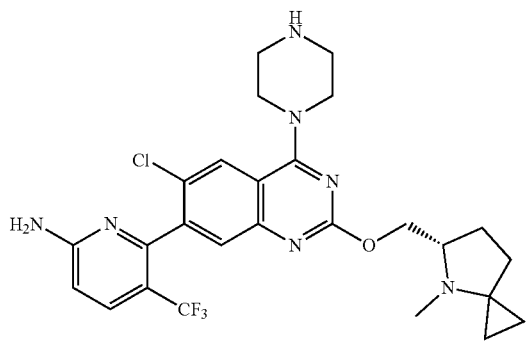 [SMILES: CN1[C@H](COc2nc(N3CCNCC3)c3cc(Cl)c(-c4nc(N)ccc4C(F)(F)F)cc3n2)CCC12CC2]

A solution of tert-butyl (S)-4-(7-(6-(bis(4-methoxybenzyl)amino)-3-(trifluoromethyl)pyridin-2-yl)-6-chloro-2-((4-methyl-4-azaspiro[2.4]heptan-5-yl)methoxy)quinazolin-4-yl)piperazine-1-carboxylate (80.0 mg, 0.09 mmol) in 2,2,2-trifluoroacetic acid (10 mL) was stirred at 50° C. for 5 hours. Upon completion, the solution was quenched with water and extracted with dichloromethane. The organic layer was collected and dried over anhydrous sodium sulfate and concentrated under vacuum. The residue was applied on a silica gel column eluting with dichloromethane/methanol (7/1) to afford (S)-6-(6-chloro-2-((4-methyl-4-azaspiro[2.4]heptan-5-yl)methoxy)-4-(piperazin-1-yl)quinazolin-7-yl)-5-(trifluoromethyl)pyridin-2-amine (40 mg, 0.073 mmol, 81.1% yield) was obtained. LC-MS: (ESI, m/z): 548.2 [M+H]$^+$ Step 5: (S)-1-(4-(7-(6-amino-3-(trifluoromethyl)pyridin-2-yl)-6-chloro-2-((4-methyl-4-azaspiro[2.4]heptan-5-yl)methoxy)quinazolin-4-yl)piperazin-1-yl)prop-2-en-1-one

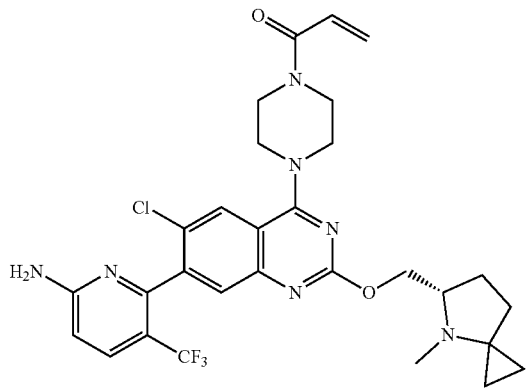 [SMILES: C=CC(=O)N1CCN(c2nc(OC[C@@H]3CCC4(CC4)N3C)nc3cc(-c4nc(N)ccc4C(F)(F)F)c(Cl)cc23)CC1]

A solution of (S)-6-(6-chloro-2-((4-methyl-4-azaspiro[2.4]heptan-5-yl)methoxy)-4-(piperazin-1-yl)quinazolin-7-yl)-5-(trifluoromethyl)pyridin-2-amine (30.0 mg, 0.05 mmol) and N,N-diisopropylethylamine (22.0 mg, 0.17 mmol) in dichloromethane (10 mL) was stirred at −78° C. for 5 minutes. Then acryloyl chloride (5.0 mg, 0.06 mmol) was added and stirred at −78° C. for 0.5 hours. Upon completion, the solution was quenched with water and extracted with dichloromethane. The organic layer was collected and dried over anhydrous sodium sulfate and concentrated under vacuum. The residue was purified by Prep-HPLC to afford (S)-1-(4-(7-(6-amino-3-(trifluoromethyl)pyridin-2-yl)-6-chloro-2-((4-methyl-4-azaspiro[2.4]heptan-5-yl)methoxy)quinazolin-4-yl)piperazin-1-yl)prop-2-en-1-one (10.8 mg, 0.018 mmol, 32.8% yield) as a white solid. LC-MS: (ESI, m/z): 602.3 [M+H]$^+$. Prep-HPLC conditions: Column: XBridge Shield RP18 OBD Column; mobile phase, A: water, B: acetonitrile, B % (40%~62% in 7 min); Detector, UV 220 nm.

Example 72

$^1$H NMR (400 MHz, CDCl$_3$, ppm) δ 7.89 (s, 1H), 7.82 (d, J=8.7 Hz, 1H), 7.68 (s, 1H), 6.72-6.50 (m, 2H), 6.48-6.23 (m, 1H), 5.89-5.68 (m, 1H), 5.03-4.82 (m, 2H), 4.56 (s, 1H), 4.34 (s, 1H), 4.02-3.73 (m, 8H), 3.17 (s, 1H), 2.24 (s, 3H), 2.20-2.11 (m, 1H), 2.01-1.89 (m, 1H), 1.89-1.72 (m, 2H), 0.91 (s, 1H), 0.67 (s, 1H), 0.52 (s, 1H), 0.31 (s, 1H).

Example 73

1-(4-(7-(6-amino-3-(trifluoromethyl)pyridin-2-yl)-6-chloro-2-((4,4-difluoro-1,2-dimethylpyrrolidin-2-yl)methoxy)quinazolin-4-yl)piperazin-1-yl)prop-2-en-1-one

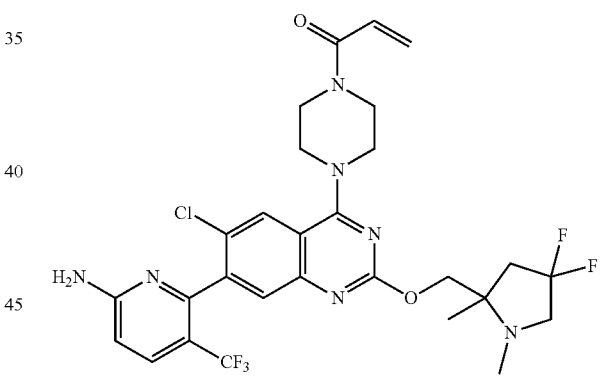

Synthetic Route

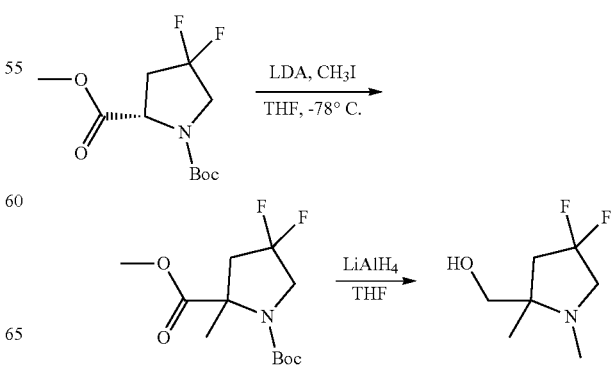

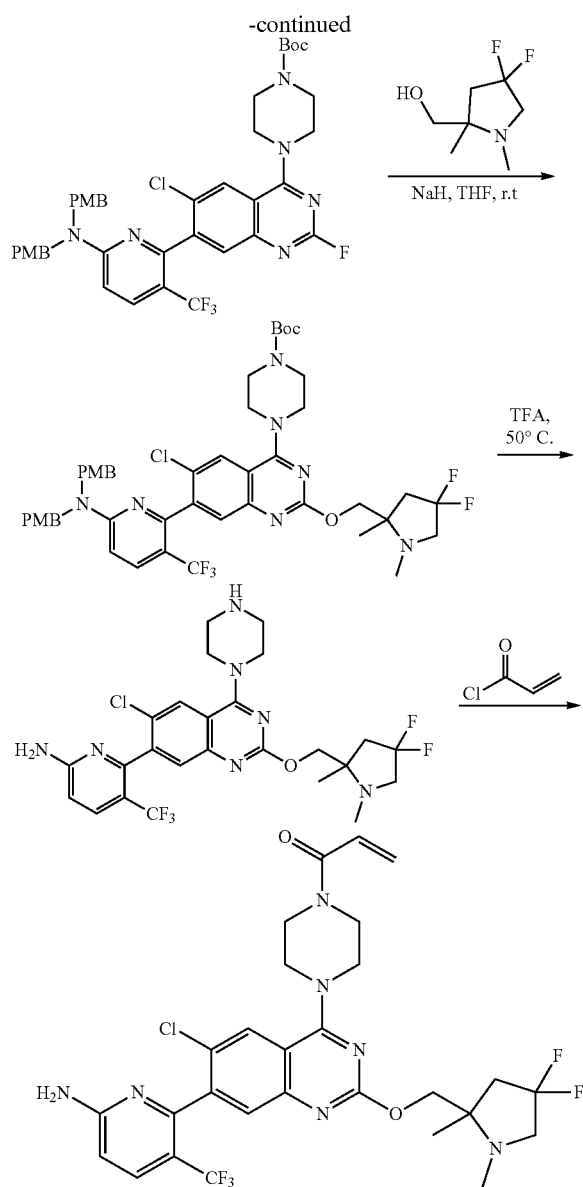

Step 1: 1-(tert-butyl) 2-methyl 4,4-difluoro-2-methylpyrrolidine-1,2-dicarboxylate

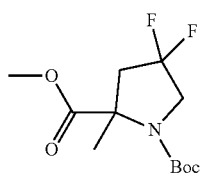 [SMILES: COC(=O)C1(C)CC(F)(F)CN1C(=O)OC(C)(C)C]

A solution of 1-tert-butyl 2-methyl (2S)-4, 4-difluoropyrrolidine-1,2-dicarboxylate (3.0 g, 11.31 mmol) and lithium diisopropylamide (6.8 mL, 13.57 mmol, 2M in tetrahydrofuran) in tetrahydrofuran (25 mL), was stirred at −78° C. for 0.5 hours under nitrogen. Iodomethane (2.09 g, 14.7 mmol) was added dropwise into the reaction system and stirred at −78° C. for 5 hours. Upon completion, the solution was diluted with water and extracted with ethyl acetate. The organic layers were collected, dried over anhydrous sodium sulfate and concentrated under vacuum. The desired crude product 1-(tert-butyl) 2-methyl 4, 4-difluoro-2-methylpyrrolidine-1,2-dicarboxylate (2.6 g, 9.3097 mmol, 82.3% yield) was obtained. LC-MS: (ESI, m/z): 280.1 [M+H]⁺

Step 2: (4, 4-difluoro-1,2-dimethylpyrrolidin-2-yl)methanol

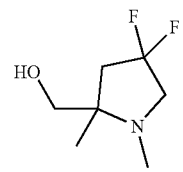

A solution of 1-(tert-butyl) 2-methyl 4,4-difluoro-2-methylpyrrolidine-1,2-dicarboxylate (2.5 g, 8.95 mmol) in tetrahydrofuran (25 mL) was stirred at 25° C. for 0.5 hours. Then lithium aluminum hydride (1.36 g, 35.81 mmol) was added into the reaction system and stirred at 25° C. for 5 hours. Upon completion, the solution was diluted with water and extracted with ethyl acetate. The organic layers were collected, dried over anhydrous sodium sulfate and concentrated to afford crude product (4,4-difluoro-1,2-dimethylpyrrolidin-2-yl)methanol (1.3 g, 7.87 mmol, 87.9% yield) was obtained. LC-MS: (ESI, m/z): 166.1 [M+H]⁺

Step 3: tert-butyl 4-(7-(6-(bis(4-methoxybenzyl)amino)-3-(trifluoromethyl)pyridin-2-yl)-6-chloro-2-((4,4-difluoro-1,2-dimethylpyrrolidin-2-yl)methoxy)quinazolin-4-yl)piperazine-1-carboxylate

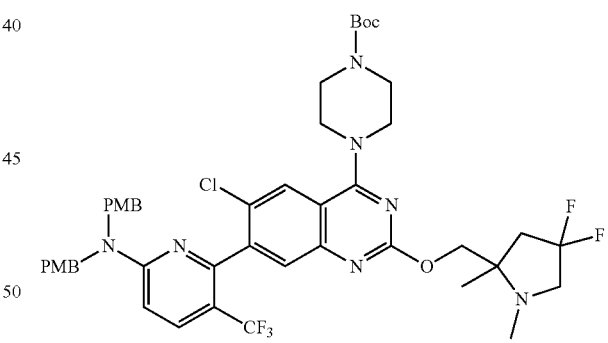

A solution of (4,4-difluoro-1,2-dimethyl-pyrrolidin-2-yl)methanol (130.0 mg, 0.79 mmol) in tetrahydrofuran (20 mL) was stirred at 25° C. for 0.5 hours. The sodium hydride (19.0 mg, 0.79 mmol) was added and stirred at 25° C. for 0.5 hours, then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (400.0 mg, 0.52 mmol) was added and stirred at 25° C. for 5 hours. Upon completion, the solution was quenched with water and extracted with ethyl acetate. The organic layer was collected and dried over anhydrous sodium sulfate and concentrated under vacuum. The residue was purified by flash chromatography on silica gel eluting with petroleum ether/ethyl acetate (9:1) to afford tert-butyl 4-(7-(6-(bis(4- methoxybenzyl)amino)-3-(trifluoromethyl)pyridin-2-yl)-6-chloro-2-((4,4-difluoro-1,2-dimethylpyrrolidin-2-yl)methoxy)quinazolin-4-yl)piperazine-1-carboxylate (286 mg, 0.31 mmol, 60.1% yield) as a yellow solid. LC-MS: (ESI, m/z): 912.4 [M+H]+

Step 4: 6-(6-chloro-2-((4,4-difluoro-1,2-dimethylpyrrolidin-2-yl)methoxy)-4-(piperazin-1-yl)quinazolin-7-yl)-5-(trifluoromethyl)pyridin-2-amine

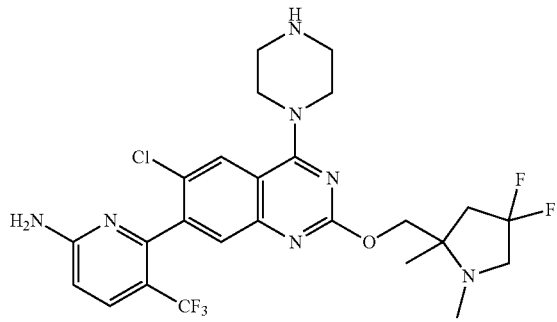 [SMILES: CN1CC(F)(F)CC1(C)COc1nc(N2CCNCC2)c2cc(Cl)c(-c3nc(N)ccc3C(F)(F)F)cc2n1]

A solution of tert-butyl 4-(7-(6-(bis(4-methoxybenzyl)amino)-3-(trifluoromethyl)pyridin-2-yl)-6-chloro-2-((4,4-difluoro-1,2-dimethylpyrrolidin-2-yl)methoxy)quinazolin-4-yl)piperazine-1-carboxylate (276.0 mg, 0.30 mmol) in 2,2,2-trifluoroacetic acid (25 mL) was stirred at 50° C. for 8 hours. Upon completion, the solution was quenched with water and extracted with ethyl acetate. The organic layer was collected and dried over anhydrous sodium sulfate and concentrated under vacuum. The residue was purified by flash chromatography on silica gel eluting with dichloromethane/methanol (97:3) to afford 6-(6-chloro-2-((4,4-difluoro-1,2-dimethylpyrrolidin-2-yl)methoxy)-4-(piperazin-1-yl)quinazolin-7-yl)-5-(trifluoromethyl)pyridin-2-amine (120 mg, 0.21 mmol, 69.4% yield) as a yellow solid. LC-MS: (ESI, m/z): 572.2 [M+H]+

Step 5: 1-(4-(7-(6-amino-3-(trifluoromethyl)pyridin-2-yl)-6-chloro-2-((4,4-difluoro-1,2-dimethylpyrrolidin-2-yl)methoxy)quinazolin-4-yl)piperazin-1-yl)prop-2-en-1-one

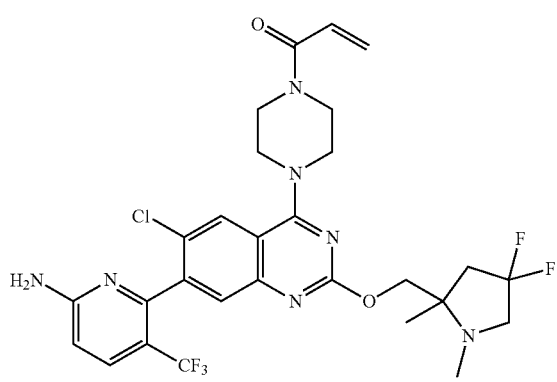 [SMILES: C=CC(=O)N1CCN(c2nc(OCC3(C)CC(F)(F)CN3C)nc3cc(-c4nc(N)ccc4C(F)(F)F)c(Cl)cc23)CC1]

A solution of 6-(6-chloro-2-((4,4-difluoro-1,2-dimethylpyrrolidin-2-yl)methoxy)-4-(piperazin-1-yl)quinazolin-7-yl)-5-(trifluoromethyl)pyridin-2-amine (110.0 mg, 0.19 mmol) and N,N-diisopropylethylamine (75.0 mg, 0.58 mmol) in dichloromethane (10 mL) was stirred at −78° C. for 5 minutes. Then acryloyl chloride (18.0 mg, 0.20 mmol) was added drop-wisely into the reaction system and stirred at −78° C. for 30 mints. Upon completion, the solution was quenched with water and extracted with dichloromethane. The organic layer was collected and dried over anhydrous sodium sulfate and concentrated under vacuum. The residue was purified by Prep-HPLC to afford 1-(4-(7-(6-amino-3-(trifluoromethyl)pyridin-2-yl)-6-chloro-2-((4,4-difluoro-1,2-dimethylpyrrolidin-2-yl)methoxy)quinazolin-4-yl)piperazin-1-yl)prop-2-en-1-one (54.5 mg, 0.09 mmol, 45.3% yield) as a white solid.

Example 73

LC-MS: (ESI, m/z): 626.2 [M+H]+, 1H NMR (300 MHz, Methanol-$d_4$) δ 8.09 (s, 1H), 7.80 (d, J=9 Hz, 1H), 7.55 (s, 1H), 6.91-6.75 (m, 1H), 6.70 (d, J=9 Hz, 1H), 6.34-6.18 (m, 1H), 5.86-5.74 (m, 1H), 4.49-4.31 (m, 2H), 4.06-3.84 (m, 8H), 3.43-3.32 (m, 1H), 3.22-3.01 (m, 1H), 2.69-2.45 (m, 1H), 2.39 (s, 3H), 2.30-2.12 (m, 1H), 1.26 (s, 3H).

Example 74

1-[4-[7-[6-amino-3-(trifluoromethyl)-2-pyridyl]-6-chloro-2-[1-methyl-1-[(2S)-1-methylpyrrolidin-2-yl]ethoxy]quinazolin-4-yl]piperazin-1-yl]prop-2-en-1-one

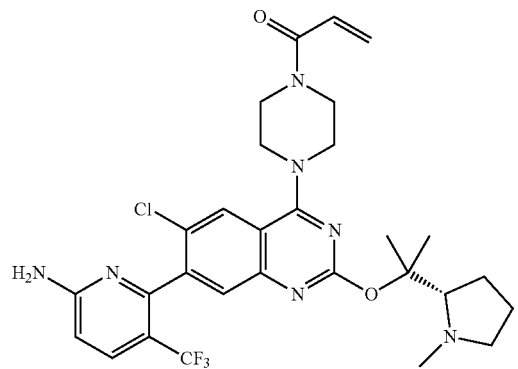

Synthetic Route

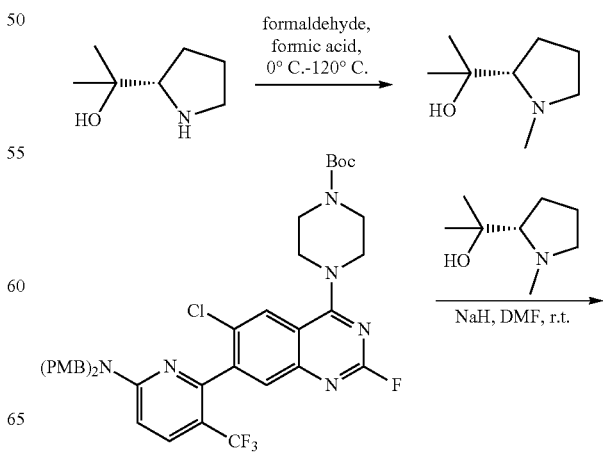

507

-continued

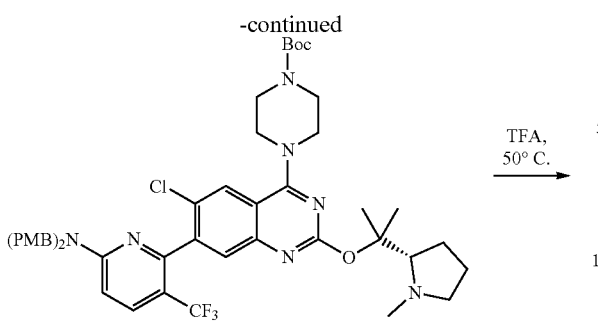

TFA, 50° C.

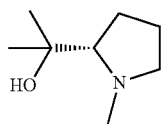

DIEA, DCM, -78° C.

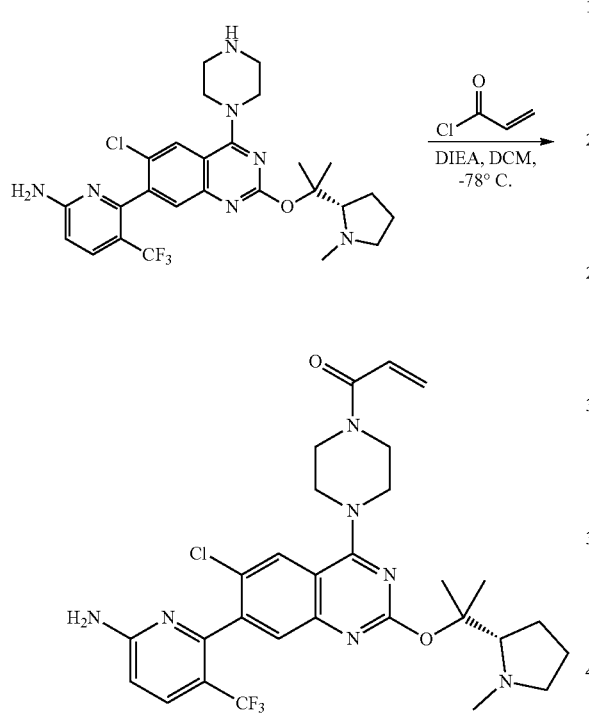

Step 1: 2-[(2S)-1-methylpyrrolidin-2-yl]propan-2-ol

2-[(2S)-pyrrolidin-2-yl]propan-2-ol (1.0 g, 7.74 mmol) was added to 0.2 mL of formic acid at 0° C., followed by 0.15 mL of 40% aqueous formaldehyde. Then mixture was refluxed at 120° C. for 24 hours. Upon completion, the mixture was acidified with 5N hydrochloric acid, and evaporated. The residue was dissolved in a minimum quantity of water, saturated with sodium hydroxide, and extracted with chloroform. The combined extracts were dried over potassium carbonate, and concentrated under vacuum. The residue was purified by flash chromatography on silica gel eluting with dichloromethane/methanol (96/4) to afford 510 mg (46%) of 2-[(2S)-1-methylpyrrolidin-2-yl]propan-2-ol as a yellowish-brown solid. LC-MS: (ESI, m/z): 144.3 [M+H]+

508

Step 2: tert-butyl (S)-4-(7-(6-(bis(4-methoxybenzyl) amino)-3-(trifluoromethyl)pyridin-2-yl)-6-chloro-2-((2-(1-methylpyrrolidin-2-yl)propan-2-yl)oxy)quinazolin-4-yl)piperazine-1-carboxylate

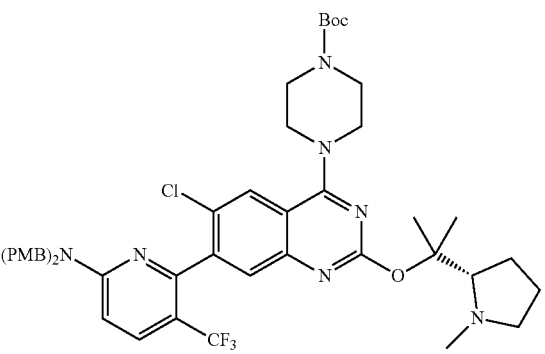

A solution of 2-[(2S)-1-methylpyrrolidin-2-yl]propan-2-ol (112.01 mg, 0.78 mmol) in N,N-dimethylformamide (22 mL) was added sodium hydride (125.13 mg, 3.13 mmol, 60% dispersion in mineral oil) at 0° C. and stirred at 25° C. for 1 hour. Then tert-butyl 4-(7-(6-(bis(4-methoxybenzyl)amino)-3-(trifluoromethyl)pyridin-2-yl)-6-chloro-2-fluoro-quinazolin-4-yl)piperazine-1-carboxylate (Intermediate 3) (300.0 mg, 0.39 mmol) was added and stirred at 25° C. for 1 hour. Upon completion, the resulting solution was quenched with water and extracted with dichloromethane. Then the organic layers were combined, washed with water, dried over anhydrous sodium sulfate and concentrated under vacuum. The residue was purified by flash chromatography on silica gel eluting with dichloromethane/methanol (4%) to afford 105 mg (30.2%) tert-butyl (S)-4-(7-(6-(bis(4-methoxybenzyl)amino)-3-(trifluoromethyl)pyridin-2-yl)-6-chloro-2-((2-(1-methylpyrrolidin-2-yl)propan-2-yl)oxy)quinazolin-4-yl)piperazine-1-carboxylate as a white solid. LC-MS: (ESI, m/z): 890.4 [M+H]+

Step 3: (S)-6-(6-chloro-2-((2-(1-methylpyrrolidin-2-yl)prop an-2-yl)oxy)-4-(piperazin-1-yl)quinazolin-7-yl)-5-(trifluoromethyl)pyridin-2-amine

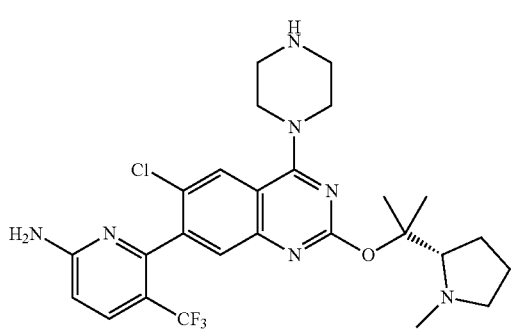

A solution of tert-butyl (S)-4-(7-(6-(bis(4-methoxybenzyl)amino)-3-(trifluoromethyl)pyridin-2-yl)-6-chloro-2-((2-(1-methylpyrrolidin-2-yl)propan-2-yl)oxy)quinazolin-4-yl) piperazine-1-carboxylate (96.0 mg, 0.11 mmol) in trifluoroacetic acid (21 mL, 0.11 mmol) was stirred at 50° C.

for 5 hours. Upon completion, the reaction was concentrated. The crude was used in the next reaction. LC-MS: (ESI, m/z): 550.4 [M+H]+

Step 4: 1-[4-[7-[6-amino-3-(trifluoromethyl)-2-pyridyl]-6-chloro-2-[1-methyl-1-[(2S)-1-methylpyrrolidin-2-yl]ethoxy]quinazolin-4-yl]piperazin-1-yl]prop-2-en-1-one

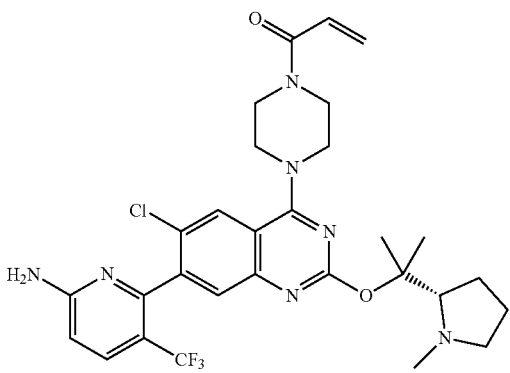

To a solution of (S)-6-(6-chloro-2-((2-(1-methylpyrrolidin-2-yl)propan-2-yl)oxy)-4-(piperazin-1-yl)quinazolin-7-yl)-5-(trifluoromethyl)pyridin-2-amine (59.0 mg, 0.11 mmol) and N,N-diisopropylethylamine (55.35 mg, 0.43 mmol) in dichloromethane (19 mL) was added acryloyl chloride (6.8 mg, 0.08 mmol) at −78° C. and stirred at −78° C. for 1 hour. Upon completion, the resulting solution was quenched with water and extracted with dichloromethane. Then the organic layers were combined, dried over anhydrous sodium sulfate and concentrated under vacuum. The residue was purified by a reversed-phase chromatography-Column, C18 silica gel; mobile phase, A: water, B: acetonitrile, B % (5% 70% in 30 min); Detector, UV 254 nm to afford a crude product. The crude product was purified directly by Prep-HPLC-Column, XBridge Prep C18 OBD Column19*15 mm 5 umC-0013; mobile phase, A: 10 mmol ammonium bicarbonate in water, B: ACN and B % (51%~73% in 7 min); Detector, UV 254 nm to afford 8 mg (12.3%) of 1-[4-[7-[6-amino-3-(trifluoromethyl)-2-pyridyl]-6-chloro-2-[1-methyl-1-[(2S)-1-methylpyrrolidin-2-yl]ethoxy]quinazolin-4-yl]piperazin-1-yl]prop-2-en-1-one as a white solid. LC-MS: (ESI, m/z): 604.4 [M+H]+.

Example 74

1H NMR (400 MHz, DMSO-d6, ppm) δ 8.00 (s, 1H), 7.77 (d, J=9.2 Hz, 1H), 7.43 (s, 1H), 6.88-6.78 (m, 3H), 6.59 (d, J=8.8 Hz, 1H), 6.16 (dd, J=16.4, 2.0 Hz, 1H), 5.73 (dd, J=10.8, 2.4 Hz, 1H), 3.83-3.79 (m, 8H), 3.12-3.09 (m, 1H), 2.98-2.96 (m, 1H), 2.37 (d, J=9.6 Hz, 3H), 2.29-2.24 (m, 1H), 1.90-1.84 (m, 1H), 1.71-1.58 (m, 3H), 1.57-1.52 (m, 6H). LC-MS: (ESI, m/z): 604.4 [M+H]+.

Examples 75a and 75b (R)-1-(4-(7-(6-amino-3-(trifluoromethyl)pyridin-2-yl)-6-chloro-2-((1-methylazetidin-2-yl)methoxy)quinazolin-4-yl)piperazin-1-yl)prop-2-en-1-one (Example 75a) and (S)-1-(4-(7-(6-amino-3-(trifluoromethyl)pyridin-2-yl)-6-chloro-2-((1-methylazetidin-2-yl)methoxy)quinazolin-4-yl)piperazin-1-yl)prop-2-en-1-one (Example 75b)

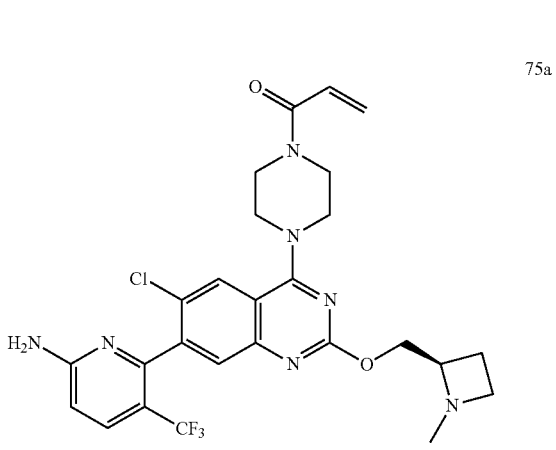

75a

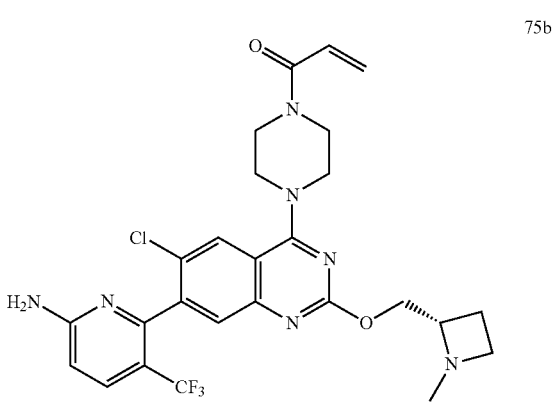

75b

Synthetic Route

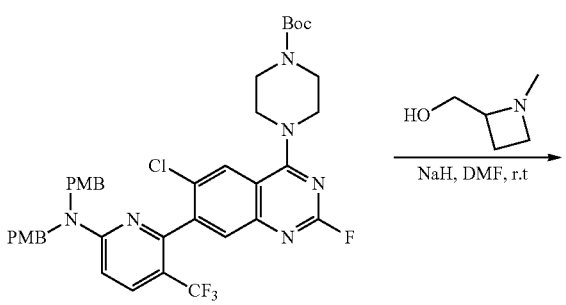

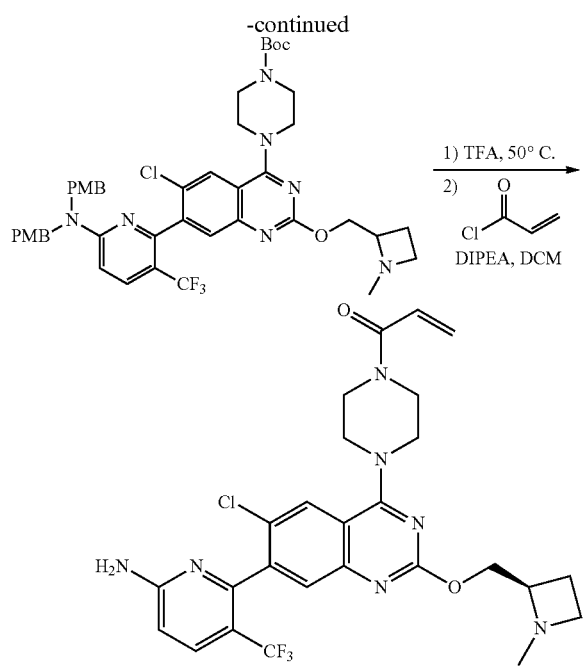

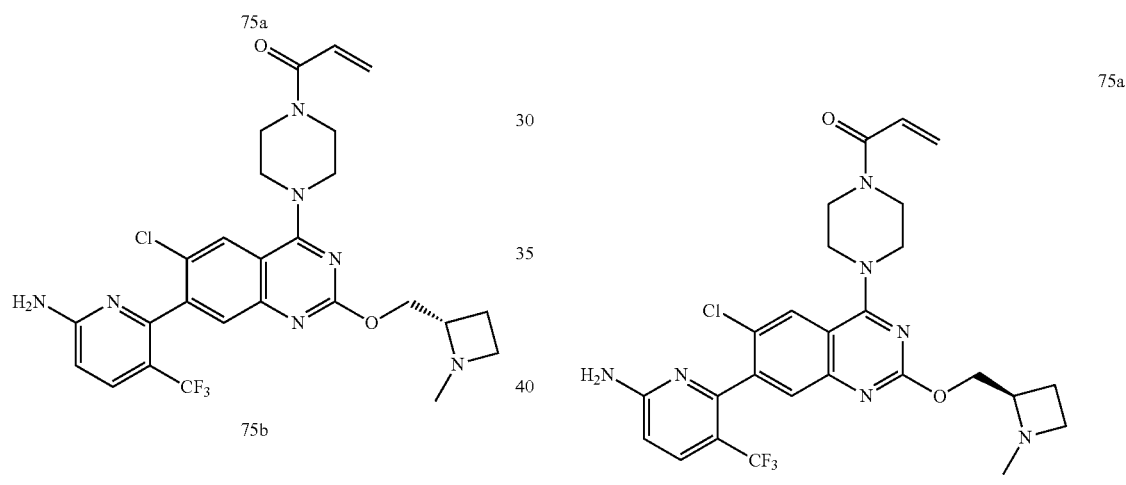

Step 1: tert-butyl 4-[7-[6-[bis[(4-methoxyphenyl)methyl]amino]-3-(trifluoromethyl)-2-pyridyl]-6-chloro-2-[(1-methylazetidin-2-yl)methoxy]quinazolin-4-yl]piperazine-1-carboxylate

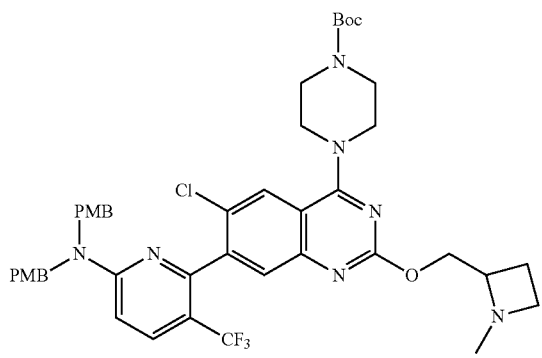

A solution of (1-methylazetidin-2-yl)methanol (39.5 mg, 0.3 mmol) and sodium hydride (60% purity) (23.4 mg, 0.5 mmol) in N,N-dimethylformamide (2 mL) was stirred at 0° C. for 30 minutes. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (150.0 mg, 0.2 mmol) was added and stirred at room temperature for 2 hours. Upon completion, the reaction was quenched with saturated ammonium chloride. The resulting solution was extracted with ethyl acetate and the organic layers were combined. The residue was purified by flash chromatography on silica gel eluting with dichloromethane/methanol (10/1) to afford tert-butyl 4-[7-[6-[bis[(4-methoxyphenyl)methyl]amino]-3-(trifluoromethyl)-2-pyridyl]-6-chloro-2-[(1-methylazetidin-2-yl)methoxy]quinazolin-4-yl]piperazine-1-carboxylate (120.0 mg, 0.1 mmol, 72% yield) as a yellow liquid. LC-MS: (ESI, m/z): 848.3 [M+H]$^+$ Step 2: (R)-1-(4-(7-(6-amino-3-(trifluoromethyl)pyridin-2-yl)-6-chloro-2-((1-methylazetidin-2-yl)methoxy)quinazolin-4-yl)piperazin-1-yl)prop-2-en-1-one (Example 75a) and (S)-1-(4-(7-(6-amino-3-(trifluoromethyl)pyridin-2-yl)-6-chloro-2-((1-methylazetidin-2-yl)methoxy)quinazolin-4-yl)piperazin-1-yl)prop-2-en-1-one (Example 75b)

A solution of tert-butyl 4-[7-[6-[bis[(4-methoxyphenyl)methyl]amino]-3-(trifluoromethyl)-2-pyridyl]-6-chloro-2-[(1-methylazetidin-2-yl)methoxy]quinazolin-4-yl]piperazine-1-carboxylate (100.0 mg, 0.1 mmol) in trifluoroacetic acid (2.6 mL, 35.3 mmol) was stirred at 50° C. for 12 hours. Upon completion, the reaction was concentrated. The resulting mixture was re-dissolved in dichloromethane (1 mL) and N,N-diisopropylethylamine (76.1 mg, 0.5 mmol) and acryloyl chloride (17.8 mg, 0.2 mmol) were added sequentially. The reaction was stirred at −78° C. for 0.5 hours. The resulting solution was quenched with water and extracted with dichloromethane. The organic layer was collected, concentrated, and purified by flash chromatography on silica gel eluting with dichloromethane/methanol (10/1) to afford the crude product. The crude product was purified by Prep-HPLC-Column: XBridge Prep OBD C18 Column, 30×150 mm 5 um; Mobile Phase A: Water (10 mmol/L $NH_4HCO_3$), Mobile Phase B:ACN; Flow rate: 60 mL/min; to afford the diastereoisomers as a colorless oil. The diastereoisomers was isolated by Prep-Chiral-HPLC (Column: CHIRALPAK IE-3, 4.6*50 mm 3 um; Mobile Phase A:(Hex:DCM=3:1)(0.1% DEA):IPA=80:20) to afford (R)-1-(4-(7-(6-amino-3-(trifluoromethyl)pyridin-2-yl)-6-chloro-2-((1-methylazetidin-2-yl)methoxy)quinazolin-4-yl)piperazin-1-yl)prop-2-en-1-one (Example 75a) (6.1 mg, 0.01 mmol, 5.5% yield) as a white solid and (S)-1-(4-(7-(6-amino-3-(trifluoromethyl)pyridin-2-yl)-6-chloro-2-((1-methylazetidin-2-yl)methoxy)quinazolin-4-yl)piperazin-1-yl)prop-2-en-1-one (Example 75b) (6.6 mg, 0.01 mmol, 6% yield) as a white solid.

Example 75a

LC-MS: (ESI, m/z): 562.2 $[M+H]^+$, $^1$H NMR (300 MHz, DMSO-$d_6$, ppm) δ 8.05 (s, 1H), 7.78 (d, J=8.7 Hz, 1H), 7.47 (s, 1H), 6.91 (s, 2H), 6.82 (dd, J=16.5, 10.2 Hz, 1H), 6.60 (d, J=8.7 Hz, 1H), 6.17 (dd, J=16.8, 2.4 Hz, 1H), 5.74 (dd, J=10.5, 2.4 Hz, 1H), 4.33 (d, J=5.4 Hz, 2H), 3.85-3.77 (m, 8H), 2.82-2.72 (m, 1H), 2.29 (s, 3H), 2.02-1.93 (m, 2H), 1.26-1.23 (m, 2H). Chiral HPLC: Column: CHIRALPAK IE-3, 4.6*50 mm 3 um; detected at 254 nm; (Hex:DCM=3:1)(0.1% DEA):IPA=80:20; Flow rate:1 mL/min; Retention time: 3.723 min; (faster peak).

Example 75b

LC-MS: (ESI, m/z): 562.2 $[M+H]^+$, $^1$H NMR (300 MHz, DMSO-$d_6$, ppm) δ 8.04 (s, 1H), 7.78 (d, J=8.7 Hz, 1H), 7.46 (s, 1H), 6.91-6.78 (m, 3H), 6.60 (d, J=8.7 Hz, 1H), 6.17 (dd, J=16.8, 2.4 Hz, 1H), 5.74 (dd, J=10.5, 2.4 Hz, 1H), 4.30 (d, J=5.4 Hz, 2H), 3.85-3.77 (m, 8H), 2.78-2.70 (m, 1H), 2.25 (s, 3H), 2.01-1.87 (m, 2H), 1.26-1.23 (m, 2H). Chiral HPLC: Column: CHIRALPAK IE-3, 4.6*50 mm 3 um; detected at 254 nm; (Hex:DCM=3:1)(0.1% DEA):IPA=80:20; Flow rate:1 mL/min; Retention time: 4.650 min; (slower peak).

Example 76

1-(4-(7-(6-amino-3-(trifluoromethyl)pyridin-2-yl)-6-chloro-2-(2-(3-(fluoromethyl)azetidin-1-yl)ethoxy)quinazolin-4-yl)piperazin-1-yl)prop-2-en-1-one

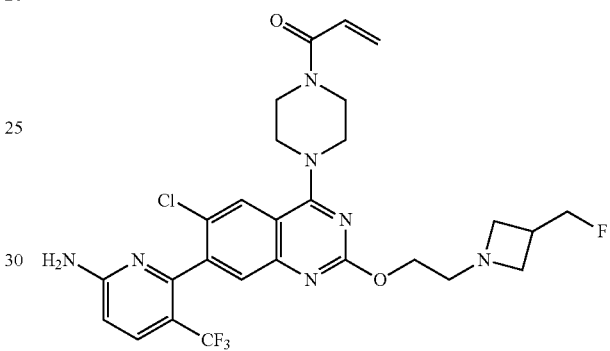

Synthetic Route

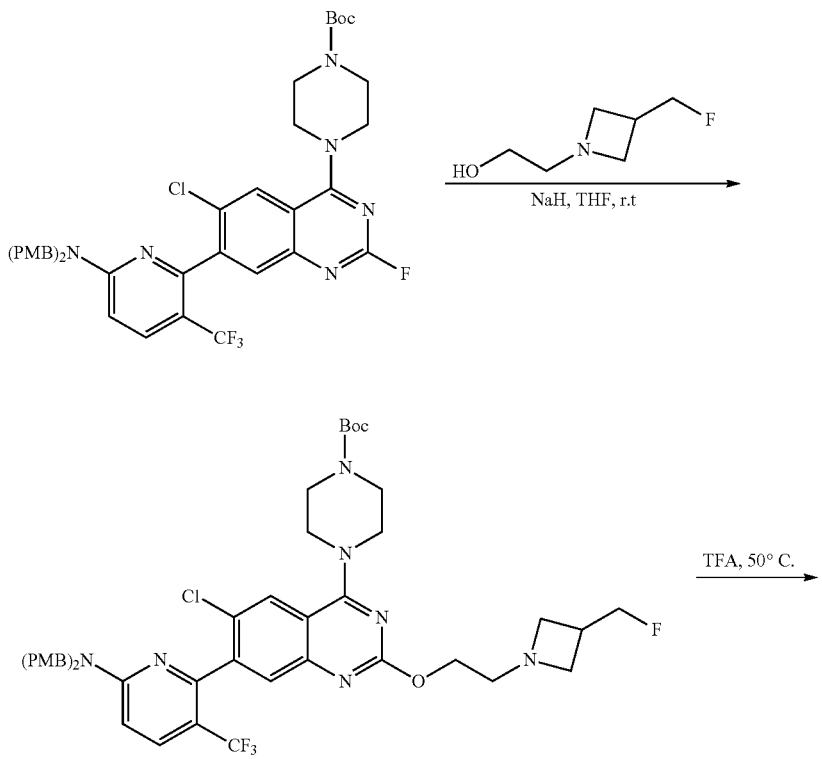

-continued

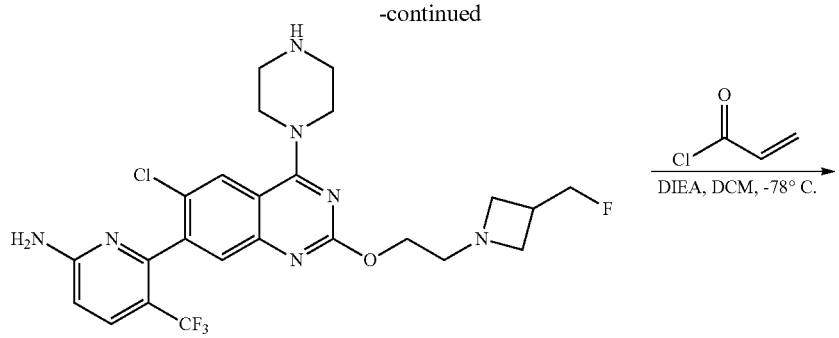

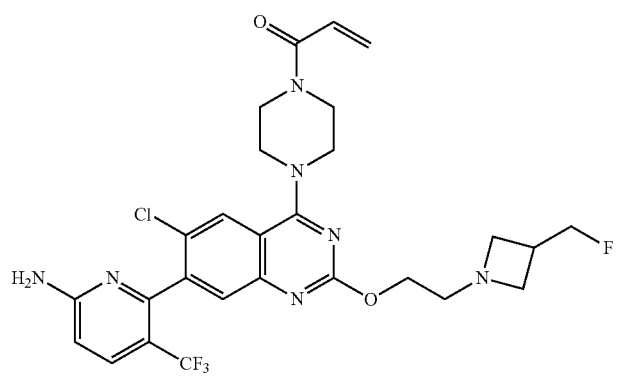

Step 1: tert-butyl 4-(7-(6-(bis(4-methoxybenzyl)amino)-3-(trifluoromethyl)pyridin-2-yl)-6-chloro-2-(2-(3-(fluoromethyl)azetidin-1-yl)ethoxy)quinazolin-4-yl)piperazine-1-carboxylate

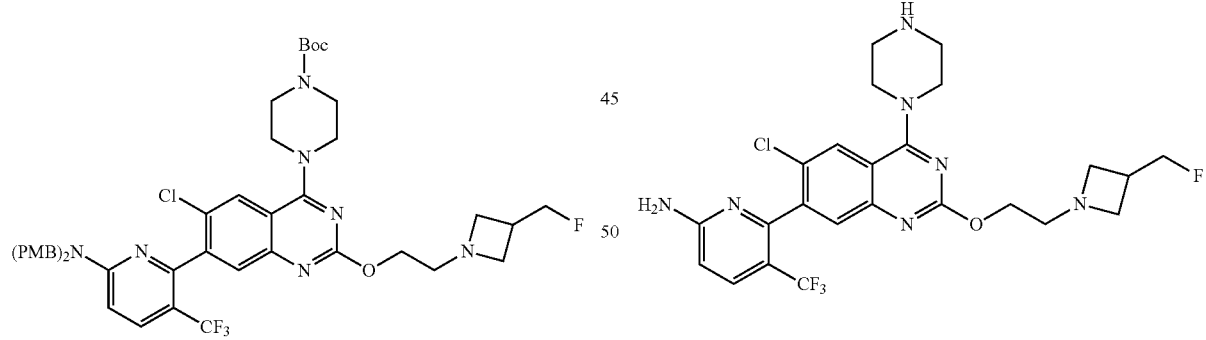

A solution of 2-[3-(fluoromethyl)azetidin-1-yl]ethanol (70.0 mg, 0.5300 mmol) and sodium hydride (20.0 mg, 0.5 mmol, 60% purity) in tetrahydrofuran (5 mL) was added and stirred at 25° C. for 5 minutes. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (200.0 mg, 0.26 mmol) was added and stirred at 25° C. for 30 minutes. Upon completion, the solution was concentrated under vacuum to get crude product. The crude product was directly used to the next step. LC-MS: (ESI, m/z): 880.3 [M+H]$^+$ Step 2: 6-(6-chloro-2-(2-(3-(fluoromethyl)azetidin-1-yl)ethoxy)-4-(piperazin-1-yl)quinazolin-7-yl)-5-(trifluoromethyl)pyridin-2-amine A solution of tert-butyl 4-(7-(6-(bis(4-methoxybenzyl)amino)-3-(trifluoromethyl)pyridin-2-yl)-6-chloro-2-(2-(3-(fluoromethyl)azetidin-1-yl)ethoxy)quinazolin-4-yl)piperazine-1-carboxylate (241.0 mg, 0.27 mmol) in 2,2,2-trifluoroacetic acid (10 mL) was stirred at 50° C. for 2 hours. Upon completion, the reaction was concentrated. The residue was purified by flash chromatography on C18 gel eluting with methanol/water (25:75) to afford 6-(6-chloro-2-(2-(3-(fluoromethyl)azetidin-1-yl)ethoxy)-4-(piperazin-1-yl)quinazolin-7-yl)-5-(trifluoromethyl)pyridin-2-amine (140 mg, 0.25 mmol, 94.7% yield) as a yellow solid. LC-MS: (ESI, m/z): 540.2 [M+H]$^+$

517

Step 3: 1-(4-(7-(6-amino-3-(trifluoromethyl)pyridin-2-yl)-6-chloro-2-(2-(3-(fluoromethyl)azetidin-1-yl)ethoxy)quinazolin-4-yl)piperazin-1-yl)prop-2-en-1-one

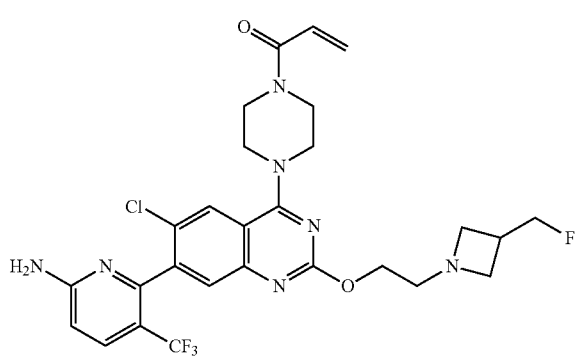 [SMILES: C=CC(=O)N1CCN(c2nc(OCCN3CC(CF)C3)nc3cc(-c4nc(N)ccc4C(F)(F)F)c(Cl)cc23)CC1]

A solution of 6-(6-chloro-2-(2-(3-(fluoromethyl)azetidin-1-yl)ethoxy)-4-(piperazin-1-yl)quinazolin-7-yl)-5-(trifluoromethyl)pyridin-2-amine (140.0 mg, 0.26 mmol) and N,N-diisopropylethylamine (0.09 mL, 0.52 mmol) in dichloromethane (10 mL) was stirred at −78° C. for 5 minutes. Then acryloyl chloride (24.0 mg, 0.27 mmol) was added and stirred at −78° C. for 1 hour. Upon completion, the reaction was concentrated. The residue was purified by flash chromatography on C18 gel eluting with acetonitrile/water (25:75) to afford crude product. The crude product was purified by Prep-HPLC-Column: Xselect CSH OBD Column 30*150 mm 5 um, n; Mobile Phase A:Water(0.1% FA), Mobile Phase B:ACN; Flow rate:60 mL/min afforded 1-(4-(7-(6-amino-3-(trifluoromethyl)pyridin-2-yl)-6-chloro-2-(2-(3-(fluoromethyl)azetidin-1-yl)ethoxy)quinazolin-4-yl)piperazin-1-yl)prop-2-en-1-one formic acid salt (16.8 mg, 0.026 mmol, 10.1% yield) as a white solid.

Example 76

LC-MS: (ESI, m/z): 594.2 [M+H]+, 1H NMR (300 MHz, DMSO, ppm) δ 8.04 (s, 1H), 7.78 (d, J=9.0 Hz, 1H), 7.46 (s, 1H), 7.00-6.67 (m, 3H), 6.60 (d, J=8.7 Hz, 1H), 6.17 (dd, J=2.1, 16.5 Hz, 1H), 5.74 (dd, J=2.1, 10.5 Hz, 1H), 4.58 (d, J=6.3 Hz, 1H), 4.42 (d, J=6.3 Hz, 1H), 4.31-4.15 (m, 2H), 3.93-3.70 (m, 8H), 3.32-3.29 (m, 2H), 3.02-2.93 (m, 2H), 2.83-2.66 (m, 3H).

518

Example 77

1-[4-[7-[6-amino-3-(trifluoromethyl)-2-pyridyl]-6-chloro-2-[[(2R, 3S)-3-fluoro-1-methyl-pyrrolidin-2-yl]methoxy]quinazolin-4-yl]piperazin-1-yl]prop-2-en-1-one

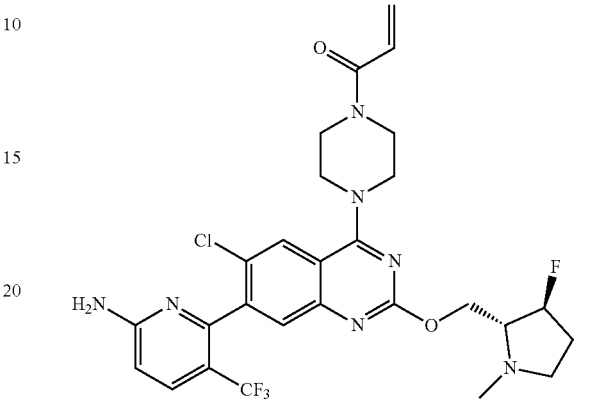

Synthetic Route

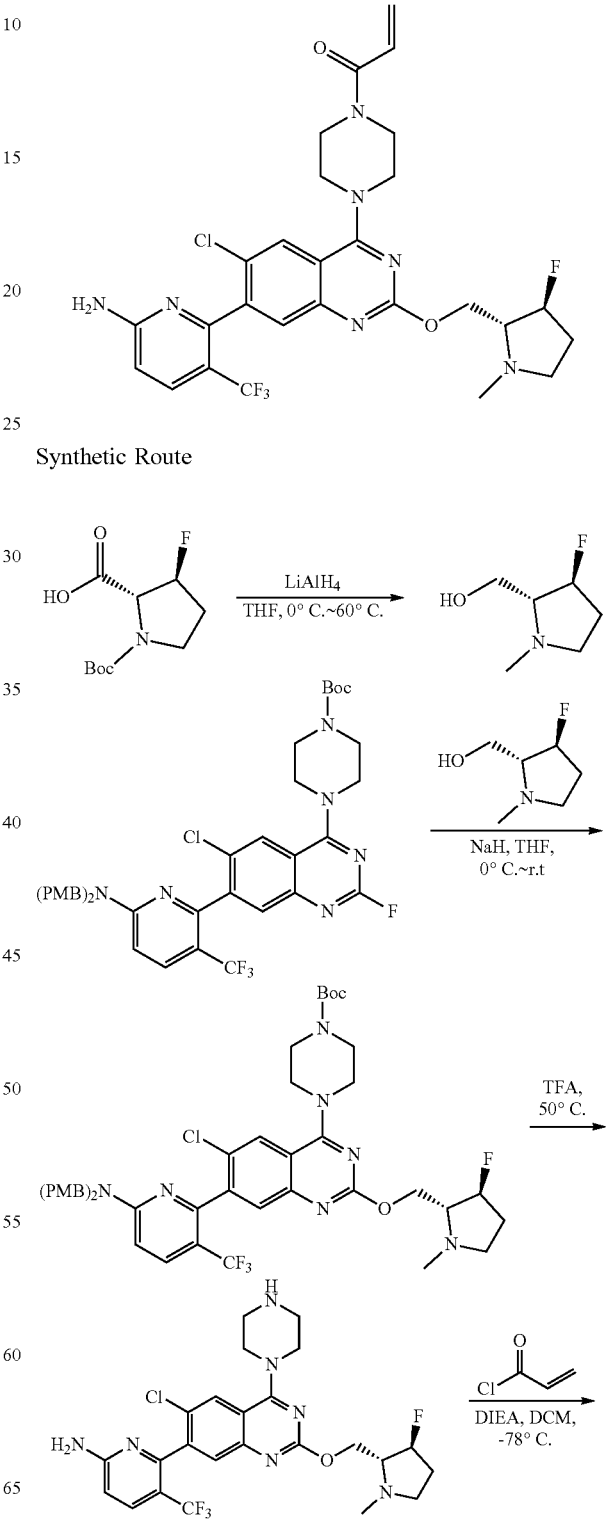

-continued

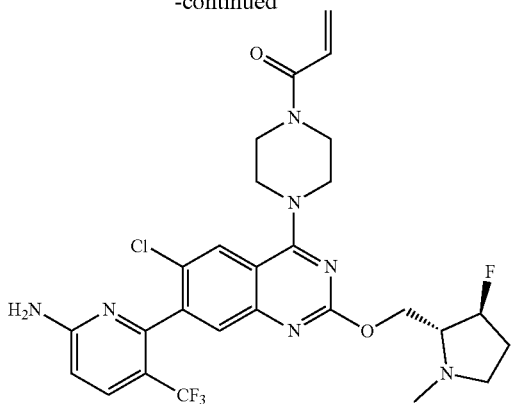

Step 1: [(2R, 3S)-3-fluoro-1-methyl-pyrrolidin-2-yl]methanol

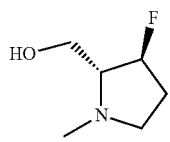

Lithium aluminum hydride (146.63 mg, 3.86 mmol) was added to a solution of (2R,3S)-1-tert-butoxycarbonyl-3-fluoro-pyrrolidine-2-carboxylic acid (450.0 mg, 1.93 mmol) in tetrahydrofuran (18 mL) at 0° C. The reaction was then heated to 60° C. for 1.5 hours. The reaction was cooled and quenched with water, filtered, and concentrated. The residue was purified by flash chromatography on silica gel eluting with dichloromethane/methanol (96/4) to afford 80 mg (31%) of [(2R, 3S)-3-fluoro-1-methyl-pyrrolidin-2-yl]methanol as a yellow oil. LC-MS: (ESI, m/z): 134.3 [M+H]$^+$.

Step 2: tert-butyl 4-[7-[6-[bis[(4-methoxyphenyl)methyl]amino]-3-(trifluoromethyl)-2-pyridyl]-6-chloro-2-[[(2R,3S)-3-fluoro-1-methyl-pyrrolidin-2-yl]methoxy]quinazolin-4-yl]piperazine-1-carboxylate

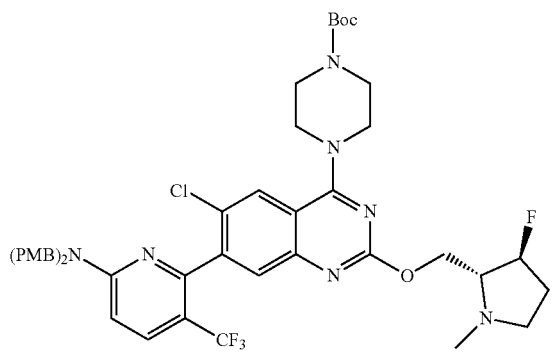

A solution of [(2R,3S)-3-fluoro-1-methyl-pyrrolidin-2-yl]methanol (138.85 mg, 1.04 mmol) in tetrahydrofuran (12 mL) was added sodium hydride (166.84 mg, 4.17 mmol) at 0° C. The reaction was warmed to 25° C. and stirred for 1 hour. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (400.0 mg, 0.52 mmol) was added and stirred at 25° C. for 1 hour. Upon completion, the reaction was quenched with water and extracted with dichloromethane. The organic layers were combined, washed with water, dried over anhydrous sodium sulfate and concentrated under vacuum. The residue was purified by flash chromatography on silica gel eluting with petroleum ether/ethyl acetate (1/1) to afford 69 mg (15%) of tert-butyl 4-[7-[6-[bis[(4-methoxy phenyl)methyl]amino]-3-(trifluoromethyl)-2-pyridyl]-6-chloro-2-[[(2R,3S)-3-fluoro-1-methyl-pyrrolidin-2-yl]methoxy]quinazolin-4-yl]piperazine-1-carboxylate as a yellow solid. LC-MS: (ESI, m/z): 880.5 [M+H]$^+$.

Step 3: 6-[6-chloro-2-[[(2R,3S)-3-fluoro-1-methyl-pyrrolidin-2-yl]methoxy]-4-piperazin-1-yl-quinazolin-7-yl]-5-(trifluoromethyl)pyridin-2-amine

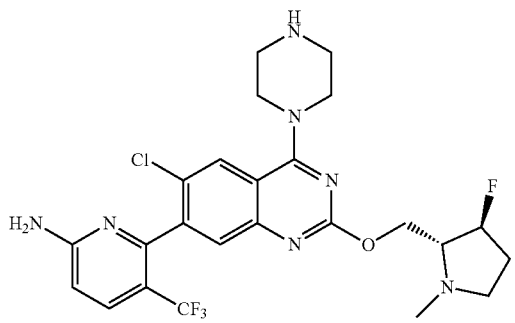

A solution of tert-butyl 4-[7-[6-[bis[(4-methoxyphenyl)methyl]amino]-3-(trifluoromethyl)-2-pyridyl]-6-chloro-2-[[(2R,3S)-3-fluoro-1-methyl-pyrrolidin-2-yl]methoxy]quinazolin-4-yl]piperazine-1-carboxylate (61.0 mg, 0.07 mmol) in trifluoroacetic acid (16 mL) was stirred at 50° C. for 3 hours. Upon completion, the reaction was concentrated. The pH was adjusted to 10 with N,N-diisopropylethylamine. The residue was purified by a reversed-phase chromatography-Column, C18 silica gel; mobile phase, A: water, B:MeCN, B % (5% 70% in 30 min); Detector, UV 254 nm to afford 37 mg of 6-[6-chloro-2-[[(2R,3S)-3-fluoro-1-methyl-pyrrolidin-2-yl]methoxy]-4-piperazin-1-yl-quinazolin-7-yl]-5-(trifluoromethyl)pyridin-2-amine as a light yellow solid. LC-MS: (ESI, m/z): 540.3 [M+H]$^+$

521

Step 4: 1-[4-[7-[6-amino-3-(trifluoromethyl)-2-pyridyl]-6-chloro-2-[[(2R,3S)-3-fluoro-1-methyl-pyrrolidin-2-yl]methoxy]quinazolin-4-yl]piperazin-1-yl]prop-2-en-1-one

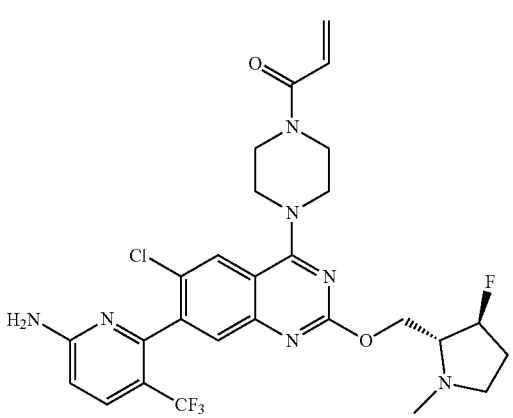 [SMILES: C=CC(=O)N1CCN(c2nc(OC[C@@H]3[C@@H](F)CCN3C)nc3cc(-c4nc(N)ccc4C(F)(F)F)c(Cl)cc23)CC1]

To a solution of 6-[6-chloro-2-[[(2R,3S)-3-fluoro-1-methyl-pyrrolidin-2-yl]methoxy]-4-piperazin-1-yl-quinazolin-7-yl]-5-(trifluoromethyl)pyridin-2-amine (37.0 mg, 0.07 mmol) and N,N-diisopropylethylamine (35.36 mg, 0.27 mmol) in dichloromethane (4.6 mL) was added acryloyl chloride (3.72 mg, 0.04 mmol) at −78° C. and stirred at −78° C. for 1 hour. Upon completion, the reaction was quenched by water and extracted with dichloromethane. The organic layers were combined, dried over anhydrous sodium sulfate and concentrated under vacuum. The crude product was purified directly by Prep-HPLC-Column, XBridge Prep C18 OBD Column19*15 mm 5 umC-0013; mobile phase, A: TFA in water, B: ACN and B % (51%~73% in 7 min); Detector, UV 254 nm to afford 7.5 mg (18.4%) of 1-[4-[7-[6-amino-3-(trifluoromethyl)-2-pyridyl]-6-chloro-2-[[(2R,3S)-3-fluoro-1-methyl-pyrrolidin-2-yl]methoxy]quinazolin-4-yl]piperazin-1-yl]prop-2-en-1-one as a white solid. LC-MS: (ESI, m/z): 594.2 [M+H]$^+$ Example 77

$^1$H NMR (400 MHz, DMSO-d$_6$, ppm) δ 8.05 (s, 1H), 7.78 (d, J=8.0 Hz, 1H), 7.46 (s, 1H), 6.91 (s, 2H), 6.98-6.78 (m, 1H), 6.59 (d, J=8.8 Hz, 1H), 6.17 (dd, J=16.8, 2.0 Hz, 1H), 5.74 (dd, J=8.8, 2.0 Hz, 1H), 5.09 (d, J=52.0, 1H), 4.39-4.35 (m, 1H), 4.15-4.13 (m, 1H), 3.90-3.86 (m, 6H), 3.76 (s, 2H), 2.94 (d, J=6.8, 1H), 2.84-2.75 (m, 1H), 2.49-2.43 (m, 4H), 1.96-1.90 (m, 2H). LC-MS: (ESI, m/z): 594.2 [M+H]$^+$.

522

Example 78a 1-(4-(7-(6-amino-3-(trifluoromethyl)pyridin-2-yl)-6-chloro-2-(((1S,2S,5R)-3-methyl-3-azabicyclo[3.1.0]hexan-2-yl)methoxy)quinazolin-4-yl)piperazin-1-yl)prop-2-en-1-one

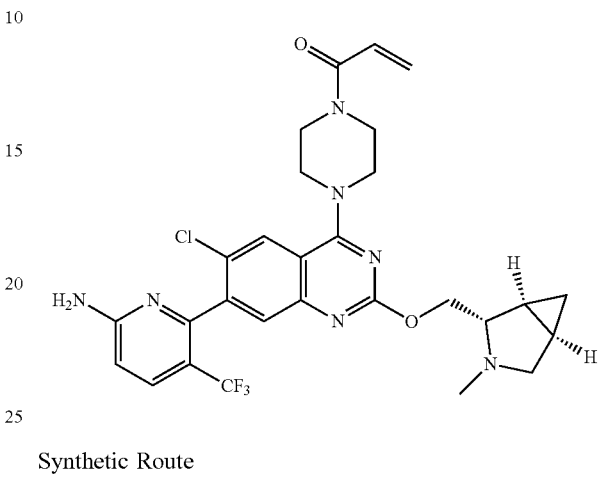

Synthetic Route

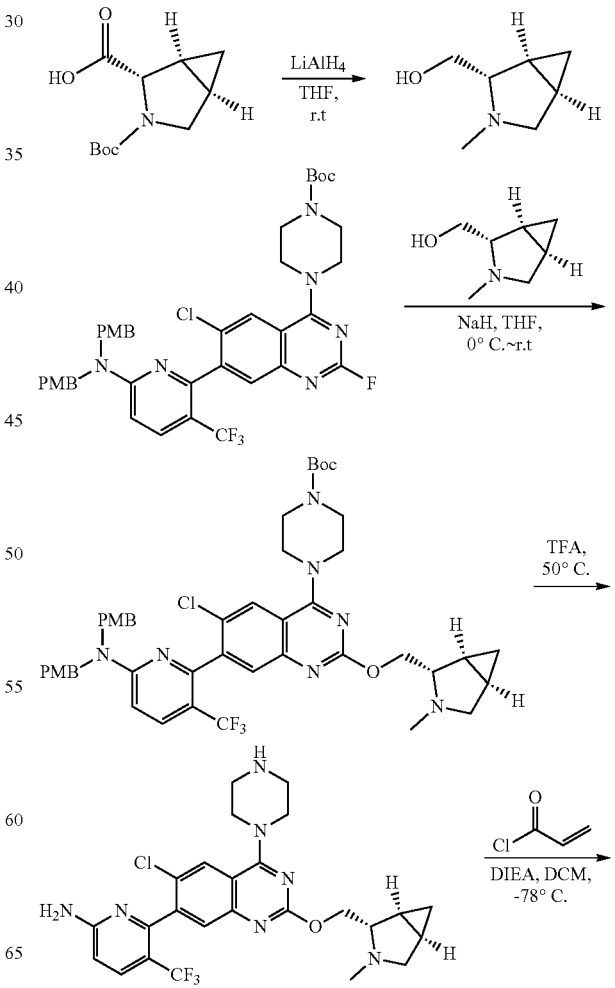

-continued

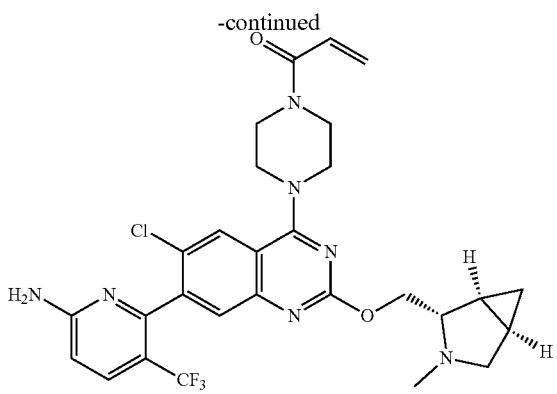

Step 1: ((1S,2S,5R)-3-methyl-3-azabicyclo[3.1.0]
hexan-2-yl)methanol

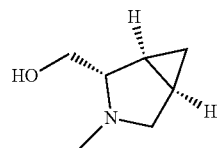

A solution of (1S,2S,5R)-3-(tert-butoxycarbonyl)-3-azabicyclo[3.1.0]hexane-2-carboxylic acid (200.0 mg, 0.88 mmol) in tetrahydrofuran (10 mL) was stirred at 25° C. for 0.5 hours. Then lithium aluminum hydride (67.0 mg, 1.77 mmol) was added and stirred at 25° C. for 6 hours. Upon completion, the reaction was quenched with water and extracted with ethyl acetate. The organic layer was collected and dried over anhydrous sodium sulfate and concentrated under vacuum to afford ((1S,2S,5R)-3-methyl-3-azabicyclo[3.1.0]hexan-2-yl)methanol (90 mg, 0.71 mmol, 80.4% yield) that was directly carried forward to the next step. LC-MS: (ESI, m/z): 128.1 [M+H]$^+$ Step 2: tert-butyl 4-(7-(6-(bis(4-methoxybenzyl)amino)-3-(trifluoromethyl)pyridin-2-yl)-6-chloro-2-(((1S,2S,5R)-3-methyl-3-azabicyclo[3.1.0]hexan-2-yl)methoxy)quinazolin-4-yl)piperazine-1-carboxylate

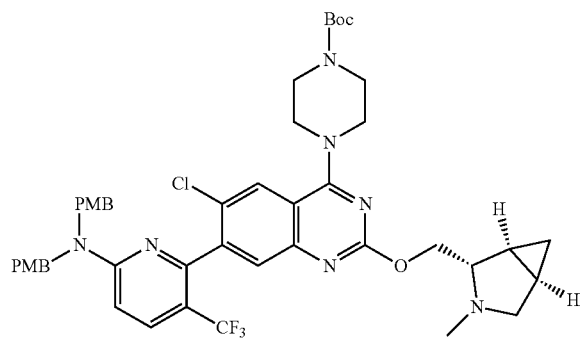

A solution of ((1S,2S,5R)-3-methyl-3-azabicyclo[3.1.0]hexan-2-yl)methanol (100.0 mg, 0.7900 mmol) and sodium hydride (32.0 mg, 1.33 mmol) in tetrahydrofuran (10 mL) was stirred at 0° C. for 0.5 hours. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (200.0 mg, 0.26 mmol) was added and the reaction was stirred at 25° C. for 3 hours. Upon completion, the reaction was quenched with water and extracted with ethyl acetate. The organic layer was collected and dried over anhydrous sodium sulfate and concentrated. The residue was purified by flash chromatography on silica gel eluting with dichloromethane/methanol (97:3) to afford tert-butyl 4-(7-(6-(bis(4-methoxybenzyl)amino)-3-(trifluoromethyl)pyridin-2-yl)-6-chloro-2-(((1S,2S,5R)-3-methyl-3-azabicyclo[3.1.0]hexan-2-yl)methoxy)quinazolin-4-yl)piperazine-1-carboxylate (56 mg, 0.06 mmol, 24.6% yield) as a yellow solid. LC-MS: (ESI, m/z): 874.4 [M+H]$^+$.

Step 3: 6-(6-chloro-2-(((1S,2S,5R)-3-methyl-3-azabicyclo[3.1.0]hexan-2-yl)methoxy)-4-(piperazin-1-yl)quinazolin-7-yl)-5-(trifluoromethyl)pyridin-2-amine

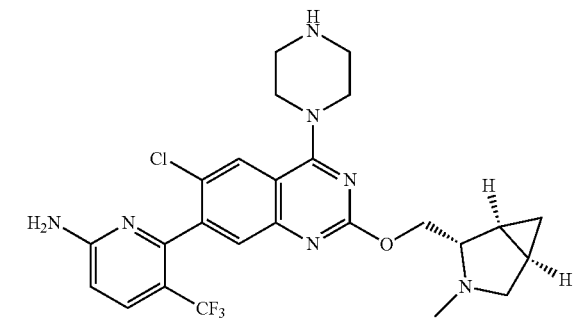 [SMILES: CN1C[C@@H]2C[C@@H]2[C@H]1COc1nc(N2CCNCC2)c2cc(Cl)c(-c3nc(N)ccc3C(F)(F)F)cc2n1]

A solution of tert-butyl 4-(7-(6-(bis(4-methoxybenzyl)amino)-3-(trifluoromethyl)pyridin-2-yl)-6-chloro-2-(((1S,2S,5R)-3-methyl-3-azabicyclo[3.1.0]hexan-2-yl)methoxy)quinazolin-4-yl)piperazine-1-carboxylate (83.0 mg, 0.09 mmol) in 2,2,2-trifluoroacetic acid (10 mL) was stirred at 50° C. for 5 hours. The reaction was concentrated to afford 6-(6-chloro-2-(((1S,2S,5R)-3-methyl-3-azabicyclo[3.1.0]hexan-2-yl)methoxy)-4-(piperazin-1-yl)quinazolin-7-yl)-5-(trifluoromethyl)pyridin-2-amine (25 mg, 0.05 mmol, 89% yield). LC-MS: (ESI, m/z): 534.2 [M+H]$^+$ Step 4: 1-(4-(7-(6-amino-3-(trifluoromethyl)pyridin-2-yl)-6-chloro-2-(((1S,2S,5R)-3-methyl-3-azabicyclo[3.1.0]hexan-2-yl)methoxy)quinazolin-4-yl)piperazin-1-yl)prop-2-en-1-one

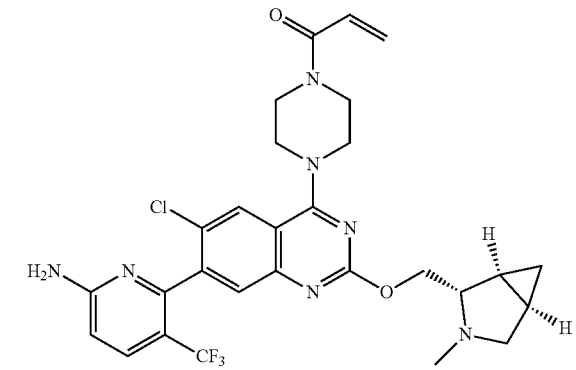 [SMILES: C=CC(=O)N1CCN(c2nc(OC[C@@H]3[C@H]4C[C@H]4CN3C)nc3cc(-c4nc(N)ccc4C(F)(F)F)c(Cl)cc23)CC1]

A solution of 6-(6-chloro-2-(((1S,2S,5R)-3-methyl-3-azabicyclo[3.1.0]hexan-2-yl)methoxy)-4-(piperazin-1-yl)quinazolin-7-yl)-5-(trifluoromethyl)pyridin-2-amine (50.0 mg, 0.09 mmol) and N,N-diisopropylethylamine (37.0 mg, 0.29 mmol) in dichloromethane (10 mL) was stirred at −78° C. for 5 minutes. Then acryloyl chloride (9.0 mg, 0.10 mmol) was added and the mixture stirred at −78° C. for 0.5 hours. Upon completion, the solution was quenched with water (2 mL) and extracted with dichloromethane (3×5 mL). The organic layer was collected and dried over anhydrous sodium sulfate and concentrated under vacuum. he crude product was further isolated by Prep-HPLC-Column: Xselect CSH OBD Column 30*150 mm 5 um, n; Mobile Phase A:Water(0.1% FA), Mobile Phase B: ACN; Flow rate:60 mL/min; to afford 1-(4-(7-(6-amino-3-(trifluoromethyl)pyridin-2-yl)-6-chloro-2-(((1S,2S,5R)-3-methyl-3-azabicyclo[3.1.0]hexan-2-yl)methoxy)quinazolin-4-yl)piperazin-1-yl)prop-2-en-1-one (15.2 mg, 0.03 mmol, 46% yield) as a white solid.

Example 78a

LC-MS: (ESI, m/z): 588.3 [M+H]$^+$, $^1$H NMR (300 MHz, Methanol-d$_4$, ppm) δ 8.09 (s, 1H), 7.80 (d, J=9 Hz, 1H), 7.54 (s, 1H), 6.83 (dd, J=16.8, 10.8 Hz, 1H), 6.71 (d, J=8.7, 1H), 6.29 (dd, J=16.8, 2.1 Hz, 1H), 5.82 (dd, J=10.5, 1.8 Hz, 1H), 4.62-4.51 (m, 1H), 4.48-4.33 (m, 1H), 4.05-3.86 (m, 8H), 3.13 (d, J=9 Hz, 1H), 3.01-2.92 (m, 1H), 2.58 (dd, J=9, 3.9 Hz, 1H), 2.43 (s, 3H), 1.76-1.61 (m, 1H), 1.58-1.39 (m, 1H), 0.82-0.63 (m, 1H), 0.45-0.26 (m, 1H).

Example 78b 1-(4-(7-(6-amino-3-(trifluoromethyl)pyridin-2-yl)-6-chloro-2-(((1R,2S,5S)-3-methyl-3-azabicyclo[3.1.0]hexan-2-yl)methoxy)quinazolin-4-yl)piperazin-1-yl)prop-2-en-1-one

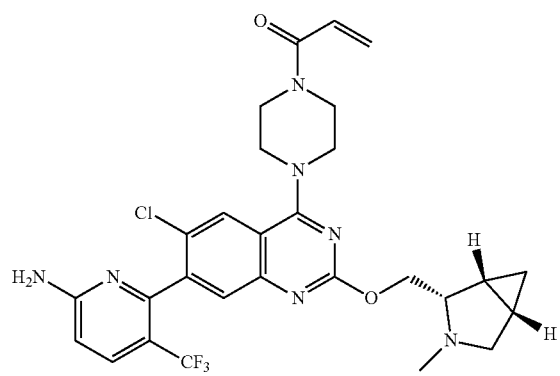 [SMILES: C=CC(=O)N1CCN(c2nc(OC[C@@H]3[C@@H]4C[C@@H]4CN3C)nc3cc(-c4nc(N)ccc4C(F)(F)F)c(Cl)cc23)CC1]

Synthetic Route

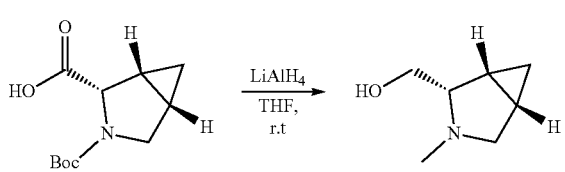

-continued

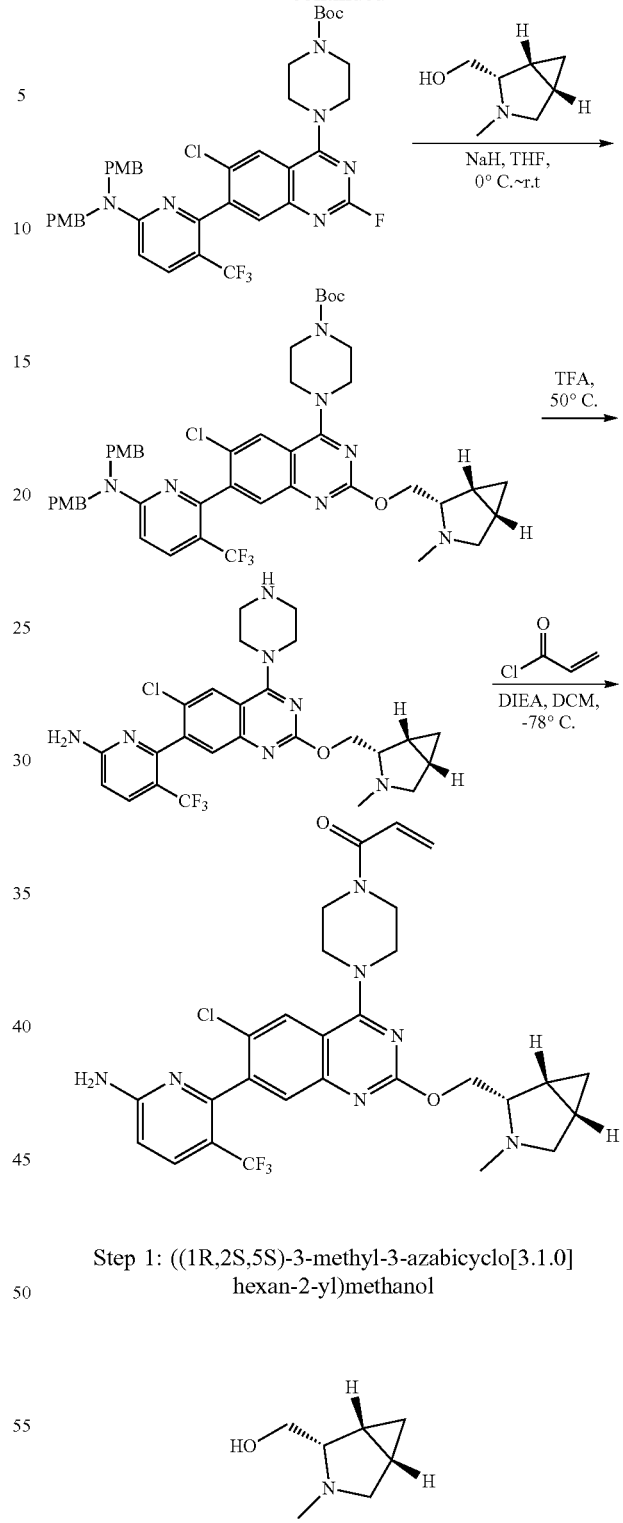

Step 1: ((1R,2S,5S)-3-methyl-3-azabicyclo[3.1.0]hexan-2-yl)methanol

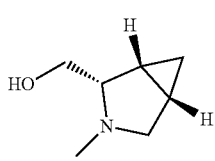

A solution of (1R,2S,5S)-3-(tert-butoxycarbonyl)-3-azabicyclo[3.1.0]hexane-2-carboxylic acid (200.0 mg, 0.88 mmol) in tetrahydrofuran (10 mL) was stirred at 25° C. for 5 minutes. Then lithium aluminum hydride (67.0 mg, 1.77 mmol) was added and stirred at 25° C. for 6 hours. Upon completion, the solution was quenched with water and extracted with ethyl acetate. The organic layer was collected and dried over anhydrous sodium sulfate and concentrated under vacuum to afford ((1R, 2S,5S)-3-methyl-3-azabicyclo[3.1.0]hexan-2-yl)methanol (86 mg, 0.68 mmol, 76.8% yield) that was carried forward to the next step without purification. LC-MS: (ESI, m/z): 128.1 [M+H]+

Step 2: tert-butyl 4-(7-(6-(bis(4-methoxybenzyl)amino)-3-(trifluoromethyl)pyridin-2-yl)-6-chloro-2-(((1R,2S,5S)-3-methyl-3-azabicyclo[3.1.0]hexan-2-yl)methoxy)quinazolin-4-yl)piperazine-1-carboxylate

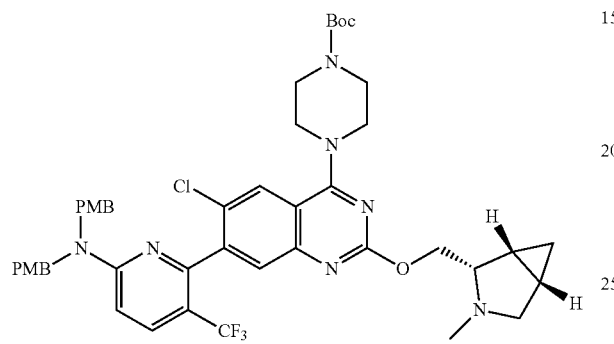

A solution of ((1R,2S,5S)-3-methyl-3-azabicyclo[3.1.0]hexan-2-yl)methanol (100.0 mg, 0.79 mmol) and sodium hydride (32.0 mg, 1.33 mmol) in tetrahydrofuran (10 mL) was stirred at 0° C. for 0.5 hours. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (200.0 mg, 0.26 mmol) was added and the reaction stirred at 25° C. for 3 hours. The reaction was concentrated and the residue was purified by silica gel chromatography eluting with dichloromethane/methanol (97:3) to afford tert-butyl 4-(7-(6-(bis(4-methoxybenzyl)amino)-3-(trifluoromethyl)pyridin-2-yl)-6-chloro-2-(((1R,2S,5S)-3-methyl-3-azabicyclo[3.1.0]hexan-2-yl)methoxy)quinazolin-4-yl)piperazine-1-carboxylate (93 mg, 0.11 mmol, 40.8% yield) as a yellow solid. LC-MS: (ESI, m/z): 874.4 [M+H]+

Step 3: 6-(6-chloro-2-(((1R,2S,5S)-3-methyl-3-azabicyclo[3.1.0]hexan-2-yl)methoxy)-4-(piperazin-1-yl)quinazolin-7-yl)-5-(trifluoromethyl)pyridin-2-amine

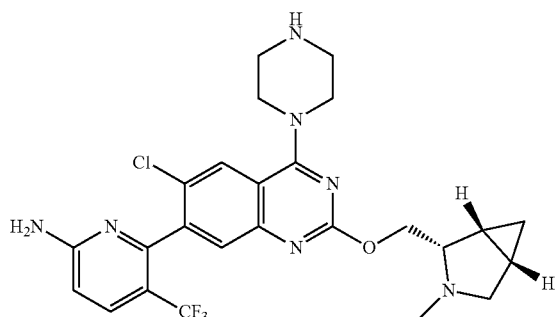

A solution of tert-butyl 4-(7-(6-(bis(4-methoxybenzyl)amino)-3-(trifluoromethyl)pyridin-2-yl)-6-chloro-2-(((1R,2S,5S)-3-methyl-3-azabicyclo[3.1.0]hexan-2-yl)methoxy)quinazolin-4-yl)piperazine-1-carboxylate (83.0 mg, 0.09 mmol) in 2,2,2-trifluoroacetic acid (10 mL) was stirred at 50° C. for 5 hours. The reaction was concentrated to afford 6-(6-chloro-2-(((1R,2S,5S)-3-methyl-3-azabicyclo[3.1.0]hexan-2-yl)methoxy)-4-(piperazin-1-yl)quinazolin-7-yl)-5-(trifluoromethyl)pyridin-2-amine (40 mg, 0.09 mmol, 70.2% yield). LC-MS: (ESI, m/z): 534.2 [M+H]+

Step 4: 1-(4-(7-(6-amino-3-(trifluoromethyl)pyridin-2-yl)-6-chloro-2-(((1R,2S,5S)-3-methyl-3-azabicyclo[3.1.0]hexan-2-yl)methoxy)quinazolin-4-yl)piperazin-1-yl)prop-2-en-1-one

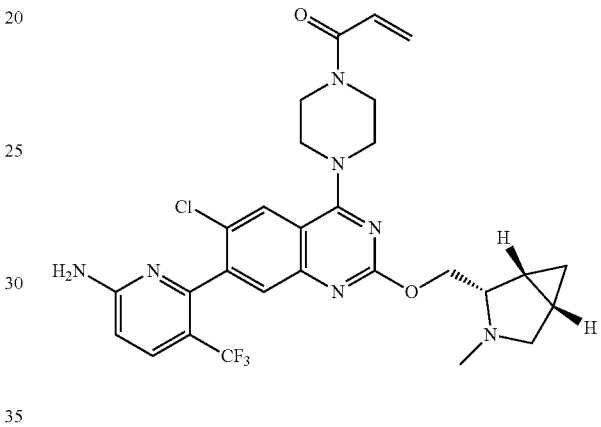

A solution of 6-(6-chloro-2-(((1R,2S,5S)-3-methyl-3-azabicyclo[3.1.0]hexan-2-yl)methoxy)-4-(piperazin-1-yl)quinazolin-7-yl)-5-(trifluoromethyl)pyridin-2-amine (50.0 mg, 0.09 mmol) and N,N-diisopropylethylamine (37.0 mg, 0.29 mmol) in dichloromethane (10 mL) was stirred at −78° C. for 0.5 hours. Then acryloyl chloride (10 mg, 0.10 mmol) was added and stirred at −78° C. for 0.5 hours. Upon completion, the solution was quenched with water and extracted with dichloromethane. The organic layer was collected and dried over anhydrous sodium sulfate and concentrated. The crude product was further isolated by Prep-HPLC-Column: Xselect CSH OBD Column 30*150 mm 5 um, n; Mobile Phase A:Water(0.1% FA), Mobile Phase B:ACN; Flow rate:60 mL/min; to afford 1-(4-(7-(6-amino-3-(trifluoromethyl)pyridin-2-yl)-6-chloro-2-(((1R,2S,5S)-3-methyl-3-azabicyclo[3.1.0]hexan-2-yl)methoxy)quinazolin-4-yl)piperazin-1-yl)prop-2-en-1-one (15.4 mg, 0.026 mmol, 37.8% yield) as a white solid.

Example 78b

LC-MS: (ESI, m/z): 588.2 [M+H]+, 1H NMR (400 MHz, Methanol-$d_4$, ppm) δ 8.11 (s, 1H), 7.82 (d, J=8.9 Hz, 1H), 7.57 (s, 1H), 6.83 (dd, J=10.8, 10.4 Hz, 1H), 6.72 (d, J=8.8 Hz, 1H), 6.29 (dd, J=16.8, 1.6 Hz, 1H), 5.82 (dd, J=10.6, 2 Hz, 1H), 4.72-4.56 (m, 1H), 4.55-4.37 (m, 1H), 4.14-3.68 (m, 8H), 3.29-3.13 (m, 2H), 2.79 (d, J=9.6 Hz, 1H), 2.54 (s, 3H), 1.68-1.52 (m, 2H), 0.83-0.69 (m, 1H), 0.63-0.47 (m, 1H).

Examples 79a and 79b
(R)-1-(4-(7-(6-amino-3-(trifluoromethyl)pyridin-2-yl)-6-chloro-2-((1-(dimethylamino)propan-2-yl)oxy)quinazolin-4-yl)piperazin-1-yl)prop-2-en-1-one and (S)-1-(4-(7-(6-amino-3-(trifluoromethyl)pyridin-2-yl)-6-chloro-2-((1-(dimethylamino)prop an-2-yl)oxy)quinazolin-4-yl)piperazin-1-yl)prop-2-en-1-one
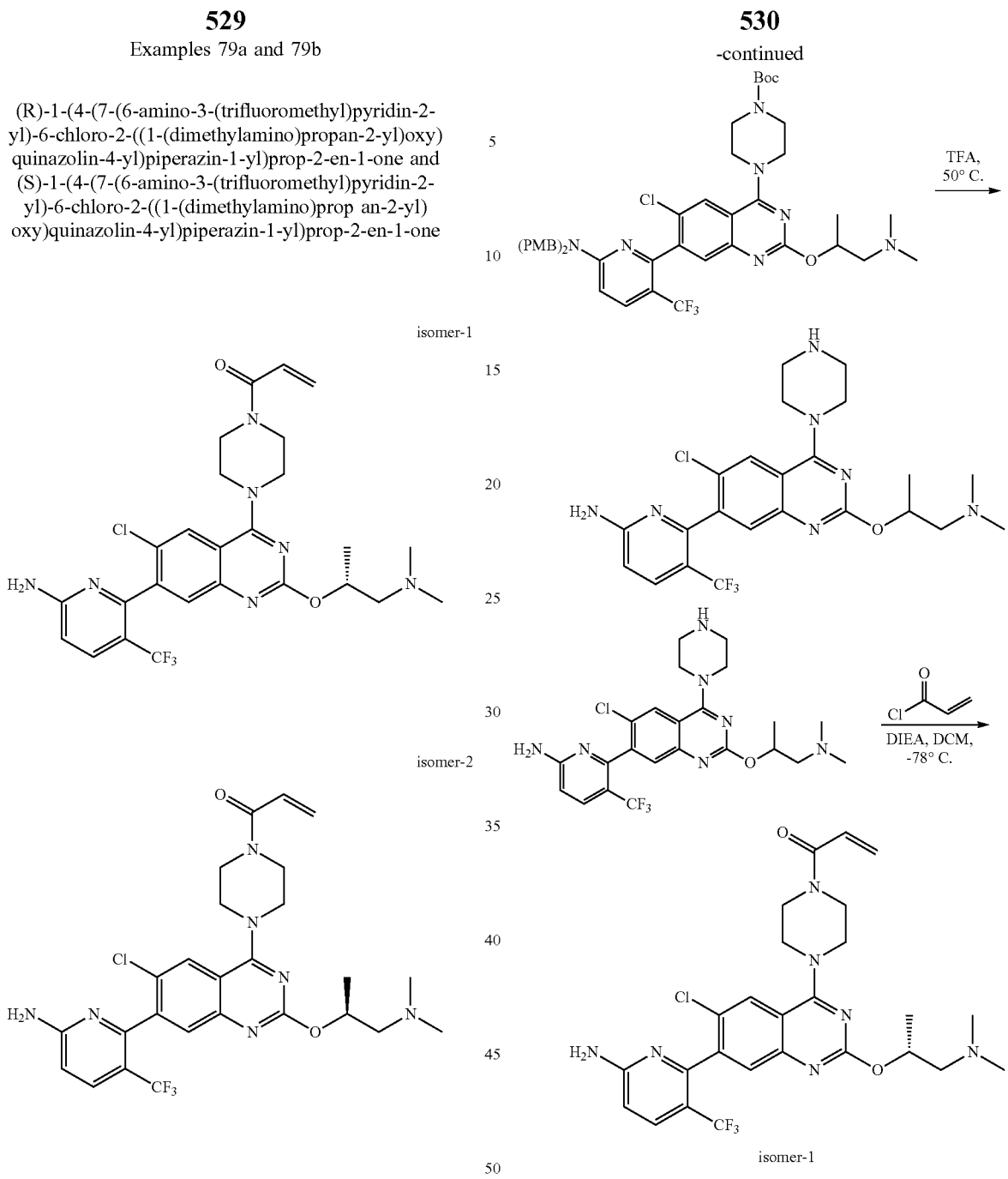
Synthetic Route
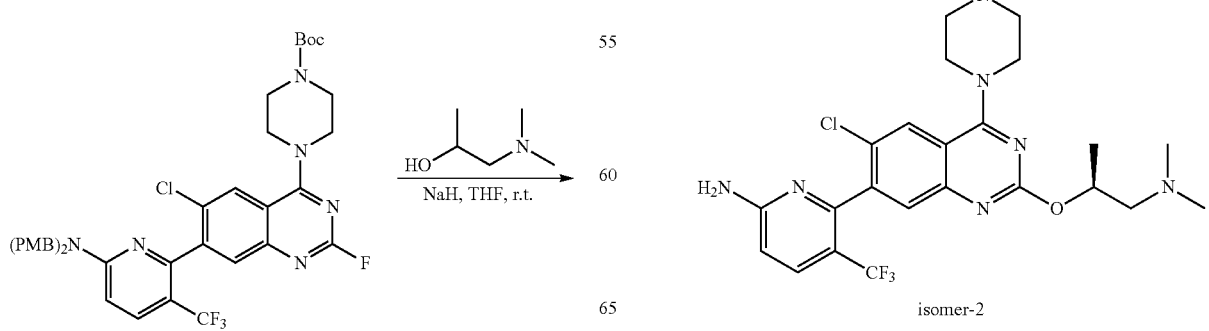

531

Step 1: tert-butyl 4-(7-(6-(bis(4-methoxybenzyl)amino)-3-(trifluoromethyl)pyridin-2-yl)-6-chloro-2-((1-(dimethylamino)propan-2-yl)oxy)quinazolin-4-yl)piperazine-1-carboxylate

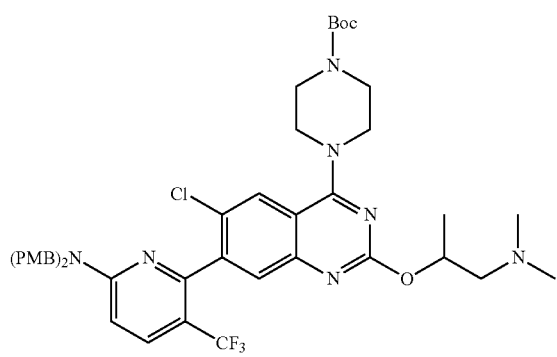

A solution of 1-dimethylamino-2-propanol (40.0 mg, 0.39 mmol) and sodium hydride (10.0 mg, 0.4200 mmol, 60% purity) in tetrahydrofuran (10 mL) was stirred at 25° C. for 15 minutes. Then tert-butyl 4-(7-(6-(bis(4-methoxybenzyl)amino)-3-(trifluoromethyl)pyridin-2-yl)-6-chloro-2-fluoro-quinazolin-4-yl)piperazine-1-carboxylate (Intermediate 3) (200.0 mg, 0.26 mmol) was added and stirred at 25° C. for 2 hours. Upon completion, the reaction was concentrated. The crude product was directly used in the next step without purification. LC-MS: (ESI, m/z): 850.2 [M+H]$^+$

Step 2: 6-(6-chloro-2-((1-(dimethylamino)propan-2-yl)oxy)-4-(piperazin-1-yl)quinazolin-7-yl)-5-(trifluoromethyl)pyridin-2-amine

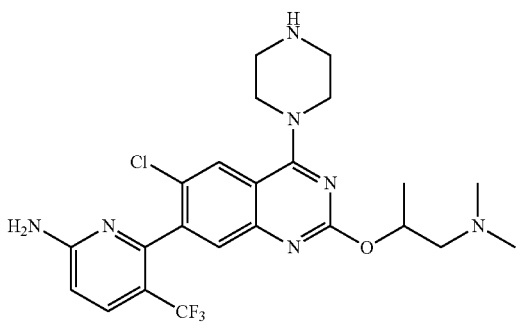 [SMILES: CC(CN(C)C)Oc1nc(N2CCNCC2)c2cc(Cl)c(-c3nc(N)ccc3C(F)(F)F)cc2n1]

A solution of tert-butyl 4-(7-(6-(bis(4-methoxybenzyl)amino)-3-(trifluoromethyl)pyridin-2-yl)-6-chloro-2-((1-(dimethylamino)propan-2-yl)oxy)quinazolin-4-yl)piperazine-1-carboxylate (243.0 mg, 0.29 mmol) in 2,2,2-trifluoroacetic acid (10 mL) was stirred at 50° C. for 2 hours. Upon completion, the reaction was concentrated under vacuum and the resulting product was directly used in the next step. LC-MS: (ESI, m/z): 510.2 [M+H]$^+$

532

Step 3: (R)-1-(4-(7-(6-amino-3-(trifluoromethyl)pyridin-2-yl)-6-chloro-2-((1-(dimethylamino)propan-2-yl)oxy)quinazolin-4-yl)piperazin-1-yl)prop-2-en-1-one and (S)-1-(4-(7-(6-amino-3-(trifluoromethyl)pyridin-2-yl)-6-chloro-2-((1-(dimethylamino)propan-2-yl)oxy)quinazolin-4-yl)piperazin-1-yl)prop-2-en-1-one

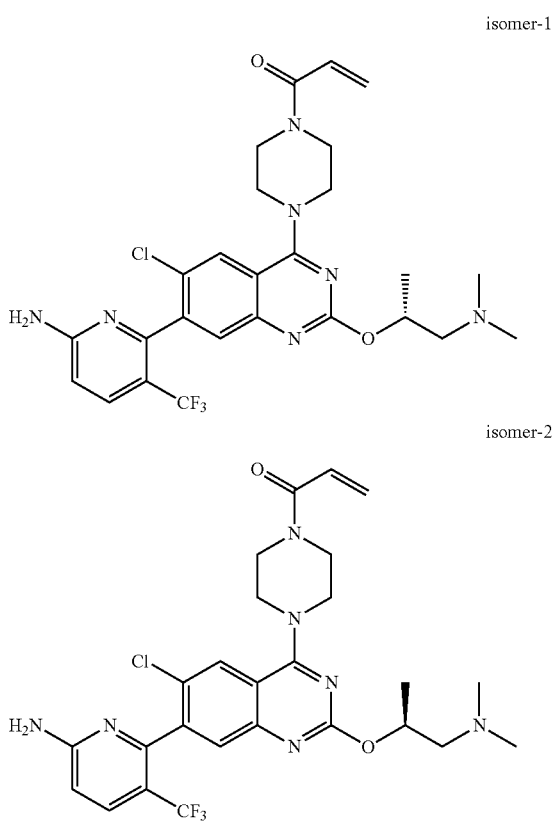

A solution of 6-(6-chloro-2-((1-(dimethylamino)propan-2-yl)oxy)-4-(piperazin-1-yl)quinazolin-7-yl)-5-(trifluoromethyl)pyridin-2-amine (60.0 mg, 0.12 mmol) and N,N-diisopropylethylamine (0.06 mL, 0.35 mmol) in dichloromethane (5 mL) was stirred at −78° C. for 5 minutes. Then acryloyl chloride (11.0 mg, 0.12 mmol) was added and stirred at −78° C. for 30 minutes. Upon completion, the reaction was concentrated to get crude product. The crude product was purified by Prep-HPLC-Column: Xselect CSH OBD Column 30*150 mm 5 um, n; Mobile Phase A:Water(0.1% FA), Mobile Phase B:ACN; Flow rate:60 mL/min. The resulting was purified by Chiral-Prep-HPLC-Column: CHIRALPAK IC, 2*25 cm, 5 um; Mobile Phase A:Hex:DCM=3:1(10 mM NH3-MeOH)-HPLC, Mobile Phase B:MeOH-HPLC; Flow rate:18 mL/min to give 1-[4-[7-[6-amino-3-(trifluoromethyl)-2-pyridyl]-6-chloro-2-[(1S)-2-(dimethylamino)-1-methyl-ethoxy]quinazolin-4-yl]piperazin-1-yl]prop-2-en-1-one (8.1 mg, 0.014 mmol, 12.2% yield) as a white solid and 1-[4-[7-[6-amino-3-(trifluoromethyl)-2-pyridyl]-6-chloro-2-[(1R)-2-(dimethylamino)-1-methyl-ethoxy]quinazolin-4-yl]piperazin-1-yl]prop-2-en-1-one (9.5 mg, 0.016 mmol, 14.3% yield) as a white solid.

Example 79a

LC-MS: (ESI, m/z): 564.2 [M+H]$^+$, $^1$H NMR (400 MHz, DMSO, ppm) δ 8.03 (s, 1H), 7.79 (d, J=8.0, 1H), 7.43 (s, 1H), 6.89 (s, 2H), 6.89-6.72 (m, 1H), 6.58 (d, J=12.0, 1H), 6.17 (dd, J=2.4, 16.8 Hz, 1H), 5.74 (dd, J=2.4, 10.4 Hz, 1H), 5.41-5.23 (m, 1H), 3.95-3.62 (m, 8H), 2.60-2.51 (m, 1H), 2.40-2.31 (m, 1H), 2.19 (s, 6H), 1.35-1.20 (m, 3H). Chiral HPLC: CHIRALPAK IC-3 (0.46*5 cm; 3 um); detected at 254 nm; (n-hexane/dichloromethane=3/1)(0.1% diethylamine)/methanol=7/3; flow rate=1.0 mL/min; Retention time: 2.2 min (faster peak).

Example 79b

LC-MS: (ESI, m/z): 564.2 [M+H]$^+$, $^1$H NMR (400 MHz, DMSO, ppm) δ 8.03 (s, 1H), 7.78 (d, J=8.8, 1H), 7.43 (s, 1H), 6.89 (s, 2H), 6.85-6.72 (m, 1H), 6.60 (d, J=8.8, 1H), 6.17 (dd, J=2.4, 16.8 Hz, 1H), 5.74 (dd, J=2.4, 10.4 Hz, 1H), 5.41-5.23 (m, 1H), 3.93-3.65 (m, 8H), 2.64-2.54 (m, 1H), 2.40-2.28 (m, 1H), 2.19 (s, 6H), 1.40-1.29 (m, 3H). Chiral HPLC: CHIRALPAK IC-3 (0.46*5 cm; 3 um); detected at 254 nm; (n-hexane/dichloromethane=3/1)(0.1% diethylamine)/methanol=7/3; flow rate=1.0 mL/min; Retention time: 3.0 min (slower peak).

Example 80

1-(4-(7-(6-amino-3-(trifluoromethyl)pyridin-2-yl)-6-chloro-2-((5-(methoxymethyl)-1-methylpyrrolidin-2-yl)methoxy)quinazolin-4-yl)piperazin-1-yl)prop-2-en-1-one

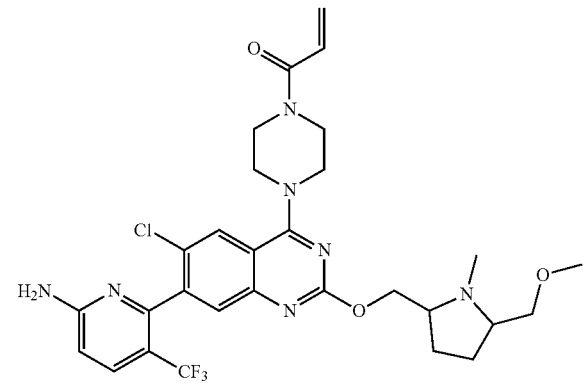 [SMILES: C=CC(=O)N1CCN(c2nc(OCC3CCC(COC)N3C)nc3cc(-c4nc(N)ccc4C(F)(F)F)c(Cl)cc23)CC1]

Synthetic Route

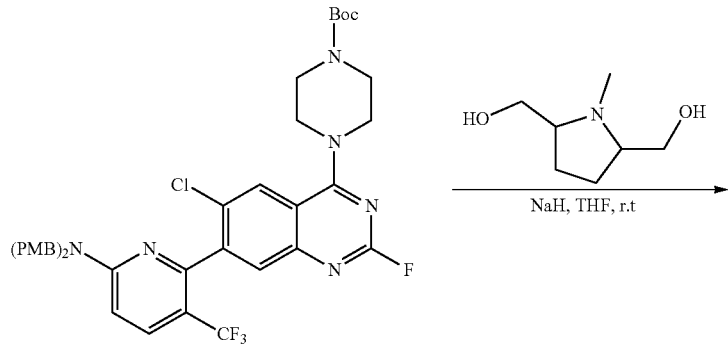

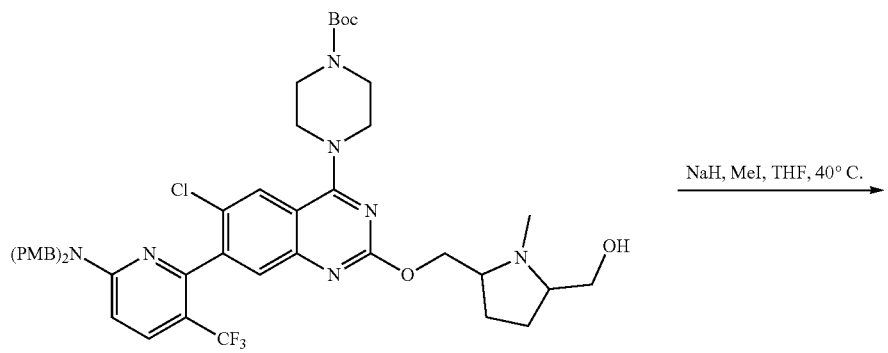

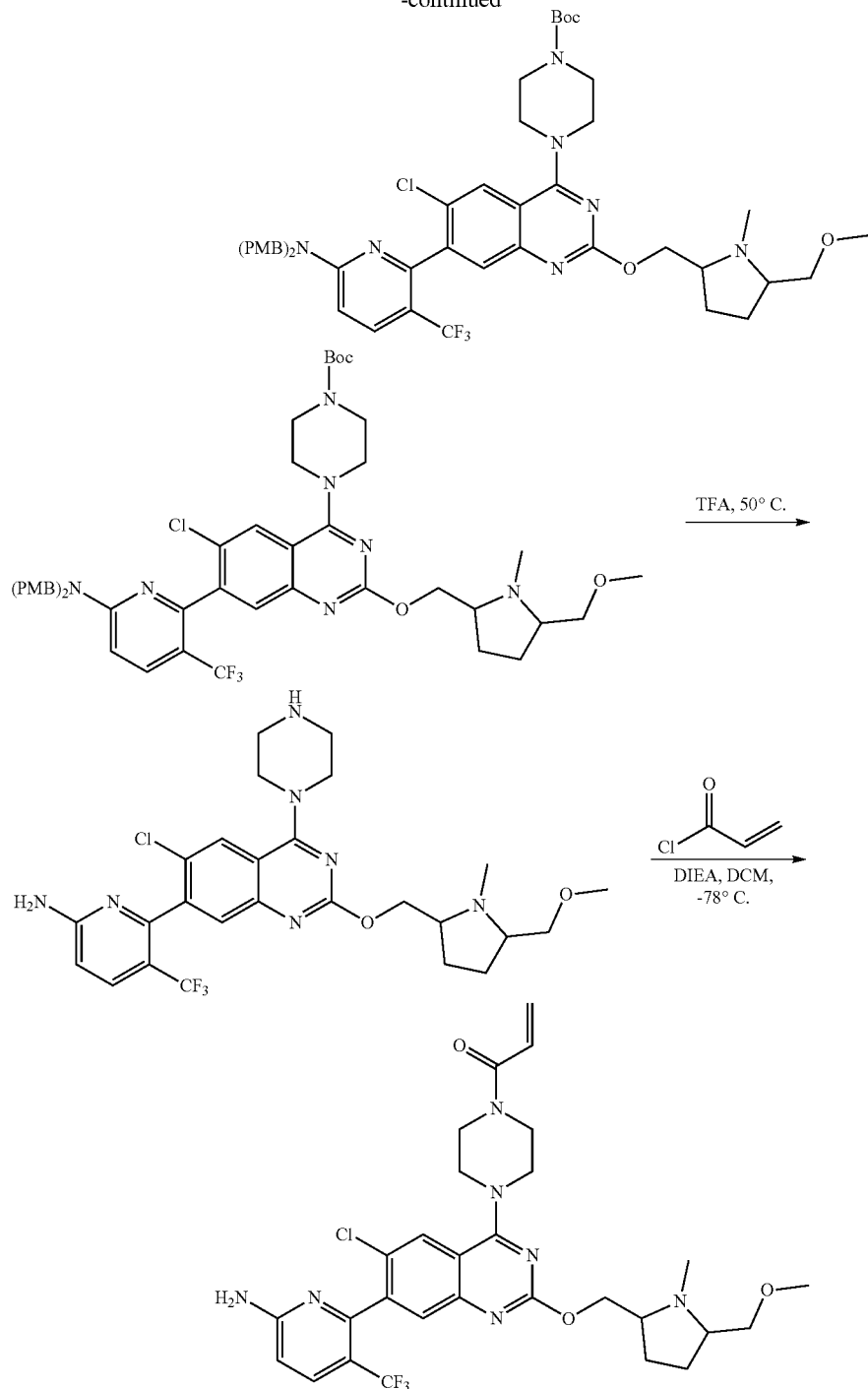

Step 1: (1-methylpyrrolidine-2,5-diyl)dimethanol

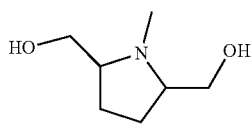

A solution of tert-butyl 2,5-bis(hydroxymethyl)pyrrolidine-1-carboxylate (1500.0 mg, 6.49 mmol) and lithium aluminum hydride (369.0 mg, 9.72 mmol) in tetrahydrofuran (60 mL) was stirred at 25° C. for 8 hours. Upon completion, the reaction was concentrated. The residue was purified by flash chromatography on silica gel eluting with methanol/dichloromethane (1:4) to afford (1-methylpyrrolidine-2,5-diyl)dimethanol (500 mg, 3.44 mmol, 53.1% yield) as a colorless oil. LC-MS: (ESI, m/z): 146.2 [M+H]$^+$ Step 2: tert-butyl 4-(7-(6-(bis(4-methoxybenzyl)amino)-3-(trifluoromethyl)pyridin-2-yl)-6-chloro-2-((5-(hydroxymethyl)-1-methylpyrrolidin-2-yl)methoxy)quinazolin-4-yl)piperazine-1-carboxylate

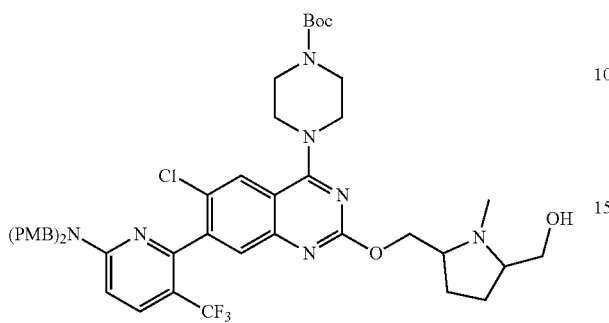

A solution of (1-methylpyrrolidine-2,5-diyl)dimethanol (76.0 mg, 0.52 mmol) and sodium hydride (40.0 mg, 1 mmol) in tetrahydrofuran (20 mL) was stirred at 25° C. for 10 minutes. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (200.0 mg, 0.26 mmol) was added and stirred at 25° C. for 2 hours. Upon completion, the reaction was quenched with water concentrated. The residue was purified by flash chromatography on silica gel eluting with methanol/dichloromethane (5:95) to afford tert-butyl 4-(7-(6-(bis(4-methoxybenzyl)amino)-3-(trifluoromethyl)pyridin-2-yl)-6-chloro-2-((5-(hydroxymethyl)-1-methylpyrrolidin-2-yl)methoxy)quinazolin-4-yl)piperazine-1-carboxylate (120 mg, 0.13 mmol, 51.4% yield) as a yellow solid. LC-MS: (ESI, m/z): 892.4 [M+H]$^+$.

Step 3: tert-butyl 4-(7-(6-(bis(4-methoxybenzyl)amino)-3-(trifluoromethyl)pyridin-2-yl)-6-chloro-2-((5-(methoxymethyl)-1-methylpyrrolidin-2-yl)methoxy)quinazolin-4-yl)piperazine-1-carboxylate

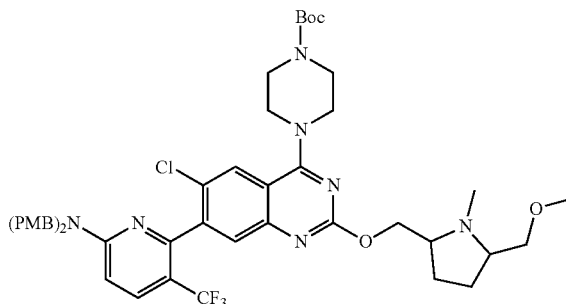

A solution of tert-butyl 4-(7-(6-(bis(4-methoxybenzyl)amino)-3-(trifluoromethyl)pyridin-2-yl)-6-chloro-2-((5-(hydroxymethyl)-1-methylpyrrolidin-2-yl)methoxy)quinazolin-4-yl)piperazine-1-carboxylate (100.0 mg, 0.11 mmol) and sodium hydride (9.0 mg, 0.23 mmol) in tetrahydrofuran (10 mL) was stirred at 40° C. for 5 minutes. Then iodomethane (32.0 mg, 0.23 mmol) was added and stirred at 40° C. for 2 hours. Upon completion, the reaction was concentrated and the residue was purified by flash chromatography on C18 gel eluting with acetonitrile/water (97:3) to afford tert-butyl 4-(7-(6-(bis(4-methoxybenzyl)amino)-3-(trifluoromethyl)pyridin-2-yl)-6-chloro-2-((5-(methoxymethyl)-1-methylpyrrolidin-2-yl)methoxy)quinazolin-4-yl)piperazine-1-carboxylate (50 mg, 0.055 mmol, 49.2% yield) as a yellow solid. LC-MS: (ESI, m/z): 906.4 [M+H]$^+$.

Step 4: 6-(6-chloro-2-((5-(methoxymethyl)-1-methylpyrrolidin-2-yl)methoxy)-4-(piperazin-1-yl)quinazolin-7-yl)-5-(trifluoromethyl)pyridin-2-amine

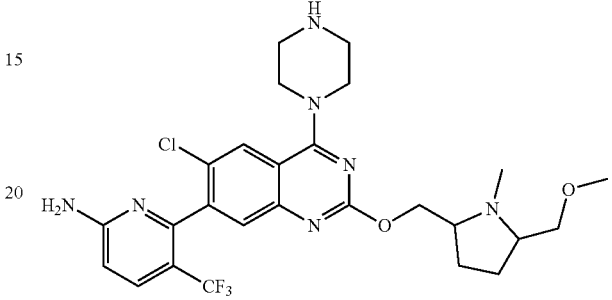

A solution of tert-butyl 4-(7-(6-(bis(4-methoxybenzyl)amino)-3-(trifluoromethyl)pyridin-2-yl)-6-chloro-2-((5-(methoxymethyl)-1-methylpyrrolidin-2-yl)methoxy)quinazolin-4-yl)piperazine-1-carboxylate (10.0 mg, 0.01 mmol) in 2,2,2-trifluoroacetic acid (0.8 mL) was stirred at 50° C. for 2 hours. Upon completion, the reaction was concentrated and crude product was directly used in the next. LC-MS: (ESI, m/z): 566.3 [M+H]$^+$ Step 5: 1-(4-(7-(6-amino-3-(trifluoromethyl)pyridin-2-yl)-6-chloro-2-((5-(methoxymethyl)-1-methylpyrrolidin-2-yl)methoxy)quinazolin-4-yl)piperazin-1-yl)prop-2-en-1-one

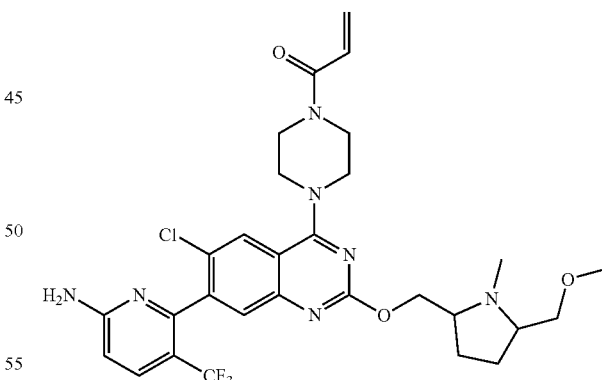

A solution of 6-(6-chloro-2-((5-(methoxymethyl)-1-methylpyrrolidin-2-yl)methoxy)-4-(piperazin-1-yl)quinazolin-7-yl)-5-(trifluoromethyl)pyridin-2-amine (100.0 mg, 0.17 mmol) and N,N-diisopropylethylamine (0.06 mL, 0.33 mmol) in dichloromethane (10 mL) was stirred at −78° C. for 5 minutes. Then acryloyl chloride (15.0 mg, 0.17 mmol) was added and stirred at −78° C. for 30 minutes. Upon completion, the reaction was quenched with water and concentrate. The resulting residue was purified by flash chromatography on C18 gel eluting with acetonitrile/water (95:5) to afford crude. The crude product was purified by Prep-HPLC-Column: XBridge Prep OBD C18 Column, 30×150 mm 5 um; Mobile Phase A:Water(10 mmol/L $NH_4HCO_3$), Mobile Phase B:ACN; Flow rate:60 mL/min to afford 1-(4-(7-(6-amino-3-(trifluoromethyl)pyridin-2-yl)-6-chloro-2-((5-(methoxymethyl)-1-methylpyrrolidin-2-yl)methoxy)quinazolin-4-yl)piperazin-1-yl)prop-2-en-1-one formate (34.4 mg, 0.051 mmol, 30.2% yield) as a white solid.

Example 80

LC-MS: (ESI, m/z): 620.4 [M+H]$^+$, $^1$H NMR (300 MHz, MeOD, ppm) δ 8.09 (s, 1H), 7.80 (d, J=8.7 Hz, 1H), 7.54 (s, 1H), 6.82 (dd, J=10.5, 16.8 Hz, 1H), 6.70 (d, J=8.4 Hz, 1H), 6.27 (dd, J=1.8, 16.8 Hz, 1H), 5.80 (dd, J=1.8, 10.5 Hz, 1H), 4.59-4.45 (m, 2H), 4.10-3.89 (m, 10H), 3.54-3.41 (m, 2H), 3.39 (s, 3H), 2.78-2.53 (m, 3H), 2.20-1.87 (m, 2H), 1.83-1.59 (m, 2H).S Examples 81a and 81b 1-((S)-4-((R)-7-(6-amino-4-methyl-3-(trifluoromethyl)pyridin-2-yl)-6,8-difluoro-2-(((2S,4R)-4-fluoro-1-methylpyrrolidin-2-yl)methoxy)quinazolin-4-yl)-3-methylpiperazin-1-yl)prop-2-en-1-one (Example 81a) and 1-((S)-4-((S)-7-(6-amino-4-methyl-3-(trifluoromethyl)pyridin-2-yl)-6,8-difluoro-2-(((2S,4R)-4-fluoro-1-methylpyrrolidin-2-yl)methoxy)quinazolin-4-yl)-3-methylpiperazin-1-yl)prop-2-en-1-one (Example 81b) (2 atropisomers)

Synthetic Route

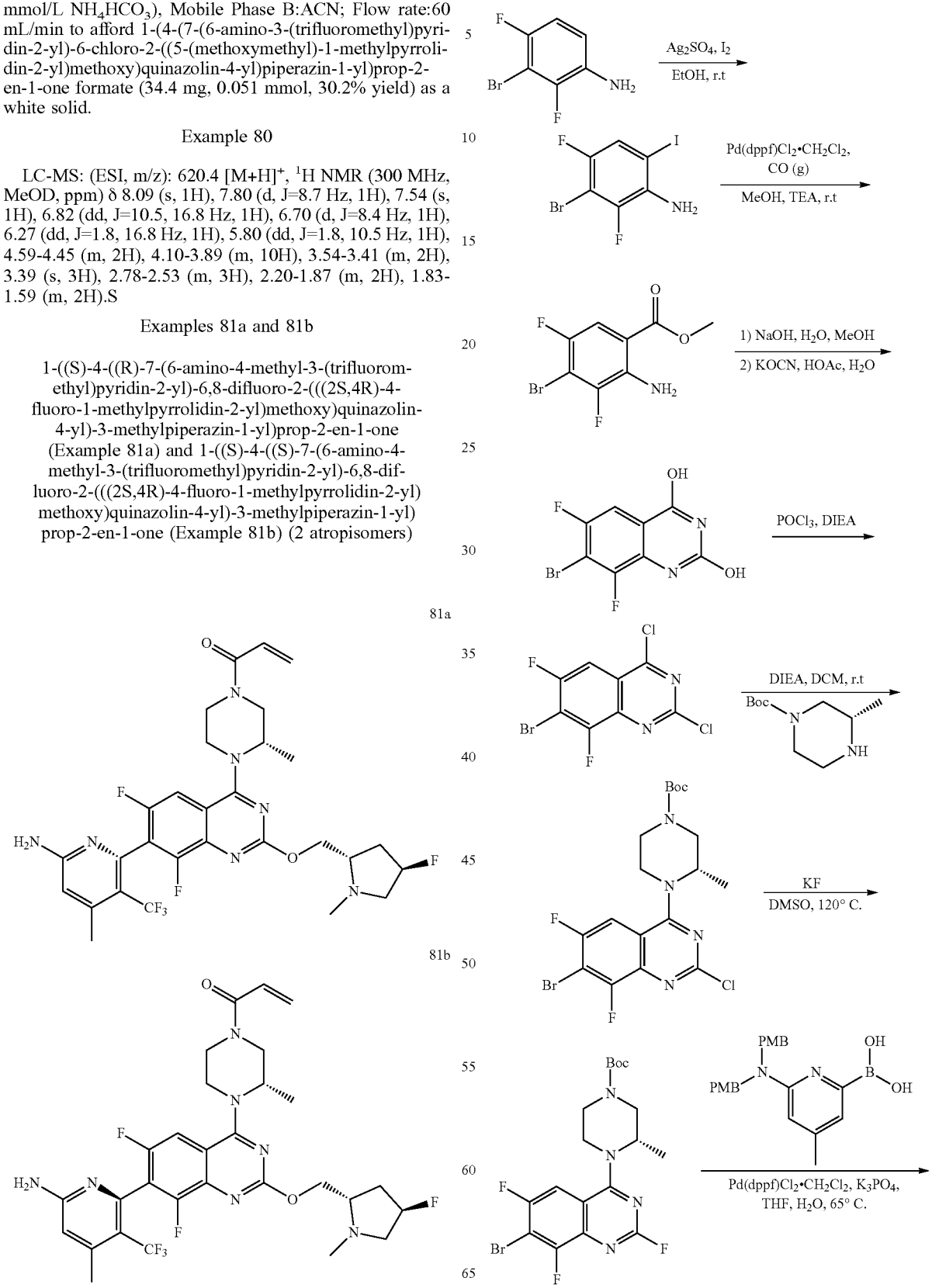

-continued

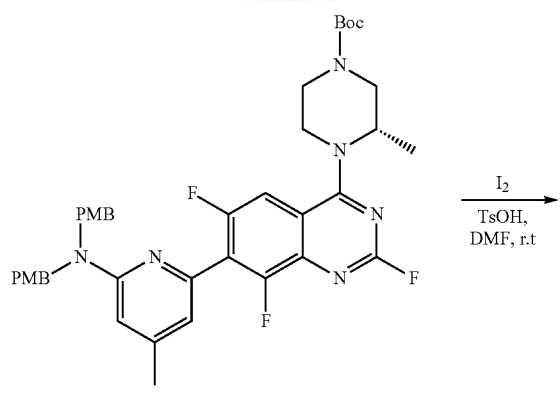

-continued

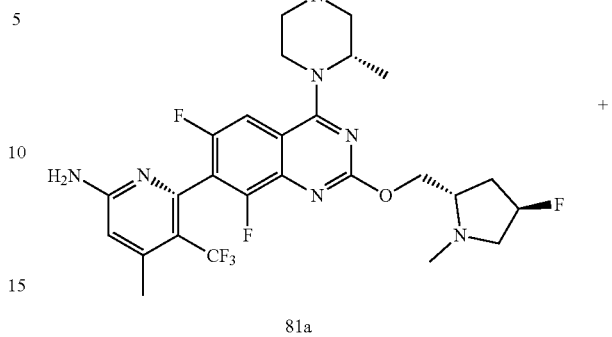

81a

+

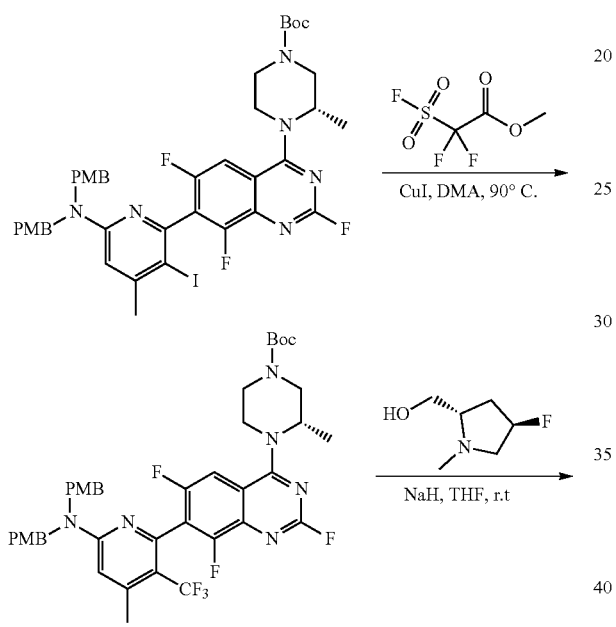

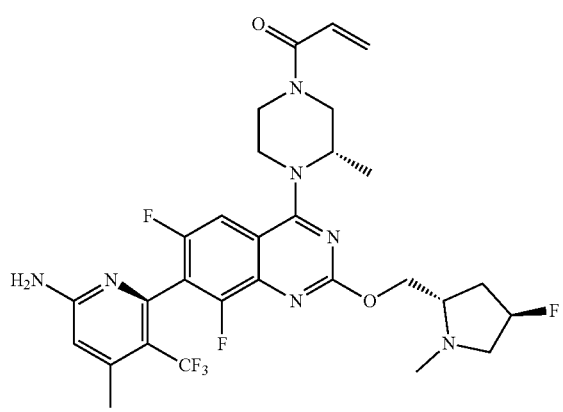

81b

Step 1: 3-bromo-2,4-difluoro-6-iodoaniline

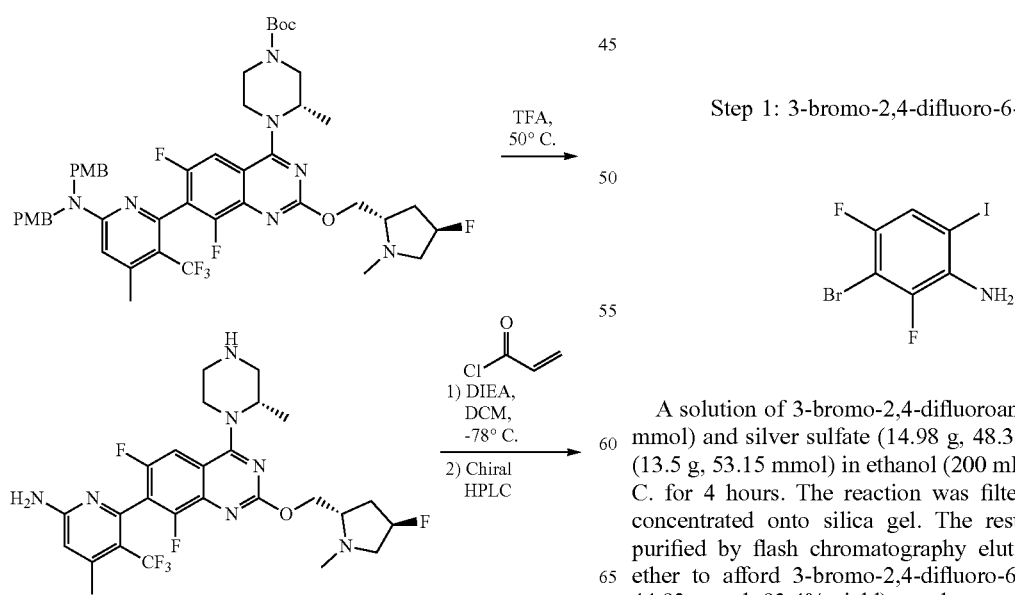

A solution of 3-bromo-2,4-difluoroaniline (10.0 g, 48.08 mmol) and silver sulfate (14.98 g, 48.32 mmol) and iodine (13.5 g, 53.15 mmol) in ethanol (200 mL) was stirred at 20° C. for 4 hours. The reaction was filtered and the filtrate concentrated onto silica gel. The resulting mixture was purified by flash chromatography eluting with petroleum ether to afford 3-bromo-2,4-difluoro-6-iodoaniline (15 g, 44.92 mmol, 93.4% yield) as a brown solid. LC-MS: (ESI, m/z): 333.9 [M+H]$^+$

Step 2: methyl 2-amino-4-bromo-3,5-difluorobenzoate

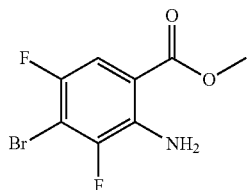

Under carbon monoxide, a solution of 3-bromo-2,4-difluoro-6-iodoaniline (15.0 g, 44.92 mmol) and 1,1'-bis(diphenylphosphino)ferrocene-palladium(II)dichloride dichloromethane complex (3.3 g, 4.51 mmol) in methanol (500 mL) was stirred at 25° C. for 5 minutes. Then triethylamine (21 mL, 314.47 mmol) was added and stirred at 25° C. for 8 hours. The solvent was concentrated and the residue was purified by flash chromatography on silica gel eluting with petroleum ether/ethyl acetate (3/97) to afford methyl 2-amino-4-bromo-3,5-difluoro-benzoate (8.6 g, 32.3 mmol) as a light yellow solid. LC-MS: (ESI, m/z): 266.0 [M+H]$^+$

Step 3: 7-bromo-6,8-difluoroquinazoline-2,4-diol

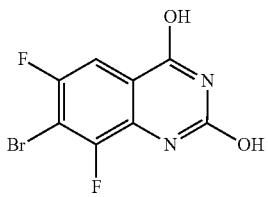 [SMILES: Oc1nc(O)c2cc(F)c(Br)c(F)c2n1]

A solution of methyl 2-amino-4-bromo-3,5-difluoro-benzoate (15.0 g, 56.4 mmol) and NaOH (4.5 g, 112.8 mmol) in water (300 mL) and methanol (300 mL) was stirred at 25° C. for 3 hours. After methyl 2-amino-4-bromo-3,5-difluorobenzoate was disappeared, the reaction system was washed with diethyl ether. Then the pH of solution was adjusted to 4 with HOAc (30 mL, 56.4 mmol). To the resulting solution KOCN (11.4 g, 140.53 mmol) was added and stirred at 40° C. for 3 hours. This operation was repeated three times until most of the intermediate was formed on LCMS. Then NaOH (90 g, 2256 mmol) was added and stirred at room temperature for 2 hours. After completion, the pH of the reaction system was adjusted to 4 with concentrated hydrochloric acid. The solids were collected after filtration and washed with water to afford 7-bromo-6,8-difluoroquinazoline-2,4-diol (5 g, 18.049 mmol, 32% yield) as a red solid. LC-MS: (ESI, m/z): 276.9 [M+H]$^+$

Step 4: 7-bromo-2,4-dichloro-6,8-difluoroquinazoline

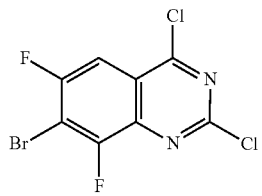

A solution of 7-bromo-6,8-difluoro-quinazoline-2,4-diol (5.0 g, 18.05 mmol) in POCl$_3$ (150 mL) was stirred at 120° C. for 5 minutes. Then N,N-diisopropylethylamine (46.7 g, 361.0 mmol) was added and stirred at 120° C. for 3 hours. After completion, the solvent was concentrated under vacuum to afford 7-bromo-2,4-dichloro-6,8-difluoro-quinazoline (4 g, yellow oil, crude) which was used for next step without purification. LC-MS: (ESI, m/z): 312.9 [M+H]$^+$

Step 5: tert-butyl (S)-4-(7-bromo-2-chloro-6,8-difluoroquinazolin-4-yl)-3-methylpiperazine-1-carboxylate

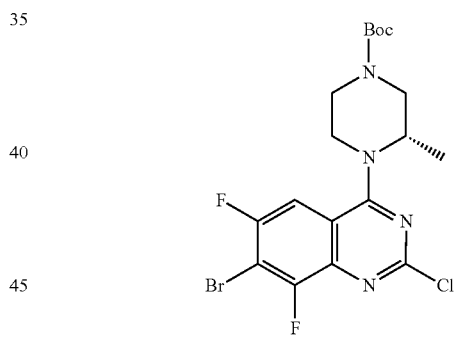

To a solution of 7-bromo-2,4-dichloro-6,8-difluoro-quinazoline (4 g, crude) in dichloromethane (120 mL) was added N,N-diisopropylethylamine (10 mL), the resulting solution was stirred at 20° C. for 5 minutes, then tert-butyl (S)-3-methylpiperazine-1-carboxylate (5.96 g, 29.8 mmol) was added and the reaction was stirred at 20° C. for 5 hours. After completion, the resulting solution was washed with brine. The organic layer was dried over anhydrous sodium sulfate and concentrated. The residue was purified by flash chromatography on silica gel eluting with petroleum ether/ ethyl acetate (1/4) to afford tert-butyl (S)-4-(7-bromo-2-chloro-6,8-difluoroquinazolin-4-yl)-3-methylpiperazine-1-carboxylate (4.6 g, 9.6 mmol, 65% yield) as a yellow solid. LC-MS: (ESI, m/z): 477.0 [M+H]$^+$ Step 6: tert-butyl (S)-4-(7-bromo-2,6,8-trifluoroquinazolin-4-yl)-3-methylpiperazine-1-carboxylate

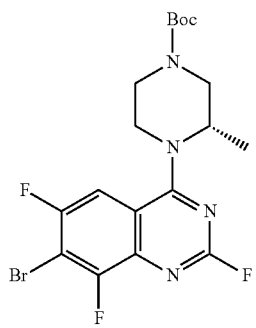

A mixture of tert-butyl (S)-4-(7-bromo-2-chloro-6,8-difluoroquinazolin-4-yl)-3-methylpiperazine-1-carboxylate (1.0 g, 2.1 mmol) and potassium fluoride (2.5 g, 43.0 mmol) in DMSO (25 mL) was stirred at 120° C. for 2 hours under nitrogen. The reaction was filtered, the the filtrate was diluted with ethyl acetate, washed with brine, dried, and concentrated. The residue was purified by flash chromatography on silica gel eluting with petroleum ether/ethyl acetate (10/1) to afford tert-butyl (S)-4-(7-bromo-2,6,8-trifluoroquinazolin-4-yl)-3-methylpiperazine-1-carboxylate (600 mg, 1.3 mmol, 62.1% yield) as a white solid. LC-MS: (ESI, m/z): 461.1 [M+H]+

Step 7: tert-butyl (S)-4-(7-(6-(bis(4-methoxybenzyl)amino)-4-methylpyridin-2-yl)-2,6,8-trifluoroquinazolin-4-yl)-3-methylpiperazine-1-carboxylate

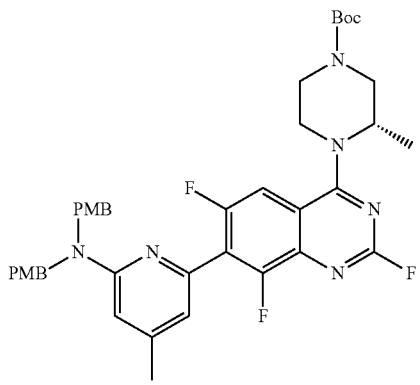

A solution of tert-butyl (S)-4-(7-bromo-2,6,8-trifluoroquinazolin-4-yl)-3-methylpiperazine-1-carboxylate (500.0 mg, 1.08 mmol), (6-(bis(4-methoxybenzyl)amino)-4-methylpyridin-2-yl)boronic acid (850.0 mg, 2.17 mmol), 1,1'-bis(diphenylphosphino)ferrocene-Palladium(II)dichloride dichloromethane complex (90.0 mg, 0.11 mmol), in tetrahydrofuran (30 mL) and water (6 mL) was added potassium phosphate (460.0 mg, 2.17 mmol) at 65° C. under nitrogen. The resulting solution was stirred at 65° C. for 3 hours. The reaction was concentrated and the residue was purified by flash chromatography on silica gel eluting with petroleum ether/ethyl acetate (9/1) to afford tert-butyl (S)-4-(7-(6-(bis(4-methoxybenzyl)amino)-4-methylpyridin-2-yl)-2,6,8-trifluoroquinazolin-4-yl)-3-methylpiperazine-1-carboxylate (650 mg, 0.89 mmol, 82.3% yield) as a yellow solid. LC-MS: (ESI, m/z): 729.3 [M+H]+.

Step 8: tert-butyl (3S)-4-(7-(6-(bis(4-methoxybenzyl)amino)-3-iodo-4-methylpyridin-2-yl)-2,6,8-trifluoroquinazolin-4-yl)-3-methylpiperazine-1-carboxylate

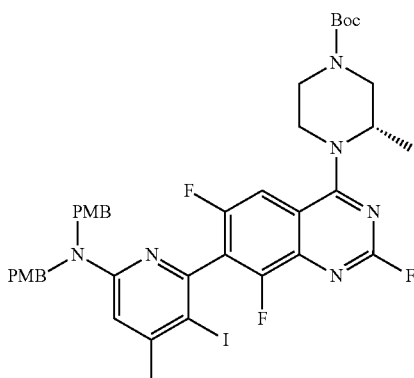

A solution of tert-butyl (S)-4-(7-(6-(bis(4-methoxybenzyl)amino)-4-methylpyridin-2-yl)-2,6,8-trifluoroquinazolin-4-yl)-3-methylpiperazine-1-carboxylate (500.0 mg, 0.69 mmol) and p-toluenesulfonic acid (12.0 mg, 0.07 mmol) in N,N-dimethylformamide (10 mL) was stirred at 25° C. for 5 minutes. Then NIS (309.0 mg, 1.37 mmol) was added and stirred at 25° C. for 3 hours. The reaction was quenched with water and extracted with dichloromethane. Then the organic layers were combined, washed with water, dried over anhydrous sodium sulfate and concentrated under vacuum. The residue was purified by flash chromatography on silica gel eluting with petroleum ether/ethyl acetate (30/1) to afford tert-butyl (3S)-4-(7-(6-(bis(4-methoxybenzyl)amino)-3-iodo-4-methylpyridin-2-yl)-2,6,8-trifluoroquinazolin-4-yl)-3-methylpiperazine-1-carboxylate (200 mg, 0.23 mmol, 34.1% yield) as a yellow solid. LC-MS: (ESI, m/z): 855.2 [M+H]+.

Step 9: tert-butyl (3S)-4-(7-(6-(bis(4-methoxybenzyl)amino)-4-methyl-3-(trifluoromethyl)pyridin-2-yl)-2,6,8-trifluoroquinazolin-4-yl)-3-methylpiperazine-1-carboxylate

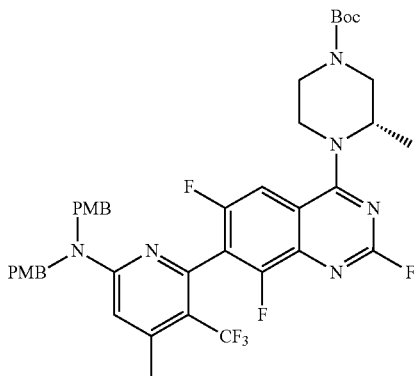

A solution of tert-butyl (3S)-4-(7-(6-(bis(4-methoxybenzyl)amino)-3-iodo-4-methylpyridin-2-yl)-2,6,8-trifluoroquinazolin-4-yl)-3-methylpiperazine-1-carboxylate (500.0 mg, 0.59 mmol) and CuI (450.0 mg, 2.36 mmol) in N,N-dimethylacetamide (20 mL) was stirred at 25° C. for 5 minutes. Then methyl 2,2-difluoro-2-(fluorosulfonyl)acetate (1130.0 mg, 5.88 mmol) was added and stirred at 90° C. for 3 hours under nitrogen. The reaction was concentrated and residue was purified by flash chromatography on silica gel eluting with petroleum ether/ethyl acetate (20/1) to afford tert-butyl (3S)-4-(7-(6-(bis(4-methoxybenzyl)amino)-4-methyl-3-(trifluoromethyl)pyridin-2-yl)-2,6,8-trifluoroquinazolin-4-yl)-3-methylpiperazine-1-carboxylate (430 mg, 0.54 mmol, 92.2% yield) as a yellow solid. LC-MS: (ESI, m/z): 797.3 [M+H]⁺.

Step 10: tert-butyl (3S)-4-(7-(6-(bis(4-methoxybenzyl)amino)-4-methyl-3-(trifluoromethyl)pyridin-2-yl)-6,8-difluoro-2-(((2S,4R)-4-fluoro-1-methylpyrrolidin-2-yl)methoxy)quinazolin-4-yl)-3-methylpiperazine-1-carboxylate

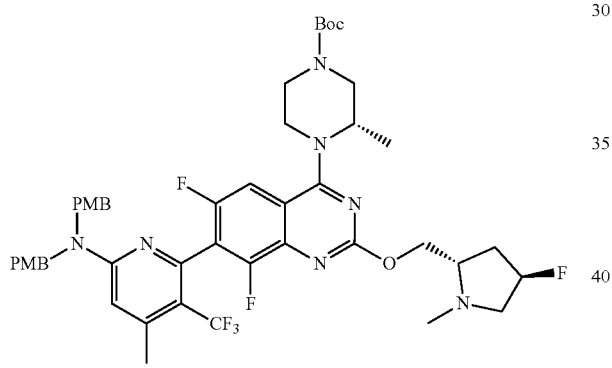

A solution of ((2S,4R)-4-fluoro-1-methylpyrrolidin-2-yl)methanol (168.0 mg, 1.26 mmol) and NaH (101.6 mg, 2.54 mmol, 60% dispersion in mineral oil) in tetrahydrofuran (20 mL) was stirred at 25° C. for 0.5 hours. Then tert-butyl (3S)-4-(7-(6-(bis(4-methoxybenzyl)amino)-4-methyl-3-(trifluoromethyl)pyridin-2-yl)-2,6,8-trifluoroquinazolin-4-yl)-3-methylpiperazine-1-carboxylate (500.0 mg, 0.63 mmol) was added and stirred at 25° C. for 2 hours. The reaction was quenched with water and extracted with dichloromethane. Then the organic layers were combined, washed with water, dried over anhydrous sodium sulfate and concentrated under vacuum. The residue was purified by flash chromatography on silica gel eluting with petroleum ether/ethyl acetate (4/1) to afford tert-butyl (3S)-4-(7-(6-(bis(4-methoxybenzyl)amino)-4-methyl-3-(trifluoromethyl)pyridin-2-yl)-6,8-difluoro-2-(((2S,4R)-4-fluoro-1-methylpyrrolidin-2-yl)methoxy)quinazolin-4-yl)-3-methylpiperazine-1-carboxylate (350 mg, 0.38 mmol, 61.3% yield) as a yellow solid. LC-MS: (ESI, m/z): 910.4 [M+H]⁺

Step 11: 6-(6,8-difluoro-2-(((2S,4R)-4-fluoro-1-methylpyrrolidin-2-yl)methoxy)-4-((S)-2-methylpiperazin-1-yl)quinazolin-7-yl)-4-methyl-5-(trifluoromethyl)pyridin-2-amine

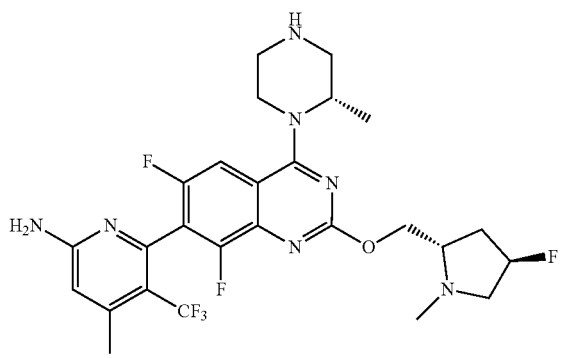 [SMILES: Cc1cc(N)nc(-c2c(F)cc3c(N4CCNC[C@@H]4C)nc(OC[C@@H]4C[C@@H](F)CN4C)nc3c2F)c1C(F)(F)F]

A solution of tert-butyl (3S)-4-(7-(6-(bis(4-methoxybenzyl)amino)-4-methyl-3-(trifluoromethyl)pyridin-2-yl)-6,8-difluoro-2-(((2S,4R)-4-fluoro-1-methylpyrrolidin-2-yl)methoxy)quinazolin-4-yl)-3-methylpiperazine-1-carboxylate (350.0 mg, 0.38 mmol) in trifluoroacetic acid (10 mL) was stirred at 50° C. for 6 hours. After completion, the solvent was concentrated under vacuum to afford 6-(6,8-difluoro-2-(((2S,4R)-4-fluoro-1-methylpyrrolidin-2-yl)methoxy)-4-((S)-2-methylpiperazin-1-yl)quinazolin-7-yl)-4-methyl-5-(trifluoromethyl)pyridin-2-amine (200 mg, crude) which was used for next step without purification. LC-MS: (ESI, m/z): 570.2 [M+H]+

Step 12: 1-((S)-4-((R)-7-(6-amino-4-methyl-3-(trifluoromethyl)pyridin-2-yl)-6,8-difluoro-2-(((2S,4R)-4-fluoro-1-methylpyrrolidin-2-yl)methoxy)quinazolin-4-yl)-3-methylpiperazin-1-yl)prop-2-en-1-one (Example 81a) and 1-((S)-4-((S)-7-(6-amino-4-methyl-3-(trifluoromethyl)pyridin-2-yl)-6,8-difluoro-2-(((2S,4R)-4-fluoro-1-methylpyrrolidin-2-yl)methoxy)quinazolin-4-yl)-3-methylpiperazin-1-yl)prop-2-en-1-one (Example 81b) (2 atropisomers)

81a

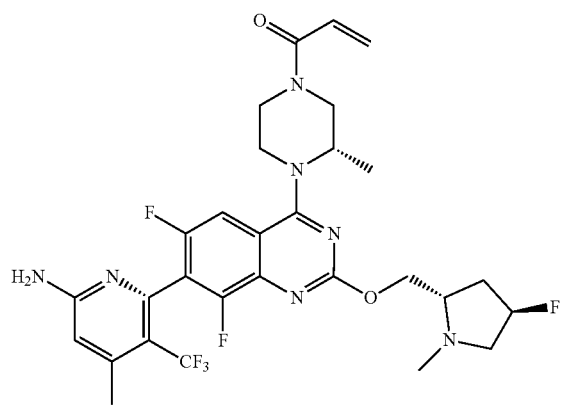

81b

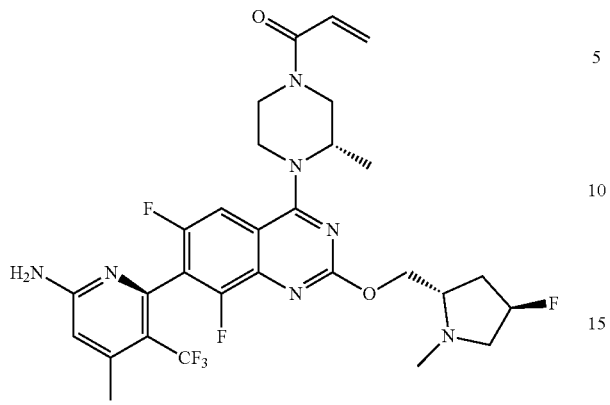

A solution of 6-(6,8-difluoro-2-(((2S,4R)-4-fluoro-1-methylpyrrolidin-2-yl)methoxy)-4-((S)-2-methylpiperazin-1-yl)quinazolin-7-yl)-4-methyl-5-(trifluoromethyl)pyridin-2-amine (400.0 mg, 0.70 mmol) and DIEA (274.0 mg, 2.12 mmol) in dichloromethane (40 mL) was stirred at −78° C. for 5 mins. Then acryloyl chloride (64.0 mg, 0.71 mmol) was added and stirred at −78° C. for 0.5 hours. After completion, the solution was quenched with water and concentrated under vacuum. The residue was purified by successive Prep-HPLC and chiral-HPLC to afford the title compounds. The stereo chemistry of title compounds was assigned based on potency.

Example 81a 1-((S)-4-((R)-7-(6-amino-4-methyl-3-(trifluoromethyl)pyridin-2-yl)-6,8-difluoro-2-(((2S,4R)-4-fluoro-1-methylpyrrolidin-2-yl)methoxy)quinazolin-4-yl)-3-methylpiperazin-1-yl)prop-2-en-1-one (67.7 mg, 0.11 mmol, 15.5% yield, white solid). $^1$H NMR (300 MHz, Methanol-$d_4$, ppm) δ 7.53 (dd, J=9.9, 8.1 Hz, 1H), 6.89-6.72 (m, 1H), 6.60 (s, 1H), 6.31-6.25 (m, 1H), 5.81 (dd, J=18, 10.5 Hz, 1H), 5.35-5.03 (m, 1H), 4.81 (s, 1H), 4.64-4.31 (m, 3H), 4.31-3.94 (m, 2H), 3.82-3.45 (m, 3H), 3.28-3.06 (m, 2H), 2.73-2.62 (m, 1H), 2.55 (s, 3H), 2.45 (d, J=1.5, 3H), 2.32-2.20 (m, 1H), 2.17-1.98 (m, 1H), 1.40 (d, J=6.6 Hz, 3H). LC-MS: (ESI, m/z): 624.3 [M+H]$^+$. Chiral HPLC: Column: CHIRALPAK IE-3, 4.6*50 mm 3 um; Mobile Phase: (Hex:DCM=3:1)(0.1% DEA):EtOH=80:20, Flow rate: 1.0 mL/min; Retention time: 1.836 min (faster peak).

Example 81b 1-((S)-4-((S)-7-(6-amino-4-methyl-3-(trifluoromethyl)pyridin-2-yl)-6,8-difluoro-2-(((2S,4R)-4-fluoro-1-methylpyrrolidin-2-yl)methoxy)quinazolin-4-yl)-3-methylpiperazin-1-yl)prop-2-en-1-one $^1$H NMR (300 MHz, Methanol-$d_4$, ppm) 67.53 (dd, J=9.9, 8.1 Hz, 1H), 6.94-6.71 (m, 1H), 6.60 (s, 1H), 6.38-6.20 (m, 1H), 5.81 (dd, J=18, 10.5 Hz, 1H), 5.45-5.03 (m, 1H), 4.81 (s, 1H), 4.64-4.31 (m, 3H), 4.31-3.94 (m, 2H), 3.82-3.45 (m, 3H), 3.28-3.06 (m, 2H), 2.79-2.60 (m, 1H), 2.55 (s, 3H), 2.45 (d, J=1.5, 3H), 2.39-2.20 (m, 1H), 2.17-1.78 (m, 1H), 1.40 (d, J=6.6 Hz, 3H). LC-MS: (ESI, m/z): 624.3 [M+H]$^+$. Chiral HPLC: Column: CHIRALPAK IE-3, 4.6*50 mm 3 um; Mobile Phase: (Hex:DCM=3:1)(0.1% DEA):EtOH=80:20, Flow rate: 1.0 mL/min; Retention time: 2.322 min (faster peak).

Examples 82a and 82b 1-((S)-4-((R)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)-2-fluoroprop-2-en-1-one (Example 82a) and 1-((S)-4-((S)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)-2-fluoroprop-2-en-1-one (Example 82b)

82a

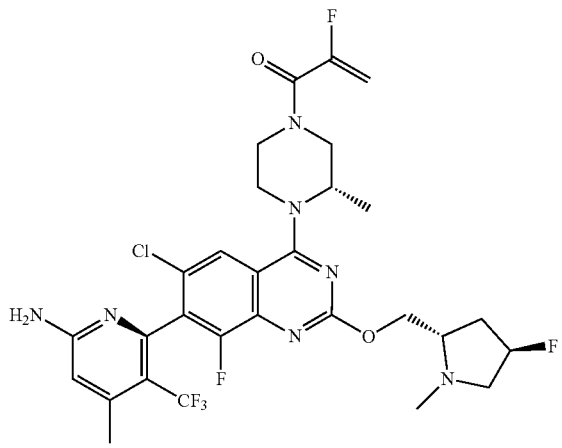

82b

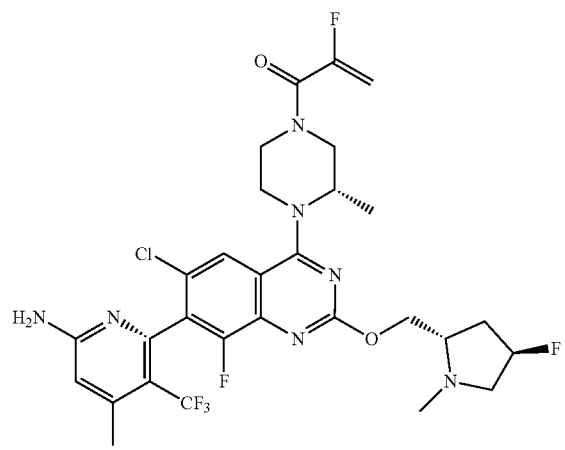

Synthetic Route

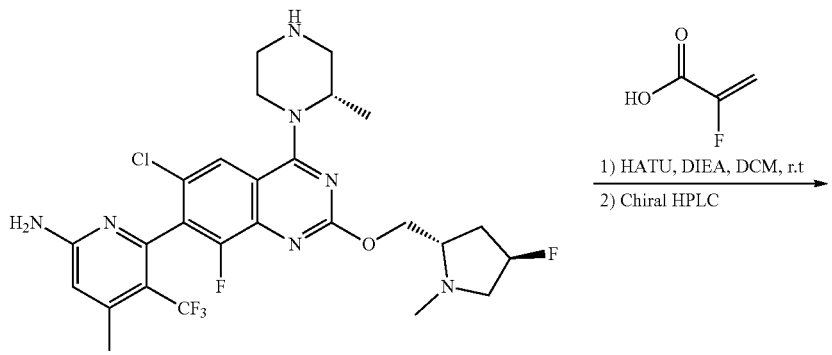

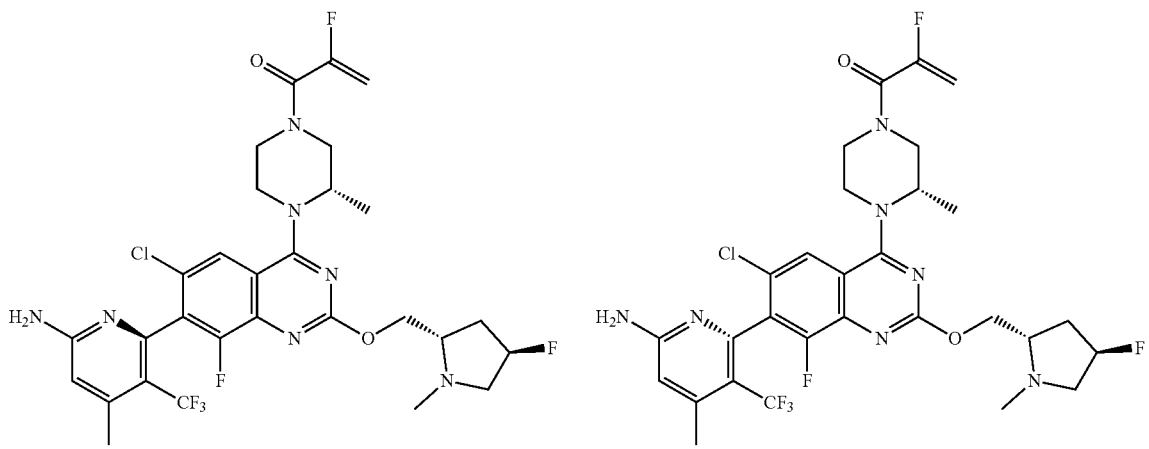

A solution of 6-[6-chloro-8-fluoro-2-[[(2S,4R)-4-fluoro-1-methyl-pyrrolidin-2-yl]methoxy]-4-[(2S)-2-methylpiperazin-1-yl]quinazolin-7-yl]-4-methyl-5-(trifluoromethyl)pyridin-2-amine (produced as an intermediate in Step 2 of Example 69) (0.6 g, 1.02 mmol), 2-fluoroacrylic acid (0.09 g, 1.02 mmol), HATU (0.58 g, 1.54 mmol) and N,N-diisopropylethylamine (397 mg, 3.07 mmol) in dichloromethane (5 mL) and was stirred at r.t. for 2 hours. Upon completion, the reaction mixture was diluted with water and extracted with dichloromethane. Then the organic layer was dried over anhydrous sodium sulfate and concentrated. The crude product was purified by Prep-HPLC and Chiral-HPLC to afford 1-((S)-4-((R)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)-2-fluoroprop-2-en-1-one (55.2 mg, 0.084 mmol, 8.2% yield) and 1-((S)-4-((S)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)-2-fluoroprop-2-en-1-one (42.8 mg, 0.065 mmol, 6.4% yield) as a yellow solid. LCMS (ESI, m/z): 658.3 [M+H]$^+$. Prep-HPLC condition: Column: XBridge Shield RP18 OBD Column, 30*150 mm, 5 um; Mobile Phase A:Water(10 mmol/L NH$_4$HCO$_3$), Mobile Phase B:ACN; Flow rate:60 mL/min. Chiral-HPLC CHIRALPAK IC, 3*25 cm, 5 um; Mobile Phase A:Hex:DCM=3:1(10 mM NH3-MeOH)-HPLC, Mobile Phase B:EtOH-HPLC; Flow rate:2 mL/min.

Example 82a $^1$H NMR (300 MHz, Methanol-d4, ppm) δ 7.82 (s, 1H), 6.60 (s, 1H), 5.42-5.02 (m, 3H), 4.82 (s, 1H), 4.50 (d, J=5.0 Hz, 2H), 4.42-3.93 (m, 3H), 3.86-3.39 (m, 4H), 3.21-3.00 (m, 1H), 2.77-2.51 (s, 4H), 2.51-2.39 (m, 3H), 2.38-1.92 (m, 2H), 1.43 (d, J=6.7 Hz, 3H).

Example 82b $^1$H NMR (300 MHz, Methanol-d4, ppm) δ 7.82 (s, 1H), 6.60 (s, 1H), 5.51-5.00 (m, 3H), 4.82 (s, 1H), 4.50 (d, J=5.0 Hz, 2H), 4.46-3.93 (m, 3H), 3.88-3.39 (m, 4H), 3.26-3.00 (m, 1H), 2.78-2.51 (m, 4H), 2.51-2.40 (m, 3H), 2.40-1.90 (m, 2H), 1.43 (d, J=6.7 Hz, 3H).

Examples 83a, 83b, 83c, and 83d 2-((R)-4-((S)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-1-(2-fluoroacryloyl)piperazin-2-yl)acetonitrile (Example 83a)

2-((S)-4-((S)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-1-(2-fluoroacryloyl)piperazin-2-yl)acetonitrile (Example 83b)

2-((R)-4-((R)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-1-(2-fluoroacryloyl)piperazin-2-yl)acetonitrile (Example 83c); and 2-((S)-4-((R)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-1-(2-fluoroacryloyl)piperazin-2-yl)acetonitrile (Example 83d)

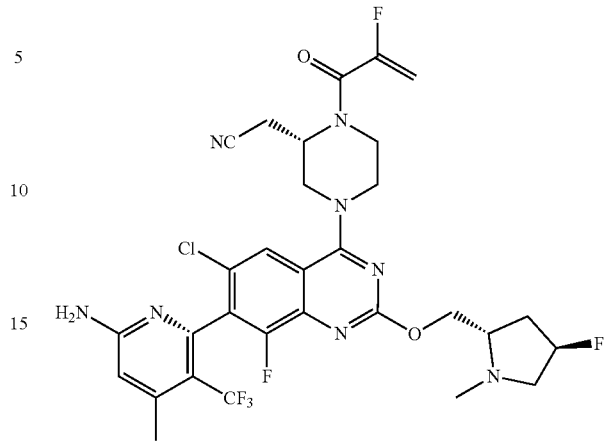

83b

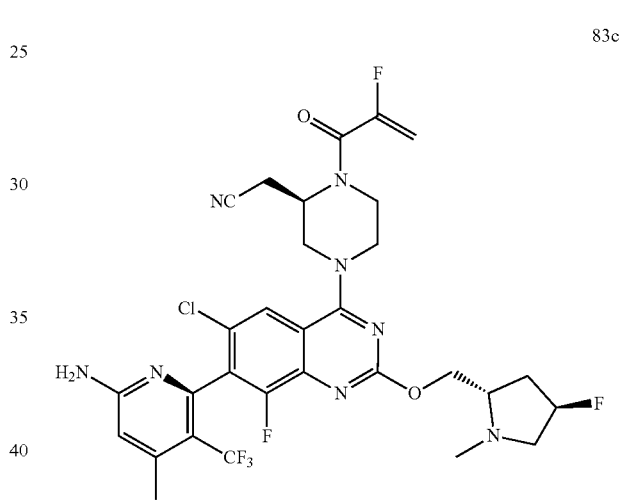

83c

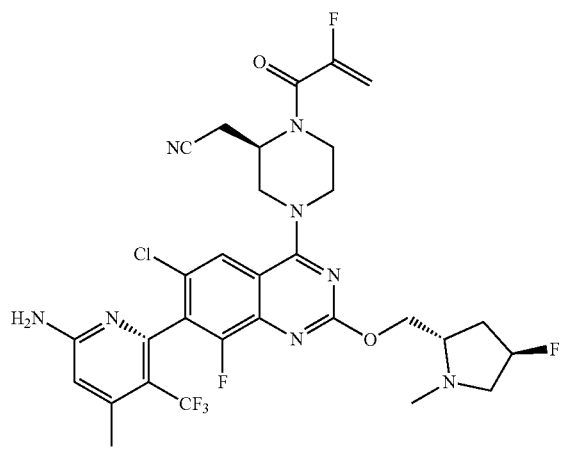

83a

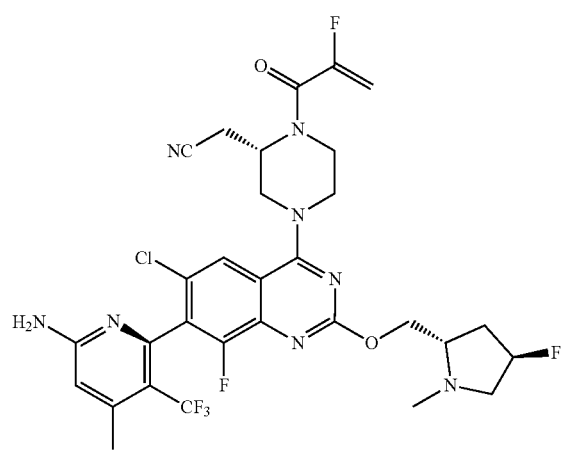

83d

Synthetic Route
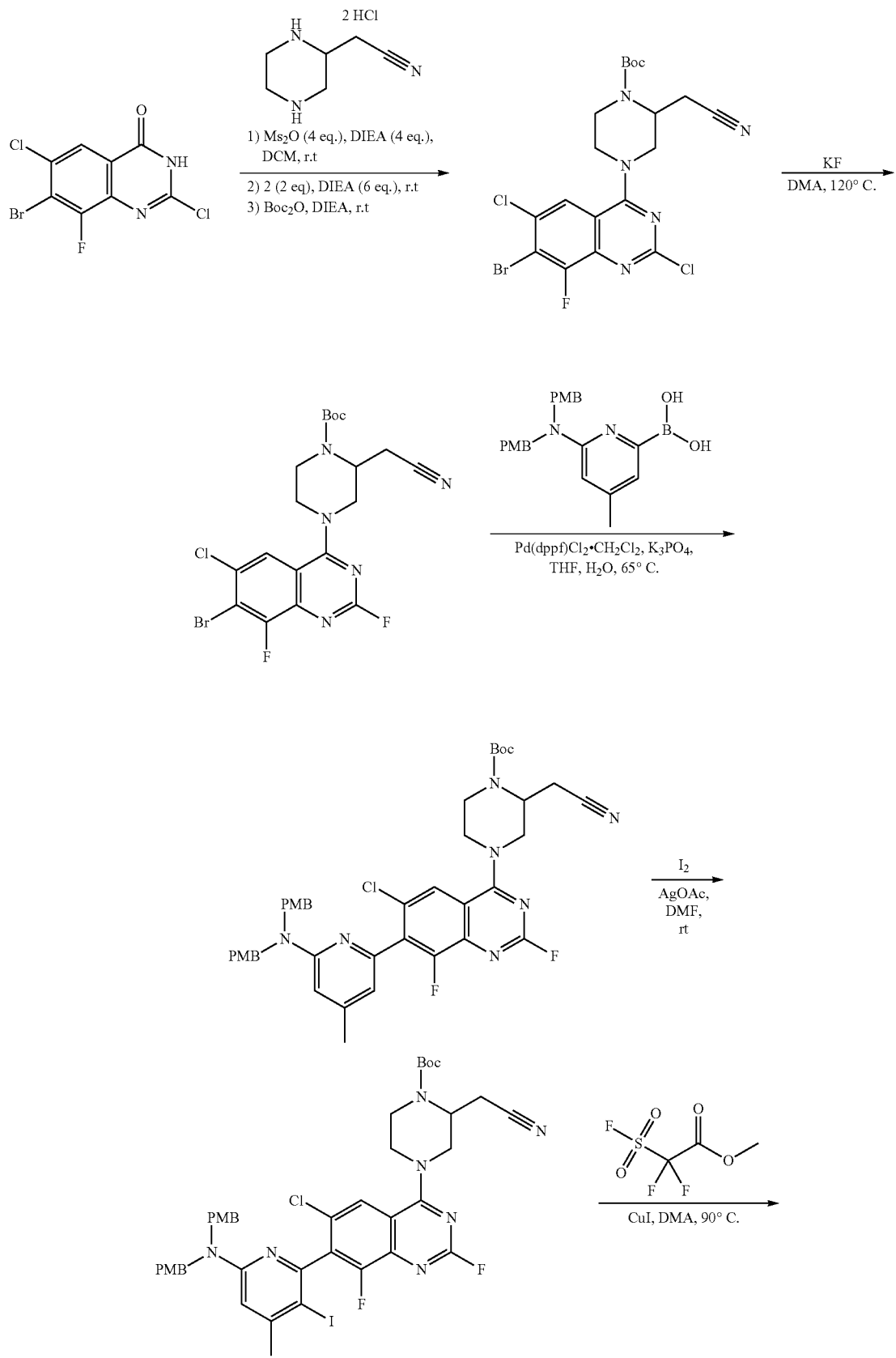

-continued
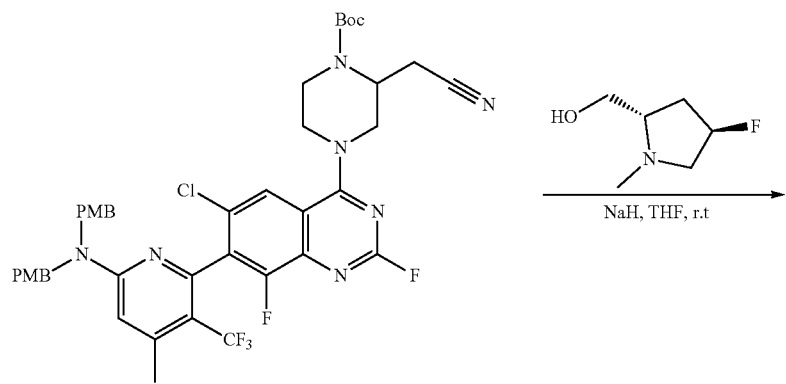
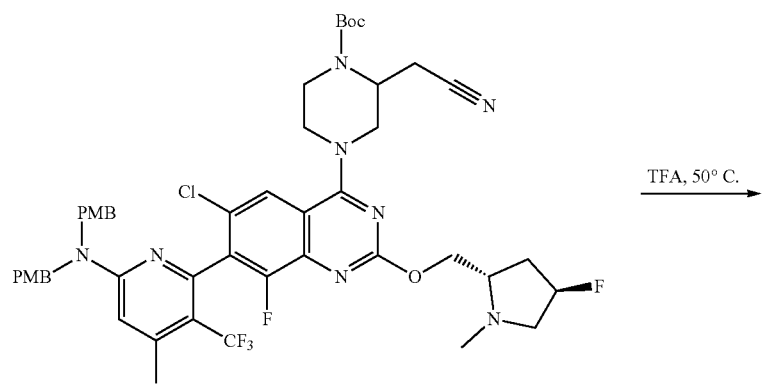
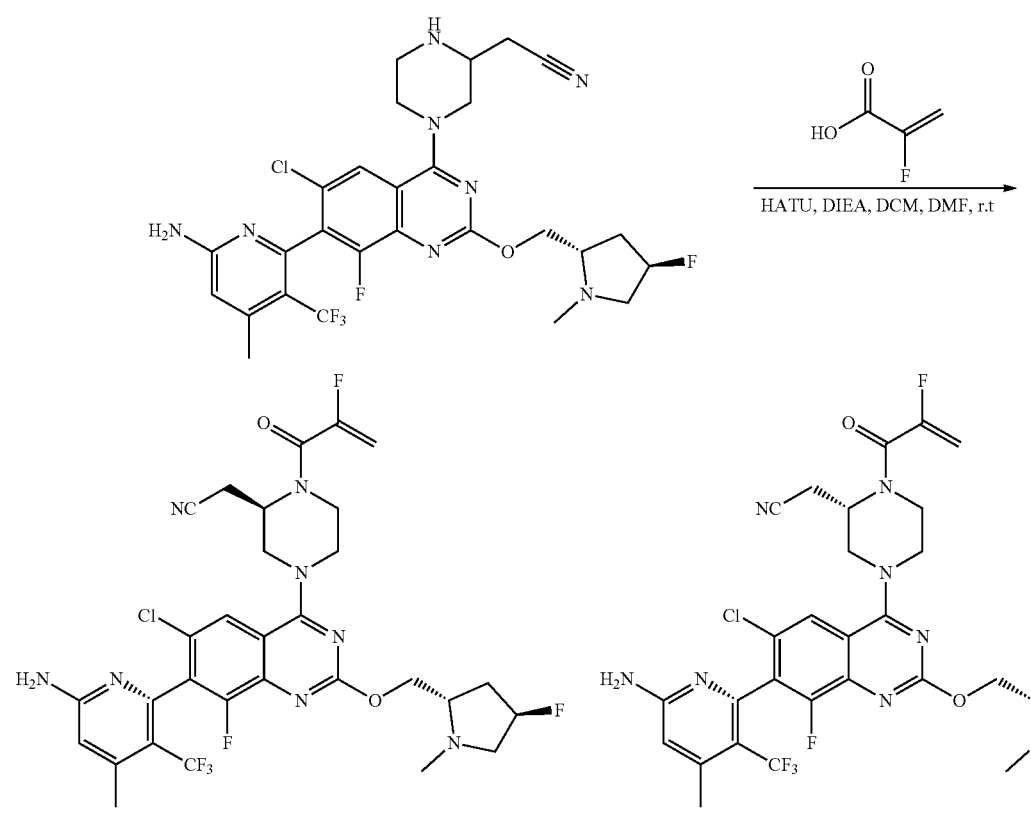
83a
83b

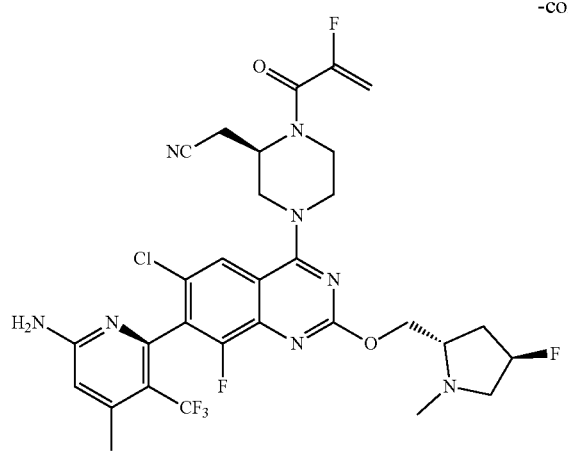

83c

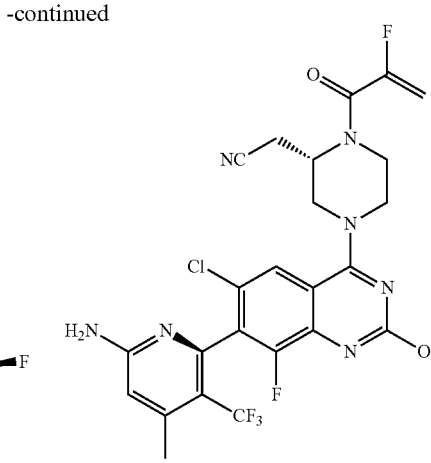

83d

Step 1: tert-butyl 4-(7-bromo-2,6-dichloro-8-fluoro-quinazolin-4-yl)-2-(cyanomethyl)piperazine-1-carboxylate Step 2: tert-butyl 4-(7-bromo-6-chloro-2,8-difluoro-quinazolin-4-yl)-2-(cyanomethyl)piperazine-1-carboxylate

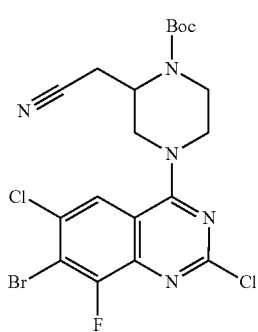 [SMILES: CC(C)(C)OC(=O)N1CCN(c2nc(Cl)nc3c(F)c(Br)c(Cl)cc23)CC1CC#N]

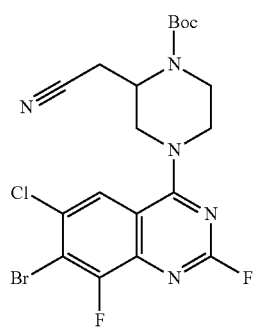 [SMILES: CC(C)(C)OC(=O)N1CCN(c2nc(F)nc3c(F)c(Br)c(Cl)cc23)CC1CC#N]

A solution of 7-bromo-2,6-dichloro-8-fluoroquinazolin-4 (3H)-one (3.9 g, 12.5 mmol) and N,N-diisopropylethylamine (6.5 g, 50.3 mmol) in dichloromethane (80 mL) was stirred at 20° C. for 5 minutes. Methanesulfonic anhydride (8.8 g, 50.3 mmol) was added and the resulting mixture was stirred at 20° C. for 20 minutes. 2-piperazin-2-ylacetonitrile (5.0 g, 40.0 mmol) and N,N-diisopropylethylamine (9.7 g, 75.5 mmol) were then added and the mixture was stirred at 20° C. for an additional 1 hour. Upon complete conversion to the desired product, di-tert-butyldicarbonate (32.7 g, 150 mmol) was added and the mixture was stirred at 20° C. for 2 hours. The reaction was poured into a separatory funnel and was washed with brine. The organic layer was dried over anhydrous sodium sulfate and concentrated. The residue was purified by flash chromatography eluting with petroleum ether/ethyl acetate (1/4) to afford tert-butyl 4-(7-bromo-2,6-dichloro-8-fluoro-quinazolin-4-yl)-2-(cyanomethyl)piperazine-1-carboxylate (4.9 g, 9.4 mmol, 75.5% yield) as a yellow solid. LC-MS: (ESI, m/z): 518.0, 520.0 [M+H]$^+$.

A solution of tert-butyl 4-(7-bromo-2,6-dichloro-8-fluoro-quinazolin-4-yl)-2-(cyanomethyl) piperazine-1-carboxylate (9.7 g, 18.7 mmol) and potassium fluoride (43.7 g, 752.6 mmol) in DMA (200 mL) was stirred at 120° C. for 3 hours. The reaction was filtered, diluted, with ethyl acetate (1 L) and washed with brine (200 mL*5). The organic layer was dried over anhydrous sodium sulfate and concentrated. The residue was purified by flash chromatography on silica gel eluting with petroleum ether/ethyl acetate (1/5) to afford tert-butyl 4-(7-bromo-6-chloro-2,8-difluoro-quinazolin-4-yl)-2-(cyanomethyl)piperazine-1-carboxylate (6.6 g, 13.1 mmol, 70.3% yield) as a yellow solid. LC-MS: (ESI, m/z): 502.0, 504.0 [M+H]$^+$.

Step 3: tert-butyl 4-[7-[6-[bis[(4-methoxyphenyl)methyl]amino]-4-methyl-2-pyridyl]-6-chloro-2,8-difluoro-quinazolin-4-yl]-2-(cyanomethyl)piperazine-1-carboxylate

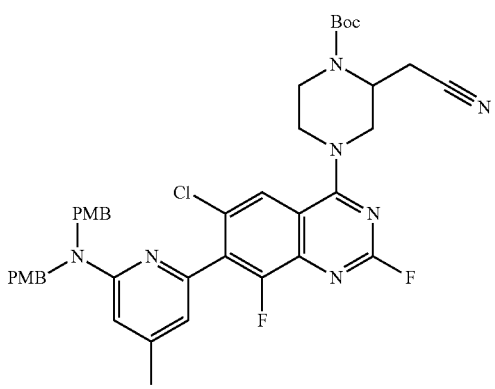

A solution of tert-butyl 4-(7-bromo-6-chloro-2,8-difluoro-quinazolin-4-yl)-2-(cyanomethyl)piperazine-1-carboxylate (5.5 g, 10.9 mmol), [6-[bis[(4-methoxyphenyl)methyl]amino]-4-methyl-2-pyridyl]boronic acid (12.0 g, 30.6 mmol), 1,1'-bis(diphenylphosphino)ferrocene-palladium(II)dichloride dichloromethane complex (1.32 g, 1.8 mmol) and potassium phosphate (5.12 g, 24.1 mmol) in tetrahydrofuran (400 mL) and water (80 mL) was stirred at 65° C. for 2 hours under nitrogen. The reaction mixture was filtered and the filtrate was diluted with dichloromethane (500 mL) and washed with brine (50 mL×5). The organic layer was dried over anhydrous sodium sulfate and concentrated. The residue was purified by flash chromatography on silica gel eluting with petroleum ether/ethyl acetate (1/3) to afford tert-butyl 4-[7-[6-[bis[(4-methoxyphenyl)methyl]amino]-4-methyl-2-pyridyl]-6-chloro-2,8-difluoro-quinazolin-4-yl]-2-(cyanomethyl)piperazine-1-carboxylate (5 g, 6.5 mmol, 59.3% yield) as a yellow solid. LC-MS: (ESI, m/z): 770.3 [M+H]$^+$.

Step 4: tert-butyl 4-[7-[6-[bis[(4-methoxyphenyl)methyl]amino]-3-iodo-4-methyl-2-pyridyl]-6-chloro-2,8-difluoro-quinazolin-4-yl]-2-(cyanomethyl)piperazine-1-carboxylate

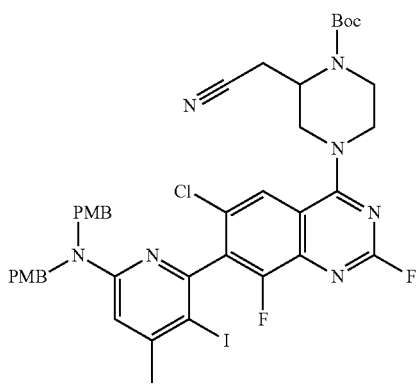

A solution of tert-butyl 4-[7-[6-[bis[(4-methoxyphenyl)methyl]amino]-4-methyl-2-pyridyl]-6-chloro-2,8-difluoro-quinazolin-4-yl]-2-(cyanomethyl)piperazine-1-carboxylate (5.0 g, 6.5 mmol) and silver acetate (2.7 g, 16.3 mmol) and iodine (4.97 g, 19.57 mmol) in N,N-dimethylformamide (50 mL) was stirred at 20° C. for 4 hours. The reaction was filtered. The filtrate was diluted with ethyl acetate (250 mL) and washed with saturated sodium thiosulfate solution (100 mL×5). The organic layer was dried over anhydrous sodium sulfate and concentrated under vacuum. The residue was purified by flash chromatography on silica gel eluting with petroleum ether/ethyl acetate (1/3) to afford tert-butyl 4-[7-[6-[bis[(4-methoxyphenyl)methyl]amino]-3-iodo-4-methyl-2-pyridyl]-6-chloro-2,8-difluoro-quinazolin-4-yl]-2-(cyanomethyl)piperazine-1-carboxylate (4.8 g, 5.4 mmol, 82.5% yield) as a yellow solid. LC-MS: (ESI, m/z): 896.2 [M+H]$^+$.

Step 5: tert-butyl 4-[7-[6-[bis[(4-methoxyphenyl)methyl]amino]-4-methyl-3-(trifluoromethyl)-2-pyridyl]-6-chloro-2,8-difluoro-quinazolin-4-yl]-2-(cyanomethyl)piperazine-1-carboxylate

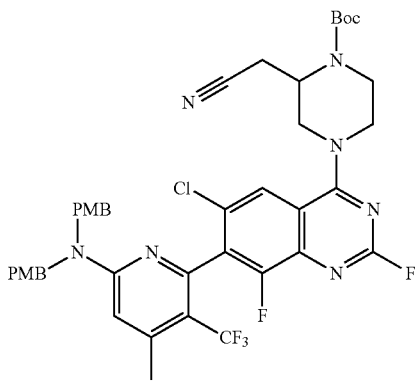

A solution of tert-butyl 4-[7-[6-[bis[(4-methoxyphenyl)methyl]amino]-3-iodo-4-methyl-2-pyridyl]-6-chloro-2,8-difluoro-quinazolin-4-yl]-2-(cyanomethyl)piperazine-1-carboxylate (2.5 g, 2.8 mmol) and methyl 2,2-difluoro-2-(fluorosulfonyl)acetate (13.4 g, 69.8 mmol) and cuprous iodide (5.3 g, 27.9 mmol) in N,N-dimethylacetamide (80 mL) was stirred at 90° C. for 6 hours. The reaction was filtered. The filtrate was diluted with ethyl acetate (400 mL) and washed with brine (100 mL×5). The organic layer was dried over anhydrous sodium sulfate and concentrated. The residue was purified by silica gel flash chromatography eluting with petroleum ether/ethyl acetate (1/3) to afford tert-butyl 4-[7-[6-[bis[(4-methoxyphenyl)methyl]amino]-4-methyl-3-(trifluoromethyl)-2-pyridyl]-6-chloro-2,8-difluoro-quinazolin-4-yl]-2-(cyanomethyl)piperazine-1-carboxylate (2.2 g, 2.6 mmol, 94.1% yield) as a yellow solid. LC-MS: (ESI, m/z): 838.4 [M+H]$^+$.

Step 6: tert-butyl 4-[7-[6-[bis[(4-methoxyphenyl)
methyl]amino]-4-fluoro-3-(trifluoromethyl)-2-
pyridyl]-6-chloro-8-fluoro-2-[[(2S,4R)-4-fluoro-1-
methyl-pyrrolidin-2-yl]methoxy]quinazolin-4-yl]-2-
prop-2-ynyl-piperazine-1-carboxylate

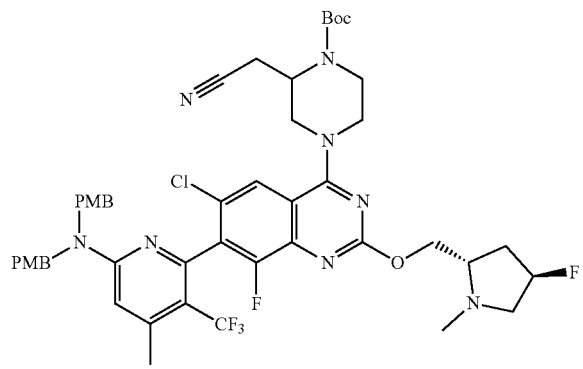

A solution of [(2S,4R)-4-fluoro-1-methyl-pyrrolidin-2-yl] methanol (420.37 mg, 3.16 mmol) in tetrahydrofuran (43 mL) was added sodium hydride (180.39 mg, 4.51 mmol, 60% dispersion in mineral oil) at 0° C. and stirred at 25° C. for 1 hour. Then tert-butyl 4-[7-[6-[bis[(4-methoxyphenyl) methyl]amino]-4-methyl-3-(trifluoromethyl)-2-pyridyl]-6-chloro-2,8-difluoro-quinazolin-4-yl]-2-(cyanomethyl)piperazine-1-carboxylate (944.0 mg, 1.13 mmol) was added and stirred at 25° C. for 1 hour. Upon completion, the reaction was quenched with water and extracted with dichloromethane. Then the organic layers were combined, washed with water, dried over anhydrous sodium sulfate and concentrated. The residue was purified by flash chromatography on silica gel eluting with dichloromethane/methanol (4%) to afford tert-butyl 4-[7-[6-[bis[(4-methoxyphenyl)methyl] amino]-4-fluoro-3-(trifluoromethyl)-2-pyridyl]-6-chloro-8-fluoro-2-[[(2S,4R)-4-fluoro-1-methyl-pyrrolidin-2-yl] methoxy]quinazolin-4-yl]-2-prop-2-ynyl-piperazine-1-carboxy late (929 mg, 0.98 mmol, 86.3% yield) as a yellow solid. LC-MS: (ESI, m/z): 951.3 [M+H]$^+$.

Step 7: 2-[4-[7-[6-amino-4-methyl-3-(trifluoromethyl)-2-pyridyl]-6-chloro-8-fluoro-2-[[(2S,4R)-4-fluoro-1-methyl-pyrrolidin-2-yl]methoxy]quinazolin-4-yl]piperazin-2-yl]acetonitrile

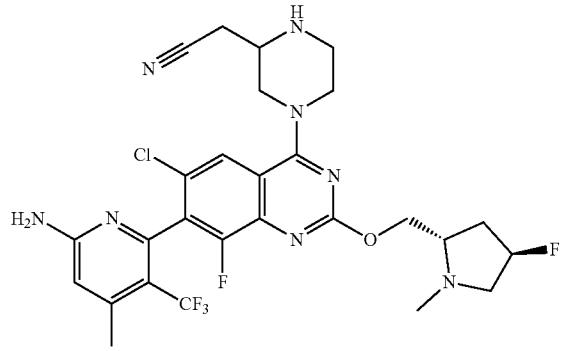 [SMILES: Cc1cc(N)nc(-c2c(Cl)cc3c(N4CCNC(CC#N)C4)nc(OC[C@@H]4C[C@@H](F)CN4C)nc3c2F)c1C(F)(F)F]

A solution of tert-butyl 4-[7-[6-[bis[(4-methoxyphenyl) methyl]amino]-4-fluoro-3-(trifluoromethyl)-2-pyridyl]-6-chloro-8-fluoro-2-[[(2S,4R)-4-fluoro-1-methyl-pyrrolidin-2-yl]methoxy]quinazolin-4-yl]-2-prop-2-ynyl-piperazine-1-carboxylate (909.0 mg, 0.96 mmol) in trifluoroacetic acid (91 mL, 0.96 mmol) was stirred at 50° C. for 3 hours. Upon completion, the reaction was concentrated and the residue was dissolved with dichloromethane and the pH was adjusted to 10 with N,N-diisopropylethylamine. The mixture was concentrated and the residue was purified by a reversed-phase chromatography-Column, C18 silica gel; mobile phase, A: water, B:MeCN, B % (5% 70% in 30 min); Detector, UV 254 nm to afford 2-[4-[7-[6-amino-4-methyl-3-(trifluoromethyl)-2-pyridyl]-6-chloro-8-fluoro-2-[[(2S,4R)-4-fluoro-1-methyl-pyrrolidin-2-yl]methoxy]quinazolin-4-yl]piperazin-2-yl]acetonitrile (373 mg, 061 mmol, 63.9%) of as a white solid. LC-MS: (ESI, m/z): 611.2 [M+H]$^+$.

Step 8: 2-((R)-4-((S)-7-(6-amino-4-methyl-3-(trifluoromethyl)pyridin-2-yl)-6-chloro-8-fluoro-2-(((2S, 4R)-4-fluoro-1-methylpyrrolidin-2-yl)methoxy)quinazolin-4-yl)-1-(2-fluoroacryloyl)piperazin-2-yl) acetonitrile (Example 83a); 2-((S)-4-((S)-7-(6-amino-4-methyl-3-(trifluoromethyl)pyridin-2-yl)-6-chloro-8-fluoro-2-4(2S,4R)-4-fluoro-1-methylpyrrolidin-2-yl)methoxy)quinazolin-4-yl)-1-(2-fluoroacryloyl)piperazin-2-yl)acetonitrile (Example 83b); 2-((R)-4-((R)-7-(6-amino-4-methyl-3-(trifluoromethyl)pyridin-2-yl)-6-chloro-8-fluoro-2-(((2S,4R)-4-fluoro-1-methylpyrrolidin-2-yl) methoxy)quinazolin-4-yl)-1-(2-fluoroacryloyl) piperazin-2-yl)acetonitrile (Example 83c); and 2-((S)-4-((R)-7-(6-amino-4-methyl-3-(trifluoromethyl)pyridin-2-yl)-6-chloro-8-fluoro-2-4(2S,4R)-4-fluoro-1-methylpyrrolidin-2-yl)methoxy)quinazolin-4-yl)-1-(2-fluoroacryloyl)piperazin-2-yl)acetonitrile (Example 83d)

83a

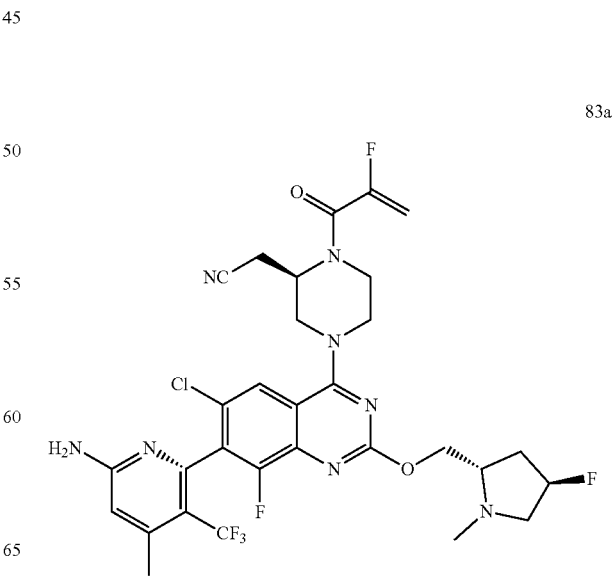

-continued

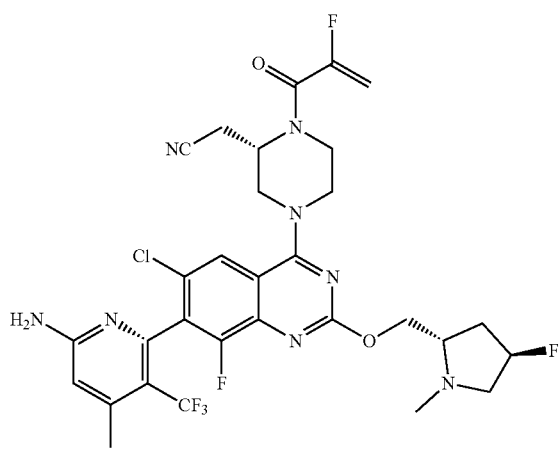

83b

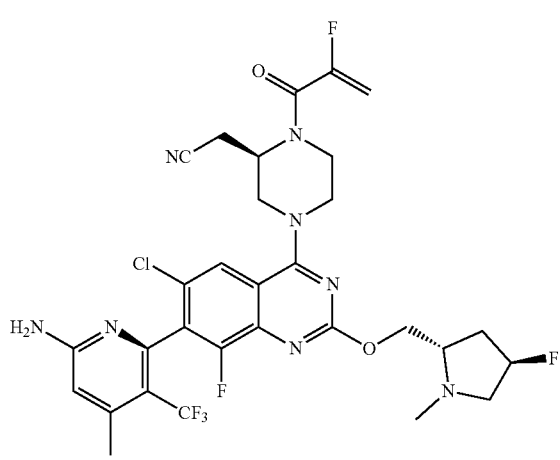

83c

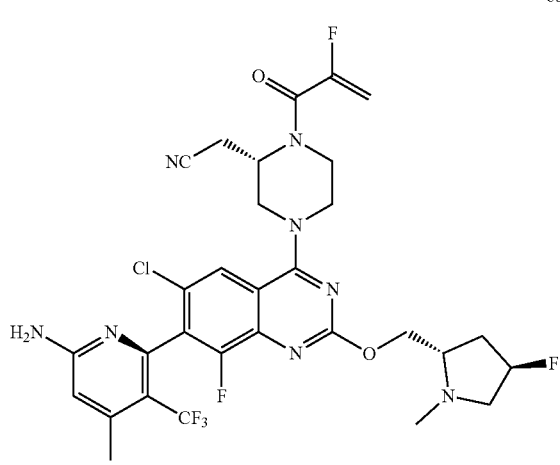

83d

A solution of 2-[4-[7-[6-amino-4-methyl-3-(trifluoromethyl)-2-pyridyl]-6-chloro-8-fluoro-2-[[(2S,4R)-4-fluoro-1-methyl-pyrrolidin-2-yl]methoxy]quinazolin-4-yl]piperazin-2-yl]acetonitrile (373.0 mg, 0.61 mmol), N,N-diisopropylethylamine (393.75 mg, 3.05 mmol), HATU (232.12 mg, 0.61 mmol) and 2-fluoroacrylic acid (71.46 mg, 0.79 mmol) in dichloromethane (10 mL) and N,N-dimethylformamide (0.5 mL) was stirred at 25° C. for 1 hour. Upon completion, the resulting reaction was concentrated. The crude product was purified directly by Prep-HPLC-Column, XBridge Prep C18 OBD Column19*15 mm 5 umC-0013; mobile phase, A: 1 mmol FA in water, B: ACN and B % (51%~73% in 7 min); Detector, UV 254 nm to afford 480 mg of 2-(4-(7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-1-(2-fluoroacryloyl)piperazin-2-yl)acetonitrile as a white solid. The product was further purified by Chiral-Prep-HPLC with following condition (Column, CHIRALPAK IE-3 4.6*50 mm 3 um; mobile phase, Hex (0.1% DEA):EtOH=50:50; Detector, 254 nm; Flow, 1.0 mL/min; Temperature: 25° C.) and (Column, CHIRAL Cellulose-SB4.6*100 mm 3 um; mobile phase, MtBE (0.1% DEA):EtOH=70:30; Detector, 254 nm; Flow, 1.0 ml/min; Temperature: 25° C.) to afford the title compounds. The stereo chemistry of title compounds was assigned based on potency data.

Example 83a 2-((R)-4-((S)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-1-(2-fluoroacryloyl)piperazin-2-yl)acetonitrile; (62.4 mg, 0.09 mmol, 15% yield, white solid). $^1$H NMR (400 MHz, Methanol-$d_4$, ppm) δ 7.96 (d, J=1.6 Hz, 1H), 6.62 (s, 1H), 5.42-5.12 (m, 3H), 5.11-4.90 (m, 1H), 4.58-4.40 (m, 4H), 4.35-4.01 (m, 1H), 3.91-3.59 (m, 3H), 3.57-3.46 (m, 1H), 3.18-3.07 (m, 3H), 2.73-2.62 (m, 1H), 2.57 (s, 3H), 2.46 (d, J=1.2 Hz, 3H), 2.36-2.25 (m, 1H), 2.12-1.96 (m, 1H). LC-MS: (ESI, m/z): 683.3 [M+H]$^+$. Chiral HPLC: CHIRAL Cellulose-SB, 4.6*100 mm, 3 um; detected at 214 nm; MtBE (0.1% DEA):EtOH=70:30; Flow=1 mL/min; Retention time: 2.041 min (First peak).

Example 83b 2-((S)-4-((S)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-1-(2-fluoroacryloyl)piperazin-2-yl)acetonitrile (64 mg, 0.09 mmol, 15.3% yield, white solid). $^1$H NMR (400 MHz, Methanol-$d_4$, ppm) δ 7.96 (d, J=1.6 Hz, 1H), 6.62 (s, 1H), 5.42-5.12 (m, 3H), 5.11-4.92 (m, 1H), 4.53-4.40 (m, 4H), 4.38-4.00 (m, 1H), 3.89-3.59 (m, 3H), 3.62-3.46 (m, 1H), 3.19-3.13 (m, 2H), 3.09-3.03 (m, 1H), 2.73-2.62 (m, 1H), 2.57 (s, 3H), 2.46 (d, J=1.6 Hz, 3H), 2.33-2.18 (m, 1H), 2.15-1.91 (m, 1H). LC-MS: (ESI, m/z): 683.3 [M+H]$^+$. Chiral HPLC: CHIRAL Cellulose-SB, 4.6*100 mm, 3 um; detected at 214 nm; MtBE (0.1% DEA):EtOH=70:30; Flow=1 mL/min; Retention time: 2.704 min (Second peak).

Example 83c 2-((R)-4-((R)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-1-(2-fluoroacryloyl)piperazin-2-yl)acetonitrile (40.2 mg, 0.0589 mmol, 9.6% yield, white solid). $^1$H NMR (400 MHz, Methanol-$d_4$, ppm) δ 7.96 (d, J=1.6 Hz, 1H), 6.62 (s, 1H), 5.42-5.11 (m, 3H), 5.08-4.93 (m, 1H), 4.66-4.39 (m, 4H), 4.38-4.10 (m, 1H), 3.89-3.49 (m, 4H), 3.19-3.04 (m, 3H), 2.76-2.63 (m, 1H), 2.59 (s, 3H), 2.46 (d, J=1.2 Hz, 3H), 2.33-2.26 (m, 1H), 2.16-1.98 (m, 1H). LC-MS: (ESI, m/z): 683.3 [M+H]$^+$. Chiral HPLC: CHIRALPAK IE-3, 4.6*50 mm, 3 um; detected at 254 nm; Hex (0.1% DEA):EtOH=50:50; Flow=1 mL/min; Retention time: 2.395 min (third peak).

Example 83d 2-((S)-4-((R)-7-(6-amino-4-methyl-3-(trifluoromethyl)pyridin-2-yl)-6-chloro-8-fluoro-2-(((2S,4R)-4-fluoro-1-methylpyrrolidin-2-yl)methoxy)quinazolin-4-yl)-1-(2-fluoroacryloyl)piperazin-2-yl)acetonitrile. (92.1 mg, 0.13 mmol, 22.1% yield, white solid). $^1$H NMR (400 MHz, Methanol-$d_4$, ppm) δ 7.96 (d, J=1.6 Hz, 1H), 6.62 (s, 1H), 5.43-5.14 (m, 3H), 5.11-4.91 (m, 1H), 4.62-4.40 (m, 4H), 4.37-3.98 (m, 1H), 3.90-3.47 (m, 4H), 3.22-3.05 (m, 3H), 2.89-2.69 (m, 1H), 2.61 (s, 3H), 2.46 (d, J=4.0 Hz, 3H), 2.39-2.28 (m, 1H), 2.15-1.99 (m, 1H). LC-MS: (ESI, m/z): 683.3 [M+H]$^+$. Chiral HPLC: CHIRALPAK IE-3, 4.6*50 mm, 3 um; detected at 254 nm; Hex (0.1% DEA):EtOH=50:50; Flow=1 mL/min; Retention time: 3.052 min (fourth peak)

Examples 84a and 84b 1-((S)-4-((R)-7-(6-amino-3,4-dimethylpyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)prop-2-en-1-one (Example 84a) and 1-((S)-4-((S)-7-(6-amino-3,4-dimethylpyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)prop-2-en-1-one (Example 84b) (2 atropisomers)

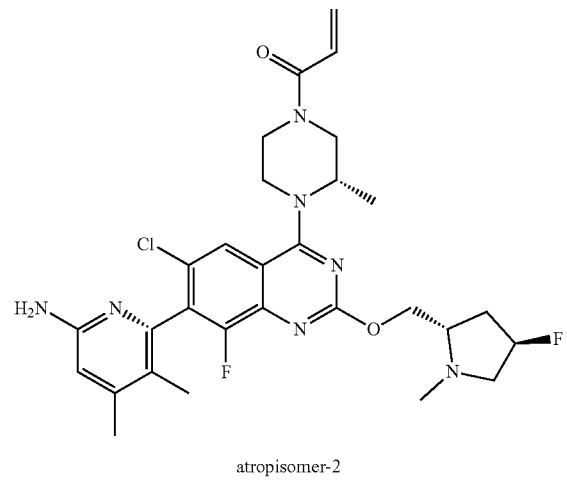

atropisomer-2

Synthetic Route

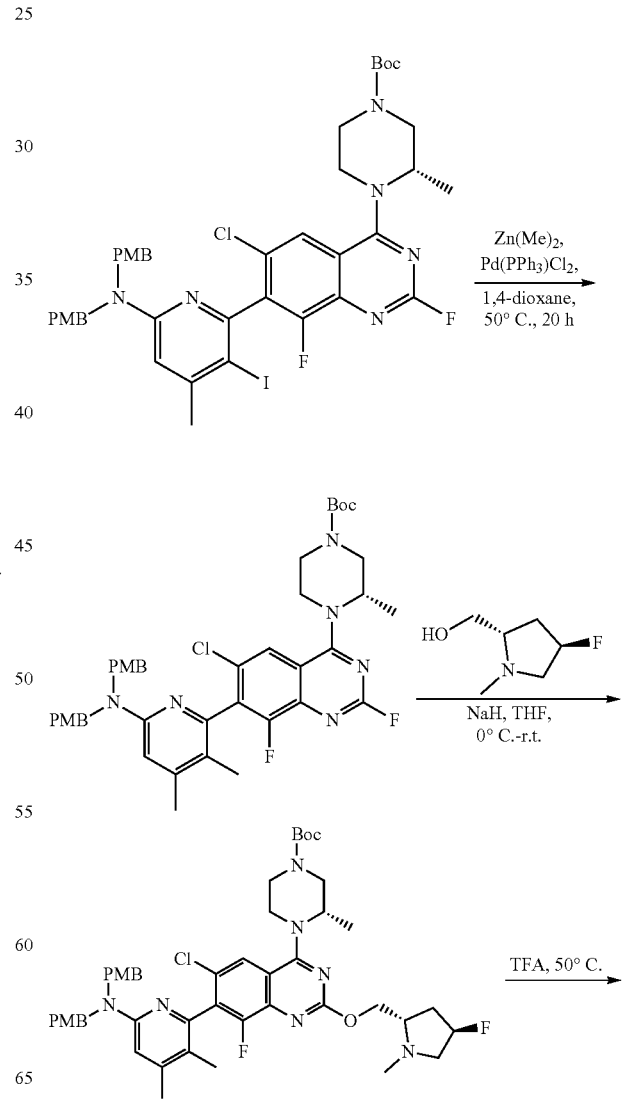

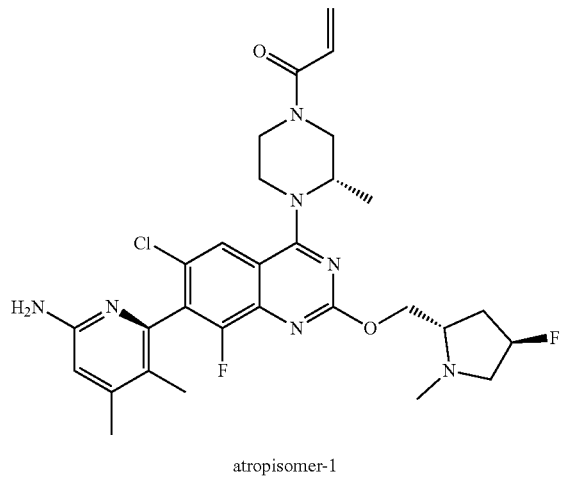

atropisomer-1

569

-continued

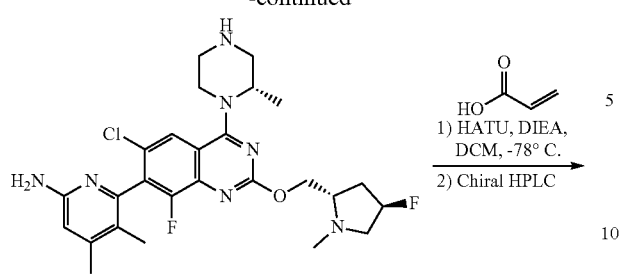

1) HATU, DIEA, DCM, -78° C.
2) Chiral HPLC

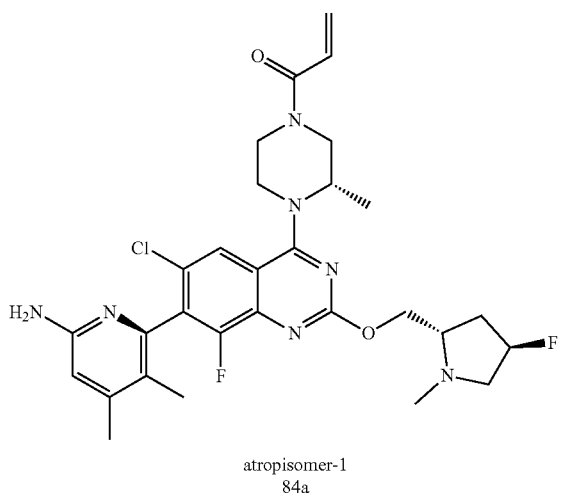

atropisomer-1
84a atropisomer-2
84b

570

Step 1: tert-butyl (3S)-4-[7-[6-[bis[(4-methoxyphenyl)methyl]amino]-3,4-dimethyl-2-pyridyl]-6-chloro-2,8-difluoro-quinazolin-4-yl]-3-methyl-piperazine-1-carboxylate

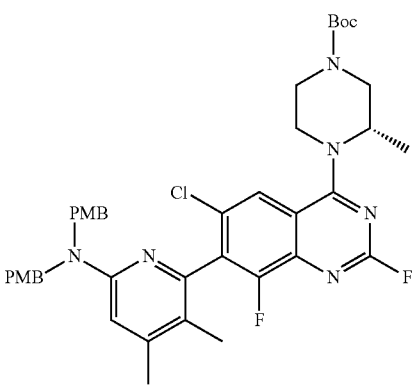

A solution of tert-butyl (3S)-4-[7-[6-[bis[(4-methoxyphenyl)methyl]amino]-3-iodo-4-methyl-2-pyridyl]-6-chloro-2,8-difluoro-quinazolin-4-yl]-3-methyl-piperazine-1-carboxylate (4.00 g, 4.5 mmol) and bis(triphenylphosphine)palladium(II) chloride (321.8 mg, 0.4 mmol) in 1,4-dioxane (40 mL) was stirred at 25° C. for 5 minutes under nitrogen. Then dimethylzinc in toluene (1.2 M) (7.6 mL, 9.1 mmol) was added and stirred at 50° C. for 20 hours. Upon completion, the reaction was quenched with water, extracted with ethyl acetate, dried over anhydrous sodium sulfate and concentrated. The residue was purified by flash chromatography on silica gel eluting with petroleum ether/ethyl acetate (10/1) to afford tert-butyl (3S)-4-[7-[6-[bis[(4-methoxyphenyl)methyl]amino]-3,4-dimethyl-2-pyridyl]-6-chloro-2,8-difluoro-quinazolin-4-yl]-3-methyl-piperazine-1-carboxylate (3.00 g, 3.9 mmol, 86.1% yield) as a yellow oil. LCMS (ESI, m/z): 759.3 [M+H]$^+$.

Step 2: tert-butyl (3S)-4-[7-[6-[bis[(4-methoxyphenyl)methyl]amino]-3,4-dimethyl-2-pyridyl]-6-chloro-8-fluoro-2-[[(2S,4R)-4-fluoro-1-methyl-pyrrolidin-2-yl]methoxy]quinazolin-4-yl]-3-methyl-piperazine-1-carboxylate

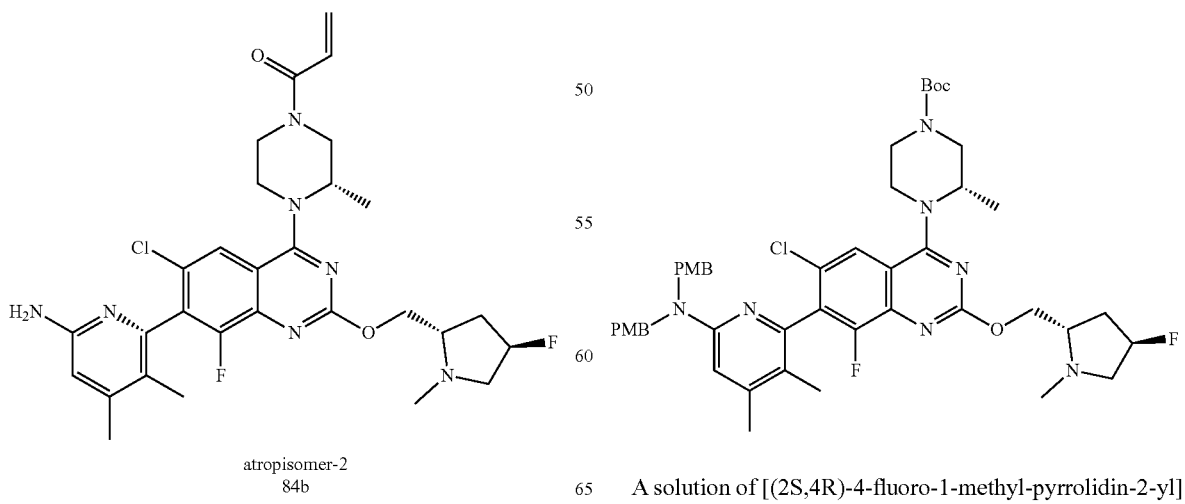

A solution of [(2S,4R)-4-fluoro-1-methyl-pyrrolidin-2-yl]methanol (1052.2 mg, 7.9 mmol) in tetrahydrofuran (30 mL) was stirred at 0° C. for 2 minutes. Then sodium hydride (60% purity) (632.1 mg, 15.8 mmol) was added and stirred at 0° C. for 10 minutes. Then tert-butyl (3S)-4-[7-[6-[bis[(4-methoxyphenyl)methyl]amino]-3,4-dimethyl-2-pyridyl]-6-chloro-2,8-difluoro-quinazolin-4-yl]-3-methyl-piperazine-1-carboxylate (3.0 g, 3.9 mmol) was added and stirred at 25° C. for 1 hour. Upon completion, the reaction was quenched by saturated ammonium chloride, extracted with ethyl acetate, dried over anhydrous sodium sulfate and concentrated under vacuum. The residue was purified by flash chromatography on silica gel eluting with dichloromethane/methanol (10/1) to afford tert-butyl (3S)-4-[7-[6-[bis[(4-methoxyphenyl)methyl]amino]-3,4-dimethyl-2-pyridyl]-6-chloro-8-fluoro-2-[[(2S,4R)-4-fluoro-1-methyl-pyrrolidin-2-yl]methoxy]quinazolin-4-yl]-3-methyl-piperazine-1-carboxylate (2.4 g, 2.7 mmol, 69.6% yield) as a yellow solid. LCMS (ESI, m/z): 872.4 [M+H]$^+$.

Step 3: 6-[6-chloro-8-fluoro-2-[[(2S,4R)-4-fluoro-1-methyl-pyrrolidin-2-yl]methoxy]-4-[(2S)-2-methylpiperazin-1-yl]quinazolin-7-yl]-4,5-dimethyl-pyridin-2-amine

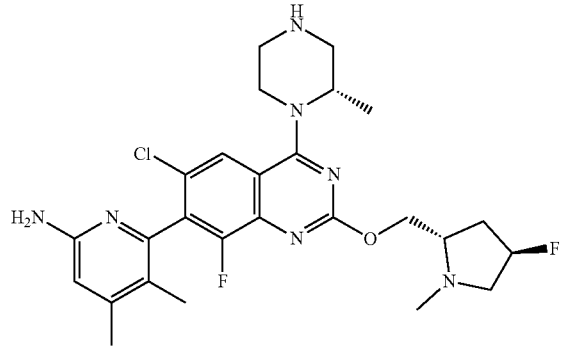 [SMILES: Cc1cc(N)nc(-c2c(Cl)cc3c(N4CCNC[C@@H]4C)nc(OC[C@@H]4C[C@@H](F)CN4C)nc3c2F)c1C]

A solution of tert-butyl (3S)-4-[7-[6-[bis[(4-methoxyphenyl)methyl]amino]-3,4-dimethyl-2-pyridyl]-6-chloro-8-fluoro-2-[[(2S,4R)-4-fluoro-1-methyl-pyrrolidin-2-yl]methoxy]quinazolin-4-yl]-3-methyl-piperazine-1-carboxylate (2.4 g, 2.7 mmol) in trifluoroacetic acid (9 g, 82.5 mmol) was stirred at 50° C. for 1 hour. Upon completion, the reaction was concentrated. The residue was purified by flash chromatography on silica gel eluting with acetonitrile/water(40:60) to afford 6-[6-chloro-8-fluoro-2-[[(2S,4R)-4-fluoro-1-methyl-pyrrolidin-2-yl]methoxy]-4-[(2S)-2-methylpiperazin-1-yl]quinazolin-7-yl]-4,5-dimethyl-pyridin-2-amine (1.2 g, 2.2 mmol, 82% yield) as a yellow solid. LCMS (ESI, m/z): 532.2 [M+H]$^+$.

Step 4: 1-((S)-4-((R)-7-(6-amino-3,4-dimethylpyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)prop-2-en-1-one (Example 84a) and 1-((S)-4-((S)-7-(6-amino-3,4-dimethylpyridin-2-yl)-6-chloro-8-fluoro-2-(((2 S,4R)-4-fluoro-1-methylpyrrolidin-2-yl)methoxy)quinazolin-4-yl)-3-methylpiperazin-1-yl)prop-2-en-1-one (Example 84b) (2 atropisomers)

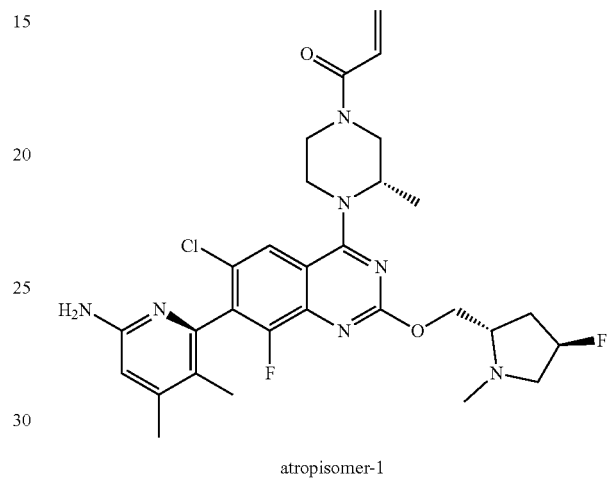

atropisomer-1

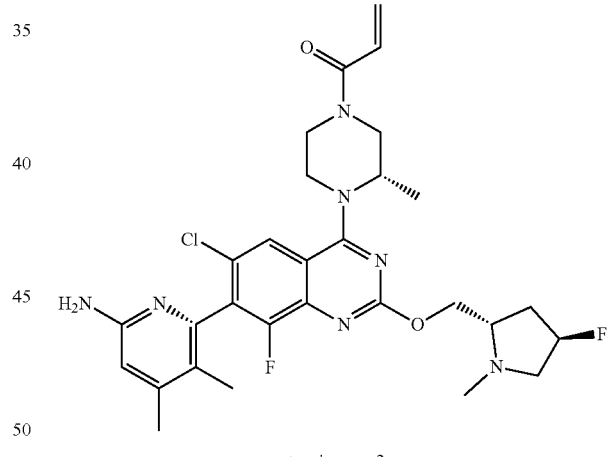

atropisomer-2

A solution of 6-[6-chloro-8-fluoro-2-[[(2S,4R)-4-fluoro-1-methyl-pyrrolidin-2-yl]methoxy]-4-[(2 S)-2-methylpiperazin-1-yl]quinazolin-7-yl]-4,5-dimethyl-pyridin-2-amine (900.0 mg, 1.6 mmol), acrylic acid (97.5 mg, 1.3 mmol) and N,N-diisopropylethylamine (654.6 mg, 5.0 mmol) in dichloromethane (9 mL) was stirred at −78° C. for 2 minutes. Then HATU (643.2 mg, 1.6 mmol) was added at −78° C. for 1 hour. Upon completion, the reaction was quenched with water, extracted with ethyl acetate, dried over anhydrous sodium sulfate and concentrated under vacuum. The residue was purified by flash chromatography on silica gel eluting with dichloromethane/methanol (10/1) to afford 197 mg crude solid. The crude product was purified by Prep-HPLC-Column: XBridge Prep OBD C18 Column, 30×150 mm 5 um; Mobile Phase A:Water(10 mmol/L NH₄HCO₃), Mobile Phase B:ACN; Flow rate:60 mL/min; to afford 117 mg of the desired product. The resulting solid was purified by Chiral-Prep-HPLC-Column, CHIRALPAK IC-3, 0.46*5 cm; 3 um; mobile phase: MtBE(0.3% IPAmine):MeOH=50:50; Detector, UV 254 nm. The faster peak was obtained at 1.142 min. The slower peak was obtained at 1.629 min. to afford 1-((S)-4-((R)-7-(6-amino-3,4-dimethylpyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)prop-2-en-1-one (38 mg, 0.06 mmol, 3.8% yield) as a white solid and 1-((S)-4-((S)-7-(6-amino-3,4-dimethylpyridin-2-yl)-6-chloro-8-fluoro-2-(((2S,4R)-4-fluoro-1-methylpyrrolidin-2-yl)methoxy)quinazolin-4-yl)-3-methylpiperazin-1-yl)prop-2-en-1-one (35.1 mg, 0.06 mmol, 3.5% yield) as a white solid.

Example 84a

¹H NMR (300 MHz, DMSO-d₆, ppm) δ 7.82 (s, 1H), 6.92-6.74 (m, 1H), 6.39 (s, 1H), 6.26-6.11 (m, 1H), 5.81-5.66 (m, 3H), 5.18 (d, J=56.2 Hz, 1H), 4.75 (s, 1H), 4.50-4.23 (m, 3H), 4.19-3.91 (m, 2H), 3.74-3.38 (m, 3H), 3.26-2.85 (m, 2H), 2.44-2.29 (m, 4H), 2.24-2.05 (m, 4H), 2.03-1.87 (m, 1H), 1.81 (s, 3H), 1.28 (d, J=6.5 Hz, 3H). LCMS (ESI, m/z):586.3 [M+H]⁺ Chiral HPLC: Column: CHIRALPAK IC-3, 4.6*50 mm 3 um; detected at 254 nm; MtBE(0.3% IPAmine):MeOH=50:50; Flow rate:1 mL/min; Retention time: 1.136 min; (faster peak).

Example 84b

¹H NMR (300 MHz, DMSO-d₆, ppm) δ 7.82 (s, 1H), 6.95-6.74 (m, 1H), 6.39 (s, 1H), 6.25-6.11 (m, 1H), 5.84-5.65 (m, 3H), 5.19 (d, J=56.1 Hz, 1H), 4.74 (s, 1H), 4.49-4.22 (m, 3H), 4.21-3.88 (m, 2H), 3.74-3.53 (m, 2H), 3.50-3.38 (m, 2H), 3.25-3.01 (m, 1H), 3.03-2.86 (m, 1H), 2.41 (s, 3H), 2.20 (s, 3H), 2.13-1.87 (m, 2H), 1.83 (s, 3H), 1.30 (d, J=6.5 Hz, 3H). LCMS (ESI, m/z):586.3 [M+H]⁺ Chiral HPLC: Column: CHIRALPAK IC-3, 4.6*50 mm 3 um; detected at 254 nm; MtBE(0.3% IPAmine):MeOH=50:50; Flow rate:1 mL/min; Retention time: 1.629 min; (slower peak).

Example 85

(E)-1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-hydroxybut-2-en-1-one

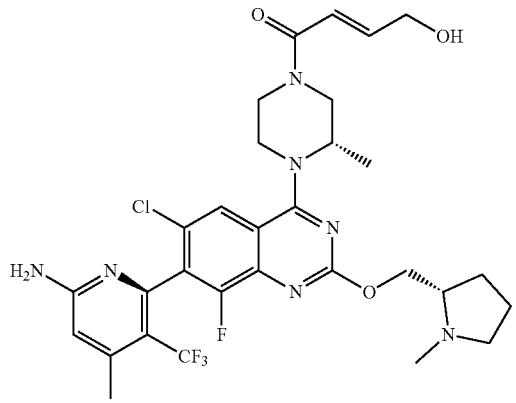

Synthetic Route

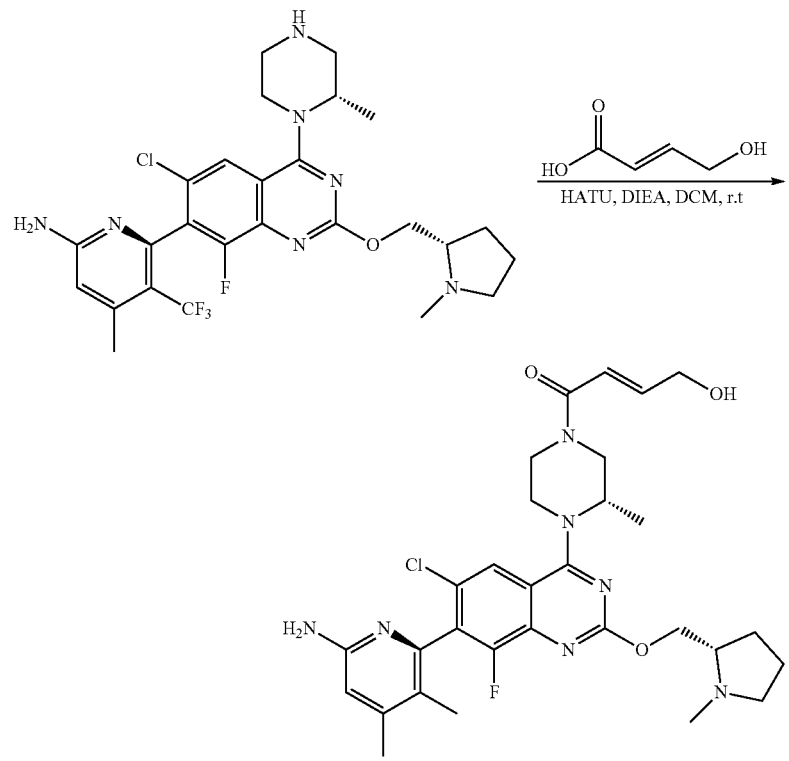

A solution of 6-((R)-6-chloro-8-fluoro-4-((S)-2-methylpiperazin-1-yl)-2-(((S)-1-methylpyrrolidin-2-yl)methoxy)quinazolin-7-yl)-4-methyl-5-(trifluoromethyl)pyridin-2-amine (see Step 11 of Example 17a/17b) (156.0 mg, 0.27 mmol), 4-hydroxy-but-2-enoicacid (42.06 mg, 0.41 mmol), N,N-diisopropylethylamine (141.72 mg, 1.1 mmol) and HATU (156.64 mg, 0.4100 mmol) in dichloromethane (6.5 mL) was stirred at 25° C. for 1 hour. Upon completion, the reaction was diluted with dichloromethane and washed with brine. Then the organic layer was dried over anhydrous sodium sulfate and concentrated. The residue was purified by a reversed-phase chromatography-Column, C18 silica gel; mobile phase, A: water, B:MeCN, B % (5%~70% in 30 min); Detector, UV 254 nm to afford 117 mg (65.3%) of desired atropisomer of (E)-1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-hydroxybut-2-en-1-one as a white solid.

Example 85

LC-MS: (ESI, m/z): 652.3 [M+H]$^+$, $^1$HNMR: (400 MHz, DMSO-d$_6$, ppm) δ 7.83 (s, 1H), 6.83-6.79 (m, 3H), 6.64-6.55 (m, 1H), 6.50 (s, 1H), 5.03-5.01 (m, 1H), 4.76 (s, 1H), 4.47-4.23 (m, 3H), 4.15-3.88 (m, 4H), 3.65-3.30 (m, 3H), 3.24-2.98 (m, 2H), 2.90-2.68 (m, 1H), 2.49-2.44 (m, 3H), 2.37-2.32 (m, 3H), 1.99-1.91 (m, 1H), 1.72-1.65 (m, 3H), 1.27 (s, 3H).

Example 86

(E)-1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-chlorobut-2-en-1-one

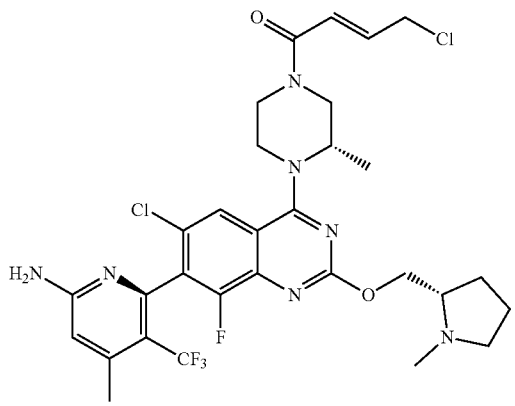

Synthetic Route

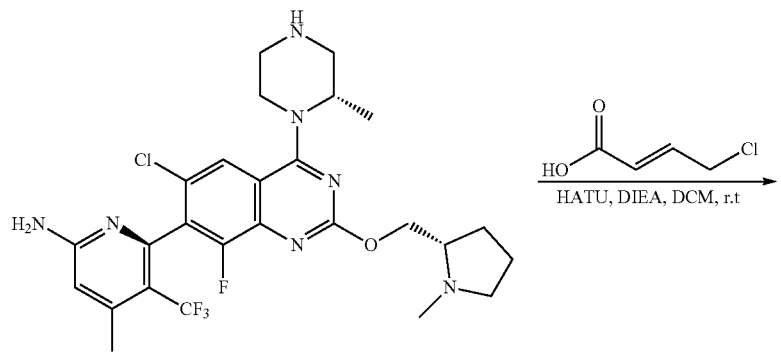

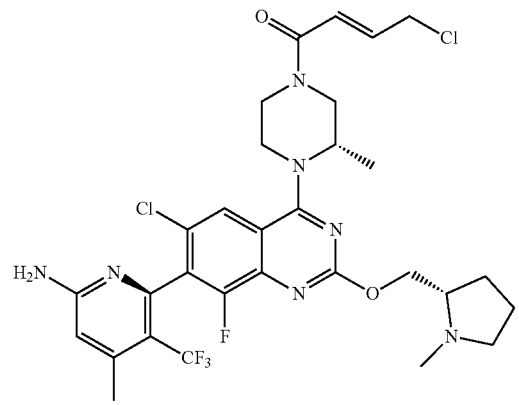

A solution of desired atropisomer of 6-((R)-6-chloro-8-fluoro-4-((S)-2-methylpiperazin-1-yl)-2-(((S)-1-methylpyrrolidin-2-yl)methoxy)quinazolin-7-yl)-4-methyl-5-(trifluoromethyl)pyridin-2-amine (see Step 11 of Example 17a/17b) (108.0 mg, 0.190 mmol), (E)-4-chlorobut-2-enoic acid (20.63 mg, 0.1700 mmol), N,N-diisopropylethylamine (98.11 mg, 0.7600 mmol) and HATU (108.44 mg, 0.2900 mmol) in dichloromethane (2 mL) was stirred at 25° C. for 1 hour. Upon completion, the reaction was washed with water and extracted with dichloromethane. The organic layer was dried over anhydrous sodium sulfate and concentrated under vacuum. The residue was purified by a reversed-phase chromatography-Column, C18 silica gel; mobile phase, A: water, B:MeCN, B % (5%~70% in 30 min); Detector, UV 254 nm to afford a white solid. The crude product was purified directly by Prep-HPLC-Column, XBridge Prep C18 OBD Column19*15 mm 5 umC-0013; mobile phase, A: 0.1% mmol FA in water, B: ACN and B % (51%~73% in 7 min); Detector, UV 254 nm to afford 44 mg (34.5%) of (E)-1-((S)-4-((R)-7-(6-amino-4-methyl-3-(trifluoromethyl)pyridin-2-yl)-6-chloro-8-fluoro-2-(((S)-1-methylpyrrolidin-2-yl)methoxy)quinazolin-4-yl)-3-methylpiperazin-1-yl)-4-chlorobut-2-en-1-one as a white solid.

Example 86

LC-MS: (ESI, m/z): 670.3 [M-41]$^+$, $^1$HNMR: (400 MHz, DMSO-d$_6$, ppm) δ 8.18 (s, 1H), 7.82 (s, 1H), 6.83-6.71 (m, 3H), 6.49 (s, 1H), 4.90-4.75 (m, 1H), 4.40-4.30 (m, 3H), 4.30-4.06 (m, 3H), 4.01-3.88 (m, 1H), 3.67-3.55 (m, 2H), 3.13-3.15 (m, 1H), 3.05-2.93 (m, 1H), 2.61-2.56 (m, 1H), 2.43-2.26 (m, 6H), 2.19-2.15 (m, 1H), 1.97-1.93 (m, 1H), 1.70-1.62 (m, 3H), 1.28-1.25 (m, 3H).

Example 87

1-[4-[7-[6-amino-3-(trifluoromethyl)-2-pyridyl]-6-chloro-2-[[(2S)-1-(oxetan-3-yl)pyrrolidin-2-yl]methoxy]quinazolin-4-yl]piperazin-1-yl]prop-2-en-1-one

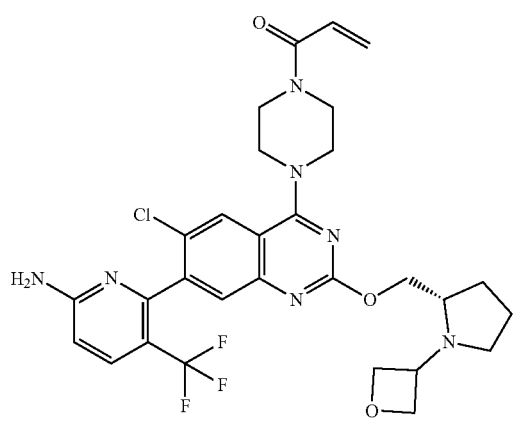 [SMILES: C=CC(=O)N1CCN(c2nc(OC[C@@H]3CCCN3C3COC3)nc3cc(-c4nc(N)ccc4C(F)(F)F)c(Cl)cc23)CC1]

Synthetic Route

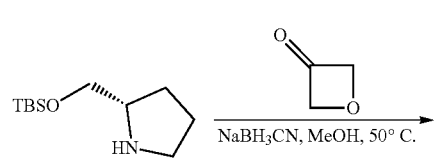

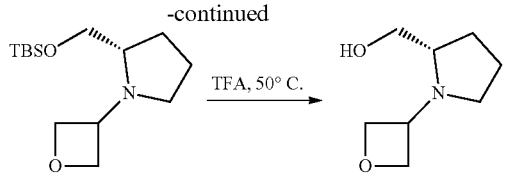

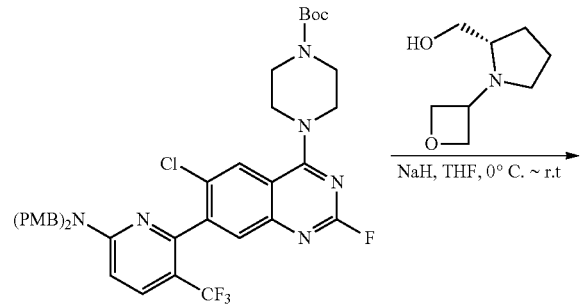

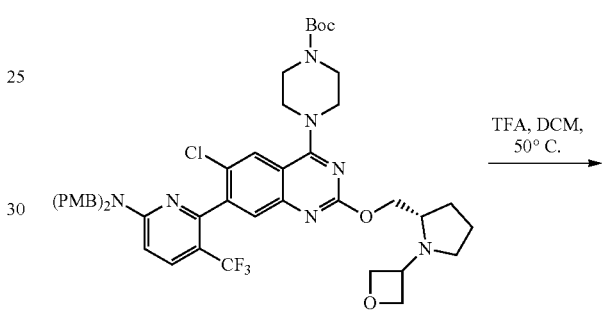

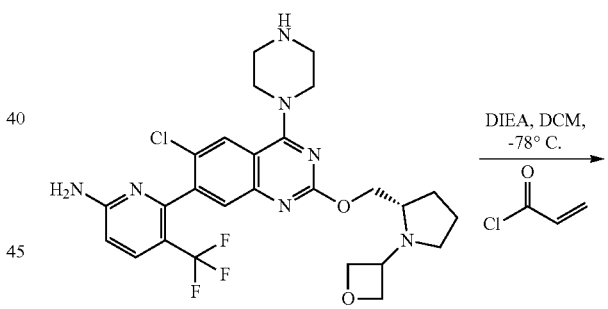

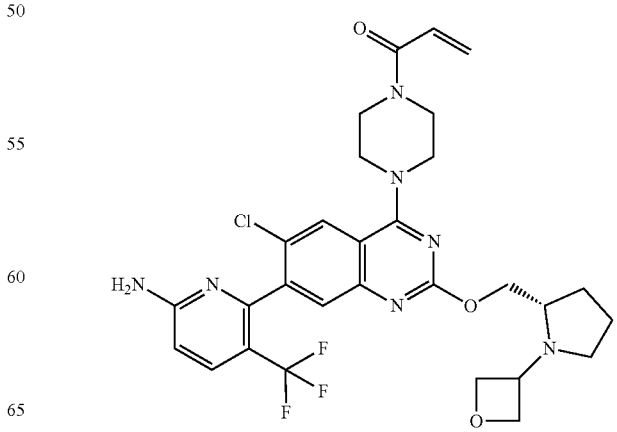

Step 1: tert-butyl-dimethyl-[[(2S)-1-(oxetan-3-yl)pyrrolidin-2-yl]methoxy]silane

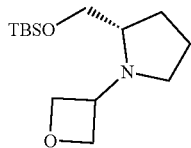 [SMILES: CC(C)(C)[Si](C)(C)OC[C@@H]1CCCN1C1COC1]

A mixture of tert-butyl-dimethyl-[[(2S)-pyrrolidin-2-yl]methoxy]silane (1600.0 mg, 7.43 mmol), 3-oxetanone (2700.0 mg, 37.47 mmol) and sodium cyanoborohydride (500.0 mg, 7.94 mmol) in methyl alcohol (10 mL) was stirred at 50° C. for 4 hours. The resulting solution was diluted with water, extracted with dichloromethane and the organic layers were combined. The resulting mixture was purified by Prep-HPLC to afford tert-butyl-dimethyl-[[(2S)-1-(oxetan-3-yl)pyrrolidin-2-yl]methoxy]silane (1200 mg, 4.41 mmol 59.5% yield) as a yellow oil. LC-MS: (ESI, m/z): 272.2 [M+H]$^+$

Step 2: [(2S)-1-(oxetan-3-yl)pyrrolidin-2-yl]methanol

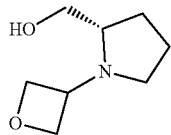 [SMILES: OC[C@@H]1CCCN1C1COC1]

To a mixture of tert-butyl-dimethyl-[[(2S)-1-(oxetan-3-yl)pyrrolidin-2-yl]methoxy]silane (1800.0 mg, 6.63 mmol) in trifluoroacetic acid (3 mL, 40.39 mmol), the mixture was stirred for 3 hours at 50° C. Upon completion, the pH was adjusted to 8.0 with N,N-diisopropylethylamine. The crude product was purified by Prep-HPLC to afford [(2S)-1-(oxetan-3-yl)pyrrolidin-2-yl]methanol (880 mg, 5.57 mmol, 84.4% yield) as a yellow oil. LC-MS: (ESI, m/z): 158.1 [M+H]$^+$.

Step 3: tert-butyl 4-[7-[6-[bis[(4-methoxyphenyl)methyl]amino]-3-(trifluoromethyl)-2-pyridyl]-6-chloro-2-[[(2S)-1-(oxetan-3-yl)pyrrolidin-2-yl]methoxy]quinazolin-4-yl]piperazine-1-carboxylate

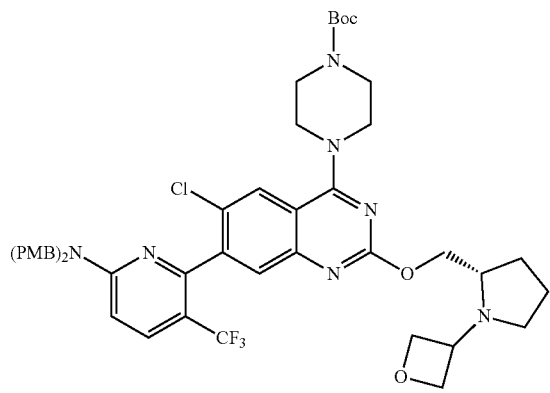

To a mixture of sodium hydride (36.0 mg, 1.5 mmol) in tetrahydrofuran (3 mL) was added [(2S)-1-(oxetan-3-yl)pyrrolidin-2-yl]methanol (90.0 mg, 0.57 mmol), the mixture was stirred for 15 minutes at 0° C. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (300.0 mg, 0.39 mmol) was added and stirred for 2 hours at room temperature. Upon completion, the reaction was quenched with saturated ammonium chloride and extracted with dichloromethane. The organic layer was dried over anhydrous sodium sulfate and concentrated under vacuum to afford crude product that directly used in the next step. LC-MS: (ESI, m/z): 904.4 [M+H]$^+$

Step 4: 6-[6-chloro-2-[[(2S)-1-(oxetan-3-yl)pyrrolidin-2-yl]methoxy]-4-piperazin-1-yl-quinazolin-7-yl]-5-(trifluoromethyl)pyridin-2-amine

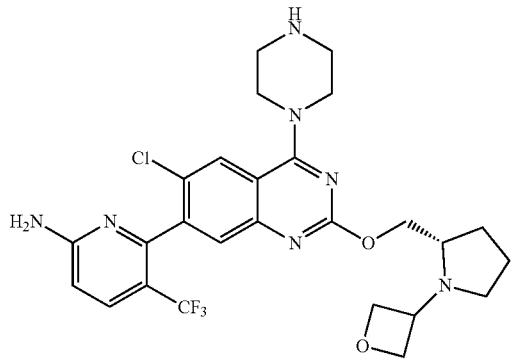 [SMILES: Nc1ccc(C(F)(F)F)c(-c2cc3nc(OC[C@@H]4CCCN4C4COC4)nc(N4CCNCC4)c3cc2Cl)n1]

To a mixture of tert-butyl 4-[7-[6-[bis[(4-methoxyphenyl)methyl]amino]-3-(trifluoromethyl)-2-pyridyl]-6-chloro-2-[[(2S)-1-(oxetan-3-yl)pyrrolidin-2-yl]methoxy]quinazolin-4-yl]piperazine-1-carboxylate (250.0 mg, 0.28 mmol) in trifluoroacetic acid (3 mL, 40.39 mmol), the mixture was stirred for 3 hours at 50° C. The reaction mixture was adjusted to pH8 with N,N-diisopropylethylamine. The resulting solution was diluted with water extracted with dichloromethane. The organic layers was dried over anhydrous sodium sulfate and concentrated under vacuum to afford 6-[6-chloro-2-[[(2S)-1-(oxetan-3-yl)pyrrolidin-2-yl]methoxy]-4-piperazin-1-yl-quinazolin-7-yl]-5-(trifluoromethyl)pyridin-2-amine (150 mg, 0.27 mmol 96.2% yield) as a crude product. The crude would be directly used in the next step without purification. LC-MS: (ESI, m/z): 564.2 [M+H]$^+$

581

Step 5: 1-[4-[7-[6-amino-3-(trifluoromethyl)-2-pyridyl]-6-chloro-2-[[(2S)-1-(oxetan-3-yl)pyrrolidin-2-yl]methoxy]quinazolin-4-yl]piperazin-1-yl]prop-2-en-1-one

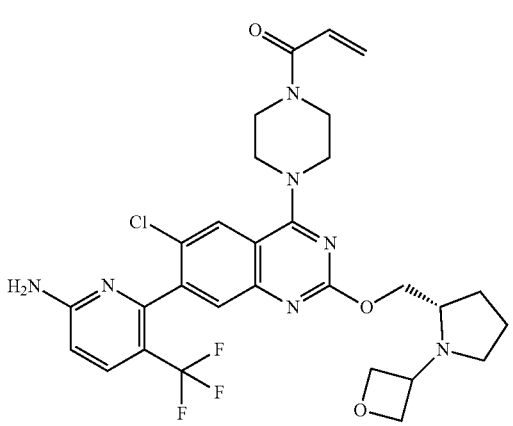 [SMILES: C=CC(=O)N1CCN(c2nc(OC[C@@H]3CCCN3C3COC3)nc3cc(-c4nc(N)ccc4C(F)(F)F)c(Cl)cc23)CC1]

To a mixture of [(2S)-1-(oxetan-3-yl)pyrrolidin-2-yl]methanol (60.0 mg, 0.11 mmol) in dichloromethane (1 mL) was added N,N-diisopropylethylamine (25.0 mg, 0.19 mmol), 6-[6-chloro-2-[[(2S)-1-(oxetan-3-yl)pyrrolidin-2-yl]methoxy]-4-piperazin-1-yl-quinazolin-7-yl]-5-(trifluoromethyl)pyridin-2-amine (60.0 mg, 0.11 mmol), and the mixture was stirred for 0.5 hours at −78° C. Upon completion, the organic layer was concentrated and the crude product was purified by Prep-HPLC-Column: Xselect CSH F-Phenyl OBD column, 19*250, 5 um; Mobile Phase A:Water(10 mmol/L NH$_4$HCO$_3$), Mobile Phase B:EtOH; Flow rate:25 mL/min; to afford 1-[4-[7-[6-amino-3-(trifluoromethyl)-2-pyridyl]-6-chloro-2-[[(2S)-1-(oxetan-3-yl)pyrrolidin-2-yl]methoxy]quinazolin-4-yl]piperazin-1-yl]prop-2-en-1-one (14.2 mg, 0.023 mmol 21.6% yield) as a white solid.

Example 87

LC-MS: (ESI, m/z): 618.3 [M+H]$^+$, $^1$H NMR (300 MHz, DMSO-d$_6$, ppm) δ 8.05 (s, 1H), 7.78 (d, J=8.9 Hz, 1H), 7.48 (d, J=2.3 Hz, 1H), 6.98-6.75 (m, 3H), 6.60 (d, J=8.8 Hz, 1H), 6.17 (dd, J=16.7, 2.4 Hz, 1H), 5.74 (dd, J=10.4, 2.4 Hz, 1H), 4.65-4.15 (m, 2H), 3.95-3.60 (m, 10H), 3.29-3.07 (m, 3H), 2.97-2.69 (m, 1H), 2.65-2.55 (m, 1H), 2.18-2.01 (m, 1H), 1.77-1.46 (m, 3H), 1.38-1.13 (m, 1H).

582

Example 88

1-(4-(7-(6-amino-3-(trifluoromethyl)pyridin-2-yl)-6-chloro-2-((1-(dimethylamino)cyclopropyl)methoxy)quinazolin-4-yl)piperazin-1-yl)prop-2-en-1-one Synthetic Route

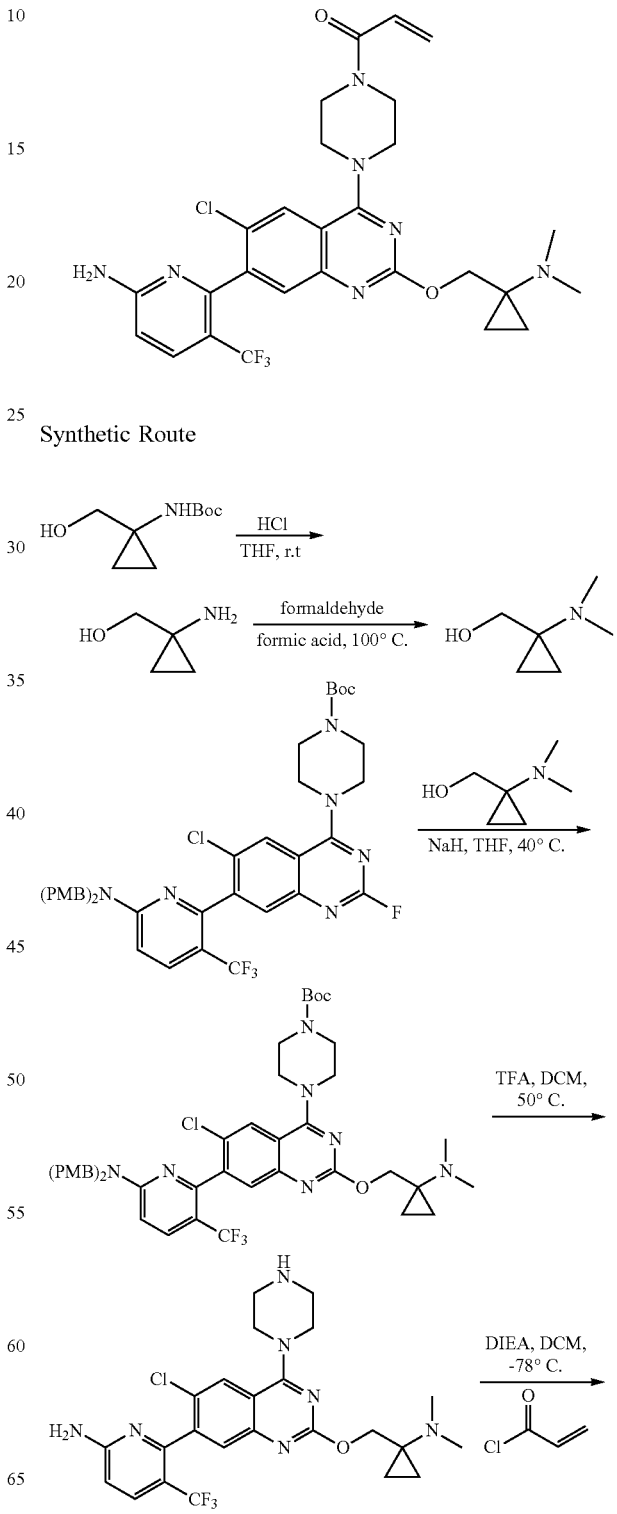

-continued

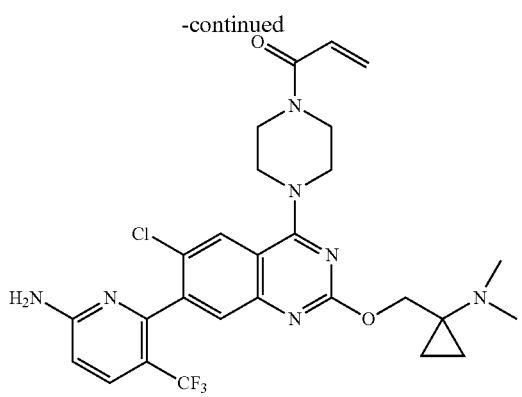

Step 1: (1-aminocyclopropyl)methanol

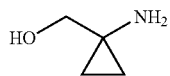

A solution of tert-butyl (1-(hydroxymethyl)cyclopropyl)carbamate (10.0 g, 53.41 mmol) in tetrahydrofuran (100 mL) was added hydrochloric acid (200 mL, 2M in tetrahydrofuran). The mixture was stirred at 25° C. for 16 hours. Upon completion, the reaction was concentrated and purified by flash chromatography using silica gel eluting with dichloromethane/methanol (4:1) to afford (1-aminocyclopropyl)methanol (4 g, 45.9 mmol, 86% yield) as a white solid. LC-MS: (ESI, m/z): 88.3 [M+H]$^+$ Step 2: (1-(dimethylamino)cyclopropyl)methanol

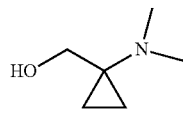

A solution of (1-aminocyclopropyl)methanol (500.0 mg, 5.74 mmol), formaldehyde (16.7 mL, 66.6 mmol) and formic acid (500.0 mg, 10.86 mmol) was stirred at 100° C. for 8 hours. Upon completion, the reaction was concentrated and sodium hydroxide was added to adjust pH to 13. The residue was purified by flash chromatography on silica gel eluting with methanol/dichloromethane (3:7) to afford (1-(dimethylamino)cyclopropyl)methanol (150 mg, 1.3 mmol, 22.7% yield) as a colorless oil. LC-MS: (ESI, m/z): 116.2 [M+H]$^+$ Step 3: tert-butyl 4-(7-(6-(bis(4-methoxybenzyl)amino)-3-(trifluoromethyl)pyridin-2-yl)-6-chloro-2-((1-(dimethyl amino)cyclopropyl)methoxy)quinazolin-4-yl)piperazine-1-carboxylate

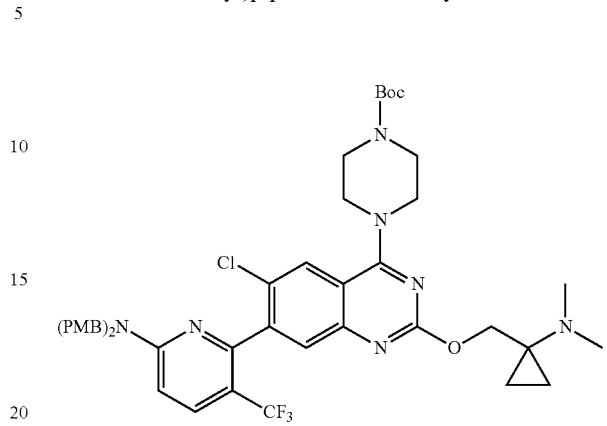

A solution of (1-(dimethylamino)cyclopropyl)methanol (60 mg, 0.50 mmol) and sodium hydride (25.0 mg, 1.1 mmol) in tetrahydrofuran (10 mL) was stirred at 40° C. for 5 minutes. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (200.0 mg, 0.3 mmol) was added and stirred at 40° C. for 1 hour. Upon completion, the reaction was concentrated to afford tert-butyl 4-(7-(6-(bis(4-methoxybenzyl)amino)-3-(trifluoromethyl)pyridin-2-yl)-6-chloro-2-((1-(dimethylamino)cyclopropyl)methoxy)quinazolin-4-yl)piperazine-1-carboxylate (250 mg, 0.17 mmol, 56.7% yield, 60% purity) as a yellow oil which was directly used in the next step. LC-MS: (ESI, m/z): 862.4 [M+H]$^+$ Step 4: 6-(6-chloro-2-((1-(dimethylamino)cyclopropyl)methoxy)-4-(piperazin-1-yl)quinazolin-7-yl)-5-(trifluoromethyl)pyridin-2-amine

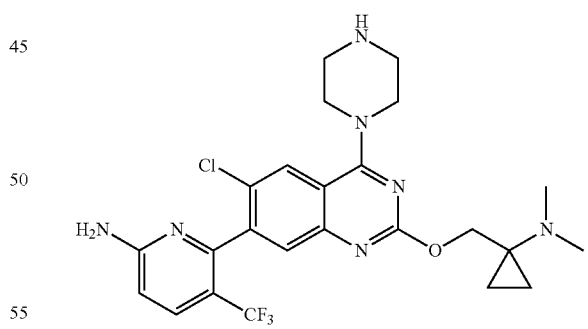

A solution of tert-butyl 4-(7-(6-(bis(4-methoxybenzyl)amino)-3-(trifluoromethyl)pyridin-2-yl)-6-chloro-2-((1-(dimethylamino)cyclopropyl)methoxy)quinazolin-4-yl)piperazine-1-carboxylate (250 mg, 0.17 mmol, 60% purity) in 2,2,2-trifluoroacetic acid (5 mL) and dichloromethane (15 mL) was stirred at 50° C. for 2 hours. The reaction was concentrated and the resulting mixture was purified by flash chromatography on C18 gel eluting with methanol/water (3:7) to afford 6-(6-chloro-2-((1-(dimethylamino)cyclopropyl)methoxy)-4-(piperazin-1-yl)quinazolin-7-yl)-5-(trifluoromethyl)pyridin-2-amine (80 mg, 0.15 mmol, 90.3% yield) as a yellow solid. LC-MS: (ESI, m/z): 522.3 [M+H]+

Step 5: 1-(4-(7-(6-amino-3-(trifluoromethyl)pyridin-2-yl)-6-chloro-2-((1-(dimethylamino)cyclopropyl)methoxy)quinazolin-4-yl)piperazin-1-yl)prop-2-en-1-one

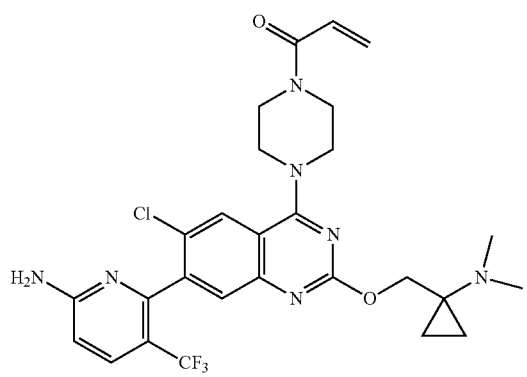 [SMILES: C=CC(=O)N1CCN(c2nc(OCC3(N(C)C)CC3)nc3cc(-c4nc(N)ccc4C(F)(F)F)c(Cl)cc23)CC1]

A solution of 6-(6-chloro-2-((1-(dimethylamino)cyclopropyl)methoxy)-4-(piperazin-1-yl)quinazolin-7-yl)-5-(trifluoromethyl)pyridin-2-amine (30.0 mg, 0.057 mmol), N,N-diisopropylethylamine (10.0 mg, 0.077 mmol) and dichloromethane (5 mL) was stirred at −78° C. for 5 minutes. Then acryloyl chloride (5.2 mg, 0.06 mmol) was added and stirred at −78° C. for 30 minutes. The reaction was concentrated and purified by flash chromatography on C18 gel eluting with acetonitrile/water (7:3) to afford crude product. The crude product was purified by Prep-HPLC-Column: XBridge Prep OBD C18 Column, 30×150 mm 5 um; Mobile Phase A:Water(10 mmol/L NH4HCO3), Mobile Phase B:ACN; Flow rate:60 mL/min; to afford 1-(4-(7-(6-amino-3-(trifluoromethyl)pyridin-2-yl)-6-chloro-2-((1-(dimethylamino)cyclopropyl)methoxy)quinazolin-4-yl)piperazin-1-yl)prop-2-en-1-one (17.3 mg, 0.03 mmol, 52.3% yield) as a white solid.

Example 88

LC-MS: (ESI, m/z): 576.2 [M+H]+, 1H NMR (300 MHz, DMSO, ppm) δ 8.04 (s, 1H), 7.77 (d, J=9.0 Hz, 1H), 7.43 (s, 1H), 6.87 (s, 2H), 6.79 (dd, J=12.0, 18.0 Hz, 1H), 6.58 (d, J=9.0 Hz, 1H), 6.15 (dd, J=3.0, 18.0 Hz, 1H), 5.72 (dd, J=3.0, 9.0 Hz, 1H), 4.40 (dd, J=12.0, 27.0 Hz, 2H), 3.93-3.80 (m, 6H), 3.81-3.72 (m, 2H), 2.34 (s, 6H), 0.75-0.53 (m, 4H).

Example 89

1-[4-[7-[6-amino-3-(trifluoromethyl)-2-pyridyl]-6-chloro-2-[[(2S,4R)-4-fluoro-1-(2-methoxyethyl)pyrrolidin-2-yl]methoxy]quinazolin-4-yl]piperazin-1-yl]prop-2-en-1-one

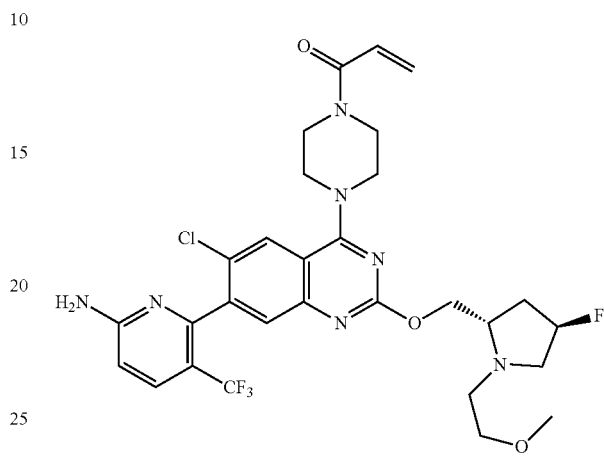

Synthetic Route

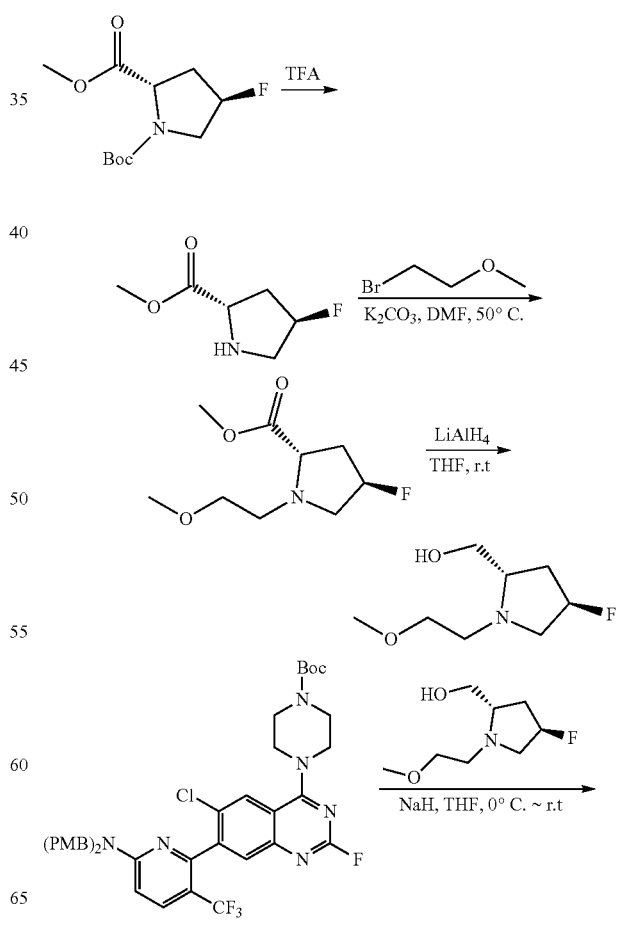

587

-continued

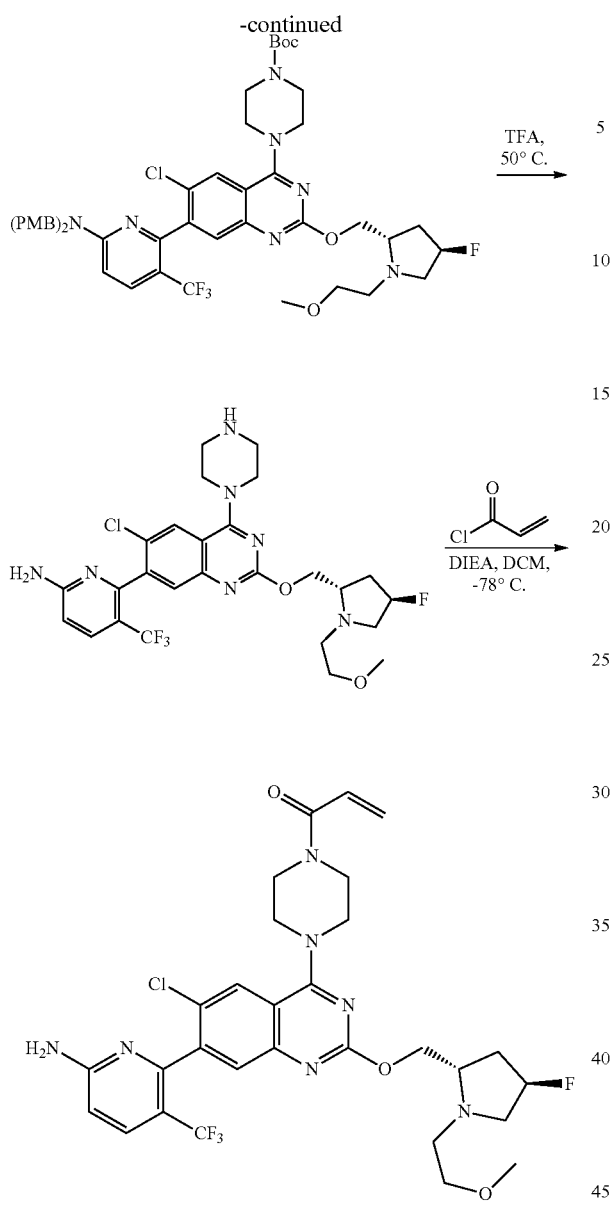

Step 1: methyl
(2S,4R)-4-fluoropyrrolidine-2-carboxylate

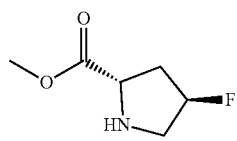

A solution of 1-(tert-butyl) 2-methyl (2S,4R)-4-fluoropyrrolidine-1,2-dicarboxylate (5.0 g, 20.22 mmol) in trifluoroacetic acid (192 mL) was stirred at 25° C. for 1 hour. Upon completion, the solvent was concentrated. The pH was adjusted to 10 with N,N-diisopropylethylamine and the mixture was concentrated and directly used in the subsequent reaction. LC-MS: (ESI, m/z): 148.0 [M+H]$^+$

588

Step 2: methyl (2S,4R)-4-fluoro-1-(2-methoxyethyl)pyrrolidine-2-carboxylate

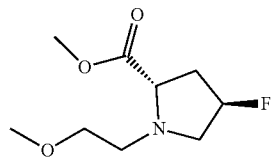

A solution of methyl (2S,4R)-4-fluoropyrrolidine-2-carboxylate (2.8 g, 19.03 mmol), 2-bromoethyl methyl ether (5.82 g, 41.86 mmol) and potassium carbonate (5.78 g, 41.86 mmol) in N,N-dimethylformamide (40.8 mL) was stirred at 50° C. for 4 hours. Upon completion, the reaction was quenched with water and extracted with ethyl acetate. Then the organic layer was dried over anhydrous sodium sulfate and concentrated under vacuum. The crude was used in the next reaction. LC-MS: (ESI, m/z): 206.1 [M+H]$^+$ Step 3: [(2S,4R)-4-fluoro-1-(2-methoxyethyl)pyrrolidin-2-yl]methanol

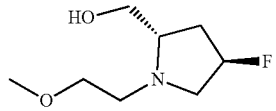

A solution of methyl (2S,4R)-4-fluoro-1-(2-methoxyethyl)pyrrolidine-2-carboxylate (1.45 g, 7.07 mmol) in tetrahydrofuran (14 mL) was stirred at 0° C. Lithium aluminium hydride (0.54 g, 14.13 mmol) was added and the reaction was stirred at 25° C. for 1 hour. The reaction was quenched with water (0.5 mL), sodium hydroxide solution (15%) (0.5 mL), water (1.5 mL) and stirred at 0° C. for 1 hour. The mixture was diluted with methanol (50 mL) and stirred at 25° C. for 30 minutes. The mixture was then filtered and concentrated. The resulting oil was redissolved in dichloromethane, dried over anhydrous sodium sulfate, filtered, and concentrated to afford the crude product which was carried further to the next step. LC-MS: (ESI, m/z): 178.3 [M+H]$^+$ Step 4: tert-butyl 4-[7-[6-[bis[(4-methoxyphenyl)methyl]amino]-3-(trifluoromethyl)-2-pyridyl]-6-chloro-2-[[(2S,4R)-4-fluoro-1-(2-methoxyethyl)pyrrolidin-2-yl]methoxy]quinazolin-4-yl]piperazine-1-carboxylate

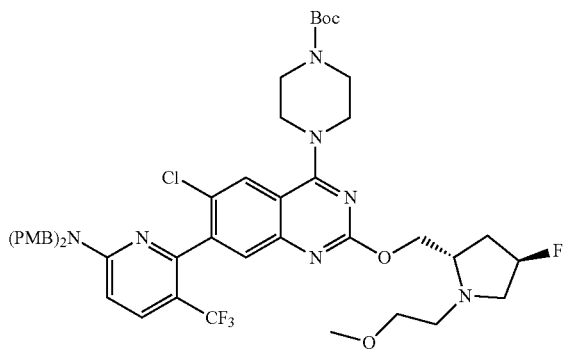

A solution of [(2S,4R)-4-fluoro-1-(2-methoxyethyl)pyrrolidin-2-yl]methanol (250.86 mg, 1.42 mmol) in tetrahydrofuran (27.84 mL) was added sodium hydride (188.74 mg, 4.72 mmol, 60% dispersion in mineral oil) at 0° C. and stirred at 25° C. for 1 hour. tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (362.0 mg, 0.4700 mmol) was added and the reaction was stirred at 25° C. for 1 hour. The reaction was quenched with water and extracted with dichloromethane. The organic layer was collected, dried over anhydrous sodium sulfate, and concentrated. The residue was purified by a reversed-phase chromatography-Column, C18 silica gel; mobile phase, A: water, B:MeCN, B % (5%~70% in 30 min); Detector, UV 254 nm to afford 180 mg (41.3%) of tert-butyl 4-[7-[6-[bis[(4-methoxyphenyl)methyl]amino]-3-(trifluoromethyl)-2-pyridyl]-6-chloro-2-[[(2S,4R)-4-fluoro-1-(2-methoxyethyl)pyrrolidin-2-yl]methoxy]quinazolin-4-yl]piperazine-1-carboxylate as a yellow solid. LC-MS: (ESI, m/z): 924.5 [M+H]+

Step 5: 6-[6-chloro-2-[[(2S,4R)-4-fluoro-1-(2-methoxyethyl)pyrrolidin-2-yl]methoxy]-4-piperazin-1-yl-quinazolin-7-yl]-5-(trifluoromethyl)pyridin-2-amine

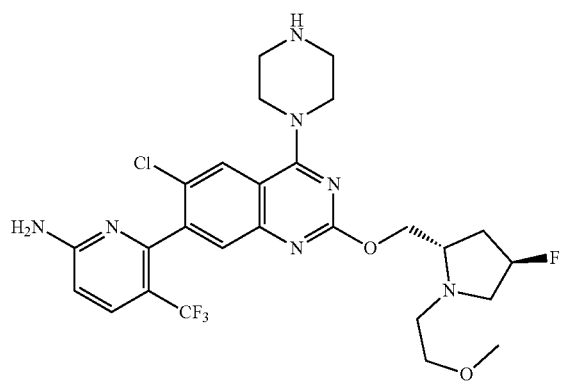 [SMILES: COCCN1C[C@H](F)C[C@H]1COc1nc(N2CCNCC2)c2cc(Cl)c(-c3nc(N)ccc3C(F)(F)F)cc2n1]

A solution of tert-butyl 4-[7-[6-[bis[(4-methoxyphenyl)methyl]amino]-3-(trifluoromethyl)-2-pyridyl]-6-chloro-2-[[(2S,4R)-4-fluoro-1-(2-methoxyethyl)pyrrolidin-2-yl]methoxy]quinazolin-4-yl]piperazine-1-carboxylate (164.0 mg, 0.18 mmol) in trifluoroacetic acid (23 mL) was stirred at 50° C. for 5 hours. Upon completion, the reaction was concentrated. The pH was adjusted to 10 with N,N-diisopropylethylamine. The residue was purified by a reversed-phase chromatography-Column, C18 silica gel; mobile phase, A: water, B:MeCN, B % (5% 70% in 30 min); Detector, UV 254 nm to afford 60 mg (57.9%) of 6-[6-chloro-2-[[(2S,4R)-4-fluoro-1-(2-methoxyethyl)pyrrolidin-2-yl]methoxy]-4-piperazin-1-yl-quinazolin-7-yl]-5-(trifluoromethyl)pyridin-2-amine as a yellow solid. LC-MS: (ESI, m/z): 584.2 [M+H]+

Step 6: 1-[4-[7-[6-amino-3-(trifluoromethyl)-2-pyridyl]-6-chloro-2-[[(2S,4R)-4-fluoro-1-(2-methoxyethyl)pyrrolidin-2-yl]methoxy]quinazolin-4-yl]piperazin-1-yl]prop-2-en-1-one

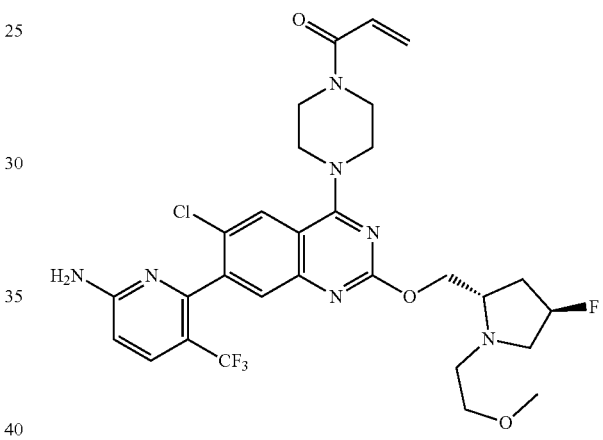

To a solution of 6-[6-chloro-2-[[(2S,4R)-4-fluoro-1-(2-methoxyethyl)pyrrolidin-2-yl]methoxy]-4-piperazin-1-yl-quinazolin-7-yl]-5-(trifluoromethyl)pyridin-2-amine (48.0 mg, 0.0800 mmol) and N,N-diisopropylethylamine (42.41 mg, 0.3300 mmol) in dichloromethane (4 mL) was added acryloyl chloride (4.46 mg, 0.0500 mmol) at −78° C. and stirred at −78° C. for 1 hour. The reaction was quenched with water and extracted with dichloromethane. Then the organic layer was dried over anhydrous sodium sulfate and concentrated. The crude product was purified directly by Prep-HPLC-Column, XBridge Prep C18 OBD Column19*15 mm 5 umC-0013; mobile phase, A: ammonium bicarbonate and NH$_3$.H$_2$O in water, B: ACN and B % (51%~73% in 7 min); Detector, UV 254 nm to afford 17 mg (32.4%) of 1-[4-[7-[6-amino-3-(trifluoromethyl)-2-pyridyl]-6-chloro-2-[[(2S,4R)-4-fluoro-1-(2-methoxyethyl)pyrrolidin-2-yl]methoxy]quinazolin-4-yl]piperazin-1-yl]prop-2-en-1-one as a white solid. LC-MS: (ESI, m/z): 638.2 [M+H]+

Example 89

$^1$H NMR (400 MHz, DMSO-d$_6$, ppm) δ 8.04 (s, 1H), 7.77 (d, J=9.2 Hz, 1H), 7.46 (s, 1H), 6.89 (s, 2H), 6.86-6.72 (m, 1H), 6.59 (d, J=8.8 Hz, 1H), 6.19 (d, J=2.4 Hz, 1H), 5.73 (dd, J=12.4, 2.0 Hz, 1H), 5.18 (d, J=48 Hz, 1H), 4.43-4.31 (m, 1H), 4.30-4.18 (m, 1H), 3.98-3.58 (m, 8H), 3.52-3.42

(m, 1H), 3.41-3.37 (m, 2H), 3.22-3.13 (m, 4H), 3.13-3.05 (m, 1H), 2.72-2.57 (m, 2H), 2.21-2.09 (m, 1H), 1.98-1.78 (m, 1H). LC-MS: (ESI, m/z): 638.2 [M+H]⁺.

Example 90

1-[4-[7-[6-amino-3-(trifluoromethyl)-2-pyridyl]-6-chloro-2-[[(2S,4R,5S)-4-fluoro-1,5-dimethyl-pyrrolidin-2-yl]methoxy]quinazolin-4-yl]piperazin-1-yl]prop-2-en-1-one Synthetic Route

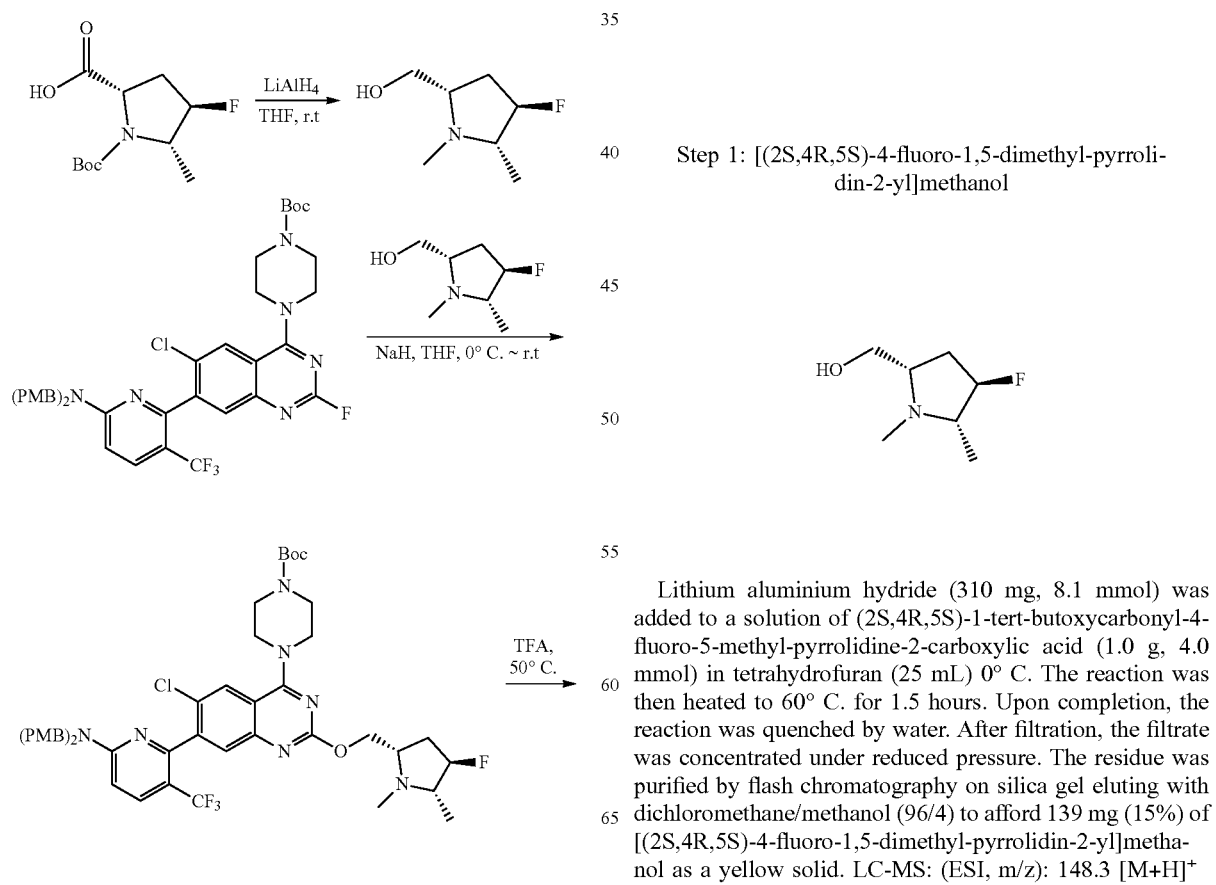

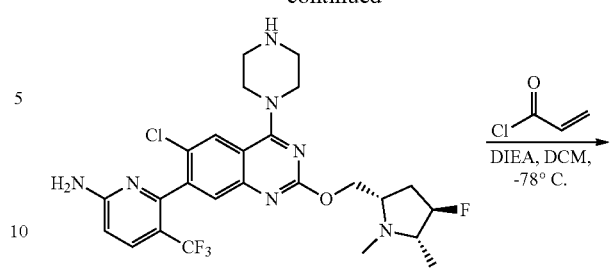

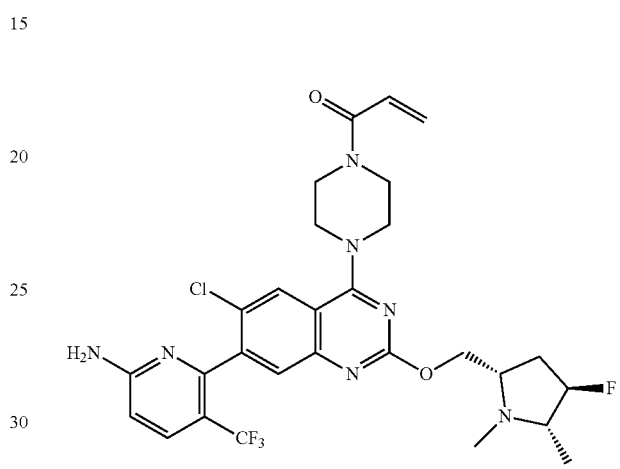

Step 1: [(2S,4R,5S)-4-fluoro-1,5-dimethyl-pyrrolidin-2-yl]methanol

Lithium aluminium hydride (310 mg, 8.1 mmol) was added to a solution of (2S,4R,5S)-1-tert-butoxycarbonyl-4-fluoro-5-methyl-pyrrolidine-2-carboxylic acid (1.0 g, 4.0 mmol) in tetrahydrofuran (25 mL) 0° C. The reaction was then heated to 60° C. for 1.5 hours. Upon completion, the reaction was quenched by water. After filtration, the filtrate was concentrated under reduced pressure. The residue was purified by flash chromatography on silica gel eluting with dichloromethane/methanol (96/4) to afford 139 mg (15%) of [(2S,4R,5S)-4-fluoro-1,5-dimethyl-pyrrolidin-2-yl]methanol as a yellow solid. LC-MS: (ESI, m/z): 148.3 [M+H]⁺

Step 2: tert-butyl 4-[7-[6-[bis[(4-methoxyphenyl)methyl]amino]-3-(trifluoromethyl)-2-pyridyl]-6-chloro-2-[[(2S,4R,5S)-4-fluoro-1,5-dimethyl-pyrrolidin-2-yl]methoxy]quinazolin-4-yl]piperazine-1-carboxylate

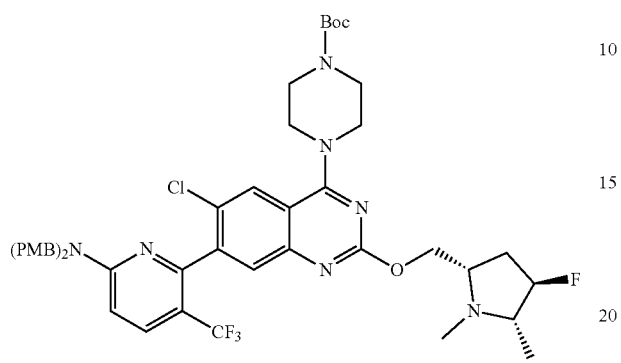

A solution of [(2S,4R,5S)-4-fluoro-1,5-dimethyl-pyrrolidin-2-yl]methanol (95.9 mg, 0.66 mmol) in tetrahydrofuran (8 mL) was added sodium hydride (62.56 mg, 1.56 mmol) at 0° C. and the mixture was stirred 30 minutes. tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (200.0 mg, 0.26 mmol) was added and stirred at 25° C. for 1 hour. The reaction was quenched with water and extracted with dichloromethane. The organic layer was dried over anhydrous sodium sulfate and concentrated. The residue was purified by flash chromatography on silica gel eluting with dichloromethane/methanol (97/3) to afford 170 mg (72.9%) of tert-butyl 4-[7-[6-[bis[(4-methoxyphenyl)methyl]amino]-3-(trifluoromethyl)-2-pyridyl]-6-chloro-2-[[(2S,4R,5S)-4-fluoro-1,5-dimethyl-pyrrolidin-2-yl]methoxy]quinazolin-4-yl]piperazine-1-carboxylate as a yellow solid. LC-MS: (ESI, m/z): 894.5 [M+H]⁺

Step 3: 6-[6-chloro-2-[[(2S,4R,5S)-4-fluoro-1,5-dimethyl-pyrrolidin-2-yl]methoxy]-4-piperazin-1-yl-quinazolin-7-yl]-5-(trifluoromethyl)pyridin-2-amine

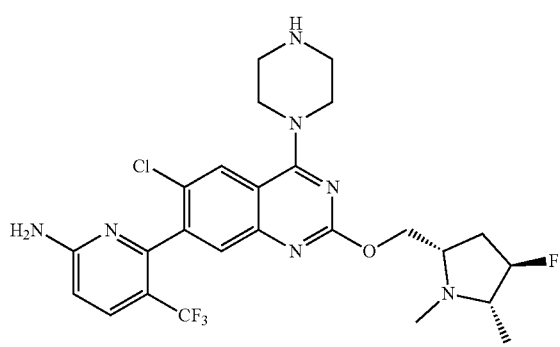 [SMILES: C[C@H]1[C@H](F)C[C@@H](COc2nc(N3CCNCC3)c3cc(Cl)c(-c4nc(N)ccc4C(F)(F)F)cc3n2)N1C]

A solution of tert-butyl 4-[7-[6-[bis[(4-methoxyphenyl)methyl]amino]-3-(trifluoromethyl)-2-pyridyl]-6-chloro-2-[[(2S,4R,5S)-4-fluoro-1,5-dimethyl-pyrrolidin-2-yl]methoxy]quinazolin-4-yl]piperazine-1-carboxylate (170.0 mg, 0.19 mmol) in trifluoroacetic acid (26 mL) was stirred at 50° C. for 3 hours. Upon completion, the reaction was concentrated. The pH was adjusted to 10 with N,N-diisopropylethylamine. The residue was purified by a reversed-phase chromatography-Column, C18 silica gel; mobile phase, A: water, B:MeCN, B % (5% 70% in 30 min); Detector, UV 254 nm to afford 105 mg of 6-[6-chloro-2-[[(2S,4R,5S)-4-fluoro-1,5-dimethyl-pyrrolidin-2-yl]methoxy]-4-piperazin-1-yl-quinazolin-7-yl]-5-(trifluoromethyl)pyridin-2-amine as a light yellow solid. LC-MS: (ESI, m/z): 554.2 [M+H]⁺

Step 4: 1-[4-[7-[6-amino-3-(trifluoromethyl)-2-pyridyl]-6-chloro-2-[[(2S,4R,5S)-4-fluoro-1,5-dimethyl-pyrrolidin-2-yl]methoxy]quinazolin-4-yl]piperazin-1-yl]prop-2-en-1-one

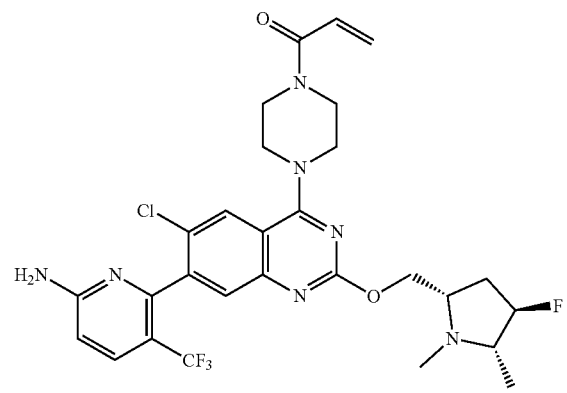 [SMILES: C=CC(=O)N1CCN(c2nc(OC[C@@H]3C[C@@H](F)[C@H](C)N3C)nc3cc(-c4nc(N)ccc4C(F)(F)F)c(Cl)cc23)CC1]

A solution of 6-[6-chloro-2-[[(2S,4R,5S)-4-fluoro-1,5-dimethyl-pyrrolidin-2-yl]methoxy]-4-piperazin-1-yl-quinazolin-7-yl]-5-(trifluoromethyl)pyridin-2-amine (105.0 mg, 0.19 mmol) and N,N-diisopropylethylamine (122.25 mg, 0.95 mmol) in dichloromethane (12 mL) was added acryloyl chloride (10.29 mg, 0.11 mmol) at −78° C. and the mixture was stirred for 1 hour (−78° C.). The reaction was quenched with water and extracted with dichloromethane. Then organic layer was dried over anhydrous sodium sulfate and concentrated. The residue was purified by a reversed-phase chromatography-Column, C18 silica gel; mobile phase, A: water, B:MeCN, B % (40%); Detector, UV 254 nm to afford the crude product which purified by Prep-HPLC-Column, XBridge Prep C18 OBD Column19*15 mm 5 umC-0013; mobile phase, A: FA in water, B: ACN and B % (51%~73% in 7 min); Detector, UV 254 nm to afford 25 mg of (21.7%) of 1-[4-[7-[6-amino-3-(trifluoromethyl)-2-pyridyl]-6-chloro-2-[[(2S,4R,5S)-4-fluoro-1,5-dimethyl-pyrrolidin-2-yl]methoxy]quinazolin-4-yl]piperazin-1-yl]prop-2-en-1-one as white solid. LC-MS: (ESI, m/z): 608.2 [M+H]⁺

Example 90

¹H NMR (400 MHz, Methanol-d₄, ppm) δ 8.10 (s, 1H), 7.81 (d, J=8.0 Hz, 1H), 7.55 (s, 1H), 6.86-6.79 (m, 1H), 6.71 (d, J=8.8 Hz, 1H), 6.29 (dd, J=8.4, 2.0 Hz, 1H), 5.82 (dd, J=10.4, 1.6 Hz, 1H), 4.88-4.62 (m, 1H), 4.54-4.44 (m, 2H), 4.00-3.93 (m, 8H), 3.15-3.11 (m, 1H), 2.75-2.62 (m, 1H), 2.51 (s, 3H), 2.26-1.98 (m, 2H), 1.21 (d, J=6.4 Hz, 3H). LC-MS: (ESI, m/z): 608.2 [M+H]⁺.

Example 91

1-[4-[7-[6-amino-3-(trifluoromethyl)-2-pyridyl]-6-chloro-2-[[(2S)-1-(2-methoxyethyl)pyrrolidin-2-yl]methoxy]quinazolin-4-yl]piperazin-1-yl]prop-2-en-1-one

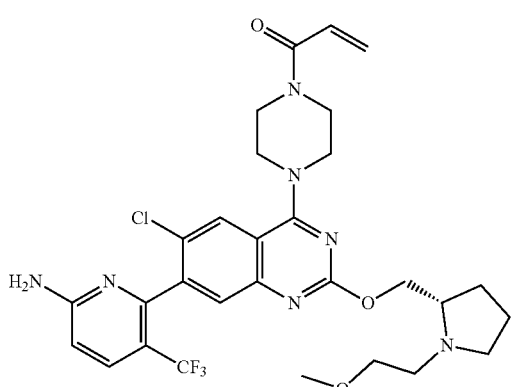

Synthetic Route

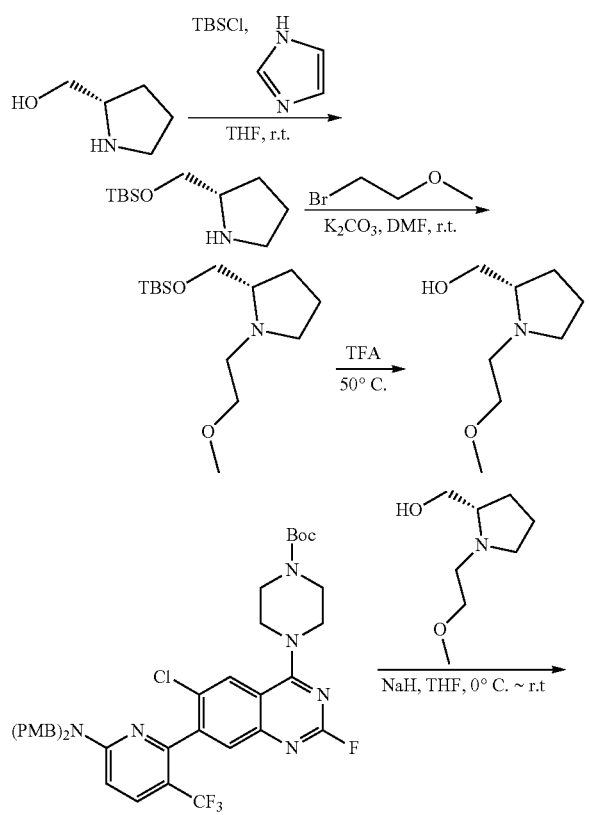

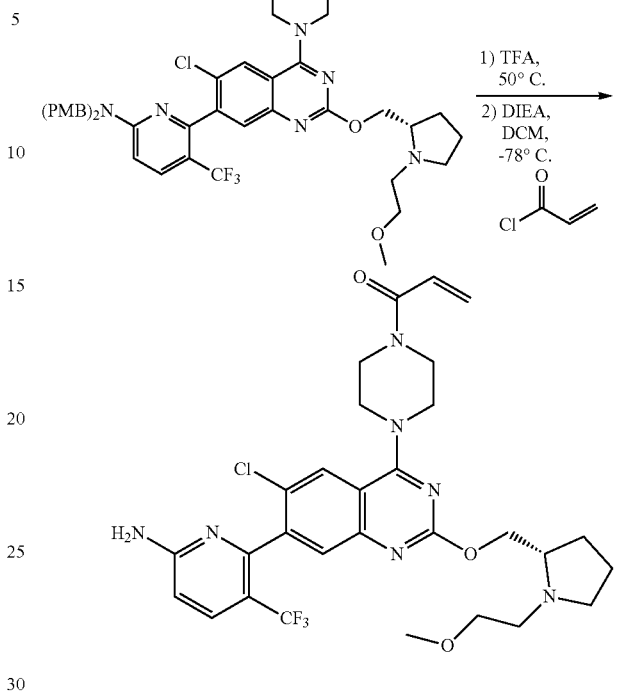

Step 1: tert-butyl-dimethyl-[[(2S)-pyrrolidin-2-yl]methoxy]silane

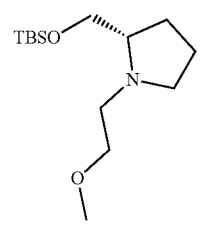

To a mixture of L-prolinol (20 g, 197.73 mmol), imidazole (4 g, 587.54 mmol) in tetrahydrofuran (200 mL) was added tert-butyldimethylchlorosilane (45 g, 298.57 mmol), the mixture was stirred for 2 hours at room temperature. Upon completion, the resulting solution was diluted with water, extracted with dichloromethane and the organic layers were combined. The organic layer was dried over anhydrous sodium sulfate and concentrated to afford crude product which directly used in the next step without purification. LC-MS: (ESI, m/z): 216.2 [M+H]$^+$

Step 2: tert-butyl-[[(2S)-1-(2-methoxyethyl)pyrrolidin-2-yl]methoxy]-dimethyl-silane A mixture of tert-butyl-dimethyl-[[(2S)-pyrrolidin-2-yl]methoxy]silane (3.8 g, 13.93 mmol), 2-bromoethyl methyl ether (3.85 g, 27.7 mmol) and potassium carbonate (5.77 g, 41.81 mmol) in N,N-dimethylformamide (30 mL) was stirred at room temperature for 2 hours. Upon completion, the reaction was diluted with water extracted with dichloromethane. The organic layer was washed with brine, dried over anhydrous sodium sulfate and concentrated to afford crude product. The crude would be directly used in the next step without purification. LC-MS: (ESI, m/z): 274.2 [M+H]$^+$ Step 3: [(2S)-1-(2-methoxyethyl)pyrrolidin-2-yl]methanol

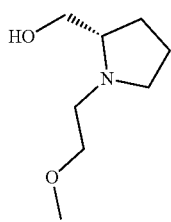

A mixture of tert-butyl-[[(2S)-1-(2-methoxyethyl)pyrrolidin-2-yl]methoxy]-dimethyl-silane (2.0 g, 7.31 mmol) in trifluoroacetic acid (2. mL, 26.93 mmol) was stirred for 4 hours at 50° C. The reaction mixture was adjusted to pH 8 with N,N-diisopropylethylamine. The crude product was purified by Prep-HPLC to afford [(2S)-1-(2-methoxyethyl)pyrrolidin-2-yl]methanol (800 mg, 5.0 mmol, 68.7% yield) as a yellow oil. LC-MS: (ESI, m/z): 160.1 [M+H]$^+$ Step 4: tert-butyl 4-[7-[6-[bis[(4-methoxyphenyl)methyl]amino]-3-(trifluoromethyl)-2-pyridyl]-6-chloro-2-[[(2S)-1-(2-methoxyethyl)pyrrolidin-2-yl]methoxy]quinazolin-4-yl]piperazine-1-carboxylate

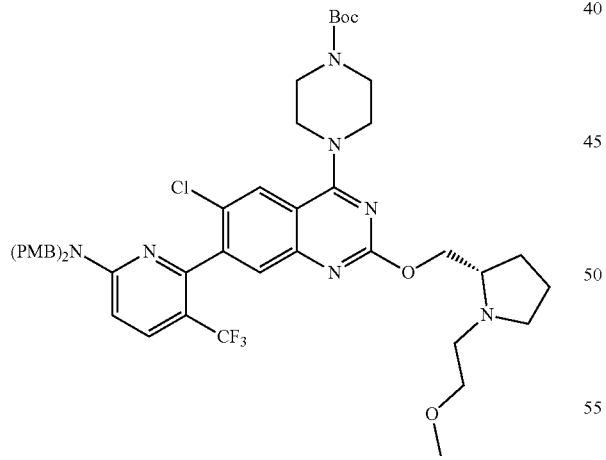

A solution of [(2S)-1-(2-methoxyethyl)pyrrolidin-2-yl]methanol (62.0 mg, 0.39 mmol) in tetrahydrofuran (1 mL) was added sodium hydride (20.0 mg, 0.83 mmol) and stirred at 0° C. for 15 minutes. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (200.0 mg, 0.26 mmol) was added and stirred at room temperature for 2 hours. The reaction was quenched with water and extracted with dichloromethane. The organic layer was concentrated and purified by flash chromatography on silica gel eluting with dichloromethane/methanol (19:1) to afford tert-butyl 4-[7-[6-[bis[(4-methoxyphenyl)methyl]amino]-3-(trifluoromethyl)-2-pyridyl]-6-chloro-2-[[(2S)-1-(2-methoxyethyl)pyrrolidin-2-yl]methoxy]quinazolin-4-yl]piperazine-1-carboxylate (120 mg, 0.125 mmol 50.8% yield) as a yellow solid. LC-MS: (ESI, m/z): 906.4 [M+H]$^+$ Step 5a: 6-[6-chloro-2-[[(2S)-1-(2-methoxyethyl)pyrrolidin-2-yl]methoxy]-4-piperazin-1-yl-quinazolin-7-yl]-5-(trifluoromethyl)pyridin-2-amine

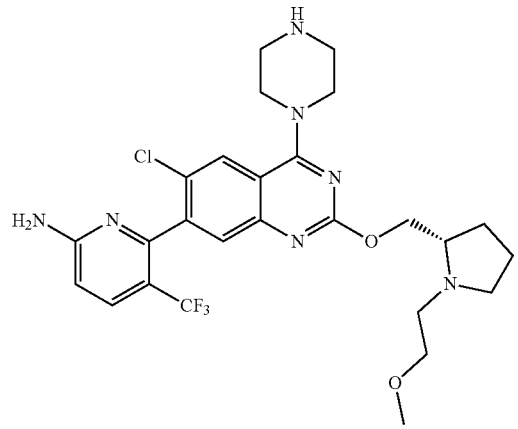 [SMILES: COCCN1CCC[C@H]1COc1nc(N2CCNCC2)c2cc(Cl)c(-c3nc(N)ccc3C(F)(F)F)cc2n1]

To tert-butyl 4-[7-[6-[bis[(4-methoxyphenyl)methyl]amino]-3-(trifluoromethyl)-2-pyridyl]-6-chloro-2-[[(2S)-1-(2-methoxyethyl)pyrrolidin-2-yl]methoxy]quinazolin-4-yl]piperazine-1-carboxylate (150.0 mg, 0.17 mmol) was added trifluoroacetic acid (1 mL, 13.23 mmol). The mixture was stirred for 2 hours at 50° C. The reaction mixture was adjusted to pH 8 with N,N-diisopropylethylamine. The crude product was purified by flash chromatography on silica gel eluting with methanol/water (3/1) to afford 6-[6-chloro-2-[[(2S)-1-(2-methoxyethyl)pyrrolidin-2-yl]methoxy]-4-piperazin-1-yl-quinazolin-7-yl]-5-(trifluoromethyl)pyridin-2-amine (80 mg, 0.14 mmol 85.4% yield) as a yellow oil. LC-MS: (ESI, m/z): 566.2 [M+H]$^+$ Step 5b: 1-[4-[7-[6-amino-3-(trifluoromethyl)-2-pyridyl]-6-chloro-2-[[(2S)-1-(2-methoxyethyl)pyrrolidin-2-yl]methoxy]quinazolin-4-yl]piperazin-1-yl]prop-2-en-1-one

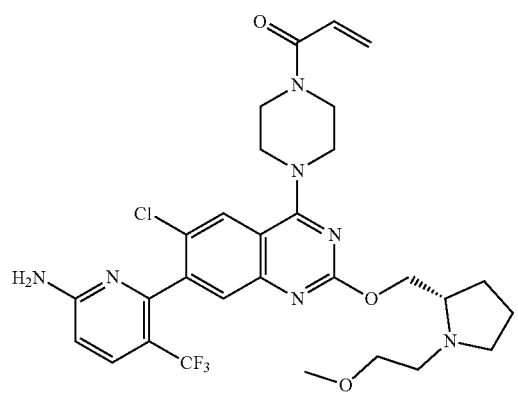 [SMILES: C=CC(=O)N1CCN(c2nc(OC[C@@H]3CCCN3CCOC)nc3cc(-c4nc(N)ccc4C(F)(F)F)c(Cl)cc23)CC1]

To a mixture of 6-[6-chloro-2-[[(2S)-1-(2-methoxyethyl)pyrrolidin-2-yl]methoxy]-4-piperazin-1-yl-quinazolin-7-yl]-5-(trifluoromethyl)pyridin-2-amine (80.0 mg, 0.14 mmol) and N,N-diisopropylethylamine (54 mg, 0.42 mmol) in dichloromethane (1 mL) was added acryloyl chloride (14.0 mg, 0.15 mmol), and the mixture was stirred for 0.5 hours at −78° C. The crude product was purified by Prep-HPLC-Column: XBridge Prep OBD C18 Column, 19*250 mm, 5 um; Mobile Phase A:Water(10 mmol/L NH$_4$HCO$_3$), Mobile Phase B:MeOH-HPLC; Flow rate:25 mL/min; to afford 1-[4-[7-[6-amino-3-(trifluoromethyl)-2-pyridyl]-6-chloro-2-[[(2S)-1-(2-methoxyethyl)pyrrolidin-2-yl]methoxy]quinazolin-4-yl]piperazin-1-yl]prop-2-en-1-one (15.1 mg, 0.024 mmol 17.2% yield) as a white solid.

Example 91

LC-MS: (ESI, m/z): 620.3 [M+H]$^+$, $^1$H NMR (300 MHz, DMSO-d$_6$, ppm) δ 8.04 (s, 1H), 7.78 (d, J=8.9 Hz, 1H), 7.46 (s, 1H), 6.96-6.74 (m, 3H), 6.60 (d, J=8.8 Hz, 1H), 6.17 (dd, J=16.6, 2.4 Hz, 1H), 5.74 (dd, J=10.4, 2.4 Hz, 1H), 4.38-4.27 (m, 1H), 4.15-3.99 (m, 1H), 3.94-3.70 (m, 8H), 3.42 (t, J=6.2 Hz, 3H), 3.21 (s, 3H), 3.09-2.95 (m, 2H), 2.84 (s, 1H), 2.31-2.18 (m, 1H), 1.95-1.80 (m, 1H), 1.75-1.54 (m, 3H).

Example 92

1-[4-[7-[6-amino-3-(trifluoromethyl)-2-pyridyl]-6-chloro-2-[[(2S,4R)-4-(difluoromethoxy)-1-methyl-pyrrolidin-2-yl]methoxy]quinazolin-4-yl]piperazin-1-yl]prop-2-en-1-one

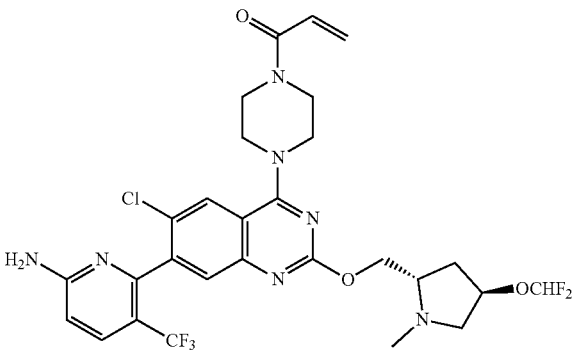 [SMILES: C=CC(=O)N1CCN(c2nc(OC[C@@H]3C[C@@H](OC(F)F)CN3C)nc3cc(-c4nc(N)ccc4C(F)(F)F)c(Cl)cc23)CC1]

Synthetic Route

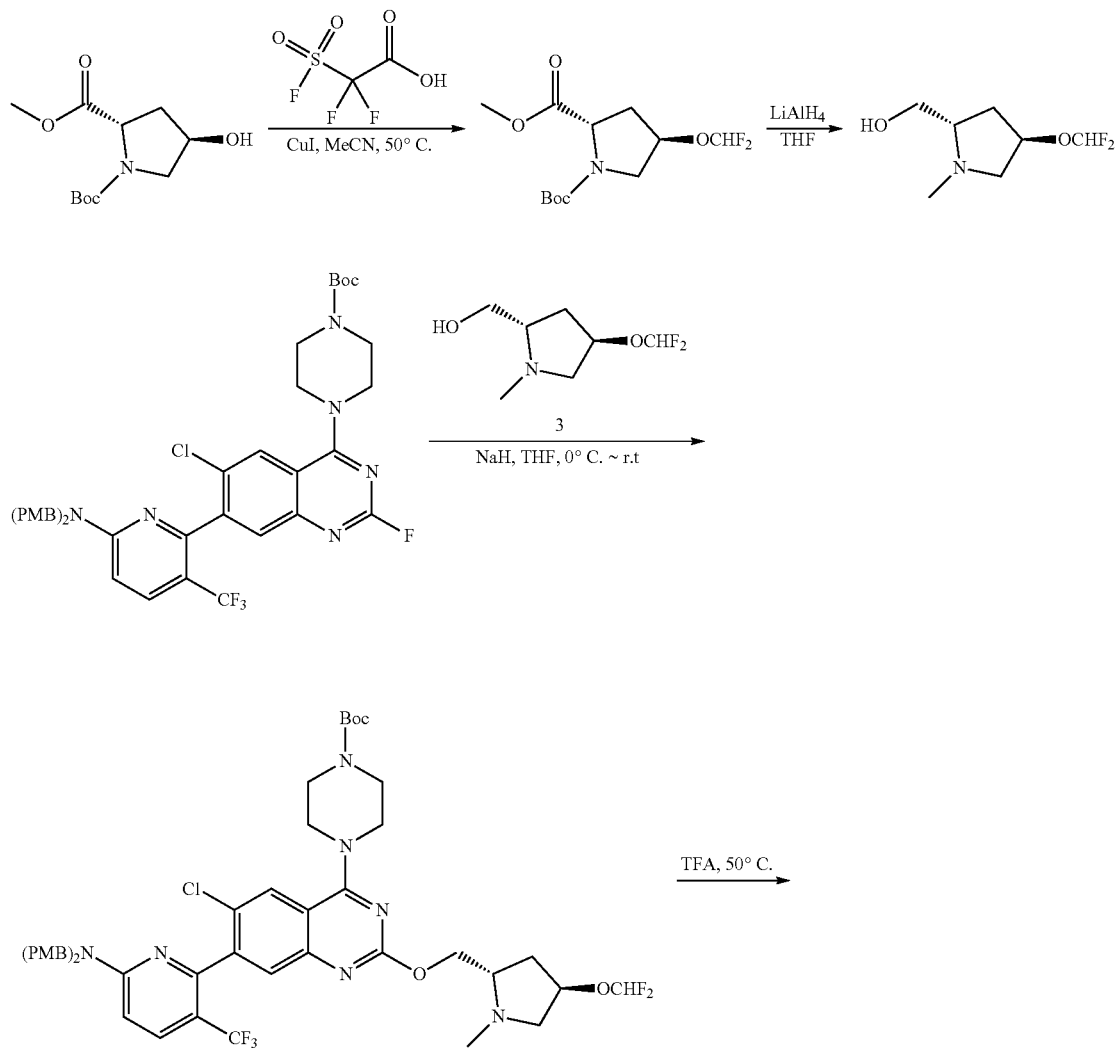

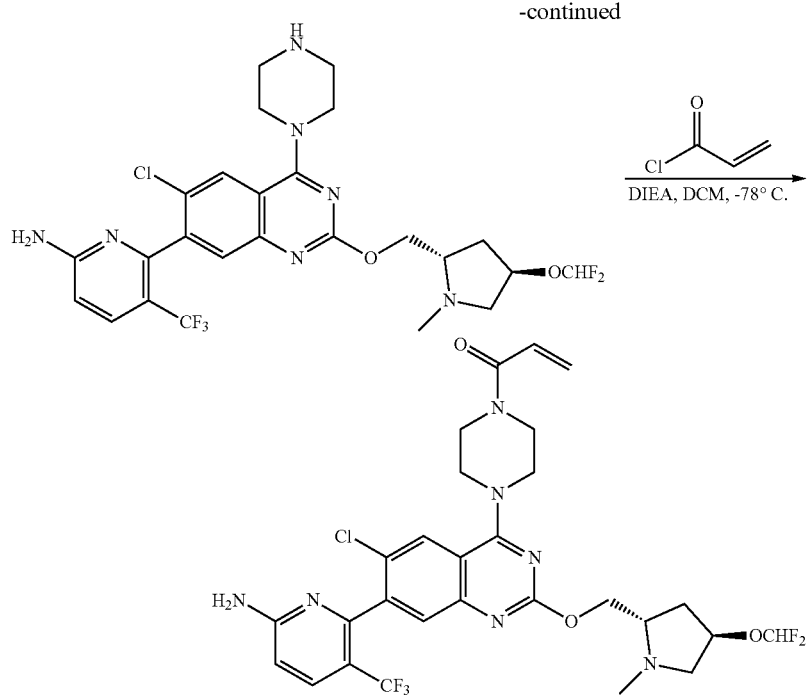

Step 1: 1-(tert-butyl) 2-methyl (2S,4R)-4-(difluoromethoxy)pyrrolidine-1,2-dicarboxylate

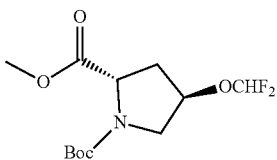 [SMILES: COC(=O)[C@@H]1C[C@@H](OC(F)F)CN1C(=O)OC(C)(C)C]

Under nitrogen, a solution of 1-(tert-butyl) 2-methyl (2S,4R)-4-hydroxypyrrolidine-1,2-dicarboxylate (4.8 g, 19.57 mmol) in acetonitrile (66 mL) was added cuprous iodide (0.74 g, 3.91 mmol) at 25° C. and stirred at 50° C. Then a solution of difluoro(fluorosulfonyl)acetic acid (4.18 g, 23.48 mmol) in acetonitrile (19.8 mL) was added and stirred at 50° C. for 1 hour. The reaction was concentrated and the residue was slurried in ethyl acetate. After filtration, the filtrate was concentrated under reduced pressure. The crude was used in the next reaction. LC-MS: (ESI, m/z): 296.3 [M+H]$^+$

Step 2: ((2S,4R)-4-(difluoromethoxy)-1-methylpyrrolidin-2-yl)methanol

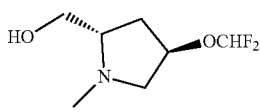

A solution of 1-(tert-butyl) 2-methyl (2S,4R)-4-(difluoromethoxy)pyrrolidine-1,2-dicarboxylate (5.0 g, 16.93 mmol) in tetrahydrofuran (66 mL) was added lithium aluminium hydride (1.29 g, 33.87 mmol) at 0° C. and was stirred at 60° C. for 30 minutes. The reaction was quenched with water and filtered. The filtrate was concentrated purified by silica gel flash chromatography using dichloromethane/methanol (96/4) to afford 320 mg (10.4%) of ((2S,4R)-4-(difluoromethoxy)-1-methylpyrrolidin-2-yl)methanol as a yellow oil. LC-MS: (ESI, m/z): 182.3 [M+H]$^+$

Step 3: tert-butyl 4-[7-[6-[bis[(4-methoxyphenyl)methyl]amino]-3-(trifluoromethyl)-2-pyridyl]-6-chloro-2-[[(2S,4R)-4-(difluoromethoxy)-1-methylpyrrolidin-2-yl]methoxy]quinazolin-4-yl]piperazine-1-carboxylate

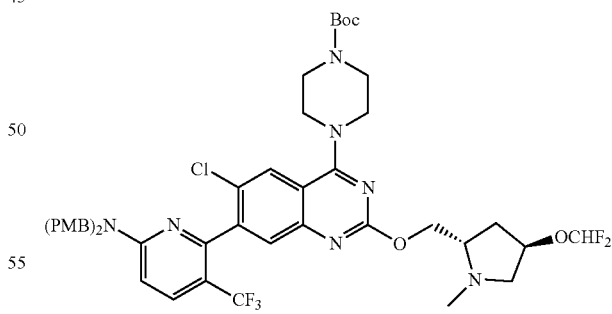

A solution of [(2S,4R)-4-(difluoromethoxy)-1-methylpyrrolidin-2-yl]methanol (183.02 mg, 1.01 mmol) in tetrahydrofuran (16.5 mL) was added sodium hydride (80.81 mg, 2.02 mmol, 60% dispersion in mineral oil) at 0° C. and stirred at 25° C. for 1 hour. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (310.0 mg, 0.40 mmol) was added and stirred at 25° C. for 1 hour. The reaction was quenched with water and extracted with dichloromethane. Then the organic layers were combined, washed with water, dried over anhydrous sodium sulfate and concentrated under vacuum. The residue was purified by flash chromatography on silica gel eluting with dichloromethane/methanol (96/4) to afford 245 mg (65.3%) of tert-butyl 4-[7-[6-[bis[(4-methoxyphenyl)methyl]amino]-3-(trifluoromethyl)-2-pyridyl]-6-chloro-2-[[(2S,4R)-4-(difluoromethoxy)-1-methyl-pyrrolidin-2-yl]methoxy]quinazolin-4-yl]piperazine-1-carboxylate as a yellow solid. LC-MS: (ESI, m/z): 928.5 [M+H]$^+$.

Step 4: 6-[6-chloro-2-[[(2S,4R)-4-(difluoromethoxy)-1-methyl-pyrrolidin-2-yl]methoxy]-4-piperazin-1-yl-quinazolin-7-yl]-5-(trifluoromethyl)pyridin-2-amine

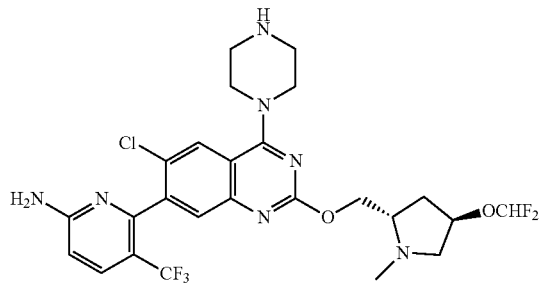 [SMILES: CN1C[C@H](OC(F)F)C[C@H]1COc1nc(N2CCNCC2)c2cc(Cl)c(-c3nc(N)ccc3C(F)(F)F)cc2n1]

A solution of tert-butyl 4-[7-[6-[bis[(4-methoxyphenyl)methyl]amino]-3-(trifluoromethyl)-2-pyridyl]-6-chloro-2-[[(2S,4R)-4-(difluoromethoxy)-1-methyl-pyrrolidin-2-yl]methoxy]quinazolin-4-yl]piperazine-1-carboxylate (229.0 mg, 0.25 mmol) in trifluoroacetic acid (29 mL) was stirred at 50° C. for 3 hours. The reaction was concentrated, the pH adjusted to 10 with N,N-diisopropylethylamine and the mixture was concentrated. The residue was purified by a reversed-phase chromatography-Column, C18 silica gel; mobile phase, A: water, B:MeOH, B % (5% 70% in 30 min); Detector, UV 254 nm to afford 93 mg of 6-[6-chloro-2-[[(2S,4R)-4-(difluoromethoxy)-1-methyl-pyrrolidin-2-yl]methoxy]-4-piperazin-1-yl-quinazolin-7-yl]-5-(trifluoromethyl)pyridin-2-amine as a yellow solid. LC-MS: (ESI, m/z): 588.4 [M+H]$^+$ Step 5: 1-[4-[7-[6-amino-3-(trifluoromethyl)-2-pyridyl]-6-chloro-2-[[(2S,4R)-4-(difluoromethoxy)-1-methyl-pyrrolidin-2-yl]methoxy]quinazolin-4-yl]piperazin-1-yl]prop-2-en-1-one

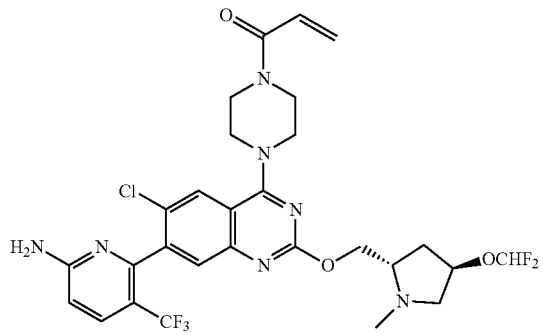 [SMILES: C=CC(=O)N1CCN(c2nc(OC[C@@H]3C[C@@H](OC(F)F)CN3C)nc3cc(-c4nc(N)ccc4C(F)(F)F)c(Cl)cc23)CC1]

To a solution of 6-[6-chloro-2-[[(2S,4R)-4-(difluoromethoxy)-1-methyl-pyrrolidin-2-yl]methoxy]-4-piperazin-1-yl-quinazolin-7-yl]-5-(trifluoromethyl)pyridin-2-amine (87.0 mg, 0.15 mmol) and N,N-diisopropylethylamine (95.44 mg, 0.74 mmol) in dichloromethane (14.5 mL) was added acryloyl chloride (10.71 mg, 0.12 mmol) at −78° C. and stirred at −78° C. for 1 hour. Upon completion, the resulting solution was quenched with water and extracted with dichloromethane. Then the organic layers were combined, washed with water, dried over anhydrous sodium sulfate and concentrated. The residue was purified by a reversed-phase chromatography-Column, C18 silica gel; mobile phase, A: water, B:MeCN, B % (40%); Detector, UV 254 nm. The mixture repurified by Prep-HPLC-Column, XBridge Prep C18 OBD Column19*15 mm 5 umC-0013; mobile phase, A: TFA in water, B: ACN and B % (51%~73% in 7 min); Detector, UV 254 nm to afford 30 mg (31.6%) of 1-[4-[7-[6-amino-3-(trifluoromethyl)-2-pyridyl]-6-chloro-2-[[(2S,4R)-4-(difluoromethoxy)-1-methyl-pyrrolidin-2-yl]methoxy]quinazolin-4-yl]piperazin-1-yl]prop-2-en-1-one as white solid. LC-MS: (ESI, m/z): 642.1 [M+H]$^+$ Example 92

$^1$H NMR (400 MHz, Methanol-d$_4$, ppm) δ 8.14 (s, 1H), 7.82 (d, J=8.8 Hz, 1H), 7.57 (s, 1H), 6.86-6.79 (m, 1H), 6.73-6.71 (m, 1H), 6.52 (s, 1H), 6.33-6.27 (m, 1H), 5.82 (dd, J=10.4, 1.6 Hz, 1H), 4.99-4.98 (m, 1H), 4.77-4.73 (m, 1H), 4.63-4.58 (m, 1H), 3.98 (d, J=3.6 Hz, 8H), 3.83-3.79 (m, 2H), 3.17-3.14 (m, 1H), 2.93 (s, 3H), 2.43-2.33 (m, 2H). LC-MS: (ESI, m/z): 642.1 [M+H]$^+$.

Example 93

1-((3S)-4-(7-(6-amino-4-methyl-3-(trifluoromethyl)pyridin-2-yl)-6-chloro-8-fluoro-2-(((S)-pyrrolidin-2-yl)methoxy)quinazolin-4-yl)-3-methylpiperazin-1-yl)prop-2-en-1-one

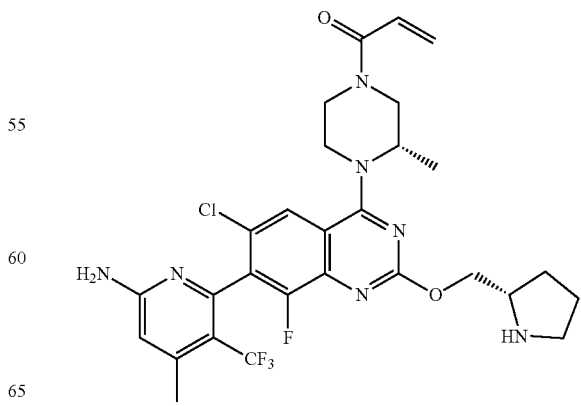

Synthetic Route

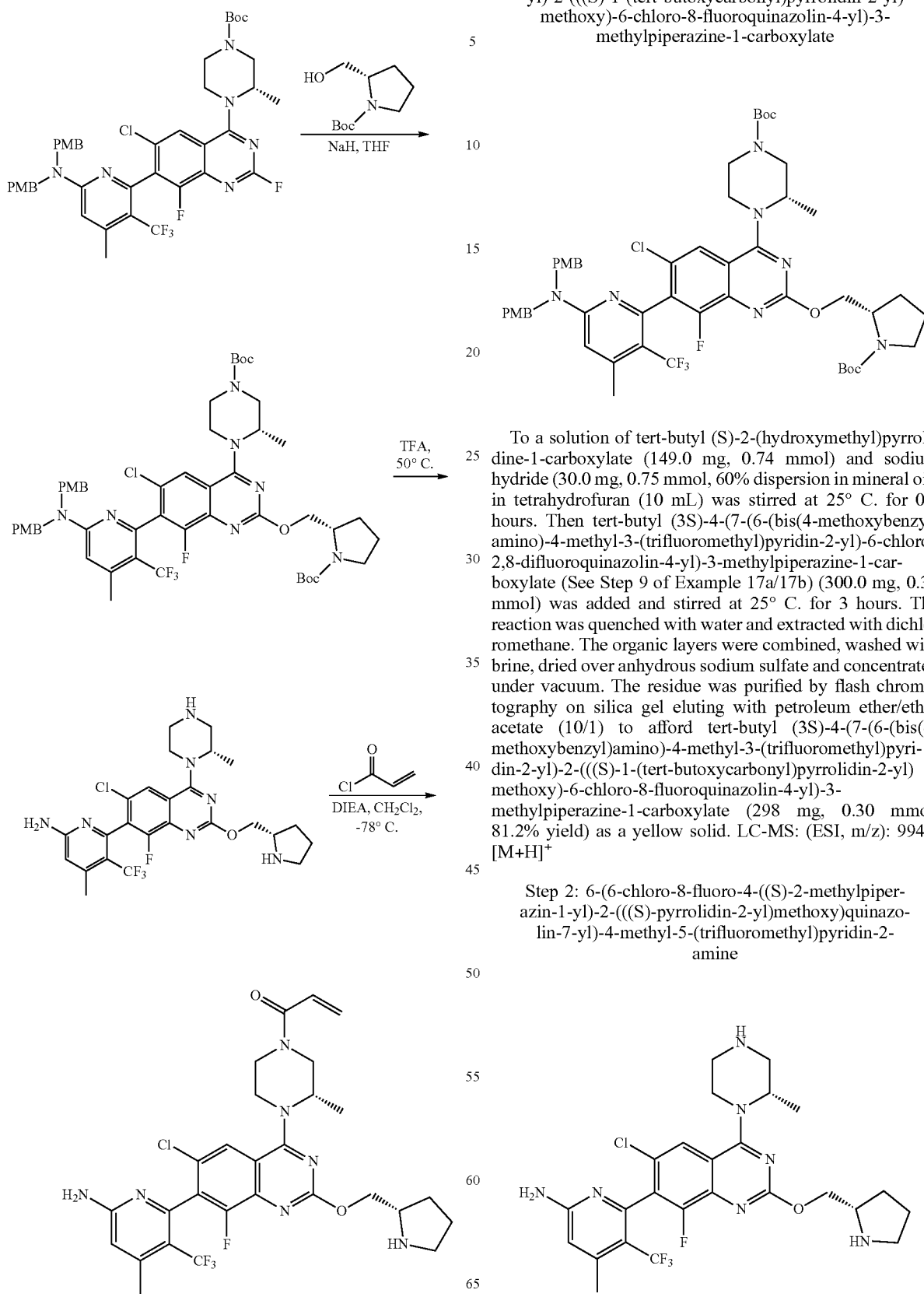

Step 1: tert-butyl (3S)-4-(7-(6-(bis(4-methoxybenzyl)amino)-4-methyl-3-(trifluoromethyl)pyridin-2-yl)-2-(((S)-1-(tert-butoxycarbonyl)pyrrolidin-2-yl)methoxy)-6-chloro-8-fluoroquinazolin-4-yl)-3-methylpiperazine-1-carboxylate To a solution of tert-butyl (S)-2-(hydroxymethyl)pyrrolidine-1-carboxylate (149.0 mg, 0.74 mmol) and sodium hydride (30.0 mg, 0.75 mmol, 60% dispersion in mineral oil) in tetrahydrofuran (10 mL) was stirred at 25° C. for 0.5 hours. Then tert-butyl (3S)-4-(7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate (See Step 9 of Example 17a/17b) (300.0 mg, 0.37 mmol) was added and stirred at 25° C. for 3 hours. The reaction was quenched with water and extracted with dichloromethane. The organic layers were combined, washed with brine, dried over anhydrous sodium sulfate and concentrated under vacuum. The residue was purified by flash chromatography on silica gel eluting with petroleum ether/ethyl acetate (10/1) to afford tert-butyl (3S)-4-(7-(6-(bis(4-methoxybenzyl)amino)-4-methyl-3-(trifluoromethyl)pyridin-2-yl)-2-(((S)-1-(tert-butoxycarbonyl)pyrrolidin-2-yl)methoxy)-6-chloro-8-fluoroquinazolin-4-yl)-3-methylpiperazine-1-carboxylate (298 mg, 0.30 mmol, 81.2% yield) as a yellow solid. LC-MS: (ESI, m/z): 994.4 [M+H]$^+$ Step 2: 6-(6-chloro-8-fluoro-4-((S)-2-methylpiperazin-1-yl)-2-(((S)-pyrrolidin-2-yl)methoxy)quinazolin-7-yl)-4-methyl-5-(trifluoromethyl)pyridin-2-amine A solution of tert-butyl (3S)-4-(7-(6-(bis(4-methoxybenzyl)amino)-4-methyl-3-(trifluoromethyl)pyridin-2-yl)-2-(((S)-1-(tert-butoxycarbonyl)pyrrolidin-2-yl)methoxy)-6-chloro-8-fluoroquinazolin-4-yl)-3-methylpiperazine-1-carboxylate (283.0 mg, 0.28 mmol) in trifluoroacetic acid (10 mL) was stirred at 50° C. for 6 hours. The reaction was concentrated. The residue was purified by flash chromatography on silica gel eluting with dichloromethane/methanol (20/1) to afford 6-(6-chloro-8-fluoro-4-((S)-2-methylpiperazin-1-yl)-2-(((S)-pyrrolidin-2-yl)methoxy)quinazolin-7-yl)-4-methyl-5-(trifluoromethyl)pyridin-2-amine (140 mg, 0.25 mmol, 88.8% yield) as a yellow solid. LC-MS: (ESI, m/z): 554.2 [M+H]$^+$ Step 3: 1-((3S)-4-(7-(6-amino-4-methyl-3-(trifluoromethyl)pyridin-2-yl)-6-chloro-8-fluoro-2-(((S)-pyrrolidin-2-yl)methoxy)quinazolin-4-yl)-3-methylpiperazin-1-yl)prop-2-en-1-one

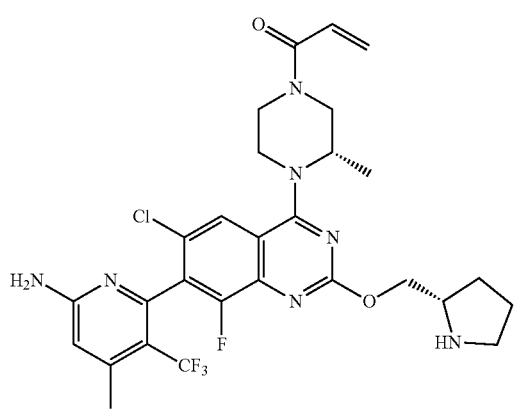 [SMILES: C=CC(=O)N1CCN(c2nc(OC[C@@H]3CCCN3)nc3c(F)c(-c4nc(N)cc(C)c4C(F)(F)F)c(Cl)cc23)[C@@H](C)C1]

A solution of 6-(6-chloro-8-fluoro-4-((S)-2-methylpiperazin-1-yl)-2-(((S)-pyrrolidin-2-yl)methoxy)quinazolin-7-yl)-4-methyl-5-(trifluoromethyl)pyridin-2-amine (70.0 mg, 0.13 mmol) and N,N-diisopropylethylamine (49.0 mg, 0.38 mmol) in dichloromethane (10 mL) was stirred at −78° C. for 5 minutes. Then acryloyl chloride (12.0 mg, 0.13 mmol) was added and stirred at −78° C. for 0.5 hours. After completion, the solution was concentrated under vacuum. The residue was purified by Prep-HPLC to afford 1-((3S)-4-(7-(6-amino-4-methyl-3-(trifluoromethyl)pyridin-2-yl)-6-chloro-8-fluoro-2-(((S)-pyrrolidin-2-yl)methoxy)quinazolin-4-yl)-3-methylpiperazin-1-yl)prop-2-en-1-one (4.3 mg, 0.0071 mmol, 5.6% yield) as a white solid.

Example 93

$^1$H NMR (400 MHz, Methanol-d$_4$, ppm) δ 7.67 (d, J=1.6 Hz, 1H), 6.92-6.73 (m, 1H), 6.60 (s, 1H), 6.29 (d, J=18.0 Hz, 1H), 5.87-5.76 (m, 1H), 4.69 (s, 1H), 4.54 (d, J=16.2 Hz, 1H), 4.41-4.23 (m, 1H), 4.22-3.96 (m, 2H), 3.95-3.81 (m, 1H), 3.80-3.52 (m, 6H), 2.46 (s, 3H), 2.28-1.77 (m, 4H), 1.37 (d, J=6.6 Hz, 3H). LC-MS: (ESI, m/z): 608.2 [M+H]$^+$.

Example 94

(S)-1-(4-(7-(6-amino-3-(trifluoromethyl)pyridin-2-yl)-6-chloro-2-((1-(2,2-difluoroethyl)pyrrolidin-2-yl)methoxy)quinazolin-4-yl)piperazin-1-yl)prop-2-en-1-one

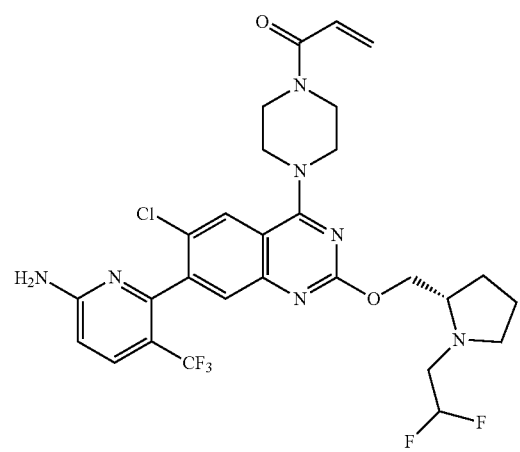 [SMILES: C=CC(=O)N1CCN(c2nc(OC[C@@H]3CCCN3CC(F)F)nc3cc(-c4nc(N)ccc4C(F)(F)F)c(Cl)cc23)CC1]

Synthetic Route

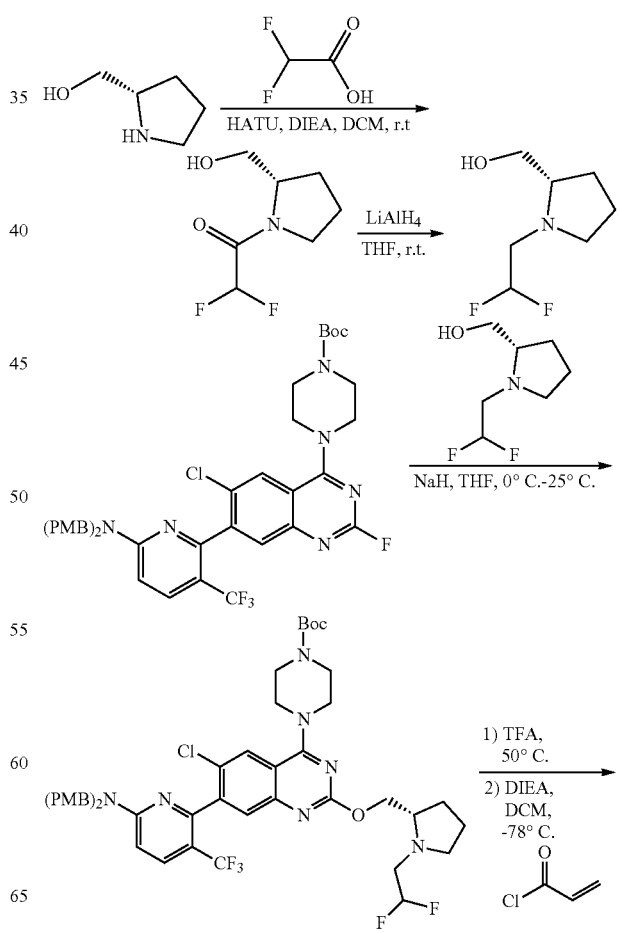

-continued

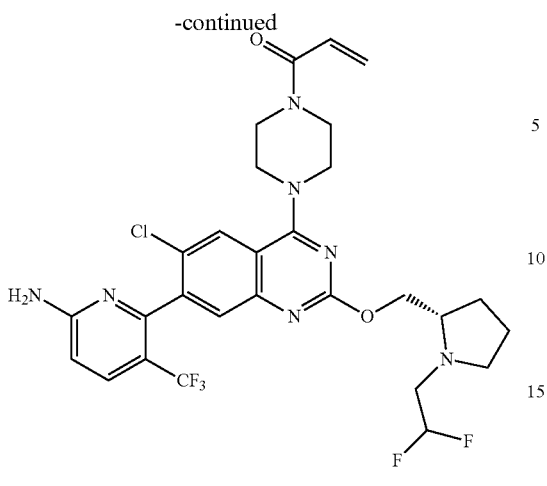

Step 1: (S)-2,2-difluoro-1-(2-(hydroxymethyl)pyrrolidin-1-yl)ethan-1-one

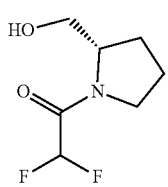 [SMILES: O=C(C(F)F)N1CCC[C@H]1CO]

A solution of (S)-pyrrolidin-2-ylmethanol (5.0 g, 49.4 mmol), 2,2-difluoroacetic acid (7.1 g, 74.1 mmol), HATU (28.2 g, 74.1 mmol) and N,N-diisopropylethylamine (19.1 g, 148.3 mmol) in dichloromethane (50 mL) was stirred at 20° C. for 1 hours. The reaction mixture was washed saturated sodium chloride (200 mL), dried (Na$_2$SO$_4$), filtered, and concentrated to afford (S)-2,2-difluoro-1-(2-(hydroxymethyl)pyrrolidin-1-yl)ethan-1-one (8.0 g, 44.7 mmol, 90.3% yield) as a brown oil. LC-MS: (ESI, m/z): 178.1 [M–H]$^+$ Step 2: (S)-(1-(2,2-difluoroethyl)pyrrolidin-2-yl)methanol

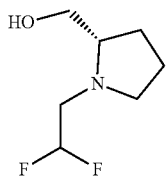

A solution of (S)-2,2-difluoro-1-(2-(hydroxymethyl)pyrrolidin-1-yl)ethan-1-one (5.0 g, 27.9 mmol) and lithium aluminum hydride (4.2 g, 111.6 mmol) in tetrahydrofuran (40 mL) was stirred at 20° C. for 1 hours. The reaction was quenched with aqueous ammonium chloride (40 mL). The mixture was filtered, and the filtrate was extracted with dichloromethane (5×40 mL). The organic layers were combined, dried with sodium sulfate, and concentrated to afford (S)-(1-(2,2-difluoroethyl)pyrrolidin-2-yl)methanol (380 mg, 2.3005 mmol, 8.2% yield) as a yellow solid. LC-MS: (ESI, m/z): 166.1 [M+H]$^+$ Step 3: tert-butyl (S)-4-(7-(6-(bis(4-methoxybenzyl)amino)-3-(trifluoromethyl)pyridin-2-yl)-6-chloro-2-((1-(2,2-difluoroethyl)pyrrolidin-2-yl)methoxy)quinazolin-4-yl)piperazine-1-carboxylate

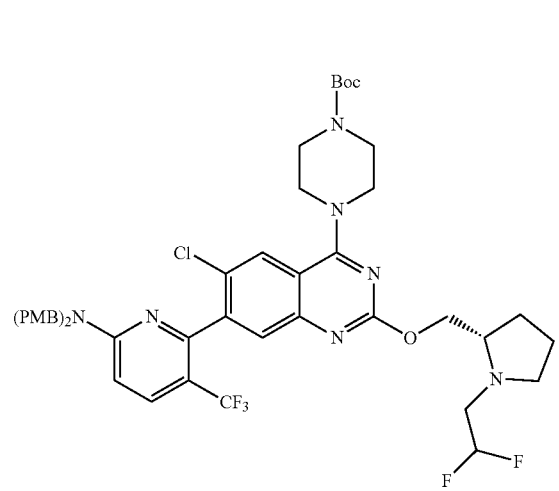

Sodium hydride (124.0 mg, 3.1 mmol) was added to a solution of (S)-(1-(2,2-difluoroethyl)pyrrolidin-2-yl)methanol (320.0 mg, 1.9 mmol) in tetrahydrofuran (8 mL). Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (297 mg, 0.4 mmol) was added and the reaction was stirred at 25° C. for 1 hour. The reaction was quenched with aqueous ammonium chloride (20 mL) and then extracted with dichloromethane. The organic layers was dried over anhydrous sodium sulfate and concentrated under vacuum. The residue was purified by silica gel flash chromatography using dichloromethane/methanol (10/1) to afford tert-butyl (S)-4-(7-(6-(bis(4-methoxybenzyl)amino)-3-(trifluoromethyl)pyridin-2-yl)-6-chloro-2-((1-(2,2-difluoroethyl)pyrrolidin-2-yl)methoxy)quinazolin-4-yl)piperazine-1-carboxylate (320 mg, 0.35 mmol, 18.1% yield) as a yellow solid. LC-MS: (ESI, m/z): 912.3 [M+H]$^+$.

Step 4: (S)-1-(4-(7-(6-amino-3-(trifluoromethyl)pyridin-2-yl)-6-chloro-2-((1-(2,2-difluoroethyl)pyrrolidin-2-yl)methoxy)quinazolin-4-yl)piperazin-1-yl)prop-2-en-1-one

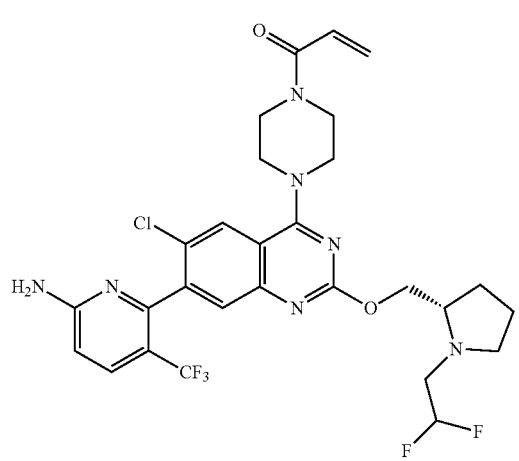 [SMILES: C=CC(=O)N1CCN(c2nc(OC[C@@H]3CCCN3CC(F)F)nc3cc(-c4nc(N)ccc4C(F)(F)F)c(Cl)cc23)CC1]

A solution of tert-butyl (S)-4-(7-(6-(bis(4-methoxybenzyl)amino)-3-(trifluoromethyl)pyridin-2-yl)-6-chloro-2-((1-(2,2-difluoroethyl)pyrrolidin-2-yl)methoxy)quinazolin-4-yl)piperazine-1-carboxylate (150.0 mg, 0.16 mmol) in trifluoroacetic acid (16 mL) was stirred at 50° C. for 12 hours and concentrated. Then resulting oil was dissolved in dichloromethane (9 mL) and N,N-diisopropylethylamine (424.0 mg, 3.3 mmol) was added. Acryloyl chloride (13.0 mg, 0.14 mmol) was added to the resulting mixture at −78° C. and the reaction was stirred for 15 minutes. The reaction was quenched with saturated ammonium chloride (30 mL). The reaction was extracted with dichloromethane (5×25 mL) and the organic layers were combined. The organic layer was dried over anhydrous sodium sulfate, filtered, and concentrated. The crude product was purified by Prep-HPLC to afford (S)-1-(4-(7-(6-amino-3-(trifluoromethyl)pyridin-2-yl)-6-chloro-2-((1-(2,2-difluoroethyl)pyrrolidin-2-yl)methoxy)quinazolin-4-yl)piperazin-1-yl)prop-2-en-1-one (33.9 mg, 0.05 mmol, 32.9% yield) as a white solid. LC-MS (ESI, m/z): 626.3 [M+H]⁺.

Example 94

¹H NMR (400 MHz, DMSO-d₆, ppm) δ 8.04 (s, 1H), 7.78 (d, J=8.8 Hz, 1H), 7.46 (s, 1H), 6.90 (s, 2H), 6.82 (dd, J=10.4, 10.8 Hz, 1H), 6.60 (d, J=8.8 Hz, 1H), 6.24-5.88 (m, 2H), 5.79-5.68 (m, 1H), 4.38-4.24 (m, 1H), 4.20-4.07 (m, 1H), 3.92-3.68 (m, 8H), 3.39-3.21 (m, 1H), 3.16-3.06 (m, 1H), 3.05-2.95 (m, 1H), 2.90-2.74 (m, 1H), 2.45-2.37 (m, 1H), 1.98-1.86 (m, 1H), 1.79-1.68 (m, 2H), 1.67-1.56 (m, 1H).

Example 95

1-(4-(7-(6-amino-3-(trifluoromethyl)pyridin-2-yl)-6-chloro-2-(((2S,4R)-4-methoxy-1-(2-methoxyethyl)pyrrolidin-2-yl)methoxy)quinazolin-4-yl)piperazin-1-yl)prop-2-en-1-one

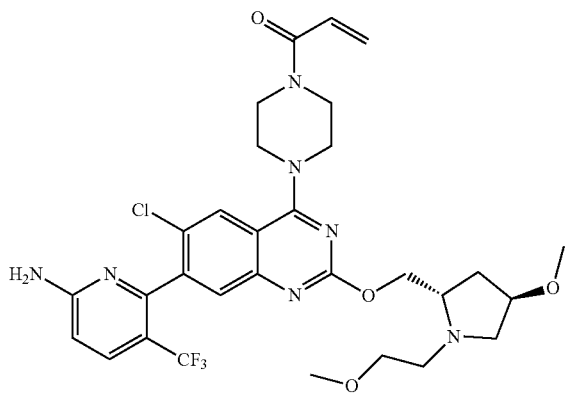 [SMILES: C=CC(=O)N1CCN(c2nc(OC[C@@H]3C[C@@H](OC)CN3CCOC)nc3cc(-c4nc(N)ccc4C(F)(F)F)c(Cl)cc23)CC1]

Synthetic Route

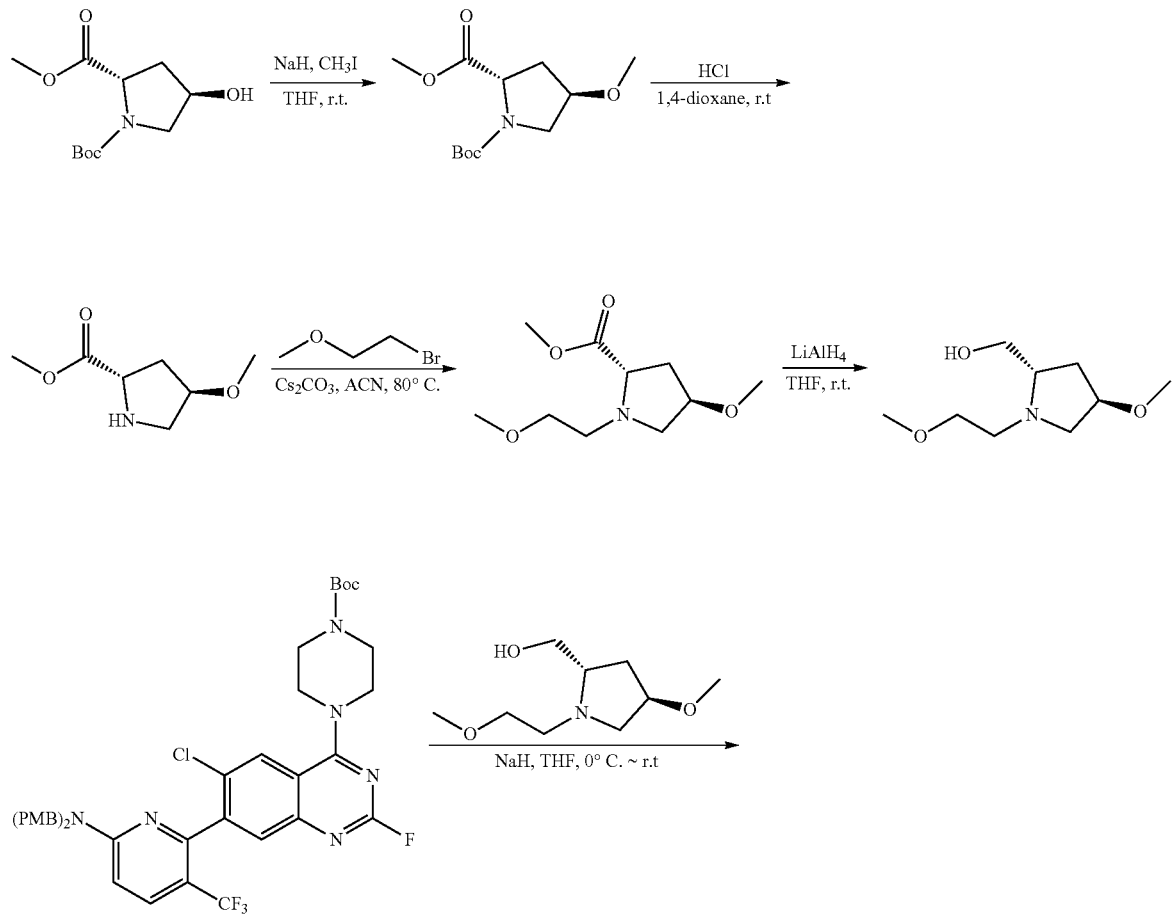

613

614

-continued

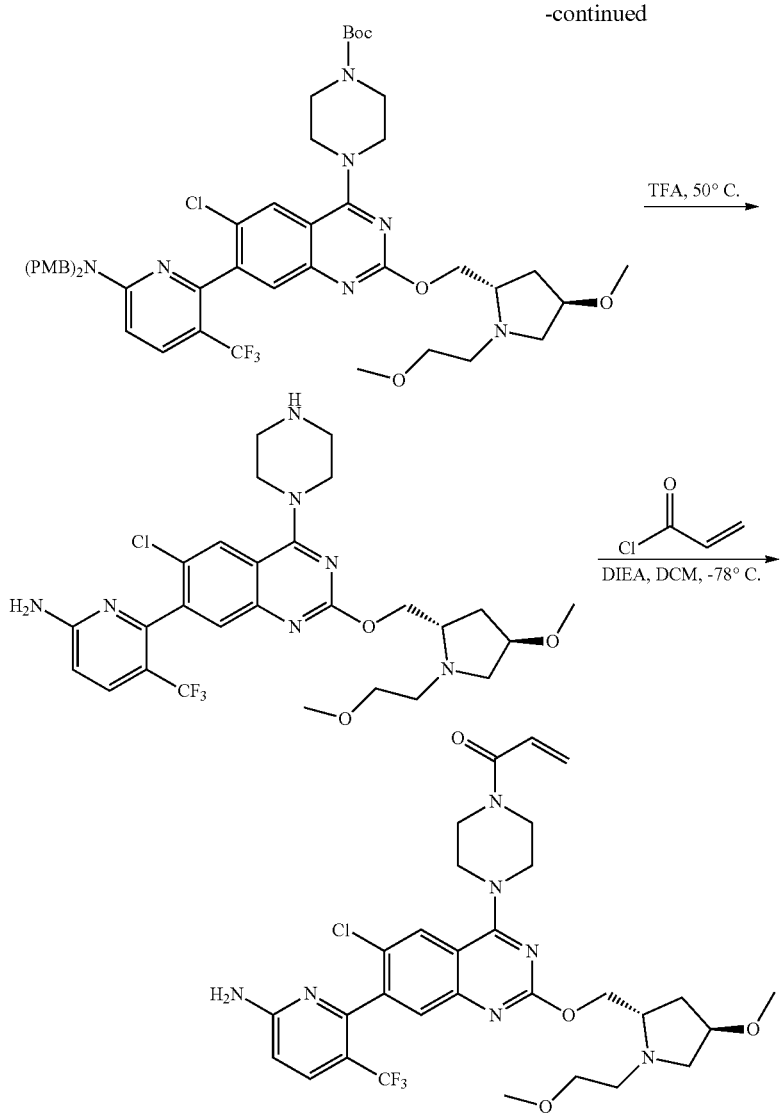

Step 1: 1-(tert-butyl) 2-methyl (2S,4R)-4-methoxy-pyrrolidine-1,2-dicarboxylate

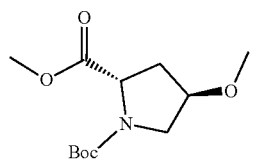

A solution of 1-(tert-butyl) 2-methyl (2S,4R)-4-hydroxy-pyrrolidine-1,2-dicarboxylate (30.0 g, 122.3 mmol) and sodium hydride (5.88 g, 245 mmol) in tetrahydrofuran (1.3 L) was stirred at 20° C. for 0.5 hours. Iodomethane (34.74 g, 244.7 mmol) was added and the reaction was stirred at 20° C. for 1 hours. The reaction was quenched with aqueous ammonium chloride (300 mL). The resulting mixture was extracted with ethyl acetate, dried over anhydrous sodium sulfate, filtered, and concentrated to afford 1-(tert-butyl) 2-methyl (2S,4R)-4-methoxypyrrolidine-1,2-dicarboxylate (22 g, 84.8 mmol, 69.4% yield) as a brown oil. LC-MS: (ESI, m/z): 260.3 [M+H]$^+$

Step 2: methyl (2S,4R)-4-methoxypyrrolidine-2-carboxylate

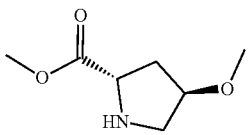

A solution of 1-(tert-butyl) 2-methyl (2S,4R)-4-methoxy-pyrrolidine-1,2-dicarboxylate (30.0 g, 115.7 mmol) and hydrogen chloride in 1,4-dioxane (200 mL) was stirred at 20° C. for 1.5 hours. The mixture was concentrated under vacuum to afford methyl (2S,4R)-4-methoxypyrrolidine-2-carboxylate (12 g, 75.4 mmol) as a brown solid. LC-MS: (ESI, m/z): 160.2 [M+H]$^+$ Step 3: methyl (2S,4R)-4-methoxy-1-(2-methoxyethyl)pyrrolidine-2-carboxylate

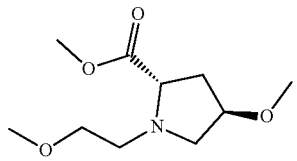

A solution of methyl (2S,4R)-4-methoxypyrrolidine-2-carboxylate (5.0 g, 31.4 mmol) and 1-bromo-2-methoxyethane (6.51 g, 46.8 mmol) and cesium carbonate (20.5 g, 62.9 mmol) in acetonitrile (150 mL) was stirred at 80° C. for 2 hours. After filtration, the filtrate was concentrated under reduced pressure to afford methyl (2S,4R)-4-methoxy-1-(2-methoxyethyl)pyrrolidine-2-carboxylate (4.4 g, 20.252 mmol, 64.5% yield) as a brown oil. LC-MS: (ESI, m/z): 218.3 [M+H]+

Step 4: ((2S,4R)-4-methoxy-1-(2-methoxyethyl)pyrrolidin-2-yl)methanol

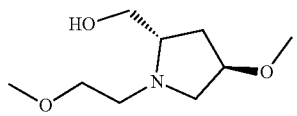

A solution of methyl (2S,4R)-4-methoxy-1-(2-methoxyethyl)pyrrolidine-2-carboxylate (2.0 g, 9.2 mmol) and lithium aluminum hydride (700.0 mg, 18.42 mmol) in tetrahydrofuran (40 mL) was stirred at 20° C. for 1 hours. The reaction was quenched with aqueous ammonium chloride aqueous, and extracted with ethyl acetate. The organic layer was dried over anhydrous sodium sulfate and concentrated to afford ((2S,4R)-4-methoxy-1-(2-methoxyethyl)pyrrolidin-2-yl)methanol (750 mg, 3.963 mmol, 43.1% yield) as a brown oil. LC-MS (ESI, m/z): 190.3 [M+H]+.

Step 5: tert-butyl 4-(7-(6-(bis(4-methoxybenzyl)amino)-3-(trifluoromethyl)pyridin-2-yl)-6-chloro-2-(((2S,4R)-4-methoxy-1-(2-methoxyethyl)pyrrolidin-2-yl)methoxy)quinazolin-4-yl)piperazine-1-carboxylate

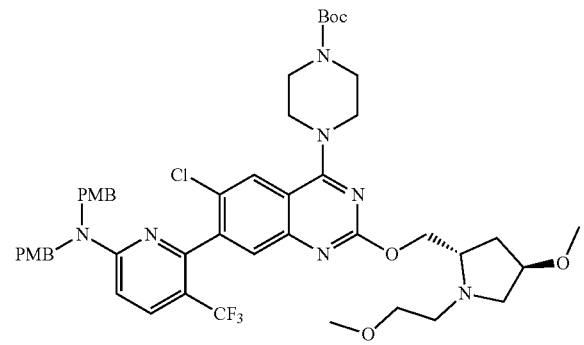

A solution of ((2S,4R)-4-methoxy-1-(2-methoxyethyl)pyrrolidin-2-yl)methanol (650.0 mg, 3.4 mmol) in tetrahydrofuran (20 mL) and sodium hydride (275.0 mg, 6.9 mmol) was added at 0° C. The resulting solution was stirred at 20° C. for 0.5 hours. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (300.0 mg, 0.39 mmol) was added and stirred at 20° C. for 1 hours. The reaction was quenched with aqueous ammonium chloride (15 mL). The resulting mixture was extracted with ethyl acetate. The organic layer was dried over anhydrous sodium sulfate and concentrated. The residue was purified by flash chromatography on silica gel eluting with dichloromethane/methyl alcohol (10/1) to afford tert-butyl 4-(7-(6-(bis(4-methoxybenzyl)amino)-3-(trifluoromethyl)pyridin-2-yl)-6-chloro-2-(((2S,4R)-4-methoxy-1-(2-methoxyethyl)pyrrolidin-2-yl)methoxy)quinazolin-4-yl)piperazine-1-carboxylate (240 mg, 0.26 mmol, 7.5% yield) as a brown solid. LC-MS (ESI, m/z): 936.6 [M+H]+.

Step 6: 6-(6-chloro-2-(((2S,4R)-4-methoxy-1-(2-methoxyethyl)pyrrolidin-2-yl)methoxy)-4-(piperazin-1-yl)quinazolin-7-yl)-5-(trifluoromethyl)pyridin-2-amine

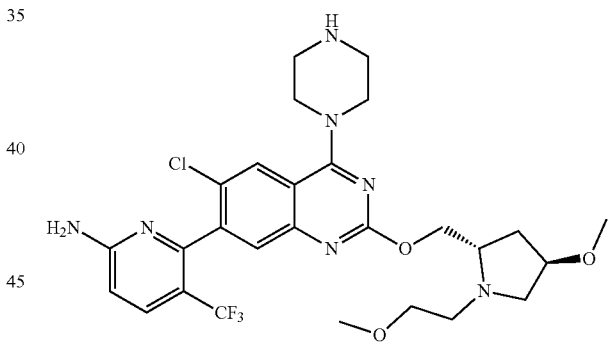

A solution of tert-butyl 4-(7-(6-(bis(4-methoxybenzyl)amino)-3-(trifluoromethyl)pyridin-2-yl)-6-chloro-2-(((2S,4R)-4-methoxy-1-(2-methoxyethyl)pyrrolidin-2-yl)methoxy)quinazolin-4-yl)piperazine-1-carboxylate (230.0 mg, 0.250 mmol) in 2,2,2-trifluoroacetic acid (50 mL) was stirred at 50° C. for 4 hours. The resulting mixture was filtered and the filtrate was concentrated to afford 6-(6-chloro-2-(((2S,4R)-4-methoxy-1-(2-methoxyethyl)pyrrolidin-2-yl)methoxy)-4-(piperazin-1-yl)quinazolin-7-yl)-5-(trifluoromethyl)pyridin-2-amine (120 mg, 0.20 mmol, 81.9% yield) as a brown solid. LC-MS (ESI, m/z): 596.2 [M+H]+.

617

Step 7: 1-(4-(7-(6-amino-3-(trifluoromethyl)pyridin-2-yl)-6-chloro-2-(((2S,4R)-4-methoxy-1-(2-methoxyethyl)pyrrolidin-2-yl)methoxy)quinazolin-4-yl)piperazin-1-yl)prop-2-en-1-one

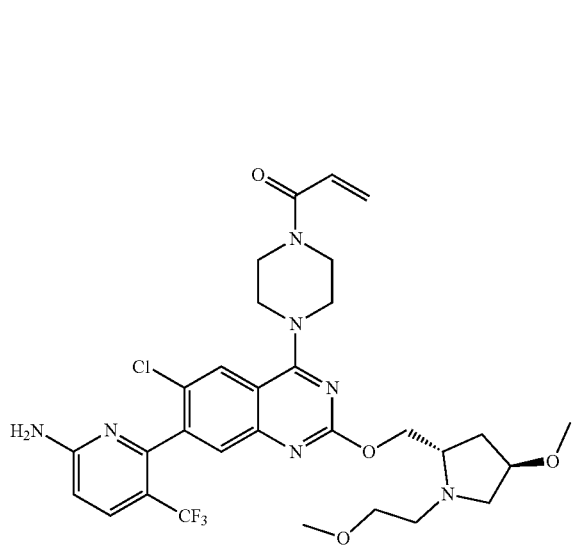 [SMILES: C=CC(=O)N1CCN(c2nc(OC[C@@H]3C[C@@H](OC)CN3CCOC)nc3cc(-c4nc(N)ccc4C(F)(F)F)c(Cl)cc23)CC1]

A solution of 6-(6-chloro-2-(((2S,4R)-4-methoxy-1-(2-methoxyethyl)pyrrolidin-2-yl)methoxy)-4-(piperazin-1-yl)quinazolin-7-yl)-5-(trifluoromethyl)pyridin-2-amine (110 mg, 0.18 mmol) and N,N-diisopropylethylamine (71.0 mg, 0.55 mmol) in dichloromethane (10 mL) was stirred at −78° C. for 5 mins. Acryloyl chloride (15.0 mg, 0.17 mmol) was added and the mixture was stirred at −78° C. for 15 minutes. The reaction was quenched by with aqueous ammonium chloride aqueous (5 mL). The resulting solution was extracted with dichloromethane (5×8 mL) and the organic layers were combined. The organic layer was dried over anhydrous sodium sulfate, filtered, and concentrated. The crude product was purified by Prep-HPLC to afford 1-(4-(7-(6-amino-3-(trifluoromethyl)pyridin-2-yl)-6-chloro-2-(((2S,4R)-4-methoxy-1-(2-methoxyethyl)pyrrolidin-2-yl)methoxy)quinazolin-4-yl)piperazin-1-yl)prop-2-en-1-one (22.2 mg, 0.034 mmol, 18.5% yield) as a white solid. LC-MS (ESI, m/z): 650.4 [M+H]$^+$.

Example 95

$^1$H NMR (400 MHz, Methanol-d$_4$) δ 8.10 (s, 1H), 7.80 (d, J=8.8 Hz, 1H), 7.57 (m, 1H), 6.87-6.76 (m, 1H), 6.70 (d, J=8.8 Hz, 1H), 6.31-6.23 (m, 1H), 5.84-5.77 (m, 1H), 4.63-4.48 (m, 2H), 4.05-3.99 (m, 5H), 3.92 (s, 4H), 3.66-3.36 (m, 5H), 3.33 (s, 5H), 3.29 (d, J=1.2 Hz, 1H), 3.05-2.78 (m, 2H), 2.55-1.88 (m, 2H).

618

Example 96

1-[4-[7-[6-amino-3-(trifluoromethyl)-2-pyridyl]-6-chloro-2-[[(4R)-4-fluoro-1,2-dimethyl-pyrrolidin-2-yl]methoxy]quinazolin-4-yl]piperazin-1-yl]prop-2-en-1-one

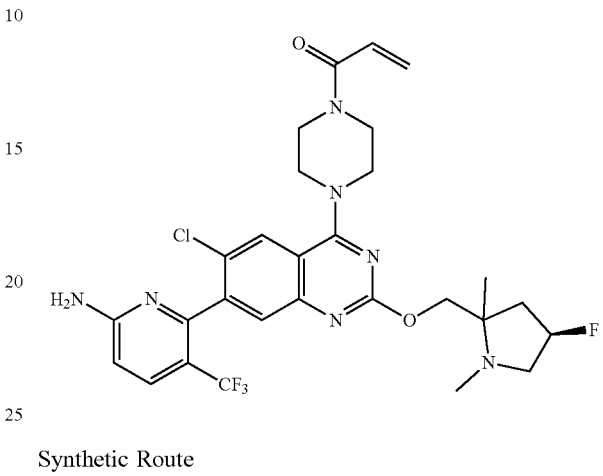

Synthetic Route

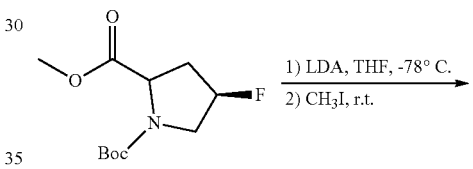

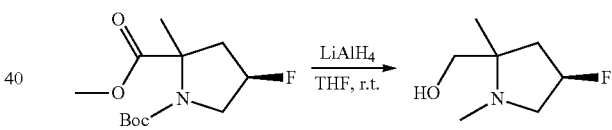

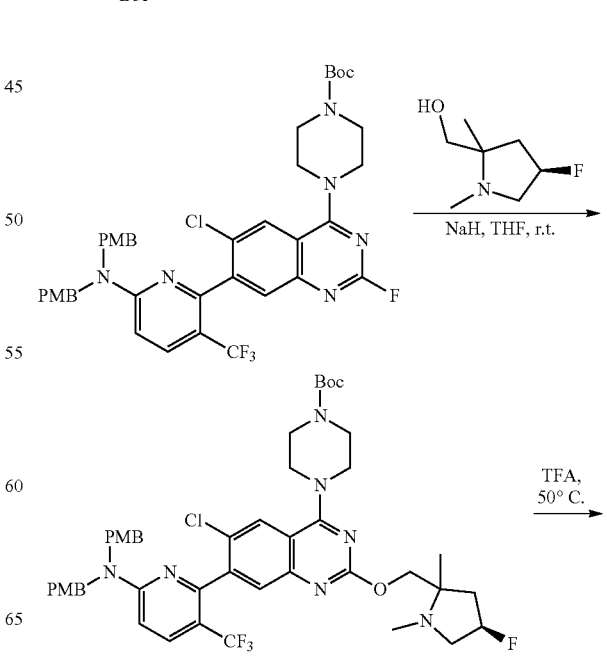

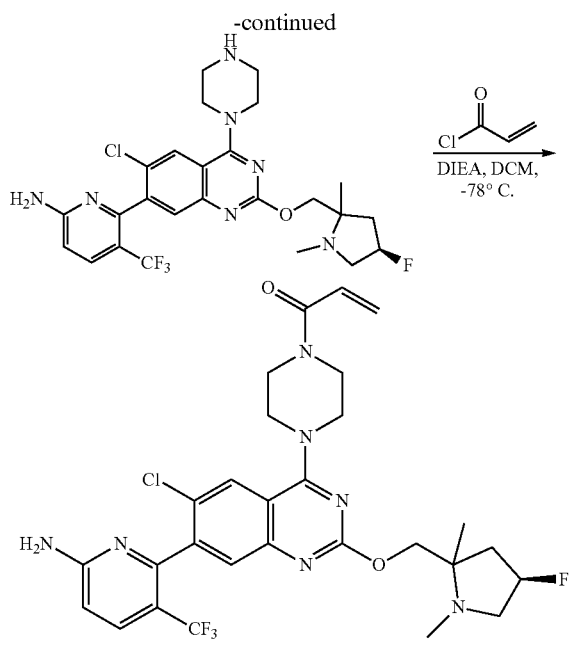

Step 1: 1-(tert-butyl) 2-methyl (4R)-4-fluoro-2-methylpyrrolidine-1,2-dicarboxylate

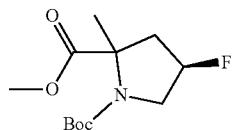 [SMILES: COC(=O)C1(C)C[C@@H](F)CN1C(=O)OC(C)(C)C]

A solution of 1-(tert-butyl) 2-methyl (4R)-4-fluoropyrrolidine-1,2-dicarboxylate (5.00 g, 20.22 mmol) in tetrahydrofuran (19 mL) was added lithium diisopropylamide (12.1 mL, 24.27 mmol, 2.0M in tetrahydrofuran) and stirred at −78° C. for 1 hour. Iodomethane (4.31 g, 30.33 mmol) was added at −78° C. and the reaction stirred at 25° C. for 1 hour. The reaction was concentrated and the crude product was used in the next reaction. LC-MS: (ESI, m/z): 206.1 [M−55]⁺

Step 2: [(4R)-4-fluoro-1,2-dimethyl-pyrrolidin-2-yl]methanol

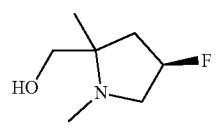

A solution of 1-(tert-butyl) 2-methyl (4R)-4-fluoro-2-methylpyrrolidine-1,2-dicarboxylate (4.00 g, crude) in tetrahydrofuran (75 mL) was added lithium aluminium hydride (1.45 g, 38.27 mmol) at 0° C. and stirred at 25° C. for 1 hour. The reaction was quenched with water, filtered, and the filtrate was concentrated. The resulting mixture was purified by flash chromatography on silica gel eluting with dichloromethane/methanol (96/4) to afford 700 mg (31.1%) of [(4R)-4-fluoro-1,2-dimethyl-pyrrolidin-2-yl]methanol as a yellow oil. LC-MS: (ESI, m/z): 148.1 [M+H]⁺

Step 3: tert-butyl 4-[7-[6-[bis[(4-methoxyphenyl)methyl]amino]-3-(trifluoromethyl)-2-pyridyl]-6-chloro-2-[[(4R)-4-fluoro-1,2-dimethyl-pyrrolidin-2-yl]methoxy]quinazolin-4-yl]piperazine-1-carboxylate

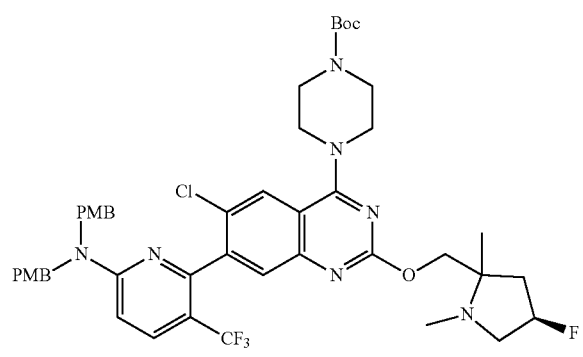

A solution of [(4R)-4-fluoro-1,2-dimethyl-pyrrolidin-2-yl]methanol (479.6 mg, 3.26 mmol) in tetrahydrofuran (14 mL) was added sodium hydride (208.5 mg, 5.21 mmol, 60% dispersion in mineral oil) at 0° C. and stirred at 25° C. for 1 hour. Then tert-butyl 4-(7-(6-(bis(4-methoxybenzyl)amino)-3-(trifluoromethyl)pyridin-2-yl)-6-chloro-2-fluoroquinazolin-4-yl)piperazine-1-carboxylate (Intermediate 3) (500.0 mg, 0.65 mmol) was added and stirred at 25° C. for 1 hour. The reaction was quenched with water and extracted with dichloromethane. Then the organic layer was dried over anhydrous sodium sulfate, filtered, and concentrated. The residue was purified by flash chromatography on silica gel eluting with dichloromethane/methanol (96/4) to afford 450 mg of (80%) of tert-butyl 4-[7-[6-[bis[(4-methoxyphenyl)methyl]amino]-3-(trifluoromethyl)-2-pyridyl]-6-chloro-2-[[(4R)-4-fluoro-1,2-dimethyl-pyrrolidin-2-yl]methoxy]quinazolin-4-yl]piperazine-1-carboxylate as a yellow oil. LC-MS: (ESI, m/z): 894.5 [M+H]⁺

Step 4: 6-[6-chloro-2-[[(4R)-4-fluoro-1,2-dimethyl-pyrrolidin-2-yl]methoxy]-4-piperazin-1-yl-quinazolin-7-yl]-5-(trifluoromethyl)pyridin-2-amine

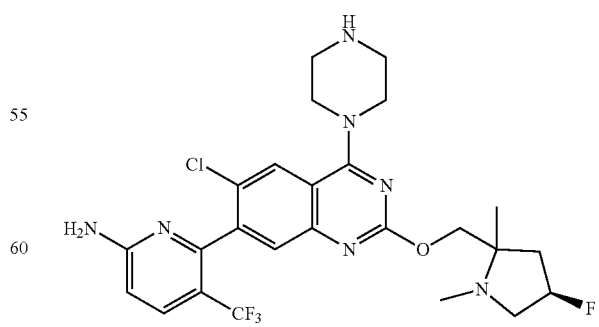

A solution of tert-butyl 4-[7-[6-[bis[(4-methoxyphenyl)methyl]amino]-3-(trifluoromethyl)-2-pyridyl]-6-chloro-2-[[(4R)-4-fluoro-1,2-dimethyl-pyrrolidin-2-yl]methoxy]quinazolin-4-yl]piperazine-1-carboxylate (420.0 mg, 0.47 mmol) in trifluoroacetic acid (42 mL) was stirred at 50° C. for 3 hours. Upon completion, the reaction was concentrated. The pH was adjusted to 10 with N,N-diisopropylethylamine and the mixture was concentrated. The crude was used in the next reaction without purification. LC-MS: (ESI, m/z): 554.2 [M+H]+

Step 5: 1-[4-[7-[6-amino-3-(trifluoromethyl)-2-pyridyl]-6-chloro-2-[[(4R)-4-fluoro-1,2-dimethyl-pyrrolidin-2-yl]methoxy]quinazolin-4-yl]piperazin-1-yl]prop-2-en-1-one

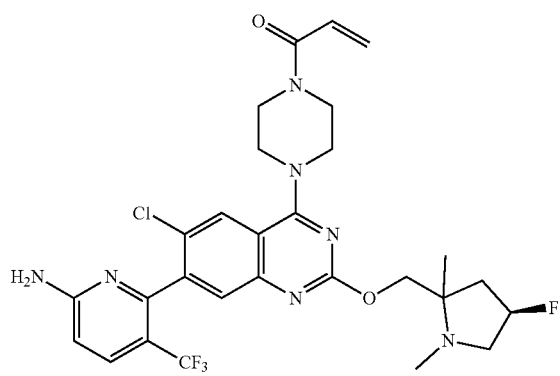 [SMILES: C=CC(=O)N1CCN(c2nc(OCC3(C)C[C@@H](F)CN3C)nc3cc(-c4nc(N)ccc4C(F)(F)F)c(Cl)cc23)CC1]

A solution of 6-[6-chloro-2-[[(4R)-4-fluoro-1,2-dimethyl-pyrrolidin-2-yl]methoxy]-4-piperazin-1-yl-quinazolin-7-yl]-5-(trifluoromethyl)pyridin-2-amine (160.0 mg, 0.29 mmol) and N,N-diisopropylethylamine (149.03 mg, 1.16 mmol) in dichloromethane (14.76 mL) was added acryloyl chloride (18.3 mg, 0.20 mmol) at −78° C. and stirred at −78° C. for 1 hour. The reaction was quenched with water and extracted with dichloromethane. The organic layer was dried over anhydrous sodium sulfate and concentrated. The residue was purified by a reversed-phase chromatography-Column, C18 silica gel; mobile phase, A: water, B: acetonitrile, B % (5%~70% in 30 min); Detector, UV 254 nm. The resulting mixture was repurified directly by Prep-HPLC-Column, XBridge Prep C18 OBD Column19*15 mm 5 umC-0013; mobile phase, A: 10 mmol/L NH4HCO3 in water, B: ACN and B % (51%~73% in 7 min); Detector, UV 254 nm to afford 47 mg (26.8%) of 1-[4-[7-[6-amino-3-(trifluoromethyl)-2-pyridyl]-6-chloro-2-[[(4R)-4-fluoro-1,2-dimethyl-pyrrolidin-2-yl]methoxy]quinazolin-4-yl]piperazin-1-yl]prop-2-en-1-one as a white solid. LC-MS: (ESI, m/z): 608.2 [M+H]+

Example 96

1H NMR (400 MHz, DMSO-d6, ppm) δ 8.04 (s, 1H), 7.78 (d, J=8.8 Hz, 1H), 7.47 (s, 1H), 6.90 (s, 2H), 6.85-6.82 (m, 1H), 6.59 (d, J=8.8 Hz, 1H), 6.19 (d, J=2.4 Hz, 1H), 5.73 (dd, J=10.4, 2.4 Hz, 1H), 5.26 (d, J=56 Hz, 1H), 4.26-4.16 (m, 2H), 3.88-3.85 (m, 6H), 3.85-3.70 (m, 2H), 3.07-2.99 (m, 1H), 2.91-2.78 (m, 1H), 2.27 (s, 3H), 2.19-2.00 (m, 2H), 1.02 (s, 3H). LC-MS: (ESI, m/z): 608.2 [M+H]+

Example 97

1-((S)-4-((R)-7-(6-amino-4-methyl-3-(trifluoromethyl)pyridin-2-yl)-6-chloro-8-fluoro-2-((2-methyl-1,2,3,4-tetrahydroisoquinolin-5-yl)oxy)quinazolin-4-yl)-3-methylpiperazin-1-yl)prop-2-en-1-one

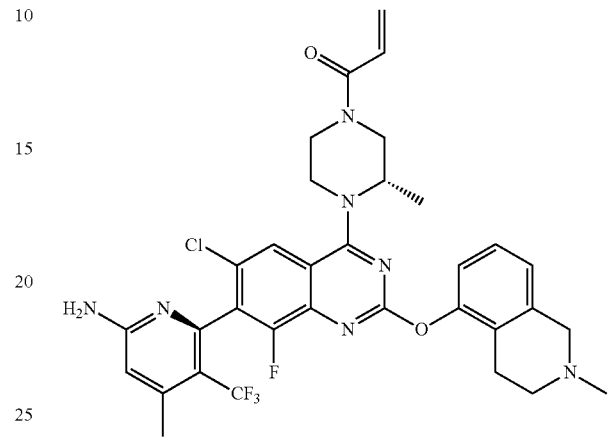

Synthetic Route

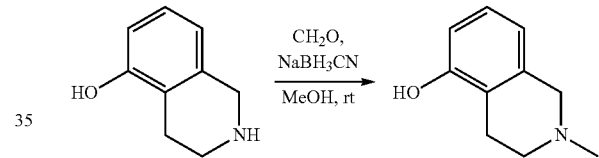

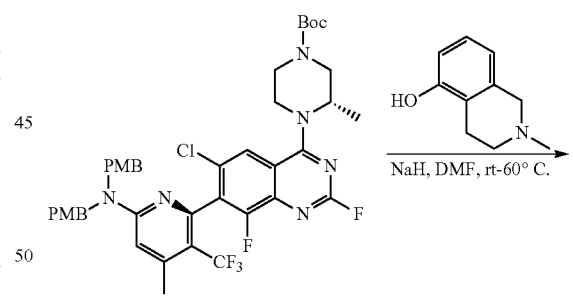

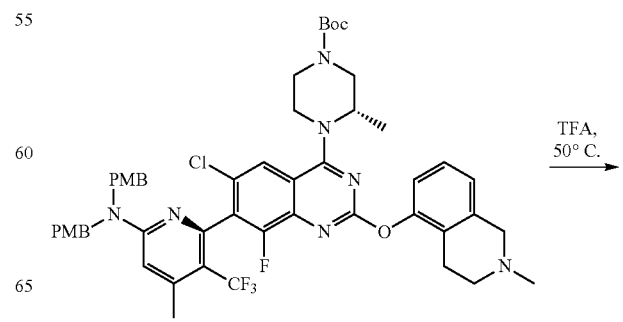

623
-continued

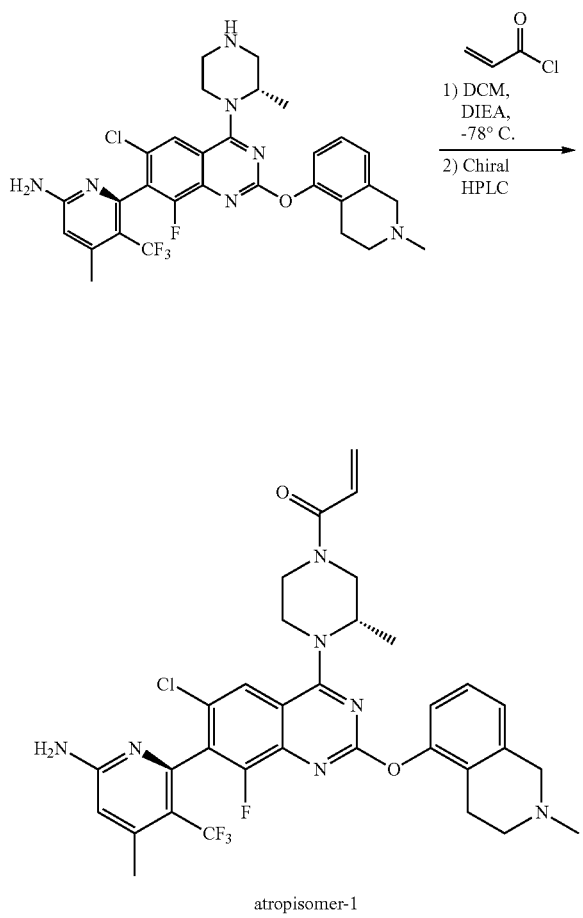

atropisomer-1

Step 1: 2-methyl-3,4-dihydro-1H-isoquinolin-5-ol

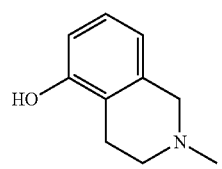

A solution of 1,2,3,4-tetrahydroisoquinolin-5-ol (1.0 g, 6.7 mmol) and formaldehyde (0.4 g, 13.4 mmol) in MeOH (10 mL) was stirred at 25° C. for 10 minutes. Then sodium cyanoborohydride (1.3 g, 20.1 mmol) was added and stirred at 25° C. for 30 minutes. Upon completion, the mixture was concentrated. The residue was purified by flash chromatography on silica gel eluting with dichloromethane/methanol (10:1) to afford 2-methyl-3,4-dihydro-1H-isoquinolin-5-ol (0.8 g, 4.5 mmol, 67.3% yield) as a white solid. LCMS (ESI, m/z): 164.2 [M+H]$^+$.

624

Step 2: tert-butyl (S)-4-((R)-7-(6-(bis(4-methoxybenzyl)amino)-4-methyl-3-(trifluoromethyl)pyridin-2-yl)-6-chloro-8-fluoro-2-((2-methyl-1,2,3,4-tetrahydroisoquinolin-5-yl)oxy)quinazolin-4-yl)-3-methylpiperazine-1-carboxylate

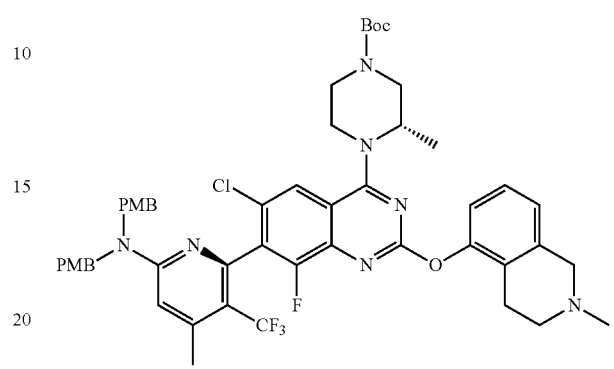

A solution of 2-methyl-3,4-dihydro-1H-isoquinolin-5-ol (0.8 g, 4.92 mmol) and sodium hydride (0.4 g, 9.84 mmol) in N,N-dimethylformamide (20 mL) was stirred at room temperature for 20 minutes. Then tert-butyl (S)-4-((R)-7-(6-(bis(4-methoxybenzyl)amino)-4-methyl-3-(trifluoromethyl)pyridin-2-yl)-6-chloro-2,8-difluoroquinazolin-4-yl)-3-methylpiperazine-1-carboxylate (See Step 9 of Example 17a/17b) (2.0 g, 2.46 mmol) was added and stirred at 60° C. for 30 minutes. The reaction was quenched with water (10 mL), diluted with dichloromethane (100 mL). The organic layer was washed with water (30 mL×3), dried over anhydrous sodium sulfate and concentrated. The residue was purified by flash chromatography on silica gel eluting with dichloromethane/methanol (10:1) to afford tert-butyl (S)-4-((R)-7-(6-(bis(4-methoxybenzyl)amino)-4-methyl-3-(trifluoromethyl)pyridin-2-yl)-6-chloro-8-fluoro-2-((2-methyl-1,2,3,4-tetrahydroisoquinolin-5-yl)oxy)quinazolin-4-yl)-3-methylpiperazine-1-carboxylate (0.8 g, 0.77 mmol, 31.3% yield) as a white solid. LCMS (ESI, m/z): 956.3 [M+H]$^+$.

Step 3: 6-((R)-6-chloro-8-fluoro-2-((2-methyl-1,2,3,4-tetrahydroisoquinolin-5-yl)oxy)-4-((S)-2-methylpiperazin-1-yl)quinazolin-7-yl)-N,N-bis(4-methoxybenzyl)-4-methyl-5-(trifluoromethyl)pyridin-2-amine

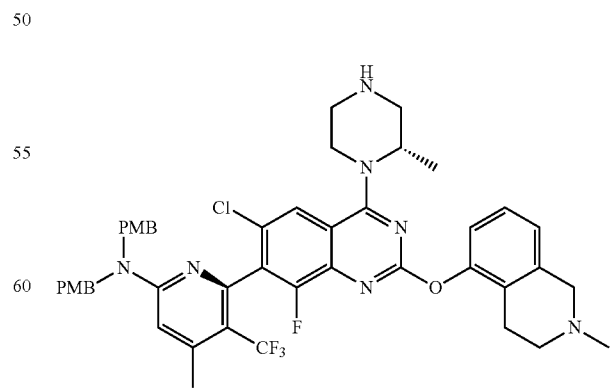

A solution of tert-butyl (S)-4-((R)-7-(6-(bis(4-methoxybenzyl)amino)-4-methyl-3-(trifluoromethyl)pyridin-2-yl)-

6-chloro-8-fluoro-2-((2-methyl-1,2,3,4-tetrahydroisoquinolin-5-yl)oxy)quinazolin-4-yl)-3-methylpiperazine-1-carboxylate (0.8 g, 0.78 mmol) in trifluoroacetic acid (10 mL) was stirred at 50° C. for 5 hours. Upon concentration pH was adjusted to 7 with N,N-diisopropylethylamine (10 mL). The resulting residue was purified by reverse phase chromatography (acetonitrile 0-40/in water) to afford 6-((R)-6-chloro-8-fluoro-2-((2-methyl-1,2,3,4-tetrahydroisoquinolin-5-yl)oxy)-4-((S)-2-methylpiperazin-1-yl)quinazolin-7-yl)-N,N-bis(4-methoxybenzyl)-4-methyl-5-(trifluoromethyl)pyridin-2-amine (0.23 g, 0.34 mmol, 43.8% yield) as a white solid. LCMS (ESI, m/z): 616.2 [M+H]⁺.

Step 4: 1-((S)-4-((R)-7-(6-amino-4-methyl-3-(trifluoromethyl)pyridin-2-yl)-6-chloro-8-fluoro-2-((2-methyl-1,2,3,4-tetrahydroisoquinolin-5-yl)oxy)quinazolin-4-yl)-3-methylpiperazin-1-yl)prop-2-en-1-one

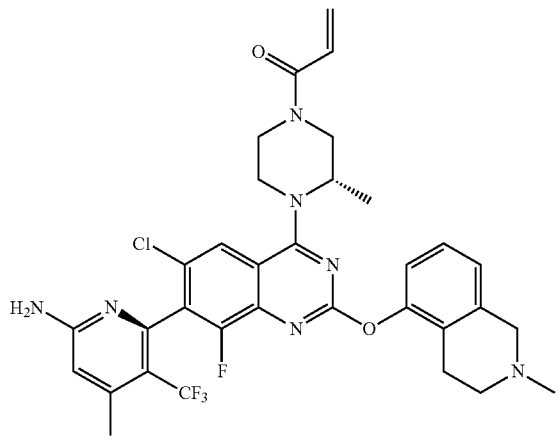

A solution of 6-((R)-6-chloro-8-fluoro-2-((2-methyl-1,2,3,4-tetrahydroisoquinolin-5-yl)oxy)-4-((S)-2-methylpiperazin-1-yl)quinazolin-7-yl)-N,N-bis(4-methoxybenzyl)-4-methyl-5-(trifluoromethyl)pyridin-2-amine (0.23 g, 0.37 mmol) and N,N-diisopropylethylamine (0.1 g, 0.75 mmol) in dichloromethane (5 mL) was stirred at −78° C. for 2 minutes. Then acryloyl chloride (0.03 g, 0.37 mmol) was added and stirred at −78° C. for 20 minutes. The reaction was quenched with water (5 mL). The reaction mixture was diluted with dichloromethane (50 mL) and washed with water (20 mL×3). The organic layer was dried over anhydrous sodium sulfate and concentrated. The residue was purified by flash chromatography on silica gel eluting with dichloromethane/methanol (10:1) to afford the crude product. The mixture was purified by Chiral-Prep-HPLC-Column: CHIRAL ART Cellulose-SB, 2*25 cm, 5 um; Mobile Phase A: Hex(8 mmol/L ammonia. methanol), Mobile Phase B: EtOH; Flow rate:18 mL/min to afford 1-((S)-4-((R)-7-(6-amino-4-methyl-3-(trifluoromethyl)pyridin-2-yl)-6-chloro-8-fluoro-2-((2-methyl-1,2,3,4-tetrahydroisoquinolin-5-yl)oxy)quinazolin-4-yl)-3-methylpiperazin-1-yl)prop-2-en-1-one (38.9 mg, 0.0575 mmol, 15.4% yield) at 6.942 min. LCMS (ESI, m/z): 670.3 [M+H]⁺

Example 97

1H NMR (400 MHz, DMSO-d₆, ppm) 7.84 (s, 1H), 7.19 (t, J=7.8 Hz, 1H), 6.99 (t, J=8.5 Hz, 2H), 6.87 (s, 2H), 6.83-6.74 (m, 1H), 6.50 (s, 1H), 6.22-6.12 (m, 1H), 5.78-5.70 (m, 1H), 4.54 (d, J=29.3 Hz, 1H), 4.30-3.86 (m, 3H), 3.55 (td, J=24.5, 23.0, 13.2 Hz, 4H), 3.24-3.02 (m, 1H), 2.60 (d, J=6.0 Hz, 2H), 2.57-2.52 (m, 2H), 2.37 (d, J=2.3 Hz, 3H), 2.32 (s, 3H), 1.19 (t, J=5.8 Hz, 3H).

The data from Examples 1-97 is summarized in Table 2.

TABLE 2

| Example No. | ¹H NMR | MS (M + H)⁺ |
|---|---|---|
| 1 | ¹H NMR (400 MHz, DMSO-d₆) δ 8.70 (s, 1H), 8.21 (s, 1H),7.84 (s, 1H), 7.63 (dd, J = 8.5, 1.0 Hz, 1H), 7.47 (ddd, J = 8.3,6.6, 1.2 Hz, 1H), 7.25 (dq, J = 8.5, 0.9 Hz, 1H), 7.07 (ddd, J =8.5, 6.7, 1.2 Hz, 1H), 6.85 (dd, J = 16.7, 10.4 Hz, 1H), 6.75 (d,J = 0.9 Hz, 1H), 6.18 (dd, J = 16.7, 2.4 Hz, 1H), 6.10 (s, 2H), 5.75 (dd, J = 10.4, 2.4 Hz, 1H), 4.01-3.73 (m, 8H). | 445.1 |
| 2 | ¹H NMR (400 MHz, DMSO-d₆) δ 8.69 (s, 1H), 8.51 (ddd, J = 4.8, 1.6, 0.7 Hz, 1H), 8.19 (s, 1H), 7.81 (ddd, J = 7.8, 1.7, 0.8 Hz, 1H), 7.76 (s, 1H), 7.42 (dd, J = 7.7, 4.7 Hz, 1H), 6.84 (dd, J = 16.7, 10.4 Hz, 1H), 6.18 (dd, J = 16.7, 2.4 Hz, 1H), 5.74 (dd, J = 10.4, 2.4 Hz, 1H), 3.95-3.75 (m, 8H), 2.14 (d, J = 0.8 Hz, 3H). | 394.1 |
| 3 | ¹H NMR (400 MHz, DMSO-d₆) δ 8.69 (s, 1H), 8.44 (dd, J = 4.0, 1.6 Hz, 1H), 8.14 (s, 1H), 8.07 (dd, J = 8.6, 1.6 Hz, 1H), 7.84 (s, 1H), 7.44 (dd, J = 8.5, 4.0 Hz, 1H), 6.84 (dd, J = 16.7, 10.5 Hz, 1H), 6.75 (s, 1H), 6.32 (s, 2H), 6.18 (dd, J = 16.7, 2.4 Hz, 1H), 5.75 (dd, J = 10.5, 2.3 Hz, 1H), 3.85 (d, J = 43.6 Hz, 8H). | 446.1 |
| 4 | ¹H NMR (400 MHz, DMSO-d₆) δ 9.13 (d, J = 1.1 Hz, 1H), 8.71 (s, 1H), 8.23 (s, 1H), 8.09 (d, J = 5.9 Hz, 1H), 7.89 (s, 1H), 7.09 (dt, J = 5.9, 1.1 Hz, 1H), 6.88 t, J = 1.1 Hz, 1H), 6.87-6.79 (m, 1H), 6.49 (s, 2H), 6.18 (dd, J = 16.7, 2.4 Hz, 1H), 5.75 (dd, J = 10.4, 2.4 Hz, 1H), 3.99-3.74 (m, 8H). | 446.1 |
| 5 | ¹H NMR (400 MHz, DMSO-d₆) δ 8.70 (s, 1H), 8.22 (s, 1H), 7.88 (s, 1H), 7.67 (dd, J = 7.4, 1.1 Hz, 1H), 7.25 (dt, J = 8.5, 1.0 Hz, 1H), 7.03 (dd, J = 8.5, 7.3 Hz, 1H), 6.98 (d, J = 1.0 Hz, 1H), 6.85 (dd, J = 16.7, 10.5 Hz, 1H), 6.49 (s, 2H), 6.18 (dd, J = 16.7, 2.4 Hz, 1H), 5.75 (dd, J = 10.5, 2.4 Hz, 1H), 3.99-3.75 (m, 8H). | 479.1 |
| 6 | ¹H NMR (400 MHz, DMSO-d₆) δ 8.69 (s, 1H), 8.19 (s, 1H), 7.80 (s, 1H), 7.14 (d, J = 9.2 Hz, 1H), 6.98 (d, J = 2.4 Hz, 1H), 6.84 (dd, J = 16.7, 10.5 Hz, 1H), 6.74-6.63 (m, 2H), 6.18 (dd, J = 16.7, 2.4 Hz, 1H), 6.03 (s, 2H), 5.75 (dd, J = 10.4, 2.4 Hz, 1H), 3.78-3.99 (m, 11H). | 475.1 |
| 7 | ¹H NMR (400 MHz, DMSO-d₆) δ 8.73 (s, 1H), 8.08 (d, J = 1.5 Hz, 1H), 7.65 (dt, J = 8.7, 0.9 Hz, 1H), 7.49 (ddd, J = 8.3, 6.7, 1.2 Hz, 1H), 7.25 (dt, J = 8.6, 1.0 Hz, 1H), 7.09 (ddd, J = 8.5, 6.7, 1.1 Hz, 1H), 6.84 (dd, J = 16.7, 10.4 Hz, 1H), 6.79 (d, J = 0.9 Hz, 1H), 6.24-6.08 (m, 3H), 5.75 (dd, J = 10.4, 2.4 Hz, 1H), 4.04-3.90 (m, 4H), 3.90-3.74 (m, 4H). | 463.1 |
| 8 | ¹H NMR (400 MHz, DMSO-d₆) δ 8.73 (s, 1H), 8.08 (d, J = 1.5 Hz, 1H), 7.65 (dt, J = 8.5, 0.9 Hz, 1H), 7.49 (ddd, J = 8.3, 6.7, 1.2 Hz, 1H), 7.25 (dt, J = 8.6, 1.0 Hz, 1H), 7.09 (ddd, J = 8.5, 6.7, 1.2 Hz, 1H), 6.84 (dd, J = 16.7, 10.5 Hz, 1H), 6.80-6.76 (m, 1H), 6.23-6.10 (m, 3H), 5.75 (dd, J = 10.5, 2.4 Hz, 1H), 4.05-3.90 (m, 4H), 3.82 (d, J = 29.0 Hz, 4H). | 463.1 |
| 9 | ¹H NMR (400 MHz, DMSO-d₆) δ 8.70 (s, 1H), 8.01 (d, J = 1.5 Hz, 1H), 7.84 (d, J = 8.9 Hz, 1H), 7.00 (s, 2H), 6.82 (dd, J = 16.7, 10.4 Hz, 1H), 6.69-6.61 (m, 1H), 6.17 (dd, J = 16.7, 2.4 Hz, 1H), 5.74 (dd, J = 10.4, 2.4 Hz, 1H), 3.92 (t, J = 5.2 Hz, 4H), 3.84 (s, 2H), 3.77 (s, 2H). | 481.1 |
| 10 | ¹H NMR (400 MHz, DMSO-d₆) δ 8.70 (s, 1H), 8.01 (d, J = 1.6 Hz, 1H), 7.84 (d, J = 8.9 Hz, 1H), 7.00 (s, 2H), 6.82 (dd, J = 16.7, 10.4 Hz, 1H), 6.69-6.61 (m, 1H), 6.17 (dd, J = 16.7, 2.4 Hz, 1H), 5.74 (dd, J = 0.4, 2.4 Hz, 1H), 3.91 (dd, J = 6.5, 4.0 Hz, 4H), 3.84 (s, 2H), 3.77 (s, 2H). | 481.1 |

TABLE 2-continued

| Example No. | ¹H NMR | MS (M + H)⁺ |
|---|---|---|
| 11 | ¹H NMR (400 MHz, DMSO-d₆) δ 8.67 (s, 1H), 8.14 (s, 1H), 7.81 (s, 1H), 6.83 (dd, J = 16.7, 10.4 Hz, 1H), 6.45 (dd, J = 4.7, 1.0 Hz, 1H), 6.17 (dd, J = 16.7, 2.4 Hz, 1H), 5.93 (s, 2H), 5.74 (dd, J = 10.4, 2.4 Hz, 1H), 3.91-3.73 (m, 8H), 2.21 (dd, J = 1.7, 0.9 Hz, 3H). | 427.1 |
| 12 | ¹H NMR (400 MHz, DMSO-d₆) δ 7.84 (s, 1H), 7.25 (d, J = 58.3 Hz, 2H), 6.84 (dd, J = 16.7, 10.5 Hz, 1H), 6.41 (dd, J = 4.7, 1.0 Hz, 1H), 6.16 (dd, J = 16.7, 2.4 Hz, 1H), 5.88 (dd, J = 10.4, 2.4 Hz, 1H), 4.77 (s, 1H), 4.36 (s, 1H), 3.90-3.59 (m, 10H), 2.19 (dd, J = 1.7, 0.8 Hz, 3H), 1.20-1.09 (m, 6H). | 546.2 |
| 13 | ¹H NMR (400 MHz, DMSO-d₆) δ 8.66 (s, 1H), 8.12 (s, 1H), 7.64 (s, 1H), 6.83 (dd, J = 16.7, 10.5 Hz, 1H), 6.40-6.36 (m, 1H), 6.17 (dd, J = 16.7, 2.4 Hz, 1H), 5.79-5.69 (m, 3H), 3.90-3.74 (m, 8H), 2.18 (d, J = 0.8 | 423.1 |
| 14 | ¹H NMR (400 MHz, DMSO-d₆) δ 8.67 (s, 1H), 8.14 (s, 1H), 7.72 (s, 1H), 6.83 (dd, J = 16.7, 10.5 Hz, 1H), 6.51 (d, J = 0.9 Hz, 1H), 6.23-6.14 (m, 3H), 5.74 (dd, J = 10.4, 2.4 Hz, 1H), 3.83 (dd, J = 39.2, 5.3 Hz, 8H), 2.28 (d, J = 0.7 Hz, 3H). | 443.1 |
| 15 | ¹H NMR (400 MHz, Methanol-d₄, ppm) δ 8.68 (s, 1H), 8.23 (s, 1H), 7.76 (s, 1H), 7.48 (dd, J = 8.4, 0.4 Hz, 1H), 6.88-6.81 (m, 1H), 6.66 (d, J = 8.4 Hz, 1H), 6.29 (dd, J = 16.8, 2.0 Hz, 1H), 5.83 (dd, J = 10.8, 2.0 Hz, 1H), 4.02 (s, 4H), 3.94 (s, 4H), 2.00 (s, 3H). | 409.1 |
| 16 | ¹H NMR (400 MHz, Methanol-d₄, ppm) δ 8.68 (s, 1H), 8.22 (s, 1H), 8.13-8.08 (m, 1H), 7.76-7.74 (m, 2H), 6.86-6.79 (m, 1H), 6.27 (dd, J = 16.8, 2.0 Hz, 1H), 5.80 (dd, J = 14.4, 2.0 Hz, 1H), 4.00 (m, 4H), 3.92 (s, 4H), 2.16 (s, 3H), 2.13 (s, 3H). | 451.2 |
| 17a | ¹H NMR: (400 MHz, CDCl₃, ppm) δ 7.64 (s, 1H), 6.70-6.55 (m, 1H), 6.48 (s, 1H), 6.42-6.35 (m, 1H), 5.82-5.75 (m, 1H), 4.90-4.79 (m, 2H), 4.78-4.40 (m, 3H), 4.35-4.28 (m, 1H), 4.18-4.00 (m, 1H), 3.99-3.76 (m, 1H), 3.72-3.45 (m, 2H), 3.31-2.98 (m, 2H), 2.81-2.70 (m, 1H), 2.55-2.45 (m, 6H), 2.35-2.25 (m, 1H), 2.11-2.01 (m, 1H), 1.95-1.72 (m, 3H), 1.36-1.34 (m, 3H). | 622.2 |
| 17b | ¹H NMR: (400 MHz, CDCl₃, ppm) δ 7.63 (s, 1H), 6.70-6.55 (m, 1H), 6.50 (s, 1H), 6.42-6.35 (m, 1H), 5.82-5.75 (m, 1H), 4.85-4.70 (m, 2H), 4.78-4.68 (m, 2H), 4.65-4.55 (m, 2H), 4.50-4.40 (m, 1H), 4.30-4.10 (m, 1H), 4.05-3.75 (m, 1H), 3.80-3.76 (m, 2H), 3.25-3.08 (m, 2H), 2.85-2.75 (m, 1H), 2.60-2.45 (m, 6H), 2.40-2.25 (m, 1H), 2.15-2.05 (m, 1H), 1.95-1.72 (m, 3H), 1.45-1.32 (m, 3H). | 622.2 |
| 18a | ¹H NMR: (400 MHz, DMSO-d₆) δ 7.82 (s, 1H), 6.85 (s, 2H), 6.83-6.68 (m, 2H), 6.50 (s, 1H), 5.20 (d, J = 2.8 Hz, 1H), 5.08 (d, J = 2,8 Hz, 1H), 4.75 (s, 1H), 4.41-4.23 (m, 2H), 4.19-3.94 (m, 3H), 3.73-3.65 (m, 1H), 3.43-3.07 (m, 2H), 2.96-2.93 (m, 1H), 2.60-2.50 (m, 1H), 2.37-2.36 (m, 6H), 2.18 (dd, J = 16.4, 8.0 Hz, 1H), 1.99-1.90 (m, 1H), 1.72-1.59 (m, 3H), 1.27 (t, J = 6.8 Hz, 3H) | 654.2 |
| 18b | ¹H NMR: (400 MHz, DMSO-d₆) δ 7.80 (s, 1H), 6.85 (s, 2H), 6.83-6.68 (m, 2H), 6.50 (s, 1H), 5.20 (d, J = 2.8 Hz, 1H), 5.08 (d, J = 2,8 Hz, 1H), 4.71 (s, 1H), 4.39-4.23 (m, 2H), 4.20-3.93 (m, 3H), 3.70-3.60 (m, 1H), 3.51-3.09 (m, 2H), 2.96-2.93 (m, 1H), 2.60-2.52 (m, 1H), 2.37-2.36 (m, 6H), 2.18 (dd, J = 16.4, 8.0 Hz, 1H), 1.99-1.90 (m, 1H), 1.72-1.59 (m, 3H), 1.30 (t, J = 8.0 Hz, 3H) | 654.2 |
| 19 | ¹H NMR (400 MHz, Methanol-d₄, ppm) δ 8.67 (s, 1H), 7.92 (s, 1H), 6.89-6.82 (m, 1H), 6.62 (s, 1H), 6.32-6.26 (m, 1H), 5.83-5.80 (m, 1H), 4.56-4.39 (m, 1H), 4.38-4.30 (m, 1H), 4.20-4.02 (m, 1H), 3.80-3.52 (m, 2H), 3.33-3.30 (m, 1H), 3.22-3.13 (m, 1H), 2.45 (s, 3H), 1.42 (d, J = 1.6 Hz, 3H). | 509.1 |
| 20 | ¹H NMR (300 MHz, Methanol-d₄, ppm) δ 8.50 (s, 1H), 7.83 (d, J = 9.0 Hz, 1H), 7.54 (s, 1H), 6.91-6.82 (m, 1H), 6.75-6.70 (m, 2H), 6.30 (dd, J = 16.8, 2.0 Hz, 1H), 5.83 (dd, J = 10.6, 2.0 Hz, 1H), 3.99-3.81 (m, 8H), 3.78-3.61 (m, 4H), 2.29-2.19 (m, 2H) | 484.2 |
| 21 | ¹H NMR (400 MHz, Methanol-d₄, ppm) δ 8.69 (s, 1H), 8.26 (s, 1H), 7.78 (d, J = 7.2 Hz, 1H), 7.67 (s, 1H), 6.84 (dd, J = 16.8, 10.4 Hz, 1H), 6.67 (d, J = 8.8 Hz, 1H), 6.29 (dd, J = 16.8, 2.0 Hz, 1H), 5.82 (dd, J = 10.4, 2.0 Hz, 1H), 4.15-4.00 (m, 4H), 3.99-3.86 (m, 4H), 2.02 (dd, J = 19.2, 18.4 Hz, 3H). | 493.2 |
| 22 | ¹H NMR (400 MHz, Methanol-d₄, ppm) δ 9.34 (s, 1H), 8.87 (s, 1H), 8.02 (s, 1H), 6.91-6.87 (m, 1H), 6.63 (s, 1H), 6.27 (dd, J = 16.8, 2.0 Hz, 1H), 5.82 (dd, J = 10.8, 2.0 Hz, 1H), 4.82-4.78 (m, 1H), 4.65(m, 1H), 4.44-4.35 (m, 1H), 3.81-3.72 (m, 1H), 3.40-3.35 (m, 1H), 2.69-2.60 (m, 2H), 2.48 (s, 3H), 2.45-2.35 (m, 1H). | 501.1 |
| 23 | ¹H NMR (300 MHz, CDCl₃, ppm) δ 8.88 (s, 1H), 8.15 (d, J = 12.3 Hz, 1H), 7.91 (s, 1H), 6.69 (d, J = 0.9 Hz, 1H), 6.51 (s, 2H), 4.85 (s, 2H), 4.47 (dd, J = 13.8, 7.8 Hz, 2H), 4.28 (d, J = 12.9 Hz, 1H), 3.88 (s, 1H), 3.40 (t, J = 15.8 Hz, 1H), 3.32-3.14 (m, 1H), 2.94 (s, 2H), 2.66-2.57 (m, 2H), 2.51 (s, 3H). | 528.1 |
| 24 | ¹H NMR (300 MHz, CDCl₃, ppm) δ 8.90 (s, 1H), 8.21-8.09 (m, 1H), 7.91 (s, 1H), 6.50 (s, 1H), 5.85-5.75 (m, 1H), 4.82 (s, 2H), 4.47-4.21 (m, 3H), 4.05-3.95 (m, 1H), 3.73 (t, J = 3.4 Hz, 1H), 3.59-3.09 (m, 4H), 2.51 (s, 3H) | 518.1 |
| 25 | ¹H NMR (300 MHz, DMSO-d₆, ppm) δ 8.73 (s, 1H), 8.10 (s, 1H), 7.86-7.75 (m, 2H), 6.96 (s, 2H), 6.93-6.88 (m, 1H), 6.63 (d, 0.9 Hz, 1H), 6.27 (t, J = 12 Hz, 1H), 5.90-5.80 (m, 1H), 5.50-5.38 (m, 1H), 4.55-4.20 (m, 3H), 3.90-3.68 (m, 2H), 3.56-3.40 (m, 1H). | 531.1 |
| 26 | ¹H NMR (400 MHz, Methanol-d₄, ppm) δ 8.68 (s, 1H), 8.18 (s, 1H), 7.71 (s, 1H), 6.61 (s, 1H), 5.38-5.32 (dd, J = 18.8, 3.6 Hz, 1H), 5.29-5.25 (dd, J = 13.2, 4.0 Hz, 1H), 4.09-3.96 (m, 4H), 3.92 (s, 4H), 2.47 (s, 3H). | 495.1 |
| 27 | ¹H NMR (300 MHz, DMSO-d₆, ppm) δ 8.71 (s, 1H), 8.04 (s, 1H), 7.51-7.45 (m, 2H), 6.87-6.80 (m, 3H), 6.41 (d, J = 5.2 Hz, 2H), 6.18 (d, J = 16.4, 2.0 Hz, 1H), 5.75(dd, J = 10.4, 2.4 Hz, 1H), 3.94-3.77 (m, 8H). | 481.1 |
| 28 | ¹H NMR (300 MHz, DMSO-d₆, ppm) δ 8.74 (s, 1H), 8.68 (s, 1H), 7.79 (d, J = 9.0 Hz, 1H), 7.66 (s, 1H), 6.89 (s, 2H), 6.86-6.80 (m, 1H), 6.60 (d, J = 8.1 Hz, 1H), 6.19 (dd, J = 16.8, 2.4 Hz, 1H), 5.75 (dd, J = 10.5, 2.4 Hz, 1H), 4.05 (m, 4H), 3.86-3.72 (m, 4H), 3.42 (s, 3H). | 507.1 |
| 29 | ¹H NMR (300 MHz, Methanol-d₄, ppm) δ 8.62 (s, 1H), 7.85 (d, J = 8.7 Hz, 1H), 7.63 (d, J = 11.4 Hz, 2H), 6.85 (dd, J = 16.8, 10.6 Hz, 1H), 6.71 (d, J = 9.0 Hz, 1H), 6.29 (dd, J = 16.8, 2.0 Hz, 1H), 5.82 (dd, J = 10.6, 1.9 Hz, 1H), 3.94 (s, 8H), 1.82 (t, J = 5.8 Hz, 1H), 0.97-0.83 (m, 3H), 0.71 (d, J = 5.6 Hz, 1H). | 469.2 |
| 30 | ¹H NMR (300 MHz, DMSO-d₆, ppm) δ 8.24 (s, 1H), 7.78 (s, 1H), 6.85-6.78 (m, 3H), 6.49 (s, 1H), 6.22-6.15 (m, 1H), 5.78-5.72 (m, 1H), 4.08-4.00 (m, 4H), 3.88-3.70 (m, 4H), 2.37 (s, 3H). | 545.1 |
| 31 | ¹H NMR (300 MHz, Methanol-d₄, ppm) δ 8.16 (s, 1H), 7.59-7.25 (m, 1H), 6.79 (dd, J = 16.8, 10.5 Hz, 1H), 6.65 (s, 1H), 6.30 (dd, J = 16.5, 1.8 Hz, 1H), 5.82 (dd, J = 10.8, 2.1 Hz, 1H), 4.27 (s, 4H), 3.94 (s, 4H), 3.09 (s, 3H), 2.45 (s, 3H). | 507.2 |
| 32 | ¹H NMR (300 MHz, Methanol-d₄, ppm) δ 8.12 (s, 1H), 7.62 (s, 1H), 6.84 (dd, J = 16.8, 10.6 Hz, 1H), 6.64-6.57 (m, 1H), 6.29 (dd, J = 16.8, 2.0 Hz, 1H), 5.82 (dd, J = 10.6, 2.0 Hz, 1H), 3.98-3.89 (m, 8H), 2.63 (s, 3H), 2.46 (s, 3H). | 491.1 |
| 33 | ¹H NMR (300 MHz, DMSO-d₆, ppm) δ 8.68 (s, 1H), 8.17 (s, 1H), 7.76 (s, 1H), 6.89-6.70 (m, 2H), 6.50 (s, 2H), 6.21-6.15 (m, 1H), 5.78-5.72 (m, 1H), 3.88-3.78 (m, 8H), 1.99 (s, 3H) | 477.1 |
| 34 | ¹H NMR (400 MHz, CDCl₃, ppm) δ 8.75 (s, 1H), 8.09 (s, 1H), 7.97 (s, 1H), 6.75-6.65 (m, 1H), 6.42-6.37 (m, 1H), 6.22 (s, 1H), 5.81 (dd, J = 7.2, 2.4 Hz, 1H), 4.98 (s, 1H), 4.05-3.80 (m, 8H), 2.19 (s, 1H), 1.25 (s, 1H), 1.14-1.07 (m, 2H), 0.88 (s, 1H). | 503.1 |
| 35 | ¹H NMR (300 MHz, DMSO-d₆, ppm) δ 8.68 (s, 1H), 8.14 (s, 1H), 7.81 (d, J = 8.9 Hz, 1H), 7.72 (s, 1H), 6.95 (s, 2H), 6.84 (dd, J = 16.5, 10.2 Hz, 1H), 6.62 (d, J = 9.0 Hz, 1H), 6.18 (dd, J = 16.8, 2.4 Hz, 1H), 5.75 (dd, J = 10.5, 2.4 Hz, 1H), 3.87-3.79(m, 8H) | 463.1 |

TABLE 2-continued

| Example No. | ¹H NMR | MS (M + H)⁺ |
|---|---|---|
| 36 | ¹H NMR (300 MHz, Methanol-d₄, ppm) δ 8.71 (s, 1H), 8.55 (s, 1H), 8.31 (s, 1H), 7.95-7.92 (m, 2H), 7.74-7.69 (m, 1H), 7.55 (d, J = 8.4 Hz, 1H), 7.47-7.42 (m, 1H), 6.85 (dd, J = 16.8, 10.8 Hz, 1H), 6.30 (dd, J = 16.8, 1.8 Hz, 1H), 5.83 (dd, J = 10.6, 1.9 Hz, 1H), 4.08-4.04 (m, 4H), 3.98-3.92 (m, 4H), 1.95-1.92 (m, 1H), 1.05-1.01 (m, 2H), 0.94-0.89 (m, 2H). | 513.2 |
| 37 | ¹H NMR (300 MHz, Methanol-d₄, ppm) δ 8.71 (d, J = 4.6 Hz, 2H), 8.33 (s, 1H), 8.01 (d, J = 8.4 Hz, 1H), 7.95 (s, 1H), 7.80-7.74 (m, 1H), 7.60-7.57 (m, 1H), 7.53-7.47 (m, 1H), 6.86 (dd, J = 16.8, 10.6 Hz, 1H), 6.31 (dd, J = 16.8, 1.9 Hz, 1H), 5.84 (dd, J = 10.6, 2.0 Hz, 1H), 4.23 (s, 2H), 4.10-4.06 (m, 4H), 3.99-3.94 (m, 4H). | 503.2 |
| 38 | ¹H NMR (400 MHz, Chloroform-d, ppm) δ 8.80 (s, 1H), 8.18-8.06 (s, 2H), 7.64 (d, J = 8.4 Hz, 1H), 7.52-7.47 (m, 1H), 7.35-7.33 (m, 1H), 7.13-7.11 (m, 1H), 6.66-6.59 (m, 2H), 6.39 (dd, J = 16.8, 1.8 Hz, 1H), 5.80 (dd, J = 10.5, 1.8 Hz, 1H), 3.95-3.82 (m, 9H), 1.35-1.34 (m, 6H). | 487.2 |
| 39 | ¹H NMR (400 MHz, Methanol-d₄, ppm) δ 8.71 (s, 1H), 8.31 (s, 1H), 7.93 (s, 1H), 7.77 (d, J = 8.4 Hz, 1H), 7.58 (ddd, J = 8.3, 6.7, 1.2 Hz, 1H), 7.45-7.42 (m, 1H), 7.23 (ddd, J = 8.4, 6.8, 1.2 Hz, 1H), 7.03 (s, 1H), 6.86 (dd, J = 16.8, 10.6 Hz, 1H), 6.31 (dd, J = 16.8, 1.9 Hz, 1H), 5.84 (dd, J = 10.6, 1.9 Hz, 1H), 4.44 (d, J = 1.9 Hz, 2H), 4.09-4.06 (m, 4H), 3.97-3.95 (m, 4H). | 484.2 |
| 40 | ¹H NMR (300 MHz, Methanol-d₄, ppm) δ 8.68 (s, 1H), 8.22 (s, 1H), 7.85 (s, 1H), 7.64-7.55 (m, 1H), 6.84 (dd, J = 16.8, 10.6 Hz, 1H), 6.74 (d, J = 9.1 Hz, 1H), 6.29 (dd, J = 16.8, 2.0 Hz, 1H), 5.82 (dd, J = 10.7, 2.0 Hz, 1H), 4.04-4.00 (m, 4H), 3.95-3.92 (m, 4H). | 479.1 |
| 41 | ¹H NMR (300 MHz, Methanol-d₄, ppm) δ 8.68 (s, 1H), 8.22 (s, 1H), 7.81-7.78 (m, 2H), 6.87-6.73 (m, 2H), 6.53-6.16 (m, 2H), 5.81 (dd, J = 10.6, 1.9 Hz, 1H), 4.03-3.99 (m, 4H), 3.93-3.91 (m, 4H). | 445.1 |
| 42 | ¹H NMR (300 MHz, Methanol-d₄, ppm) δ 8.68 (s, 1H), 8.17 (s, 1H), 8.07 (d, J = 9.0 Hz, 1H), 7.84 (s, 1H), 6.84 (dd, J = 16.8, 10.6 Hz, 1H), 6.76 (d, J = 9.0 Hz, 1H), 6.29 (dd, J = 16.8, 2.0 Hz, 1H), 5.82 (dd, J = 10.6, 2.0 Hz, 1H), 4.05-3.92 (m, 8H), 2.99 (s, 3H). | 473.1 |
| 43 | ¹H NMR (300 MHz, CDCl₃, ppm) δ 8.80 (s, 1H), 8.01 (s, 1H), 7.97 (s, 1H), 7.62 (d, J = 9.0 Hz, 1H), 6.70 (d, J = 8.6 Hz, 1H), 6.64 (dd, J = 16.8, 10.5 Hz, 1H), 6.40 (dd, J = 16.8, 1.9 Hz, 1H), 5.80 (dd, J = 10.5, 1.9 Hz, 1H), 5.12 (brs, 2H), 3.94-3.85 (m, 8H), 3.34-2.99 (m, 2H). | 477.1 |
| 44 | ¹H NMR (300 MHz, Methanol-d₄, ppm) δ 8.67 (s, 1H), 8.18 (s, 1H), 7.71 (s, 1H), 6.84 (dd, J = 16.8, 10.6 Hz, 1H), 6.61 (m, 1H), 6.29 (dd, J = 16.8, 2.0 Hz, 1H), 5.82 (dd, J = 10.6, 2.0 Hz, 1H), 4.03-3.91 (m, 8H), 2.48-2.46 (m, 3H). | 477.1 |
| 45 | ¹H NMR (300 MHz, Methanol-d₄, ppm) δ 8.22 (s, 1H), 7.85 (d, J = 9.0 Hz, 1H), 7.56 (s, 1H), 6.84-6.75 (m, 2H), 6.31 (dd, J = 16.8, 1.9 Hz, 1H), 5.84 (dd, J = 10.6, 1.9 Hz, 1H), 4.31 (brs, 4H), 4.04-3.92 (m, 6H), 3.49 (t, J = 5.9 Hz, 2H), 2.99 (s, 6H). | 549.2 |
| 46a | ¹H NMR (400 MHz, Methanol-d₄, ppm) δ 8.79 (s, 1H), 8.31 (d, J = 1.8 Hz, 1H), 7.85-7.83 (m, 2H), 6.74 (dd, J = 8.9, 0.9 Hz, 1H), 5.67 (brs, 1H), 5.55 (d, J = 4.0, 1.3 Hz, 1H), 5.45-5.40 (m, 1H), 4.71 (dq, J = 14.1, 2.3 Hz, 1H), 4.52-4.47 (m, 1H), 4.38-4.34 (m, 1H), 3.83 (brs, 1H), 3.72 (ddd, J = 13.9, 10.2, 3.6 Hz, 1H), 3.54-3.43 (m, 1H). | 506.1 |
| 46b | ¹H NMR (400 MHz, Methanol-d₄, ppm) δ 8.79 (s, 1H), 8.31 (d, J = 1.8 Hz, 1H), 7.85-7.83 (m, 2H), 6.74 (dd, J = 8.9, 0.9 Hz, 1H), 5.67 (brs, 1H), 5.55 (d, J = 4.0, 1.3 Hz, 1H), 5.45-5.40 (m, 1H), 4.71 (dq, J = 14.1, 2.3 Hz, 1H), 4.52-4.47 (m, 1H), 4.38-4.34 (m, 1H), 3.83 (brs, 1H), 3.72 (ddd, J = 13.9, 10.2, 3.6 Hz, 1H), 3.54-3.43 (m, 1H). | 506.1 |
| 47 | ¹H NMR (300 MHz, CDCl3, ppm) δ 8.77 (s, 1H), 7.91 (s, 1H), 7.22-7.18 (m, 2H), 6.66 (dd, J = 16.8, 10.5 Hz, 1H), 6.56 (d, J = 8.5 Hz, 1H), 6.38 (dd, J = 16.8, 1.9 Hz, 1H), 5.79 (dd, J = 10.5, 1.9 Hz, 1H), 4.65 (brs, 2H), 3.92-3.78 (m, 11H), 1.65-1.55 (m, 1H), 0.69-0.66 (m, 2H), 0.55-0.49 (m, 2H). | 431.2 |
| 48 | ¹H NMR (300 MHz, DMSO-d₆, ppm) δ 8.69 (s, 1H), 8.14 (s, 1H), 7.83 (s, 1H), 7.49-7.40 (m, 2H), 6.89-6.76 (m, 3H), 6.35 (s, 2H), 6.18 (dd, J = 16.7, 2.4 Hz, 1H), 5.75 (dd, J = 10.4, 2.4 Hz, 1H), 3.88 (brs, 6H), 3.79 (brs, 2H). | 463.1 |
| 49 | ¹H NMR (300 MHz, Methanol-d₄, ppm) δ 8.70 (s, 1H), 8.31 (s, 1H), 7.90 (s, 1H), 7.73 (dd, J = 9.2, 5.4 Hz, 1H), 7.42-7.35 (m, 1H), 6.99-6.93 (m, 2H), 6.85 (dd, J = 16.8, 10.6 Hz, 1H), 6.29 (dd, J = 16.8, 1.9 Hz, 1H), 5.82 (dd, J = 10.6, 2.0 Hz, 1H), 4.09-4.04 (m, 4H), 3.96-3.93 (m, 4H). | 463.1 |
| 50 | ¹H NMR (300 MHz, Methanol-d4, ppm} δ 9.33 (s, 1H), 8.33 (s, 1H), 7.98 (s, 1H), 7.82 (d, J = 8.9 Hz, 1H), 6.73 (dd, J = 9.0, 1.1 Hz, 1H), 6.47-6.38 (m, 1H), 6.29 (dd, J = 17.0, 2.1 Hz, 1H), 5.78 (ddd, J = 10.2, 2.3, 1.0 Hz, 1H), 5.00-4.88 (m, 2H), 4.84-4.76 (m, 1H), 4.64-4.50 (m, 2H). | 434.1 |
| 51 | ¹H NMR (300 MHz, Methanol-d₄, ppm) δ 8.68 (s, 1H), 8.24 (s, 1H), 7.80 (s, 1H), 7.62 (d, J = 8.6 Hz, 1H), 6.84 (dd, J = 16.8, 10.6 Hz, 1H), 6.72 (d, J = 8.7 Hz, 1H), 6.29 (dd, J = 16.8, 2.0 Hz, 1H), 5.82 (dd, J = 10.6, 2.0 Hz, 1H), 4.06-4.01 (m, 4H), 3.98-3.93 (m, 4H), 3.43-3.36 (m, 1H), 3.16-3.00 (m, 1H). | 477.1 |
| 52 | ¹H NMR (400 MHz, DMSO-d₆, ppm) δ 8.67 (s, 1H), 8.11 (s, 1H), 7.65 (s, 1H), 6.88-6.81 (m, 3H), 6.54 (s, 1H), 6.18 (dd, J = 16.7, 2.4 Hz, 1H), 5.75 (dd, J = 10.4, 2.4 Hz, 1H), 3.86 (brs, 7H), 3.78 (brs, 1H), 2.74-2.68 (m, 2H), 1.24 (t, J = 7.4 Hz, 3H). | 491.1 |
| 53 | ¹H NMR (400 MHz, Methanol-d₄, ppm) δ 8.68 (s, 1H), 8.20 (s, 1H), 7.80-7.76 (m, 2H), 6.85 (dd, J = 16.8, 10.6 Hz, 1H), 6.65 (d, J = 9.0, 0.9 Hz, 1H), 6.30 (dd, J = 16.8, 1.9 Hz, 1H), 5.83 (dd, J = 10.6, 2.0 Hz, 1H), 4.03-4.01 (m, 4H), 3.96-3.91 (m, 4H), 2.91 (s, 3H). | 477.1 |
| 54 | ¹H NMR (400 MHz, Methanol-d₄, ppm) δ 8.69 (s, 1H), 8.12 (s, 1H), 7.84 (d, J = 8.9 Hz, 1H), 7.77 (s, 1H), 6.92-6.80 (m, 1H), 6.74 (d, J = 8.9, 0.8 Hz, 1H), 6.31 (dd, J = 16.9, 5.7 Hz, 1H), 5.84 (dd, J = 10.7, 1.9 Hz, 1H), 4.59-4.41 (m, 1H), 4.34-4.29 (m, 1H), 4.23-4.05 (m, 1H), 3.85-3.60 (m, 2H), 3.39-3.37 (m, 1H), 3.26-3.19 (m, 1H), 1.44 (d, J = 6.8 Hz, 3H). | 477.1 |
| 55 | 1H NMR (400 MHz, DMSO-d6) δ 8.17-8.06 (m, 1H), 7.42 (d, J = 3.2 Hz, 1H), 6.77 (d, J = 2.9 Hz, 2H), 6.46 (s, 1H), 5.48-5.18 (m, 2H), 4.86 (s, 1H), 4.36 (dt, J = 11.3, 5.7 Hz, 1H), 4.21 (qd, J = 10.4, 9.0, 6.0 Hz, 3H), 3.11-2.93 (m, 2H), 2.63 (s, 1H), 2.40-2.34 (m, 6H), 2.23 (q, J = 8.4 Hz, 2H), 2.02-1.88 (m, 1H), 1.67 (tdd, J = 16.1, 9.6, 4.8 Hz, 3H). | 647.3 |
| 56 | 1H NMR (400 MHz, DMSO-d6) δ 8.10 (d, J = 3.9 Hz, 1H), 7.43 (d, J = 3.1 Hz, 1H), 6.77 (d, J = 2.8 Hz, 2H), 6.46 (s, 1H), 5.41 (dd, J = 18.0, 4.1 Hz, 1H), 5.37-5.08 (m, 2H), 4.39 (ddd, J = 11.5, 7.6, 4.7 Hz, 1H), 4.25 (ddq, J = 24.9, 12.6, 5.3 Hz, 3H), 2.92 (dd, J = 10.2, 5.3 Hz, 2H), 2.40 (s, 3H), 2.38-2.33 (m, 3H), 2.22-2.04 (m, 1H), 1.91 (dddd, J = 33.6, 14.8, 9.8, 5.9 Hz, 1H). | 665.3 |
| 57 | 1H NMR (400 MHz, DMSO-d6) δ 8.04 (d, J = 1.5 Hz, 1H), 7.42 (d, J = 1.7 Hz, 1H), 6.78 (d, J = 2.9 Hz, 2H), 6.46 (s, 1H), 5.43-5.18 (m, 2H), 4.74 (d, J = 43.0 Hz, 3H), 4.43-4.12 (m, 5H), 2.99-2.93 (m, 1H), 2.63-2.53 (m, 1H), 2.36 (s, 6H), 2.18 (q, J = 8.6 Hz, 1H), 2.01-1.89 (m, 1H), 1.74-1.56 (m, 4H). | 640.3 |
| 58 | 1H NMR (400 MHz, DMSO-d6) δ 8.08 (d, J = 10.5 Hz, 1H), 7.43 (d, J = 2.5 Hz, 1H), 6.77 (s, 2H), 6.46 (d, J = 1.5 Hz, 1H), 5.49-4.92 (m, 4H), 4.64 (s, 1H), 4.38 (dt, J = 10.6, 5.1 Hz, 1H), 4.34-4.22 (m, 1H), 4.21-3.93 (m, 2H), 3.71 (d, J = 29.2 Hz, 2H), 3.53-3.37 (m, 2H), 3.07-2.84 (m, 2H), 2.40 (dd, J = 2.4, 1.1 Hz, 4H), 2.38-2.34 (m, 3H), 2.13 (ddd, J = 25.1, 10.7, 4.0 Hz, 1H), 2.02-1.80 (m, 1H), 1.15 (d, J = 8.5 Hz, 3H). | 679.3 |

TABLE 2-continued

| Example No. | $^1$H NMR | MS (M + H)$^+$ |
|---|---|---|
| 59a | $^1$H NMR (300 MHz, DMSO, ppm) δ 8.12 (d, J = 21 Hz, 1H), 6.84 (s, 3H), 6.50 (s, 1H), 6.18 (d, J = 36.0 Hz, 1H), 5.75 (dd, J = 2.4, 10.2 Hz, 1H), 4.75-4.63 (m, 1H), 4.47-4.00 (m, 5H), 3.67-3.55 (m, 2H), 3.25-3.16 (m, 1H), 3.02-2.92 (m, 1H), 2.66-2.55 (m, 1H), 2.38 (s, 6H), 2.25-2.15 (m, 1H), 2.02-1.85 (m, 1H), 1.75-1.55 (m, 3H), 1.45-1.26 (m, 3H). | 688.2 |
| 59b | $^1$H NMR (300 MHz, DMSO, ppm) δ 8.13 (s, 1H), 6.92-6.84 (m, 3H), 6.51 (s, 1H), 6.20 (d, J = 30.0 Hz, 1H), 5.75 (dd, J = 2.4, 10.2 Hz, 1H), 4.75 (s, 1H), 4.45-4.35 (m, 1H), 4.30-3.90 (m, 4H), 3.80-3.55 (m, 2H), 3.28-3.04 (m, 1H), 3.01-2.90 (m, 1H), 2.65-2.55 (m, 1H), 2.43-2.31 (m, 6H), 2.23-2.11 (m, 1H), 2.04-1.87 (m, 1H), 1.75-1.55 (m, 3H), 1.34 (d, J = 6.6 Hz, 3H). | 688.2 |
| 60 | 1H NMR (400 MHz, DMSO-d6), ppm) δ 8.97 (d, J = 4.9 Hz, 1H), 8.22 (d, J = 5.2 Hz, 1H), 7.79 (d, J = 5.3 Hz, 1H), 6.97-6.71 (m, 3H), 6.55-6.46 (m, 1H), 6.20 (dd, J = 16.7, 2.4 Hz, 1H), 5.75 (dd, J = 10.4, 2.4 Hz, 1H), 4.15-3.89 (m, 4H), 3.65 (s, 2H), 2.38 (d, J = 2.5 Hz, 3H), 1.01 (d, J = 6.4 Hz, 6H). | 505.1 |
| 61 | $^1$H NMR (300 MHz, DMSO-d6, ppm) δ 7.94 (d, J = 3.9 Hz, 1H), 7.41 (s, 1H), 6.95-6.72 (m, 3H), 6.47 (s, 1H), 6.18 (d, J = 18.3 Hz, 1H), 5.75 (d, J = 10.5, 2.4 Hz, 1H), 4.70 (s, 1H), 4.46-4.31 (m, 2H), 4.31-3.92 (m, 4H), 3.73-3.51 (m, 2H), 3.01-2.91 (m, 1H), 2.64-2.53 (m, 1H), 2.36 (s, 6H), 2.25-2.12 (m, 1H), 2.00-1.90 (m, 1H), 1.77-1.56 (m, 3H), 1.26 (d, J = 6.0 Hz, 3H). | 604.2 |
| 62a | $^1$H NMR (300 MHz, Methanol-d$_4$, ppm) δ 7.84 (s, 1H), 6.88-6.76 (m, 1H), 6.53 (s, 1H), 6.35-6.28 (m, 1H), 5.85-5.82 (m, 1H), 4.57-4.40 (m, 3H), 4.30-4.03 (m, 2H), 3.81-3.55 (m, 2H), 3.42-3.35 (m, 1H), 3.27-3.20 (m, 1H), 3.16-3.09 (m, 1H), 2.89 (s, 3H), 2.84-2.80 (m, 1H), 2.54 (s, 3H), 2.46 (s, 3H), 2.42-2.35 (m, 1H), 2.17-2.08 (m, 1H), 1.90-1.74 (m, 3H), 1.43 (s, 3H). | 636.1 |
| 62b | $^1$H NMR (300 MHz, Methanol-d$_4$, ppm) δ 7.84 (s, 1H), 6.91-6.75 (m, 1H), 6.53 (s, 1H), 6.35-6.28 (m, 1H), 5.85-5.82 (m, 1H), 4.57-4.40 (m, 3H), 4.30-4.03 (m, 2H), 3.81-3.55 (m, 2H), 3.42-3.34 (m, 1H), 3.27-3.20 (m, 1H), 3.16-3.09 (m, 1H), 2.89 (s, 3H), 2.84-2.80 (m, 1H), 2.54 (s, 3H), 2.46 (s, 3H), 2.42-2.35 (m, 1H), 2.17-2.08 (m, 1H), 1.90-1.75 (m, 3H), 1.45 (d, J = 9 Hz, 3H). | 636.1 |
| 63a | $^1$H NMR (300 MHz, CDCl$_3$, ppm) δ 7.74 (s, 1H), 7.64 (d, J = 8.4 Hz, 1H), 7.54-7.49 (m, 1H), 7.39 (d, J = 8.4 Hz, 1H), 7.28-7.15 (m, 1H), 6.88 (s, 1H), 6.69-6.55 (m, 1H), 6.39 (dd, J = 1.8, 16.5 Hz, 1H), 5.79 (dd, J = 1.8, 10.5 Hz, 1H), 4.90-4.70 (m, 1H), 4.67-4.50 (m, 3H), 4.39-4.27(m, 1H), 4.23-4.11 (m, 1H), 4.05-3.85 (m, 1H), 3.72-3.41 (m, 2H), 3.40-2.95 (m, 2H), 2.82-2.75 (m, 1H), 2.52(s, 3H), 2.42-1.95 (m, 1H), 1.95-1.69 (m, 3H), 1.50-1.25 (m, 3H). | 590.2 |
| 63b | $^1$H NMR (300 MHz, CDCl$_3$, ppm) δ 7.73 (s, 1H), 7.65 (d, J = 8.1 Hz, 1H), 7.55-7.50 (m, 1H), 7.40 (d, J = 8.4 Hz, 1H), 7.21-7.18 (m, 1H), 6.89 (s, 1H), 6.78-6.50 (m, 1H), 6.40 (dd, J = 2.1, 16.8 Hz, 1H), 5.80 (d, J = 11.1 Hz, 1H), 4.80-4.67 (m, 1H), 4.65-4.45 (m, 3H), 4.45-4.32(m, 1H), 4.32-4.17 (m, 1H), 4.12-3.75 (m, 1H), 3.78-3.43 (m, 2H), 3.30-3.00 (m, 2H), 2.97-2.70 (m, 1H), 2.55(s, 3H), 2.45-2.30 (m, 1H), 2.17-2.03 (m, 1H), 1.99-1.66 (m, 4H), 1.54-1.35 (m, 3H). | 590.2 |
| 64a | $^1$H NMR (400 MHz, Methanol-d$_4$, ppm) δ 7.85 (d, J = 1.6 Hz, 1H), 6.92-6.77 (m, 1H), 6.62 (s, 1H), 6.30 (dd, J = 16.8, 3.2 Hz, 1H), 5.82 (dd, J = 10.8, 8.8 Hz, 1H), 4.82-4.78 (m, 1H), 4.52-4.48 (m, 2H), 4.31-4.28 (m, 1H), 4.28-4.01 (m, 2H), 3.87-3.52 (m, 2H), 3.40-3.44 (m, 1H), 3.32-3.17 (m, 1H), 2.92 (s, 3H), 2.61-2.58 (m, 1H), 2.46 (d, J = 1.2 Hz, 3H), 2.37-2.27 (m, 2H), 2.10-2.05 (m, 1H), 1.43 (d, J = 6.8 Hz, 3H). | 636.2 |
| 64b | $^1$H NMR (400 MHz, Methanol-d$_4$, ppm) δ 7.85 (d, J = 1.6 Hz, 1H), 6.92-6.77 (m, 1H), 6.62 (s, 1H), 6.30 (dd, J = 16.8, 3.2 Hz, 1H), 5.81 (dd, J = 10.8, 8.8 Hz, 1H), 4.85-4.77 (m, 1H), 4.53-4.49 (m, 2H), 4.31-4.28 (m, 1H), 4.28-4.01 (m, 2H), 3.87-3.52 (m, 2H), 3.36-3.34 (m, 1H), 3.30-3.17 (m, 1H), 2.92 (s, 3H), 2.61-2.58 (m, 1H), 2.46 (d, J = 1.2 Hz, 3H), 2.37-2.27 (m, 2H), 2.11-2.05 (m, 1H), 1.43 (d, J = 6.8 Hz, 3H). | 636.2 |
| 65 | $^1$H NMR (400 MHz, DMSO-d6, ppm) δ 7.94 (t, J = 7.2 Hz, 1H), 7.41 (s, 1H), 7.23-7.08 (m, 1H), 6.78 (s, 2H), 6.69-6.62 (m, 1H), 6.53-6.45 (m, 1H), 4.84-4.63 (m, 1H), 4.43-4.22 (m, 2H), 4.19-3.98 (m, 3H), 3.98-3.80 (m, 1H), 3.78-3.42 (m, 2H), 3.28-3.08 (m, 1H), 2.97-2.92 (m, 1H), 2.63-2.55 (m, 1H), 2.41-2.33 (m, 6H), 2.18 (q, J = 8.4 Hz, 1H), 2.01-1.92 (m, 1H), 1.73-1.58 (m, 3H), 1.35-1.23 (m, 3H). | 654.3 |
| 66 | $^1$H NMR (400 MHz, DMSO-d$_6$), ppm) δ 7.93 (s, 1H), 7.42 (d, J = 3.4 Hz, 1H), 6.89-6.80 (m, 1H), 6.77 (s, 2H), 6.46 (s, 1H), 6.19 (d, J = 16.4 Hz, 1H), 5.75 (dd, J = 10.4, 2.4 Hz, 1H), 5.40 (s, 1H), 4.70 (s, 1H), 4.40-4.19 (m, 1H), 4.15-3.89 (m, 2H), 3.62-3.40 (m, 2H), 3.25-3.05 (m, 2H), 2.40-2.25 (m, 8H), 2.13-1.97 (m, 3H), 1.68-1.52 (s, 4H), 1.39-1.25 (m, 3H). | 618.2 |
| 67a | $^1$H NMR (300 MHz, DMSO, ppm) δ 8.01-7.74 (m, 2H), 7.73-7.60 (m, 1H), 7.40-7.30 (m, 1H), 7.25-7.17 (m, 1H), 6.75-7.00 (m, 1H), 6.33 (s, 2H), 6.22-6.09 (m, 1H), 5.74 (dd, J = 2.4, 10.5 Hz, 1H), 4.80 (s, 1H), 4.42-3.95 (m, 5H), 3.87-3.37 (m, 2H), 3.29-3.02 (m, 1H), 2.98-2.83 (m, 1H), 2.68-2.54 (m, 1H), 2.32 (s, 3H), 2.19-2.09 (m, 1H), 2.00-1.85 (m, 1H), 1.70-1.52 (m, 3H), 1.38-1.25 (m, 3H). | 608.2 |
| 67b | $^1$H NMR (300 MHz, DMSO, ppm) δ 8.05-7.75 (m, 2H), 7.73-7.53 (m, 1H), 7.51-7.30 (m, 1H), 7.27-7.10 (m, 1H), 7.00-6.6.63 (m, 1H), 6.33 (s, 2H), 6.22-6.15 (d, J = 21, 1H), 5.74 (dd, J = 2.4, 10.5 Hz, 1H), 4.80 (s, 1H), 4.42-3.95 (m, 5H), 3.87-3.37 (m, 2H), 3.29-3.02 (m, 1H), 2.98-2.83 (m, 1H), 2.68-2.54 (m, 1H), 2.32 (s, 3H), 2.19-2.09 (m, 1H), 2.01-1.87 (m, 1H), 1.80-1.53 (m, 3H), 1.33-1.17 (m, 3H). | 608.2 |
| 68a | $^1$H NMR (400 MHz, DMSO-d$_6$, ppm) δ 7.81 (s, 1H), 6.85 (s, 2H), 6.49 (s, 1H), 5.37-5.20 (m, 2H), 4.76 (s, 1H), 4.39 (dd, J = 10.8, 6.0 Hz, 1H), 4.18-4.11 (m, 3H), 4.11-3.93 (m, 1H), 3.91-3.69 (m, 2H), 3.20-3.03 (m, 1H), 2.96-2.92 (m, 1H), 2.60-2.57 (m, 1H), 2.37-2.35 (m, 6H), 2.19-2.14 (m, 1H), 1.96-1.92 (m, 1H), 1.70-1.62 (m, 3H), 1.28 (d, J = 6.8 Hz, 3H). | 640.2 |
| 68b | $^1$H NMR (400 MHz, DMSO-d$_6$, ppm) δ 7.79 (s, 1H), 6.84 (s, 2H), 6.49 (s, 1H), 5.37-5.19 (m, 2H), 4.73 (s, 1H), 4.37 (dd, J = 10.8, 6.0 Hz, 1H), 4.18-4.01 (m, 3H), 4.01-3.79 (m, 1H), 3.79-3.66 (m, 2H), 3.31-3.03 (m, 1H), 2.96-2.92 (m, 1H), 2.59-2.56 (m, 1H), 2.37-2.35 (m, 6H), 2.18-2.14 (m, 1H), 1.97-1.93 (m, 1H), 1.70-1.62 (m, 3H), 1.31 (d, J = 6.8 Hz, 3H). | 640.2 |
| 69 | $^1$H NMR (400 MHz, DMSO-d$_6$, ppm) δ 7.80 (s, 1H), 6.85 (s, 3H), 6.50 (s, 1H), 6.25-6.12 (m, 1H), 5.74 (dd, J = 10.4, 2.4 Hz, 1H), 5.19 (d, J = 56.6 Hz, 1H), 4.71 (s, 1H), 4.51-4.19 (m, 3H), 4.19-3.91 (m, 2H), 3.61 (d, J = 12.3 Hz, 2H), 3.45 (m, J = 25.6, 11.5, 5.3 Hz, 1H), 3.25-3.02 (m, 1H), 2.93 (dd, J = 10.1, 5.3 Hz, 1H), 2.42-2.34 (m, 7H), 2.24-2.05 (m, 1H), 1.92 (m, J = 33.7, 14.9, 10.0, 6.0 Hz, 1H), 1.30 (d, J = 6.6 Hz, 3H). | 640.2 |
| 70 | $^1$H NMR (400 MHz, DMSO-d$_6$, ppm) δ 8.04 (s, 1H), 7.78 (d, J = 8.8 Hz, 1H), 7.46 (s, 1H), 6.90 (s, 2H), 6.82 (dd, J = 10.0, 16.4 Hz, 1H), 6.60 (d, J = 8.8 Hz, 1H), 6.17 (dd, J = 2.4, 16.8 Hz, 1H), 5.74 (dd, J = 2.0, 10.4 Hz, 1H), 4.36-4.33 (m, 1H), 4.19-4.15 (m, 1H), 3.85-3.77 (m, 8H), 2.96-2.95 (m, 1H), 2.68-2.65 (m, 1H), 2.35 (s, 3H), 2.19-2.13 (m, 1H), 1.97-1.88 (m, 1H), 1.68-1.60 (m, 3H). | 576.2 |

TABLE 2-continued

| Example No. | ¹H NMR | MS (M + H)⁺ |
|---|---|---|
| 71 | ¹H NMR (300 MHz, Methanol-d₄, ppm) δ 8.09 (s, 1H), 7.80 (d, J = 9.0 Hz, 1H), 7.54 (s, 1H), 6.89-6.77 (m, 1H), 6.71-6.66 (m, 1H), 6.31-6.25 (m, 1H), 5.86-5.75 (m, 1H), 4.52-4.48 (m, 2H), 4.10 (s, 1H), 3.98 (s, 4H), 3.93 (s, 4H), 3.56-3.36 (m, 3H), 3.17 (s, 1H), 2.60 (s, 3H), 2.56-2.47 (m, 1H), 2.12 (s, 1H), 2.00 (d, J = 8.2 Hz, 1H), 1.18 (t, J = 7.0 Hz, 3H). | 620.3 |
| 72 | ¹H NMR (400 MHz, CDCl₃, ppm) δ 7.89 (s, 1H), 7.82 (d, J = 8.7 Hz, 1H), 7.68 (s, 1H), 6.69-6.56 (m, 1H), 6.43-6.34 (m, 1H), 5.85-5.75 (m, 1H), 4.90 (d, J = 7.1 Hz, 2H), 4.58 (s, 1H), 4.34 (s, 1H), 4.01-3.73 (m, 8H), 3.17 (s, 1H), 2.24 (s, 3H), 1.92 (s, 1H), 1.80 (s, 2H), 0.91 (s, 1H), 0.67 (s, 1H), 0.52 (s, 1H), 0.31 (s, 1H). | 602.2 |
| 73 | ¹H NMR (300 MHz, Methanol-d₄) δ 8.09 (s, 1H), 7.80 (d, J = 9 Hz, 1H), 7.55 (s, 1H), 6.91-6.75 (m, 1H), 6.70 (d, J = 9 Hz, 1H), 6.34-6.18 (m, 1H), 5.86-5.74 (m, 1H), 4.49-4.31 (m, 2H), 4.06-3.84 (m, 8H), 3.43-3.32 (m, 1H), 3.22-3.01 (m, 1H), 2.69-2.45 (m, 1H), 2.39 (s, 3H), 2.30-2.12 (m, 1H), 1.26 (s, 3H). | 626.2 |
| 74 | ¹H NMR (400 MHz, DMSO-d₆, ppm) δ 8.00 (s, 1H), 7.77 (d, J = 9.2 Hz, 1H), 7.43 (s, 1H), 6.88-6.78 (m, 3H), 6.59 (d, J = 8.8 Hz, 1H), 6.16 (dd, J = 16.4, 2.0 Hz, 1H), 5.73 (dd, J = 10.8, 2.4 Hz, 1H), 3.83-3.79 (m, 8H), 3.12-3.09 (m, 1H), 2.98-2.96 (m, 1H), 2.37 (d, J = 9.6 Hz, 3H), 2.29-2.24 (m, 1H), 1.90-1.84 (m, 1H), 1.71-1.58 (m, 3H), 1.57-1.52 (m, 6H). | 604.4 |
| 75a | ¹H NMR (300 MHz, DMSO-d₆, ppm) δ 8.05 (s, 1H), 7.78 (d, J = 8.7 Hz, 1H), 7.47 (s, 1H), 6.91 (s, 2H), 6.82 (dd, J = 16.5, 10.2 Hz, 1H), 6.60 (d, J = 8.7 Hz, 1H), 6.17 (dd, J = 16.8, 2.4 Hz, 1H), 5.74 (dd, J = 10.5, 2.4 Hz, 1H), 4.33 (d, J = 5.4 Hz, 2H), 3.85-3.77 (m, 8H), 2.82-2.72 (m, 1H), 2.29 (s, 3H), 2.02-1.93 (m, 2H), 1.26-1.23 (m, 2H). | 562.2 |
| 75b | ¹H NMR (300 MHz, DMSO-d₆, ppm) δ 8.04 (s, 1H), 7.78 (d, J = 8.7 Hz, 1H), 7.46 (s, 1H), 6.91-6.78 (m, 3H), 6.60 (d, J = 8.7 Hz, 1H), 6.17 (dd, J = 16.8, 2.4 Hz, 1H), 5.74 (dd, J = 10.5, 2.4 Hz, 1H), 4.30 (d, J = 5.4 Hz, 2H), 3.85-3.77 (m, 8H), 2.78-2.70 (m, 1H), 2.25 (s, 3H), 2.01-1.87 (m, 2H), 1.26-1.23 (m, 2H). | 562.2 |
| 76 | ¹H NMR (300 MHz, DMSO, ppm) δ 8.04 (s, 1H), 7.78 (d, J = 9.0 Hz, 1H), 7.46 (s, 1H), 7.00-6.67 (m, 3H), 6.60 (d, J = 8.7 Hz, 1H), 6.17 (dd, J = 2.1, 16.5 Hz, 1H), 5.74 (dd, J = 2.1, 10.5 Hz, 1H), 4.58 (d, J = 6.3 Hz, 1H), 4.42 (d, J = 6.3 Hz, 1H), 4.31-4.15 (m, 2H), 3.93-3.70 (m, 8H), 3.32-3.29 (m, 2H), 3.02-2.93 (m, 2H), 2.83-2.66 (m, 3H). | 594.2 |
| 77 | ¹H NMR (400 MHz, DMSO-d₆, ppm) δ 8.05 (s, 1H), 7.78 (d, J = 8.0 Hz, 1H), 7.46 (s, 1H), 6.91 (s, 2H), 6.98-6.78 (m, 1H), 6.59 (d, J = 8.8 Hz, 1H), 6.17 (dd, J = 16.8, 2.0 Hz, 1H), 5.74 (dd, J = 8.8, 2.0 Hz, 1H), 5.09 (d, J = 52.0, 1H), 4.39-4.35 (m, 1H), 4.15-4.13 (m, 1H), 3.90-3.86 (m, 6H), 3.76 (s, 2H), 2.94 (d, J = 6.8, 1H), 2.84-2.75 (m, 1H), 2.49-2.43 (m, 4H), 1.96-1.90 (m, 2H). | 594.2 |
| 78a | ¹H NMR (300 MHz, Methanol-d₄, ppm) δ 8.09 (s, 1H), 7.80 (d, J = 9 Hz, 1H), 7.54 (s, 1H), 6.83 (dd, J = 16.8, 10.8 Hz, 1H), 6.71 (dd, J = 8.7 Hz, 1H), 6.29 (dd, J = 16.8, 2.1 Hz, 1H), 5.82 (dd, J = 10.5, 1.8 Hz, 1H), 4.62-4.51 (m, 1H), 4.48-4.33 (m, 1H), 4.05-3.86 (m, 8H), 3.13 (d, J = 9 Hz, 1H), 3.01-2.92 (m, 1H), 2.58 (dd, J = 9, 3.9 Hz, 1H), 2.43 (s, 3H), 1.76-1.61 (m, 1H), 1.58-1.39 (m, 1H), 0.82-0.63 (m, 1H), 0.45-0.26 (m, 1H). | 588.3 |
| 78b | ¹H NMR (400 MHz, Methanol-d₄, ppm) δ 8.11 (s, 1H), 7.82 (d, J = 8.9 Hz, 1H), 7.57 (s, 1H), 6.83 (dd, J = 10.8, 10.4 Hz, 1H), 6.72 (d, J = 8.8 Hz, 1H), 6.29 (dd, J = 16.8, 1.6 Hz, 1H), 5.82 (dd, J = 10.6, 2 Hz, 1H), 4.72-4.56 (m, 1H), 4.55-4.37 (m, 1H), 4.14-3.68 (m, 8H), 3.29-3.13 (m, 2H), 2.79 (d, J = 9.6 Hz, 1H), 2.54 (s, 3H), 1.68-1.52 (m, 2H), 0.83-0.69 (m, 1H), 0.63-0.47 (m, 1H). | 588.2 |
| 79a | ¹H NMR (400 MHz, DMSO, ppm) δ 8.03 (s, 1H), 7.79 (d, J = 8.0, 1H), 7.43 (s, 1H), 6.89 (s, 2H), 6.89-6.72 (m, 1H), 6.58 (d, J = 12.0, 1H), 6.17 (dd, J = 2.4, 16.8 Hz, 1H), 5.74 (dd, J = 2.4, 10.4 Hz, 1H), 5.41-5.23 (m, 1H), 3.95-3.62 (m, 8H), 2.60-2.51 (m, 1H), 2.40-2.31 (m, 1H), 2.19 (s, 6H), 1.35-1.20 (m, 3H). | 564.2 |
| 79b | ¹H NMR (400 MHz, DMSO, ppm) δ 8.03 (s, 1H), 7.78 (d, J = 8.8, 1H), 7.43 (s, 1H), 6.89 (s, 2H), 6.85-6.72 (m, 1H), 6.60 (d, J = 8.8, 1H), 6.17 (dd, J = 2.4, 16.8 Hz, 1H), 5.74 (dd, J = 2.4, 10.4 Hz, 1H), 5.41-5.23 (m, 1H), 3.93-3.65 (m, 8H), 2.64-2.54 (m, 1H), 2.40-2.28 (m, 1H), 2.19 (s, 6H), 1.40-1.29 (m, 3H). | 564.2 |
| 80 | ¹H NMR (300 MHz, MeOD, ppm) δ 8.09 (s, 1H), 7.80 (d, J = 8.7 Hz, 1H), 7.54 (s, 1H), 6.82 (dd, J = 10.5, 16.8 Hz, 1H), 6.70 (d, J = 8.4 Hz, 1H), 6.27 (dd, J = 1.8, 16.8 Hz, 1H), 5.80 (dd, J = 1.8, 10.5 Hz, 1H), 4.59-4.45 (m, 2H), 4.10-3.89 (m, 10H), 3.54-3.41 (m, 2H), 3.39 (s, 3H), 2.78-2.53 (m, 3H), 2.20-1.87 (m, 2H), 1.83-1.59 (m, 2H). | 620.4 |
| 81a | ¹H NMR (300 MHz, Methanol-d₄, ppm) δ 7.53 (dd, J = 9.9, 8.1 Hz, 1H), 6.89-6.72 (m, 1H), 6.60 (s, 1H), 6.31-6.25 (m, 1H), 5.81 (dd, J = 18, 10.5 Hz, 1H), 5.35-5.03 (m, 1H), 4.81 (s, 1H), 4.64-4.31 (m, 3H), 4.31-3.94 (m, 2H), 3.82-3.45 (m, 3H), 3.28-3.06 (m, 2H), 2.73-2.62 (m, 1H), 2.55 (s, 3H), 2.45 (d, J = 1.5, 3H), 2.32-2.20 (m, 1H), 2.17-1.98 (m, 1H), 1.40 (d, J = 6.6 Hz, 3H). | 624.3 |
| 81b | ¹H NMR (300 MHz, Methanol-d₄, ppm) δ 7.53 (dd, J = 9.9, 8.1 Hz, 1H), 6.94-6.71 (m, 1H), 6.60 (s, 1H), 6.38-6.20 (m, 1H), 5.81 (dd, J = 18, 10.5 Hz, 1H), 5.45-5.03 (m, 1H), 4.81 (s, 1H), 4.64-4.31 (m, 3H), 4.31-3.94 (m, 2H), 3.82-3.45 (m, 3H), 3.28-3.06 (m, 2H), 2.79-2.60 (m, 1H), 2.55 (s, 3H), 2.45 (d, J = 1.5, 3H), 2.39-2.20 (m, 1H), 2.17-1.78 (m, 1H), 1.40 (d, J = 6.6 Hz, 3H). | 624.3 |
| 82a | ¹H NMR (300 MHz, Methanol-d4, ppm) δ 7.82 (s, 1H), 6.60 (s, 1H), 5.42-5.02 (m, 3H), 4.82 (s, 1H), 4.50 (d, J = 5.0 Hz, 2H), 4.42-3.93 (m, 3H), 3.86-3.39 (m, 4H), 3.21-3.00 (m, 1H), 2.77-2.51 (m, 4H), 2.51-2.39 (m, 3H), 2.38-1.92 (m, 2H), 1.43 (d, J = 6.7 Hz, 3H). | 658.3 |
| 82b | ¹H NMR (300 MHz, Methanol-d4, ppm) δ 7.82 (s, 1H), 6.60 (s, 1H), 5.51-5.00 (m, 3H), 4.82 (s, 1H), 4.50 (d, J = 5.0 Hz, 2H), 4.46-3.93 (m, 3H), 3.88-3.39 (m, 4H), 3.26-3.00 (m, 1H), 2.78-2.51 (m, 4H), 2.51-2.40 (m, 3H), 2.40-1.90 (m, 2H), 1.43 (d, J = 6.7 Hz, 3H). | 658.3 |
| 83a | ¹H NMR (400 MHz, Methanol-d₄, ppm) δ 7.96 (d, J = 1.6 Hz, 1H), 6.62 (s, 1H), 5.42-5.12 (m, 3H), 5.11-4.90 (m, 1H), 4.58-4.40 (m, 4H), 4.35-4.01 (m, 1H), 3.91-3.59 (m, 3H), 3.57-3.46 (m, 1H), 3.18-3.07 (m, 3H), 2.73-2.62 (m, 1H), 2.57 (s, 3H), 2.46 (d, J = 1.2 Hz, 3H), 2.36-2.25 (m, 1H), 2.12-1.96 (m, 1H). | 683.3 |
| 83b | ¹H NMR (400 MHz, Methanol-d₄, ppm) δ 7.96 (d, J = 1.6 Hz, 1H), 6.62 (s, 1H), 5.42-5.12 (m, 3H), 5.11-4.92 (m, 1H), 4.53-4.40 (m, 4H), 4.38-4.00 (m, 1H), 3.89-3.59 (m, 3H), 3.62-3.46 (m, 1H), 3.19-3.13 (m, 2H), 3.09-3.03 (m, 1H), 2.73-2.62 (m, 1H), 2.57 (s, 3H), 2.46 (d, J = 1.6 Hz, 3H), 2.33-2.18 (m, 1H), 2.15-1.91 (m, 1H). | 683.3 |
| 83c | ¹H NMR (400 MHz, Methanol-d₄, ppm) δ 7.96 (d, J = 1.6 Hz, 1H), 6.62 (s, 1H), 5.42-5.12 (m, 3H), 5.08-4.93 (m, 1H), 4.66-4.39 (m, 4H), 4.38-4.10 (m, 1H), 3.89-3.49 (m, 4H), 3.19-3.04 (m, 3H), 2.76-2.63 (m, 1H), 2.59 (s, 3H), 2.46 (d, J = 1.2 Hz, 3H), 2.33-2.26 (m, 1H), 2.16-1.98 (m, 1H). | 683.3 |
| 83d | ¹H NMR (400 MHz, Methanol-d₄, ppm) δ 7.96 (d, J = 1.6 Hz, 1H), 6.62 (s, 1H), 5.43-5.14 (m, 3H), 5.11-4.91 (m, 1H), 4.62-4.40 (m, 4H), 4.37-3.98 (m, 1H), 3.90-3.47 (m, 4H), 3.22-3.05 (m, 3H), 2.89-2.69 (m, 1H), 2.61 (s, 3H), 2.46 (d, J = 4.0 Hz, 3H), 2.39-2.28 (m, | 683.3 |

TABLE 2-continued

| Example No. | ¹H NMR | MS (M + H)⁺ |
|---|---|---|
| | 1H), 2.15-1.99 (m, 1H). | |
| 84a | ¹H NMR (300 MHz, DMSO-d₆, ppm) δ 7.82 (s, 1H), 6.92-6.74 (m, 1H), 6.39 (s, 1H), 6.26-6.11 (m, 1H), 5.81-5.66 (m, 3H), 5.18 (d, J = 56.2 Hz, 1H), 4.75 (s, 1H), 4.50-4.23 (m, 3H), 4.19-3.91 (m, 2H), 3.74-3.38 (m, 3H), 3.26-2.85 (m, 2H), 2.44-2.29 (m, 4H), 2.24-2.05 (m, 4H), 2.03-1.87 (m, 1H), 1.81 (s, 3H), 1.28 (d, J = 6.5 Hz, 3H). | 586.3 |
| 84b | ¹H NMR (300 MHz, DMSO-d₆, ppm) δ 7.82 (s, 1H), 6.95-6.74 (m, 1H), 6.39 (s, 1H), 6.25-6.11 (m, 1H), 5.84-5.65 (m, 3H), 5.19 (d, J = 56.1 Hz, 1H), 4.74 (s, 1H), 4.49-4.22 (m, 3H), 4.21-3.88 (m, 2H), 3.74-3.53 (m, 2H), 3.50-3.38 (m, 2H), 3.25-3.01 (m, 1H), 3.03-2.86 (m, 1H), 2.41 (s, 3H), 2.20 (s, 3H), 2.13-1.87 (m, 2H), 1.83 (s, 3H), 1.30 (d, J = 6.5 Hz, 3H). | 586.3 |
| 85 | ¹H NMR: (400 MHz, DMSO-d₆, ppm) δ 7.83 (s, 1H), 6.83-6.79 (m, 3H), 6.64-6.55 (m, 1H), 6.50 (s, 1H), 5.03-5.01 (m, 1H), 4.76 (s, 1H), 4.47-4.23 (m, 3H), 4.15-3.88 (m, 4H), 3.65-3.30 (m, 3H), 3.24-2.98 (m, 2H), 2.90-2.68 (m, 1H), 2.49-2.44 (m, 3H), 2.37-2.32 (m, 3H), 1.99-1.91 (m, 1H), 1.72-1.65 (m, 3H), 1.27 (s, 3H). | 652.3 |
| 86 | ¹HNMR: (400 MHz, DMSO-d₆, ppm) δ 8.18 (s, 1H), 7.82 (s, 1H), 6.83-6.71 (m, 3H), 6.49 (s, 1H), 4.90-4.75 (m, 1H), 4.40-4.30 (m, 3H), 4.30-4.06 (m, 3H), 4.01-3.88 (m, 1H), 3.67-3.55 (m, 2H), 3.13-3.15 (m, 1H), 3.05-2.93 (m, 1H), 2.61-2.56 (m, 1H), 2.43-2.26 (m, 6H), 2.19-2.15 (m, 1H), 1.97-1.93 (m, 1H), 1.70-1.62 (m, 3H), 1.28-1.25 (m, 3H). | 670.3 |
| 87 | ¹H NMR (300 MHz, DMSO-d₆, ppm) δ 8.05 (s, 1H), 7.78 (d, J = 8.9 Hz, 1H), 7.48 (d, J = 2.3 Hz, 1H), 6.98-6.75 (m, 3H), 6.60 (d, J = 8.8 Hz, 1H), 6.17 (dd, J = 16.7, 2.4 Hz, 1H), 5.74 (dd, J = 10.4, 2.4 Hz, 4.65-4.15 (m, 2H), 3.95-3.60 (m, 10H), 3.29-3.07 (m, 3H), 2.97-2.69 (m, 1H), 2.65-2.55 (m, 1H), 2.18-2.01 (m, 1H), 1.77-1.46 (m, 3H), 1.38-1.13 (m, 1H). | 618.3 |
| 88 | ¹H NMR (300 MHz, DMSO, ppm) δ 8.04 (s, 1H), 7.77 (d, J = 9.0 Hz, 1H), 7.43 (s, 1H), 6.87 (s, 2H), 6.79 (dd, J = 12.0, 18.0 Hz, 1H), 6.58 (d, J = 9.0 Hz, 1H), 6.15 (dd, J = 3.0, 18.0 Hz, 1H), 5.72 (dd, J = 3.0, 9.0 Hz, 1H), 4.40 (dd, J = 12.0, 27.0 Hz, 2H), 3.93-3.80 (m, 6H), 3.81-3.72 (m, 2H), 2.34 (s, 6H), 0.75-0.53 (m, 4H). | 576.2 |
| 89 | ¹H NMR (400 MHz, DMSO-d₆, ppm) δ 8.04 (s, 1H), 7.77 (d, J = 9.2 Hz, 1H), 7.46 (s, 1H), 6.89 (s, 2H), 6.86-6.72 (m, 1H), 6.59 (d, J = 8.8 Hz, 1H), 6.19 (d, J = 2.4 Hz, 1H), 5.73 (dd, J = 12.4, 2.0 Hz, 1H), 5.18 (d, J = 48 Hz, 1H), 4.43-4.31(m, 1H), 4.30-4.18 (m, 1H), 3.98-3.58 (m, 8H), 3.52-3.42 (m, 1H), 3.41-3.37 (m, 2H), 3.22-3.13 (m, 4H), 3.13-3.05 (m, 1H), 2.72-2.57 (m, 2H), 2.21-2.09 (m, 1H), 1.98-1.78 (m, 1H). | 638.2 |
| 90 | ¹H NMR (400 MHz, Methanol-d₄,ppm) δ 8.10 (s, 1H), 7.81 (d, J = 8.0 Hz, 1H), 7.55 (s, 1H), 6.86-6.79 (m, 1H), 6.71 (d, J = 8.8 Hz, 1H), 6.29 (dd, J = 8.4,2.0 Hz, 1H), 5.82 (dd,J = 10.4, 1.6 Hz, 1H), 4.88-4.62 (m, 1H), 4.54-4.44 (m, 2H), 4.00-3.93 (m, 8H), 3.15-3.11 (m, 1H), 2.75-2.62 (m, 1H), 2.51 (s, 3H), 2.26-1.98 (m, 2H), 1.21 (d, J = 6.4 Hz, 3H). | 608.2 |
| 91 | ¹H NMR (300 MHz, DMSO-d₆, ppm) δ 8.04 (s, 1H), 7.78 (d, J = 8.9 Hz, 1H), 7.46 (s, 1H), 6.96-6.74 (m, 3H), 6.60 (d, J = 8.8 Hz, 1H), 6.17 (dd, J = 16.6, 2.4 Hz, 1H), 5.74 (dd, J = 10.4, 2.4 Hz, 1H), 4.38-4.27 (m, 1H), 4.15-3.99 (m, 1H), 3.94-3.70 (m, 8H), 3.42 (t, J = 6.2 Hz, 3H), 3.21 (s, 3H), 3.09-2.95 (m, 2H), 2.84 (s, 1H), 2.31-2.18 (m, 1H), 1.95-1.80 (m, 1H), 1.75-1.54 (m, 3H). | 620.3 |
| 92 | ¹H NMR (400 MHz, Methanol-d₄, ppm) δ 8.14 (s, 1H), 7.82 (d, J = 8.8 Hz, 1H), 7.57 (s, 1H), 6.86-6.79 (m, 1H), 6.73-6.71 (m, 1H), 6.52 (s, 1H), 6.33-6.27 (m, 1H), 5.82 (dd, J = 10.4, 1.6 Hz, 1H), 4.99-4.98 (m, 1H), 4.77-4.73 (m, 1H), 4.63-4.58 (m, 1H), 3.98 (d, J = 3.6 Hz, 8H), 3.83-3.79 (m, 2H), 3.17-3.14 (m, 1H), 2.93 (s, 3H), 2.43-2.33 (m, 2H). | 642.1 |
| 93 | ¹H NMR (400 MHz, Methanol-d₄, ppm) δ 7.67 (d, J = 1.6 Hz, 1H), 6.92-6.73 (m, 1H), 6.60 (s, 1H), 6.29 (d, J = 18.0 Hz, 1H), 5.87-5.76 (m, 1H), 4.69 (s, 1H), 4.54 (d, J = 16.2 Hz, 1H), 4.41-4.23 (m, 1H), 4.22-3.96 (m, 2H), 3.95-3.81 (m, 1H), 3.80-3.52 (m, 6H), 2.46 (s, 3H), 2.28-1.77 (m, 4H), 1.37 (d, J = 6.6 Hz, 3H). | 608.3 |
| 94 | ¹H NMR (400 MHz, DMSO-d₆, ppm) δ 8.04 (s, 1H), 7.78 (d, J = 8.8 Hz, 1H), 7.46 (s, 1H), 6.90 (s, 2H), 6.82 (dd, J = 10.4, 10.8 Hz, 1H), 6.60 (d, J = 8.8 Hz, 1H), 6.24-5.88 (m, 2H), 5.79-5.68 (m, 1H), 4.38-4.24 (m, 1H), 4.20-4.07 (m, 1H), 3.92-3.68 (m, 8H), 3.39-3.21 (m, 1H), 3.16-3.06 (m, 1H), 3.05-2.95 (m, 1H), 2.90-2.74 (m, 1H), 2.45-2.37 (m, 1H), 1.98-1.86 (m, 1H), 1.79-1.68 (m, 2H), 1.67-1.56 (m, 1H). | 626.3 |
| 95 | ¹H NMR (400 MHz, Methanol-d₄) 58.10 (s, 1H), 7.80 (d, J = 8.8 Hz, 1H), 7.57 (m, 1H), 6.87-6.76 (m, 1H), 6.70 (d, J = 8.8 Hz, 1H), 6.31-6.23 (m, 1H), 5.84-5.77 (m, 1H), 4.63-4.48 (m, 2H), 4.05-3.99 (m, 5H), 3.92 (s, 4H), 3.66-3.36 (m, 5H), 3.33 (s, 5H), 3.29 (d. J = 1.2 Hz, 1H), 3.05-2.78 (m, 2H), 2.55-1.88 (m, 2H). | 650.4 |
| 96 | ¹H NMR (400 MHz, DMSO-d₆, ppm) δ 8.04 (s, 1H), 7.78 (d, J = 8.8 Hz, 1H), 7.47 (s, 1H), 6.90 (s, 2H), 6.85-6.82 (m, 1H), 6.59 (d, J = 8.8 Hz, 1H), 6.19 (d, J = 2.4 Hz, 1H), 5.73 (dd, J = 10.4, 2.4 Hz, 1H), 5.26 (d, J = 56 Hz, 1H), 4.26-4.16 (m, 2H), 3.88-3.85 (m, 6H), 3.85-3.70 (m, 2H), 3.07-2.99 (m, 1H), 2.91-2.78 (m, 1H), 2.27 (s, 3H), 2.19-2.00 (m, 2H), 1.02 (s, 3H). | 608.2 |
| 97 | ¹H NMR (400 MHz, DMSO-d₆) 7.84 (s, 1H), 7.19 (t, J = 7.8 Hz, 1H), 6.99 (t, J = 8.5 Hz, 2H), 6.87 (s, 2H), 6.83-6.74 (m, 1H), 6.50 (s, 1H), 6.22-6.12 (m, 1H), 5.78-5.70 (m, 1H), 4.54 (d, J = 29.3 Hz, 1H), 4.30-3.86 (m, 3H), 3.55 (td, J = 24.5, 23.0, 13.2 Hz, 4H), 3.24-3.02 (m, 1H), 2.60 (d, J = 6.0 Hz, 2H), 2.57-2.52 (m, 2H), 2.37 (d, J = 2.3 Hz, 3H), 2.32 (s, 3H), 1.19 (t, J = 5.8 Hz, 3H). | 670.3 |

Biological Examples

K-Ras G12C, SOS1, Raf RBD Homogeneous Time Resolved Fluorescence (HTRF) Assay for Inhibition of GTP Exchange To determine the potency of compounds for inhibiting nucleotide exchange, various concentrations were incubated with K-Ras G12C (25 nM in reaction, 12.5 nM final). After 18 hours at room temperature, the SOS1 GTP exchange factor (1.67 nM during exchange, 1.25 nM final) was added to initiate nucleotide exchange to GTP (200 μM during exchange, 150 μM final). The level of GTP exchange was assessed by addition of a Ras binding domain derived from C-Raf and the HTRF detection antibodies Tb-anti-FLAG and D2-anti-his (Cis-Bio) at 50 nM, 1 nM and 12.5 nM, respectively. After 2 hours, the ratio of 665 nm to 615 nM emission with 320 nM excitation was measured on an Envision plate reader (Perkin Elmer).

The final reaction volume was 20 μl in a ProxiPlate-384F Plus (Perkin Elmer), in buffer containing 20 mM HEPES, 150 mM NaCl, 1 mM MgCl2, 0.1% BSA, 0.03% Tween-20 and 1 mM DTT. K-Ras G12C (residues 2-188) and SOS1 (residues 564-1049) had N-terminal 6-His and the Raf-RBD construct (residues 51-186 of RAF1) had an N-terminal Flag-tag. All constructs were expressed in E. coli and had a Tev cleavage site between the tag and protein of interest that was not used during purification. HTRF data are presented below in Table 3.

Western Blot Assay for in Cell Alkylation of K-Ras G12C

HCC1171 cells were maintained in RPMI1640 supplemented with 10% FBS. Cells were plated in a 96-well plate at 20,000 cells/well and the following day compounds were added to the cells. After 18 hours at 37° C., cells were lysed in RIPA buffer (Sigma R0278) with 0.5% SDS and protease/phosphatase inhibitor cocktail. After through mixing to enable complete lysis, the lysates were cleared by centrifugation before 20 μl was transferred from each well and combined with loading buffer and reducing agent. After heating for 10 minutes at 95° C., 15 μl of each sample was loaded onto a 4-20% Tris-Glycine gel and electrophoresed at 110V for 165 minutes in SDS-PAGE running buffer. Gels were transferred to a nitrocellulose membrane, blocked for 1 hour and stained overnight at 4° C. with primary antibody against K-Ras (polyclonal Proteintech 12063-1-AP). The membrane was then washed thoroughly and counterstained with anti-rabbit IRDye 800CW (LI-COR 926-32211) for one hour at room temperature. After final washes, the membrane was imaged on a LI-COR Odyssey CLx at medium resolution. Alkylated K-Ras was visible by an electrophoretic shift from unmodified K-Ras. To quantify this affect, the LICOR software was used to draw a rectangle over alkylated and unalkylated bands for each well and measured the total fluorescent intensity (FI) in each of these bands. The following formula was then used to calculate % alkylation: $FI_{(alkylated)}/(FI_{(alkylated)}+FI_{(unalkylated)})*100$ for each well.

A 7 point dose response curve was used to determine the $IC_{50}$ for each compound. Cell alkylation data are presented below in Table 3.

Table 3 provides the results of the HTRF and Western Blot Assays as previously described above.

TABLE 3

| Example No. | K-Ras G12C HTRF IC50 (μM) | K-Ras G12C-alkylation HCC1171 Western EC50 (μM) |
|---|---|---|
| 1 | 0.084 | 0.56 |
| 2 | 4.1 | 16 |
| 3 | 6.9 | 21 |
| 4 | ND | >30 |
| 5 | 0.9 | 2.8 |
| 6 | 5.1 | 10 |
| 7 | 0.017 | 0.075 |
| 8 | 0.24 | 0.72 |
| 9 | 0.014 | 0.093 |
| 10 | 0.4 | 2.3 |
| 11 | 1.2 | 4.7 |
| 12 | 1.4 | 8.1 |
| 13 | 0.18 | 1.3 |
| 14 | 0.064 | 0.4 |
| 15 | 0.45 | 2.8 |
| 16 | 3 | 8.2 |
| 17a | <0.01 | 0.002 |
| 17b | 0.6 | 0.56 |
| 18a | 0.008 | 0.0032 |
| 18b | 0.96 | 0.6 |
| 19 | 0.013 | 0.019 |
| 20 | 0.15 | 2.3 |
| 21 | 0.24 | 2.8 |
| 22 | 0.23 | 2.9 |
| 23 | 0.2 | 0.91 |
| 24 | 0.81 | 6.3 |
| 25 | 0.29 | 4.2 |
| 26 | 0.032 | 0.14 |
| 27 | 0.032 | 0.14 |
| 28 | 0.54 | 7.8 |
| 29 | 0.071 | 0.83 |
| 30 | 0.35 | 7.8 |
| 31 | 0.033 | 0.2 |
| 32 | 0.019 | 0.2 |
| 33 | 0.36 | 2.1 |
| 34 | 1 | 3.4 |
| 35 | 0.061 | 0.45 |
| 36 | 4 | 5.5 |
| 37 | 19 | ND |
| 38 | 9.2 | 7.1 |
| 39 | 2.1 | 10 |
| 40 | 0.2 | 1.1 |
| 41 | 0.59 | 16 |
| 42 | >150 | ND |
| 43 | 0.35 | 3.2 |
| 44 | 0.015 | 0.062 |
| 45 | 0.059 | 2.4 |
| 46a | 0.76 | 4.8 |
| 46b | 0.032 | 0.27 |
| 47 | 0.75 | 3.9 |
| 48 | 0.032 | 0.14 |
| 49 | 0.053 | 0.25 |
| 50 | 0.88 | 5.3 |
| 51 | 0.29 | 2.8 |
| 52 | 0.025 | 0.086 |
| 53 | 0.87 | 3.4 |
| 54 | 0.035 | 0.14 |
| 55 | <0.01 | 0.026 |
| 56 | 0.011 | 0.026 |
| 57 | <0.010 | 0.23 |
| 58 | 0.014 | 0.033 |
| 59a | <0.010 | 0.0036 |
| 59b | 0.084 | 0.024 |
| 60 | 0.014 | 0.072 |
| 61 | <0.010 | 0.002 |
| 62a | <0.010 | 0.004 |
| 62b | 0.71 | 0.53 |
| 63a | 0.007 | 0.004 |
| 63b | 0.16 | 0.047 |
| 64a | 3.3 | 2.5 |
| 64b | <0.010 | 0.031 |
| 65 | 0.013 | 0.0076 |
| 66 | 0.011 | 0.028 |
| 67a | <0.010 | 0.004 |
| 67b | 0.073 | 0.032 |
| 68a | <0.010 | 0.013 |
| 68b | 2.6 | 2.6 |
| 69 | <0.010 | 0.001 |
| 70 | <0.010 | 0.019 |
| 71 | 0.011 | 0.018 |
| 72 | 0.013 | 0.055 |
| 73 | 0.026 | 0.11 |
| 74 | 0.012 | 0.11 |
| 75a | <0.010 | 0.1 |
| 75b | <0.010 | 0.035 |
| 76 | 0.013 | 0.14 |
| 77 | <0.010 | 0.025 |
| 78a | <0.010 | 0.056 |
| 78b | <0.010 | 0.04 |
| 79a | 0.022 | 0.15 |
| 79b | 0.017 | 0.14 |
| 80 | 0.01 | 0.071 |
| 81a | 0.01 | 0.0019 |
| 81b | 0.2 | 0.032 |
| 82a | <0.010 | 0.01 |
| 82b | 0.88 | 1.3 |
| 83a | 4 | 1 |
| 83b | 2.9 | 0.97 |
| 83c | 0.01 | 0.031 |
| 83d | 0.02 | 0.0014 |
| 84a | 0.01 | 0.0055 |
| 84b | 0.21 | 0.09 |
| 85 | 0.012 | 0.11 |
| 86 | 0.028 | 0.0047 |
| 87 | 0.023 | 0.18 |
| 88 | 0.025 | 0.24 |
| 89 | 0.011 | 0.029 |

TABLE 3-continued

| Example No. | K-Ras G12C HTRF IC50 (μM) | K-Ras G12C-alkylation HCC1171 Western EC50 (μM) |
| --- | --- | --- |
| 90 | 0.012 | 0.055 |
| 91 | 0.012 | 0.04 |
| 92 | 0.012 | 0.018 |
| 93 | 0.079 | 0.13 |
| 94 | 0.023 | 0.13 |
| 95 | 0.013 | 0.072 |
| 96 | <0.010 | 0.022 |
| 97 | <0.010 | 0.022 |

ND = not determined

Whole Blood Stability Assay

A whole blood stability assay was performed using fresh blood with a drug final concentration of 1 μM. The drug-blood mixtures were incubated at 37° C. for 180 minutes. The half-life of exemplary compounds are set forth in Table 4.

TABLE 4

| Example No. | Half-Life (min) |
| --- | --- |
| 17a | 360 |
| 18a | 240 |
| 19 | 160 |
| 59a | 390 |
| 61 | 160 |
| 62a | 310 |
| 65 | 37 |
| 67a | 250 |
| 68a | >540 |
| 69 | >540 |
| 70 | 61 |
| 71 | 91 |
| 81a | 47 |
| 83d | >540 |
| 84a | 420 |
| 86 | 290 |
| 92 | 180 |

K-Ras G12C Viability and Selectivity 3D Culture CTG Assay

A proliferation assessment may assess the effect of compounds on viability and the specificity for K-Ras G12C driven cancer cell lines. A proliferation assessment is carried out using 3 G12C-driven (H358, HCC1171 and HCC1792) and 2 non-G12C-driven (PC-9 and A427) lines in ultra-low attachment plates to encourage growth of 3D spheroids. On day 1, 1000 cells per well are seeded into 384-well black clear round bottom ultra-low attachment plates (Corning 3830) in 50 μl of RPMI1640 media supplemented with 10% FBS and 2 mM L-Glutamine. On the following day, various concentrations of compounds are added, using a dose response titration starting at 20 uM and keeping the final DMSO amount constant at 0.3%. Seven days after addition of compounds, the amount of viable cells are determined by adding 40 μl of CTG 3D reagent (Promega G9683) which lyses the cells and generates a luciferase signal in proportion to the amount of ATP released. Plates are shaken vigorously for 25 minutes. Plates are then incubated for an additional 10 minutes. Plates are then centrifuged briefly prior to reading luminescence on an Envision plate reader (Perkin Elmer). Luminescence from wells treated with DMSO only is used to determine total proliferation and 1 uM Staurosporine use to determine 100% inhibition.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually.

What is claimed is:

1. A compound having a Formula (II):

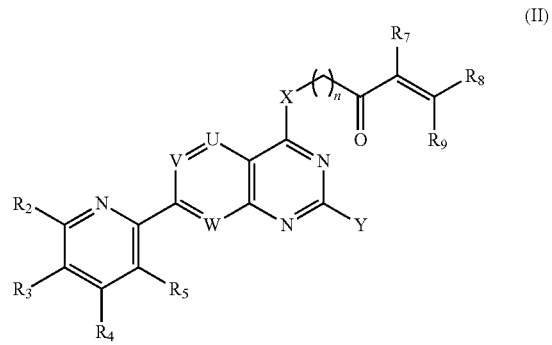

or a pharmaceutically acceptable salt thereof;
wherein,
$R_2$ is $NH_2$;
$R_3$ and $R_4$ are each independently selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and cyclopropyl;
$R_5$ is selected from the group consisting of H, $NH_2$, halo, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ haloalkylthio, $C_{1-6}$ alkylamino, and $C_{3-7}$ cycloalkyl,
or wherein $R_4$ and $R_5$, together with the atoms to which they are each bonded, form $C_{6-14}$ aryl or 5- to 10-membered heteroaryl; each of which is optionally substituted with 1 to 4 substituents, wherein each substituent is independently selected from the group consisting of OH, $NH_2$, halo, $C_{1-3}$ alkyl, $C_{1-3}$ haloalkyl, $C_{1-3}$ alkoxy, and $C_{1-3}$ haloalkoxy;
$R_7$ is selected from the group consisting of H, cyano, and halo; and $R_8$ and $R_9$ are each independently selected from the group consisting of H, $C_{1-6}$ alkyl, $C_{1-6}$ haloalkyl, $C_{1-6}$ hydroxyalkyl, cyano, and halo; wherein $C_{1-6}$ alkyl is optionally substituted with one substituent selected from the group consisting of: methanesulfonyl (mesyl), p-toluenesulfonyl (tosyl), an alkyl or aryl sulfonate leaving group, $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy;
or
$R_7$ and $R_8$ together form a triple bond between the carbons to which they are attached, or $R_7$ and $R_8$ together with the carbons to which they are each bonded form a $C_{3-7}$ cycloalkenyl optionally substituted with one or two halo substituents; and Ry is selected from the group consisting of H, $C_{1-6}$ alkyl, $C_{1-6}$ haloalkyl, cyano, and halo; wherein $C_{1-6}$ alkyl is optionally substituted with one substituent selected from the group consisting of: $C_{1-6}$ alkanoylamino, $C_{1-6}$ alkoxy, $C_{1-6}$ alkylamino, $C_{1-6}$ alkylsulfonylamino, $C_{6-12}$ dialkylamino, and $C_{1-6}$ haloalkoxy;
X is 4- to 7-membered heterocyclyl optionally substituted with 1 to 4 substituents, wherein each substituent is independently selected from the group consisting of OH, NH2, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;
Y is $Y_1$;
$Y_1$ is H;
U is $C(R_{6a})$;
V is $C(R_{6b})$;
W is $C(R_{6c})$;
each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{1-6}$ haloalkoxy, $C_{1-6}$ haloalkyl, 5- to 10-membered heteroaryl, and 4- to 10-membered heterocyclyl; and
n is selected from the group consisting of 0, 1, and 2.

2. The compound of claim 1, or a pharmaceutically acceptable salt thereof, wherein $R_3$ and $R_4$ are independently selected from the group consisting of H, halo, $C_{1-6}$ alkyl, $C_{1-6}$ haloalkyl, and cyclopropyl and $R_5$ is selected from the group consisting of H, halo, $C_{1-6}$ alkyl, $C_{1-6}$ haloalkyl, $C_{1-6}$ haloalkoxy, $C_{1-6}$ alkylamino, and $C_{3-7}$ cycloalkyl.

3. The compound of claim 1, or a pharmaceutically acceptable salt thereof, wherein $R_4$ and $R_5$, together with the atoms to which they are each bonded, form an unsubstituted $C_6$ aryl or 5- to 10-membered heteroaryl; or wherein $R_4$ and $R_5$, together with the atoms to which they are each bonded, form a Ce aryl or 5- to 10-membered heteroaryl substituted with 1 substituent, independently selected from the group consisting of halo, $C_{1-3}$ alkyl, $C_{1-3}$ haloalkyl, $C_{1-3}$ alkoxy, and $C_{1-3}$ haloalkoxy.

4. A compound having a Formula (IV):

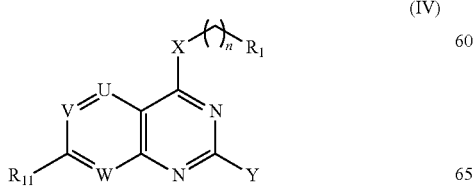

(IV)

or a pharmaceutically acceptable salt thereof;
wherein,
$R_1$ is an electrophilic moiety capable of forming a covalent bond with a cysteine residue at position 12 of a K-Ras G12C mutant protein;
X is 4- to 7-membered heterocyclyl optionally substituted with 1 to 4 substituents, wherein each substituent is independently selected from the group consisting of OH, $NH_2$, halo, cyano, carboxy, carbamoyl, $C_{1-6}$ alkyl, $C_{1-6}$ aminoalkyl, $C_{1-6}$ carbamoylalkyl, $C_{1-6}$ carboxyalkyl, $C_{1-6}$ cyanoalkyl, $C_{1-6}$ haloalkyl, $C_{1-6}$ hydroxyalkyl, and 4- to 7-membered heterocyclyl; wherein two geminal substituents may be taken together to form $C_{3-7}$ spirocycloalkyl or 4- to 7-membered spiroheterocyclyl;
Y is $Y_1$;
$Y_1$ is H;
U is $C(R_{6a})$;
V is $C(R_{6b})$;
W is $C(R_{6c})$;
each of $R_{6a}$, $R_{6b}$, and $R_{6c}$ are independently selected from the group consisting of H, OH, $NH_2$, halo, cyano, carbamoyl, $C_{2-6}$ alkenyl, $C_{1-6}$ alkoxy, $C_{1-6}$ alkyl, $C_{1-6}$ alkyl substituted with a 4- to 10-membered heterocyclyl substituent, $C_{1-6}$ alkylsulfanyl, $C_{1-6}$ alkylsulfonyl, $C_{1-6}$ alkylthio, $C_{1-6}$ haloalkylthio, $C_{2-6}$ alkynyl, $C_{1-6}$ alkylamino, $C_{6-14}$ aryl, $C_{1-6}$ aminoalkyl, $C_{1-6}$ carbamoylalkyl, $C_{1-6}$ carboxyalkyl, $C_{1-6}$ cyanoalkyl, $C_{3-7}$ cycloalkyl, $C_{1-6}$ haloalkoxy, $C_{1-6}$ haloalkyl, 5- to 10-membered heteroaryl, and 4- to 10-membered heterocyclyl;
n is selected from the group consisting of 0, 1, and 2; and
$R_{11}$ is selected from the group consisting of:

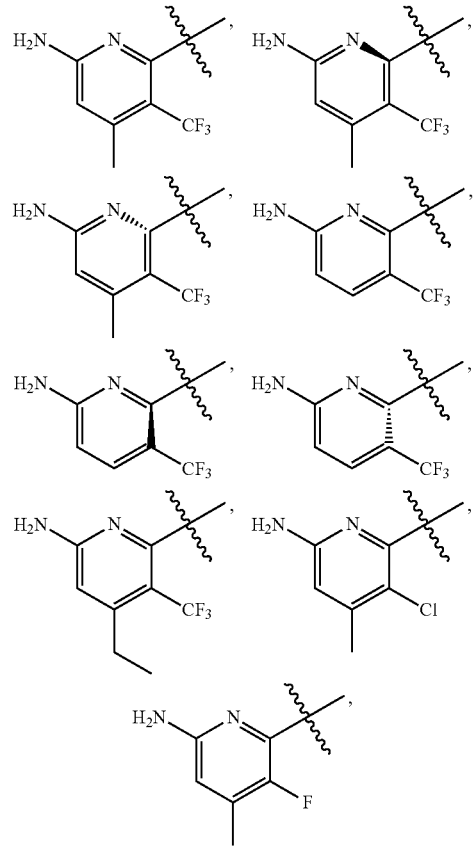

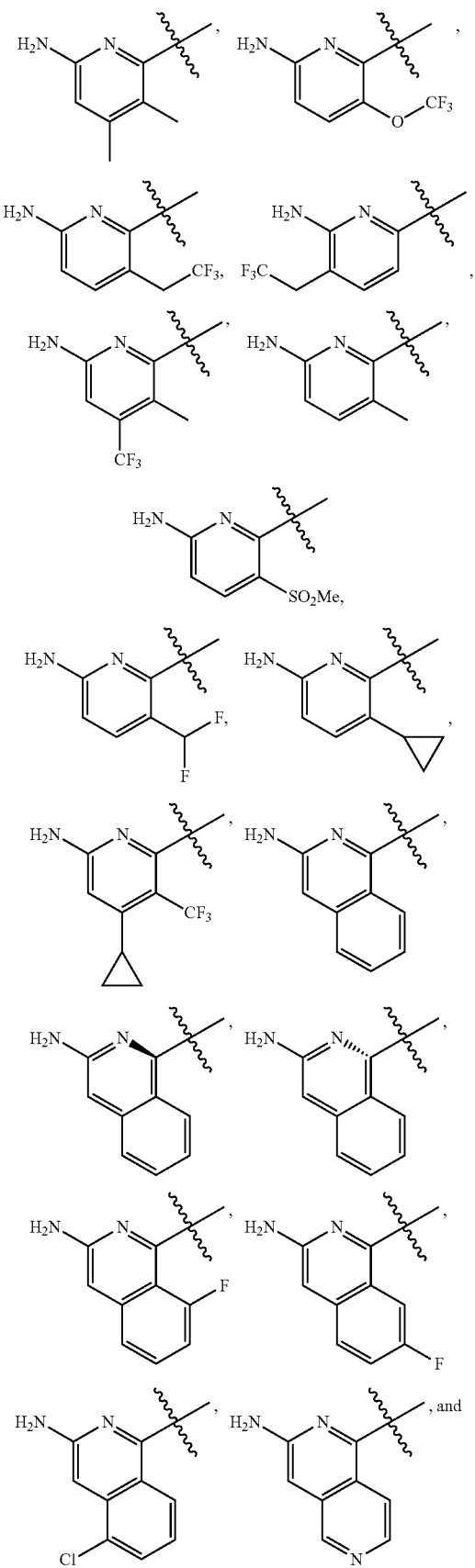
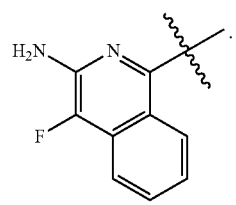
5. The compound of claim 4, or a pharmaceutically acceptable salt thereof, wherein $R_{6a}$ is H.
6. The compound of claim 1, or a pharmaceutically acceptable salt thereof, wherein X is selected from the group consisting of:
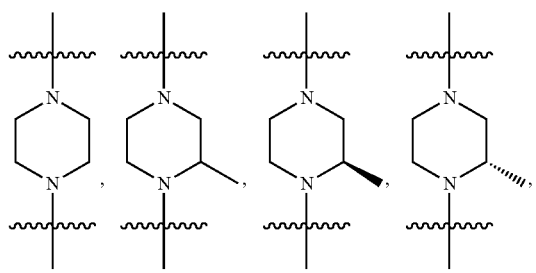
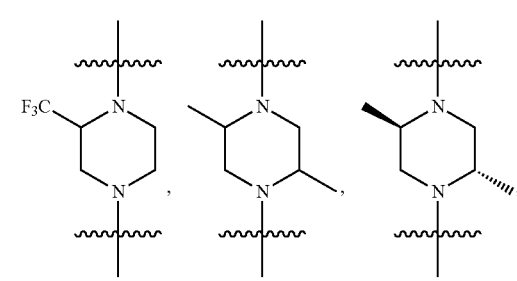
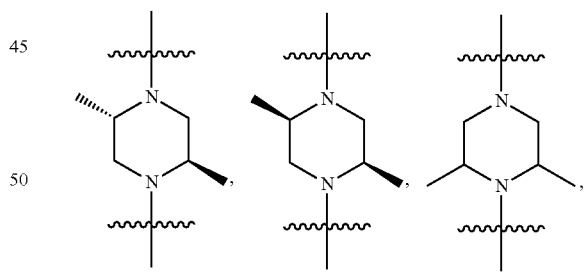
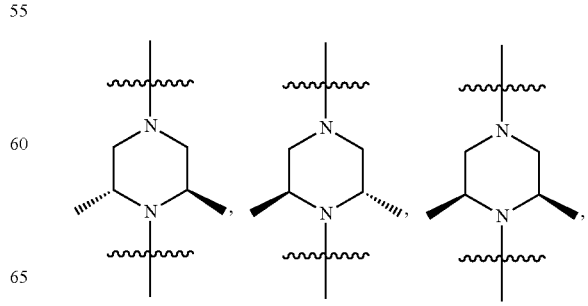

-continued
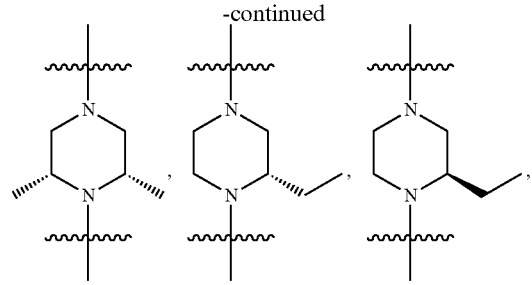
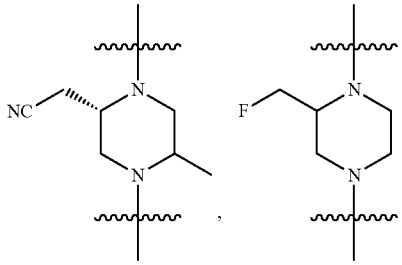
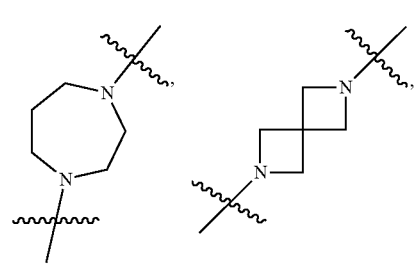
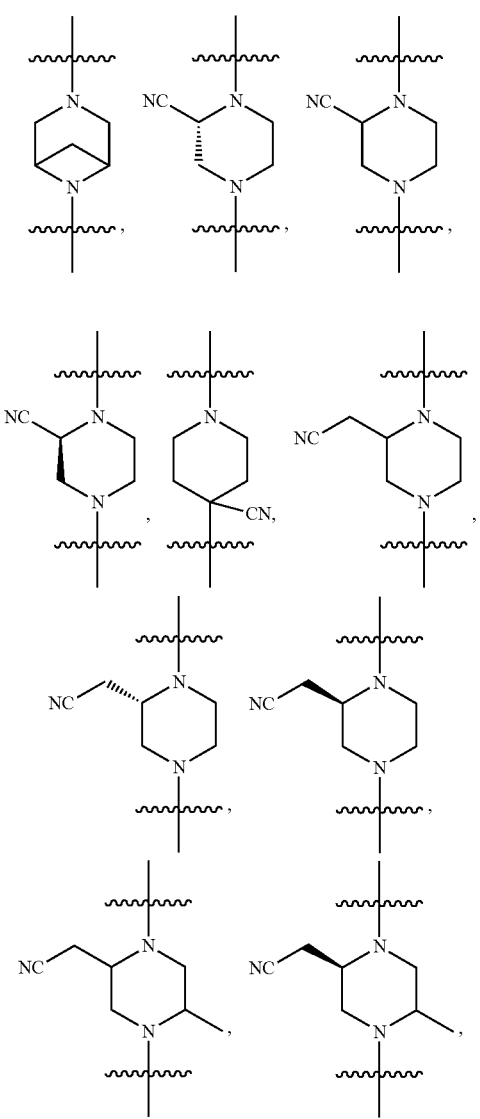
7. The compound of claim 4, or a pharmaceutically acceptable salt thereof, wherein X is selected from the group consisting of:

-continued
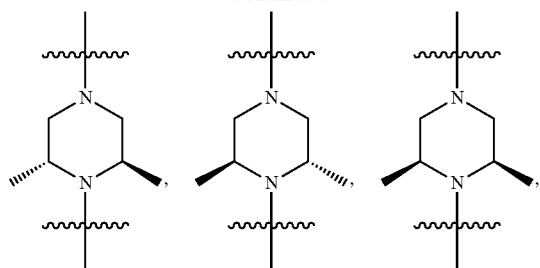
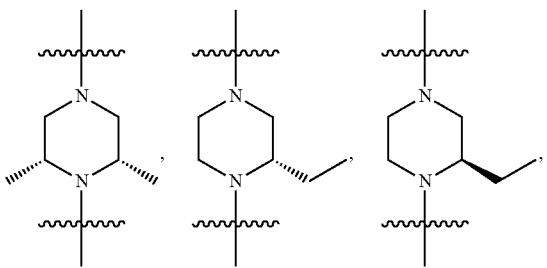
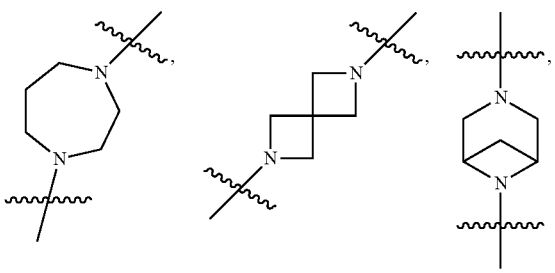
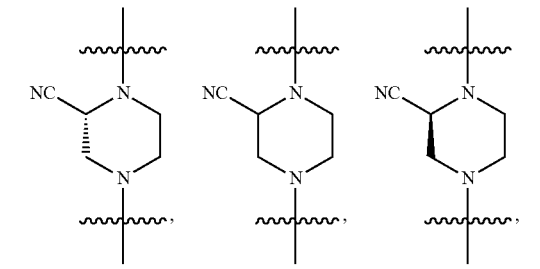
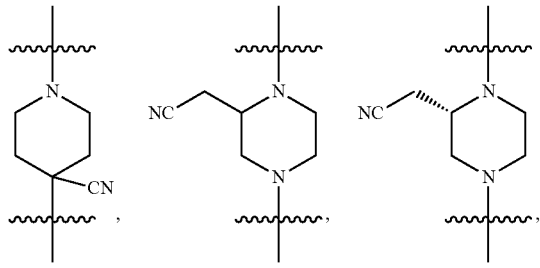
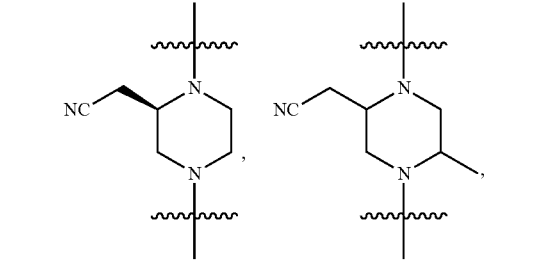
-continued
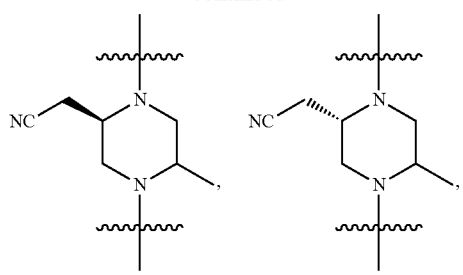
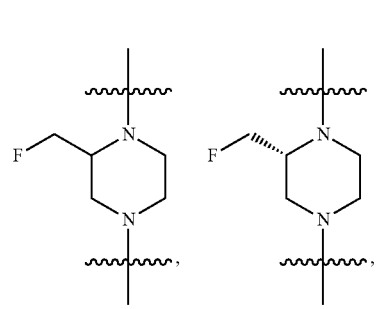
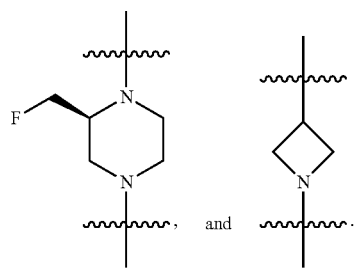
and
8. The compound of claim 1, or a pharmaceutically acceptable salt thereof, wherein X is selected from the group consisting of
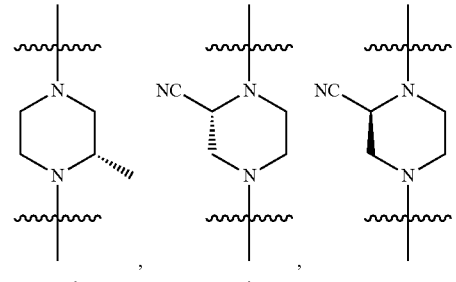
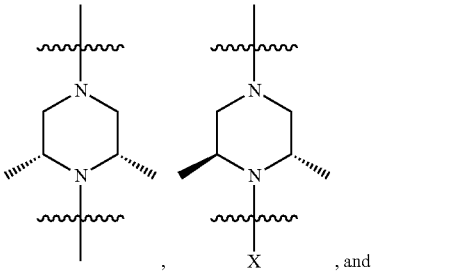
, X , and -continued

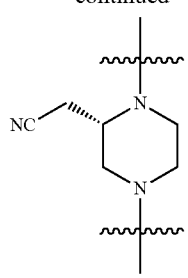

,

9. The compound of claim 4, or a pharmaceutically acceptable salt thereof, wherein X is

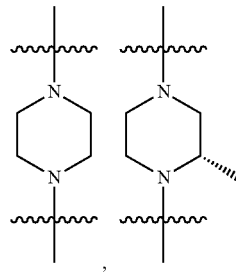 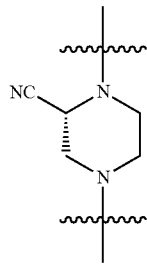 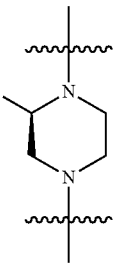

,

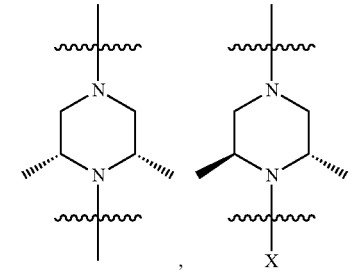

,or

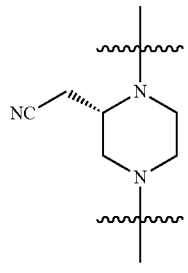

.

10. The compound of claim 4, or a pharmaceutically acceptable salt thereof, wherein $R_1$ is selected from the group consisting of:

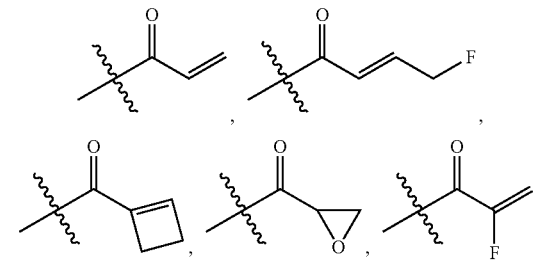

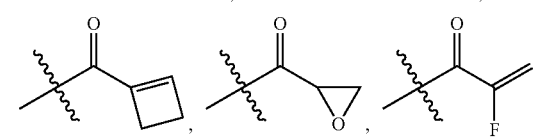

-continued

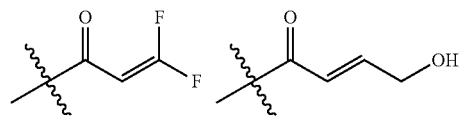

, and

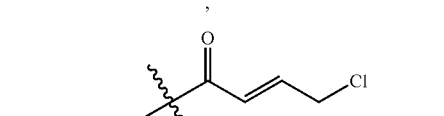

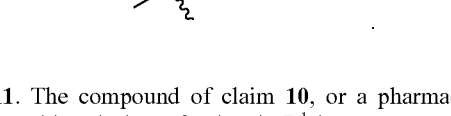

.

11. The compound of claim 10, or a pharmaceutically acceptable salt thereof, wherein $R^1$ is

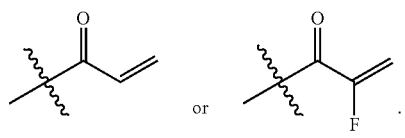 or 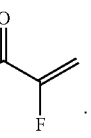

.

12. The compound of claim 1, or a pharmaceutically acceptable salt thereof, wherein $R_7$ is H, cyano, or halo; and $R_8$ and $R_9$ are each H.

13. The compound of claim 1, or a pharmaceutically acceptable salt thereof, wherein $R_7$, $R_8$, and $R_9$ are each H.

14. A compound or a pharmaceutically acceptable salt thereof selected from the group consisting of:

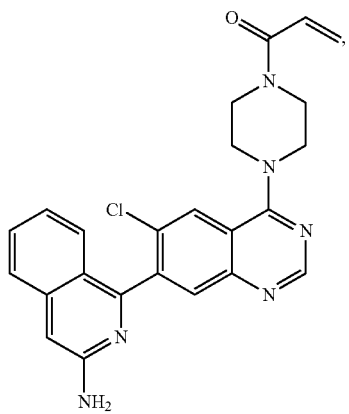

651
-continued
652
-continued
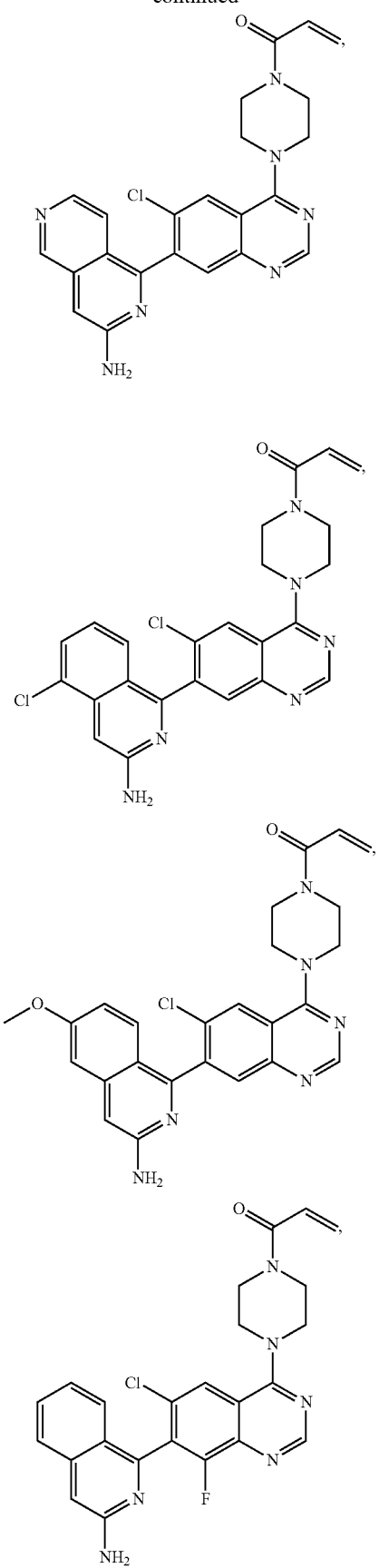
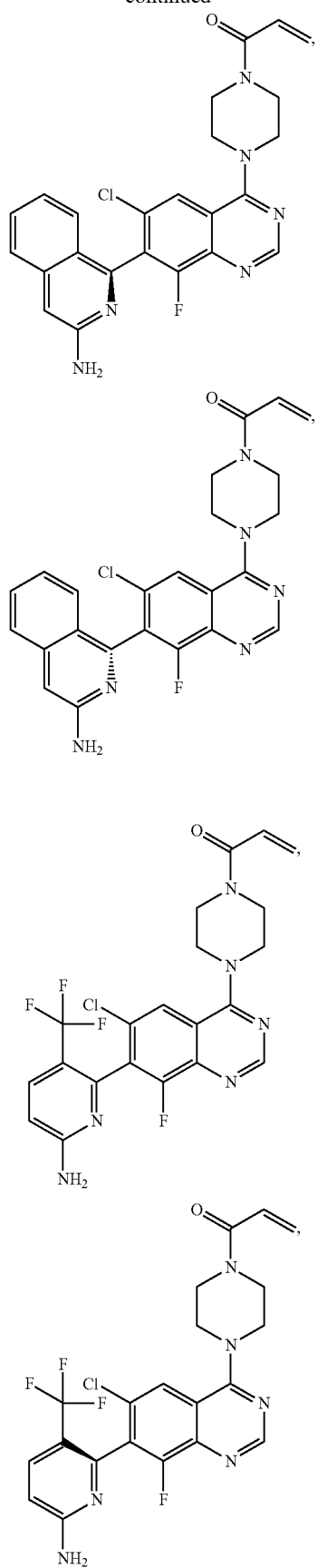

-continued

655
-continued
656
-continued
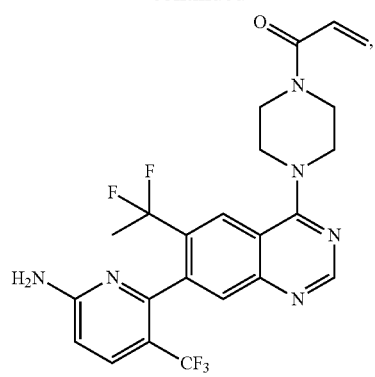
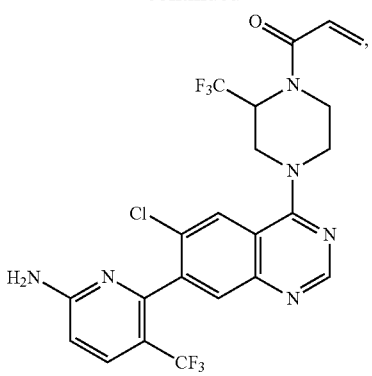

657
-continued
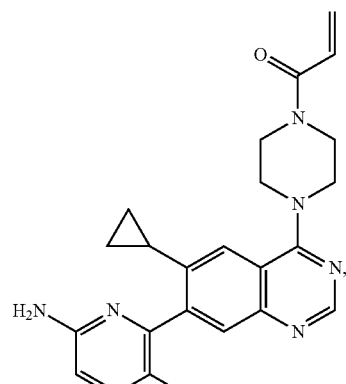
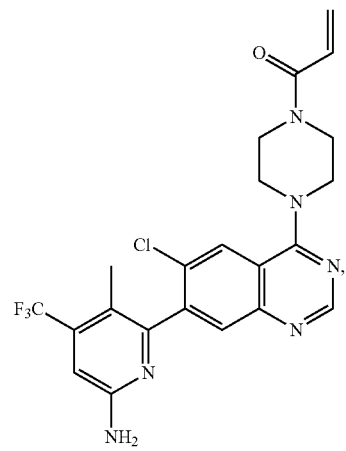
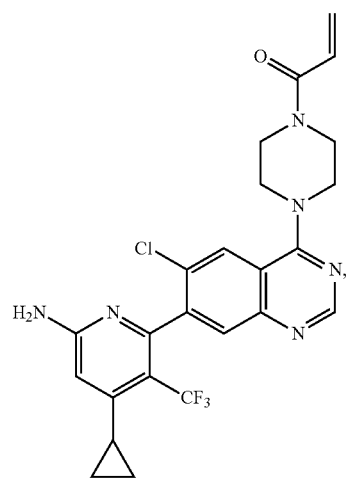
658
-continued
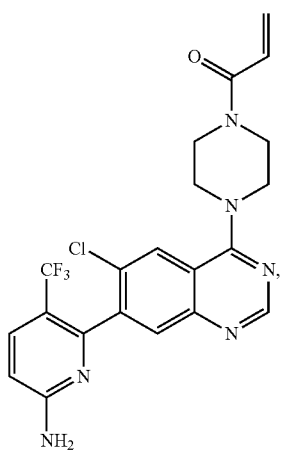
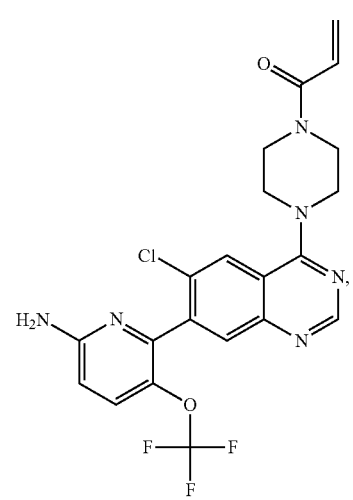
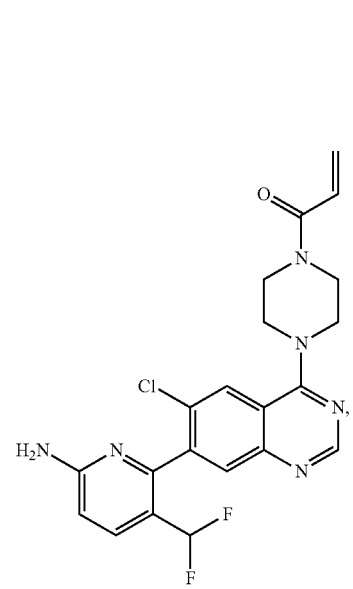

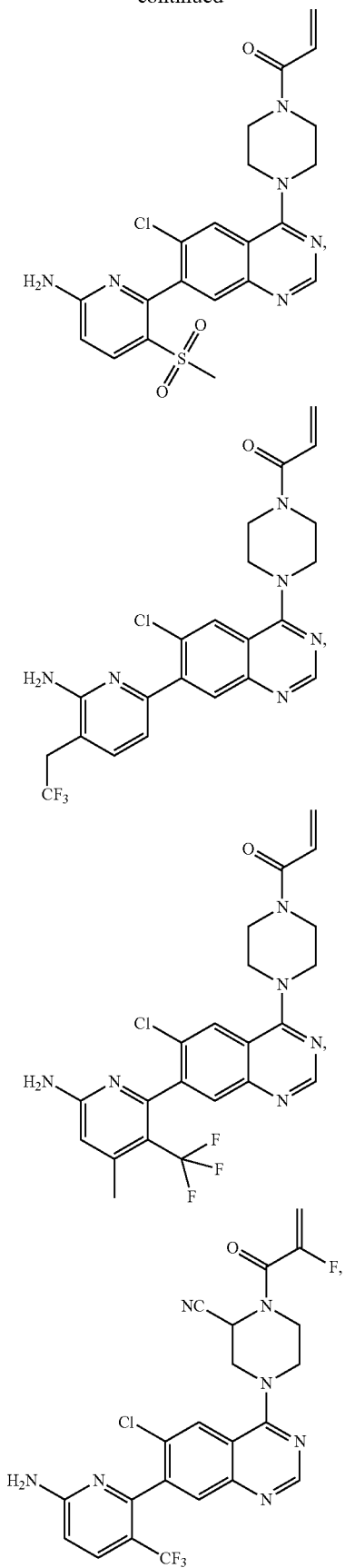
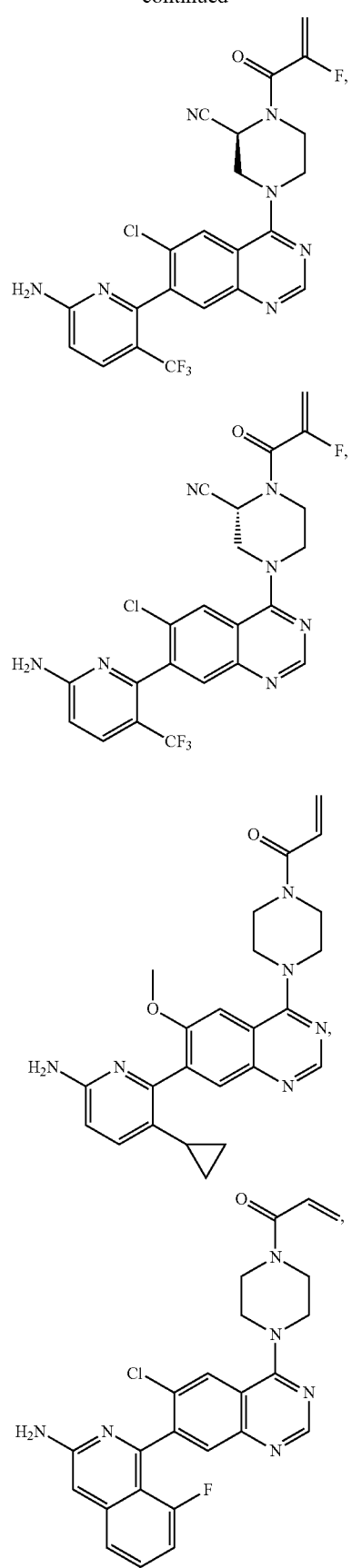

-continued
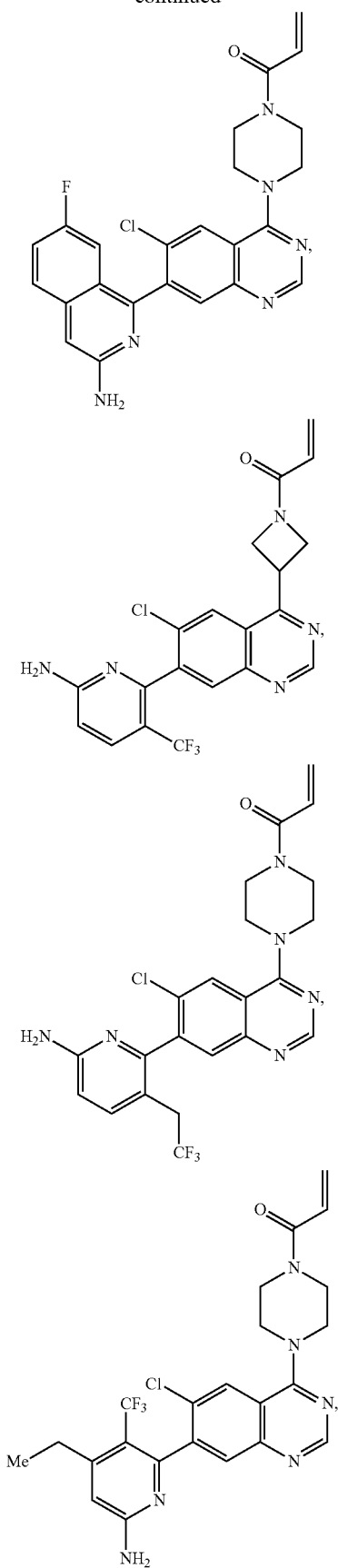
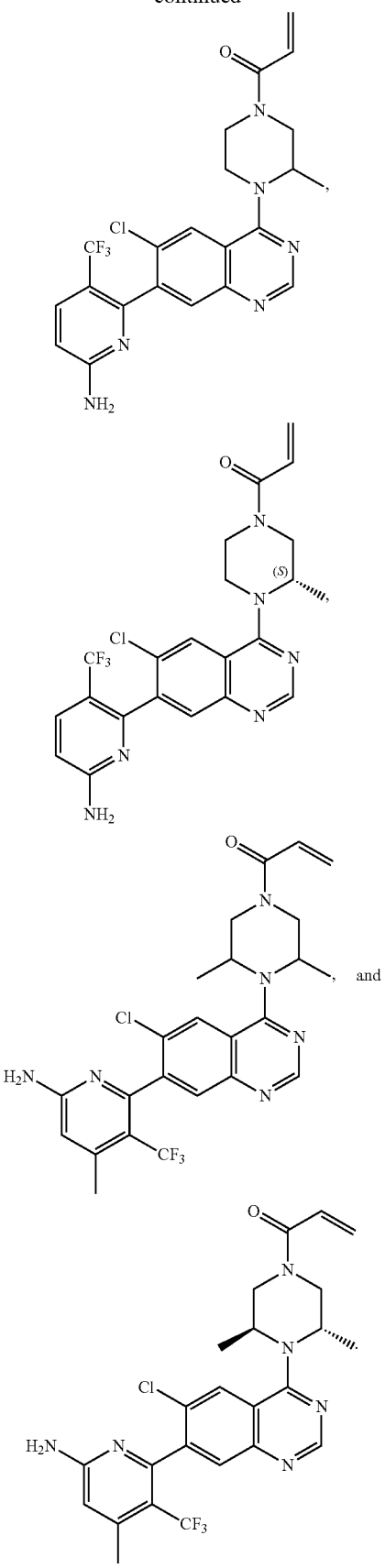

15. A pharmaceutical composition comprising the compound of claim 1, or a pharmaceutically acceptable salt thereof, and a pharmaceutically acceptable excipient.

* * * * *